US011603531B1

(12) United States Patent
Luzzio et al.

(10) Patent No.: US 11,603,531 B1
(45) Date of Patent: Mar. 14, 2023

(54) METHODS AND COMPOSITIONS FOR MODULATING SPLICING

(71) Applicant: SKYHAWK THERAPEUTICS, INC., Waltham, MA (US)

(72) Inventors: Michael Luzzio, Noank, CT (US); Kathleen McCarthy, Somerville, MA (US); William Haney, Wayland, MA (US)

(73) Assignee: SKYHAWK THERAPEUTICS, INC., Waltham, MA (US)

( * ) Notice: Subject to any disclaimer, the term of this patent is extended or adjusted under 35 U.S.C. 154(b) by 0 days.

(21) Appl. No.: 17/502,824

(22) Filed: Oct. 15, 2021

Related U.S. Application Data

(63) Continuation of application No. 16/781,524, filed on Feb. 4, 2020, now Pat. No. 11,162,101, which is a continuation of application No. PCT/US2018/045282, filed on Aug. 3, 2018.

(60) Provisional application No. 62/562,948, filed on Sep. 25, 2017, provisional application No. 62/562,927, filed on Sep. 25, 2017, provisional application No. 62/541,202, filed on Aug. 4, 2017.

(51) Int. Cl.
| | |
|---|---|
| *C12N 15/113* | (2010.01) |
| *C07D 401/14* | (2006.01) |
| *C07D 403/14* | (2006.01) |
| *C07D 451/02* | (2006.01) |
| *C07D 451/04* | (2006.01) |
| *C07D 451/14* | (2006.01) |
| *C07D 471/04* | (2006.01) |
| *C07D 471/08* | (2006.01) |
| *C07D 487/08* | (2006.01) |
| *C07D 491/08* | (2006.01) |
| *C07D 471/10* | (2006.01) |

(52) U.S. Cl.
CPC .......... *C12N 15/113* (2013.01); *C07D 401/14* (2013.01); *C07D 403/14* (2013.01); *C07D 451/02* (2013.01); *C07D 451/04* (2013.01); *C07D 451/14* (2013.01); *C07D 471/04* (2013.01); *C07D 471/08* (2013.01); *C07D 471/10* (2013.01); *C07D 487/08* (2013.01); *C07D 491/08* (2013.01); *C12N 2310/321* (2013.01); *C12N 2310/333* (2013.01)

(58) Field of Classification Search
CPC ............ C12N 15/113; C12N 2310/321; C12N 2310/333; C07D 401/14; C07D 403/14; C07D 451/02; C07D 451/04; C07D 451/14; C07D 471/04; C07D 471/08; C07D 471/10; C07D 487/08; C07D 491/08
USPC .................................................... 514/210.16
See application file for complete search history.

(56) References Cited

U.S. PATENT DOCUMENTS

| | | |
|---|---|---|
| 4,873,192 A | 10/1989 | Kunkel |
| 5,276,036 A | 1/1994 | Bourguignon et al. |
| 7,135,484 B2 | 11/2006 | Dart et al. |
| 7,160,876 B2 | 1/2007 | Ji et al. |
| 7,220,741 B2 | 5/2007 | Peters et al. |
| 7,309,487 B2 | 12/2007 | Inana et al. |
| 7,309,699 B2 | 12/2007 | Ji et al. |
| 7,399,765 B2 | 7/2008 | Bunnelle et al. |
| 7,528,132 B2 | 5/2009 | Chan et al. |
| 7,655,657 B2 | 2/2010 | Stoner et al. |
| 7,674,794 B2 | 3/2010 | Ji et al. |
| 7,834,178 B2 | 11/2010 | Li et al. |
| 7,838,657 B2 | 11/2010 | Singh et al. |
| 7,872,017 B2 | 1/2011 | Ji et al. |
| 7,902,222 B2 | 3/2011 | Ji et al. |
| 7,919,514 B2 | 4/2011 | Monenschein et al. |
| 7,973,015 B2 | 7/2011 | Van Ommen et al. |
| 8,014,953 B2 | 9/2011 | Brenner et al. |
| 8,133,724 B2 | 3/2012 | Qiu et al. |
| 8,283,116 B1 | 10/2012 | Bhattacharyya et al. |
| 8,437,067 B2 | 5/2013 | Hattori et al. |
| 8,603,457 B2 | 12/2013 | Yu et al. |
| 8,609,662 B2 | 12/2013 | Feuerbach et al. |
| 8,609,852 B2 | 12/2013 | Cosford et al. |
| 8,633,019 B2 | 1/2014 | Paushkin et al. |
| 8,729,263 B2 | 5/2014 | Cheung et al. |
| 8,802,642 B2 | 8/2014 | Singh et al. |
| 8,853,241 B2 | 10/2014 | Ji et al. |
| 8,933,090 B2 | 1/2015 | Feuerbach et al. |
| 8,940,762 B2 | 1/2015 | Lee et al. |
| 8,969,346 B2 | 3/2015 | Ashcraft et al. |
| 9,040,712 B2 | 5/2015 | Axford et al. |
| 9,078,823 B2 | 7/2015 | Gunderson et al. |
| 9,133,123 B2 | 9/2015 | Ashcraft et al. |
| 9,163,017 B2 | 10/2015 | Degoey et al. |

(Continued)

FOREIGN PATENT DOCUMENTS

| | | |
|---|---|---|
| CA | 2068770 A1 | 11/1992 |
| DE | 69200895 T2 | 6/1995 |

(Continued)

OTHER PUBLICATIONS

Agrawal, et al., Targeting splicing abnormalities in cancer, Curr Opin Genet Dev., Feb. 2018;48:67-74. doi: 10.1016/j.gde.2017.10. 010. Epub Nov. 12, 2017. PMID: 29136527.

(Continued)

*Primary Examiner* — Kristin A Vajda
(74) *Attorney, Agent, or Firm* — Wilson Sonsini Goodrich & Rosati

(57) ABSTRACT

Described herein are small molecule splicing modulator compounds that modulate splicing of mRNA, such as pre-mRNA, encoded by genes, and methods of use of the small molecule splicing modulator compounds for modulating splicing and treating diseases and conditions.

22 Claims, 31 Drawing Sheets

Specification includes a Sequence Listing.

(56) References Cited

U.S. PATENT DOCUMENTS

| | | |
|---|---|---|
| 9,243,245 B2 | 1/2016 | De Kimpe et al. |
| 9,371,336 B2 | 6/2016 | Lee et al. |
| 9,394,539 B1 | 7/2016 | Paushkin et al. |
| 9,399,649 B2 | 7/2016 | Chen et al. |
| 9,447,075 B2 | 9/2016 | Cuny et al. |
| 9,464,065 B2 | 10/2016 | Schultz et al. |
| 9,475,811 B2 | 10/2016 | Feuerbach et al. |
| 9,545,404 B2 | 1/2017 | Cheung et al. |
| 9,586,955 B2 | 3/2017 | Qi et al. |
| 9,604,965 B2 | 3/2017 | Ashcraft et al. |
| 9,617,268 B2 | 4/2017 | Woll et al. |
| 9,714,422 B2 | 7/2017 | Vorechovsky et al. |
| 9,717,750 B2 | 8/2017 | Bennett et al. |
| 9,730,886 B2 | 8/2017 | Yang et al. |
| 9,745,577 B2 | 8/2017 | Vorechovsky et al. |
| 9,879,007 B2 | 1/2018 | Qi et al. |
| 9,895,358 B2 | 2/2018 | Androphy et al. |
| 9,914,722 B2 | 3/2018 | Yang et al. |
| 9,956,223 B2 | 5/2018 | Ebeling et al. |
| 9,963,699 B2 | 5/2018 | Bennett et al. |
| 9,982,260 B2 | 5/2018 | Kendall et al. |
| 10,006,027 B2 | 6/2018 | Bennett et al. |
| 10,053,697 B1 | 8/2018 | Smolke et al. |
| 10,076,519 B2 | 9/2018 | Ashcraft et al. |
| 10,093,678 B2 | 10/2018 | Shishido et al. |
| 10,112,923 B2 | 10/2018 | Congreve et al. |
| 10,195,196 B2 | 2/2019 | Cheung et al. |
| 10,196,639 B2 | 2/2019 | Vorechovsky et al. |
| 10,252,984 B2 | 4/2019 | Stewart et al. |
| 10,358,427 B2 | 7/2019 | Chong et al. |
| 10,377,742 B2 | 8/2019 | Goff et al. |
| 2008/0044824 A1 | 2/2008 | Giordano et al. |
| 2008/0131892 A1 | 6/2008 | Becker et al. |
| 2010/0305089 A1 | 12/2010 | Ji et al. |
| 2011/0178121 A1 | 7/2011 | Lee et al. |
| 2012/0172352 A1 | 7/2012 | Page et al. |
| 2012/0172353 A1 | 7/2012 | Peters et al. |
| 2013/0165416 A1 | 6/2013 | Wagner et al. |
| 2014/0051672 A1 | 2/2014 | Cheung et al. |
| 2015/0158867 A1 | 6/2015 | Schrimpf et al. |
| 2015/0259391 A1 | 9/2015 | Petsko et al. |
| 2016/0145270 A1 | 5/2016 | Dakka et al. |
| 2016/0184305 A1 | 6/2016 | Cheung et al. |
| 2017/0145411 A1 | 5/2017 | Collard et al. |
| 2017/0239225 A1 | 8/2017 | Androphy et al. |
| 2017/0268066 A1 | 9/2017 | Gai et al. |
| 2017/0334977 A1 | 11/2017 | Butovsky et al. |
| 2017/0355956 A1 | 12/2017 | Kiledjian et al. |
| 2018/0002694 A1 | 1/2018 | Vorechovsky et al. |
| 2018/0009754 A1 | 1/2018 | Long et al. |
| 2018/0078601 A1 | 3/2018 | Mastaloudis et al. |
| 2018/0134707 A1 | 5/2018 | Youngman et al. |
| 2018/0142240 A1 | 5/2018 | Bennett et al. |
| 2018/0170923 A1 | 6/2018 | Metzger et al. |
| 2018/0271803 A1 | 9/2018 | Hybertson et al. |
| 2018/0289682 A1 | 10/2018 | Kenyon et al. |
| 2018/0344680 A1 | 12/2018 | Zhang et al. |
| 2018/0344737 A1 | 12/2018 | Ebeling et al. |
| 2019/0000844 A1 | 1/2019 | Babu et al. |
| 2019/0016707 A1 | 1/2019 | Kane, Jr. et al. |
| 2019/0030058 A1 | 1/2019 | Bennett et al. |
| 2019/0040040 A1 | 2/2019 | Hodgetts et al. |
| 2019/0048057 A1 | 2/2019 | Colonna et al. |
| 2019/0070213 A1 | 3/2019 | Aznarez et al. |
| 2019/0083489 A1 | 3/2019 | Christiano |
| 2019/0134152 A1 | 5/2019 | Durham |
| 2019/0142858 A1 | 5/2019 | Ranum et al. |
| 2019/0160062 A1 | 5/2019 | Cheung et al. |
| 2019/0167815 A1 | 6/2019 | Holmes et al. |
| 2019/0231808 A1 | 8/2019 | Richter et al. |
| 2019/0264211 A1 | 8/2019 | Vorechovsky et al. |
| 2019/0292540 A1 | 9/2019 | Singh et al. |
| 2019/0330615 A1 | 10/2019 | Bhattacharyya et al. |
| 2020/0224199 A1 | 7/2020 | Luzzio et al. |
| 2020/0277289 A1 | 9/2020 | Luzzio et al. |

FOREIGN PATENT DOCUMENTS

| | | |
|---|---|---|
| EP | 0327155 A2 | 8/1989 |
| EP | 0514277 A1 | 11/1992 |
| EP | 2417257 B1 | 3/2016 |
| EP | 3027600 A1 | 6/2016 |
| EP | 3053577 A1 | 8/2016 |
| EP | 2480228 B1 | 11/2016 |
| EP | 3359685 A1 | 8/2018 |
| EP | 3368069 A1 | 9/2018 |
| EP | 3373972 A1 | 9/2018 |
| EP | 3411080 A2 | 12/2018 |
| EP | 3423158 A1 | 1/2019 |
| EP | 3436443 A1 | 2/2019 |
| EP | 3442960 A1 | 2/2019 |
| EP | 3155128 B1 | 5/2019 |
| EP | 3583951 A1 | 12/2019 |
| EP | 2948448 B1 | 1/2020 |
| WO | WO-9113885 A1 | 9/1991 |
| WO | WO-2006113704 A2 | 10/2006 |
| WO | WO-2007137030 A2 | 11/2007 |
| WO | WO-2009006959 A1 | 1/2009 |
| WO | WO-2011090669 A1 | 7/2011 |
| WO | WO-2013063458 A2 | 5/2013 |
| WO | WO-2013117693 A1 | 8/2013 |
| WO | WO-2014028459 A1 | 2/2014 |
| WO | WO-2014111751 A1 | 7/2014 |
| WO | WO-2014111837 A1 | 7/2014 |
| WO | WO-2014111838 A1 | 7/2014 |
| WO | WO-2015024876 A2 | 2/2015 |
| WO | WO-2016128343 A1 | 8/2016 |
| WO | WO-2016196386 A1 | 12/2016 |
| WO | WO-2017100726 A1 | 6/2017 |
| WO | WO-2018006074 A2 | 1/2018 |
| WO | WO-2018006074 A3 | 2/2018 |
| WO | WO-2018151326 A1 | 8/2018 |
| WO | WO-2018204412 A1 | 11/2018 |
| WO | WO-2018232039 A1 | 12/2018 |
| WO | WO-2019005980 A1 | 1/2019 |
| WO | WO-2019005993 A1 | 1/2019 |
| WO | WO-2019028440 A1 | 2/2019 |
| WO | WO-2019057123 A1 | 3/2019 |
| WO | WO-2019075265 A1 | 4/2019 |
| WO | WO-2019191092 A1 | 10/2019 |
| WO | WO-2019191229 A1 | 10/2019 |
| WO | WO-2019199972 A1 | 10/2019 |
| WO | WO-2020004594 A1 | 1/2020 |
| WO | WO-2020005873 A1 | 1/2020 |
| WO | WO-2020005877 A1 | 1/2020 |
| WO | WO-2020005882 A1 | 1/2020 |
| WO | WO-2020028814 A1 | 2/2020 |
| WO | WO-2020073949 A1 | 4/2020 |
| WO | WO-2021174163 A1 | 9/2021 |
| WO | WO-2021174164 A1 | 9/2021 |
| WO | WO-2021174165 A1 | 9/2021 |
| WO | WO-2021174167 A1 | 9/2021 |
| WO | WO-2021174170 A1 | 9/2021 |
| WO | WO-2021174174 A1 | 9/2021 |
| WO | WO-2021174176 A1 | 9/2021 |
| WO | WO-2021207530 A1 | 10/2021 |
| WO | WO-2021207532 A1 | 10/2021 |
| WO | WO-2021207550 A1 | 10/2021 |
| WO | WO-2021207554 A1 | 10/2021 |

OTHER PUBLICATIONS

Almada et al., "Promoter directionality is controlled by U1 snRNP and polyadenylation signals", Nature, Jul. 18, 2013, vol. 499, pp. 360-363.

Bertram K, et al., Cryo-EM structure of a human spliceosome activated for step 2 of splicing, Nature. Feb. 16, 2017;542(7641):318-323. doi: 10.1038/nature21079. Epub Jan. 11, 2017. PMID: 28076346.

Bertram K, et al., Cryo-EM Structure of a Pre-catalytic Human Spliceosome Primed for Activation, Cell. Aug. 10, 2017;170(4):701-713.e11. doi:10.1016/j.cell.2017.07.011. Epub Aug. 3, 2017. PMID: 28781166.

(56) References Cited

OTHER PUBLICATIONS

Betz et al. KlenTaq polymerase replicates unnatural base pairs by inducing a Watson-Crick geometry. Nat Chem Biol 8:612-614 (2012).

Birman et al., "Second-harmonic generation-based methods to detect and characterize ligand-induced RNA conformational changes", Methods, Sep. 2019, vol. 167, pp. 92-104.

Boutz et al., "Detained introns are a novel, widespread class of post-transcriptionally spliced introns", (Nov. 10, 2014) Genes & Development, 29:63-80,Cold Spring Harbor Press Laboratory, ISSN 0890-9369/15.

Braun et al., "Coordinated Splicing of Regulatory Detained Introns within Oncogenic Transcripts Creates and Exploitable Vulnerability in Malignant Glioma", Cancer Cell, 2017, vol. 32, pp. 411-426.

Butko et al, "Detection of Ligand-Induced Conformational Changes in Oligonucleotides by Second-Harmonic Generation at a Supported Lipid Bilayer Interface", Anal. Chem, 2016, vol. 88, pp. 10482-10489.

Cheng et al., "Probes and drugs that interfere with protein translation via targeting to the RNAs or RNA-protein interactions", Methods, 2019, vol. 167, pp. 124-133.

Cheung et al., Discovery of Small Molecule Splicing Modulators of Survival Motor Neuron-2 (SMN2) forthe Treatment of Spinal Muscular Atrophy (SMA), J Med Chem., Dec. 27, 2018;61(24):11021-11036. doi: 10.1021/acs.jmedchem.8b01291. Epub Dec. 13, 2018. PMID: 30407821.

Cho, Aesop, Recent Advances in Oral Prodrug Discovery. Annual Reports in Medicinal Chemistry, vol. 41, 395-407, (2006).

Clark et al., "Long-read sequencing reveals the splicing profile of the calcium channel gene CACNA1C in human brain", bioRxiv 260562; pp. 1-19, doi: https://doi.org/10.1101/260562. 2018.

Clery et al., "switchSENSE: A new technology to study protein-RNA interactions", Methods, Apr. 2017, vol. 118-119, pp. 137-145.

Cooper, Thomas A., "Use of minigene systems to dissect alternative splicing elements", Methods, Dec. 2005, vol. 37, Issue 4, pp. 331-340.

Cretu C, et al., Structural Basis of Splicing Modulation by Antitumor Macrolide Compounds, Mol Cell. Apr. 19, 2018;70(2):265-273.e8. doi:10.1016/j.molcel.2018.03.011. Epub Apr. 12, 2018. PMID: 29656923.

Czech, Christian et al., Biomarker for Spinal Muscular Atrophy: Expression of SMN in Peripheral Blood of SMA Patients and Healthy Controls, PloS one vol. 10,10 e0139950. Oct. 15, 2015, doi:10.1371/journal.pone.0139950.

European Search Report for EP Application No. 20165378.9 dated Jun. 25, 2020.

Fica, Sebastian M, and Kiyoshi Nagai, Cryo-electron microscopy snapshots of the spliceosome: structural insights into a dynamic ribonucleoprotein machine, Nature structural & molecular biology vol. 24,10 (2017): 791-799. doi:10.1038/nsmb.3463.

Finci, Lorenzo I et al., The cryo-EM structure of the SF3b spliceosome complex bound to a splicing modulator reveals a pre-mRNA substrate competitive mechanism of action, Genes& development vol. 32,3-4 (2018): 309-320. doi:10.1101/gad.311043.117.

Henderson et al., "Generation of small molecule-binding RNA arrays and their application to fluorogen-binding RNA aptamers", Methods, 2019, vol. 167, pp. 39-53.

Hermann T, Patel DJ, RNA bulges as architectural and recognition motifs, Structure.Mar. 15, 2000;8(3):R47-54. doi: 10.1016/s0969-2126(00)00110-6. PMID: 10745015.

Hug, Nele et al. , Mechanism and regulation of the nonsense-mediated decay pathway, Nucleic acids research vol. 44,4 (2016): 1483-95. doi:10.1093/nar/gkw010.

International Search Report and Written Opinion for PCT/US2020/16894 dated May 15, 2020.

International Search Report and Written Opinion dated Apr. 29, 2020, for PCT/US20/16671.

International Search Report and Written Opinion dated Feb. 4, 2020 for PCT/US2020/016647.

International Search Report and Written Opinion dated Jun. 15, 2020, for PCT/US2020/016682.

International Search Report and Written Opinion dated May 12, 2020, for PCT/US20/16677.

International Search Report and Written Opinion dated May 27, 2020, for PCT/US2020/01640.

International Search Report and Written Opinion dated May 27, 2020 for PCT/US2020/17086.

International Search Report and Written Opinion dated May 29, 2020 for PCT/US20/16897.

"International Search Report and Written Opinion for corresponding PCT Application No. PCT/US2018/045282 dated Dec. 12, 2018".

International Search Report and Written Opinion for PCT/US20/16568 dated Jun. 18, 2020.

International Search Report and Written Opinion for PCT/US20/16638 dated Jun. 18, 2020.

International Search Report and Written Opinion for PCT/US20/16676 dated Jun. 3, 2020.

International Search Report and Written Opinion for PCT/US2020/016671 dated Apr. 29, 2020.

Kastner B, et al., Structural Insights into Nuclear pre-mRNA Splicing in Higher Eukaryotes, Cold Spring Harb Perspect Biol. Nov. 1, 2019;11(11):a032417. doi:10.1101/cshperspect.a032417. PMID: 30765414; PMCID: PMC6824238.

Kletzl et al., "The oral splicing modifier RG7800 increases full length survival of motor neuron 2 mRNA and survival of motor neuron protein: Results from trials in healthy adults and patients with spinal and muscular atrophy", Neuromuscular Disorders, 2019, vol. 29, Issue 1, pp. 21-29.

Knezevic et al., "Quantitation of Affinity, Avidity, and Binding Kinetics of Protein Analytes with a Dynamically Switchable Biosurface", J. Am. Chem. Soc., 2012, vol. 134, pp. 15225-15228.

Kondo, Yasushi et al., Crystal structure of human U1 snRNP, a small nuclear ribonucleoprotein particle, reveals the mechanism of 5' splice site recognition, eLife vol. 4e04986. Jan. 2, 2015, doi:10.7554/eLife.04986.

Lee et al., "Mechanisms and Regulation of Alternative Pre-mRNA Splicing", Annual Review of Biochemistry, 2015, vol. 84, pp. 291-323.

Li et al., "Annotation-free quantification of RNA splicing using LeafCutter", Nat Genet., Jan. 2018, vol. 50, No. 1, pp. 151-158. doi:10.1038/s41588-017-0004-9.

Li, Xueni et al., CryoEM structure of *Saccharomyces cerevisiae* U1 snRNP offers insight into alternative splicing, Nature communications vol. 8,1 1035. Oct. 19, 2017, doi:10.1038/s41467-017-01241-9.

Martin et al., "Using SHAPE-MaP to probe small molecule-RNA interactions", Methods, Sep. 2019, vol. 167, pp. 105-116.

Mashalidis et al., "A three-stage biophysical screening cascade for fragment-based drug discovery", Nature Protocols, 2013, vol. 8, No. 11 pp. 2309-2324.

Mcgovern-Gooch et al., "Fluorescence-based investigations of RNA-small molecule interactions", Methods, Sep. 2019, vol. 167, pp. 54-65, doi: 10.1016/j.ymeth.2019.05.017..

Montes, Matias et al., RNA Splicing and Disease: Animal Models to Therapies, Trends in genetics : TIG vol. 35,1 (2019): 68-87. doi:10.1016/j.tig.2018.10.002.

Murata et al., "Modulating RNA secondary and tertiary structures by mismatch binding ligands", Methods, 2019, vol. 167, pp. 78-91.

Muto Y, et al., The structure and biochemical properties of the human spliceosomal protein U1C, J Mol Biol. Jul. 30, 2004;341(1):185-98. doi: 10.1016/j.jmb.2004.04.078. PMID:15312772.

Nelissen, R L et al., Zinc finger-like structure in U1-specific protein C is essential for specific binding to U1 snRNP, Nucleic acids research vol. 19,3 (1991): 449-54.doi:10.1093/nar/19.3.449.

"Oltean, "Modulators of alternative splicing as novel therapeutics in cancer", World J Clin Oncol 2015, 6, 92-95".

Palacino J, et al., SMN2 splice modulators enhance U1-pre-mRNAassociation and rescue SMA mice, Nat Chem Biol. Jul. 2015;11(7):511-7. doi:10.1038/nchembio.1837. Epub Jun. 1, 2015. Erratum in: Nat Chem Biol. Sep. 2015;11(9):741. Erratum in: Nat Chem Biol. Apr. 2016;12(4):304. PMID: 26030728.

(56) References Cited

OTHER PUBLICATIONS

Parra et al., "An important class of intron retention events in human erythroblasts is regulated by cryptic exons proposed to function as splicing decoys", RNA, 24(9):1255-1265, Cold Spring Harbor Press Laboratory for the RNA Society, 2018.
Pawellek, Andrea et al., Identification of small molecule inhibitors of pre-mRNA splicing, The Journal of Biological Chemistry, Dec. 12, 2014, vol. 289(50):34683-34698.
Pawellek, Andrea et al., Identification of small molecule inhibitors of pre-mRNA splicing, The Journal of biological chemistry vol. 289,50 (2014): 34683-98.doi:10.1074/jbc.M114.590976.
Pinard E, et al., Discovery of a Novel Class of Survival Motor Neuron 2 Splicing Modifiers for the Treatment of Spinal Muscular Atrophy, J Med Chem. May 25, 2017;60(10):4444-4457. doi: 10.1021/acs.jmedchem.7b00406. EpubMay 4, 2017.PMID: 28441483.
Plaschka C, Newman AJ, Nagai K., Structural Basis of Nuclear pre-mRNA Splicing: Lessons from Yeast, Cold Spring Harb Perspect Biol. May 1, 2019;11 (5):a032391. doi:10.1101/cshperspect. a032391. PMID: 30765413; PMCID: PMC6496352.
Poirier, Agnès et al., Risdiplam distributes and increases SMN protein in both the central nervous system and peripheral organs, Pharmacology research & perspectives vol. 6,6 e00447. Nov. 29, 2018, doi:10.1002/prp2.447.
Ramesh, R., et al., Quest for Novel Chemical Entities through Incorporation of Silicon in Drug Scaffold, J. Medicinal Chemistry, 2018, 61, 3779-3798.
Ratni et al., "Rewriting the (tran)script: Application to spinal muscular atrophy", Progress in Medicinal Chemistry, 2019, vol. 58, pp. 119-156.
Ratni H, et al., Discovery of Risdiplam, a Selective Survival of Motor Neuron-2 ( SMN2) Gene Splicing Modifier for the Treatment of Spinal Muscular Atrophy (SMA), J Med Chem. Aug. 9, 2018;61 (15):6501-6517. doi: 10.1021/acs.jmedchem.8b00741. Epub Jul. 25, 2018.PMID: 30044619.
Ratni H, et al., Specific Correction of Alternative Survival Motor Neuron 2 Splicing by Small Molecules: Discovery of a Potential Novel Medicine To Treat Spinal Muscular Atrophy, J Med Chem. Jul. 14, 2016;59(13):6086-100. doi:10.1021/acs.jmedchem. 6b00459. Epub Jul. 6, 2016. PMID: 27299419.
Rizvi et al., "Discovery of Selective RNA-Binding Small Molecules by Affinity-Selection Mass Spectrometry", ACS Chem Biol., 2018, vol. 13, No. 3, pp. 820-831.
Rizvi et al., "RNA-ALIS: Methodology for screening soluble RNAs as small molecule targets using ALIS affinity-selection mass spectrometry", Methods, Sep. 1, 2019, vol. 167, pp. 28-38.
Roca, Xavier et al., Widespread recognition of 5' splice sites by noncanonical base-pairing to U1snRNA involving bulged nucleotides, Genes & development vol. 26,10 (2012):1098-109. doi:10.1101/ gad.190173.112.
Romero-Barrios, Natali et al., Splicing regulation by long noncoding RNAs, Nucleic acids research vol. 46,5 (2018): 2169-2184. doi:10.1093/nar/gky095.
Rooseboom et al. Enzyme-catalyzed activation of anticancer prodrugs. Pharmacological Reviews 56:53-102 (2004).
Rosenberg et al., "Learning the Sequence Determinants of Alternative Splicing from Millions of Random Sequences", Cell, 2015, vol. 163, pp. 698-711.
Scotti et al., "RNA mis-splicing in disease", Nat Rev Genet., Jan. 2016, vol. 17, No. 1, pp. 19-32, doi: 10.1038/nrg.2015.3.
Shi Y., The Spliceosome: A Protein-Directed Metalloribozyme, J MolBiol. Aug. 18, 2017;429(17):2640-2653. doi: 10.1016/j.jmb. 2017.07.010. Epub Jul. 19, 2017. PMID: 28733144.
Sibley, Christopher R et al., Lessons from non-canonical splicing,Nature reviews. Genetics vol. 17,7 (2016): 407-421. doi:10.1038/nrg.2016. 46.
Silvers et al., "Differential Scanning Fluorimetry for Monitoring RNA Stability", ChemBioChem, May 4, 2015, vol. 16, No. 7, pp. 1109-1114.
Smola et al., "Selective 2'-hydroxyl acylation analyzed by primer extension and mutational profiling (SHAPE-MaP) for direct, versatile, and accurate RNA structure analysis", Nat Protoc., Nov. 2015, vol. 10, No. 11, pp. 1643-1669. doi:10.1038/nprot.2015.103.
Spraggon et al., "U1 snRNP-Dependent Suppression of Polyadenylation: Physiological Role and Therapeutic Opportunities in Cancer", International Journal of Cell Biology, 2013, vol. 2013, Article ID 846510, pp. 1-10, doi.org/10.1155/2013/846510.
Sturm, Stefan et al., A phase 1 healthy male volunteer single escalating dose study of the pharmacokinetics and pharmacodynamics of risdiplam(RG7916, RO7034067), a SMN2 splicing modifier, British journal of clinical pharmacology vol. 85,1 (2019): 181-193. doi:10.1111/bcp.13786.
Supplementary European Search Report dated Dec. 11, 2020 for Application No. EP 18 84 0857, (10 pages).
Taladriz-Sender et al., "Splice-switching small molecules: A new therapeutic approach to modulate gene expression", Methods, Sep. 2019, vol. 167, pp. 134-142, doi: 10.1016/j.ymeth.2019.06.011.
Tan et al., Noncanonical registers and base pairs in human 5' splice-site selection, Nucleic Acids Research, 2016, vol. 44, No. 8, pp. 3908-3921. doi:10.1093/narlgkw163.
Teng, Teng et al. ,Splicing modulators act at the branch point adenosine binding pocket defined by the PHF5A-SF3b complex, Nature communications vol. 8 15522. May 25, 2017,doi:10.1038/ ncomms15522.
Thompson et al., "NMR characterization of RNA small molecule interactions", Methods, 2019, vol. 167, pp. 66-77.
Tilgner et al., "Comprehensive transcriptome analysis using synthetic long-read sequencing reveals molecular co-association of distant splicing events", Nat Biotechnol., Jul. 2015, vol. 33, No. 7, pp. 736-742, doi: 10.1038/nbt.3242.
Treutlein et al., "Cartography of neurexin alternative splicing mapped by single-molecule long-read mRNA sequencing", PNAS, Apr. 1, 2014, 111 (13) E1291-E1299.
Co-pending U.S. Appl. No. 16/818,590, filed Mar. 13, 2020.
Van Nostrand et al., "Robust transcriptosome-wide discovery of RNA binding protein binding sites with enhanced CLIP (eCLIP)", Nat Methods, Jun. 2016, vol. 13, No. 6, pp. 508-514. doi:10.1038/ nmeth.3810.
Vaquero-Garcia et al., "A new view of transcriptome complexity and regulation through the lens of local splicing variations", eLife, 2016, 5:e11752, pp. 1-30, DOI: 10.7554/eLife.11752.
Verbist et al., "Using transcriptomics to guide lead optimization in drug discovery projects: Lessons learned from the QSTAR project", Drug Discovery Today, May 2015, vol. 20, No. 5, pp. 505-513.
Vo et al., "Biosensor-surface plasmon resonance: A strategy to help establish a new generation of RNA-specific small molecules", Methods, 2019, vol. 167, pp. 15-27.
Wahl MC, Will CL, Luhrmann R, The spliceosome: design principles of a dynamic RNP machine, Cell. Feb. 20, 2009;136(4):701-18. doi:10.1016/j.cell.2009.02.009. PMID: 19239890.
Wan R, et al., Structure of an Intron Lariat Spliceosome from *Saccharomyces cerevisiae*, Cell. Sep. 21, 2017;171(1):120-132.e12. doi:10.1016/j.cell.2017.08.029. Epub Sep. 14, 2017. PMID: 28919079.
Weber, Gert et al., Functional organization of the Sm core in the crystal structure of human U1 snRNP, The EMBO journal vol. 29,24 (2010): 4172-84. doi:10.1038/emboj.2010.295.
Wicks et al., "Fluorescent indicator displacement assays to identify and characterize small molecule interactions with RNA", Methods, 2019, vol. 167, pp. 3-14.
Will, Cindy L, and Reinhard Lührmann, Spliceosome structure and function, Cold Spring Harbor perspectives in biology vol. 3,7 a003707. Jul. 1, 2011, doi:10.1101/cshperspect.a003707.
Wong et al., "Quantitative Activity Profile and Context Dependence of All Human 5' Splice Sites", Molecular Cell, May 2018, vol. 71, pp. 1012-1026.
Xiao, Jinbo et al., Discovery, Synthesis and Biological Evaluation of Novel SMN Protein Modulators, J. Med. Chem, Sep. 22, 2011; 54(18): 6215-6233.
Yan, Chuangye et al. , Molecular Mechanisms of pre-mRNA Splicing through Structural Biology of the Spliceosome, Cold Spring Harbor perspectives in biology vol. 11,1 a032409. Jan. 2, 2019,doi:10.1101/cshperspect.a032409.
Yan et al., "miRNA inhibition by proximity-enabled Dicer inactivation", Methods, 2019, vol. 167, pp. 117-123.

(56) References Cited

OTHER PUBLICATIONS

Ye et al., "DRUG-seq for miniaturized high-throughput transcriptome profiling in drug discovery", Nature Communications, 2018, 9:4307, pp. 1-9, doi.org/10.1038/s41467-018-06500-x.

Zaworski, Phillip et al., SMN Protein Can Be Reliably Measured in Whole Blood with an Electrochemiluminescence (ECL) Immunoassay: Implications for Clinical Trials, PloS one vol. 11,3e0150640. Mar. 8, 2016, doi:10.1371/journal.pone.0150640.

Zubradt et al., "DMS-MaPseq for genome-wide or targeted RNA structure probing in vivo", Nat Methods, Jan. 2017, vol. 14, No. 1, pp. 75-82. doi:10.1038/nmeth.4057.

SMN2

A: 3'-GUCCAΨΨCAUA-5'
B: 5'--GGGUAAGU$_A$CU-3'

FIG. 6A

FOXM1

A: 3'-GUCAΨΨCAUA-5'
B: 5'-CAGUAAGUGX-3'
           CU

FIG. 6B

IKBKAP

A: 3'-GU$^C$CAΨΨCAUA-5'
B: 5'-CA$_A$GUAAGUG--3'

FIG. 6C

MADD1

A: 3'-GUCCAΨΨC$^U$AA-5'
B: 5'--AGGUGGGUU-3'

FIG. 6D

KRAS

A: 3'-GUCCAΨΨCAUA-5'
B: 5'-CAGGUAAGUA--3'

FIG. 6E

Impact of Stereochemistry on Cell Activity

Compound 1
Cell$_{A-673}$ = 18 nM

Compound 2
Cell$_{A-673}$ > 100 mM

METHODS AND COMPOSITIONS FOR MODULATING SPLICING

CROSS REFERENCE

This application is a continuation of U.S. Non-provisional application Ser. No. 16/781,524, filed on Feb. 4, 2020, which is a continuation of International Application No. PCT/US2018/045282, filed on Aug. 3, 2018, which claims priority to U.S. Provisional Application No. 62/541,202, filed on Aug. 4, 2017; U.S. Provisional Application No. 62/562,927, filed on Sep. 25, 2017; and U.S. Provisional Application No. 62/562,948, filed on Sep. 25, 2017, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Apr. 8, 2021, is named 51503-705_308_SL.txt and is 29,851 bytes in size.

BACKGROUND

The majority of protein-coding genes in the human genome are composed of multiple exons (coding regions) that are separated by introns (non-coding regions). Gene expression results in a single precursor messenger RNA (pre-mRNA). The intron sequences are subsequently removed from the pre-mRNA by a process called splicing, which results in the mature messenger RNA (mRNA). By including different combinations of exons, alternative splicing gives rise to multiple mRNAs encoding distinct protein isoforms. The spliceosome, an intracellular complex of multiple proteins and ribonucleoproteins, catalyzes splicing.

Current therapeutic approaches to direct and control mRNA expression require methods such as gene therapy, genome editing, or a wide range of oligonucleotide technologies (antisense, RNAi, etc.). Gene therapy and genome editing act upstream of transcription of mRNA by influencing the DNA code and thereby changing mRNA expression. Oligonucleotides modulate the action of RNA via canonical base/base hybridization. The appeal of this approach is in the design of the basic pharmacophore of an oligonucleotide, which can be defined in a straightforward fashion by known base pairing to the target sequence subject. Each of these therapeutic modalities suffers from substantial technical, clinical, and regulatory challenges. Some limitations of oligonucleotides as therapeutics (e.g., antisense, RNAi) include unfavorable pharmacokinetics, lack of oral bioavailability, and lack of blood-brain-barrier penetration, with the latter precluding delivery to the brain or spinal cord after parenteral drug administration for the treatment of diseases (e.g., neurological diseases, brain cancers). In addition, oligonucleotides are not taken up effectively into solid tumors without a complex delivery system such as lipid nanoparticles. Further, most of the oligonucleotides taken up into cells and tissues remain in non-functional compartments (e.g., endosomes) and does not gain access to the cytosol and/or nucleus where the target is located.

Additionally, to anneal to a target, oligonucleotide therapies require access to complementary base pairs of the target. This approach assumes that pre-mRNA sequences exist as a linear strand of RNA in the cell. However, pre-mRNA is rarely linear; it has complex secondary and tertiary structure. Further, cis-acting elements (e.g., protein binding elements) and trans-acting factors (e.g., splicing complex components) can create additional two-dimensional and three-dimensional complexity (e.g., by binding to the pre-mRNA). These features can be potency- and efficacy-limiting for oligonucleotide therapies.

SUMMARY

The novel small molecule splicing modulators (SMSMs) described herein do not suffer from the limitations above, nor the structural and steric hindrances that greatly limit oligonucleotide therapies (e.g., by blocking hybridization to pre-mRNA targets). Small molecules have been essential in uncovering the mechanisms, regulations, and functions of many cellular processes, including DNA replication, transcription, and translation. While several recent reports have described screens for small molecule effectors of splicing, only a small number of constitutive or alternative splicing modulators have been identified and many of the small-molecule inhibitors lack specificity, lack selectivity, lack potency, exhibit toxicity, or are not orally available. Targeting the RNA transcriptome with small-molecule modulators represents an untapped therapeutic approach to treat a variety of RNA-mediated diseases. Accordingly, there remains a need to develop small-molecule RNA modulators useful as therapeutic agents. There is need in the art for novel modulators of splicing or splicing-dependent processes. Provided herein are small molecule splicing modulators and uses thereof that fulfill this need.

Provided herein is a compound that has the structure of Formula (IV), or a pharmaceutically acceptable salt or solvate thereof.

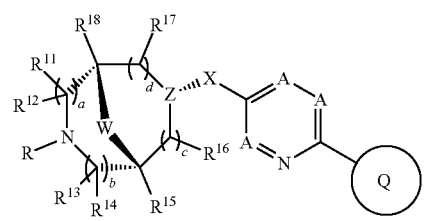

Formula (IV)

wherein,
each A is independently N or $CR^4$;
each RA is independently selected from H, D, halogen, —CN, —OH, —$OR^1$, =O, =N—$OR^1$, —$SR^1$, —S(=O)$R^1$, —S(=O)$_2R^1$, —N($R^1$)$_2$, —$NR^1$S(=O)(=$NR^1$)$R^2$, —$NR^1$S(=O)$_2R^2$, —S(=O)$_2$N($R^1$)$_2$, —C(=O)$R^1$, —OC(=O)$R^1$, —C(=O)$OR^1$, —OC(=O)$OR^1$, —C(=O)N($R^1$)$_2$, —OC(=O)N($R^1$)$_2$, —$NR^1$C(=O)$R^1$, —P(=O)($R^2$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, and substituted or unsubstituted monocyclic heteroaryl;
ring Q is monocyclic aryl, bicyclic aryl, monocyclic heteroaryl, or fused bicyclic heteroaryl; X is —O—, —$NR^3$—, —$CR^4R^5$—, —C(=O)—, —C(=$CR^2_2$)—, —S—, —S(=O)—, —S(=O)$_2$—, or —S(=O)(=$NR^1$)—;
each $R^1$ is independently H, D, substituted or unsubstituted $C_1$-$C_6$ alkyl, —$CD_3$, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each $R^2$ is independently H, D, substituted or unsubstituted $C_1$-$C_6$ alkyl, substituted or unsubstituted $C_1$-$C_6$ haloalkyl, substituted or unsubstituted aryl, substituted or unsubstituted monocyclic heteroaryl, —$OR^1$, —$N(R^1)_2$, —$CH_2OR^1$, —C(=O)$OR^1$, —OC(=O)$R^1$, —C(=O)$N(R^1)_2$, or —$NR^1$C(=O)$R^1$;

$R^3$ is —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl;

$R^4$ is H, D, F, —CN, —$OR^1$, —$SR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^5$ is H, D, F, —CN, —$OR^1$, —$SR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or $R^4$ and R taken in combination with the carbon atom to which they attach, form a substituted or unsubstituted $C_{3-8}$ cycloalkyl or a substituted or unsubstituted $C_{2-7}$ heterocycloalkyl;

Z is $CR^2$; and $R^2$ is independently H, D, substituted or unsubstituted $C_1$-$C_6$ alkyl, substituted or unsubstituted $C_1$-$C_6$ haloalkyl or —$CH_2OR^1$;

W is substituted or unsubstituted $C_1$-$C_4$ alkylene, substituted or unsubstituted $C_2$-$C_4$ alkenylene, or substituted or unsubstituted $C_1$-$C_4$ heteroalkylene;

R is selected from the group consisting of H, a substituted or unsubstituted $C_{1-6}$ alkyl, substituted or unsubstituted $C_1$-$C_6$ fluoroalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, and substituted or unsubstituted heteroaryl, wherein alkyl is optionally substituted with hydroxy, amino, substituted or unsubstituted mono-$C_{1-6}$ alkylamino, or substituted or unsubstituted di-$C_{1-6}$ alkylamino;

$R^{11}$, $R^{12}$, $R^{13}$, $R^{14}$, $R^{15}$, $R^{16}$, $R^{17}$, and $R^{18}$ are each independently selected from the group consisting of H, F, $OR^1$, substituted or unsubstituted $C_{1-6}$ alkyl, a substituted or unsubstituted $C_{1-6}$ fluoroalkyl, substituted or unsubstituted $C_1$-$C_6$ heteroalkyl, wherein alkyl is optionally substituted with hydroxy, amino, methoxy, substituted or unsubstituted mono-$C_{1-6}$ alkylamino or substituted or unsubstituted di-$C_{1-6}$ alkylamino;

$R^{11}$ and $R^{13}$, taken in combination form a substituted or unsubstituted $C_{1-3}$ alkylene group or a substituted or unsubstituted $C_{1-3}$ heteroalkylene group; or $R^{11}$ and $R^{15}$, taken in combination form a substituted or unsubstituted $C_{1-3}$ alkylene group; or $R^{16}$ and $R^{17}$, taken in combination form a substituted or unsubstituted $C_{1-3}$ alkylene group; or $R^{13}$ and $R^{14}$, taken in combination with the carbon atom to which they attach, form a spirocyclic $C_{3-8}$ cycloalkyl;

or $R^{17}$ and $R^2$, taken in combination form a substituted or unsubstituted $C_{1-3}$ alkylene group; or when X is —$NR^3$—, then $R^3$ and $R^2$ are optionally taken together with the intervening atoms to which they are attached to form a 4, 5, or 6-membered ring; or when X is —$NR^3$—, then $R^3$ and $R^{16}$ are optionally taken together with the intervening atoms to which they are attached to form a 4, 5, or 6-membered ring;

a and b are each independently selected from 0, 1, 2, or 3;

c and d are each independently selected from 1, 2, 3, or 4; and wherein the compound of Formula (IV) has a stereochemical purity of at least 80%.

In some embodiments, W is substituted or unsubstituted $C_1$-$C_4$ alkylene.

In some embodiments,

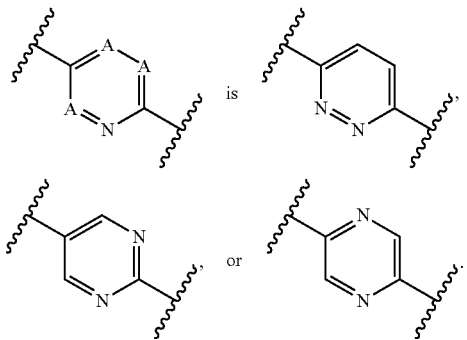

In some embodiments,

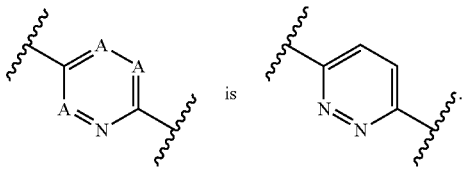

In some embodiments, X is —O—, —$NR^3$—, —S—, —$CR^4R$—, —C(=O)—, or —C(=$CR^2_2$)—.

In some embodiments, X is —O—, —$NR^3$—, or —C(=O)—.

In some embodiments, ring Q is substituted or unsubstituted aryl.

In some embodiments, ring Q is 2-hydroxy-phenyl substituted with: 0, 1, 2, or 3 substituents independently selected from $C_{1-6}$ alkyl, oxo, oxime, hydroxy, halo-$C_{1-6}$ alkyl, dihalo-$C_{1-6}$ alkyl, trihalo-$C_{1-6}$ alkyl, $C_{1-6}$ alkoxy, $C_{1-6}$ alkoxy-$C_{3-7}$ cycloalkyl, halo-$C_{1-6}$ alkoxy, dihalo-$C_{1-6}$ alkoxy, trihalo-$C_{1-6}$ alkoxy, hydroxy, cyano, halogen, amino, mono-$C_{1-6}$ alkylamino, di-$C_{1-6}$ alkylamino, aryl, heteroaryl, $C_{1-6}$ alkyl substituted with hydroxy, $C_{1-6}$ alkoxy substituted with aryl, amino, —C(=O)NH—$C_{1-6}$ alkyl-heteroaryl, —NHC(=O)—$C_{1-6}$ alkylheteroaryl, $C_{1-6}$ alkyl-C(=O)NH-heteroaryl, $C_{1-6}$ alkyl-NHC(=O)-heteroaryl, $C_{3-7}$ cycloalkyl, 5-7 membered cycloalkenyl, or 5, 6 or 9 membered heterocycle containing 1 or 2 heteroatoms independently, selected from S, O, and N, wherein two $C_{1-6}$ alkyl groups can combine with the atoms to which they are bound to form a 5-6 membered ring; wherein heteroaryl has 5, 6, 9, or 10 ring atoms, 1, 2 or 3 ring heteroatoms selected from N, O, and S, and is substituted with 0, 1, or 2 substituents independently selected from oxo, hydroxy, nitro, halogen, $C_{1-6}$ alkyl, $C_{1-6}$ alkenyl, $C_{1-6}$ alkoxy, $C_{3-7}$ cycloalkyl, $C_{1-6}$ alkyl-OH, trihalo-$C_{1-6}$ alkyl, mono-$C_{1-6}$ alkylamino, di-$C_{1-6}$ alkylamino, —C(=O)NH$_2$, —NH$_2$, —NO$_2$, hydroxy-$C_{1-6}$ alkylamino, hydroxy-$C_{1-6}$ alkyl, 4-7 membered heterocycle-$C_{1-6}$ alkyl, amino-$C_{1-6}$ alkyl, mono-$C_{1-6}$ alkylamino-$C_{1-6}$ alkyl, and di-$C_{1-6}$ alkylamino-$C_{1-6}$ alkyl.

In some embodiments, ring Q is

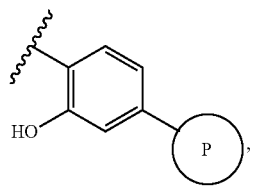

wherein ring P is aryl or heteroaryl.

In some embodiments, ring Q is

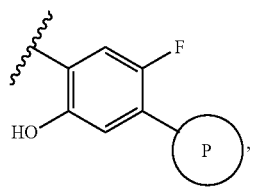

wherein ring P is aryl or heteroaryl.

In some embodiments, ring P is heteroaryl selected from the group consisting of:

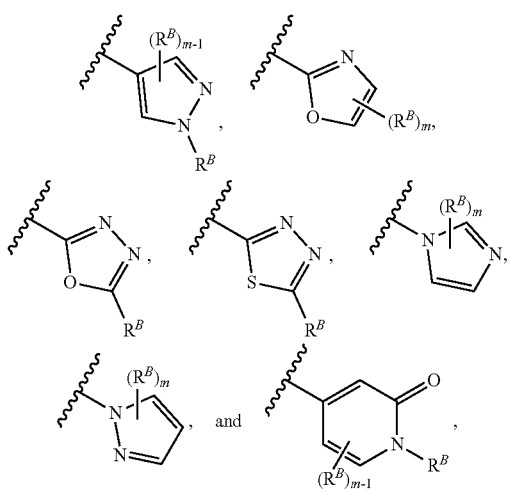

wherein each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3

In some embodiments, ring P is heteroaryl selected from the group consisting of:

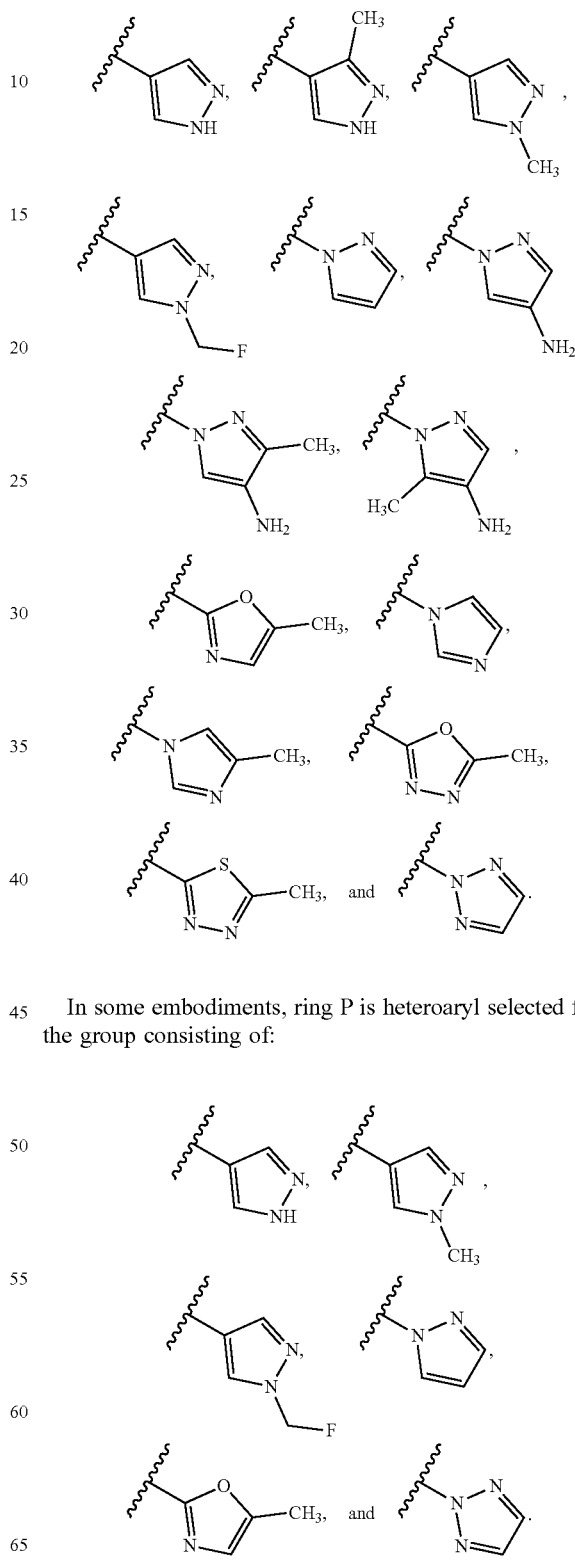

In some embodiments, ring P is heteroaryl selected from the group consisting of:

In some embodiments, ring P is heteroaryl selected from the group consisting of:

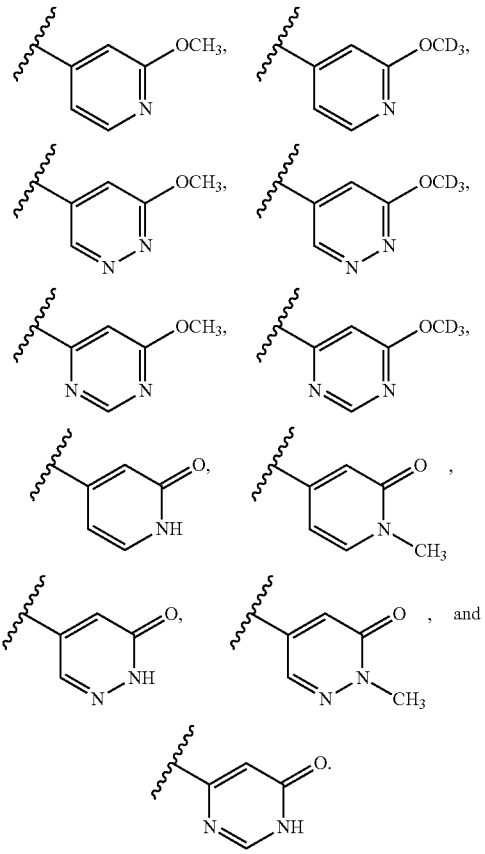

In some embodiments, ring P is heteroaryl selected from the group consisting of:

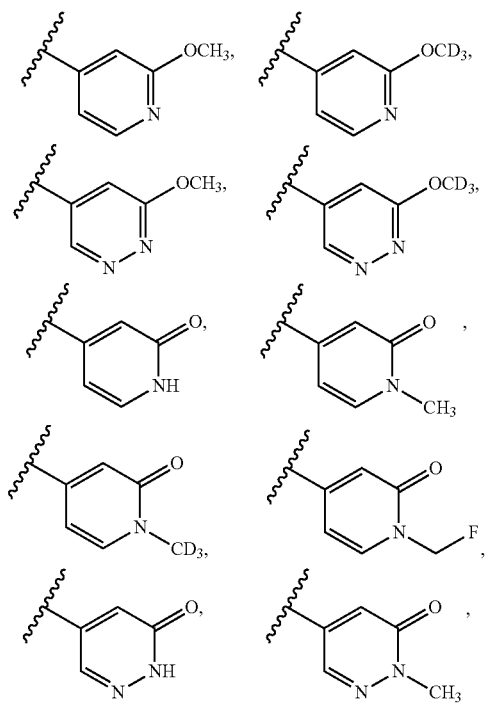

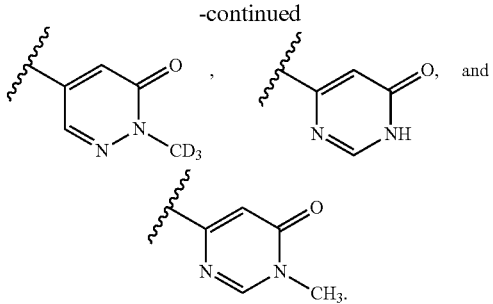

In some embodiments, ring Q is 2-naphthyl optionally substituted at the 3 position with hydroxy and additionally substituted with 0, 1, or 2 substituents selected from hydroxy, cyano, halogen, $C_{1-6}$ alkyl, $C_{2-6}$ alkenyl, $C_{1-6}$ alkoxy, wherein the alkoxy is unsubstituted or substituted with hydroxy, $C_{1-6}$ alkoxy, amino, —NHC(=O)—$C_{1-6}$ alkyl, —NHC(=O)—$C_{1-6}$ alkyl, $C_{1-6}$ alkylene-4-7 membered heterocycle, 4-7 membered heterocycle, mono-$C_{1-6}$ alkylamino, and di-$C_{1-6}$ alkylamino.

In some embodiments, ring Q is

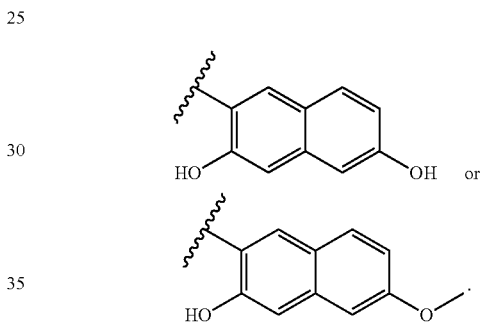

In some embodiments, ring Q is

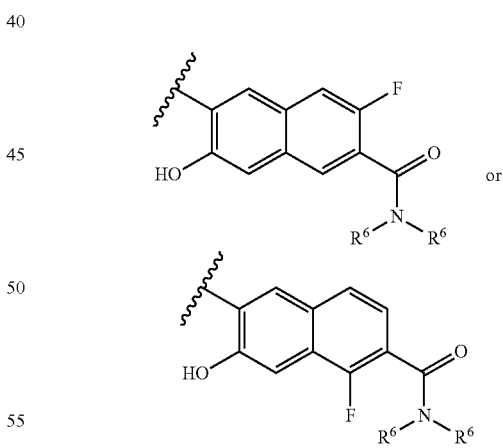

and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, ring Q is monocyclic heteroaryl or fused bicyclic heteroaryl.

In some embodiments, ring Q is a 5 or 6 membered monocyclic heteroaryl having 1-4 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from cyano, $C_{1-6}$ alkyl, mono-$C_{1-6}$ alkylamino, di-$C_{1-6}$ alkylamino, hydroxy-$C_{1-6}$ alkylamino, hydroxy-$C_{1-6}$ alkyl, amino-$C_{1-6}$ alkyl and mono-$C_{1-6}$ alkylamino-$C_{1-6}$ alkyl, and di-$C_{1-6}$ alkylamino-$C_{1-6}$ alkyl.

In some embodiments, ring Q is fused bicyclic heteroaryl having 8 to 10 ring atoms, 1, 2, or 3 ring heteroatoms independently selected from N, O or S, and which is substituted with 0, 1, or 2 substituents independently selected from cyano, oxime, halogen, hydroxy, $C_{1-6}$ alkyl, $C_{24}$ alkenyl, $C_{24}$ alkynyl, $C_{1-6}$ alkoxy, $C_{1-6}$ alkoxy substituted with hydroxy, amino, mono-$C_{1-6}$ alkylamino, and di-$C_{1-6}$ alkylamino.

In some embodiments, ring Q is a monocyclic heterocycle selected from the group consisting of:

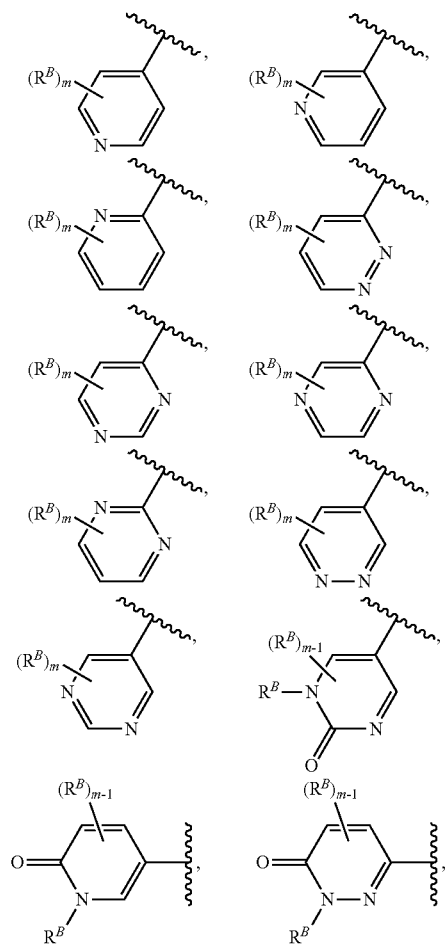

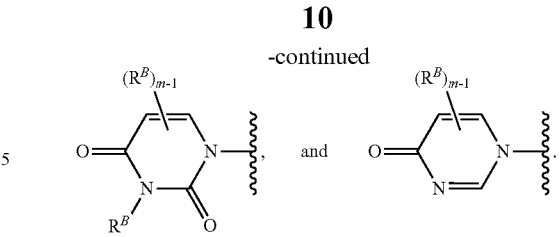

In some embodiments, ring Q is a 6-5 fused heteroaryl, 6-6 fused heteroaryl, 5-6 fused heteroaryl, 5-5 fused heteroaryl, 7-5 fused heteroaryl, or 5-7 fused heteroaryl.

In some embodiments, ring Q is a 6-5 fused heteroaryl, 6-6 fused heteroaryl, or 5-6 fused heteroaryl, selected from the group consisting of

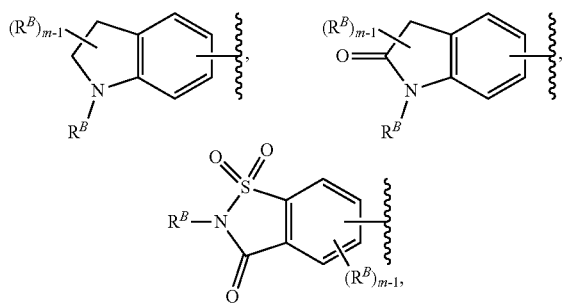

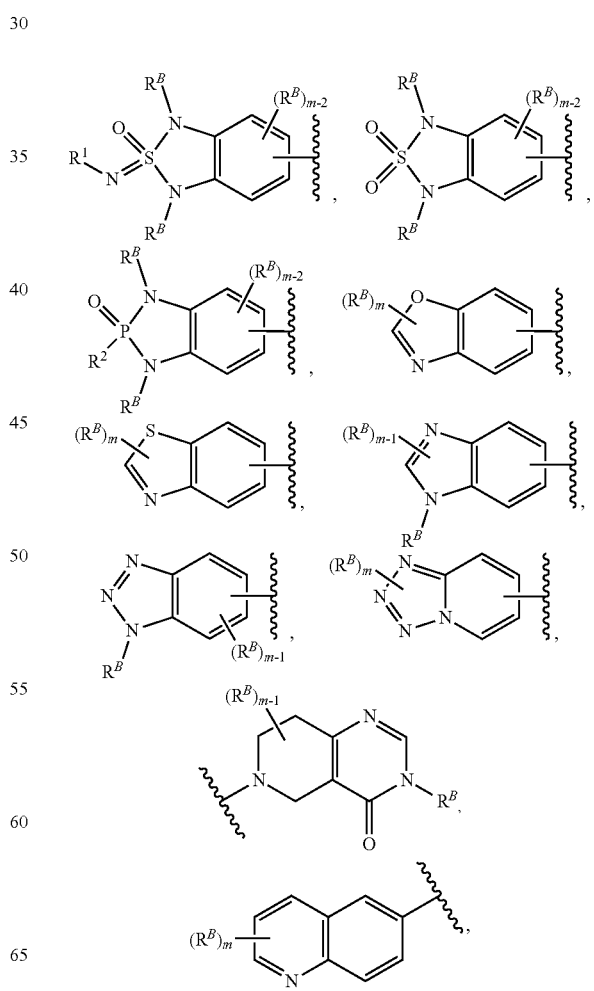

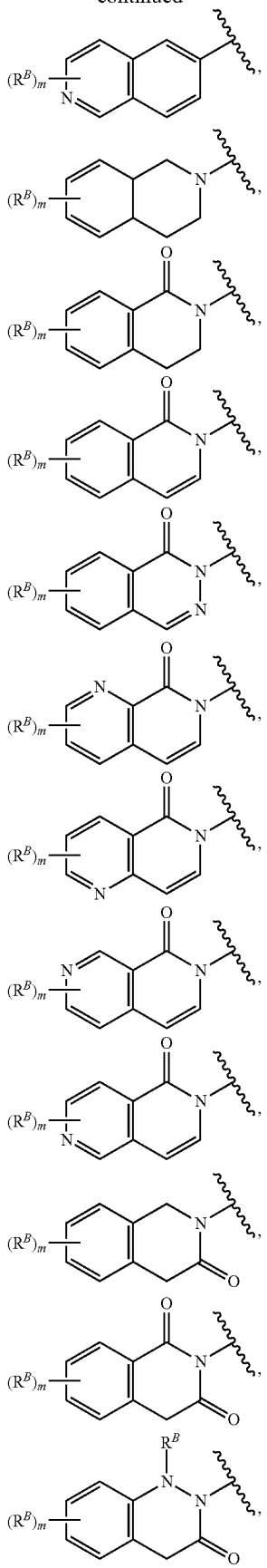
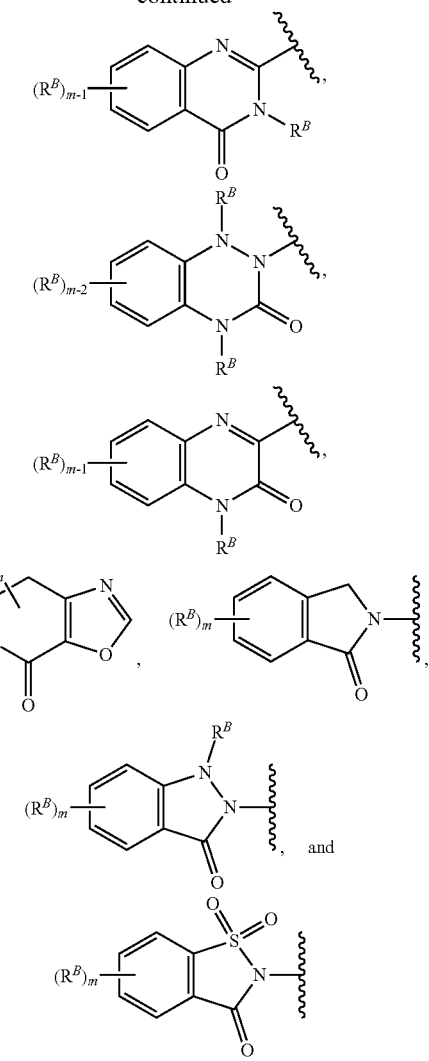
In some embodiments, ring Q is
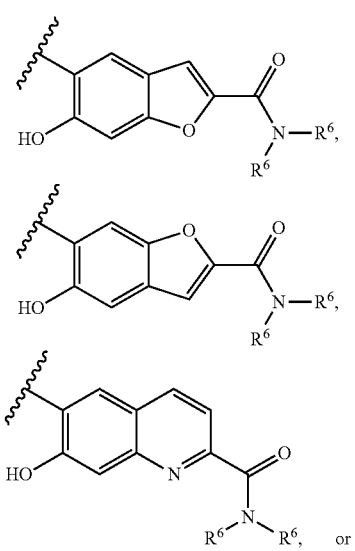

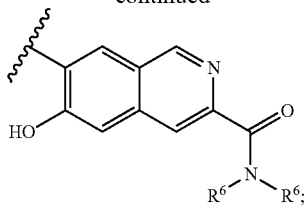

substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl In some embodiments, X is —$NR^3$—.

In some embodiments, $R^3$ is —$OR^1$, substituted or unsubstituted $C_1$-$C_6$ alkyl, substituted or unsubstituted $C_1$-$C_6$ haloalkyl, substituted or unsubstituted $C_1$-$C_6$ heteroalkyl, or substituted or unsubstituted $C_3$-$C_8$ cycloalkyl.

In some embodiments, $R^3$ is $C_3$-$C_8$ cycloalkyl that is selected from cyclopropyl, cyclobutyl, cyclopentyl, or cyclohexyl.

In some embodiments, $R^3$ is cyclopropyl.

In some embodiments, $R^3$ is $C_3$-$C_8$ cycloalkyl that is selected from cyclopentenyl, or cyclohexenyl.

In some embodiments, $R^3$ is —$CH_3$ or —$CF_3$.

In some embodiments, $R^3$ is —$CD_3$.

In some embodiments, $R^3$ is —$OCH_3$, —$OCH_2CH_3$, —$OCH_2CH_2OH$ or —$OCH_2CH_2OCH_3$.

In some embodiments, $R^3$ is —$OCD_3$.

In some embodiments,

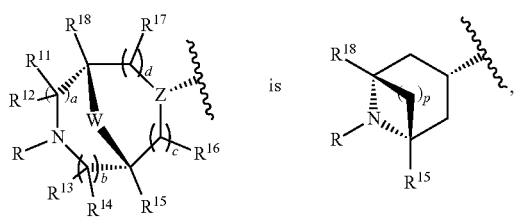

wherein p is 1, 2, or 3.

In some embodiments, R is H; $R^{15}$ and $R^{18}$ are H; and p is 2 or 3.

In some embodiments, R is H; $R^{15}$ and $R^{18}$ are H; and p is 2.

In some embodiments, R is H; $R^{15}$ and $R^{18}$ are H; and p is 3.

In some embodiments, R is H; $R^{15}$ and $R^{18}$ are $CH_3$; and p is 2 or 3.

In some embodiments, R is H; $R^{15}$ and $R^{18}$ are $CH_3$; and p is 2.

In some embodiments, R is H; $R^{15}$ and $R^{18}$ are $CH_3$; and p is 3.

In some embodiments,

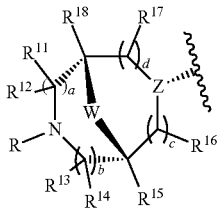 is 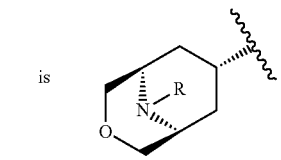

or

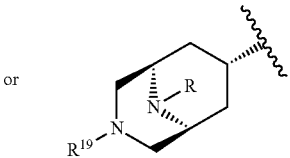

wherein $R^{19}$ is H, D, —CN, —OH, —$OR^1$, —$SR^1$, —S(=O)$R^1$, —S(=O)$_2R^1$, —$CH_2$—N($R^1$)$_2$, —S(=O)$_2$N($R^1$)$_2$, —C(=O)$R^1$, —$CO_2R^1$, —C(=O)N($R^1$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, or substituted or unsubstituted $C_2$-$C_8$ heterocycloalkyl.

Provided herein is a composition comprising a small molecule splicing modulator compound (SMSM); wherein the SMSM interacts with an unpaired bulged nucleobase of an RNA duplex, and wherein the RNA duplex comprises a splice site.

Provided herein is composition comprising a complex comprising a small molecule splicing modulator compound (SMSM) bound to an RNA duplex, wherein the SMSM interacts with an unpaired bulged nucleobase of an RNA duplex, and wherein the RNA duplex comprises a splice site.

In some embodiments, the duplex RNA comprises an alpha helix.

In some embodiments, the unpaired bulged nucleobase is located on an external portion of a helix of the duplex RNA In some embodiments, the unpaired bulged nucleobase is located within an internal portion of the helix of the duplex RNA.

In some embodiments, the SMSM forms one or more intermolecular interactions with the duplex RNA.

In some embodiments, the SMSM forms one or more intermolecular interactions with the unpaired bulged nucleobase.

In some embodiments, the intermolecular interaction is selected from the group comprising an ionic interaction, a hydrogen bond, a dipole-dipole interaction or a van der Waals interaction.

In some embodiments, a first portion of the SMSM interacts with the unpaired bulged nucleobase on a first RNA strand of the RNA duplex.

In some embodiments, a second portion of the SMSM interacts with one or more nucleobases of a second RNA strand of the RNA duplex, wherein the first RNA strand is not the second RNA strand.

In some embodiments, a rate of exchange of the unpaired bulged nucleobase from within the interior of a helix of the duplex RNA to an exterior portion of the helix is reduced.

In some embodiments, the SMSM reduces a rate of rotation of the unpaired bulged nucleobase.

In some embodiments, the SMSM reduces a rate of rotation of the unpaired bulged nucleobase around a phosphate backbone of an RNA strand of the RNA duplex.

In some embodiments, the SMSM modulates a distance of the unpaired bulged nucleobase from a second nucleobase of the duplex RNA.

In some embodiments, the SMSM reduces the distance of the unpaired bulged nucleobase from a second nucleobase of the duplex RNA.

In some embodiments, the unpaired bulged nucleobase is located within the interior of a helix of the duplex RNA of the complex.

In some embodiments, the SMSM reduces a size of a bulge of the RNA duplex.

In some embodiments, the SMSM removes a bulge of the RNA duplex.

In some embodiments, the SMSM stabilizes a bulge of the RNA duplex.

In some embodiments, the SMSM modulates splicing at the splice site of the RNA duplex.

In some embodiments, the SMSM increases splicing at the splice site of the RNA duplex.

In some embodiments, the SMSM reduces splicing at the splice site of the RNA duplex.

In some embodiments, the unpaired bulged nucleobase has modulated base stacking within an RNA strand of the RNA duplex.

In some embodiments, the unpaired bulged nucleobase has increased base stacking within an RNA strand of the RNA duplex.

In some embodiments, the unpaired bulged nucleobase has decreased base stacking within an RNA strand of the RNA duplex.

In some embodiments, the SMSM is not an aptamer.

In some embodiments, the RNA duplex comprises pre-mRNA.

In some embodiments, the unpaired bulged nucleobase is free to rotate around a phosphate backbone of an RNA strand of the RNA duplex in the absence of the SMSM Provided herein is a method of modulating splicing comprising contacting a small molecule splicing modulator compound (SMSM) to cells, wherein the SMSM kills the cells at an IC50 of less than 50 nM.

Provided herein is a method of modulating splicing comprising contacting a small molecule splicing modulator compound (SMSM) to cells, wherein the SMSM modulates splicing at a splice site sequence of a pre-mRNA that encodes a mRNA, wherein the mRNA encodes a target protein or a functional RNA, and wherein a total amount of the mRNA is increased at least about 10% compared to the total amount of the mRNA encoding the target protein or functional RNA produced in control cells.

Provided herein is a method of modulating splicing comprising contacting a small molecule splicing modulator compound (SMSM) to cells, wherein the SMSM modulates splicing at a splice site sequence of a pre-mRNA that encodes a mRNA, wherein the mRNA encodes a target protein or a functional RNA, and wherein a total amount of the mRNA, the target protein and/or the functional RNA is at least 10% lower than the total amount of the mRNA, the target protein and/or the functional RNA in control cells.

Provided herein is a method of modulating splicing comprising contacting a small molecule splicing modulator compound (SMSM) to cells, wherein the SMSM modulates splicing at a splice site sequence of a pre-mRNA that encodes a first mRNA isoform associated with a disease or condition and a second mRNA isoform, wherein a total amount of the first mRNA isoform is decreased by at least about 10% compared to the total amount of the first mRNA isoform in control cells, and/or a total amount of the second mRNA isoform is increased by at least about 10% compared to the total amount of the first mRNA isoform in control cells.

Provided herein is a method of modulating splicing comprising contacting a small molecule splicing modulator compound (SMSM) to cells comprising an amount of a first mRNA isoform and an amount of a second mRNA isoform present in the cells; wherein a ratio of the first mRNA isoform to the second mRNA isoform is decreased at least 1.2 fold; wherein the first and second mRNAs are encoded by a pre-MRNA comprising a splice site sequence, and wherein the first mRNA isoform is associated with a disease or condition and a second mRNA isoform.

Provided herein is a method of modulating splicing, comprising contacting a small molecule splicing modulator compound (SMSM) to a cell comprising a polynucleotide with a splice site sequence, wherein the SMSM modulates exon inclusion, exon exclusion, pseudo exon inclusion, intron retention, or splicing at a cryptic splice site of the polynucleotide, and wherein the SMSM modulates splicing of the splice site sequence.

Provided herein is a method of modulating splicing, comprising contacting a small molecule splicing modulator compound (SMSM) to a cell comprising a polynucleotide with a splice site sequence, thereby modulating splicing of the polynucleotide, wherein the splice site sequence comprises a splice site sequence selected from the group consisting of splice site sequences of Table 2A, Table 2B, Table 2C or Table 2D.

Provided herein is a method of modulating splicing, comprising contacting a small molecule splicing modulator compound (SMSM) to a cell comprising a polynucleotide with a splice site sequence, wherein the splice site sequence comprises a sequence selected from GGAguaag and AGAguaag.

Provided herein is a method of modulating splicing, comprising contacting a small molecule splicing modulator compound (SMSM) to a cell comprising a polynucleotide with a splice site sequence, wherein the splice site sequence comprises at least one bulged nucleotide at the −3, −2, −1, +1, +2, +3, +4, +5 or +6 position of the splice site sequence.

Provided herein is a method of modulating splicing, comprising contacting a small molecule splicing modulator compound (SMSM) to a cell comprising a polynucleotide with a splice site sequence, wherein the splice site sequence comprises a mutant nucleotide at the −3, −2, −1, +1, +2, +3, +4, +5 or +6 position of the splice site sequence.

Provided herein is a method of modulating splicing, comprising contacting a small molecule splicing modulator compound (SMSM) to a cell comprising a polynucleotide with a splice site sequence, thereby modulating splicing of the polynucleotide, wherein the splice site sequence comprises a sequence selected from the group consisting of NGAgunvrn, NHAdddddn, NNBnnnnnn, and NHAddmhvk; wherein N or n is A, U, G or C; B is C, G, or U; H or h is A, C, or U; d is a, g, or u; m is a or c; r is a or g; v is a, c or g; k is g or u.

Provided herein is a method of modulating splicing, comprising contacting a small molecule splicing modulator compound (SMSM) to a cell comprising a polynucleotide with a splice site sequence, thereby modulating splicing of the polynucleotide, wherein the splice site sequence comprises a sequence selected from the group consisting of NNBgunnnn, NNBhunnnn, or NNBgvnnnn; wherein N or n is A, U, G or C; B is C, G, or U; H or h is A, C, or U; d is a, g, or u; m is a or c; r is a or g; v is a, c or g; k is g or u.

In some embodiments, the splice site sequence comprises a sequence selected from the group consisting of NNBgurrrn, NNBguwwdn, NNBguvmvn, NNBguvbbn, NNBgukddn, NNBgubnbd, NNBhunngn, NNBhurmhd, or NNBgvdnvn; wherein N or n is A, U, G or C; B is C, G, or U; H or h is A, C, or U; d is a, g, or u; m is a or c; r is a or g; v is a, c org; k is g or u.

In some embodiments, the nucleotide at the −3, −2, −1, +1, +2, +3, +4, +5 or +6 position of the splice site sequence is a bulged nucleotide.

In some embodiments, the nucleotide at the −3, −2, −1, +1, +2, +3, +4, +5 or +6 position of the splice site sequence is mutated nucleotide.

In some embodiments, the splice site sequence comprises a sequence selected from the group consisting of splice site sequences of Table 2A, Table 2B, Table 2C or Table 2D.

Provided herein is a method of modulating splicing, comprising contacting a small molecule splicing modulator compound (SMSM) to a cell comprising a polynucleotide with a splice site sequence, thereby modulating splicing of the polynucleotide, wherein the polynucleotide is encoded by a gene selected from the group consisting of genes of Table 2A, Table 2B, Table 2C or Table 2D.

In some embodiments, the gene is SMN2.

In some embodiments, modulating splicing of the polynucleotide comprises inhibiting skipping of exon 7.

In some embodiments, the gene is DMD.

In some embodiments, modulating splicing of the polynucleotide comprises promoting skipping of exon 51.

Provided herein is a method of modulating splicing comprising contacting a small molecule splicing modulator compound (SMSM) to a cell; wherein the SMSM interacts with an unpaired bulged nucleobase of an RNA duplex in the cell; wherein the duplex RNA comprises a splice site sequence; and wherein the SMSM modulates splicing of the RNA duplex.

Provided herein is a method for modulating the relative position of a first nucleobase relative to a second nucleobase, wherein the first nucleobase and the second nucleobase are within a duplex RNA, the method comprising contacting a small molecule splicing modulator compound (SMSM) to the duplex RNA, or a pharmaceutically acceptable salt thereof, wherein the first nucleobase is an unpaired bulged nucleobase of the RNA duplex; wherein the duplex RNA comprises a splice site sequence.

In some embodiments, the duplex RNA comprises a helix.

In some embodiments, the unpaired bulged nucleobase is located on an external portion of a helix of the duplex RNA prior to contacting the SMSM.

In some embodiments, the SMSM forms one or more intermolecular interactions with the duplex RNA.

In some embodiments, the SMSM forms one or more intermolecular interactions with the unpaired bulged nucleobase.

In some embodiments, the intermolecular interaction is selected from the group comprising an ionic interaction, a hydrogen bond, a dipole-dipole interaction or a van der Waals interaction.

In some embodiments, a rate of exchange of the unpaired bulged nucleobase from within the interior of a helix of the duplex RNA to an exterior portion of the helix is reduced.

In some embodiments, a rate of rotation of the unpaired bulged nucleobase is reduced.

In some embodiments, a rate of rotation of the unpaired bulged nucleobase around a phosphate backbone of an RNA strand of the RNA duplex is reduced.

In some embodiments, a distance of the unpaired bulged nucleobase from a second nucleobase of the duplex RNA is modulated after contacting the SMSM.

In some embodiments, the distance of the unpaired bulged nucleobase from a second nucleobase of the duplex RNA is reduced.

In some embodiments, the unpaired bulged nucleobase is located within the interior of the helix of the duplex RNA.

In some embodiments, a size of a bulge of the RNA duplex is reduced.

In some embodiments, a bulge of the RNA duplex is removed or maintained.

In some embodiments, splicing at the splice site of the RNA duplex is promoted.

In some embodiments, base stacking of the unpaired bulged nucleobase within an RNA strand of the RNA duplex is increased after contacting the SMSM.

In some embodiments, the distance of the unpaired bulged nucleobase from a second nucleobase of the duplex RNA is increased or maintained.

In some embodiments, a bulge of the RNA duplex is stabilized after contacting the SMSM.

In some embodiments, the unpaired bulged nucleobase is located on an exterior portion of a helix of the duplex RNA.

In some embodiments, a size of a bulge of the RNA duplex is increased.

In some embodiments, splicing at the splice site of the RNA duplex is inhibited.

In some embodiments, splicing is inhibited at the splice site

In some embodiments, base stacking of the unpaired bulged nucleobase within an RNA strand of the RNA duplex is reduced after contacting the SMSM.

In some embodiments, the RNA duplex comprises pre-mRNA.

Provided herein is a method of treating a subject with a tumor comprising administering a small molecule splicing modulator compound (SMSM) to the subject, wherein a size of the tumor is reduced.

Provided herein is a method of treating a subject with a tumor comprising administering a small molecule splicing modulator compound (SMSM) to the subject, wherein tumor growth is inhibited by at least 20.

Provided herein is a method of the treatment, prevention and/or delay of progression of a condition or disease comprising administering a small molecule splicing modulator compound (SMSM) to a subject, wherein the SMSM modulates splicing of a splice site of a polynucleotide in a cell of the subject, wherein the condition or disease is associated with splicing of the splice site.

In some embodiments, the subject has the disease or condition.

Provided herein is a method of treating a subject with a disease or condition comprising administering a small molecule splicing modulator compound (SMSM) to a subject with a disease or condition selected from the group consisting of diseases of Table 2A, Table 2B, Table 2C and Table 2D.

Provided herein is a method of treating a subject with a disease or condition comprising administering a small molecule splicing modulator compound (SMSM) to a subject with a disease or condition, wherein the SMSM is selected from the group consisting of the SMSMs of Table 1A, Table 1B or Table 1C.

Provided herein is a method of treating a subject with a disease or condition comprising administering a small molecule splicing modulator compound (SMSM) to a subject with a disease or condition, wherein the SMSM binds to a pre-mRNA comprising a splice site sequence selected from the group consisting of splice site sequences of Table 2A, Table 2B, Table 2C or Table 2D.

In some embodiments, the disease or condition is spinal muscular atrophy.

In some embodiments, the disease or condition is Duchenne's muscular dystrophy.

In some embodiments, the SMSM is selected from the group consisting of SMSMs of Table 1A, Table 1B and Table 1C.

In some embodiments, the SMSM is a compound described herein.

In some embodiments, the method further comprises administering an additional therapeutic molecule to the subject.

In some embodiments, the subject is a mammal.

In some embodiments, the mammal is a human.

In some embodiments, the polynucleotide is a pre-mRNA.

In some embodiments, modulating splicing comprises preventing, inhibiting or reducing splicing at the splice site sequence of the polynucleotide.

In some embodiments, modulating splicing comprises enhancing, promoting or increasing splicing at the splice site sequence of the polynucleotide.

In some embodiments, the splice site sequence is a 5' splice site sequence, a 3' splice site sequence, a branch point splice site sequence or a cryptic splice site sequence.

In some embodiments, the splice site comprises a mutation, the splice site comprises a bulge, the splice site comprises a mutation and a bulge, the splice site does not comprises a mutation, the splice site does not comprises a bulge, or the splice site does not comprises a mutation and does not comprise a bulge.

In some embodiments, the bulge is a bulge caused by the mutation.

In some embodiments, a bulged nucleotide is a mutant nucleotide.

In some embodiments, a bulged nucleotide is not a mutant nucleotide.

In some embodiments, the SMSM decreases a KD of splicing complex component to the polynucleotide.

In some embodiments, the SMSM increases a KD of splicing complex component to the polynucleotide.

In some embodiments, the SMSM inhibits binding of a splicing complex component to the polynucleotide at the splice site sequence, upstream of the splice site sequence or downstream of the splice site sequence.

In some embodiments, the SMSM promotes binding of a splicing complex component to the polynucleotide at the splice site sequence, upstream of the splice site sequence or downstream of the splice site sequence.

In some embodiments, the polynucleotide is RNA.

In some embodiments, the RNA is a pre-mRNA.

In some embodiments, the RNA is a heterogeneous nuclear RNA.

The In some embodiments, the splice site sequence is a 5' splice site sequence, a 3' splice site sequence, a branch point (BP) splice site sequence, an exonic splicing enhancer (ESE) sequence, an exonic splicing silencer (ESS) sequence, an intronic splicing enhancer (ISE) sequence, an intronic splicing silencer (ISS) sequence, a polypyrimidine tract sequence, or any combination thereof.

The In some embodiments, the polynucleotide is at least 5, 6, 7, 8, 9, 10, 15, 20, 25, 50, 100, 250, 500, 750, 1,000, 2,000, 5,000, 10,000, 50,000, 100,000, 500,000, or 1,000,000 nucleotides in length.

In some embodiments, the SMSM binds to the splice site sequence of the polynucleotide.

In some embodiments, the SMSM interacts with a bulge of the splice site sequence of the polynucleotide.

In some embodiments, the polynucleotide comprises a cis-acting element sequence.

In some embodiments, the cis-acting element sequence does not comprise a bulge.

In some embodiments, the cis-acting element sequence does not comprise a mutation.

In some embodiments, the cis-acting element sequence comprises a mutation, a bulge, or a combination thereof, at the cis-acting element sequence, 1-1000 nucleobases upstream of the cis-acting element sequence or 1-1000 nucleobases downstream of the cis-acting element sequence.

In some embodiments, the cis-acting element sequence comprises a regulatory element sequence that modulates recruitment of a splicing complex component to the polynucleotide.

In some embodiments, the cis-acting element sequence comprises a regulatory element sequence that modulates recruitment of a spliceosome to the polynucleotide.

In some embodiments, the regulatory element sequence comprises an exonic splicing enhancer (ESE) sequence, an exonic splicing silencer (ESS) sequence, an intronic splicing enhancer (ISE) sequence, an intronic splicing silencer (ISS) sequence, and combinations thereof.

In some embodiments, the SMSM binds to the splicing complex component.

In some embodiments, the splicing complex component is 9G8, A1 hnRNP, A2 hnRNP, ASD-1, ASD-2b, ASF, B1 hnRNP, C1 hnRNP, C2 hnRNP, CBP20, CBP80, CELF, F hnRNP, FBP11, Fox-1, Fox-2, G hnRNP, H hnRNP, hnRNP 1, hnRNP 3, hnRNP C, hnRNP G, hnRNP K, hnRNP M, hnRNP U, Hu, HUR, I hnRNP, K hnRNP, KH-type splicing regulatory protein (KSRP), L hnRNP, M hnRNP, mBBP, muscle-blind like (MBNL), NF45, NFAR, Nova-1, Nova-2, nPTB, P54/SFRS11, polypyrimidine tract binding protein (PTB), PRP19 complex proteins, R hnRNP, RNPC1, SAM68, SC35, SF, SF1/BBP, SF2, SF3 a, SF3B, SFRS10, Sm proteins, SR proteins, SRm300, SRp20, SRp30c, SRP35C, SRP36, SRP38, SRp40, SRp55, SRp75, SRSF, STAR, GSG, SUP-12, TASR-1, TASR-2, TIA, TIAR, TRA2, TRA2a/b, U hnRNP, U1 snRNP, U11 snRNP, U12 snRNP, U1-C, U2 snRNP, U2AF1-RS2, U2AF35, U2AF65, U4 snRNP, U5 snRNP, U6 snRNP, Urp, YB1, or any combination thereof.

In some embodiments, the splicing complex component comprises RNA.

In some embodiments, the splicing complex component is a small nuclear RNA (snRNA).

In some embodiments, the snRNA comprises U1 snRNA, U2 snRNA, U4 snRNA, U5 snRNA, U6 snRNA, U11 snRNA, U12 snRNA, U4atac snRNA, U5 snRNA, U6 atac snRNA, or any combination thereof.

In some embodiments, the splicing complex component comprises a protein.

In some embodiments, the splicing complex component comprises a small nuclear ribonucleoprotein (snRNP).

In some embodiments, the snRNP comprises U1 snRNP, U2 snRNP, U4 snRNP, U5 snRNP, U6 snRNP, U11 snRNP, U12 snRNP, U4atac snRNP, U5 snRNP, U6 atac snRNP, or any combinations thereof.

In some embodiments, the protein is a serine/arginine-rich (SR) protein.

In some embodiments, the splice site sequence comprises abase that is mismatched to a base of a snRNA sequence.

In some embodiments, a bulge is due to mismatched base pairing between the splice site sequence and a snRNA sequence.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 6A depicts an exemplary SMN2 pre-mRNA sequence with a bulge (SEQ ID NOs 115-116, respectively, in order of appearance).

FIG. 6B depicts an exemplary pre-mRNA sequence with a bulge (SEQ ID NOs 117-118, respectively, in order of appearance).

FIG. 6C depicts an exemplary pre-mRNA sequence with a bulge (SEQ ID NOs 115 and 119, respectively, in order of appearance).

FIG. 6D depicts an exemplary pre-mRNA sequence with a bulge (SEQ ID NOs 115 and 120, respectively, in order of appearance).

FIG. 6E depicts an exemplary pre-mRNA sequence without a bulge (SEQ ID NOs 115 and 121, respectively, in order of appearance).

DETAILED DESCRIPTION

Figure 1:
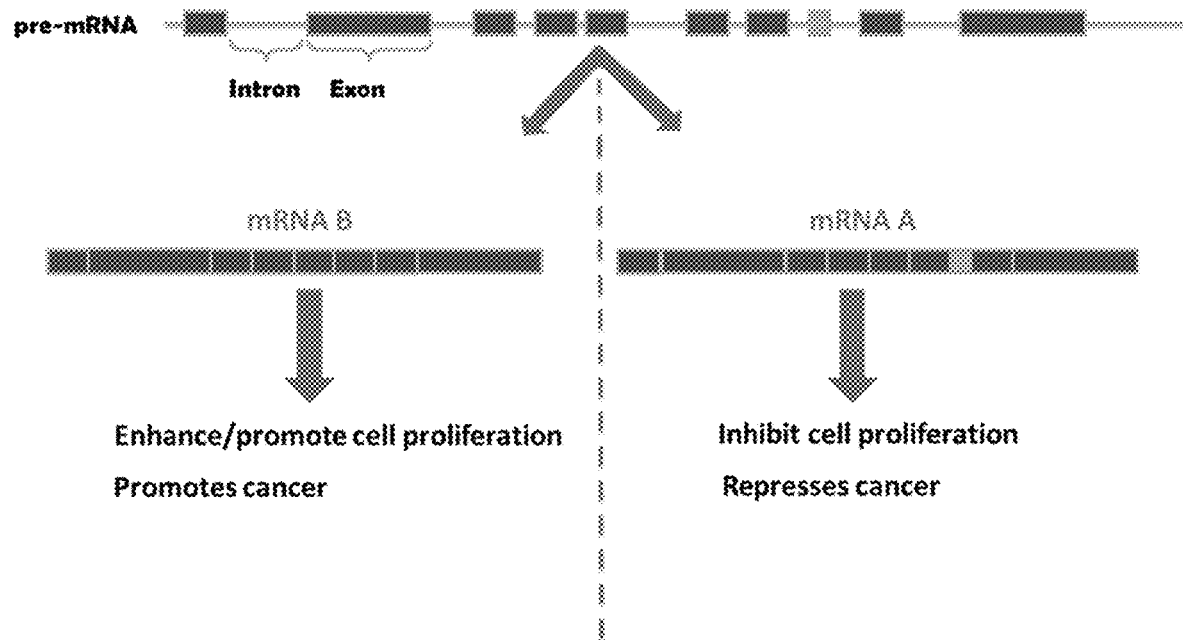
FIG. 1 depicts a diagram of alternative splicing of an exemplary pre-MRNA. One mRNA isoform depicted encodes a protein that enhances or promotes cell proliferation and/or cancer. The other mRNA isoform depicted encodes a protein that enhances or inhibits cell proliferation and/or cancer. The two isoforms differ by a single exon.
Figure 2:
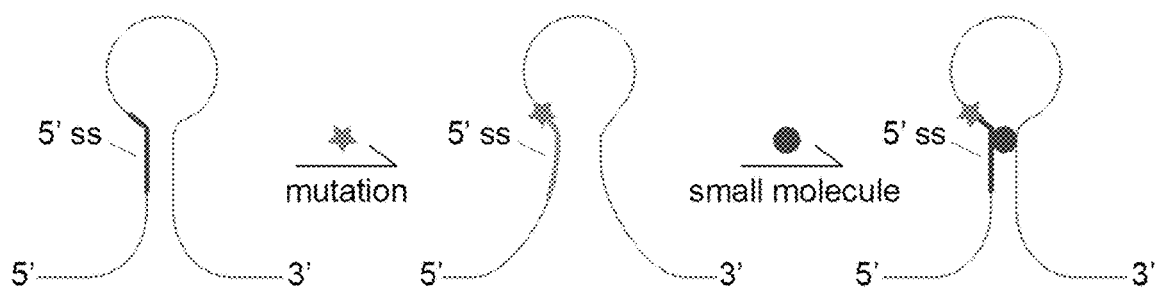
FIG. 2 depicts a diagram of an RNA (left), the RNA with a mutation (middle), and a small molecule bound to the RNA with the mutation (right). The mutation depicted disrupts a stem-loop that contains the mutated base increasing 5'ss accessibility. Access to the 5' splice site can is decreased by the depicted stem loop-stabilizing small molecule splicing modulator. In this case the resulting mRNA isoform has skipped one exon by a small molecule splicing modulator.
Figure 3:
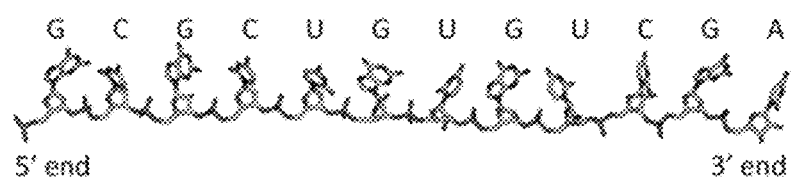
FIG. 3 depicts diagrams of an exemplary primary RNA structure (top) (SEQ ID NO: 114), exemplary secondary RNA structures (middle) and exemplary tertiary RNA structures (bottom).
Figure 3:
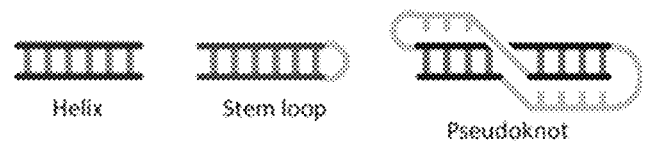
Figure 3:
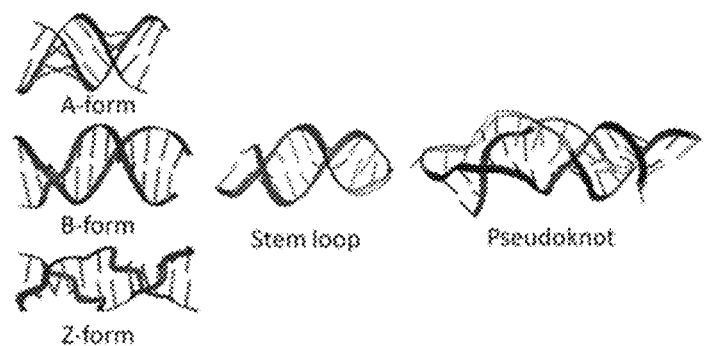

Certain specific details of this description are set forth in order to provide a thorough understanding of various embodiments. However, one skilled in the art will understand that the present disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below.

Definitions

The terms "compound(s) of this disclosure", "compound(s) of the present disclosure", "small molecule steric modulator(s)", "small molecule splicing modulator(s)" "steric modulator(s)", "splicing modulator(s)", "compound(s) that modify splicing" and "compound(s) modifying splicing", "SMSM" or "small molecule that binds a target RNA," are interchangeably used herein and refer to compounds as disclosed herein and stereoisomers, tautomers, solvates, and salts (e.g., pharmaceutically acceptable salts) thereof. The terms "compound(s) of this disclosure", "compound(s) of the present disclosure", "small molecule steric modulator(s)", "small molecule splicing modulator(s)" "steric modulator(s)", "splicing modulator(s)", "compound(s) that modify splicing" and "compound(s) modifying splicing", "SMSM" or "small molecule that binds a target RNA," denote a small molecule compound that binds to a cell component (e.g., DNA, RNA, pre-mRNA, protein, RNP, snRNA, carbohydrates, lipids, co-factors, nutrients and/or metabolites) and modulates splicing of a target polynucleotide, e.g., a pre-mRNA. For example, an SMSM can bind directly or indirectly to a target polynucleotide, e.g., RNA (e.g., a pre-mRNA) with a mutated, non-mutated, bulged and/or aberrant splice site, resulting in modulation of splicing of the target polynucleotide. For example, an SMSM can bind directly or indirectly to a protein, e.g., a spliceosome protein or a ribonuclear protein, resulting in steric modulation of the protein and modulation of splicing of a target RNA. For example, an SMSM can bind directly or indirectly to a spliceosome component, e.g., a spliceosome protein or snRNA resulting in steric modulation of the spliceosome protein or snRNA and modulation of splicing of target polynucleotide. These terms specifically exclude compounds consisting of oligonucleotides. These terms include small molecule compounds that may bind to one or more secondary or tertiary structure elements of a target RNA. These sites include RNA triplexes, 3WJs, 4WJs, parallel-Y junctions, hairpins, bulge loops, pseudoknots, internal loops, and other higher-order RNA structural motifs.

The term "RNA" (ribonucleic acid) as used herein, means naturally-occurring or synthetic oligoribonucleotides independent of source (e.g., the RNA may be produced by a human, animal, plant, virus, or bacterium, or may be synthetic in origin), biological context (e.g., the RNA may be in the nucleus, circulating in the blood, in vitro, cell lysate, or isolated or pure form), or physical form (e.g., the RNA may be in single-, double-, or triple-stranded form (including RNA-DNA hybrids), may include epigenetic modifications, native post-transcriptional modifications, artificial modifications (e.g., obtained by chemical or in vitro modification), or other modifications, may be bound to, e.g., metal ions, small molecules, proteins such as chaperones, or co-factors, or may be in a denatured, partially denatured, or folded state including any native or unnatural secondary or tertiary structure such as quadruplexes, hairpins, triplexes, three way junctions (3WJs), four way junctions (4WJs), parallel-Y junctions, hairpins, bulge loops, pseudoknots, and internal loops, etc., and any transient forms or structures adopted by the RNA). In some embodiments, the RNA is 20, 22, 50, 75, or 100 or more nucleotides in length. In some embodiments, the RNA is 250 or more nucleotides in length. In some embodiments, the RNA is 350, 450, 500, 600, 750, or 1,000, 2,000, 3,000, 4,000, 5,000, 7,500, 10,000, 15,000, 25,000, 50,000, or more nucleotides in length. In some embodiments, the RNA is between 250 and 1,000 nucleotides in length. In some embodiments, the RNA is a pre-RNA, pre-miRNA, or pretranscript. In some embodiments, the RNA is a non-coding RNA (ncRNA), messenger RNA (mRNA), micro-RNA (miRNA), a ribozyme, riboswitch, lncRNA, lincRNA, snoRNA, snRNA, scaRNA, piRNA, ceRNA, pseudo-gene, viral RNA, fungal RNA, parasitic RNA, or bacterial RNA.

The term "target polynucleotide" or "target RNA," as used herein, means any type of polynucleotide or RNA, respectively, having a splice site capable of being modulated by a small molecule compound described herein. For example, a target polynucleotide" or "target RNA," may have a secondary or tertiary structure capable of binding a small molecule compound described herein.

"Steric alteration", "steric modification" or "steric modulation" herein refers to changes in the spatial orientation of chemical moieties with respect to each other. A person of ordinary skill in the art would recognize steric mechanisms include, but are not limited to, steric hindrance, steric shielding, steric attraction, chain crossing, steric repulsions, steric inhibition of resonance, and steric inhibition of protonation.

Any open valency appearing on a carbon, oxygen, sulfur or nitrogen atom in the structures herein indicates the presence of hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination arylalkylheterocycloalkyl refers to a heterocycloalkyl-radical which is substituted by an alkyl which is substituted by an aryl.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The following abbreviations are used throughout the specification: acetic acid (AcOH); ethyl acetate (EtOAc); butyl alcohol (n-BuOH); 1,2-dichloroethane (DCE); dichloromethane ($CH_2Cl_2$, DCM); diisopropylethylamine (Diipea); dimethylformamide (DMF); hydrogen chloride (HCl); methanol (MeOH); methoxymethyl bromide (MOMBr); N-methyl-2-pyrrolidone (NMP); methyl Iodide (Mel); n-propanol (n-PrOH); p-methoxybenzyl (PMB); triethylamine ($Et_3N$); [1,1'-Bis(diphenylphosphino)ferrocene] dichloropalladium(II); (Pd(dppf)$Cl_2$); sodium ethane thiolate (EtSNa); sodium acetate (NaOAc); sodium hydride (NaH); sodium hydroxide (NaOH); tetrahydropyran (THP); tetrahydrofuran (THF).

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

The term "oxo" refers to the =O substituent.

The term "thioxo" refers to the =S substituent.

The term "halo", "halogen", and "halide" are used interchangeably herein and denote fluoro, chloro, bromo, or iodo.

The term "alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

The term "alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

The term "alkylamino" refers to a radical of the formula —NHR or —NRR where each R is, independently, an alkyl radical as defined above. Unless stated otherwise specifically in the specification, an alkylamino group may be optionally substituted as described below.

The term "alkenyl" refers to a type of alkyl group in which at least one carbon-carbon double bond is present. In one embodiment, an alkenyl group has the formula —C(R)=CR$_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=CH$_2$, —C(CH$_3$)=CH$_2$, —CH=CHCH$_3$, —C(CH$_3$)=CHCH$_3$, and —CH$_2$CH=CH$_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$, —C≡CCH$_2$CH$_3$, —CH$_2$C≡CH.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

The term "aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted. In some embodiments, an aryl group is partially reduced to form a cycloalkyl group defined herein. In some embodiments, an aryl group is fully reduced to form a cycloalkyl group defined herein.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms.

The term "haloalkoxy" denotes an alkoxy group wherein at least one of the hydrogen atoms of the alkoxy group has been replaced by same or different halogen atoms, particularly fluoro atoms. Examples of haloalkoxyl include mono-fluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The terms "carbocyclic" or "carbocycle" refer to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted.

The term "bridged" refers to any ring structure with two or more rings that contains abridge connecting two bridgehead atoms. The bridgehead atoms are defined as atoms that are the part of the skeletal framework of the molecule and which are bonded to three or more other skeletal atoms. In some embodiments, the bridgehead atoms are C, N, or P. In some embodiments, the bridge is a single atom or a chain of atoms that connects two bridgehead atoms. In some embodiments, the bridge is a valence bond that connects two bridgehead atoms. In some embodiments, the bridged ring system is cycloalkyl. In some embodiments, the bridged ring system is heterocycloalkyl.

The term "fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with one or more N, S, and O atoms. The non-limiting examples of fused heterocyclyl or heteroaryl ring structures include 6-5 fused heterocycle, 6-6 fused heterocycle, 5-6 fused heterocycle, 5-5 fused heterocycle, 7-5 fused heterocycle, and 5-7 fused heterocycle.

The term "haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

The term "haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

The term "fluoroalkyl" refers to an alkyl in which one or more hydrogen atoms are replaced by a fluorine atom. In one aspect, a fluoroalkyl is a $C_1$-$C_6$ fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g. —NH—, —N(alkyl)-, or —N(aryl)-), sulfur (e.g. —S—, —S(=O)—, or —S(=O)$_2$—), or combinations thereof. In some embodiments, a heteroalkyl is attached to the rest of the molecule at a carbon atom of the heteroalkyl. In some embodiments, a heteroalkyl is attached to the rest of the molecule at a heteroatom of the heteroalkyl. In some embodiments, a heteroalkyl is a $C_1$-$C_6$ heteroalkyl. Representative heteroalkyl groups include, but are not limited to —OCH$_2$OMe, —OCH$_2$CH$_2$OH, —OCH$_2$CH$_2$OMe, or —OCH$_2$CH$_2$OCH$_2$CH$_2$NH$_2$.

The term "heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

The term "heterocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heterocycle" or "heterocyclic" refers to heteroaromatic rings (also known as heteroaryls) and heterocycloalkyl rings (also known as heteroalicyclic groups) that includes at least one heteroatom selected from nitrogen, oxygen and sulfur, wherein each heterocyclic group has from 3 to 12 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 12 atoms in its ring system and aromatic heterocyclic groups include rings having 5 to 12 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3 h-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The term "heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-6 N atoms in the ring. In some embodiments, a heteroaryl contains 1-4 N atoms in the ring. In some embodiments, a heteroaryl contains 4-6 N atoms in the ring. In some embodiments, a heteroaryl contains 0-4 N atoms, 0-1 O atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl. In some embodiments, a heteroaryl group is partially reduced to form a heterocycloalkyl group defined herein. In some embodiments, a heteroaryl group is fully reduced to form a heterocycloalkyl group defined herein.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$ alkyl), —C(=O)NH$_2$, —C(=O)NH(C$_1$-C$_4$ alkyl), —C(=O)N(C$_1$-C$_4$ alkyl)$_2$, —S(=O)$_2$NH$_2$, —S(=O)$_2$NH(C$_1$-C$_4$ alkyl), —S(=O)$_2$N(C$_1$-C$_4$ alkyl)$_2$, C$_1$-C$_4$ alkyl, C$_3$-C$_6$ cycloalkyl, C$_1$-C$_4$ fluoroalkyl, C$_1$-C$_4$ heteroalkyl, C$_1$-C$_4$ alkoxy, C$_1$-C$_4$ fluoroalkoxy, —SC$_1$-C$_4$ alkyl, —S(=O)C$_1$-C$_4$ alkyl, and —S(=O)$_2$(C$_1$-C$_4$ alkyl). In some embodiments, optional substituents are independently selected from D, halogen, —CN, —NH$_2$, —OH, —NH(CH$_3$), —N(CH$_3$)$_2$, —NH(cyclopropyl), —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

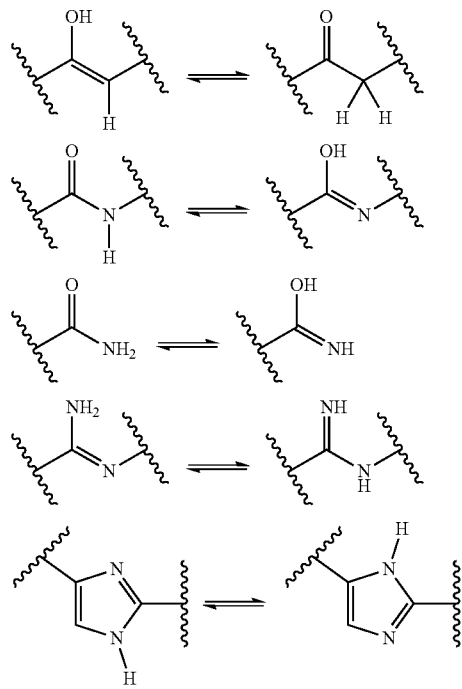

-continued

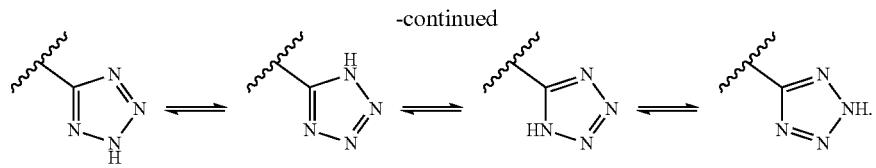

The terms "administer," "administering", "administration," and the like, as used herein, refer to the methods that may be used to enable delivery of compounds or compositions to the desired site of biological action. These methods include, but are not limited to oral routes (p.o.), intraduodenal routes (i.d.), parenteral injection (including intravenous (i.v.), subcutaneous (s.c.), intraperitoneal (i.p.), intramuscular (i.m.), intravascular or infusion (inf.)), topical (top.) and rectal (p.r.) administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated; for example a reduction and/or alleviation of one or more signs, symptoms, or causes of a disease, or any other desired alteration of a biological system. For example, an "effective amount" for therapeutic uses can be an amount of an agent that provides a clinically significant decrease in one or more disease symptoms. An appropriate "effective" amount may be determined using techniques, such as a dose escalation study, in individual cases.

The terms "enhance" or "enhancing," as used herein, means to increase or prolong either in amount, potency or duration a desired effect. For example, in regard to enhancing splicing of a target, the term "enhancing" can refer to the ability to increase or prolong splicing, either in amount, potency or duration, of a the target.

The term "subject" or "patient" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human. The term "animal" as used herein comprises human beings and non-human animals. In one embodiment, a "non-human animal" is a mammal, for example a rodent such as rat or a mouse. In one embodiment, a non-human animal is a mouse.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "preventing" or "prevention" of a disease state denotes causing the clinical symptoms of the disease state not to develop in a subject that can be exposed to or predisposed to the disease state, but does not yet experience or display symptoms of the disease state.

The terms "pharmaceutical composition" and "pharmaceutical formulation" (or "formulation") are used interchangeably and denote a mixture or solution comprising a therapeutically effective amount of an active pharmaceutical ingredient together with one or more pharmaceutically acceptable excipients to be administered to a subject, e.g., a human in need thereof.

The term "pharmaceutical combination" as used herein, means a product that results from mixing or combining more than one active ingredient and includes both fixed and non-fixed combinations of the active ingredients. The term "fixed combination" means that the active ingredients, e.g., a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., administration of three or more active ingredients.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use. "Pharmaceutically acceptable" can refer a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents, excipients, preservatives or lubricants used in formulating pharmaceutical products.

The term "pharmaceutically acceptable salts" denotes salts which are not biologically or otherwise undesirable. Pharmaceutically acceptable salts include both acid and base addition salts. A "pharmaceutically acceptable salt" can refer to a formulation of a compound that does not cause significant irritation to an organism to which it is administered and/or does not abrogate the biological activity and properties of the compound. In some embodiments, pharmaceutically acceptable salts are obtained by reacting an SMSM compound of any one of Formulas (I)-(V) with an acid. Pharmaceutically acceptable salts are also obtained by reacting a compound of any one of Formulas (I)-(V) or with a base to form a salt.

The term "nucleic acid" as used herein generally refers to one or more nucleobases, nucleosides, or nucleotides, and the term includes polynucleobases, polynucleosides, and polynucleotides.

The term "polynucleotide", as used herein generally refers to a molecule comprising two or more linked nucleic acid subunits, e.g., nucleotides, and can be used interchangeably with "oligonucleotide". For example, a polynucleotide may include one or more nucleotides selected from adenosine (A), cytosine (C), guanine (G), thymine (T) and uracil (U), or variants thereof. A nucleotide generally includes a nucleoside and at least 1, 2, 3, 4, 5, 6, 7, 8, 9, 10, or more phosphate ($PO_3$) groups. A nucleotide can include a nucleobase, a five-carbon sugar (either ribose or deoxyribose), and one or more phosphate groups. Ribonucleotides include nucleotides in which the sugar is ribose. Deoxyribonucleotides include nucleotides in which the sugar is deoxyribose. A nucleotide can be a nucleoside monophosphate, nucleoside diphosphate, nucleoside triphosphate or a nucleoside polyphosphate. For example, a nucleotide can be a deoxyribonucleoside polyphosphate, such as a deoxyribonucleoside triphosphate (dNTP), Exemplary dNTPs include deoxyadenosine triphosphate (dATP), deoxycytidine triphosphate (dCTP), deoxyguanosine triphosphate (dGTP), uridine triphosphate (dUTP) and deoxythymidine triphosphate (dTTP). dNTPs can also include detectable tags, such as luminescent tags or markers (e.g., fluorophores). For example, a nucleotide can be a purine (i.e., A or G, or variant thereof) or a pyrimidine (i.e., C, T or U, or variant thereof). In some examples, a polynucleotide is deoxyribonucleic acid (DNA), ribonucleic acid (RNA), or derivatives or variants thereof. Exemplary polynucleotides include, but are not limited to, short interfering RNA (siRNA), a microRNA (miRNA), a plasmid DNA (pDNA), a short hairpin RNA (shRNA), small nuclear RNA (snRNA), messenger RNA (mRNA), precursor mRNA (pre-mRNA), antisense RNA (asRNA), and heteronuclear RNA (hnRNA), and encompasses both the nucleotide sequence and any structural embodiments thereof, such as single-stranded, double-stranded, triple-stranded, helical, hairpin, stem loop, bulge, etc. In some cases, a polynucleotide is circular. A polynucleotide can have various lengths. For example, a polynucleotide can have a length of at least about 7 bases, 8 bases, 9 bases, 10 bases, 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. A polynucleotide can be isolated from a cell or a tissue. For example, polynucleotide sequences may comprise isolated and purified DNA/RNA molecules, synthetic DNA/RNA molecules, and/or synthetic DNA/RNA analogs.

Polynucleotides may include one or more nucleotide variants, including nonstandard nucleotide(s), non-natural nucleotide(s), nucleotide analog(s) and/or modified nucleotides. Examples of modified nucleotides include, but are not limited to diaminopurine, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 5-methyl-2-thiouracil, 3-(3-amino-3-N-2-carboxypropyl)uracil, (acp3)w, 2,6-diaminopurine and the like. In some cases, nucleotides may include modifications in their phosphate moieties, including modifications to a triphosphate moiety. Non-limiting examples of such modifications include phosphate chains of greater length (e.g., a phosphate chain having, 4, 5, 6, 7, 8, 9, 10 or more phosphate moieties) and modifications with thiol moieties (e.g., alpha-thiotriphosphate and beta-thiotriphosphates). Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone. Nucleic acid molecules may also contain amine-modified groups, such as amino ally 1-dUTP (aa-dUTP) and aminohexhylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure can provide higher density in bits per cubic mm, higher safety (resistant to accidental or purposeful synthesis of natural toxins), easier discrimination in photo-programmed polymerases, or lower secondary structure. Such alternative base pairs compatible with natural and mutant polymerases for de novo and/or amplification synthesis are described in Betz K, Malyshev D A, Lavergne T, Welte W, Diederichs K, Dwyer T J, Ordoukhanian P, Romesberg F E, Marx A. Nat. Chem. Biol. 2012 July; 8(7):612-4, which is herein incorporated by reference for all purposes.

As used herein, the terms "polypeptide", "protein" and "peptide" are used interchangeably and refer to a polymer of amino acid residues linked via peptide bonds and which may be composed of two or more polypeptide chains. The terms "polypeptide", "protein" and "peptide" refer to a polymer of at least two amino acid monomers joined together through amide bonds. An amino acid may be the L-optical isomer or the D-optical isomer. More specifically, the terms "polypeptide", "protein" and "peptide" refer to a molecule composed of two or more amino acids in a specific order; for example, the order as determined by the base sequence of nucleotides in the gene or RNA coding for the protein. Proteins are essential for the structure, function, and regulation of the body's cells, tissues, and organs, and each protein has unique functions. Examples are hormones, enzymes, antibodies, and any fragments thereof. In some cases, a protein can be a portion of the protein, for example, a domain, a subdomain, or a motif of the protein. In some cases, a protein can be a variant (or mutation) of the protein, wherein one or more amino acid residues are inserted into, deleted from, and/or substituted into the naturally occurring (or at least a known) amino acid sequence of the protein. A protein or a variant thereof can be naturally occurring or recombinant.

Methods for detection and/or measurement of polypeptides in biological material are well known in the art and include, but are not limited to, Western-blotting, flow cytometry, ELISAs, RIAs, and various proteomics techniques. An exemplary method to measure or detect a polypeptide is an immunoassay, such as an ELISA. This type of protein quantitation can be based on an antibody capable of capturing a specific antigen, and a second antibody capable of detecting the captured antigen. Exemplary assays for detection and/or measurement of polypeptides are described in Harlow, E. and Lane, D. Antibodies: A Laboratory Manual, (1988), Cold Spring Harbor Laboratory Press.

Methods for detection and/or measurement of RNA in biological material are well known in the art and include, but are not limited to, Northern-blotting, RNA protection assay, RT PCR. Suitable methods are described in Molecular Cloning: A Laboratory Manual (Fourth Edition) By Michael R. Green, Joseph Sambrook, Peter MacCallum 2012, 2,028 pp, ISBN 978-1-936113-42-2.

As used here, a "small molecular weight compound" can be used interchangeably with "small molecule" or "small organic molecule". Small molecules refer to compounds other than peptides or oligonucleotides; and typically have molecular weights of less than about 2000 Daltons, e.g., less than about 900 Daltons.

A ribonucleoprotein (RNP) refers to a nucleoprotein that contains RNA. A RNP can be a complex of a ribonucleic acid and an RNA-binding protein. Such a combination can also be referred to as a protein-RNA complex. These complexes can function in a number of biological functions that include, but are not limited to, DNA replication, gene expression, metabolism of RNA, and pre-mRNA splicing. Examples of RNPs include the ribosome, the enzyme telomerase, vault ribonucleoproteins, RNase P, heterogeneous nuclear RNPs (hnRNPs) and small nuclear RNPs (snRNPs).

Nascent RNA transcripts from protein-coding genes and mRNA processing intermediates, collectively referred to as pre-mRNA, are generally bound by proteins in the nuclei of eukaryotic cells. From the time nascent transcripts first emerge from RNA polymerase (e.g., RNA polymerase II) until mature mRNAs are transported into the cytoplasm, the RNA molecules are associated with an abundant set of splicing complex components (e.g., nuclear proteins and snRNAs). These proteins can be components of hnRNPs, which can contain heterogeneous nuclear RNA (hnRNA) (e.g., pre-mRNA and nuclear RNA complexes) of various sizes.

Splicing complex components function in splicing and/or splicing regulation. Splicing complex components can include, but are not limited to, ribonuclear proteins (RNPs), splicing proteins, small nuclear RNAs (snRNAs), small nuclear ribonucleoproteins (snRNPs), and heterogeneous nuclear ribonucleoproteins (hnRNPs). Splicing complex components include, but are not limited to, those that may be required for splicing, such as constitutive splicing, alternative splicing, regulated splicing and splicing of specific messages or groups of messages. A group of related proteins, the serine arginine rich proteins (SR proteins), can function in constitutive pre-mRNA splicing and may also regulate alternative splice-site selection in a concentration-dependent manner. SR proteins typically have a modular structure that consists of one or two RNA-recognition motifs (RRMs) and a C-terminal rich in arginine and serine residues (RS domain). Their activity in alternative splicing may be antagonized by members of the hnRNP A/B family of proteins. Splicing complex components can also include proteins that are associated with one or more snRNAs. SR proteins in human include, but are not limited to, SC35, SRp55, SRp40, SRm300, SFRS10, TASR-1, TASR-2, SF2/ASF, 9G8, SRp75, SRp30c, SRp20 and P54/SFRS11. Other splicing complex components in human that can be involved in splice site selection include, but are not limited to, U2 snRNA auxiliary factors (e.g. U2AF65, U2AF35), Urp/U2AF1-RS2, SF1/BBP, CBP80, CBP 20, SF1 and PTB/hnRNP1. hnRNP proteins in humans include, but are not limited to, A1, A2/B1, L, M, K, U, F, H, G, R, I and C1/C2. Human genes encoding hnRNPs include HNRNPA0, HNRNPA1, HNRNPA1L1, HNRNPA1L2, HNRNPA3, HNRNPA2B1, HNRNPAB, HNRNPB1, HNRNPC, HNRNPCL1, HNRNPD, HNRPDL, HNRNPF, HNRNPH1, HNRNPH2, HNRNPH3, HNRNPK, HNRNPL, HNRPLL, HNRNPM, HNRNPR, HNRNPU, HNRNPUL1, HNRNPUL2, HNRNPUL3, and FMR1. Splicing complex components may be stably or transiently associated with a snRNP or with a transcript.

The term "intron" refers to both the DNA sequence within a gene and the corresponding sequence in the unprocessed RNA transcript. As part of the RNA processing pathway, introns can be removed by RNA splicing either shortly after or concurrent with transcription. Introns are found in the genes of most organisms and many viruses. They can be located in a wide range of genes, including those that generate proteins, ribosomal RNA (rRNA), and transfer RNA (tRNA).

An "exon" can be any part of a gene that encodes apart of the final mature RNA produced by that gene after introns have been removed by RNA splicing. The term "exon" refers to both the DNA sequence within a gene and to the corresponding sequence in RNA transcripts.

A "spliceosome" can be assembled from snRNAs and protein complexes. The spliceosome can remove introns from a transcribed pre-mRNA.

"Medium effective dose" ($ED_{50}$) is the dose at which 50% of a population expresses a specified response. "Medium lethal dose" ($LD_{50}$) is the dose at which 50% of a population dies. "Medium toxic dose" ($TD_{50}$) is the dose at which 50% of a population expresses a specified toxic effect. One particularly useful pharmacological indicator is the "therapeutic index" which is traditionally defined as the ratio of $LD_{50}$ to $ED_{50}$ or the ratio of $TD_{50}$ to $ED_{50}$. Therapeutic index provides a simple and useful indicator of the benefit versus adverse effect of a drug. Those drugs which have a high therapeutic index have a large therapeutic window, i.e., the drugs may be administered over a wider range of effective doses without incurring significant adverse events. Conversely, drugs having a small therapeutic index have a small therapeutic window (small range of effective doses without incurring significant adverse events).

The term "AUC" as used herein refers to an abbreviation for "area under the curve" in a graph of the concentration of a therapeutic agent over time in a certain part or tissue, such as blood or plasma, of a subject to whom the therapeutic agent has been administered.

Small Molecule Splicing Modulators (SMSMs)

It has now been found that compounds of this invention, and pharmaceutically acceptable compositions thereof, are effective as agents for use in treating, preventing, or ameliorating a disease or condition associated with a target RNA. The present invention provides the unexpected discovery that certain small chemical molecules can modify splicing events in pre-mRNA molecules, herein referred to as small molecule splicing modulators (SMSMs). These SMSMs can modulate specific splicing events in specific pre-mRNA molecules. These SMSMs can operate by a variety of mechanisms to modify splicing events. For example, the SMSMs of this invention can: 1) interfere with the formation and/or function and/or other properties of splicing complexes, spliceosomes, and/or their components such as hnRNPs, snRNPs, SR-proteins and other splicing factors or elements, resulting in the prevention or induction of a splicing event in a pre-mRNA molecule. As another example; 2) prevent and/or modify post-transcriptional regulation (e.g., splicing) of gene products, such as hnRNPs, snRNPs, SR-proteins and other splicing factors, which can subsequently be involved in the formation and/or function of a spliceosome or splicing complex component; 3) prevent and/or modify phosphorylation, glycosylation and/or other modifications of gene products including, but not limited to, hnRNPs, snRNPs, SR-proteins and other splicing factors, which can subsequently be involved in the formation and/or function of a spliceosome or splicing complex component; 4) bind to and/or otherwise affect specific pre-mRNA so that a specific splicing event is prevented or induced, e.g., via a mechanism that does not involve base pairing with RNA in a sequence-specific manner. The small molecules of this invention are different from and are not related to antisense or antigene oligonucleotides.

Described herein are compounds modifying splicing of gene products for use in the treatment, prevention and/or delay of progression of diseases or conditions (e.g., cancer). Described herein are compounds modifying splicing of gene products wherein the compounds induce a transcriptionally inactive variant or transcript of a gene product. Described herein are compounds modifying splicing of gene products wherein the compounds repress a transcriptionally active variant or transcript of a gene product.

In one aspect, described herein is a compound that has the structure of Formula (I), or a pharmaceutically acceptable salt or solvate thereof:

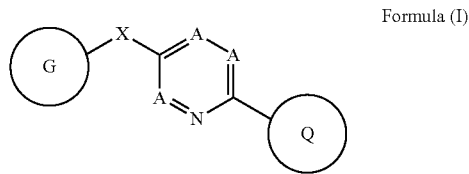

Formula (I)

wherein,
each A is independently N or $CR^A$;
each $R^A$ is independently selected from H, D, halogen, —CN, —OH, —$OR^1$, =O, =N—$OR^1$, —$SR^1$, —S(=O)$R^1$, —S(=O)$_2R^1$, —$N(R^1)_2$, —$NR^1S(=O)(=NR^1)R^2$, —$NR^1S(=O)_2R^2$, —S(=O)$_2N(R^1)_2$, —C(=O)$R^1$, —OC(=O)$R^1$, —C(=O)$OR^1$, —OC(=O)$OR^1$, —C(=O)N($R^1)_2$, —OC(=O)N($R^1)_2$, —$NR^1C(=O)R^1$, —P(=O)($R^2)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, and substituted or unsubstituted monocyclic heteroaryl;
ring Q is aryl, monocyclic heteroaryl, or fused bicyclic heteroaryl;
X is —$NR^3$—, —$CR^4R^-$, —C(=O)—, —S—, —S(=O)—, —S(=O)$_2$—, or —S(=O)(=$NR^1$); each $R^1$ is independently H, D, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each $R^2$ is independently H, D, substituted or unsubstituted $C_1$-$C_6$ alkyl, substituted or unsubstituted $C_1$-$C_6$ haloalkyl, substituted or unsubstituted aryl, substituted or unsubstituted monocyclic heteroaryl, —$OR^1$, —$N(R^1)_2$, —$CH_2OR^1$, —C(=O)$OR^1$, —OC(=O)$R^1$, —C(=O)N($R^1)_2$, or —$NR^1C(=O)R^1$;
$R^3$ is —$OR^1$, —$N(R^1)_2$, substituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl, wherein substituted $C_1$-$C_6$ alkyl comprises one or more substituents other than —OH, —$NH_2$, and —$CO_2H$, wherein substituted or unsubstituted $C_1$-$C_6$ heteroalkyl comprises at least 2 O atoms, 2 N atoms, or S atom, and wherein substituted $C_3$-$C_8$ cycloalkyl comprises at least 1 substituent selected from D, halogen, and —$OR^1$;
$R^4$ is D, F, —CN, —$OR^1$, —$SR^1$, —$N(R^1)_2$, substituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;
$R^5$ is H, D, F, —CN, —$OR^1$, —$SR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;
ring G is a group of the Formula

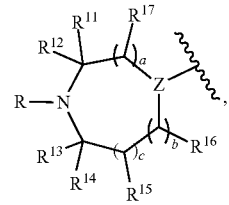

wherein
Z is N or $CR^7$; and $R^7$ is H, D, substituted or unsubstituted $C_1$-$C_6$ alkyl, substituted or unsubstituted $C_1$-$C_6$ haloalkyl or —$CH_2OR^1$;
a, b, and c are each independently selected from 0, 1, or 2;
$R^{11}$, $R^{12}$, $R^{11}$, $R^{14}$, $R^{15}$, $R^{11}$, and $R^{17}$ are each independently selected from the group consisting of H, F, $OR^1$, substituted or unsubstituted $C_{1-6}$ alkyl, a substituted or unsubstituted $C_{1-6}$ fluoroalkyl, substituted or unsubstituted $C_1$-$C_6$ heteroalkyl, wherein alkyl is optionally substituted with hydroxy, amino, methoxy, substituted or unsubstituted mono-$C_{1-6}$ alkylamino or substituted or unsubstituted di-$C_{1-6}$ alkylamino; or
R and $R^{13}$, taken in combination form a fused 5 or 6 membered heterocyclic ring having 0 or 1 additional ring heteroatoms selected from N, O or S; or
$R^{11}$ and $R^{13}$, taken in combination form a substituted or unsubstituted $C_{1-3}$ alkylene group; or
$R^{11}$ and $R^{15}$, taken in combination form a substituted or unsubstituted $C_{1-3}$ alkylene group; or
$R^{11}$ and $R^{17}$, taken in combination form a substituted or unsubstituted $C_{1-3}$ alkylene group; or R$^{16}$ and R$^{17}$, taken in combination form a substituted or unsubstituted C$_{1-3}$ alkylene group; or R$^{16}$ and R$^{17}$, taken in combination form a bond; or R$^{13}$ and R$^4$, taken in combination with the carbon atom to which they attach, form a spirocyclic C$_{3-8}$ cycloalkyl; or R$^{16}$ and R$^2$, taken in combination form a double bond; or R$^{17}$ and R$^2$, taken in combination form a substituted or unsubstituted C$_{1-3}$ alkylene group; or when Z is CR$^7$, then R$^3$ and R$^7$ are optionally taken together with the intervening atoms to which they are attached form a 4, 5, or 6-membered ring; or when X is —NR$^3$—, then R$^3$ and R$^{16}$ are optionally taken together with the intervening atoms to which they are attached form a 4, 5, or 6-membered ring; or when Z is CR$^7$ and X is —CR$^4$R$^5$—, then R$^7$ and R$^5$ are optionally taken in combination form a double bond.

For any and all of the embodiments, substituents are selected from among a subset of the listed alternatives. For example, in some embodiments, a is 0, 1, or 2. In other embodiments, a is 0. In some other embodiments, a is 1. In some other embodiments, a is 2.

In some embodiments,

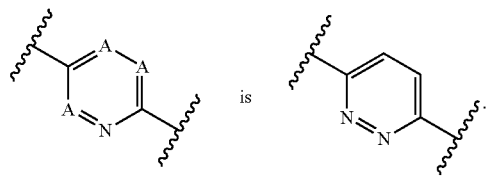

is

In some embodiments,

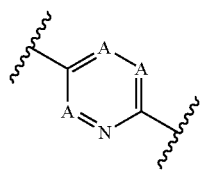

is

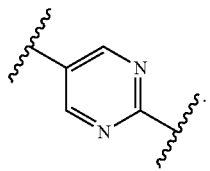 [SMILES: *c1cnc(*)nc1]

In some embodiments, Z is N and X is —NR$^3$—, —CH(CH$_2$OR$^1$)—, —CH(OR$^1$)—, —C(=O)—, —S(=O)—, —S(=O)$_2$—, or —S(=O)(=NR$^1$)—. In some embodiments, Z is N. In some embodiments, X is —NR$^3$—. In some embodiments, X is —CH(CH$_2$OR$^1$)—. In some embodiments, X is —CH(CH$_2$OH)—. In some embodiments, X is —CH(CH$_2$OCH$_3$)—. In some embodiments, X is —CH(OR$^1$)—. In some embodiments, X is —CH(OH)—. In some embodiments, X is —CH(OCH$_3$)—. In some embodiments, X is —C(=O)—. In some embodiments, X is —S(=O)—. In some embodiments, X is —S(=O)$_2$—. In some embodiments, X is —S(=O)(=NR$^1$)—.

In some embodiments, R$^3$ is H, —OR$^1$, —N(R$^1$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl.

In some embodiments, R$^3$ is —OR$^1$, —N(R$^1$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl.

In some embodiments, Z is CR$^7$ and X is —C(=O)—, —CH(CH$_2$OR$^1$)—, or —CH(OR$^1$)—. In some embodiments, Z is CR$^7$. In some embodiments, X is —C(=O)—. In some embodiments, X is —CH(CH$_2$OR$^1$)—. In some embodiments, X is —CH(OR$^1$)—.

In some embodiments, ring Q is substituted or unsubstituted aryl. In some embodiments, ring Q is substituted aryl. In some embodiments, ring Q is unsubstituted aryl.

In some embodiments, ring Q is substituted phenyl. In some embodiments, ring Q is 2-hydroxy-phenyl which is substituted with: 0, 1, 2, or 3 substituents independently selected from C$_{1-6}$ alkyl, oxo, oxime, hydroxy, halo-C$_{1-6}$ alkyl, dihalo-C$_{1-6}$ alkyl, trihalo-C$_{1-6}$ alkyl, C$_{1-6}$ alkoxy, C$_{1-6}$ alkoxy-C$_{3-7}$ cycloalkyl, halo-C$_{1-6}$ alkoxy, dihalo-C$_{1-6}$ alkoxy, trihalo-C$_{1-6}$ alkoxy, hydroxy, cyano, halogen, amino, mono-C$_{1-6}$ alkylamino, di-C$_{1-6}$ alkylamino, heteroaryl, C$_{1-6}$ alkyl substituted with hydroxy, C$_{1-6}$ alkoxy substituted with aryl, amino, —C(=O)NH—C$_{1-6}$ alkyl-heteroaryl, —NHC(=O)—C$_{1-6}$ alkylheteroaryl, C$_{1-6}$ alkyl-C(=O)NH-heteroaryl, C$_{1-6}$ alkyl-NHC(=O)-heteroaryl, C$_{3-7}$ cycloalkyl, 5-7 membered cycloalkenyl, or 5, 6 or 9 membered heterocycle containing 1 or 2 heteroatoms independently, selected from S, O and N.

In some embodiments, ring Q is 2-hydroxy-phenyl which is substituted with two C$_{1-6}$ alkyl. In some embodiments, two C$_{1-6}$ alkyl groups can combine with the atoms to which they are bound to form a 5-6 membered ring.

In some embodiments, ring Q is 2-hydroxy-phenyl which is substituted with heteroaryl. In some embodiments, heteroaryl has 5, 6, 9, or 10 ring atoms, 1, 2 or 3 ring heteroatoms selected from N, O and S, and is substituted with 0, 1, or 2 substituents independently selected from oxo, hydroxy, nitro, halogen, C$_{1-6}$ alkyl, C$_{1-6}$ alkenyl, C$_{1-6}$ alkoxy, C$_{3-7}$ cycloalkyl, C$_{1-6}$ alkyl-OH, trihalo-C$_{1-6}$ alkyl, mono-C$_{1-6}$ alkylamino, di-C$_{1-6}$ alkylamino, —C(=O)NH$_2$, —NH$_2$, —NO$_2$, hydroxy-C$_{1-6}$ alkylamino, hydroxy-C$_{1-6}$ alkyl, 4-7 membered heterocycle-C$_{1-6}$ alkyl, amino-C$_{1-6}$ alkyl, mono-C$_{1-6}$ alkylamino-C$_{1-6}$ alkyl, and di-C$_{1-6}$ alkylamino-C$_{1-6}$ alkyl.

In some embodiments, ring Q is 2-hydroxy-phenyl which is substituted with a heteroaryl selected from the group consisting of:

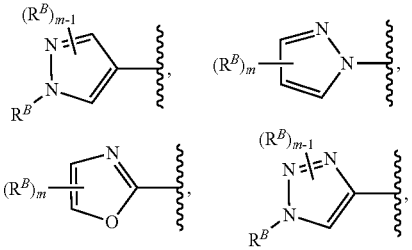

-continued

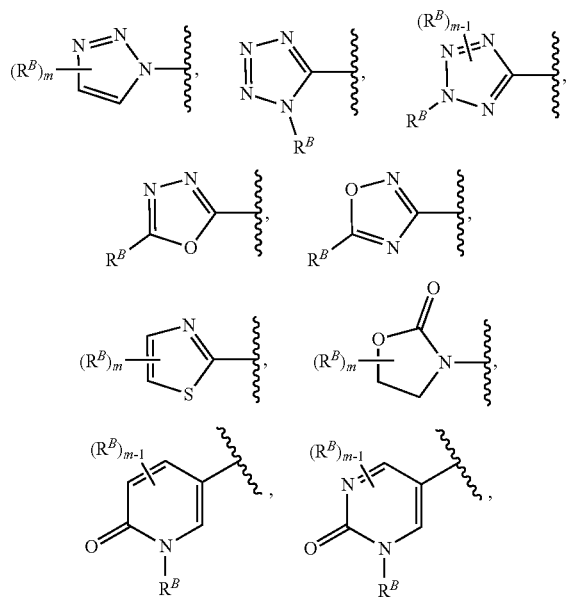

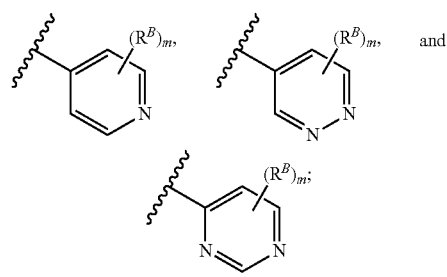

wherein each $R^B$ is independently selected from cyano, halogen, hydroxy, substituted or unsubstituted $C_{1-6}$ alkyl, —$OCH_3$, —$OCD_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-s}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is

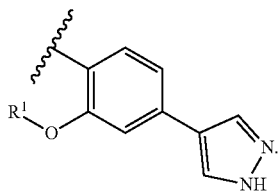

In some embodiments, ring Q is

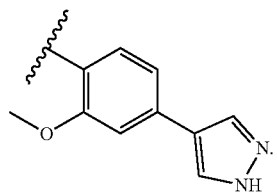 [SMILES: *c1ccc(-c2cn[nH]c2)cc1OC]

In some embodiments, ring Q is

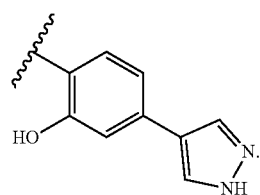 [SMILES: *c1ccc(-c2cn[nH]c2)cc1O]

In some embodiments, ring Q is

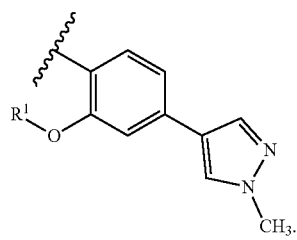

In some embodiments, ring Q is

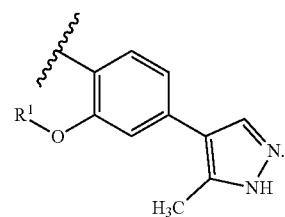

In some embodiments, ring Q

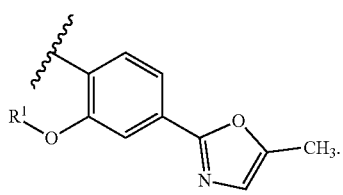

In some embodiments, ring Q is

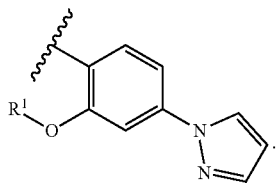

In some embodiments, ring Q is

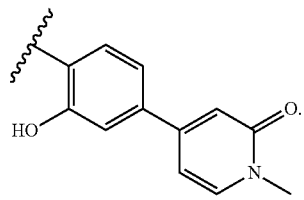 [SMILES: *c1ccc(-c2ccn(C)c(=O)c2)cc1O]

In some embodiments, ring Q is

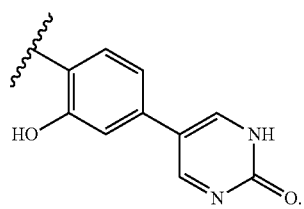 [SMILES: *c1ccc(-c2cnc(=O)[nH]c2)cc1O]

In some embodiments, ring Q is

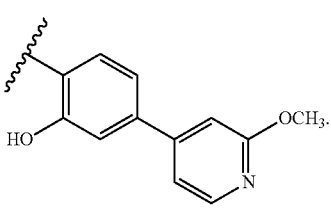

In some embodiments, ring Q is

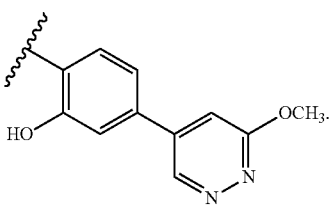

In some embodiments, ring Q is

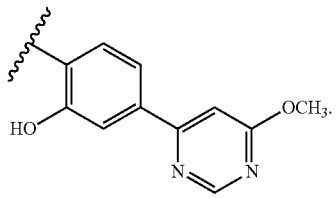

In some embodiments, ring Q is

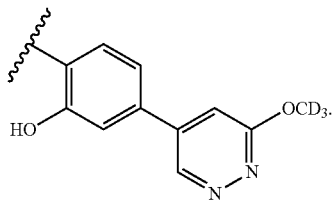 [SMILES: *c1ccc(-c2cnnc(OC)c2)cc1O]

In some embodiments, ring Q is

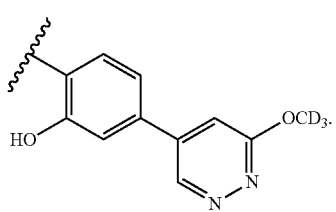

In some embodiments, ring Q is

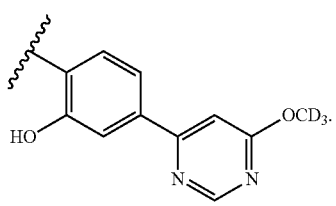

In some embodiments, ring Q is 2-naphthyl optionally substituted at the 3 position with hydroxy and additionally substituted with 0, 1, or 2 substituents selected from hydroxy, cyano, halogen, $C_{1-6}$ alkyl, $C_{2-6}$ alkenyl, $C_{1-6}$ alkoxy, wherein the alkoxy is unsubstituted or substituted with hydroxy, $C_{1-6}$ alkoxy, amino, —NHC(=O)—$C_{1-6}$ alkyl, —NHC(=O)—$C_{1-6}$ alkyl, $C_{1-6}$ alkylene-4-7 membered heterocycle, 4-7 membered heterocycle, mono-$C_{1-6}$ alkylamino, and di-$C_{1-6}$ alkylamino.

In some embodiments, ring Q is monocyclic heteroaryl or fused bicyclic heteroaryl.

In some embodiments, ring Q is a 5 or 6 membered monocyclic heteroaryl having 1-4 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from cyano, $C_{1-6}$ alkyl, mono-$C_{1-6}$ alkylamino, di-$C_{1-6}$ alkylamino, hydroxy-$C_{1-6}$ alkylamino, hydroxy-$C_{1-6}$ alkyl, amino-$C_{1-6}$ alkyl and mono-$C_{1-6}$ alkylamino-$C_{1-6}$ alkyl, and di-$C_{1-6}$ alkylamino-$C_{1-6}$ alkyl.

In some embodiments, ring Q is a 5 membered monocyclic heteroaryl selected from the group consisting of

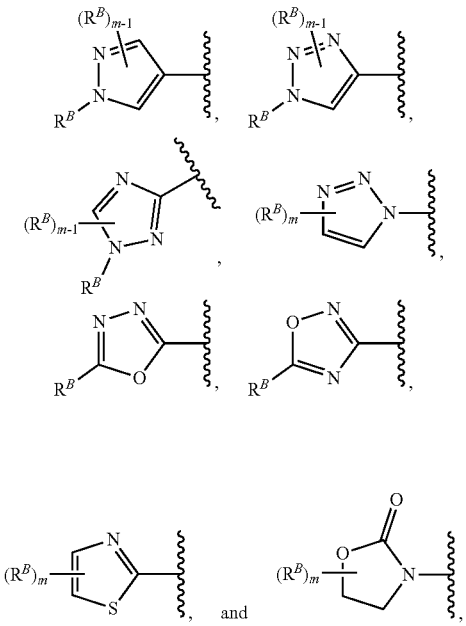

wherein
each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a 6 membered monocyclic heteroaryl selected from the group consisting of

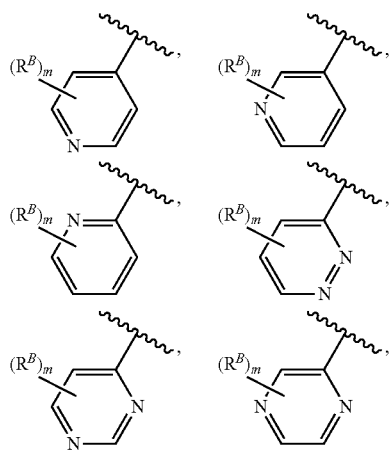

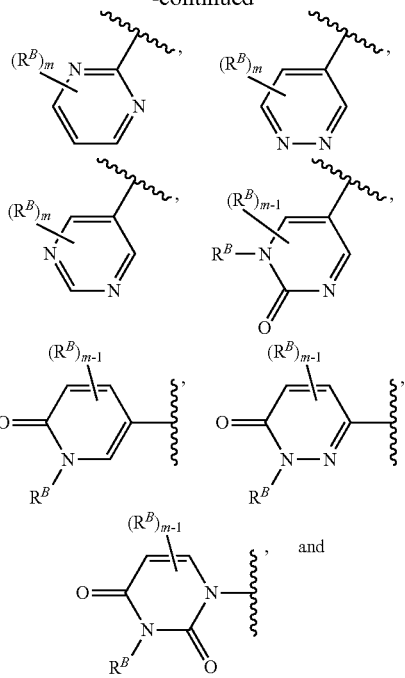

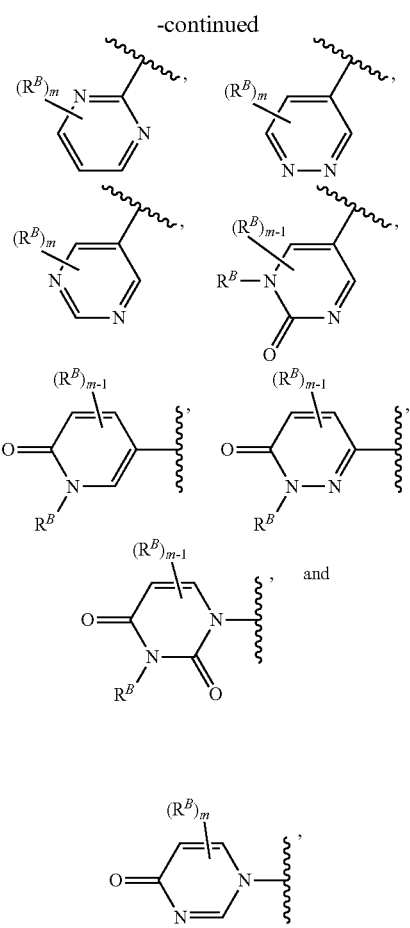

wherein
each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a fused bicyclic heteroaryl having 8 to 10 ring atoms, 1, 2, or 3 ring heteroatoms independently selected from N, O or S, and which is substituted with 0, 1, or 2 substituents independently selected from cyano, oxime, halogen, hydroxy, $C_{1-6}$ alkyl, $C_{24}$ alkenyl, $C_{24}$ alkynyl, $C_{1-6}$ alkoxy, $C_{1-6}$ alkoxy substituted with hydroxy, amino, mono-$C_{1-6}$ alkylamino, and di-$C_{1-6}$ alkylamino.

In some embodiments, ring Q is a 6-5 fused heteroaryl, 6-6 fused heteroaryl, 5-6 fused heteroaryl, 5-5 fused heteroaryl, 7-5 fused heteroaryl, or 5-7 fused heteroaryl.

In some embodiments, ring Q is a 6-5 fused heteroaryl, 6-6 fused heteroaryl, or 5-6 fused heteroaryl, selected from the group consisting of:

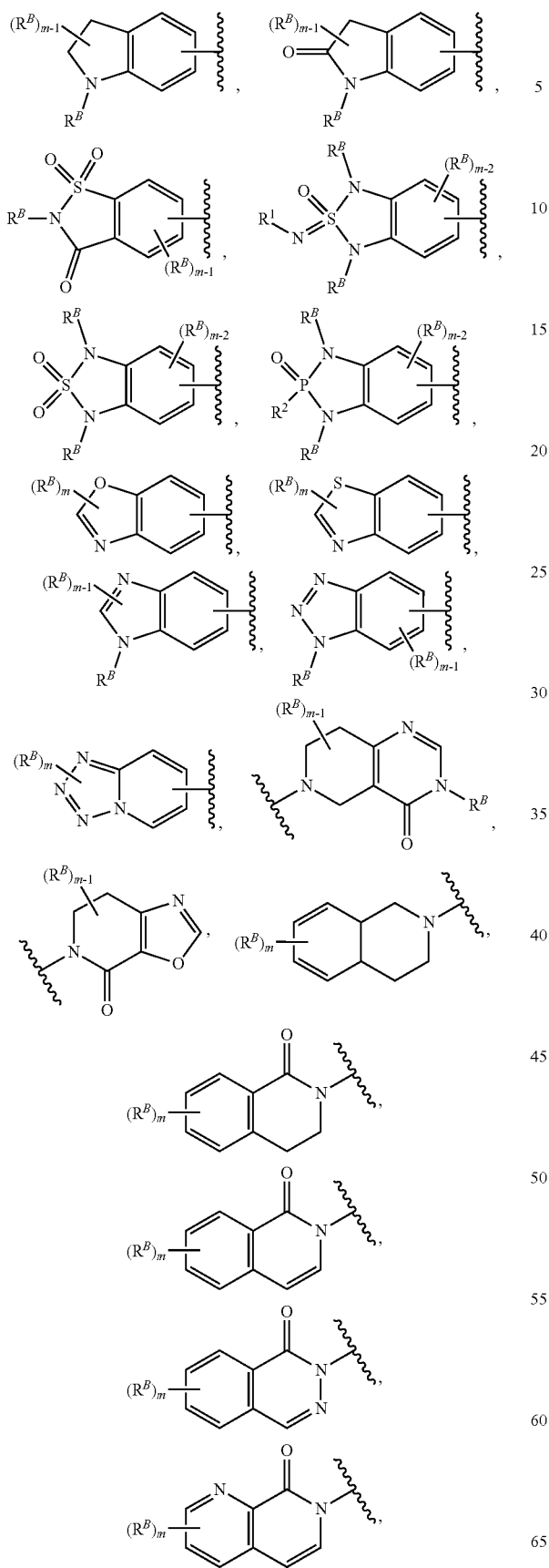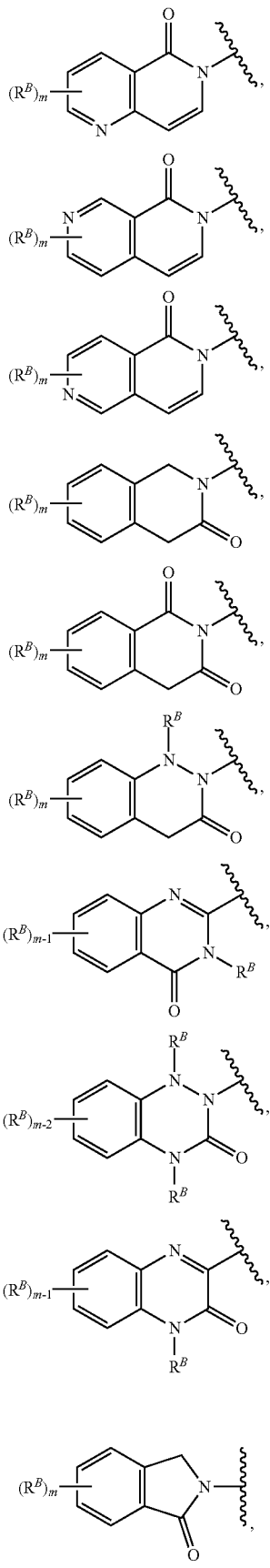

-continued

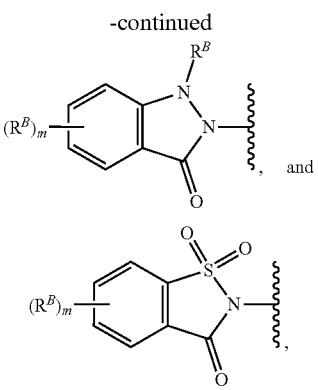, and

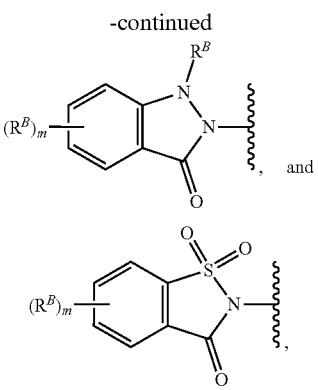, wherein each $R^B$ is independently selected from cyano, halogen, hydroxy, substituted or unsubstituted $C_{1-6}$ alkyl, —$OCH_3$, —$OCD_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 1, 2, or 3.

In some embodiments, X is S.

In some embodiments, X is —$NR^3$—.

In some embodiments, $R^3$ is —$OR^1$. In some embodiments, $R^3$ is —$OCH_3$. In some embodiments, $R^3$ is —$OCH_2CH_3$. In some embodiments, $R^3$ is —$OCH_2CH_2CH_3$. In some embodiments, $R^3$ is —$OCH(CH_3)_2$.

In some embodiments, $R^3$ is substituted $C_1$-$C_6$ alkyl comprises one or more substituents other than —OH, —$NH_2$, and —$CO_2H$. In some embodiments, $R^3$ is —$CD_3$.

In some embodiments, $R^3$ is substituted or unsubstituted $C_1$-$C_6$ haloalkyl. In some embodiments, $R^3$ is $CF_3$. In some embodiments, $R^3$ is —$CH_2CH_2F$. In some embodiments, $R^3$ is —$CH_2CH_2CH_2F$. In some embodiments, $R^3$ is —$CH_2CF_3$. In some embodiments, $R^3$ is —$CH_2CH_2CF_3$.

In some embodiments, $R^3$ is substituted or unsubstituted $C_1$-$C_6$ heteroalkyl. In some embodiments, the substituted or unsubstituted $C_1$-$C_6$ heteroalkyl comprises at least 2 O atoms or S atom. In some embodiments, $R^3$ is —$OCH_2CH_2OCH_3$ or —$OCH_2CH_2OCF_3$. In some embodiments, $R^3$ is —$CH_2CH_2OCH_3$. In some embodiments, $R^3$ is —$OCH_2CH_2OCF_3$. In some embodiments, $R^3$ is —$CH_2CH_2SCH_3$ or —$CH_2SCH_3$. In some embodiments, $R^3$ is —$CH_2CH_2SCH_3$. In some embodiments, $R^3$ is —$CH_2SCH_3$.

In some embodiments, $R^3$ is substituted or unsubstituted $C_3$-$C_8$ cycloalkyl. In some embodiments, $R^3$ is substituted or unsubstituted $C_3$-$C_8$ cycloalkyl. In some embodiments, $R^3$ is cyclopropyl, cyclobutyl, cyclopentyl, cyclohexyl, cycloheptyl, or cyclooctyl. In some embodiments, $R^3$ is cyclopentenyl, cyclohexenyl, cycloheptenyl, or cyclooctenyl.

In some embodiments, X is —$NR^3$— and ring G is

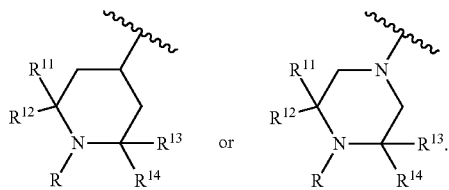

In some embodiments, X is —$NR^3$— and ring G is

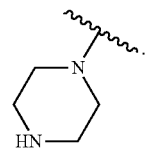

In some embodiments, X is —$NR^3$— and ring G is

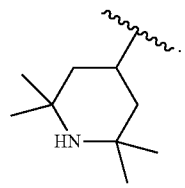

In some embodiments, X is —$NR^3$— and ring G is

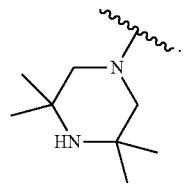

In some embodiments, ring G is

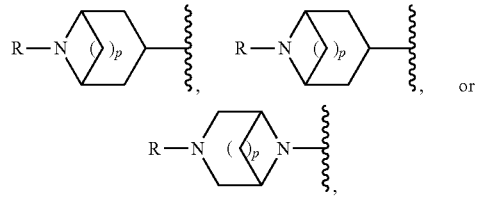

wherein p is 1 or 2. In some embodiments, ring G is

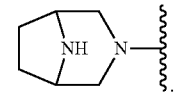

In some embodiments, ring G is

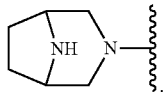

In some embodiments, ring G is

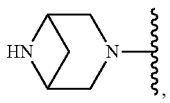

In some embodiments, ring G is

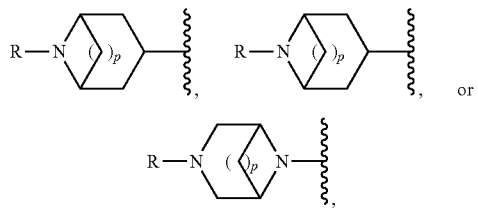

wherein p is 1 or 2. In some embodiments, ring G is

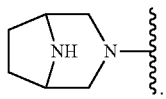

In some embodiments, ring G is

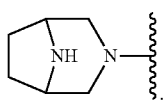

In some embodiments, ring G is

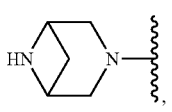

In some embodiments, ring G is

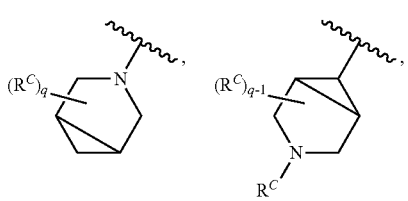

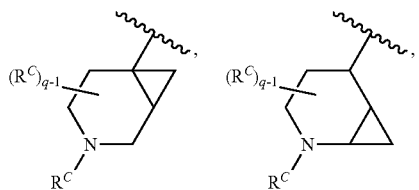

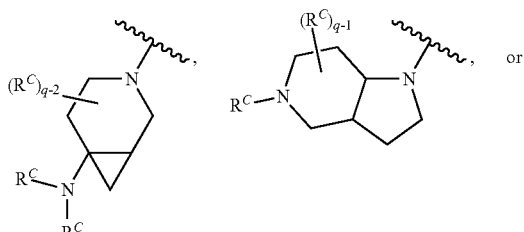

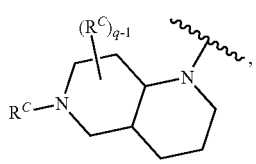

wherein each $R^C$ is independently selected from H, D, F, —CN, —OH, —OR$^1$, —SR$^1$, —S(=O)R$^1$, —S(=O)$_2$R$^1$, —N(R$^1$)$_2$, —CH$_2$—N(R$^1$)$_2$, —NHS(=O)$_2$R$^1$, —S(=O)$_2$N(R$^1$)$_2$, —C(=O)R$^1$, —OC(=O)R$^1$, —CO$_2$R$^1$, —OCO$_2$R$^1$, —C(=O)N(R$^1$)$_2$, —OC(=O)N(R$^1$)$_2$, —NR$^1$C(=O)N(R$^1$)$_2$, —NR$^1$C(=O)R$^1$, —NR$^1$C(=O)OR$^1$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, and substituted or unsubstituted C$_2$-C$_8$ heterocycloalkyl; and q is 0, 1, 2, 3, 4, 5, or 6.

In some embodiments, ring G is

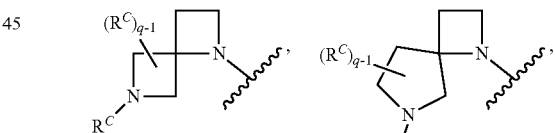

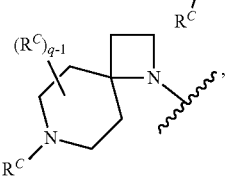

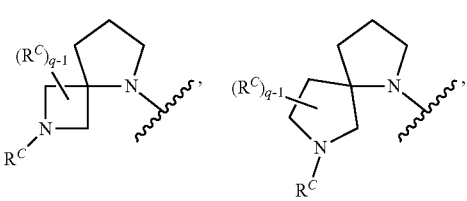

-continued

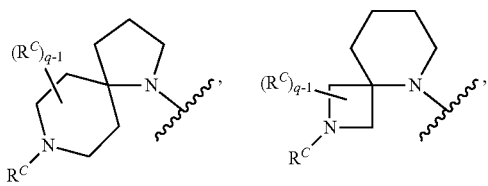

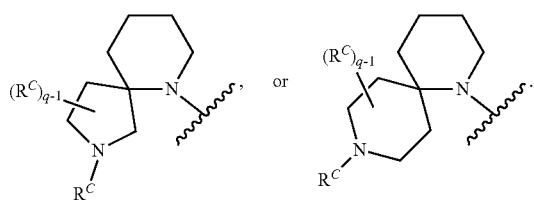

In some embodiments,

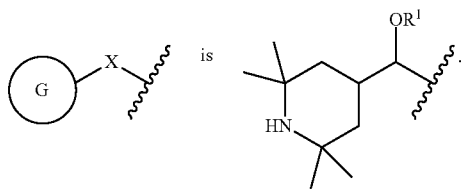

is

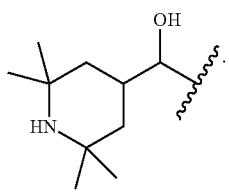 [SMILES: *C(O)C1CC(C)(C)NC(C)(C)C1]

In some embodiments,

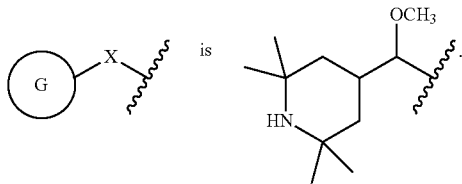

In some embodiments,

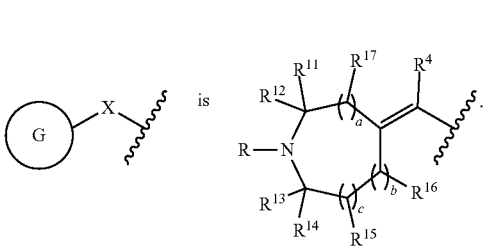

In some embodiments,

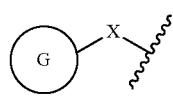

is

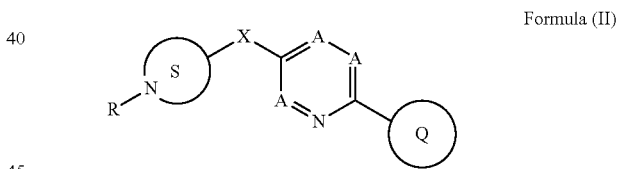

In some embodiments, a compound of Formula (I) is selected from a compound in Table 1A, Table 1B or Table 1C.

In one aspect, described herein is a compound that has the structure of Formula (II), or a pharmaceutically acceptable salt or solvate thereof:

Formula (II)

wherein,
each A is independently N or $CR^4$;
each $R^A$ is independently selected from H, D, halogen, —CN, —OH, —$OR^1$, =O, =N—$OR^1$, —$SR^1$, —S(=O)$R^1$, —S(=O)$_2R^1$, —N($R^1$)$_2$, —$NR^1$S(=O)(=$NR^1$)$R^2$, —$NR^1$S(=O)$_2R^2$, —S(=O)$_2$N($R^1$)$_2$, —C(=O)$R^1$, —OC(=O)$R^1$, —C(=O)$OR^1$, —OC(=O)$OR^1$, —C(=O)N($R^1$)$_2$, —OC(=O)N($R^1$)$_2$, —$NR^1$C(=O)$R^1$, —P(=O)($R^2$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, and substituted or unsubstituted monocyclic heteroaryl;
ring Q is monocyclic aryl, bicyclic aryl, monocyclic heteroaryl, or fused bicyclic heteroaryl;
X is —O—, —$NR^3$—, —$CR^4R$—, —C(=O)—, —C(=C($R^2$)$_2$)—, —S—, —S(=O)—, —S(=O)$_2$—, or —S(=O)(=$NR^1$)—; ring S is fused bicyclic heterocycle;
R is selected from the group consisting of H, a substituted or unsubstituted $C_{1-6}$ alkyl, substituted or unsubstituted $C_{1-6}$ fluoroalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, and substituted or unsubstituted heteroaryl, wherein alkyl is optionally substituted with hydroxy, amino, substituted or unsubstituted mono-$C_{1-6}$ alkylamino, or substituted or unsubstituted di-$C_{1-6}$ alkylamino;

each $R^1$ is independently H, D, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each $R^2$ is independently H, D, substituted or unsubstituted $C_1$-$C_6$ alkyl, substituted or unsubstituted $C_1$-$C_6$ haloalkyl, substituted or unsubstituted aryl, substituted or unsubstituted monocyclic heteroaryl, —$OR^1$, —$N(R^1)_2$, —$CH_2OR^1$, —$C(=O)OR^1$, —$OC(=O)R^1$, —$C(=O)N(R^1)_2$, or —$NR^1C(=O)R^1$;

$R^3$ is H, —$OR^1$, —$N(R^1)_2$, substituted or unsubstituted $C_1$-$C_6$ alkyl, —$CD_3$, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^4$ is H, D, F, —CN, —$OR^1$, —$SR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^5$ is H, D, F, —CN, —$OR^1$, —$SR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or $R^4$ and R taken in combination with the carbon atom to which they attach, form a substituted or unsubstituted $C_{3-8}$ cycloalkyl or a substituted or unsubstituted $C_{2-7}$ heterocycloalkyl; and wherein the compound of Formula (II) has a stereochemical purity of at least 80%.

For any and all of the embodiments, substituents are selected from among a subset of the listed alternatives. For example, in some embodiments, a is 0, 1, or 2. In other embodiments, a is 0. In some other embodiments, a is 1. In some other embodiments, a is 2.

In some embodiments,

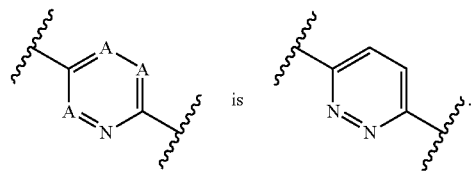 is 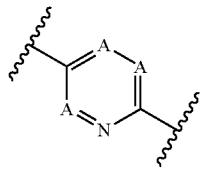.

In some embodiments

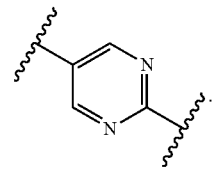 [SMILES: *c1cnc(*)nc1] is

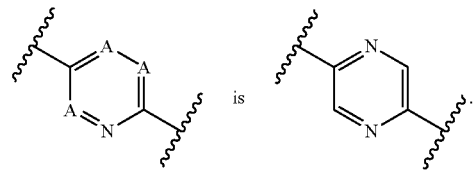

In some embodiments,

In some embodiments, X is —O—, —$NR^3$—, —S—, —$CR^4R^5$—, —C(=O)—, or —$C(=CR^2_2)$—. In some embodiments, X is —O—. In some embodiments, X is —$NR^3$—. In some embodiments, X is —S—. In some embodiments, X is —$CR^4R^5$—. In some embodiments, X is —C(=O)—. In some embodiments, X is —$C(=CR^2_2)$—.

In some embodiments, X is —$CH(CH_2OR^1)$— or —$CH(OR^1)$—. In some embodiments, X is —$CH(CH_2OR^1)$—. In some embodiments, X is —$CH(OR^1)$—.

In some embodiments, $R^3$ is H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl.

In some embodiments, $R^3$ is —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl.

In some embodiments, ring Q is substituted or unsubstituted monocyclic aryl. In some embodiments, ring Q is substituted monocyclic aryl. In some embodiments, ring Q is unsubstituted monocyclic aryl.

In some embodiments, ring Q is substituted phenyl. In some embodiments, ring Q is 2-hydroxy-phenyl which is substituted with: 0, 1, 2, or 3 substituents independently selected from $C_{1-6}$ alkyl, oxo, oxime, hydroxy, halo-$C_{1-6}$ alkyl, dihalo-$C_{1-6}$ alkyl, trihalo-$C_{1-6}$ alkyl, $C_{1-6}$ alkoxy, $C_{1-6}$ alkoxy-$C_{3-7}$ cycloalkyl, halo-$C_{1-6}$ alkoxy, dihalo-$C_{1-6}$ alkoxy, trihalo-$C_{1-6}$ alkoxy, hydroxy, cyano, halogen, amino, mono-$C_{1-6}$ alkylamino, di-$C_{1-6}$ alkylamino, heteroaryl, $C_{1-6}$ alkyl substituted with hydroxy, $C_{1-6}$ alkoxy substituted with aryl, amino, —C(=O)NH—$C_{1-6}$ alkyl-heteroaryl, —NHC(=O)—$C_{1-6}$ alkylheteroaryl, $C_{1-6}$ alkyl-C(=O)NH-heteroaryl, $C_{1-6}$ alkyl-NHC(=O)-heteroaryl, $C_{3-7}$ cycloalkyl, 5-7 membered cycloalkenyl, or 5, 6 or 9 membered heterocycle containing 1 or 2 heteroatoms independently, selected from S, O and N.

In some embodiments, ring Q is 2-hydroxy-phenyl which is substituted with two $C_{1-6}$ alkyl. In some embodiments, two $C_{1-6}$ alkyl groups can combine with the atoms to which they are bound to form a 5-6 membered ring.

In some embodiments, ring Q is 2-hydroxy-phenyl which is substituted with heteroaryl. In some embodiments, heteroaryl has 5, 6, 9, or 10 ring atoms, 1, 2 or 3 ring heteroatoms selected from N, O and S, and is substituted with 0, 1, or 2 substituents independently selected from oxo, hydroxy, nitro, halogen, $C_{1-6}$ alkyl, $C_{1-6}$ alkenyl, $C_{1-6}$ alkoxy, $C_{3-7}$ cycloalkyl, $C_{1-6}$ alkyl-OH, trihalo-$C_{1-6}$ alkyl, mono-$C_{1-6}$ alkylamino, di-$C_{1-6}$ alkylamino, —C(=O)NH$_2$, —NH$_2$, —NO$_2$, hydroxy-$C_{1-6}$ alkylamino, hydroxy-$C_{1-6}$ alkyl, 4-7 membered heterocycle-$C_{1-6}$ alkyl, amino-$C_{1-6}$ alkyl, mono-$C_{1-6}$ alkylamino-$C_{1-6}$ alkyl, and di-$C_{1-6}$ alkylamino-$C_{1-6}$ alkyl.

In some embodiments, ring Q is

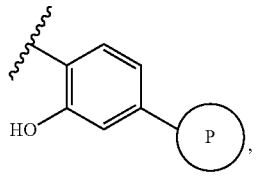

wherein ring P is aryl or heteroaryl. In some embodiments, ring Q is

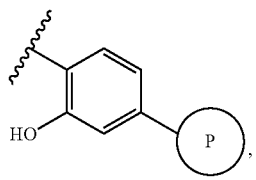

wherein ring P is aryl. In some embodiments, ring Q is

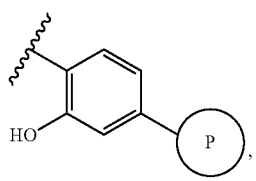

wherein ring P is heteroaryl In some embodiments, the heteroaryl is selected from the group consisting of:

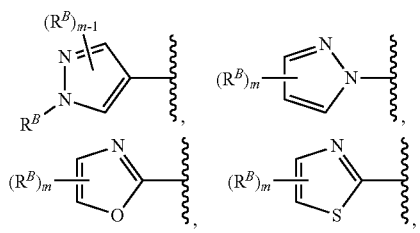

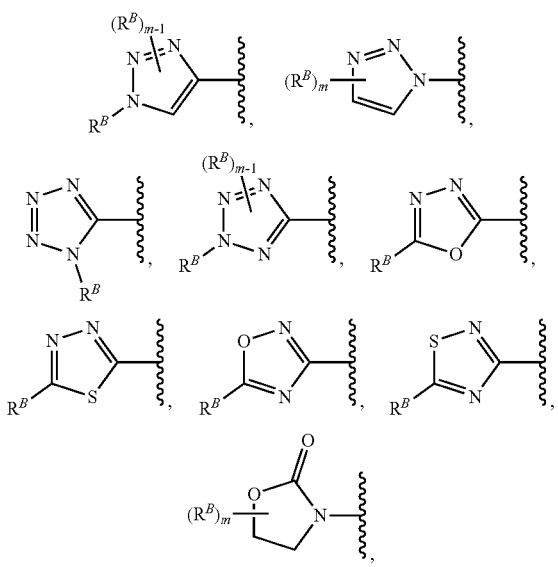

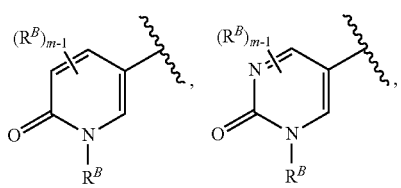

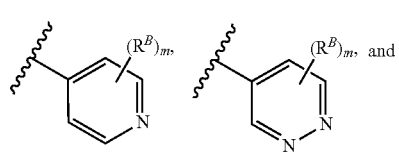

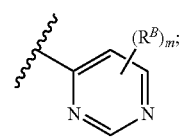

wherein each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is
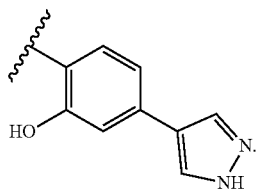 [SMILES: *c1ccc(-c2cn[nH]c2)cc1O]
In some embodiments, ring Q is
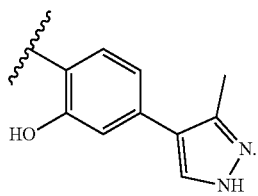
In some embodiments, ring Q is
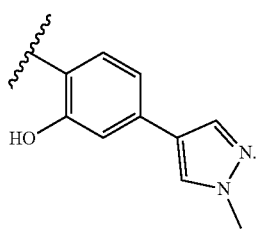 [SMILES: *c1ccc(-c2cnn(C)c2)cc1O]
In some embodiments, ring Q is
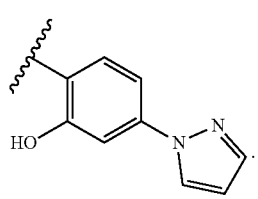 [SMILES: *c1ccc(-n2cccn2)cc1O]
In some embodiments, ring Q is
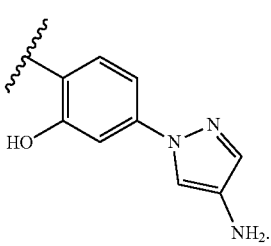 [SMILES: *c1ccc(-n2cc(N)cn2)cc1O]
In some embodiments, ring Q is
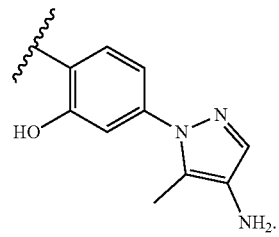 [SMILES: *c1ccc(-n2ncc(N)c2C)cc1O]
In some embodiments, ring Q is
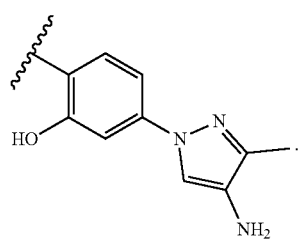 [SMILES: *c1ccc(-n2cc(N)c(C)n2)cc1O]
In some embodiments, ring Q is
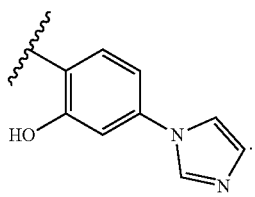 [SMILES: *c1ccc(-n2ccnc2)cc1O]
In some embodiments, ring Q is
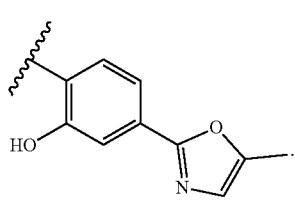 [SMILES: *c1ccc(-c2ncc(C)o2)cc1O]

In some embodiments, ring Q
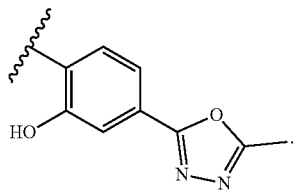 [SMILES: *c1ccc(-c2nnc(C)o2)cc1O]
In some embodiments, ring Q is
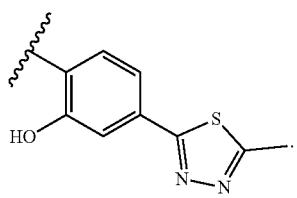
In some embodiments, ring Q is
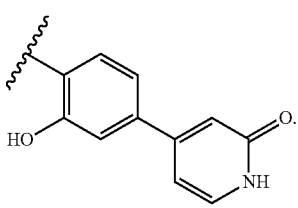 [SMILES: *c1ccc(-c2cc[nH]c(=O)c2)cc1O]
In some embodiments, ring Q is
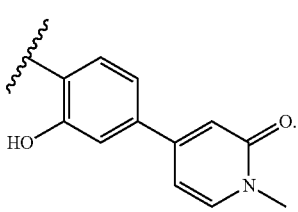 [SMILES: *c1ccc(-c2ccn(C)c(=O)c2)cc1O]
In some embodiments, ring Q is
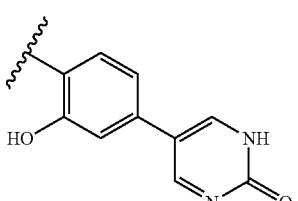
In some embodiments, ring Q is
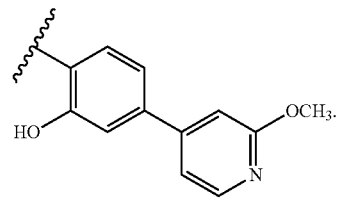
In some embodiments, ring Q is
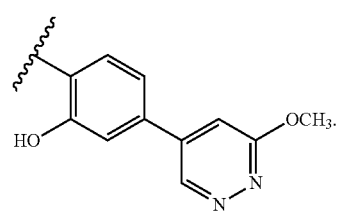
In some embodiments, ring Q is
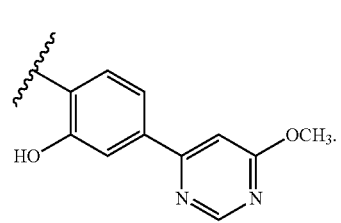
In some embodiments, ring Q is
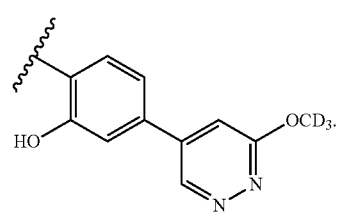
In some embodiments, ring Q is
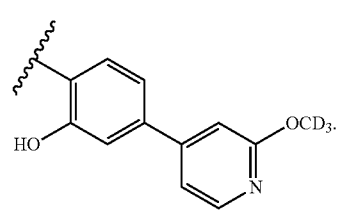

In some embodiments, ring Q is

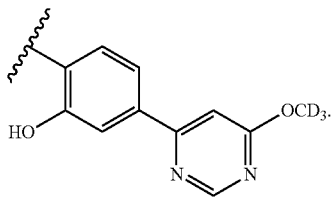

In some embodiments, ring Q is 2-naphthyl optionally substituted at the 3 position with hydroxy and additionally substituted with 0, 1, or 2 substituents selected from hydroxy, cyano, halogen, $C_{1-6}$ alkyl, $C_{2-6}$ alkenyl, $C_{1-6}$ alkoxy, wherein the alkoxy is unsubstituted or substituted with hydroxy, $C_{1-6}$ alkoxy, amino, —NHC(=O)—$C_{1-6}$ alkyl, —NHC(=O)—$C_{1-6}$ alkyl, $C_{1-6}$ alkylene-4-7 membered heterocycle, 4-7 membered heterocycle, mono-$C_{1-6}$ alkylamino, and di-$C_{1-6}$ alkylamino.

In some embodiments, ring Q is

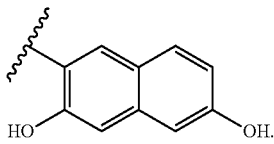 [SMILES: *c1cc2ccc(O)cc2cc1O]

In some embodiments, ring Q is

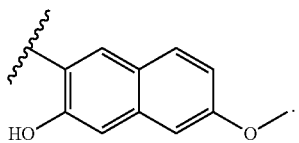 [SMILES: *c1cc2ccc(OC)cc2cc1O]

In some embodiments, ring Q is

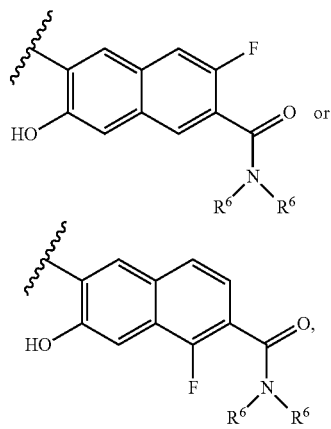

and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, ring Q is monocyclic heteroaryl or fused bicyclic heteroaryl.

In some embodiments, ring Q is a 5 or 6 membered monocyclic heteroaryl having 1-4 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from cyano, $C_{1-6}$ alkyl, mono-$C_{1-6}$ alkylamino, di-$C_{1-6}$ alkylamino, hydroxy-$C_{1-6}$ alkylamino, hydroxy-$C_{1-6}$ alkyl, amino-$C_1$-alkyl and mono-$C_{1-6}$ alkylamino-$C_{1-6}$ alkyl, and di-$C_{1-6}$ alkylamino-$C_{1-6}$ alkyl.

In some embodiments, ring Q is a 5 membered monocyclic heteroaryl selected from the group consisting of:

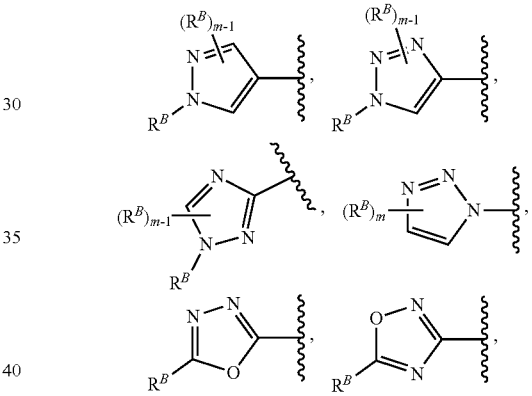

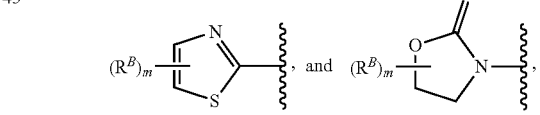

wherein each $R^B$ is independently selected from cyano, halogen, hydroxy, substituted or unsubstituted $C_{1-6}$ alkyl, —$OCH_3$, —$OCD_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a 6 membered monocyclic heteroaryl selected from the group consisting of:

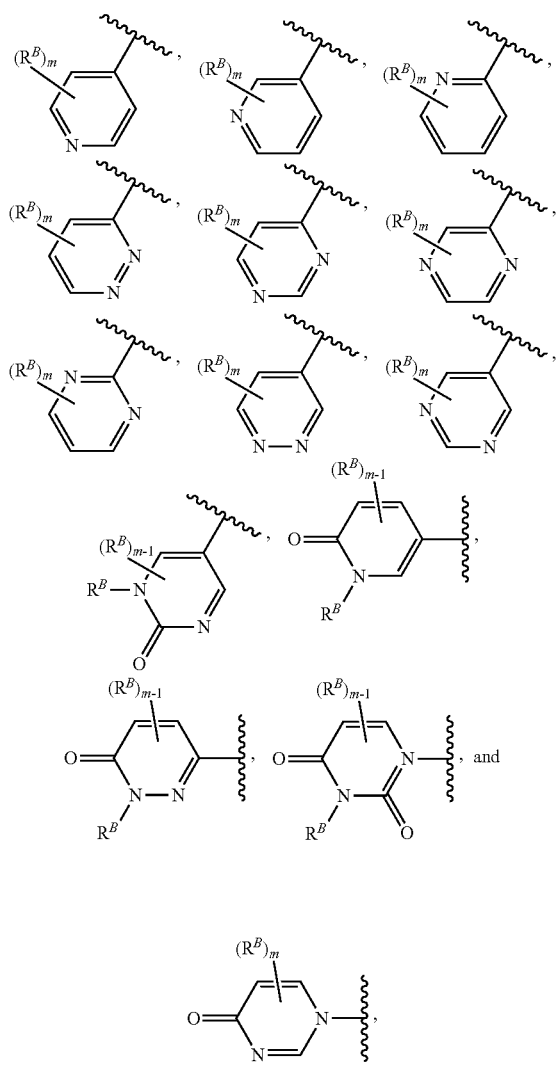

wherein
each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_2$-s heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a fused bicyclic heteroaryl having 8 to 10 ring atoms, 1, 2, or 3 ring heteroatoms independently selected from N, O or S, and which is substituted with 0, 1, or 2 substituents independently selected from cyano, oxime, halogen, hydroxy, $C_{1-6}$ alkyl, $C_{24}$ alkenyl, $C_{24}$ alkynyl, $C_{1-6}$ alkoxy, $C_{1-6}$ alkoxy substituted with hydroxy, amino, mono-$C_{1-6}$ alkylamino, and di-$C_{1-6}$ alkylamino.

In some embodiments, ring Q is a 6-5 fused heteroaryl, 6-6 fused heteroaryl, 5-6 fused heteroaryl, 5-5 fused heteroaryl, 7-5 fused heteroaryl, or 5-7 fused heteroaryl.

In some embodiments, ring Q is a 6-5 fused heteroaryl, 6-6 fused heteroaryl, or 5-6 fused heteroaryl, selected from the group consisting of:

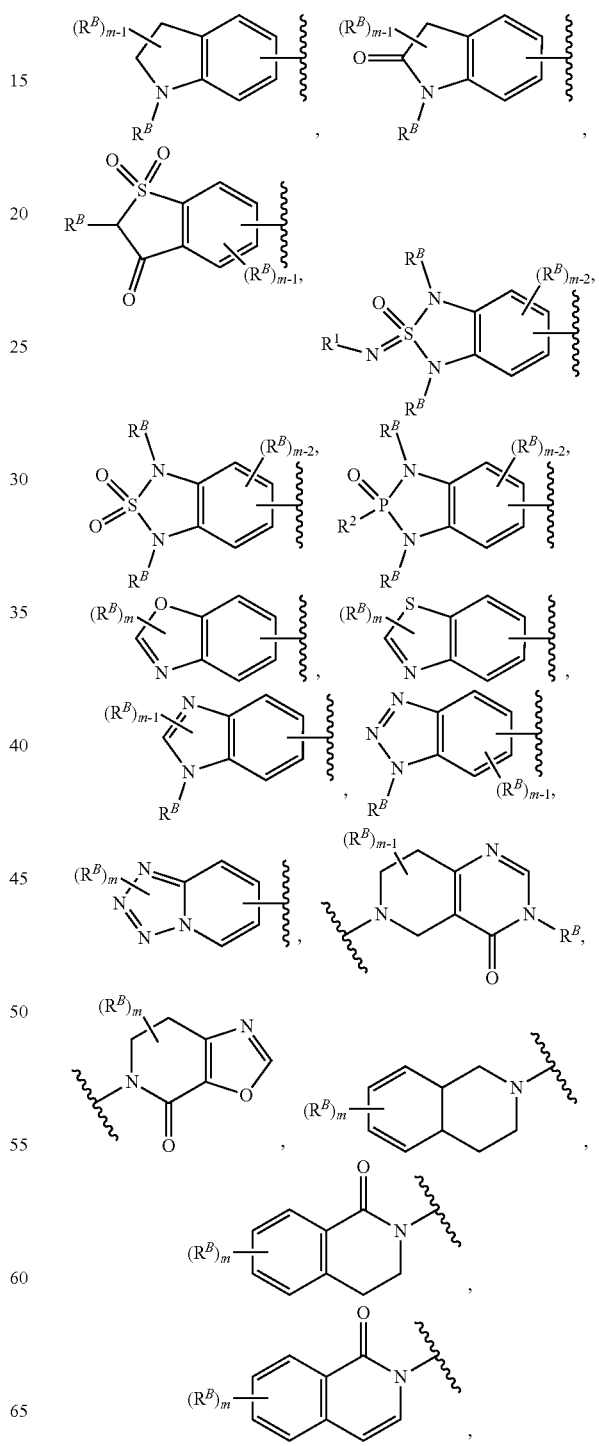

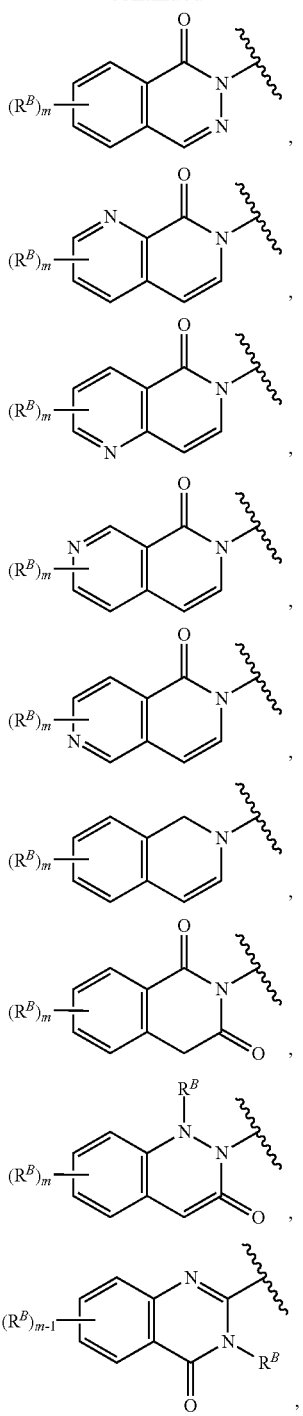

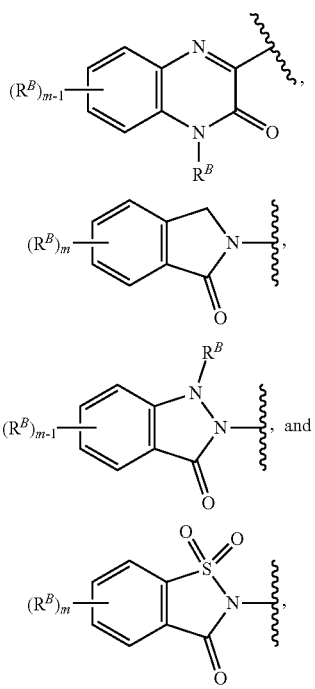

wherein each $R^B$ is independently selected from cyano, halogen, hydroxy, substituted or unsubstituted $C_{1-6}$alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 1, 2, or 3.

In some embodiments, ring Q is

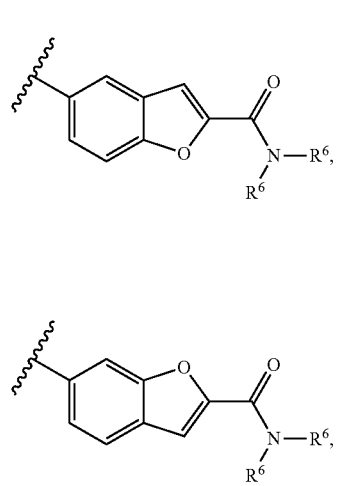

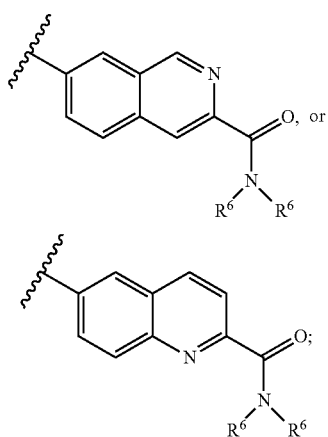

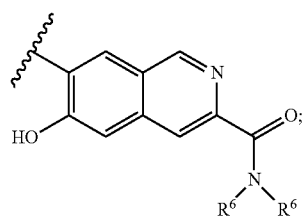

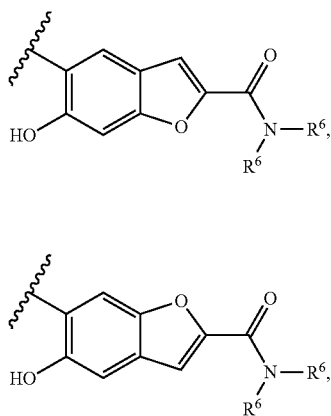

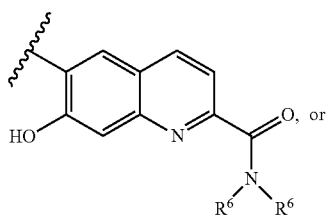

and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, ring Q is and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, X is —$NR^3$—.

In some embodiments, $R^3$ is —$OR^1$. In some embodiments, $R^3$ is —$OCH_3$. In some embodiments, $R^3$ is —$OCH_2CH_3$. In some embodiments, $R^3$ is —$OCH_2CH_2CH_3$. In some embodiments, $R^3$ is —$OCH(CH_3)_2$.

In some embodiments, $R^3$ is —$CD_3$.

In some embodiments, $R^3$ is substituted or unsubstituted $C_1$-$C_6$ haloalkyl. In some embodiments, $R^3$ is $CF_3$. In some embodiments, $R^3$ is —$CH_2CH_2F$. In some embodiments, $R^3$ is —$CH_2CH_2CH_2F$. In some embodiments, $R^3$ is —$CH_2CF_3$. In some embodiments, $R^3$ is —$CH_2CH_2CF_3$.

In some embodiments, $R^3$ is substituted or unsubstituted $C_1$-$C_6$ heteroalkyl. In some embodiments, $R^3$ is —$OCH_2CH_2OCH_3$ or —$OCH_2CH_2OCF_3$. In some embodiments, $R^3$ is —$CH_2CH_2OCH_3$.

In some embodiments, $R^3$ is substituted or unsubstituted $C_3$-$C_8$ cycloalkyl. In some embodiments, $R^3$ is cyclopropyl, cyclobutyl, cyclopentyl, cyclohexyl, cycloheptyl, or cyclooctyl.

In some embodiments, $R^3$ is cyclopentenyl, cyclohexenyl, cycloheptenyl, or cyclooctenyl.

In some embodiments,

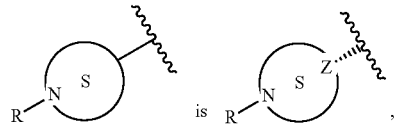

wherein Z is $CR^7$, and $R^7$ is H, D, substituted or unsubstituted $C_1$-$C_6$ alkyl, substituted or unsubstituted $C_1$-$C_6$ haloalkyl, or —$CH_2OR^1$.

In some embodiments,

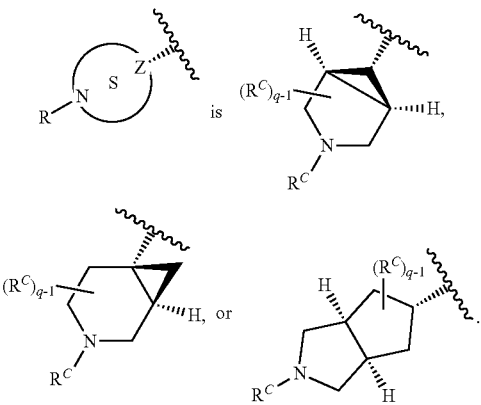

In some embodiments,

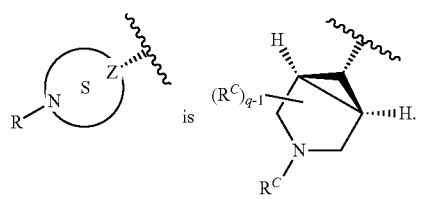

In some embodiments,

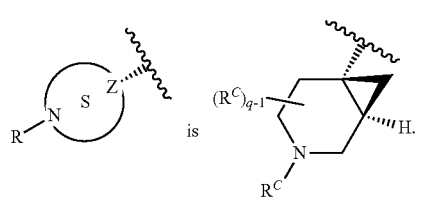

In some embodiments,

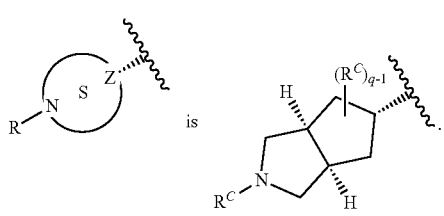

In some embodiments,

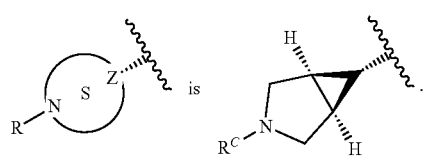

In some embodiments,

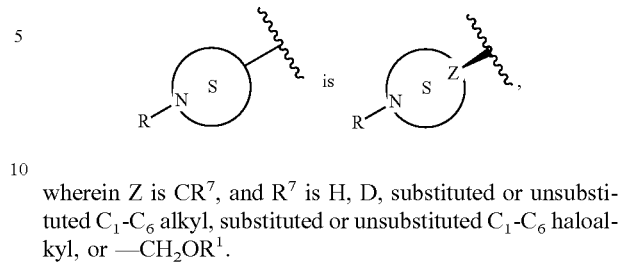

wherein Z is $CR^7$, and $R^7$ is H, D, substituted or unsubstituted $C_1$-$C_6$ alkyl, substituted or unsubstituted $C_1$-$C_6$ haloalkyl, or —$CH_2OR^1$.

In some embodiments,

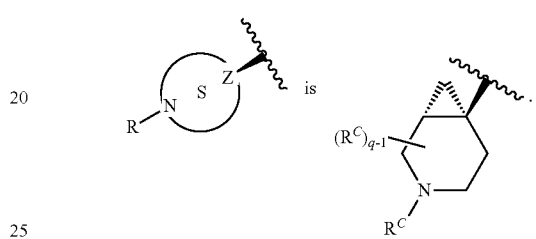

In some embodiments,

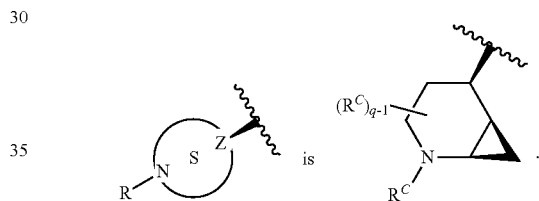

In some embodiments,

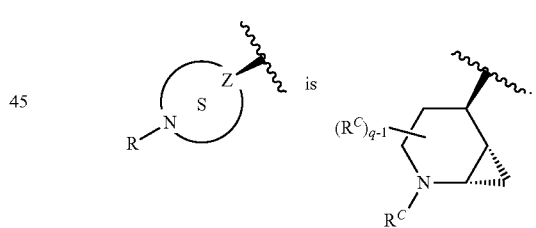

In some embodiments,

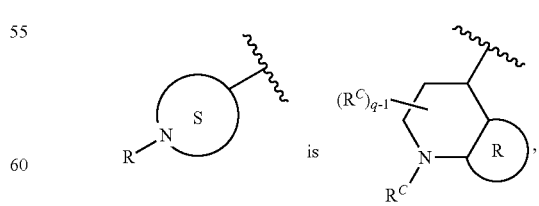

wherein ring R is substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl.

In some embodiments,

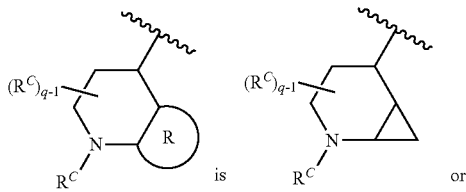

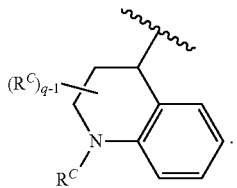

In some embodiments,

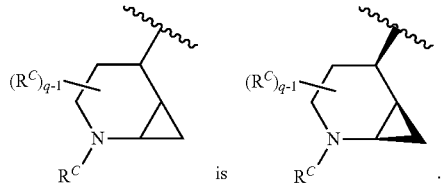

In some embodiments,

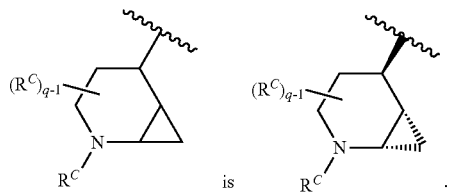

In some embodiments,

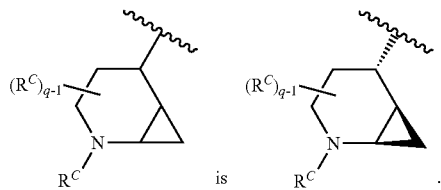

In some embodiments,

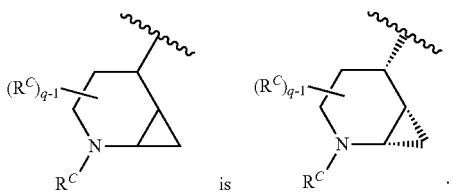

In some embodiments,

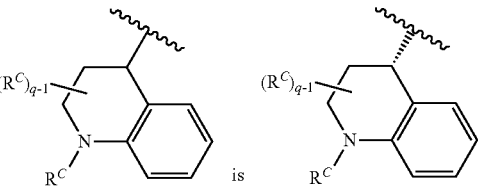

In some embodiments,

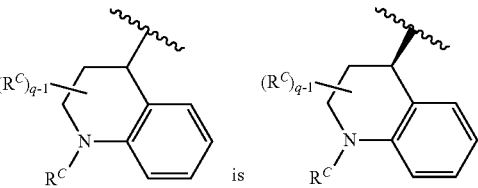

In some embodiments, the compound of Formula (II) is not racemic. In some preferred embodiments, the compound of Formula (II) is substantially free of other isomers. In some preferred embodiments, the compound of Formula (V) is a single isomer substantially free of other isomers. In some preferred embodiments, the compound of Formula (II) comprises 25% or less of other isomers. In some preferred embodiments, the compound of Formula (II) comprises 20% or less of other isomers. In some preferred embodiments, the compound of Formula (II) comprises 15% or less of other isomers. In some preferred embodiments, the compound of Formula (II) comprises 10% or less of other isomers. In some preferred embodiments, the compound of Formula (II) comprises 5% or less of other isomers. In some preferred embodiments, the compound of Formula (II) comprises 1% or less of other isomers.

In some preferred embodiments, the compound of Formula (II) has a stereochemical purity of at least 75%. In some preferred embodiments, the compound of Formula (II) has a stereochemical purity of at least 80%. In some preferred embodiments, the compound of Formula (II) has a stereochemical purity of at least 85%. In some preferred embodiments, the compound of Formula (II) has a stereochemical purity of at least 90%. In some preferred embodiments, the compound of Formula (II) has a stereochemical purity of at least 95%. In some preferred embodiments, the compound of Formula (II) has a stereochemical purity of at least 96%. In some preferred embodiments, the compound of Formula (II) has a stereochemical purity of at least 97%. In some preferred embodiments, the compound of Formula (II) has a stereochemical purity of at least 98%. In some preferred embodiments, the compound of Formula (II) has a stereochemical purity of at least 99%.

In some preferred embodiments, the asymmetric carbon atom ($CR^7$) of the compound of Formula (I) is present in enantiomerically enriched form. In certain embodiments, the asymmetric carbon atom ($CR^7$) of the compound of Formula (II) has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (S)- or (R)-configuration.

In some embodiments, a compound of Formula (II) is selected from a compound in Table 1A, Table 1B or Table 1C.

Any combination of the groups described above for the various variables is contemplated herein. Throughout the specification, groups and substituents thereof are chosen by one skilled in the field to provide stable moieties and compounds.

In one aspect, described herein is a compound that has the structure of Formula (III), or a pharmaceutically acceptable salt or solvate thereof:

Formula (III)

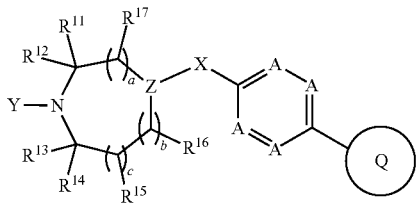

wherein, each A is independently N or $CR^A$;

each $R^A$ is independently selected from H, D, halogen, —CN, —OH, —$OR^1$, =O, =N—$OR^1$, —$SR^1$, —S(=O) $R^1$, —S(=O)$_2R^1$, —N($R^1$)$_2$, —$NR^1$S(=O)(=$NR^1$)$R^2$, —$NR^1$S(=O)$_2R^2$, —S(=O)$_2$N($R^1$)$_2$, —C(=O)$R^1$, —OC(=O)$R^1$, —C(=O)$OR^1$, —OC(=O)$OR^1$, —C(=O)N($R^1$)$_2$, —OC(=O)N($R^1$)$_2$, —$NR^1$C(=O)$R^1$, —P(=O)($R^2$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, and substituted or unsubstituted monocyclic heteroaryl;

ring Q is substituted or unsubstituted monocyclic aryl, substituted or unsubstituted bicyclic aryl, substituted or unsubstituted monocyclic heteroaryl, or substituted or unsubstituted fused bicyclic heteroaryl;

X is —$NR^3$—, —$CR^4R$—, —C(=O)—, —O—, —S—, —S(=O)—, —S(=O)$_2$—, or —S(=O)(=$NR^1$)—; each $R^1$ is independently H, D, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

each $R^2$ is independently H, D, substituted or unsubstituted $C_1$-$C_6$ alkyl, substituted or unsubstituted $C_1$-$C_6$ haloalkyl, substituted or unsubstituted aryl, substituted or unsubstituted monocyclic heteroaryl, —$OR^1$, —N($R^1$)$_2$, —$CH_2OR^1$, —C(=O)$OR^1$, —OC(=O)$R^1$, —C(=O)N($R^1$)$_2$, or —$NR^1$C(=O)$R^1$;

$R^3$ is —$OR^1$, —N($R^1$)$_2$, substituted or unsubstituted $C_1$-$C_6$ alkyl, —$CD_3$, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^4$ is H, D, F, —CN, —$OR^1$, —$SR^1$, —N($R^1$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^5$ is H, D, F, —CN, —$OR^1$, —$SR^1$, —N($R^1$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

Z is N or $CR^7$; and $R^7$ is H, D, substituted or unsubstituted $C_1$-$C_6$ alkyl, substituted or unsubstituted $C_1$-$C_6$ haloalkyl or —$CH_2OR^1$;

a, b, and c are each independently selected from 0, 1, or 2;

$R^{11}$, $R^{12}$, $R^{13}$ and $R^{14}$ are each independently selected from the group consisting of H, F, $OR^1$, substituted or unsubstituted $C_{1-6}$ alkyl, a substituted or unsubstituted $C_{1-6}$ fluoroalkyl, substituted or unsubstituted $C_1$-$C_6$ heteroalkyl, wherein alkyl is optionally substituted with hydroxy, amino, methoxy, substituted or unsubstituted mono-$C_{1-6}$ alkylamino or substituted or unsubstituted di-$C_{1-6}$ alkylamino;

$R^{15}$, $R^{16}$, and $R^{17}$ are each independently selected from H, F, $OR^1$, and substituted or unsubstituted $C_{1-6}$ alkyl; or $R^{11}$ and $R^{13}$, taken in combination form a bond or substituted or unsubstituted $C_{1-3}$ alkylene group; or $R^{11}$ and $R^{15}$, taken in combination form a substituted or unsubstituted $C_{1-3}$ alkylene group; or $R^{11}$ and $R^{17}$, taken in combination form a substituted or unsubstituted $C_{1-3}$ alkylene group; or $R^{16}$ and $R^{17}$, taken in combination form a bond or substituted or unsubstituted $C_{1-3}$ alkylene group; or $R^{13}$ and $R^{14}$, taken in combination with the carbon atom to which they attach, form a spirocyclic $C_{3-8}$ cycloalkyl; or when Z is $CR^7$, then $R^{16}$ and $R^7$, are optionally taken together with the intervening atoms to which they are attached to form a double bond or a substituted or unsubstituted $C_{1-3}$ alkylene group; or when Z is $CR^7$ and X is $NR^3$, then $R^3$ and $R^7$ are optionally taken together with the intervening atoms to which they are attached to form a substituted or unsubstituted $C_{1-3}$ alkylene group; or when Z is $CR^7$ and X is $NR^3$, then $R^3$ and $R^{16}$ are optionally taken together with the intervening atoms to which they are attached to form a substituted or unsubstituted $C_{1-3}$ alkylene group; or when Z is $CR^7$ and X is —$CR^4R^5$—, then $R^7$ and R are optionally taken in combination to form a double bond; and Y is W-L-V, wherein W is —C(=O)—, —S(=O)—, —S(=O)$_2$—, —S(=O)(=$NR^1$)—, —C(=O)O—, —C(=O)$NR^1$—, —S(=O)$NR^1$—, or —S(=O)$_2NR^1$—;

L is absent, substituted or unsubstituted $C_1$-$C_4$alkylene, substituted or unsubstituted $C_2$-$C_4$alkenylene, substituted or unsubstituted $C_2$-$C_4$alkynylene, substituted or unsubstituted $C_1$-$C_4$ heteroalkylene, substituted or unsubstituted $C_1$-$C_4$cycloalkylene, substituted or unsubstituted $C_1$-$C_4$ heterocycloalkylene, substituted or unsubstituted arylene, or substituted or unsubstituted monocyclic heteroarylene, or a combination thereof, and V is —CN, —$OR^1$, —$SR^1$, —S(=O)$R^1$, —S(=O)$_2R^1$, —N($R^1$)$_2$, —$NR^1$S(=O)(=$NR^1$)$R^2$, —$NR^1$S(=O)$_2R^2$, —S(=O)$_2$N($R^1$)$_2$, —C(=O)$R^1$, —OC(=O)$R^1$, —C(=O)$OR^1$, —OC(=O)$OR^1$, —C(=O)N($R^1$)$_2$, —OC(=O)N($R^1$)$_2$, —$NR^1$C(=O)$R^1$, substituted or unsubstituted $C_1$-$C_4$alkyl, substituted or unsubstituted $C_1$-$C_4$fluoroalkyl, substituted or unsubstituted $C_1$-$C_4$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted monocyclic heteroaryl.

For any and all of the embodiments, substituents are selected from among a subset of the listed alternatives. For example, in some embodiments, a is 0, 1, or 2. In other embodiments, a is 0. In some other embodiments, a is 1. In some other embodiments, a is 2.

In some other embodiments,

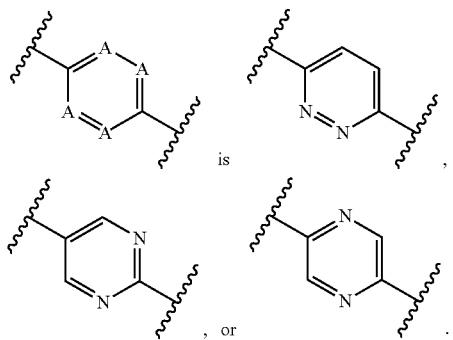

is

In some other embodiments,

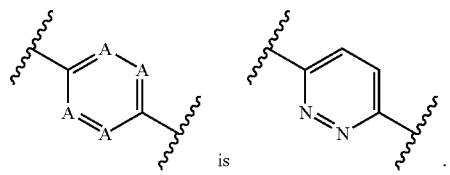

In some other embodiments, is

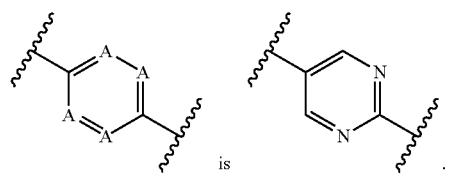

In some other embodiments,

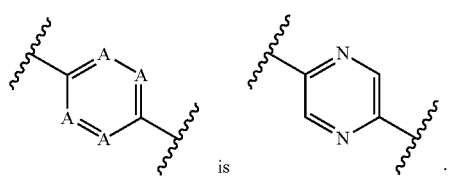

In some other embodiments,

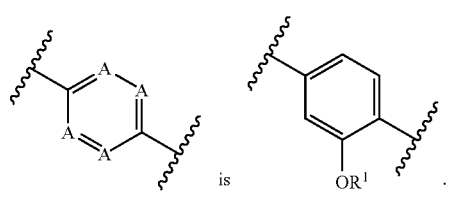

In some embodiments, Z is N. In some embodiments, Z is $CR^7$.

In some embodiments, X is —O—, —$NR^3$—, —S—, —$CR^4R^5$—, —C(=O)—, —C(=C($R^2$)$_2$)—, —S(=O)—, —S(=O)$_2$—, or —S(=O)(=$NR^1$)—. In some embodiments, X is —O—. In some embodiments, X is —$NR^3$—. In some embodiments, X is —S—. In some embodiments, X is —$CR^4R^5$—. In some embodiments, X is —C(=O)—. In some embodiments, X is —C(=C($R^2$)$_2$)—. In some embodiments, X is —S(=O)—. In some embodiments, X is —S(=O)$_2$—. In some embodiments, X is —S(=O)(=$NR^1$)—.

In some embodiments, X is —CH(CH$_2$O$R^1$)— or —CH(O$R^1$)—. In some embodiments, X is —CH(CH$_2$O$R^1$)—. In some embodiments, X is —CH(O$R^1$)—.

In some embodiments, $R^3$ is H, —O$R^1$, —N($R^1$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl.

In some embodiments, $R^3$ is —O$R^1$, —N($R^1$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, or substituted or unsubstituted $C_2$-$C_7$ heterocycloalkyl.

In some embodiments, ring Q is substituted or unsubstituted monocyclic aryl. In some embodiments, ring Q is substituted monocyclic aryl. In some embodiments, ring Q is unsubstituted monocyclic aryl.

In some embodiments, ring Q is substituted phenyl. In some embodiments, ring Q is 2-hydroxy-phenyl which is substituted with: 0, 1, 2, or 3 substituents independently selected from $C_{1-6}$ alkyl, oxo, oxime, hydroxy, halo-$C_{1-6}$ alkyl, dihalo-$C_{1-6}$ alkyl, trihalo-$C_{1-6}$ alkyl, $C_{1-6}$ alkoxy, $C_{1-6}$ alkoxy-$C_{3-7}$ cycloalkyl, halo-$C_{1-6}$ alkoxy, dihalo-$C_{1-6}$ alkoxy, trihalo-$C_{1-6}$ alkoxy, hydroxy, cyano, halogen, amino, mono-$C_{1-6}$ alkylamino, di-$C_{1-6}$ alkylamino, heteroaryl, $C_{1-6}$ alkyl substituted with hydroxy, $C_{1-6}$ alkoxy substituted with aryl, amino, —C(=O)NH—$C_{1-6}$ alkyl-heteroaryl, —NHC(=O)—$C_{1-6}$ alkylheteroaryl, $C_{1-6}$ alkyl-C(=O)NH-heteroaryl, $C_{1-6}$ alkyl-NHC(=O)-heteroaryl, $C_{3-7}$ cycloalkyl, 5-7 membered cycloalkenyl, or 5, 6 or 9 membered heterocycle containing 1 or 2 heteroatoms independently, selected from S, O and N.

In some embodiments, ring Q is 2-hydroxy-phenyl which is substituted with two $C_{1-6}$ alkyl. In some embodiments, two $C_{1-6}$ alkyl groups can combine with the atoms to which they are bound to form a 5-6 membered ring.

In some embodiments, ring Q is 2-hydroxy-phenyl which is substituted with heteroaryl. In some embodiments, heteroaryl has 5, 6, 9, or 10 ring atoms, 1, 2 or 3 ring heteroatoms selected from N, O and S, and is substituted with 0, 1, or 2 substituents independently selected from oxo, hydroxy, nitro, halogen, $C_{1-6}$ alkyl, $C_{1-6}$ alkenyl, $C_{1-6}$ alkoxy, $C_{3-7}$ cycloalkyl, $C_{1-6}$ alkyl-OH, trihalo-$C_{1-6}$ alkyl, mono-$C_{1-6}$ alkylamino, di-$C_{1-6}$ alkylamino, —C(=O)NH$_2$, —NH$_2$, —NO$_2$, hydroxy-$C_{1-6}$ alkylamino, hydroxy-$C_{1-6}$ alkyl, 4-7 membered heterocycle-$C_{1-6}$ alkyl, amino-$C_{1-6}$ alkyl, mono-$C_{1-6}$ alkylamino-$C_{1-6}$ alkyl, and di-$C_{1-6}$ alkylamino-$C_{1-6}$ alkyl.

In some embodiments, ring Q is

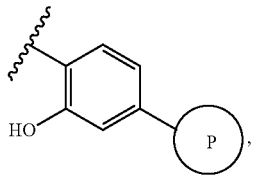

wherein ring P is aryl or heteroaryl. In some embodiments, ring Q is

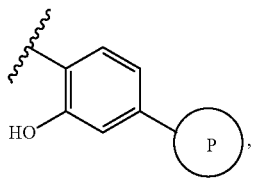

wherein ring P is aryl. In some embodiments, ring Q is

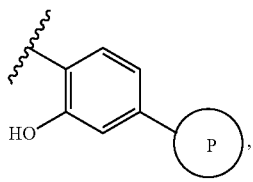

wherein ring P is heteroaryl.

In some embodiments, ring Q is

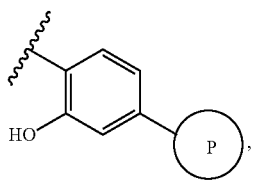

wherein ring P is heteroaryl, wherein the heteroaryl is selected from the group consisting of:

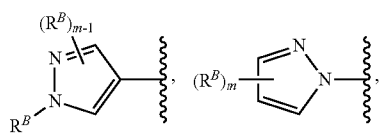

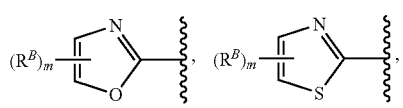

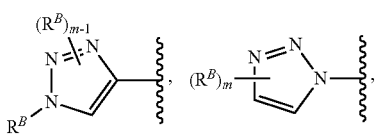

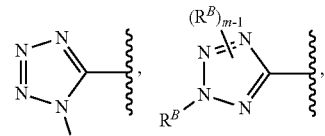

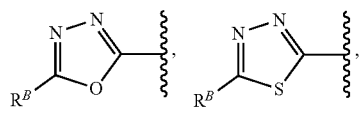

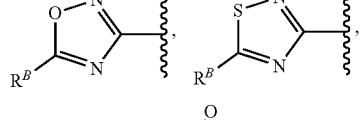

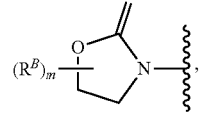

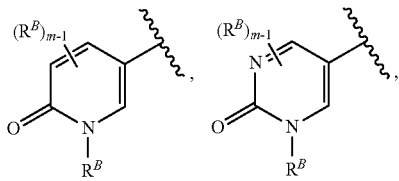

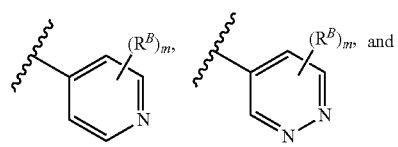

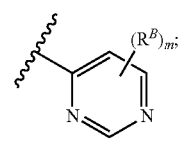

wherein each $R^B$ is independently selected from cyano, halogen, hydroxy, substituted or unsubstituted $C_{1-6}$ alkyl, —$OCH_3$, $OCD_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is
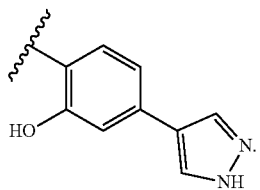 [SMILES: *c1ccc(-c2cn[nH]c2)cc1O]
In some embodiments, ring Q is
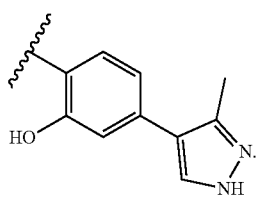
In some embodiments, ring Q is
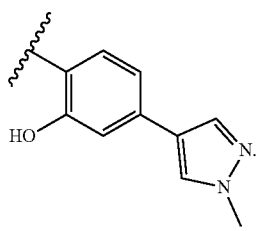 [SMILES: *c1ccc(-c2cnn(C)c2)cc1O]
In some embodiments, ring Q is
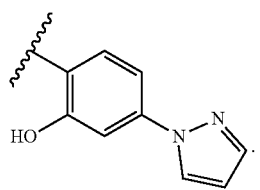 [SMILES: *c1ccc(-n2cccn2)cc1O]
In some embodiments, ring Q is
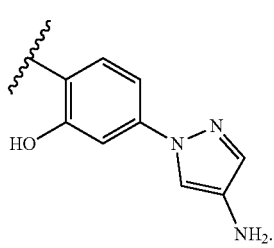 [SMILES: *c1ccc(-n2cc(N)cn2)cc1O]
In some embodiments, ring Q is
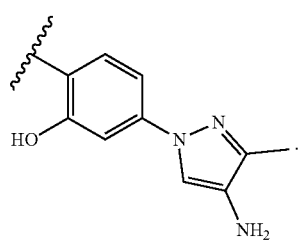 [SMILES: *c1ccc(-n2cc(N)c(C)n2)cc1O]
In some embodiments, ring Q is
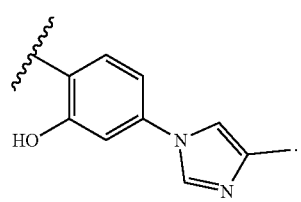 [SMILES: *c1ccc(-n2cnc(C)c2)cc1O]
In some embodiments, ring Q
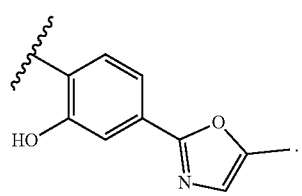
In some embodiments, ring Q is
In some embodiments, ring Q In some embodiments, ring Q is
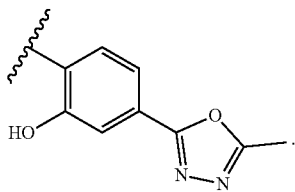 [SMILES: *c1ccc(-c2nnc(C)o2)cc1O]
In some embodiments, ring Q is
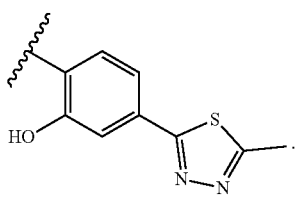 [SMILES: *c1ccc(-c2nnc(C)s2)cc1O]
In some embodiments, ring Q is
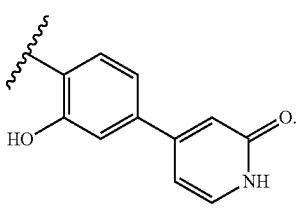 [SMILES: *c1ccc(-c2cc[nH]c(=O)c2)cc1O]
In some embodiments, ring Q is
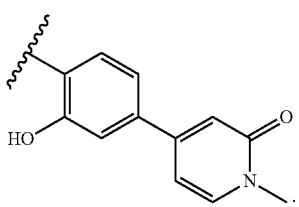
In some embodiments, ring Q is
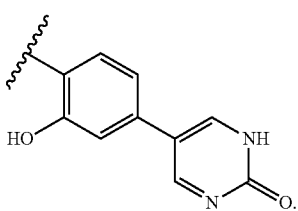 [SMILES: *c1ccc(-c2cnc(=O)[nH]c2)cc1O]
In some embodiments, ring Q is
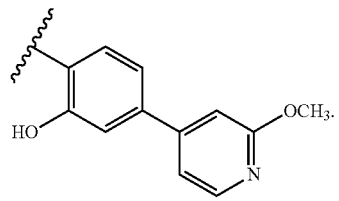
In some embodiments, rig Q is
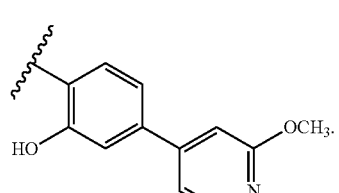
In some embodiments, ring Q is
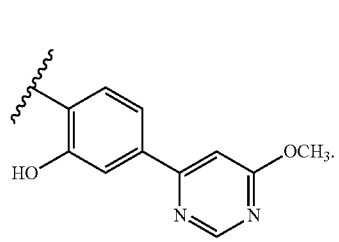
In some embodiments, ring Q is
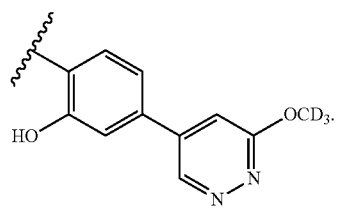
In some embodiments, ring Q is
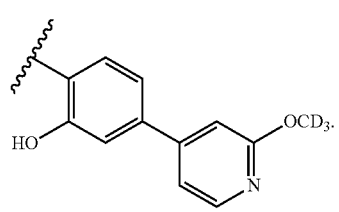

In some embodiments, ring Q is

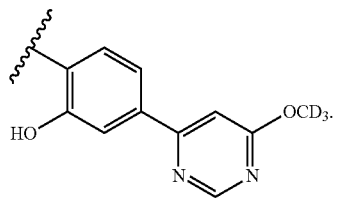

In some embodiments, ring Q is 2-naphthyl optionally substituted at the 3 position with hydroxy and additionally substituted with 0, 1, or 2 substituents selected from hydroxy, cyano, halogen, $C_{1-6}$ alkyl, $C_{2-6}$ alkenyl, $C_{1-6}$ alkoxy, wherein the alkoxy is unsubstituted or substituted with hydroxy, $C_{1-6}$ alkoxy, amino, —NHC(=O)—$C_{1-6}$ alkyl, —NHC(=O)—$C_{1-6}$ alkyl, $C_{1-6}$ alkylene-4-7 membered heterocycle, 4-7 membered heterocycle, mono-$C_{1-6}$ alkylamino, and di-$C_{1-6}$ alkylamino.

In some embodiments, ring Q is

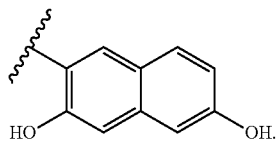 [SMILES: *c1cc2ccc(O)cc2cc1O]

In some embodiments, ring Q is

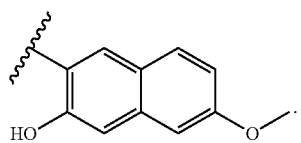 [SMILES: *c1cc2ccc(OC)cc2cc1O]

In some embodiments, ring Q is

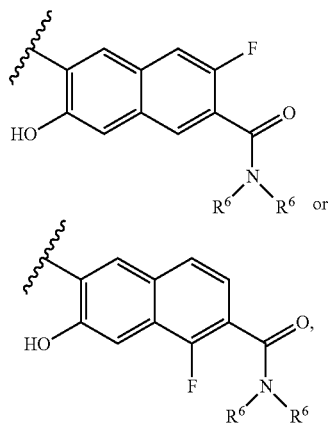

and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, ring Q is monocyclic heteroaryl or fused bicyclic heteroaryl.

In some embodiments, ring Q is a 5 or 6 membered monocyclic heteroaryl having 1-4 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from cyano, $C_{1-6}$ alkyl, mono-$C_{1-6}$ alkylamino, di-$C_{1-6}$ alkylamino, hydroxy-$C_{1-6}$ alkylamino, hydroxy-$C_{1-6}$ alkyl, amino-$C_{1-6}$ alkyl and mono-$C_{1-6}$ alkylamino-$C_{1-6}$ alkyl, and di-$C_{1-6}$ alkylamino-$C_{1-6}$ alkyl.

In some embodiments, ring Q is a 5 membered monocyclic heteroaryl selected from the group consisting of:

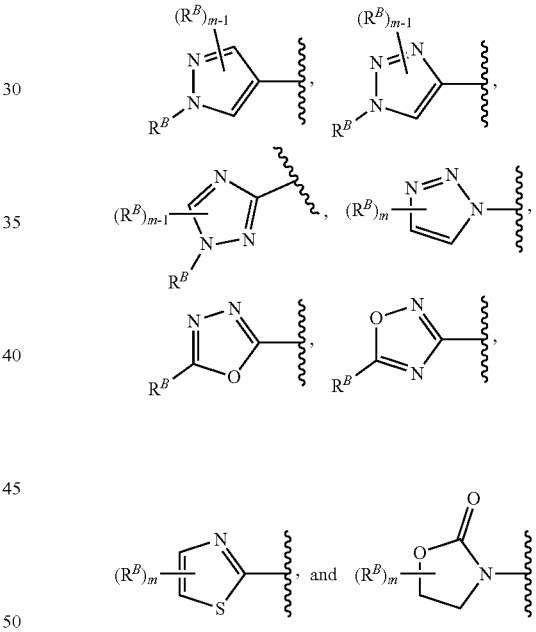

wherein
each $R^B$ is independently selected from cyano, halogen, hydroxy, substituted or unsubstituted $C_{1-6}$ alkyl, —$OCH_3$, —$OCD_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.-

In some embodiments, ring Q is a 6 membered monocyclic heteroaryl selected from the group consisting of:

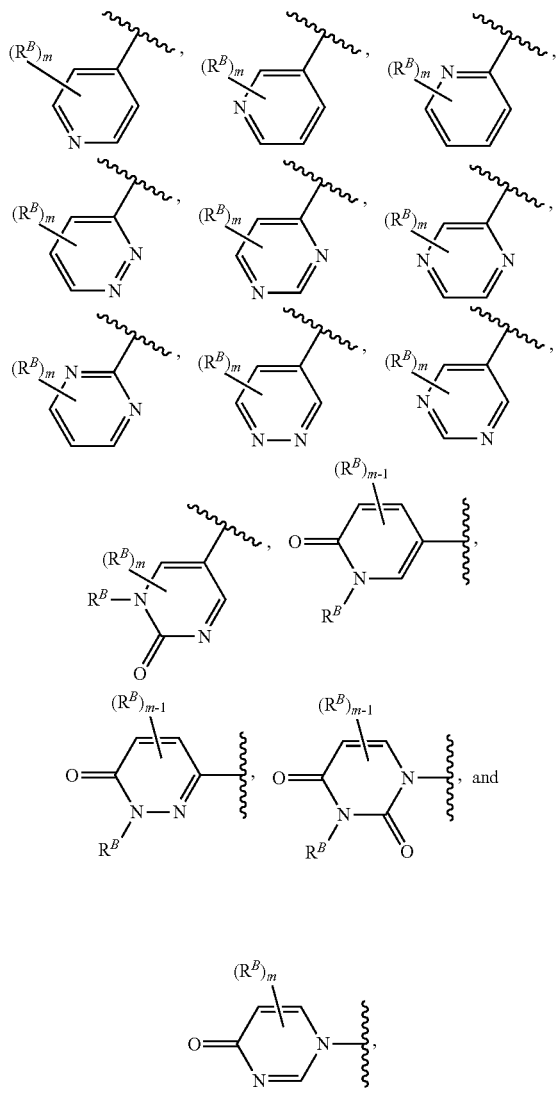

wherein
each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a fused bicyclic heteroaryl having 8 to 10 ring atoms, 1, 2, or 3 ring heteroatoms independently selected from N, O or S, and which is substituted with 0, 1, or 2 substituents independently selected from cyano, oxime, halogen, hydroxy, $C_{1-6}$ alkyl, $C_{24}$ alkenyl, $C_{24}$ alkynyl, $C_{1-6}$ alkoxy, $C_{1-6}$ alkoxy substituted with hydroxy, amino, mono-$C_{1-6}$ alkylamino, and di-$C_{1-6}$ alkylamino.

In some embodiments, ring Q is a 6-5 fused heteroaryl, 6-6 fused heteroaryl, 5-6 fused heteroaryl, 5-5 fused heteroaryl, 7-5 fused heteroaryl, or 5-7 fused heteroaryl.

In some embodiments, ring Q is a 6-5 fused heteroaryl, 6-6 fused heteroaryl, or 5-6 fused heteroaryl, selected from the group consisting of

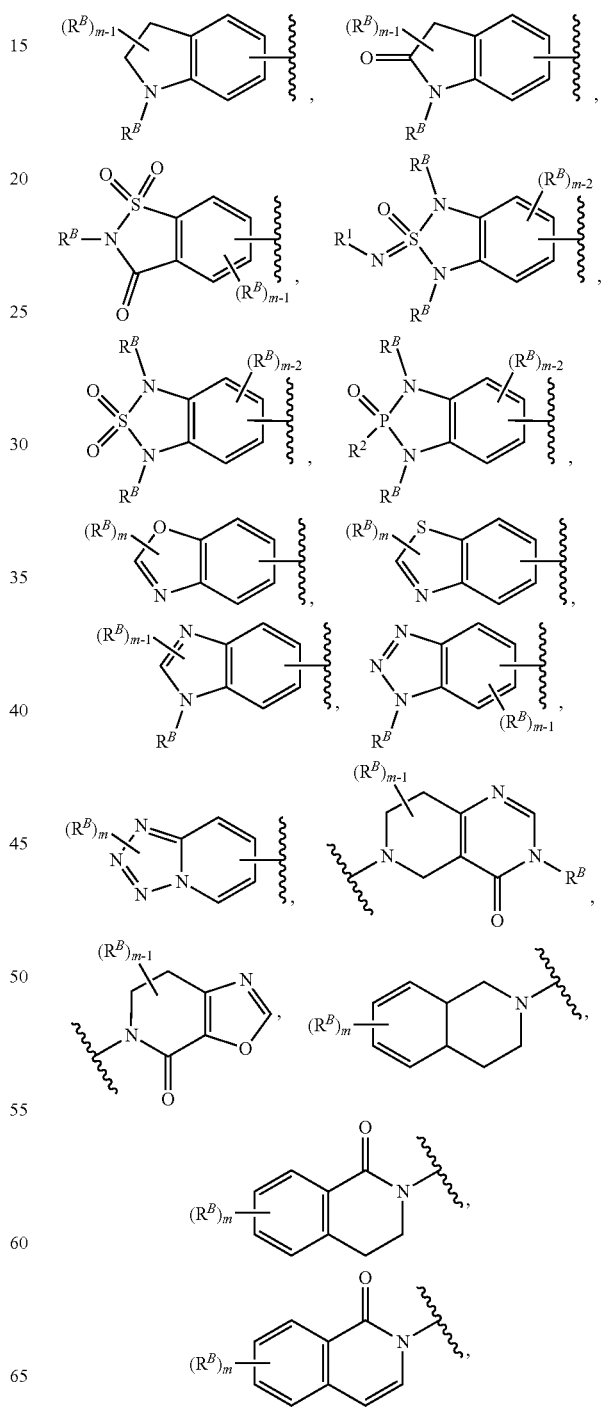

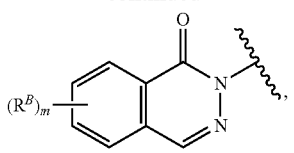

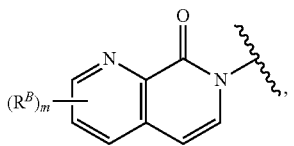

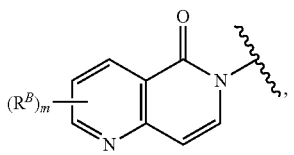

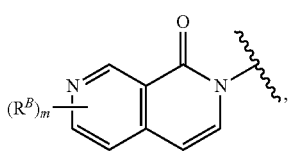

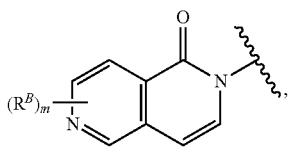

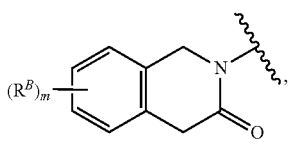

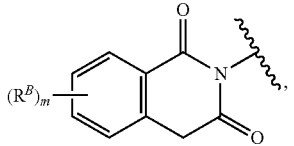

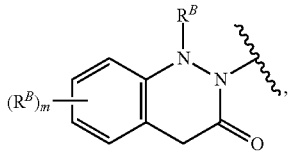

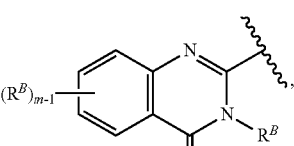

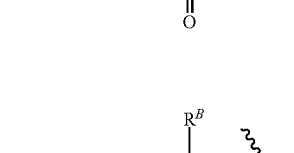

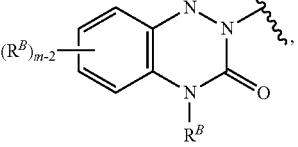

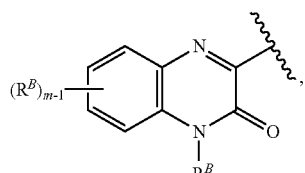

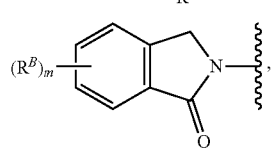

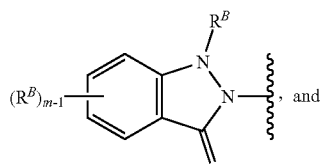

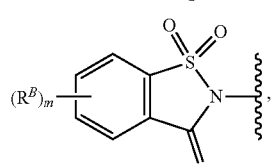

wherein each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 1, 2, or 3.

In some embodiments, ring Q is

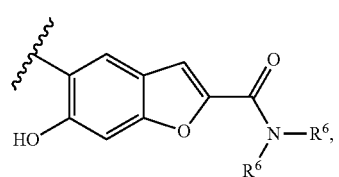

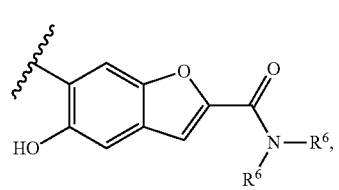

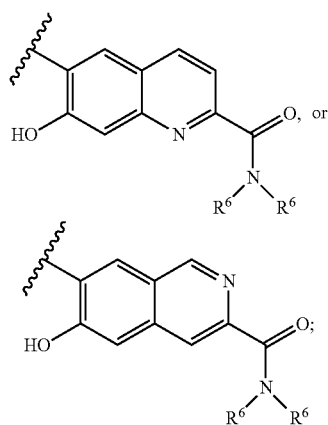

and each $R^6$ is independently H, $-OR^1$, $-N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, Z is $CR^7$ and X is $-NR^3-$, $-CR^4R-$, $-C(=O)-$, $-S-$, or $-O-$. In some embodiments, Z is $CR^7$ and X is $-NR^3-$. In some embodiments, Z is $CR^7$ and X is $-CR^4R^5-$. In some embodiments, Z is $CR^7$ and X is $-C(=O)-$. In some embodiments, Z is $CR^7$ and X is $-S-$. In some embodiments, Z is $CR^7$ and X is $-O-$.

In some embodiments, Z is $CR^7$ and X is $-NR^3-$.

In some embodiments, each $R^7$ is independently H, D, substituted or unsubstituted $C_1$-$C_6$ alkyl, substituted or unsubstituted $C_1$-$C_6$ haloalkyl, or $-CH_2OR^1$.

In some embodiments, $R^3$ is $-OR^1$, substituted or unsubstituted $C_1$-$C_6$ haloalkyl, substituted or unsubstituted $C_1$-$C_6$ heteroalkyl, or substituted or unsubstituted $C_3$-$C_8$ cycloalkyl. In some embodiments, $R^3$ is $-OR^1$. In some embodiments, $R^3$ is substituted or unsubstituted $C_1$-$C_6$ haloalkyl. In some embodiments, $R^3$ is substituted or unsubstituted $C_1$-$C_6$ heteroalkyl. In some embodiments, $R^3$ is substituted or unsubstituted $C_3$-$C_8$ cycloalkyl. In some embodiments, $R^3$ is $-CD_3$.

In some embodiments, $R^3$ is cyclopropyl. In some embodiments, $R^3$ is cyclobutyl. In some embodiments, $R^3$ is cyclopentyl. In some embodiments, $R^3$ is cyclohexyl. In some embodiments, $R^3$ is cycloheptyl. In some embodiments, $R^3$ is cyclooctyl.

In some embodiments, $R^3$ is cyclopentenyl. In some embodiments, $R^3$ is cyclohexenyl. In some embodiments, $R^3$ is cycloheptenyl. In some embodiments, $R^3$ is cyclooctenyl.

In some embodiments, $R^3$ is $-CF_3$, $-CH_2CH_2F$, $-CH_2CF_3$, or $-CH_2CH_2CH_2F$. In some embodiments, $R^3$ is $-CF_3$. In some embodiments, $R^3$ is $-CH_2CH_2F$. In some embodiments, $R^3$ is $-CH_2CF_3$. In some embodiments, $R^3$ is $-CH_2CH_2CH_2F$.

In some embodiments, $R^3$ is $-OCH_3$. In some embodiments, $R^3$ is $-OCH_2CH_3$. In some embodiments, $R^3$ is $-OCH_2CH_2OH$. In some embodiments, $R^3$ is $-CH_2CH_2OCH_3$. In some embodiments, $R^3$ is $-OCH_2CH_2OCH_3$.

In some embodiments,

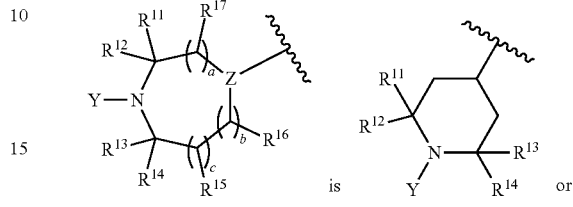

is

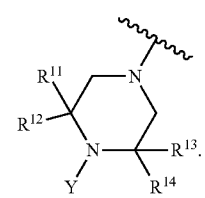

In some embodiments,

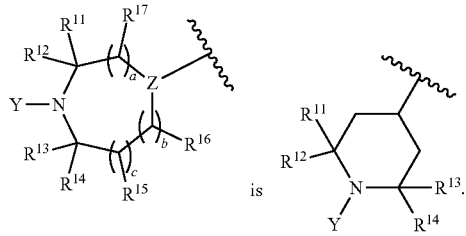

is

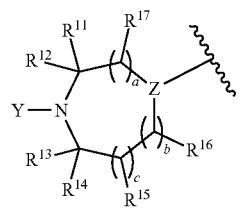

In some embodiments,

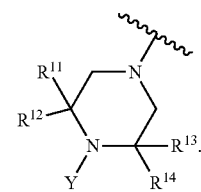

is

In some embodiments,

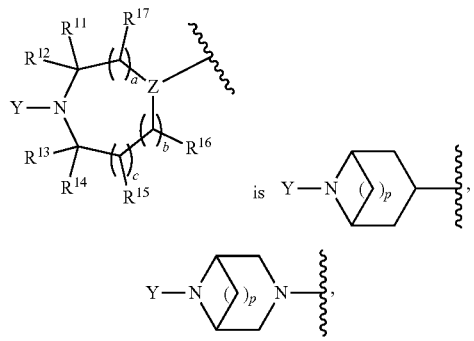

or

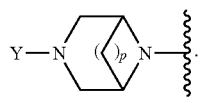

In some embodiments,

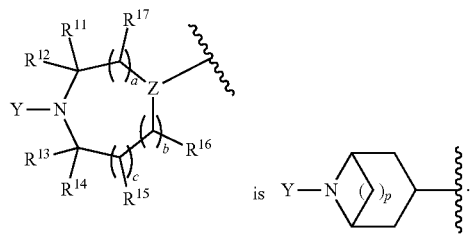

In some embodiments,

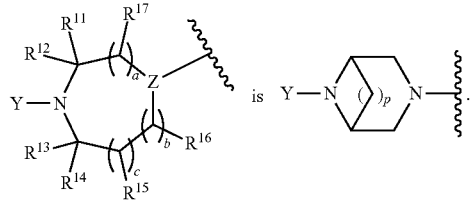

In some embodiments,

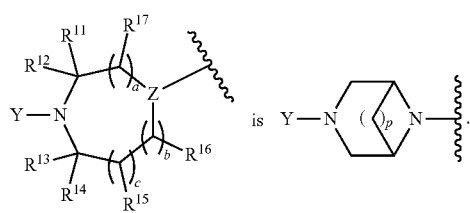

In some embodiments, p is 1 or 2. In some embodiments, p is 1. In some embodiments, p is 2.

In some embodiments,

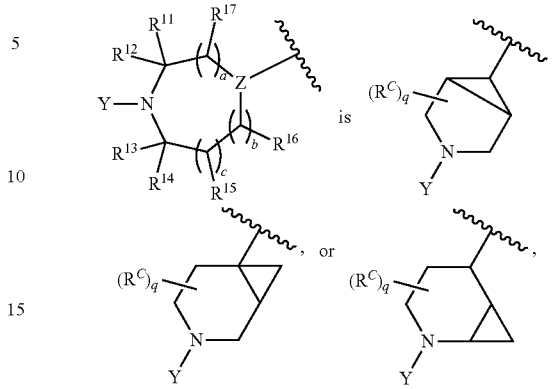

wherein
each $R^C$ is independently selected from D, F, —CN, —OH, —OR$^1$, —SR$^1$, —S(=O)R$^1$, —S(=O)$_2$R$^1$, —N(R$^1$)$_2$, —CH$_2$—N(R$^1$)$_2$, —NHS(=O)$_2$R$^1$, —S(=O)$_2$N(R$^1$)$_2$, —C(=O)R$^1$, —OC(=O)R$^1$, —CO$_2$R$^1$, —OCO$_2$R$^1$, —C(=O)N(R$^1$)$_2$, —OC(=O)N(R$^1$)$_2$, —NR$^1$C(=O)N(R$^1$)$_2$, —NR$^1$C(=O)R$^1$, —NR$^1$C(=O)OR$^1$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, and substituted or unsubstituted C$_2$-C$_8$ heterocycloalkyl; and q is 0, 1, 2, 3, 4, 5, or 6.

In some embodiments,

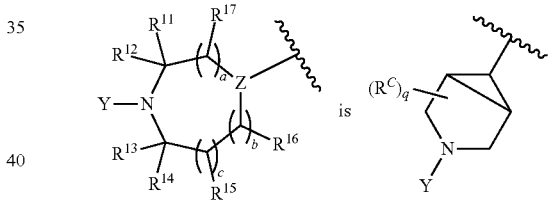

In some embodiments,

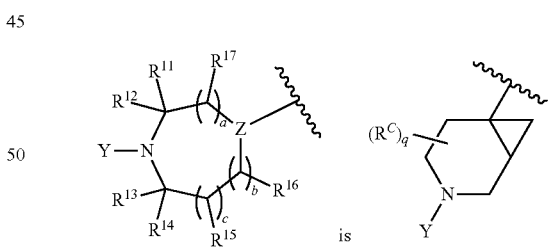

In some embodiments,

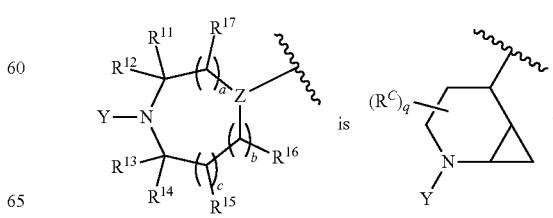

In some embodiments,

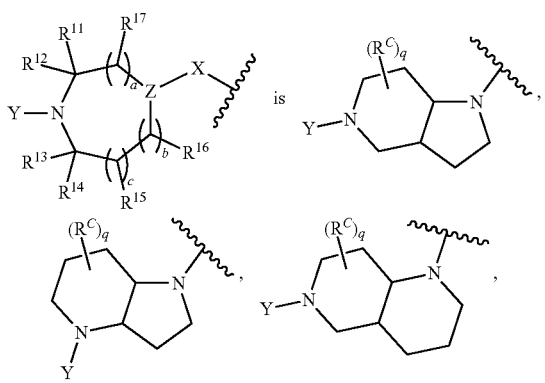

is

In some embodiments,

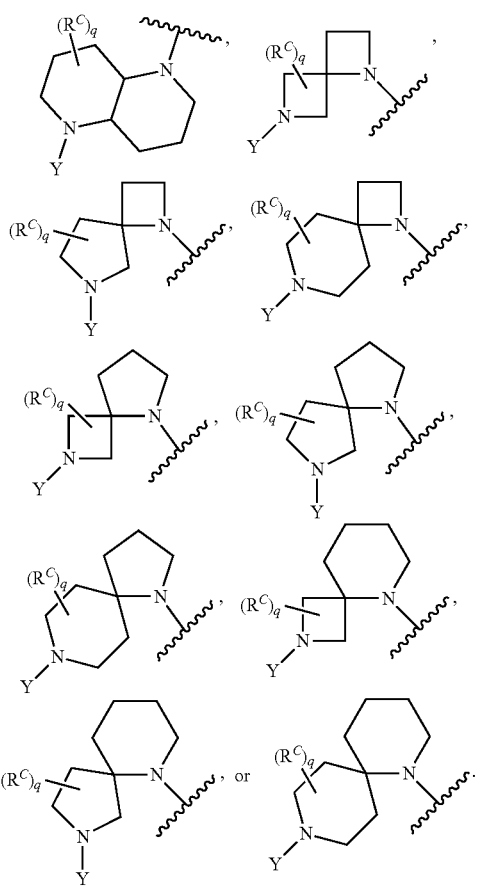

In some embodiments,

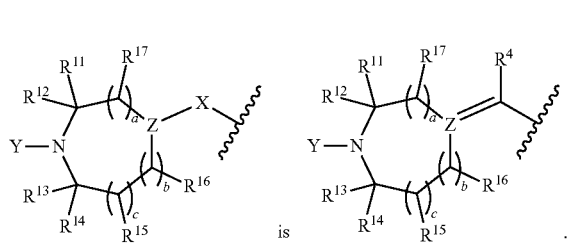

In some embodiments, Y is —C(=O)(CH$_2$)$_y$NH$_2$, —S(=O)(CH$_2$)$_y$NH$_2$, or —S(=O)$_2$(CH$_2$)$_y$NH$_2$, wherein y is 0, 1, or 2. In some embodiments, Y is —C(=O)NH$_2$. In some embodiments, Y is —C(=O)CH$_2$NH$_2$. In some embodiments, Y is —C(=O)CH$_2$CH$_2$NH$_2$. In some embodiments, Y is —S(=O)NH$_2$. In some embodiments, Y is —S(=O)CH$_2$NH$_2$. In some embodiments, Y is —S(=O)CH$_2$CH$_2$NH$_2$. In some embodiments, Y is —S(=O)$_2$NH$_2$. In some embodiments, Y is —S(=O)$_2$CH$_2$NH$_2$. In some embodiments, Y is —S(=O)$_2$CH$_2$CH$_2$NH$_2$.

In some embodiments, Y is —C(=O)(CH$_2$)$_y$CH=CH$_2$ or —C(=O)(CH$_2$)$_y$C≡CH, wherein y is 0, 1, or 2. In some embodiments, Y is —C(=O)CH=CH$_2$. In some embodiments, Y is —C(=O)CH$_2$CH=CH$_2$. In some embodiments, Y is —C(=O)CH$_2$CH$_2$CH=CH$_2$. In some embodiments, Y is —C(=O)CH≡CH$_2$. In some embodiments, Y is —C(=O)CH$_2$CH≡CH$_2$. In some embodiments, Y is —C(=O)CH$_2$CH$_2$CH≡CH$_2$.

In some embodiments, Y is

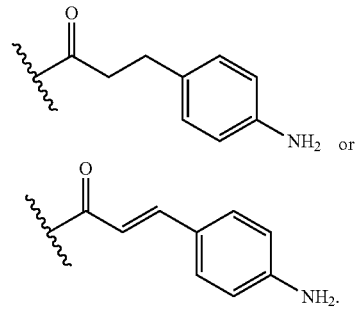

In some embodiments, Y is

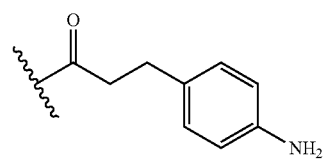 [SMILES: *C(=O)CCc1ccc(N)cc1]

In some embodiments Y is

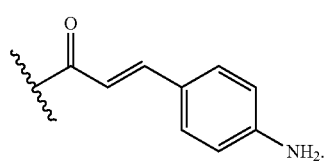 [SMILES: *C(=O)/C=C/c1ccc(N)cc1]

In some embodiments, Y is

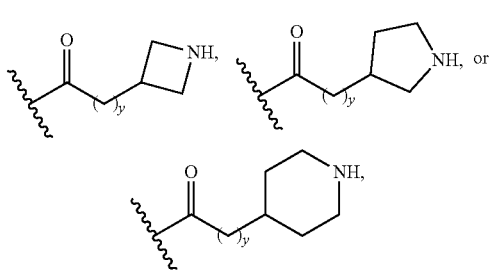

wherein y is 0, 1, or 2.

In some embodiments, Y is

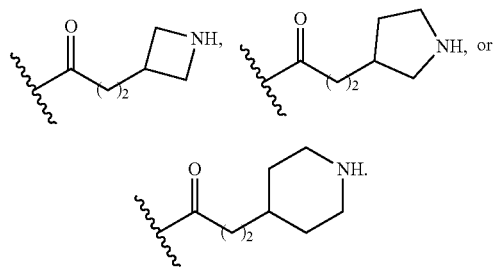

In some embodiments, Y is

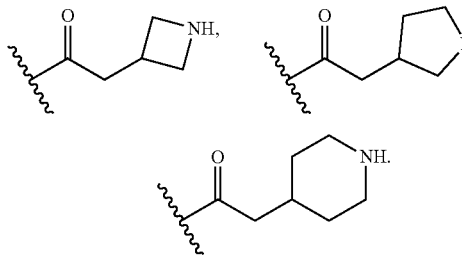

In some embodiments, Y is

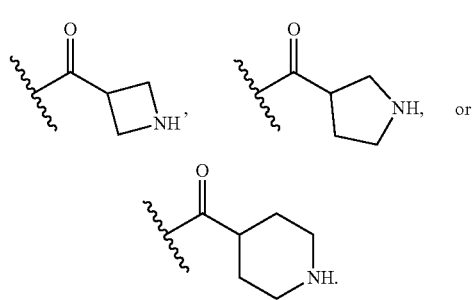

In some embodiments, Y is

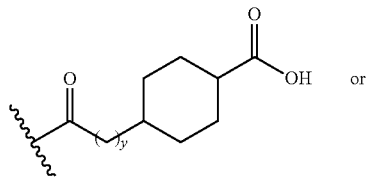

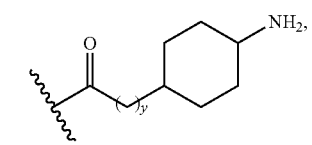

wherein y is 0, 1 or 2.

In some embodiments, In some embodiments, Y is

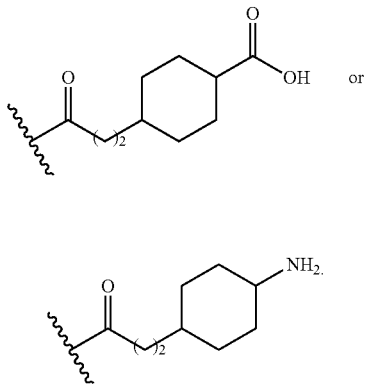

In some embodiments, In some embodiments, Y is

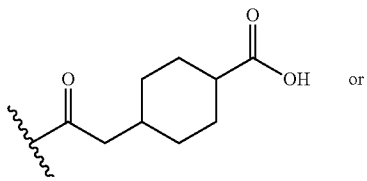

In some embodiments, Y is

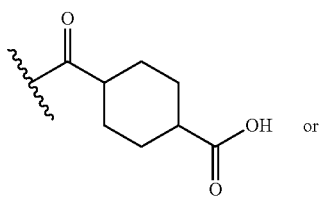

In some embodiments, a compound of Formula (III) is selected from a compound in Table 1A, Table 1B or Table 1C.

In one aspect, described herein is a compound that has the structure of Formula (IV), or a pharmaceutically acceptable salt or solvate thereof:

Formula (IV)

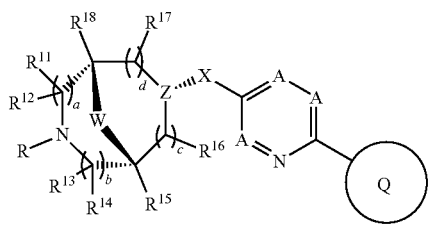

wherein,
each A is independently N or CR$^4$;
each R$^A$ is independently selected from H, D, halogen, —CN, —OH, —OR$^1$, =O, =N—OR$^1$, —SR$^1$, —S(=O) R$^1$, —S(=O)$_2$R$^1$, —N(R$^1$)$_2$, —NR$^1$S(=O)(=NR)R$^2$, —NR$^1$S(=O)$_2$R$^2$, —S(=O)$_2$N(R$^1$)$_2$, —C(=O)R$^1$, —OC (=O)R$^1$, —C(=O)OR$^1$, —OC(=O)OR$^1$, —C(=O) N(R$^1$)$_2$, —OC(=O)N(R$^1$)$_2$, —NR$^1$C(=O)R$^1$, —P(=O) (R$^2$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, and substituted or unsubstituted monocyclic heteroaryl;
ring Q is monocyclic aryl, bicyclic aryl, monocyclic heteroaryl, or fused bicyclic heteroaryl;
X is —O—, —NR$^3$—, —CR$^4$R—, —C(=O)—, —C(=CR$^2$$_2$)—, —S—, —S(=O)—, —S(=O)$_2$—, or —S(=O)(=NR$^1$)—; each R$^1$ is independently H, D, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;
each R$^2$ is independently H, D, substituted or unsubstituted C$_1$-C$_6$ alkyl, substituted or unsubstituted C$_1$-C$_6$ haloalkyl, substituted or unsubstituted aryl, substituted or unsubstituted monocyclic heteroaryl, —OR$^1$, —N(R$^1$)$_2$, —CH$_2$OR$^1$, —C(=O)OR$^1$, —OC(=O)R$^1$, —C(=O)N(R$^1$)$_2$, or —NR$^1$C(=O)R$^1$;
R$^3$ is H, —OR$^1$, —N(R$^1$)$_2$, substituted or unsubstituted C$_1$-C$_6$ alkyl, —CD$_3$, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;
R$^4$ is H, D, F, —CN, —OR$^1$, —SR$^1$, —N(R$^1$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_1$-C$_6$ alkylene-OR$^1$, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;
R$^5$ is H, D, F, —CN, —OR$^1$, —SR$^1$, —N(R$^1$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_1$-C$_6$ alkylene-OR$^1$, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl; or
R$^4$ and R$^5$ taken in combination with the carbon atom to which they attach, form a substituted or unsubstituted C$_{3-8}$ cycloalkyl or a substituted or unsubstituted C$_{2-7}$ heterocycloalkyl;

Z is CR$^7$; and R$^7$ is H, D, substituted or unsubstituted C$_1$-C$_6$ alkyl, substituted or unsubstituted C$_1$-C$_6$ haloalkyl or —CH$_2$OR$^1$;
W is substituted or unsubstituted C$_1$-C$_4$alkylene, substituted or unsubstituted C$_2$-C$_4$alkenylene, or substituted or unsubstituted C$_1$-C$_4$ heteroalkylene;
R is selected from the group consisting of H, a substituted or unsubstituted C$_{1-6}$ alkyl, substituted or unsubstituted C$_{1-6}$ fluoroalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, and substituted or unsubstituted heteroaryl, wherein alkyl is optionally substituted with hydroxy, amino, substituted or unsubstituted mono-C$_1$-alkylamino, or substituted or unsubstituted di-C$_{1-6}$ alkylamino;
R$^{11}$, R$^{12}$, R$^{13}$, R$^{14}$, R$^{15}$, R$^{16}$, R$^{17}$, and R$^{18}$ are each independently selected from the group consisting of H, F, OR$^1$, substituted or unsubstituted C$_{1-6}$ alkyl, a substituted or unsubstituted C$_{1-6}$ fluoroalkyl, substituted or unsubstituted C$_1$-C$_6$ heteroalkyl, wherein alkyl is optionally substituted with hydroxy, amino, methoxy, substituted or unsubstituted mono-C$_1$-alkylamino or substituted or unsubstituted di-C$_{1-6}$ alkylamino;
R$^{11}$ and R$^{13}$, taken in combination form a substituted or unsubstituted C$_{1-3}$ alkylene group or a substituted or unsubstituted C$_{1-3}$ heteroalkylene group; or
R$^{11}$ and R$^1$, taken in combination form a substituted or unsubstituted C$_{1-3}$ alkylene group; or
R$^{16}$ and R$^{17}$, taken in combination form a substituted or unsubstituted C$_{1-3}$ alkylene group; or
R$^{13}$ and R$^{14}$, taken in combination with the carbon atom to which they attach, form a spirocyclic C$_{3-8}$ cycloalkyl; or
R$^{17}$ and R$^2$, taken in combination form a substituted or unsubstituted C$_{1-3}$ alkylene group; or
when X is —NR$^3$—, then R$^3$ and R$^2$ are optionally taken together with the intervening atoms to which they are attached to form a 4, 5, or 6-membered ring; or
when X is —NR$^3$—, then R$^3$ and R$^{16}$ are optionally taken together with the intervening atoms to which they are attached to form a 4, 5, or 6-membered ring;
a and b are each independently selected from 0, 1, 2, or 3;
c and d are each independently selected from 1, 2, 3, or 4; and
wherein the compound of Formula (IV) has a stereochemical purity of at least 80%.

For any and all of the embodiments, substituents are selected from among a subset of the listed alternatives. For example, in some embodiments, a is 0, 1, or 2. In other embodiments, a is 0. In some other embodiments, a is 1. In some other embodiments, a is 2.

In some embodiments, W is substituted or unsubstituted C$_1$-C$_4$ alkylene.

In some embodiments,

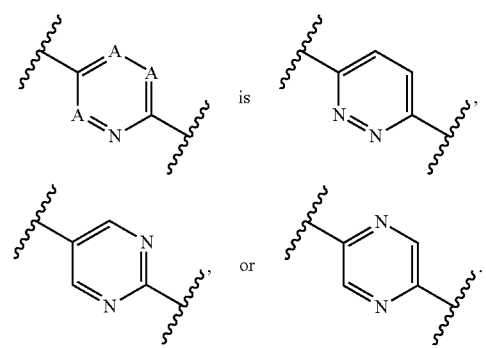

In some embodiments,

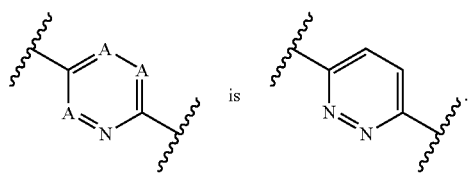 is

In some embodiments,

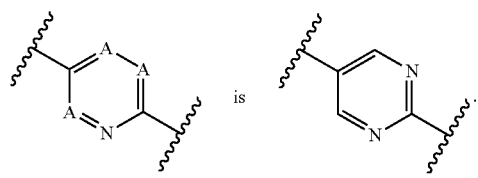 is is

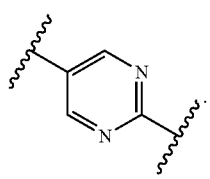 [SMILES: *c1cnc(*)nc1]

In some embodiments,

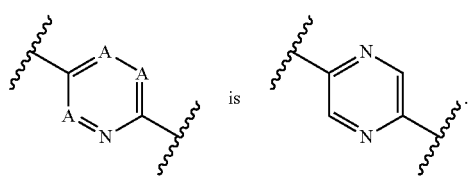 is

In some embodiments, X is —O—, —NR$^3$—, —S—, —CR$^4$R—, —C(=O)—, or —C(=CR$^2{}_2$)—. In some embodiments, X is —O—, —NR$^3$—, or —C(=O)—. In some embodiments, X is —O—. In some embodiments, X is —NR$^3$—. In some embodiments, X is —S—. In some embodiments, X is —CR$^4$R$^5$—. In some embodiments, X is —C(=O)—. In some embodiments, X is —C(=CR$^2{}_2$)—.

In some embodiments, X is —CH(CH$_2$OR$^1$)— or —CH(OR$^1$)—. In some embodiments, X is —CH(CH$_2$OR$^1$)—. In some embodiments, X is —CH(OR$^1$)—.

In some embodiments, R$^3$ is H, —OR$^1$, —N(R$^1$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl.

In some embodiments, R$^3$ is —OR$^1$, —N(R$^1$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, or substituted or unsubstituted C$_2$-C$_7$ heterocycloalkyl.

In some embodiments, ring Q is substituted or unsubstituted monocyclic aryl. In some embodiments, ring Q is substituted monocyclic aryl. In some embodiments, ring Q is unsubstituted monocyclic aryl.

In some embodiments, ring Q is substituted phenyl. In some embodiments, ring Q is 2-hydroxy-phenyl which is substituted with: 0, 1, 2, or 3 substituents independently selected from C$_{1-6}$ alkyl, oxo, oxime, hydroxy, halo-C$_{1-6}$ alkyl, dihalo-C$_{1-6}$ alkyl, trihalo-C$_{1-6}$ alkyl, C$_{1-6}$ alkoxy, C$_{1-6}$ alkoxy-C$_{3-7}$ cycloalkyl, halo-C$_{1-6}$ alkoxy, dihalo-C$_{1-6}$ alkoxy, trihalo-C$_{1-6}$ alkoxy, hydroxy, cyano, halogen, amino, mono-C$_{1-6}$ alkylamino, di-C$_{1-6}$ alkylamino, heteroaryl, C$_{1-6}$ alkyl substituted with hydroxy, C$_{1-6}$ alkoxy substituted with aryl, amino, —C(=O)NH—C$_{1-6}$ alkyl-heteroaryl, —NHC(=O)—C$_{1-6}$ alkylheteroaryl, C$_{1-6}$ alkyl-C(=O)NH-heteroaryl, C$_{1-6}$ alkyl-NHC(=O)-heteroaryl, C$_{3-7}$ cycloalkyl, 5-7 membered cycloalkenyl, or 5, 6 or 9 membered heterocycle containing 1 or 2 heteroatoms independently, selected from S, O and N.

In some embodiments, ring Q is 2-hydroxy-phenyl which is substituted with two C$_{1-6}$ alkyl. In some embodiments, two C$_{1-6}$ alkyl groups can combine with the atoms to which they are bound to form a 5-6 membered ring.

In some embodiments, ring Q is 2-hydroxy-phenyl which is substituted with heteroaryl. In some embodiments, heteroaryl has 5, 6, 9, or 10 ring atoms, 1, 2 or 3 ring heteroatoms selected from N, O and S, and is substituted with 0, 1, or 2 substituents independently selected from oxo, hydroxy, nitro, halogen, C$_{1-6}$ alkyl, C$_{1-6}$ alkenyl, C$_{1-6}$ alkoxy, C$_{3-7}$ cycloalkyl, C$_{1-6}$ alkyl-OH, trihalo-C$_{1-6}$ alkyl, mono-C$_{1-6}$ alkylamino, di-C$_{1-6}$ alkylamino, —C(=O)NH$_2$, —NH$_2$, —NO$_2$, hydroxy-C$_{1-6}$ alkylamino, hydroxy-C$_{1-6}$ alkyl, 4-7 membered heterocycle-C$_{1-6}$ alkyl, amino-C$_{1-6}$ alkyl, mono-C$_{1-6}$ alkylamino-C$_{1-6}$ alkyl, and di-C$_{1-6}$ alkylamino-C$_{1-6}$ alkyl.

In some embodiments, ring Q is

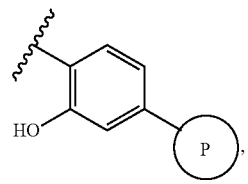, wherein ring P is aryl or heteroaryl. In some embodiments, ring Q is

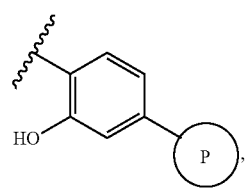, wherein ring P is aryl. In some embodiments, ring Q is

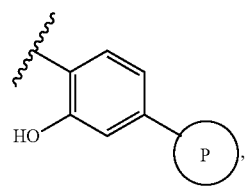, wherein ring P is heteroaryl. In some embodiments, ring Q is

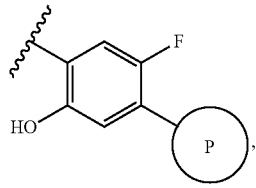

wherein ring P is aryl or heteroaryl. In some embodiments, ring Q is

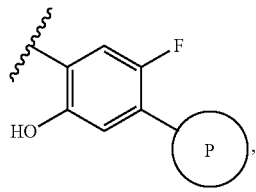

wherein ring P is aryl.
In some embodiments, ring Q

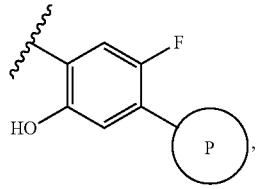

wherein ring P is heteroaryl. In some embodiments, ring P is heteroaryl and the heteroaryl is selected from the group consisting of:

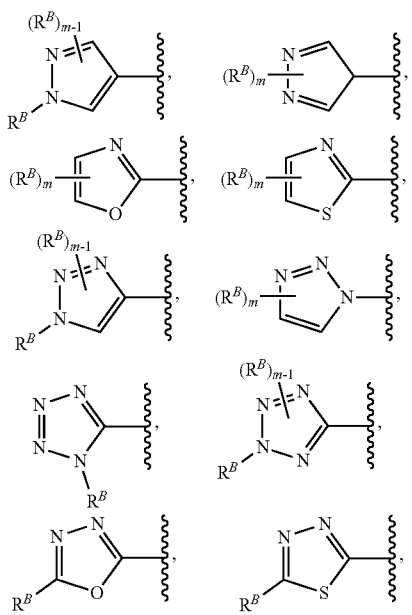

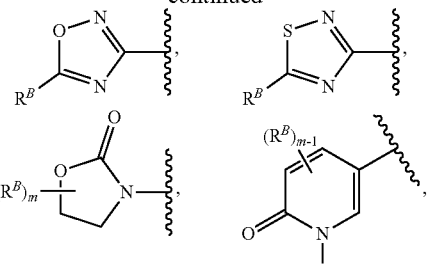

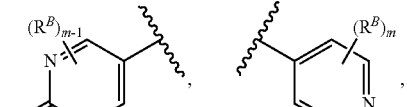

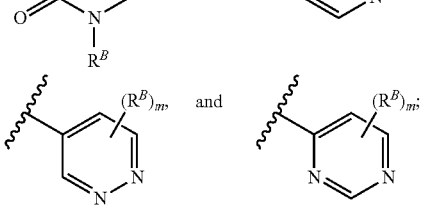

wherein
each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring P is heteroaryl selected from the group consisting of:

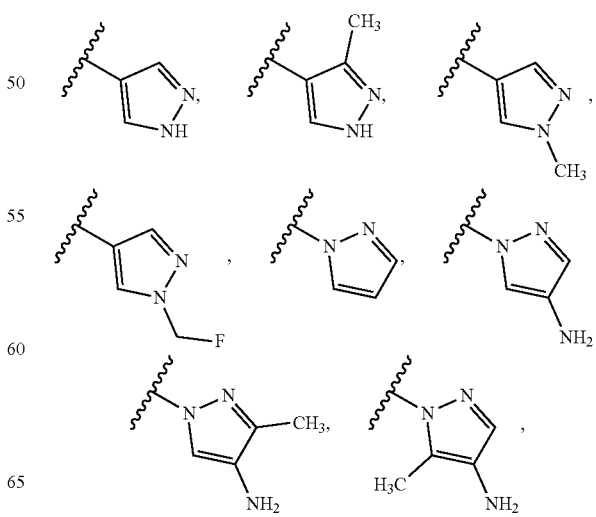

-continued
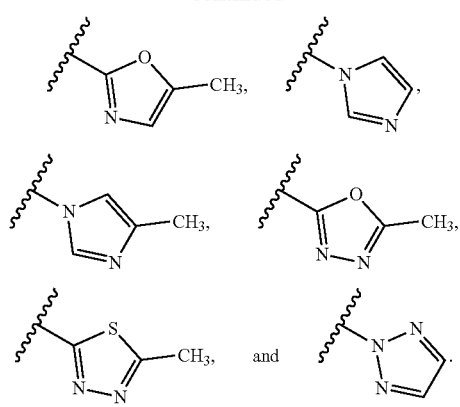
In some embodiments, ring P is heteroaryl selected from the group consisting of:
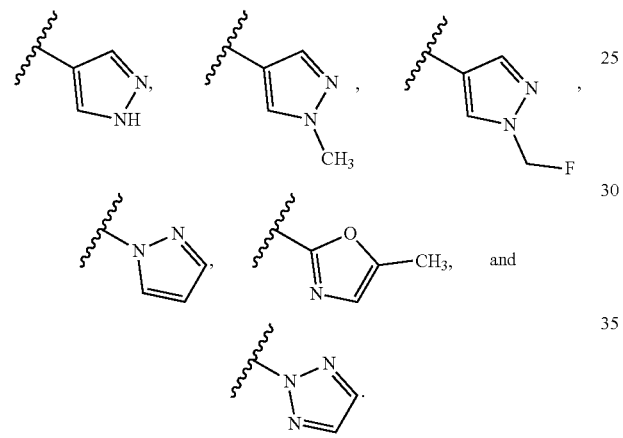
In some embodiments, ring P is heteroaryl selected from the group consisting of:
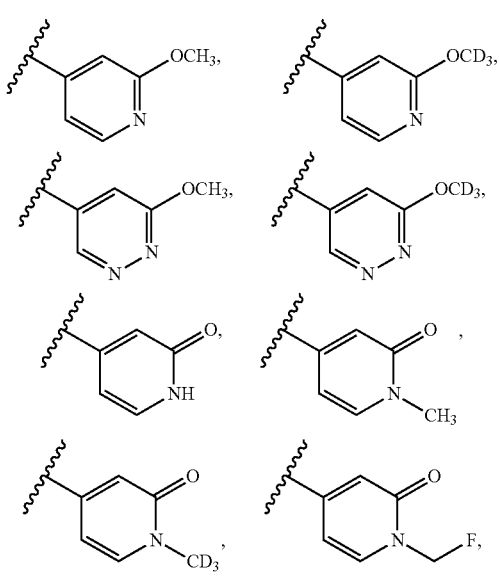
-continued
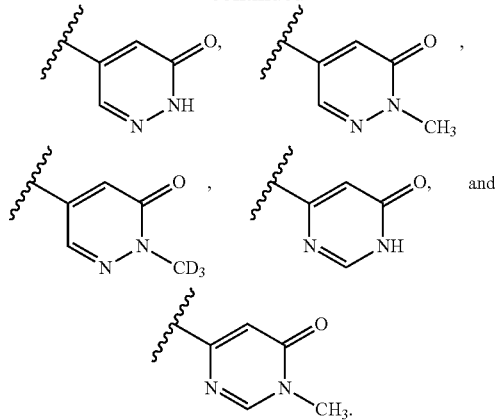
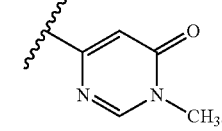
In some embodiments, ring P is heteroaryl selected from the group consisting of:
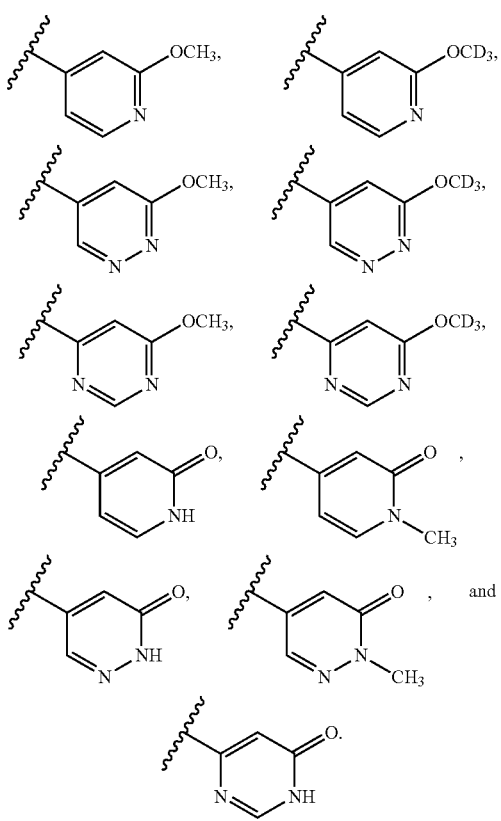
In some embodiments, ring Q is
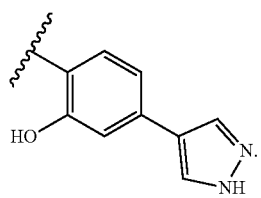 [SMILES: *c1ccc(-c2cn[nH]c2)cc1O]

In some embodiments, ring Q is
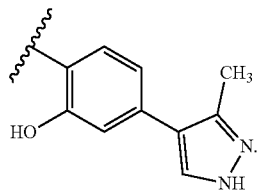 [SMILES: *c1ccc(-c2c[nH]nc2C)cc1O]
In some embodiments, ring Q is
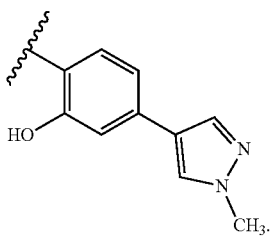 [SMILES: *c1ccc(-c2cnn(C)c2)cc1O]
In some embodiments, ring Q
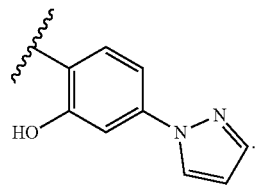 [SMILES: *c1ccc(-n2cccn2)cc1O]
In some embodiments, ring Q is
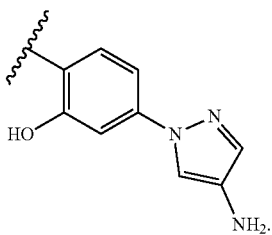
In some embodiments, ring Q is
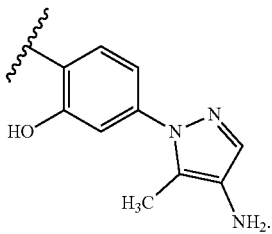 [SMILES: *c1ccc(-n2ncc(N)c2C)cc1O]
In some embodiments, ring Q is
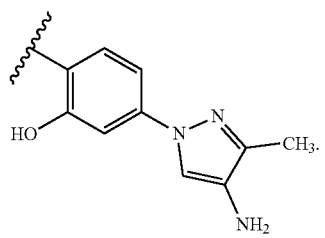 [SMILES: *c1ccc(-n2cc(N)c(C)n2)cc1O]
In some embodiments,
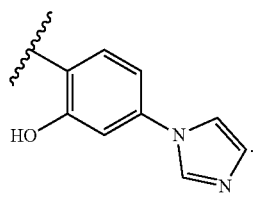 [SMILES: *c1ccc(-n2ccnc2)cc1O]
ring Q is
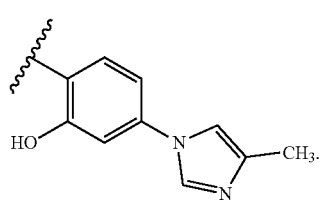 [SMILES: *c1ccc(-n2cnc(C)c2)cc1O]
In some embodiments, ring Q is
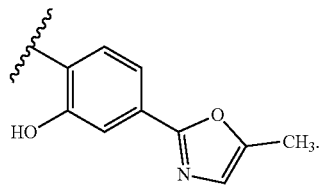 [SMILES: *c1ccc(-c2ncc(C)o2)cc1O]
In some embodiments, ring Q is
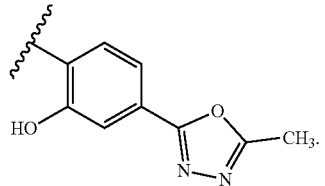 [SMILES: *c1ccc(-c2nnc(C)o2)cc1O]

In some embodiments, ring Q is
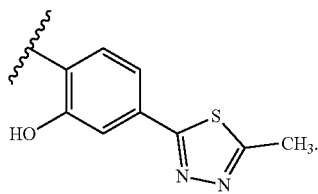 [SMILES: *c1ccc(-c2nnc(C)s2)cc1O]
In some embodiments, ring Q is
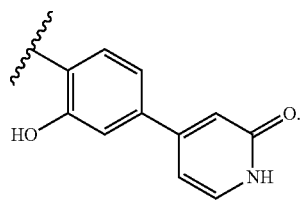 [SMILES: *c1ccc(-c2cc[nH]c(=O)c2)cc1O]
In some embodiments, ring Q is
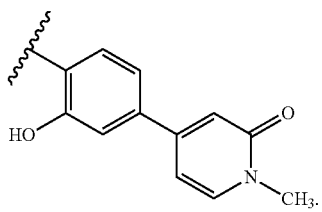 [SMILES: *c1ccc(-c2ccn(C)c(=O)c2)cc1O]
In some embodiments, ring Q is
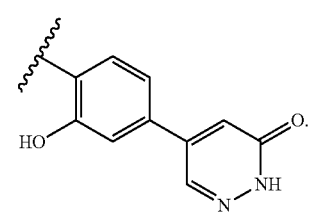 [SMILES: *c1ccc(-c2cn[nH]c(=O)c2)cc1O]
In some embodiments, ring Q is
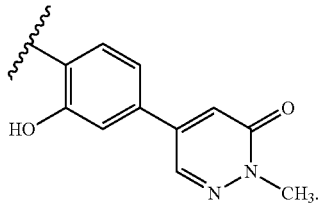 [SMILES: *c1ccc(-c2cnn(C)c(=O)c2)cc1O]
In some embodiments, ring Q is
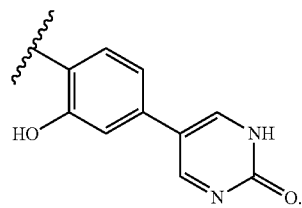 [SMILES: *c1ccc(-c2cnc(=O)[nH]c2)cc1O]
In some embodiments, ring Q is
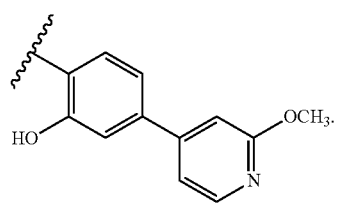
In some embodiments, ring Q is
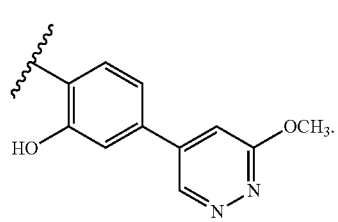
In some embodiments, ring Q is
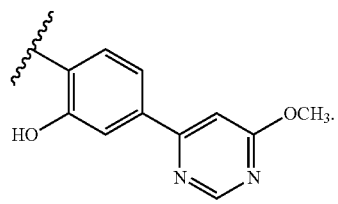
In some embodiments, ring Q is
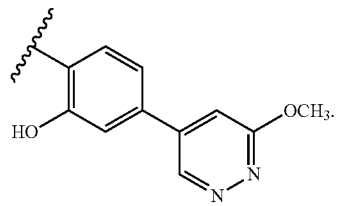

In some embodiments, ring Q is

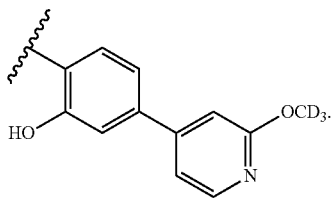

In some embodiments, ring Q is

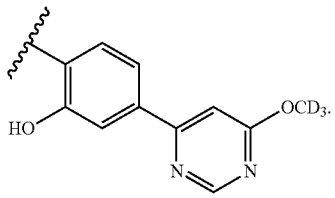

In some embodiments, ring Q is 2-naphthyl optionally substituted at the 3 position with hydroxy and additionally substituted with 0, 1, or 2 substituents selected from hydroxy, cyano, halogen, $C_{1-6}$ alkyl, $C_{2-6}$ alkenyl, $C_{1-6}$ alkoxy, wherein the alkoxy is unsubstituted or substituted with hydroxy, $C_{1-6}$ alkoxy, amino, —NHC(=O)—$C_{1-6}$ alkyl, —NHC(=O)—$C_{1-6}$ alkyl, $C_{1-6}$ alkylene-4-7 membered heterocycle, 4-7 membered heterocycle, mono-$C_{1-6}$ alkylamino, and di-$C_{1-6}$ alkylamino.

In some embodiments, ring Q is

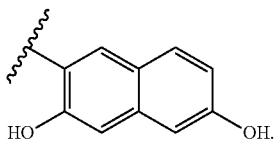 [SMILES: *c1cc2ccc(O)cc2cc1O]

In some embodiments, ring Q is

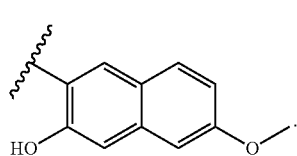 [SMILES: *c1cc2ccc(OC)cc2cc1O]

In some embodiments, ring Q is

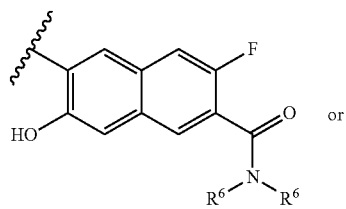

or

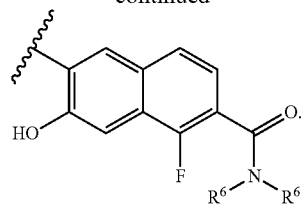

and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, ring Q is monocyclic heteroaryl or fused bicyclic heteroaryl.

In some embodiments, ring Q is a 5 or 6 membered monocyclic heteroaryl having 1-4 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from cyano, $C_{1-6}$ alkyl, mono-$C_{1-6}$ alkylamino, di-$C_{1-6}$ alkylamino, hydroxy-$C_{1-6}$ alkylamino, hydroxy-$C_{1-6}$ alkyl, amino-$C_{1-6}$ alkyl and mono-$C_{1-6}$ alkylamino-$C_{1-6}$ alkyl, and di-$C_{1-6}$ alkylamino-$C_{1-6}$ alkyl.

In some embodiments, ring Q is a 5 membered monocyclic heteroaryl selected from the group consisting of:

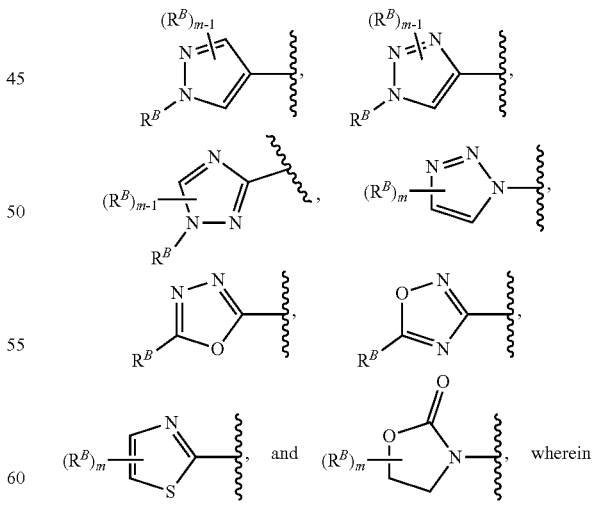

wherein each $R^B$ is independently selected from cyano, halogen, hydroxy, substituted or unsubstituted $C_{1-6}$ alkyl, —$OCH_3$, —$OCD_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a 6 membered monocyclic heteroaryl selected from the group consisting of:

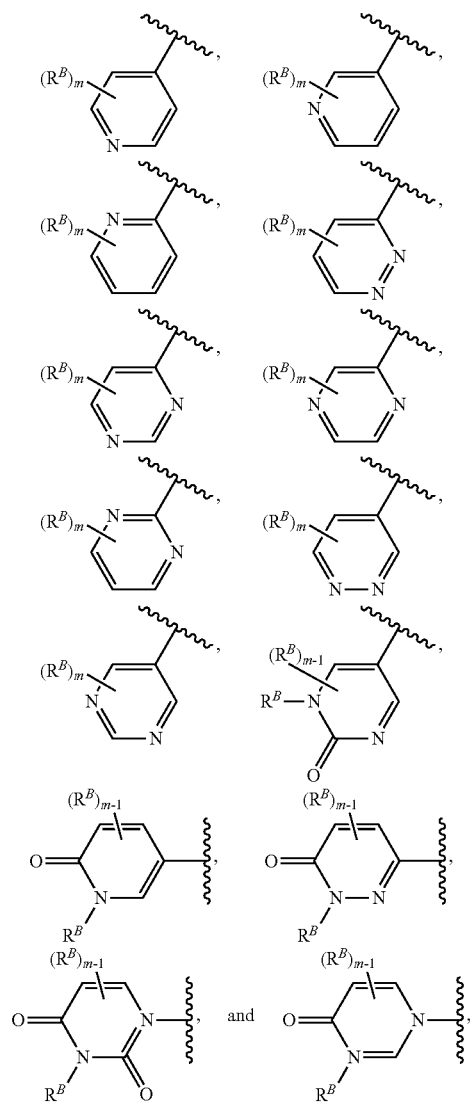

wherein
each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a fused bicyclic heteroaryl having 8 to 10 ring atoms, 1, 2, or 3 ring heteroatoms independently selected from N, O or S, and which is substituted with 0, 1, or 2 substituents independently selected from cyano, oxime, halogen, hydroxy, $C_{1-6}$ alkyl, $C_{24}$ alkenyl, $C_{24}$ alkynyl, $C_{1-6}$ alkoxy, $C_{1-6}$ alkoxy substituted with hydroxy, amino, mono-$C_{1-6}$ alkylamino, and di-$C_{1-6}$ alkylamino.

In some embodiments, ring Q is a 6-5 fused heteroaryl, 6-6 fused heteroaryl, 5-6 fused heteroaryl, 5-5 fused heteroaryl, 7-5 fused heteroaryl, or 5-7 fused heteroaryl.

In some embodiments, ring Q is a 6-5 fused heteroaryl, 6-6 fused heteroaryl, or 5-6 fused heteroaryl, selected from the group consisting of:

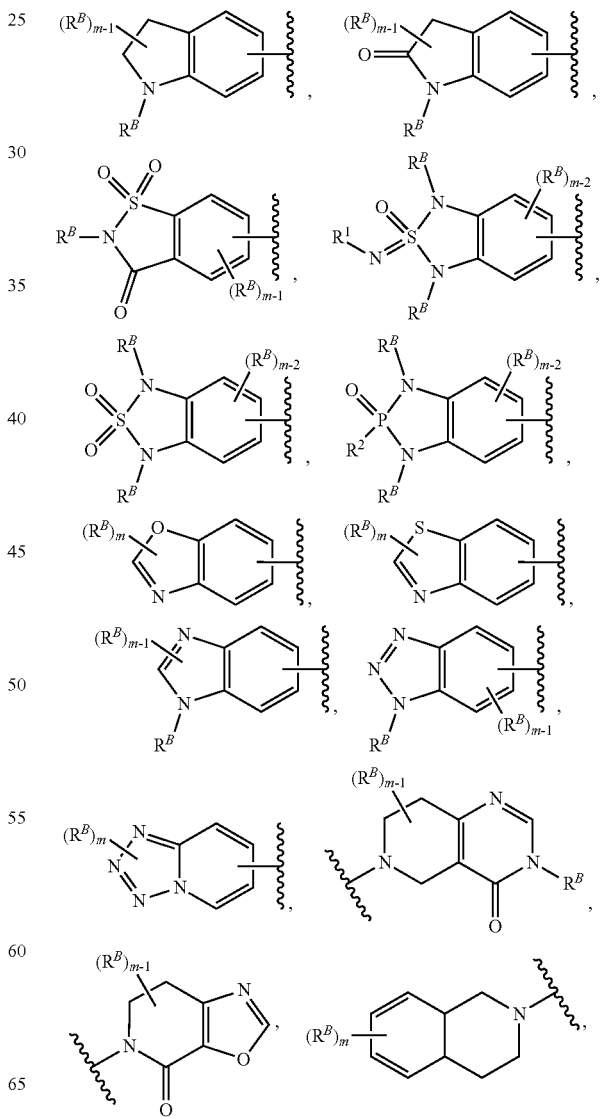

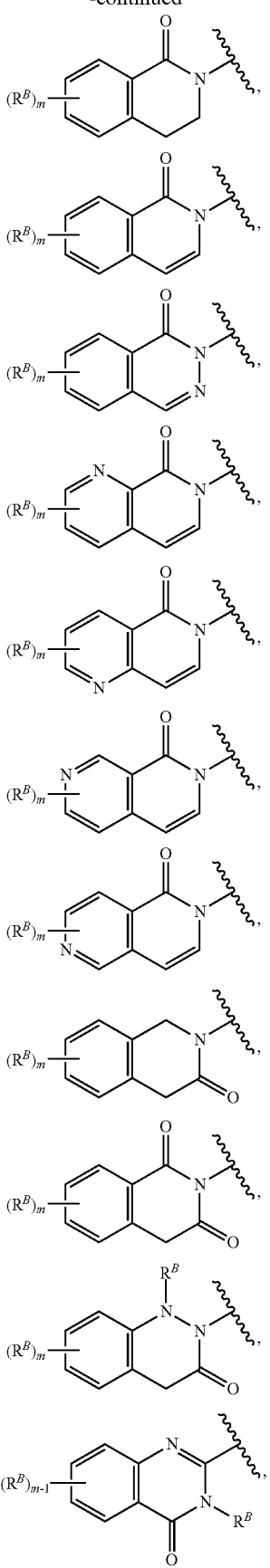

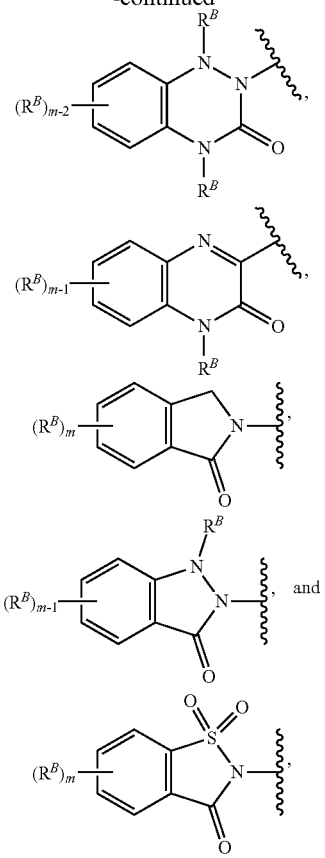

wherein each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_2$-s heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$alkyl-heteroaryl, substituted or unsubstituted $C_{1-6}$alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$alkoxy, amino, mono-$C_{1-6}$alkylamino and di-$C_{1-6}$alkylamino; and m is 1, 2, or 3.

In some embodiments, ring Q is

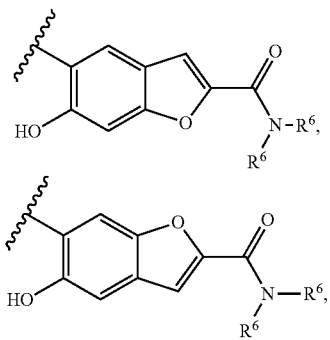

-continued

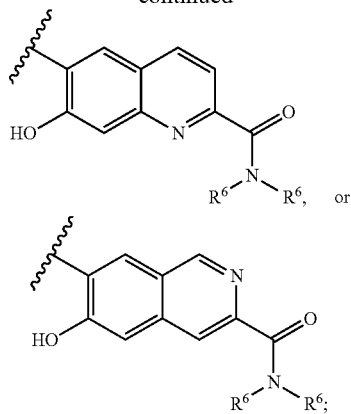

and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, X is —$NR^3$—.

In some embodiments, $R^3$ is —$OR^1$, substituted or unsubstituted $C_1$-$C_6$ alkyl, substituted or unsubstituted $C_1$-$C_6$ haloalkyl, substituted or unsubstituted $C_1$-$C_6$ heteroalkyl, or substituted or unsubstituted $C_3$-$C_8$ cycloalkyl.

In some embodiments, $R^3$ is —$OR^1$. In some embodiments, $R^3$ is —$OCH_3$, —$OCH_2CH_3$, —$OCH_2CH_2OH$ or —$OCH_2CH_2OCH_3$. In some embodiments, $R^3$ is —$OCH_3$. In some embodiments, $R^3$ is —$OCH_2CH_3$. In some embodiments, $R^3$ is —$OCH_2CH_2CH_3$. In some embodiments, $R^3$ is —$OCH(CH_3)_2$. In some embodiments, $R^3$ is —$OCD_3$.

In some embodiments, $R^3$ is —$CD_3$.

In some embodiments, $R^3$ is substituted or unsubstituted $C_1$-$C_6$ haloalkyl. In some embodiments, $R^3$ is $CF_3$. In some embodiments, $R^3$ is —$CH_2CH_2F$. In some embodiments, $R^3$ is —$CH_2CH_2CH_2F$. In some embodiments, $R^3$ is —$CH_2CF_3$. In some embodiments, $R^3$ is —$CH_2CH_2CF_3$.

In some embodiments, $R^3$ is —$CH_3$ or —$CF_3$.

In some embodiments, $R^3$ is substituted or unsubstituted $C_1$-$C_6$ heteroalkyl. In some embodiments, $R^3$ is —$OCH_2CH_2OCH_3$ or —$OCH_2CH_2OCF_3$. In some embodiments, $R^3$ is —$CH_2CH_2OCH_3$.

In some embodiments, $R^3$ is substituted or unsubstituted $C_3$-$C_8$ cycloalkyl. In some embodiments, $R^3$ is cyclopropyl, cyclobutyl, cyclopentyl, cyclohexyl, cycloheptyl, or cyclooctyl. In some embodiments, $R^3$ is cyclopropyl, cyclobutyl, cyclopentyl, or cyclohexyl. In some embodiments, $R^3$ is cyclopropyl. In some embodiments, $R^3$ is cyclobutyl. In some embodiments, $R^3$ is cyclopentyl. In some embodiments, $R^3$ is cyclohexyl.

In some embodiments, $R^3$ is cyclopentenyl, cyclohexenyl, cycloheptenyl, or cyclooctenyl. In some embodiments, $R^3$ is cyclopentenyl or cyclohexenyl. In some embodiments, $R^3$ is cyclopentenyl. In some embodiments, $R^3$ is cyclohexenyl.

In some embodiments,

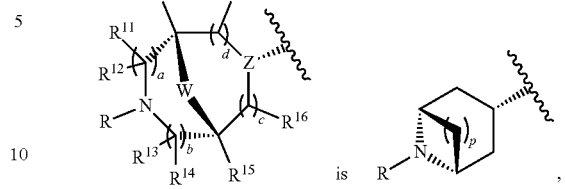

wherein p is 1, 2, or 3.

In some embodiments,

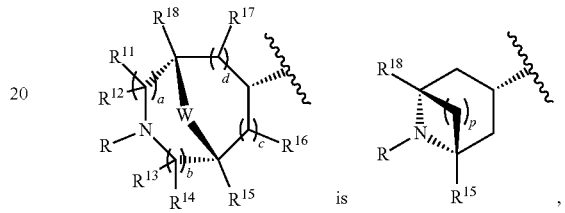

wherein p is 1, 2, or 3. In some embodiments, R is H; $R^{15}$ and $R^{18}$ are H; and p is 2 or 3. In some embodiments, R is H; $R^{15}$ and $R^{18}$ are H; and p is 2. In some embodiments, R is H; $R^5$ and $R^{18}$ are H; and p is 3. In some embodiments, R is H; $R^{15}$ and R are $CH_3$; and p is 2 or 3. In some embodiments, R is H; $R^5$ and $R^{18}$ are $CH_3$; and p is 2. In some embodiments, R is H; $R^{15}$ and $R^{18}$ are $CH_3$; and p is 3.

In some preferred embodiments, X is in equatorial position of

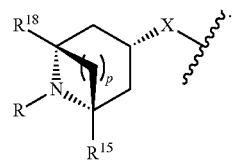

In some embodiments,

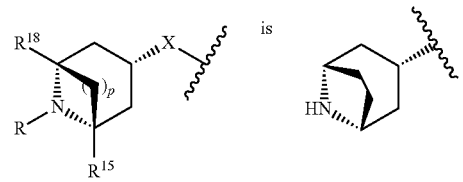

In some embodiments,

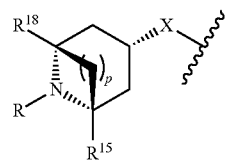

is

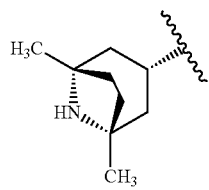

In some embodiments,

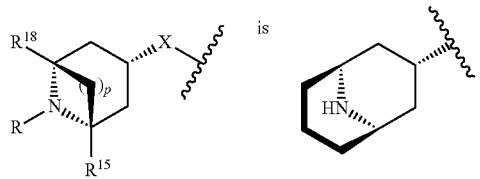

In some embodiments,

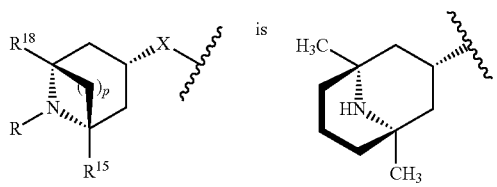

In some preferred embodiments, X is in equatorial position of

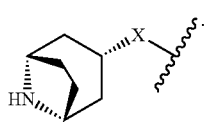

In some other preferred embodiments,

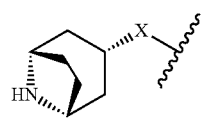

has a structure of

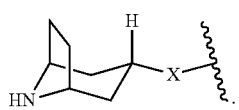

In some preferred embodiments, X is in equatorial position of

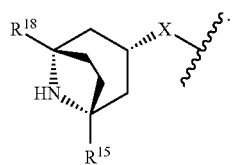

In some other preferred embodiments,

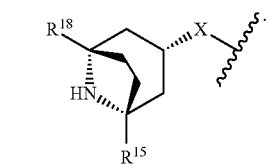

has a structure of

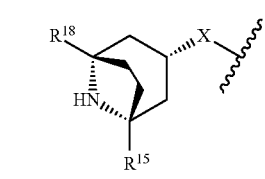

In some preferred embodiments, X is in equatorial position of

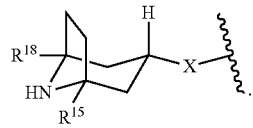

In some other preferred embodiments

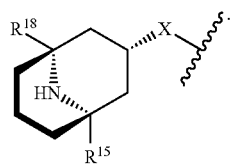

has a structure of

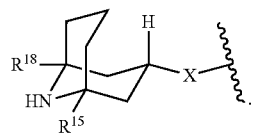

In some embodiments,

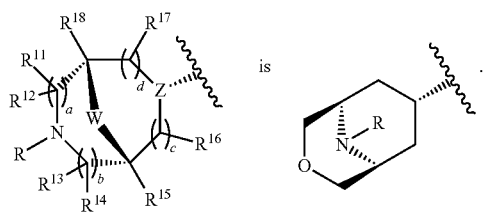

In some preferred embodiments, X is in equatorial position of

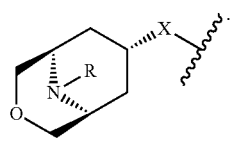

In some embodiments,

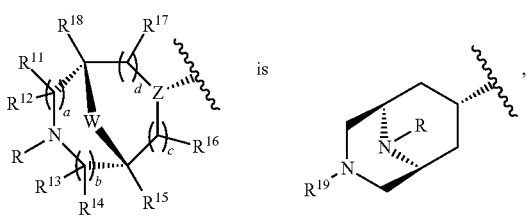

wherein $R^{19}$ is H, D, —CN, —OH, —OR$^1$, —SR$^1$, —S(=O)R$^1$, —S(=O)$_2$R$^1$, —CH$_2$—N(R$^1$)$_2$, —S(=O)$_2$N(R$^1$)$_2$, —C(=O)R$^1$, —CO$_2$R$^1$, —C(=O)N(R$^1$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, or substituted or unsubstituted C$_2$-C$_8$ heterocycloalkyl.

In some preferred embodiments, X is in equatorial position of

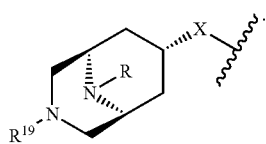

In some embodiments, the compound of Formula (IV) is not racemic. In some preferred embodiments, the compound of Formula (IV) is substantially free of other isomers. In some preferred embodiments, the compound of Formula (IV) is substantially free of other isomers. In some preferred embodiments, the compound of Formula (IV) comprises 25% or less of other isomers. In some preferred embodiments, the compound of Formula (IV) comprises 20% or less of other isomers. In some preferred embodiments, the compound of Formula (IV) comprises 15% or less of other isomers. In some preferred embodiments, the compound of Formula (IV) comprises 10% or less of other isomers. In some preferred embodiments, the compound of Formula (IV) comprises 5% or less of other isomers. In some preferred embodiments, the compound of Formula (IV) comprises 1% or less of other isomers.

In some preferred embodiments, the compound of Formula (IV) has a stereochemical purity of at least 75%. In some preferred embodiments, the compound of Formula (IV) has a stereochemical purity of at least 80%. In some preferred embodiments, the compound of Formula (IV) has a stereochemical purity of at least 85%. In some preferred embodiments, the compound of Formula (IV) has a stereochemical purity of at least 90%. In some preferred embodiments, the compound of Formula (IV) has a stereochemical purity of at least 95%. In some preferred embodiments, the compound of Formula (IV) has a stereochemical purity of at least 96%. In some preferred embodiments, the compound of Formula (IV) has a stereochemical purity of at least 97%. In some preferred embodiments, the compound of Formula (IV) has a stereochemical purity of at least 98%. In some preferred embodiments, the compound of Formula (IV) has a stereochemical purity of at least 99%.

In some preferred embodiments, the asymmetric carbon atom (CR$^7$) of the compound of Formula (IV) is present in enantiomerically enriched form. In certain embodiments, the asymmetric carbon atom (CR$^7$) of the compound of Formula (IV) has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (S)- or (R)-configuration.

In some embodiments, a compound of Formula (IV) is selected from a compound in Table 1A, Table 1B or Table 1C.

In another aspect, described herein is a compound that has the structure of Formula (V), or a pharmaceutically acceptable salt or solvate thereof:

Formula (V)

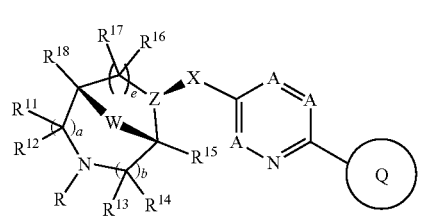

wherein,
each A is independently N or CR$^4$;
each R$^4$ is independently selected from H, D, halogen, —CN, —OH, —OR$^1$, =O, =N—OR$^1$, —SR$^1$, —S(=O)R$^1$, —S(=O)$_2$R$^1$, —N(R$^1$)$_2$, —NR$^1$S(=O)(=NR$^1$)R$^2$, —NR$^1$S(=O)$_2$R$^2$, —S(=O)$_2$N(R$^1$)$_2$, —C(=O)R$^1$, —OC(=O)R$^1$, —C(=O)OR$^1$, —OC(=O)OR$^1$, —C(=O)N(R$^1$)$_2$, —OC(=O)N(R$^1$)$_2$, —NR$^1$C(=O)R$^1$, —P(=O)(R$^2$)$_2$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, and substituted or unsubstituted monocyclic heteroaryl;
ring Q is monocyclic aryl, bicyclic aryl, monocyclic heteroaryl, or fused bicyclic heteroaryl;
X is —O—, —NR$^3$—, —CR$^4$R$^5$—, —C(=O)—, —C(=CR$^2$$_2$)—, —S—, —S(=O)—, —S(=O)$_2$—, or —S(=O)(=NR$^1$)—;
each R$^1$ is independently H, D, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted $C_2$-$C_7$ heterocycloalkyl, substituted or unsubstituted aryl, or substituted or unsubstituted heteroaryl;

each $R^2$ is independently H, D, substituted or unsubstituted $C_1$-$C_6$ alkyl, substituted or unsubstituted $C_1$-$C_6$ haloalkyl, substituted or unsubstituted aryl, substituted or unsubstituted monocyclic heteroaryl, —$OR^1$, —$N(R^1)_2$, —$CH_2OR^1$, —$C(=O)OR^1$, —$OC(=O)R^1$, —$C(=O)N(R^1)_2$, or —$NR^1C(=O)R^1$;

$R^3$ is H, —$OR^1$, —$N(R^1)_2$, substituted or unsubstituted $C_1$-$C_6$ alkyl, —$CD_3$, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^4$ is H, D, F, —CN, —$OR^1$, —$SR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^5$ is H, D, F, —CN, —$OR^1$, —$SR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_1$-$C_6$ alkylene-$OR^1$, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or $R^4$ and R taken in combination with the carbon atom to which they attach, form a substituted or unsubstituted $C_{3-8}$ cycloalkyl or a substituted or unsubstituted $C_{2-7}$ heterocycloalkyl;

Z is $CR^7$; and $R^7$ is H, D, substituted or unsubstituted $C_1$-$C_6$ alkyl, substituted or unsubstituted $C_1$-$C_6$ haloalkyl or —$CH_2OR^1$;

W is substituted or unsubstituted $C_1$-$C_4$ alkylene, substituted or unsubstituted $C_2$-$C_4$ alkenylene, or substituted or unsubstituted $C_1$-$C_4$ heteroalkylene;

R is selected from the group consisting of H, a substituted or unsubstituted $C_{1-6}$ alkyl, substituted or unsubstituted $C_{1-6}$ fluoroalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, and substituted or unsubstituted heteroaryl, wherein alkyl is optionally substituted with hydroxy, amino, substituted or unsubstituted mono-$C_{1-6}$ alkylamino, or substituted or unsubstituted di-$C_{1-6}$ alkylamino;

$R^{11}$, $R^{12}$, $R^{13}$, $R^{14}$, $R^{15}$, $R^{16}$, $R^{17}$, and $R^{18}$ are each independently selected from the group consisting of H, F, $OR^1$, substituted or unsubstituted $C_{1-6}$ alkyl, a substituted or unsubstituted $C_{1-6}$ fluoroalkyl, substituted or unsubstituted $C_1$-$C_6$ heteroalkyl, wherein alkyl is optionally substituted with hydroxy, amino, methoxy, substituted or unsubstituted mono-$C_{1-6}$ alkylamino or substituted or unsubstituted di-$C_{1-6}$ alkylamino;

$R^{11}$ and $R^{13}$, taken in combination form a substituted or unsubstituted $C_{1-3}$ alkylene group or a substituted or unsubstituted $C_{1-3}$ heteroalkylene group; or $R^{11}$ and $R^{13}$, taken in combination form a substituted or unsubstituted $C_{1-3}$ alkylene group; or $R^{16}$ and $R^{17}$, taken in combination form a substituted or unsubstituted $C_{1-3}$ alkylene group; or $R^{13}$ and $R^{14}$, taken in combination with the carbon atom to which they attach, form a spirocyclic $C_{3-8}$ cycloalkyl; or $R^{17}$ and $R^2$, taken in combination form a substituted or unsubstituted $C_{1-3}$ alkylene group; or when X is —$NR^3$—, then $R^3$ and $R^2$ are optionally taken together with the intervening atoms to which they are attached to form a 4, 5, or 6-membered ring; or when X is —$NR^3$—, then $R^3$ and $R^{16}$ are optionally taken together with the intervening atoms to which they are attached to form a 4, 5, or 6-membered ring;

a, b, and e are each independently selected from 0, 1, or 2; and wherein the compound of Formula (V) has a stereochemical purity of at least 80%.

For any and all of the embodiments, substituents are selected from among a subset of the listed alternatives. For example, in some embodiments, a is 0, 1, or 2. In other embodiments, a is 0. In some other embodiments, a is 1. In some other embodiments, a is 2.

In some embodiments,

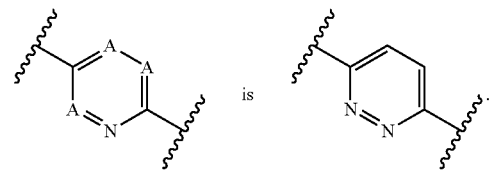

In some embodiments,

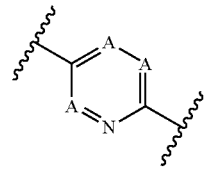

In some embodiments,

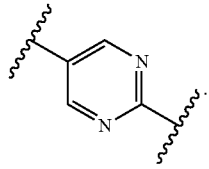 [SMILES: *c1cnc(*)nc1]

In some embodiments,

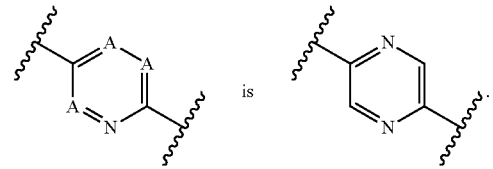

In some embodiments, X is —O—, —$NR^3$—, —S—, —$CR^4R^5$—, —C(=O)—, or —C(=$CR^2_2$)—. In some embodiments, X is —O—. In some embodiments, X is —$NR^3$—. In some embodiments, X is —S—. In some embodiments, X is —$CR^4R^5$—. In some embodiments, X is —C(=O)—. In some embodiments, X is —C(=$CR^2_2$)—.

In some embodiments, X is —CH($CH_2OR^1$)— or —CH($OR^1$)—. In some embodiments, X is —CH($CH_2OR^1$)—. In some embodiments, X is —CH($OR^1$)—.

In some embodiments, R³ is H, —OR¹, —N(R¹)₂, substituted or unsubstituted C₁-C₆ alkyl, substituted or unsubstituted C₁-C₆ haloalkyl, substituted or unsubstituted C₁-C₆ heteroalkyl, substituted or unsubstituted C₃-C₈ cycloalkyl, or substituted or unsubstituted C₂-C₇ heterocycloalkyl.

In some embodiments, R³ is —OR¹, —N(R¹)₂, substituted or unsubstituted C₁-C₆ alkyl, substituted or unsubstituted C₁-C₆ haloalkyl, substituted or unsubstituted C₁-C₆ heteroalkyl, substituted or unsubstituted C₃-C₈ cycloalkyl, or substituted or unsubstituted C₂-C₇ heterocycloalkyl.

In some embodiments, ring Q is substituted or unsubstituted monocyclic aryl. In some embodiments, ring Q is substituted monocyclic aryl. In some embodiments, ring Q is unsubstituted monocyclic aryl.

In some embodiments, ring Q is substituted phenyl. In some embodiments, ring Q is 2-hydroxy-phenyl which is substituted with: 0, 1, 2, or 3 substituents independently selected from C₁₋₆ alkyl, oxo, oxime, hydroxy, halo-C₁₋₆ alkyl, dihalo-C₁₋₆ alkyl, trihalo-C₁₋₆ alkyl, C₁₋₆ alkoxy, C₁₋₆ alkoxy-C₃₋₇ cycloalkyl, halo-C₁₋₆ alkoxy, dihalo-C₁₋₆ alkoxy, trihalo-C₁₋₆ alkoxy, hydroxy, cyano, halogen, amino, mono-C₁₋₆ alkylamino, di-C₁₋₆ alkylamino, heteroaryl, C₁₋₆ alkyl substituted with hydroxy, C₁₋₆ alkoxy substituted with aryl, amino, —C(=O)NH—C₁₋₆ alkyl-heteroaryl, —NHC(=O)—C₁₋₆ alkylheteroaryl, C₁₋₆ alkyl-C(=O)NH-heteroaryl, C₁₋₆ alkyl-NHC(=O)-heteroaryl, C₃₋₇ cycloalkyl, 5-7 membered cycloalkenyl, or 5, 6 or 9 membered heterocycle containing 1 or 2 heteroatoms independently, selected from S, O and N.

In some embodiments, ring Q is 2-hydroxy-phenyl which is substituted with two C₁₋₆ alkyl. In some embodiments, two C₁₋₆ alkyl groups can combine with the atoms to which they are bound to form a 5-6 membered ring.

In some embodiments, ring Q is 2-hydroxy-phenyl which is substituted with heteroaryl. In some embodiments, heteroaryl has 5, 6, 9, or 10 ring atoms, 1, 2 or 3 ring heteroatoms selected from N, O and S, and is substituted with 0, 1, or 2 substituents independently selected from oxo, hydroxy, nitro, halogen, C₁₋₆ alkyl, C₁₋₆ alkenyl, C₁₋₆ alkoxy, C₃₋₇ cycloalkyl, C₁₋₆ alkyl-OH, trihalo-C₁₋₆ alkyl, mono-C₁₋₆ alkylamino, di-C₁₋₆ alkylamino, —C(=O)NH₂, —NH₂, —NO₂, hydroxy-C₁₋₆ alkylamino, hydroxy-C₁₋₆ alkyl, 4-7 membered heterocycle-C₁₋₆ alkyl, amino-C₁₋₆ alkyl, mono-C₁₋₆ alkylamino-C₁₋₆ alkyl, and di-C₁₋₆ alkylamino-C₁₋₆ alkyl.

In some embodiments, ring Q is

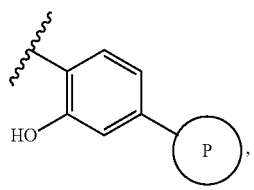

wherein ring P is aryl or heteroaryl. In some embodiments, ring Q is

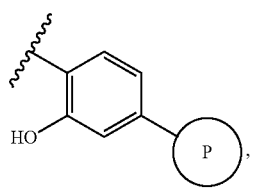

wherein ring P is aryl. In some embodiments, ring Q is

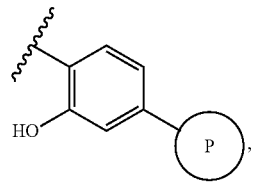

wherein ring P is heteroaryl In some embodiments, the heteroaryl is selected from the group consisting of.

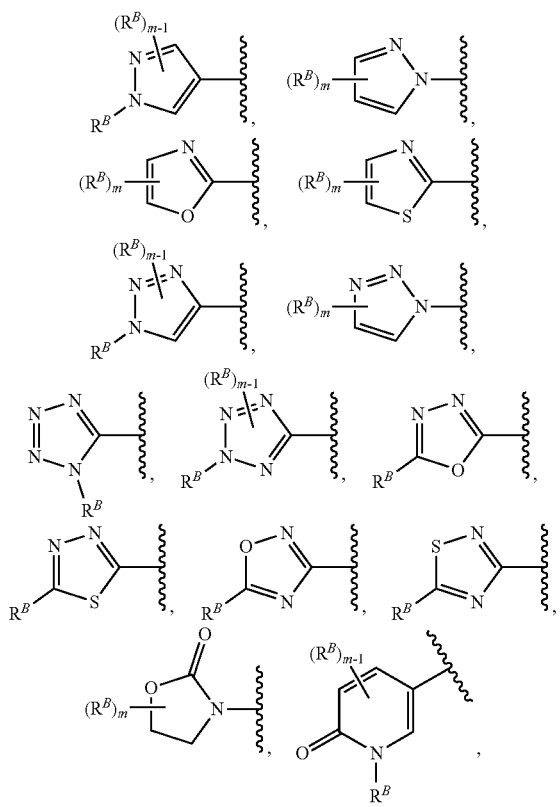

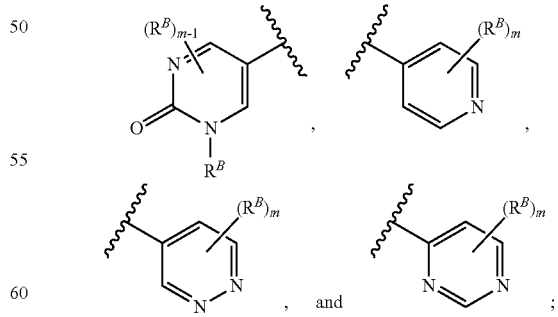

wherein
each R^B is independently selected from cyano, halogen, hydroxy, substituted or unsubstituted C₁₋₆ alkyl, —OCH₃, —OCD₃, substituted or unsubstituted C₂₋₆ alkenyl, substituted or unsubstituted C₂₋₆ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is

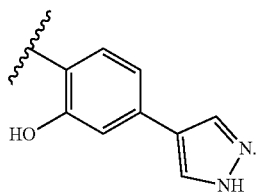 [SMILES: *c1ccc(-c2cn[nH]c2)cc1O]

In some embodiments, ring Q is

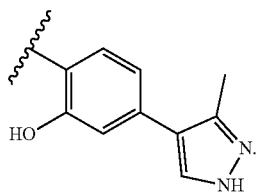 [SMILES: *c1ccc(-c2c[nH]nc2C)cc1O]

In some embodiments, ring Q is

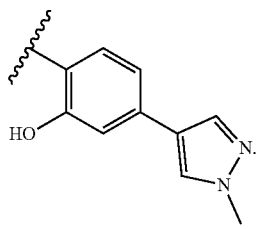 [SMILES: *c1ccc(-c2cnn(C)c2)cc1O]

In some embodiments, ring Q is

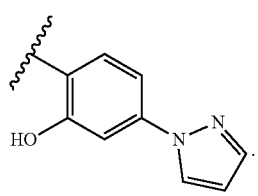 [SMILES: *c1ccc(-n2cccn2)cc1O]

In some embodiments, ring Q is

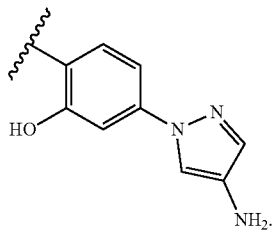

In some embodiments, ring Q is

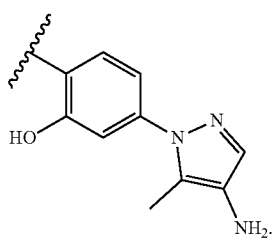 [SMILES: *c1ccc(-n2ncc(N)c2C)cc1O]

In some embodiments, ring Q is

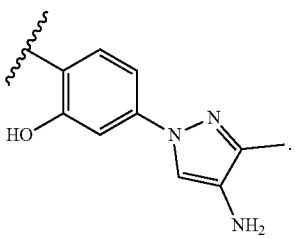 [SMILES: *c1ccc(-n2cc(N)c(C)n2)cc1O]

In some embodiments, ring Q is

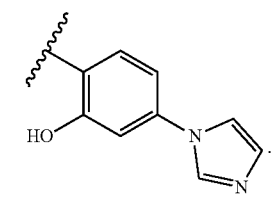

In some embodiments, ring Q is

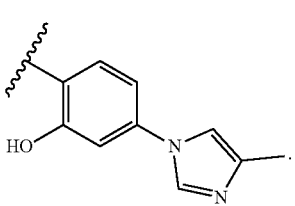 [SMILES: *c1ccc(-n2cnc(C)c2)cc1O]

In some embodiments, ring Q is
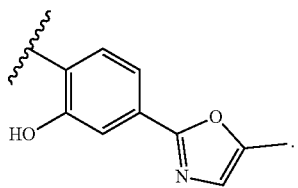 [SMILES: *c1ccc(-c2ncc(C)o2)cc1O]
In some embodiments, ring Q is
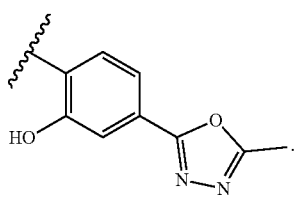
In some embodiments, ring Q is
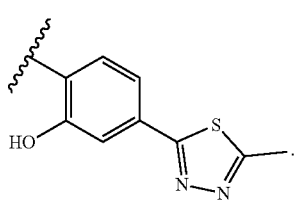
In some embodiments, ring Q is
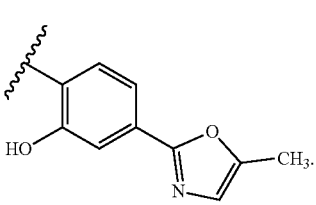 [SMILES: *c1ccc(-c2ncc(C)o2)cc1O]
In some embodiments, ring Q is
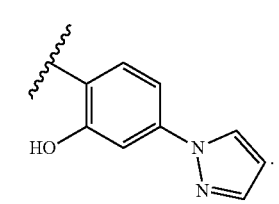
In some embodiments, ring Q is
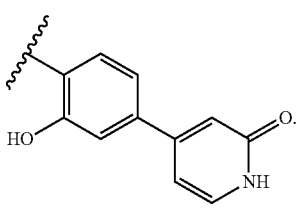 [SMILES: *c1ccc(-c2cc[nH]c(=O)c2)cc1O]
In some embodiments, ring Q is
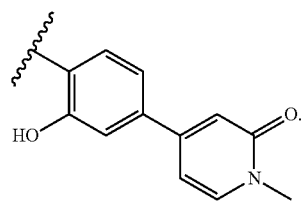 [SMILES: *c1ccc(-c2ccn(C)c(=O)c2)cc1O]
In some embodiments, ring Q is
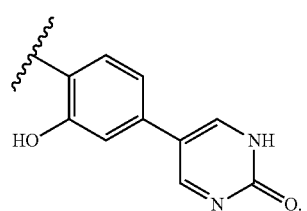 [SMILES: *c1ccc(-c2cnc(=O)[nH]c2)cc1O]
In some embodiments, ring Q is
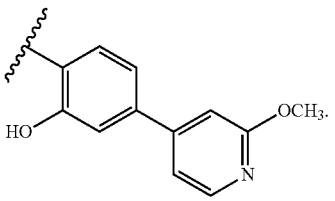
In some embodiments, ring Q is
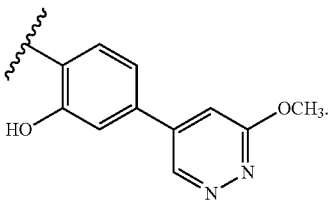
In some embodiments, ring Q is
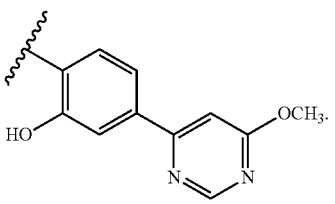

In some embodiments, ring Q is

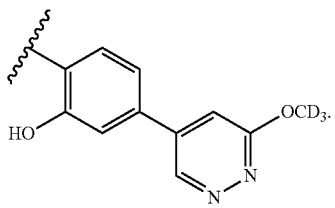

In some embodiments, ring Q is

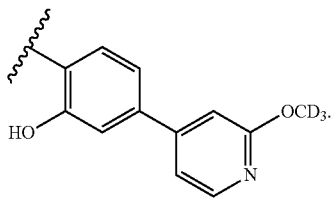

In some embodiments, ring Q is

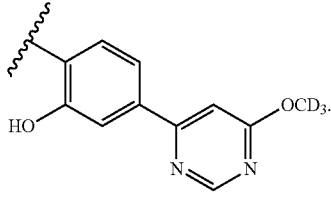

In some embodiments, ring Q is 2-naphthyl optionally substituted at the 3 position with hydroxy and additionally substituted with 0, 1, or 2 substituents selected from hydroxy, cyano, halogen, $C_{1-6}$ alkyl, $C_{2-6}$ alkenyl, $C_{1-6}$ alkoxy, wherein the alkoxy is unsubstituted or substituted with hydroxy, $C_{1-6}$ alkoxy, amino, —NHC(=O)—$C_{1-6}$ alkyl, —NHC(=O)—$C_{1-6}$ alkyl, $C_{1-6}$ alkylene-4-7 membered heterocycle, 4-7 membered heterocycle, mono-$C_{1-6}$ alkylamino, and di-$C_{1-6}$ alkylamino.

In some embodiments, ring Q is

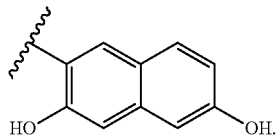 [SMILES: *c1cc2ccc(O)cc2cc1O]

In some embodiments, ring Q is

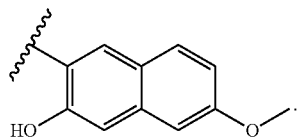 [SMILES: *c1cc2ccc(OC)cc2cc1O]

In some embodiments, ring Q is

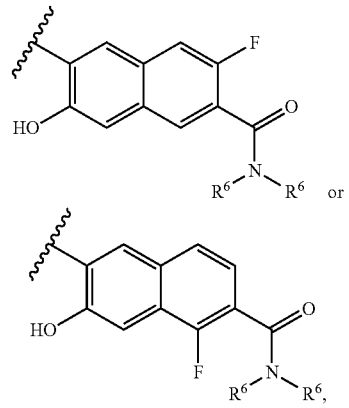

and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, ring Q is monocyclic heteroaryl or fused bicyclic heteroaryl.

In some embodiments, ring Q is a 5 or 6 membered monocyclic heteroaryl having 1-4 ring nitrogen atoms and which is substituted by phenyl or a heteroaryl having 5 or 6 ring atoms, 1 or 2 ring heteroatoms independently selected from N, O and S and is substituted with 0, 1, or 2 substituents independently selected from cyano, $C_{1-6}$ alkyl, mono-$C_{1-6}$ alkylamino, di-$C_{1-6}$ alkylamino, hydroxy-$C_{1-6}$ alkylamino, hydroxy-$C_{1-6}$ alkyl, amino-$C_{1-6}$ alkyl and mono-$C_{1-6}$ alkylamino-$C_1$-alkyl, and di-$C_{1-6}$ alkylamino-$C_{1-6}$ alkyl.

In some embodiments, ring Q is a 5 membered monocyclic heteroaryl selected from the group consisting of:

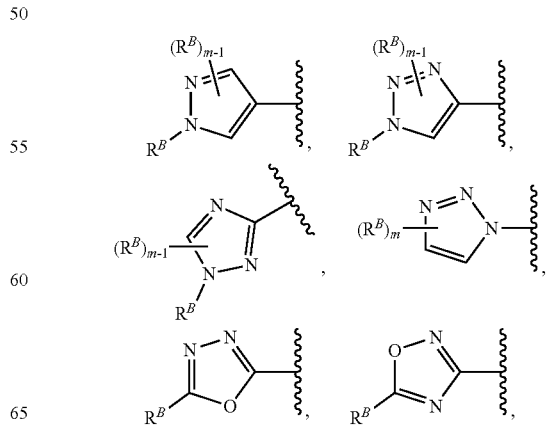

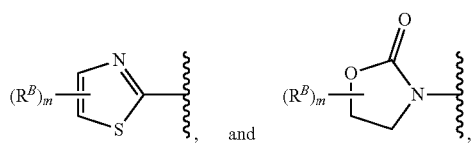

wherein
each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a 6 membered monocyclic heteroaryl selected from the group consisting of:

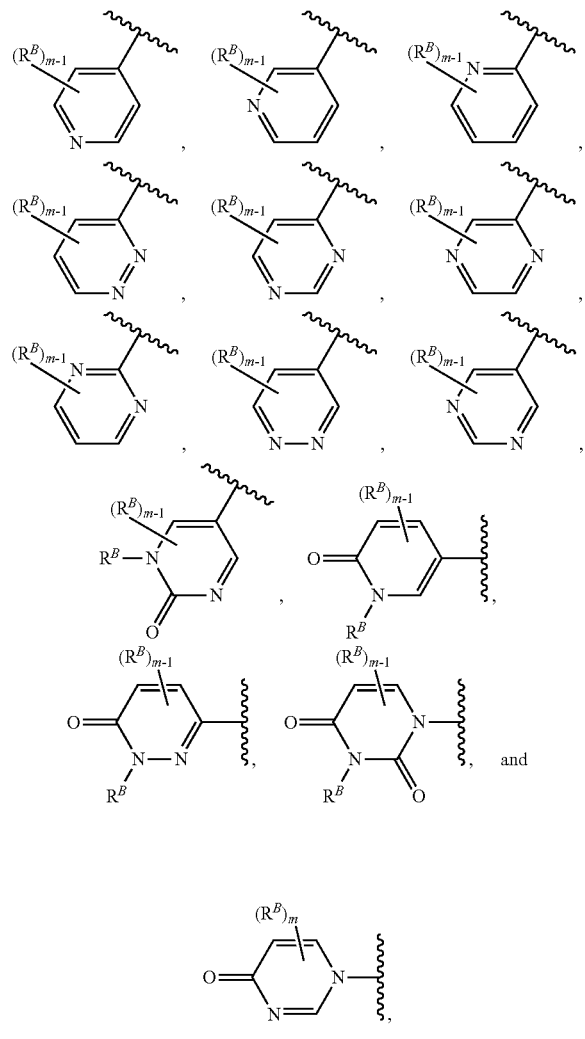

wherein
each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 0, 1, 2, or 3.

In some embodiments, ring Q is a fused bicyclic heteroaryl having 8 to 10 ring atoms, 1, 2, or 3 ring heteroatoms independently selected from N, O or S, and which is substituted with 0, 1, or 2 substituents independently selected from cyano, oxime, halogen, hydroxy, $C_{1-6}$ alkyl, $C_{24}$ alkenyl, $C_{24}$ alkynyl, $C_{1-6}$ alkoxy, $C_{1-6}$ alkoxy substituted with hydroxy, amino, mono-$C_{1-6}$ alkylamino, and di-$C_{1-6}$ alkylamino.

In some embodiments, ring Q is a 6-5 fused heteroaryl, 6-6 fused heteroaryl, 5-6 fused heteroaryl, 5-5 fused heteroaryl, 7-5 fused heteroaryl, or 5-7 fused heteroaryl.

In some embodiments, ring Q is a 6-5 fused heteroaryl, 6-6 fused heteroaryl, or 5-6 fused heteroaryl, selected from the group consisting of:

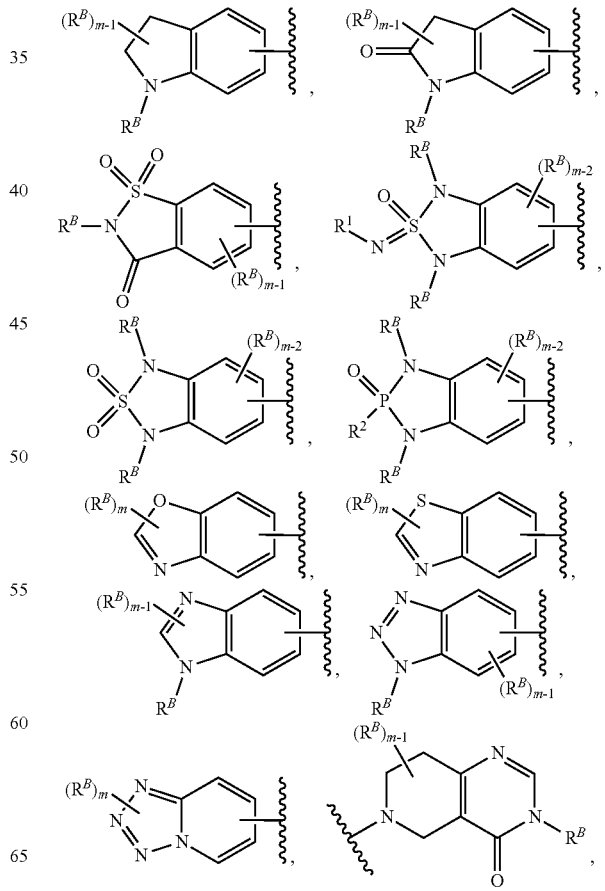

137
-continued

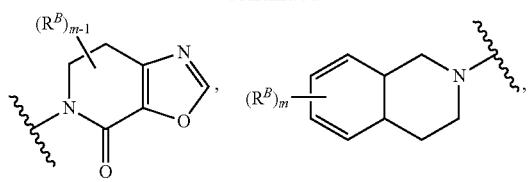
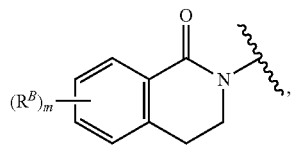
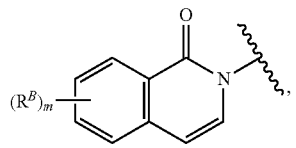
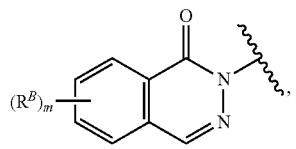
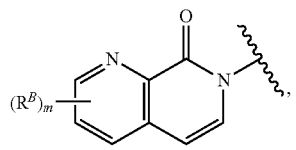
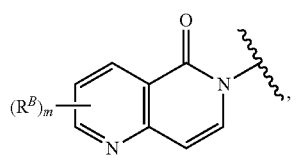
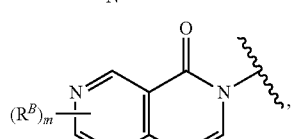
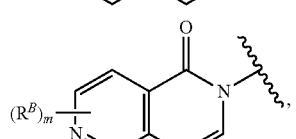
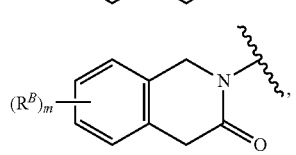
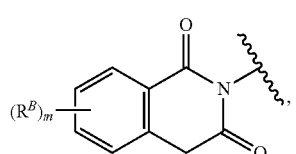
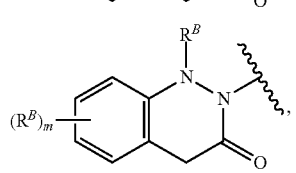

138
-continued

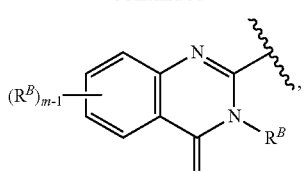
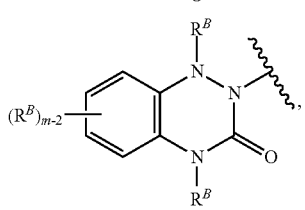
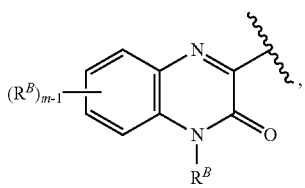
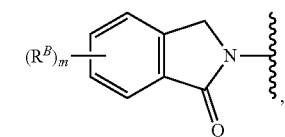
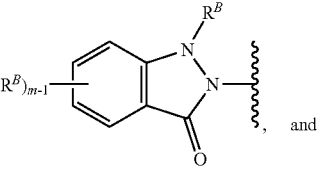
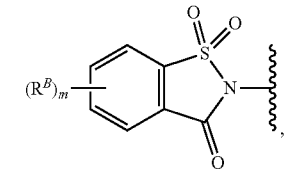

wherein each $R^B$ is independently selected from cyano, halogen, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, substituted or unsubstituted $C_{1-6}$ alkoxy-heteroaryl, and $C_{1-6}$ alkoxy substituted with hydroxy, $C_{1-6}$ alkoxy, amino, mono-$C_{1-6}$ alkylamino and di-$C_{1-6}$ alkylamino; and m is 1, 2, or 3.

In some embodiments, ring Q is

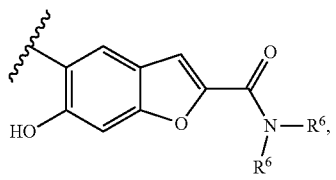

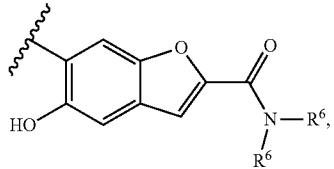

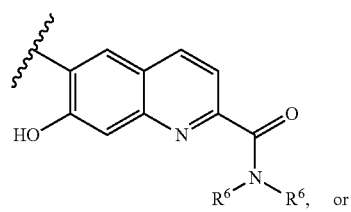

, or

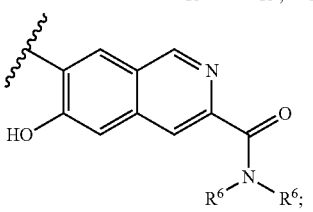

;

and each $R^6$ is independently H, —$OR^1$, —$N(R^1)_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; or two $R^6$ are taken together with the N atom to which they are attached to form a substituted or unsubstituted $C_2$-$C_6$ heterocycloalkyl. In some embodiments, each $R^6$ is independently H, substituted or unsubstituted $C_1$-$C_6$ alkyl, substituted or unsubstituted $C_1$-$C_6$ heteroalkyl, or substituted or unsubstituted $C_3$-$C_8$ cycloalkyl. In some embodiments, each $R^6$ is independently H, substituted or unsubstituted $C_1$-$C_4$ alkyl, or substituted or unsubstituted $C_3$-$C_6$ cycloalkyl.

In some embodiments, X is —$NR^3$—.

In some embodiments, $R^3$ is —$OR^1$, substituted or unsubstituted $C_1$-$C_6$ alkyl, substituted or unsubstituted $C_1$-$C_6$ haloalkyl, substituted or unsubstituted $C_1$-$C_6$ heteroalkyl, or substituted or unsubstituted $C_3$-$C_8$ cycloalkyl.

In some embodiments, $R^3$ is —$OR^1$. In some embodiments, $R^3$ is —$OCH_3$, —$OCH_2CH_3$, —$OCH_2CH_2OH$ or —$OCH_2CH_2OCH_3$. In some embodiments, $R^3$ is —$OCH_3$. In some embodiments, $R^3$ is —$OCH_2CH_3$. In some embodiments, $R^3$ is —$OCH_2CH_2CH_3$. In some embodiments, $R^3$ is —$OCH(CH_3)_2$. In some embodiments, $R^3$ is —$OCD_3$.

In some embodiments, $R^3$ is —$CD_3$.

In some embodiments, $R^3$ is substituted or unsubstituted $C_1$-$C_6$ haloalkyl. In some embodiments, $R^3$ is $CF_3$. In some embodiments, $R^3$ is —$CH_2CH_2F$. In some embodiments, $R^3$ is —$CH_2CH_2CH_2F$. In some embodiments, $R^3$ is —$CH_2CF_3$. In some embodiments, $R^3$ is —$CH_2CH_2CF_3$.

In some embodiments, $R^3$ is —$CH_3$ or —$CF_3$.

In some embodiments, $R^3$ is substituted or unsubstituted $C_1$-$C_6$ heteroalkyl. In some embodiments, $R^3$ is —$OCH_2CH_2OCH_3$ or —$OCH_2CH_2OCF_3$. In some embodiments, $R^3$ is —$CH_2CH_2OCH_3$.

In some embodiments, $R^3$ is substituted or unsubstituted $C_3$-$C_8$ cycloalkyl. In some embodiments, $R^3$ is cyclopropyl, cyclobutyl, cyclopentyl, cyclohexyl, cycloheptyl, or cyclooctyl. In some embodiments, $R^3$ is cyclopropyl, cyclobutyl, cyclopentyl, or cyclohexyl. In some embodiments, $R^3$ is cyclopropyl. In some embodiments, $R^3$ is cyclobutyl. In some embodiments, $R^3$ is cyclopentyl. In some embodiments, $R^3$ is cyclohexyl.

In some embodiments, $R^3$ is cyclopentenyl, cyclohexenyl, cycloheptenyl, or cyclooctenyl. In some embodiments, $R^3$ is cyclopentenyl or cyclohexenyl. In some embodiments, $R^3$ is cyclopentenyl. In some embodiments, $R^3$ is cyclohexenyl.

In some embodiments,

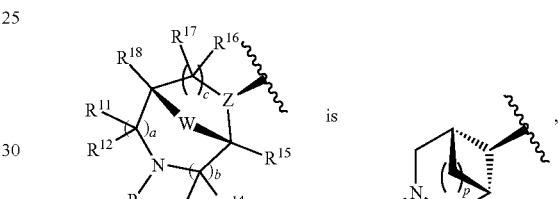

wherein p is 1, 2, or 3.

In some preferred embodiments, X is in equatorial position of

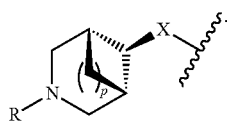

.

In some embodiments,

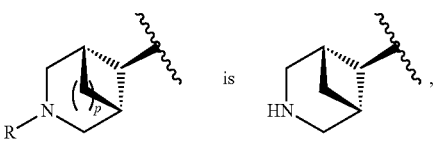

,

In some embodiments,

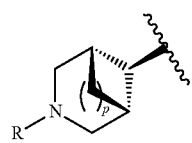

is

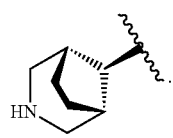

In some preferred embodiments, X is in equatorial position of

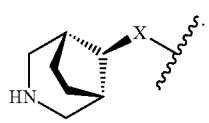

In some other preferred embodiments

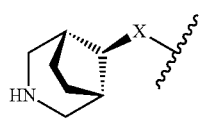

has a structure of

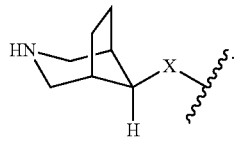

In some embodiments,

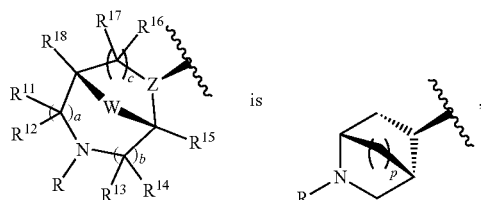 is 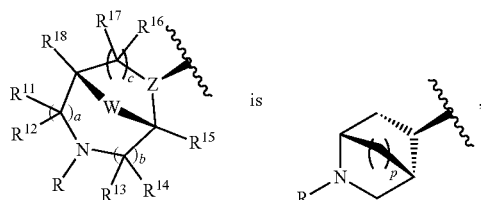, wherein p is 1, 2, or 3.

In some preferred embodiments, X is in equatorial position of R

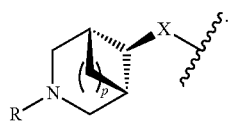

In some embodiments,

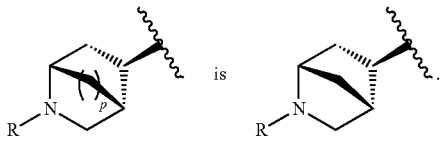 is 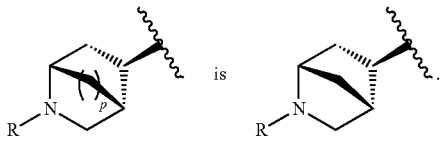.

In some embodiments,

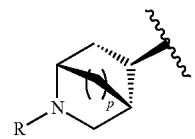

is

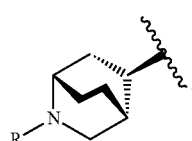

In some embodiments,

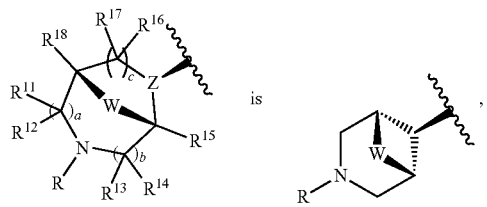 is 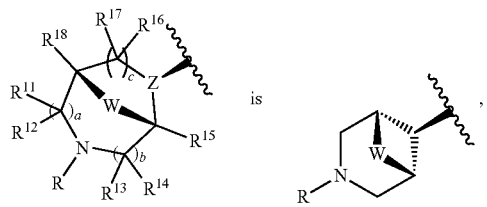, wherein W is —CH$_2$OCH$_2$—.

In some preferred embodiments, X is in equatorial position of

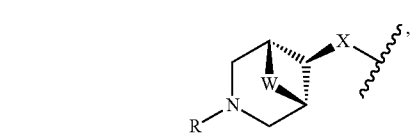

wherein W is —CH$_2$OCH$_2$—.

In some embodiments,

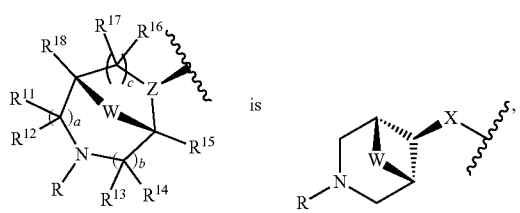 is 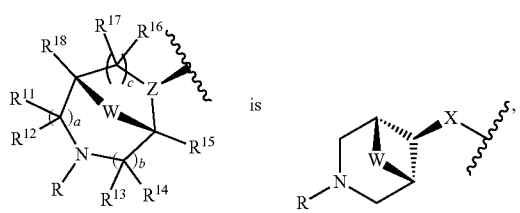, wherein W is —CH$_2$N(R$^{19}$)CH$_2$—, wherein R$^{19}$ is H, D, —CN, —OH, —OR$^1$, —SR$^1$, —S(=O)R$^1$, —S(=O)$_2$R$^1$, —CH$_2$—N(R$^1$)$_2$, —S(=O)$_2$N(R$^1$)$_2$, —C(=O)R$^1$, —CO$_2$R$^1$, —C(=O)N(R$^1$)$_2$, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, or substituted or unsubstituted $C_2$-$C_8$ heterocycloalkyl.

In some preferred embodiments, X is in equatorial position of

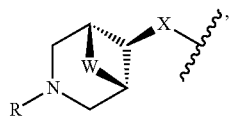

wherein W is —$CH_2N(R^{19})CH_2$—.

In some embodiments, the compound of Formula (V) is not racemic. In some preferred embodiments, the compound of Formula (V) is substantially free of other isomers. In some preferred embodiments, the compound of Formula (V) is a single isomer substantially free of other isomers. In some preferred embodiments, the compound of Formula (V) comprises 25% or less of other isomers. In some preferred embodiments, the compound of Formula (V) comprises 20% or less of other isomers. In some preferred embodiments, the compound of Formula (V) comprises 15% or less of other isomers. In some preferred embodiments, the compound of Formula (V) comprises 10% or less of other isomers. In some preferred embodiments, the compound of Formula (V) comprises 5% or less of other isomers. In some preferred embodiments, the compound of Formula (V) comprises 1% or less of other isomers.

In some preferred embodiments, the compound of Formula (V) has a stereochemical purity of at least 75%. In some preferred embodiments, the compound of Formula (V) has a stereochemical purity of at least 80%. In some preferred embodiments, the compound of Formula (V) has a stereochemical purity of at least 85%. In some preferred embodiments, the compound of Formula (V) has a stereochemical purity of at least 90%. In some preferred embodiments, the compound of Formula (V) has a stereochemical purity of at least 95%. In some preferred embodiments, the compound of Formula (V) has a stereochemical purity of at least 96%. In some preferred embodiments, the compound of Formula (V) has a stereochemical purity of at least 97%. In some preferred embodiments, the compound of Formula (V) has a stereochemical purity of at least 98%. In some preferred embodiments, the compound of Formula (V) has a stereochemical purity of at least 99%.

In some embodiments, the asymmetric carbon atom ($CR^7$) of the compound of Formula (V) is present in enantiomerically enriched form. In certain embodiments, the asymmetric carbon atom ($CR^7$) of the compound of Formula (V) has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (S)- or (R)-configuration.

In some embodiments, a compound of Formula (V) is selected from a compound in Table 1A, Table 1B or Table 1C Any combination of the groups described above for the various variables is contemplated herein. Throughout the specification, groups and substituents thereof are chosen by one skilled in the field to provide stable moieties and compounds.

In some embodiments, a compound of Formula (I), (II), (III), (IV) or (V) is selected from:
(6-(2-hydroxy-4-(1H-pyrazol-4-yl)phenyl)pyridazin-3-yl) (piperazin-1-yl)methanone;
2-(6-(piperidin-4-ylthio)pyridazin-3-yl)-5-(1H-pyrazol-4-yl)phenol;
(3,6-diazabicyclo[3.1.1]heptan-3-yl)(6-(2-hydroxy-4-(1H-pyrazol-4-yl)phenyl)pyridazin-3-yl)methanone;
2-(6-((6-azabicyclo[3.1.1]heptan-3-yl)(2-fluoroethyl) amino)pyridazin-3-yl)-5-(1H-pyrazol-4-yl)phenol;
(3,8-diazabicyclo[3.2.1]octan-3-yl)(6-(2-hydroxy-4-(1H-pyrazol-4-yl)phenyl)pyridazin-3-yl)methanone;
2-(6-((8-azabicyclo[3.2.1]octan-3-yl)(2-fluoroethyl)amino) pyridazin-3-yl)-5-(1H-pyrazol-4-yl)phenol;
2-(6-(octahydro-1,6-naphthyridin-1(2H)-yl)pyridazin-3-yl)-5-(1H-pyrazol-4-yl)phenol;
2-(6-(methoxy(2,2,6,6-tetramethylpiperidin-4-yl)amino) pyridazin-3-yl)-5-(1H-pyrazol-4-yl)phenol;
2-(6-(hydroxy(2,2,6,6-tetramethylpiperidin-4-yl)methyl) pyridazin-3-yl)-5-(1H-pyrazol-4-yl)phenol;
(6-(2-hydroxy-4-(1H-pyrazol-4-yl)phenyl)pyridazin-3-yl) (3,3,5,5-tetramethylpiperazin-1-yl)methanone;
(6-(2-hydroxy-4-(1H-pyrazol-4-yl)phenyl)pyridazin-3-yl) (2,2,6,6-tetramethylpiperidin-4-yl)methanone;
5-(1H-pyrazol-4-yl)-2-(6-((2,2,6,6-tetramethylpiperidin-4-yl)thio)pyridazin-3-yl)phenol;
2-(6-((2-methoxyethoxy)(2,2,6,6-tetramethylpiperidin-4-yl) amino)pyridazin-3-yl)-5-(1H-pyrazol-4-yl)phenol;
5-(1H-pyrazol-4-yl)-2-(6-((2,2,6,6-tetramethylpiperidin-4-ylidene)methyl)pyridazin-3-yl)phenol;
5-(1H-pyrazol-4-yl)-2-(6-((2,2,6,6-tetramethylpiperidin-4-yl)(trifluoromethyl)amino)pyridazin-3-yl)phenol;
2-(6-((2-fluoroethyl)(2,2,6,6-tetramethylpiperidin-4-yl) amino)pyridazin-3-yl)-5-(1H-pyrazol-4-yl)phenol;
5-(1H-pyrazol-4-yl)-2-(6-((2,2,6,6-tetramethylpiperidin-4-yl)(2,2,2-trifluoroethyl)amino)pyridazin-3-yl)phenol;
2-(6-((3-fluoropropyl)(2,2,6,6-tetramethylpiperidin-4-yl) amino)pyridazin-3-yl)-5-(1H-pyrazol-4-yl)phenol;
5-(1H-pyrazol-4-yl)-2-(6-((2,2,6,6-tetramethylpiperidin-4-yl)(3,3,3-trifluoropropyl)amino)pyridazin-3-yl)phenol;
3-(6-((2-fluoroethyl)(2,2,6,6-tetramethylpiperidin-4-yl) amino)pyridazin-3-yl)-7-methoxynaphthalen-2-ol;
2-(6-((2-fluoroethyl)(2,2,6,6-tetramethylpiperidin-4-yl) amino)pyridazin-3-yl)-5-(1-methyl-1H-pyrazol-4-yl)phenol;
2-(6-((2-fluoroethyl)(2,2,6,6-tetramethylpiperidin-4-yl) amino)pyridazin-3-yl)-5-(5-methyl-1H-pyrazol-4-yl)phenol;
2-(6-((2-fluoroethyl)(2,2,6,6-tetramethylpiperidin-4-yl) amino)pyridazin-3-yl)-5-(5-methyloxazol-2-yl)phenol;
2-(6-((2-fluoroethyl)(2,2,6,6-tetramethylpiperidin-4-yl) amino)pyridazin-3-yl)-5-(1H-pyrazol-1-yl)phenol;
5-(4-(6-((2-fluoroethyl)(2,2,6,6-tetramethylpiperidin-4-yl) amino)pyridazin-3-yl)-3-hydroxyphenyl)pyridin-2(1H)-one;
5-(4-(6-((2-fluoroethyl)(2,2,6,6-tetramethylpiperidin-4-yl) amino)pyridazin-3-yl)-3-hydroxyphenyl)pyrimidin-2 (1H)-one;
2-(6-((2-methoxyethoxy)(2,2,6,6-tetramethylpiperidin-4-yl) methyl)pyridazin-3-yl)-5-(1H-pyrazol-4-yl)phenol;
2-(6-(((1R,3s,5S)-8-azabicyclo[3.2.1]octan-3-yl)oxy) pyridazin-3-yl)-5-(1H-pyrazol-4-yl)phenol;
2-(6-(((1R,3s,5S)-8-azabicyclo[3.2.1]octan-3-yl)oxy) pyridazin-3-yl)-5-(5-methyloxazol-2-yl)phenol;
2-(6-(((1R,3s,5S)-8-azabicyclo[3.2.1]octan-3-yl)oxy) pyridazin-3-yl)-5-(4-methyl-1H-imidazol-1-yl)phenol;

2-(6-(((1R,3s,5S)-8-azabicyclo[3.2.1]octan-3-yl)oxy)
pyridazin-3-yl)-5-(1H-imidazol-1-yl)phenol;
2-(6-(((1R,3s,5S)-8-azabicyclo[3.2.1]octan-3-yl)oxy)
pyridazin-3-yl)-5-(3-methyl-1H-pyrazol-4-yl)phenol;
2-(6-(((1R,3s,5S)-8-azabicyclo[3.2.1]octan-3-yl)oxy)
pyridazin-3-yl)-5-(1-methyl-1H-pyrazol-4-yl)phenol;
2-(6-(((1R,3s,5S)-8-azabicyclo[3.2.1]octan-3-yl)oxy)
pyridazin-3-yl)-5-(1H-pyrazol-1-yl)phenol;
4-(4-(6-(((1R,3s,5S)-8-azabicyclo[3.2.1]octan-3-yl)oxy)
pyridazin-3-yl)-3-hydroxyphenyl)pyridin-2(1H)-one;
4-(4-(6-(((1R,3s,5S)-8-azabicyclo[3.2.1]octan-3-yl)oxy)
pyridazin-3-yl)-3-hydroxyphenyl)-1-methylpyridin-2
(1H)-one;
2-(6-(((1R,3s,5S)-8-azabicyclo[3.2.1]octan-3-yl)oxy)
pyridazin-3-yl)-5-(4-amino-1H-pyrazol-1-yl)phenol;
2-(6-(((1R,3s,5S)-8-azabicyclo[3.2.1]octan-3-yl)oxy)
pyridazin-3-yl)-5-(4-amino-5-methyl-1H-pyrazol-1-yl)
phenol;
2-(6-(((1R,3s,5S)-8-azabicyclo[3.2.1]octan-3-yl)oxy)
pyridazin-3-yl)-5-(4-amino-3-methyl-1H-pyrazol-1-yl)
phenol;
2-(6-(((1R,3s,5S)-8-azabicyclo[3.2.1]octan-3-yl)oxy)
pyridazin-3-yl)-5-(5-methyl-1,3,4-oxadiazol-2-yl)phenol;
2-(6-(((1R,3s,5S)-8-azabicyclo[3.2.1]octan-3-yl)oxy)
pyridazin-3-yl)-5-(5-methyl-1,3,4-thiadiazol-2-yl)phenol;
3-(6-(((1R,3s,5S)-8-azabicyclo[3.2.1]octan-3-yl)oxy)
pyridazin-3-yl)-7-methoxynaphthalen-2-ol;
3-(6-(((1R,3s,5S)-8-azabicyclo[3.2.1]octan-3-yl)oxy)
pyridazin-3-yl)naphthalene-2,7-diol;
6-(6-(((1R,3s,5S)-8-azabicyclo[3.2.1]octan-3-yl)oxy)
pyridazin-3-yl)isoquinolin-7-ol;
6-(6-(((1R,3s,5S)-8-azabicyclo[3.2.1]octan-3-yl)oxy)
pyridazin-3-yl)-1-methylisoquinolin-7-ol;
2-(6-(((1R,3s,5S)-8-azabicyclo[3.2.1]octan-3-yl)(methyl)
amino)pyridazin-3-yl)-5-(1H-pyrazol-4-yl)phenol;
2-(6-(((1R,3s,5S)-8-azabicyclo[3.2.1]octan-3-yl)thio)
pyridazin-3-yl)-5-(1H-pyrazol-4-yl)phenol;
((1R,3s,5S)-8-azabicyclo[3.2.1]octan-3-yl)(6-(2-hydroxy-4-
(1H-pyrazol-4-yl)phenyl)pyridazin-3-yl)methanone;
2-(6-(1-((1R,3s,5S)-8-azabicyclo[3.2.1]octan-3-yl)vinyl)
pyridazin-3-yl)-5-(1H-pyrazol-4-yl)phenol;
2-(6-(((1R,3s,5S)-8-azabicyclo[3.2.1]octan-3-yl)(methyl)
amino)pyridazin-3-yl)-5-(5-methyloxazol-2-yl)phenol;
2-(6-(((1R,3s,5S)-8-azabicyclo[3.2.1]octan-3-yl)(methyl)
amino)pyridazin-3-yl)-5-(4-methyl-1H-imidazol-1-yl)
phenol;
2-(6-(((1R,3s,5S)-8-azabicyclo[3.2.1]octan-3-yl)(methyl)
amino)pyridazin-3-yl)-5-(1H-imidazol-1-yl)phenol;
2-(6-(((1R,3s,5S)-8-azabicyclo[3.2.1]octan-3-yl)(methyl)
amino)pyridazin-3-yl)-5-(3-methyl-1H-pyrazol-4-yl)phenol;
2-(6-(((1R,3s,5S)-8-azabicyclo[3.2.1]octan-3-yl)(methyl)
amino)pyridazin-3-yl)-5-(1-methyl-1H-pyrazol-4-yl)phenol;
2-(6-(((1R,3s,5S)-8-azabicyclo[3.2.1]octan-3-yl)(methyl)
amino)pyridazin-3-yl)-5-(1H-pyrazol-1-yl)phenol;
4-(4-(6-(((1R,3s,5S)-8-azabicyclo[3.2.1]octan-3-yl)
(methyl)amino)pyridazin-3-yl)-3-hydroxyphenyl)pyridin-2(1H)-one;
4-(4-(6-(((1R,3s,5S)-8-azabicyclo[3.2.1]octan-3-yl)
(methyl)amino)pyridazin-3-yl)-3-hydroxyphenyl)-1-methylpyridin-2(1H)-one;
2-(6-(((1R,3s,5S)-8-azabicyclo[3.2.1]octan-3-yl)(methyl)
amino)pyridazin-3-yl)-5-(4-amino-1H-pyrazol-1-yl)phenol;
2-(6-(((1R,3s,5S)-8-azabicyclo[3.2.1]octan-3-yl)(methyl)
amino)pyridazin-3-yl)-5-(4-amino-5-methyl-1H-pyrazol-1-yl)phenol;
2-(6-(((1R,3s,5S)-8-azabicyclo[3.2.1]octan-3-yl)(methyl)
amino)pyridazin-3-yl)-5-(4-amino-3-methyl-1H-pyrazol-1-yl)phenol;
2-(6-(((1R,3s,5S)-8-azabicyclo[3.2.1]octan-3-yl)(methyl)
amino)pyridazin-3-yl)-5-(5-methyl-1,3,4-oxadiazol-2-yl)phenol;
2-(6-(((1R,3s,5S)-8-azabicyclo[3.2.1]octan-3-yl)(methyl)
amino)pyridazin-3-yl)-5-(5-methyl-1,3,4-thiadiazol-2-yl)phenol;
3-(6-(((1R,3s,5S)-8-azabicyclo[3.2.1]octan-3-yl)(methyl)
amino)pyridazin-3-yl)-7-methoxynaphthalen-2-ol;
3-(6-(((1R,3s,5S)-8-azabicyclo[3.2.1]octan-3-yl)(methyl)
amino)pyridazin-3-yl)naphthalene-2,7-diol;
6-(6-(((1R,3s,5S)-8-azabicyclo[3.2.1]octan-3-yl)(methyl)
amino)pyridazin-3-yl)isoquinolin-7-ol;
6-(6-(((1R,3s,5S)-8-azabicyclo[3.2.1]octan-3-yl)(methyl)
amino)pyridazin-3-yl)-1-methylisoquinolin-7-ol;
2-(6-(((1R,3s,5S)-1,5-dimethyl-8-azabicyclo[3.2.1]octan-3-yl)(methyl)amino)pyridazin-3-yl)-3-fluoro-5-(1H-pyrazol-4-yl)phenol;
2-(6-(((1R,3s,5S)-1,5-dimethyl-8-azabicyclo[3.2.1]octan-3-yl)(methyl)amino)pyridazin-3-yl)-3,4-difluoro-5-(1H-pyrazol-4-yl)phenol;
4-(4-(6-(((1R,3s,5S)-1,5-dimethyl-8-azabicyclo[3.2.1]octan-3-yl)(methyl)amino)pyridazin-3-yl)-3-fluoro-5-hydroxyphenyl)-1-methylpyridin-2(1H)-one;
4-(4-(6-(((1R,3s,5S)-1,5-dimethyl-8-azabicyclo[3.2.1]octan-3-yl)(methyl)amino)pyridazin-3-yl)-2,3-difluoro-5-hydroxyphenyl)-1-methylpyridin-2(1H)-one;
2-(6-(((1R,3s,5S)-1,5-dimethyl-8-azabicyclo[3.2.1]octan-3-yl)(methyl)amino)pyridazin-3-yl)-3-fluoro-5-(2-methoxypyridin-4-yl)phenol;
2-(6-(((1R,3s,5S)-1,5-dimethyl-8-azabicyclo[3.2.1]octan-3-yl)(methyl)amino)pyridazin-3-yl)-3,4-difluoro-5-(2-methoxypyridin-4-yl)phenol;
2-(6-(((1R,3s,5S)-1,5-dimethyl-8-azabicyclo[3.2.1]octan-3-yl)(methyl)amino)pyridazin-3-yl)-3-fluoro-5-(6-methoxypyridazin-4-yl)phenol;
2-(6-(((1R,3s,5S)-1,5-dimethyl-8-azabicyclo[3.2.1]octan-3-yl)(methyl)amino)pyridazin-3-yl)-3,4-difluoro-5-(6-methoxypyridazin-4-yl)phenol;
5-(4-(6-(((1R,3s,5S)-1,5-dimethyl-8-azabicyclo[3.2.1]octan-3-yl)(methyl)amino)pyridazin-3-yl)-3-fluoro-5-hydroxyphenyl)-2-methylpyridazin-3(2H)-one;
5-(4-(6-(((1R,3s,5S)-1,5-dimethyl-8-azabicyclo[3.2.1]octan-3-yl)(methyl)amino)pyridazin-3-yl)-2,3-difluoro-5-hydroxyphenyl)-2-methylpyridazin-3(2H)-one;
2-(6-(cyclopropyl((1R,3s,5S)-1,5-dimethyl-8-azabicyclo[3.2.1]octan-3-yl)amino)pyridazin-3-yl)-3-fluoro-5-(6-methoxypyridazin-4-yl)phenol;
2-(6-(cyclopropyl((1R,3s,5S)-1,5-dimethyl-8-azabicyclo[3.2.1]octan-3-yl)amino)pyridazin-3-yl)-3,4-difluoro-5-(6-methoxypyridazin-4-yl)phenol;
2-(6-(((1R,3s,5S)-1,5-dimethyl-8-azabicyclo[3.2.1]octan-3-yl)(methyl)amino)pyridazin-3-yl)-3-fluoro-5-(6-methoxypyrimidin-4-yl)phenol;
2-(6-(((1R,3s,5S)-1,5-dimethyl-8-azabicyclo[3.2.1]octan-3-yl)(methyl)amino)pyridazin-3-yl)-3,4-difluoro-5-(6-methoxypyrimidin-4-yl)phenol;
2-(6-(((1R,3s,5S)-1,5-dimethyl-8-azabicyclo[3.2.1]octan-3-yl)(2-fluoroethyl)amino)pyridazin-3-yl)-5-(1H-pyrazol-4-yl)phenol;

2-(6-(((1R,3s,5S)-1,5-dimethyl-8-azabicyclo[3.2.1]octan-3-yl)(2-fluoroethyl)amino)pyridazin-3-yl)-4-fluoro-5-(1H-pyrazol-4-yl)phenol;

2-(6-(((1R,3s,5S)-1,5-dimethyl-8-azabicyclo[3.2.1]octan-3-yl)(2-fluoroethyl)amino)pyridazin-3-yl)-3-fluoro-5-(1H-pyrazol-4-yl)phenol;

2-(6-(((1R,3s,5S)-1,5-dimethyl-8-azabicyclo[3.2.1]octan-3-yl)(2-fluoroethyl)amino)pyridazin-3-yl)-3,4-difluoro-5-(1H-pyrazol-4-yl)phenol;

2-(6-(((1R,3s,5S)-1,5-dimethyl-8-azabicyclo[3.2.1]octan-3-yl)(methyl)amino)pyridazin-3-yl)-3-fluoro-5-(2-(methoxy-d3)pyridin-4-yl)phenol;

2-(6-(((1R,3s,5S)-1,5-dimethyl-8-azabicyclo[3.2.1]octan-3-yl)(methyl)amino)pyridazin-3-yl)-3,4-difluoro-5-(2-(methoxy-d3)pyridin-4-yl)phenol;

2-(6-(((1R,3s,5S)-1,5-dimethyl-8-azabicyclo[3.2.1]octan-3-yl)(methyl)amino)pyridazin-3-yl)-3-fluoro-5-(6-(methoxy-d3)pyridazin-4-yl)phenol;

2-(6-(((1R,3s,5S)-1,5-dimethyl-8-azabicyclo[3.2.1]octan-3-yl)(methyl)amino)pyridazin-3-yl)-3,4-difluoro-5-(6-(methoxy-d3)pyridazin-4-yl)phenol;

2-(6-(((1R,3s,5S)-1,5-dimethyl-8-azabicyclo[3.2.1]octan-3-yl)(methyl-d3)amino)pyridazin-3-yl)-3-fluoro-5-(2-(methoxy-d3)pyridin-4-yl)phenol;

2-(6-(((1R,3s,5S)-1,5-dimethyl-8-azabicyclo[3.2.1]octan-3-yl)(methyl-d3)amino)pyridazin-3-yl)-3,4-difluoro-5-(2-(methoxy-d3)pyridin-4-yl)phenol;

2-(6-(((1R,3s,5S)-1,5-dimethyl-8-azabicyclo[3.2.1]octan-3-yl)(methyl-d3)amino)pyridazin-3-yl)-3-fluoro-5-(6-(methoxy-d3)pyridazin-4-yl)phenol;

2-(6-(((1R,3s,5S)-1,5-dimethyl-8-azabicyclo[3.2.1]octan-3-yl)(methyl-d3)amino)pyridazin-3-yl)-3,4-difluoro-5-(6-(methoxy-d3)pyridazin-4-yl)phenol;

2-(6-(((1R,3s,5S)-1,5-dimethyl-8-azabicyclo[3.2.1]octan-3-yl)(methyl)amino)pyridazin-3-yl)-3-fluoro-5-(1-methyl-1H-pyrazol-4-yl)phenol;

2-(6-(((1R,3s,5S)-1,5-dimethyl-8-azabicyclo[3.2.1]octan-3-yl)(methyl)amino)pyridazin-3-yl)-3,4-difluoro-5-(1-methyl-1H-pyrazol-4-yl)phenol;

2-(6-(((1R,3s,5S)-1,5-dimethyl-8-azabicyclo[3.2.1]octan-3-yl)(methyl)amino)pyridazin-3-yl)-4-fluoro-5-(1,2,3-triazin-5-yl)phenol;

2-(6-(((1R,3s,5S)-1,5-dimethyl-8-azabicyclo[3.2.1]octan-3-yl)(methyl)amino)pyridazin-3-yl)-3,4-difluoro-5-(1,2,3-triazin-5-yl)phenol;

2-(6-(((1R,3s,5S)-1,5-dimethyl-8-azabicyclo[3.2.1]octan-3-yl)(methyl)amino)pyridazin-3-yl)-3-fluoro-5-(1,2,3-triazin-5-yl)phenol;

2-(6-(((1R,3s,5S)-1,5-dimethyl-9-azabicyclo[3.3.1]nonan-3-yl)(methyl)amino)pyridazin-3-yl)-4-fluoro-5-(6-methoxypyridazin-4-yl)phenol;

2-(6-(((1R,3s,5S)-1,5-dimethyl-9-azabicyclo[3.3.1]nonan-3-yl)(methyl)amino)pyridazin-3-yl)-3,4-difluoro-5-(6-methoxypyridazin-4-yl)phenol;

2-(6-(((1R,3s,5S)-1,5-dimethyl-9-azabicyclo[3.3.1]nonan-3-yl)(methyl)amino)pyridazin-3-yl)-3-fluoro-5-(6-methoxypyridazin-4-yl)phenol;

2-(6-(((1R,3s,5S)-1,5-dimethyl-9-azabicyclo[3.3.1]nonan-3-yl)(methyl)amino)pyridazin-3-yl)-3,4-difluoro-5-(6-methoxypyrimidin-4-yl)phenol;

2-(6-(((1R,3s,5S)-1,5-dimethyl-9-azabicyclo[3.3.1]nonan-3-yl)(methyl)amino)pyridazin-3-yl)-3-fluoro-5-(6-methoxypyrimidin-4-yl)phenol;

2-(6-(cyclopropyl((1R,3s,5S)-1,5-dimethyl-9-azabicyclo[3.3.1]nonan-3-yl)amino)pyridazin-3-yl)-4-fluoro-5-(6-methoxypyridazin-4-yl)phenol;

2-(6-(cyclopropyl((1R,3s,5S)-1,5-dimethyl-9-azabicyclo[3.3.1]nonan-3-yl)amino)pyridazin-3-yl)-3,4-difluoro-5-(6-methoxypyridazin-4-yl)phenol;

2-(6-(cyclopropyl((1R,3s,5S)-1,5-dimethyl-9-azabicyclo[3.3.1]nonan-3-yl)amino)pyridazin-3-yl)-3-fluoro-5-(6-methoxypyridazin-4-yl)phenol;

2-(6-(((1R,3s,5S)-1,5-dimethyl-9-azabicyclo[3.3.1]nonan-3-yl)(2-fluoroethyl)amino)pyridazin-3-yl)-4-fluoro-5-(6-methoxypyridazin-4-yl)phenol;

2-(6-(((1R,3s,5S)-1,5-dimethyl-9-azabicyclo[3.3.1]nonan-3-yl)(2-fluoroethyl)amino)pyridazin-3-yl)-3,4-difluoro-5-(6-methoxypyridazin-4-yl)phenol;

2-(6-(((1R,3s,5S)-1,5-dimethyl-9-azabicyclo[3.3.1]nonan-3-yl)(2-fluoroethyl)amino)pyridazin-3-yl)-3-fluoro-5-(6-methoxypyridazin-4-yl)phenol;

2-(6-(((1R,3s,5S)-1,5-dimethyl-9-azabicyclo[3.3.1]nonan-3-yl)oxy)pyridazin-3-yl)-4-fluoro-5-(6-methoxypyridazin-4-yl)phenol;

2-(6-(((1R,3s,5S)-1,5-dimethyl-9-azabicyclo[3.3.1]nonan-3-yl)oxy)pyridazin-3-yl)-3,4-difluoro-5-(6-methoxypyridazin-4-yl)phenol;

2-(6-(((1R,3s,5S)-1,5-dimethyl-9-azabicyclo[3.3.1]nonan-3-yl)oxy)pyridazin-3-yl)-3-fluoro-5-(6-methoxypyridazin-4-yl)phenol;

4-(4-(6-(((1R,3s,5S)-1,5-dimethyl-9-azabicyclo[3.3.1]nonan-3-yl)oxy)pyridazin-3-yl)-2-fluoro-5-hydroxyphenyl)-1-methylpyridin-2(1H)-one;

4-(4-(6-(((1R,3s,5S)-1,5-dimethyl-9-azabicyclo[3.3.1]nonan-3-yl)oxy)pyridazin-3-yl)-2,3-difluoro-5-hydroxyphenyl)-1-methylpyridin-2(1H)-one;

4-(4-(6-(((1R,3s,5S)-1,5-dimethyl-9-azabicyclo[3.3.1]nonan-3-yl)oxy)pyridazin-3-yl)-3-fluoro-5-hydroxyphenyl)-1-methylpyridin-2(1H)-one;

4-(4-(6-(((1R,3s,5S)-1,5-dimethyl-9-azabicyclo[3.3.1]nonan-3-yl)(methyl)amino)pyridazin-3-yl)-2-fluoro-5-hydroxyphenyl)-1-methylpyridin-2(1H)-one;

4-(4-(6-(((1R,3s,5S)-1,5-dimethyl-9-azabicyclo[3.3.1]nonan-3-yl)(methyl)amino)pyridazin-3-yl)-2,3-difluoro-5-hydroxyphenyl)-1-methylpyridin-2(1H)-one;

4-(4-(6-(((1R,3s,5S)-1,5-dimethyl-9-azabicyclo[3.3.1]nonan-3-yl)(methyl)amino)pyridazin-3-yl)-3-fluoro-5-hydroxyphenyl)-1-methylpyridin-2(1H)-one;

2-(6-(((1R,3s,5S)-1,5-dimethyl-8-azabicyclo[3.2.1]octan-3-yl)(methyl)amino)-4-fluoropyridazin-3-yl)-4-fluoro-5-(1H-pyrazol-4-yl)phenol;

2-(6-(((1R,3s,5S)-1,5-dimethyl-8-azabicyclo[3.2.1]octan-3-yl)(methyl)amino)-5-fluoropyridazin-3-yl)-4-fluoro-5-(1H-pyrazol-4-yl)phenol;

2-(6-(((1R,3s,5S)-1,5-dimethyl-9-azabicyclo[3.3.1]nonan-3-yl)(methyl)amino)-4-fluoropyridazin-3-yl)-4-fluoro-5-(1H-pyrazol-4-yl)phenol;

2-(6-(((1R,3s,5S)-1,5-dimethyl-9-azabicyclo[3.3.1]nonan-3-yl)(methyl)amino)-5-fluoropyridazin-3-yl)-4-fluoro-5-(1H-pyrazol-4-yl)phenol;

7-(6-(((1R,3s,5S)-1,5-dimethyl-8-azabicyclo[3.2.1]octan-3-yl)(methyl)amino)pyridazin-3-yl)-6-hydroxy-N-methylisoquinoline-3-carboxamide;

7-(6-(((1R,3s,5S)-1,5-dimethyl-9-azabicyclo[3.3.1]nonan-3-yl)(methyl)amino)pyridazin-3-yl)-6-hydroxy-N-methylisoquinoline-3-carboxamide;

6-(6-(((1R,3s,5S)-1,5-dimethyl-9-azabicyclo[3.3.1]nonan-3-yl)(methyl)amino)pyridazin-3-yl)-7-hydroxy-N-methylquinoline-2-carboxamide;

6-(6-(((1R,3s,5S)-1,5-dimethyl-9-azabicyclo[3.3.1]nonan-3-yl)(methyl)amino)pyridazin-3-yl)-1-fluoro-7-hydroxy-N-methyl-2-naphthamide;

6-(6-((((1R,3s,5S)-1,5-dimethyl-9-azabicyclo[3.3.1]nonan-3-yl)(methyl)amino)pyridazin-3-yl)-3-fluoro-7-hydroxy-N-methyl-2-naphthamide;

6-(6-((((1R,3s,5S)-1,5-dimethyl-8-azabicyclo[3.2.1]octan-3-yl)(methyl)amino)pyridazin-3-yl)-3-fluoro-7-hydroxy-N-methyl-2-naphthamide;

6-(6-((((1R,3s,5S)-1,5-dimethyl-8-azabicyclo[3.2.1]octan-3-yl)(methyl)amino)pyridazin-3-yl)-1-fluoro-7-hydroxy-N-methyl-2-naphthamide;

2-(6-(cyclopropyl(2,2,6,6-tetramethylpiperidin-4-yl)amino)pyridazin-3-yl)-5-(1H-pyrazol-4-yl)phenol;

2-(6-(cyclobutyl(2,2,6,6-tetramethylpiperidin-4-yl)amino)pyridazin-3-yl)-5-(1H-pyrazol-4-yl)phenol;

2-(6-(octahydro-1H-pyrrolo[3,2-c]pyridin-1-yl)pyridazin-3-yl)-5-(1H-pyrazol-4-yl)phenol;

2-(6-(1,7-diazaspiro[3.5]nonan-1-yl)pyridazin-3-yl)-5-(1H-pyrazol-4-yl)phenol;

2-(6-((2-methoxyethyl)(2,2,6,6-tetramethylpiperidin-4-yl)amino)pyridazin-3-yl)-5-(1H-pyrazol-4-yl)phenol;

2-(5-(methyl(2,2,6,6-tetramethylpiperidin-4-yl)amino)pyrimidin-2-yl)-5-(1H-pyrazol-4-yl)phenol;

2-(5-(methyl(2,2,6,6-tetramethylpiperidin-4-yl)amino)pyridin-2-yl)-5-(1H-pyrazol-4-yl)phenol;

2-(5-(methyl(2,2,6,6-tetramethylpiperidin-4-yl)amino)pyrazin-2-yl)-5-(1H-pyrazol-4-yl)phenol;

2-(6-((((1R,5S,6s)-3-azabicyclo[3.1.0]hexan-6-yl)(methyl)amino)pyridazin-3-yl)-5-(1H-pyrazol-4-yl)phenol;

2-(6-((((1R,3s,5S)-8-azabicyclo[3.2.1]octan-3-yl)(methyl)amino)pyridazin-3-yl)-5-(1H-pyrazol-4-yl)phenol;

2-(6-((((1R,3r,5S)-8-azabicyclo[3.2.1]octan-3-yl)(methyl)amino)pyridazin-3-yl)-5-(1H-pyrazol-4-yl)phenol;

2-(6-(((1R,3s,5S)-8-azabicyclo[3.2.1]octan-3-yl)oxy)pyridazin-3-yl)-5-(1H-pyrazol-4-yl)phenol;

2-(6-(((1R,3r,5S)-8-azabicyclo[3.2.1]octan-3-yl)oxy)pyridazin-3-yl)-5-(1H-pyrazol-4-yl)phenol;

2-(6-(methyl((3R,5r,6S)-octahydrocyclopenta[c]pyrrol-5-yl)amino)pyridazin-3-yl)-5-(1H-pyrazol-4-yl)phenol;

2-(6-(methyl((3R,5s,6S)-octahydrocyclopenta[c]pyrrol-5-yl)amino)pyridazin-3-yl)-5-(1H-pyrazol-4-yl)phenol;

2-(6-((((1R,5S,8s)-3-azabicyclo[3.2.1]octan-8-yl)(methyl)amino)pyridazin-3-yl)-5-(1H-pyrazol-4-yl)phenol;

2-(6-((((1R,5S,8r)-3-azabicyclo[3.2.1]octan-8-yl)(methyl)amino)pyridazin-3-yl)-5-(1H-pyrazol-4-yl)phenol;

2-(6-((((1R,4R,5S)-2-azabicyclo[2.2.1]heptan-5-yl)(methyl)amino)pyridazin-3-yl)-5-(1H-pyrazol-4-yl)phenol;

2-(6-((((1S,4S,5R)-2-azabicyclo[2.2.1]heptan-5-yl)(methyl)amino)pyridazin-3-yl)-5-(1H-pyrazol-4-yl)phenol;

2-(6-((((1R,4R,5R)-2-azabicyclo[2.2.1]heptan-5-yl)(methyl)amino)pyridazin-3-yl)-5-(1H-pyrazol-4-yl)phenol;

2-(6-((((1S,4S,5S)-2-azabicyclo[2.2.1]heptan-5-yl)(methyl)amino)pyridazin-3-yl)-5-(1H-pyrazol-4-yl)phenol;

2-(6-((((1R,3r,5S)-1,5-dimethyl-8-azabicyclo[3.2.1]octan-3-yl)(methyl)amino)pyridazin-3-yl)-5-(1H-pyrazol-4-yl)phenol;

2-(6-((((1R,3s,5S)-1,5-dimethyl-8-azabicyclo[3.2.1]octan-3-yl)(methyl)amino)pyridazin-3-yl)-5-(1H-pyrazol-4-yl)phenol;

2-(6-(((1R,3s,5S)-1,5-dimethyl-8-azabicyclo[3.2.1]octan-3-yl)oxy)pyridazin-3-yl)-5-(1H-pyrazol-4-yl)phenol;

2-(6-(((1R,3r,5S)-1,5-dimethyl-8-azabicyclo[3.2.1]octan-3-yl)oxy)pyridazin-3-yl)-5-(1H-pyrazol-4-yl)phenol;

2-(6-((((1R,5S,7r)-3-oxa-9-azabicyclo[3.3.1]nonan-7-yl)(methyl)amino)pyridazin-3-yl)-5-(1H-pyrazol-4-yl)phenol;

2-(6-((((1R,5S,7s)-3-oxa-9-azabicyclo[3.3.1]nonan-7-yl)(methyl)amino)pyridazin-3-yl)-5-(1H-pyrazol-4-yl)phenol;

2-(6-((((1R,5S,7r)-1,5-dimethyl-3-oxa-9-azabicyclo[3.3.1]nonan-7-yl)(methyl)amino)pyridazin-3-yl)-5-(1H-pyrazol-4-yl)phenol;

2-(6-((((1R,5S,7s)-1,5-dimethyl-3-oxa-9-azabicyclo[3.3.1]nonan-7-yl)(methyl)amino)pyridazin-3-yl)-5-(1H-pyrazol-4-yl)phenol;

2-(6-(((1R,5S,7s)-3-oxa-9-azabicyclo[3.3.1]nonan-7-yl)oxy)pyridazin-3-yl)-5-(1H-pyrazol-4-yl)phenol;

2-(6-(((1R,5S,7r)-3-oxa-9-azabicyclo[3.3.1]nonan-7-yl)oxy)pyridazin-3-yl)-5-(1H-pyrazol-4-yl)phenol;

2-(6-((((1R,3s,5S)-9-azabicyclo[3.3.1]nonan-3-yl)(methyl)amino)pyridazin-3-yl)-5-(1H-pyrazol-4-yl)phenol;

2-(6-((((1R,3s,5S)-8-azabicyclo[3.2.1]octan-3-yl)(methyl)amino)pyridazin-3-yl)-4-fluoro-5-(1H-pyrazol-4-yl)phenol;

6-(6-((((1R,3s,5S)-8-azabicyclo[3.2.1]octan-3-yl)(methyl)amino)pyridazin-3-yl)quinolin-7-ol;

3-(6-((((1R,3s,5S)-8-azabicyclo[3.2.1]octan-3-yl)(methyl)amino)pyridazin-3-yl)-7-methoxynaphthalen-2-ol;

6-(6-((((1R,3s,5S)-8-azabicyclo[3.2.1]octan-3-yl)(methyl)amino)pyridazin-3-yl)-5-hydroxy-3-methylbenzo[d]oxazol-2(3H)-one;

3-(6-((((1R,3s,5S)-8-azabicyclo[3.2.1]octan-3-yl)(methyl)amino)pyridazin-3-yl)-7-(fluoromethoxy)naphthalen-2-ol;

3-(6-((((1R,3s,5S)-8-azabicyclo[3.2.1]octan-3-yl)(methyl)amino)pyridazin-3-yl)-7-(difluoromethoxy)naphthalen-2-ol;

2-(6-((((1R,3s,5S)-1,5-dimethyl-8-azabicyclo[3.2.1]octan-3-yl)(methyl)amino)pyridazin-3-yl)-4-fluoro-5-(1H-pyrazol-4-yl)phenol;

4-(4-(6-((((1R,3s,5S)-1,5-dimethyl-8-azabicyclo[3.2.1]octan-3-yl)(methyl)amino)pyridazin-3-yl)-3-hydroxyphenyl)-1-methylpyridin-2(1H)-one;

4-(4-(6-((((1R,3s,5S)-1,5-dimethyl-8-azabicyclo[3.2.1]octan-3-yl)(methyl)amino)pyridazin-3-yl)-2-fluoro-5-hydroxyphenyl)-1-methylpyridin-2(1H)-one;

5-(4-(6-((((1R,3s,5S)-1,5-dimethyl-8-azabicyclo[3.2.1]octan-3-yl)(methyl)amino)pyridazin-3-yl)-3-hydroxyphenyl)-2-methylpyridazin-3(2H)-one;

2-(6-((((1R,3s,5S)-1,5-dimethyl-8-azabicyclo[3.2.1]octan-3-yl)(methyl)amino)pyridazin-3-yl)-5-(1-(methyl-d3)-1H-pyrazol-4-yl)phenol;

2-(6-((((1R,3s,5S)-1,5-dimethyl-8-azabicyclo[3.2.1]octan-3-yl)(methyl)amino)pyridazin-3-yl)-5-(2-(methoxy-d3)pyridin-4-yl)phenol;

2-(6-((((1R,3s,5S)-1,5-dimethyl-8-azabicyclo[3.2.1]octan-3-yl)(methyl)amino)pyridazin-3-yl)-5-(2-methoxypyridin-4-yl)phenol;

2-(6-((((1R,3s,5S)-1,5-dimethyl-8-azabicyclo[3.2.1]octan-3-yl)(methyl)amino)pyridazin-3-yl)-5-(1-(fluoromethyl)-1H-pyrazol-4-yl)phenol;

2-(6-((((1R,3s,5S)-1,5-dimethyl-8-azabicyclo[3.2.1]octan-3-yl)(methyl)amino)pyridazin-3-yl)-5-(4-fluoro-1H-pyrazol-1-yl)phenol;

2-(6-((((1R,3s,5S)-1,5-dimethyl-8-azabicyclo[3.2.1]octan-3-yl)(methyl)amino)pyridazin-3-yl)-5-(4-fluoro-1H-imidazol-1-yl)phenol;

2-(6-((((1R,3s,5S)-1,5-dimethyl-8-azabicyclo[3.2.1]octan-3-yl)(methyl)amino)pyridazin-3-yl)-5-(4-methyl-1H-imidazol-1-yl)phenol;

4-(4-(6-((((1R,3s,5S)-1,5-dimethyl-8-azabicyclo[3.2.1]octan-3-yl)(methyl)amino)pyridazin-3-yl)-5-hydroxy-2-methylphenyl)-1-methylpyridin-2(1H)-one;

5-(1-(difluoromethyl)-1H-pyrazol-4-yl)-2-(6-((((1R,3s,5S)-1,5-dimethyl-8-azabicyclo[3.2.1]octan-3-yl)(methyl)amino)pyridazin-3-yl)phenol;

4-(4-(6-(((1R,3s,5S)-1,5-dimethyl-8-azabicyclo[3.2.1]octan-3-yl)(methyl)amino)pyridazin-3-yl)-3-hydroxyphenyl)-1-methylpyrimidin-2(1H)-one;

4-(4-(6-(((1R,3s,5S)-1,5-dimethyl-8-azabicyclo[3.2.1]octan-3-yl)(methyl)amino)pyridazin-3-yl)-3-hydroxyphenyl)-1-methyl-1,3,5-triazin-2(1H)-one;

2-(6-(((1R,3s,5S)-1,5-dimethyl-8-azabicyclo[3.2.1]octan-3-yl)(methyl)amino)pyridazin-3-yl)-4-methyl-5-(1H-pyrazol-4-yl)phenol;

4-(4-(6-(((1R,3s,5S)-1,5-dimethyl-8-azabicyclo[3.2.1]octan-3-yl)(methyl)amino)pyridazin-3-yl)-3-hydroxyphenyl)pyridin-2(1H)-one;

4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)pyridin-2(1H)-one;

5-(2-(difluoromethoxy)pyridin-4-yl)-2-(6-(((1R,3s,5S)-1,5-dimethyl-8-azabicyclo[3.2.1]octan-3-yl)(methyl)amino)pyridazin-3-yl)phenol;

2-(6-(((1R,3s,5S)-1,5-dimethyl-8-azabicyclo[3.2.1]octan-3-yl)(methyl)amino)pyridazin-3-yl)-5-(1-(trifluoromethyl)-1H-pyrazol-4-yl)phenol;

4-(4-(6-(((1R,3s,5S)-1,5-dimethyl-8-azabicyclo[3.2.1]octan-3-yl)(methyl)amino)pyridazin-3-yl)-3-hydroxyphenyl)-1-(fluoromethyl)pyridin-2(1H)-one;

6-(6-(((1R,3s,5S)-1,5-dimethyl-8-azabicyclo[3.2.1]octan-3-yl)(methyl)amino)pyridazin-3-yl)-5-hydroxy-N-methylbenzofuran-2-carboxamide;

2-(6-(((1R,3s,5S)-1,5-dimethyl-8-azabicyclo[3.2.1]octan-3-yl)(methyl)amino)pyridazin-3-yl)-5-(2-fluoro-6-methoxypyridin-4-yl)phenol;

4-(4-(6-(((1R,3s,5S)-1,5-dimethyl-8-azabicyclo[3.2.1]octan-3-yl)(methyl)amino)pyridazin-3-yl)-3-hydroxyphenyl)-6-fluoropyridin-2-ol;

2-(6-(((1R,3s,5S)-1,5-dimethyl-8-azabicyclo[3.2.1]octan-3-yl)(methyl)amino)pyridazin-3-yl)-5-(6-methoxypyridazin-4-yl)phenol;

5-(6-(((1R,3s,5S)-1,5-dimethyl-8-azabicyclo[3.2.1]octan-3-yl)(methyl)amino)pyridazin-3-yl)-6-hydroxy-N-methylbenzofuran-2-carboxamide;

4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1-(fluoromethyl)pyridin-2(1H)-one;

6-(4-(6-(((1R,3s,5S)-1,5-dimethyl-8-azabicyclo[3.2.1]octan-3-yl)(methyl)amino)pyridazin-3-yl)-3-hydroxyphenyl)-3-methylpyrimidin-4(3H)-one;

4-(4-(6-(((1R,3s,5S)-1,5-dimethyl-8-azabicyclo[3.2.1]octan-3-yl)(methyl)amino)pyridazin-3-yl)-3-hydroxyphenyl)-1-methyl-1H-pyrrole-2-carbonitrile;

1-(4-(6-(((1R,3s,5S)-1,5-dimethyl-8-azabicyclo[3.2.1]octan-3-yl)(methyl)amino)pyridazin-3-yl)-3-hydroxyphenyl)-1H-imidazole-4-carbonitrile;

1-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1H-imidazole-4-carbonitrile;

6-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-3-methylpyrimidin-4(3H)-one;

4-(4-(6-(((1R,3s,5S)-1,5-dimethyl-8-azabicyclo[3.2.1]octan-3-yl)(methyl)amino)pyridazin-3-yl)-3-hydroxyphenyl)picolinonitrile;

1-(4-(6-(((1R,3s,5S)-1,5-dimethyl-8-azabicyclo[3.2.1]octan-3-yl)(methyl)amino)pyridazin-3-yl)-3-hydroxyphenyl)-1H-pyrazole-4-carbonitrile;

2-(6-(((1R,3s,5S)-1,5-dimethyl-8-azabicyclo[3.2.1]octan-3-yl)(ethyl)amino)pyridazin-3-yl)-5-(1H-pyrazol-4-yl)phenol;

2-(6-(((1R,3s,5S)-1,5-dimethyl-8-azabicyclo[3.2.1]octan-3-yl)(ethyl)amino)pyridazin-3-yl)-4-fluoro-5-(1H-pyrazol-4-yl)phenol;

1-(4-(6-(((1R,3s,5S)-1,5-dimethyl-8-azabicyclo[3.2.1]octan-3-yl)(methyl)amino)pyridazin-3-yl)-3-hydroxyphenyl)-1H-pyrrole-3-carbonitrile;

5-(2,6-difluoropyridin-4-yl)-2-(6-(((1R,3s,5S)-1,5-dimethyl-8-azabicyclo[3.2.1]octan-3-yl)(methyl)amino)pyridazin-3-yl)phenol;

2-(6-(((1R,3s,5S)-1,5-dimethyl-8-azabicyclo[3.2.1]octan-3-yl)(methyl)amino)pyridazin-3-yl)-5-(6-(methoxy-d3)pyridazin-4-yl)phenol;

2-(6-(((1R,3s,5S)-1,5-dimethyl-8-azabicyclo[3.2.1]octan-3-yl)(methyl)amino)pyridazin-3-yl)-4-fluoro-5-(6-(methoxy-d3)pyridazin-4-yl)phenol;

2-(6-(((1R,3s,5S)-1,5-dimethyl-8-azabicyclo[3.2.1]octan-3-yl)(methyl)amino)pyridazin-3-yl)-5-(2-fluoro-6-(methoxy-d3)pyridin-4-yl)phenol;

2-(6-(((1R,3s,5S)-1,5-dimethyl-8-azabicyclo[3.2.1]octan-3-yl)(methyl)amino)pyridazin-3-yl)-4-fluoro-5-(2-fluoro-6-(methoxy-d3)pyridin-4-yl)phenol;

4-(6-(((1R,3s,5S)-1,5-dimethyl-8-azabicyclo[3.2.1]octan-3-yl)(methyl)amino)pyridazin-3-yl)-3'-methoxy-[1,1'-biphenyl]-3-ol;

4-(6-(((1R,3s,5S)-1,5-dimethyl-8-azabicyclo[3.2.1]octan-3-yl)(methyl)amino)pyridazin-3-yl)-4'-fluoro-3'-methoxy-[1,1'-biphenyl]-3-ol;

2-(6-(((1R,3s,5S)-1,5-dimethyl-8-azabicyclo[3.2.1]octan-3-yl)(methyl)amino)pyridazin-3-yl)-5-(5-methoxypyridin-3-yl)phenol;

2-(6-(((1R,3s,5S)-1,5-dimethyl-8-azabicyclo[3.2.1]octan-3-yl)(methyl)amino)pyridazin-3-yl)-5-(6-fluoro-5-methoxypyridin-3-yl)phenol;

2-(6-(((1R,3s,5S)-1,5-dimethyl-8-azabicyclo[3.2.1]octan-3-yl)(methyl)amino)pyridazin-3-yl)-4-fluoro-5-(6-methoxypyridazin-4-yl)phenol;

2-(6-(((1R,3s,5S)-1,5-dimethyl-8-azabicyclo[3.2.1]octan-3-yl)(methyl-d3)amino)pyridazin-3-yl)-4-fluoro-5-(1H-pyrazol-4-yl)phenol;

2-(6-(((1R,3s,5S)-1,5-dimethyl-8-azabicyclo[3.2.1]octan-3-yl)(methyl)amino)pyridazin-3-yl)-5-(6-methoxypyrimidin-4-yl)phenol;

2-(6-(((1R,3s,5S)-1,5-dimethyl-8-azabicyclo[3.2.1]octan-3-yl)(methyl)amino)pyridazin-3-yl)-4-fluoro-5-(6-methoxypyrimidin-4-yl)phenol;

2-(6-(((1R,3s,5S)-8-azabicyclo[3.2.1]octan-3-yl)(methyl)amino)pyridazin-3-yl)-5-(1H-imidazol-1-yl)phenol;

2-(6-(((1R,3s,5S)-8-azabicyclo[3.2.1]octan-3-yl)(methyl)amino)pyridazin-3-yl)-5-(4-methyl-1H-imidazol-1-yl)phenol;

2-(6-(((1R,3s,5S)-8-azabicyclo[3.2.1]octan-3-yl)(methyl)amino)pyridazin-3-yl)-5-(5-methyl-1,3,4-oxadiazol-2-yl)phenol;

2-(6-(((1R,3s,5S)-8-azabicyclo[3.2.1]octan-3-yl)(methyl)amino)pyridazin-3-yl)-5-(1H-pyrazol-1-yl)phenol;

2-(6-(((1R,3s,5S)-8-azabicyclo[3.2.1]octan-3-yl)(methyl)amino)pyridazin-3-yl)-5-(4-methyl-1H-pyrazol-1-yl)phenol;

2-(6-(((1R,3s,5S)-8-azabicyclo[3.2.1]octan-3-yl)(methyl)amino)pyridazin-3-yl)-5-(3-methyl-1H-pyrazol-1-yl)phenol;

2-(6-(((1R,3s,5S)-8-azabicyclo[3.2.1]octan-3-yl)(methyl)amino)pyridazin-3-yl)-5-(2H-1,2,3-triazol-2-yl)phenol;

2-(6-(((1R,3s,5S)-8-azabicyclo[3.2.1]octan-3-yl)(methyl)amino)pyridazin-3-yl)-5-(1H-1,2,3-triazol-1-yl)phenol;

2-(6-(((1R,3s,5S)-8-azabicyclo[3.2.1]octan-3-yl)(methyl)
amino)pyridazin-3-yl)-5-(4-methyl-1H-1,2,3-triazol-1-
yl)phenol;
2-(6-(((1R,3s,5S)-8-azabicyclo[3.2.1]octan-3-yl)(methyl)
amino)pyridazin-3-yl)-5-(1H-1,2,3-triazol-4-yl)phenol;
2-(6-(((1R,3s,5S)-8-azabicyclo[3.2.1]octan-3-yl)(methyl)
amino)pyridazin-3-yl)-5-(1H-tetrazol-5-yl)phenol;
2-(6-(((1R,3s,5S)-8-azabicyclo[3.2.1]octan-3-yl)(methyl)
amino)pyridazin-3-yl)-5-(2-methyloxazol-5-yl)phenol;
2-(6-(((1R,3s,5S)-8-azabicyclo[3.2.1]octan-3-yl)(methyl)
amino)pyridazin-3-yl)-5-(3-methylisoxazol-5-yl)phenol;
2-(6-(((1R,3s,5S)-8-azabicyclo[3.2.1]octan-3-yl)(methyl)
amino)pyridazin-3-yl)-5-(2-methyl-1H-imidazol-1-yl)
phenol;
2-(6-(((1R,3s,5S)-8-azabicyclo[3.2.1]octan-3-yl)(methyl)
amino)pyridazin-3-yl)-5-(2,4-dimethyl-1H-imidazol-1-
yl)phenol;
2-(6-(((1R,3s,5S)-8-azabicyclo[3.2.1]octan-3-yl)(methyl)
amino)pyridazin-3-yl)-5-(5-(trifluoromethyl)-1,3,4-oxa-
diazol-2-yl)phenol;
2-(6-(((1R,3s,5S)-8-azabicyclo[3.2.1]octan-3-yl)(methyl)
amino)pyridazin-3-yl)-5-(5-methyl-1H-tetrazol-1-yl)phe-
nol;
2-(6-(((1R,3s,5S)-8-azabicyclo[3.2.1]octan-3-yl)(methyl)
amino)pyridazin-3-yl)-5-(5-methyl-2H-tetrazol-2-yl)phe-
nol;
2-(6-(((1R,3s,5S)-8-azabicyclo[3.2.1]octan-3-yl)(methyl)
amino)pyridazin-3-yl)-5-(4H-1,2,4-triazol-4-yl)phenol;
2-(6-(((1R,3s,5S)-8-azabicyclo[3.2.1]octan-3-yl)(methyl)
amino)pyridazin-3-yl)-5-(6-methylpyridin-3-yl)phenol;
2-(6-(((1R,3s,5S)-8-azabicyclo[3.2.1]octan-3-yl)(methyl)
amino)pyridazin-3-yl)-5-(2-methylpyrimidin-5-yl)phe-
nol;
5-(4-(6-(((1R,3s,5S)-8-azabicyclo[3.2.1]octan-3-yl)
(methyl)amino)pyridazin-3-yl)-3-hydroxyphenyl)-2-
methylpyridazin-3(2H)-one;
2-(6-(((1R,3s,5S)-8-azabicyclo[3.2.1]octan-3-yl)(methyl)
amino)pyridazin-3-yl)-5-(6-methylpyridazin-3-yl)phe-
nol;
4-(4-(6-(((1R,3s,5S)-8-azabicyclo[3.2.1]octan-3-yl)
(methyl)amino)pyridazin-3-yl)-3-hydroxyphenyl)-1-
methylpyridin-2(1H)-one;
5-(4-(6-(((1R,3s,5S)-8-azabicyclo[3.2.1]octan-3-yl)
(methyl)amino)pyridazin-3-yl)-3-hydroxyphenyl)-1-
methylpyridin-2(1H)-one;
2-(6-(((1R,3s,5S)-8-azabicyclo[3.2.1]octan-3-yl)(methyl)
amino)pyridazin-3-yl)-5-(4-(trifluoromethyl)-1H-imida-
zol-1-yl)phenol;
2-(6-(((1R,3s,5S)-8-azabicyclo[3.2.1]octan-3-yl)(methyl)
amino)pyridazin-3-yl)-5-(1H-1,2,4-triazol-1-yl)phenol;
2-(6-(((1R,3s,5S)-8-azabicyclo[3.2.1]octan-3-yl)(methyl)
amino)pyridazin-3-yl)-5-(3-methyl-1H-1,2,4-triazol-1-
yl)phenol;
2-(6-(((1R,3s,5S)-8-azabicyclo[3.2.1]octan-3-yl)oxy)
pyridazin-3-yl)-5-(1H-imidazol-1-yl)phenol;
2-(6-(((1R,3s,5S)-8-azabicyclo[3.2.1]octan-3-yl)oxy)
pyridazin-3-yl)-5-(4-methyl-1H-imidazol-1-yl)phenol;
2-(6-(((1R,3s,5S)-8-azabicyclo[3.2.1]octan-3-yl)oxy)
pyridazin-3-yl)-5-(5-methyl-1,3,4-oxadiazol-2-yl)phenol;
2-(6-(((1R,3s,5S)-8-azabicyclo[3.2.1]octan-3-yl)oxy)
pyridazin-3-yl)-5-(1H-pyrazol-1-yl)phenol;
2-(6-(((1R,3s,5S)-8-azabicyclo[3.2.1]octan-3-yl)oxy)
pyridazin-3-yl)-5-(4-methyl-1H-pyrazol-1-yl)phenol;
2-(6-(((1R,3s,5S)-8-azabicyclo[3.2.1]octan-3-yl)oxy)
pyridazin-3-yl)-5-(3-methyl-1H-pyrazol-1-yl)phenol;
2-(6-(((1R,3s,5S)-8-azabicyclo[3.2.1]octan-3-yl)oxy)
pyridazin-3-yl)-5-(2H-1,2,3-triazol-2-yl)phenol;
2-(6-(((1R,3s,5S)-8-azabicyclo[3.2.1]octan-3-yl)oxy)
pyridazin-3-yl)-5-(1H-1,2,3-triazol-1-yl)phenol;
2-(6-(((1R,3s,5S)-8-azabicyclo[3.2.1]octan-3-yl)oxy)
pyridazin-3-yl)-5-(1H-1,2,3-triazol-4-yl)phenol;
2-(6-(((1R,3s,5S)-8-azabicyclo[3.2.1]octan-3-yl)oxy)
pyridazin-3-yl)-5-(1H-tetrazol-5-yl)phenol;
2-(6-(((1R,3s,5S)-8-azabicyclo[3.2.1]octan-3-yl)oxy)
pyridazin-3-yl)-5-(2-methyloxazol-5-yl)phenol;
2-(6-(((1R,3s,5S)-8-azabicyclo[3.2.1]octan-3-yl)oxy)
pyridazin-3-yl)-5-(3-methylisoxazol-5-yl)phenol;
2-(6-(((1R,3s,5S)-8-azabicyclo[3.2.1]octan-3-yl)oxy)
pyridazin-3-yl)-5-(5-methyl-1H-tetrazol-1-yl)phenol;
2-(6-(((1R,3s,5S)-8-azabicyclo[3.2.1]octan-3-yl)oxy)
pyridazin-3-yl)-5-(5-methyl-2H-tetrazol-2-yl)phenol;
4-(4-(6-(((1R,3s,5S)-1,5-dimethyl-9-azabicyclo[3.3.1]
nonan-3-yl)(methyl)amino)pyridazin-3-yl)-3-hydroxy-
phenyl)-1-methylpyridin-2(1H)-one;
5-(4-(6-(((1R,3s,5S)-1,5-dimethyl-9-azabicyclo[3.3.1]
nonan-3-yl)(methyl)amino)pyridazin-3-yl)-3-hydroxy-
phenyl)-2-methylpyridazin-3(2H)-one;
5-(6-(((1R,3s,5S)-1,5-dimethyl-9-azabicyclo[3.3.1]nonan-
3-yl)(methyl)amino)pyridazin-3-yl)-6-hydroxy-N-meth-
ylbenzofuran-2-carboxamide;
2-(6-(((1R,3s,5S)-1,5-dimethyl-9-azabicyclo[3.3.1]nonan-
3-yl)oxy)pyridazin-3-yl)-5-(1H-pyrazol-4-yl)phenol;
2-(6-(((1R,3s,5S)-1,5-dimethyl-9-azabicyclo[3.3.1]nonan-
3-yl)oxy)pyridazin-3-yl)-4-fluoro-5-(1H-pyrazol-4-yl)
phenol;
4-(4-(6-(((1R,3s,5S)-1,5-dimethyl-9-azabicyclo[3.3.1]
nonan-3-yl)(methyl)amino)pyridazin-3-yl)-2-fluoro-5-
hydroxyphenyl)-1-(fluoromethyl)pyridin-2(1H)-one;
4-(4-(6-(((1R,3s,5S)-1,5-dimethyl-9-azabicyclo[3.3.1]
nonan-3-yl)(methyl)amino)pyridazin-3-yl)-2-fluoro-5-
hydroxyphenyl)-1-methylpyridin-2(1H)-one;
6-(4-(6-(((1R,3s,5S)-1,5-dimethyl-9-azabicyclo[3.3.1]
nonan-3-yl)(methyl)amino)pyridazin-3-yl)-3-hydroxy-
phenyl)-3-methylpyrimidin-4(3H)-one;
2-(6-(((1R,3s,5S)-1,5-dimethyl-9-azabicyclo[3.3.1]nonan-
3-yl)(methyl)amino)pyridazin-3-yl)-5-(6-methoxy-
pyridazin-4-yl)phenol;
2-(6-(((1R,3s,5S)-1,5-dimethyl-9-azabicyclo[3.3.1]nonan-
3-yl)(methyl)amino)pyridazin-3-yl)-5-(6-(methoxy-d3)
pyridazin-4-yl)phenol;
2-(6-(((1R,3s,5S)-1,5-dimethyl-9-azabicyclo[3.3.1]nonan-
3-yl)(methyl)amino)pyridazin-3-yl)-4-fluoro-5-(6-
(methoxy-d3)pyridazin-4-yl)phenol;
2-(6-(((1R,3s,5S)-1,5-dimethyl-9-azabicyclo[3.3.1]nonan-
3-yl)(methyl)amino)pyridazin-3-yl)-5-(6-methoxypy-
rimidin-4-yl)phenol;
2-(6-(((1R,3s,5S)-9-azabicyclo[3.3.1]nonan-3-yl)(methyl)
amino)pyridazin-3-yl)-4-fluoro-5-(1H-pyrazol-4-yl)phe-
nol;
2-(6-(((1R,3s,5S)-9-azabicyclo[3.3.1]nonan-3-yl)(methyl)
amino)pyridazin-3-yl)-5-(1H-imidazol-1-yl)phenol;
2-(6-(((1R,3s,5S)-9-azabicyclo[3.3.1]nonan-3-yl)(methyl)
amino)pyridazin-3-yl)-5-(2-methyloxazol-5-yl)phenol;
2-(6-(((1R,3s,5S)-9-azabicyclo[3.3.1]nonan-3-yl)(methyl)
amino)pyridazin-3-yl)-4-fluoro-5-(2-methyloxazol-5-yl)
phenol;
2-(6-(((1R,3s,5S)-9-azabicyclo[3.3.1]nonan-3-yl)(methyl)
amino)pyridazin-3-yl)-5-(2H-1,2,3-triazol-2-yl)phenol;
2-(6-(((1R,3s,5S)-9-azabicyclo[3.3.1]nonan-3-yl)oxy)
pyridazin-3-yl)-5-(1H-pyrazol-4-yl)phenol;
2-(6-(((1R,3r,5S)-9-azabicyclo[3.3.1]nonan-3-yl)oxy)
pyridazin-3-yl)-5-(1H-pyrazol-4-yl)phenol;
2-(6-(((1R,3s,5S)-9-azabicyclo[3.3.1]nonan-3-yl)oxy)
pyridazin-3-yl)-4-fluoro-5-(1H-pyrazol-4-yl)phenol;

2-(6-((((1R,3s,5S)-9-azabicyclo[3.3.1]nonan-3-yl)(methyl) amino)pyridazin-3-yl)-5-(1H-1,2,3-triazol-1-yl)phenol;

5-(4-(6-(((1R,3s,5S)-9-azabicyclo[3.3.1]nonan-3-yl) (methyl)amino)pyridazin-3-yl)-3-hydroxyphenyl)-2-methylpyridazin-3(2H)-one;

5-(4-(6-(((1R,3s,5S)-9-azabicyclo[3.3.1]nonan-3-yl) (methyl)amino)pyridazin-3-yl)-3-hydroxyphenyl)-2-(methyl-d3)pyridazin-3(2H)-one;

5-(4-(6-(((1R,3s,5S)-8-azabicyclo[3.2.1]octan-3-yl) (methyl)amino)pyridazin-3-yl)-3-hydroxyphenyl)-2-(methyl-d3)pyridazin-3(2H)-one;

4-(4-(6-(((1R,3s,5S)-9-azabicyclo[3.3.1]nonan-3-yl) (methyl)amino)pyridazin-3-yl)-3-hydroxyphenyl)-1-methylpyridin-2(1H)-one;

4-(4-(6-(((1R,3s,5S)-9-azabicyclo[3.3.1]nonan-3-yl) (methyl)amino)pyridazin-3-yl)-3-hydroxyphenyl)-1-(methyl-d3)pyridin-2(1H)-one;

4-(4-(6-(((1R,3s,5S)-9-azabicyclo[3.3.1]nonan-3-yl) (methyl)amino)pyridazin-3-yl)-2-fluoro-5-hydroxyphenyl)-1-methylpyridin-2(1H)-one;

5-(4-(6-(((1R,3s,5S)-9-azabicyclo[3.3.1]nonan-3-yl) (methyl)amino)pyridazin-3-yl)-2-fluoro-5-hydroxyphenyl)-2-methylpyridazin-3(2H)-one;

2-(6-((((1R,3s,5S)-9-azabicyclo[3.3.1]nonan-3-yl)(methyl) amino)pyridazin-3-yl)-5-(1-methyl-1H-pyrazol-4-yl)phenol;

2-(6-((((1R,3s,5S)-9-azabicyclo[3.3.1]nonan-3-yl)(methyl) amino)pyridazin-3-yl)-5-(1-(methyl-d3)-1H-pyrazol-4-yl)phenol;

2-(6-((((1R,3s,5S)-9-azabicyclo[3.3.1]nonan-3-yl)(methyl) amino)pyridazin-3-yl)-5-(2-methoxypyridin-4-yl)phenol;

4-(4-(6-(((1R,3s,5S)-9-azabicyclo[3.3.1]nonan-3-yl) (methyl)amino)pyridazin-3-yl)-3-hydroxyphenyl)-1,6-dimethylpyridin-2(1H)-one;

4-(4-(6-(((1R,3s,5S)-9-azabicyclo[3.3.1]nonan-3-yl) (methyl)amino)pyridazin-3-yl)-3-hydroxyphenyl)-1-(fluoromethyl)pyridin-2(1H)-one;

4-(6-(((1R,3s,5S)-9-azabicyclo[3.3.1]nonan-3-yl)(methyl) amino)pyridazin-3-yl)-3'-methoxy-4'-methyl-[1,1'-biphenyl]-3-ol;

4-(4-(6-(((1R,3s,5S)-9-azabicyclo[3.3.1]nonan-3-yl) (methyl)amino)pyridazin-3-yl)-3-hydroxyphenyl)pyridin-2(1H)-one;

6-(6-(((1R,3s,5S)-9-azabicyclo[3.3.1]nonan-3-yl)(methyl) amino)pyridazin-3-yl)-5-hydroxy-N-methylbenzofuran-2-carboxamide;

6-(6-(((1R,3s,5S)-9-azabicyclo[3.3.1]nonan-3-yl)(methyl) amino)pyridazin-3-yl)-5-hydroxy-N,N-dimethylbenzofuran-2-carboxamide;

6-(6-(((1R,3s,5S)-9-azabicyclo[3.3.1]nonan-3-yl)(methyl) amino)pyridazin-3-yl)-N-cyclopropyl-5-hydroxybenzofuran-2-carboxamide;

5-(6-(((1R,3s,5S)-9-azabicyclo[3.3.1]nonan-3-yl)(methyl) amino)pyridazin-3-yl)-6-hydroxy-N-methylbenzofuran-2-carboxamide;

5-(6-(((1R,3s,5S)-9-azabicyclo[3.3.1]nonan-3-yl)(methyl) amino)pyridazin-3-yl)-6-hydroxy-N,N-dimethylbenzofuran-2-carboxamide;

5-(6-(((1R,3s,5S)-9-azabicyclo[3.3.1]nonan-3-yl)(methyl) amino)pyridazin-3-yl)-N-cyclopropyl-6-hydroxybenzofuran-2-carboxamide;

6-(4-(6-(((1R,3s,5S)-9-azabicyclo[3.3.1]nonan-3-yl) (methyl)amino)pyridazin-3-yl)-3-hydroxyphenyl)-3-methylpyrimidin-4(3H)-one;

2-(6-((((1R,3s,5S)-9-azabicyclo[3.3.1]nonan-3-yl)(methyl) amino)pyridazin-3-yl)-5-(1-(difluoromethyl)-1H-pyrazol-4-yl)phenol;

2-(6-(cyclopropyl((1R,3s,5S)-1,5-dimethyl-8-azabicyclo [3.2.1]octan-3-yl)amino)pyridazin-3-yl)-5-(1H-pyrazol-4-yl)phenol;

2-(6-((((1R,3s,5S)-1,5-dimethyl-8-azabicyclo[3.2.1]octan-3-yl)(methyl)amino)pyridazin-3-yl)-5-(2-(methyl-d3)oxazol-5-yl)phenol;

2-(6-((((1R,3s,5S)-1,5-dimethyl-8-azabicyclo[3.2.1]octan-3-yl)(methyl)amino)pyridazin-3-yl)-4-fluoro-5-(2-(methyl-d3)oxazol-5-yl)phenol;

4-(4-(6-((((1R,3s,5S)-1,5-dimethyl-9-azabicyclo[3.3.1] nonan-3-yl)(methyl)amino)pyridazin-3-yl)-3-hydroxyphenyl)-1-methylpyrimidin-2(1H)-one;

4-(4-(6-((((1R,3s,5S)-1,5-dimethyl-9-azabicyclo[3.3.1] nonan-3-yl)(methyl)amino)pyridazin-3-yl)-3-hydroxyphenyl)pyridin-2(1H)-one;

4-(4-(6-((((1R,3s,5S)-1,5-dimethyl-9-azabicyclo[3.3.1] nonan-3-yl)(methyl)amino)pyridazin-3-yl)-2-fluoro-5-hydroxyphenyl)pyridin-2(1H)-one;

5-(2-(difluoromethoxy)pyridin-4-yl)-2-(6-((((1R,3s,5S)-1,5-dimethyl-9-azabicyclo[3.3.1]nonan-3-yl)(methyl)amino) pyridazin-3-yl)phenol;

3-amino-1-(4-(cyclopropyl(6-(2-hydroxy-4-(1H-pyrazol-4-yl)phenyl)pyridazin-3-yl)amino)-2,2,6,6-tetramethylpiperidin-1-yl)propan-1-one;

3-amino-1-(4-(6-(2-hydroxy-4-(1H-pyrazol-4-yl)phenyl) pyridazine-3-carbonyl)-2,2,6,6-tetramethylpiperidin-1-yl)propan-1-one;

3-amino-1-(4-((6-(2-hydroxy-4-(1H-pyrazol-4-yl)phenyl) pyridazin-3-yl)thio)-2,2,6,6-tetramethylpiperidin-1-yl) propan-1-one;

3-amino-1-((1R,3s,5S)-3-((6-(2-hydroxy-4-(1H-pyrazol-4-yl)phenyl)pyridazin-3-yl)oxy)-8-azabicyclo[3.2.1]octan-8-yl)propan-1-one;

3-amino-1-(4-((6-(2-hydroxy-4-(1H-pyrazol-4-yl)phenyl) pyridazin-3-yl)(methyl)amino)-2,2,6,6-tetramethylpiperidin-1-yl)propan-1-one;

3-amino-1-(4-((6-(2-hydroxy-4-(1H-pyrazol-4-yl)phenyl) pyridazin-3-yl)oxy)-2,2,6,6-tetramethylpiperidin-1-yl) propan-1-one;

3-amino-1-((1R,5S)-6-((6-(2-hydroxy-4-(1H-pyrazol-4-yl) phenyl)pyridazin-3-yl)(methyl)amino)-3-azabicyclo [3.1.0]hexan-3-yl)propan-1-one;

3-amino-1-(4-(cyclobutyl(6-(2-hydroxy-4-(1H-pyrazol-4-yl)phenyl)pyridazin-3-yl)amino)-2,2,6,6-tetramethylpiperidin-1-yl)propan-1-one;

3-amino-1-(4-((6-(2-hydroxy-4-(1H-pyrazol-4-yl)phenyl) pyridazin-3-yl)(methoxy)amino)-2,2,6,6-tetramethylpiperidin-1-yl)propan-1-one;

3-amino-1-(1-(6-(2-hydroxy-4-(1H-pyrazol-4-yl)phenyl) pyridazin-3-yl)octahydro-5H-pyrrolo[3,2-c]pyridin-5-yl) propan-1-one;

3-amino-1-(1-(6-(2-hydroxy-4-(1H-pyrazol-4-yl)phenyl) pyridazin-3-yl)octahydro-1,6-naphthyridin-6(2H)-yl)propan-1-one;

3-amino-1-(1-(6-(2-hydroxy-4-(1H-pyrazol-4-yl)phenyl) pyridazin-3-yl)-1,7-diazaspiro[3.5]nonan-7-yl)propan-1-one;

3-amino-1-(4-((6-(2-hydroxy-4-(1H-pyrazol-4-yl)phenyl) pyridazin-3-yl)thio)piperidin-1-yl)propan-1-one;

3-amino-1-(4-((6-(2-hydroxy-4-(1H-pyrazol-4-yl)phenyl) pyridazin-3-yl)oxy)-2,2,6,6-tetramethylpiperidin-1-yl) propan-1-one;

3-amino-1-(4-((6-(2-hydroxy-4-(1H-pyrazol-4-yl)phenyl) pyridazin-3-yl)(methyl)amino)-2,2,6,6-tetramethylpiperidin-1-yl)propan-1-one;

3-amino-1-(4-((6-(2-hydroxy-4-(1H-pyrazol-4-yl)phenyl) pyridazin-3-yl)(2-methoxyethoxy)amino)-2,2,6,6-tetramethylpiperidin-1-yl)propan-1-one;
3-amino-1-(4-((6-(2-hydroxy-4-(1H-pyrazol-4-yl)phenyl) pyridazin-3-yl)methylene)-2,2,6,6-tetramethylpiperidin-1-yl)propan-1-one;
3-amino-1-(4-(6-(2-hydroxy-4-(1H-pyrazol-4-yl)phenyl) pyridazine-3-carbonyl)piperidin-1-yl)propan-1-one;
3-amino-1-(4-(hydroxy(6-(2-hydroxy-4-(1H-pyrazol-4-yl) phenyl)pyridazin-3-yl)methyl)-2,2,6,6-tetramethylpiperidin-1-yl)propan-1-one;
3-amino-1-(4-((6-(2-hydroxy-4-(1H-pyrazol-4-yl)phenyl) pyridazin-3-yl)(methoxy)methyl)-2,2,6,6-tetramethylpiperidin-1-yl)propan-1-one;
3-amino-1-(4-(6-(2-hydroxy-4-(1H-pyrazol-4-yl)phenyl) pyridazine-3-carbonyl)-2,2,6,6-tetramethylpiperazin-1-yl)propan-1-one;
3-amino-1-(4-((6-(2-hydroxy-4-(1H-pyrazol-4-yl)phenyl) pyridazin-3-yl)(trifluoromethyl)amino)-2,2,6,6-tetramethylpiperidin-1-yl)propan-1-one;
3-amino-1-(4-((2-fluoroethyl)(6-(2-hydroxy-4-(1H-pyrazol-4-yl)phenyl)pyridazin-3-yl)amino)-2,2,6,6-tetramethylpiperidin-1-yl)propan-1-one;
3-amino-1-(4-((6-(2-hydroxy-4-(1H-pyrazol-4-yl)phenyl) pyridazin-3-yl)(2,2,2-trifluoroethyl)amino)-2,2,6,6-tetramethylpiperidin-1-yl)propan-1-one;
3-amino-1-(4-((3-fluoropropyl)(6-(2-hydroxy-4-(1H-pyrazol-4-yl)phenyl)pyridazin-3-yl)amino)-2,2,6,6-tetramethylpiperidin-1-yl)propan-1-one;
3-amino-1-(4-((6-(2-hydroxy-4-(1H-pyrazol-4-yl)phenyl) pyridazin-3-yl)(2-methoxyethyl)amino)-2,2,6,6-tetramethylpiperidin-1-yl)propan-1-one;
3-amino-1-((1R,3s,5S)-3-((6-(2-hydroxy-4-(1H-pyrazol-4-yl)phenyl)pyridazin-3-yl)oxy)-8-azabicyclo[3.2.1]octan-8-yl)propan-1-one;
3-amino-1-((1R,3r,5S)-3-((6-(2-hydroxy-4-(1H-pyrazol-4-yl)phenyl)pyridazin-3-yl)oxy)-8-azabicyclo[3.2.1]octan-8-yl)propan-1-one;
3-amino-1-((1R,3s,5S)-3-((6-(2-hydroxy-4-(1H-pyrazol-4-yl)phenyl)pyridazin-3-yl)(methyl)amino)-8-azabicyclo[3.2.1]octan-8-yl)propan-1-one;
3-amino-1-((1R,3r,5S)-3-((6-(2-hydroxy-4-(1H-pyrazol-4-yl)phenyl)pyridazin-3-yl)(methyl)amino)-8-azabicyclo[3.2.1]octan-8-yl)propan-1-one;
3-amino-1-(3-((6-(2-hydroxy-4-(1H-pyrazol-4-yl)phenyl) pyridazin-3-yl)oxy)-8-azabicyclo[3.2.1]octan-8-yl)propan-1-one;
3-amino-1-(4-((5-(2-hydroxy-4-(1H-pyrazol-4-yl)phenyl) pyrazin-2-yl)(methyl)amino)piperidin-1-yl)propan-1-one;
3-amino-1-(4-((5-(2-hydroxy-4-(1H-pyrazol-4-yl)phenyl) pyrazin-2-yl)(methyl)amino)-2,2,6,6-tetramethylpiperidin-1-yl)propan-1-one;
3-amino-1-(4-((5-(2-hydroxy-4-(1H-pyrazol-4-yl)phenyl) pyrazin-2-yl)oxy)-2,2,6,6-tetramethylpiperidin-1-yl)propan-1-one;
3-amino-1-(4-((6-(2-hydroxy-4-(1H-pyrazol-4-yl)phenyl) pyridin-3-yl)(methyl)amino)-2,2,6,6-tetramethylpiperidin-1-yl)propan-1-one;
3-amino-1-(4-((2-(2-hydroxy-4-(1H-pyrazol-4-yl)phenyl) pyrimidin-5-yl)(methyl)amino)-2,2,6,6-tetramethylpiperidin-1-yl)propan-1-one;
5-(4-(5-((1-(3-aminopropanoyl)-2,2,6,6-tetramethylpiperidin-4-yl)(methyl)amino)pyrazin-2-yl)-3-hydroxyphenyl) pyrimidin-2(1H)-one;
1-(4-((4-(5-(1H-pyrazol-4-yl)pyrimidin-2-yl)-3-hydroxyphenyl)(methyl)amino)-2,2,6,6-tetramethylpiperidin-1-yl)-3-aminopropan-1-one;
2'-(4-((1-(3-aminopropanoyl)piperidin-4-yl)(methyl) amino)-2-hydroxyphenyl)-[5,5'-bipyrimidin]-2(1H)-one;
(E)-3-(4-aminophenyl)-1-(4-((6-(2-hydroxy-4-(1H-pyrazol-4-yl)phenyl)pyridazin-3-yl)(methyl)amino)-2,2,6,6-tetramethylpiperidin-1-yl)prop-2-en-1-one;
3-(4-aminophenyl)-1-(4-((6-(2-hydroxy-4-(1H-pyrazol-4-yl)phenyl)pyridazin-3-yl)(methyl)amino)-2,2,6,6-tetramethylpiperidin-1-yl)propan-1-one;
1-(4-((6-(2-hydroxy-4-(1H-pyrazol-4-yl)phenyl)pyridazin-3-yl)(methyl)amino)-2,2,6,6-tetramethylpiperidin-1-yl)-2-(piperidin-4-yl)ethan-1-one;
4-(4-((6-(2-hydroxy-4-(1H-pyrazol-4-yl)phenyl)pyridazin-3-yl)(methyl)amino)-2,2,6,6-tetramethylpiperidine-1-carbonyl)cyclohexane-1-carboxylic acid;
1-(4-((6-(2-hydroxy-4-(1H-pyrazol-4-yl)phenyl)pyridazin-3-yl)(methyl)amino)-2,2,6,6-tetramethylpiperidin-1-yl)-2-(2-(methylamino)ethoxy)ethan-1-one;
4-((6-(2-hydroxy-4-(1H-pyrazol-4-yl)phenyl)pyridazin-3-yl)(methyl)amino)-2,2,6,6-tetramethyl-N-(3-(methylamino)propyl)piperidine-1-carboxamide;
(4-((6-(2-hydroxy-4-(1H-pyrazol-4-yl)phenyl)pyridazin-3-yl)(methyl)amino)-2,2,6,6-tetramethylpiperidin-1-yl)(piperidin-4-yl)methanone;
1-(4-((6-(2-hydroxy-4-(1H-pyrazol-4-yl)phenyl)pyridazin-3-yl) (methyl)amino)-2,2,6,6-tetramethylpiperidin-1-yl)-2-(methyl(2-(methylamino)ethyl)amino)ethan-1-one;
2-(azetidin-3-yl)-1-(4-((6-(2-hydroxy-4-(1H-pyrazol-4-yl) phenyl)pyridazin-3-yl)(methyl)amino)-2,2,6,6-tetramethylpiperidin-1-yl)ethan-1-one;
1-(4-((6-(2-hydroxy-4-(1H-pyrazol-4-yl)phenyl)pyridazin-3-yl)(methyl)amino)-2,2,6,6-tetramethylpiperidin-1-yl) pent-4-yn-1-one.

Exemplary SMSM compounds are summarized in Table 1A, Table 1B and Table 1C.

TABLE 1A

| SMSM# | Structure | Name |
|---|---|---|
| 1 | 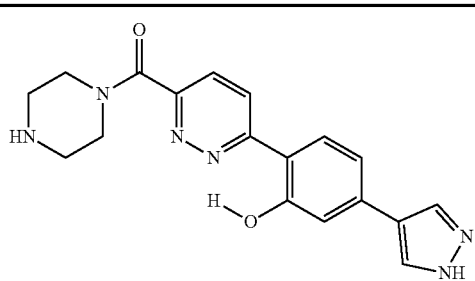 | (6-(2-hydroxy-4-(1H-pyrazol-4-yl)phenyl)pyridazin-3-yl)(piperazin-1-yl)methanone |

TABLE 1A-continued

Exemplary SMSM compounds

| SMSM# | Structure | Name |
| --- | --- | --- |
| 2 | 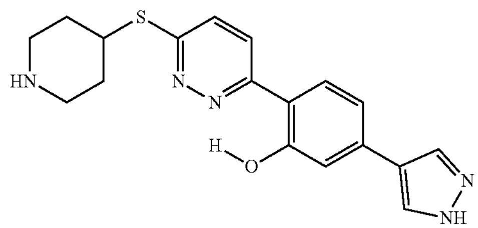 [SMILES: Oc1cc(-c2cn[nH]c2)ccc1-c1ccc(SC2CCNCC2)nn1] | 2-(6-(piperidin-4-ylthio)pyridazin-3-yl)-5-(1H-pyrazol-4-yl)phenol |
| 3 | 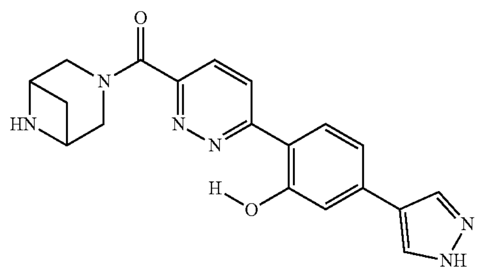 [SMILES: O=C(c1ccc(-c2ccc(-c3cn[nH]c3)cc2O)nn1)N1CC2CC(C1)N2] | (3,6-diazabicyclo[3.1.1]heptan-3-yl)(6-(2-hydroxy-4-(1H-pyrazol-4-yl)phenyl)pyridazin-3-yl)methanone |
| 4 | 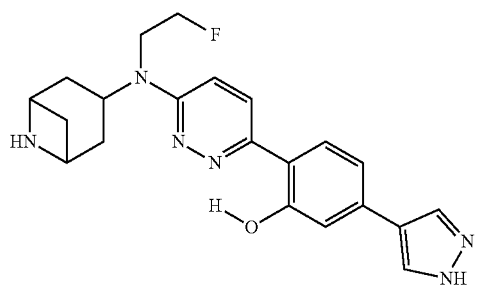 [SMILES: Oc1cc(-c2cn[nH]c2)ccc1-c1ccc(N(CCF)C2CC3CC(C2)N3)nn1] | 2-(6-((6-azabicyclo[3.1.1]heptan-3-yl)(2-fluoroethyl)amino)pyridazin-3-yl)-5-(1H-pyrazol-4-yl)phenol |
| 5 | 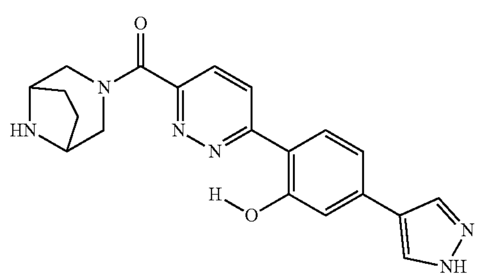 [SMILES: O=C(c1ccc(-c2ccc(-c3cn[nH]c3)cc2O)nn1)N1CC2CCC(C1)N2] | (3,8-diazabicyclo[3.2.1]octan-3-yl)(6-(2-hydroxy-4-(1H-pyrazol-4-yl)phenyl)pyridazin-3-yl)methanone |
| 6 | 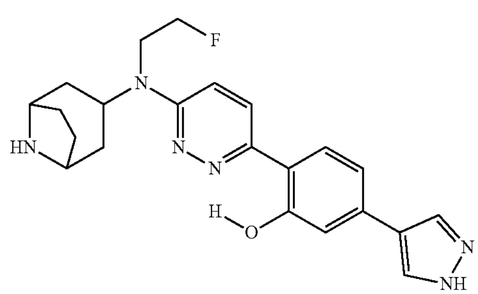 [SMILES: Oc1cc(-c2cn[nH]c2)ccc1-c1ccc(N(CCF)C2CC3CCC(C2)N3)nn1] | 2-(6-((8-azabicyclo[3.2.1]octan-3-yl)(2-fluoroethyl)amino)pyridazin-3-yl)-5-(1H-pyrazol-4-yl)phenol |

TABLE 1A-continued

Exemplary SMSM compounds

| SMSM# | Structure | Name |
|---|---|---|
| 7 | 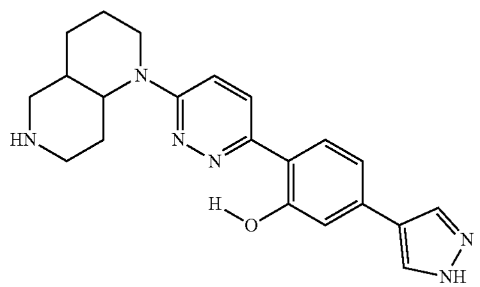 [SMILES: Oc1cc(-c2cn[nH]c2)ccc1-c1ccc(N2CCCC3CNCCC32)nn1] | 2-(6-(octahydro-1,6-naphthyridin-1(2H)-yl)pyridazin-3-yl)-5-(1H-pyrazol-4-yl)phenol |
| 8 | 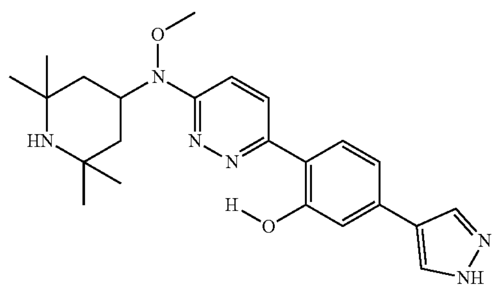 [SMILES: CON(c1ccc(-c2ccc(-c3cn[nH]c3)cc2O)nn1)C1CC(C)(C)NC(C)(C)C1] | 2-(6-(methoxy(2,2,6,6-tetramethylpiperidin-4-yl)amino)pyridazin-3-yl)-5-(1H-pyrazol-4-yl)phenol |
| 9 | 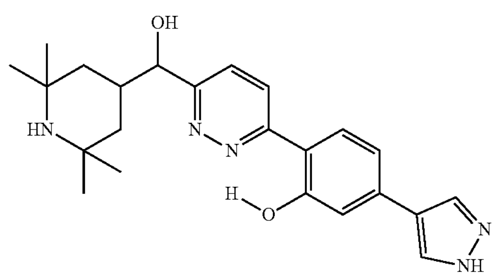 [SMILES: CC1(C)CC(C(O)c2ccc(-c3ccc(-c4cn[nH]c4)cc3O)nn2)CC(C)(C)N1] | 2-(6-(hydroxy(2,2,6,6-tetramethylpiperidin-4-yl)methyl)pyridazin-3-yl)-5-(1H-pyrazol-4-yl)phenol |
| 10 | 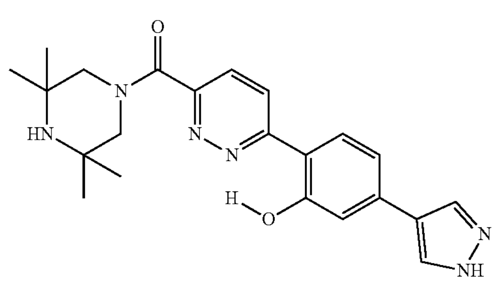 [SMILES: CC1(C)CC(C(=O)c2ccc(-c3ccc(-c4cn[nH]c4)cc3O)nn2)CC(C)(C)N1] | (6-(2-hydroxy-4-(1H-pyrazol-4-yl)phenyl)pyridazin-3-yl)(3,3,5,5-tetramethylpiperazin-1-yl)methanone |
| 11 | 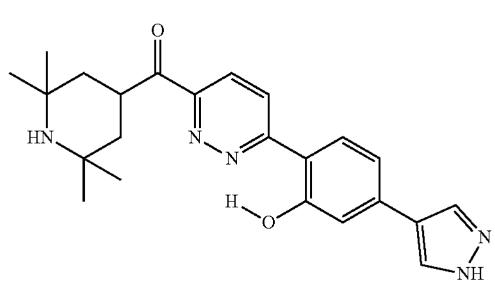 | (6-(2-hydroxy-4-(1H-pyrazol-4-yl)phenyl)pyridazin-3-yl)(2,2,6,6-tetramethylpiperidin-4-yl)methanone |

TABLE 1A-continued

Exemplary SMSM compounds

| SMSM# | Structure | Name |
|---|---|---|
| 12 | 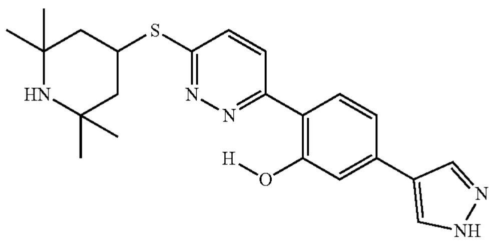 [SMILES: CC1(C)CC(Sc2ccc(-c3ccc(-c4cn[nH]c4)cc3O)nn2)CC(C)(C)N1] | 5-(1H-pyrazol-4-yl)-2-(6-((2,2,6,6-tetramethylpiperidin-4-yl)thio)pyridazin-3-yl)phenol |
| 13 | 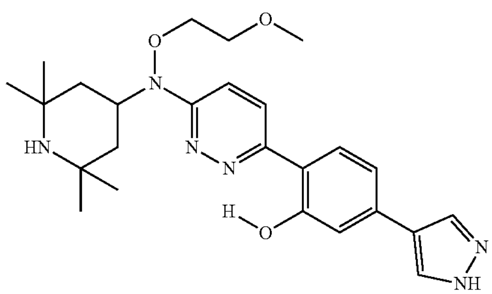 [SMILES: COCCON(c1ccc(-c2ccc(-c3cn[nH]c3)cc2O)nn1)C1CC(C)(C)NC(C)(C)C1] | 2-(6-((2-methoxyethoxy)(2,2,6,6-tetramethylpiperidin-4-yl)amino)pyridazin-3-yl)-5-(1H-pyrazol-4-yl)phenol |
| 14 | 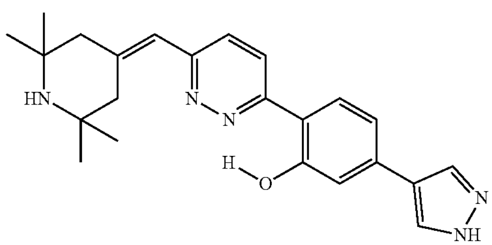 [SMILES: CC1(C)CC(=Cc2ccc(-c3ccc(-c4cn[nH]c4)cc3O)nn2)CC(C)(C)N1] | 5-(1H-pyrazol-4-yl)-2-(6-((2,2,6,6-tetramethylpiperidin-4-ylidene)methyl)pyridazin-3-yl)phenol |
| 15 | 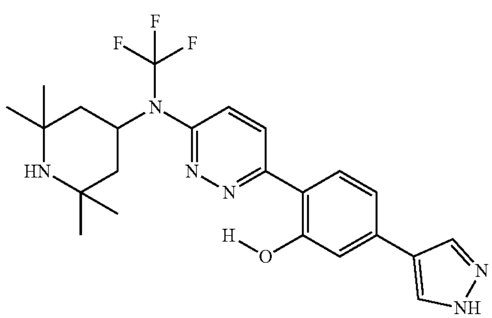 [SMILES: CC1(C)CC(N(c2ccc(-c3ccc(-c4cn[nH]c4)cc3O)nn2)C(F)(F)F)CC(C)(C)N1] | 5-(1H-pyrazol-4-yl)-2-(6-((2,2,6,6-tetramethylpiperidin-4-yl)(trifluoromethyl)amino)pyridazin-3-yl)phenol |
| 16 | 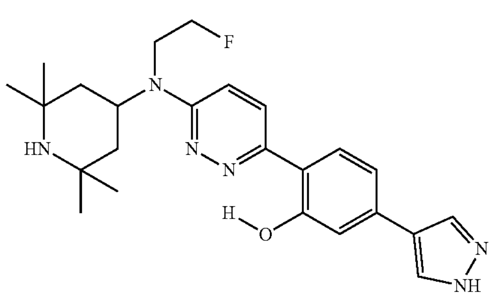 [SMILES: CC1(C)CC(N(CCF)c2ccc(-c3ccc(-c4cn[nH]c4)cc3O)nn2)CC(C)(C)N1] | 2-(6-((2-fluoroethyl)(2,2,6,6-tetramethylpiperidin-4-yl)amino)pyridazin-3-yl)-5-(1H-pyrazol-4-yl)phenol |

TABLE 1A-continued

Exemplary SMSM compounds

| SMSM# | Structure | Name |
|---|---|---|
| 17 | 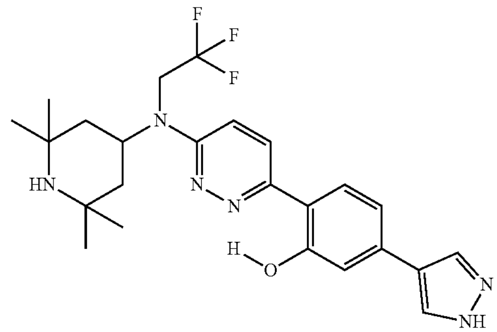 [SMILES: CC1(C)CC(N(CC(F)(F)F)c2ccc(-c3ccc(-c4cn[nH]c4)cc3O)nn2)CC(C)(C)N1] | 5-(1H-pyrazol-4-yl)-2-(6-((2,2,6,6-tetramethylpiperidin-4-yl)(2,2,2-trifluoroethyl)amino)pyridazin-3-yl)phenol |
| 18 | 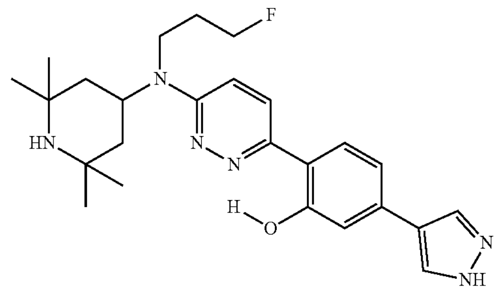 [SMILES: CC1(C)CC(N(CCCF)c2ccc(-c3ccc(-c4cn[nH]c4)cc3O)nn2)CC(C)(C)N1] | 2-(6-((3-fluoropropyl)(2,2,6,6-tetramethylpiperidin-4-yl)amino)pyridazin-3-yl)-5-(1H-pyrazol-4-yl)phenol |
| 19 | 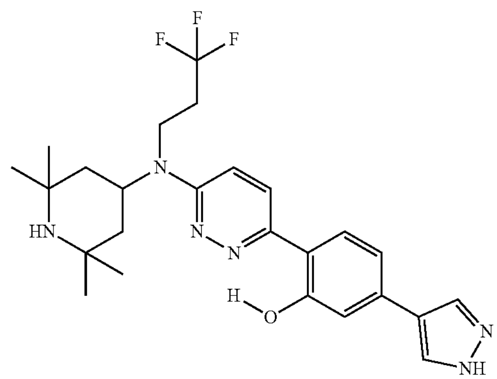 [SMILES: CC1(C)CC(N(CCC(F)(F)F)c2ccc(-c3ccc(-c4cn[nH]c4)cc3O)nn2)CC(C)(C)N1] | 5-(1H-pyrazol-4-yl)-2-(6-((2,2,6,6-tetramethylpiperidin-4-yl)(3,3,3-trifluoropropyl)amino)pyridazin-3-yl)phenol |
| 20 | 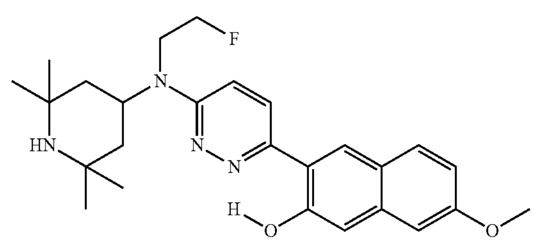 | 3-(6-((2-fluoroethyl)(2,2,6,6-tetramethylpiperidin-4-yl)amino)pyridazin-3-yl)-7-methoxynaphthalen-2-ol |
| 21 | 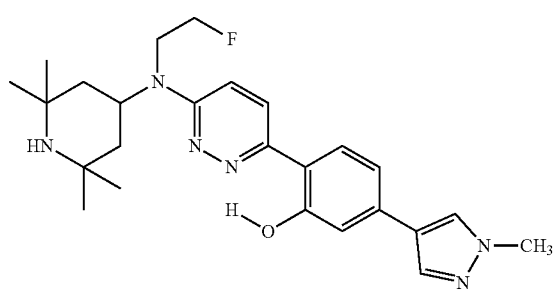 | 2-(6-((2-fluoroethyl)(2,2,6,6-tetramethylpiperidin-4-yl)amino)pyridazin-3-yl)-5-(1-methyl-1H-pyrazol-4-yl)phenol |

TABLE 1A-continued

Exemplary SMSM compounds

| SMSM# | Structure | Name |
|---|---|---|
| 22 | 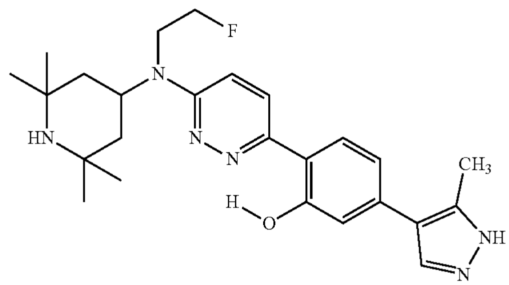 [SMILES: Cc1[nH]ncc1-c1ccc(-c2ccc(N(CCF)C3CC(C)(C)NC(C)(C)C3)nn2)c(O)c1] | 2-(6-((2-fluoroethyl)(2,2,6,6-tetramethylpiperidin-4-yl)amino)pyridazin-3-yl)-5-(5-methyl-1H-pyrazol-4-yl)phenol |
| 23 | 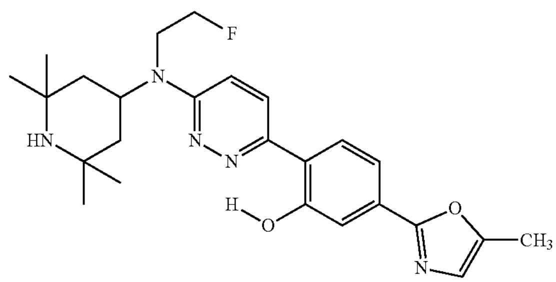 | 2-(6-((2-fluoroethyl)(2,2,6,6-tetramethylpiperidin-4-yl)amino)pyridazin-3-yl)-5-(5-methyloxazol-2-yl)phenol |
| 24 | 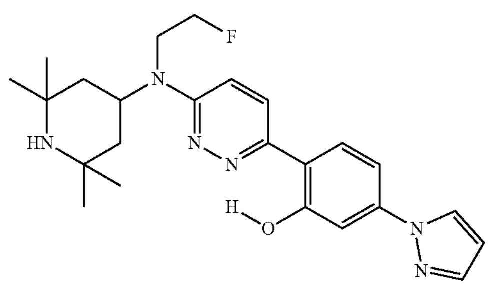 [SMILES: CC1(C)CC(N(CCF)c2ccc(-c3ccc(-n4cccn4)cc3O)nn2)CC(C)(C)N1] | 2-(6-((2-fluoroethyl)(2,2,6,6-tetramethylpiperidin-4-yl)amino)pyridazin-3-yl)-5-(1H-pyrazol-1-yl)phenol |
| 25 | 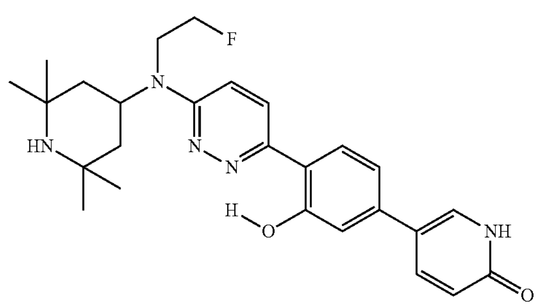 [SMILES: CC1(C)CC(N(CCF)c2ccc(-c3ccc(-c4ccc(=O)[nH]c4)cc3O)nn2)CC(C)(C)N1] | 5-(4-(6-((2-fluoroethyl)(2,2,6,6-tetramethylpiperidin-4-yl)amino)pyridazin-3-yl)-3-hydroxyphenyl)pyridin-2(1H)-one |
| 26 | 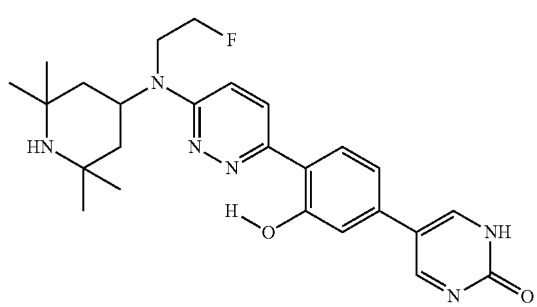 [SMILES: CC1(C)CC(N(CCF)c2ccc(-c3ccc(-c4cnc(=O)[nH]c4)cc3O)nn2)CC(C)(C)N1] | 5-(4-(6-((2-fluoroethyl)(2,2,6,6-tetramethylpiperidin-4-yl)amino)pyridazin-3-yl)-3-hydroxyphenyl)pyrimidin-2(1H)-one |

TABLE 1A-continued

Exemplary SMSM compounds

| SMSM# | Structure | Name |
|---|---|---|
| 27 | 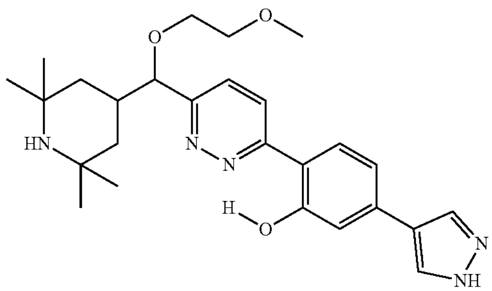 | 2-(6-((2-methoxyethoxy)(2,2,6,6-tetramethylpiperidin-4-yl)methyl)pyridazin-3-yl)-5-(1H-pyrazol-4-yl)phenol |
| 28 | 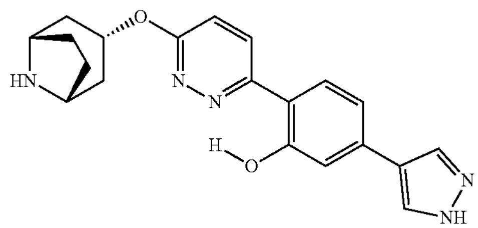 [SMILES: Oc1cc(-c2cn[nH]c2)ccc1-c1ccc(O[C@@H]2C[C@H]3CC[C@@H](C2)N3)nn1] | 2-(6-(((1R,3s,5S)-8-azabicyclo[3.2.1]octan-3-yl)oxy)pyridazin-3-yl)-5-(1H-pyrazol-4-yl)phenol |
| 29 | 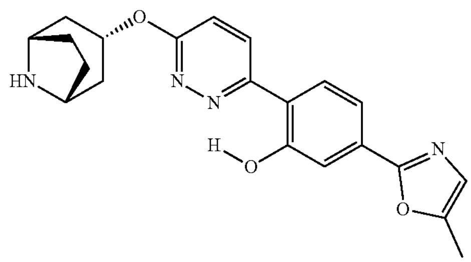 [SMILES: Cc1cnc(-c2ccc(-c3ccc(O[C@@H]4C[C@H]5CC[C@@H](C4)N5)nn3)c(O)c2)o1] | 2-(6-(((1R,3s,5S)-8-azabicyclo[3.2.1]octan-3-yl)oxy)pyridazin-3-yl)-5-(5-methyloxazol-2-yl)phenol |
| 30 | 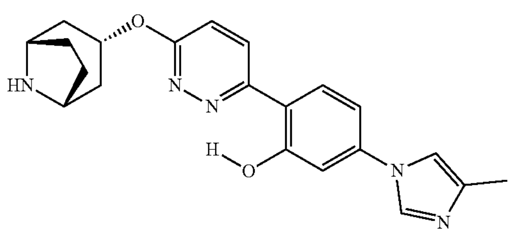 [SMILES: Cc1cn(-c2ccc(-c3ccc(O[C@@H]4C[C@H]5CC[C@@H](C4)N5)nn3)c(O)c2)cn1] | 2-(6-(((1R,3s,5S)-8-azabicyclo[3.2.1]octan-3-yl)oxy)pyridazin-3-yl)-5-(4-methyl-1H-imidazol-1-yl)phenol |
| 31 | 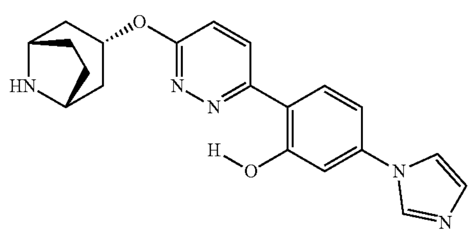 [SMILES: Oc1cc(-n2ccnc2)ccc1-c1ccc(O[C@@H]2C[C@H]3CC[C@@H](C2)N3)nn1] | 2-(6-(((1R,3s,5S)-8-azabicyclo[3.2.1]octan-3-yl)oxy)pyridazin-3-yl)-5-(1H-imidazol-1-yl)phenol |
| 32 | 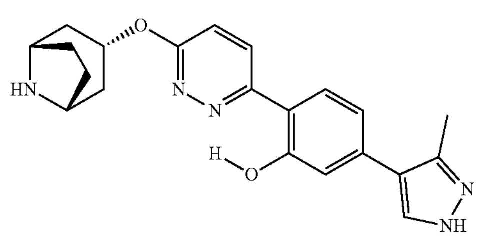 [SMILES: Cc1n[nH]cc1-c1ccc(-c2ccc(O[C@@H]3C[C@H]4CC[C@@H](C3)N4)nn2)c(O)c1] | 2-(6-(((1R,3s,5S)-8-azabicyclo[3.2.1]octan-3-yl)oxy)pyridazin-3-yl)-5-(3-methyl-1H-pyrazol-4-yl)phenol |

TABLE 1A-continued

Exemplary SMSM compounds

| SMSM# | Structure | Name |
|---|---|---|
| 33 | 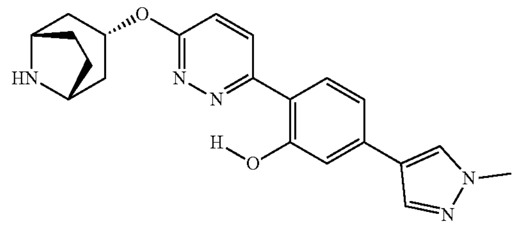 [SMILES: Cn1cc(-c2ccc(-c3ccc(O[C@@H]4C[C@H]5CC[C@@H](C4)N5)nn3)c(O)c2)cn1] | 2-(6-(((1R,3s,5S)-8-azabicyclo[3.2.1]octan-3-yl)oxy)pyridazin-3-yl)-5-(1-methyl-1H-pyrazol-4-yl)phenol |
| 34 | 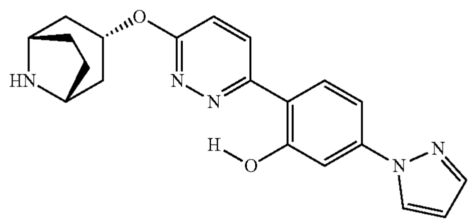 [SMILES: Oc1cc(-n2cccn2)ccc1-c1ccc(O[C@@H]2C[C@H]3CC[C@@H](C2)N3)nn1] | 2-(6-(((1R,3s,5S)-8-azabicyclo[3.2.1]octan-3-yl)oxy)pyridazin-3-yl)-5-(1H-pyrazol-1-yl)phenol |
| 35 | 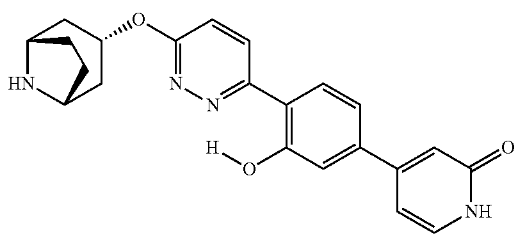 [SMILES: O=c1cc(-c2ccc(-c3ccc(O[C@@H]4C[C@H]5CC[C@@H](C4)N5)nn3)c(O)c2)cc[nH]1] | 4-(4-(6-(((1R,3s,5S)-8-azabicyclo[3.2.1]octan-3-yl)oxy)pyridazin-3-yl)-3-hydroxyphenyl)pyridin-2(1H)-one |
| 36 | 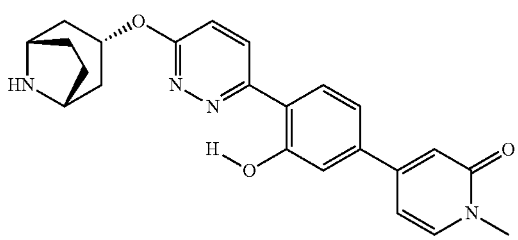 [SMILES: Cn1ccc(-c2ccc(-c3ccc(O[C@@H]4C[C@H]5CC[C@@H](C4)N5)nn3)c(O)c2)cc1=O] | 4-(4-(6-(((1R,3s,5S)-8-azabicyclo[3.2.1]octan-3-yl)oxy)pyridazin-3-yl)-3-hydroxyphenyl)-1-methylpyridin-2(1H)-one |
| 37 | 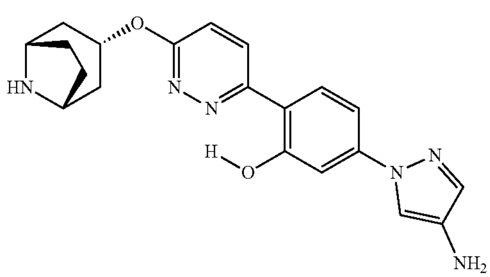 [SMILES: Nc1cnn(-c2ccc(-c3ccc(O[C@@H]4C[C@H]5CC[C@@H](C4)N5)nn3)c(O)c2)c1] | 2-(6-(((1R,3s,5S)-8-azabicyclo[3.2.1]octan-3-yl)oxy)pyridazin-3-yl)-5-(4-amino-1H-pyrazol-1-yl)phenol |
| 38 | 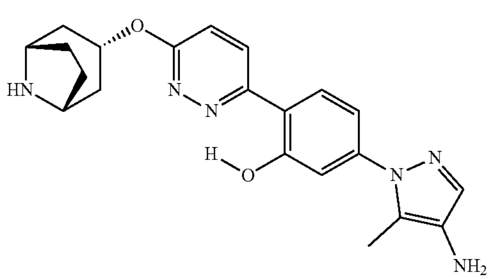 [SMILES: Cc1c(N)cnn1-c1ccc(-c2ccc(O[C@@H]3C[C@H]4CC[C@@H](C3)N4)nn2)c(O)c1] | 2-(6-(((1R,3s,5S)-8-azabicyclo[3.2.1]octan-3-yl)oxy)pyridazin-3-yl)-5-(4-amino-5-methyl-1H-pyrazol-1-yl)phenol |

TABLE 1A-continued

Exemplary SMSM compounds

| SMSM# | Structure | Name |
|---|---|---|
| 39 | 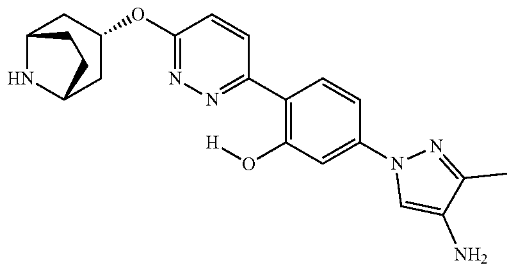 [SMILES: Cc1nn(-c2ccc(-c3ccc(O[C@@H]4C[C@H]5CC[C@@H](C4)N5)nn3)c(O)c2)cc1N] | 2-(6-(((1R,3s,5S)-8-azabicyclo[3.2.1]octan-3-yl)oxy)pyridazin-3-yl)-5-(4-amino-3-methyl-1H-pyrazol-1-yl)phenol |
| 40 | 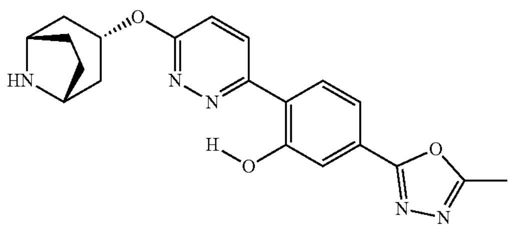 [SMILES: Cc1nnc(-c2ccc(-c3ccc(O[C@@H]4C[C@H]5CC[C@@H](C4)N5)nn3)c(O)c2)o1] | 2-(6-(((1R,3s,5S)-8-azabicyclo[3.2.1]octan-3-yl)oxy)pyridazin-3-yl)-5-(5-methyl-1,3,4-oxadiazol-2-yl)phenol |
| 41 | 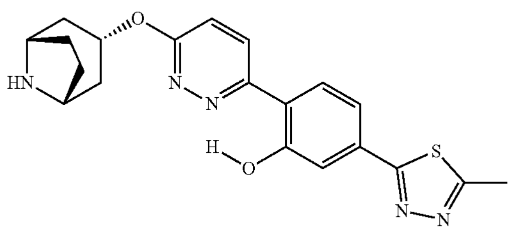 [SMILES: Cc1nnc(-c2ccc(-c3ccc(O[C@@H]4C[C@H]5CC[C@@H](C4)N5)nn3)c(O)c2)s1] | 2-(6-(((1R,3s,5S)-8-azabicyclo[3.2.1]octan-3-yl)oxy)pyridazin-3-yl)-5-(5-methyl-1,3,4-thiadiazol-2-yl)phenol |
| 42 | 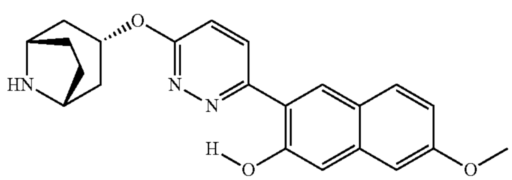 [SMILES: COc1ccc2cc(-c3ccc(O[C@@H]4C[C@H]5CC[C@@H](C4)N5)nn3)c(O)cc2c1] | 3-(6-(((1R,3s,5S)-8-azabicyclo[3.2.1]octan-3-yl)oxy)pyridazin-3-yl)-7-methoxynaphthalen-2-ol |
| 43 | 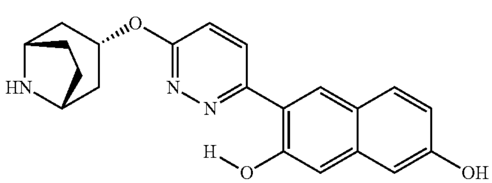 [SMILES: Oc1ccc2cc(-c3ccc(O[C@@H]4C[C@H]5CC[C@@H](C4)N5)nn3)c(O)cc2c1] | 3-(6-(((1R,3s,5S)-8-azabicyclo[3.2.1]octan-3-yl)oxy)pyridazin-3-yl)naphthalene-2,7-diol |
| 44 | 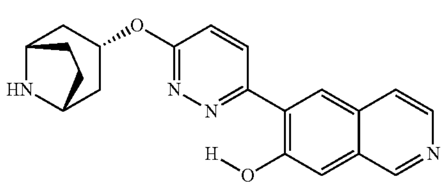 [SMILES: Oc1cc2cnccc2cc1-c1ccc(O[C@@H]2C[C@H]3CC[C@@H](C2)N3)nn1] | 6-(6-(((1R,3s,5S)-8-azabicyclo[3.2.1]octan-3-yl)oxy)pyridazin-3-yl)isoquinolin-7-ol |
| 45 | 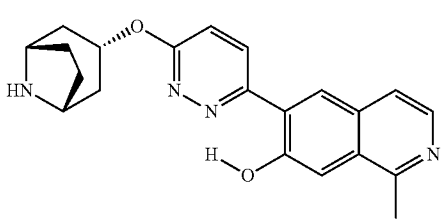 [SMILES: Cc1nccc2cc(-c3ccc(O[C@@H]4C[C@H]5CC[C@@H](C4)N5)nn3)c(O)cc12] | 6-(6-(((1R,3s,5S)-8-azabicyclo[3.2.1]octan-3-yl)oxy)pyridazin-3-yl)-1-methylisoquinolin-7-ol |

TABLE 1A-continued

Exemplary SMSM compounds

| SMSM# | Structure | Name |
|---|---|---|
| 46 | 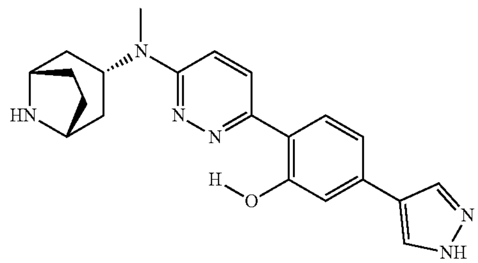 [SMILES: CN(c1ccc(-c2ccc(-c3cn[nH]c3)cc2O)nn1)[C@@H]1C[C@H]2CC[C@@H](C1)N2] | 2-(6-(((1R,3s,5S)-8-azabicyclo[3.2.1]octan-3-yl)(methyl)amino)pyridazin-3-yl)-5-(1H-pyrazol-4-yl)phenol |
| 47 | 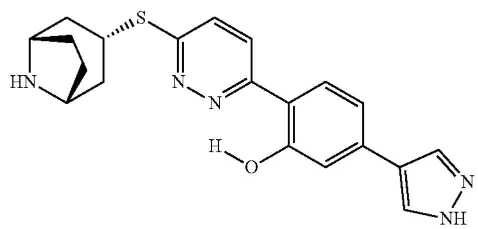 [SMILES: Oc1cc(-c2cn[nH]c2)ccc1-c1ccc(S[C@@H]2C[C@H]3CC[C@@H](C2)N3)nn1] | 2-(6-(((1R,3s,5S)-8-azabicyclo[3.2.1]octan-3-yl)thio)pyridazin-3-yl)-5-(1H-pyrazol-4-yl)phenol |
| 48 | 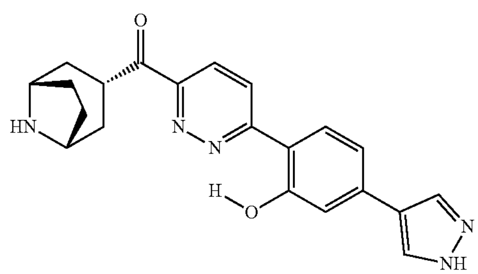 [SMILES: O=C(c1ccc(-c2ccc(-c3cn[nH]c3)cc2O)nn1)[C@@H]1C[C@H]2CC[C@@H](C1)N2] | ((1R,3s,5S)-8-azabicyclo[3.2.1]octan-3-yl)(6-(2-hydroxy-4-(1H-pyrazol-4-yl)phenyl)pyridazin-3-yl)methanone |
| 49 | 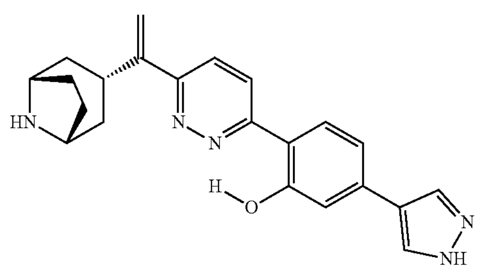 [SMILES: C=C(c1ccc(-c2ccc(-c3cn[nH]c3)cc2O)nn1)[C@@H]1C[C@H]2CC[C@@H](C1)N2] | 2-(6-(1-((1R,3s,5S)-8-azabicyclo[3.2.1]octan-3-yl)vinyl)pyridazin-3-yl)-5-(1H-pyrazol-4-yl)phenol |
| 50 | 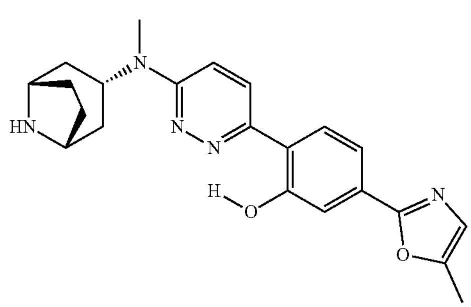 [SMILES: Cc1cnc(-c2ccc(-c3ccc(N(C)[C@@H]4C[C@H]5CC[C@@H](C4)N5)nn3)c(O)c2)o1] | 2-(6-(((1R,3s,5S)-8-azabicyclo[3.2.1]octan-3-yl)(methyl)amino)pyridazin-3-yl)-5-(5-methyloxazol-2-yl)phenol |

TABLE 1A-continued

Exemplary SMSM compounds

| SMSM# | Structure | Name |
|---|---|---|
| 51 | 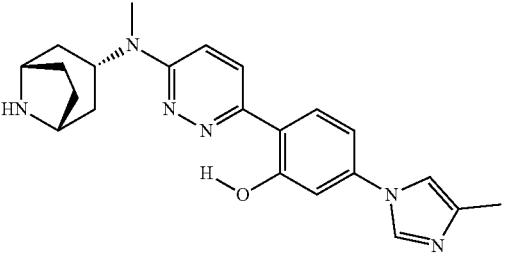 [SMILES: Cc1cn(-c2ccc(-c3ccc(N(C)[C@@H]4C[C@H]5CC[C@@H](C4)N5)nn3)c(O)c2)cn1] | 2-(6-(((1R,3s,5S)-8-azabicyclo[3.2.1]octan-3-yl)(methyl)amino)pyridazin-3-yl)-5-(4-methyl-1H-imidazol-1-yl)phenol |
| 52 | 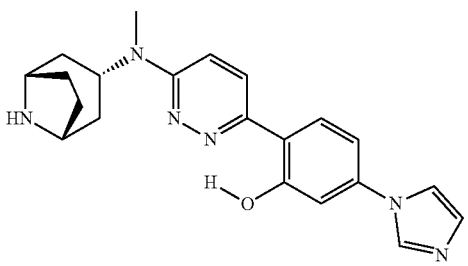 [SMILES: CN(c1ccc(-c2ccc(-n3ccnc3)cc2O)nn1)[C@@H]1C[C@H]2CC[C@@H](C1)N2] | 2-(6-(((1R,3s,5S)-8-azabicyclo[3.2.1]octan-3-yl)(methyl)amino)pyridazin-3-yl)-5-(1H-imidazol-1-yl)phenol |
| 53 | 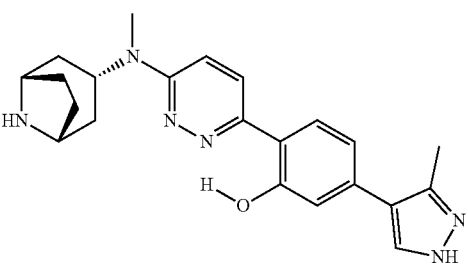 [SMILES: Cc1n[nH]cc1-c1ccc(-c2ccc(N(C)[C@@H]3C[C@H]4CC[C@@H](C3)N4)nn2)c(O)c1] | 2-(6-(((1R,3s,5S)-8-azabicyclo[3.2.1]octan-3-yl)(methyl)amino)pyridazin-3-yl)-5-(3-methyl-1H-pyrazol-4-yl)phenol |
| 54 | 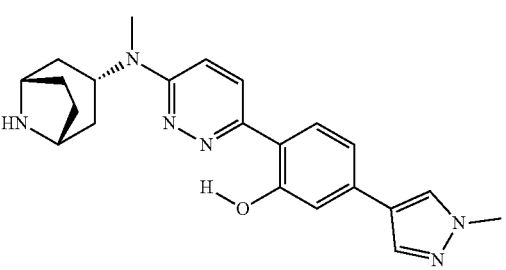 [SMILES: CN(c1ccc(-c2ccc(-c3cnn(C)c3)cc2O)nn1)[C@@H]1C[C@H]2CC[C@@H](C1)N2] | 2-(6-(((1R,3s,5S)-8-azabicyclo[3.2.1]octan-3-yl)(methyl)amino)pyridazin-3-yl)-5-(1-methyl-1H-pyrazol-4-yl)phenol |
| 55 | 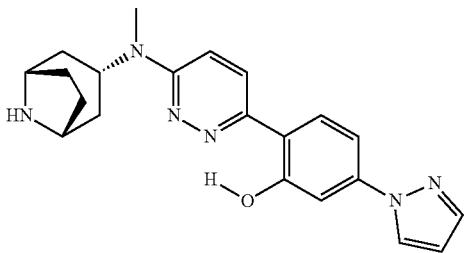 [SMILES: CN(c1ccc(-c2ccc(-n3cccn3)cc2O)nn1)[C@@H]1C[C@H]2CC[C@@H](C1)N2] | 2-(6-(((1R,3s,5S)-8-azabicyclo[3.2.1]octan-3-yl)(methyl)amino)pyridazin-3-yl)-5-(1H-pyrazol-1-yl)phenol |

TABLE 1A-continued

Exemplary SMSM compounds

| SMSM# | Structure | Name |
|---|---|---|
| 56 | 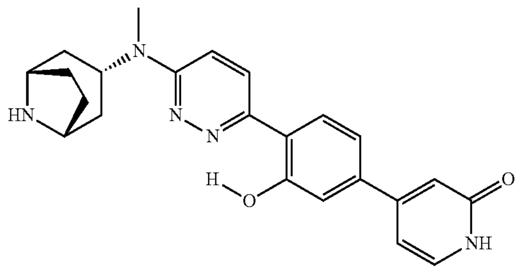 [SMILES: CN(c1ccc(-c2ccc(-c3cc[nH]c(=O)c3)cc2O)nn1)[C@@H]1C[C@H]2CC[C@@H](C1)N2] | 4-(4-(6-((((1R,3s,5S)-8-azabicyclo[3.2.1]octan-3-yl)(methyl)amino)pyridazin-3-yl)-3-hydroxyphenyl)pyridin-2(1H)-one |
| 57 | 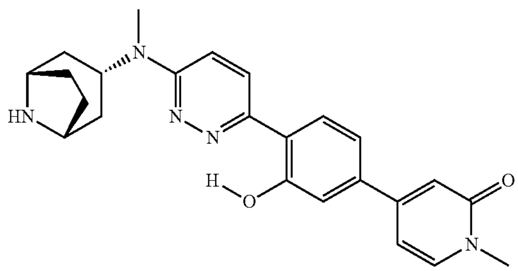 [SMILES: CN(c1ccc(-c2ccc(-c3ccn(C)c(=O)c3)cc2O)nn1)[C@@H]1C[C@H]2CC[C@@H](C1)N2] | 4-(4-(6-(((1R,3s,5S)-8-azabicyclo[3.2.1]octan-3-yl)(methyl)amino)pyridazin-3-yl)-3-hydroxyphenyl)-1-methylpyridin-2(1H)-one |
| 58 | 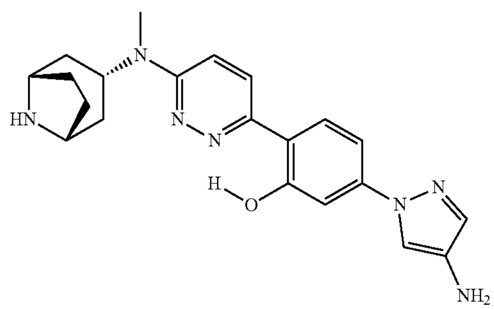 [SMILES: CN(c1ccc(-c2ccc(-n3cc(N)cn3)cc2O)nn1)[C@@H]1C[C@H]2CC[C@@H](C1)N2] | 2-(6-(((1R,3s,5S)-8-azabicyclo[3.2.1]octan-3-yl)(methyl)amino)pyridazin-3-yl)-5-(4-amino-1H-pyrazol-1-yl)phenol |
| 59 | 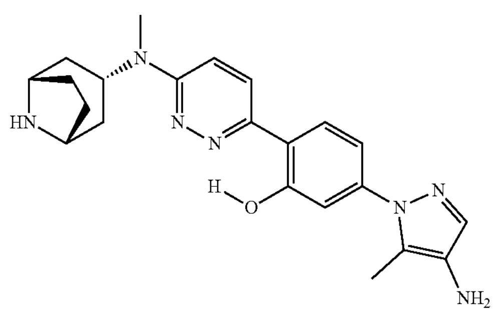 [SMILES: Cc1c(N)cnn1-c1ccc(-c2ccc(N(C)[C@@H]3C[C@H]4CC[C@@H](C3)N4)nn2)c(O)c1] | 2-(6-(((1R,3s,5S)-8-azabicyclo[3.2.1]octan-3-yl)(methyl)amino)pyridazin-3-yl)-5-(4-amino-5-methyl-1H-pyrazol-1-yl)phenol |
| 60 | 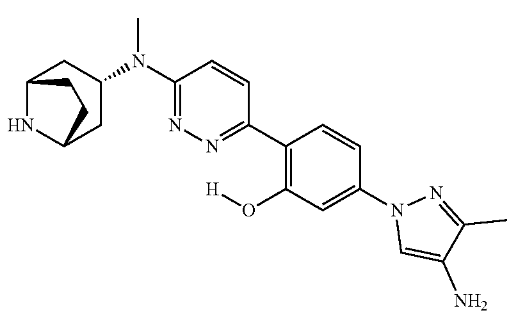 [SMILES: Cc1nn(-c2ccc(-c3ccc(N(C)[C@@H]4C[C@H]5CC[C@@H](C4)N5)nn3)c(O)c2)cc1N] | 2-(6-(((1R,3s,5S)-8-azabicyclo[3.2.1]octan-3-yl)(methyl)amino)pyridazin-3-yl)-5-(4-amino-3-methyl-1H-pyrazol-1-yl)phenol |

TABLE 1A-continued

Exemplary SMSM compounds

| SMSM# | Structure | Name |
|---|---|---|
| 61 | 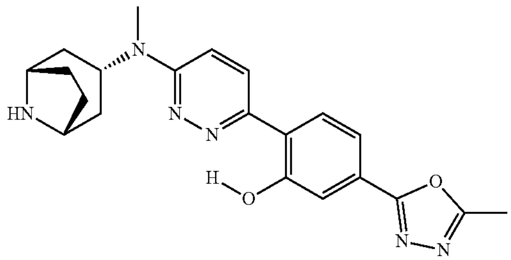 [SMILES: Cc1nnc(-c2ccc(-c3ccc(N(C)[C@@H]4C[C@H]5CC[C@@H](C4)N5)nn3)c(O)c2)o1] | 2-(6-(((1R,3s,5S)-8-azabicyclo[3.2.1]octan-3-yl)(methyl)amino)pyridazin-3-yl)-5-(5-methyl-1,3,4-oxadiazol-2-yl)phenol |
| 62 | 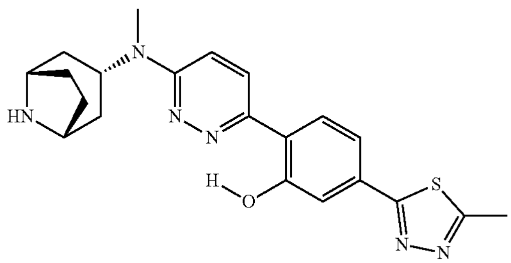 [SMILES: Cc1nnc(-c2ccc(-c3ccc(N(C)[C@@H]4C[C@H]5CC[C@@H](C4)N5)nn3)c(O)c2)s1] | 2-(6-(((1R,3s,5S)-8-azabicyclo[3.2.1]octan-3-yl)(methyl)amino)pyridazin-3-yl)-5-(5-methyl-1,3,4-thiadiazol-2-yl)phenol |
| 63 | 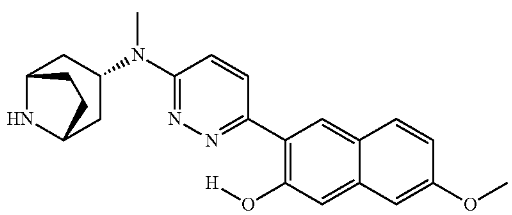 [SMILES: COc1ccc2cc(-c3ccc(N(C)[C@@H]4C[C@H]5CC[C@@H](C4)N5)nn3)c(O)cc2c1] | 3-(6-(((1R,3s,5S)-8-azabicyclo[3.2.1]octan-3-yl)(methyl)amino)pyridazin-3-yl)-7-methoxynaphthalen-2-ol |
| 64 | 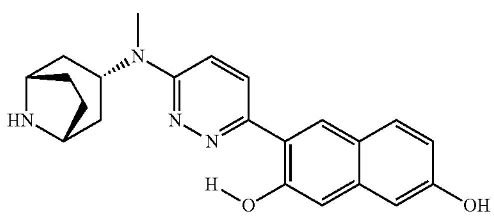 [SMILES: CN(c1ccc(-c2cc3ccc(O)cc3cc2O)nn1)[C@@H]1C[C@H]2CC[C@@H](C1)N2] | 3-(6-(((1R,3s,5S)-8-azabicyclo[3.2.1]octan-3-yl)(methyl)amino)pyridazin-3-yl)naphthalene-2,7-diol |
| 65 | 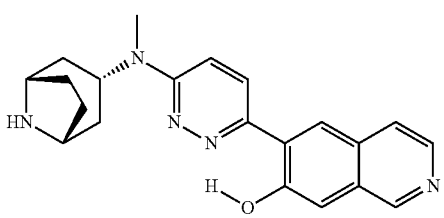 [SMILES: CN(c1ccc(-c2cc3ccncc3cc2O)nn1)[C@@H]1C[C@H]2CC[C@@H](C1)N2] | 6-(6-(((1R,3s,5S)-8-azabicyclo[3.2.1]octan-3-yl)(methyl)amino)pyridazin-3-yl)isoquinolin-7-ol |
| 66 | 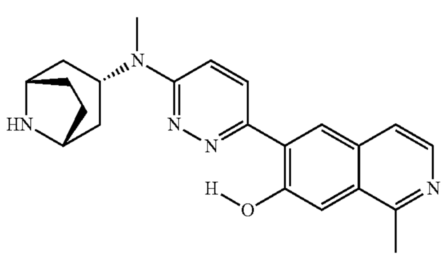 [SMILES: Cc1nccc2cc(-c3ccc(N(C)[C@@H]4C[C@H]5CC[C@@H](C4)N5)nn3)c(O)cc12] | 6-(6-(((1R,3s,5S)-8-azabicyclo[3.2.1]octan-3-yl)(methyl)amino)pyridazin-3-yl)-1-methylisoquinolin-7-ol |

TABLE 1A-continued

Exemplary SMSM compounds

| SMSM# | Structure | Name |
|---|---|---|
| 67 | 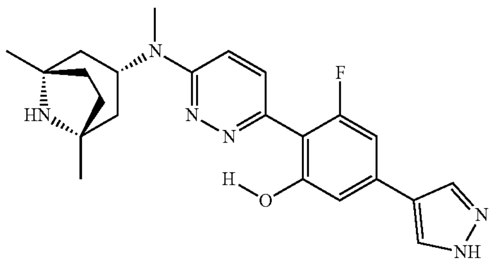 [SMILES: CN(c1ccc(-c2c(O)cc(-c3cn[nH]c3)cc2F)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-3-fluoro-5-(1H-pyrazol-4-yl)phenol |
| 68 | 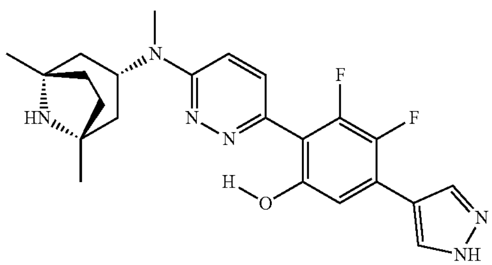 [SMILES: CN(c1ccc(-c2c(O)cc(-c3cn[nH]c3)c(F)c2F)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-3,4-difluoro-5-(1H-pyrazol-4-yl)phenol |
| 69 | 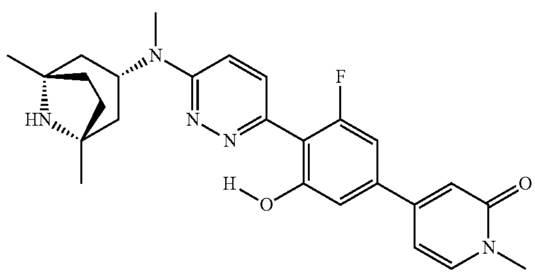 [SMILES: CN(c1ccc(-c2c(O)cc(-c3ccn(C)c(=O)c3)cc2F)nn1)[C@H]1C[C@]2(C)CC[C@](C)(C1)N2] | 4-(4-(6-(((1R,3s,5S)-1,5-dimethyl-8-azabicyclo[3.2.1]octan-3-yl)(methyl)amino)pyridazin-3-yl)-3-fluoro-5-hydroxyphenyl)-1-methylpyridin-2(1H)-one |
| 70 | 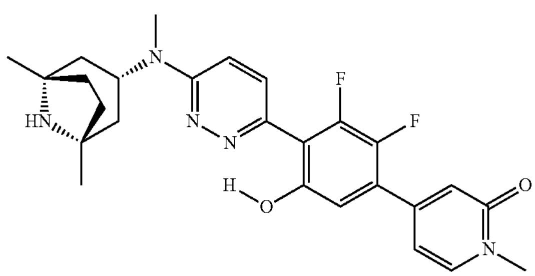 | 4-(4-(6-(((1R,3s,5S)-1,5-dimethyl-8-azabicyclo[3.2.1]octan-3-yl)(methyl)amino)pyridazin-3-yl)-2,3-difluoro-5-hydroxyphenyl)-1-methylpyridin-2(1H)-one |
| 71 | 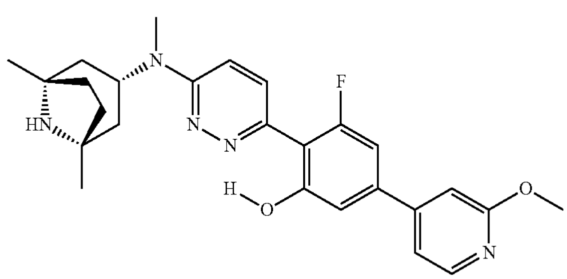 | 2-(6-(((1R,3s,5S)-1,5-dimethyl-8-azabicyclo[3.2.1]octan-3-yl)(methyl)amino)pyridazin-3-yl)-3-fluoro-5-(2-methoxypyridin-4-yl)phenol |

TABLE 1A-continued

Exemplary SMSM compounds

| SMSM# | Structure | Name |
|---|---|---|
| 72 | 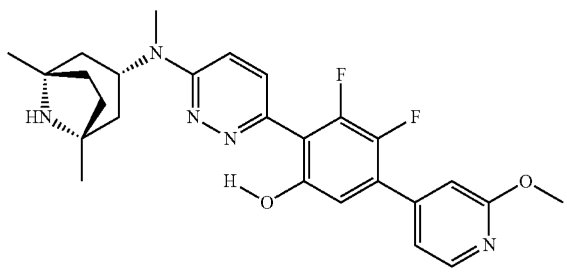 | 2-(6-(((1R,3s,5S)-1,5-dimethyl-8-azabicyclo[3.2.1]octan-3-yl)(methyl)amino)pyridazin-3-yl)-3,4-difluoro-5-(2-methoxypyridin-4-yl)phenol |
| 73 | 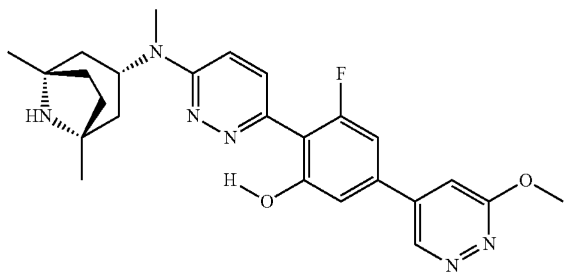 | 2-(6-(((1R,3s,5S)-1,5-dimethyl-8-azabicyclo[3.2.1]octan-3-yl)(methyl)amino)pyridazin-3-yl)-3-fluoro-5-(6-methoxypyridazin-4-yl)phenol |
| 74 | 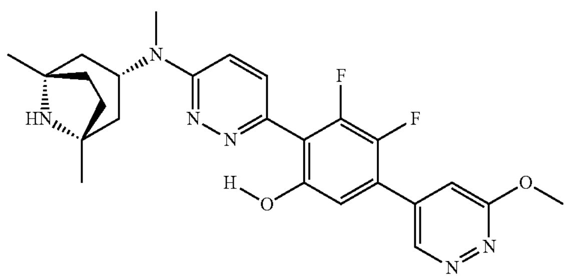 | 2-(6-(((1R,3s,5S)-1,5-dimethyl-8-azabicyclo[3.2.1]octan-3-yl)(methyl)amino)pyridazin-3-yl)-3,4-difluoro-5-(6-methoxypyridazin-4-yl)phenol |
| 75 | 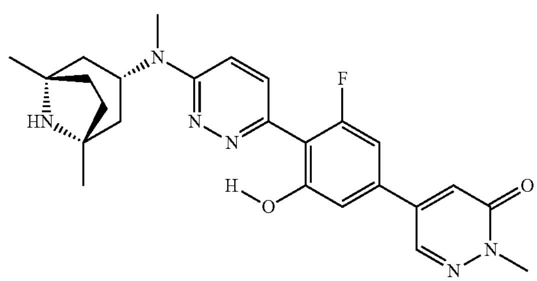 | 5-(4-(6-(((1R,3s,5S)-1,5-dimethyl-8-azabicyclo[3.2.1]octan-3-yl)(methyl)amino)pyridazin-3-yl)-3-fluoro-5-hydroxyphenyl)-2-methylpyridazin-3(2H)-one |
| 76 | 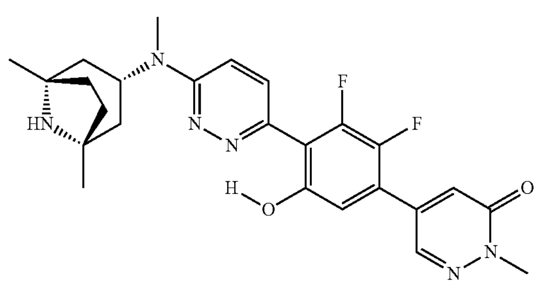 | 5-(4-(6-(((1R,3s,5S)-1,5-dimethyl-8-azabicyclo[3.2.1]octan-3-yl)(methyl)amino)pyridazin-3-yl)-2,3-difluoro-5-hydroxyphenyl)-2-methylpyridazin-3(2H)-one |

TABLE 1A-continued

Exemplary SMSM compounds

| SMSM# | Structure | Name |
|---|---|---|
| 77 | 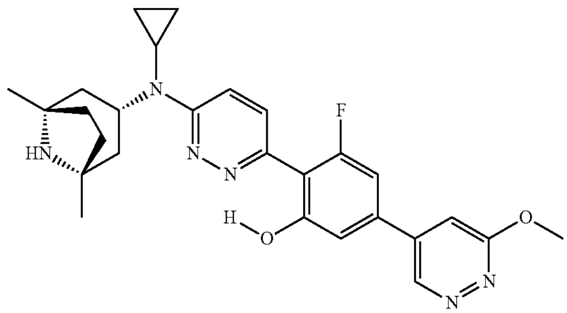 | 2-(6-(cyclopropyl((1R,3s,5S)-1,5-dimethyl-8-azabicyclo[3.2.1]octan-3-yl)amino)pyridazin-3-yl)-3-fluoro-5-(6-methoxypyridazin-4-yl)phenol |
| 78 | 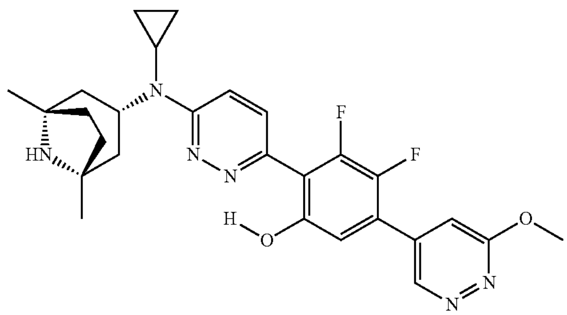 | 2-(6-(cyclopropyl((1R,3s,5S)-1,5-dimethyl-8-azabicyclo[3.2.1]octan-3-yl)amino)pyridazin-3-yl)-3,4-difluoro-5-(6-methoxypyridazin-4-yl)phenol |
| 79 | 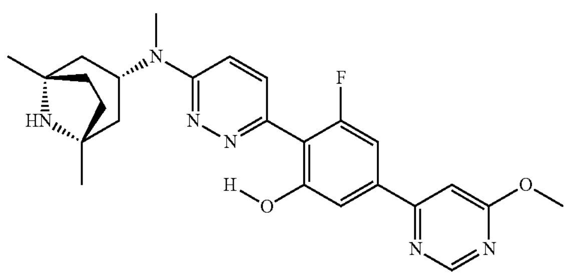 | 2-(6-(((1R,3s,5S)-1,5-dimethyl-8-azabicyclo[3.2.1]octan-3-yl)(methyl)amino)pyridazin-3-yl)-3-fluoro-5-(6-methoxypyrimidin-4-yl)phenol |
| 80 | 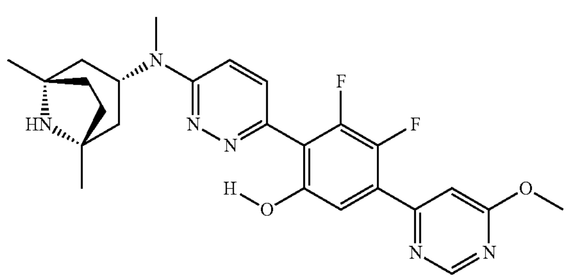 | 2-(6-(((1R,3s,5S)-1,5-dimethyl-8-azabicyclo[3.2.1]octan-3-yl)(methyl)amino)pyridazin-3-yl)-3,4-difluoro-5-(6-methoxypyrimidin-4-yl)phenol |
| 81 | 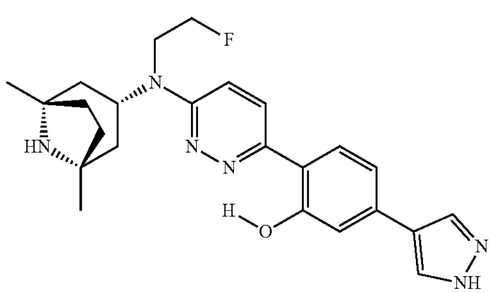 [SMILES: C[C@]12CC[C@](C)(C[C@@H](N(CCF)c3ccc(-c4ccc(-c5cn[nH]c5)cc4O)nn3)C1)N2] | 2-(6-(((1R,3s,5S)-1,5-dimethyl-8-azabicyclo[3.2.1]octan-3-yl)(2-fluoroethyl)amino)pyridazin-3-yl)-5-(1H-pyrazol-4-yl)phenol |

TABLE 1A-continued

Exemplary SMSM compounds

| SMSM# | Structure | Name |
|---|---|---|
| 82 | 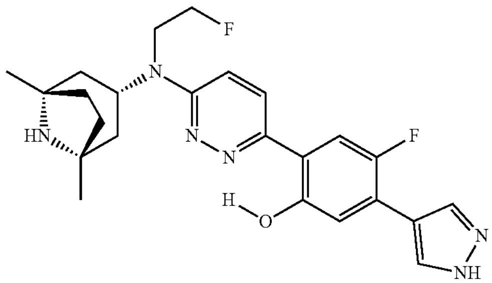 [SMILES: C[C@]12CC[C@](C)(C[C@@H](N(CCF)c3ccc(-c4cc(F)c(-c5cn[nH]c5)cc4O)nn3)C1)N2] | 2-(6-(((1R,3s,5S)-1,5-dimethyl-8-azabicyclo[3.2.1]octan-3-yl)(2-fluoroethyl)amino)pyridazin-3-yl)-4-fluoro-5-(1H-pyrazol-4-yl)phenol |
| 83 | 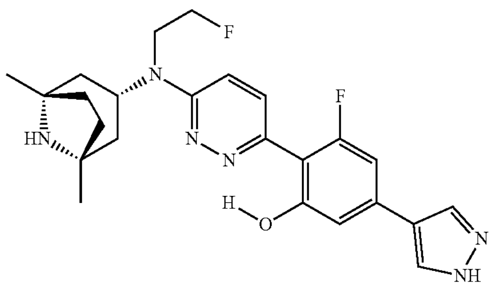 [SMILES: C[C@]12CC[C@](C)(C[C@@H](N(CCF)c3ccc(-c4c(O)cc(-c5cn[nH]c5)cc4F)nn3)C1)N2] | 2-(6-(((1R,3s,5S)-1,5-dimethyl-8-azabicyclo[3.2.1]octan-3-yl)(2-fluoroethyl)amino)pyridazin-3-yl)-3-fluoro-5-(1H-pyrazol-4-yl)phenol |
| 84 | 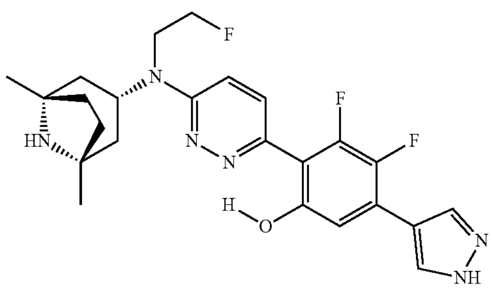 [SMILES: C[C@]12CC[C@](C)(C[C@@H](N(CCF)c3ccc(-c4c(O)cc(-c5cn[nH]c5)c(F)c4F)nn3)C1)N2] | 2-(6-(((1R,3s,5S)-1,5-dimethyl-8-azabicyclo[3.2.1]octan-3-yl)(2-fluoroethyl)amino)pyridazin-3-yl)-3,4-difluoro-5-(1H-pyrazol-4-yl)phenol |
| 85 | 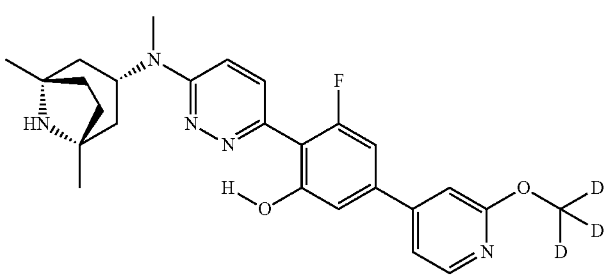 [SMILES: [2H]C([2H])([2H])Oc1cc(-c2cc(O)c(-c3ccc(N(C)[C@H]4C[C@]5(C)CC[C@](C)(C4)N5)nn3)c(F)c2)ccn1] | 2-(6-(((1R,3s,5S)-1,5-dimethyl-8-azabicyclo[3.2.1]octan-3-yl)(methyl)amino)pyridazin-3-yl)-3-fluoro-5-(2-(methoxy-d3)pyridin-4-yl)phenol |
| 86 | 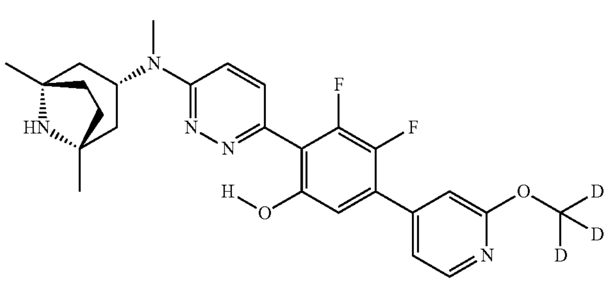 [SMILES: [2H]C([2H])([2H])Oc1cc(-c2cc(O)c(-c3ccc(N(C)[C@H]4C[C@]5(C)CC[C@](C)(C4)N5)nn3)c(F)c2F)ccn1] | 2-(6-(((1R,3s,5S)-1,5-dimethyl-8-azabicyclo[3.2.1]octan-3-yl)(methyl)amino)pyridazin-3-yl)-3,4-difluoro-5-(2-(methoxy-d3)pyridin-4-yl)phenol |

TABLE 1A-continued

Exemplary SMSM compounds

| SMSM# | Structure | Name |
|---|---|---|
| 87 | 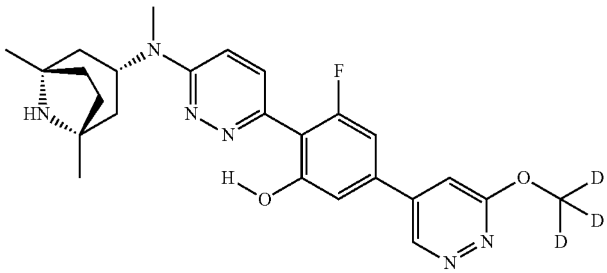 [SMILES: [2H]C([2H])([2H])Oc1cc(-c2cc(O)c(-c3ccc(N(C)[C@H]4C[C@]5(C)CC[C@](C)(C4)N5)nn3)c(F)c2)cnn1] | 2-(6-(((1R,3s,5S)-1,5-dimethyl-8-azabicyclo[3.2.1]octan-3-yl)(methyl)amino)pyridazin-3-yl)-3-fluoro-5-(6-(methoxy-d3)pyridazin-4-yl)phenol |
| 88 | 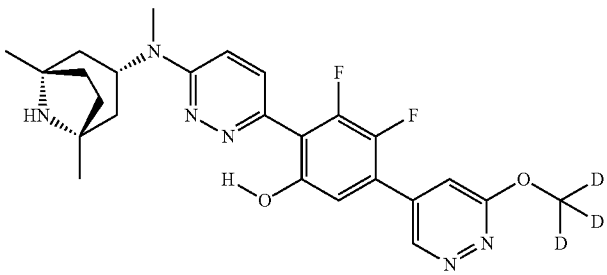 [SMILES: [2H]C([2H])([2H])Oc1cc(-c2cc(O)c(-c3ccc(N(C)[C@H]4C[C@]5(C)CC[C@](C)(C4)N5)nn3)c(F)c2F)cnn1] | 2-(6-(((1R,3s,5S)-1,5-dimethyl-8-azabicyclo[3.2.1]octan-3-yl)(methyl)amino)pyridazin-3-yl)-3,4-difluoro-5-(6-(methoxy-d3)pyridazin-4-yl)phenol |
| 89 | 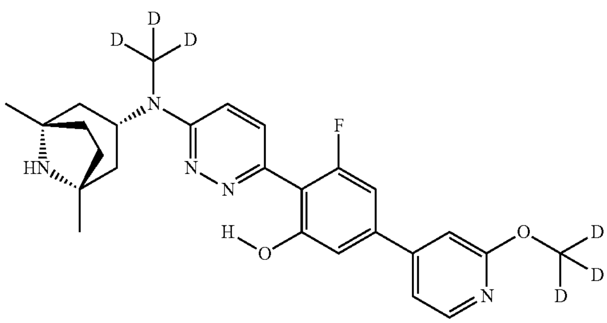 [SMILES: [2H]C([2H])([2H])Oc1cc(-c2cc(O)c(-c3ccc(N([C@H]4C[C@]5(C)CC[C@](C)(C4)N5)C([2H])([2H])[2H])nn3)c(F)c2)ccn1] | 2-(6-(((1R,3s,5S)-1,5-dimethyl-8-azabicyclo[3.2.1]octan-3-yl)(methyl-d3)amino)pyridazin-3-yl)-3-fluoro-5-(2-(methoxy-d3)pyridin-4-yl)phenol |
| 90 | 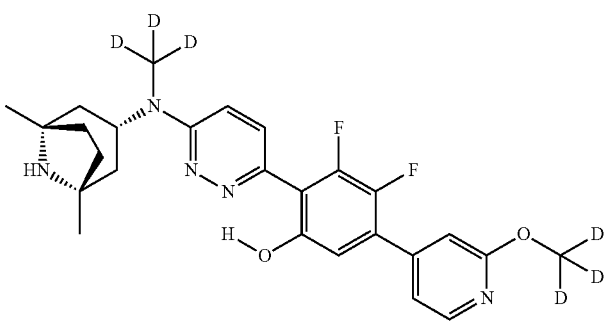 [SMILES: [2H]C([2H])([2H])Oc1cc(-c2cc(O)c(-c3ccc(N([C@H]4C[C@]5(C)CC[C@](C)(C4)N5)C([2H])([2H])[2H])nn3)c(F)c2F)ccn1] | 2-(6-(((1R,3s,5S)-1,5-dimethyl-8-azabicyclo[3.2.1]octan-3-yl)(methyl-d3)amino)pyridazin-3-yl)-3,4-difluoro-5-(2-(methoxy-d3)pyridin-4-yl)phenol |
| 91 | 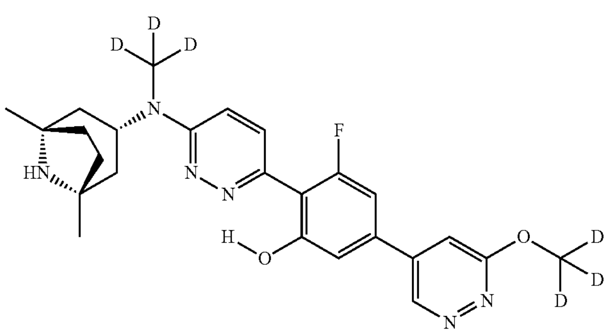 [SMILES: [2H]C([2H])([2H])Oc1cc(-c2cc(O)c(-c3ccc(N([C@H]4C[C@]5(C)CC[C@](C)(C4)N5)C([2H])([2H])[2H])nn3)c(F)c2)cnn1] | 2-(6-(((1R,3s,5S)-1,5-dimethyl-8-azabicyclo[3.2.1]octan-3-yl)(methyl-d3)amino)pyridazin-3-yl)-3-fluoro-5-(6-(methoxy-d3)pyridazin-4-yl)phenol |

TABLE 1A-continued

Exemplary SMSM compounds

| SMSM# | Structure | Name |
|---|---|---|
| 92 | 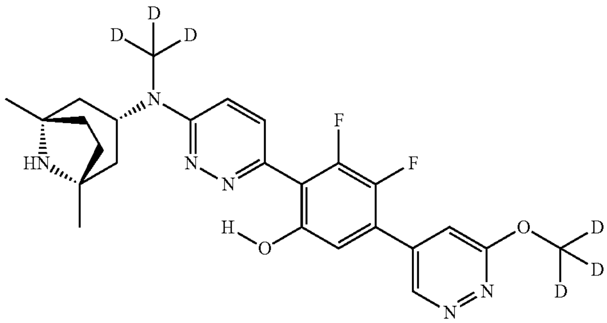 [SMILES: [2H]C([2H])([2H])Oc1cc(-c2cc(O)c(-c3ccc(N([C@H]4C[C@]5(C)CC[C@](C)(C4)N5)C([2H])([2H])[2H])nn3)c(F)c2F)cnn1] | 2-(6-(((1R,3s,5S)-1,5-dimethyl-8-azabicyclo[3.2.1]octan-3-yl)(methyl-d3)amino)pyridazin-3-yl)-3,4-difluoro-5-(6-(methoxy-d3)pyridazin-4-yl)phenol |
| 93 | 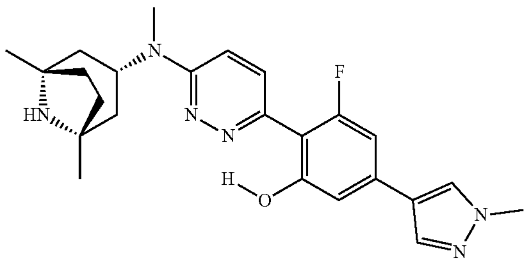 | 2-(6-(((1R,3s,5S)-1,5-dimethyl-8-azabicyclo[3.2.1]octan-3-yl)(methyl)amino)pyridazin-3-yl)-3-fluoro-5-(1-methyl-1H-pyrazol-4-yl)phenol |
| 94 | 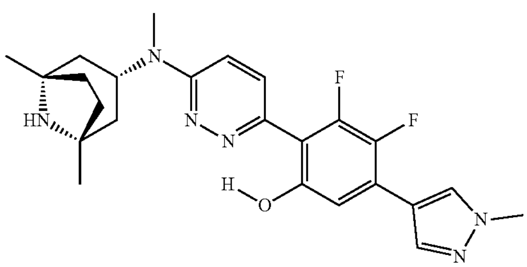 | 2-(6-(((1R,3s,5S)-1,5-dimethyl-8-azabicyclo[3.2.1]octan-3-yl)(methyl)amino)pyridazin-3-yl)-3,4-difluoro-5-(1-methyl-1H-pyrazol-4-yl)phenol |
| 95 | 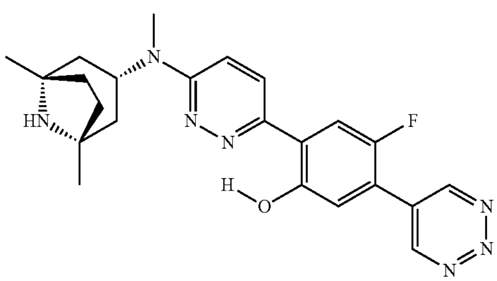 [SMILES: CN(c1ccc(-c2cc(F)c(-c3cnnnc3)cc2O)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-4-fluoro-5-(1,2,3-triazin-5-yl)phenol |
| 96 | 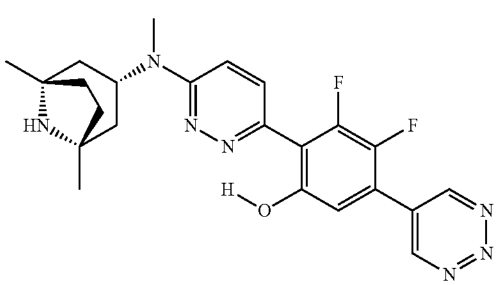 [SMILES: CN(c1ccc(-c2c(O)cc(-c3cnnnc3)c(F)c2F)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-3,4-difluoro-5-(1,2,3-triazin-5-yl)phenol |

TABLE 1A-continued

Exemplary SMSM compounds

| SMSM# | Structure | Name |
|---|---|---|
| 97 | 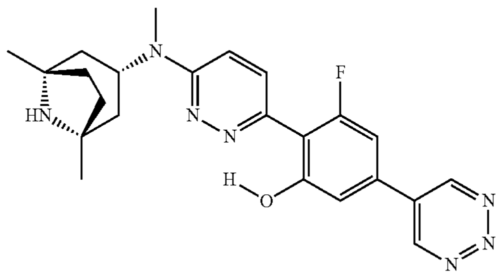 [SMILES: CN(c1ccc(-c2c(O)cc(-c3cnnnc3)cc2F)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-3-fluoro-5-(1,2,3-triazin-5-yl)phenol |
| 98 | 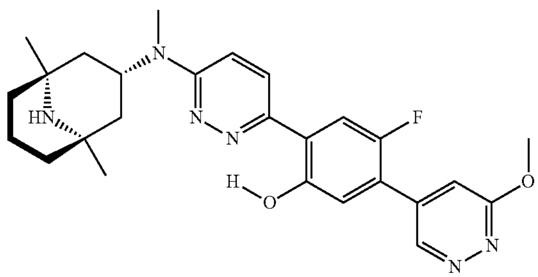 | 2-(6-(((1R,3s,5S)-1,5-dimethyl-9-azabicyclo[3.3.1]nonan-3-yl)(methyl)amino)pyridazin-3-yl)-4-fluoro-5-(6-methoxypyridazin-4-yl)phenol |
| 99 | 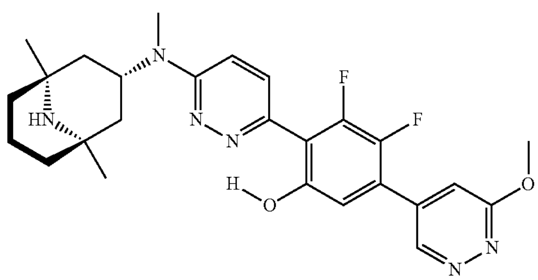 | 2-(6-(((1R,3s,5S)-1,5-dimethyl-9-azabicyclo[3.3.1]nonan-3-yl)(methyl)amino)pyridazin-3-yl)-3,4-difluoro-5-(6-methoxypyridazin-4-yl)phenol |
| 100 | 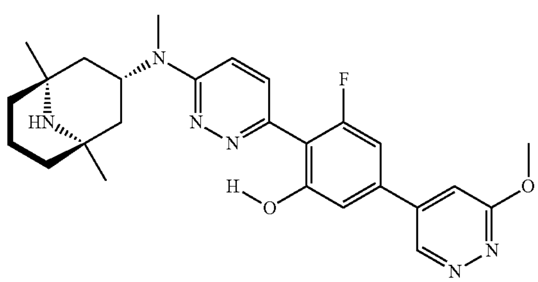 | 2-(6-(((1R,3s,5S)-1,5-dimethyl-9-azabicyclo[3.3.1]nonan-3-yl)(methyl)amino)pyridazin-3-yl)-3-fluoro-5-(6-methoxypyridazin-4-yl)phenol |
| 101 | 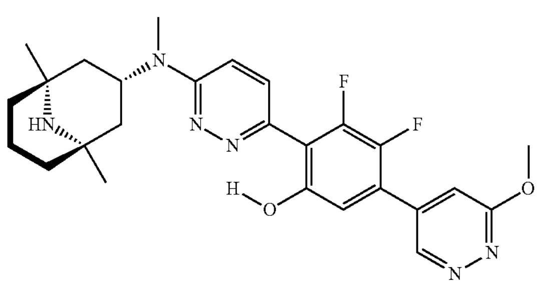 | 2-(6-(((1R,3s,5S)-1,5-dimethyl-9-azabicyclo[3.3.1]nonan-3-yl)(methyl)amino)pyridazin-3-yl)-3,4-difluoro-5-(6-methoxypyrimidin-4-yl)phenol |

TABLE 1A-continued

Exemplary SMSM compounds

| SMSM# | Structure | Name |
|---|---|---|
| 102 | 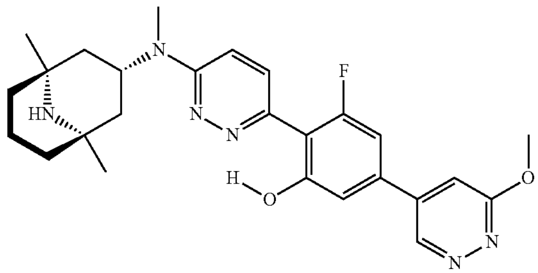 | 2-(6-(((1R,3s,5S)-1,5-dimethyl-9-azabicyclo[3.3.1]nonan-3-yl)(methyl)amino)pyridazin-3-yl)-3-fluoro-5-(6-methoxypyrimidin-4-yl)phenol |
| 103 | 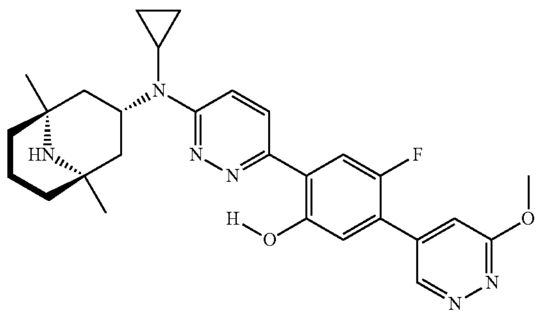 | 2-(6-(cyclopropyl((1R,3s,5S)-1,5-dimethyl-9-azabicyclo[3.3.1]nonan-3-yl)amino)pyridazin-3-yl)-4-fluoro-5-(6-methoxypyridazin-4-yl)phenol |
| 104 | 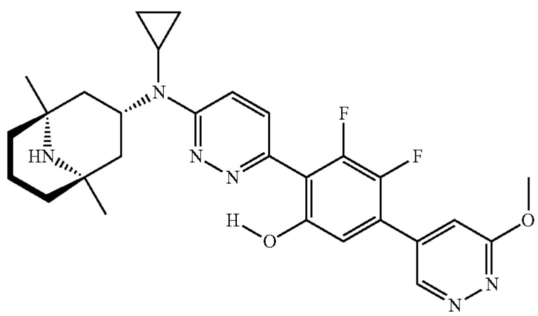 | 2-(6-(cyclopropyl((1R,3s,5S)-1,5-dimethyl-9-azabicyclo[3.3.1]nonan-3-yl)amino)pyridazin-3-yl)-3,4-difluoro-5-(6-methoxypyridazin-4-yl)phenol |
| 105 | 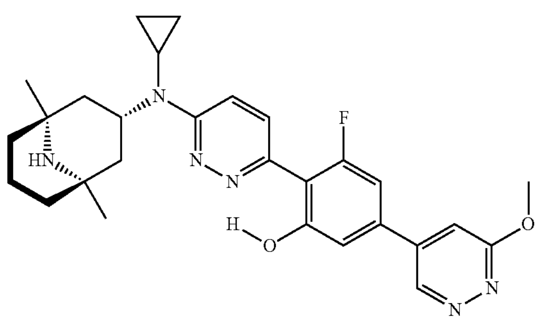 | 2-(6-(cyclopropyl((1R,3s,5S)-1,5-dimethyl-9-azabicyclo[3.3.1]nonan-3-yl)amino)pyridazin-3-yl)-3-fluoro-5-(6-methoxypyridazin-4-yl)phenol |
| 106 | 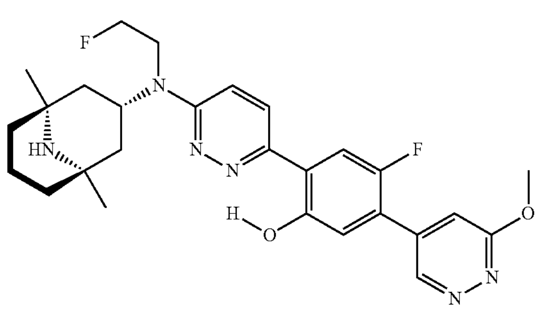 | 2-(6-(((1R,3s,5S)-1,5-dimethyl-9-azabicyclo[3.3.1]nonan-3-yl)(2-fluoroethyl)amino)pyridazin-3-yl)-4-fluoro-5-(6-methoxypyridazin-4-yl)phenol |

TABLE 1A-continued

Exemplary SMSM compounds

| SMSM# | Structure | Name |
|---|---|---|
| 107 | 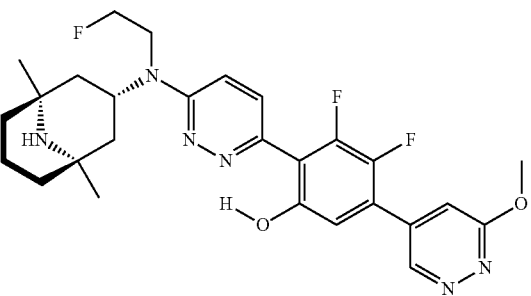 | 2-(6-(((1R,3s,5S)-1,5-dimethyl-9-azabicyclo[3.3.1]nonan-3-yl)(2-fluoroethyl)amino)pyridazin-3-yl)-3,4-difluoro-5-(6-methoxypyridazin-4-yl)phenol |
| 108 | 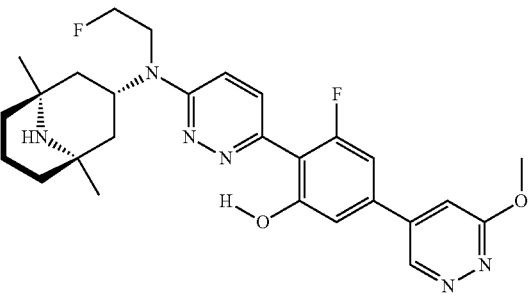 | 2-(6-(((1R,3s,5S)-1,5-dimethyl-9-azabicyclo[3.3.1]nonan-3-yl)(2-fluoroethyl)amino)pyridazin-3-yl)-3-fluoro-5-(6-methoxypyridazin-4-yl)phenol |
| 109 | 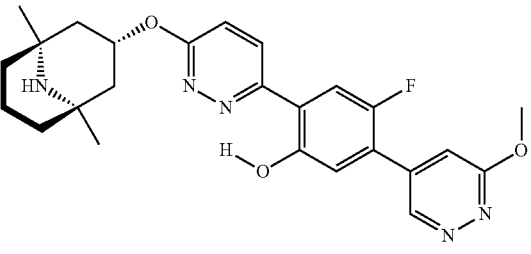 | 2-(6-(((1R,3s,5S)-1,5-dimethyl-9-azabicyclo[3.3.1]nonan-3-yl)oxy)pyridazin-3-yl)-4-fluoro-5-(6-methoxypyridazin-4-yl)phenol |
| 110 | 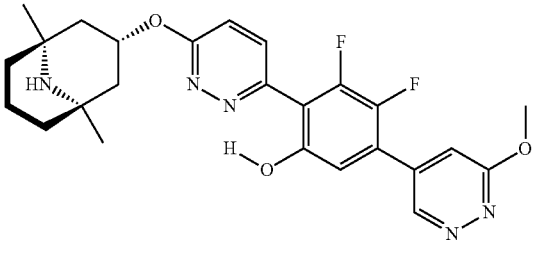 | 2-(6-(((1R,3s,5S)-1,5-dimethyl-9-azabicyclo[3.3.1]nonan-3-yl)oxy)pyridazin-3-yl)-3,4-difluoro-5-(6-methoxypyridazin-4-yl)phenol |
| 111 | 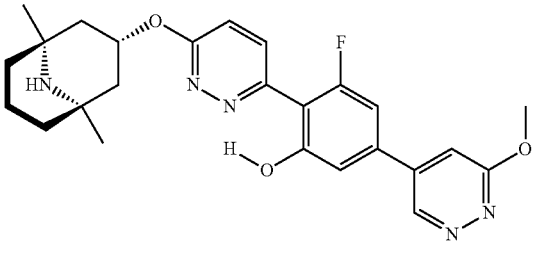 | 2-(6-(((1R,3s,5S)-1,5-dimethyl-9-azabicyclo[3.3.1]nonan-3-yl)oxy)pyridazin-3-yl)-3-fluoro-5-(6-methoxypyridazin-4-yl)phenol |

TABLE 1A-continued

Exemplary SMSM compounds

| SMSM# | Structure | Name |
|---|---|---|
| 112 | 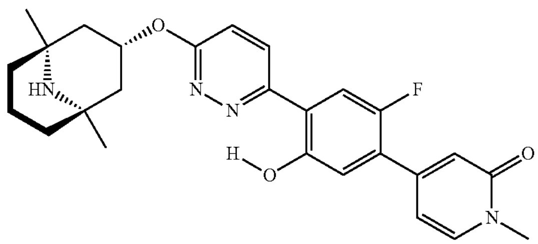 | 4-(4-(6-(((1R,3s,5S)-1,5-dimethyl-9-azabicyclo[3.3.1]nonan-3-yl)oxy)pyridazin-3-yl)-2-fluoro-5-hydroxyphenyl)-1-methylpyridin-2(1H)-one |
| 113 | 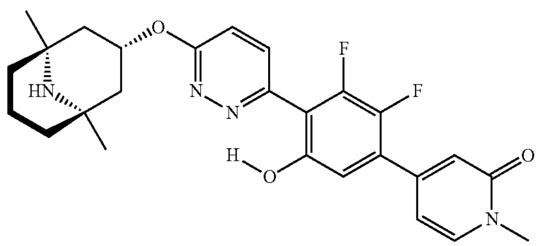 | 4-(4-(6-(((1R,3s,5S)-1,5-dimethyl-9-azabicyclo[3.3.1]nonan-3-yl)oxy)pyridazin-3-yl)-2,3-difluoro-5-hydroxyphenyl)-1-methylpyridin-2(1H)-one |
| 114 | 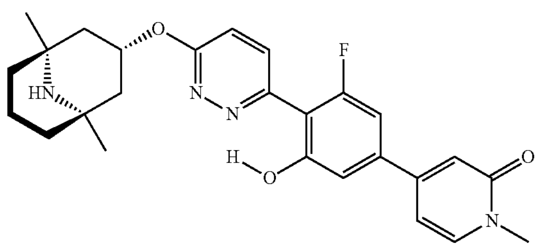 | 4-(4-(6-(((1R,3s,5S)-1,5-dimethyl-9-azabicyclo[3.3.1]nonan-3-yl)oxy)pyridazin-3-yl)-3-fluoro-5-hydroxyphenyl)-1-methylpyridin-2(1H)-one |
| 115 | 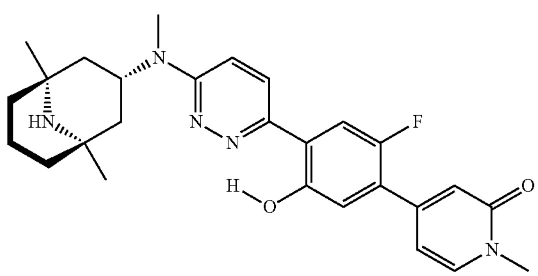 | 4-(4-(6-(((1R,3s,5S)-1,5-dimethyl-9-azabicyclo[3.3.1]nonan-3-yl)(methyl)amino)pyridazin-3-yl)-2-fluoro-5-hydroxyphenyl)-1-methylpyridin-2(1H)-one |
| 116 | 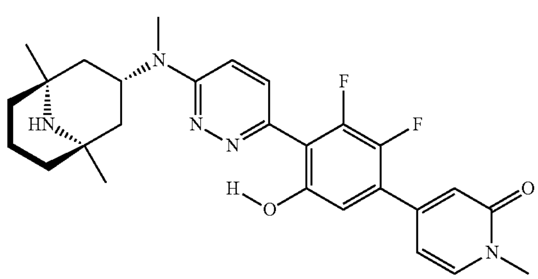 | 4-(4-(6-(((1R,3s,5S)-1,5-dimethyl-9-azabicyclo[3.3.1]nonan-3-yl)(methyl)amino)pyridazin-3-yl)-2,3-difluoro-5-hydroxyphenyl)-1-methylpyridin-2(1H)-one |
| 117 | 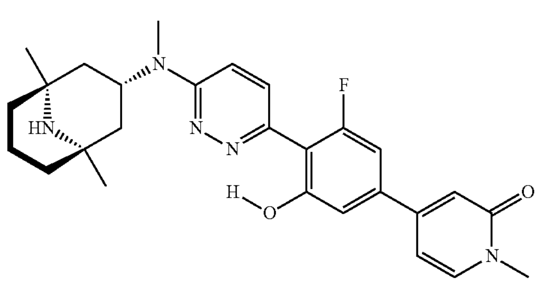 | 4-(4-(6-(((1R,3s,5S)-1,5-dimethyl-9-azabicyclo[3.3.1]nonan-3-yl)(methyl)amino)pyridazin-3-yl)-3-fluoro-5-hydroxyphenyl)-1-methylpyridin-2(1H)-one |

TABLE 1A-continued

Exemplary SMSM compounds

| SMSM# | Structure | Name |
|---|---|---|
| 118 | 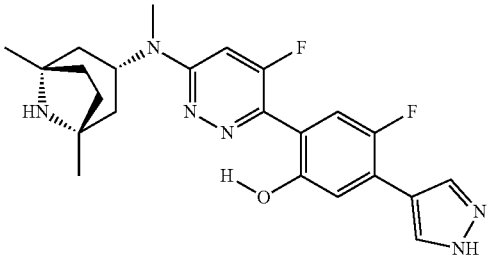 [SMILES: CN(c1cc(F)c(-c2cc(F)c(-c3cn[nH]c3)cc2O)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)-4-fluoropyridazin-3-yl)-4-fluoro-5-(1H-pyrazol-4-yl)phenol |
| 119 | 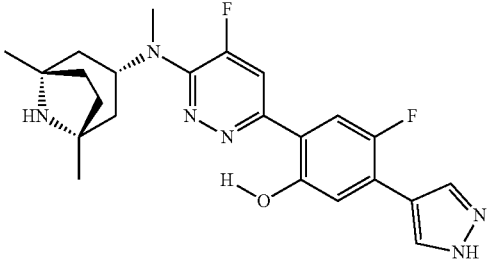 [SMILES: CN(c1nnc(-c2cc(F)c(-c3cn[nH]c3)cc2O)cc1F)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)-5-fluoropyridazin-3-yl)-4-fluoro-5-(1H-pyrazol-4-yl)phenol |
| 120 | 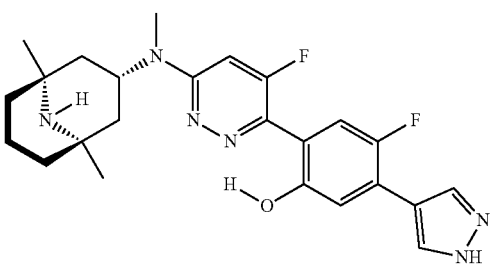 | 2-(6-(((1R,3s,5S)-1,5-dimethyl-9-azabicyclo[3.3.1]nonan-3-yl)(methyl)amino)-4-fluoropyridazin-3-yl)-4-fluoro-5-(1H-pyrazol-4-yl)phenol |
| 121 | 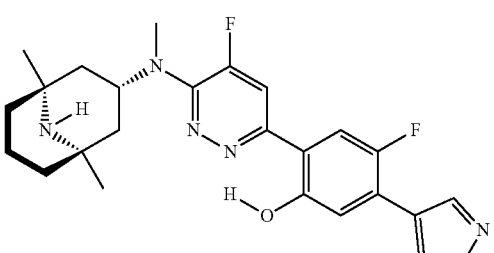 | 2-(6-(((1R,3s,5S)-1,5-dimethyl-9-azabicyclo[3.3.1]nonan-3-yl)(methyl)amino)-5-fluoropyridazin-3-yl)-4-fluoro-5-(1H-pyrazol-4-yl)phenol |
| 122 | 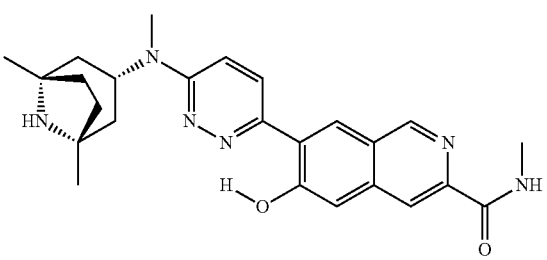 | 7-(6-(((1R,3s,5S)-1,5-dimethyl-8-azabicyclo[3.2.1]octan-3-yl)(methyl)amino)pyridazin-3-yl)-6-hydroxy-N-methylisoquinoline-3-carboxamide |

TABLE 1A-continued

Exemplary SMSM compounds

| SMSM# | Structure | Name |
|---|---|---|
| 123 | 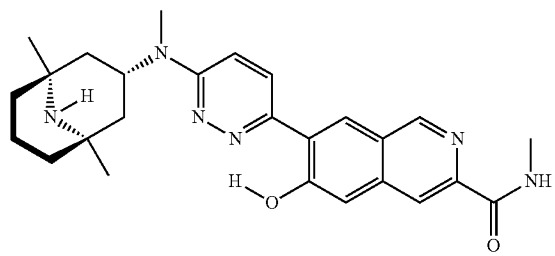 | 7-(6-(((1R,3s,5S)-1,5-dimethyl-9-azabicyclo[3.3.1]nonan-3-yl)(methyl)amino)pyridazin-3-yl)-6-hydroxy-N-methylisoquinoline-3-carboxamide |
| 124 | 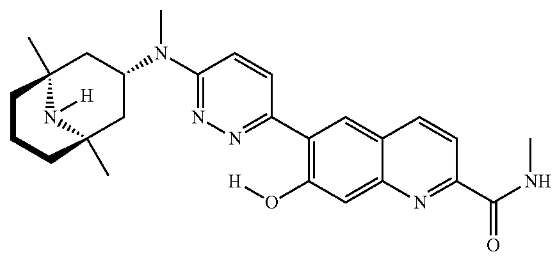 | 6-(6-(((1R,3s,5S)-1,5-dimethyl-9-azabicyclo[3.3.1]nonan-3-yl)(methyl)amino)pyridazin-3-yl)-7-hydroxy-N-methylquinoline-2-carboxamide |
| 125 | 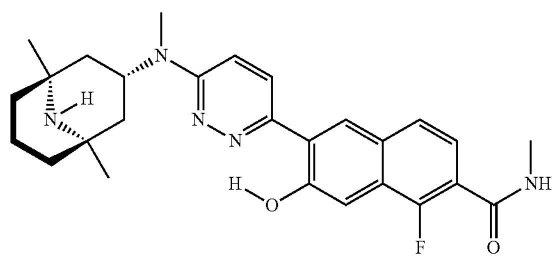 | 6-(6-(((1R,3s,5S)-1,5-dimethyl-9-azabicyclo[3.3.1]nonan-3-yl)(methyl)amino)pyridazin-3-yl)-1-fluoro-7-hydroxy-N-methyl-2-naphthamide |
| 126 | 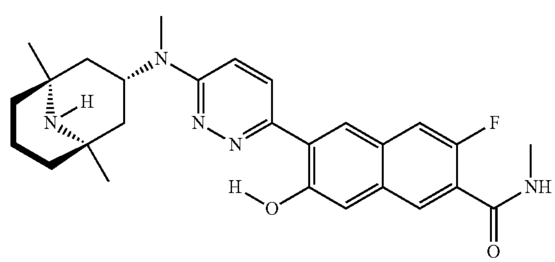 | 6-(6-(((1R,3s,5S)-1,5-dimethyl-9-azabicyclo[3.3.1]nonan-3-yl)(methyl)amino)pyridazin-3-yl)-3-fluoro-7-hydroxy-N-methyl-2-naphthamide |
| 127 | 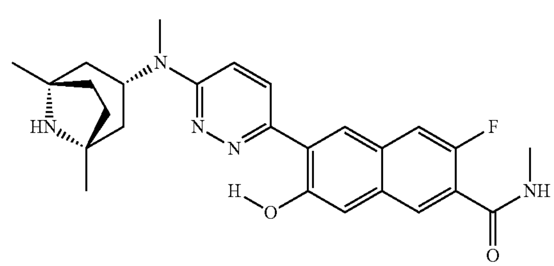 | 6-(6-(((1R,3s,5S)-1,5-dimethyl-8-azabicyclo[3.2.1]octan-3-yl)(methyl)amino)pyridazin-3-yl)-3-fluoro-7-hydroxy-N-methyl-2-naphthamide |

TABLE 1A-continued
Exemplary SMSM compounds
| SMSM# | Structure | Name |
|---|---|---|
| 128 | 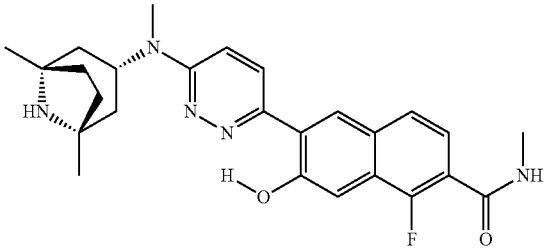 | 6-(6-(((1R,3s,5S)-1,5-dimethyl-8-azabicyclo[3.2.1]octan-3-yl)(methyl)amino)pyridazin-3-yl)-1-fluoro-7-hydroxy-N-methyl-2-naphthamide |

TABLE 1B

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 129 | 251-500 | >1000 | >1000 | 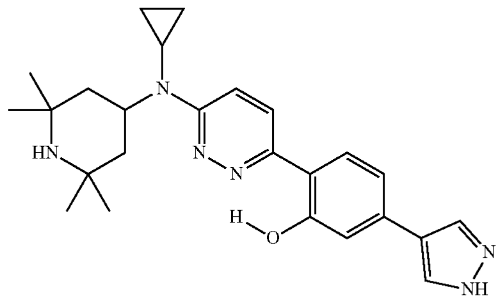 [SMILES: CC1(C)CC(N(c2ccc(-c3ccc(-c4cn[nH]c4)cc3O)nn2)C2CC2)CC(C)(C)N1] | 2-(6-(cyclopropyl(2,2,6,6-tetramethylpiperidin-4-yl)amino)pyridazin-3-yl)-5-(1H-pyrazol-4-yl)phenol | $^1$H NMR (500 MHz, DMSO-d$_6$) δ 13.79 (s, 1H), 12.99 (s, 1H), 8.25 (d, J = 9.8 Hz, 1H), 8.23-7.96 (m, 2H), 7.85 (d, J = 8 Hz, 1H), 7.58 (d, J = 9.8 Hz, 1H), 7.26-7.16 (m, 2H), 5.04-4.72 (m, 1H), 2.62-2.53 (m, 1H), 1.80-1.61 (m, 4H), 1.23 (s, $_6$ h), 1.09 (s, $_6$ h), 1.03-0.94 (m, 2H), 0.70-0.59 (m, 2H). | 433.2 |
| 130 | >1000 | >1000 | >1000 | 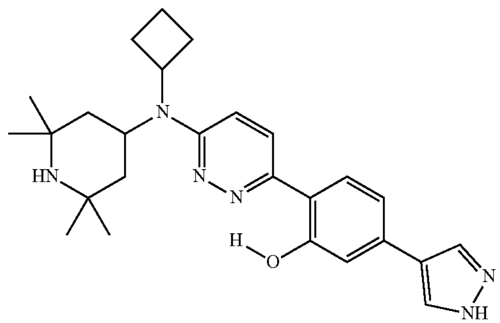 [SMILES: CC1(C)CC(N(c2ccc(-c3ccc(-c4cn[nH]c4)cc3O)nn2)C2CCC2)CC(C)(C)N1] | 2-(6-(cyclobutyl(2,2,6,6-tetramethylpiperidin-4-yl)amino)pyridazin-3-yl)-5-(1H-pyrazol-4-yl)phenol | $^1$H NMR (500 MHz, Methanol-d$_4$) δ 8.06 (d, J = 10 Hz, 1H), 8.02 (s, 2H), 7.78-7.74 (m, 1H), 7.32 (d, J = 10 Hz, 1H), 7.19 (s, 2H), 4.47-4.29 (m, 2H), 2.48-2.32 (m, 4H), 2.29-2.16 (m, 2H), 1.90-1.77 (m, 2H), 1.73-1.64 (m, 2H), 1.38 (s, $_6$ h), 1.26 (s, $_6$ h). | 447.2 |
| 131 | >1000 | 101-250 | 251-500 | 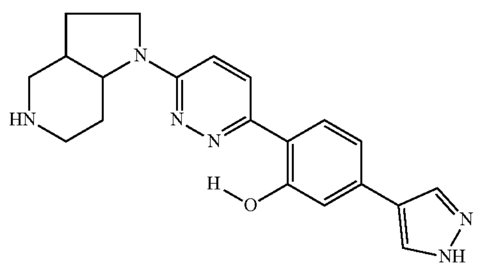 [SMILES: Oc1cc(-c2cn[nH]c2)ccc1-c1ccc(N2CCC3CNCCC32)nn1] | 2-(6-(octahydro-1H-pyrrolo[3,2-c]pyridin-1-yl)pyridazin-3-yl)-5-(1H-pyrazol-4-yl)phenol | $^1$H NMR (400 MHz, Methanol-d$_4$) δ 8.11 (d, J = 8 Hz, 1H), 7.91 (s, 2H), 7.64 (d, J = 6.8 Hz, 1H), 7.23 (d, J = 8 Hz, 1H), 7.12-7.08 (m, 2H), 4.35-4.31 (m, 1H), 3.70-3.20 (m, 5H), 3.04-2.98 (m, 1H), 2.80-1.70 (m, $_7$ h). | 363.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 132 | >1000 | | >1000 | 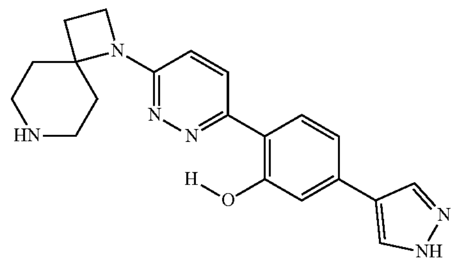 [SMILES: Oc1cc(-c2cn[nH]c2)ccc1-c1ccc(N2CCC23CCNCC3)nn1] | 2-(6-(1,7-diazaspiro[3.5]nonan-1-yl)pyridazin-3-yl)-5-(1H-pyrazol-4-yl)phenol | $^1$H NMR (500 MHz, Methanol-d$_4$) δ 8.27 (d, J = 9.6 Hz, 1H), 8.05 (s, 2H), 7.72 (d, J = 8.2 Hz, 1H), 7.28 (dd, J = 8.2, 1.7 Hz, 1H), 7.23 (q, J = 4.0 Hz, 2H), 4.20-4.17 (m, 2H), 3.55-3.52 (m, 2H), 3.18-3.08 (m, 2H), 2.92-2.84 (m, 2H), 2.52 (t, J = 7.5 Hz, 2H), 2.24-2.21 (m, 2H). | 363.2 |
| 133 | >1000 | 501-1000 | >1000 | 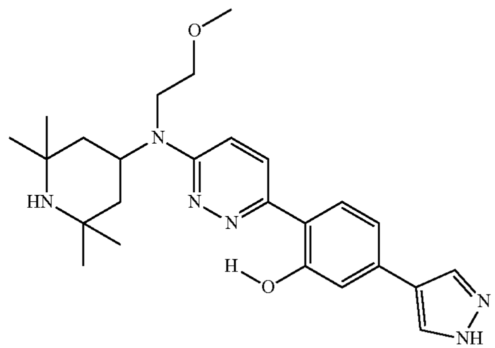 [SMILES: COCCN(c1ccc(-c2ccc(-c3cn[nH]c3)cc2O)nn1)C1CC(C)(C)NC(C)(C)C1] | 2-(6-((2-methoxyethyl)(2,2,6,6-tetramethylpiperidin-4-yl)amino)pyridazin-3-yl)-5-(1H-pyrazol-4-yl)phenol | $^1$H NMR (500 MHz, Methanol-d$_4$) δ 8.06 (d, J = 9.9 Hz, 1H), 8.01 (s, 2H), 7.75 (d, J = 8.6 Hz, 1H), 7.37 (d, J = 9.9 Hz, 1H), 7.24-7.13 (m, 2H), 5.07-4.96 (m, 1H), 3.72-3.56 (m, 4H), 3.40 (s, $_6$ h), 1.87-1.69 (m, 4H), 1.46 (s, $_6$ h), 1.31 (s, $_6$ h). | 451.3 |
| 134 | >1000 | >1000 | >1000 | 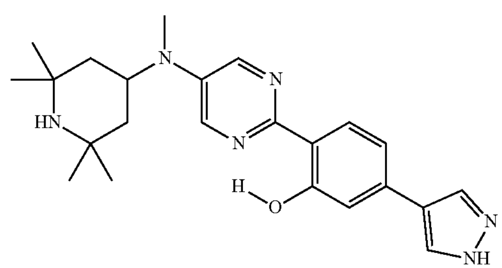 [SMILES: CN(c1cnc(-c2ccc(-c3cn[nH]c3)cc2O)nc1)C1CC(C)(C)NC(C)(C)C1] | 2-(5-(methyl(2,2,6,6-tetramethylpiperidin-4-yl)amino)pyrimidin-2-yl)-5-(1H-pyrazol-4-yl)phenol | $^1$H NMR (500 MHz, Methanol-d$_4$) δ 8.46 (s, 2H), 8.28 (d, J = 8.2 Hz, 1H), 8.01 (s, 2H), 7.20-7.10 (m, 2H), 4.26-4.23 (m, 1H), 2.92 (s, $_3$ h), 1.76-1.72 (m, 2H), 1.57-1.52 (m, 2H), 1.39 (s, $_6$ h), 1.25 (s, $_6$ h). | 407.4 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 135 | >1000 | >1000 | >1000 | 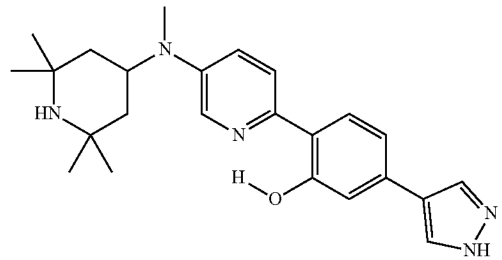 [SMILES: CN(c1ccc(-c2ccc(-c3cn[nH]c3)cc2O)nc1)C1CC(C)(C)NC(C)(C)C1] | 2-(5-(methyl(2,2,6,6-tetramethylpiperidin-4-yl)amino)pyridin-2-yl)-5-(1H-pyrazol-4-yl)phenol | $^1$H NMR (500 MHz, Methanol-d$_4$) δ 8.17 (d, J = 3.0 Hz, 1H), 7.98 (s, 2H), 7.93 (d, J = 9.1 Hz, 1H), 7.79 (d, J = 8.3 Hz, 1H), 7.45 (dd, J = 9.2, 3.1 Hz, 1H), 7.13 (d, J = 8.1 Hz, 1H), 7.11 (s, 1H), 4.26-4.23 (m, 1H), 2.90 (s, 3 h), 1.77-1.73 (m, 2H), 1.60-1.53 (m, 2H), 1.42 (s, 6 h), 1.32 (s, 1H), 1.27 (s, 6 h). | 406.1 |
| 136 | 501-1000 | 101-250 | 251-500 | 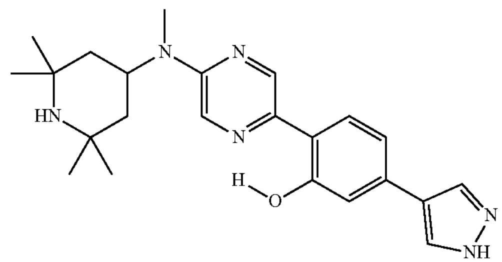 [SMILES: CN(c1cnc(-c2ccc(-c3cn[nH]c3)cc2O)cn1)C1CC(C)(C)NC(C)(C)C1] | 2-(5-(methyl(2,2,6,6-tetramethylpiperidin-4-yl)amino)pyrazin-2-yl)-5-(1H-pyrazol-4-yl)phenol | $^1$H NMR (500 MHz, Methanol-d$_4$) δ 8.72 (d, J = 1.5 Hz, 1H), 7.93 (d, J = 1.5 Hz, 1H), 7.86 (s, 2H), 7.70 (d, J = 8.3 Hz, 1H), 7.09-7.02 (m, 1H), 7.01 (d, J = 1.8 Hz, 1H), 5.08 (t, J = 12.5 Hz, 1H), 2.90 (s, 3 h), 1.61-1.44 (m, 4H), 1.30 (s, 6 h), 1.16 (s, 6 h). | 407.3 |
| 137 | >1000 | >1000 | >1000 | 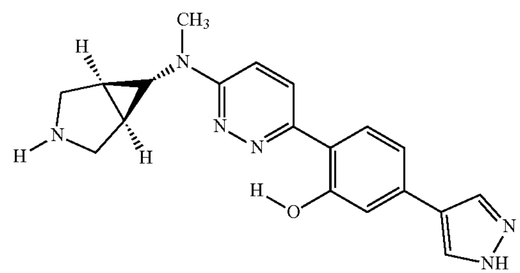 [SMILES: CN(c1ccc(-c2ccc(-c3cn[nH]c3)cc2O)nn1)[C@H]1[C@@H]2CNC[C@@H]21] | 2-(6-(((1R,5S,6s)-3-azabicyclo[3.1.0]hexan-6-yl)(methyl)amino)pyridazin-3-yl)-5-(1H-pyrazol-4-yl)phenol | $^1$H NMR (500 MHz, DMSO-d$_6$) δ 13.78 (s, 1H), 12.99 (s, 1H), 8.34-7.95 (m, 4H), 7.83 (d, J = 8.1 Hz, 1H), 7.42 (d, J = 9.8 Hz, 1H), 7.21 (s, 2H), 3.17 (s, 3 h), 3.11 (d, J = 11.2 Hz, 2H), 2.77 (d, J = 11.0 Hz, 2H), 2.54-2.51 (m, 1H), 1.76 (s, 2H). | 349.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 138 | 10-100 | 10-100 | 10-100 | 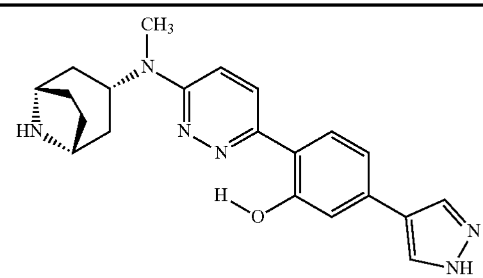 | 2-(6-(((1R,3s,5S)-8-azabicyclo[3.2.1]octan-3-yl)(methyl)amino)pyridazin-3-yl)-5-(1H-pyrazol-4-yl)phenol | $^1$H NMR (500 MHz, Methanol-d$_4$) δ 8.12 (d, J = 9.8 Hz, 1H), 8.02 (s, 2H), 7.77 (d, J = 8.3 Hz, 1H), 7.33 (d, J = 9.9 Hz, 1H), 7.20 (d, J = 7.2 Hz, 2H), 5.23-5.07 (m, 1H), 3.88-3.86 (m, 2H), 3.02 (s, 3 h), 2.14-2.00 (m, 6 h), 1.83-1.81 (m, 2H). | 377.2 |
| 139 | >1000 | >1000 | >1000 | 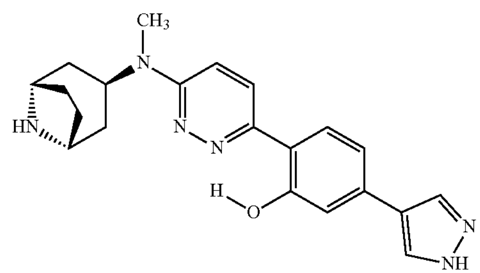 [SMILES: CN(c1ccc(-c2ccc(-c3cn[nH]c3)cc2O)nn1)[C@H]1C[C@H]2CC[C@@H](C1)N2] | 2-(6-(((1R,3r,5S)-8-azabicyclo[3.2.1]octan-3-yl)(methyl)amino)pyridazin-3-yl)-5-(1H-pyrazol-4-yl)phenol | $^1$H NMR (500 MHz, Methanol-d$_4$) δ 7.99 (s, 2H), 7.72-7.64 (m, 1H), 7.60 (d, J = 8.2 Hz, 1H), 7.21-7.07 (m, 3 h), 3.91-3.81 (m, 3 h), 3.71 (s, 3 h), 2.68-2.58 (m, 2H), 2.34-2.17 (m, 2H), 2.03-1.94 (m, 2H), 1.86-1.75 (m, 2H). | 377.2 |
| 140 | 101-250 | 10-100 | 10-100 | 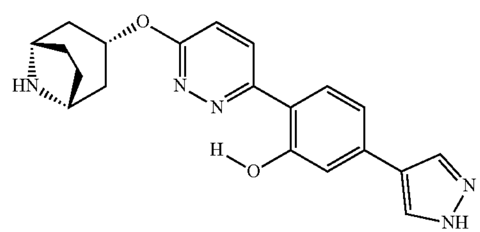 [SMILES: Oc1cc(-c2cn[nH]c2)ccc1-c1ccc(O[C@@H]2C[C@H]3CC[C@@H](C2)N3)nn1] | 2-(6-(((1R,3s,5S)-8-azabicyclo[3.2.1]octan-3-yl)oxy)pyridazin-3-yl)-5-(1H-pyrazol-4-yl)phenol | $^1$H NMR (500 MHz, Methanol-d$_4$) δ 8.28 (d, J = 9.5 Hz, 1H), 8.03 (s, 2H), 7.82 (d, J = 8.8 Hz, 1H), 7.26-7.19 (m, 3 h), 5.61-5.57 (m, 1H), 3.68 (s, 2H), 2.34-2.31 (m, 2H), 1.95 (s, 4H), 1.80-1.74 (m, 2H). | 364.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 141 | >1000 | >1000 | >1000 | 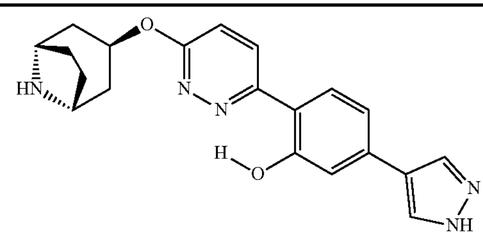 | 2-(6-(((1R,3r,5S)-8-azabicyclo[3.2.1]octan-3-yl)oxy)pyridazin-3-yl)-5-(1H-pyrazol-4-yl)phenol | 1H NMR (500 MHz, Methanol-d$_4$) δ 8.32 (d, J = 9.6 Hz, 1H), 8.04 (s, 2H), 7.84 (d, J = 8.8 Hz, 1H), 7.31 (d, J = 9.5 Hz, 1H), 7.25-7.20 (m, 2H), 5.53-5.50 (m, 1H), 3.57 (s, 2H), 2.23-2.09 (m, 6 h), 1.96-1.82 (m, 2H). | 364.0 |
| 142 | >1000 | 251-500 | 501-1000 | 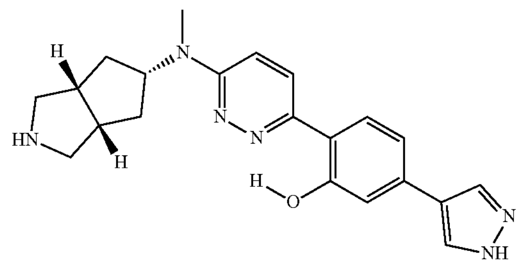 [SMILES: CN(c1ccc(-c2ccc(-c3cn[nH]c3)cc2O)nn1)[C@H]1C[C@H]2CNC[C@H]2C1] | 2-(6-(methyl((3R,5r,6S)-octahydrocyclopenta[c]pyrrol-5-yl)amino)pyridazin-3-yl)-5-(1H-pyrazol-4-yl)phenol | $^1$H NMR (500 MHz, Methanol-d$_4$) δ 8.09 (d, J = 10.1 Hz, 1H), 8.02 (s, 2H), 7.76 (d, J = 8.5 Hz, 1H), 7.37 (d, J = 9.6 Hz, 1H), 7.23-7.17 (m, 2H), 4.77-4.70 (m, 1H), 3.08 (s, 3 h), 2.97-2.71 (m, 6 h), 2.18-2.03 (m, 2H), 1.70-1.51 (m, 2H). | 377.2 |
| 143 | >1000 | 251-500 | 501-1000 | 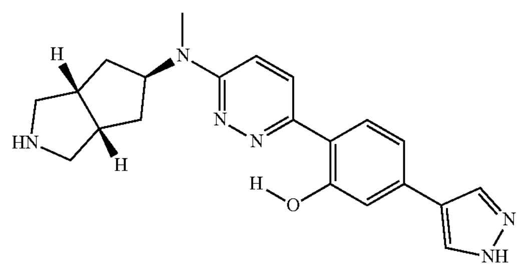 [SMILES: CN(c1ccc(-c2ccc(-c3cn[nH]c3)cc2O)nn1)[C@@H]1C[C@H]2CNC[C@H]2C1] | 2-(6-(methyl((3R,5s,6S)-octahydrocyclopenta[c]pyrrol-5-yl)amino)pyridazin-3-yl)-5-(1H-pyrazol-4-yl)phenol | $^1$H NMR (500 MHz, Methanol-d$_4$) δ 8.11 (d, J = 9.9 Hz, 1H), 8.02 (s, 2H), 7.79-7.75 (m, 1H), 7.39 (d, J = 9.9 Hz, 1H), 7.20 (d, J = 7.2 Hz, 2H), 5.07-4.99 (m, 1H), 3.31-3.25 (m, 2H), 3.05 (s, 3 h), 2.87-2.81 (m, 2H), 2.78-2.72 (m, 2H), 2.10-2.00 (m, 2H), 1.81-1.73 (m, 2H). | 377.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 144 | 501-1000 | >1000 | >1000 | 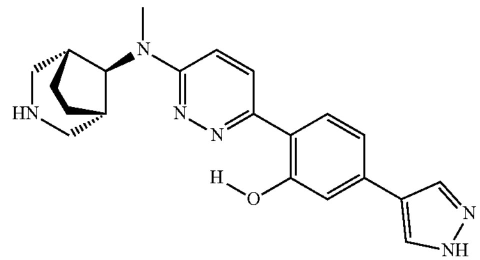 | 2-(6-(((1R,5S,8s)-3-azabicyclo[3.2.1]octan-8-yl)(methyl)amino)pyridazin-3-yl)-5-(1H-pyrazol-4-yl)phenol | $^1$H NMR (500 MHz, DMSO-d$_6$) δ 13.87 (s, 1H), 12.98 (s, 1H), 8.20 (d, J = 10.0 Hz, 1H), 8.10 (s, 2H), 7.83 (d, J = 8.3 Hz, 1H), 7.33 (d, J = 9.9 Hz, 1H), 7.23-7.16 (m, 2H), 3.93 (s, 1H), 3.11 (s, 3 h), 2.88-2.82 (m, 2H), 2.72-2.65 (m, 2H), 2.28 (s, 2H), 1.80-1.63 (m, 4H). | 377.2 |
| 145 | >1000 | >1000 | >1000 | 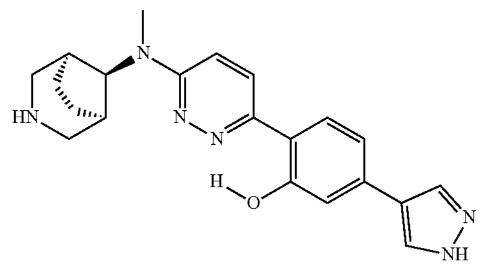 | 2-(6-(((1R,5S,8r)-3-azabicyclo[3.2.1]octan-8-yl)(methyl)amino)pyridazin-3-yl)-5-(1H-pyrazol-4-yl)phenol | $^1$H NMR (500 MHz, DMSO-d$_6$) δ 13.74 (s, 1H), 12.99 (s, 1H), 8.29 (d, J = 9.9 Hz, 1H), 8.13 (s, 3 h), 7.89 (d, J = 8.2 Hz, 1H), 7.56 (d, J = 9.8 Hz, 1H), 7.24-7.19 (m, 2H), 3.69-3.63 (m, 1H), 3.19 (s, 3 h), 2.93-2.86 (m, 2H), 2.71 (s, 2H), 2.47-2.40 (m, 2H), 1.86-1.71 (m, 4H). | 377.2 |
| 146 | >1000 | 101-250 | 251-500 | 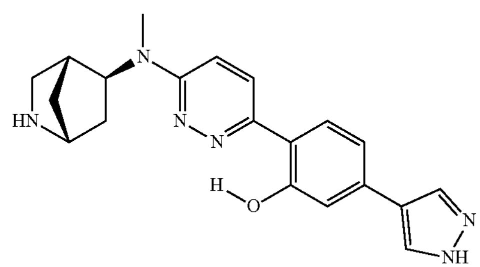 [SMILES: CN(c1ccc(-c2ccc(-c3cn[nH]c3)cc2O)nn1)[C@H]1C[C@H]2C[C@@H]1CN2] | 2-(6-(((1R,4R,5S)-2-azabicyclo[2.2.1]heptan-5-yl)(methyl)amino)pyridazin-3-yl)-5-(1H-pyrazol-4-yl)phenol | $^1$H NMR (500 MHz, Methanol-d$_4$) δ 8.15 (d, J = 9.9 Hz, 1H), 8.02 (s, 2H), 7.79 (d, J = 8.8 Hz, 1H), 7.45 (d, J = 9.8 Hz, 1H), 7.25-7.15 (m, 2H), 4.41-4.39 (m, 1H), 3.77 (s, 1H), 3.23 (s, 3 h), 3.22-3.97 (m, 3 h), 2.33-1.77 (m, 4H). | 363.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 147 | >1000 | 101-250 | 251-500 | 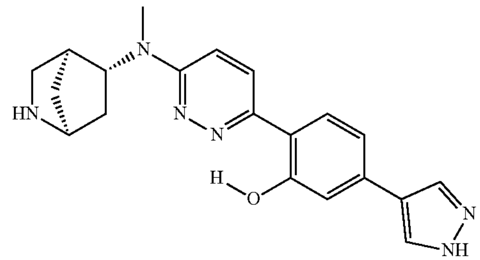 [SMILES: CN(c1ccc(-c2ccc(-c3cn[nH]c3)cc2O)nn1)[C@@H]1C[C@@H]2C[C@H]1CN2] | 2-(6-((1S,4S,5R)-2-azabicyclo[2.2.1]heptan-5-yl)(methyl)amino)pyridazin-3-yl)-5-(1H-pyrazol-4-yl)phenol | $^1$H NMR (500 MHz, Methanol-d$_4$) δ 8.15 (d, J = 9.9 Hz, 1H), 8.02 (s, 2H), 7.79 (d, J = 8.9 Hz, 1H), 7.45 (d, J = 9.8 Hz, 1H), 7.25-7.15 (m, 2H), 4.41-4.38 (m, 1H), 3.78 (s, 1H), 3.22 (s, $_3$ h), 3.22-3.97 (m, $_3$ h), 2.33-1.78 (m, 4H). | 363.1 |
| 148 | >1000 | >1000 | >1000 | 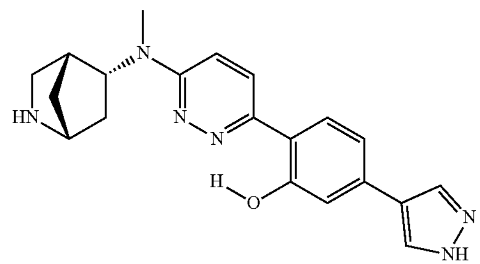 [SMILES: CN(c1ccc(-c2ccc(-c3cn[nH]c3)cc2O)nn1)[C@@H]1C[C@H]2C[C@@H]1CN2] | 2-(6-(((1R,4R,5R)-2-azabicyclo[2.2.1]heptan-5-yl)(methyl)amino)pyridazin-3-yl)-5-(1H-pyrazol-4-yl)phenol | $^1$H NMR (500 MHz, Methanol-d$_4$) δ 8.09 (d, J = 10.0 Hz, 1H), 8.02 (s, 2H), 7.75 (d, J = 8.8 Hz, 1H), 7.36 (d, J = 9.9 Hz, 1H), 7.20-7.19 (m, 2H), 4.41-4.39 (m, 1H), 3.87 (s, 1H), 3.14 (s, $_3$ h), 3.11-2.83 (m, $_3$ h), 2.41-1.77 (m, 4H). | 363.1 |
| 149 | >1000 | 251-500 | >1000 | 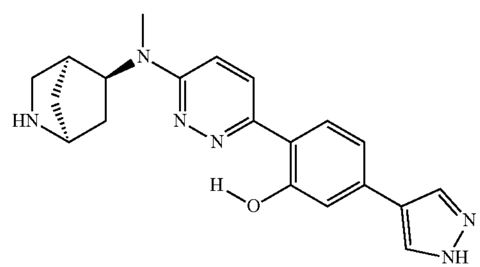 [SMILES: CN(c1ccc(-c2ccc(-c3cn[nH]c3)cc2O)nn1)[C@H]1C[C@@H]2C[C@H]1CN2] | 2-(6-((1S,4S,5S)-2-azabicyclo[2.2.1]heptan-5-yl)(methyl)amino)pyridazin-3-yl)-5-(1H-pyrazol-4-yl)phenol | $^1$H NMR (500 MHz, Methanol-d$_4$) δ 8.09 (d, J = 10.0 Hz, 1H), 8.02 (s, 2H), 7.75 (d, J = 8.8 Hz, 1H), 7.36 (d, J = 9.9 Hz, 1H), 7.20-7.19 (m, 2H), 4.41-4.39 (m, 1H), 3.87 (s, 1H), 3.14 (s, $_3$ h), 3.11-2.83 (m, $_3$ h), 2.41-1.77 (m, 4H). | 363.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 150 | >1000 | | | 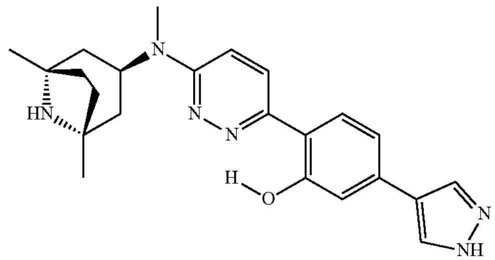 [SMILES: CN(c1ccc(-c2ccc(-c3cn[nH]c3)cc2O)nn1)[C@@H]1C[C@]2(C)CC[C@](C)(C1)N2] | 2-(6-(((1R,3r,5S)-1,5-dimethyl-8-azabicyclo[3.2.1]octan-3-yl)(methyl)amino)pyridazin-3-yl)-5-(1H-pyrazol-4-yl)phenol | 1H NMR (500 MHz, DMSO-d$_6$) δ 13.83 (s, 1H), 12.99 (s, 1H), 8.20 (d, J = 10.0 Hz, 1H), 7.84 (d, J = 8.3 Hz, 1H), 7.36 (d, J = 9.9 Hz, 1H), 7.25-7.09 (m, 2H), 4.93-4.88 (m, 1H), 2.93 (s, 3H), 1.84-1.75 (m, 2H), 1.60-1.51 (m, 6H), 1.19 (s, 6H). | 405.2 |
| 151 | <10 | <10 | <10 | 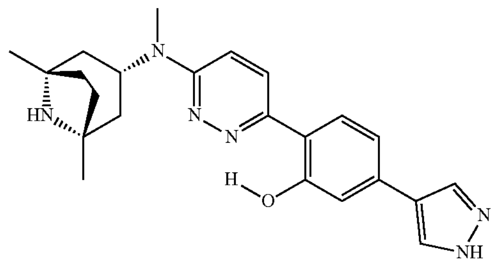 [SMILES: CN(c1ccc(-c2ccc(-c3cn[nH]c3)cc2O)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-5-(1H-pyrazol-4-yl)phenol | $^1$H NMR (400 MHz, DMSO-d$_6$) δ 13.87 (s, 1H), 12.99 (s, 1H), 8.20-7.95 (m, 2H), 7.83 (d, J = 8.3 Hz, 1H), 7.34 (d, J = 9.9 Hz, 1H), 7.24-7.05 (m, 2H), 4.91-4.88 (m, 1H), 2.92 (s, 3H), 1.86-1.64 (m, 4H), 1.58-1.50 (m, 4H), 1.24 (s, 6H). | 405.2 |
| 152 | 101-250 | 10-100 | 10-100 | 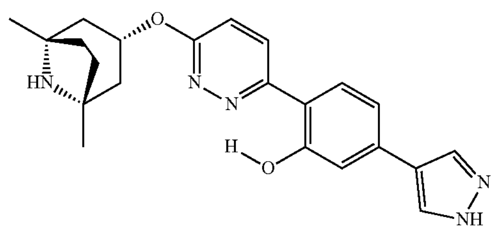 [SMILES: C[C@]12CC[C@](C)(C[C@@H](Oc3ccc(-c4ccc(-c5cn[nH]c5)cc4O)nn3)C1)N2] | 2-(6-(((1R,3s,5S)-1,5-dimethyl-8-azabicyclo[3.2.1]octan-3-yl)oxy)pyridazin-3-yl)-5-(1H-pyrazol-4-yl)phenol | $^1$H NMR (500 MHz, DMSO-d$_6$) δ 13.04 (s, 2H), 8.44 (d, J = 9.6 Hz, 1H), 8.15 (s, 2H), 7.92 (d, J = 8.4 Hz, 1H), 7.36 (d, J = 9.4 Hz, 1H), 7.27-7.20 (m, 2H), 5.54-5.44 (m, 1H), 2.18-2.11 (m, 2H), 1.91 (s, 1H), 1.80-1.74 (m, 2H), 1.51-1.45 (m, 2H), 1.37 (t, J = 11.3 Hz, 2H), 1.18 (s, 6H). | 392.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 153 | >1000 | >1000 | >1000 | 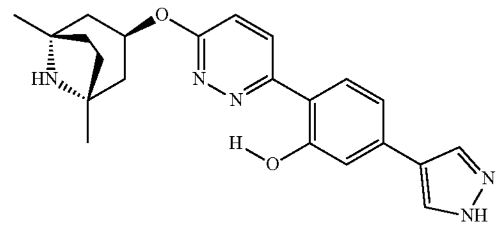 [SMILES: C[C@]12CC[C@](C)(C[C@H](Oc3ccc(-c4ccc(-c5cn[nH]c5)cc4O)nn3)C1)N2] | 2-(6-(((1R,3r,5S)-1,5-dimethyl-8-azabicyclo[3.2.1]octan-3-yl)oxy)pyridazin-3-yl)-5-(1H-pyrazol-4-yl)phenol | 1H NMR (500 MHz, DMSO-d$_6$) δ 13.27 (s, 1H), 13.02 (s, 1H), 8.45 (d, J = 9.6 Hz, 1H), 8.15 (s, 2H), 7.93 (d, J = 8.1 Hz, 1H), 7.38 (d, J = 9.5 Hz, 1H), 7.27-7.14 (m, 2H), 5.61-5.46 (m, 1H), 2.13-2.05 (m, 2H), 1.93-1.87 (m, 2H), 1.80-1.72 (m, 2H), 1.52-1.41 (m, 2H), 1.13 (s, $_6$ h). | 392.2 |
| 154 | 10-100 | 10-100 | 10-100 | 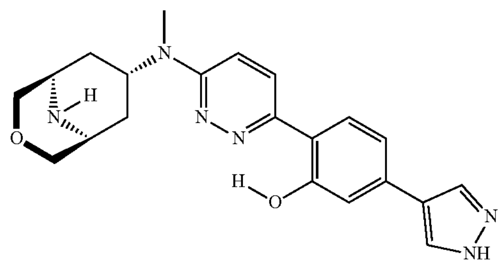 | 2-(6-(((1R,5S,7r)-3-oxa-9-azabicyclo[3.3.1]nonan-7-yl)(methyl)amino)pyridazin-3-yl)-5-(1H-pyrazol-4-yl)phenol | 1H NMR (500 MHz, DMSO-d$_6$) δ 13.86 (s, 1H), 13.00 (s, 1H), 8.23-8.18 (m, $_6$ h), 7.82 (d, J = 8.3 Hz, 1H), 7.32-7.04 (m, $_3$ h), 5.81 (s, 1H), 3.81 (d, J = 10.8 Hz, 2H), 3.73 (d, J = 10.8 Hz, 2H), 2.94 (d, J = 9.4 Hz, 4H), 2.31 (s, 1H), 2.06-1.91 (m, 2H), 1.77-1.72 (m, 2H). | 393.2 |
| 155 | >1000 | >1000 | >1000 | 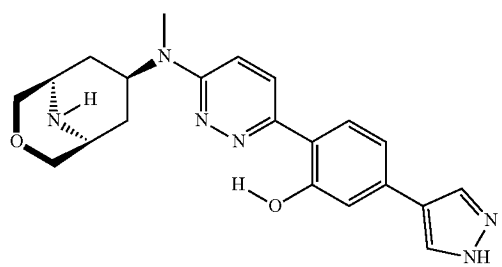 | 2-(6-(((1R,5S,7s)-3-oxa-9-azabicyclo[3.3.1]nonan-7-yl)(methyl)amino)pyridazin-3-yl)-5-(1H-pyrazol-4-yl)phenol | 1H NMR (500 MHz, DMSO-d$_6$) δ 13.90 (s, 1H), 12.98 (s, 1H), 8.27-8.21 (m, 2H), 7.98 (s, 1H), 7.86 (d, J = 8.3 Hz, 1H), 7.47 (d, J = 10.0 Hz, 1H), 7.27-7.10 (m, 2H), 4.75 (s, 1H), 3.57-3.51 (m, 4H), 3.09-2.94 (m, 5H), 2.58 (s, 1H), 2.00-1.85 (m, 2H), 1.77-1.72 (m, 2H). | 393.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 156 | 10-100 | | | 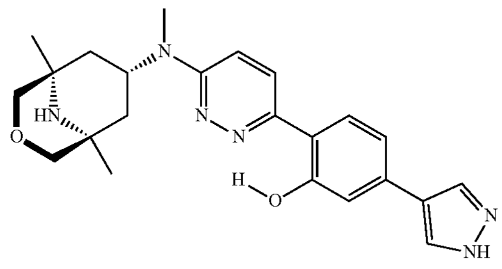 | 2-(6-(((1R,5S,7r)-1,5-dimethyl-3-oxa-9-azabicyclo[3.3.1]nonan-7-yl)(methyl)amino)pyridazin-3-yl)-5-(1H-pyrazol-4-yl)phenol | ¹H NMR (500 MHz, DMSO-d$_6$) δ 13.86 (s, 1H), 12.97 (s, 1H), 8.26 (s, 1H), 8.21 (d, J = 10.1 Hz, 1H), 7.97 (s, 1H), 7.81 (d, J = 8.4 Hz, 1H), 7.27-7.08 (m, $_3$ b), 5.90-5.82 (m, 1H), 3.70 (d, J = 10.8 Hz, 2H), 3.15 (d, J = 8.7 Hz, 2H), 2.91 (s, $_3$ h), 1.90-1.86 (m, 1H), 1.72-1.68 (m, 2H), 1.53-1.50 (m, 2H), 0.91 (s, $_6$ h). | 421.3 |
| 157 | >1000 | | | 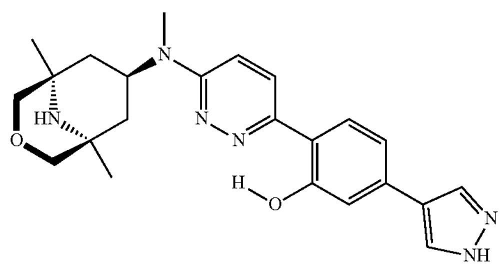 | 2-(6-(((1R,5S,7s)-1,5-dimethyl-3-oxa-9-azabicyclo[3.3.1]nonan-7-yl)(methyl)amino)pyridazin-3-yl)-5-(1H-pyrazol-4-yl)phenol | ¹H NMR (500 MHz, DMSO-d$_6$) δ 13.88 (s, 1H), 12.98 (s, 1H), 8.22 (d, J = 10.1 Hz, 1H), 7.98 (s, 1H), 7.85 (d, J = 8.3 Hz, 1H), 7.44 (d, J = 9.9 Hz, 1H), 7.29-7.05 (m, 2H), 4.65-4.61 (m, 1H), 3.36 (d, J = 10.2 Hz, 2H), 2.99 (s, $_3$ h), 2.97 (d, J = 10.2 Hz, 2H), 1.72-1.76 (m 2H), 1.45-1.41 (m, 2H), 0.96 (s, $_6$ h). | 421.3 |
| 158 | >1000 | >1000 | >1000 | 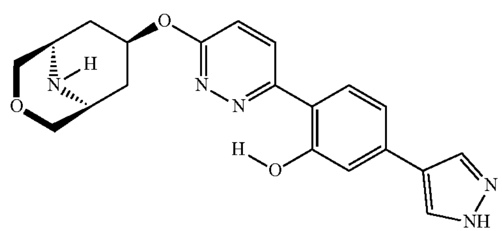 | 2-(6-((1R,5S,7s)-3-oxa-9-azabicyclo[3.3.1]nonan-7-yl)oxy)pyridazin-3-yl)-5-(1H-pyrazol-4-yl)phenol | ¹H NMR (500 MHz, DMSO-d$_6$): δ 13.32 (s, 1H), 13.02 (s, 1H), 8.44 (d, J = 9.6 Hz, 1H), 8.14 (s, 2H), 7.92 (d, J = 8.3 Hz, 1H), 7.36 (d, J = 9.5 Hz, 1H), 7.27-7.11 (m, 2H), 5.47-5.43 (m, 1H), 3.58-3.53 (m, 4H), 3.02 (d, J = 9.0 Hz, 2H), 2.43 (s, 2H), 2.37 (s, 1H), 1.76-1.64 (m, 2H). | 380.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 159 | 501-1000 | 251-500 | 501-1000 | 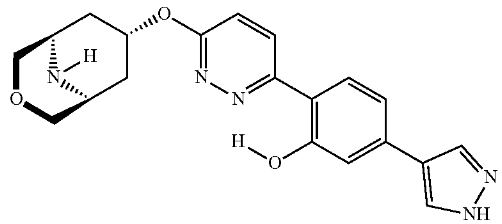 | 2-(6-((1R,5S,7r)-3-oxa-9-azabicyclo[3.3.1]nonan-7-yl)oxy)pyridazin-3-yl)-5-(1H-pyrazol-4-yl)phenol | $^1$H NMR (500 MHz, DMSO-d$_6$): δ 13.29 (s, 1H), 13.03 (s, 1H), 8.44 (d, J = 9.4 Hz, 1H), 8.15 (s, 2H), 7.92 (d, J = 8.1 Hz, 1H), 7.37 (d, J = 9.4 Hz, 1H), 7.30-7.15 (m, 2H), 6.27 (s, 1H), 3.73-3.66 (m, 4H), 3.00 (s, 2H), 2.42-2.25 (m, 3 h), 1.86-1.81 (m, 2H). | 380.2 |
| 160 | <10 | <10 | <10 | 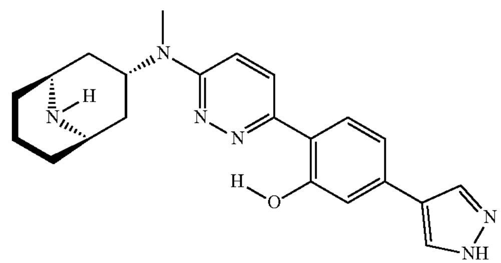 | 2-(6-((1R,3s,5S)-9-azabicyclo[3.3.1]nonan-3-yl)(methyl)amino)pyridazin-3-yl)-5-(1H-pyrazol-4-yl)phenol | $^1$H NMR (500 MHz, DMSO-d$_6$) δ 13.82 (s, 1H), 12.98 (s, 1H), 8.20 (d, J = 10.0 Hz, 1H), 8.12 (s, 2H), 7.83 (d, J = 8.4 Hz, 1H), 7.30 (d, J = 9.9 Hz, 1H), 7.21 (d, J = 1.8 Hz, 1H), 7.18 (dd, J = 8.2, 1.8 Hz, 1H), 5.71-5.56 (m, 1H), 3.21-3.13 (m, 2H), 2.92 (s, 3 h), 2.05-1.91 (m, 2H), 1.85-1.75 (m, 2H), 1.74-1.59 (m, 5H). | 391.2 |
| 161 | <10 | <10 | <10 | 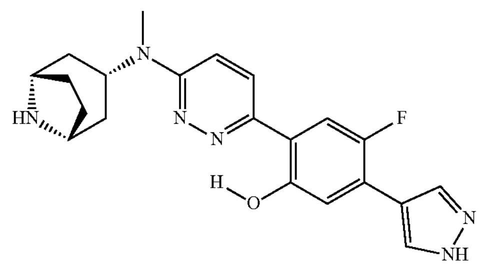 [SMILES: CN(c1ccc(-c2cc(F)c(-c3cn[nH]c3)cc2O)nn1)[C@@H]1C[C@H]2CC[C@@H](C1)N2] | 2-(6-(((1R,3s,5S)-8-azabicyclo[3.2.1]octan-3-yl)(methyl)amino)pyridazin-3-yl)-4-fluoro-5-(1H-pyrazol-4-yl)phenol | $^1$H NMR (500 MHz, DMSO-d$_6$) δ 13.48 (s, 1H), 13.14 (s, 1H), 8.24 (d, J = 10.0 Hz, 1H), 8.11 (s, 2H), 7.84 (d, J = 12.6 Hz, 1H), 7.41 (d, J = 9.8 Hz, 1H), 7.30 (d, J = 7.0 Hz, 1H), 5.06-4.95 (m, 1H), 3.87 (s, 2H), 2.97 (s, 3 h), 2.09-1.84 (m, 6 h), 1.74-1.64 (m, 2H). | 395.2 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 162 | 251-500 | | | 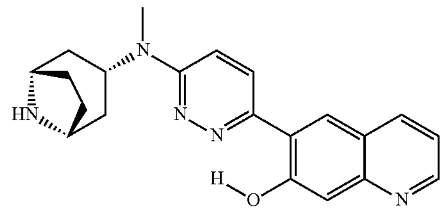 [SMILES: CN(c1ccc(-c2cc3cccnc3cc2O)nn1)[C@@H]1C[C@H]2CC[C@@H](C1)N2] | 6-(6-(((1R,3s,5S)-8-azabicyclo[3.2.1]octan-3-yl)(methyl)amino)pyridazin-3-yl)quinolin-7-ol | $^1$H NMR (400 MHz, Methanol-d$_4$) δ 8.73-8.67 (m, 1H), 8.31-8.24 (m, 2H), 8.18 (d, J = 9.6 Hz, 1H), 7.39 (s, 1H), 7.34-7.29 (m, 1H), 7.26 (d, J = 9.8 Hz, 1H), 5.18-5.04 (m, 1H), 3.73-3.64 (m, 2H), 2.99 (s, 3 h), 2.03-1.91 (m, 6 h), 1.75-1.68 (m, 2H). | 362.2 |
| 163 | 101-250 | 10-100 | | 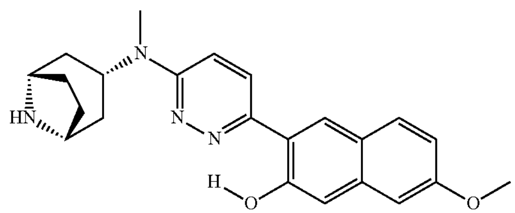 [SMILES: COc1ccc2cc(-c3ccc(N(C)[C@@H]4C[C@H]5CC[C@@H](C4)N5)nn3)c(O)cc2c1] | 3-(6-(((1R,3s,5S)-8-azabicyclo[3.2.1]octan-3-yl)(methyl)amino)pyridazin-3-yl)-7-methoxynaphthalen-2-ol | $^1$H NMR (500 MHz, DMSO-d$_6$) δ 13.30 (s, 1H), 8.44 (s, 1H), 8.35 (d, J = 9.9 Hz, 1H), 7.79 (d, J = 9.0 Hz, 1H), 7.48 (d, J = 9.9 Hz, 1H), 7.20 (s, 1H), 7.12 (d, J = 2.1 Hz, 1H), 6.96 (dd, J = 8.9, 2.4 Hz, 1H), 5.12-5.08 (m, 1H), 4.13-4.09 (m, 2H), 3.86 (s, 3 h), 3.01 (s, 3 h), 2.25-3.21 (m, 2H), 2.10-2.05 (m, 4H), 1.81-1.77 (m, 2H). | 391.1 |
| 164 | 251-500 | 10-100 | 10-100 | 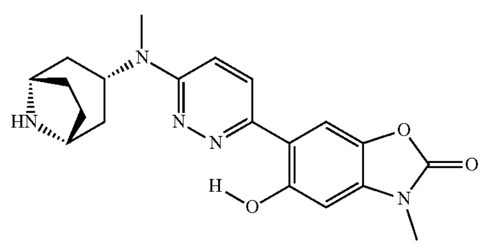 [SMILES: CN(c1ccc(-c2cc3oc(=O)n(C)c3cc2O)nn1)[C@@H]1C[C@H]2CC[C@@H](C1)N2] | 6-(6-(((1R,3s,5S)-8-azabicyclo[3.2.1]octan-3-yl)(methyl)amino)pyridazin-3-yl)-5-hydroxy-3-methylbenzo[d]oxazol-2(3H)-one | $^1$H NMR (500 MHz, DMSO-d$_6$) δ 14.25 (s, 1H), 8.22 (d, J = 10.1 Hz, 1H), 7.92 (s, 1H), 7.41 (d, J = 10.0 Hz, 1H), 6.86 (s, 1H), 5.00-4.88 (m, 1H), 3.77 (s, 2H), 3.41 (s, 3 h), 2.94 (s, 3 h), 2.02-1.82 (m, 6 h), 1.69-1.59 (m, 2H). | 382.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 165 | 10-100 | | | 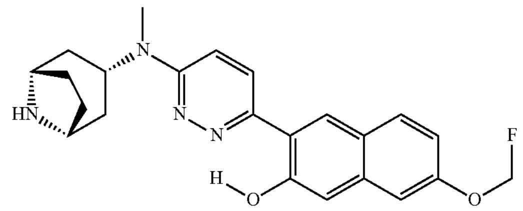 [SMILES: CN(c1ccc(-c2cc3ccc(OCF)cc3cc2O)nn1)[C@@H]1C[C@H]2CC[C@@H](C1)N2] | 3-(6-((((1R,3s,5S)-8-azabicyclo[3.2.1]octan-3-yl)(methyl)amino)pyridazin-3-yl)-7-(fluoromethoxy)naphthalen-2-ol | $^1$H NMR (500 MHz, DMSO-d$_6$) δ 13.31 (s, 1H), 8.78 (s, 1H), 8.51 (s, 1H), 8.36 (d, J = 9.8 Hz, 1H), 7.90 (d, J = 8.8 Hz, 1H), 7.49 (d, J = 9.7 Hz, 1H), 7.38 (s, 1H), 7.27 (s, 1H), 7.11 (d, J = 8.6 Hz, 1H), 5.98 (d, J = 54.3 Hz, 2H), 5.12-5.08 (m, 1H), 4.15-4.11 (m, 2H), 2.99 (s, $_3$ h), 2.26-1.96 (m, $_6$ h), 1.83-1.80 (m, 2H). | 409.1 |
| 166 | 501-1000 | | | 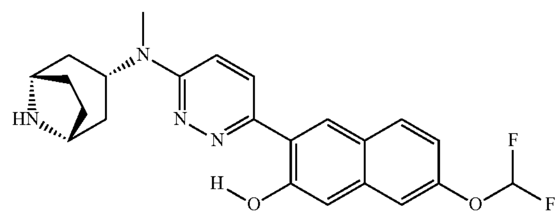 [SMILES: CN(c1ccc(-c2cc3ccc(OC(F)F)cc3cc2O)nn1)[C@@H]1C[C@H]2CC[C@@H](C1)N2] | 3-(6-((((1R,3s,5S)-8-azabicyclo[3.2.1]octan-3-yl)(methyl)amino)pyridazin-3-yl)-7-(difluoromethoxy)naphthalen-2-ol | $^1$H NMR (500 MHz, DMSO-d$_6$) δ 8.54 (s, 1H), 8.34 (d, J = 9.9 Hz, 1H), 7.95 (d, J = 9.0 Hz, 1H), 7.54-7.35 (m, $_3$ h), 7.30 (s, 1H), 7.15-7.13 (m, 1H), 6.98 (t, J = 74.5 Hz, 1H), 5.05-5.01 (m, 1H), 3.83-3.79 (m, 2H), 2.99 (s, $_3$ h), 2.14-1.82 (m, $_6$ h), 1.69-1.65 (m, 2H). | 427.1 |
| 167 | <10 | <10 | <10 | 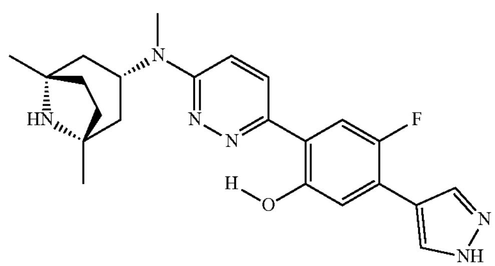 [SMILES: CN(c1ccc(-c2cc(F)c(-c3cn[nH]c3)cc2O)nn1)[C@H]1C[C@]2(C)CC[C@](C)(C1)N2] | 2-(6-((((1R,3s,5S)-1,5-dimethyl-8-azabicyclo[3.2.1]octan-3-yl)(methyl)amino)pyridazin-3-yl)-4-fluoro-5-(1H-pyrazol-4-yl)phenol | $^1$H NMR (500 MHz, DMSO-d$_6$) δ 13.56 (s, 1H), 13.14 (s, 1H), 8.21 (d, J = 9.9 Hz, 1H), 8.11 (s, 2H), 7.81 (d, J = 12.6 Hz, 1H), 7.35 (d, J = 9.9 Hz, 1H), 7.30 (d, J = 7.0 Hz, 1H), 5.00-4.87 (m, 1H), 2.93 (s, $_3$ h), 1.83-1.77 (m, 2H), 1.56-1.39 (m, $_6$ h), 1.17 (s, $_6$ h). | 423.3 |

TABLE 1B-continued

Exemplary SMSM compounds

| SMSM # | A-673 IC$_{50}$ (nM)[a] | Splice EC$_{50}$ (nM)[b] | Splice IC$_{50}$ (nM)[c] | Structure | Name | Proton NMR | M + H (MS) |
|---|---|---|---|---|---|---|---|
| 168 | <10 | >1000 | <10 | 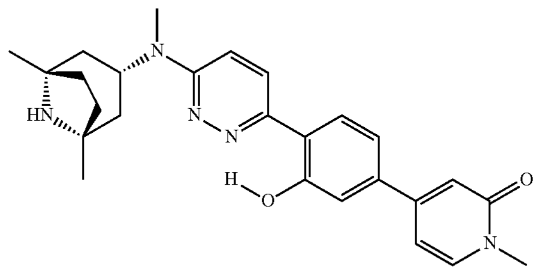 | 4-(4-(6-(((1R,3s,5S)-1,5-dimethyl-8-azabicyclo[3.2.1]octan-3-yl)(methyl)amino)pyridazin-3-yl)-3-hydroxyphenyl)-1-methylpyridin-2(1H)-one | $^1$H NMR (500 MHz, DMSO-d$_6$) δ 13.75 (s, 1H), 8.25 (d, J = 10.0 Hz, 1H), 7.97 (d, J = 8.2 Hz, 1H), 7.78 (d, J = 7.1 Hz, 1H), 7.38 (d, J = 9.9 Hz, 1H), 7.29-7.22 (m, 2H), 6.70 (s, 1H), 6.61 (d, J = 7.2 Hz, 1H), 4.94 (s, 1H), 3.46 (s, 3 h), 2.94 (s, 3 h), 1.88-1.83 (m, 2H), 1.61-1.42 (m, 6 h), 1.23 (s, 6 h). | 446.3 |
| 169 | <10 | >1000 | <10 | 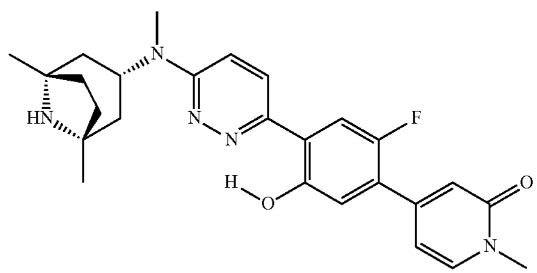 | 4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1-methylpyridin-2(1H)-one | $^1$H NMR (500 MHz, DMSO-d$_6$) δ 13.50 (s, 1H), 8.25 (d, J = 10.0 Hz, 1H), 7.91 (d, J = 12.4 Hz, 1H), 7.78 (d, J = 7.1 Hz, 1H), 7.37 (d, J = 9.9 Hz, 1H), 7.08 (d, J = 6.9 Hz, 1H), 6.58 (s, 1H), 6.45 (dt, J = 7.1, 1.9 Hz, 1H), 5.07-4.77 (m, 1H), 3.46 (s, 6 h), 2.94 (s, 6 h), 1.85-1.76 (m, 2H), 1.60-1.43 (m, 6 h), 1.18 (s, 6 h). | 464.2 |
| 170 | <10 | <10 | <10 | 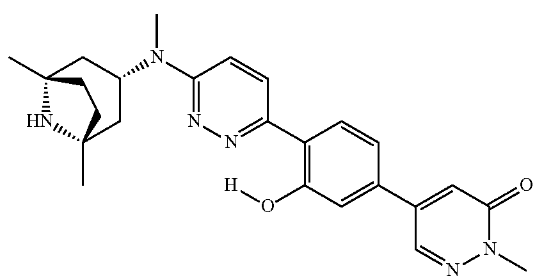 | 5-(4-(6-(((1R,3s,5S)-1,5-dimethyl-8-azabicyclo[3.2.1]octan-3-yl)(methyl)amino)pyridazin-3-yl)-3-hydroxyphenyl)-2-methylpyridazin-3(2H)-one | $^1$H NMR (500 MHz, DMSO-d$_6$) δ 8.40 (d, J = 9.9 Hz, 1H), 8.33 (s, 1H), 7.98 (d, J = 8.2 Hz, 1H), 7.30-7.12 (m, 4H), 4.95 (s, 1H), 3.68 (s, 3 h), 2.92 (s, 3 h), 1.86-1.811 (m, 3 h), 1.56-1.51 (m, 6 h), 1.17 (s, 6 h). | 447.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 171 | 10-100 | | | 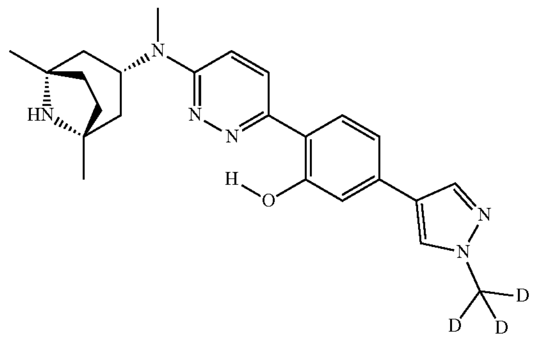 [SMILES: [2H]C([2H])([2H])n1cc(-c2ccc(-c3ccc(N(C)[C@H]4C[C@]5(C)CC[C@](C)(C4)N5)nn3)c(O)c2)cn1] | 2-(6-((((1R,3s,5S)-1,5-dimethyl-8-azabicyclo[3.2.1]octan-3-yl)(methyl)amino)pyridazin-3-yl)-5-(1-(methyl-d3)-1H-pyrazol-4-yl)phenol | $^1$H NMR (500 MHz, DMSO-d$_6$) δ 8.25-8.13 (m, 2H), 7.91 (d, J = 0.6 Hz, 1H), 7.83 (d, J = 9.0 Hz, 1H), 7.36 (d, J = 9.9 Hz, 1H), 7.19-7.11 (m, 2H), 4.97-4.89 (m, 1H), 2.94 (s, $_3$ h), 1.92-1.86 (m, 2H), 1.70-1.58 (m, $_6$ h), 1.25 (s, $_6$ h). | 422.3 |
| 172 | <10 | | | 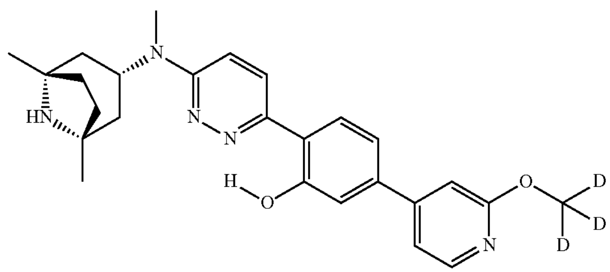 [SMILES: [2H]C([2H])([2H])Oc1cc(-c2ccc(-c3ccc(N(C)[C@H]4C[C@]5(C)CC[C@](C)(C4)N5)nn3)c(O)c2)ccn1] | 2-(6-((((1R,3s,5S)-1,5-dimethyl-8-azabicyclo[3.2.1]octan-3-yl)(methyl)amino)pyridazin-3-yl)-5-(2-(methoxy-d3)pyridin-4-yl)phenol | $^1$H NMR (500 MHz, DMSO-d$_6$) δ 13.87 (s, 1H), 8.28-8.19 (m, 2H), 8.02-7.95 (m, 1H), 7.42-7.30 (m, 4H), 7.14 (s, 1H), 5.01-4.85 (m, 1H), 2.94 (s, $_3$ h), 1.87-1.78 (m, $_6$ h), 1.57-1.44 (m, $_6$ h), 1.17 (s, $_6$ h). | 449.3 |
| 173 | <10 | | | 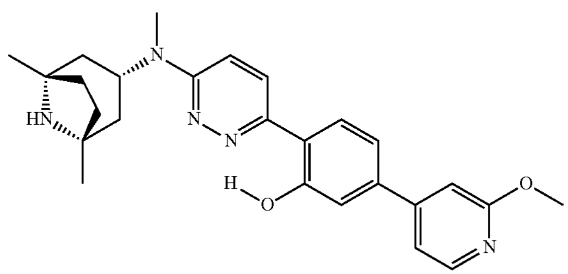 | 2-(6-((((1R,3s,5S)-1,5-dimethyl-8-azabicyclo[3.2.1]octan-3-yl)(methyl)amino)pyridazin-3-yl)-5-(2-methoxypyridin-4-yl)phenol | $^1$H NMR (500 MHz, DMSO-d$_6$) δ 13.87 (s, 1H), 8.27-8.23 (m, 2H), 8.00 (d, J = 8.9 Hz, 1H), 7.48-7.25 (m, 4H), 7.14 (s, 1H), 4.94 (s, 1H), 3.90 (s, $_3$ h), 2.95 (s, $_3$ h), 1.82 (d, J = 7.1 Hz, 2H), 1.59-1.53 (m, $_6$ h), 1.18 (s, $_6$ h). | 446.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 174 | <10 | | | 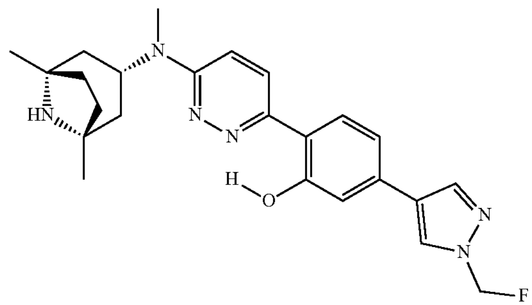 [SMILES: CN(c1ccc(-c2ccc(-c3cnn(CF)c3)cc2O)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-5-(1-(fluoromethyl)-1H-pyrazol-4-yl)phenol | $^1$H NMR (500 MHz, DMSO-d$_6$) δ 13.78 (s, 1H), 9.11 (s, 1H), 8.76 (s, 1H), 8.58 (s, 1H), 8.27 (d, J = 10.0 Hz, 1H), 7.92 (d, J = 8.3 Hz, 1H), 7.46 (d, J = 9.9 Hz, 1H), 7.22 (d, J = 16.5 Hz, 2H), 6.17 (d, J = 53.5 Hz, 2H), 5.12-5.08 (m, 1H), 2.99 (s, 3 h), 2.18 (m, 2H), 2.10-1.98 (m, 2H), 1.93-1.76 (m, 4H), 1.44 (s, 6 h). | 437.2 |
| 175 | 10-100 | | | 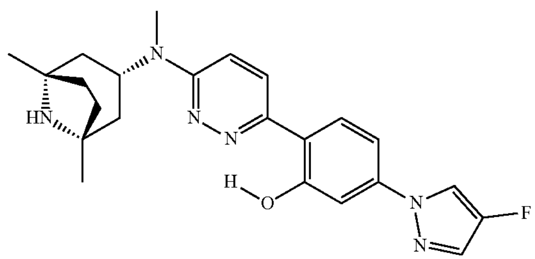 [SMILES: CN(c1ccc(-c2ccc(-n3cc(F)cn3)cc2O)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-5-(4-fluoro-1H-pyrazol-1-yl)phenol | $^1$H NMR (500 MHz, DMSO-d$_6$) δ 14.04 (s, 1H), 8.77 (d, J = 4.5 Hz, 1H), 8.27 (d, J = 10.0 Hz, 1H), 8.03 (d, J = 8.5 Hz, 1H), 7.86 (d, J = 4.2 Hz, 1H), 7.46 (d, J = 9.9 Hz, 1H), 7.42-7.33 (m, 2H), 5.06 (s, 1H), 3.00 (s, 3 h), 2.21-1.97 (m, 4H), 1.93-1.70 (m, 4H), 1.43 (s, 6 h). | 423.3 |
| 176 | 10-100 | | | 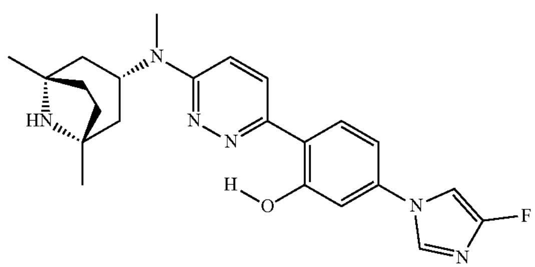 [SMILES: CN(c1ccc(-c2ccc(-n3cnc(F)c3)cc2O)nn1)[C@H]1C[C@]2(C)CC[C@](C)(C1)N2] | 2-(6-(((1R,3s,5S)-1,5-dimethyl-8-azabicyclo[3.2.1]octan-3-yl)(methyl)amino)pyridazin-3-yl)-5-(4-fluoro-1H-imidazol-1-yl)phenol | $^1$H NMR (500 MHz, DMSO-d$_6$) δ 8.25 (d, J = 10.0 Hz, 1H), 8.14 (s, 1H), 8.02 (d, J = 8.7 Hz, 1H), 7.64 (dd, J = 8.1, 1.7 Hz, 1H), 7.38 (d, J = 9.9 Hz, 1H), 7.29 (d, J = 2.3 Hz, 1H), 7.23 (dd, J = 8.6, 2.3 Hz, 1H), 4.93 (s, 1H), 2.94 (s, 3 h), 1.86-1.81 (m, 2H), 1.58-1.42 (m, 6 h), 1.17 (s, 6 h). | 423.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 177 | 10-100 | <10 | <10 | 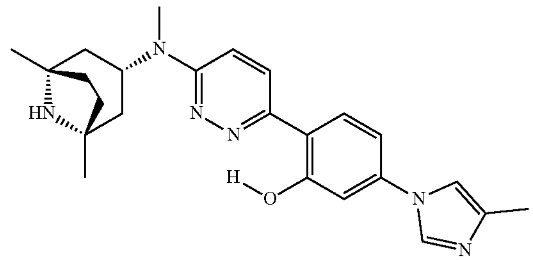 | 2-(6-(((1R,3s,5S)-1,5-dimethyl-8-azabicyclo[3.2.1]octan-3-yl)(methyl)amino)pyridazin-3-yl)-5-(4-methyl-1H-imidazol-1-yl)phenol | $^1$H NMR (500 MHz, DMSO-d$_6$) δ 8.21-8.26 (m, 2H), 7.99 (d, J = 8 Hz, 1H), 7.51 (s, 1H), 7.45 (d, J = 8 Hz, 1H), 7.19-7.21 (m, 2H), 5.06-5.09 (m, 1H), 2.97 (s, 3 h), 2.16-2.21 (m, 7 h), 1.81-2.01 (m, 4H), 1.43 (s, 6 h). | 420.2 |
| 178 | 251-500 | | | 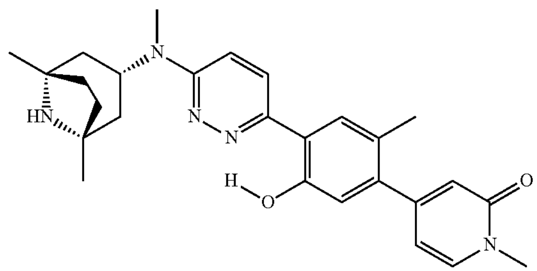 [SMILES: Cc1cc(-c2ccc(N(C)[C@H]3C[C@]4(C)CC[C@](C)(C3)N4)nn2)c(O)cc1-c1ccn(C)c(=O)c1] | 4-(4-(6-(((1R,3s,5S)-1,5-dimethyl-8-azabicyclo[3.2.1]octan-3-yl)(methyl)amino)pyridazin-3-yl)-5-hydroxy-2-methylphenyl)-1-methylpyridin-2(1H)-one | $^1$H NMR (500 MHz, DMSO-d$_6$) δ 13.39 (s, 1H), 8.21 (d, J = 10.0 Hz, 1H), 7.80 (s, 1H), 7.74 (d, J = 6.9 Hz, 1H), 7.35 (d, J = 9.9 Hz, 1H), 6.77 (s, 1H), 6.32 (d, J = 1.9 Hz, 1H), 6.25 (dd, J = 6.9, 2.0 Hz, 1H), 5.00-4.89 (m, 1H), 3.47 (s, 3 h), 2.93 (s, 6 h), 2.25 (s, 3 h), 1.84-1.78 (m, 2H), 1.56-1.46 (m, 6 h), 1.17 (s, 6 h). | 460.3 |
| 179 | 10-100 | | | 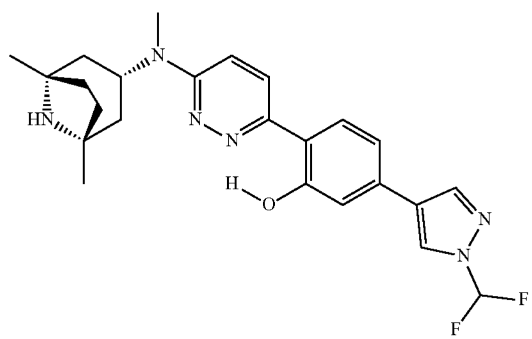 [SMILES: CN(c1ccc(-c2ccc(-c3cnn(C(F)F)c3)cc2O)nn1)[C@H]1C[C@]2(C)CC[C@](C)(C1)N2] | 5-(1-(difluoromethyl)-1H-pyrazol-4-yl)-2-(6-(((1R,3s,5S)-1,5-dimethyl-8-azabicyclo[3.2.1]octan-3-yl)(methyl)amino)pyridazin-3-yl)phenol | $^1$H NMR (500 MHz, DMSO-d$_6$) δ 13.92 (s, 1H), 8.79 (s, 1H), 8.34 (s, 1H), 8.23 (d, J = 10.0 Hz, 1H), 7.91 (d, J = 8.5 Hz, 1H), 7.84 (t, J = 59.5 Hz, 1H), 7.38 (d, J = 10.0 Hz, 1H), 7.33-7.25 (m, 2H), 5.03-4.81 (m, 1H), 2.94 (s, 3 h), 1.90-1.81 (m, 2H), 1.66-1.48 (m, 6 h), 1.21 (s, 6 h). | 455.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 180 | 101–250 | 10–100 | 10–100 | 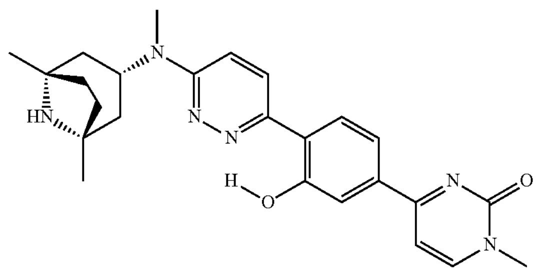 | 4-(4-(6-(((1R,3s,5S)-1,5-dimethyl-8-azabicyclo[3.2.1]octan-3-yl)(methyl)amino)pyridazin-3-yl)-3-hydroxyphenyl)-1-methylpyrimidin-2(1H)-one | $^1$H NMR (500 MHz, DMSO-d$_6$) δ 13.72 (s, 1H), 8.29-8.25 (m, 2H), 8.02 (d, J = 8.8 Hz, 1H), 7.67 (d, J = 7.7 Hz, 2H), 7.38-7.36 (m, 1H), 7.12-7.10 (m, 1H), 4.96 (s, 1H), 3.47 (s, 3 h), 2.95 (s, 3 h), 1.85-1.76 (m, 3 h), 1.54-1.48 (m, 6 h), 1.17 (s, 6 h). | 447.3 |
| 181 | 251–500 | 10–100 | 10–100 | 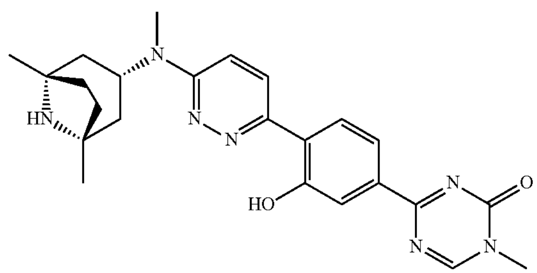 [SMILES: CN(c1ccc(-c2ccc(-c3ncn(C)c(=O)n3)cc2O)nn1)[C@H]1C[C@]2(C)CC[C@](C)(C1)N2] | 4-(4-(6-(((1R,3s,5S)-1,5-dimethyl-8-azabicyclo[3.2.1]octan-3-yl)(methyl)amino)pyridazin-3-yl)-3-hydroxyphenyl)-1-methyl-1,3,5-triazin-2(1H)-one | $^1$H NMR (500 MHz, DMSO-d$_6$) δ 8.83 (s, 1H), 8.27 (d, J = 9.9 Hz, 1H), 8.03 (d, J = 8.5 Hz, 1H), 7.84 (d, J = 7.5 Hz, 2H), 7.36 (d, J = 9.9 Hz, 1H), 5.05-4.87 (m, 1H), 3.43 (s, 6 h), 2.95 (s, 3 h), 1.91-1.75 (m, 6 h), 1.57-1.47 (m, 6 h), 1.17 (s, 6 h). | 448.2 |
| 182 | 10–100 | <10 | <10 | 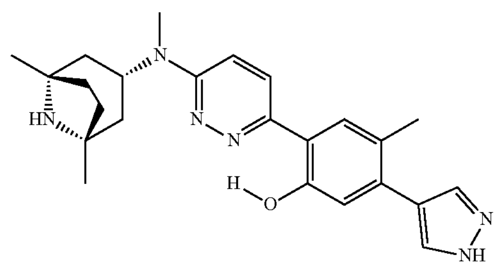 [SMILES: Cc1cc(-c2ccc(N(C)[C@H]3C[C@]4(C)CC[C@](C)(C3)N4)nn2)c(O)cc1-c1cn[nH]c1] | 2-(6-(((1R,3s,5S)-1,5-dimethyl-8-azabicyclo[3.2.1]octan-3-yl)(methyl)amino)pyridazin-3-yl)-4-methyl-5-(1H-pyrazol-4-yl)phenol | $^1$H NMR (500 MHz, DMSO-d$_6$) δ 13.37 (s, 1H), 13.01 (s, 1H), 8.19 (d, J = 9.9 Hz, 1H), 7.94 (s, 2H), 7.73 (s, 1H), 7.34 (d, J = 9.8 Hz, 1H), 7.00 (s, 1H), 5.00-4.92 (m, 1H), 2.93 (s, 3 h), 2.38 (s, 3 h), 1.84-1.76 (m, 2H), 1.60-1.42 (m, 6 h), 1.17 (s, 6 h). | 419.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 183 | 10-100 | | | 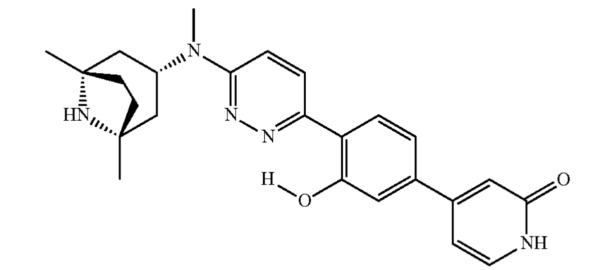 [SMILES: CN(c1ccc(-c2ccc(-c3cc[nH]c(=O)c3)cc2O)nn1)[C@H]1C[C@]2(C)CC[C@](C)(C1)N2] | 4-(4-(6-(((1R,3s,5S)-1,5-dimethyl-8-azabicyclo[3.2.1]octan-3-yl)(methyl)amino)pyridazin-3-yl)-3-hydroxyphenyl)pyridin-2(1H)-one | $^1$H NMR (500 MHz, DMSO-d$_6$) δ 13.81 (s, 1H), 11.88 (s, 1H), 8.24 (d, J = 10.0 Hz, 1H), 7.97 (d, J = 8.4 Hz, 1H), 7.44 (d, J = 6.9 Hz, 1H), 7.38 (d, J = 9.8 Hz, 1H), 7.30-7.18 (m, 2H), 6.61 (s, 1H), 6.54 (d, J = 6.8 Hz, 1H), 4.93 (s, 1H), 2.94 (s, 3 h), 1.86-1.82 (m, 2H), 1.58-1.52 (m, 6 h), 1.18 (s, 6 h). | 432.3 |
| 184 | 10-100 | | | 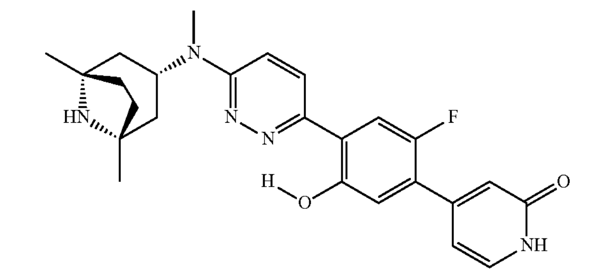 [SMILES: CN(c1ccc(-c2cc(F)c(-c3cc[nH]c(=O)c3)cc2O)nn1)[C@H]1C[C@]2(C)CC[C@](C)(C1)N2] | 4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)pyridin-2(1H)-one | $^1$H NMR (500 MHz, DMSO-d$_6$) δ 13.48 (s, 1H), 8.25 (d, J = 10.0 Hz, 1H), 7.91 (d, J = 12.3 Hz, 1H), 7.46 (d, J = 6.7 Hz, 1H), 7.37 (d, J = 9.9 Hz, 1H), 7.06 (d, J = 6.9 Hz, 1H), 6.50 (s, 1H), 6.39 (dt, J = 6.9, 1.8 Hz, 1H), 5.00-4.89 (m, 1H), 2.94 (s, 3 h), 1.85-1.77 (m, 2H), 1.60-1.39 (m, 6 h), 1.17 (s, 6 h). | 450.2 |
| 185 | 501-1000 | | | 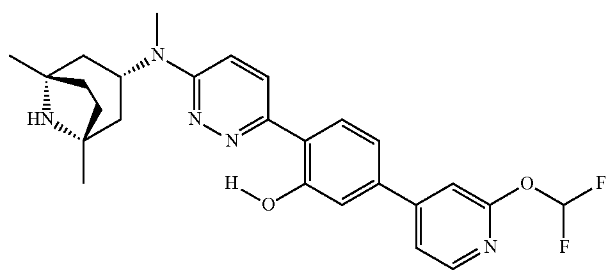 [SMILES: CN(c1ccc(-c2ccc(-c3ccnc(OC(F)F)c3)cc2O)nn1)[C@H]1C[C@]2(C)CC[C@](C)(C1)N2] | 5-(2-(difluoromethoxy)pyridin-4-yl)-2-(6-(((1R,3s,5S)-1,5-dimethyl-8-azabicyclo[3.2.1]octan-3-yl)(methyl)amino)pyridazin-3-yl)phenol | $^1$H NMR (500 MHz, DMSO-d$_6$) δ 13.94 (s, 1H), 8.33 (d, J = 5.3 Hz, 1H), 8.28 (d, J = 10.0 Hz, 1H), 8.03 (d, J = 8.2 Hz, 1H), 7.78 (t, J = 73.5 Hz, 1H), 7.67 (dd, J = 5.4, 1.6 Hz, 1H), 7.49-7.34 (m, 4H), 4.95-4.94 (m, 1H), 2.95 (s, 3 h), 1.92-1.79 (m, 2H), 1.64-1.47 (m, 6 h), 1.20 (s, 6 h). | 482.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 186 | >1000 | 10-100 | 101-250 | 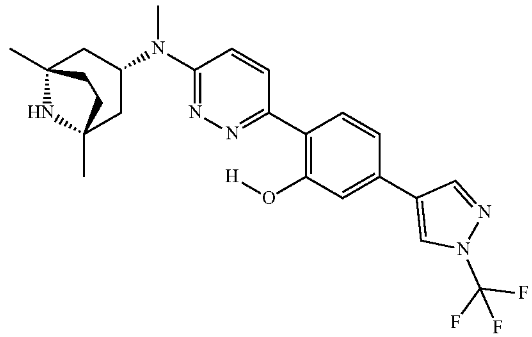 [SMILES: CN(c1ccc(-c2ccc(-c3cnn(C(F)(F)F)c3)cc2O)nn1)[C@H]1C[C@]2(C)CC[C@](C)(C1)N2] | 2-(6-((((1R,3s,5S)-1,5-dimethyl-8-azabicyclo[3.2.1]octan-3-yl)(methyl)amino)pyridazin-3-yl)-5-(1-(trifluoromethyl)-1H-pyrazol-4-yl)phenol | $^1$H NMR (500 MHz, DMSO-d$_6$) δ 13.97 (s, 1H), 9.06 (s, 1H), 8.54 (s, 1H), 8.26 (d, J = 10.0 Hz, 1H), 7.94 (d, J = 8.4 Hz, 1H), 7.41-7.36 (m, 2H), 7.33 (dd, J = 7.8, 1.7 Hz, 1H), 4.97 (s, 1H), 2.95 (s, 3 h), 1.98-1.86 (m, 2H), 1.67-1.54 (m, 6 h), 1.23 (s, 6 h). | 473.2 |
| 187 | 10-100 | <10 | <10 | 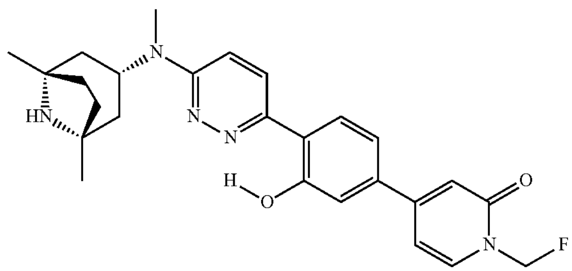 [SMILES: CN(c1ccc(-c2ccc(-c3ccn(CF)c(=O)c3)cc2O)nn1)[C@H]1C[C@]2(C)CC[C@](C)(C1)N2] | 4-(4-(6-((((1R,3s,5S)-1,5-dimethyl-8-azabicyclo[3.2.1]octan-3-yl)(methyl)amino)pyridazin-3-yl)-3-hydroxyphenyl)-1-(fluoromethyl)pyridin-2(1H)-one | $^1$H NMR (500 MHz, DMSO-d$_6$) δ 13.88 (s, 1H), 8.25 (d, J = 10.0 Hz, 1H), 8.01-7.95 (m, 1H), 7.90 (d, J = 7.3 Hz, 1H), 7.38 (d, J = 10.0 Hz, 1H), 7.35-7.27 (m, 2H), 6.81 (d, J = 1.9 Hz, 1H), 6.73 (dd, J = 7.3, 2.0 Hz, 1H), 5.98 (d, J = 51.1 Hz, 2H), 5.01-4.87 (m, 1H), 2.95 (s, 3 h), 1.88-1.75 (m, 2H), 1.61-1.43 (m, 6 h), 1.18 (s, 6 h). | 464.1 |
| 188 | 10-100 | <10 | 10-100 | 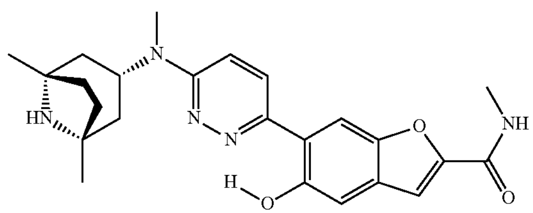 | 6-(6-((((1R,3s,5S)-1,5-dimethyl-8-azabicyclo[3.2.1]octan-3-yl)(methyl)amino)pyridazin-3-yl)-5-hydroxy-N-methylbenzofuran-2-carboxamide | $^1$H NMR (500 MHz, DMSO-d$_6$) δ 13.35 (s, 1H), 8.63 (d, J = 4.6 Hz, 1H), 8.28 (d, J = 10.0 Hz, 1H), 8.12 (s, 1H), 7.45-7.30 (m, 2H), 7.20 (s, 1H), 4.92 (s, 2H), 2.95 (s, 3 h), 2.80 (d, J = 4.6 Hz, 3 h), 1.91-1.73 (m, 3 h), 1.57-1.42 (m, 6 h), 1.17 (s, 6 h). | 436.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 189 | 10-100 | | | 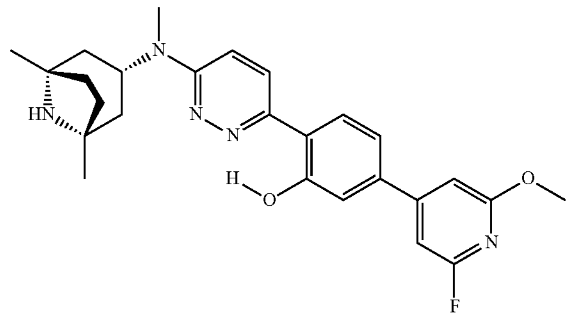 | 2-(6-(((1R,3s,5S)-1,5-dimethyl-8-azabicyclo[3.2.1]octan-3-yl)(methyl)amino)pyridazin-3-yl)-5-(2-fluoro-6-methoxypyridin-4-yl)phenol | 1H NMR (500 MHz, DMSO-d6) δ 13.90 (s, 1H), 8.28 (d, J = 9.8 Hz, 1H), 8.01 (d, J = 8.3 Hz, 1H), 7.44-7.36 (m, 3H), 7.14 (s, 2H), 5.03-4.91 (m, 2H), 3.89 (s, 3H), 2.96 (s, 3H), 1.97-1.85 (m, 2H), 1.72-1.50 (m, 6H), 1.23 (s, 6H). | 464.3 |
| 190 | 101-250 | | | 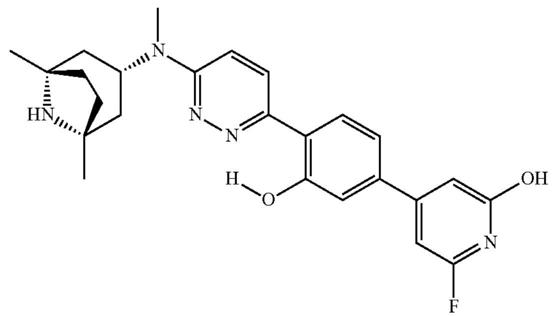 [SMILES: CN(c1ccc(-c2ccc(-c3cc(O)nc(F)c3)cc2O)nn1)[C@H]1C[C@]2(C)CC[C@](C)(C1)N2] | 4-(4-(6-(((1R,3s,5S)-1,5-dimethyl-8-azabicyclo[3.2.1]octan-3-yl)(methyl)amino)pyridazin-3-yl)-3-hydroxyphenyl)-6-fluoropyridin-2-ol | $^1$H NMR (500 MHz, DMSO-d$_6$) δ 13.86 (s, 1H), 8.25 (d, J = 10.0 Hz, 1H), 7.99 (d, J = 8.9 Hz, 1H), 7.39 (d, J = 9.9 Hz, 1H), 7.34-7.28 (m, 2H), 6.88-6.78 (m, 2H), 5.02-4.88 (m, 1H), 2.95 (s, 3 h), 1.89-1.82 (m, 2H), 1.63-1.50 (m, 6 h), 1.20 (s, 6 h). | 450.2 |
| 191 | <10 | | | 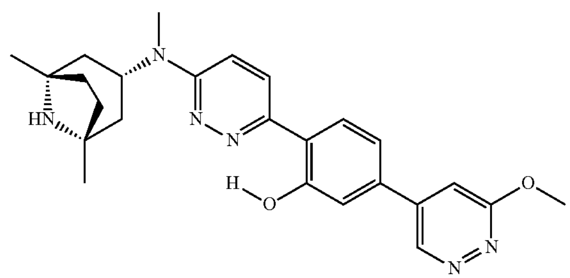 | 2-(6-(((1R,3s,5S)-1,5-dimethyl-8-azabicyclo[3.2.1]octan-3-yl)(methyl)amino)pyridazin-3-yl)-5-(6-methoxypyridazin-4-yl)phenol | $^1$H NMR (500 MHz, DMSO-d$_6$) δ 9.34 (s, 1H), 8.30 (d, J = 9.9 Hz, 1H), 8.04 (d, J = 8.2 Hz, 1H), 7.55 (s, 1H), 7.48 (s, 1H), 7.45 (d, J = 8.3 Hz, 1H), 7.37 (d, J = 9.9 Hz, 1H), 5.00-4.87 (m, 1H), 4.08 (s, 3 h), 2.94 (s, 3 h), 1.88-1.76 (m, 3 h), 1.57-1.44 (m, 6 h), 1.17 (s, 6 h). | 447.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 192 | 10-100 | <10 | <10 | 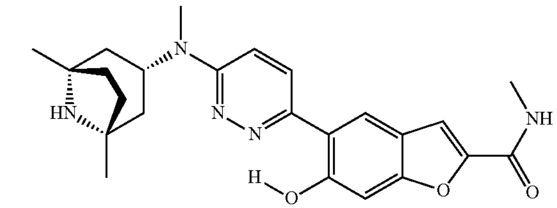 | 5-(6-(((1R,3s,5S)-1,5-dimethyl-8-azabicyclo[3.2.1]octan-3-yl)(methyl)amino)pyridazin-3-yl)-6-hydroxy-N-methylbenzofuran-2-carboxamide | $^1$H NMR (500 MHz, DMSO-d$_6$) δ 8.55-8.56 (m, 1H), 8.28 (s, 1H), 8.24 (d, J = 10.1 Hz, 1H), 7.43 (d, J = 0.7 Hz, 1H), 7.40 (d, J = 10.0 Hz, 1H), 7.11 (s, 1H), 4.94-4.90 (m, 1H), 2.95 (s, 3h), 2.79 (d, J = 4.6 Hz, 3h), 1.83-1.79 (m, 2H), 1.54-1.49 (m, J = 15.2, 7.8 Hz, 6h), 1.18 (d, J = 10.6 Hz, 6h). | 436.3 |
| 193 | <10 | | | 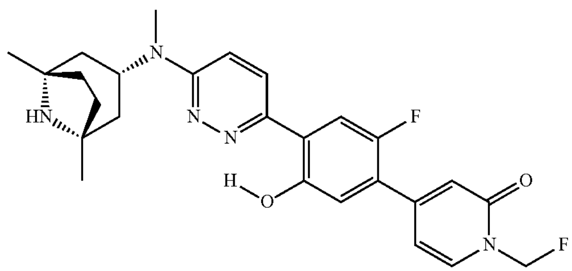 [SMILES: CN(c1ccc(-c2cc(F)c(-c3ccn(CF)c(=O)c3)cc2O)nn1)[C@H]1C[C@]2(C)CC[C@](C)(C1)N2] | 4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1-(fluoromethyl)pyridin-2(1H)-one | $^1$H NMR (500 MHz, DMSO-d$_6$) δ 13.45 (s, 1H), 8.29 (d, J = 9.9 Hz, 1H), 7.95 (d, J = 12.5 Hz, 1H), 7.90 (d, J = 7.2 Hz, 1H), 7.43 (d, J = 9.8 Hz, 1H), 7.14 (d, J = 6.9 Hz, 1H), 6.68 (s, 1H), 6.59-6.51 (m, 1H), 5.99 (d, J = 50.8 Hz, 2H), 5.16-4.89 (m, 1H), 2.99 (s, 3h), 2.07-1.61 (m, 8h), 1.32 (s, 6h). | 482.2 |
| 194 | 10-100 | | | 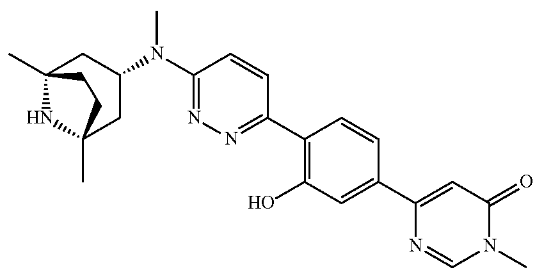 | 6-(4-(6-(((1R,3s,5S)-1,5-dimethyl-8-azabicyclo[3.2.1]octan-3-yl)(methyl)amino)pyridazin-3-yl)-3-hydroxyphenyl)-3-methylpyrimidin-4(3H)-one | $^1$H NMR (500 MHz, DMSO-d$_6$) δ 13.67 (s, 1H), 8.56 (s, 1H), 8.26 (d, J = 9.9 Hz, 1H), 7.99 (d, J = 8.3 Hz, 1H), 7.64-7.58 (m, 2H), 7.40 (d, J = 9.9 Hz, 1H), 7.00 (s, 1H), 5.06-4.88 (m, 1H), 3.44 (s, 3h), 2.96 (s, 3h), 2.03-1.86 (m, 2H), 1.82-1.53 (m, 6h), 1.32-1.18 (m, 6h). | 447.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 195 | 501-1000 | | | 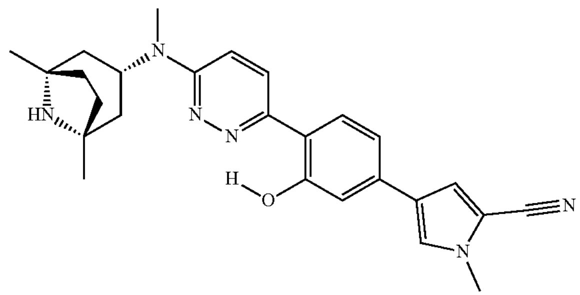 [SMILES: CN(c1ccc(-c2ccc(-c3cc(C#N)n(C)c3)cc2O)nn1)[C@H]1C[C@]2(C)CC[C@](C)(C1)N2] | 4-(4-(6-(((1R,3s,5S)-1,5-dimethyl-8-azabicyclo[3.2.1]octan-3-yl)(methyl)amino)pyridazin-3-yl)-3-hydroxyphenyl)-1-methyl-1H-pyrrole-2-carbonitrile | $^1$H NMR (500 MHz, DMSO-d$_6$) δ 13.85 (s, 1H), 8.19 (d, J = 9.8 Hz, 1H), 7.84 (d, J = 8.3 Hz, 1H), 7.76 (s, 1H), 7.44 (d, J = 1.8 Hz, 1H), 7.35 (d, J = 9.8 Hz, 1H), 7.14 (d, J = 10.3 Hz, 2H), 4.99-4.85 (m, 1H), 3.79 (s, 3H), 2.93 (s, 3H), 1.86-1.78 (m, 2H), 1.56-1.49 (m, 6H), 1.17 (s, 6H). | 443.3 |
| 196 | 251-500 | | | 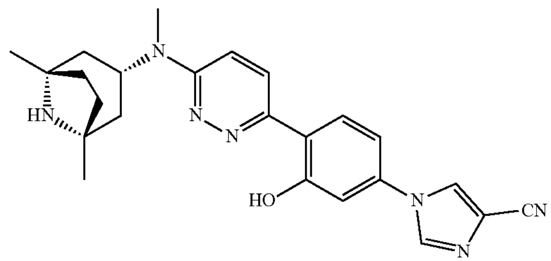 [SMILES: CN(c1ccc(-c2ccc(-n3cnc(C#N)c3)cc2O)nn1)[C@H]1C[C@]2(C)CC[C@](C)(C1)N2] | 1-(4-(6-((((1R,3s,5S)-1,5-dimethyl-8-azabicyclo[3.2.1]octan-3-yl)(methyl)amino)pyridazin-3-yl)-3-hydroxyphenyl)-1H-imidazole-4-carbonitrile | $^1$H NMR (500 MHz, DMSO-d$_6$) δ 8.83 (s, 1H), 8.62 (s, 1H), 8.27 (d, J = 9.3 Hz, 1H), 8.07 (d, J = 7.5 Hz, 1H), 7.48-7.15 (m, 2H), 4.94 (s, 1H), 2.94 (s, 3 h), 1.93-1.70 (m, 2H), 1.63-1.42 (m, $_6$ h), 1.17 (s, $_6$ h). | 430.0 |
| 197 | >1000 | | | 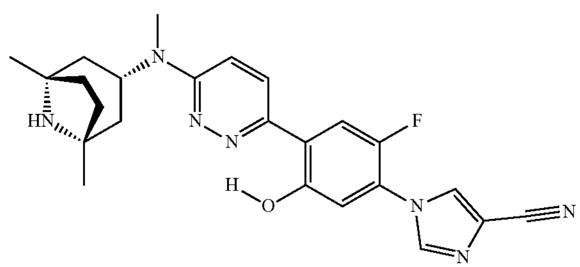 | 1-(4-(6-((((1R,3s,5S)-1,5-dimethyl-8-azabicyclo[3.2.1]octan-3-yl)(methyl)amino)pyridazin-3-yl)-2-fluoro-5-hydroxyphenyl)-1H-imidazole-4-carbonitrile | $^1$H NMR (500 MHz, DMSO-d$_6$) δ 9.00 (d, J = 9.5 Hz, 1H), 8.44 (s, 1H), 8.15 (s, 1H), 7.75 (d, J = 13.7 Hz, 1H), 6.90 (d, J = 9.7 Hz, 1H), 6.21 (d, J = 7.1 Hz, 1H), 5.06-4.91 (m, 1H), 2.85 (s, 3H), 1.81-1.78 (m, 2H), 1.52-1.45 (m, 6H), 1.16 (s, 6H). | 448.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 198 | <10 | | | 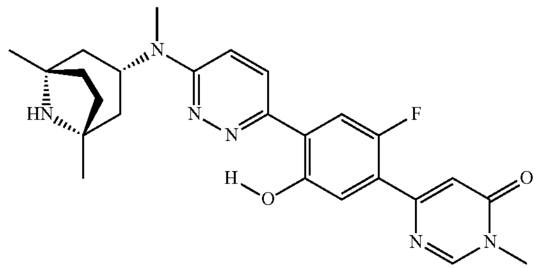 | 6-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-3-methylpyrimidin-4(3H)-one | $^1$H NMR (500 MHz, Methanol-d$_4$) δ 8.51 (s, 1H), 8.14 (d, J = 9.9 Hz, 1H), 7.73-7.64 (m, 2H), 7.33 (d, J = 9.8 Hz, 1H), 7.02 (s, 1H), 5.19-5.11 (m, 1H), 3.59 (s, 3H), 3.03 (s, 3H), 2.08-2.02 (m, 2H), 1.78-1.65 (m, 6H), 1.33 (s, 6H). | 465.4 |
| 199 | 10-100 | | | 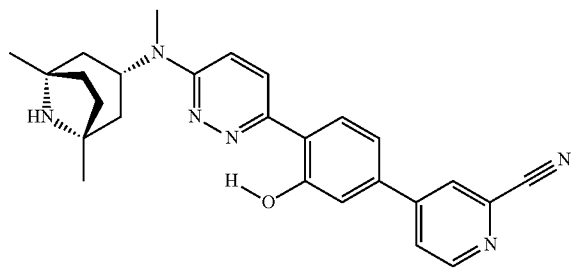 | 4-(4-(6-(((1R,3s,5S)-1,5-dimethyl-8-azabicyclo[3.2.1]octan-3-yl)(methyl)amino)pyridazin-3-yl)-3-hydroxyphenyl)picolinonitrile | 1H NMR (500 MHz, DMSO-d6) δ 8.70 (d, J = 5.2 Hz, 1H), 8.61-8.55 (m, 1H), 8.29 (d, J = 1.8 Hz, 1H), 7.99-7.92 (m, 2H), 7.14-7.07 (m, 2H), 6.99 (d, J = 8.1 Hz, 1H), 5.04-4.89 (m, 1H), 2.89 (s, 3H), 1.83-1.78 (m, 2H), 1.53-1.46 (m, 6H), 1.17 (s, 6H). | 441.0 |
| 200 | 101-250 | | | 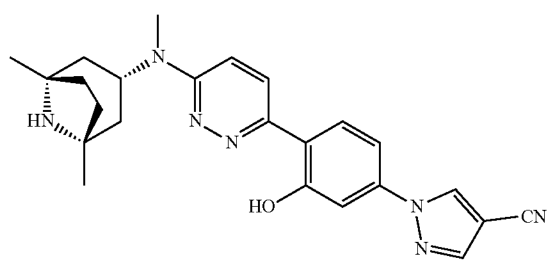 [SMILES: CN(c1ccc(-c2ccc(-n3cc(C#N)cn3)cc2O)nn1)[C@H]1C[C@]2(C)CC[C@](C)(C1)N2] | 1-(4-(6-(((1R,3s,5S)-1,5-dimethyl-8-azabicyclo[3.2.1]octan-3-yl)(methyl)amino)pyridazin-3-yl)-3-hydroxyphenyl)-1H-pyrazole-4-carbonitrile | $^1$H NMR (500 MHz, DMSO-d$_6$) δ 9.40 (s, 1H), 8.38 (s, 1H), 8.24 (d, J = 9.9 Hz, 1H), 8.06 (d, J = 8.8 Hz, 1H), 7.57-7.24 (m, 3 h), 4.93 (s, 1H), 2.94 (s, 3 h), 1.88-1.73 (m, 2H), 1.64-1.36 (m, 6 h), 1.17 (s, 6 h). | 430.0 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 201 | 10-100 | | | 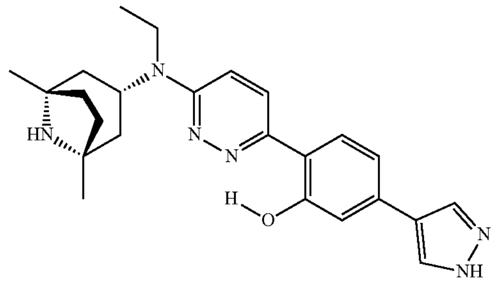 | 2-(6-(((1R,3s,5S)-1,5-dimethyl-8-azabicyclo[3.2.1]octan-3-yl)(ethyl)amino)pyridazin-3-yl)-5-(1H-pyrazol-4-yl)phenol | $^{1}$H NMR (500 MHz, DMSO-d$_6$) δ 13.81 (s, 1H), 12.98 (s, 1H), 8.22-7.98 (m, 3H), 7.82 (d, J = 8.2 Hz, 1H), 7.30 (d, J = 9.9 Hz, 1H), 7.23-7.15 (m, 2H), 4.98-4.83 (m, 1H), 3.48-3.44 (m, 2H), 1.93-1.82 (m, 2H), 1.65-1.49 (m, 6H), 1.21 (s, 6H), 1.14 (t, J = 6.9 Hz, 3H). | 419.0 |
| 202 | 10-100 | | | 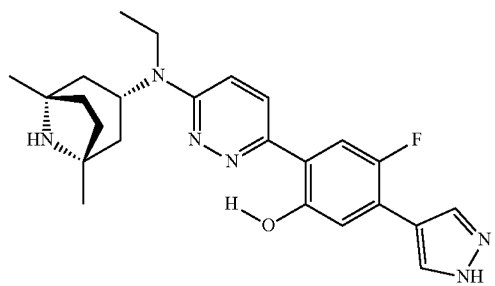 | 2-(6-(((1R,3s,5S)-1,5-dimethyl-8-azabicyclo[3.2.1]octan-3-yl)(ethyl)amino)pyridazin-3-yl)-4-fluoro-5-(1H-pyrazol-4-yl)phenol | $^{1}$H NMR (500 MHz, DMSO-d$_6$) δ 13.56 (s, 1H), 13.14 (s, 1H), 8.18 (d, J = 9.9 Hz, 1H), 8.11 (s, 2H), 7.80 (d, J = 12.5 Hz, 1H), 7.34-7.24 (m, 2H), 4.98-4.79 (m, 1H), 3.51-3.43 (m, 2H), 1.84-1.76 (m, 2H), 1.64-1.43 (m, 6H), 1.21-1.10 (m, 9H). | 437.0 |
| 203 | 10-100 | | | 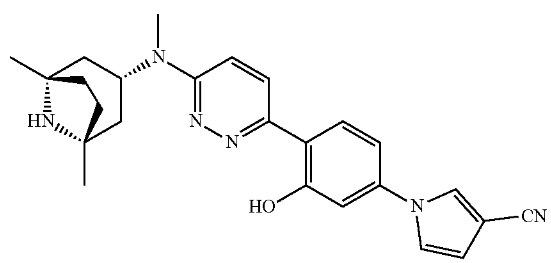 | 1-(4-(6-(((1R,3s,5S)-1,5-dimethyl-8-azabicyclo[3.2.1]octan-3-yl)(methyl)amino)pyridazin-3-yl)-3-hydroxyphenyl)-1H-pyrrole-3-carbonitrile | $^{1}$H NMR (500 MHz, DMSO-d$_6$) δ 14.2 (s, 1H), 8.35-8.32 (m, 1H), 8.25 (d, J = 10.0 Hz, 1H), 8.01 (d, J = 8.8 Hz, 1H), 7.67-7.63 (m, 1H), 7.38 (d, J = 10.0 Hz, 1H), 7.28 (d, J = 2.4 Hz, 1H), 7.27-7.20 (m, 1H), 6.76-6.69 (m, 1H), 4.92 (s, 1H), 2.94 (s, 3H), 1.83-1.76 (m, 2H), 1.54-1.45 (m, 6H), 1.17 (s, 6H). | 429.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 204 | 100-500 | | | 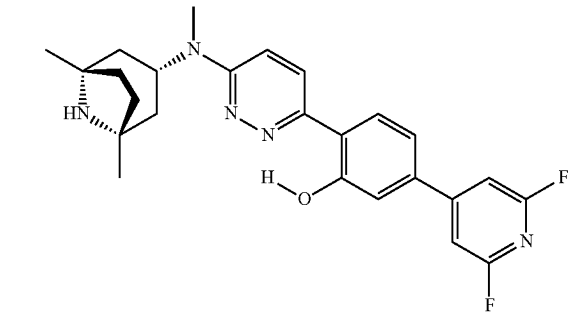 | 5-(2,6-difluoropyridin-4-yl)-2-(6-((((1R,3s,5S)-1,5-dimethyl-8-azabicyclo[3.2.1]octan-3-yl)(methyl)amino)pyridazin-3-yl)phenol | ¹H NMR (500 MHz, DMSO-d₆) δ 8.32 (d, J = 9.9 Hz, 1H), 8.04 (d, J = 8.4 Hz, 1H), 7.62 (s, 2H), 7.51-7.42 (m, 2H), 7.37 (d, J = 9.9 Hz, 1H), 5.02-4.89 (m, 1H), 2.94 (s, 3H), 1.89-1.75 (m, 3H), 1.56-1.45 (m, 6H), 1.17 (s, 6H). | 452.2 |
| 205 | <10 | | | 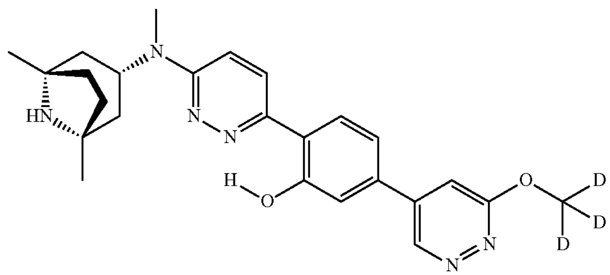 | 2-(6-((((1R,3s,5S)-1,5-dimethyl-8-azabicyclo[3.2.1]octan-3-yl)(methyl)amino)pyridazin-3-yl)-5-(6-(methoxy-d3)pyridazin-4-yl)phenol | ¹H NMR (500 MHz, DMSO-d₆) δ 14.00 (s, 1H), 9.35 (s, 1H), 8.40-8.18 (m, 1H), 8.12-7.94 (m, 1H), 7.66-7.23 (m, 4H), 5.09-4.81 (m, 1H), 2.95 (s, ₃ h), 1.86-1.76 (m, 2H), 1.60-1.43 (m, ₆ h), 1.17 (s, ₆ h). | 450.3 |
| 206 | <10 | | | 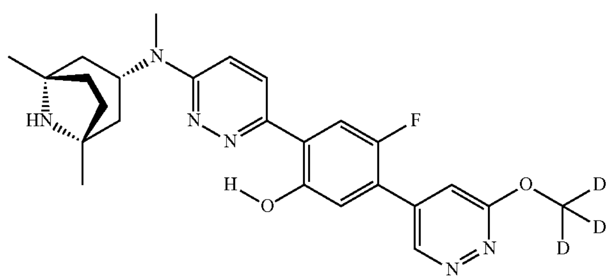 | 2-(6-((((1R,3s,5S)-1,5-dimethyl-8-azabicyclo[3.2.1]octan-3-yl)(methyl)amino)pyridazin-3-yl)-4-fluoro-5-(6-(methoxy-d3)pyridazin-4-yl)phenol | ¹H NMR (500 MHz, DMSO-d₆) δ 9.21-9.01 (m, 1H), 8.48-8.29 (m, 1H), 8.02-7.78 (m, 1H), 7.44-7.07 (m, 3H), 5.06-4.79 (m, 1H), 2.93 (s, 3H), 1.87-1.77 (m, 2H), 1.58-1.43 (m, 6H), 1.17 (s, 6H). | 468.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 207 | 10-100 | | | 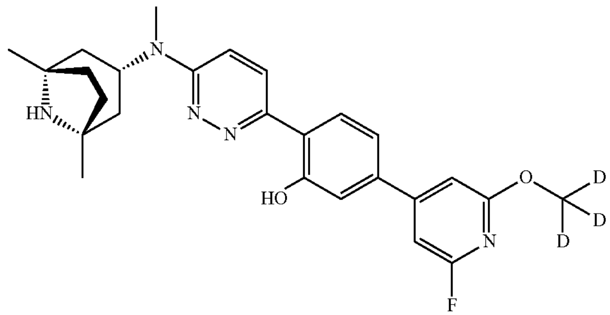 | 2-(6-(((1R,3s,5S)-1,5-dimethyl-8-azabicyclo[3.2.1]octan-3-yl)(methyl)amino)pyridazin-3-yl)-5-(2-fluoro-6-(methoxy-d3)pyridin-4-yl)phenol | $^1$H NMR (500 MHz, DMSO-d$_6$) δ 13.88 (s, 1H), 8.29 (d, J = 9.9 Hz, 1H), 8.02 (d, J = 8.2 Hz, 1H), 7.45-7.36 (m, 3H), 7.13 (s, 2H), 5.06-4.95 (m, 1H), 2.97 (s, 3H), 2.04-1.90 (m, 2H), 1.80-1.52 (m, 6H), 1.28 (s, 6H). | 467.3 |
| 208 | >1000 | | | 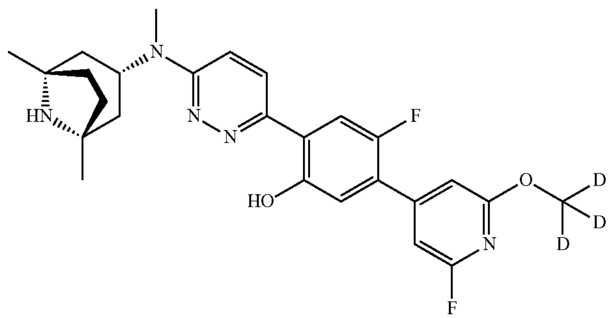 | 2-(6-(((1R,3s,5S)-1,5-dimethyl-8-azabicyclo[3.2.1]octan-3-yl)(methyl)amino)pyridazin-3-yl)-4-fluoro-5-(2-fluoro-6-(methoxy-d3)pyridin-4-yl)phenol | $^1$H NMR (500 MHz, DMSO-d$_6$) δ 13.61 (s, 1H), 8.28 (d, J = 10.0 Hz, 1H), 7.96 (d, J = 12.3 Hz, 1H), 7.38 (d, J = 9.8 Hz, 1H), 7.20 (d, J = 6.9 Hz, 1H), 6.99 (d, J = 6.8 Hz, 2H), 5.00-4.90 (m, 1H), 2.95 (s, 3H), 1.84-1.78 (m, 2H), 1.54-1.47 (m, 6H), 1.17 (s, 6H). | 485.3 |
| 209 | >1000 | | | 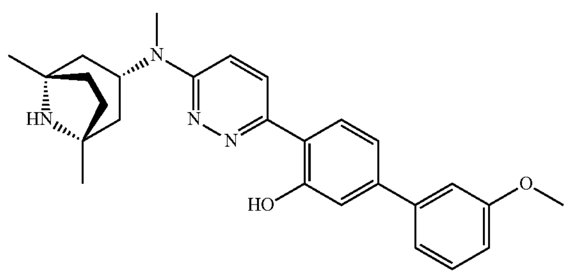 | 4(6-(((1R,3s,5S)-1,5-dimethyl-8-azabicyclo[3.2.1]octan-3-yl)(methyl)amino)pyridazin-3-yl)-3'-methoxy-[1,1'-biphenyl]-3-ol | $^1$H NMR (500 MHz, DMSO-d$_6$) δ 13.80 (s, 1H), 8.22 (d, J = 9.9 Hz, 1H), 7.94 (d, J = 8.8 Hz, 1H), 7.43-7.33 (m, 2H), 7.31-7.20 (m, 4H), 6.99-6.93 (m, 1H), 5.04-4.76 (m, 1H), 3.84 (s, 3H), 2.94 (s, 3H), 1.86-1.79 (m, 2H), 1.56-1.45 (m, 6H), 1.17 (s, 6H). | 445.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 210 | 251–500 | | | 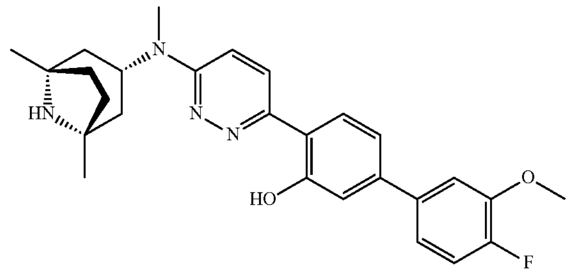 | 4-(6-(((1R,3s,5S)-1,5-dimethyl-8-azabicyclo[3.2.1]octan-3-yl)(methyl)amino)pyridazin-3-yl)-4'-fluoro-3'-methoxy-[1,1'-biphenyl]-3-ol | $^1$H NMR (500 MHz, DMSO-d$_6$) δ 13.95-13.18 (m, 1H), 8.24 (d, J = 9.4 Hz, 1H), 7.94 (d, J = 7.9 Hz, 1H), 7.44 (d, J = 8.3 Hz, 1H), 7.36 (d, J = 9.5 Hz, 1H), 7.37-7.15 (m, 4H), 4.99-4.93 (m, 1H), 3.95 (s, 3H), 2.94 (s, 3H), 1.92-1.66 (m, 3H), 1.62-1.29 (m, 6H), 1.17 (s, 6H). | 463.2 |
| 211 | 251–500 | | | 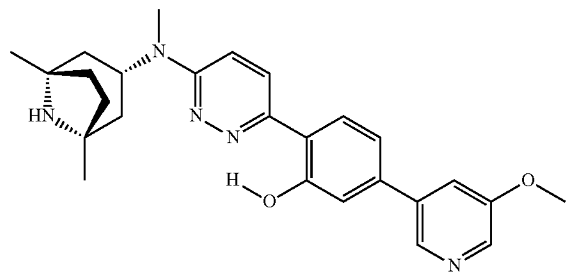 | 2-(6-(((1R,3s,5S)-1,5-dimethyl-8-azabicyclo[3.2.1]octan-3-yl)(methyl)amino)pyridazin-3-yl)-5-(5-methoxypyridin-3-yl)phenol | $^1$H NMR (500 MHz, DMSO-d$_6$) δ 13.90 (s, 1H), 8.54 (d, J = 1.9 Hz, 1H), 8.30 (d, J = 2.7 Hz, 1H), 8.26 (d, J = 10.0 Hz, 1H), 7.99 (d, J = 8.3 Hz, 1H), 7.67 (s, 1H), 7.42-7.29 (m, 1H), 3.93 (s, 3 h), 2.94 (s, 3 h), 1.86-1.75 (m, 2H), 1.58-1.45 (m, $_6$ h), 1.17 (s, $_6$ h). | 446.3 |
| 212 | | | | 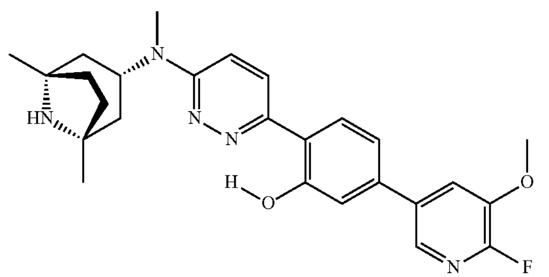 | 2-(6-(((1R,3s,5S)-1,5-dimethyl-8-azabicyclo[3.2.1]octan-3-yl)(methyl)amino)pyridazin-3-yl)-5-(6-fluoro-5-methoxypyridin-3-yl)phenol | $^1$H NMR (500 MHz, DMSO-d6) δ 13.95 (s, 1H), 8.26 (d, J = 9.9 Hz, 1H), 8.08 (s, 1H), 7.99 (d, J = 8.3 Hz, 1H), 7.95-7.91 (m, 1H), 7.40-7.30 (m, 3H), 5.02-4.80 (m, 1H), 4.00 (s, 3H), 2.94 (s, 3H), 1.85-1.76 (m, 2H), 1.56-1.48 (m, 6H), 1.17 (s, 6H). | 464.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 213 | <10 | | | 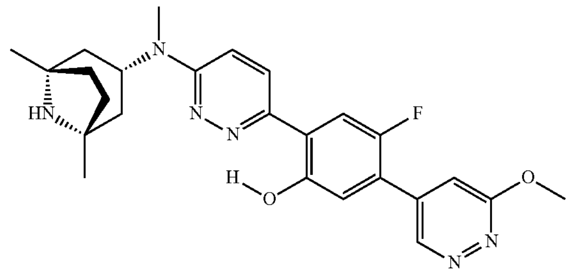 | 2-(6-((((1R,3s,5S)-1,5-dimethyl-8-azabicyclo[3.2.1]octan-3-yl)(methyl)amino)pyridazin-3-yl)-4-fluoro-5-(6-methoxypyridazin-4-yl)phenol | $^1$H NMR (500 MHz, DMSO-d$_6$) δ 9.15 (s, 1H), 8.32 (d, J = 9.8 Hz, 1H), 7.97 (d, J = 12.3 Hz, 1H), 7.42 (s, 1H), 7.34 (d, J = 9.8 Hz, 1H), 7.26 (d, J = 6.8 Hz, 1H), 5.06-4.87 (m, 1H), 4.09 (s, 3H), 2.94 (s, 3H), 1.85-1.75 (m, 2H), 1.56-1.45 (m, 6H), 1.17 (s, 6H). | 465.4 |
| 214 | | | | 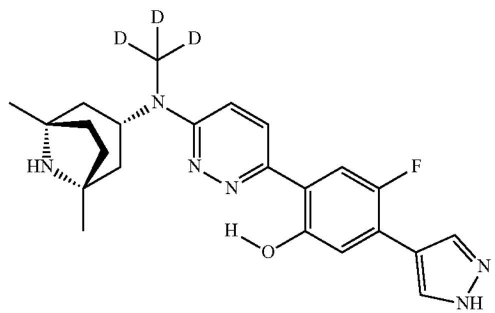 | 2-(6-((((1R,3s,5S)-1,5-dimethyl-8-azabicyclo[3.2.1]octan-3-yl)(methyl-d3)amino)pyridazin-3-yl)-4-fluoro-5-(1H-pyrazol-4-yl)phenol | $^1$H NMR (500 MHz, DMSO-d$_6$) δ 13.56 (s, 1H), 13.14 (s, 1H), 8.21 (d, J = 10.0 Hz, 1H), 8.11 (s, 2H), 7.82 (d, J = 12.6 Hz, 1H), 7.35 (d, J = 9.8 Hz, 1H), 7.30 (d, J = 6.9 Hz, 1H), 5.02-4.88 (m, 1H), 1.86-1.77 (m, 2H), 1.57-1.45 (m, 6H), 1.18 (s, 6H). | 426.1 |
| 215 | | | | 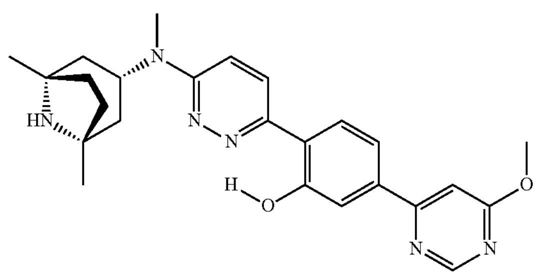 | 2-(6-((((1R,3s,5S)-1,5-dimethyl-8-azabicyclo[3.2.1]octan-3-yl)(methyl)amino)pyridazin-3-yl)-5-(6-methoxypyrimidin-4-yl)phenol | $^1$H NMR (500 MHz, DMSO-d$_6$) δ 8.81 (s, 1H), 8.54 (s, 1H), 7.94 (d, J = 7.9 Hz, 1H), 7.47 (s, 1H), 7.36 (s, 2H), 7.16 (d, 1H), 5.02-4.90 (m, 1H), 3.96 (s, 3H), 2.90 (s, 3H), 1.92-1.69 (m, 3H), 1.60-1.36 (m, 6H), 1.12 (s, 6H). | 447.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 216 | | | | 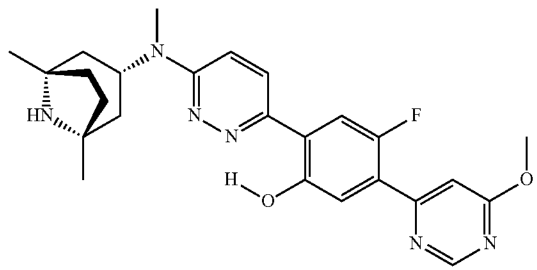 | 2-(6-(((1R,3s,5S)-1,5-dimethyl-8-azabicyclo[3.2.1]octan-3-yl)(methyl)amino)pyridazin-3-yl)-4-fluoro-5-(6-methoxypyrimidin-4-yl)phenol | $^1$H NMR (500 MHz, DMSO-d$_6$) δ 13.23 (s, 1H), 8.92 (s, 1H), 8.29 (d, J = 9.8 Hz, 1H), 7.96 (d, J = 13.0 Hz, 1H), 7.61 (d, J = 6.9 Hz, 1H), 7.40 (d, J = 9.9 Hz, 1H), 7.30 (s, 1H), 5.12-4.90 (m, 1H), 3.99 (s, 3H), 2.97 (s, 3H), 2.02-1.88 (m, 2H), 1.84-1.55 (m, 6H), 1.28 (s, 6H). | 485.1 |
| 217 | 10-100 | <10 | 10-100 | 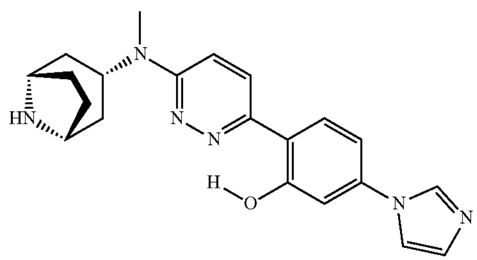 | 2-(6-(((1R,3s,5S)-8-azabicyclo[3.2.1]octan-3-yl)(methyl)amino)pyridazin-3-yl)-5-(1H-imidazol-1-yl)phenol | $^1$H NMR (500 MHz, DMSO-d$_6$) δ 8.35 (s, 1H), 8.25 (d, J = 9.9 Hz, 1H), 8.00 (d, J = 8.6 Hz, 1H), 7.83 (d, J = 1.5 Hz, 1H), 7.36 (d, J = 9.8 Hz, 1H), 7.30 (s, 1H), 7.21 (d, J = 9.6 Hz, 1H), 7.10 (s, 1H), 4.98-4.83 (m, 1H), 3.48 (s, 2H), 2.92 (s, $_3$ h), 1.84-1.68 (m, $_6$ h), 1.56-1.47 (m, 2H). | 377.2 |
| 218 | 10-100 | <10 | <10 | 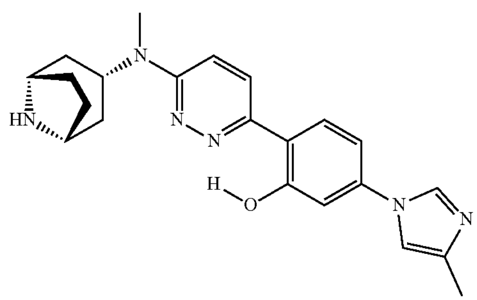 | 2-(6-(((1R,3s,5S)-8-azabicyclo[3.2.1]octan-3-yl)(methyl)amino)pyridazin-3-yl)-5-(4-methyl-1H-imidazol-1-yl)phenol | $^1$H NMR (500 MHz, DMSO-d$_6$) δ 14.23 (s, 1H), 8.25-8.20 (m, 2H), 7.98 (d, J = 8.6 Hz, 1H), 7.52 (s, 1H), 7.38 (d, J = 10.0 Hz, 1H), 7.21 (d, J = 2.3 Hz, 1H), 7.18 (dd, J = 8.5, 2.5 Hz, 1H), 4.98-4.79 (m, 1H), 3.53-3.45 (m, 2H), 2.93 (s, $_3$ h), 2.16 (s, $_3$ h), 1.85-1.70 (m, $_6$ h), 1.59-1.48 (m, 2H). | 391.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 219 | >1000 | 10-100 | 10-100 | 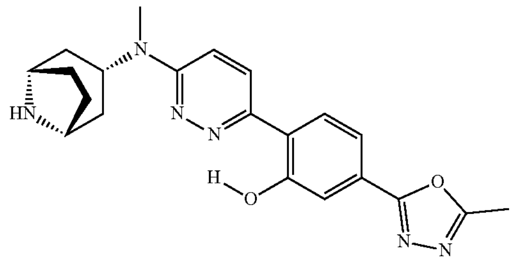 | 2-(6-(((1R,3s,5S)-8-azabicyclo[3.2.1]octan-3-yl)(methyl)amino)pyridazin-3-yl)-5-(5-methyl-1,3,4-oxadiazol-2-yl)phenol | $^1$H NMR (500 MHz, DMSO-d$_6$) δ 13.68 (s, 1H), 9.09 (s, 1H), 8.29 (d, J = 9.9 Hz, 1H), 8.12 (d, J = 8.4 Hz, 1H), 7.54-7.44 (m, 3 h), 5.13-4.94 (m, 1H), 4.14-4.05 (m, 2H), 3.02 (s, 3 h), 2.60 (s, 3 h), 2.33-2.21 (m, 2H), 2.09-1.99 (m, 4H), 1.80-1.72 (m, 2H). | 393.2 |
| 220 | 10-100 | <10 | 10-100 | 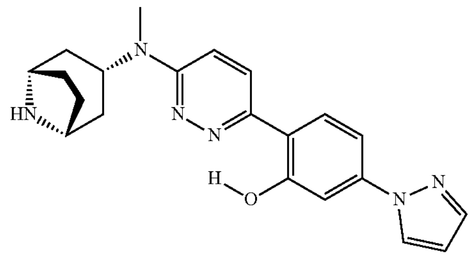 | 2-(6-(((1R,3s,5S)-8-azabicyclo[3.2.1]octan-3-yl)(methyl)amino)pyridazin-3-yl)-5-(1H-pyrazol-1-yl)phenol | $^1$H NMR (500 MHz, DMSO-d$_6$) δ 14.11 (s, 1H), 8.58 (d, J = 2.3 Hz, 1H), 8.21 (d, J = 10.0 Hz, 1H), 8.0 (d, J = 1.4 Hz, 1H), 7.76 (d, J = 1.4 Hz, 1H), 7.47-7.40 (m, 2H), 7.38 (d, J = 9.9 Hz, 1H), 6.62-6.51 (m, 1H), 4.92-4.88 (m, 1H), 3.50 (s, 2H), 2.95 (s, 3 h), 1.98-1.69 (m, 6 h), 1.56-1.52 (m, 2H). | 377.4 |
| 221 | 101-250 | 10-100 | 10-100 | 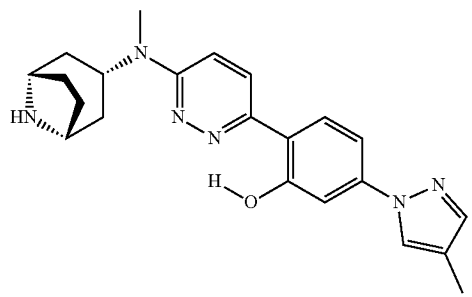 | 2-(6-(((1R,3s,5S)-8-azabicyclo[3.2.1]octan-3-yl)(methyl)amino)pyridazin-3-yl)-5-(4-methyl-1H-pyrazol-1-yl)phenol | $^1$H NMR (500 MHz, DMSO) δ 8.33 (s, 1H), 8.20 (d, J = 10.0 Hz, 1H), 7.96 (d, J = 9.4 Hz, 1H), 7.58 (s, 1H), 7.38-7.32 (m, 3 h), 4.94-4.83 (m, 1H), 3.48 (s, 2H), 2.93 (s, 6 h), 2.10 (s, 3 h), 1.83-1.69 (m, 6 h), 1.56-1.48 (m, 2H). | 391.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 222 | 10-100 | <10 | 10-100 | 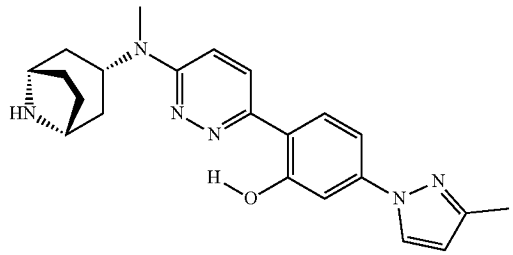 | 2-(6-(((1R,3s,5S)-8-azabicyclo[3.2.1]octan-3-yl)(methyl)amino)pyridazin-3-yl)-5-(3-methyl-1H-pyrazol-1-yl)phenol | $^1$H NMR (500 MHz, DMSO) δ 8.44 (d, J = 2.4 Hz, 1H), 8.20 (d, J = 10.0 Hz, 1H), 7.95 (d, J = 8.8 Hz, 1H), 7.41-7.32 (m, $_3$ h), 6.34 (d, J = 2.3 Hz, 1H), 4.99-4.83 (m, 1H), 3.50 (s, 2H), 2.93 (s, $_3$ h), 2.28 (s, $_3$ h), 1.85-1.69 (m, $_6$ h), 1.53 (m, 2H). | 391.3 |
| 223 | 10-100 | <10 | <10 | 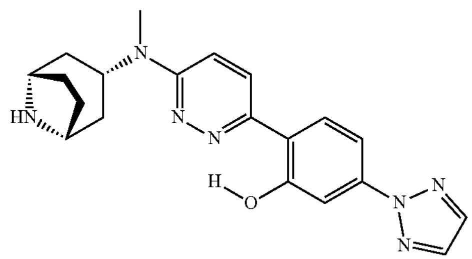 | 2-(6-(((1R,3s,5S)-8-azabicyclo[3.2.1]octan-3-yl)(methyl)amino)pyridazin-3-yl)-5-(2H-1,2,3-triazol-2-yl)phenol | $^1$H NMR (500 MHz, Methanol-d$_4$) δ 8.13 (d, J = 9.9 Hz, 1H), 7.97-7.89 (m, $_3$ h), 7.70-7.63 (m, 2H), 7.32 (d, J = 9.9 Hz, 1H), 5.21-5.00 (m, 1H), 3.79-3.57 (m, 2H), 3.01 (s, $_3$ h), 2.11-1.89 (m, $_6$ h), 1.80-1.67 (m, 2H). | 378.3 |
| 224 | 101-250 | <10 | 10-100 | 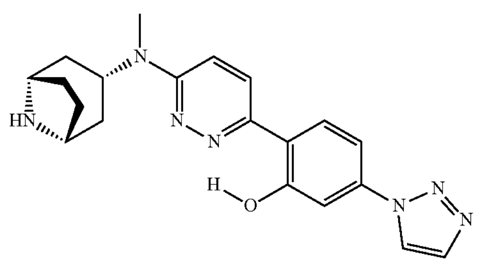 | 2-(6-(((1R,3s,5S)-8-azabicyclo[3.2.1]octan-3-yl)(methyl)amino)pyridazin-3-yl)-5-(1H-1,2,3-triazol-1-yl)phenol | $^1$H NMR (500 MHz, DMSO-d$_6$) δ 8.91 (s, 1H), 8.26 (d, J = 9.9 Hz, 1H), 8.10 (d, J = 8.5 Hz, 1H), 7.99 (s, 1H), 7.55-7.48 (m, 2H), 7.43-7.35 (m, 1H), 5.00-4.86 (m, 1H), 3.50 (s, 2H), 2.95 (s, $_3$ h), 1.85-1.70 (m, $_6$ h), 1.61-1.48 (m, 2H). | 378.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 225 | 10-100 | 10-100 | 10-100 | 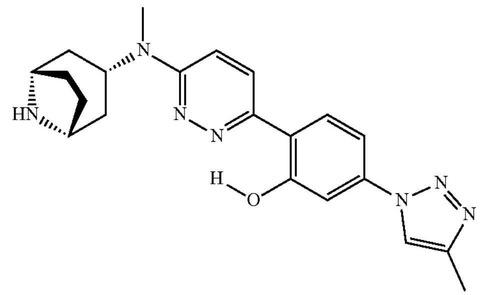 | 2-(6-(((1R,3s,5S)-8-azabicyclo[3.2.1]octan-3-yl)(methyl)amino)pyridazin-3-yl)-5-(4-methyl-1H-1,2,3-triazol-1-yl)phenol | $^1$H NMR (500 MHz, DMSO-d$_6$) δ 8.60 (s, 1H), 8.26 (d, J = 9.9 Hz, 1H), 8.07 (d, J = 8.4 Hz, 1H), 7.45-7.37 (m, 3 h), 4.93 (s, 2H), 3.48 (s, 2H), 2.94 (s, 3 h), 2.33 (s, 3 h), 1.84-1.66 (m, 6 h), 1.56-1.52 (m, 2H). | 392.2 |
| 226 | 101-250 | 10-100 | 10-100 | 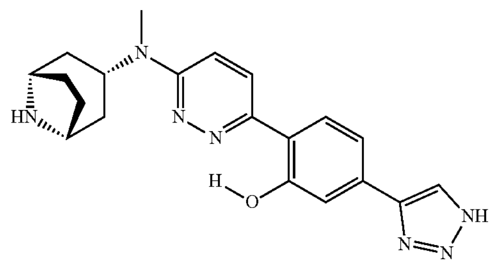 | 2-(6-(((1R,3s,5S)-8-azabicyclo[3.2.1]octan-3-yl)(methyl)amino)pyridazin-3-yl)-5-(1H-1,2,3-triazol-4-yl)phenol | $^1$H NMR (500 MHz, Methanol-d$_4$) δ 8.19-8.12 (m, 2H), 7.85 (d, J = 8.8 Hz, 1H), 7.49-7.41 (m, 2H), 7.34 (d, J = 9.9 Hz, 1H), 5.20-5.13 (m, 1H), 3.84 (s, 2H), 3.02 (s, 3 h), 2.12-2.01 (m, 6 h), 1.84-1.77 (m, 2H). | 378.3 |
| 227 | >1000 | >1000 | >1000 | 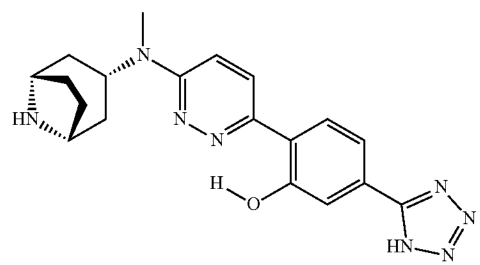 | 2-(6-(((1R,3s,5S)-8-azabicyclo[3.2.1]octan-3-yl)(methyl)amino)pyridazin-3-yl)-5-(1H-tetrazol-5-yl)phenol | $^1$H NMR (500 MHz, DMSO-d$_6$) δ 13.44 (s, 1H), 8.23 (d, J = 9.9 Hz, 1H), 7.89 (d, J = 8.3 Hz, 1H), 7.55 (dd, J = 8.2, 1.5 Hz, 1H), 7.53 (d, J = 1.5 Hz, 1H), 7.44 (d, J = 9.8 Hz, 1H), 5.05-5.01 (m, 1H), 4.09-4.05 (m, 2H), 2.96 (s, 3 h), 2.13-1.98 (m, 6 h), 1.81-1.77 (m, 2H). | 379.3 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 228 | 10-100 | <10 | 10-100 | 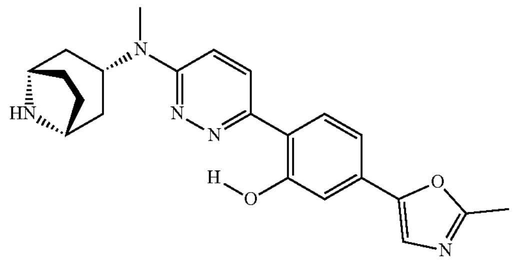 | 2-(6-(((1R,3s,5S)-8-azabicyclo[3.2.1]octan-3-yl)(methyl)amino)pyridazin-3-yl)-5-(2-methyloxazol-5-yl)phenol | $^1$H NMR (500 MHz, Methanol-d$_4$) δ 8.13 (d, J = 9.9 Hz, 1H), 7.84 (d, J = 8.5 Hz, 1H), 7.43 (s, 1H), 7.33 (d, J = 9.8 Hz, 1H), 7.30-7.24 (m, 2H), 5.15-5.07 (m, 1H), 3.72 (s, 2H), 3.02 (s, 3 h), 2.56 (s, 3 h), 2.05-1.95 (m, 6 h), 1.77-1.71 (m, 2H). | 392.2 |
| 229 | >1000 | >1000 | >1000 | 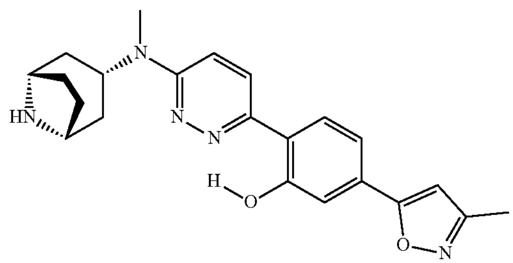 | 2-(6-(((1R,3s,5S)-8-azabicyclo[3.2.1]octan-3-yl)(methyl)amino)pyridazin-3-yl)-5-(3-methylisoxazol-5-yl)phenol | $^1$H NMR (400 MHz, DMSO-d$_6$) δ 7.41 (d, J = 8.5 Hz, 1H), 7.03 (m, 4H), 6.15 (s, 1H), 5.00-4.86 (m, 1H), 3.48 (s, 2H), 2.87 (s, 3 h), 2.19 (s, 3 h), 1.82-1.65 (m, 6 h), 1.57-1.42 (m, 2H). | 392.3 |
| 230 | >1000 | 101-250 | 501-1000 | 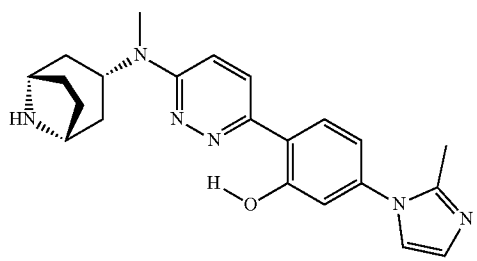 | 2-(6-(((1R,3s,5S)-8-azabicyclo[3.2.1]octan-3-yl)(methyl)amino)pyridazin-3-yl)-5-(2-methyl-1H-imidazol-1-yl)phenol | $^1$H NMR (500 MHz, DMSO-d$_6$) δ 13.99 (s, 1H), 8.26 (d, J = 10.0 Hz, 1H), 8.03 (d, J = 8.3 Hz, 1H), 7.43 (d, J = 9.9 Hz, 1H), 7.34 (s, 1H), 7.04-6.97 (m, 2H), 6.92 (d, J = 1.4 Hz, 1H), 4.98-4.96 (m, 1H), 3.78 (s, 2H), 2.98 (s, 3 h), 2.36 (s, 3 h), 2.09-1.96 (m, 2H), 1.89 (s, 4H), 1.68-1.59 (m, 2H). | 391.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 231 | >1000 | 251-500 | 501-1000 | 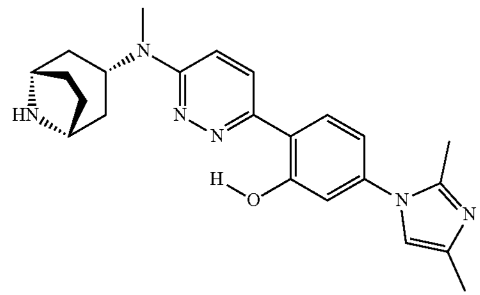 | 2-(6-(((1R,3s,5S)-8-azabicyclo[3.2.1]octan-3-yl)(methyl)amino)pyridazin-3-yl)-5-(2,4-dimethyl-1H-imidazol-1-yl)phenol | $^1$H NMR (500 MHz, DMSO-d$_6$) δ 14.04 (s, 1H), 8.23 (d, J = 10.0 Hz, 1H), 7.99 (d, J = 8.6 Hz, 1H), 7.39 (d, J = 9.9 Hz, 1H), 7.02 (d, J = 1.3 Hz, 1H), 6.98-6.92 (m, 2H), 4.97-4.82 (m, 1H), 3.54 (s, 2H), 2.94 (s, 3 h), 2.31 (s, 6 h), 2.09 (s, 3 h), 1.86-1.70 (m, 6 h), 1.59-1.50 (m, 2H). | 405.3 |
| 232 | >1000 | 101-250 | 501-1000 | 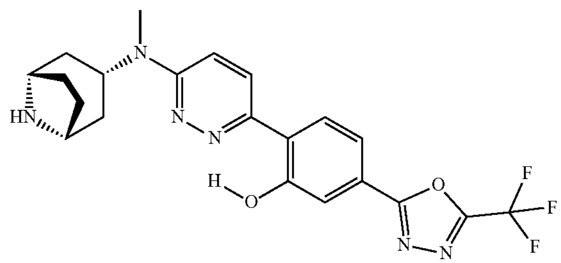 | 2-(6-(((1R,3s,5S)-8-azabicyclo[3.2.1]octan-3-yl)(methyl)amino)pyridazin-3-yl)-5-(5-(trifluoromethyl)-1,3,4-oxadiazol-2-yl)phenol | $^1$H NMR (500 MHz, Methanol-d$_4$) δ 8.26 (d, J = 9.9 Hz, 1H), 8.05 (d, J = 8.1 Hz, 1H), 7.74-7.66 (m, 2H), 7.41 (d, J = 9.9 Hz, 1H), 5.57-5.36 (m, 1H), 4.23-4.21 (m, 2H), 3.08 (s, 3 h), 2.36-2.16 (m, 6 h), 2.01-1.98 (m, 2H). | 447.2 |
| 233 | >1000 | | | 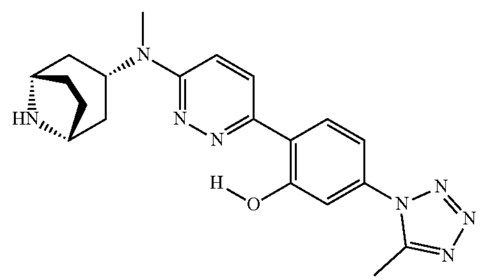 | 2-(6-(((1R,3s,5S)-8-azabicyclo[3.2.1]octan-3-yl)(methyl)amino)pyridazin-3-yl)-5-(5-methyl-1H-tetrazol-1-yl)phenol | $^1$H NMR (400 MHz, DMSO-d$_6$) δ 9.01 (s, 1H), 8.88 (s, 1H), 8.34 (d, J = 9.9 Hz, 1H), 8.11 (d, J = 8.5 Hz, 1H), 7.63 (d, J = 9.9 Hz, 1H), 7.29-7.24 (m, 2H), 5.19-4.84 (m, 1H), 4.33-3.98 (m, 2H), 3.02 (s, 3 h), 2.49 (s, 3 h), 2.28-1.81 (m, 8 h). | 393.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 234 | 10-100 | 10-100 | 10-100 | 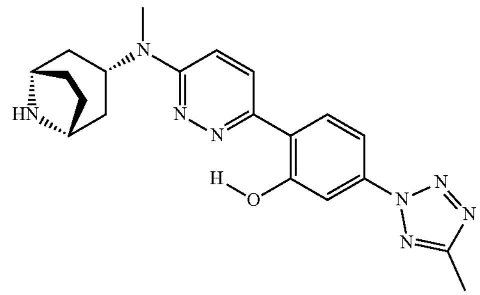 | 2-(6-(((1R,3s,5S)-8-azabicyclo[3.2.1]octan-3-yl)(methyl)amino)pyridazin-3-yl)-5-(5-methyl-2H-tetrazol-2-yl)phenol | $^1$H NMR (400 MHz, DMSO-d$_6$) δ 13.94 (s, 1H), 8.93 (s, 1H), 8.29 (d, J = 9.9 Hz, 1H), 8.18 (d, J = 8.6 Hz, 1H), 7.69-7.52 (m, 2H), 7.49 (d, J = 10.0 Hz, 1H), 5.14-4.99 (m, 1H), 4.10 (s, 2H), 3.01 (s, 3 h), 2.60 (s, 3 h), 2.30-2.14 (m, 2H), 2.14-1.94 (m, 4H), 1.85-1.67 (m, 2H). | 393.2 |
| 235 | >1000 | | | 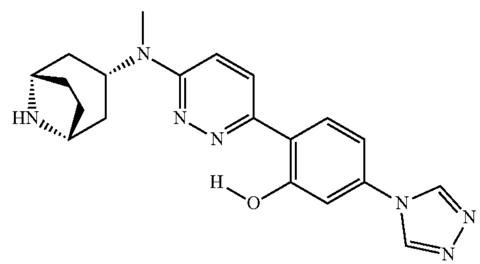 [SMILES: CN(c1ccc(-c2ccc(-n3cnnc3)cc2O)nn1)[C@@H]1C[C@H]2CC[C@@H](C1)N2] | 2-(6-(((1R,3s,5S)-8-azabicyclo[3.2.1]octan-3-yl)(methyl)amino)pyridazin-3-yl)-5-(4H-1,2,4-triazol-4-yl)phenol | $^1$H NMR (500 MHz, DMSO-d$_6$) δ 14.27 (s, 1H), 9.23 (s, 2H), 9.01-8.53 (m, 1H), 8.33 (d, J = 10.0 Hz, 1H), 8.11 (d, J = 8.6 Hz, 1H), 7.49 (d, J = 9.8 Hz, 1H), 7.38 (s, 1H), 7.31 (d, J = 8.2 Hz, 1H), 5.06-5.06 (m, 1H), 4.11 (s, 2H), 2.99 (s, 3 h), 2.23-1.95 (m, 6 h), 1.85-1.79 (m, 2H). | 378.2 |
| 236 | 101-250 | | | 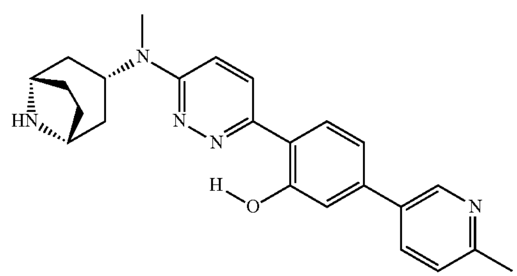 | 2-(6-(((1R,3s,5S)-8-azabicyclo[3.2.1]octan-3-yl)(methyl)amino)pyridazin-3-yl)-5-(6-methylpyridin-3-yl)phenol | $^1$H NMR (400 MHz, DMSO-d$_6$) δ 13.86 (s, 1H), 8.81 (d, J = 2.4 Hz, 1H), 8.24 (d, J = 10.0 Hz, 1H), 8.06-7.93 (m, 2H), 7.40-7.23 (m, 4H), 5.03-4.77 (m, 1H), 3.50 (s, 2H), 3.31 (s, 3 h), 2.94 (s, 3 h), 1.85-1.67 (m, 6 h), 1.58-1.47 (m, 2H). | 402.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 237 | 501-1000 | | | 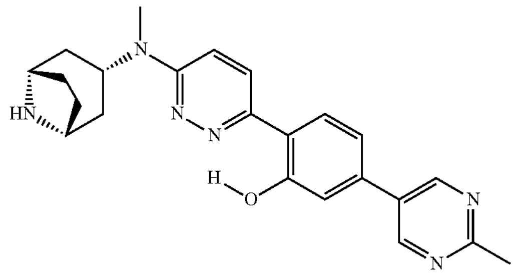 [SMILES: Cc1ncc(-c2ccc(-c3ccc(N(C)[C@@H]4C[C@H]5CC[C@@H](C4)N5)nn3)c(O)c2)cn1] | 2-(6-((((1R,3s,5S)-8-azabicyclo[3.2.1]octan-3-yl)(methyl)amino)pyridazin-3-yl)-5-(2-methylpyrimidin-5-yl)phenol | $^1$H NMR (400 MHz, DMSO-d$_6$) δ 13.87 (s, 1H), 9.07 (s, 2H), 8.30 (d, J = 9.9 Hz, 1H), 8.04 (d, J = 8.3 Hz, 1H), 7.45 (d, J = 10.0 Hz, 1H), 7.40-7.32 (m, 2H), 5.10-4.93 (m, 1H), 3.93 (s, 2H), 2.99 (s, 3 h), 2.67 (s, 3 h), 2.18-2.06 (m, 2H), 2.03-1.90 (m, 4H), 1.75-1.67 (m, 2H). | 403.1 |
| 238 | 10-100 | <10 | 10-100 | 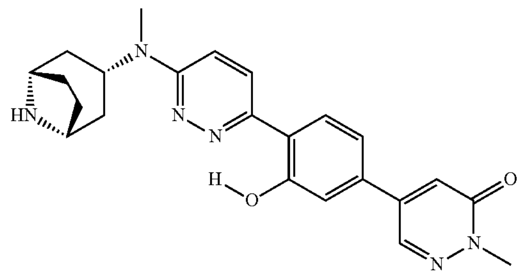 [SMILES: CN(c1ccc(-c2ccc(-c3cnn(C)c(=O)c3)cc2O)nn1)[C@@H]1C[C@H]2CC[C@@H](C1)N2] | 5-(4-(6-((((1R,3s,5S)-8-azabicyclo[3.2.1]octan-3-yl)(methyl)amino)pyridazin-3-yl)-3-hydroxyphenyl)-2-methylpyridazin-3(2H)-one | $^1$H NMR (400 MHz, DMSO-d$_6$) δ 13.95 (s, 1H), 8.39 (d, J = 2.2 Hz, 1H), 8.27 (d, J = 9.8 Hz, 1H), 8.01 (d, J = 8.1 Hz, 1H), 7.44-7.34 (m, 3 h), 7.26 (d, J = 2.2 Hz, 1H), 4.99-4.84 (m, 1H), 3.69 (s, 3 h), 3.50 (s, 2H), 2.94 (s, 3 h), 1.84-1.71 (m, 6 h), 1.57-1.50 (m, 2H). | 419.2 |
| 239 | 251-500 | <10 | <10 | 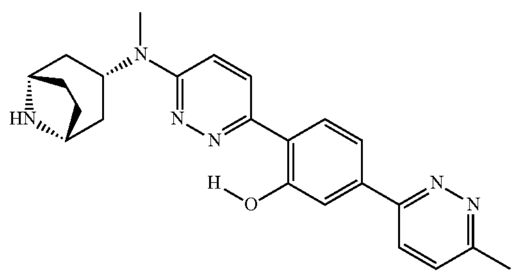 [SMILES: Cc1ccc(-c2ccc(-c3ccc(N(C)[C@@H]4C[C@H]5CC[C@@H](C4)N5)nn3)c(O)c2)nn1] | 2-(6-((((1R,3s,5S)-8-azabicyclo[3.2.1]octan-3-yl)(methyl)amino)pyridazin-3-yl)-5-(6-methylpyridazin-3-yl)phenol | $^1$H NMR (400 MHz, DMSO-d$_6$) δ 13.80 (s, 1H), 8.27 (d, J = 10.0 Hz, 1H), 8.18 (d, J = 8.8 Hz, 1H), 8.05 (d, J = 8.8 Hz, 1H), 7.77-7.69 (m, 2H), 7.66 (d, J = 8.8 Hz, 1H), 7.40 (d, J = 9.9 Hz, 1H), 5.02-4.89 (m, 1H), 3.56 (s, 2H), 2.95 (s, 3 h), 2.67 (s, 3 h), 1.93-1.65 (m, 6 h), 1.60-1.50 (m, 2H). | 403.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Name | Structure | Proton NMR | M + H (MS) |
|---|---|---|---|---|---|---|---|
| 240 | 10-100 | <10 | <10 | 4-(4-(6-(((1R,3s,5S)-8-azabicyclo[3.2.1]octan-3-yl)(methyl)amino)pyridazin-3-yl)-3-hydroxyphenyl)-1-methylpyridin-2(1H)-one | 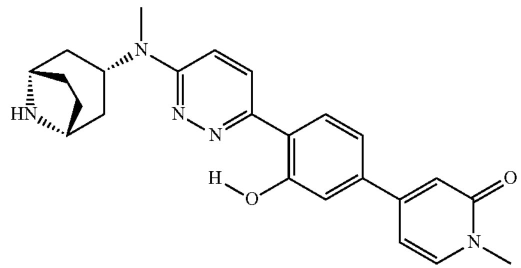 [SMILES: CN(c1ccc(-c2ccc(-c3ccn(C)c(=O)c3)cc2O)nn1)[C@@H]1C[C@H]2CC[C@@H](C1)N2] | $^1$H NMR (400 MHz, DMSO-d$_6$) δ 13.84 (s, 1H), 8.24 (d, J = 10.0 Hz, 1H), 7.97 (d, J = 8.2 Hz, 1H), 7.77 (d, J = 7.2 Hz, 1H), 7.37 (d, J = 10.0 Hz, 1H), 7.29-7.21 (m, 2H), 6.70 (d, J = 2.1 Hz, 1H), 6.64-6.59 (m, 1H), 4.99-4.82 (m, 1H), 3.52-3.43 (m, 5H), 2.94 (s, 3 h), 1.84-1.68 (m, 6 h), 1.58-1.49 (m, 2H). | 418.1 |
| 241 | 101-250 | <10 | 10-100 | 5-(4-(6-(((1R,3s,5S)-8-azabicyclo[3.2.1]octan-3-yl)(methyl)amino)pyridazin-3-yl)-3-hydroxyphenyl)-1-methylpyridin-2(1H)-one | 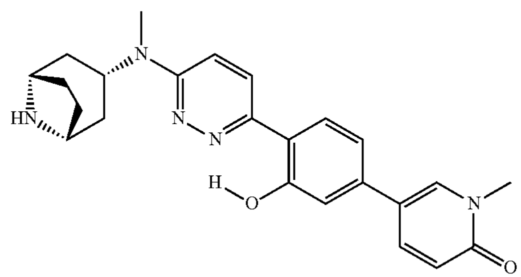 [SMILES: CN(c1ccc(-c2ccc(-c3ccc(=O)n(C)c3)cc2O)nn1)[C@@H]1C[C@H]2CC[C@@H](C1)N2] | $^1$H NMR (400 MHz, DMSO-d$_6$) δ 13.91 (s, 1H), 8.32-8.15 (m, 2H), 7.97-7.82 (m, 2H), 7.36 (d, J = 9.9 Hz, 1H), 7.20-7.11 (m, 2H), 6.48 (d, J = 9.5 Hz, 1H), 5.04-4.73 (m, 1H), 3.52 (s, 3 h), 3.48 (s, 2H), 2.93 (s, 3 h), 1.86-1.65 (m, 6 h), 1.59-1.47 (m, 2H). | 418.2 |
| 242 | 251-500 | 10-100 | 101-250 | 2-(6-(((1R,3s,5S)-8-azabicyclo[3.2.1]octan-3-yl)(methyl)amino)pyridazin-3-yl)-5-(4-(trifluoromethyl)-1H-imidazol-1-yl)phenol | 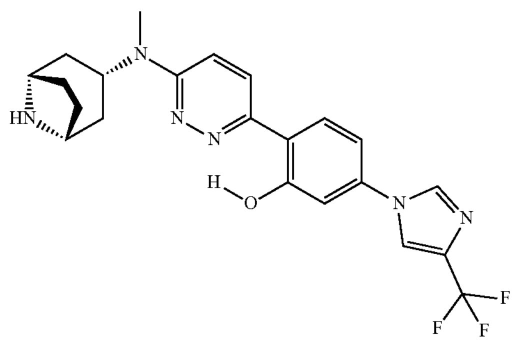 | $^1$H NMR (500 MHz, DMSO-d$_6$) δ 14.27 (s, 1H), 8.57 (d, J = 14.3 Hz, 2H), 8.34 (d, J = 10.0 Hz, 1H), 8.10 (d, J = 8.7 Hz, 1H), 7.49 (d, J = 10.0 Hz, 1H), 7.39 (d, J = 2.3 Hz, 1H), 7.33 (dd, J = 8.6, 2.3 Hz, 1H), 5.08-5.04 (m, 1H), 4.12-4.08 (m, 2H), 3.01 (s, 3 h), 2.28-2.24 (m, 2H), 2.08-2.04 (m, 4H), 1.80-1.76 (m, 2H). | 445.1 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 243 | 10-100 | <10 | 10-100 | 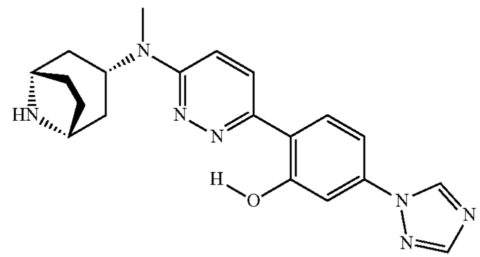 | 2-(6-(((1R,3s,5S)-8-azabicyclo[3.2.1]octan-3-yl)(methyl)amino)pyridazin-3-yl)-5-(1H-1,2,4-triazol-1-yl)phenol | $^1$H NMR (500 MHz, DMSO-d$_6$) δ 14.10 (s, 1H), 9.39 (s, 1H), 9.33-8.89 (m, 1H), 8.36-8.19 (m, 2H), 8.10 (d, J = 8.7 Hz, 1H), 7.49-7.45 (m, 2H), 5.06 (s, 1H), 4.10 (s, 2H), 3.01 (s, 3 h), 2.29-2.22 (m, 2H), 2.12-1.94 (m, 4H), 1.85-1.77 (m, 2H). | 378.2 |
| 244 | 101-250 | 10-100 | 10-100 | 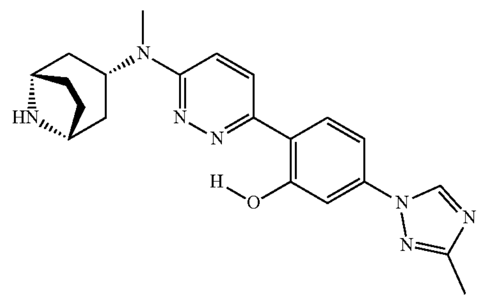 | 2-(6-(((1R,3s,5S)-8-azabicyclo[3.2.1]octan-3-yl)(methyl)amino)pyridazin-3-yl)-5-(3-methyl-1H-1,2,4-triazol-1-yl)phenol | $^1$H NMR (500 MHz, DMSO-d$_6$) δ 9.23 (s, 1H), 8.23 (d, J = 9.9 Hz, 1H), 8.03 (d, J = 8.6 Hz, 1H), 7.48-7.27 (m, 3 h), 4.91 (s, 1H), 3.50 (s, 2H), 2.94 (s, 3 h), 2.37 (s, 3 h), 1.89-1.64 (m, 6 h), 1.55-1.52 (m, 2H). | 392.3 |
| 245 | 501-1000 | 10-100 | 101-250 | 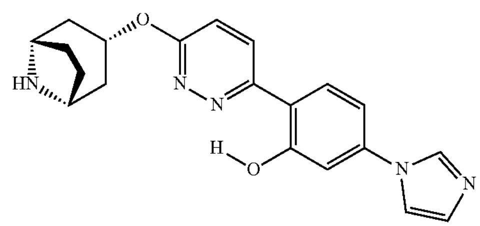 | 2-(6-(((1R,3s,5S)-8-azabicyclo[3.2.1]octan-3-yl)oxy)pyridazin-3-yl)-5-(1H-imidazol-1-yl)phenol | $^1$H NMR (500 MHz, DMSO-d$_6$) δ 8.48 (d, J = 9.5 Hz, 1H), 8.39 (s, 1H), 8.09 (d, J = 8.7 Hz, 1H), 7.86 (s, 1H), 7.42 (d, J = 9.4 Hz, 1H), 7.36-7.27 (m, 2H), 7.12 (s, 1H), 5.56-5.46 (m, 1H), 3.58-3.56 (m, 2H), 2.24-2.13 (m, 2H), 1.83-1.71 (m, 4H), 1.67-1.58 (m, 2H). | 364.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 246 | 251–500 | 10–100 | 101–250 | 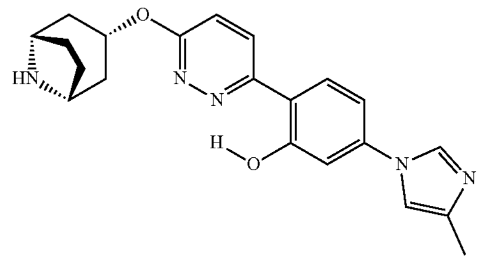 | 2-(6-(((1R,3s,5S)-8-azabicyclo[3.2.1]octan-3-yl)oxy)pyridazin-3-yl)-5-(4-methyl-1H-imidazol-1-yl)phenol | $^1$H NMR (500 MHz, DMSO-d$_6$) δ 8.46 (d, J = 9.6 Hz, 1H), 8.26 (d, J = 1.4 Hz, 1H), 8.06 (d, J = 8.7 Hz, 1H), 7.54 (s, 1H), 7.40 (d, J = 9.4 Hz, 1H), 7.30-7.20 (m, 2H), 5.54-5.43 (m, 1H), 3.55-3.48 (m, 2H), 2.20-2.11 (m, 5H), 1.75-1.55 (m, 6 h). | 378.1 |
| 247 | >1000 | | | 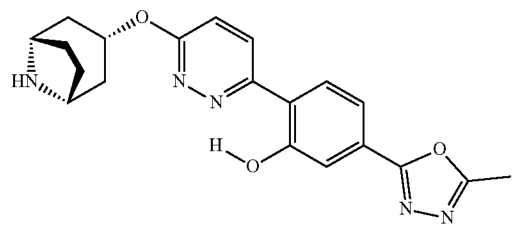 | 2-(6-(((1R,3s,5S)-8-azabicyclo[3.2.1]octan-3-yl)oxy)pyridazin-3-yl)-5-(5-methyl-1,3,4-oxadiazol-2-yl)phenol | $^1$H NMR (500 MHz, DMSO-d$_6$) δ 8.40 (d, J = 9.5 Hz, 1H), 8.11 (d, J = 8.1 Hz, 1H), 7.56-7.53 (m, 2H), 7.38 (d, J = 9.4 Hz, 1H), 5.70-5.37 (m, 1H), 3.63-3.60 (m, 2H), 2.60 (s, 3 h), 2.23-2.19 (m, 2H), 1.77-1.74 (m, 4H), 1.68-1.63 (m, 2H). | 380.2 |
| 248 | 501–1000 | | | 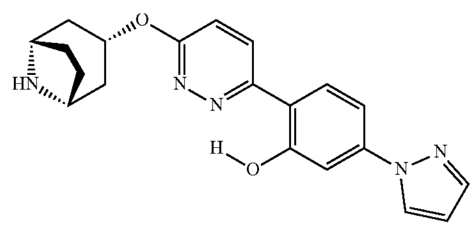 | 2-(6-(((1R,3s,5S)-8-azabicyclo[3.2.1]octan-3-yl)oxy)pyridazin-3-yl)-5-(1H-pyrazol-1-yl)phenol | $^1$H NMR (500 MHz, DMSO-d$_6$) δ 8.60 (d, J = 2.5 Hz, 1H), 8.44 (d, J = 9.5 Hz, 1H), 8.07 (d, J = 8.7 Hz, 1H), 7.78 (d, J = 1.5 Hz, 1H), 7.51 (d, J = 2.2 Hz, 1H), 7.48 (dd, J = 8.7, 2.2 Hz, 1H), 7.41 (d, J = 9.5 Hz, 1H), 6.66-6.50 (m, 1H), 5.57-5.49 (m, 1H), 3.69 (s, 2H), 2.27-2.21 (m, 2H), 1.85-1.63 (m, 6 h). | 364.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 249 | 501-1000 | 101-250 | 251-500 | 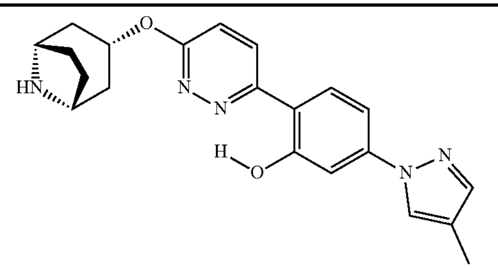 | 2-(6-(((1R,3s,5S)-8-azabicyclo[3.2.1]octan-3-yl)oxy)pyridazin-3-yl)-5-(4-methyl-1H-pyrazol-1-yl)phenol | $^1$H NMR (500 MHz, DMSO-d$_6$) δ 8.45 (d, J = 9.5 Hz, 1H), 8.32 (s, 1H), 8.02 (d, J = 8.7 Hz, 1H), 7.58 (s, 1H), 7.39 (s, 1H), 7.33 (d, J = 9.4 Hz, 2H), 5.54-5.44 (m, 1H), 3.50 (s, 2H), 2.19-2.12 (m, 2H), 2.10 (s, 3 h), 1.78-1.66 (m, 4H), 1.61-1.57 (m, 2H). | 378.3 |
| 250 | 501-1000 | 10-100 | 101-250 | 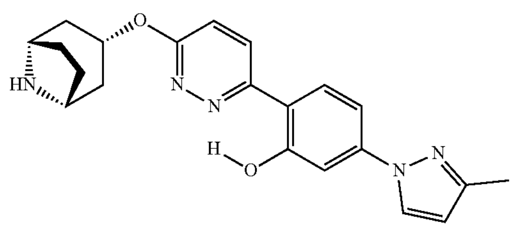 | 2-(6-(((1R,3s,5S)-8-azabicyclo[3.2.1]octan-3-yl)oxy)pyridazin-3-yl)-5-(3-methyl-1H-pyrazol-1-yl)phenol | $^1$H NMR (500 MHz, DMSO-d$_6$) δ 8.46 (d, J = 2.4 Hz, 1H), 8.44-8.39 (m, 1H), 8.03 (d, J = 8.7 Hz, 1H), 7.44 (d, J = 2.2 Hz, 1H), 7.40 (d, J = 2.1 Hz, 1H), 7.37 (d, J = 9.5 Hz, 1H), 6.36 (d, J = 2.4 Hz, 1H), 5.54-5.44 (m, 1H), 3.50 (s, 2H), 2.28 (s, 3 h), 2.19-2.11 (m, 2H), 1.76-1.66 (m, 4H), 1.64-1.54 (m, 2H). | 378.3 |
| 251 | 251-500 | 10-100 | 101-250 | 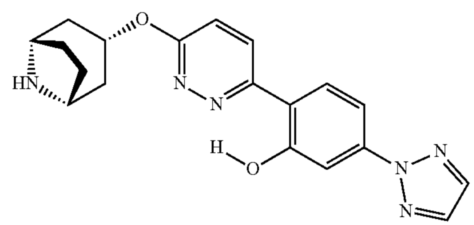 | 2-(6-(((1R,3s,5S)-8-azabicyclo[3.2.1]octan-3-yl)oxy)pyridazin-3-yl)-5-(2H-1,2,3-triazol-2-yl)phenol | $^1$H NMR (500 MHz, Methanol-d$_4$) δ 8.25 (d, J = 9.5 Hz, 1H), 7.89 (d, J = 9.2 Hz, 1H), 7.85 (s, 2H), 7.64-7.57 (m, 2H), 7.23-7.19 (m, 1H), 5.69-5.41 (m, 1H), 4.11 (s, 2H), 2.64-2.40 (m, 2H), 2.21-2.03 (m, 4H), 1.96-1.89 (m, 2H). | 365.1 |

TABLE 1B-continued

Exemplary SMSM compounds

| SMSM # | A-673 IC$_{50}$ (nM)[a] | Splice EC$_{50}$ (nM)[b] | Splice IC$_{50}$ (nM)[c] | Structure | Name | Proton NMR | M + H (MS) |
|---|---|---|---|---|---|---|---|
| 252 | 501-1000 | 101-250 | 251-500 | 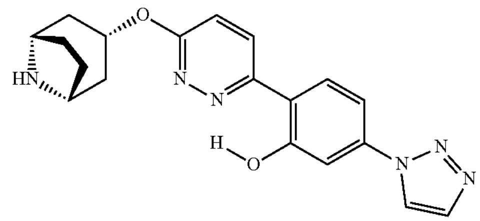 | 2-(6-(((1R,3s,5S)-8-azabicyclo[3.2.1]octan-3-yl)oxy)pyridazin-3-yl)-5-(1H-1,2,3-triazol-1-yl)phenol | $^1$H NMR (500 MHz, Methanol-d$_4$) δ 8.63 (d, J = 1.1 Hz, 1H), 8.38 (d, J = 9.5 Hz, 1H), 8.08 (d, J = 8.6 Hz, 1H), 7.94 (d, J = 1.1 Hz, 1H), 7.62-7.42 (m, 2H), 7.31 (d, J = 9.5 Hz, 1H), 5.76-5.53 (m, 1H), 3.80 (s, 2H), 2.53-2.29 (m, 2H), 2.09- | 365.2 |
| 253 | 501-1000 | 251-500 | 251-500 | 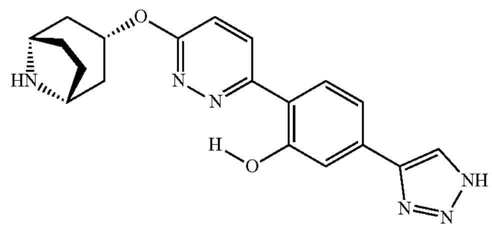 | 2-(6-(((1R,3s,5S)-8-azabicyclo[3.2.1]octan-3-yl)oxy)pyridazin-3-yl)-5-(1H-1,2,3-triazol-4-yl)phenol | $^1$H NMR (500 MHz, DMSO-d$_6$) δ 8.45-8.42 (m, 2H), 8.02 (d, J = 8.3 Hz, 1H), 7.51 (d, J = 1.5 Hz, 1H), 7.47 (dd, J = 8.2, 1.5 Hz, 1H), 7.38 (d, J = 9.5 Hz, 1H), 5.50 (m, 1H), 3.53 (s, 2H), 2.17 (m, 2H), 1.73 (m, 4H), 1.61 (m, 2H). | 385.2 |
| 254 | >1000 | >1000 | >1000 | 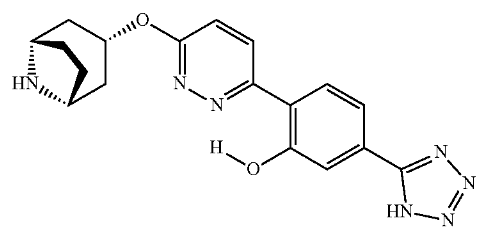 | 2-(6-(((1R,3s,5S)-8-azabicyclo[3.2.1]octan-3-yl)oxy)pyridazin-3-yl)-5-(1H-tetrazol-5-yl)phenol | $^1$H NMR (500 MHz, DMSO-d$_6$) δ 12.51 (s, 1H), 8.53 (s, 1H), 8.42 (d, J = 9.6 Hz, 1H), 7.94 (d, J = 8.1Hz, 1H), 7.63-7.56 (m, 2H), 7.40 (d, J = 9.4 Hz, 1H), 5.67-5.48 (m, 1H), 4.14-4.09 (m, 2H), 2.45-2.41 (m, 2H), 2.10-1.86 (m, 6 h). | 366.1 |
| 255 | 501-1000 | 101-250 | 101-250 | 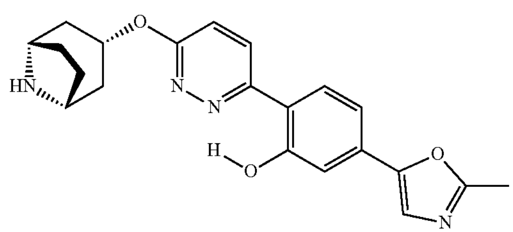 | 2-(6-(((1R,3s,5S)-8-azabicyclo[3.2.1]octan-3-yl)oxy)pyridazin-3-yl)-5-(2-methyloxazol-5-yl)phenol | $^1$H NMR (500 MHz, DMSO) δ 8.44 (d, J = 9.5 Hz, 1H), 8.01 (d, J = 8.3 Hz, 1H), 7.63 (s, 1H), 7.36 (d, J = 9.4 Hz, 1H), 7.27 (s, 1H), 7.25 (d, J = 8.4 Hz, 1H), 5.63-5.34 (m, 1H), 3.52-3.49 (m, 2H), 2.50 (s, 3 h), 2.18-2.12 (m, 2H), 1.79-1.52 (m, 6 h). | 378.9 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 256 | >1000 | >1000 | >1000 | 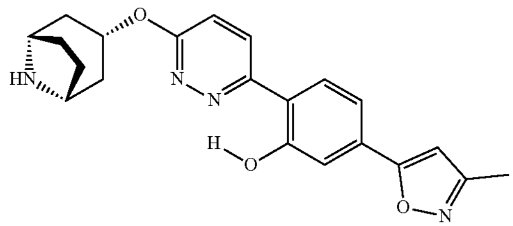 | 2-(6-(((1R,3s,5S)-8-azabicyclo[3.2.1]octan-3-yl)oxy)pyridazin-3-yl)-5-(3-methylisoxazol-5-yl)phenol | $^1$H NMR (400 MHz, DMSO-d$_6$) δ 7.44 (d, J = 8.4 Hz, 1H), 7.33 (d, J = 9.1Hz, 1H), 7.15-6.97 (m, 3 h), 6.18 (s, 1H), 5.57-5.40 (m, 1H), 3.50 (s, 2H), 2.23-2.08 (m, 5H), 1.76-1.64 (m, 4H), 1.60-1.55 (m, 2H). | 379.1 |
| 257 | >1000 | | | 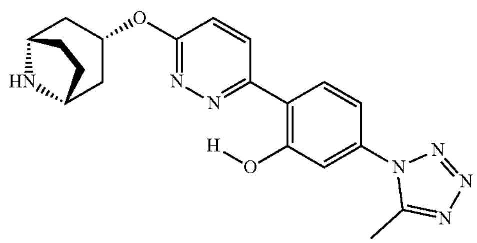 | 2-(6-((((1R,3s,5S)-8-azabicyclo[3.2.1]octan-3-yl)oxy)pyridazin-3-yl)-5-(5-methyl-1H-tetrazol-1-yl)phenol | $^1$H NMR (400 MHz, DMSO-d$_6$) δ 12.88 (s, 1H), 8.88 (s, 1H), 8.46 (d, J = 9.5 Hz, 1H), 8.17 (d, J = 8.4 Hz, 1H), 7.50-7.28 (m, 3 h), 5.62-5.58 (m, 1H), 4.15 (s, 2H), 2.63 (s, 3 h), 2.48-2.92 (m, 8 h). | 380.2 |
| 258 | 251-500 | 10-100 | 101-250 | 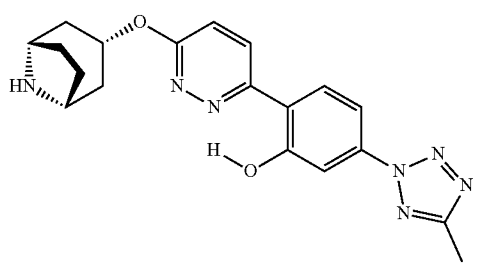 | 2-(6-((((1R,3s,5S)-8-azabicyclo[3.2.1]octan-3-yl)oxy)pyridazin-3-yl)-5-(5-methyl-2H-tetrazol-2-yl)phenol | $^1$H NMR (400 MHz, DMSO-d$_6$) δ 12.65 (s, 1H), 8.98 (s, 1H), 8.42 (d, J = 9.5 Hz, 1H), 8.17 (d, J = 8.6 Hz, 1H), 7.77-7.60 (m, 2H), 7.45 (d, J = 9.4 Hz, 1H), 5.68-5.44 (m, 1H), 4.13 (s, 2H), 2.61 (s, 3 h), 2.48-2.39 (m, 2H), 2.08-2.00 (m, 6 h). | 380.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 259 | <10 | | | 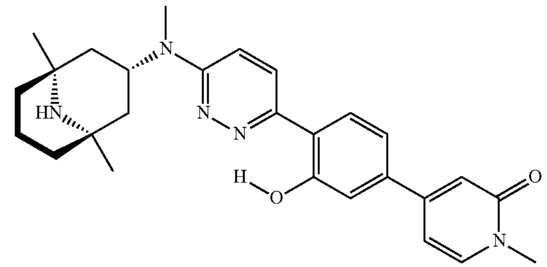 | 4-(4-(6-(((1R,3s,5S)-1,5-dimethyl-9-azabicyclo[3.3.1]nonan-3-yl)(methyl)amino)pyridazin-3-yl)-3-hydroxyphenyl)-1-methylpyridin-2(1H)-one | $^1$H NMR (500 MHz, DMSO-d$_6$) δ 13.8 (s, 1H), 8.21 (d, J = 9.9 Hz, 1H), 7.95 (d, J = 8.4 Hz, 1H), 7.78 (d, J = 7.0 Hz, 1H), 7.36-7.24 (m, 3 h), 6.78-6.63 (m, 2H), 5.77 (s, 1H), 3.48 (s, 3 h), 2.88 (s, 3 h), 2.08-2.01 (m, 1H), 1.67-0.99 (m, 15H). | 460.3 |
| 260 | <10 | | | 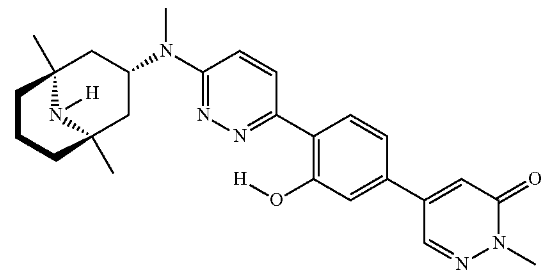 | 5-(4-(6-(((1R,3s,5S)-1,5-dimethyl-9-azabicyclo[3.3.1]nonan-3-yl)(methyl)amino)pyridazin-3-yl)-3-hydroxyphenyl)-2-methylpyridazin-3(2H)-one | $^1$H NMR (500 MHz, DMSO-d$_6$) δ 13.95 (s, 1H), 8.39 (d, J = 2.2 Hz, 1H), 8.28 (d, J = 10.0 Hz, 1H), 8.01 (d, J = 8.3 Hz, 1H), 7.48-7.35 (m, 2H), 7.30 (d, J = 9.7 Hz, 1H), 7.26 (d, J = 2.2 Hz, 1H), 5.85-5.63 (m, 1H), 3.69 (s, 3 h), 2.89 (s, 3 h), 1.72-1.55 (m, 4H), 1.51-1.37 (m, 2H), 1.37-1.17 (m, 4H), 1.04 (s, 6 h). | 461.2 |
| 261 | 10-100 | | | 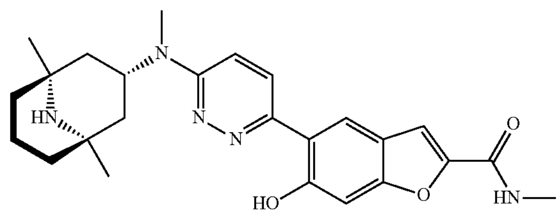 | 5-(6-(((1R,3s,5S)-1,5-dimethyl-9-azabicyclo[3.3.1]nonan-3-yl)(methyl)amino)pyridazin-3-yl)-6-hydroxy-N-methylbenzofuran-2-carboxamide | $^1$H NMR (500 MHz, Methanol-d$_4$) δ 8.22 (d, J = 9.9 Hz, 1H), 8.16 (s, 1H), 7.46 (s, 1H), 7.36 (d, J = 9.8 Hz, 1H), 7.11 (s, 1H), 6.13-6.00 (m, 1H), 3.01 (s, 3 h), 2.97 (s, 3 h), 2.49-2.36 (m, 1H), 2.17-2.08 (m, 4H), 2.05-1.77 (m, 5H), 1.49 (s, 6 h). | 450.0 |

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 262 | 101-250 | | | 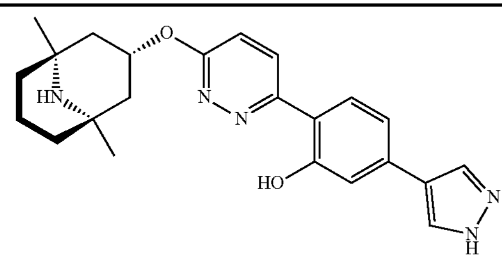 | 2-(6-(((1R,3s,5S)-1,5-dimethyl-9-azabicyclo[3.3.1]nonan-3-yl)oxy)pyridazin-3-yl)-5-(1H-pyrazol-4-yl)phenol | $^1$H NMR (500 MHz, DMSO-d$_6$) δ 13.03 (s, 1H), 8.77-8.58 (m, 1H), 8.48 (d, J = 9.7 Hz, 1H), 8.30 (s, 1H), 8.00 (s, 1H), 7.94 (d, J = 8.3 Hz, 1H), 7.43 (d, J = 9.6 Hz, 1H), 7.25 (d, J = 10.2 Hz, 1H), 6.16-6.01 (m, 1H), 2.61-2.52 (m, 2H), 2.02-1.86 (m, 3 h), 1.83-1.71 (m, 3 h), 1.69-1.57 (m, 2H), 1.37 (s, 6 h). | 406.2 |
| 263 | <10 | | | 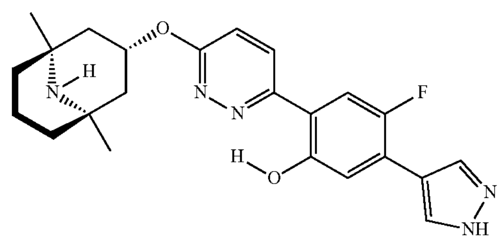 | 2-(6-(((1R,3s,5S)-1,5-dimethyl-9-azabicyclo[3.3.1]nonan-3-yl)oxy)pyridazin-3-yl)-4-fluoro-5-(1H-pyrazol-4-yl)phenol | $^1$H NMR (500 MHz, DMSO-d$_6$) δ 13.20 (s, 1H), 8.74-8.59 (m, 2H), 8.49 (d, J = 9.6 Hz, 1H), 8.25 (s, 1H), 8.01 (s, 1H), 7.92 (d, J = 12.4 Hz, 1H), 7.45 (d, J = 9.6 Hz, 1H), 7.36 (d, J = 6.9 Hz, 10H), 6.14-5.96 (m, 3H), 1.98-1.88 (m, 3H), 1.80-1.72 (m, 3H), 1.68-1.58 (m, 2H), 1.37 (s, 6H). | 424.3 |
| 264 | | | | 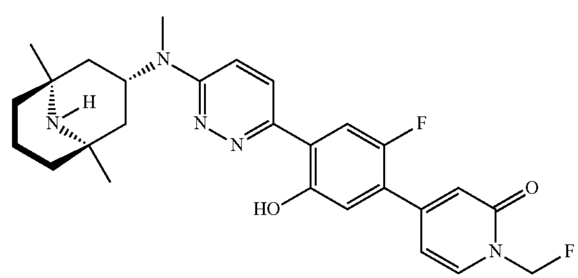 | 4-(4-(6-(((1R,3s,5S)-1,5-dimethyl-9-azabicyclo[3.3.1]nonan-3-yl)(methyl)amino)pyridazin-3-yl)-2-fluoro-5-hydroxyphenyl)-1-(fluoromethyl)pyridin-2(1H)-one | $^1$H NMR (500 MHz, DMSO-d$_6$) δ 13.52 (s, 1H), 8.27 (d, J = 10.0 Hz, 1H), 7.93 (d, J = 12.5 Hz, 1H), 7.90 (d, J = 7.2 Hz, 1H), 7.29 (d, J = 9.9 Hz, 1H), 7.13 (d, J = 6.9 Hz, 1H), 6.68 (s, 1H), 6.56 (d, J = 7.2 Hz, 1H), 5.99 (d, J = 50.9 Hz, 2H), 5.85-5.64 (m, 1H), 2.89 (s, 3H), 2.08 (s, 1H), 1.73-1.54 | 496.2 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 265 | <10 | | | 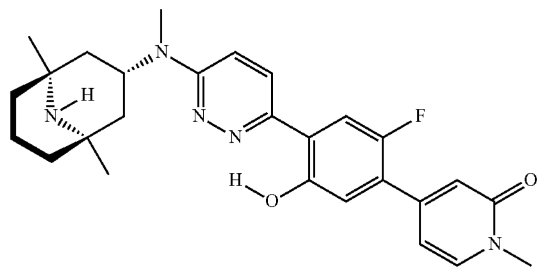 | 4-(4-(6-((((1R,3s,5S)-1,5-dimethyl-9-azabicyclo[3.3.1]nonan-3-yl)(methyl)amino)pyridazin-3-yl)-2-fluoro-5-hydroxyphenyl)-1-methylpyridin-2(1H)-one | $^1$H NMR (500 MHz, DMSO-d$_6$) δ 13.47 (s, 1H), 8.26 (d, J = 10.0 Hz, 1H), 7.90 (d, J = 12.5 Hz, 1H), 7.78 (d, J = 7.0 Hz, 1H), 7.28 (d, J = 9.8 Hz, 1H), 7.08 (d, J = 6.9 Hz, 1H), 6.58 (d, J = 1.7 Hz, 1H), 6.47-6.43 (m, 1H), 5.83-5.67 (m, 1H), 3.46 (s, 3 h), 2.89 (s, 3 h), 1.69-1.56 (m, 5H), 1.49-1.26 (m, 5H), 1.04 (s, 6 h). | 478.2 |
| 266 | 10-100 | | | 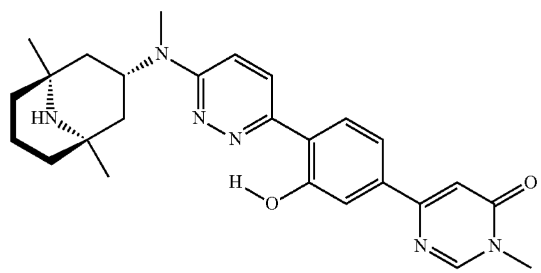 | 6-(4-(6-((((1R,3s,5S)-1,5-dimethyl-9-azabicyclo[3.3.1]nonan-3-yl)(methyl)amino)pyridazin-3-yl)-3-hydroxyphenyl)-3-methylpyrimidin-4(3H)-one | $^1$H NMR (500 MHz, DMSO-d$_6$) δ 13.50 (s, 1H), 8.57 (s, 1H), 8.31 (d, J = 10.0 Hz, 1H), 8.00 (d, J = 8.4 Hz, 1H), 7.65-7.61 (m, 2H), 7.37 (d, J = 9.9 Hz, 1H), 7.00 (s, 1H), 5.95-5.85 (m, 1H), 3.44 (s, 3H), 2.93 (s, 3H), 2.19-2.12 (m, 1H), 2.01-1.88 (m, 6H), 1.80-1.74 (m, 1H), 1.68-1.61 (m, 2H), 1.36 (s, 6H). | 461.0 |
| 267 | | | | 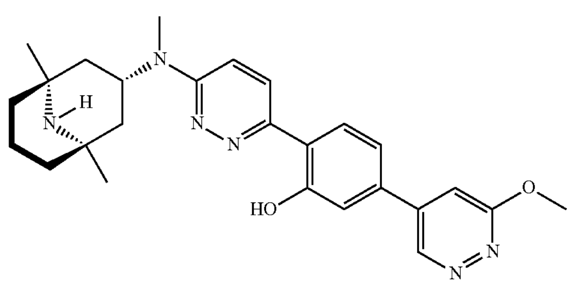 | 2-(6-((((1R,3s,5S)-1,5-dimethyl-9-azabicyclo[3.3.1]nonan-3-yl)(methyl)amino)pyridazin-3-yl)-5-(6-methoxypyridazin-4-yl)phenol | $^1$H NMR (500 MHz, DMSO-d$_6$) δ 13.89 (s, 1H), 9.35 (s, 1H), 8.34 (d, J = 8.8 Hz, 1H), 8.06 (d, J = 8.2 Hz, 1H), 7.56 (s, 1H), 7.55-7.46 (m, 2H), 7.36 (d, J = 8.1 Hz, 1H), 5.91-5.76 (m, 1H), 4.09 (s, 3H), 2.92 (s, 3H), 2.19-2.05 (m, 1H), 1.96-1.67 (m, 6H), 1.64-1.45 (m, 3H), 1.37-1.09 (m, 6H). | 461.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 268 | <10 | | | 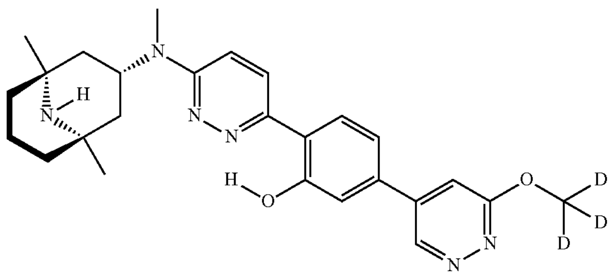 | 2-(6-(((1R,3s,5S)-1,5-dimethyl-9-azabicyclo[3.3.1]nonan-3-yl)(methyl)amino)pyridazin-3-yl)-5-(6-(methoxy-d3)pyridazin-4-yl)phenol | $^1$H NMR (500 MHz, DMSO-d$_6$) δ 13.90 (s, 1H), 9.35 (s, 1H), 8.30 (d, J = 10.0 Hz, 1H), 8.03 (d, J = 8 Hz, 1H), 7.47-7.50 (m, 3H), 7.31 (d, J = 9 Hz, 1H), 5.75 (m, 1H), 2.90 (s, 3H), 2.00 (m, 1H), 1.28-1.68 (m, 9H), 1.12 (s, 6H). | 464.0 |
| 269 | <10 | | | 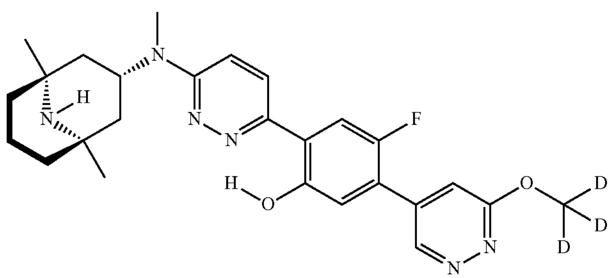 | 2-(6-(((1R,3s,5S)-1,5-dimethyl-9-azabicyclo[3.3.1]nonan-3-yl)(methyl)amino)pyridazin-3-yl)-4-fluoro-5-(6-(methoxy-d3)pyridazin-4-yl)phenol | $^1$H NMR (500 MHz, DMSO-d$_6$) δ 13.66 (s, 1H), 9.17 (d, J = 1.7 Hz, 1H), 8.30 (d, J = 10.0 Hz, 1H), 7.99 (d, J = 12.4 Hz, 1H), 7.44 (s, 1H), 7.39-7.17 (m, 2H), 5.92-5.64 (m, 1H), 2.89 (s, 3H), 2.17-1.95 (m, 1H), 1.78-1.54 (m, 5H), 1.52-1.38 (m, 2H), 1.38-1.26 (m, 2H), 1.05 (s, 6H). | 482.2 |
| 270 | | | | 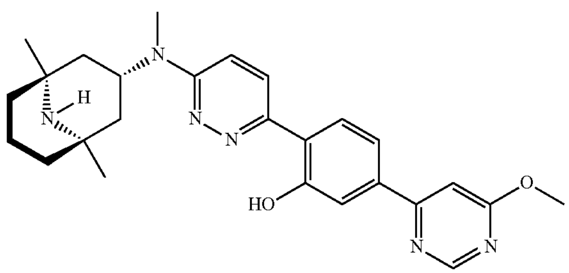 | 2-(6-(((1R,3s,5S)-1,5-dimethyl-9-azabicyclo[3.3.1]nonan-3-yl)(methyl)amino)pyridazin-3-yl)-5-(6-methoxypyrimidin-4-yl)phenol | $^1$H NMR (500 MHz, DMSO-d$_6$) δ 13.77 (s, 1H), 8.87 (s, 1H), 8.28 (d, J = 10.0 Hz, 1H), 8.01 (d, J = 3.5 Hz, 1H), 7.76-7.74 (m, 2H), 7.54 (s, 1H), 5.74 (m, 1H), 3.99 (s, 3H), 2.90 (s, 3H), 2.08 (m, 1H), 1.67-1.62 (m, 5H), 1.46-1.44 (m, 2H), 1.34-1.28 (m, 2H), 1.04 (s, 6H). | 461.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 271 | <10 | | | 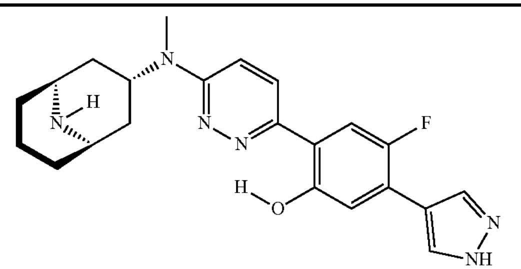 | 2-(6-((1R,3s,5S)-9-azabicyclo[3.3.1]nonan-3-yl)(methyl)amino)pyridazin-3-yl)-4-fluoro-5-(1H-pyrazol-4-yl)phenol | ¹H NMR (500 MHz, Methanol-d₄) δ 8.13-8.03 (m, ₃ h), 7.61 (d, J = 12.4 Hz, 1H), 7.30 (d, J = 9.9 Hz, 1H), 7.25 (d, J = 6.7 Hz, 1H), 5.84-5.73 (m, 1H), 3.52-3.48 (m, 2H), 3.02 (s, ₃ h), 2.28-2.18 (m, ₃ h), 2.10-2.00 (m, 2H), 1.98-1.90 (m, 4H), 1.90-1.82 (m, 1H). | 409.1 |
| 272 | 10-100 | | | 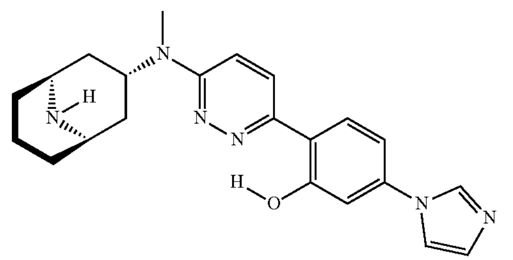 | 2-(6-((1R,3s,5S)-9-azabicyclo[3.3.1]nonan-3-yl)(methyl)amino)pyridazin-3-yl)-5-(1H-imidazol-1-yl)phenol | ¹H NMR (500 MHz, DMSO-d₆) δ 14.13 (s, 1H), 9.21 (s, 1H), 8.37 (s, 1H), 8.31 (d, J = 9 Hz, 1H), 8.03 (d, J = 7.5 Hz, 1H), 7.82 (s, 1H), 7.39 (d, J = 9.5 Hz, 1H), 7.30 (s, 1H), 7.25 (d, J = 7 Hz, 1H), 7.11 (s, 1H), 5.70-5.75 (m, 1H), 3.73 (s, 2H), 2.99 (s, ₃ h), 2.31-2.39 (m, 2H), 2.01-2.08 (m, ₃ h), 1.75-1.90 (m, 4H), 1.70-1.75 (m, 1H). | 391.3 |
| 273 | <10 | | | 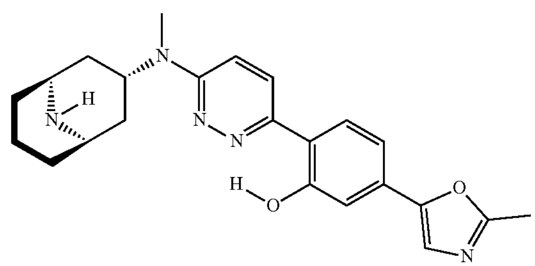 | 2-(6-((1R,3s,5S)-9-azabicyclo[3.3.1]nonan-3-yl)(methyl)amino)pyridazin-3-yl)-5-(2-methyloxazol-5-yl)phenol | ¹H NMR (500 MHz, DMSO-d₆) δ 13.74 (s, 1H), 9.20 (s, 1H), 8.28 (d, J = 10 Hz, 1H), 8.00 (s, 1H), 7.62 (s, 1H), 7.38 (d, J = 10 Hz, 1H), 7.25-7.23 (m, 2H), 5.75 (s, 1H), 3.75 (s, 2H), 2.96 (s, 3 h), 2.28-2.37 (m, 3 h), 1.76-2.01 (m, ₁₀ h). | 406.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 274 | <10 | <10 | <10 | 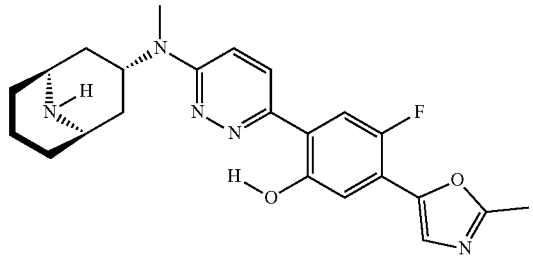 | 2-(6-(((1R,3s,5S)-9-azabicyclo[3.3.1]nonan-3-yl)(methyl)amino)pyridazin-3-yl)-4-fluoro-5-(2-methyloxazol-5-yl)phenol | $^1$H NMR (500 MHz, DMSO-d$_6$) δ 13.32 (s, 1H), 8.30 (d, J = 9.9 Hz, 1H), 7.96 (d, J = 12.5 Hz, 1H), 7.44 (d, J = 3.5 Hz, 1H), 7.37 (d, J = 9.9 Hz, 1H), 7.22 (d, J = 6.5 Hz, 1H), 5.84-5.70 (m, 1H), 3.76-3.68 (m, 2H), 2.97 (s, 3 h), 2.52 (s, 3 h), 2.38-2.27 (m, 2H), 2.09-1.75 (m, 8 h). | 424.2 |
| 275 | <10 | <10 | <10 | 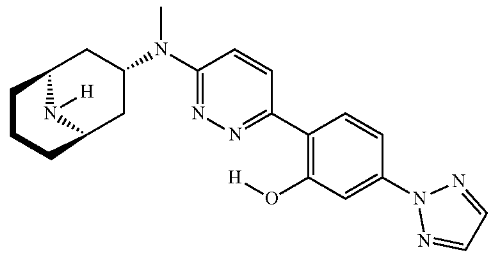 | 2-(6-(((1R,3s,5S)-9-azabicyclo[3.3.1]nonan-3-yl)(methyl)amino)pyridazin-3-yl)-5-(2H-1,2,3-triazol-2-yl)phenol | $^1$H NMR (500 MHz, DMSO-d$_6$) δ 13.81 (s, 1H), 8.28 (d, J = 10.0 Hz, 1H), 8.15 (s, 2H), 8.10 (d, J = 8.7 Hz, 1H), 7.66-7.50 (m, 2H), 7.40 (d, J = 9.9 Hz, 1H), 5.89-5.59 (m, 1H), 3.76 (s, 2H), 2.96 (s, 3 h), 2.38-2.32 (m, 2H), 2.11-1.83 (m, 8 h). | 392.3 |
| 276 | 101-250 | <10 | <10 | 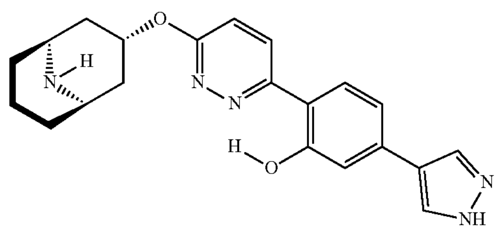 | 2-(6-(((1R,3s,5S)-9-azabicyclo[3.3.1]nonan-3-yl)oxy)pyridazin-3-yl)-5-(1H-pyrazol-4-yl)phenol | $^1$H NMR (500 MHz, DMSO-d$_6$) δ 13.21 (s, 1H), 13.02 (s, 1H), 8.44 (d, J = 9.6 Hz, 1H), 8.18 (s, 2H), 7.93 (d, J = 8.3 Hz, 1H), 7.38 (d, J = 9.5 Hz, 1H), 7.30-7.25 (m, 2H), 6.05 (s, 1H), 3.20 (s, 2H), 2.32-2.25 (m, 2H), 1.94-1.82 (m, 4H), 1.76-1.70 (m, 4H). | 378.2 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 277 | >1000 | >1000 | >1000 | 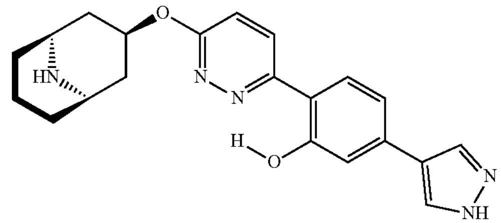 | 2-(6-((1R,3r,5S)-9-azabicyclo[3.3.1]nonan-3-yl)oxy)pyridazin-3-yl)-5-(1H-pyrazol-4-yl)phenol | $^1$H NMR (500 MHz, DMSO-d$_6$) δ 13.29 (s, 1H), 13.21-12.89 (m, 1H), 8.45 (d, J = 9.6 Hz, 1H), 8.15 (s, 2H), 7.93 (d, J = 8.3 Hz, 1H), 7.40 (d, J = 9.5 Hz, 1H), 7.28-7.18 (m, 2H), 5.40-5.35 (m, 1H), 3.29 (d, J = 9.4 Hz, 2H), 2.48-2.42 (m, 2H), 2.15-2.08 (m, 1H), 1.69-1.58 (m, 4H), 1.48-1.45 (m, 6 h). | 378.3 |
| 278 | 10-100 | <10 | <10 | 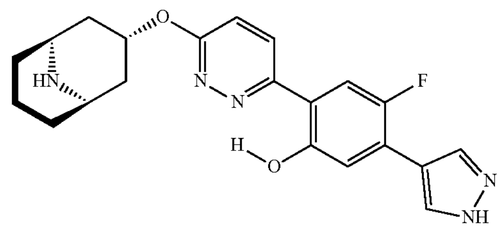 | 2-(6-((1R,3s,5S)-9-azabicyclo[3.3.1]nonan-3-yl)oxy)pyridazin-3-yl)-4-fluoro-5-(1H-pyrazol-4-yl)phenol | $^1$H NMR (500 MHz, DMSO-d$_6$) δ 8.43 (d, J = 9.5 Hz, 1H), 8.13 (s, 2H), 7.89 (d, J = 12.2 Hz, 1H), 7.42-7.31 (m, 2H), 6.12-6.00 (m, 1H), 3.24-3.18 (m, 2H), 2.28-2.20 (m, 2H), 2.07 (s, 3 h), 1.85-1.60 (m, 8 h). | 396.1 |
| 279 | 10-100 | <10 | <10 | 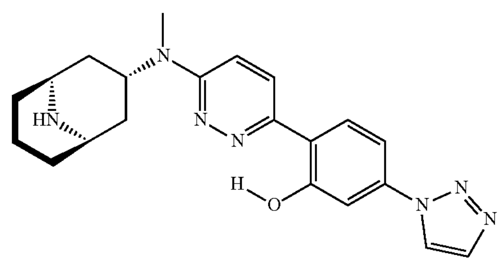 | 2-(6-((1R,3s,5S)-9-azabicyclo[3.3.1]nonan-3-yl)(methyl)amino)pyridazin-3-yl)-5-(1H-1,2,3-triazol-1-yl)phenol | $^1$H NMR (500 MHz, DMSO-d$_6$) δ 14.08 (s, 1H), 8.92 (s, 1H), 8.79-8.41 (m, 1H), 8.31 (d, J = 10.0 Hz, 1H), 8.13 (d, J = 8.6 Hz, 1H), 8.00 (s, 1H), 7.57-7.48 (m, 2H), 7.41 (d, J = 9.9 Hz, 1H), 5.88-5.58 (m, 1H), 3.68 (s, 2H), 2.96 (s, 3 h), 2.37-2.31 (m, 2H), 2.07-1.65 (m, 8 h). | 392.3 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 280 | 10-100 | <10 | <10 | 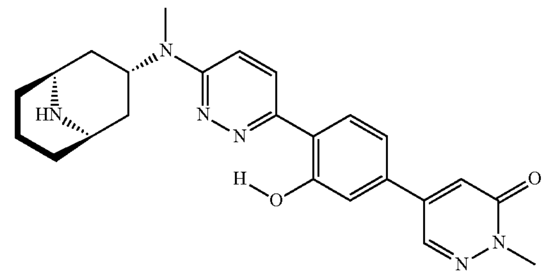 | 5-(4-(6-(((1R,3s,5S)-9-azabicyclo[3.3.1]nonan-3-yl)(methyl)amino)pyridazin-3-yl)-3-hydroxyphenyl)-2-methylpyridazin-3(2H)-one | $^1$H NMR (500 MHz, DMSO-d$_6$) δ 13.87 (s, 1H), 8.40 (d, J = 2.2 Hz, 1H), 8.33 (d, J = 10.0 Hz, 1H), 8.04 (d, J = 8.3 Hz, 1H), 7.45-7.35 (m, 6 h), 7.27 (d, J = 2.2 Hz, 1H), 5.73 (m, 1H), 3.69 (s, 3 h), 3.59 (s, 2H), 2.96 (s, 3 h), 2.22 (m, 2H), 2.09-1.79 (m, 8 h), 1.79-1.69 (m, 1H). | 433.1 |
| 281 | <10 | <10 | <10 | 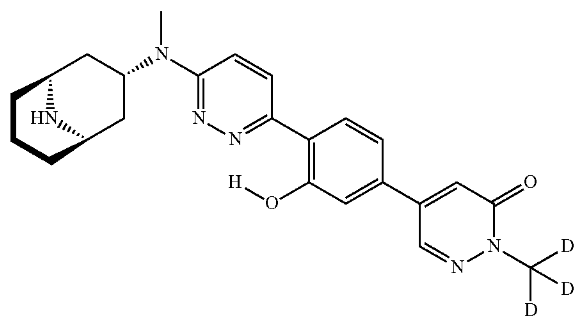 | 5-(4-(6-(((1R,3s,5S)-9-azabicyclo[3.3.1]nonan-3-yl)(methyl)amino)pyridazin-3-yl)-3-hydroxyphenyl)-2-(methyl-d3)pyridazin-3(2H)-one | $^1$H NMR (500 MHz, DMSO-d$_6$) δ 8.39 (d, J = 2.1 Hz, 1H), 8.31 (d, J = 9.9 Hz, 1H), 8.03 (d, J = 8.3 Hz, 1H), 7.44-7.38 (m, 2H), 7.35 (d, J = 9.9 Hz, 1H), 7.27 (d, J = 2.1 Hz, 1H), 5.75-5.63 (m, 1H), 2.95 (s, 3 h), 2.13-1.95 (m, 3 h), 1.92-1.81 (m, 2H), 1.73 (m, 5H). | 436.1 |
| 282 | 10-100 | <10 | 10-100 | 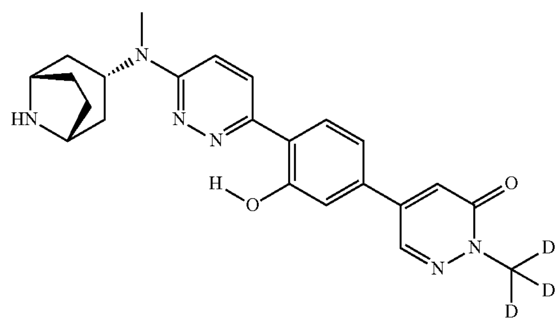 [SMILES: [2H]C([2H])([2H])n1ncc(-c2ccc(-c3ccc(N(C)[C@@H]4C[C@H]5CC[C@@H](C4)N5)nn3)c(O)c2)cc1=O] | 5-(4-(6-(((1R,3s,5S)-8-azabicyclo[3.2.1]octan-3-yl)(methyl)amino)pyridazin-3-yl)-3-hydroxyphenyl)-2-(methyl-d3)pyridazin-3(2H)-one | $^1$H NMR (500 MHz, DMSO-d$_6$) δ 8.39 (d, J = 2.2 Hz, 1H), 8.28 (d, J = 10.0 Hz, 1H), 8.02 (d, J = 8.2 Hz, 1H), 7.44-7.36 (m, 3 h), 7.27 (d, J = 2.2 Hz, 1H), 5.02-4.86 (m, 1H), 3.55 (s, 2H), 2.95 (s, 3 h), 1.88-1.72 (m, 6 h), 1.59-1.46 (m, 2H). | 422.2 |

TABLE 1B-continued

Exemplary SMSM compounds

| SMSM # | A-673 IC$_{50}$ (nM)[a] | Splice EC$_{50}$ (nM)[b] | Splice IC$_{50}$ (nM)[c] | Structure | Name | Proton NMR | M + H (MS) |
|---|---|---|---|---|---|---|---|
| 283 | <10 | | <10 | 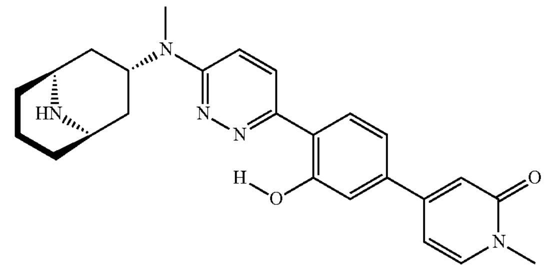 | 4-(4-(6-((1R,3s,5S)-9-azabicyclo[3.3.1]nonan-3-yl)(methyl)amino)pyridazin-3-yl)-3-hydroxyphenyl)-1-methylpyridin-2(1H)-one | $^1$H NMR (500 MHz, DMSO-d$_6$) δ 8.22 (d, J = 9.9 Hz, 1H), 7.96 (d, J = 8.3 Hz, 1H), 7.78 (d, J = 7.1 Hz, 1H), 7.34-7.25 (m, 3 h), 6.74 (d, J = 2.0 Hz, 1H), 6.67 (dd, J = 7.1, 2.1 Hz, 1H), 5.74-5.60 (m, 1H), 3.48 (s, 3 h), 3.25-3.15 (m, 2H), 2.94 (s, 3 h), 2.09-1.92 (m, 3 h), 1.90-1.79 (m, 2H), 1.74-1.61 (m, 5H). | 432.1 |
| 284 | <10 | >1000 | <10 | 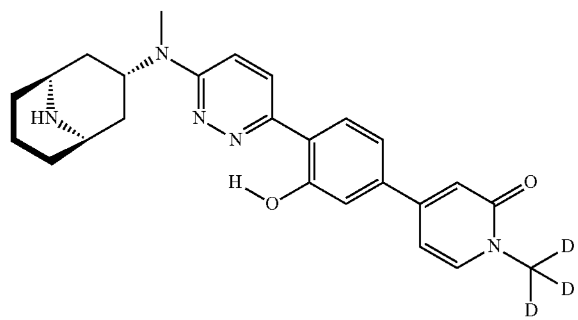 | 4-(4-(6-((1R,3s,5S)-9-azabicyclo[3.3.1]nonan-3-yl)(methyl)amino)pyridazin-3-yl)-3-hydroxyphenyl)-1-(methyl-d3)pyridin-2(1H)-one | $^1$H NMR (500 MHz, DMSO-d$_6$) δ 13.75 (s, 1H), 8.28 (d, J = 9.9 Hz, 1H), 7.98 (d, J = 8.3 Hz, 1H), 7.77 (d, J = 7.1 Hz, 1H), 7.36 (d, J = 10.0 Hz, 1H), 7.30-7.24 (m, 2H), 6.70 (d, J = 2.1 Hz, 1H), 6.61 (dd, J = 7.2, 2.1 Hz, 1H), 5.75-5.64 (m, 1H), 3.45 (s, 2H), 2.95 (s, 3 h), 2.15-1.72 (m, 10 h). | 435.3 |
| 285 | <10 | >1000 | <10 | 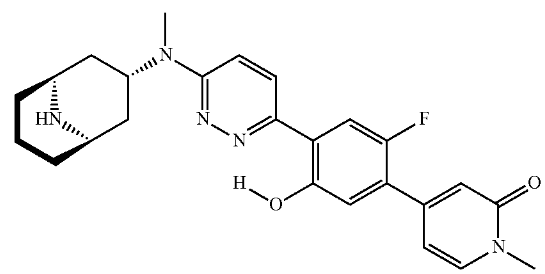 | 4-(4-(6-((1R,3s,5S)-9-azabicyclo[3.3.1]nonan-3-yl)(methyl)amino)pyridazin-3-yl)-2-fluoro-5-hydroxyphenyl)-1-methylpyridin-2(1H)-one | $^1$H NMR (500 MHz, DMSO-d$_6$) δ 13.47 (s, 1H), 8.27 (d, J = 9.9 Hz, 1H), 7.91 (d, J = 12.4 Hz, 1H), 7.78 (d, J = 7.1 Hz, 1H), 7.32 (d, J = 9.9 Hz, 1H), 7.08 (d, J = 6.9 Hz, 1H), 6.58 (s, 1H), 6.45 (d, J = 7.1 Hz, 1H), 5.73-5.61 (m, 1H), 3.46 (s, 3 h), 3.24-3.15 (m, 2H), 2.94 (s, 3 h), 2.06-1.93 (m, 3 h), 1.86-1.76 (m, 2H), 1.74-1.60 (m, 5H). | 450.2 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 286 | <10 | | | 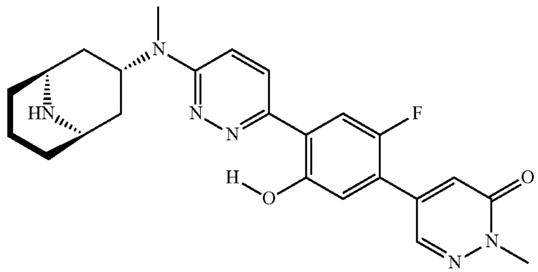 | 5-(4-(6-(((1R,3s,5S)-9-azabicyclo[3.3.1]nonan-3-yl)(methyl)amino)pyridazin-3-yl)-2-fluoro-5-hydroxyphenyl)-2-methylpyridazin-3(2H)-one | $^{1}$H NMR (500 MHz, DMSO-d$_6$) δ 8.29 (d, J = 9.9 Hz, 1H), 8.19 (t, J = 2.0 Hz, 1H), 7.97 (d, J = 12.3 Hz, 1H), 7.33 (d, J = 9.9 Hz, 1H), 7.24 (d, J = 6.9 Hz, 1H), 7.15 (d, J = 2.0 Hz, 1H), 5.76-5.62 (m, 1H), 3.70 (s, 3 h), 3.21-3.15 (m, 2H), 2.94 (s, 3 h), 2.06-1.92 (m, 3 h), 1.84-1.75 (m, 2H), 1.74-1.62 (m, 5H). | 451.2 |
| 287 | <10 | | | 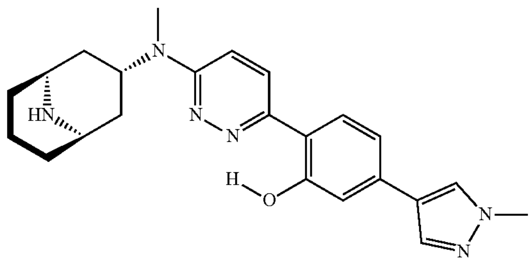 | 2-(6-((1R,3s,5S)-9-azabicyclo[3.3.1]nonan-3-yl)(methyl)amino)pyridazin-3-yl)-5-(1-methyl-1H-pyrazol-4-yl)phenol | $^{1}$H NMR (500 MHz, DMSO-d$_6$) δ 8.18 (d, J = 9.4 Hz, 2H), 7.91 (s, 1H), 7.82 (d, J = 8.8 Hz, 1H), 7.30 (d, J = 9.9 Hz, 1H), 7.15 (s, 2H), 5.70-5.54 (m, 1H), 3.87 (s, 3 h), 3.31-3.19 (m, 2H), 2.93 (s, 3 h), 2.08-1.66 (m, 10 h). | 405.2 |
| 288 | 10-100 | | | 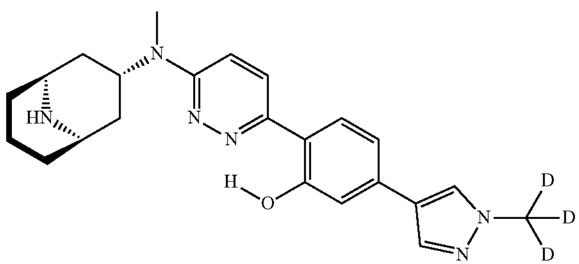 | 2-(6-((1R,3s,5S)-9-azabicyclo[3.3.1]nonan-3-yl)(methyl)amino)pyridazin-3-yl)-5-(1-(methyl-d3)-1H-pyrazol-4-yl)phenol | $^{1}$H NMR (500 MHz, DMSO-d$_6$) δ 8.17 (d, J = 9.6 Hz, 2H), 7.91 (s, 1H), 7.82 (d, J = 8.8 Hz, 1H), 7.30 (d, J = 9.9 Hz, 1H), 7.16 (d, J = 5.5 Hz, 2H), 5.63-5.60 (m, 1H), 3.24 (s, 2H), 2.92 (s, 3 h), 2.05-1.94 (m, 3 h), 1.85 (s, 2H), 1.73-1.63 (m, 5H). | 408.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 289 | <10 | | | 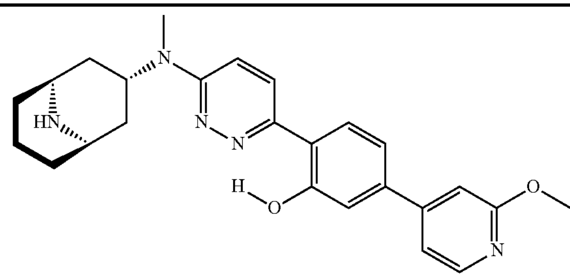 | 2-(6-((1R,3s,5S)-9-azabicyclo[3.3.1]nonan-3-yl)(methyl)amino)pyridazin-3-yl)-5-(2-methoxypyridin-4-yl)phenol | $^1$H NMR (500 MHz, Methanol-d$_4$) δ 8.33 (d, J = 9.8 Hz, 1H), 8.24 (d, J = 5.5 Hz, 1H), 7.89 (d, J = 8.4 Hz, 1H), 7.64-7.59 (m, 1H), 7.41-7.35 (m, 2H), 7.34-7.31 (m, 1H), 7.15 (d, J = 1.5 Hz, 1H), 5.86 (s, 1H), 4.02 (s, 3 h), 3.89 (s, 2H), 3.08 (s, 3 h), 2.44-2.35 (m, 2H), 2.24-2.33 (m, 1H), 2.21-2.07 (m, 6 h), 1.96-1.89 (m, 1H). | 432.1 |
| 290 | 251-500 | | | 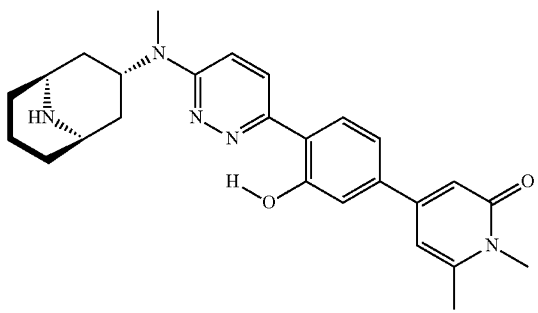 | 4-(4-(6-(((1R,3s,5S)-9-azabicyclo[3.3.1]nonan-3-yl)(methyl)amino)pyridazin-3-yl)-3-hydroxyphenyl)-1,6-dimethylpyridin-2(1H)-one | $^1$H NMR (500 MHz, DMSO-d$_6$) δ 8.25 (d, J = 10.0 Hz, 1H), 7.96 (d, J = 8.2 Hz, 1H), 7.33 (d, J = 9.9 Hz, 1H), 7.30-7.22 (m, 2H), 6.64-6.57 (m, 2H), 5.75-5.62 (m, 1H), 3.35 (d, J = 5.3 Hz, 2H), 3.32 (s, 3 h), 2.94 (s, 3 h), 2.44 (s, 3 h), 2.12-1.68 (m, 10 h). | 446.3 |
| 291 | <10 | | | 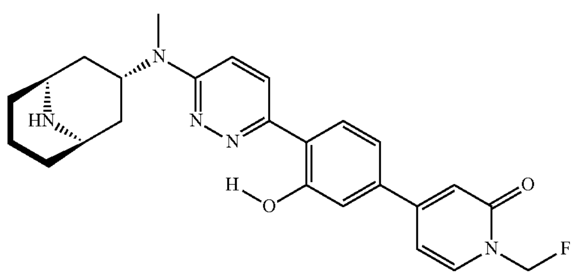 | 4-(4-(6-((1R,3s,5S)-9-azabicyclo[3.3.1]nonan-3-yl)(methyl)amino)pyridazin-3-yl)-3-hydroxyphenyl)-1-(fluoromethyl)pyridin-2(1H)-one | $^1$H NMR (500 MHz, DMSO-d$_6$) δ 13.79 (s, 1H), 8.30 (d, J = 9.9 Hz, 1H), 8.01 (d, J = 8.2 Hz, 1H), 7.90 (d, J = 7.3 Hz, 1H), 7.41-7.25 (m, 3 h), 6.81 (d, J = 1.6 Hz, 1H), 6.77-6.68 (m, 1H), 5.99 (d, J = 51 Hz, 2H), 5.72-5.69 (m, 1H), 3.50 (s, 2H), 2.96 (s, 3 h), 2.26-2.12 (m, 2H), 2.07-1.63 (m, 8 h). | 450.3 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 292 | >1000 | | | 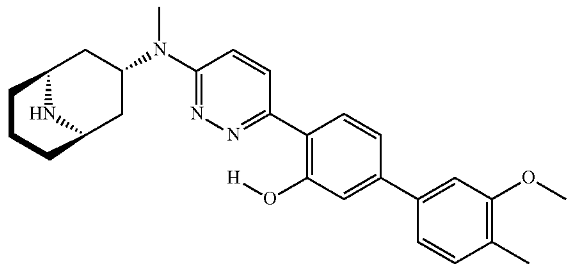 | 4-(6-(((1R,3s,5S)-9-azabicyclo[3.3.1]nonan-3-yl)(methyl)amino)pyridazin-3-yl)-3'-methoxy-4'-methyl-[1,1'-biphenyl]-3-ol | $^1$H NMR (500 MHz, DMSO-d$_6$) δ 8.18 (d, J = 9.7 Hz, 1H), 7.90 (d, J = 8.1 Hz, 1H), 7.34-7.15 (m, 6 h), 5.64-5.56 (m, 1H), 3.89 (s, 3 h), 3.23 (s, 2H), 2.94 (s, 3 h), 2.20 (s, 3 h), 2.06-1.75 (m, 3 h), 1.58-1.45 (m, 3 h), 1.65-1.49 (m, 5H). | 445.1 |
| 293 | 10-100 | | | 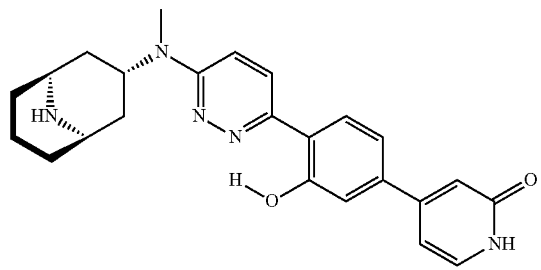 | 4-(4-(6-(((1R,3s,5S)-9-azabicyclo[3.3.1]nonan-3-yl)(methyl)amino)pyridazin-3-yl)-3-hydroxyphenyl)pyridin-2(1H)-one | $^1$H NMR (500 MHz, DMSO-d$_6$) δ 8.25 (d, J = 10.0 Hz, 1H), 7.97 (d, J = 8.2 Hz, 1H), 7.45 (d, J = 6.8 Hz, 1H), 7.32 (d, J = 9.9 Hz, 1H), 7.28-7.20 (m, 2H), 6.62 (d, J = 1.3 Hz, 1H), 6.55 (dd, J = 6.9, 1.7 Hz, 1H), 5.65-5.59 (m, 1H), 3.17 (s, 2H), 2.94 (s, 3 h), 2.01-1.91 (m, 3 h), 1.83-1.65 (m, 8 h). | 418.1 |
| 294 | 501-1000 | | | 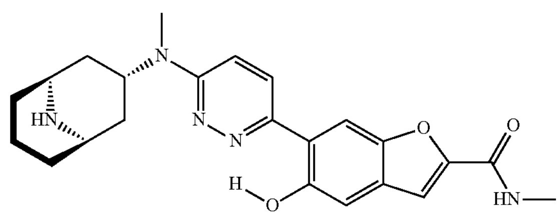 | 6-(6-(((1R,3s,5S)-9-azabicyclo[3.3.1]nonan-3-yl)(methyl)amino)pyridazin-3-yl)-5-hydroxy-N-methylbenzofuran-2-carboxamide | $^1$H NMR (500 MHz, DMSO-d$_6$) δ 13.29 (s, 1H), 8.62 (q, J = 4.6 Hz, 1H), 8.30 (d, J = 10.0 Hz, 1H), 8.12 (s, 1H), 7.39 (s, 1H), 7.32 (d, J = 9.9 Hz, 1H), 7.20 (s, 1H), 5.71-5.59 (m, 1H), 3.27 (s, 2H), 2.94 (s, 3 h), 2.81 (d, J = 4.7 Hz, 3 h), 2.08-1.96 (m, 2H), 1.90-1.78 (m, 2H), 1.73-1.67 (m, 5H). | 422.1 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 295 | 251-500 | | | 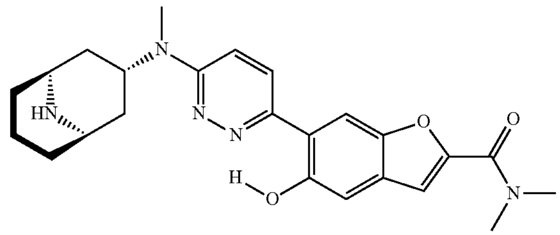 | 6-(6-(((1R,3s,5S)-9-azabicyclo[3.3.1]nonan-3-yl)(methyl)amino)pyridazin-3-yl)-5-hydroxy-N,N-dimethylbenzofuran-2-carboxamide | $^1$H NMR (500 MHz, Methanol-d$_4$) δ 8.20 (d, J = 9.9 Hz, 1H), 8.04 (s, 1H), 7.34-7.28 (m, 2H), 7.21 (s, 1H), 5.83-5.70 (m, 1H), 3.45-3.37 (m, 5H), 3.17 (s, $_3$ h), 3.03 (s, $_3$ h), 2.27-2.14 (m, $_3$ h), 2.09-1.96 (m, 2H), 1.96-1.80 (m, 5H). | 436.3 |
| 296 | 101-250 | <10 | 10-100 | 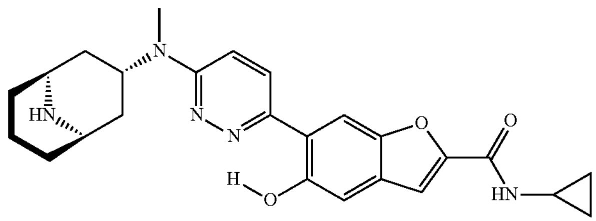 | 6-(6-((1R,3s,5S)-9-azabicyclo[3.3.1]nonan-3-yl)(methyl)amino)pyridazin-3-yl)-N-cyclopropyl-5-hydroxybenzofuran-2-carboxamide | $^1$H NMR (500 MHz, DMSO-d$_6$) δ 13.31 (s, 1H), 8.68 (d, J = 4.4 Hz, 1H), 8.27 (d, J = 9.8 Hz, 1H), 8.11 (s, 1H), 7.40 (s, 1H), 7.32 (d, J = 9.9 Hz, 1H), 7.20 (s, 1H), 5.80-5.51 (m, 1H), 3.23 (s, 2H), 2.94 (s, $_3$ h), 2.91-2.80 (m, 1H), 2.05-1.93 (m, $_3$ h), 1.87-1.78 (m, 2H), 1.73-1.63 (m, 5H), 0.75-0.59 (m, 4H). | 448.2 |
| 297 | 10-100 | | | 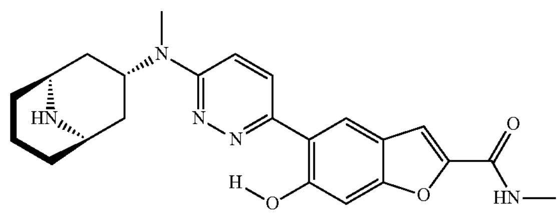 | 5-(6-((1R,3s,5S)-9-azabicyclo[3.3.1]nonan-3-yl)(methyl)amino)pyridazin-3-yl)-6-hydroxy-N-methylbenzofuran-2-carboxamide | $^1$H NMR (500 MHz, DMSO-d$_6$) δ 8.60-8.56 (m, 1H), 8.28 (s, 1H), 8.26 (d, J = 10.0 Hz, 1H), 7.43 (s, 1H), 7.36 (d, J = 9.9 Hz, 1H), 7.12 (s, 1H), 5.68-5.65 (m, 1H), 3.27-3.23 (m, 2H), 2.93 (s, $_3$ h), 2.79 (d, J = 4.6 Hz, $_3$ h), 2.09-1.92 (m, $_3$ h), 1.85-1.81 (m, 2H), 1.71-1.67 (m, 5H). | 422.1 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 298 | 10-100 | | | 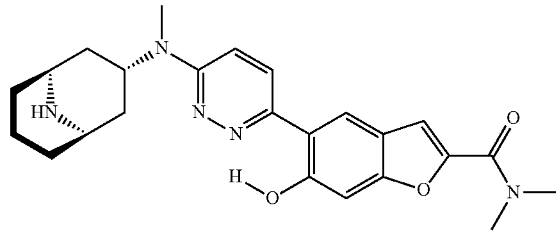 | 5-(6-((1R,3s,5S)-9-azabicyclo[3.3.1]nonan-3-yl)(methyl)amino)pyridazin-3-yl)-6-hydroxy-N,N-dimethylbenzofuran-2-carboxamide | $^1$H NMR (500 MHz, DMSO-d$_6$) δ 8.25-8.23 (m, 2H), 7.36-7.34 (m, 2H), 7.16 (s, 1H), 5.66-5.64 (m, 1H), 3.29-3.25 (m, 2H), 3.20 (s, 3 h), 3.03 (s, 3 h), 2.93 (s, 3 h), 2.00-1.96 (m, 3 h), 1.82-1.78 (m, 2H), 1.71-1.67 (m, 5H). | 436.0 |
| 299 | 10-100 | | | 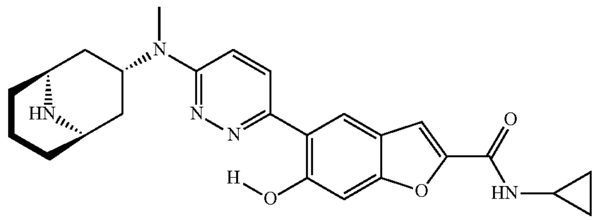 | 5-(6-((1R,3s,5S)-9-azabicyclo[3.3.1]nonan-3-yl)(methyl)amino)pyridazin-3-yl)-N-cyclopropyl-6-hydroxybenzofuran-2-carboxamide | $^1$H NMR (500 MHz, DMSO-d$_6$) δ 8.64 (d, J = 4.0 Hz, 1H), 8.30 (d, J = 10.0 Hz, 1H), 8.29 (s, 1H), 7.45 (s, 1H), 7.40 (d, J = 10.0 Hz, 1H), 7.11 (s, 1H), 5.75-5.72 (m, 1H), 3.69-3.65 (m, 2H), 2.95 (s, 3 h), 2.86-2.84 (m, 1H), 2.22 (s, 2H), 2.13-1.65 (m, 8 h), 0.82-0.52 (m, 4H). | 448.3 |
| 300 | 10-100 | | | 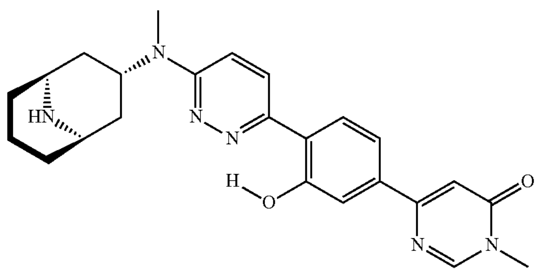 | 6-(4-(6-((((1R,3s,5S)-9-azabicyclo[3.3.1]nonan-3-yl)(methyl)amino)pyridazin-3-yl)-3-hydroxyphenyl)-3-methylpyrimidin-4(3H)-one | $^1$H NMR (500 MHz, DMSO-d$_6$) δ 13.71 (s, 1H), 8.56 (s, 1H), 8.26 (d, J = 9.9 Hz, 1H), 7.97 (d, J = 8.2 Hz, 1H), 7.64-7.58 (m, 2H), 7.31 (d, J = 9.9 Hz, 1H), 7.00 (s, 1H), 5.72-5.61 (m, 1H), 3.44 (s, 3 h), 3.21-3.16 (m, 2H), 2.94 (s, 3 h), 2.03-1.93 (m, 2H), 1.86-1.76 (m, 2H), 1.74-1.62 (m, 5H). | 433.3 |

TABLE 1B-continued

Exemplary SMSM compounds

| SMSM # | A-673 IC$_{50}$ (nM)$^A$ | Splice EC$_{50}$ (nM)$^B$ | Splice IC$_{50}$ (nM)$^C$ | Structure | Name | Proton NMR | M + H (MS) |
|---|---|---|---|---|---|---|---|
| 301 | 10-100 | | | 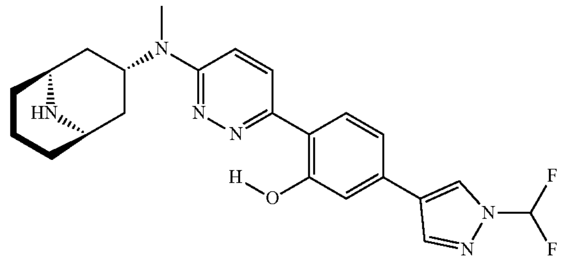 | 2-(6-(((1R,3s,5S)-9-azabicyclo[3.3.1]nonan-3-yl)(methyl)amino)pyridazin-3-yl)-5-(1-(difluoromethyl)-1H-pyrazol-4-yl)phenol | $^1$H NMR (500 MHz, DMSO-d$_6$) δ 13.86 (s, 1H), 8.80 (s, 1H), 8.35 (s, 1H), 8.27 (d, J = 10.0 Hz, 1H), 7.92 (d, J = 8.3 Hz, 1H), 7.85 (t, J = 59.5 Hz, 1H), 7.38-7.23 (m, 3 h), 5.82-5.64 (m, 1H), 3.54 (s, 2H), 2.95 (s, 3 h), 2.25-2.15 (m, 2H), 2.03-1.70 (m, 8 h). | 441.3 |
| 302 | 10-100 | | | 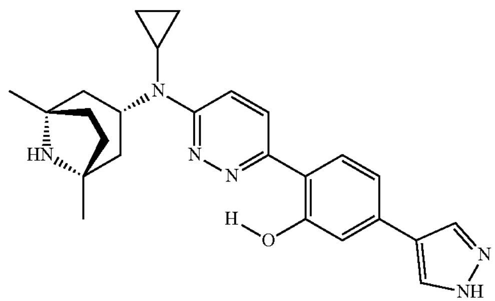 | 2-(6-(cyclopropyl((1R,3s,5S)-1,5-dimethyl-8-azabicyclo[3.2.1]octan-3-yl)amino)pyridazin-3-yl)-5-(1H-pyrazol-4-yl)phenol | 1H NMR (500 MHz, DMSO-d$_6$) δ 8.25 (d, J = 9.8 Hz, 1H), 8.12 (s, 2H), 7.84 (d, J = 8.3 Hz, 1H), 7.54 (d, J = 9.7 Hz, 1H), 7.21 (s, 1H), 7.17 (d, J = 8.0 Hz, 1H), 4.81-4.65 (m, 1H), 1.87-1.63 (m, 7H), 1.47 (d, J = 7.2 Hz, 2H), 1.17 (s, 6H), 0.98 (d, J = 5.5 Hz, 2H), 0.65 (s, 2H). | 431.2 |
| 303 | 10-100 | | | 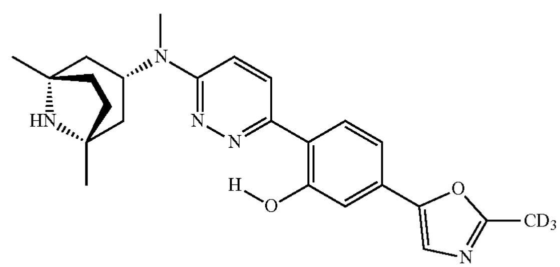 | 2-(6-(((1R,3s,5S)-1,5-dimethyl-8-azabicyclo[3.2.1]octan-3-yl)(methyl)amino)pyridazin-3-yl)-5-(2-(methyl-d3)oxazol-5-yl)phenol | $^1$H NMR (500 MHz, DMSO-d$_6$) δ 13.89 (s, 1H), 8.22 (d, J = 10.0 Hz, 1H), 7.95 (d, J = 8.8 Hz, 1H), 7.61 (s, 1H), 7.37 (d, J = 9.9 Hz, 1H), 7.25-7.18 (m, 2H), 5.02-4.90 (m, 1H), 2.94 (s, 3 h), 1.89-1.80 (m, 2H), 1.65-1.52 (m, 6 h), 1.18 (s, 6 h). | 423.3 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 304 | 10-100 | >1000 | <10 | 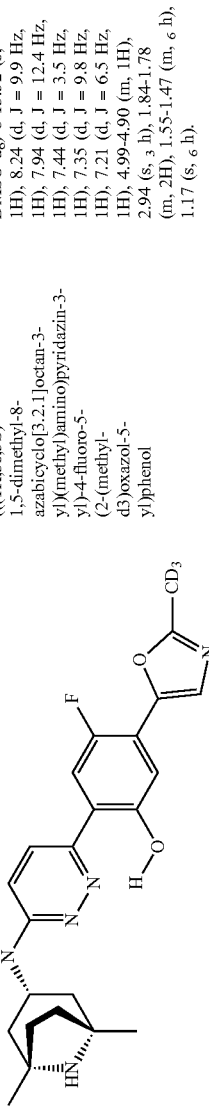 | 2-(6-(((1R,3s,5S)-1,5-dimethyl-8-azabicyclo[3.2.1]octan-3-yl)(methyl)amino)pyridazin-3-yl)-4-fluoro-5-(2-(methyl-d3)oxazol-5-yl)phenol | $^1$H NMR (500 MHz, DMSO-d$_6$) δ 13.52 (s, 1H), 8.24 (d, J = 9.9 Hz, 1H), 7.94 (d, J = 12.4 Hz, 1H), 7.44 (d, J = 3.5 Hz, 1H), 7.35 (d, J = 9.8 Hz, 1H), 7.21 (d, J = 6.5 Hz, 1H), 4.99-4.90 (m, 1H), 2.94 (s, 3h), 1.84-1.78 (m, 2H), 1.55-1.47 (m, 6 h), 1.17 (s, 6 h). | 441.3 |
| 305 | 101-250 | | | 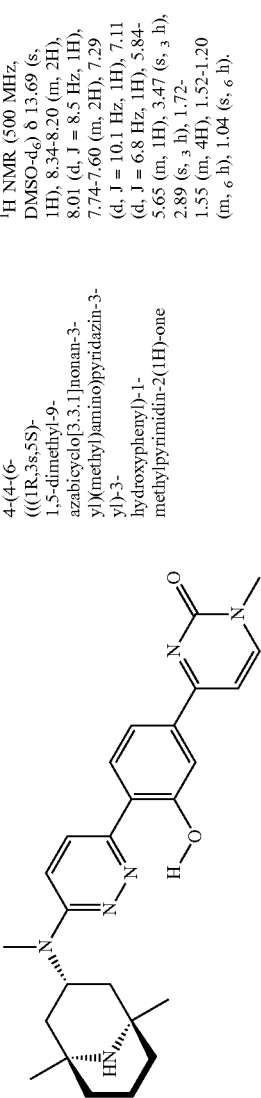 | 4-(4-(6-(((1R,3s,5S)-1,5-dimethyl-9-azabicyclo[3.3.1]nonan-3-yl)(methyl)amino)pyridazin-3-yl)-3-hydroxyphenyl)-1-methylpyrimidin-2(1H)-one | $^1$H NMR (500 MHz, DMSO-d$_6$) δ 13.69 (s, 1H), 8.34-8.20 (m, 2H), 8.01 (d, J = 8.5 Hz, 1H), 7.74-7.60 (m, 2H), 7.29 (d, J = 10.1 Hz, 1H), 7.11 (d, J = 6.8 Hz, 1H), 5.84-5.65 (m, 1H), 3.47 (s, 3 h), 2.89 (s, 3 h), 1.72-1.55 (m, 4H), 1.52-1.20 (m, 6 h), 1.04 (s, 6 h). | 461.3 |
| 306 | <10 | | | 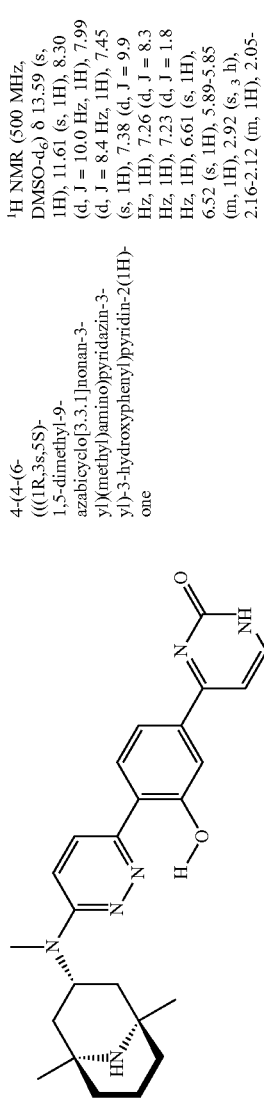 | 4-(4-(6-(((1R,3s,5S)-1,5-dimethyl-9-azabicyclo[3.3.1]nonan-3-yl)(methyl)amino)pyridazin-3-yl)-3-hydroxyphenyl)pyridin-2(1H)-one | $^1$H NMR (500 MHz, DMSO-d$_6$) δ 13.59 (s, 1H), 11.61 (s, 1H), 8.30 (d, J = 10.0 Hz, 1H), 7.99 (d, J = 8.4 Hz, 1H), 7.45 (s, 1H), 7.38 (d, J = 9.9 Hz, 1H), 7.26 (d, J = 8.3 Hz, 1H), 7.23 (d, J = 1.8 Hz, 1H), 6.61 (s, 1H), 6.52 (s, 1H), 5.89-5.85 (m, 1H), 2.92 (s, 3 h), 2.16-2.12 (m, 1H), 2.05-1.84 (m, 6 h), 1.74-1.70 (m, 3 h), 1.36 (s, 6 h). | 446.0 |

TABLE 1B-continued

Exemplary SMSM compounds

| SMSM # | A-673 IC$_{50}$ (nM)[A] | Splice EC$_{50}$ (nM)[B] | Splice IC$_{50}$ (nM)[C] | Structure | Name | Proton NMR | M + H (MS) |
|---|---|---|---|---|---|---|---|
| 307 | 10-100 | <10 | <10 | 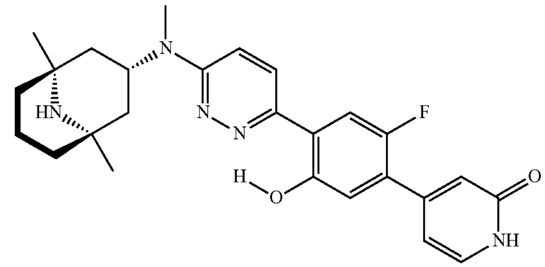 | 4-(4-(6-(((1R,3s,5S)-1,5-dimethyl-9-azabicyclo[3.3.1]nonan-3-yl)(methyl)amino)pyridazin-3-yl)-2-fluoro-5-hydroxyphenyl)pyridin-2(1H)-one | $^1$H NMR (500 MHz, DMSO-d$_6$) δ 13.25 (s, 1H), 11.71 (s, 1H), 9.17 (s, 1H), 8.65 (s, 1H), 8.31 (d, J = 10.0 Hz, 1H), 7.93 (d, J = 12.3 Hz, 1H), 7.47 (d, J = 1.3 Hz, 1H), 7.36 (d, J = 9.9 Hz, 1H), 7.07 (d, J = 6.9 Hz, 1H), 6.50 (s, 1H), 6.38 (d, J = 7.2 Hz, 1H), 5.89 (m, 1H), 2.96 (s, 3 h), 2.14 (m, 1H), 2.06-1.84 (m, 6 h), 1.80-1.60 (m, 3 h), 1.38 (s, 6 h). | 464.0 |
| 308 | 501-1000 | | | 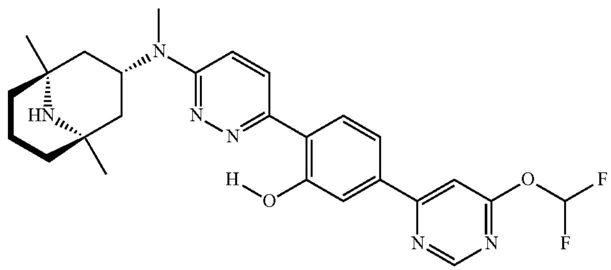 | 5-(2-(difluoromethoxy)pyridin-4-yl)-2-(6-(((1R,3s,5S)-1,5-dimethyl-9-azabicyclo[3.3.1]nonan-3-yl)(methyl)amino)pyridazin-3-yl)phenol | $^1$H NMR (500 MHz, DMSO-d$_6$) δ 13.76 (s, 1H), 9.25-9.12 (m, 1H), 8.70-8.59 (m, 1H), 8.38-8.30 (m, 2H), 8.07-8.01 (m, 1H), 7.77 (t, J = 73 Hz, 1H), 7.68-7.65 (m, 1H), 7.48-7.34 (m, 4H), 5.96-5.83 (m, 1H), 2.97 (s, 3 h), 2.05-1.86 (m, 5H), 1.79-1.61 (m, 3 h), 1.39 (s, 6 h). | 496.3 |

[A]Cell viability
[B]FoxM1 A mRNA increase (exon excluded)
[C]FoxM1 BC mRNA decrease (exon included)

TABLE 1C

Exemplary SMSM compounds

| SMSM# | Structure | Name |
|---|---|---|
| 309 | 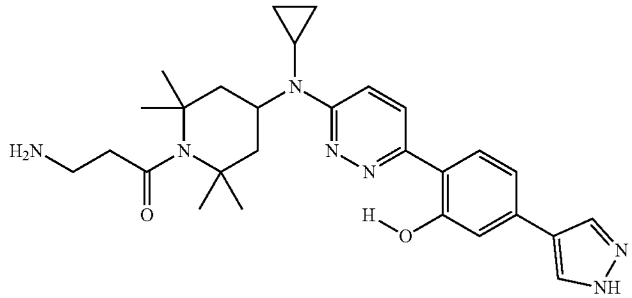 [SMILES: CC1(C)CC(N(c2ccc(-c3ccc(-c4cn[nH]c4)cc3O)nn2)C2CC2)CC(C)(C)N1C(=O)CCN] | 3-amino-1-(4-(cyclopropyl(6-(2-hydroxy-4-(1H-pyrazol-4-yl)phenyl)pyridazin-3-yl)amino)-2,2,6,6-tetramethylpiperidin-1-yl)propan-1-one |
| 310 | 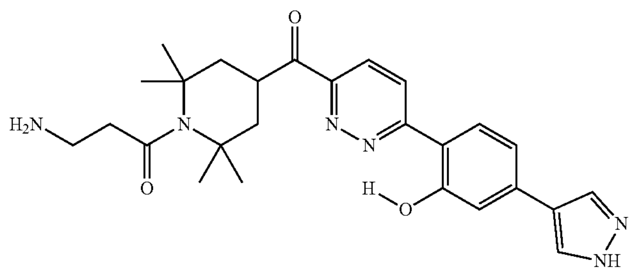 | 3-amino-1-(4-(6-(2-hydroxy-4-(1H-pyrazol-4-yl)phenyl)pyridazine-3-carbonyl)-2,2,6,6-tetramethylpiperidin-1-yl)propan-1-one |
| 311 | 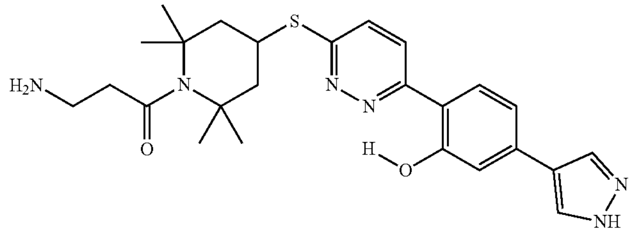 [SMILES: CC1(C)CC(Sc2ccc(-c3ccc(-c4cn[nH]c4)cc3O)nn2)CC(C)(C)N1C(=O)CCN] | 3-amino-1-(4-((6-(2-hydroxy-4-(1H-pyrazol-4-yl)phenyl)pyridazin-3-yl)thio)-2,2,6,6-tetramethylpiperidin-1-yl)propan-1-one |
| 312 | 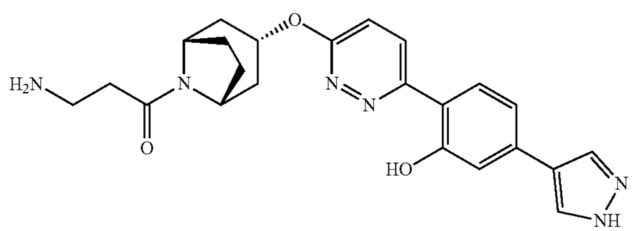 [SMILES: NCCC(=O)N1[C@@H]2CC[C@H]1C[C@H](Oc1ccc(-c3ccc(-c4cn[nH]c4)cc3O)nn1)C2] | 3-amino-1-((1R,3s,5S)-3-((6-(2-hydroxy-4-(1H-pyrazol-4-yl)phenyl)pyridazin-3-yl)oxy)-8-azabicyclo[3.2.1]octan-8-yl)propan-1-one |
| 313 | 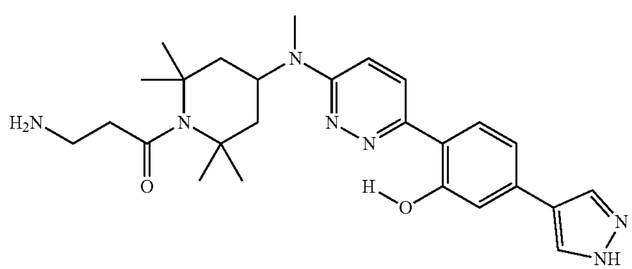 [SMILES: CN(c1ccc(-c2ccc(-c3cn[nH]c3)cc2O)nn1)C1CC(C)(C)N(C(=O)CCN)C(C)(C)C1] | 3-amino-1-(4-((6-(2-hydroxy-4-(1H-pyrazol-4-yl)phenyl)pyridazin-3-yl)(methyl)amino)-2,2,6,6-tetramethylpiperidin-1-yl)propan-1-one |
| 314 | 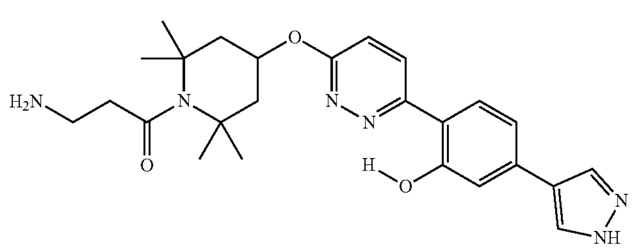 | 3-amino-1-(4-((6-(2-hydroxy-4-(1H-pyrazol-4-yl)phenyl)pyridazin-3-yl)oxy)-2,2,6,6-tetramethylpiperidin-1-yl)propan-1-one |

TABLE 1C-continued

Exemplary SMSM compounds

| SMSM# | Structure | Name |
|---|---|---|
| 315 | 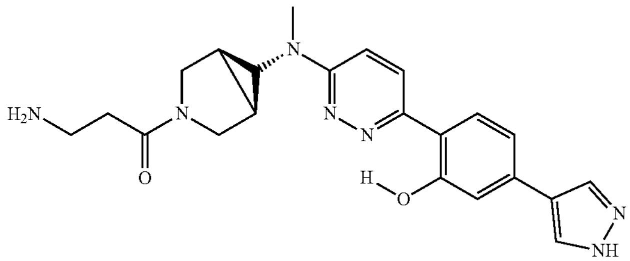 | 3-amino-1-((1R,5S)-6-((6-(2-hydroxy-4-(1H-pyrazol-4-yl)phenyl)pyridazin-3-yl)(methyl)amino)-3-azabicyclo[3.1.0]hexan-3-yl)propan-1-one |
| 316 | 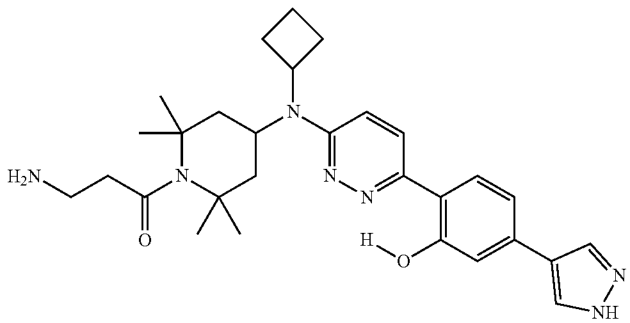 [SMILES: CC1(C)CC(N(c2ccc(-c3ccc(-c4cn[nH]c4)cc3O)nn2)C2CCC2)CC(C)(C)N1C(=O)CCN] | 3-amino-1-(4-(cyclobutyl(6-(2-hydroxy-4-(1H-pyrazol-4-yl)phenyl)pyridazin-3-yl)amino)-2,2,6,6-tetramethylpiperidin-1-yl)propan-1-one |
| 317 | 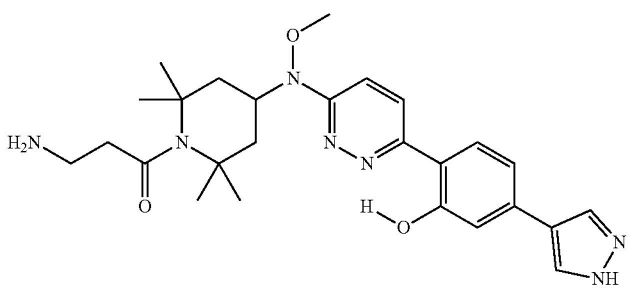 [SMILES: CON(c1ccc(-c2ccc(-c3cn[nH]c3)cc2O)nn1)C1CC(C)(C)N(C(=O)CCN)C(C)(C)C1] | 3-amino-1-(4-((6-(2-hydroxy-4-(1H-pyrazol-4-yl)phenyl)pyridazin-3-yl)(methoxy)amino)-2,2,6,6-tetramethylpiperidin-1-yl)propan-1-one |
| 318 | 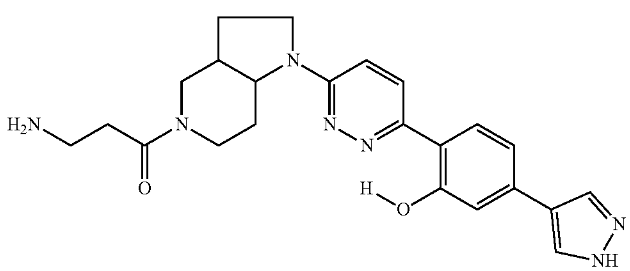 [SMILES: NCCC(=O)N1CCC2C(CCN2c2ccc(-c3ccc(-c4cn[nH]c4)cc3O)nn2)C1] | 3-amino-1-(1-(6-(2-hydroxy-4-(1H-pyrazol-4-yl)phenyl)pyridazin-3-yl)octahydro-5H-pyrrolo[3,2-c]pyridin-5-yl)propan-1-one |
| 319 | 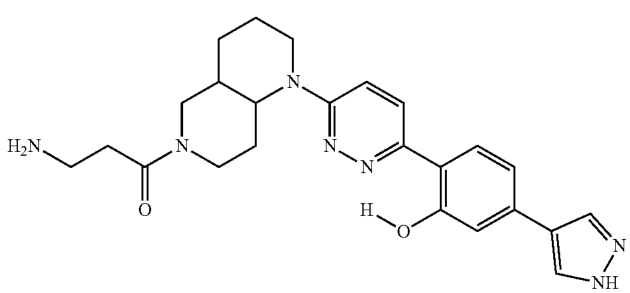 [SMILES: NCCC(=O)N1CCC2C(CCCN2c2ccc(-c3ccc(-c4cn[nH]c4)cc3O)nn2)C1] | 3-amino-1-(1-(6-(2-hydroxy-4-(1H-pyrazol-4-yl)phenyl)pyridazin-3-yl)octahydro-1,6-naphthyridin-6(2H)-yl)propan-1-one |

333
334

TABLE 1C-continued

Exemplary SMSM compounds

| SMSM# | Structure | Name |
|---|---|---|
| 320 | 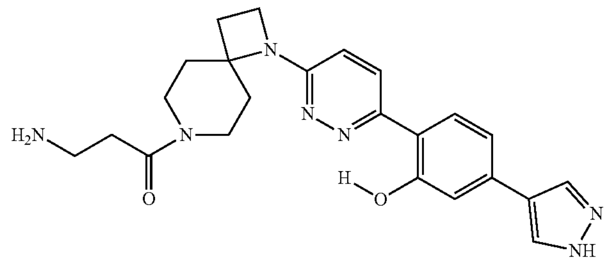 [SMILES: NCCC(=O)N1CCC2(CC1)CCN2c1ccc(-c2ccc(-c3cn[nH]c3)cc2O)nn1] | 3-amino-1-(1-(6-(2-hydroxy-4-(1H-pyrazol-4-yl)phenyl)pyridazin-3-yl)-1,7-diazaspiro[3.5]nonan-7-yl)propan-1-one |
| 321 | 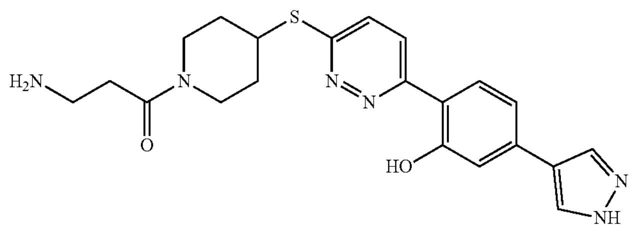 [SMILES: NCCC(=O)N1CCC(Sc2ccc(-c3ccc(-c4cn[nH]c4)cc3O)nn2)CC1] | 3-amino-1-(4-((6-(2-hydroxy-4-(1H-pyrazol-4-yl)phenyl)pyridazin-3-yl)thio)piperidin-1-yl)propan-1-one |
| 322 | 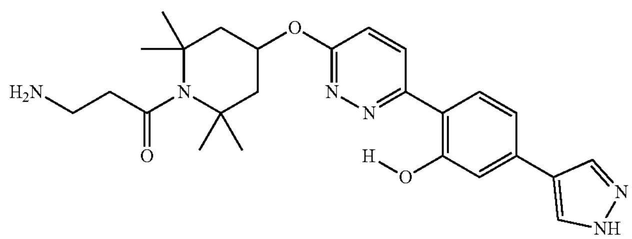 | 3-amino-1-(4-((6-(2-hydroxy-4-(1H-pyrazol-4-yl)phenyl)pyridazin-3-yl)oxy)-2,2,6,6-tetramethylpiperidin-1-yl)propan-1-one |
| 323 | 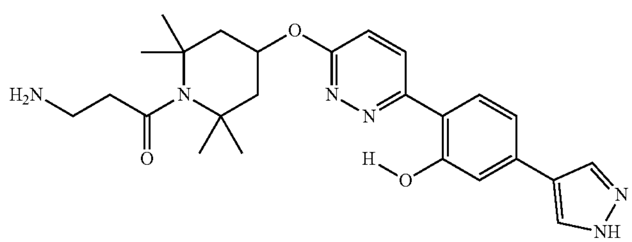 [SMILES: CC1(C)CC(Oc2ccc(-c3ccc(-c4cn[nH]c4)cc3O)nn2)CC(C)(C)N1C(=O)CCN] | 3-amino-1-(4-((6-(2-hydroxy-4-(1H-pyrazol-4-yl)phenyl)pyridazin-3-yl)(methyl)amino)-2,2,6,6-tetramethylpiperidin-1-yl)propan-1-one |
| 324 | 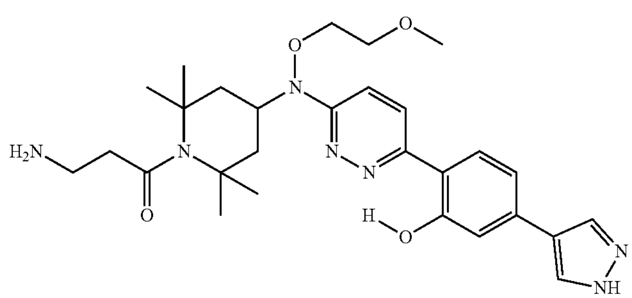 [SMILES: COCCON(c1ccc(-c2ccc(-c3cn[nH]c3)cc2O)nn1)C1CC(C)(C)N(C(=O)CCN)C(C)(C)C1] | 3-amino-1-(4-((6-(2-hydroxy-4-(1H-pyrazol-4-yl)phenyl)pyridazin-3-yl)(2-methoxyethoxy)amino)-2,2,6,6-tetramethylpiperidin-1-yl)propan-1-one |
| 325 | 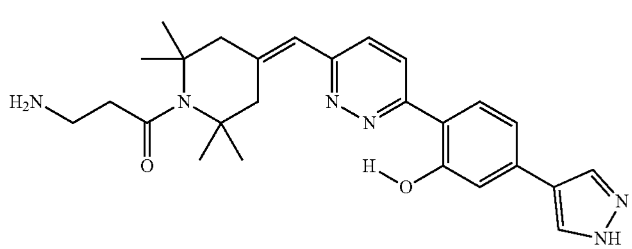 [SMILES: CC1(C)CC(=Cc2ccc(-c3ccc(-c4cn[nH]c4)cc3O)nn2)CC(C)(C)N1C(=O)CCN] | 3-amino-1-(4-((6-(2-hydroxy-4-(1H-pyrazol-4-yl)phenyl)pyridazin-3-yl)methylene)-2,2,6,6-tetramethylpiperidin-1-yl)propan-1-one |

TABLE 1C-continued

Exemplary SMSM compounds

| SMSM# | Structure | Name |
|---|---|---|
| 326 | 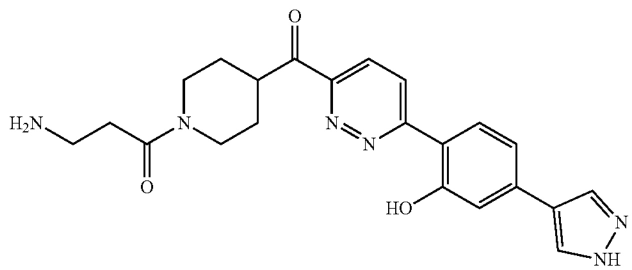 [SMILES: NCCC(=O)N1CCC(C(=O)c2ccc(-c3ccc(-c4cn[nH]c4)cc3O)nn2)CC1] | 3-amino-1-(4-(6-(2-hydroxy-4-(1H-pyrazol-4-yl)phenyl)pyridazine-3-carbonyl)piperidin-1-yl)propan-1-one |
| 327 | 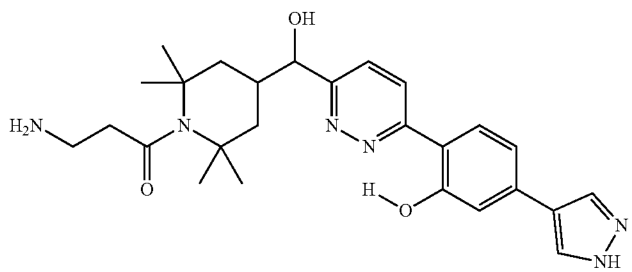 [SMILES: CC1(C)CC(C(O)c2ccc(-c3ccc(-c4cn[nH]c4)cc3O)nn2)CC(C)(C)N1C(=O)CCN] | 3-amino-1-(4-(hydroxy(6-(2-hydroxy-4-(1H-pyrazol-4-yl)phenyl)pyridazin-3-yl)methyl)-2,2,6,6-tetramethylpiperidin-1-yl)propan-1-one |
| 328 | 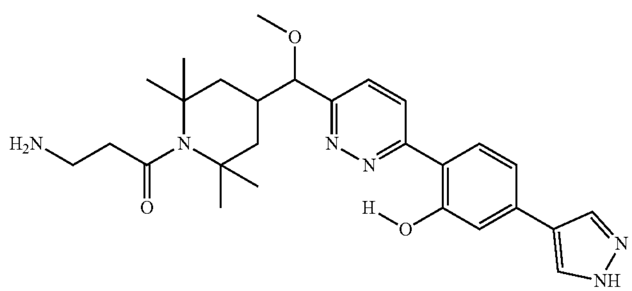 [SMILES: COC(c1ccc(-c2ccc(-c3cn[nH]c3)cc2O)nn1)C1CC(C)(C)N(C(=O)CCN)C(C)(C)C1] | 3-amino-1-(4-((6-(2-hydroxy-4-(1H-pyrazol-4-yl)phenyl)pyridazin-3-yl)(methoxy)methyl)-2,2,6,6-tetramethylpiperidin-1-yl)propan-1-one |
| 329 | 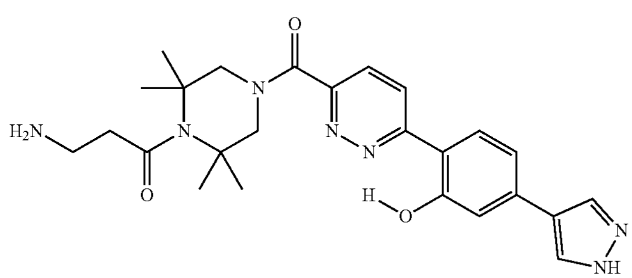 [SMILES: CC1(C)CN(C(=O)c2ccc(-c3ccc(-c4cn[nH]c4)cc3O)nn2)CC(C)(C)N1C(=O)CCN] | 3-amino-1-(4-(6-(2-hydroxy-4-(1H-pyrazol-4-yl)phenyl)pyridazine-3-carbonyl)-2,2,6,6-tetramethylpiperazin-1-yl)propan-1-one |
| 330 | 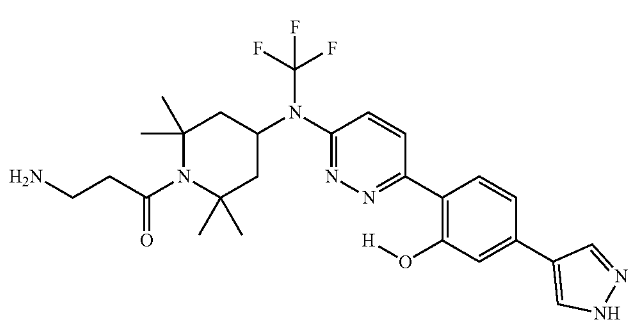 [SMILES: CC1(C)CC(N(c2ccc(-c3ccc(-c4cn[nH]c4)cc3O)nn2)C(F)(F)F)CC(C)(C)N1C(=O)CCN] | 3-amino-1-(4-((6-(2-hydroxy-4-(1H-pyrazol-4-yl)phenyl)pyridazin-3-yl)(trifluoromethyl)amino)-2,2,6,6-tetramethylpiperidin-1-yl)propan-1-one |

TABLE 1C-continued

Exemplary SMSM compounds

| SMSM# | Structure | Name |
|---|---|---|
| 331 | 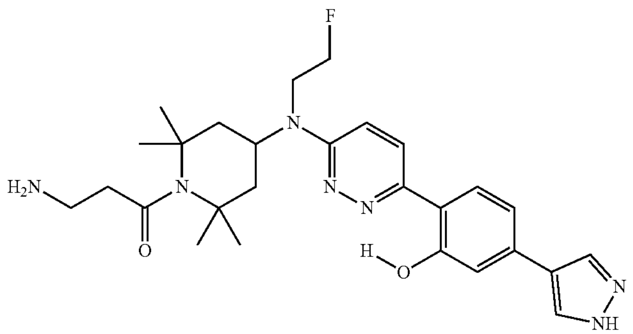 [SMILES: CC1(C)CC(N(CCF)c2ccc(-c3ccc(-c4cn[nH]c4)cc3O)nn2)CC(C)(C)N1C(=O)CCN] | 3-amino-1-(4-((2-fluoroethyl)(6-(2-hydroxy-4-(1H-pyrazol-4-yl)phenyl)pyridazin-3-yl)amino)-2,2,6,6-tetramethylpiperidin-1-yl)propan-1-one |
| 332 | 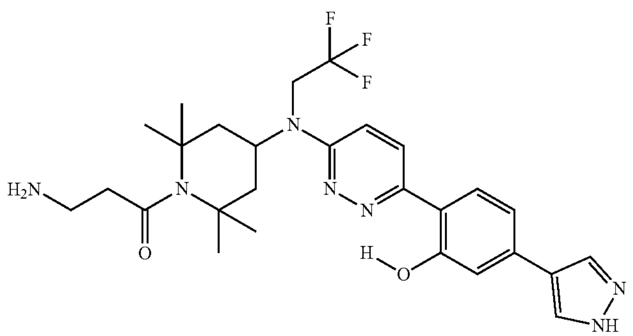 [SMILES: CC1(C)CC(N(CC(F)(F)F)c2ccc(-c3ccc(-c4cn[nH]c4)cc3O)nn2)CC(C)(C)N1C(=O)CCN] | 3-amino-1-(4-((6-(2-hydroxy-4-(1H-pyrazol-4-yl)phenyl)pyridazin-3-yl)(2,2,2-trifluoroethyl)amino)-2,2,6,6-tetramethylpiperidin-1-yl)propan-1-one |
| 333 | 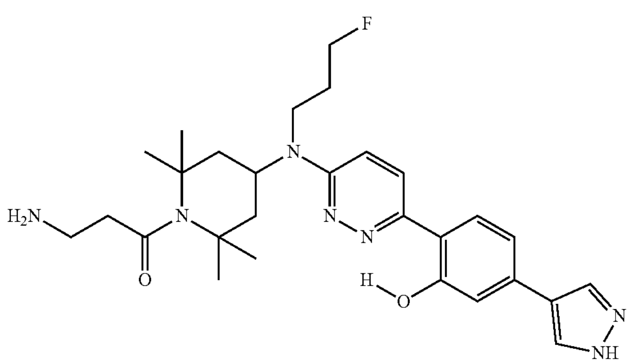 [SMILES: CC1(C)CC(N(CCCF)c2ccc(-c3ccc(-c4cn[nH]c4)cc3O)nn2)CC(C)(C)N1C(=O)CCN] | 3-amino-1-(4-((3-fluoropropyl)(6-(2-hydroxy-4-(1H-pyrazol-4-yl)phenyl)pyridazin-3-yl)amino)-2,2,6,6-tetramethylpiperidin-1-yl)propan-1-one |
| 334 | 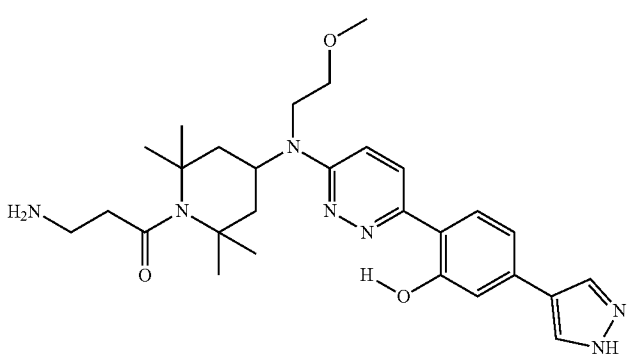 [SMILES: COCCN(c1ccc(-c2ccc(-c3cn[nH]c3)cc2O)nn1)C1CC(C)(C)N(C(=O)CCN)C(C)(C)C1] | 3-amino-1-(4-((6-(2-hydroxy-4-(1H-pyrazol-4-yl)phenyl)pyridazin-3-yl)(2-methoxyethyl)amino)-2,2,6,6-tetramethylpiperidin-1-yl)propan-1-one |

TABLE 1C-continued

Exemplary SMSM compounds

| SMSM# | Structure | Name |
|---|---|---|
| 335 | 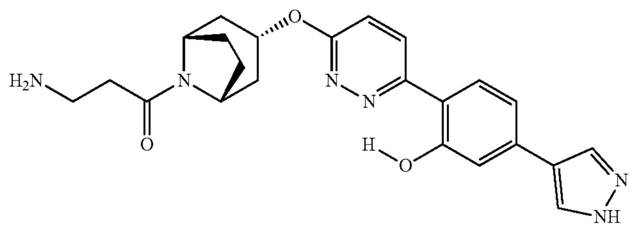 [SMILES: NCCC(=O)N1[C@@H]2CC[C@H]1C[C@H](Oc1ccc(-c3ccc(-c4cn[nH]c4)cc3O)nn1)C2] | 3-amino-1-((1R,3s,5S)-3-((6-(2-hydroxy-4-(1H-pyrazol-4-yl)phenyl)pyridazin-3-yl)oxy)-8-azabicyclo[3.2.1]octan-8-yl)propan-1-one |
| 336 | 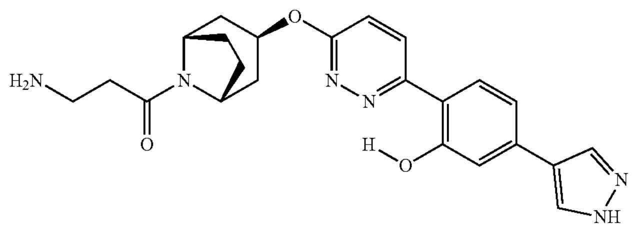 [SMILES: NCCC(=O)N1[C@@H]2CC[C@H]1C[C@@H](Oc1ccc(-c3ccc(-c4cn[nH]c4)cc3O)nn1)C2] | 3-amino-1-((1R,3r,5S)-3-((6-(2-hydroxy-4-(1H-pyrazol-4-yl)phenyl)pyridazin-3-yl)oxy)-8-azabicyclo[3.2.1]octan-8-yl)propan-1-one |
| 337 | 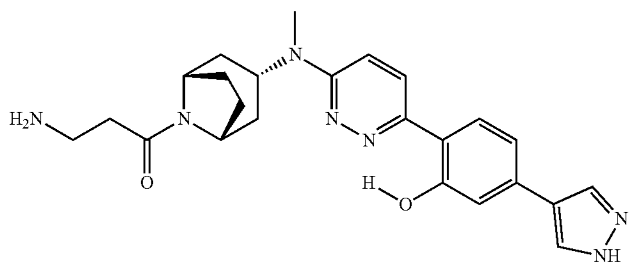 [SMILES: CN(c1ccc(-c2ccc(-c3cn[nH]c3)cc2O)nn1)[C@@H]1C[C@H]2CC[C@@H](C1)N2C(=O)CCN] | 3-amino-1-((1R,3s,5S)-3-((6-(2-hydroxy-4-(1H-pyrazol-4-yl)phenyl)pyridazin-3-yl)(methyl)amino)-8-azabicyclo[3.2.1]octan-8-yl)propan-1-one |
| 338 | 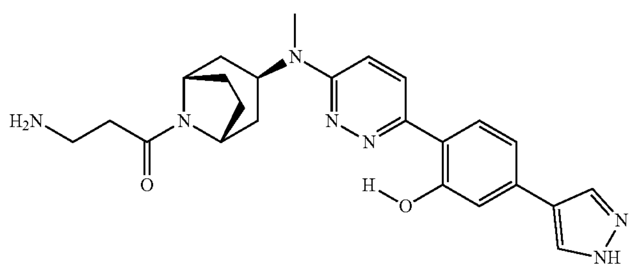 [SMILES: CN(c1ccc(-c2ccc(-c3cn[nH]c3)cc2O)nn1)[C@H]1C[C@H]2CC[C@@H](C1)N2C(=O)CCN] | 3-amino-1-((1R,3r,5S)-3-((6-(2-hydroxy-4-(1H-pyrazol-4-yl)phenyl)pyridazin-3-yl)(methyl)amino)-8-azabicyclo[3.2.1]octan-8-yl)propan-1-one |
| 339 | 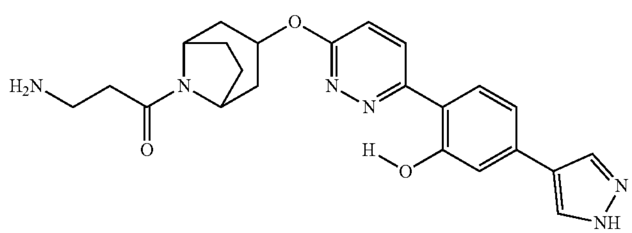 [SMILES: NCCC(=O)N1C2CCC1CC(Oc1ccc(-c3ccc(-c4cn[nH]c4)cc3O)nn1)C2] | 3-amino-1-(3-((6-(2-hydroxy-4-(1H-pyrazol-4-yl)phenyl)pyridazin-3-yl)oxy)-8-azabicyclo[3.2.1]octan-8-yl)propan-1-one |
| 340 | 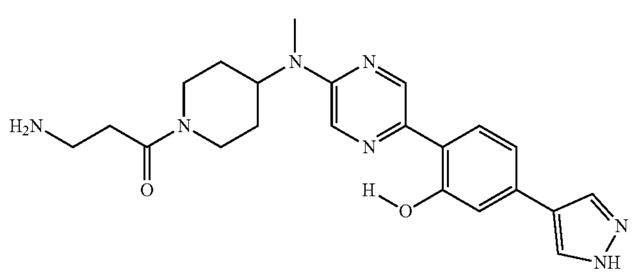 [SMILES: CN(c1cnc(-c2ccc(-c3cn[nH]c3)cc2O)cn1)C1CCN(C(=O)CCN)CC1] | 3-amino-1-(4-((5-(2-hydroxy-4-(1H-pyrazol-4-yl)phenyl)pyrazin-2-yl)(methyl)amino)piperidin-1-yl)propan-1-one |

TABLE 1C-continued

Exemplary SMSM compounds

| SMSM# | Structure | Name |
|---|---|---|
| 341 | 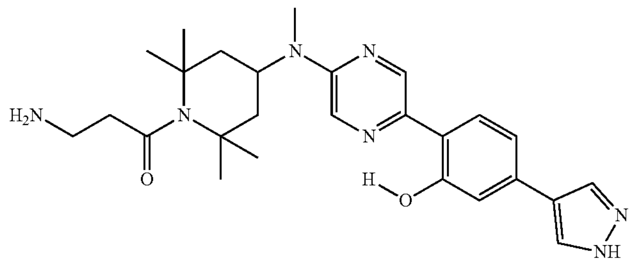 [SMILES: CN(c1cnc(-c2ccc(-c3cn[nH]c3)cc2O)cn1)C1CC(C)(C)N(C(=O)CCN)C(C)(C)C1] | 3-amino-1-(4-((5-(2-hydroxy-4-(1H-pyrazol-4-yl)phenyl)pyrazin-2-yl)(methyl)amino)-2,2,6,6-tetramethylpiperidin-1-yl)propan-1-one |
| 342 | 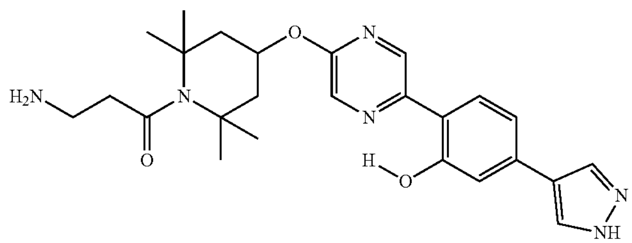 [SMILES: CC1(C)CC(Oc2cnc(-c3ccc(-c4cn[nH]c4)cc3O)cn2)CC(C)(C)N1C(=O)CCN] | 3-amino-1-(4-((5-(2-hydroxy-4-(1H-pyrazol-4-yl)phenyl)pyrazin-2-yl)oxy)-2,2,6,6-tetramethylpiperidin-1-yl)propan-1-one |
| 343 | 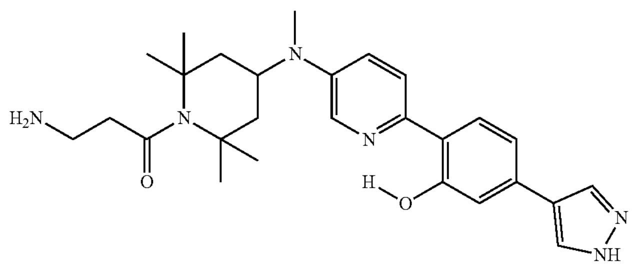 [SMILES: CN(c1ccc(-c2ccc(-c3cn[nH]c3)cc2O)nc1)C1CC(C)(C)N(C(=O)CCN)C(C)(C)C1] | 3-amino-1-(4-((6-(2-hydroxy-4-(1H-pyrazol-4-yl)phenyl)pyridin-3-yl)(methyl)amino)-2,2,6,6-tetramethylpiperidin-1-yl)propan-1-one |
| 344 | 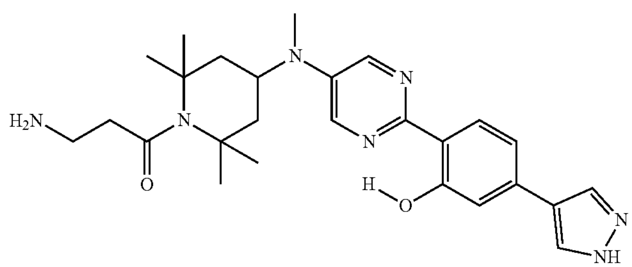 [SMILES: CN(c1cnc(-c2ccc(-c3cn[nH]c3)cc2O)nc1)C1CC(C)(C)N(C(=O)CCN)C(C)(C)C1] | 3-amino-1-(4-((2-(2-hydroxy-4-(1H-pyrazol-4-yl)phenyl)pyrimidin-5-yl)(methyl)amino)-2,2,6,6-tetramethylpiperidin-1-yl)propan-1-one |
| 345 | 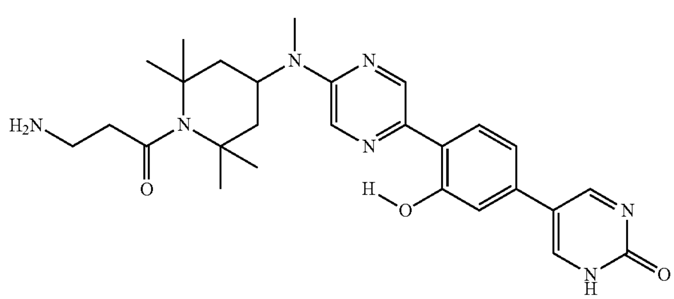 [SMILES: CN(c1cnc(-c2ccc(-c3cnc(=O)[nH]c3)cc2O)cn1)C1CC(C)(C)N(C(=O)CCN)C(C)(C)C1] | 5-(4-(5-((1-(3-aminopropanoyl)-2,2,6,6-tetramethylpiperidin-4-yl)(methyl)amino)pyrazin-2-yl)-3-hydroxyphenyl)pyrimidin-2(1H)-one |

TABLE 1C-continued

Exemplary SMSM compounds

| SMSM# | Structure | Name |
|---|---|---|
| 346 | 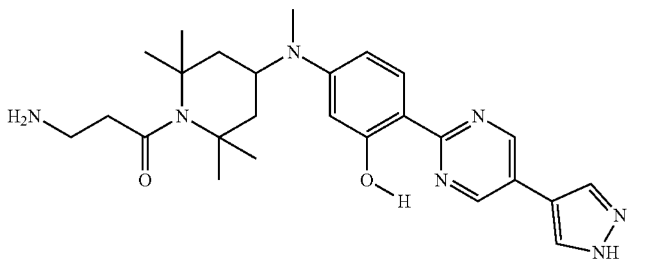 [SMILES: CN(c1ccc(-c2ncc(-c3cn[nH]c3)cn2)c(O)c1)C1CC(C)(C)N(C(=O)CCN)C(C)(C)C1] | 1-(4-((4-(5-(1H-pyrazol-4-yl)pyrimidin-2-yl)-3-hydroxyphenyl)(methyl)amino)-2,2,6,6-tetramethylpiperidin-1-yl)-3-aminopropan-1-one |
| 347 | 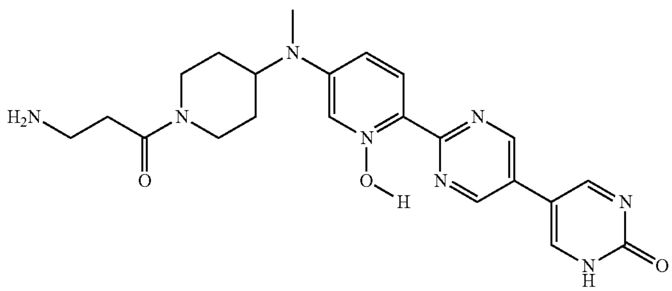 | 2'-(4-((1-(3-aminopropanoyl)piperidin-4-yl)(methyl)amino)-2-hydroxyphenyl)-[5,5'-bipyrimidin]-2(1H)-one |
| 348 | 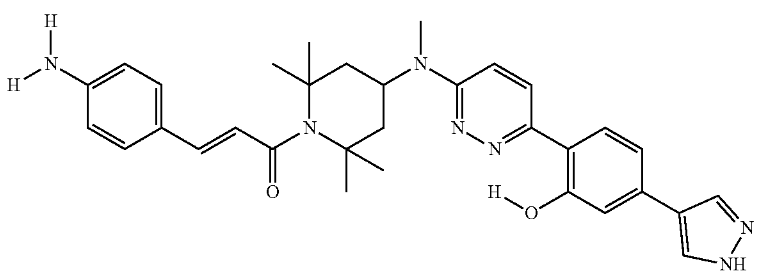 [SMILES: CN(c1ccc(-c2ccc(-c3cn[nH]c3)cc2O)nn1)C1CC(C)(C)N(C(=O)/C=C/c2ccc(N)cc2)C(C)(C)C1] | (E)-3-(4-aminophenyl)-1-(4-((6-(2-hydroxy-4-(1H-pyrazol-4-yl)phenyl)pyridazin-3-yl)(methyl)amino)-2,2,6,6-tetramethylpiperidin-1-yl)prop-2-en-1-one |
| 349 | 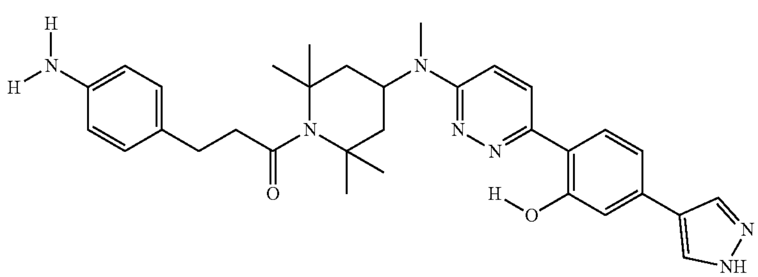 [SMILES: CN(c1ccc(-c2ccc(-c3cn[nH]c3)cc2O)nn1)C1CC(C)(C)N(C(=O)CCc2ccc(N)cc2)C(C)(C)C1] | 3-(4-aminophenyl)-1-(4-((6-(2-hydroxy-4-(1H-pyrazol-4-yl)phenyl)pyridazin-3-yl)(methyl)amino)-2,2,6,6-tetramethylpiperidin-1-yl)propan-1-one |
| 350 | 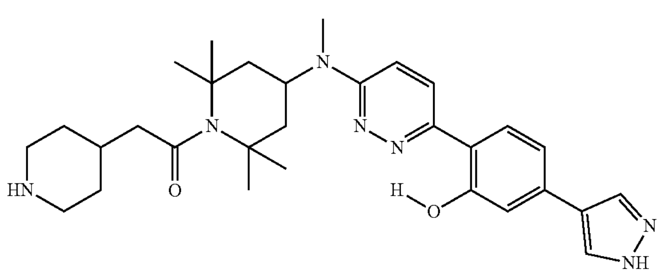 [SMILES: CN(c1ccc(-c2ccc(-c3cn[nH]c3)cc2O)nn1)C1CC(C)(C)N(C(=O)CC2CCNCC2)C(C)(C)C1] | 1-(4-((6-(2-hydroxy-4-(1H-pyrazol-4-yl)phenyl)pyridazin-3-yl)(methyl)amino)-2,2,6,6-tetramethylpiperidin-1-yl)-2-(piperidin-4-yl)ethan-1-one |

TABLE 1C-continued

Exemplary SMSM compounds

| SMSM# | Structure | Name |
|---|---|---|
| 351 | 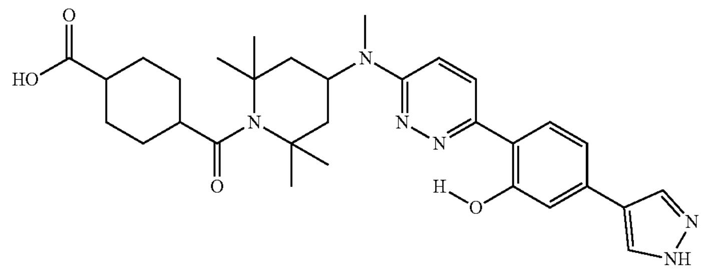 [SMILES: CN(c1ccc(-c2ccc(-c3cn[nH]c3)cc2O)nn1)C1CC(C)(C)N(C(=O)C2CCC(C(=O)O)CC2)C(C)(C)C1] | 4-(4-((6-(2-hydroxy-4-(1H-pyrazol-4-yl)phenyl)pyridazin-3-yl)(methyl)amino)-2,2,6,6-tetramethylpiperidine-1-carbonyl)cyclohexane-1-carboxylic acid |
| 352 | 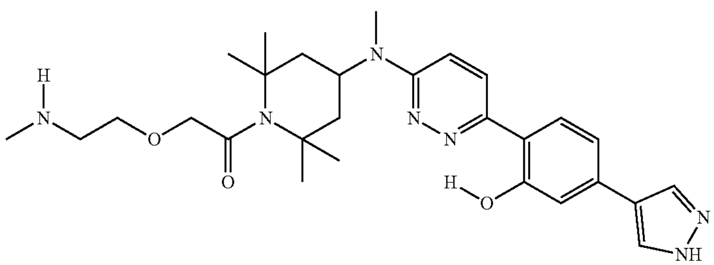 [SMILES: CNCCOCC(=O)N1C(C)(C)CC(N(C)c2ccc(-c3ccc(-c4cn[nH]c4)cc3O)nn2)CC1(C)C] | 1-(4-((6-(2-hydroxy-4-(1H-pyrazol-4-yl)phenyl)pyridazin-3-yl)(methyl)amino)-2,2,6,6-tetramethylpiperidin-1-yl)-2-(2-(methylamino)ethoxy)ethan-1-one |
| 353 | 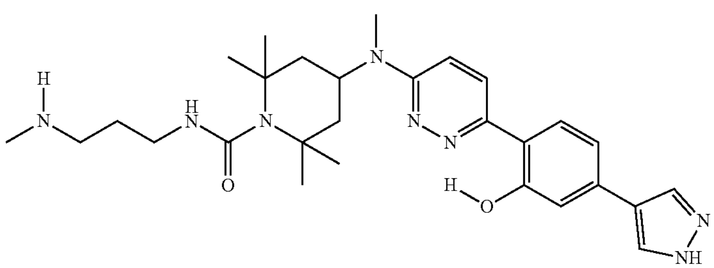 [SMILES: CNCCCNC(=O)N1C(C)(C)CC(N(C)c2ccc(-c3ccc(-c4cn[nH]c4)cc3O)nn2)CC1(C)C] | 4-((6-(2-hydroxy-4-(1H-pyrazol-4-yl)phenyl)pyridazin-3-yl)(methyl)amino)-2,2,6,6-tetramethyl-N-(3-(methylamino)propyl)piperidine-1-carboxamide |
| 354 | 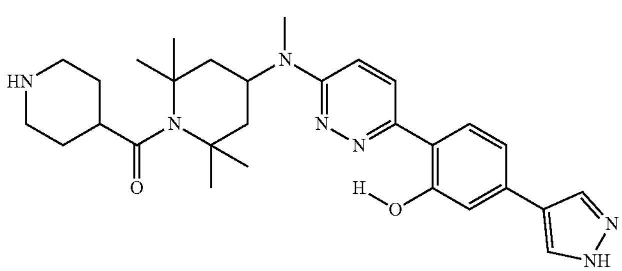 [SMILES: CN(c1ccc(-c2ccc(-c3cn[nH]c3)cc2O)nn1)C1CC(C)(C)N(C(=O)C2CCNCC2)C(C)(C)C1] | (4-((6-(2-hydroxy-4-(1H-pyrazol-4-yl)phenyl)pyridazin-3-yl)(methyl)amino)-2,2,6,6-tetramethylpiperidin-1-yl)(piperidin-4-yl)methanone |
| 355 | 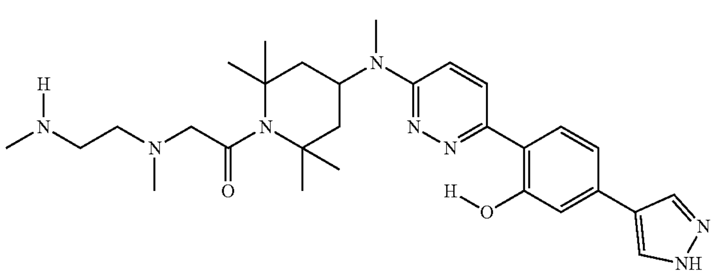 [SMILES: CNCCN(C)CC(=O)N1C(C)(C)CC(N(C)c2ccc(-c3ccc(-c4cn[nH]c4)cc3O)nn2)CC1(C)C] | 1-(4-((6-(2-hydroxy-4-(1H-pyrazol-4-yl)phenyl)pyridazin-3-yl)(methyl)amino)-2,2,6,6-tetramethylpiperidin-1-yl)-2-(methyl(2-(methylamino)ethyl)amino)ethan-1-one |

TABLE 1C-continued

Exemplary SMSM compounds

| SMSM# | Structure | Name |
|---|---|---|
| 356 | 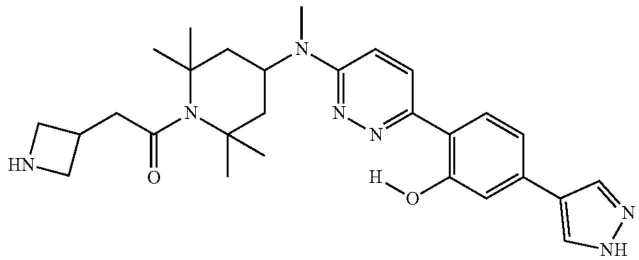 [SMILES: CN(c1ccc(-c2ccc(-c3cn[nH]c3)cc2O)nn1)C1CC(C)(C)N(C(=O)CC2CNC2)C(C)(C)C1] | 2-(azetidin-3-yl)-1-(4-((6-(2-hydroxy-4-(1H-pyrazol-4-yl)phenyl)pyridazin-3-yl)(methyl)amino)-2,2,6,6-tetramethylpiperidin-1-yl)ethan-1-one |
| 357 | 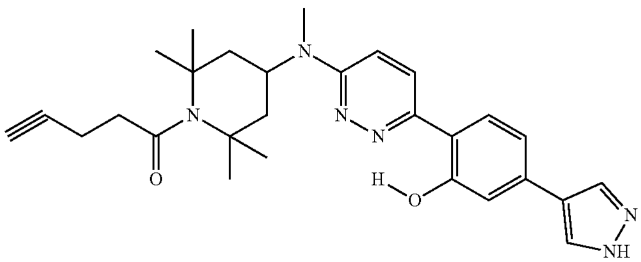 [SMILES: C#CCCC(=O)N1C(C)(C)CC(N(C)c2ccc(-c3ccc(-c4cn[nH]c4)cc3O)nn2)CC1(C)C] | 1-(4-((6-(2-hydroxy-4-(1H-pyrazol-4-yl)phenyl)pyridazin-3-yl)(methyl)amino)-2,2,6,6-tetramethylpiperidin-1-yl)pent-4-yn-1-one |

In some embodiments, a compound is selected from:
6-chloro-N-(2,2,6,6-tetramethylpiperidin-4-yl)pyridazin-3-amine;
6-chloro-N-cyclopropyl-N-(2,2,6,6-tetramethylpiperidin-4-yl)pyridazin-3-amine;
6-(4-chloro-2-methoxyphenyl)-N-cyclopropyl-N-(2,2,6,6-tetramethylpiperidin-4-yl)pyridazin-3-amine;
N-cyclopropyl-6-(2-methoxy-4-(1H-pyrazol-4-yl)phenyl)-N-(2,2,6,6-tetramethylpiperidin-4-yl)pyridazin-3-amine;
tert-butyl (1R,3S,5S)-3-((6-chloropyridazin-3-yl)amino)-8-azabicyclo[3.2.1]octane-8-carboxylate;
tert-butyl (1R,3s,5S)-3-((6-chloropyridazin-3-yl)(methyl)amino)-8-azabicyclo[3.2.1]octane-8-carboxylate;
tert-butyl(1R,3s,5S)-3-((6-(4-chloro-2-methoxyphenyl)pyridazin-3-yl)(methyl)amino)-8-azabicyclo[3.2.1]octane-8-carboxylate;
tert-butyl(1R,3s,5S)-3-((6-(2-methoxy-4-(1H-pyrazol-4-yl)phenyl)pyridazin-3-yl)(methyl)amino)-8-azabicyclo[3.2.1]octane-8-carboxylate;
tert-butyl(1R,3s,5S)-3-((6-(2-hydroxy-4-(1H-pyrazol-4-yl)phenyl)pyridazin-3-yl)(methyl)amino)-8-azabicyclo[3.2.1]octane-8-carboxylate;
tert-butyl (1R,3s,5S)-3-((6-chloropyridazin-3-yl)(methyl)amino)-9-azabicyclo[3.3.1]nonane-9-carboxylate;
tert-butyl(1R,3s,5S)-3-((6-(2-(methoxymethoxy)-4-(1-(tetrahydro-2H-pyran-2-yl)-1H-pyrazol-4-yl)phenyl)pyridazin-3-yl)(methyl)amino)-9-azabicyclo[3.3.1]nonane-9-carboxylate;
(1R,3s,5S)—N-(6-chloropyridazin-3-yl)-9-(4-methoxybenzyl)-1,5-dimethyl-9-azabicyclo[3.3.1]nonan-3-amine;
(1R,3s,5S)—N-(6-chloropyridazin-3-yl)-9-(4-methoxybenzyl)-N,1,5-trimethyl-9-azabicyclo[3.3.1]nonan-3-amine;
(1R,3s,5S)-9-(4-methoxybenzyl)-N-(6-(2-(methoxymethoxy)-4-(1-(tetrahydro-2H-pyran-2-yl)-1H-pyrazol-4-yl)phenyl)pyridazin-3-yl)-N,1,5-trimethyl-9-azabicyclo[3.3.1]nonan-3-amine;
tert-butyl(1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate;
tert-butyl(1R,3s,5S)-3-((6-(5-fluoro-2-(methoxymethoxy)-4-(1H-pyrazol-4-yl)phenyl)pyridazin-3-yl)(methyl)amino)-1,5-dimethyl-8-azabicyclo[3.2.1]octane-8-carboxylate;
(1R,3s,5S)—N-(6-chloropyridazin-3-yl)-9-(4-methoxybenzyl)-N,1,5-trimethyl-9-azabicyclo[3.3.1]nonan-3-amine;
(1R,3s,5S)—N-(6-(4-chloro-5-fluoro-2-(methoxymethoxy)phenyl) pyridazin-3-yl)-9-(4-methoxybenzyl)-N,1,5-trimethyl-9-azabicyclo[3.3.1]nonan-3-amine;
(1R,3s,5S)—N-(6-(5-fluoro-2-(methoxymethoxy)-4-(1H-pyrazol-4-yl)phenyl)pyridazin-3-yl)-9-(4-methoxybenzyl)-N,1,5-trimethyl-9-azabicyclo[3.3.1]nonan-3-amine;
tert-butyl(1R,3s,5S)-3-((6-(2-(methoxymethoxy)-4-(1-methyl-2-oxo-1,2-dihydropyridin-4-yl)phenyl)pyridazin-3-yl)(methyl)amino)-1,5-dimethyl-8-azabicyclo[3.2.1]octane-8-carboxylate;
tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate;
2tert-butyl(1R,3s,5S)-3-((6-(5-fluoro-2-(methoxymethoxy)-4-(1-methyl-2-oxo-1,2-dihydropyridin-4-yl)phenyl) pyridazin-3-yl)(methyl)amino)-1,5-dimethyl-8-azabicyclo[3.2.1]octane-8-carboxylate;
(1R,3s,5S)-3-(6-chloropyridazin-3-yloxy)-1,5-dimethyl-8-azabicyclo[3.2.1]octane; and
(1R,3s,5S)-3-((6-(2-(methoxymethoxy)-4-(1-(tetrahydro-2H-pyran-2-yl)-1H-pyrazol-4-yl)phenyl)pyridazin-3-yl)oxy)-1,5-dimethyl-8-azabicyclo[3.2.1]octane.

In some embodiments, an SMSM described herein, possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews*, 56:53-102, 2004; Aesop Cho, "Recent Advances in Oral Prodrug Discovery", Annual Reports in Medicinal Chemistry, Vol. 41, 395-407, 2006; T. Higuchi and V. Stella, *Pro-drugs as Novel Delivery Systems*, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^2$H, $_3$h, $^{13}$C, $^{14}$C, $^5$N, $^{18}$O, $^{17}$O, $^{35}$S, $^{18}$F, $^3_6$ cl. In one aspect, isotopically-labeled compounds described herein, for example those into which radioactive isotopes such as $^3$H and $1^4$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. In some embodiments, solvates of compounds described herein are conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, an SMSM has a molecular weight of at most about 2000 Daltons, 1500 Daltons, 1000 Daltons or 900 Daltons. In some embodiments, an SMSM has a molecular weight of at least 100 Daltons, 200 Daltons, 300 Daltons, 400 Daltons or 500 Daltons. In some embodiments, an SMSM does not comprise a phosphodiester linkage.

Methods of Making Compounds

Compounds described herein can be synthesized using standard synthetic techniques or using methods known in the art in combination with methods described herein. Unless otherwise indicated, conventional methods of mass spectroscopy, NMR, HPLC, protein chemistry, biochemistry, recombinant DNA techniques and pharmacology can be employed. Compounds can be prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions. The starting materials can be available from commercial sources or can be readily prepared. By way of example only, provided are schemes for preparing the SMSMs described herein.

In some embodiments, a scheme for preparing an SMSM described herein is Scheme 1:

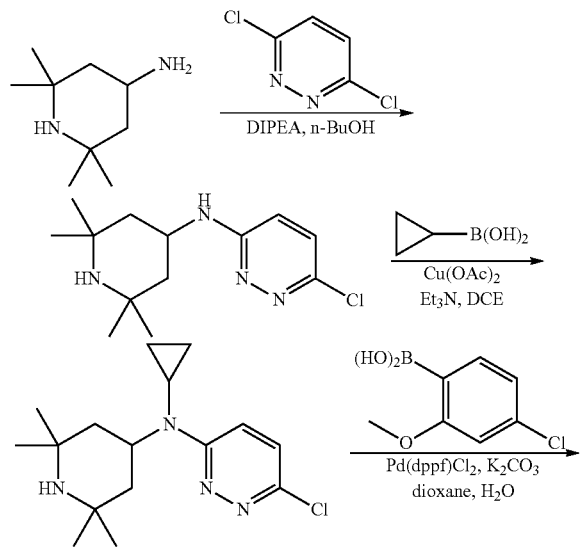

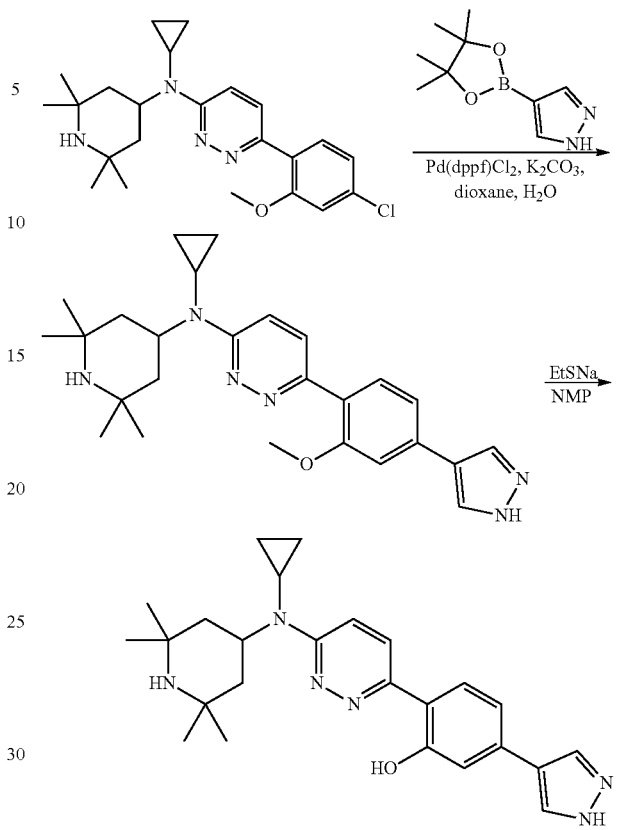

In some embodiments, a scheme for preparing an SMSM described herein is Scheme 2:

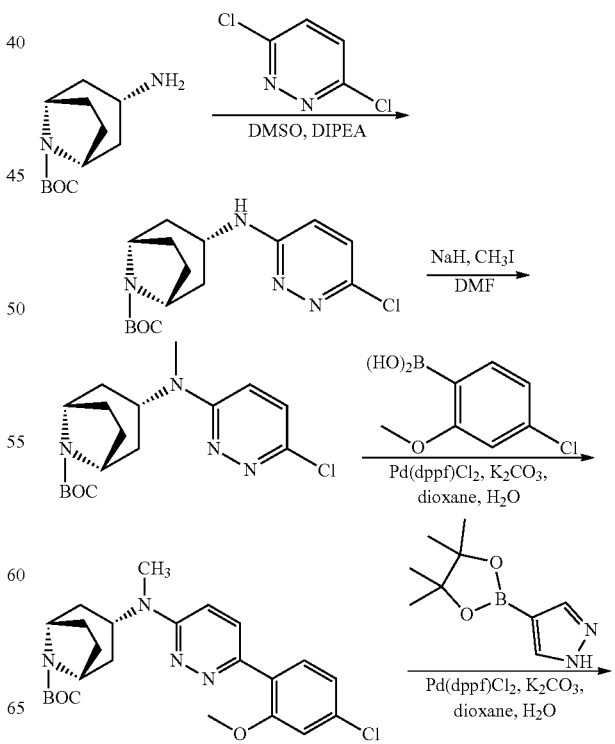

353
-continued
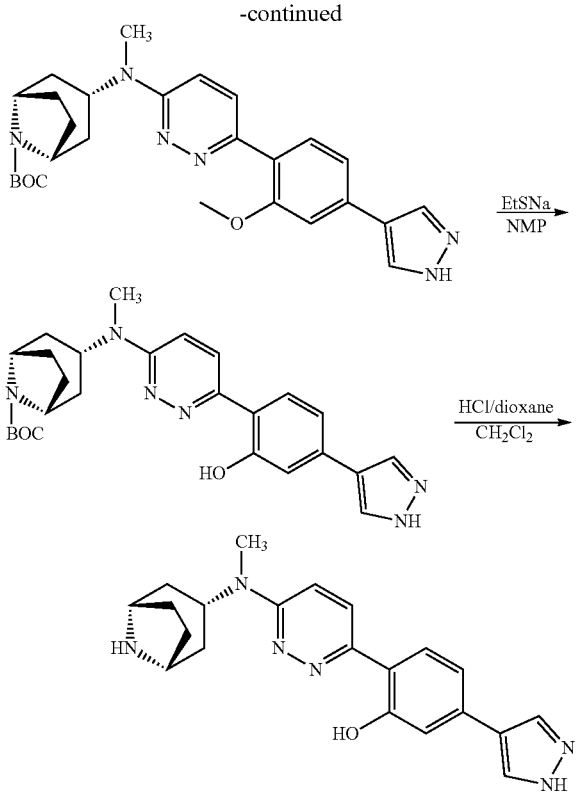
In some embodiments, a scheme for preparing an SMSM described herein is Scheme 3:
354
-continued
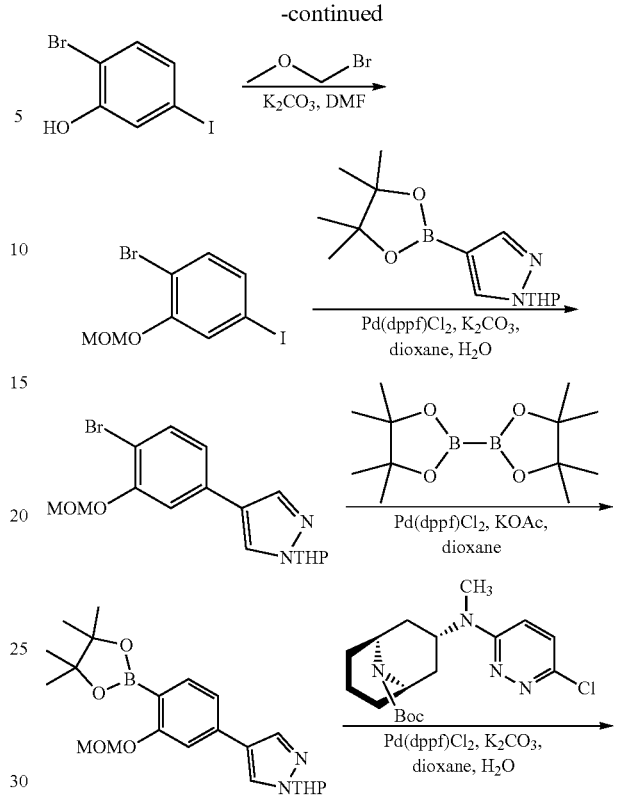
In some embodiments, a scheme for preparing an SMSM described herein is Scheme 4:
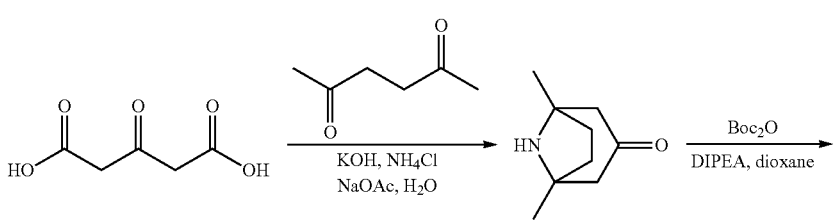

-continued
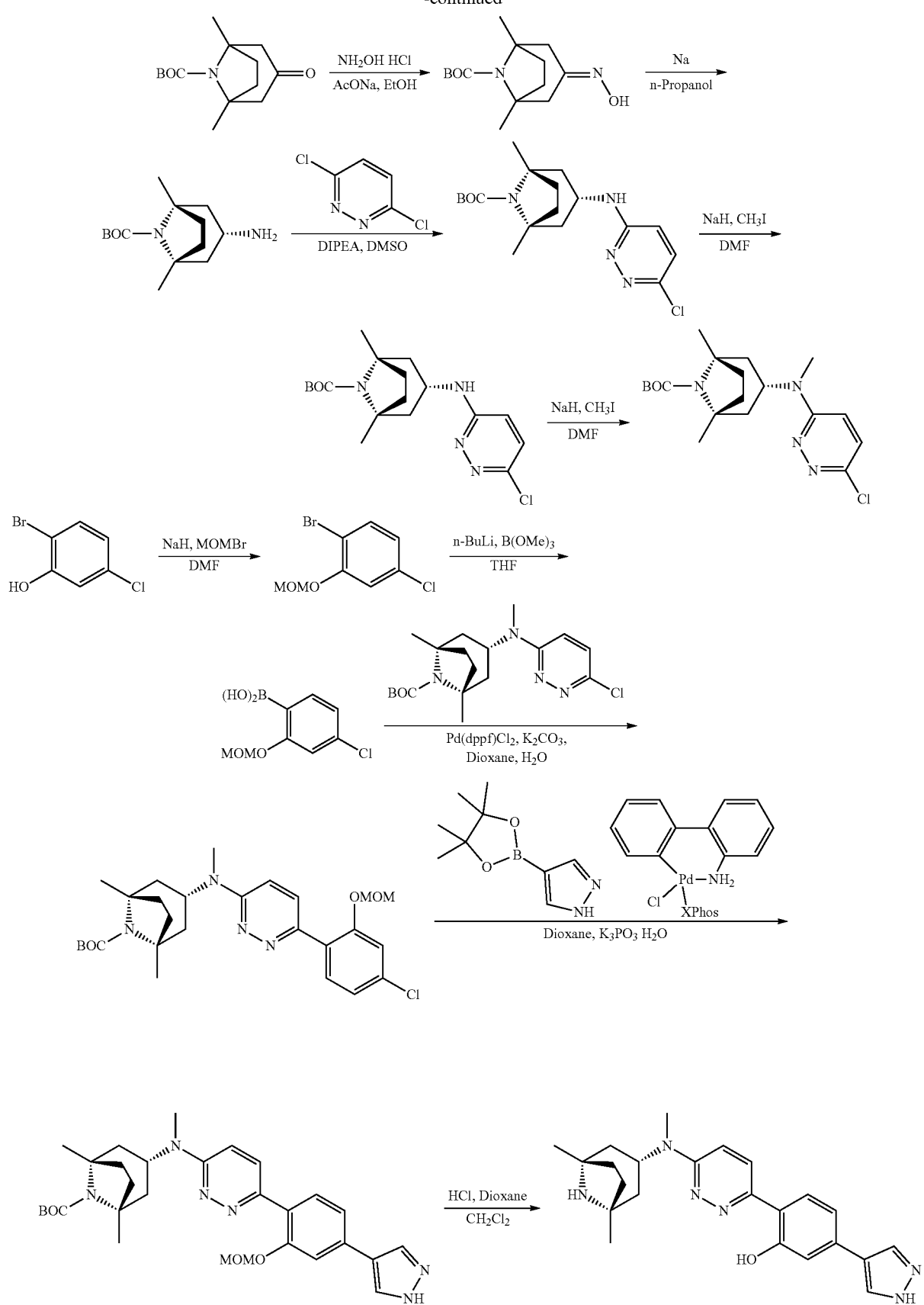

In some embodiments, a scheme for preparing an SMSM described herein is Scheme 5:
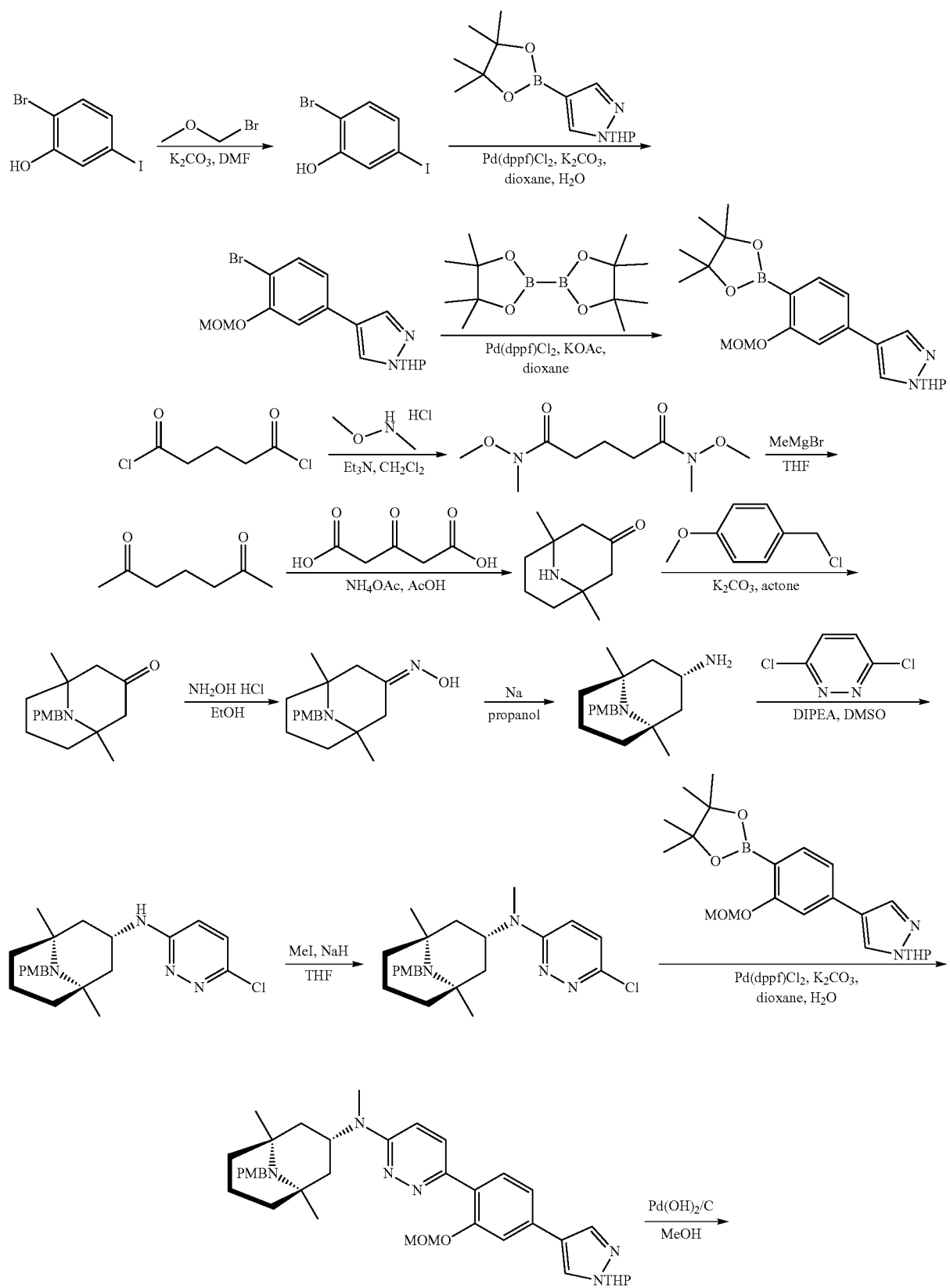

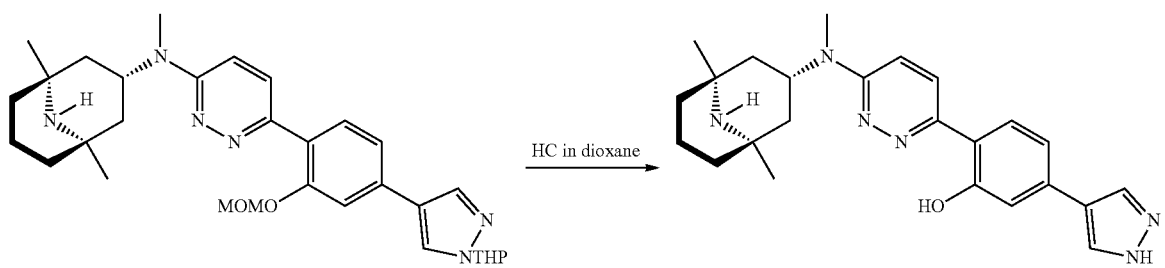
In some embodiments, a scheme for preparing an SMSM described herein is Scheme 6:
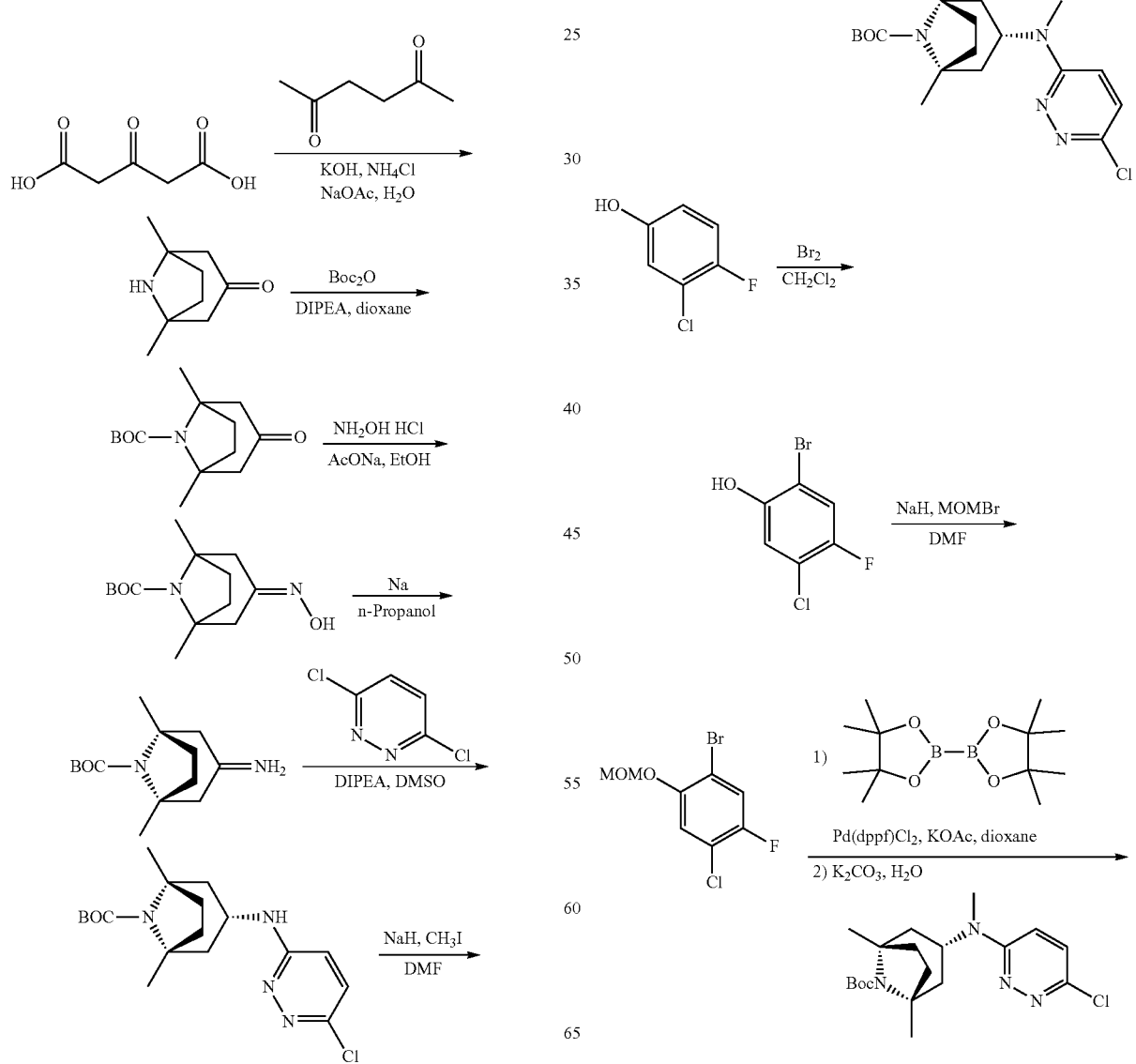

361
-continued
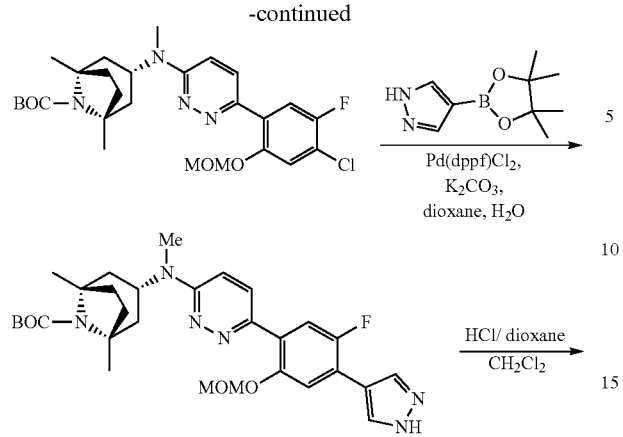
362
-continued
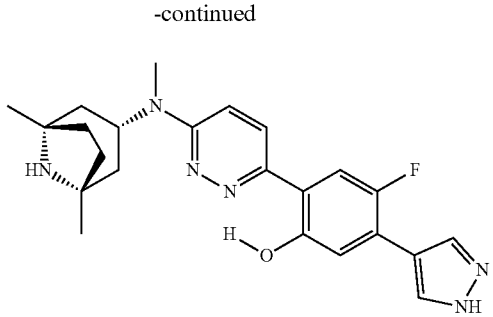
In some embodiments, a scheme for preparing an SMSM described herein is Scheme 7:
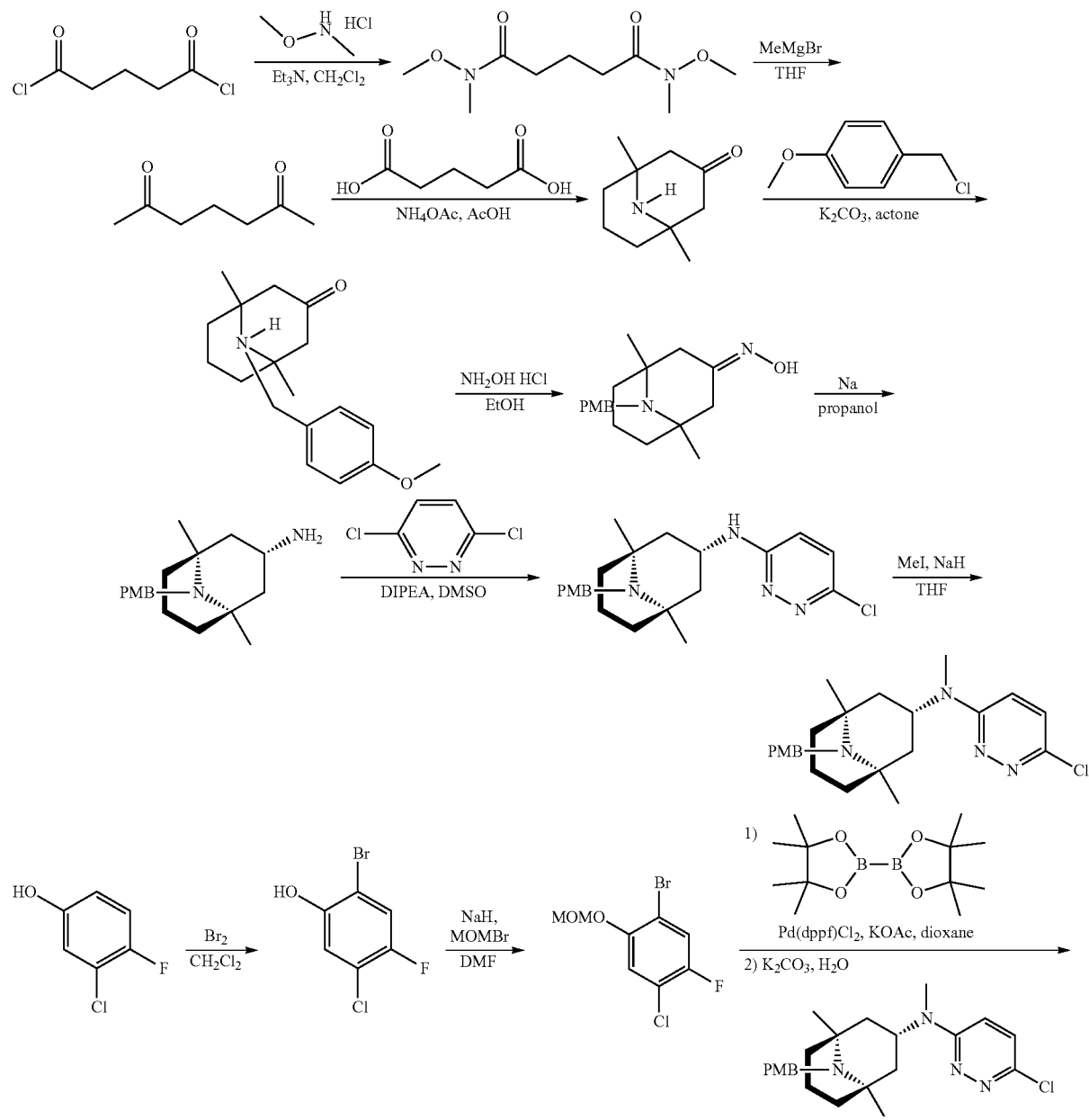

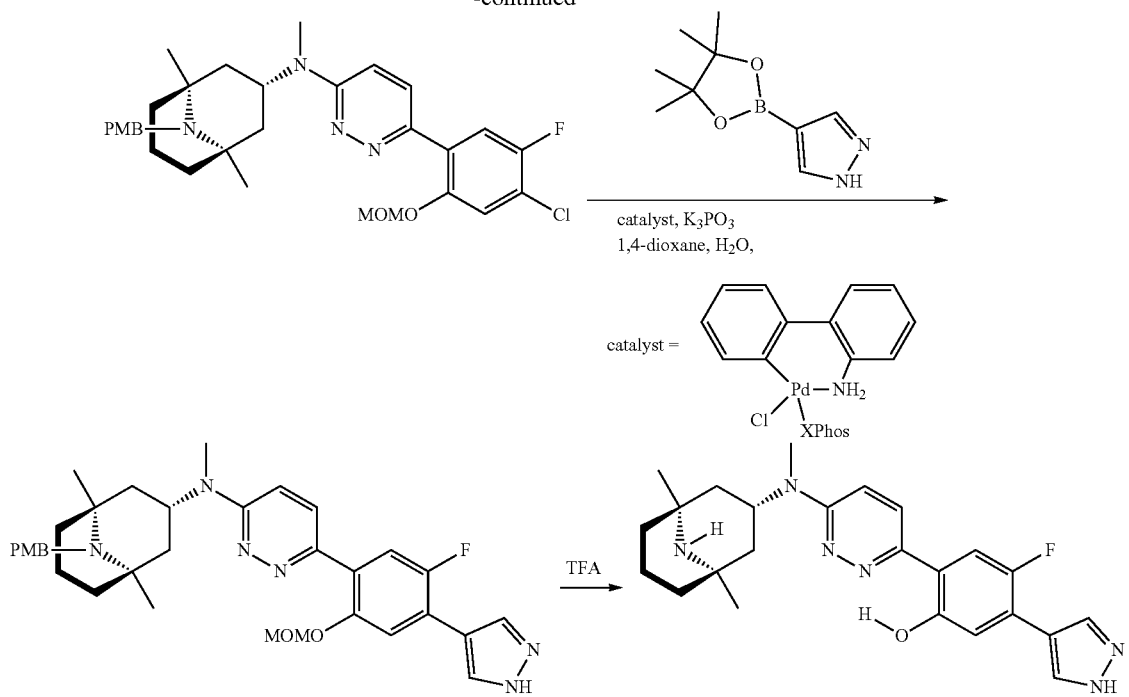
In some embodiments, a scheme for preparing an SMSM described herein is Scheme 8:
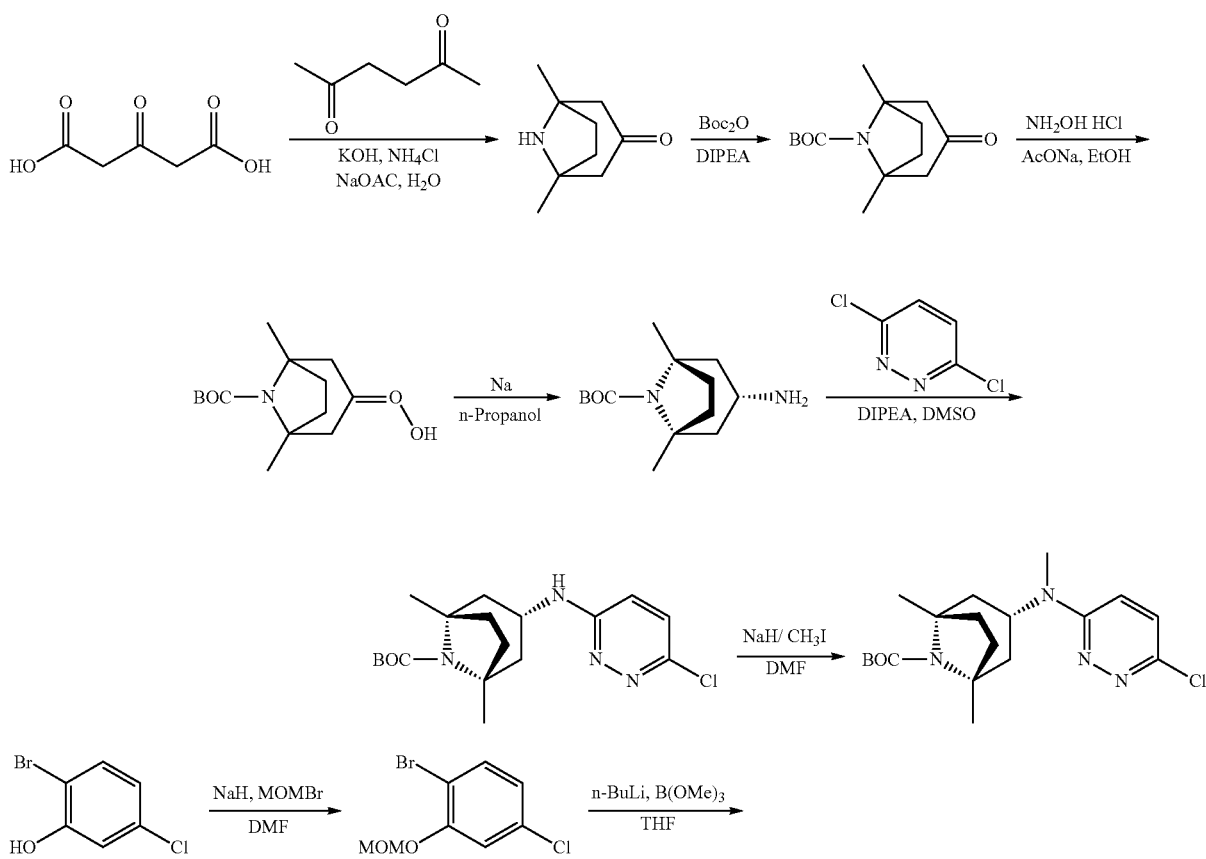

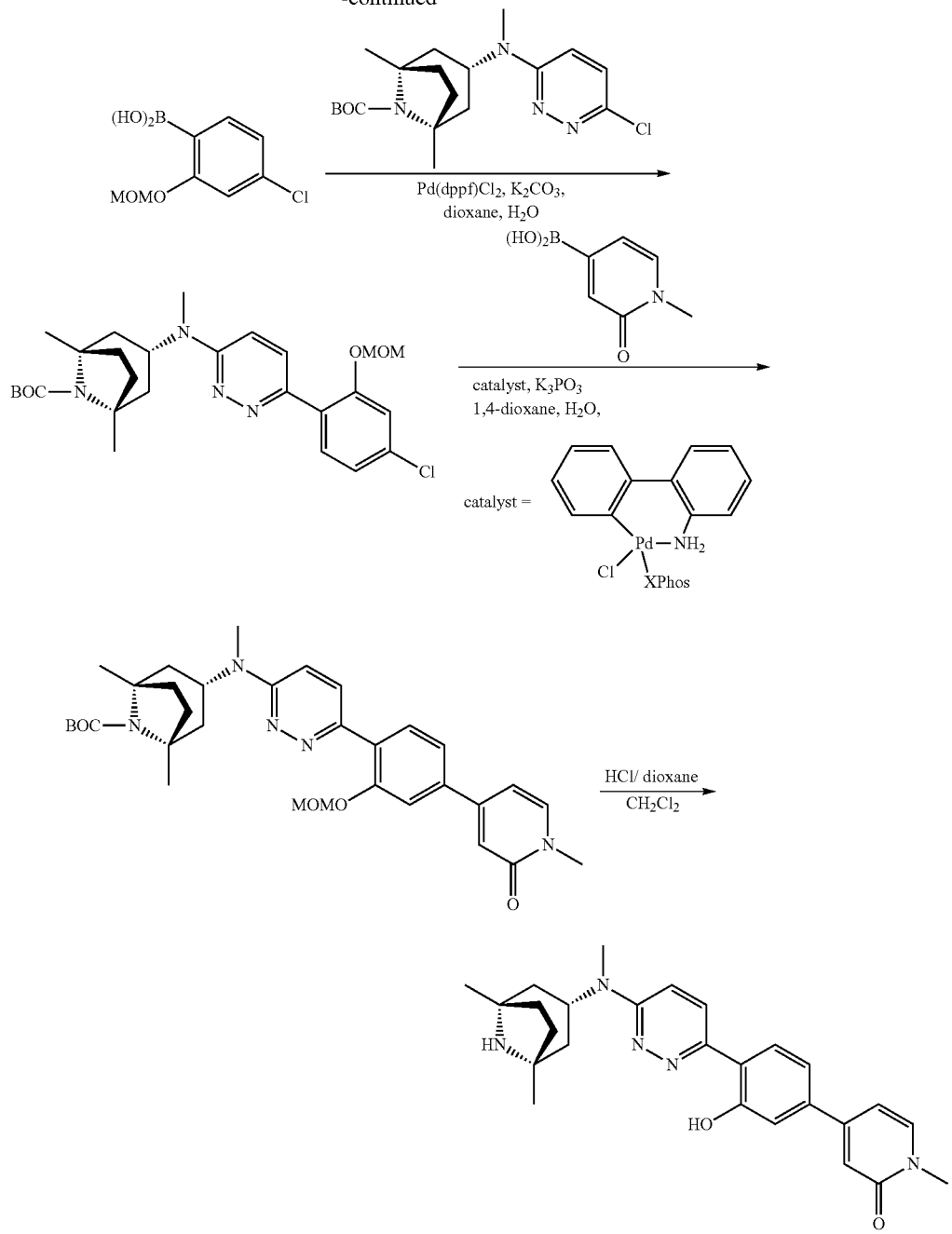
In some embodiments, a scheme for preparing an SMSM described herein is Scheme 9:
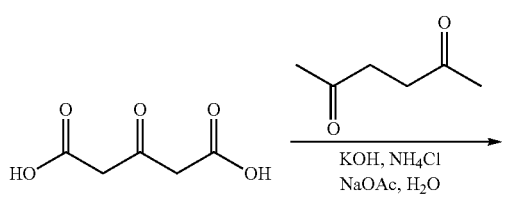
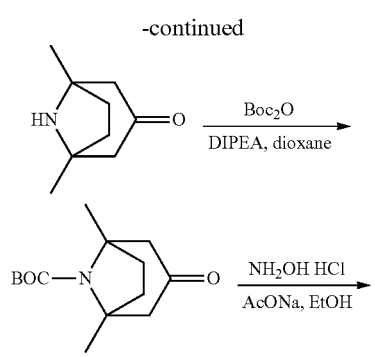

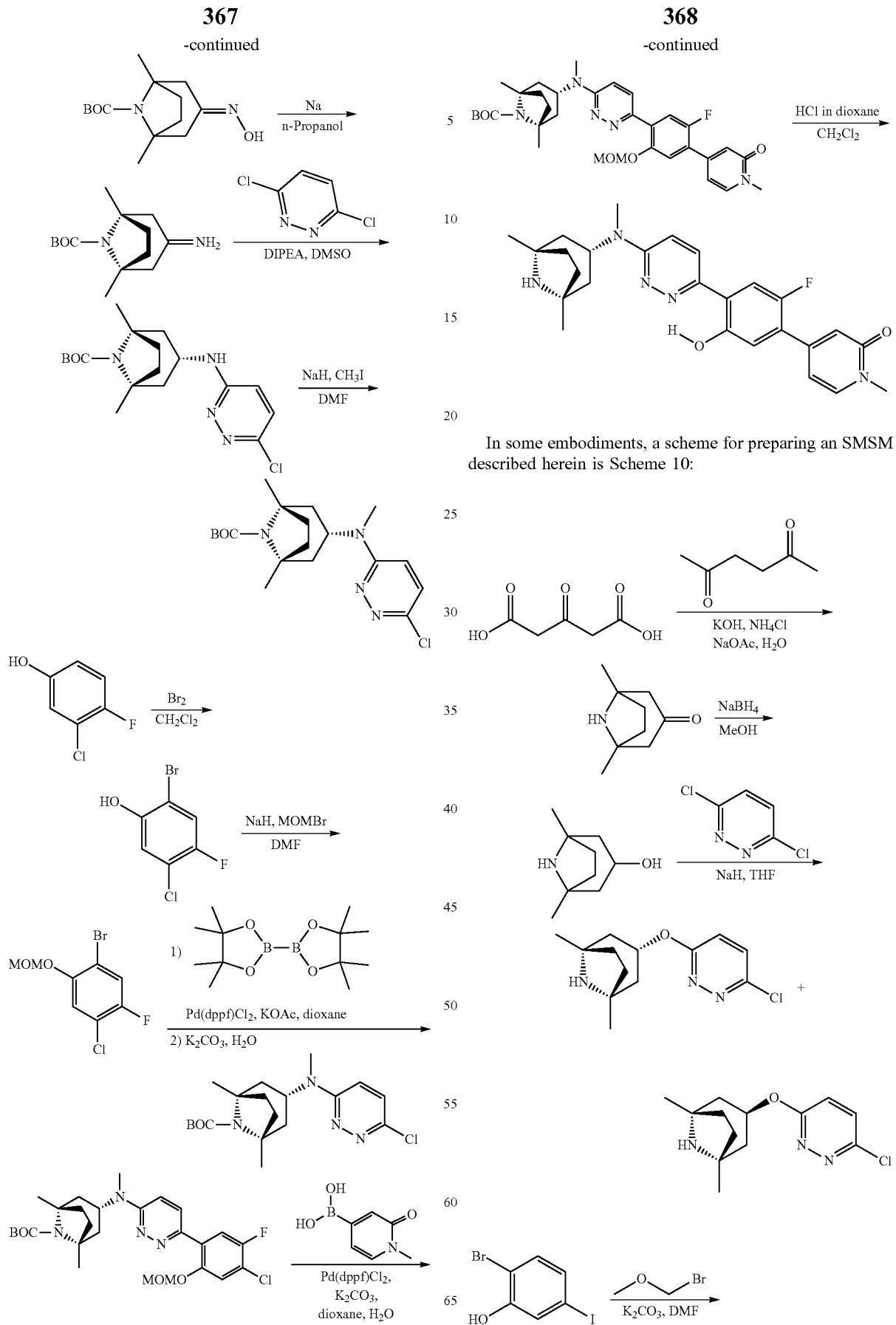
In some embodiments, a scheme for preparing an SMSM described herein is Scheme 10:

369
-continued
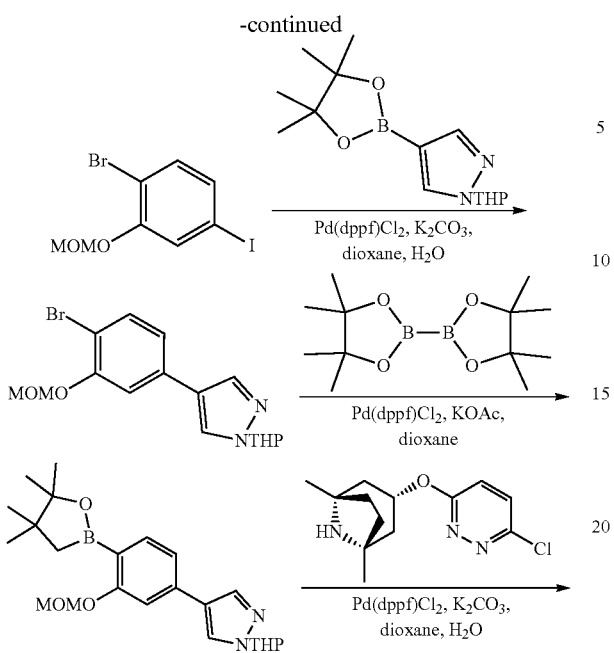
370
-continued
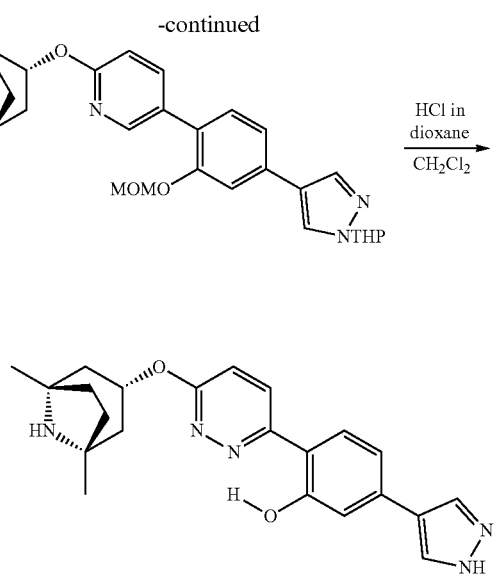
In some embodiments, a scheme for preparing an SMSM described herein is Scheme 11:
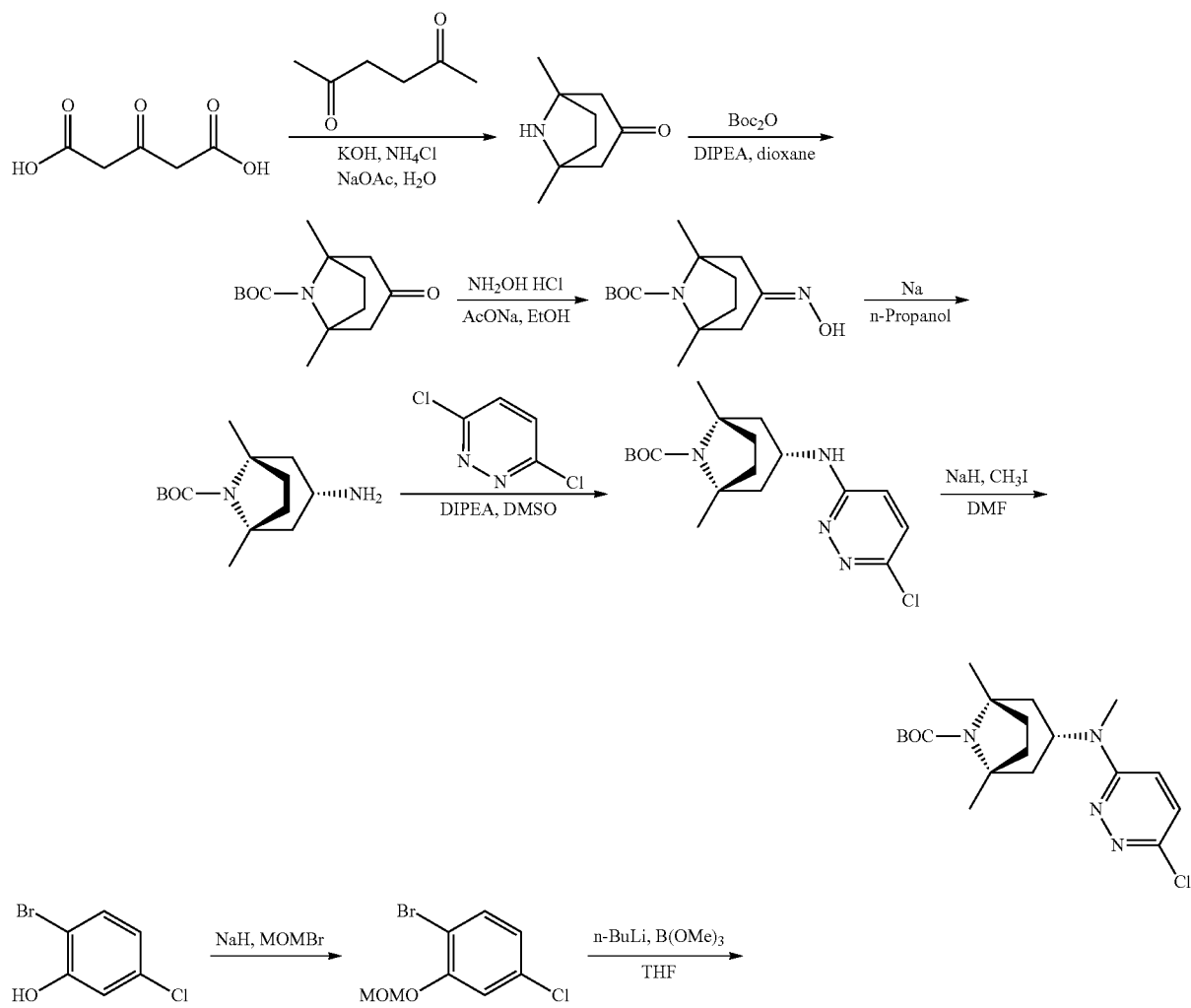

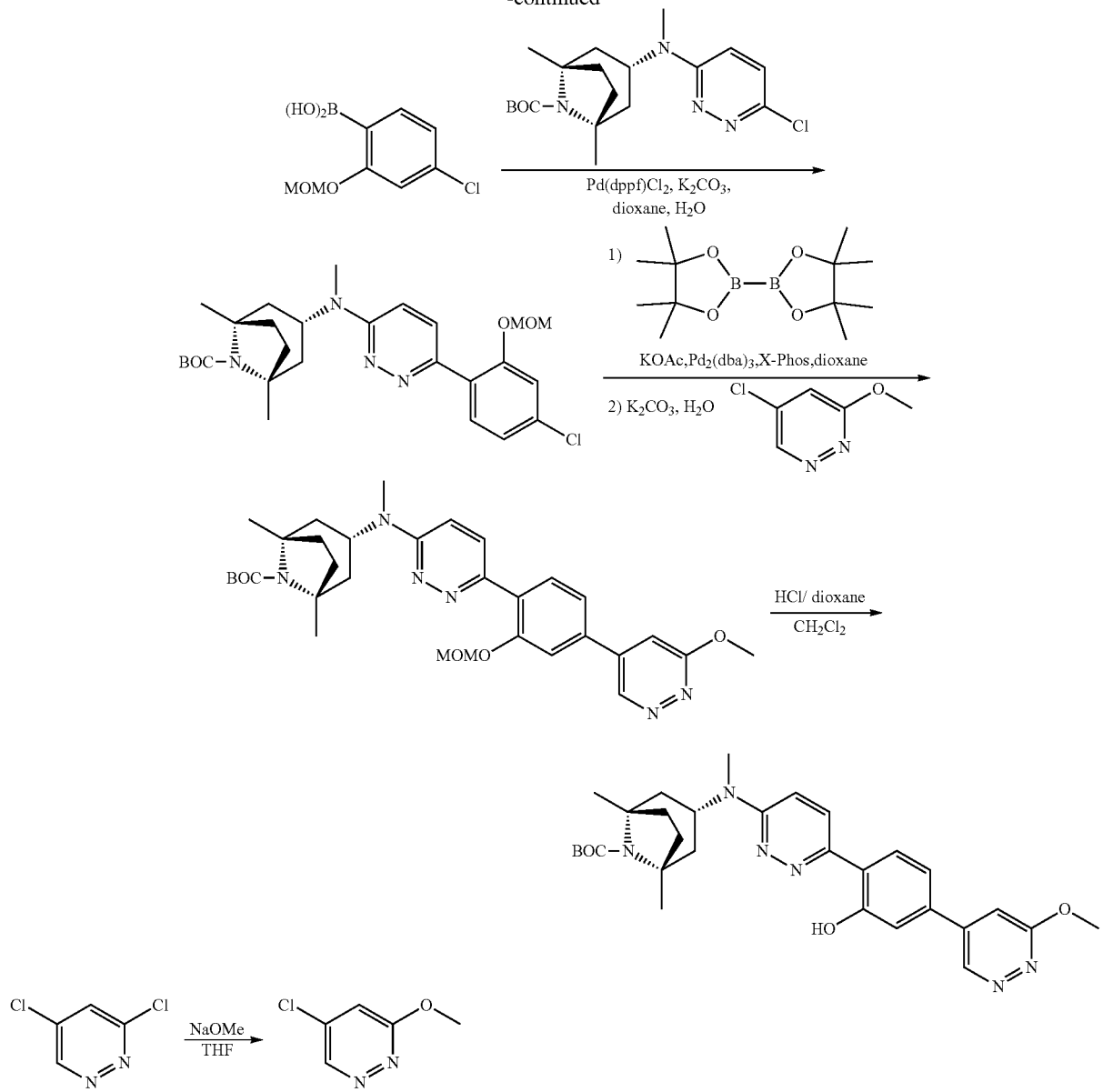
In some embodiments, a scheme for preparing an SMSM described herein is Scheme 12:
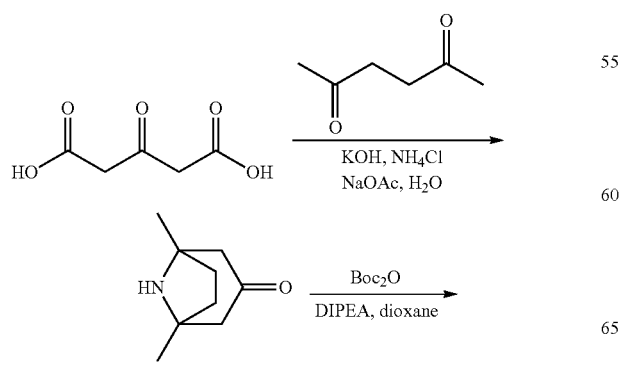
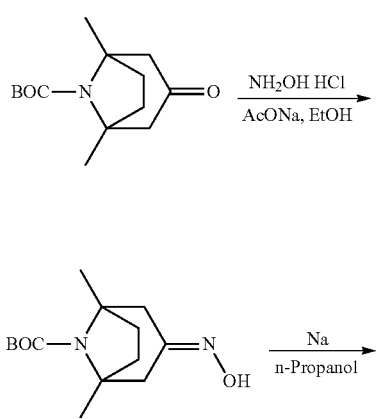

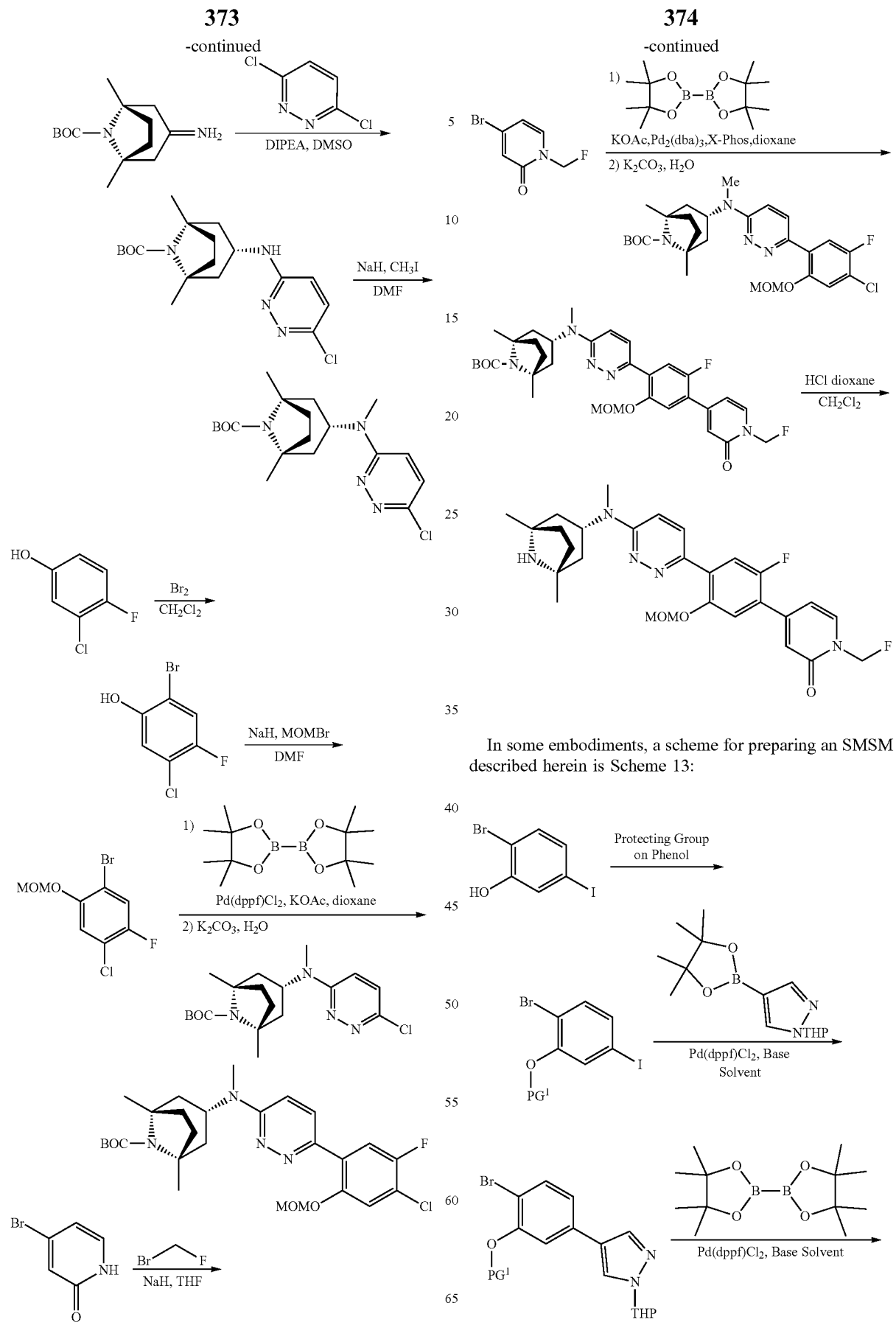
In some embodiments, a scheme for preparing an SMSM described herein is Scheme 13:

375
-continued
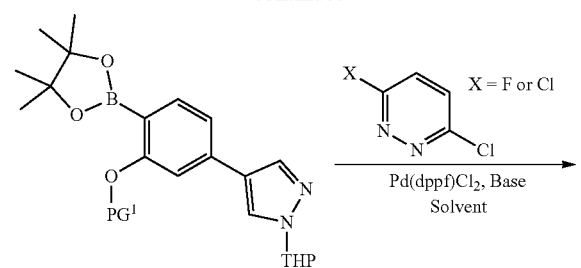
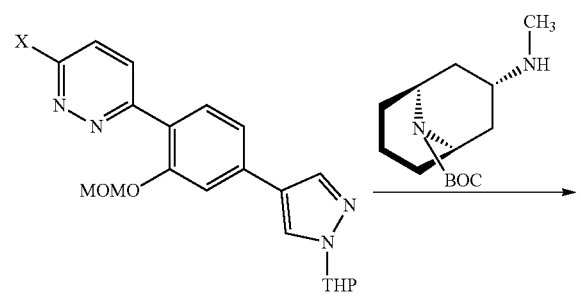
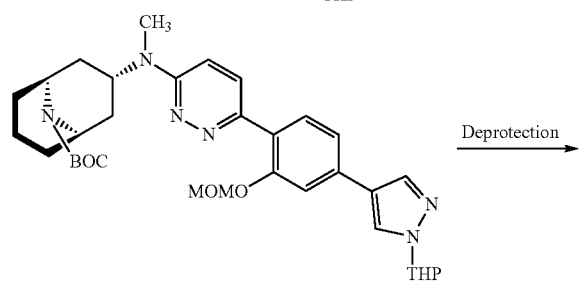
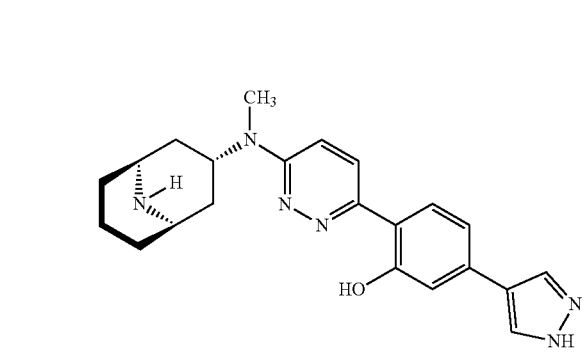
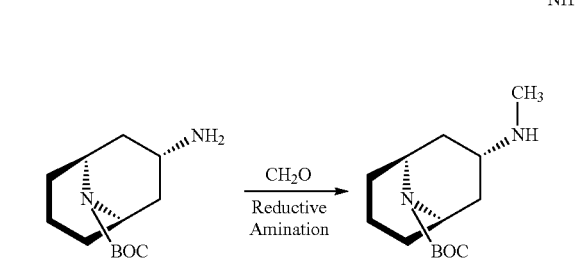
In some embodiments, a scheme for preparing an SMSM described herein is Scheme 14
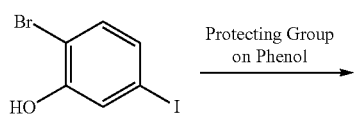
376
-continued
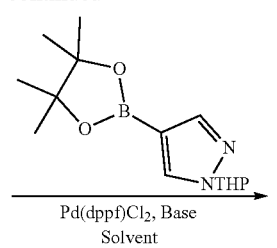
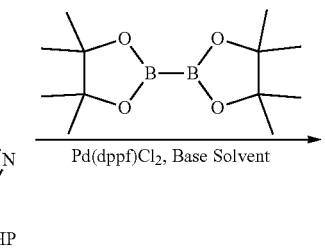
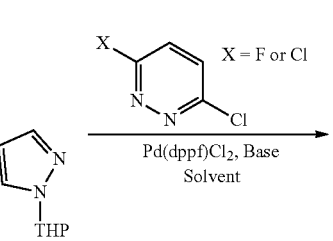

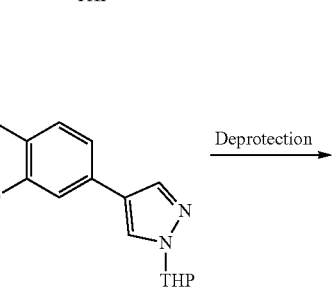
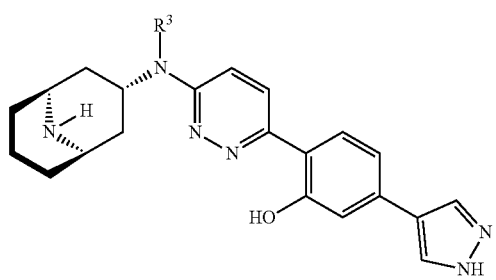

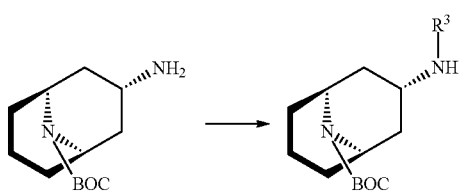
In some embodiments, a scheme for preparing an SMSM described herein is Scheme 15:
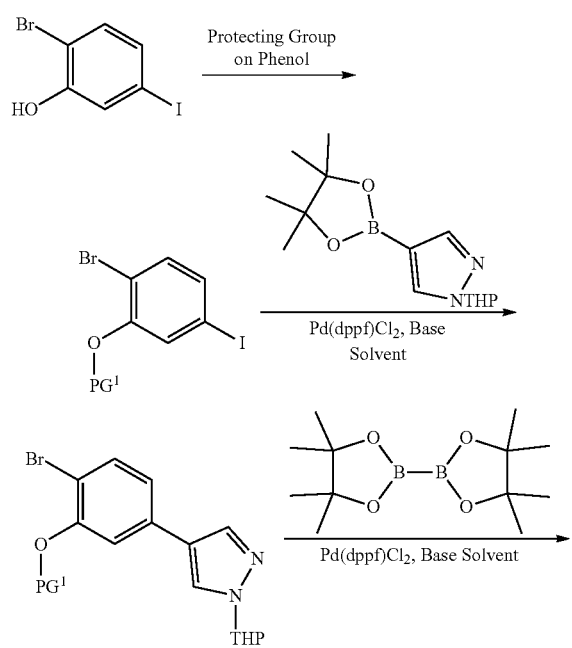
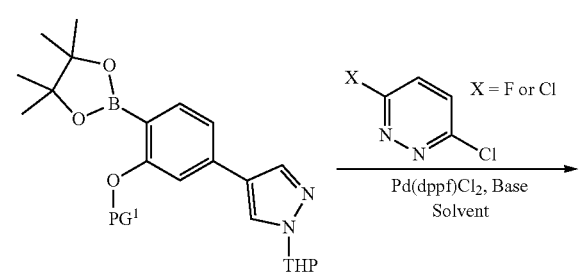
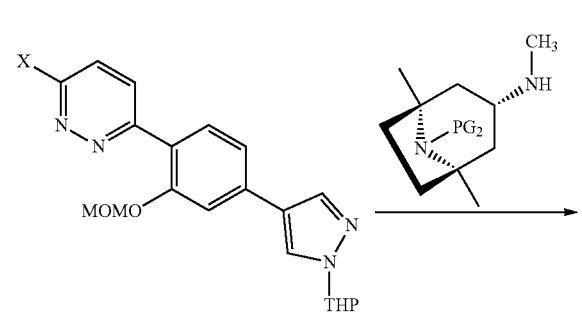
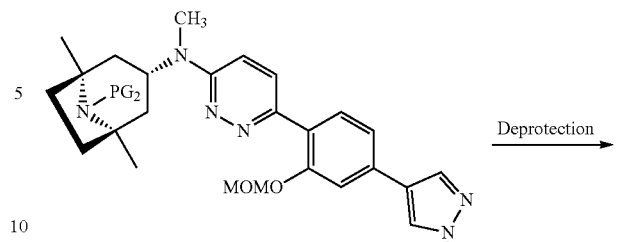
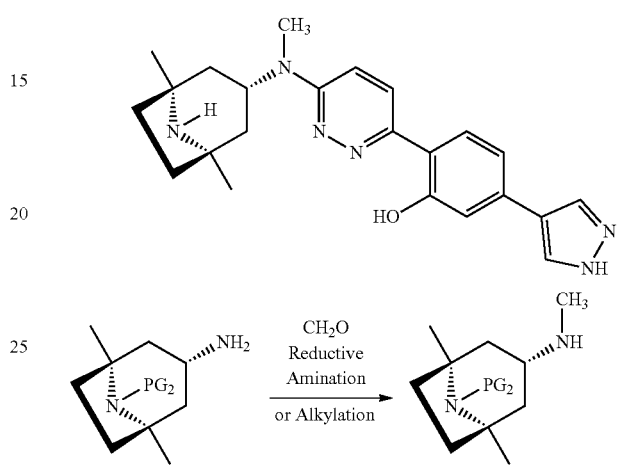
In some embodiments, a scheme for preparing an SMSM described herein is Scheme 16
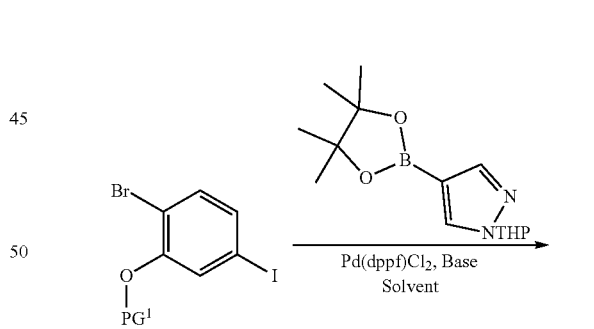
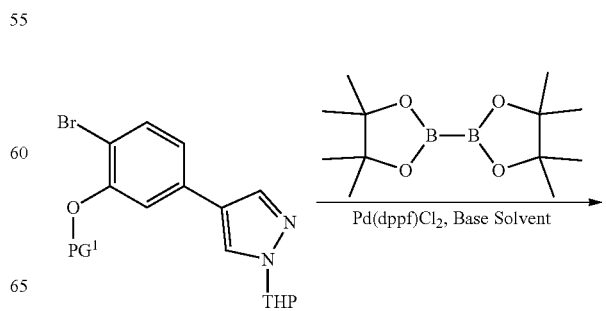

379
-continued
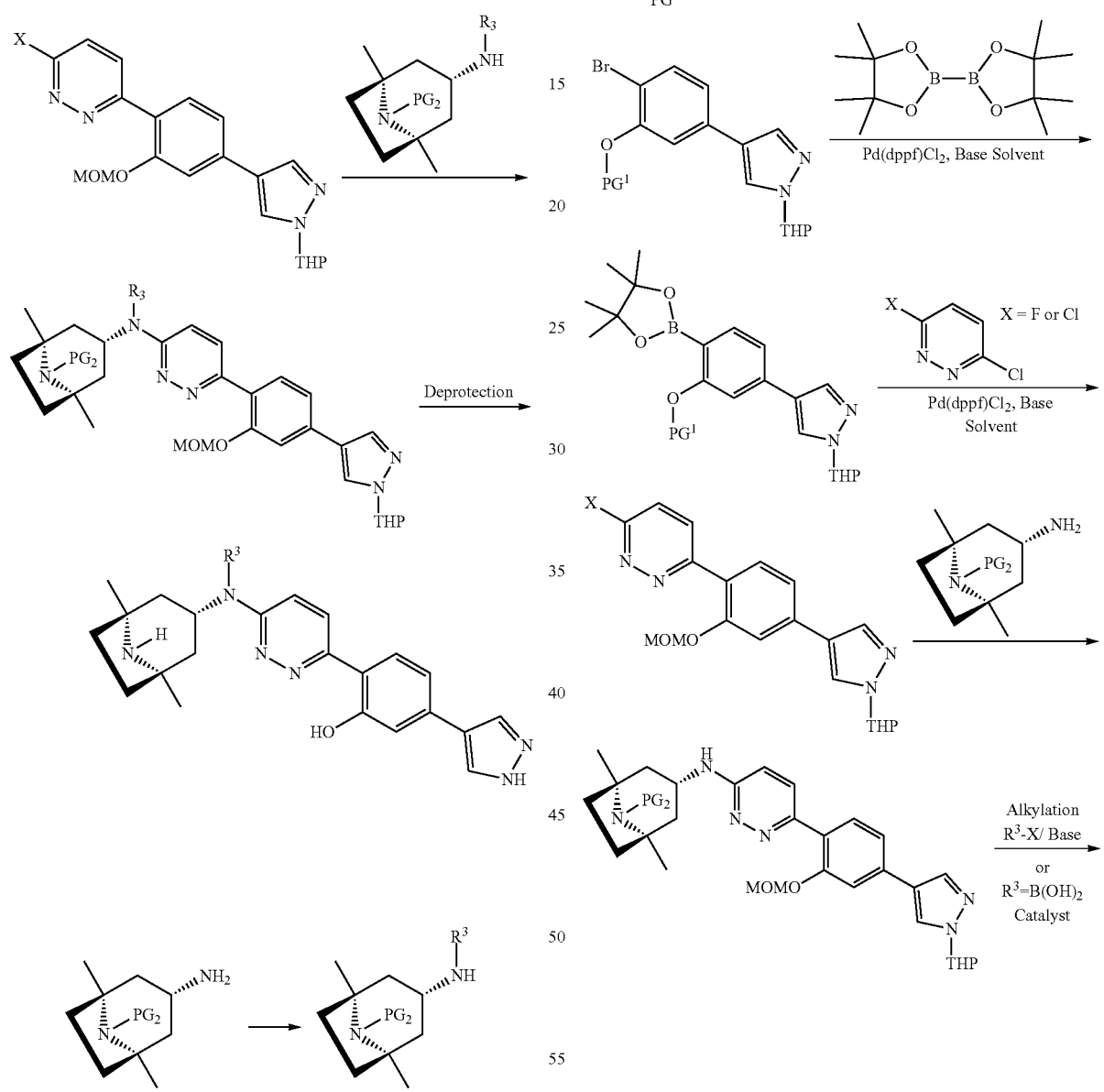
In some embodiments, a scheme for preparing an SMSM described herein is Scheme 17:
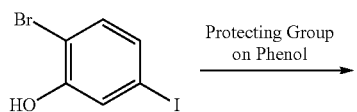
380
-continued
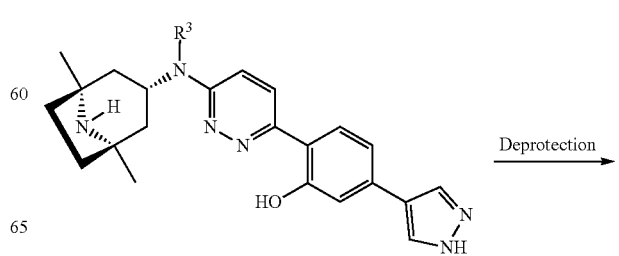

381
-continued
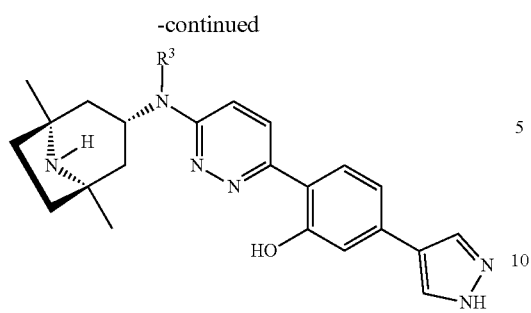
In some embodiments, a scheme for preparing an SMSM described herein is Scheme 18:
382
-continued
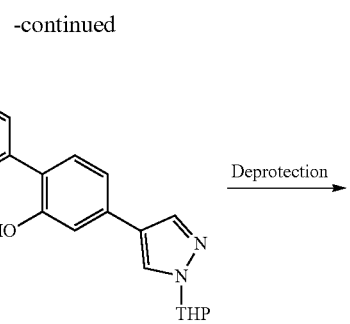
In some embodiments, a scheme for preparing an SMSM described herein is Scheme 19:
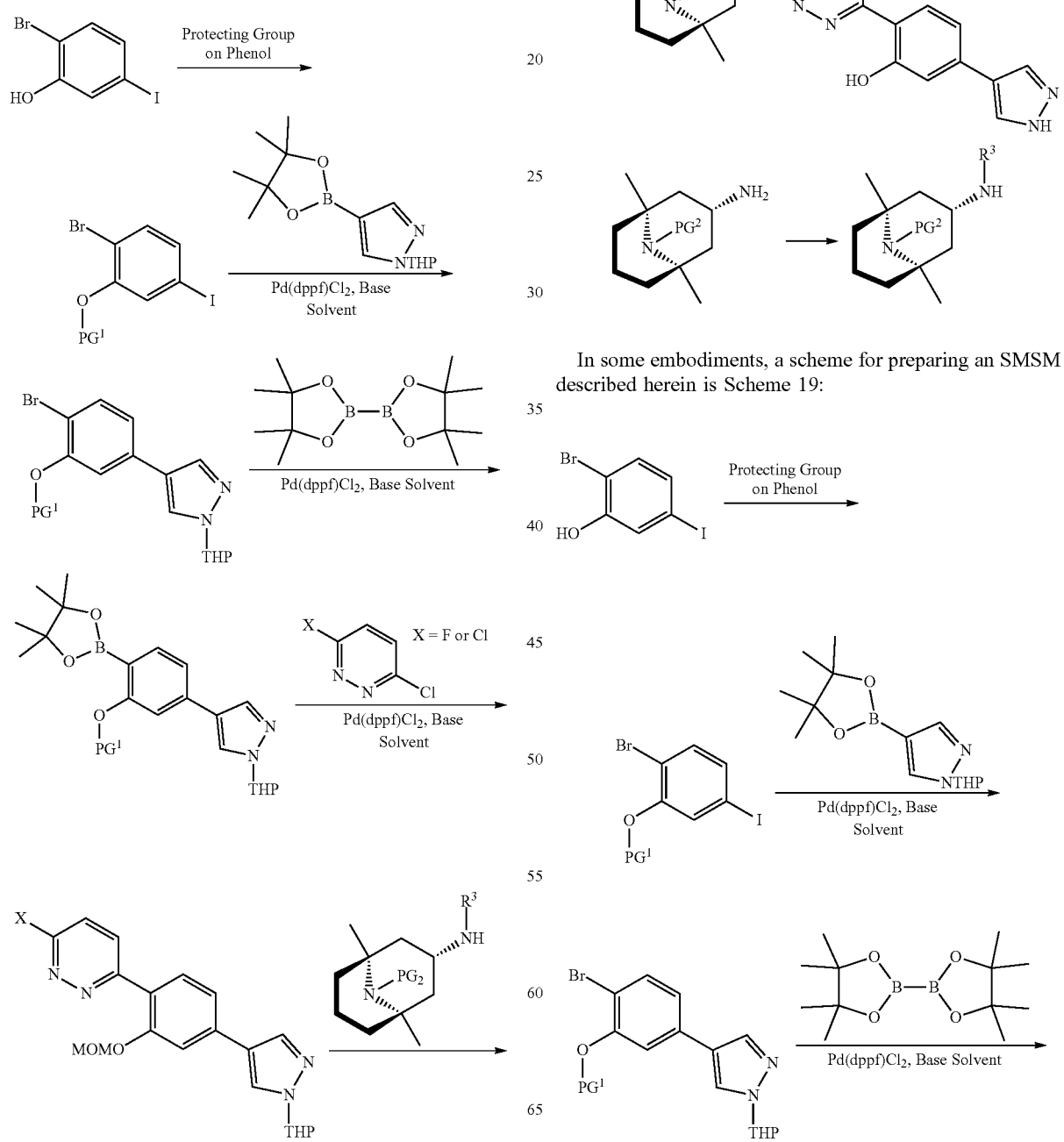

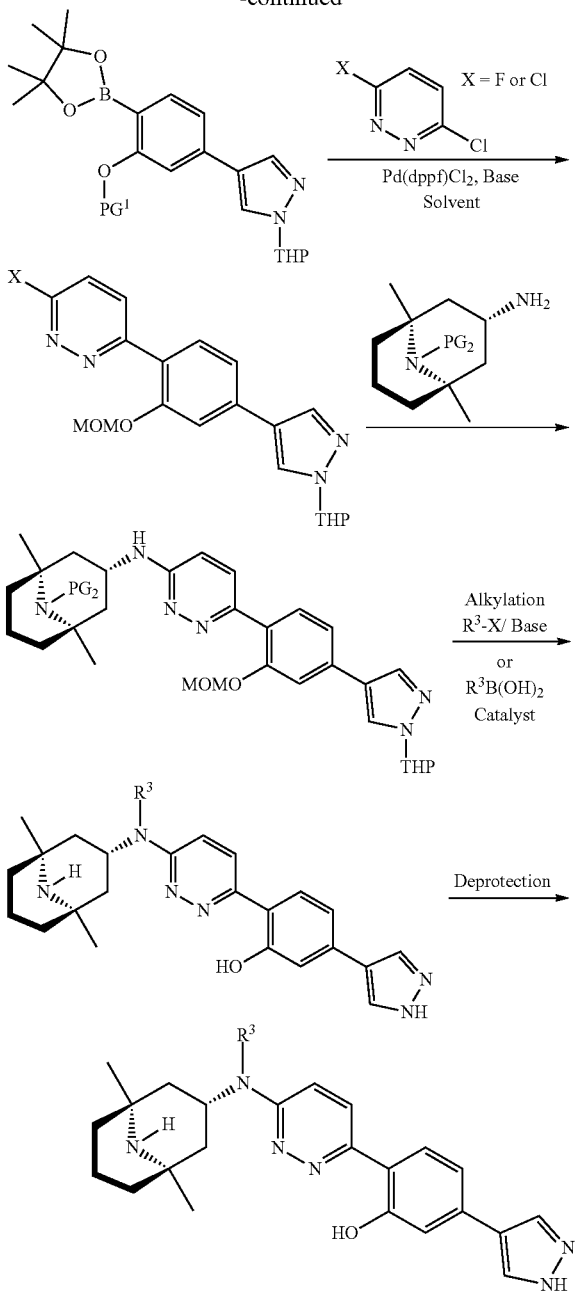

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3 527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

SMSMs can be made using known techniques and further chemically modified, in some embodiments, to facilitate intranuclear transfer to, e.g., a splicing complex component, a spliceosome or a pre-mRNA molecule. One of ordinary skill in the art will appreciate the standard medicinal chemistry approaches for chemical modifications for intranuclear transfer (e.g., reducing charge, optimizing size, and/or modifying lipophilicity).

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition can be a mixture of an SMSM described herein with one or more other chemical components (i.e. pharmaceutically acceptable ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, antifoaming agents, antioxidants, preservatives, or one or more combination thereof. The pharmaceutical composition facilitates administration of the compound to an organism.

The compositions described herein can be administered to the subject in a variety of ways, including parenterally, intravenously, intradermally, intramuscularly, colonically, rectally or intraperitoneally. In some embodiments, the small molecule splicing modulator or a pharmaceutically acceptable salt thereof is administered by intraperitoneal injection, intramuscular injection, subcutaneous injection, or intravenous injection of the subject. In some embodiments, the pharmaceutical compositions can be administered parenterally, intravenously, intramuscularly or orally. The oral agents comprising a small molecule splicing modulator can be in any suitable form for oral administration, such as liquid, tablets, capsules, or the like. The oral formulations can be further coated or treated to prevent or reduce dissolution in stomach. The compositions of the present invention can be administered to a subject using any suitable methods known in the art. Suitable formulations for use in the present invention and methods of delivery are generally well known in the art. For example, the small molecule splicing modulators described herein can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

Pharmaceutical formulations described herein can be administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical formulation is in the form of a tablet. In other embodiments, pharmaceutical formulations containing an SMSM described herein are in the form of a capsule. In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, an SMSM described herein can be formulated for use as an aerosol, a mist or a powder. For buccal or sublingual administration, the compositions may take the form of tablets, lozenges, or gels formulated in a conventional manner. In some embodiments, an SMSM described herein can be prepared as transdermal dosage forms. In some embodiments, an SMSM described herein can be formulated into a pharmaceutical composition suitable for intramuscular, subcutaneous, or intravenous injection. In some embodiments, an SMSM described herein can be administered topically and can be formulated into a variety of topically administrable compositions, such as solutions, suspensions, lotions, gels, pastes, medicated sticks, balms, creams or ointments. In some embodiments, an SMSM described herein can be formulated in rectal compositions such as enemas, rectal gels, rectal foams, rectal aerosols, suppositories, jelly suppositories, or retention enemas.

Splicing

Extensive posttranscriptional processing occurs before eukaryotic pre-mRNA matures and exits from the nucleus to the cytoplasm, including the addition of a 7-methylguanosine cap at the 5' end, the cleavage and addition of a poly-A tail at the 3' end as well as the removal of intervening sequences or introns by the spliceosome. The vast majority of higher eukaryotic genes contain multiple introns that are spliced out with high precision and fidelity in order to maintain the reading frame of the exons. Splicing of pre-mRNA can utilize the recognition of short consensus sequences at the boundaries and within introns and exons by an array of small nuclear ribonucleoprotein (snRNP) complexes (e.g., snRNPs U1, U2, U4, U5, U6, U11, U12m U4atc and U6 atc) and a large number of proteins, including spliceosomal proteins and positively as well as negatively acting splicing modulators.

Serine-arginine-rich (SR)-domain-containing proteins generally serve to promote constitutive splicing. They can also modulate alternative splicing by binding to intronic or exonic splicing enhancer (ISE) or ESE, respectively) sequences. Other pre-mRNA binding proteins, such as hnRNPs, regulate splicing by binding to intronic or exonic splicing suppressor (ISS or ESS, respectively) sequences and can also act as general splicing modulators. The SR protein family is a class of at least 10 proteins that have a characteristic serine/arginine rich domain in addition to an RNA-binding. SR proteins are generally thought to enhance splicing by simultaneously binding to U170K, a core component of the U1 snRNP, at the 5' splice site, and the U2AF35 at the 3' splice site, thus bridging the two ends of the intron. While this particular function of SR proteins seems to be redundant, as any individual SR protein can commit a pre-mRNA for constitutive splicing, the role of the various SR proteins in alternative splicing of specific pre-mRNAs is distinct due in part to their ability to recognize and bind to unique consensus sequences. Phosphorylation of the RS domain of SR proteins can lead to the regulation of their protein interactions, RNA binding, localization, trafficking, and role in alternative splicing. Several cellular kinases that phosphorylate SR proteins have been identified, including SR protein Kinase (SRPKs), Cdc2-like kinases (Clks), pre-mRNA processing mutant 4 (PRP4), and topoisomerase I. Optimal phosphorylation of SR proteins may be required for proper functioning as both hypo- and hyper-phosphorylation of the RS domains may be detrimental to their role in constitutive and alternative splicing.

In higher eukaryotes, the vast majority of genes contain one or more introns, which creates a situation in which the exons are spliced together to generate mature mRNA and microRNA (miRNA). In the host nucleus, pre-mRNA splicing is the mechanism by which introns are removed from a pre-mRNA and the exons are ligated together to generate mature mRNAs and pre-miRNA that is then exported to the cytoplasm for translation into the polypeptide gene product. Splicing of pre-mRNA can occur in cis, where two exons derive from two adjacent cotranscribed sequences, or in trans, when the two exons come from different pre-mRNA transcripts. The ratio of the different protein products (isoforms) may be due to the frequency of alternative splicing events within a pre-mRNA that leads to different amounts of distinct splice variants. In some embodiments, alternative splicing of a pre-mRNA may lead to 2, 3, 4, 5, 6, 7, 8, 9, 10, 11, 12, 13, 14, 15, 16, 17, 18, 19 or 20 protein isoforms being expressed.

Aberrations in splicing are thought to be the cause of roughly half of all inherited diseases. Aberrant splicing due to mutations in consensus sequences involved in exon-intron boundary recognition is responsible for up to 15% of inherited diseases. In addition, defects in the splicing machinery itself due to the loss or gain of function of splicing factors and modulators are causes of a wide range of human ailments from cancer to neurodegenerative diseases. Both constitutive and alternative splicing are subject to regulation by upstream signaling pathways. This regulation can be essential during development, in tissue specific expression of certain isoforms, during the cell cycle and in response to extrinsic signaling molecules.

Alternative splicing allows for a single gene to express different isoforms of mRNA, thus playing a major role in contributing to the cellular complexity in higher eukaryotes without the need to expand the genome. Splicing can also be subject to regulation by upstream signaling pathways. For example, an upstream signaling pathway may modulate alternative splicing and increase or decrease expression levels of different isoforms of mRNA.

Alternative splicing events are highly regulated by numerous splicing factors in a tissue type-, developmental stage-, and signal-dependent manner. Furthermore, non-mutation based causes of splicing defects and defects in the splicing machinery itself, e.g., due to the loss/gain of function of splicing factors or their relative stoichiometry, cause of a wide range of human ailments, ranging from cancer to neurodegenerative diseases. In many diseases the disease state is caused by an alteration of the ratio of different isoforms of two or more proteins expressed from a gene. In some embodiments, the alteration in the ratio of the protein products is due to changes in the frequency of alternative splicing events within a pre-mRNA, leading to changes in the ratio of splice variants produced. In some embodiments, alternative splicing of a pre-mRNA may lead to 2, 3, 4, 5, 6, 7, 8, 9, 10, 11, 12, 13, 14, 15, 16, 17, 18, 19 or 20 protein isoforms being expressed. In some embodiments, a change in the splice variant ratio is caused by genetic mutation.

In eukaryotes, the vast majority of splicing processes are catalyzed by the spliceosome, an RNA-protein complex that occurs in unique steps and may comprise a subset of several hundred different proteins, in addition to five spliceosomal snRNAs. These factors are responsible for the accurate positioning of the spliceosome on the 5' and 3' splice site sequences. The reason why so many factors are needed reflects the observation that exon recognition can be affected by many pre-mRNA features such as exon length, sequence recognition, the presence of enhancer and silencer elements, the strength of upstream splicing signals, the promoter architecture, and the rate of RNA processivity, secondary and tertiary RNA structure.

All mammalian diseases are ultimately mediated by the transcriptome. Insofar as messenger mRNA (mRNA) is part of the transcriptome, and all protein expression derives from mRNAs, there is the potential to intervene in protein-mediated diseases by modulating the expression of the relevant protein and by, in turn, modulating the translation of the corresponding upstream mRNA. But mRNA is only a small portion of the transcriptome: other transcribed RNAs also regulate cellular biology either directly by the structure and function of RNA structures (e.g., ribonucleoproteins) as well as via protein expression and action, including (but not limited to) microRNA (miRNA), long noncoding RNA (lncRNA), long intergenic noncoding RNA (lincRNA), small nucleolar RNA (snoRNA), small nuclear RNA (snRNA), small Cajal body-specific RNA (scaRNA), piwi-interacting RNA (piRNA), competing endogenous (ceRNA), and pseudo-genes. Drugs that intervene at this level have the potential of modulating any and all cellular processes. Existing therapeutic modalities such as antisense RNA or siRNA, in most cases, have yet to overcome significant challenges such as drug delivery, absorption, distribution to target organs, pharmacokinetics, and cell penetration. In contrast, small molecules have a long history of successfully surmounting these barriers and these qualities, which make them suitable as drugs, are readily optimized through a series of analogues to overcome such challenges. In sharp contrast, the application of small molecules as ligands for RNA that yield therapeutic benefit has received little to no attention from the drug discovery community.

DNA sequences in the chromosome are transcribed into pre-mRNAs which contain coding regions (exons) and generally also contain intervening non-coding regions (introns). Introns are removed from pre-mRNAs through splicing. Pre-mRNA splicing proceeds by a two-step mechanism. In the first step, the 5' splice site is cleaved, resulting in a "free" 5' exon and a lariat intermediate. In the second step, the 5' exon is ligated to the 3' exon with release of the intron as the lariat product. These steps are catalyzed in a complex of small nuclear ribonucleoproteins and proteins called the spliceosome.

In most cases, the splicing reaction occurs within the same pre-mRNA molecule, which is termed cis-splicing. Splicing between two independently transcribed pre-mRNAs is termed trans-splicing.

Introns are portions of eukaryotic DNA, which intervene between the coding portions, or "exons," of that DNA. Introns and exons are transcribed into RNA termed "primary transcript, precursor to mRNA" (or "pre-mRNA"). Introns can be removed from the pre-mRNA so that the native protein encoded by the exons can be produced (the term "native protein" as used herein refers to naturally occurring, wild type, or functional protein). The removal of introns from pre-mRNA and subsequent joining of the exons is carried out in the splicing process.

The splicing process is a series of reactions, which are carried out on RNA after transcription but before translation and which are mediated by splicing factors. Thus, a "pre-mRNA" can be an RNA that contains both exons and intron(s), and a mature mRNA ("mRNA") can be an RNA in which the intron(s) have been removed and the exons joined together sequentially so that the protein may be translated therefrom by the ribosomes.

Introns can be defined by a set of "splice elements" that are part of the splicing machinery and may be required for splicing and which are relatively short, conserved RNA segments that bind the various splicing factors, which carry out the splicing reactions. Thus, each intron is defined by a 5' splice site, a 3' splice site, and a branch point situated therebetween. Splice elements also comprise exon splicing enhancers and silencers, situated in exons, and intron splicing enhancers and silencers situated in introns at a distance from the splice sites and branch points. In addition to splice site and branch points these elements control alternative aberrant and constitutive splicing.

Initial RNA transcripts (pre-mRNA) of most eukaryotic genes are retained in the nucleus until non-coding intron sequences are removed by the spliceosome to produce mature messenger RNA (mRNA). The splicing that occurs can vary, so the synthesis of alternative protein products from the same primary transcript can be affected by tissue-specific or developmental signals. A significant fraction of human genetic diseases, including a number of cancers, are believed to result from deviations in the normal pattern of pre-mRNA splicing. The spliceosome is a complex comprising ribonucleoprotein (snRNP) particles composed of small nuclear RNAs and proteins. snRNA components of the spliceosome can promote the two transesterification reactions of splicing.

Two unique spliceosomes coexist in most eukaryotes: the U2-dependent spliceosome, which catalyzes the removal of U2-type introns, and the less abundant U12-dependent spliceosome, which is present in only a subset of eukaryotes and splices the rare U12-type class of introns. The U2-dependent spliceosome is assembled from the U1, U2, U5, and U4/U6 snRNPs and numerous non-snRNP proteins. The U2 snRNP is recruited with two weakly bound protein subunits, SF3a and SF3b, during the first ATP-dependent step in spliceosome assembly. SF3b is composed of seven conserved proteins, including PHF5α, SF3b155, SF3b145, SF3b130, SF3b49, SF3b14a, and SF3b10.

Splicing or RNA splicing typically refers to the editing of the nascent precursor messenger RNA (pre-mRNA) transcript into a mature messenger RNA (mRNA). Splicing is a biochemical process which includes the removal of introns followed by exon ligation. Sequential transesterification reactions are initiated by a nucleophilic attack of the 5' splice site (5'ss) by the branch adenosine (branch point; BP) in the downstream intron resulting in the formation of an intron lariat intermediate with a 2', 5'-phosphodiester linkage. This is followed by a 5'ss-mediated attack on the 3' splice site (3'ss), leading to the removal of the intron lariat and the formation of the spliced RNA product.

Splicing can be regulated by various cis-acting elements and trans-acting factors. Cis-acting elements are sequences of the mRNA and can include core consensus sequences and other regulatory elements. Core consensus sequences typically can refer to conserved RNA sequence motifs, including the 5'ss, 3'ss, polypyrimidine tract and BP region, which can function for spliceosome recruitment. BP refers to a partially conserved sequence of pre-mRNA, generally less than 50 nucleotides upstream of the 3'ss. BP reacts with the 5'ss during the first step of the splicing reaction. Other regulatory cis-acting elements can include exonic splicing enhancer (ESE), exonic splicing silencer (ESS), intronic splicing enhancer (ISE), and intronic splicing silencer (ISS). Trans-acting factors can be proteins or ribonucleoproteins which bind to cis-acting elements.

Splice site identification and regulated splicing can be accomplished principally by two dynamic macromolecular machines, the major (U2-dependent) and minor (U12-dependent) spliceosomes. Each spliceosome contains five snRNPs: U1, U2, U4, U5 and U6 snRNPs for the major spliceosome (which processes ~95.5% of all introns); and U11, U12, U4atac, U5 and $U_6$ atac snRNPs for the minor spliceosome. Spliceosome recognition of consensus sequence elements at the 5'ss, 3'ss and BP sites is one of the steps in the splicing pathway, and can be modulated by ESEs, ISEs, ESSs, and ISSs, which can be recognized by auxiliary splicing factors, including SR proteins and hnRNPs. Polypyrimidine tract-binding protein (PTBP) can bind to the polypyrimidine tract of introns and may promote RNA looping.

Alternative splicing is a mechanism by which a single gene may eventually give rise to several different proteins. Alternative splicing can be accomplished by the concerted action of a variety of different proteins, termed "alternative splicing regulatory proteins," that associate with the pre-mRNA, and cause distinct alternative exons to be included in the mature mRNA. These alternative forms of the gene's transcript can give rise to distinct isoforms of the specified protein. Sequences in pre-mRNA molecules that can bind to alternative splicing regulatory proteins can be found in introns or exons, including, but not limited to, ISS, ISE, ESS, ESE, and polypyrimidine tract. Many mutations can alter splicing patterns. For example, mutations can be cis-acting elements, and can be located in core consensus sequences (e.g. 5'ss, 3'ss and BP) or the regulatory elements that modulate spliceosome recruitment, including ESE, ESS, ISE, and ISS.

A cryptic splice site, for example, a cryptic 5'ss and a cryptic 3'ss, can refer to a splice site that is not normally recognized by the spliceosome and therefore are in the dormant state. Cryptic splice site can be recognized or activated, for example, by mutations in cis-acting elements or trans-acting factors, or structural configurations, such as bulges.

Splicing Modulation

The present invention contemplates use of small molecules with favorable drug properties that modulate the activity of splicing of a target RNA. Provided herein are small molecule splicing modulators (SMSMs) that modulate splicing of a target polynucleotide. In some embodiments, the SMSMs bind and modulate target RNA. In some embodiments, provided herein is a library of SMSMs that bind and modulate one or more target RNAs. In some embodiments, the target RNA is mRNA. In some embodiments, the target RNA is mRNA a noncoding RNA. In some embodiments, the target RNA is a pre-mRNA. In some embodiments, the target RNA is hnRNA. In some embodiments, the small molecules modulate splicing of the target RNA. In some embodiments, a small molecule provided herein modulates splicing at a sequence of the target RNA. In some embodiments, a small molecule provided herein modulates splicing at a cryptic splice site sequence of the target RNA. In some embodiments, a small molecule provided herein binds to a target RNA. In some embodiments, a small molecule provided herein binds to a splicing complex component. In some embodiments, a small molecule provided herein binds to a target RNA and a splicing complex component.

Thus, provided herein are methods of preventing or inducing a splicing event in a pre-mRNA molecule, comprising contacting the pre-mRNA molecule and/or other elements of the splicing machinery (e.g., within a cell) with a compound provided herein to prevent or induce the splicing event in the pre-mRNA molecule. The splicing event that is prevented or induced can be, e.g., an aberrant splicing event, a constitutive splicing event or an alternate splicing event.

Further provided herein is a method of identifying a compound capable of preventing or inducing a splicing event in a pre-mRNA molecule, comprising contacting the compound with splicing elements and/or factors involved in alternative, aberrant and/or constitutive splicing as described herein (e.g., within cells) under conditions whereby a positive (prevention or induction of splicing) or negative (no prevention or induction of splicing) effect is produced and detected and identifying a compound that produces a positive effect as a compound capable of preventing or inducing a splicing event.

In some embodiments, a small molecule compound described herein in a pharmaceutically acceptable carrier prevents or induces an alternative or aberrant splicing event in a pre-mRNA molecule. As noted above, the small molecule compounds provided herein are not antisense or antigene oligonucleotides. Table 1A, Table 1B and Table 1C show the chemical structure and name of exemplary compounds and is not intended to be all-inclusive.

In some embodiments, provided herein is a method of upregulating expression of a native protein in a cell containing a DNA encoding the native protein, wherein the DNA contains a mutation or no mutation that causes downregulation of the native protein by aberrant and/or alternate splicing thereof. For example, the DNA can encode a pre-mRNA that has a mutation or an aberrant secondary or tertiary structure that causes downregulation of one or more isoforms of a protein. The method can comprise introducing into the cell a small molecule provided herein that prevents an aberrant splicing event, whereby the native intron is removed by correct splicing and the native protein is produced by the cell. In some embodiments, a method comprises introducing into a cell a small molecule provided herein that modulates an alternate splicing event to produce a protein that has a different function than the protein that would be produced without modulation of alternate splicing.

In some embodiments, provided herein is a method of downregulating expression of a native protein in a cell containing a DNA encoding the native protein, wherein the DNA contains a mutation or no mutation that causes upregulation of the native protein by aberrant and/or alternate splicing thereof. For example, the DNA can encode a pre-mRNA that has a mutation or an aberrant secondary or tertiary structure that causes upregulation of one or more isoforms of a protein. The method can comprise introducing into the cell a small molecule provided herein that prevents an aberrant splicing event, whereby the native intron is removed by correct splicing and the native protein is produced by the cell. In some embodiments, a method comprises introducing into a cell a small molecule provided herein that modulates an alternate splicing event to produce a protein that has a different function than the protein that would be produced without modulation of alternate splicing. For example, a method can comprise preventing aberrant splicing in a pre-mRNA molecule containing a mutation or an aberrant secondary or tertiary structure and/or preventing an alternative splicing event. When present in the pre-mRNA, the mutation or aberrant secondary or tertiary structure can cause a pre-mRNA to splice incorrectly and produce an aberrant mRNA or mRNA fragment different from the mRNA ordinarily resulting from a pre-mRNA without the mutation or aberrant secondary or tertiary structure. For example, s pre-mRNA molecule can contain: (i) a first set of splice elements defining a native intron which can be removed by splicing when the mutation or aberrant secondary or tertiary structure is absent to produce a first mRNA molecule encoding a native protein, and (ii) a second set of splice elements induced by the mutation or aberrant secondary or tertiary structure which defines an aberrant intron different from the native intron, which aberrant intron is removed by splicing when the mutation or aberrant secondary or tertiary structure is present to produce an aberrant second mRNA molecule different from the first mRNA molecule. The method can comprise contacting the pre-mRNA molecule and/or other factors and/or elements of the splicing machinery as described herein (e.g., within a cell) with a compound described herein to prevent or promote an aberrant splicing event in a pre-mRNA molecule, whereby the native intron is removed by correct splicing and native protein production is increased in the cell.

Also provided herein is a method of upregulating expression of a RNA that would otherwise be downregulated by modulating an alternative splicing event in the RNA. The method can comprise contacting a pre-mRNA molecule and/or other elements and/or factors of the splicing machinery with a compound described herein to modulate alternate splicing events, whereby a native splicing event is inhibited and an alternate splicing event is promoted that upregulates expression of a RNA that is otherwise downregulated when under the control of the native splicing event.

Also provided herein is a method of downregulating expression of a RNA that would otherwise be upregulated by modulating an alternative splicing event in the RNA. The method can comprise contacting a pre-mRNA molecule and/or other elements and/or factors of the splicing machinery with a compound described herein to modulate alternate splicing events, whereby a native splicing event is inhibited and an alternate splicing event is promoted that downregulates expression of a RNA that is otherwise upregulated when under the control of the native splicing event.

The methods, compounds and compositions described herein have a variety of uses. For example, they are useful in any process where it is desired to have a means for downregulating expression of a RNA to be expressed until a certain time, after which it is desired to upregulate RNA expression. For such use, the RNA to be expressed may be any RNA encoding a protein to be produced so long as the gene contains a native intron. The RNA may be mutated by any suitable means, such as site-specific mutagenesis (see, T. Kunkel, U.S. Pat. No. 4,873,192) to deliberately create an aberrant second set of splice elements which define an aberrant intron which substantially downregulates expression of the gene. A sequence encoding the RNA may be inserted into a suitable expression vector and the expression vector inserted into a host cell (e.g., a eukaryotic cell such as a yeast, insect, or mammalian cell (e.g., human, rat)) by standard recombinant techniques. The host cell can then be grown in culture by standard techniques. When it is desired to upregulate expression of the mutated gene, a suitable compound of the present invention, in a suitable formulation, can be added to the culture medium so that expression of the gene is upregulated.

Also provided herein is a method of altering the ratio of splice variants produced from a gene. The method can comprise contacting a pre-mRNA molecule and/or other elements and/or factors of the splicing machinery with a compound or compounds described herein to modulate alternative splicing events. The compound or compounds of this invention can be used to act upon 1, 2, 3, 4, 5, 6, 7, 8, 9, 10, 11, 12, 13, 14, 15, 16, 17, 18, 19 or 20 alternative splicing events that may occur within a pre-mRNA. In some embodiments, a first splice variant may be downregulated or inhibited and/or a second splice variant may be upregulated, resulting in an altered ratio of splice variants of the two or more RNA. In some embodiments, a first splice variant may be upregulated while a second splice variant may be unaffected, thereby altering the ratio of the RNA. In some embodiments, a first splice variant may be downregulated while a second splicing event may be unaffected thereby altering the ratio of the RNA.

The methods, compounds and formulations described herein are also useful as in vitro or in vivo tools to examine and modulate splicing events in human or animal RNAs encoded by genes, e.g., those developmentally and/or tissue regulated (e.g., alternate splicing events).

The compounds and formulations described herein are also useful as therapeutic agents in the treatment of disease involving aberrant and/or alternate splicing. Thus, in some embodiments, a method of treating a subject having a condition or disorder associated with an alternative or aberrant splicing event in a pre-mRNA molecule, comprises administering to the subject a therapeutically effective amount of a compound described herein to modulate an alternative splicing event or prevent an aberrant splicing event, thereby treating the subject. The method can, e.g., restore a correct splicing event in a pre-mRNA molecule. The method can, e.g., utilize a small molecule compound described herein in a pharmaceutically acceptable carrier.

Formulations containing the small molecules described herein can comprise a physiologically or pharmaceutically acceptable carrier, such as an aqueous carrier. Thus, formulations for use in the methods described herein include, but are not limited to, those suitable for oral administration, parenteral administration, including subcutaneous, intradermal, intramuscular, intravenous and intra-arterial administration, as well as topical administration (e.g., administration of an aerosolized formulation of respirable particles to the lungs of a patient afflicted with cystic fibrosis or lung cancer or a cream or lotion formulation for transdermal administration of patients with psoriasis). The formulations may conveniently be presented in unit dosage form and may be prepared by any of the methods well known in the art. The most suitable route of administration in any given case may depend upon the subject, the nature and severity of the condition being treated, and the particular active compound, which is being used, as would be readily determined by one of skill in the art.

Also provided herein are methods for the use of a compound described herein having the characteristics set forth above for the preparation of a medicament for upregulating or downregulating RNA expression in a patient having a disorder associated with aberrant or alternate splicing of a pre-mRNA molecule, as discussed above. In some embodiments, the medicament upregulates gene expression. In other embodiments, the medicament downregulates gene expression. In the manufacture of at medicament according to the invention, the compound can be admixed with, inter alia, a pharmaceutically acceptable carrier. The carrier may be a solid or a liquid. One or more compounds may be incorporated in any combination in the formulations described herein, which may be prepared by any of the well-known techniques of pharmacy, such as admixing the components, and/or including one or more accessory therapeutic ingredients.

The present inventors identify herein low molecular weight compounds (sometimes referred to herein as small molecules, which block mRNA splicing and/or enhance (facilitate, augment) mRNA splicing. The splicing that can be regulated by the methods described herein include alternative splicing, e.g., exon skipping, intron retention, pseudo-exons skipping, exon exclusion, partial intron exclusion and others. Depending on factors such as the splicing sequence and the RNA (or gene encoding the RNA) or exon involved, modulation of splicing can be accomplished in the presence of, or in the absence of, antisense oligonucleotides (AOs) that are specific for splicing sequences of interest. In some embodiments, a small molecule and an AO act synergistically.

In some aspects, a method comprises contacting a splice modulating compound (e.g., a SMSM) to a pre-mRNA that modulates splicing of the pre-mRNA to favor expression of a transcript that promotes cell proliferation. For example, an SMSM described herein can increase one or more isoforms of a transcript that promotes cell proliferation. For example, an SMSM described herein can decrease expression one or more isoforms of a transcript that prevents or inhibits cell proliferation.

In some aspects, a method comprises contacting a splice modulating compound (e.g., a SMSM) to a pre-mRNA that modulates splicing of the pre-mRNA to favor expression of a transcript that prevents or inhibits cell proliferation. For example, an SMSM described herein can increase one or more isoforms of a transcript that prevents or inhibits cell proliferation. For example, an SMSM described herein can decrease expression one or more isoforms of a transcript that promotes cell proliferation.

In some embodiments, a method of modulating splicing of pre-mRNA comprises using an SMSM to decrease expression or functionality of one or more isoforms of a transcript in a subject. The method can comprise administering an SMSM, or a composition comprising an SMSM, to a subject, wherein the SMSM binds to a pre-mRNA or a splicing complex component and modulates splicing of the pre-mRNA to favor expression of one or more isoforms of a transcript. The method can comprise administering an SMSM, or a composition comprising an SMSM, to a subject, wherein the SMSM binds to a pre-mRNA or a splicing complex component and modulates splicing of the pre-mRNA to disfavor expression of one or more isoforms of a transcript.

In some embodiments, the present invention provides a method of treating a subject afflicted with a disease or condition associated with aberrant splicing of a pre-mRNA. The method can comprise administering an SMSM, or a composition comprising an SMSM, to a subject, wherein the SMSM binds to a pre-mRNA or a splicing complex component and modulates splicing of the pre-mRNA to inhibit expression of one or more isoforms of a transcript. The method can comprise administering an SMSM, or a composition comprising an SMSM, to a subject, wherein the SMSM binds to a pre-mRNA or a splicing complex component and modulates the splicing of the pre-mRNA to increase expression of one or more isoforms of a transcript.

A number of diseases are associated with expression of an aberrant gene product (e.g., an RNA transcript or protein) of a gene. For example, aberrant amounts of a RNA transcript may lead to disease due to corresponding changes in protein expression. Changes in the amount of a particular RNA transcript may be the result of several factors. First, changes in the amount of RNA transcripts may be due to an aberrant level of transcription of a particular gene, such as by the perturbation of a transcription factor or a portion of the transcription process, resulting in a change in the expression level of a particular RNA transcript. Second, changes in the splicing of particular RNA transcripts, such as by perturbation of a particular splicing process or mutations in the gene that lead to modified splicing can change the levels of a particular RNA transcript. Changes to the stability of a particular RNA transcript or to components that maintain RNA transcript stability, such as the process of poly-A tail incorporation or an effect on certain factors or proteins that bind to and stabilize RNA transcripts, may lead to changes in the levels of a particular RNA transcript. The level of translation of particular RNA transcripts can also affect the amount of those transcripts, affecting or upregulating RNA transcript decay processes. Finally, aberrant RNA transport or RNA sequestration may also lead to changes in functional levels of RNA transcripts, and may have an effect on the stability, further processing, or translation of the RNA transcripts.

In some embodiments, provided herein are methods for modulating the amount of one, two, three or more RNA transcripts encoded by a pre-mRNA, comprising contacting a cell with an SMSM compound or a pharmaceutically acceptable salt thereof. In some embodiments, the cell is contacted with an SMSM compound or a pharmaceutically acceptable salt thereof in a cell culture. In other embodiments, the cell is contacted with an SMSM compound or a pharmaceutically acceptable salt thereof in a subject (e.g., a non-human animal subject or a human subject).

In some embodiments, provided herein are methods for treatment, prevention and/or delay of progression of a disease or condition comprising administering an effective amount of a small molecule splicing modulator as described herein to a subject, in particular to a mammal.

In some embodiments, provided herein are compositions and methods for treating a disease or condition, including histeric modulator compounds or pharmaceutically acceptable salts thereof that promote prevention or correction of exon skipping of a pre-mRNA. The invention further provides compositions and methods for increasing production of mature mRNA and, in turn, protein, in cells of a subject in need thereof, for example, a subject that can benefit from increased production of protein. The invention further provides compositions and methods for decreasing production of mature mRNA and, in turn, protein, in cells of a subject in need thereof, for example, a subject that can benefit from decreased production of protein. In one embodiment, the described methods may be used to treat subjects having a disease or condition caused by a mutation in a gene, including missense, splicing, frameshift and nonsense mutations, as well as whole gene deletions, which result in deficient protein production. In another embodiment, the described methods may be used to treat subjects having a disease or condition not caused by gene mutation. In some embodiments, the compositions and methods of the present invention are used to treat subjects having a disease or condition, who can benefit from increased production of protein. In some embodiments, the compositions and methods of the present invention are used to treat subjects having a disease or condition, who can benefit from increased production of protein. In some embodiments, the compositions and methods of the present invention are used to treat subjects having a disease or condition, who can benefit from decreased production of a protein.

In some embodiments, provided herein are methods of treating a disease or condition in a subject in need thereof by increasing the expression of a target protein or functional RNA by cells of the subject, wherein the cells have a mutation that causes, e.g., exon skipping or intron inclusion, or a portion thereof, of pre-mRNA, wherein the pre-mRNA encodes the target protein or functional RNA. The method can comprise contacting cells of a subject with an SMSM compound or a pharmaceutically acceptable salt thereof that targets the pre-mRNA encoding the target protein or functional RNA or splicing complex component, whereby splicing of an exon from a pre-mRNA encoding a target protein or functional RNA is prevented or inhibited, thereby increasing a level of mRNA encoding the target protein or functional RNA, and increasing the expression of the target protein or functional RNA in the cells of the subject. In some embodiments, also disclosed herein is a method of increasing expression of a target protein by cells having a mutation or aberrant secondary or tertiary RNA structure that causes exon skipping of pre-mRNA, the pre-mRNA comprising a mutation or aberrant secondary or tertiary RNA structure that causes exon skipping. The method can comprise contacting the cells with an SMSM compound or a pharmaceutically acceptable salt thereof that targets a pre-mRNA encoding a target protein or functional RNA, whereby splicing of an exon from a pre-mRNA encoding a target protein or functional RNA is prevented or inhibited, thereby increasing the level of mRNA encoding functional protein, and increasing the expression of protein in the cells. In some embodiments, the target protein is a tumor suppressor. In some embodiments, the target protein is a tumor promoter. In some embodiments, the target protein or the functional RNA is a compensating protein or a compensating functional RNA that functionally augments or replaces a target protein or functional RNA that is deficient in amount or activity in the subject. In some embodiments, the cells are in or from a subject having a condition caused by a deficient amount or activity of the protein. In some embodiments, the deficient amount of the target protein is caused by haploinsufficiency of the target protein, wherein the subject has a first allele encoding a functional target protein, and a second allele from which the target protein is not produced, or a second allele encoding a nonfunctional target protein, and wherein an SMSM compound or a pharmaceutically acceptable salt thereof binds to a targeted portion of a pre-mRNA transcribed from the first allele. In some embodiments, the target protein is produced in a form that is fully-functional compared to the equivalent protein produced from mRNA in which an exon has been skipped or is missing. In some embodiments, the pre-mRNA is encoded by a genetic sequence with at least about 80%, 85%, 90%, 95%, 96%, 97%, 98%, 99% or 100% sequence identity to a pre-mRNA. In some embodiments, an SMSM compound or a pharmaceutically acceptable salt thereof increases the amount of the target protein or the functional RNA by modulating alternative splicing of pre-mRNA transcribed from a gene encoding the functional RNA or target protein. In some embodiments, an SMSM compound or a pharmaceutically acceptable salt thereof increases the amount of the target protein or the functional RNA by modulating aberrant splicing resulting from mutation of the gene encoding the target protein or the functional RNA.

In some embodiments, the total amount of the mRNA encoding the target protein or functional RNA produced in the cell contacted with an SMSM compound or a pharmaceutically acceptable salt thereof is increased at least about 10%, at least about 20%, at least about 50%, at least about 60%, at least about 70%, at least about 80%, at least about 90%, at least about 100%, at least about 150%, at least about 200%, at least about 250%, at least about 300%, at least about 400%, or at least about 500%, compared to the total amount of the mRNA encoding the target protein or functional RNA produced in a control cell.

In some embodiments, the total amount of the mRNA encoding the target protein or functional RNA produced in the cell contacted with than SMSM compound or a pharmaceutically acceptable salt thereof is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, or about 200% to about 250%, compared to the total amount of the mRNA encoding the target protein or functional RNA produced in a control cell.

In some embodiments, the total amount of target protein produced by the cell contacted with an SMSMS compound or a pharmaceutically acceptable salt thereof is increased at least about 20%, at least about 50%, at least about 100%, at least about 150%, at least about 200%, at least about 250%, or at least about 300%, compared to the total amount of target protein produced by a control cell. In some embodiments, the total amount of target protein produced by the cell contacted with an SMSM compound or a pharmaceutically acceptable salt thereof is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, or about 200% to about 250%, compared to the total amount of target protein produced by a control cell.

In some embodiments, a total amount of the mRNA encoding the target protein or functional RNA produced in the cell contacted with an SMSM compound or a pharmaceutically acceptable salt thereof is increased at least about 1.1-fold, at least about 1.5-fold, at least about 2-fold, at least about 2.5-fold, at least about 3-fold, at least about 3.5-fold, at least about 4-fold, at least about 5-fold, or at least about 10-fold compared to the total amount of the mRNA encoding the target protein or functional RNA produced in a control cell. In some embodiments, a total amount of an mRNA encoding the target protein or functional RNA produced in a cell contacted with an SMSM compound or a pharmaceutically acceptable salt thereof is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, or about 4 to about 9-fold, compared to a total amount of the mRNA encoding the target protein or functional RNA produced in a control cell.

In some embodiments, a total amount of target protein produced by a cell contacted with an SMSM compound or a pharmaceutically acceptable salt thereof is increased at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the total amount of target protein produced by a control cell. In some embodiments, the total amount of target protein produced by the cell contacted with an SMSM compound or a pharmaceutically acceptable salt thereof is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, or about 4 to about 9-fold, compared to a total amount of target protein produced by a control cell.

In some embodiments, the total amount of the mRNA encoding the target protein or functional RNA produced in the cell contacted with an SMSM compound or a pharmaceutically acceptable salt thereof is decreased at least about 10%, at least about 20%, at least about 30%, at least about 40%, at least about 50%, at least about 60%, at least about 70%, at least about 80%, at least about 90%, or at least about 100%, compared to the total amount of the mRNA encoding the target protein or functional RNA produced in a control cell.

In some embodiments, the total amount of the mRNA encoding the target protein or functional RNA produced in the cell contacted with an SMSM compound or a pharmaceutically acceptable salt thereof is decreased about 10% to about 100%, about 20% to about 100%, about 30% to about 100%, about 40% to about 100%, about 50% to about 100%, about 60% to about 100%, about 70% to about 100%, about 80% to about 100% about 90% to about 100%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, 70% to about 80%, about 70% to about 90%, or about 80% to about 90%, compared to the total amount of the mRNA encoding the target protein or functional RNA produced in a control cell.

In some embodiments, the total amount of target protein produced by the cell contacted with an SMSM compound or a pharmaceutically acceptable salt thereof is decreased at least about 10%, at least about 20%, at least about 30%, at least about 40%, at least about 50%, at least about 60%, at least about 70%, at least about 80%, at least about 90%, or at least about 100%, compared to the total amount of target protein produced by a control cell. In some embodiments, the total amount of target protein produced by the cell contacted with an SMSM compound or a pharmaceutically acceptable salt thereof is decreased about 10% to about 100%, about 20% to about 100%, about 30% to about 100%, about 40% to about 100%, about 50% to about 100%, about 60% to about 100%, about 70% to about 100%, about 80% to about 100% about 90% to about 100%, about 20% to about 30%, about 20% to about 40%, about 20% to about 50%, about 20% to about 60%, about 20% to about 70%, about 20% to about 80%, about 20% to about 90%, about 30% to about 40%, about 30% to about 50%, about 30% to about 60%, about 30% to about 70%, about 30% to about 80%, about 30% to about 90%, about 40% to about 50%, about 40% to about 60%, about 40% to about 70%, about 40% to about 80%, about 40% to about 90%, about 50% to about 60%, about 50% to about 70%, about 50% to about 80%, about 50% to about 90%, about 60% to about 70%, about 60% to about 80%, about 60% to about 90%, 70% to about 80%, about 70% to about 90%, or about 80% to about 90%, compared to the total amount of target protein produced by a control cell.

In some embodiments, the difference in amount between a first splice variant and a second splice variant encoding a target protein or functional RNA isoform produced in the cell contacted with an SMSM compound or a pharmaceutically acceptable salt thereof is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 20%, at least about 50%, at least about 100%, at least about 150%, at least about 200%, at least about 250%, or at least about 300%, compared to the difference in amounts between the two splice variants produced by a control cell. In some embodiments, the difference in amount between a first protein isoform expressed from a first splice variant and a second protein isoform expressed from a second splice variant produced by the cell contacted with an SMSM compound or a pharmaceutically acceptable salt thereof is increased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 20%, at least about 50%, at least about 100%, at least about 150%, at least about 200%, at least about 250%, or at least about 300%, compared to the difference in amounts between two protein isoforms produced from the splice variants produced by a control cell.

In some embodiments, the difference in amount between a first splice variant and a second splice variant encoding a target protein or functional RNA isoform produced in the cell contacted with an SMSM compound or a pharmaceutically acceptable salt thereof is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the difference in amounts between the two splice variants produced by a control cell. In some embodiments, the difference in amount between a first protein isoform expressed from a first splice variant and a second protein isoform expressed from a second splice variant produced by the cell contacted with an SMSM compound or a pharmaceutically acceptable salt thereof is increased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the difference in amounts between two protein isoforms expressed from the splice variants produced by a control cell.

In some embodiments, a difference in amount between a first splice variant and a second splice variant encoding a target protein or functional RNA isoform produced in a cell contacted with an SMSM compound or a pharmaceutically acceptable salt thereof is decreased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 20%, at least about 50%, at least about 100%, at least about 150%, at least about 200%, at least about 250%, or at least about 300%, compared to the difference in amounts between the two splice variants produced by a control cell. In some embodiments, a difference in amount between a first protein isoform expressed from a first splice variant and a second protein isoform expressed from a second splice variant produced by a cell contacted with an SMSM compound or a pharmaceutically acceptable salt thereof is decreased about 20% to about 300%, about 50% to about 300%, about 100% to about 300%, about 150% to about 300%, about 20% to about 50%, about 20% to about 100%, about 20% to about 150%, about 20% to about 200%, about 20% to about 250%, about 50% to about 100%, about 50% to about 150%, about 50% to about 200%, about 50% to about 250%, about 100% to about 150%, about 100% to about 200%, about 100% to about 250%, about 150% to about 200%, about 150% to about 250%, about 200% to about 250%, at least about 20%, at least about 50%, at least about 100%, at least about 150%, at least about 200%, at least about 250%, or at least about 300%, compared to a difference in amounts between two protein isoforms produced from the splice variants produced by a control cell.

In some embodiments, the difference in amount between a first splice variant and a second splice variant encoding a target protein or functional RNA isoform produced in the cell contacted with an SMSM compound or a pharmaceutically acceptable salt thereof is decreased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the difference in amounts between the two splice variants produced by a control cell. In some embodiments, the difference in amount between a first protein isoform expressed from a first splice variant and a second protein isoform expressed from a second splice variant produced by the cell contacted with an SMSM compound or a pharmaceutically acceptable salt thereof is decreased about 1.1 to about 10-fold, about 1.5 to about 10-fold, about 2 to about 10-fold, about 3 to about 10-fold, about 4 to about 10-fold, about 1.1 to about 5-fold, about 1.1 to about 6-fold, about 1.1 to about 7-fold, about 1.1 to about 8-fold, about 1.1 to about 9-fold, about 2 to about 5-fold, about 2 to about 6-fold, about 2 to about 7-fold, about 2 to about 8-fold, about 2 to about 9-fold, about 3 to about 6-fold, about 3 to about 7-fold, about 3 to about 8-fold, about 3 to about 9-fold, about 4 to about 7-fold, about 4 to about 8-fold, about 4 to about 9-fold, at least about 1.1-fold, at least about 1.5-fold, at least about 2-fold, at least about 2.5-fold, at least about 3-fold, at least about 3.5-fold, at least about 4-fold, at least about 5-fold, or at least about 10-fold, compared to the difference in amounts between two protein isoforms express from the splice variants produced by a control cell.

The ratio of a first isoform and a second isoform may contribute to a number of conditions or diseases. In some embodiments, a subject without a condition or disease has a first isoform to second isoform ratio of 1:1. In some embodiments, a subject with a condition or disease described herein has a first isoform to second isoform ratio of about 1:1.2, 1:1.4, 1:1.6, 1:1.8, 1:2, 1:2.5, 1:3, 1:3.5, 1:4, 1:4.5 or 1:5. In some embodiments, a subject with a condition or disease described herein has a first isoform to second isoform ratio from about 1:1 to about 1:1.1, about 1:1 to about 1:1.2, about 1:1 to about 1:1.3, about 1:1 to about 1:1.4, about 1:1 to about 1:1.5, about 1:1 to about 1:1.6, about 1:1 to about 1:1.8, about 1:1 to about 1:2, about 1:1 to about 1:3, about 1:1 to about 1:3.5, about 1:1 to about 1:4, about 1:1 to about 1:4.5, about 1:1 to about 1:5, 1:2 to about 1:3, about 1:2 to about 1:4, about 1:2 to about 1:5, about 1:3 to about 1:4, about 1:3 to about 1:5, or about 1:4 to about 1:5.

In some embodiments, binding of an SMSM compound or a pharmaceutically acceptable salt thereof to pre-mRNA prevents splicing out of one or more exons and/or introns and/or proteins thereof, from the population of pre-mRNAs to produce mRNA encoding the target protein or functional RNA. In some embodiments, the cell comprises a population of pre-mRNAs transcribed from the gene encoding the target protein or functional RNA, wherein the population of pre-mRNAs comprises a mutation that causes the splicing out of one or more exons, and wherein an SMSM compound or a pharmaceutically acceptable salt thereof binds to the mutation that causes the splicing out of the one or more exons in the population of pre-mRNAs. In some embodiments, the binding of an SMSM compound or a pharmaceutically acceptable salt thereof to the mutation that causes the splicing out of the one or more exons prevents splicing out of the one or more exons from the population of pre-mRNAs to produce mRNA encoding the target protein or functional RNA. In some embodiments, the condition is a disease or disorder. In some embodiments, the method further comprises assessing protein expression. In some embodiments, an SMSM compound or a pharmaceutically acceptable salt thereof binds to a targeted portion of a pre-mRNA.

In some embodiments, the binding of an SMSM compound or a pharmaceutically acceptable salt thereof catalyzes the inclusion of a missing exon or removal of an undesired retained intron or portions thereof, resulting in healthy mRNA and proteins. In some embodiments, the binding of an SMSM compound or a pharmaceutically acceptable salt thereof has minimal to no effect on non-diseased cells.

In some embodiments, an SMSM kills cells at an $IC_{50}$ of less than 50 nM. In some embodiments, the cells are primary cells. In some embodiments, an SMSM kills the cells at an $IC_{50}$ of less than 48 nM, 45 nM, 40 nM, 35 nM, 30 nM, 25 nM, 20 nM, 15 nM, 10 nM, 5 nM, 3 nM, or 1 nM.

In some embodiments, an SMSM modulates splicing at a splice site sequence of a polynucleotide of the primary cells. In some embodiments, an SMSM modulates proliferation or survival of the primary cells. In some embodiments, the primary cells are primary diseased cells. In some embodiments, the primary diseased cells are primary cancer cells. In some embodiments, the SMSM is present at a concentration of at least about 1 nM, 10 nM, 100 nM, 1 µM, 10 µM, 100 µM, 1 mM, 10 mM, 100 mM, or 1 M. In some embodiments, at least about 5%, 10%, 25%, 30%, 40%, 50%, 60%, 70%, 75%, 80%, 85%, 90%, 95%, 97%, 98%, 99% or 100% of the primary diseased cells are killed. In some embodiments, at least about 5%, 10%, 25%, 30%, 40%, 50%, 60%, 70%, 75%, 80%, 85%, 90%, 95%, 97%, 98%, 99% or 100% of the primary diseased cells undergo apoptosis. In some embodiments, at least about 5%, 10%, 25%, 30%, 40%, 50%, 60%, 70%, 75%, 80%, 85%, 90%, 95%, 97%, 98%, 99% or 100% of the primary diseased cells undergo necrosis. In some embodiments, proliferation is reduced or inhibited in at least about 5%, 10%, 25%, 30%, 40%, 50%, 60%, 70%, 75%, 80%, 85%, 90%, 95%, 97%, 98%, 99% or 100% of the primary diseased cells. In some embodiments, the primary diseased cells are non-transformed cells.

In some embodiments, an SMSM reduces a size of a tumor in a subject. In some embodiments, a size of a tumor in a subject administered an SMSM or a pharmaceutically acceptable salt thereof is reduced by at least about 1%, 5%, 10%, 15%, 20%, 25%, 30%, 35%, 40%, 45%, 50%, 55%, 60%, 70%, 75%, 80%, 85%, 90%, 95%, 96%, 97%, 98%, or 99% in the subject. In some embodiments, a diameter of a tumor in a subject administered an SMSM or a pharmaceutically acceptable salt thereof is reduced by at least about 1%, 5%, 10%, 15%, 20%, 25%, 30%, 35%, 40%, 45%, 50%, 55%, 60%, 70%, 75%, 80%, 85%, 90%, 95%, 96%, 97%, 98%, or 99%. In some embodiments, a volume of the tumor is reduced by at least about 1%, 5%, 10%, 15%, 20%, 25%, 30%, 35%, 40%, 45%, 50%, 55%, 60%, 70%, 75%, 80%, 85%, 90%, 95%, 96%, 97%, 98%, or 99% in the subject. In some embodiments, the tumor is malignant.

In some embodiments, a method comprises contacting an SMSM to primary non-diseased cells. In some embodiments, at most about 1%, 5%, 10%, 15%, 20%, 25%, or 50% of the primary non-diseased cells are killed. In some embodiments, at most about 1%, 5%, 10%, 15%, 20%, 25%, or 50% of the primary non-diseased cells undergo apoptosis. In some embodiments, at most about 1%, 5%, 10%, 15%, 20%, 25%, or 50% of the primary non-diseased cells undergo necrosis. In some embodiments, proliferation is reduced or inhibited in at most about 1%, 5%, 10%, 15%, 20%, 25%, or 50% of the primary non-diseased cells. In some embodiments, the primary non-diseased cells are of the same tissue as the primary diseased cells. In some embodiments, the primary non-diseased cells are differentiated cells.

An SMSM can modulate splicing at a splice site of a polynucleotide and does not exhibit significant toxicity. In some embodiments, an SMSM penetrates the blood brain barrier (BBB) when administered to a subject.

In some embodiments, an SMSM has a brain/blood AUC of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 40, or higher.

In some embodiments, an SMSM has a half-life of at least about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, or 1000 hours in a human.

In some embodiments, an SMSM is stable at room temperature for at least 1, 2, 3, 4, 5, 6, 7, 8, 9, 10, 11, 12, 13, 14, 15, 16, 17, 18, 19, 20, 21, 22, 23 or 24 hours; or at least 1, 2, 3, 4, 5, 6, 7, 8, 9, 10, 11, or 12 months; or at least 1, 2, 3, 4, or 5 years. In some embodiments, an SMSM is stable at 4° C. for at least 1, 2, 3, 4, 5, 6, 7, 8, 9, 10, 11, 12, 13, 14, 15, 16, 17, 18, 19, 20, 21, 22, 23 or 24 hours; or for at least 1, 2, 3, 4, 5, 6, 7, 8, 9, 10, 11, or 12 months; or at least 1, 2, 3, 4, or 5 years. In some embodiments, an SMSM is stable at room temperature in water or an organic solvent for at least 1, 2, 3, 4, 5, 6, 7, 8, 9, 10, 11, 12, 13, 14, 15, 16, 17, 18, 19, 20, 21, 22, 23 or 24 hours; or at least 1, 2, 3, 4, 5, 6, 7, 8, 9, 10, 11, or 12 months; or at least 1, 2, 3, 4, or 5 years. In some embodiments, an SMSM is stable at 4° C. in water or an organic solvent for at least 1, 2, 3, 4, 5, 6, 7, 8, 9, 10, 11, 12, 13, 14, 15, 16, 17, 18, 19, 20, 21, 22, 23 or 24 hours; or for at least 1, 2, 3, 4, 5, 6, 7, 8, 9, 10, 11, or 12 months; or at least 1, 2, 3, 4, or 5 years.

In some embodiments, an SMSM has an cell viability $IC_{50}$ of 0.01-10 nM, 0.01-5 nM, 0.01-2.5 nM, 0.01-1 nM, 0.01-0.75 nM, 0.01-0.5 nM, 0.01-0.25 nM, 0.01-0.1 nM, 0.1-100 nM, 0.1-50 nM, 0.1-25 nM, 0.1-10 nM, 0.1-7.5 nM, 0.1-5 nM, 0.1-2.5 nM, 2-1000 nM, 2-500 nM, 2-250 nM, 2-100 nM, 2-75 nM, 2-50 nM, 2-25 nM, 2-10 nM, 10-1000 nM, 10-500 nM, 10-250 nM, 10-100 nM, 10-75 nM, 10-50 nM, 10-25 nM, 25-1000 nM, 25-500 nM, 25-250 nM, 25-100 nM, 25-75 nM, 25-50 nM, 50-1000 nM, 50-500 nM, 50-250 nM, 50-100 nM, 50-75 nM, 60-70 nM, 100-1000 nM, 100-500 nM, 100-250 nM, 250-1000 nM, 250-500 nM, or 500-1000 nM.

In some embodiments, an SMSM has an cell viability $IC_{50}$ of at most 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 30 nM, 35 nM, 40 nM, 45 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 90 nM, 95 nM, 100 nM, 110 nM, 120 nM, 130 nM, 140 nM, 150 nM, 160 nM, 170 nM, 180 nM, 190 nM, 200 nM, 210 nM, 220 nM, 230 nM, 240 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, or 10 µM.

In some embodiments, an SMSM reduces cell proliferation of diseased cells by more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when the cells are treated with the SMSM at a concentration of 2-1000 nM, 2-500 nM, 2-250 nM, 2-100 nM, 2-75 nM, 2-50 nM, 2-25 nM, 2-10 nM, 10-1000 nM, 10-500 nM, 10-250 nM, 10-100 nM, 10-75 nM, 10-50 nM, 10-25 nM, 25-1000 nM, 25-500 nM, 25-250 nM, 25-100 nM, 25-75 nM, 25-50 nM, 50-1000 nM, 50-500 nM, 50-250 nM, 50-100 nM, 50-75 nM, 60-70 nM, 100-1000 nM, 100-500 nM, 100-250 nM, 250-1000 nM, 250-500 nM, or 500-1000 nM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM reduces cell proliferation of diseased cells by more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when the cells are treated with the SMSM at a concentration of at least 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 30 nM, 35 nM, 40 nM, 45 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 90 nM, 95 nM, 100 nM, 110 nM, 120 nM, 130 nM, 140 nM, 150 nM, 160 nM, 170 nM, 180 nM, 190 nM, 200 nM, 210 nM, 220 nM, 230 nM, 240 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, or 10 µM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM reduces viability of diseased cells by more than 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. when the cells are treated with the SMSM at a concentration of 2-1000 nM, 2-500 nM, 2-250 nM, 2-100 nM, 2-75 nM, 2-50 nM, 2-25 nM, 2-10 nM, 10-1000 nM, 10-500 nM, 10-250 nM, 10-100 nM, 10-75 nM, 10-50 nM, 10-25 nM, 25-1000 nM, 25-500 nM, 25-250 nM, 25-100 nM, 25-75 nM, 25-50 nM, 50-1000 nM, 50-500 nM, 50-250 nM, 50-100 nM, 50-75 nM, 60-70 nM, 100-1000 nM, 100-500 nM, 100-250 nM, 250-1000 nM, 250-500 nM, or 500-1000 nM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM reduces viability of diseased cells by more than 10%, 11%, 12%, 13%, 14%, 15%, 16%, 17%, 18%, 19%, 20%, 21%, 22%, 23%, 24%, 25%, 30%, 35%, 40%, 45%, 50%, 51%, $5^2$%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% when the cells are treated with the SMSM at a concentration of at least 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 30 nM, 35 nM, 40 nM, 45 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 90 nM, 95 nM, 100 nM, 110 nM, 120 nM, 130 nM, 140 nM, 150 nM, 160 nM, 170 nM, 180 nM, 190 nM, 200 nM, 210 nM, 220 nM, 230 nM, 240 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, or 10 µM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM does not reduce viability of non-diseased cells by more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, or 50 when the cells are treated with the SMSM at a concentration of 2-1000 nM, 2-500 nM, 2-250 nM, 2-100 nM, 2-75 nM, 2-50 nM, 2-25 nM, 2-10 nM, 10-1000 nM, 10-500 nM, 10-250 nM, 10-100 nM, 10-75 nM, 10-50 nM, 10-25 nM, 25-1000 nM, 25-500 nM, 25-250 nM, 25-100 nM, 25-75 nM, 25-50 nM, 50-1000 nM, 50-500 nM, 50-250 nM, 50-100 nM, 50-75 nM, 60-70 nM, 100-1000 nM, 100-500 nM, 100-250 nM, 250-1000 nM, 250-500 nM, or 500-1000 nM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM does not reduce viability of non-diseased cells by more than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, or 50% when the cells are treated with the SMSM at a concentration of at least 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 30 nM, 35 nM, 40 nM, 45 nM, 50 nM, 51 nM, 52 nM, 53 nM, 54 nM, 55 nM, 56 nM, 57 nM, 58 nM, 59 nM, 60 nM, 61 nM, 62 nM, 63 nM, 64 nM, 65 nM, 66 nM, 67 nM, 68 nM, 69 nM, 70 nM, 71 nM, 72 nM, 73 nM, 74 nM, 75 nM, 76 nM, 77 nM, 78 nM, 79 nM, 80 nM, 81 nM, 82 nM, 83 nM, 84 nM, 85 nM, 90 nM, 95 nM, 100 nM, 110 nM, 120 nM, 130 nM, 140 nM, 150 nM, 160 nM, 170 nM, 180 nM, 190 nM, 200 nM, 210 nM, 220 nM, 230 nM, 240 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 µM, or 10 µM for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 21, 32, 33, 34, 35, 36, 37, 38, 39, 40, 41, 42, 43, 44, 45, 46, 47, or 48 hours.

In some embodiments, an SMSM reduces a size of a tumor in a subject by at least 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

In some embodiments, an SMSM inhibits tumor growth of a tumor in a subject by at least 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%.

SMSM Targets

Aberrant splicing of mRNA, such as pre-mRNA, can result in a defective protein and can cause a disease or a disorder in a subject. The compositions and methods described herein can reduce this aberrant splicing of mRNA, such as pre-mRNA, and treat a disease or a disorder caused by this aberrant splicing.

Diseases associated with changes to RNA transcript amount are often treated with a focus on the aberrant protein expression. However, if the processes responsible for the aberrant changes in RNA levels, such as components of the splicing process or associated transcription factors or associated stability factors, could be targeted by treatment with a small molecule, it would be possible to restore protein expression levels such that the unwanted effects of the expression of aberrant levels of RNA transcripts or associated proteins. Therefore, there is a need for methods of modulating the amount of RNA transcripts encoded by certain genes as a way to prevent or treat diseases associated with aberrant expression of the RNA transcripts or associated proteins.

Structural Targets

Mutations and/or aberrant secondary or tertiary RNA structures in cis-acting elements can induce three-dimensional structural change in pre-mRNA. Mutations and/or aberrant secondary RNA structures in cis-acting elements can induce three-dimensional structural change in pre-mRNA when the pre-mRNA is, for example, bound to at least one snRNA, or at least one snRNP, or at least one other auxiliary splicing factor. For example, non-canonical base pairing of a non-canonical splice site sequence to a snRNA can form a bulge. For example, a bulge can be formed when the 5'ss is bound to U1-U12 snRNA or a portion thereof. For example, a bulge can be induced to form when 5'ss containing at least one mutation is bound to U1-U12 snRNA or a portion thereof. For example, a bulge can be formed when the cryptic 5'ss is bound to U1-U12 snRNA or a portion thereof. For example, a bulge can be induced to form when cryptic 5'ss containing at least one mutation is bound to U1-U12 snRNA or a portion thereof. For example, a bulge can be formed when the 3'ss is bound to U2 snRNA or a portion thereof. For example, a bulge can be induced to form when the 3'ss is bound to U2 snRNA or a portion thereof. For example, a bulge can be formed when the cryptic 3'ss is bound to U2 snRNA or a portion thereof. For example, a bulge can be induced to form when the cryptic 3'ss is bound to U2 snRNA or a portion thereof. The protein components of U1 and U2 may or may not present to form the bulge. Exemplary 5' splice site mutations and/or with aberrant secondary and/or tertiary structures that can induce a bulge structure are shown in Table 2A, Table 2B, Table 2C and Table 2D. A polynucleotide in the methods disclosed herein can contain any one of exemplary the 5' splice site sequences summarized in Table 2A, Table 2B, Table 2C and Table 2D.

In some embodiments, a small molecule can bind to a bulge. In some embodiments, a bulge is naturally occurring. In some embodiments, a bulge is formed by non-canonical base-pairing between the splice site and the small nuclear RNA. For example, a bulge can be formed by non-canonical base-pairing between the 5'ss and U1-U12 snRNA. The bulge can comprise 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, or 15 nucleotides. In some embodiments, 3-dimensional structural changes can be induced by a mutation without bulge formation. In some embodiments, a bulge may be formed without any mutation in a splice site. In some embodiments, a recognition portion can be formed by a mutation in any of the cis-acting elements. In some embodiments, a small molecule can bind to a recognition portion that is induced by a mutation. In some embodiments, a mutation and/or aberrant secondary or tertiary RNA structure at an authentic 5' splice site can result in splicing at a cryptic 5' splice site. In some embodiments, a mutation and/or aberrant secondary or tertiary RNA structure can be in one of the regulatory elements including ESEs, ESSs, ISEs, and ISSs.

In some embodiments, a target of an SMSM is a pre-mRNA comprising a splice site sequence with a bulged nucleotide in an exon. In some embodiments, a target of an SMSM is a pre-mRNA comprising a splice site sequence with a bulged nucleotide upstream (5') of the splice site of the splice site sequence. In some embodiments, a target of an SMSM is a pre-mRNA comprising a splice site sequence with a bulged nucleotide at the −1 position relative to the splice site of the splice site sequence. For example, a target of an SMSM can be a pre-mRNA comprising a splice site sequence of NNN*nnnnnn, wherein N* represents a bulged nucleotide. In some embodiments, a target of an SMSM is a pre-mRNA comprising a splice site sequence with a bulged nucleotide at the −2 position relative to the splice site of the splice site sequence. For example, a target of an SMSM can be a pre-mRNA comprising a splice site sequence of NN*Nnnnnnn, wherein N* represents a bulged nucleotide. In some embodiments, a target of an SMSM is a pre-mRNA comprising a splice site sequence with a bulged nucleotide at the −3 position relative to the splice site of the splice site sequence. For example, a target of an SMSM can be a pre-mRNA comprising a splice site sequence of N*NNnnnnnn, wherein N* represents a bulged nucleotide.

In some embodiments, a target of an SMSM is a pre-mRNA comprising a splice site sequence with a bulged nucleotide in an intron. In some embodiments, a target of an SMSM is a pre-mRNA comprising a splice site sequence with a bulged nucleotide downstream (3') of the splice site of the splice site sequence.

In some embodiments, a target of an SMSM is a pre-mRNA comprising a splice site sequence with a bulged nucleotide at the +1 position relative to the splice site of the splice site sequence. For example, a target of an SMSM can be a pre-mRNA comprising a splice site sequence of NNNn*nnnnn, wherein n* represents a bulged nucleotide. In some embodiments, a target of an SMSM is a pre-mRNA comprising a splice site sequence with a bulged nucleotide at the +2 position relative to the splice site of the splice site sequence. For example, a target of an SMSM can be a pre-mRNA comprising a splice site sequence of NNNnn*nnnn, wherein n* represents a bulged nucleotide. In some embodiments, a target of an SMSM is a pre-mRNA comprising a splice site sequence with a bulged nucleotide at the +3 position relative to the splice site of the splice site sequence. For example, a target of an SMSM can be a pre-mRNA comprising a splice site sequence of NNNnnn*nnn, wherein n* represents a bulged nucleotide. In some embodiments, a target of an SMSM is a pre-mRNA comprising a splice site sequence with a bulged nucleotide at the +4 position relative to the splice site of the splice site sequence. For example, a target of an SMSM can be a pre-mRNA comprising a splice site sequence of NNNnnnn*nn, wherein n* represents a bulged nucleotide. In some embodiments, a target of an SMSM is a pre-mRNA comprising a splice site sequence with a bulged nucleotide at the +5 position relative to the splice site of the splice site sequence. For example, a target of an SMSM can be a pre-mRNA comprising a splice site sequence of NNNnnnnn*n, wherein n* represents a bulged nucleotide. In some embodiments, a target of an SMSM is a pre-mRNA comprising a splice site sequence with a bulged nucleotide at the +6 position relative to the splice site of the splice site sequence. For example, a target of an SMSM can be a pre-mRNA comprising a splice site sequence of NNNnnnnnn*, wherein n* represents a bulged nucleotide. In some embodiments, a target of an SMSM is a pre-mRNA comprising a splice site sequence with a bulged nucleotide at the +7 position relative to the splice site of the splice site sequence. For example, a target of an SMSM can be a pre-mRNA comprising a splice site sequence of NNNnnnnnnn*, wherein n* represents a bulged nucleotide.

In some embodiments, a target of an SMSM is a pre-mRNA comprising a splice site sequence with one or more bulged nucleotides at the −1, −2, −3, +1, +2, +3, +4, +5, +6 and/or +7 position relative to the splice site of the splice site sequence. For example, a target of an SMSM can be a pre-mRNA comprising a splice site sequence of NNN*nnnnnn, NN*Nnnnnnn, N*NNnnnnnn, NNNn*nnnnn, NNNnn*nnnn, NNNnnn*nnn, NNNnnnn*nn, NNNnnnnn*n, NNNnnnnnn*, or NNNnnnnnnn*, wherein N* or n* represents a bulged nucleotide.

In some embodiments, a target of an SMSM is a pre-mRNA comprising a splice site sequence with one or more bulged nucleotides at the −1, −2, and/or −3 position relative to the splice site of the splice site sequence. For example, a target of an SMSM can be a pre-mRNA comprising a splice site sequence of NNN*nnnnnn, NN*Nnnnnnn, or N*NNnnnnnn, wherein N* represents a bulged nucleotide.

In some embodiments, a target of an SMSM is a pre-mRNA comprising a splice site sequence with one or more bulged nucleotides at the +1, +2, +3, +4, +5, +6 and/or +7 position relative to the splice site of the splice site sequence. For example, a target of an SMSM can be a pre-mRNA comprising a splice site sequence of NNNn*nnnnn, NNNnn*nnnn, NNNnnn*nnn, NNNnnnn*nn, NNNnnnnn*n, NNNnnnnnn*, or NNNnnnnnnn*, wherein n* represents a bulged nucleotide.

In some embodiments, a target of an SMSM is a pre-mRNA comprising a splice site sequence with a bulged nucleotide at the −1 position relative to the splice site of the splice site sequence and a bulged nucleotide at the −2 position relative to the splice site of the splice site sequence. For example, a target of an SMSM can be a pre-mRNA comprising a splice site sequence of NN*N*nnnnnn, wherein N* represents a bulged nucleotide. In some embodiments, a target of an SMSM is a pre-mRNA comprising a splice site sequence with a bulged nucleotide at the −2 position relative to the splice site of the splice site sequence and a bulged nucleotide at the −3 position relative to the splice site of the splice site sequence. For example, a target of an SMSM can be a pre-mRNA comprising a splice site sequence of N*N*Nnnnnnn, wherein N* represents a bulged nucleotide.

In some embodiments, an SMSM interacts with a bulged nucleotide of an RNA duplex comprising a splice site. In some embodiments, the RNA duplex comprises pre-mRNA. In some embodiments, an SMSM binds to an RNA duplex and interacts with an unpaired bulged nucleobase of an RNA duplex comprising a splice site. In some embodiments, a first portion of the SMSM interacts with the bulged nucleotide on a first RNA strand of the RNA duplex. In some embodiments, a second portion of the SMSM interacts with one or more nucleotides of a second RNA strand of the RNA duplex, wherein the first RNA strand is not the second RNA strand. In some embodiments, the SMSM forms one or more intermolecular interactions with the duplex RNA, for example, an ionic interaction, a hydrogen bond, a dipole-dipole interaction or a van der Waals interaction. In some embodiments, the SMSM forms one or more intermolecular interactions with the bulged nucleotide, for example, an ionic interaction, a hydrogen bond, a dipole-dipole interaction or a van der Waals interaction.

In some embodiments, the duplex RNA comprises an alpha helix. In some embodiments, the bulged nucleotide is located on an external portion of a helix of the duplex RNA. In some embodiments, the bulged nucleotide is located within an internal portion of the helix of the duplex RNA.

In some embodiments, a rate of exchange of the bulged nucleotide from within the interior of a helix of the duplex RNA to an exterior portion of the helix is reduced.

In some embodiments, the SMSM modulates a distance of the bulged nucleotide from a second nucleotide of the duplex RNA. In some embodiments, the SMSM reduces the distance of the bulged nucleotide from a second nucleotide of the duplex RNA. In some embodiments, the SMSM increases the distance of the bulged nucleotide from a second nucleotide of the duplex RNA.

In some embodiments, the bulged nucleotide is located within the interior of a helix of the duplex RNA of the complex. In some embodiments, the bulged nucleotide has modulated base stacking within an RNA strand of the RNA duplex. In some embodiments, the bulged nucleotide has increased base stacking within an RNA strand of the RNA duplex. In some embodiments, the bulged nucleotide has decreased base stacking within an RNA strand of the RNA duplex.

In some embodiments, the SMSM modulates splicing at the splice site of the RNA duplex. In some embodiments, the SMSM increases splicing at the splice site of the RNA duplex. In some embodiments, the SMSM reduces splicing at the splice site of the RNA duplex. In some embodiments, the SMSM reduces a size of a bulge of the RNA duplex. In some embodiments, the SMSM removes a bulge of the RNA duplex. In some embodiments, the SMSM stabilizes a bulge of the RNA duplex.

In some embodiments, the unpaired bulged nucleotide is free to rotate around a phosphate backbone of an RNA strand of the RNA duplex in the absence of the SMSM. In some embodiments, the SMSM reduces a rate of rotation of the unpaired bulged nucleotide. In some embodiments, the SMSM reduces a rate of rotation of the unpaired bulged nucleotide around a phosphate backbone of an RNA strand of the RNA duplex.

In some embodiments, the SMSM is not an aptamer.

Also, provided herein is a method of modulating splicing comprising contacting a small molecule splicing modulator compound (SMSM) to a cell; wherein the SMSM interacts with an unpaired bulged nucleotide of an RNA duplex in the cell; wherein the duplex RNA comprises a splice site; and wherein the SMSM modulates splicing of the RNA duplex.

Provided herein is a method for modulating the relative position of a first nucleotide relative to a second nucleotide, wherein the first nucleotide and the second nucleotide are within a duplex RNA, the method comprising contacting a small molecule splicing modulator compound (SMSM) to the duplex RNA, or a pharmaceutically acceptable salt thereof, wherein the first nucleotide is a bulged nucleotide of the RNA duplex; wherein the duplex RNA comprises a splice site.

In some embodiments, the duplex RNA comprises a helix.

In some embodiments, the bulged nucleotide is located on an external portion of a helix of the duplex RNA prior to contacting the SMSM.

In some embodiments, SMSM forms one or more intermolecular interactions with the duplex RNA.

In some embodiments, the SMSM forms one or more intermolecular interactions with an unpaired bulged nucleotide. In some embodiments, the intermolecular interaction is selected from the group comprising an ionic interaction, a hydrogen bond, a dipole-dipole interaction or a van der Waals interaction. In some embodiments, a rate of exchange of the unpaired bulged nucleotide from within the interior of a helix of the duplex RNA to an exterior portion of the helix is reduced. In some embodiments, a rate of rotation of the unpaired bulged nucleotide is reduced. In some embodiments, a rate of rotation of the unpaired bulged nucleotide around a phosphate backbone of an RNA strand of the RNA duplex is reduced. In some embodiments, a distance of the unpaired bulged nucleotide from a second nucleotide of the duplex RNA is modulated after contacting the SMSM. In some embodiments, the distance of the unpaired bulged nucleotide from a second nucleotide of the duplex RNA is reduced. In some embodiments, unpaired bulged nucleotide is located within the interior of the helix of the duplex RNA. In some embodiments, a size of a bulge of the RNA duplex is reduced. In some embodiments, a bulge of the RNA duplex is removed or maintained.

In some embodiments, splicing at the splice site of the RNA duplex is promoted. In some embodiments, base stacking of the unpaired bulged nucleotide within an RNA strand of the RNA duplex is increased after contacting the SMSM. In some embodiments, the distance of the unpaired bulged nucleotide from a second nucleotide of the duplex RNA is increased or maintained. In some embodiments, a bulge of the RNA duplex is stabilized after contacting the SMSM. In some embodiments, the unpaired bulged nucleotide is located on an exterior portion of a helix of the duplex RNA. In some embodiments, a size of a bulge of the RNA duplex is increased. In some embodiments, splicing at the splice site of the RNA duplex is inhibited. In some embodiments, splicing is inhibited at the splice site. In some embodiments, base stacking of the unpaired bulged nucleotide within an RNA strand of the RNA duplex is reduced after contacting the SMSM.

Exemplary sites targeted by the SMSMs described herein include 5' splice sites, 3' splice sites, polypyrimidine tracts, branch sites, splicing enhancers and silencer elements. Mutations or aberrant secondary or tertiary RNA structures at hot spots can create mRNA sites or scaffold sequences that can be targeted. For example, many exons are flanked by the intronic dinucleotides GT and AG at the 5' and 3' splice sites, respectively. For example, mutations or aberrant secondary or tertiary RNA structures at these sites can cause, e.g., exclusion of an adjacent exon or inclusion of an adjacent intron. Many factors influence the complex pre-mRNA splicing process, including several hundred different proteins, at least five spliceosomal snRNAs, sequences on the mRNA, sequence length, enhancer and silencer elements, and strength of splicing signals. Exemplary sites targeted by the SMSMs described herein include secondary and sometimes tertiary structures of RNA. For example, exemplary sites targeted by the SMSMs described herein include a stem loop, hairpin, branch point sequence (BPS), polypyrimidine tract (PPT), 5' splice site (5'ss) and 3' splice site (3'ss), duplex snRNA and splice sites and trans acting protein binding to RNA. The target pre-mRNA can comprise a defective sequence, such as a sequence that produces a deficient protein, such as a protein with altered function such as enzyme activity, or expression, such as lack of expression. In some embodiments, the defective sequence impacts the structure of the RNA. In some embodiments, the defect sequence impacts recognition by snRNP.

In addition to consensus splice site sequences, structural constraints, including those resulting from mutations, can affect cis-acting sequences such as exonic/intronic splicing enhancers (ESE/ISE) or silencer elements (ESS/ISS).

In some embodiments, a mutation in native DNA and/or pre-mRNA, or an aberrant secondary or tertiary structure of RNA, creates a new splice site sequence. For example, a mutation or aberrant RNA structure may cause native regions of the RNA that are normally dormant, or play no role as splicing elements, to become activated and serve as splice sites or splice elements. Such splice sites and elements can be referred to as "cryptic". For example, a native intron may become divided into two aberrant introns, with a new exon situated there between. For example, a mutation may create a new splice site between a native 5' splice site and a native branch point. For example, a mutation may activate a cryptic branch point sequence between a native splice site and a native branch point. For example, a mutation may create a new splice site between a native branch point and a native splice site and may further activate a cryptic splice site and a cryptic branch point sequentially upstream from the aberrant mutated splice site.

In some embodiments, a mutation or misexpression of trans-acting proteins that regulate splicing activity may cause native regions of the RNA that are normally dormant, or play no role as splicing elements, to become activated and serve as splice sites or splice elements. For example, a mutation or misexpression of an SR protein may cause native regions of the RNA that are normally dormant, or play no role as splicing elements, to become activated and serve as splice sites or splice elements.

In some embodiments, a mutation in native DNA and/or pre-mRNA inhibits splicing at a splice site. For example, a mutation may result in a new splice site upstream from (i.e., 5' to) a native splice site sequence and downstream from (i.e., 3' to) a native branch point sequence. The native splice site sequence and the native branch point sequence may serve as members of both the native set of splice site sequences and the aberrant set of splice site sequences.

In some embodiments, a native splice element (e.g., a branch point) is also a member of the set of aberrant splice elements. For example, SMSMs provided herein can block the native element and activate a cryptic element (e.g., a cryptic 5'ss, a cryptic 3'ss or a cryptic branch point), which may recruit remaining members of the native set of splice elements to promote correct splicing over incorrect splicing. In some embodiments, an activated cryptic splice element is in an intron. In some embodiments, an activated cryptic splice element is in an exon. The compounds and methods provided herein can be used to block or activate a variety of different splice elements, depending on the type of aberrant splice element (e.g., mutated splice element or non-mutated splice element) and/or depending on regulation of a splice element (e.g., regulation by upstream signaling pathways). For example, the compounds and methods provided herein can block a mutated element, a non-mutated element, a cryptic element, or a native element; it may block a 5' splice site, a 3' splice site, or a branch point.

In some embodiments, an alternate splicing event can be modulated by employing the compounds provided herein. For example, a compound provided herein can be introduced into a cell in which a gene is present that encodes a pre-mRNA that comprises alternate splice sites. In some embodiments, in the absence of the compound, a first splicing event occurs to produce a gene product having a particular function. For example, in the presence of the compound provided herein, the first splicing event can be inhibited. In some embodiments, in the presence of the compound provided herein, the first splicing event can be inhibited and a second or alternate splicing event occurs, resulting in expression of the same gene to produce a gene product having a different function.

In some embodiments, a first inhibited splicing event (e.g., a splicing event inhibited by a mutation, a mutation-induced bulge or a non-mutation induced bulge), is promoted or enhanced in the presence of a compound provided herein. In some embodiments, the first inhibited splicing event (e.g., a splicing event inhibited by a mutation, a mutation-induced bulge or a non-mutation induced bulge), is promoted or enhanced in the presence of a compound provided herein. For example, the inhibition of the first splicing event (e.g., a splicing event inhibited by a mutation, a mutation-induced bulge or a non-mutation induced bulge) can be restored to a corresponding first splicing event that is uninhibited, in the presence of a compound provided herein; or the inhibition of the first splicing event can be decreased, in the presence of a compound provided herein. In some embodiments, a second or alternate splicing event occurs, resulting in expression of the same gene to produce a gene product having a different function.

Target Polynucleotides

The compounds described herein can modulate splicing of gene products, such as those shown in Table 2A, Table 2B, Table 2C and Table 2D. In some embodiments, the compounds described herein are use in the treatment, prevention and/or delay of progression of diseases or conditions (e.g., cancer and neurodegenerative diseases). In some embodiments, the compounds described herein can modulate splicing and induce a transcriptionally inactive variant or transcript of a gene product, such as those shown in Table 2A, Table 2B, Table 2C and Table 2D. In some embodiments, the compounds described herein modulate splicing and repress a transcriptionally active variant or transcript of a gene product, such as those shown in Table 2A, Table 2B, Table 2C and Table 2D.

Modulation of splicing by the compounds described herein includes, but is not limited to, modulation of naturally occurring splicing, splicing of an RNA expressed in a diseased cell, splicing of cryptic splice site sequences of an RNA or alternative splicing. Modulation of splicing by the compounds described herein can restore or promote correct splicing or a desired splicing event. Modulation of splicing by the compounds described herein includes, but is not limited to, prevention of aberrant splicing events, e.g., splicing events caused by mutations or aberrant secondary or tertiary structures of RNA that are associated with conditions and diseases. In some embodiments, the compounds described herein prevent or inhibit splicing at a splice site sequence. In some embodiments, the compounds described herein promote or increase splicing at a splice site sequence. In some embodiments, the compounds described herein modulate splicing at a specific splice site sequence.

The compositions and methods described herein can be used to modulate splicing of a target RNA, e.g., pre-mRNAs, encoded by genes. Examples of genes encoding a target RNA, e.g., a pre-mRNA, include, but are not limited to the genes in Table 2A. Examples of genes encoding a target RNA of the compositions and methods described herein, e.g., a pre-mRNA, include, but are not limited to ABCA4, ABCD1, ACADM, ACADSB, ADA, ADAMTS13, AGL, AGT, ALB, ALDH3A2, ALG6, ANGPTL3, APC, APOA1, APOB, APOC3, AR, ATM, ATP7A, ATP7B, ATR, ATXN2, ATXN3, B2M, BCL2-like 11 (BIM), BMP2K, BRCA1, BRCA2, BTK, C3, CACNA1B, CACNA1C, CALCA, CAT, CD33, CD46, CDH1, CDH23, CFB, CFTR, CHM, CLCN1, COL11A1, COL11A2, COL1A1, COL1A2, COL2A1, COL3A1, COL4A5, COL6A1, COL7A1, COL9A2, COLQ, CREBBP, CSTB, CUL4B, CYBB, CYP17, CYP19, CYP27A1, DES, DGAT2, DMD, DUX4, DYSF, EGFR, EMD, ETV4, F11, F13A1, F5, F7, F8, FAH, FANCA, FANCC, FANCG, FBN1, FECH, FGA, FGFR2, FGG, FIX, FLNA, FOXM1, FRAS1, GALC, GBA, GCGR, GH1, GHR, GHV, GLA, HADHA, HBA2, HBB, HEXA, HEXB, HLCS, HMBS, HMGCL, HNF1A, HPRT1, HPRT2, HSF4, HSPG2, HTT, IDH1, IDS, IKBKAP, IL7RA, INSR, ITGB2, ITGB3, ITGB4, JAG1, KLKB1, KRAS, KRT5, L1CAM, LAMA2, LAMA3, LDLR, LGALS3, LMNA, LPA, LPL, LRRK2, MADD, MAPT, MET, MLH1, MSH2, MSTR, MTHFR, MUT, MVK, NF1, NF2, NR1H4, OAT, OPA1, OTC, OXT, PAH, PBGD, PCCA, PDH1, PGK1, PHEX, PKD2, PKLR, PKM1, PKM2, PLEKHM1, PLKR, POMT2, PRDM1, PRKAR1A, PROC, PSEN, PTCH1, PTEN, PYGM, RP6KA3, RPGR, RSK2, SBCAD, SCN5A, SCNA, SERPINA1, SH2DIA, SLC12A3, SLC6A8, SMN2, SOD1, SPINK5, SPTA1, TMPRSS6, TP53, TRAPPC2, TSC1, TSC2, TSHB, TTN, TTR, UBE3A, UGT1A1 and USH2A.

Examples of genes encoding a target RNA, e.g., a pre-mRNA, include, but are not limited to the genes in Table 2B. Examples of genes encoding a target RNA of the compositions and methods described herein, e.g., a pre-mRNA, include, but are not limited to ABCD1, APOB, AR, ATM, BRCA1, C3, CFTR, COL1A1, COL3A1, COL6A1, COL7A1, CYP19, CYP27A1, DMD, F5, F7, FAH, FBN1, FGA, GCK, GHV, HBA2, HBB, HMGCL, HPRT1, HXA, IDS, ITGB2, ITGB3, KRT5, LDLR, LMNA, LPL, MTHFR, NF1, NF2, PBGD, PGK1, PKD1, PTEN, RPGR, TP53, TSC2, UGT1A1 and YGM.

Examples of genes encoding a target RNA, e.g., a pre-mRNA, include, but are not limited to the genes in Table 2C. Examples of genes encoding a target RNA of the compositions and methods described herein, e.g., a pre-mRNA, include, but are not limited to genes encoding a target RNA, e.g., a pre-mRNA, with a splice site comprising a splice site sequence of AGAguaag. Examples of genes encoding a target RNA of the compositions and methods described herein, e.g., a pre-mRNA, include, but are not limited to ABCA9, ABCB1, ABCB5, ACADL, ACSS2, ADAL, ADAM10, ADAM15, ADAMTS20, ADAMTS6, ADAMTS9, ADCY10, ADCY8, AFP, AGL, AHCTF1, AKAP10, AKAP3, ALAS1, ALS2CL, AMBRA1, ANK3, ANTXR2, ANXA10, ANXA11, AP2A2, AP4E1, APOB, ARFGEF1, ARFGEF2, ARHGAP1, ARHGAP18, ARHGEF18, ARHGEF2, ARPC3, ARS2, ASHIL, ASNSD1, ASPM, ATAD5, ATG4A, ATP11C, ATP6V1G3, BBOX1, BCS1L, BMPR2, BRCC3, BRSK2, C10orf137, C11orf70, C12orf51, C13orf1, C13orf15, C14orf118, C15orf29, C15orf42, C16orf33, C16orf38, C16orf48, C18orf8, C19orf42, C1orf107, C1orf114, C1orf130, C1orf149, C1orf27, C1orf71, C1orf94, C1R, C20orf74, C21orf70, C3orf23, C4orf18, C5orf34, C8B, C8orf33, C9orf114, C9orf86, C9orf98, CA11, CAB39, CACNA2D1, CALCOCO2, CAMK1D, CAMKK1, CAPN9, CAPSL, CBX1, CBX3, CCDC102B, CCDC11, CCDC15, CCDC18, CCDC5, CCDC81, CD4, CDC14A, CDC16, CDC2L5, CDC42BPB, CDCA8, CDH10, CDH11, CDH24, CDH8, CDH9, CDK5RAP2, CDK8, CELSR3, CENP1, CENTB2, CENTG2, CEP110, CEP170, CEP192, CETP, CFH, CHAF1A, CHD9, CHIC2, CHN1, CLIC2, CLINT1, CLPB, CMIP, CNOT1, CNOT7, COG3, COLH1A1, COL12A1, COL14A1, COL19A1, COL1A1, COL1A2, COL22A1, COL24A1, COL25A1, COL29A1, COL2A1, COL3A1, COL4A1, COL4A2, COL4A5, COL4A6, COL5A2, COL9A1, COMTD, COPA, COPB2, COPS7B, COPZ2, CPSF2, CPXM2, CR1, CREBBP, CRKRS, CSEIL, CT45-6, CUBN, CUL5, CXorf41, CYP3A4, CYP3A43, CYP3A5, DCC, DCTN3, DDA1, DDX1, DDX24, DDX4, DENND2D, DEPDC2, DHFR, DHRS7, DIP2A, DMD, DNAH3, DNAH8, DNAI1, DNAJA4, DNAJC13, DNAJC7, DNTTIP2, DOCK11, DOCK4, DPP4, DSCC1, DYNCIH1, ECM2, EDEM3, EFCAB3, EFCAB4B, EIF3A, ELA1, ELA2A, EMCN, EML5, ENPP3, EPB41L5, EPHA3, EPHB1, EPHB3, EPS15, ERCC8, ERGIC3, ERMN, ERMP1, ERN1, ERN2, ETS2, EVC2, EXO1, EXOC4, F3, FAM13A1, FAM13B1, FAM13C1, FAM184A, FAM19A1, FAM20A, FAM23B, FAM65C, FANCA, FANCM, FANK1, FAR2, FBX015, FBXO18, FBXO38, FEZ2, FGFR10P, FGFR10P2, FGFR2, FGR, FLJ35848, FLJ36070, FLNA, FN1, FNBP1L, FOLH1, FRAS, FUT9, FZD3, FZD6, GAB1, GALNT3, GART, GAS2L3, GCG, GJA1, GLT8D1, GNAS, GNB5, GOLGB1, GOLT1A, GOLT1B, GPATCH1, GPR160, GRAMD3, GRHPR, GRIA1, GRIA3, GRIA4, GRIN2B, GRM3, GRM4, GRN, GSDMB, GSTCD, GTPBP4, HDAC3, HDAC5, HDX, HEPACAM2, HERC1, HIPK3, HNRNPH1, HSPA9, HSPG2, HTT, ICA1, IFI44L, IL1R2, IL5RA, IMMT, INPP5D, INTU, IPO4, IPO8, ISL2, IWS1, JAK1, JAK2, KATNAL2, KCNN2, KCNT2, KIAA0256, KIAA0586, KIAA1033, KIAA1219, KIAA1622, KIF15, KIF16B, KIF5A, KIF5B, KIF9, KIN, KIR2DL5B, KIR3DL2, KIR3DL3, KLF12, KLF3, KPNA5, KREMEN1, KRIT1, KRTCAP2, L1CAM, L3MBTL, L3MBTL2, LACE1, LAMA2, LAMB1, LGMN, LHCGR, LHX6, LIMCH1, LIMK2, LMBRD1, LMBRD2, LMLN, LMO2, LOC390110, LPCAT2, LRP4, LRPPRC, LRRC19, LRRC42, LUM, LVRN, LYST, MADD, MAGI1, MAGT1, MALT1, MAP4K4, MAPK8IP3, MAPK9, MATN2, MCF2L2, MDGA2, MEGF10, MEGF11, MEMO1, MGAM, MGAT4A, MGC34774, MIB1, MIER2, MKL2, MLANA, MLL5, MLX, MME, MPI, MRAP2, MRPL39, MRPS28, MRPS35, MTDH, MTF2, MUC2, MYB, MYCBP2, MYH2, MYO19, MYO3A, MYO9B, MYOM2, MYOM3, NAG, NARG1, NARG2, NCOA1, NDFIP2, NEDD4, NEK1, NEK5, NFIA, NFIX, NFRKB, NKAP, NLRC3, NLRC5, NME7, NOL10, NOS1, NOS2A, NOTCH1, NPM1, NR4A3, NRXN1, NSMAF, NSMCE2, NT5C3, NUBP1, NUBPL, NUMA1, NUP160, NUP98, NUPL1, OBFC2B, OLIG2, OSBPL11, OSBPL8, OSGEPL1, PADI4, PAH, PAN2, PAPOLG, PARVB, PAWR, PCNX, PCOTH, PDCD4, PDE8B, PDIA3, PDK4, PDS5A, PDS5B, PHACTR4, PHKB, PHLDB2, PHTF1, PIAS1, PIGF, PIGN, PIGT, PIK3C2G, PIK3CG, PIK3R1, PIWIL3, PKHDIL1, PLCB1, PLCB4, PLCG1, PLD1, PLEKHA5, PLEKHA7, PLXNC1, POLN, POLR3D, POMT2, POSTN, PPFIA2, PPPIRi2A, PPP3CB, PPP4C, PPP4R1L, PPP4R2, PRAME, PRC1, PRIM1, PRIM2, PRKG1, PRMT7, PROCR, PROSC, PROX1, PRPF40B, PRPF4B, PRRG2, PSD3, PSMAL, PTK2, PTK2B, PTPN11, PTPN22, PTPN3, PTPN4, PTPRD, PTPRK, PTPRM, PUS10, PVRL2, QRSL1, RAB11FIP2, RAB23, RBICC1, RBM39, RBM45, REC8, RFC4, RHPN2, RLN3, RNF32, RNFT1, ROCK1, ROCK2, RP1, RP11-265F1, RP13-36C9, RPAP3, RPN, RTEL1, RYR3, SAAL1, SAE1, SCN11A, SCN1A, SCN3A, SCO1, SCYL3, SDK2, SEC24A, SEC24D, SEC31A, SEL1L, SENP3, SENP6, SENP7, SETD3, SETD4, SGCE, SGOL2, SGPL1, SH3PXD2A, SH3PXD2B, SH3RF2, SH3TC2, SIPA1L2, SIPA1L3, SKAP1, SKIV2L2, SLC13A1, SLC28A3, SLC38A1, SLC38A4, SLC39A10, SLC4A2, SMARCA1, SMARCA5, SMC5, SNRK, SNRP70, SNX6, SPAG9, SPATA13, SPATA4, SPATS1, SPECC1L, SPP2, SRP 72, SSX3, SSX5, SSX9, STAG1, STAMBPL1, STARD6, STK17B, STX3, STXBP1, SUCLG2, SULF2, SUPT16H, SYCP1, SYTL5, TAF2, TBC1D3G, TBC1D8B, TBCEL, TBK1, TCEB3, TCF12, TCP11L2, TDRD3, TEAD1, TET2, TFRC, TG, THOC2, TIAL1, TIAM2, TIMM50, TLK2, TMEMI56, TMEM27, TMF1, TNFRSF10A, TNFRSF10B, TNFRSF8, TNK2, TNKS, TNKS2, TOM1L1, TOP2B, TP53INP1, TP63, TRAF3IP3, TRIM44, TRIM65, TRIML1, TRIML2, TRPM7, TTC17, TTLL5, TTN, TTPAL, UHRF1BP1, UNC45B, UNC5C, USP38, USP39, USP6, UTP15, UTP18, UTRN, UTX, UTY, UVRAG, UXT, VAPA, VPS29, VPS35, VTI1A, VTI1B, VWA3B, WDFY2, WDR17, WDR26, WDR44, WDR67, WDTC1, WRNIP1, WWC3, XRN1, XRN2, XX-FW88277, YARS, ZBTB20, ZC3HAV1, ZC3HC1, ZNF114, ZNF365, ZNF37A, ZNF618 and ZWINT.

Examples of genes encoding a target RNA, e.g., a pre-mRNA, include, but are not limited to the genes in Table 2D. Examples of genes encoding a target RNA of the compositions and methods described herein, e.g., a pre-mRNA, include, but are not limited to genes encoding a target RNA, e.g., a pre-mRNA, with a splice site comprising a splice site sequence of GGAgtaag. Examples of genes encoding a target RNA of the compositions and methods described herein, e.g., a pre-mRNA, include, but are not limited to ABCC9, ACTG2, ADAM22, ADAM32, ADAMTS12, ADCY3, ADRBK2, AFP, AKNA, APOH, ARHGAP26, ARHGAP8, ATGI6L2, ATP13A5, B4GALNT3, BBS4, BRSK1, BTAF1, C11orf30, C11orf65, C14orf101, C15orf60, C1orf87, C2orf55, C4orf29, C6orf118, C9orf43, CACHD1, CACNA1G, CACNA1H, CAPN3, CARKD, CCDC131, CCDC146, CD1B, CDK6, CEL, CGN, CGNL1, CHL1, CLEC16A, CLK1, CLPTM1, CMYA5, CNGA3, CNTN6, COL11A1, COL15A1, COL17A1, COL1A1, COL2A1, CRYZ, CSTF3, CYFIP2, CYP24A1, CYP4F2, CYP4F3, DAZ2, DCBLD1, DCUN1D4, DDEF1, DDX1, DHRS9, DMTF1, DOCK10, DPP3, DPY19L2P2, DVL3, EFNA4, EFTUD2, EPHA4, EPHB2, ERBB4, ERCC1, FAM134A, FAM16NA, FAM176B, FCGBP, FGD6, FKBP3, GAPDH, GBGT1, GFM1, GPR158, GRIA1, GSTCD, GSTO2, HCK, HLA-DPB1, HLA-G, HLTF, HP1BP3, HPGD, HSF2BP, INTS3, IQGAP2, ITFG1, ITGAL, ITGB1, ITIH1, ITPR2, JMJD1C, KALRN, KCNN2, KIAA0528, KIAA0564, KIAA1166, KIAA1409, KIAA1787, KIF3B, KLHL20, KLK12, LAMA1, LARP7, LENG1, LOC389634, LRWD1, LYN, MAP2K1, MCM6, MEGF10, MGAM, MGAT5, MGC16169, MKKS, MPDZ, MRPL11, MS4A13, MSMB, MTIF2, NDC80, NEB, NEK11, NFE2L2, NFKBIL2, NKAIN2, NLRC3, NLRC5, NLRP13, NLRP7, NLRP8, NT5C, NUDT5, NUP88, OBFC2A, OPN4, OPTN, PARD3, PBRM1, PCBP4, PDE10A, PDLIM5, PDXK, PDZRN3, PEL12, PGM2, PIP5K1A, PITRM1, PKIB, PMFBP1, POMT2, PRKCA, PRODH, PRUNE2, PTPRN2, PTPRT, RALBP1, RALGDS, RBL2, RFT1, RFTN1, RIF1, RMND5B, RNF11, RNGTT, RPS6KA6, RRM1, RRP1B, RTF1, RUFY1, SCN2A, SCN4A, SCN8A, SDK1, SEZ6, SFRS12, SH3BGRL2, SIVA1, SLC22A17, SLC25A14, SLC6A11, SLC6A13, SLC6A6, SMTN, SNCA1P, SNX6, STAT6, SUPT6H, SV2C, SYCP2, SYT6, TAF2, TBC1D26, TBC1D29, TBPL1, TECTB, TEK, TGM7, TGS1, TM4SF20, TM6SF1, TMEM194A, TMEM77, TOM1L2, TP53BP2, TP53I3, TRPM3, TRPM5, TSPAN7, TTLL9, TUSC3, TXNDC10, UCK1, USH2A, USP1, UTP20, VPS39, WDR16, ZC3H7A, ZFYVE1, ZNF169 and ZNF326.

The SMSM compounds and methods of their use described herein can modulate splicing, such as aberrant splicing of polynucleotide encoded by a gene, e.g., an ABCA4, ABCA9, ABCB1, ABCB5, ABCC9, ABCD1, ACADL, ACADM, ACADSB, ACSS2, ACTG2, ADA, ADAL, ADAM10, ADAM15, ADAM22, ADAM32, ADAMTS12, ADAMTS13, ADAMTS20, ADAMTS6, ADAMTS9, ADCY10, ADCY3, ADCY8, ADRBK2, AFP, AGL, AGT, AHCTF1, AKAP10, AKAP3, AKNA, ALAS1, ALB, ALDH3A2, ALG6, ALS2CL, AMBRA1, ANGPTL3, ANK3, ANTXR2, ANXA10, ANXA11, AP2A2, AP4E1, APC, APOA1, APOB, APOC3, APOH, AR, ARFGEF1, ARFGEF2, ARHGAP1, ARHGAP18, ARHGAP26, ARHGAP8, ARHGEF18, ARHGEF2, ARPC3, ARS2, ASH1L, ASNSD1, ASPM, ATAD5, ATG16L2, ATG4A, ATM, ATP11C, ATP13A5, ATP6V1G3, ATP7A, ATP7B, ATR, ATXN2, ATXN3, B2M, B4GALNT3, BBOX1, BBS4, BCL2-like 11 (BIM), BCS1L, BMP2K, BMPR2, BRCA1, BRCA2, BRCC3, BRSK1, BRSK2, BTAF1, BTK, C10orf137, C11orf30, C11orf65, C11orf70, C12orf51, C13orf1, C13orf15, C14orf101, C14orf118, C15orf29, C15orf42, C15orf60, C16orf33, C16orf38, C16orf48, C18orf8, C19orf42, C1orf107, C1orf114, C1orf130, C1orf149, C1orf27, C1orf71, C1orf87, C1orf94, C1R, C20orf74, C21orf70, C2orf55, C3, C3orf23, C4orf18, C4orf29, C5orf34, C6orf118, C8B, C8orf33, C9orf114, C9orf43, C9orf86, C9orf98, CA11, CAB39, CACHD1, CACNA1B, CACNA1C, CACNA1G, CACNA1H, CACNA2D1, CALCA, CALCOCO2, CAMK1D, CAMKK1, CAPN3, CAPN9, CAPSL, CARKD, CAT, CBX1, CBX3, CCDC102B, CCDC11, CCDC131, CCDC146, CCDC15, CCDC18, CCDC5, CCDC81, CD1B, CD33, CD4, CD46, CDC14A, CDC16, CDC2L5, CDC42BPB, CDCA8, CDH1, CDH10, CDH11, CDH23, CDH24, CDH8, CDH9, CDK5RAP2, CDK6, CDK8, CEL, CELSR3, CENP1, CENTB2, CENTG2, CEP110, CEP170, CEP192, CETP, CFB, CFH, CFTR, CGN, CGNL1, CHAF1A, CHD9, CHIC2, CHL1, CHM, CHN1, CLCN1, CLEC16A, CLIC2, CLINT1, CLK1, CLPB, CLPTM1, CMIP, CMYA5, CNGA3, CNOT1, CNOT7, CNTN6, COG3, COL11A1, COL11A2, COL12A1, COL14A1, COL15A1, COL17A1, COL19A1, COL1A1, COL1A2, COL22A1, COL24A1, COL25A1, COL29A1, COL2A1, COL3A1, COL4A1, COL4A2, COL4A5, COL4A6, COL5A2, COL6A1, COL7A1, COL9AM, COL9A2, COLQ, COMTD1, COPA, COPB2, COPS7B, COPZ2, CPSF2, CPXM2, CR1, CREBBP, CRKRS, CRYZ, CSE1L, CSTB, CSTF3, CT45-6, CUBN, CUL4B, CUL5, CXorf41, CYBB, CYFIP2, CYP17, CYP19, CYP24A1, CYP27A1, CYP3A4, CYP3A43, CYP3A5, CYP4F2, CYP4F3, DAZ2, DCBLD1, DCC, DCTN3, DCUN1D4, DDA1, DDEF1, DDX1, DDX24, DDX4, DENND2D, DEPDC2, DES, DGAT2, DHFR, DHRS7, DHRS9, DIP2A, DMD, DMTF1, DNAH3, DNAH8, DNA1, DNAJA4, DNAJC13, DNAJC7, DNTTIP2, DOCK10, DOCK11, DOCK4, DPP3, DPP4, DPY19L2P2, DSCC1, DUX4, DVL3, DYNC1H1, DYSF, ECM2, EDEM3, EFCAB3, EFCAB4B, EFNA4, EFTUD2, EGFR, EIF3A, ELA1, ELA2A, EMCN, EMD, EML5, ENPP3, EPB41L5, EPHA3, EPHA4, EPHB1, EPHB2, EPHB3, EPS15, ERBB4, ERCC1, ERCC8, ERGIC3, ERMN, ERMP1, ERN1, ERN2, ETS2, ETV4, EVC2, EXO1, EXOC4, F11, F13A1, F3, F5, F7, F8, FAH, FAM134A, FAM13A1, FAM13B1, FAM13C1, FAM16NA, FAM76B, FAM184A, FAM19A1, FAM20A, FAM23B, FAM65C, FANCA, FANCC, FANCG, FANCM, FANK, FAR2, FBN1, FBXO15, FBXO18, FBXO38, FCGBP, FECH, FEZ2, FGA, FGD6, FGFR10P, FGFR10P2, FGFR2, FGG, FGR, FIX, FKBP3, FLJ35848, FLJ36070, FLNA, FN1, FNBP1L, FOLH1, FOXAM, FRAS1, FUT9, FZD3, FZD6, GAB1, GALC, GALNT3, GAPDH, GART, GAS2L3, GBA, GBGT1, GCG, GCGR, GCK, GFM1, GH1, GHR, GHV, GJA1, GLA, GLT8D1, GNAS, GNB5, GOLGB1, GOLT1A, GOLT1B, GPATCH1, GPR158, GPR160, GRAMD3, GRHPR, GRIA1, GRIA3, GRIA4, GRIN2B, GRM3, GRM4, GRN, GSDMB, GSTCD, GSTO2, GTPBP4, HADHA, HBA2, HBB, HCK, HDAC3, HDAC5, HDX, HEPACAM2, HERC1, HEXA, HEXB, HIPK3, HLA-DPB1, HLA-G, HLCS, HLTF, HMBS, HMGCL, HNFA, HNRNPH1, HP1BP3, HPGD, HPRT, HPRT2, HSF2BP, HSF4, HSPA9, HSPG2, HTT, HXA, ICA1, IDH1, IDS, IFI44L, IKBKAP, IL1R2, IL5RA, IL7RA, IMMT, INPP5D, INSR, INTS3, INTU, IP04, IP08, IQGAP2, ISL2, ITFG1, ITGAL, ITGB1, ITGB2, ITGB3, ITGB4, ITIH1, ITPR2, IWS1, JAG1, JAK1, JAK2, JMJD1C, KALRN, KATNAL2, KCNN2, KCNT2, KIAA0256, KIAA0528, KIAA0564, KIAA0586, KIAA1033, KIAA1166, KIAA1219, KIAA1409, KIAA1622, KIAA1787, KIF15, KIF16B, KIF3B, KIF5A, KIF5B, KIF9, KIN, KIR2DL5B, KIR3DL2, KIR3DL3, KLF12, KLF3, KLHL20, KLK12, KLKB1, KPNA5, KRAS, KREMEN1, KRIT1, KRT5, KRTCAP2, L1CAM, L3MBTL, L3MBTL2, LACE1, LAMA1, LAMA2, LAMA3, LAMB1, LARP7, LDLR, LENG1, LGALS3, LGMN, LHCGR, LHX6, LIMCH1, LIMK2, LMBRD1, LMBRD2, LMLN, LMNA, LMO2, LOC389634, LOC390110, LPA, LPCAT2, LPL, LRP4, LRPPRC, LRRC19, LRRC42, LRRK2, LRWD1, LUM, LVRN, LYN, LYST, MADD, MAGI1, MAGT1, MALT1, MAP2K1, MAP4K4, MAPK8IP3, MAPK9, MAPT, MATN2, MCF2L2, MCM6, MDGA2, MEGF10, MEGF11, MEMO1, MET, MGAM, MGAT4A, MGAT5, MGC16169, MGC34774, MIB1, MIER2, MKKS, MKL2, MLANA, MLH1, MLL5, MLX, MME, MPDZ, MPI, MRAP2, MRPL11, MRPL39, MRPS28, MRPS35, MS4A13, MSH2, MSMB, MST1R, MTDH, MTF2, MTHFR, MTIF2, MUC2, MUT, MVK, MYB, MYCBP2, MYH2, MYO19, MYO3A, MYO9B, MYOM2, MYOM3, NAG, NARG1, NARG2, NCOA1, NDC80, NDFIP2, NEB, NEDD4, NEK1, NEK11, NEK5, NF1, NF2, NFE2L2, NFIA, NFIX, NFKBIL2, NFRKB, NKAIN2, NKAP, NLRC3, NLRC5, NLRP13, NLRP7, NLRP8, NME7, NOL10, NOS1, NOS2A, NOTCH1, NPM, NR1H4, NR4A3, NRXN1, NSMAF, NSMCE2, NT5C, NT5C3, NUBP, NUBPL, NUDT5, NUMA1, NUP160, NUP88, NUP98, NUPL1, OAT, OBFC2A, OBFC2B, OLIG2, OPA1, OPN4, OPTN, OSBPL11, OSBPL8, OSGEPL1, OTC, OXT, PADI4, PAH, PAN2, PAPOLG, PARD3, PARVB, PAWR, PBGD, PBRM1, PCBP4, PCCA, PCNX, PCOTH, PDCD4, PDE10A, PDE8B, PDH1, PDIA3, PDK4, PDLIM5, PDS5A, PDS5B, PDXK, PDZRN3, PELI2, PGK1, PGM2, PHACTR4, PHEX, PHKB, PHLDB2, PHTF1, PIAS1, PIGF, PIGN, PIGT, PIK3C2G, PIK3CG, PIK3R1, PIP5KIA, PITRM1, PIWIL3, PKD1, PKD2, PKHD1L1, PKIB, PKLR, PKM1, PKM2, PLCB1, PLCB4, PLCG1, PLD1, PLEKHA5, PLEKHA7, PLEKHM1, PLKR, PLXNC1, PMFBP1, POLN, POLR3D, POMT2, POSTN, PPFIA2, PPPIR12A, PPP3CB, PPP4C, PPP4R1L, PPP4R2, PRAME, PRC1, PRDM1, PRIM1, PRIM2, PRKAR1A, PRKCA, PRKG1, PRMT7, PROC, PROCR, PRODH, PROSC, PROX1, PRPF40B, PRPF4B, PRRG2, PRUNE2, PSD3, PSEN1, PSMAL, PTCH1, PTEN, PTK2, PTK2B, PTPN11, PTPN22, PTPN3, PTPN4, PTPRD, PTPRK, PTPRM, PTPRN2, PTPRT, PUS10, PVRL2, PYGM, QRSL1, RAB11FIP2, RAB23, RALBP1, RALGDS, RB1CC1, RBL2, RBM39, RBM45, REC8, RFC4, RFT1, RFTN1, RHPN2, RIF1, RLN3, RMND5B, RNF11, RNF32, RNFT1, RNGTT, ROCK1, ROCK2, RP1, RP11-265F1, RP13-36C9, RP6KA3, RPAP3, RPGR, RPN1, RPS6KA6, RRRM1, RRP1B, RSK2, RTELa, RTFa, RUFY1, RYR3, SAAL1, SAE1, SBCAD, SCN11A, SCN1A, SCN2A, SCN3A, SCN4A, SCN5A, SCN8A, SCNA, SCO1, SCYL3, SDK1, SDK2, SEC24A, SEC24D, SEC31A, SEL1L, SENP3, SENP6, SENP7, SERPINA1, SETD3, SETD4, SEZ6, SFRS12, SGCE, SGOL2, SGPL1, SH2D1A, SH3BGRL2, SH3PXD2A, SH3PXD2B, SH3RF2, SH3TC2, SIPA1L2, SIPA1L3, SIVA1, SKAP1, SKIV2L2, SLC12A3, SLC13A1, SLC22A17, SLC25A14, SLC28A3, SLC38A1, SLC38A4, SLC39A10, SLC4A2, SLC6A11, SLC6A13, SLC6A6, SLC6A8, SMARCA1, SMARCA5, SMC5, SMN2, SMTN, SNCA1P, SNRK, SNRP70, SNX6, SOD1, SPAG9, SPATA13, SPATA4, SPATS1, SPECC1L, SPINK5, SPP2, SPTA1, SRP 72, SSX3, SSX5, SSX9, STAG1, STAMBPL1, STARD6, STAT6, STK17B, STX3, STXBP1, SUCLG2, SULF2, SUPT16H, SUPT6H, SV2C, SYCP1, SYCP2, SYT6, SYTL5, TAF2, TBC1D26, TBC1D29, TBC1D3G, TBC1D8B, TBCEL, TBK1, TBPL1, TCEB3, TCF12, TCP11L2, TDRD3, TEAD1, TECTB, TEK, TET2, TFRC, TG, TGM7, TGS1, THOC2, TIAL1, TIAM2, TIMM50, TLK2, TM4SF20, TM6SF1, TMEMI56, TMEM194A, TMEM27, TMEM77, TMF1, TMPRSS6, TNFRSF10A, TNFRSF10B, TNFRSF8, TNK2, TNKS, TNKS2, TOM1L1, TOM1L2, TOP2B, TP53, TP53BP2, TP53I3, TP53INP1, TP63, TRAF3IP3, TRAPPC2, TRIM44, TRIM65, TRIML1, TRIML2, TRPM3, TRPM5, TRPM7, TSC1, TSC2, TSHB, TSPAN7, TTC17, TTLL5, TTLL9, TTN, TTPAL, TTR, TUSC3, TXNDC10, UBE3A, UCK1, UGT1A1, UHRF1BP1, UNC45B, UNC5C, USH2A, USP1, USP38, USP39, USP6, UTP15, UTP18, UTP20, UTRN, UTX, UTY, UVRAG, UXT, VAPA, VPS29, VPS35, VPS39, VTI1A, VTI1B, VWA3B, WDFY2, WDR16, WDR17, WDR26, WDR44, WDR67, WDTC1, WRNIP1, WWC3, XRN1, XRN2, XX-FW88277, YARS, YGM, ZBTB20, ZC3H7A, ZC3HAV1, ZC3HC1, ZFYVE1, ZNF114, ZNF169, ZNF326, ZNF365, ZNF37A, ZNF618 or ZWINT gene.

For example, provided herein are splice modulating compounds that modulate splicing, such as aberrant splicing of ABCA4, ABCA9, ABCB1, ABCB5, ABCC9, ABCD1, ACADL, ACADM, ACADSB, ACSS2, ACTG2, ADA, ADAL, ADAM10, ADAM15, ADAM22, ADAM32, ADAMTS12, ADAMTS13, ADAMTS20, ADAMTS6, ADAMTS9, ADCY10, ADCY3, ADCY8, ADRBK2, AFP, AGL, AGT, AHCTF1, AKAP10, AKAP3, AKNA, ALAS1, ALB, ALDH3A2, ALG6, ALS2CL, AMBRA1, ANGPTL3, ANK3, ANTXR2, ANXA10, ANXA11, AP2A2, AP4E1, APC, APOA1, APOB, APOC3, APOH, AR, ARFGEF1, ARFGEF2, ARHGAP1, ARHGAP18, ARHGAP26, ARHGAP8, ARHGEF18, ARHGEF2, ARPC3, ARS2, ASH1L, ASNSD1, ASPM, ATAD5, ATG16L2, ATG4A, ATM, ATP11C, ATP13A5, ATP6V1G3, ATP7A, ATP7B, ATR, ATXN2, ATXN3, B2M, B4GALNT3, BBOX1, BBS4, BCL2-like 11 (BIM), BCS1L, BMP2K, BMPR2, BRCA1, BRCA2, BRCC3, BRSK1, BRSK2, BTAF1, BTK, C10orf137, C11orf30, C11orf65, C11orf70, C12orf51, C13orf1, C13orf15, C14orf101, C14orf118, C15orf29, C15orf42, C15orf60, C16orf33, C16orf38, C16orf48, C18orf8, C19orf42, C1orf107, C1orf114, C1orf130, C1orf149, C1orf27, C1orf71, C1orf87, C1orf94, C1R, C20orf74, C21orf70, C2orf55, C3, C3orf23, C4orf18, C4orf29, C5orf34, C6orf118, C8B, C8orf33, C9orf114, C9orf43, C9orf86, C9orf98, CA11, CAB39, CACHD1, CACNA1B, CACNA1C, CACNA1G, CACNA1H, CACNA2D1, CALCA, CALCOCO2, CAMK1, CAMKK1, CAPN3, CAPN9, CAPSL, CARKD, CAT, CBX1, CBX3, CCDC102B, CCDC11, CCDC131, CCDC146, CCDC15, CCDC18, CCDC5, CCDC81, CD1B, CD33, CD4, CD46, CDC14A, CDC16, CDC2L5, CDC42BPB, CDCA8, CDH1, CDH10, CDH11, CDH23, CDH24, CDH8, CDH9, CDK5RAP2, CDK6, CDK8, CEL, CELSR3, CENP1, CENTB2, CENTG2, CEP110, CEP170, CEP192, CETP, CFB, CFH, CFTR, CGN, CGNL1, CHAF1A, CHD9, CHIC2, CHL1, CHM, CHN1, CLCN1, CLEC16A, CLIC2, CLINT1, CLK1, CLPB, CLPTM1, CMIP, CMYA5, CNGA3, CNOT1, CNOT7, CNTN6, COG3, COL11A1, COL11A2, COL12A1, COL14A1, COL15A1, COL17A1, COL19A1, COL1A1, COL1A2, COL22A1, COL24A1, COL25A1, COL29A1, COL2A1, COL3A1, COL4A1, COL4A2, COL4A5, COL4A6, COL5A2, COL6A1, COL7A1, COL9A1, COL9A2, COLQ, COMTD1, COPA, COPB2, COPS7B, COPZ2, CPSF2, CPXM2, CR1, CREBBP, CRKRS, CRYZ, CSE1L, CSTB, CSTF3, CT45-6, CUBN, CUL4B, CUL5, CXorf41, CYBB, CYFIP2, CYP17, CYP19, CYP24A1, CYP27A1, CYP3A4, CYP3A43, CYP3A5, CYP4F2, CYP4F3, DAZ2, DCBLD1, DCC, DCTN3, DCUN1D4, DDA1, DDEF1, DDX1, DDX24, DDX4, DENND2D, DEPDC2, DES, DGAT2, DHFR, DHRS7, DHRS9, DIP2A, DMD, DMTF1, DNAH3, DNAH8, DNAI1, DNAJA4, DNAJC13, DNAJC7, DNTTIP2, DOCK10, DOCK11, DOCK4, DPP3, DPP4, DPY19L2P2, DSCC1, DUX4, DVL3, DYNC1H1, DYSF, ECM2, EDEM3, EFCAB3, EFCAB4B, EFNA4, EFTUD2, EGFR, EIF3A, ELA1, ELA2A, EMCN, EMD, EML5, ENPP3, EPB41L5, EPHA3, EPHA4, EPHB1, EPHB2, EPHB3, EPS15, ERBB4, ERCC1, ERCC8, ERGIC3, ERMN, ERMP1, ERN1, ERN2, ETS2, ETV4, EVC2, EXO1, EXOC4, F11, F13A1, F3, F5, F7, F8, FAH, FAM134A, FAM13A1, FAM13B1, FAM13C1, FAM161A, FAM176B, FAM184A, FAM19A1, FAM20A, FAM23B, FAM65C, FANCA, FANCC, FANCG, FANCM, FANK1, FAR2, FBN1, FBXO15, FBXO18, FBXO38, FCGBP, FECH, FEZ2, FGA, FGD6, FGFR1OP, FGFR1OP2, FGFR2, FGG, FGR, FIX, FKBP3, FLJ35848, FLJ36070, FLNA, FN1, FNBP1L, FOLH1, FOXM1, FRAS1, FUT9, FZD3, FZD6, GAB1, GALC, GALNT3, GAPDH, GART, GAS2L3, GBA, GBGT1, GCG, GCGR, GCK, GFM1, GH1, GHR, GHV, GJA1, GLA, GLT8D1, GNAS, GNB5, GOLGB1, GOLT1A, GOLT1B, GPATCH1, GPR158, GPR160, GRAMD3, GRHPR, GRIA1, GRIA3, GRIA4, GRIN2B, GRM3, GRM4, GRN, GSDMB, GSTCD, GSTO2, GTPBP4, HADHA, HBA2, HBB, HCK, HDAC3, HDAC5, HDX, HEPACAM2, HERC1, HEXA, HEXB, HIPK3, HLA-DPB1, HLA-G, HLCS, HLTF, HMBS, HMGCL, HNF1A, HNRNPH1, HP1BP3, HPGD, HPRT1, HPRT2, HSF2BP, HSF4, HSPA9, HSPG2, HTT, HXA, ICA1, IDH1, IDS, IFI44L, IKBKAP, IL1R2, IL5RA, IL7RA, IMMT, INPP5D, INSR, INTS3, INTU, IP04, IP08, IQGAP2, ISL2, ITFG1, ITGAL, ITGB1, ITGB2, ITGB3, ITGB4, ITIH1, ITPR2, IWS1, JAG1, JAK1, JAK2, JMJD1C, KALRN, KATNAL2, KCNN2, KCNT2, KIAA0256, KIAA0528, KIAA0564, KIAA0586, KIAA1033, KIAA1166, KIAA1219, KIAA1409, KIAA1622, KIAA1787, KIF15, KIF16B, KIF3B, KIF5A, KIF5B, KIF9, KIN, KIR2DL5B, KIR3DL2, KIR3DL3, KLF12, KLF3, KLHL20, KLK12, KLKB1, KPNA5, KRAS, KREMEN1, KRIT1, KRT5, KRTCAP2, L1CAM, L3MBTL, L3MBTL2, LACE1, LAMA1, LAMA2, LAMA3, LAMB1, LARP7, LDLR, LENG1, LGALS3, LGMN, LHCGR, LHX6, LIMCH1, LIMK2, LMBRD1, LMBRD2, LMLN, LMNA, LMO2, LOC389634, LOC390110, LPA, LPCAT2, LPL, LRP4, LRPPRC, LRRC19, LRRC42, LRRK2, LRWD1, LUM, LVRN, LYN, LYST, MADD, MAGI1, MAGT1, MALT1, MAP2K1, MAP4K4, MAPK8IP3, MAPK9, MAPT, MATN2, MCF2L2, MCM6, MDGA2, MEGF10, MEGF11, MEMO1, MET, MGAM, MGAT4A, MGAT5, MGC16169, MGC34774, MIB1, MIER2, MKKS, MKL2, MLANA, MLH1, MLL5, MLX, MME, MPDZ, MPI, MRAP2, MRPL11, MRPL39, MRPS28, MRPS35, MS4A13, MSH2, MSMB, MST1R, MTDH, MTF2, MTHFR, MTIF2, MUC2, MUT, MVK, MYB, MYCBP2, MYH2, MYO19, MYO3A, MYO9B, MYOM2, MYOM3, NAG, NARG1, NARG2, NCOA1, NDC80, NDFIP2, NEB, NEDD4, NEK1, NEK11, NEK5, NF1, NF2, NFE2L2, NFIA, NFIX, NFKBIL2, NFRKB, NKAIN2, NKAP, NLRC3, NLRC5, NLRP13, NLRP7, NLRP8, NME7, NOL10, NOS1, NOS2A, NOTCH1, NPM1, NR1H4, NR4A3, NRXN1, NSMAF, NSMCE2, NT5C, NT5C3, NUBP1, NUBPL, NUDT5, NUMA1, NUP160, NUP88, NUP98, NUPL1, OAT, OBFC2A, OBFC2B, OLIG2, OPAL, OPN4, OPTN, OSBPL11, OSBPL8, OSGEPL1, OTC, OXT, PADI4, PAH, PAN2, PAPOLG, PARD3, PARVB, PAWR, PBGD, PBRM1, PCBP4, PCCA, PCNX, PCOTH, PDCD4, PDE10A, PDE8B, PDH1, PDIA3, PDK4, PDLIM5, PDS5A, PDS5B, PDXK, PDZRN3, PELI2, PGK1, PGM2, PHACTR4, PHEX, PHKB, PHLDB2, PHTF1, PIAS1, PIGF, PIGN, PIGT, PIK3C2G, PIK3CG, PIK3R1, PIP5KIA, PITRM1, PIWIL3, PKD1, PKD2, PKHDIL1, PKIB, PKLR, PKM1, PKM2, PLCB1, PLCB4, PLCG1, PLD1, PLEKHA5, PLEKHA7, PLEKHM1, PLKR, PLXNC1, PMFBP1, POLN, POLR3D, POMT2, POSTN, PPFIA2, PPP1R12A, PPP3CB, PPP4C, PPP4R1L, PPP4R2, PRAME, PRC1, PRDM1, PRIM1, PRIM2, PRKAR1A, PRKCA, PRKG1, PRMT7, PROC, PROCR, PRODH, PROSC, PROX1, PRPF40B, PRPF4B, PRRG2, PRUNE2, PSD3, PSEN1, PSMAL, PTCH1, PTEN, PTK2, PTK2B, PTPN11, PTPN22, PTPN3, PTPN4, PTPRD, PTPRK, PTPRM, PTPRN2, PTPRT, PUS10, PVRL2, PYGM, QRSL1, RAB11FIP2, RAB23, RALBP1, RALGDS, RB1CC1, RBL2, RBM39, RBM45, REC8, RFC4, RFT1, RFTN1, RHPN2, RIF1, RLN3, RMND5B, RNF11, RNF32, RNFT1, RNGTT, ROCK1, ROCK2, RP1, RP11-265F1, RP13-36C9, RP6KA3, RPAP3, RPGR, RPN1, RPS6KA6, RRM1, RRP1B, RSK2, RTEL1, RTF1, RUFY1, RYR3, SAAL1, SAE1, SBCAD, SCN11A, SCN1A, SCN2A, SCN3A, SCN4A, SCN5A, SCN8A, SCNA, SCO1, SCYL3, SDK1, SDK2, SEC24A, SEC24D, SEC31A, SEL1L, SENP3, SENP6, SENP7, SERPINA1, SETD3, SETD4, SEZ6, SFRS12, SGCE, SGOL2, SGPL1, SH2D1A, SH3BGRL2, SH3PXD2A, SH3PXD2B, SH3RF2, SH3TC2, SIPA1L2, SIPA1L3, SIVA1, SKAP1, SKIV2L2, SLC12A3, SLC13A1, SLC22A17, SLC25A14, SLC28A3, SLC38A1, SLC38A4, SLC39A10, SLC4A2, SLC6A11, SLC6A13, SLC6A6, SLC6A8, SMARCA1, SMARCA5, SMC5, SMN2, SMTN, SNCA1P, SNRK, SNRP70, SNX6, SOD1, SPAG9, SPATA13, SPATA4, SPATS1, SPECC1L, SPINK5, SPP2, SPTA1, SRP72, SSX3, SSX5, SSX9, STAG1, STAMBPL1, STARD6, STAT6, STK17B, STX3, STXBP1, SUCLG2, SULF2, SUPT16H, SUPT6H, SV2C, SYCP1, SYCP2, SYT6, SYTL5, TAF2, TBC1D26, TBC1D29, TBC1D3G, TBC1D8B, TBCEL, TBK1, TBPL1, TCEB3, TCF12, TCP11L2, TDRD3, TEAD1, TECTB, TEK, TET2, TFRC, TG, TGM7, TGS1, THOC2, TIAL1, TIAM2, TIMM50, TLK2, TM4SF20, TM6SF1, TMEM156, TMEM194A, TMEM27, TMEM77, TMF1, TMPRSS6, TNFRSF10A, TNFRSF10B, TNFRSF8, TNK2, TNKS, TNKS2, TOM1L1, TOM1L2, TOP2B, TP53, TP53BP2, TP53I3, TP53INP1, TP63, TRAF3IP3, TRAPPC2, TRIM44, TRIM65, TRIML1, TRIML2, TRPM3, TRPM5, TRPM7, TSC1, TSC2, TSHB, TSPAN7, TTC17, TTLL5, TTLL9, TTN, TTPAL, TTR, TUSC3, TXNDC10, UBE3A, UCK1, UGT1A1, UHRF1BP1, UNC45B, UNC5C, USH2A, USP1, USP38, USP39, USP6, UTP15, UTP18, UTP20, UTRN, UTX, UTY, UVRAG, UXT, VAPA, VPS29, VPS35, VPS39, VTI1A, VTI1B, VWA3B, WDFY2, WDR16, WDR17, WDR26, WDR44, WDR67, WDTC1, WRNIP1, WWC3, XRN1, XRN2, XX-FW88277, YARS, YGM, ZBTB20, ZC3H7A, ZC3HAV1, ZC3HC1, ZFYVE1, ZNF114, ZNF169, ZNF326, ZNF365, ZNF37A, ZNF618 or a ZWINT mRNA, such as pre-mRNA.

In some embodiments, the SMSM compounds and methods of their use described herein can modulate splicing of a pre-mRNA of ABCA4. In some embodiments, the SMSM compounds and methods of their use described herein can modulate splicing of a pre-mRNA of ABCA9. In some embodiments, the SMSM compounds and methods of their use described herein can modulate splicing of a pre-mRNA of ABCB1. In some embodiments, the SMSM compounds and methods of their use described herein can modulate splicing of a pre-mRNA of ABCB5. In some embodiments, the SMSM compounds and methods of their use described herein can modulate splicing of a pre-mRNA of ABCC9. In some embodiments, the SMSM compounds and methods of their use described herein can modulate splicing of a pre-mRNA of ABCD 1. In some embodiments, the SMSM compounds and methods of their use described herein can modulate splicing of a pre-mRNA of ACADL. In some embodiments, the SMSM compounds and methods of their use described herein can modulate splicing of a pre-mRNA of ACADM. In some embodiments, the SMSM compounds and methods of their use described herein can modulate splicing of a pre-mRNA of ACADSB. In some embodiments, the SMSM compounds and methods of their use described herein can modulate splicing of a pre-mRNA of ACSS2. In some embodiments, the SMSM compounds and methods of their use described herein can modulate splicing of a pre-mRNA of ACTG2. In some embodiments, the SMSM compounds and methods of their use described herein can modulate splicing of a pre-mRNA of ADA. In some embodiments, the SMSM compounds and methods of their use described herein can modulate splicing of a pre-mRNA of ADAL. In some embodiments, the SMSM compounds and methods of their use described herein can modulate splicing of a pre-mRNA of ADAM10. In some embodiments, the SMSM compounds and methods of their use described herein can modulate splicing of a pre-mRNA of ADAM15. In some embodiments, the SMSM compounds and methods of their use described herein can modulate splicing of a pre-mRNA of ADAM22. In some embodiments, the SMSM compounds and methods of their use described herein can modulate splicing of a pre-mRNA of ADAM32. In some embodiments, the SMSM compounds and methods of their use described herein can modulate splicing of a pre-mRNA of ADAMTS12. In some embodiments, the SMSM compounds and methods of their use described herein can modulate splicing of a pre-mRNA of ADAMTS13. In some embodiments, the SMSM compounds and methods of their use described herein can modulate splicing of a pre-mRNA of ADAMTS20. In some embodiments, the SMSM compounds and methods of their use described herein can modulate splicing of a pre-mRNA of ADAMTS6. In some embodiments, the SMSM compounds and methods of their use described herein can modulate splicing of a pre-mRNA of ADAMTS9. In some embodiments, the SMSM compounds and methods of their use described herein can modulate splicing of a pre-mRNA of ADCY10. In some embodiments, the SMSM compounds and methods of their use described herein can modulate splicing of a pre-mRNA of ADCY3. In some embodiments, the SMSM compounds and methods of their use described herein can modulate splicing of a pre-mRNA of ADCY8. In some embodiments, the SMSM compounds and methods of their use described herein can modulate splicing of a pre-mRNA of ADRBK2. In some embodiments, the SMSM compounds and methods of their use described herein can modulate splicing of a pre-mRNA of AFP. In some embodiments, the SMSM compounds and methods of their use described herein can modulate splicing of a pre-mRNA of AGL. In some embodiments, the SMSM compounds and methods of their use described herein can modulate splicing of a pre-mRNA of AGT. In some embodiments, the SMSM compounds and methods of their use described herein can modulate splicing of a pre-mRNA of AHCTF1. In some embodiments, the SMSM compounds and methods of their use described herein can modulate splicing of a pre-mRNA of AKAP10. In some embodiments, the SMSM compounds and methods of their use described herein can modulate splicing of a pre-mRNA of AKAP3. In some embodiments, the SMSM compounds and methods of their use described herein can modulate splicing of a pre-mRNA of AKNA. In some embodiments, the SMSM compounds and methods of their use described herein can modulate splicing of a pre-mRNA of ALAS1. In some embodiments, the SMSM compounds and methods of their use described herein can modulate splicing of a pre-mRNA of ALB. In some embodiments, the SMSM compounds and methods of their use described herein can modulate splicing of a pre-mRNA of ALDH3A2. In some embodiments, the SMSM compounds and methods of their use described herein can modulate splicing of a pre-mRNA of ALG6. In some embodiments, the SMSM compounds and methods of their use described herein can modulate splicing of a pre-mRNA of ALS2CL. In some embodiments, the SMSM compounds and methods of their use described herein can modulate splicing of a pre-mRNA of AMBRA1. In some embodiments, the SMSM compounds and methods of their use described herein can modulate splicing of a pre-mRNA of ANGPTL3. In some embodiments, the SMSM compounds and methods of their use described herein can modulate splicing of a pre-mRNA of ANK3. In some embodiments, the SMSM compounds and methods of their use described herein can modulate splicing of a pre-mRNA of ANTXR2. In some embodiments, the SMSM compounds and methods of their use described herein can modulate splicing of a pre-mRNA of ANXA10. In some embodiments, the SMSM compounds and methods of their use described herein can modulate splicing of a pre-mRNA of ANXA 11. In some embodiments, the SMSM compounds and methods of their use described herein can modulate splicing of a pre-mRNA of AP2A2. In some embodiments, the SMSM compounds and methods of their use described herein can modulate splicing of a pre-mRNA of AP4E1. In some embodiments, the SMSM compounds and methods of their use described herein can modulate splicing of a pre-mRNA of APC. In some embodiments, the SMSM compounds and methods of their use described herein can modulate splicing of a pre-mRNA of APOAL. In some embodiments, the SMSM compounds and methods of their use described herein can modulate splicing of a pre-mRNA of APOB. In some embodiments, the SMSM compounds and methods of their use described herein can modulate splicing of a pre-mRNA of APOC3. In some embodiments, the SMSM compounds and methods of their use described herein can modulate splicing of a pre-mRNA of APOH. In some embodiments, the SMSM compounds and methods of their use described herein can modulate splicing of a pre-mRNA of AR. In some embodiments, the SMSM compounds and methods of their use described herein can modulate splicing of a pre-mRNA of ARFGEF1. In some embodiments, the SMSM compounds and methods of their use described herein can modulate splicing of a pre-mRNA of ARFGEF2. In some embodiments, the SMSM compounds and methods of their use described herein can modulate splicing of a pre-mRNA of ARHGAP1. In some embodiments, the SMSM compounds and methods of their use described herein can modulate splicing of a pre-mRNA of ARHGAP18. In some embodiments, the SMSM compounds and methods of their use described herein can modulate splicing of a pre-mRNA of ARHGAP26. In some embodiments, the SMSM compounds and methods of their use described herein can modulate splicing of a pre-mRNA of ARHGAP8. In some embodiments, the SMSM compounds and methods of their use described herein can modulate splicing of a pre-mRNA of ARHGEF18. In some embodiments, the SMSM compounds and methods of their use described herein can modulate splicing of a pre-mRNA of ARHGEF2. In some embodiments, the SMSM compounds and methods of their use described herein can modulate splicing of a pre-mRNA of ARPC3. In some embodiments, the SMSM compounds and methods of their use described herein can modulate splicing of a pre-mRNA of ARS2. In some embodiments, the SMSM compounds and methods of their use described herein can modulate splicing of a pre-mRNA of ASH1L. In some embodiments, the SMSM compounds and methods of their use described herein can modulate splicing of a pre-mRNA of ASNSD1. In some embodiments, the SMSM compounds and methods of their use described herein can modulate splicing of a pre-mRNA of ASPM. In some embodiments, the SMSM compounds and methods of their use described herein can modulate splicing of a pre-mRNA of ATAD5. In some embodiments, the SMSM compounds and methods of their use described herein can modulate splicing of a pre-mRNA of ATG16L2. In some embodiments, the SMSM compounds and methods of their use described herein can modulate splicing of a pre-mRNA of ATG4A. In some embodiments, the SMSM compounds and methods of their use described herein can modulate splicing of a pre-mRNA of ATM. In some embodiments, the SMSM compounds and methods of their use described herein can modulate splicing of a pre-mRNA of ATP1 IC. In some embodiments, the SMSM compounds and methods of their use described herein can modulate splicing of a pre-mRNA of ATP13A5. In some embodiments, the SMSM compounds and methods of their use described herein can modulate splicing of a pre-mRNA of ATP6V1G3. In some embodiments, the SMSM compounds and methods of their use described herein can modulate splicing of a pre-mRNA of ATP7A. In some embodiments, the SMSM compounds and methods of their use described herein can modulate splicing of a pre-mRNA of ATP7B. In some embodiments, the SMSM compounds and methods of their use described herein can modulate splicing of a pre-mRNA of ATR. In some embodiments, the SMSM compounds and methods of their use described herein can modulate splicing of a pre-mRNA of ATXN2. In some embodiments, the SMSM compounds and methods of their use described herein can modulate splicing of a pre-mRNA of ATXN3. In some embodiments, the SMSM compounds and methods of their use described herein can modulate splicing of a pre-mRNA of B2M. In some embodiments, the SMSM compounds and methods of their use described herein can modulate splicing of a pre-mRNA of B4GALNT3. In some embodiments, the SMSM compounds and methods of their use described herein can modulate splicing of a pre-mRNA of BBOX1. In some embodiments, the SMSM compounds and methods of their use described herein can modulate splicing of a pre-mRNA of BBS4. In some embodiments, the SMSM compounds and methods of their use described herein can modulate splicing of a pre-mRNA of BCL2-like 11 (BIM). In some embodiments, the SMSM compounds and methods of their use described herein can modulate splicing of a pre-mRNA of BCS1L. In some embodiments, the SMSM compounds and methods of their use described herein can modulate splicing of a pre-mRNA of BMP2K. In some embodiments, the SMSM compounds and methods of their use described herein can modulate splicing of a pre-mRNA of BMPR2. In some embodiments, the SMSM compounds and methods of their use described herein can modulate splicing of a pre-mRNA of BRCA1. In some embodiments, the SMSM compounds and methods of their use described herein can modulate splicing of a pre-mRNA of BRCA2. In some embodiments, the SMSM compounds and methods of their use described herein can modulate splicing of a pre-mRNA of BRCC3. In some embodiments, the SMSM compounds and methods of their use described herein can modulate splicing of a pre-mRNA of BRSK1. In some embodiments, the SMSM compounds and methods of their use described herein can modulate splicing of a pre-mRNA of BRSK2. In some embodiments, the SMSM compounds and methods of their use described herein can modulate splicing of a pre-mRNA of BTAF1. In some embodiments, the SMSM compounds and methods of their use described herein can modulate splicing of a pre-mRNA of BTK. In some embodiments, the SMSM compounds and methods of their use described herein can modulate splicing of a pre-mRNA of C10orf137. In some embodiments, the SMSM compounds and methods of their use described herein can modulate splicing of a pre-mRNA of C1orf30. In some embodiments, the SMSM compounds and methods of their use described herein can modulate splicing of a pre-mRNA of C11orf65. In some embodiments, the SMSM compounds and methods of their use described herein can modulate splicing of a pre-mRNA of C1orf70. In some embodiments, the SMSM compounds and methods of their use described herein can modulate splicing of a pre-mRNA of C12orf51. In some embodiments, the SMSM compounds and methods of their use described herein can modulate splicing of a pre-mRNA of C13orf1. In some embodiments, the SMSM compounds and methods of their use described herein can modulate splicing of a pre-mRNA of C13orf15. In some embodiments, the SMSM compounds and methods of their use described herein can modulate splicing of a pre-mRNA of C14orf101. In some embodiments, the SMSM compounds and methods of their use described herein can modulate splicing of a pre-mRNA of C14orf118. In some embodiments, the SMSM compounds and methods of their use described herein can modulate splicing of a pre-mRNA of C15orf29. In some embodiments, the SMSM compounds and methods of their use described herein can modulate splicing of a pre-mRNA of C15orf42. In some embodiments, the SMSM compounds and methods of their use described herein can modulate splicing of a pre-mRNA of C15orf60. In some embodiments, the SMSM compounds and methods of their use described herein can modulate splicing of a pre-mRNA of C16orf33. In some embodiments, the SMSM compounds and methods of their use described herein can modulate splicing of a pre-mRNA of C16orf38. In some embodiments, the SMSM compounds and methods of their use described herein can modulate splicing of a pre-mRNA of C16orf48. In some embodiments, the SMSM compounds and methods of their use described herein can modulate splicing of a pre-mRNA of C18orf8. In some embodiments, the SMSM compounds and methods of their use described herein can modulate splicing of a pre-mRNA of C19orf42. In some embodiments, the SMSM compounds and methods of their use described herein can modulate splicing of a pre-mRNA of C1orf107. In some embodiments, the SMSM compounds and methods of their use described herein can modulate splicing of a pre-mRNA of C1orf114. In some embodiments, the SMSM compounds and methods of their use described herein can modulate splicing of a pre-mRNA of C1orf130. In some embodiments, the SMSM compounds and methods of their use described herein can modulate splicing of a pre-mRNA of C1orf149. In some embodiments, the SMSM compounds and methods of their use described herein can modulate splicing of a pre-mRNA of C1orf27. In some embodiments, the SMSM compounds and methods of their use described herein can modulate splicing of a pre-mRNA of C1orf71. In some embodiments, the SMSM compounds and methods of their use described herein can modulate splicing of a pre-mRNA of C1orf87. In some embodiments, the SMSM compounds and methods of their use described herein can modulate splicing of a pre-mRNA of C1orf94. In some embodiments, the SMSM compounds and methods of their use described herein can modulate splicing of a pre-mRNA of C1R. In some embodiments, the SMSM compounds and methods of their use described herein can modulate splicing of a pre-mRNA of C20orf74. In some embodiments, the SMSM compounds and methods of their use described herein can modulate splicing of a pre-mRNA of C21orf70. In some embodiments, the SMSM compounds and methods of their use described herein can modulate splicing of a pre-mRNA of C2orf55. In some embodiments, the SMSM compounds and methods of their use described herein can modulate splicing of a pre-mRNA of C3. In some embodiments, the SMSM compounds and methods of their use described herein can modulate splicing of a pre-mRNA of C3orf23. In some embodiments, the SMSM compounds and methods of their use described herein can modulate splicing of a pre-mRNA of C4orf18. In some embodiments, the SMSM compounds and methods of their use described herein can modulate splicing of a pre-mRNA of C4orf29. In some embodiments, the SMSM compounds and methods of their use described herein can modulate splicing of a pre-mRNA of C5orf34. In some embodiments, the SMSM compounds and methods of their use described herein can modulate splicing of a pre-mRNA of C6orf118. In some embodiments, the SMSM compounds and methods of their use described herein can modulate splicing of a pre-mRNA of C8B. In some embodiments, the SMSM compounds and methods of their use described herein can modulate splicing of a pre-mRNA of C8orf33. In some embodiments, the SMSM compounds and methods of their use described herein can modulate splicing of a pre-mRNA of C9orf114. In some embodiments, the SMSM compounds and methods of their use described herein can modulate splicing of a pre-mRNA of C9orf43. In some embodiments, the SMSM compounds and methods of their use described herein can modulate splicing of a pre-mRNA of C9orf86. In some embodiments, the SMSM compounds and methods of their use described herein can modulate splicing of a pre-mRNA of C9orf98. In some embodiments, the SMSM compounds and methods of their use described herein can modulate splicing of a pre-mRNA of CA11. In some embodiments, the SMSM compounds and methods of their use described herein can modulate splicing of a pre-mRNA of CAB39. In some embodiments, the SMSM compounds and methods of their use described herein can modulate splicing of a pre-mRNA of CACHD1. In some embodiments, the SMSM compounds and methods of their use described herein can modulate splicing of a pre-mRNA of CACNA1B. In some embodiments, the SMSM compounds and methods of their use described herein can modulate splicing of a pre-mRNA of CACNA1C. In some embodiments, the SMSM compounds and methods of their use described herein can modulate splicing of a pre-mRNA of CACNA1G. In some embodiments, the SMSM compounds and methods of their use described herein can modulate splicing of a pre-mRNA of CACNA1H. In some embodiments, the SMSM compounds and methods of their use described herein can modulate splicing of a pre-mRNA of CACNA2D1. In some embodiments, the SMSM compounds and methods of their use described herein can modulate splicing of a pre-mRNA of CALCA. In some embodiments, the SMSM compounds and methods of their use described herein can modulate splicing of a pre-mRNA of CALCOCO2. In some embodiments, the SMSM compounds and methods of their use described herein can modulate splicing of a pre-mRNA of CAMK1D. In some embodiments, the SMSM compounds and methods of their use described herein can modulate splicing of a pre-mRNA of CAMKK1. In some embodiments, the SMSM compounds and methods of their use described herein can modulate splicing of a pre-mRNA of CAPN3. In some embodiments, the SMSM compounds and methods of their use described herein can modulate splicing of a pre-mRNA of CAPN9. In some embodiments, the SMSM compounds and methods of their use described herein can modulate splicing of a pre-mRNA of CAPSL. In some embodiments, the SMSM compounds and methods of their use described herein can modulate splicing of a pre-mRNA of CARKD. In some embodiments, the SMSM compounds and methods of their use described herein can modulate splicing of a pre-mRNA of CAT. In some embodiments, the SMSM compounds and methods of their use described herein can modulate splicing of a pre-mRNA of CBX1. In some embodiments, the SMSM compounds and methods of their use described herein can modulate splicing of a pre-mRNA of CBX3. In some embodiments, the SMSM compounds and methods of their use described herein can modulate splicing of a pre-mRNA of CCDC102B. In some embodiments, the SMSM compounds and methods of their use described herein can modulate splicing of a pre-mRNA of CCDC11. In some embodiments, the SMSM compounds and methods of their use described herein can modulate splicing of a pre-mRNA of CCDC131. In some embodiments, the SMSM compounds and methods of their use described herein can modulate splicing of a pre-mRNA of CCDC146. In some embodiments, the SMSM compounds and methods of their use described herein can modulate splicing of a pre-mRNA of CCDC15. In some embodiments, the SMSM compounds and methods of their use described herein can modulate splicing of a pre-mRNA of CCDC18. In some embodiments, the SMSM compounds and methods of their use described herein can modulate splicing of a pre-mRNA of CCDC5. In some embodiments, the SMSM compounds and methods of their use described herein can modulate splicing of a pre-mRNA of CCDC81. In some embodiments, the SMSM compounds and methods of their use described herein can modulate splicing of a pre-mRNA of CD1B. In some embodiments, the SMSM compounds and methods of their use described herein can modulate splicing of a pre-mRNA of CD33. In some embodiments, the SMSM compounds and methods of their use described herein can modulate splicing of a pre-mRNA of CD4. In some embodiments, the SMSM compounds and methods of their use described herein can modulate splicing of a pre-mRNA of CD46. In some embodiments, the SMSM compounds and methods of their use described herein can modulate splicing of a pre-mRNA of CDC14A. In some embodiments, the SMSM compounds and methods of their use described herein can modulate splicing of a pre-mRNA of CDC16. In some embodiments, the SMSM compounds and methods of their use described herein can modulate splicing of a pre-mRNA of CDC2L5. In some embodiments, the SMSM compounds and methods of their use described herein can modulate splicing of a pre-mRNA of CDC42BPB. In some embodiments, the SMSM compounds and methods of their use described herein can modulate splicing of a pre-mRNA of CDCA8. In some embodiments, the SMSM compounds and methods of their use described herein can modulate splicing of a pre-mRNA of CDH1. In some embodiments, the SMSM compounds and methods of their use described herein can modulate splicing of a pre-mRNA of CDH10. In some embodiments, the SMSM compounds and methods of their use described herein can modulate splicing of a pre-mRNA of CDH11. In some embodiments, the SMSM compounds and methods of their use described herein can modulate splicing of a pre-mRNA of CDH23. In some embodiments, the SMSM compounds and methods of their use described herein can modulate splicing of a pre-mRNA of CDH24. In some embodiments, the SMSM compounds and methods of their use described herein can modulate splicing of a pre-mRNA of CDH8. In some embodiments, the SMSM compounds and methods of their use described herein can modulate splicing of a pre-mRNA of CDH9. In some embodiments, the SMSM compounds and methods of their use described herein can modulate splicing of a pre-mRNA of CDK5RAP2. In some embodiments, the SMSM compounds and methods of their use described herein can modulate splicing of a pre-mRNA of CDK6. In some embodiments, the SMSM compounds and methods of their use described herein can modulate splicing of a pre-mRNA of CDK8. In some embodiments, the SMSM compounds and methods of their use described herein can modulate splicing of a pre-mRNA of CEL. In some embodiments, the SMSM compounds and methods of their use described herein can modulate splicing of a pre-mRNA of CELSR3. In some embodiments, the SMSM compounds and methods of their use described herein can modulate splicing of a pre-mRNA of CENP1. In some embodiments, the SMSM compounds and methods of their use described herein can modulate splicing of a pre-mRNA of CENTB2. In some embodiments, the SMSM compounds and methods of their use described herein can modulate splicing of a pre-mRNA of CENTG2. In some embodiments, the SMSM compounds and methods of their use described herein can modulate splicing of a pre-mRNA of CEP110. In some embodiments, the SMSM compounds and methods of their use described herein can modulate splicing of a pre-mRNA of CEP170. In some embodiments, the SMSM compounds and methods of their use described herein can modulate splicing of a pre-mRNA of CEP192. In some embodiments, the SMSM compounds and methods of their use described herein can modulate splicing of a pre-mRNA of CETP. In some embodiments, the SMSM compounds and methods of their use described herein can modulate splicing of a pre-mRNA of CFB. In some embodiments, the SMSM compounds and methods of their use described herein can modulate splicing of a pre-mRNA of CFH. In some embodiments, the SMSM compounds and methods of their use described herein can modulate splicing of a pre-mRNA of CFTR. In some embodiments, the SMSM compounds and methods of their use described herein can modulate splicing of a pre-mRNA of CGN. In some embodiments, the SMSM compounds and methods of their use described herein can modulate splicing of a pre-mRNA of CGNL1. In some embodiments, the SMSM compounds and methods of their use described herein can modulate splicing of a pre-mRNA of CHAF1A. In some embodiments, the SMSM compounds and methods of their use described herein can modulate splicing of a pre-mRNA of CHD9. In some embodiments, the SMSM compounds and methods of their use described herein can modulate splicing of a pre-mRNA of CHIC2. In some embodiments, the SMSM compounds and methods of their use described herein can modulate splicing of a pre-mRNA of CHL1. In some embodiments, the SMSM compounds and methods of their use described herein can modulate splicing of a pre-mRNA of CHM. In some embodiments, the SMSM compounds and methods of their use described herein can modulate splicing of a pre-mRNA of CHN1. In some embodiments, the SMSM compounds and methods of their use described herein can modulate splicing of a pre-mRNA of CLCN1. In some embodiments, the SMSM compounds and methods of their use described herein can modulate splicing of a pre-mRNA of CLEC16A. In some embodiments, the SMSM compounds and methods of their use described herein can modulate splicing of a pre-mRNA of CLIC2. In some embodiments, the SMSM compounds and methods of their use described herein can modulate splicing of a pre-mRNA of CLINTT1. In some embodiments, the SMSM compounds and methods of their use described herein can modulate splicing of a pre-mRNA of CLK1. In some embodiments, the SMSM compounds and methods of their use described herein can modulate splicing of a pre-mRNA of CLPB. In some embodiments, the SMSM compounds and methods of their use described herein can modulate splicing of a pre-mRNA of CLPTM1. In some embodiments, the SMSM compounds and methods of their use described herein can modulate splicing of a pre-mRNA of CMIP. In some embodiments, the SMSM compounds and methods of their use described herein can modulate splicing of a pre-mRNA of CMYA5. In some embodiments, the SMSM compounds and methods of their use described herein can modulate splicing of a pre-mRNA of CNGA3. In some embodiments, the SMSM compounds and methods of their use described herein can modulate splicing of a pre-mRNA of CNOT1. In some embodiments, the SMSM compounds and methods of their use described herein can modulate splicing of a pre-mRNA of CNOT7. In some embodiments, the SMSM compounds and methods of their use described herein can modulate splicing of a pre-mRNA of CNTN6. In some embodiments, the SMSM compounds and methods of their use described herein can modulate splicing of a pre-mRNA of COG3. In some embodiments, the SMSM compounds and methods of their use described herein can modulate splicing of a pre-mRNA of COL11A1. In some embodiments, the SMSM compounds and methods of their use described herein can modulate splicing of a pre-mRNA of COL11A2. In some embodiments, the SMSM compounds and methods of their use described herein can modulate splicing of a pre-mRNA of COL12A1. In some embodiments, the SMSM compounds and methods of their use described herein can modulate splicing of a pre-mRNA of COL14A1. In some embodiments, the SMSM compounds and methods of their use described herein can modulate splicing of a pre-mRNA of COL15A1. In some embodiments, the SMSM compounds and methods of their use described herein can modulate splicing of a pre-mRNA of COL17A1. In some embodiments, the SMSM compounds and methods of their use described herein can modulate splicing of a pre-mRNA of COL19A1. In some embodiments, the SMSM compounds and methods of their use described herein can modulate splicing of a pre-mRNA of COL1A1. In some embodiments, the SMSM compounds and methods of their use described herein can modulate splicing of a pre-mRNA of COL1A2. In some embodiments, the SMSM compounds and methods of their use described herein can modulate splicing of a pre-mRNA of COL22A1. In some embodiments, the SMSM compounds and methods of their use described herein can modulate splicing of a pre-mRNA of COL24A1. In some embodiments, the SMSM compounds and methods of their use described herein can modulate splicing of a pre-mRNA of COL25A1. In some embodiments, the SMSM compounds and methods of their use described herein can modulate splicing of a pre-mRNA of COL29A1. In some embodiments, the SMSM compounds and methods of their use described herein can modulate splicing of a pre-mRNA of COL2A1. In some embodiments, the SMSM compounds and methods of their use described herein can modulate splicing of a pre-mRNA of COL3A1. In some embodiments, the SMSM compounds and methods of their use described herein can modulate splicing of a pre-mRNA of COL4A 1. In some embodiments, the SMSM compounds and methods of their use described herein can modulate splicing of a pre-mRNA of COL4A2. In some embodiments, the SMSM compounds and methods of their use described herein can modulate splicing of a pre-mRNA of COL4A5. In some embodiments, the SMSM compounds and methods of their use described herein can modulate splicing of a pre-mRNA of COL4A6. In some embodiments, the SMSM compounds and methods of their use described herein can modulate splicing of a pre-mRNA of COL5A2. In some embodiments, the SMSM compounds and methods of their use described herein can modulate splicing of a pre-mRNA of COL6A1. In some embodiments, the SMSM compounds and methods of their use described herein can modulate splicing of a pre-mRNA of COL7A1. In some embodiments, the SMSM compounds and methods of their use described herein can modulate splicing of a pre-mRNA of COL9A 1. In some embodiments, the SMSM compounds and methods of their use described herein can modulate splicing of a pre-mRNA of COL9A2. In some embodiments, the SMSM compounds and methods of their use described herein can modulate splicing of a pre-mRNA of COLQ. In some embodiments, the SMSM compounds and methods of their use described herein can modulate splicing of a pre-mRNA of COMTD1. In some embodiments, the SMSM compounds and methods of their use described herein can modulate splicing of a pre-mRNA of COPA. In some embodiments, the SMSM compounds and methods of their use described herein can modulate splicing of a pre-mRNA of COPB2. In some embodiments, the SMSM compounds and methods of their use described herein can modulate splicing of a pre-mRNA of COPS7B. In some embodiments, the SMSM compounds and methods of their use described herein can modulate splicing of a pre-mRNA of COPZ2. In some embodiments, the SMSM compounds and methods of their use described herein can modulate splicing of a pre-mRNA of CPSF2. In some embodiments, the SMSM compounds and methods of their use described herein can modulate splicing of a pre-mRNA of CPXM2. In some embodiments, the SMSM compounds and methods of their use described herein can modulate splicing of a pre-mRNA of CR$^1$. In some embodiments, the SMSM compounds and methods of their use described herein can modulate splicing of a pre-mRNA of CREBBP. In some embodiments, the SMSM compounds and methods of their use described herein can modulate splicing of a pre-mRNA of CRKRS. In some embodiments, the SMSM compounds and methods of their use described herein can modulate splicing of a pre-mRNA of CRYZ. In some embodiments, the SMSM compounds and methods of their use described herein can modulate splicing of a pre-mRNA of CSE1L. In some embodiments, the SMSM compounds and methods of their use described herein can modulate splicing of a pre-mRNA of CSTB. In some embodiments, the SMSM compounds and methods of their use described herein can modulate splicing of a pre-mRNA of CSTF3. In some embodiments, the SMSM compounds and methods of their use described herein can modulate splicing of a pre-mRNA of CT45-6. In some embodiments, the SMSM compounds and methods of their use described herein can modulate splicing of a pre-mRNA of CUBN. In some embodiments, the SMSM compounds and methods of their use described herein can modulate splicing of a pre-mRNA of CUL4B. In some embodiments, the SMSM compounds and methods of their use described herein can modulate splicing of a pre-mRNA of CUL5. In some embodiments, the SMSM compounds and methods of their use described herein can modulate splicing of a pre-mRNA of CXorf41. In some embodiments, the SMSM compounds and methods of their use described herein can modulate splicing of a pre-mRNA of CYBB. In some embodiments, the SMSM compounds and methods of their use described herein can modulate splicing of a pre-mRNA of CYFIP2. In some embodiments, the SMSM compounds and methods of their use described herein can modulate splicing of a pre-mRNA of CYP17. In some embodiments, the SMSM compounds and methods of their use described herein can modulate splicing of a pre-mRNA of CYP19. In some embodiments, the SMSM compounds and methods of their use described herein can modulate splicing of a pre-mRNA of CYP24A1. In some embodiments, the SMSM compounds and methods of their use described herein can modulate splicing of a pre-mRNA of CYP27A1. In some embodiments, the SMSM compounds and methods of their use described herein can modulate splicing of a pre-mRNA of CYP3A4. In some embodiments, the SMSM compounds and methods of their use described herein can modulate splicing of a pre-mRNA of CYP3A43. In some embodiments, the SMSM compounds and methods of their use described herein can modulate splicing of a pre-mRNA of CYP3A5. In some embodiments, the SMSM compounds and methods of their use described herein can modulate splicing of a pre-mRNA of CYP4F2. In some embodiments, the SMSM compounds and methods of their use described herein can modulate splicing of a pre-mRNA of CYP4F3. In some embodiments, the SMSM compounds and methods of their use described herein can modulate splicing of a pre-mRNA of DAZ2. In some embodiments, the SMSM compounds and methods of their use described herein can modulate splicing of a pre-mRNA of DCBLD1. In some embodiments, the SMSM compounds and methods of their use described herein can modulate splicing of a pre-mRNA of DCC. In some embodiments, the SMSM compounds and methods of their use described herein can modulate splicing of a pre-mRNA of DCTN3. In some embodiments, the SMSM compounds and methods of their use described herein can modulate splicing of a pre-mRNA of DCUN1D4. In some embodiments, the SMSM compounds and methods of their use described herein can modulate splicing of a pre-mRNA of DDA1. In some embodiments, the SMSM compounds and methods of their use described herein can modulate splicing of a pre-mRNA of DDEF1. In some embodiments, the SMSM compounds and methods of their use described herein can modulate splicing of a pre-mRNA of DDX1. In some embodiments, the SMSM compounds and methods of their use described herein can modulate splicing of a pre-mRNA of DDX24. In some embodiments, the SMSM compounds and methods of their use described herein can modulate splicing of a pre-mRNA of DDX4. In some embodiments, the SMSM compounds and methods of their use described herein can modulate splicing of a pre-mRNA of DENND2D. In some embodiments, the SMSM compounds and methods of their use described herein can modulate splicing of a pre-mRNA of DEPDC2. In some embodiments, the SMSM compounds and methods of their use described herein can modulate splicing of a pre-mRNA of DES. In some embodiments, the SMSM compounds and methods of their use described herein can modulate splicing of a pre-mRNA of DGAT2. In some embodiments, the SMSM compounds and methods of their use described herein can modulate splicing of a pre-mRNA of DHFR. In some embodiments, the SMSM compounds and methods of their use described herein can modulate splicing of a pre-mRNA of DHRS7. In some embodiments, the SMSM compounds and methods of their use described herein can modulate splicing of a pre-mRNA of DHRS9. In some embodiments, the SMSM compounds and methods of their use described herein can modulate splicing of a pre-mRNA of DIP2A. In some embodiments, the SMSM compounds and methods of their use described herein can modulate splicing of a pre-mRNA of DMD. For example, the SMSM compounds and methods of their use described herein can modulate splicing of exon 51a pre-mRNA of DMD. In some embodiments, the SMSM compounds and methods of their use described herein can modulate splicing of a pre-mRNA of DMTF1. In some embodiments, the SMSM compounds and methods of their use described herein can modulate splicing of a pre-mRNA of DNAH3. In some embodiments, the SMSM compounds and methods of their use described herein can modulate splicing of a pre-mRNA of DNAH8. In some embodiments, the SMSM compounds and methods of their use described herein can modulate splicing of a pre-mRNA of DNAI1. In some embodiments, the SMSM compounds and methods of their use described herein can modulate splicing of a pre-mRNA of DNAJA4. In some embodiments, the SMSM compounds and methods of their use described herein can modulate splicing of a pre-mRNA of DNAJC13. In some embodiments, the SMSM compounds and methods of their use described herein can modulate splicing of a pre-mRNA of DNAJC7. In some embodiments, the SMSM compounds and methods of their use described herein can modulate splicing of a pre-mRNA of DNTTIP2. In some embodiments, the SMSM compounds and methods of their use described herein can modulate splicing of a pre-mRNA of DOCK10. In some embodiments, the SMSM compounds and methods of their use described herein can modulate splicing of a pre-mRNA of DOCK 11. In some embodiments, the SMSM compounds and methods of their use described herein can modulate splicing of a pre-mRNA of DOCK4. In some embodiments, the SMSM compounds and methods of their use described herein can modulate splicing of a pre-mRNA of DPP3. In some embodiments, the SMSM compounds and methods of their use described herein can modulate splicing of a pre-mRNA of DPP4. In some embodiments, the SMSM compounds and methods of their use described herein can modulate splicing of a pre-mRNA of DPY19L2P2. In some embodiments, the SMSM compounds and methods of their use described herein can modulate splicing of a pre-mRNA of DSCC1. In some embodiments, the SMSM compounds and methods of their use described herein can modulate splicing of a pre-mRNA of DUX4. In some embodiments, the SMSM compounds and methods of their use described herein can modulate splicing of a pre-mRNA of DVL3. In some embodiments, the SMSM compounds and methods of their use described herein can modulate splicing of a pre-mRNA of DYNC1H1. In some embodiments, the SMSM compounds and methods of their use described herein can modulate splicing of a pre-mRNA of DYSF. In some embodiments, the SMSM compounds and methods of their use described herein can modulate splicing of a pre-mRNA of ECM2. In some embodiments, the SMSM compounds and methods of their use described herein can modulate splicing of a pre-mRNA of EDEM3. In some embodiments, the SMSM compounds and methods of their use described herein can modulate splicing of a pre-mRNA of EFCAB3. In some embodiments, the SMSM compounds and methods of their use described herein can modulate splicing of a pre-mRNA of EFCAB4B. In some embodiments, the SMSM compounds and methods of their use described herein can modulate splicing of a pre-mRNA of EFNA4. In some embodiments, the SMSM compounds and methods of their use described herein can modulate splicing of a pre-mRNA of EFTUD2. In some embodiments, the SMSM compounds and methods of their use described herein can modulate splicing of a pre-mRNA of EGFR. In some embodiments, the SMSM compounds and methods of their use described herein can modulate splicing of a pre-mRNA of EIF3A. In some embodiments, the SMSM compounds and methods of their use described herein can modulate splicing of a pre-mRNA of ELA 1. In some embodiments, the SMSM compounds and methods of their use described herein can modulate splicing of a pre-mRNA of ELA2A. In some embodiments, the SMSM compounds and methods of their use described herein can modulate splicing of a pre-mRNA of EMCN. In some embodiments, the SMSM compounds and methods of their use described herein can modulate splicing of a pre-mRNA of EMD. In some embodiments, the SMSM compounds and methods of their use described herein can modulate splicing of a pre-mRNA of EML5. In some embodiments, the SMSM compounds and methods of their use described herein can modulate splicing of a pre-mRNA of ENPP3. In some embodiments, the SMSM compounds and methods of their use described herein can modulate splicing of a pre-mRNA of EPB41L5. In some embodiments, the SMSM compounds and methods of their use described herein can modulate splicing of a pre-mRNA of EPHA3. In some embodiments, the SMSM compounds and methods of their use described herein can modulate splicing of a pre-mRNA of EPHA4. In some embodiments, the SMSM compounds and methods of their use described herein can modulate splicing of a pre-mRNA of EPHB1. In some embodiments, the SMSM compounds and methods of their use described herein can modulate splicing of a pre-mRNA of EPHB2. In some embodiments, the SMSM compounds and methods of their use described herein can modulate splicing of a pre-mRNA of EPHB3. In some embodiments, the SMSM compounds and methods of their use described herein can modulate splicing of a pre-mRNA of EPS15. In some embodiments, the SMSM compounds and methods of their use described herein can modulate splicing of a pre-mRNA of ERBB4. In some embodiments, the SMSM compounds and methods of their use described herein can modulate splicing of a pre-mRNA of ERCC1. In some embodiments, the SMSM compounds and methods of their use described herein can modulate splicing of a pre-mRNA of ERCC8. In some embodiments, the SMSM compounds and methods of their use described herein can modulate splicing of a pre-mRNA of ERGIC3. In some embodiments, the SMSM compounds and methods of their use described herein can modulate splicing of a pre-mRNA of ERMN. In some embodiments, the SMSM compounds and methods of their use described herein can modulate splicing of a pre-mRNA of ERMP1. In some embodiments, the SMSM compounds and methods of their use described herein can modulate splicing of a pre-mRNA of ERN1. In some embodiments, the SMSM compounds and methods of their use described herein can modulate splicing of a pre-mRNA of ERN2. In some embodiments, the SMSM compounds and methods of their use described herein can modulate splicing of a pre-mRNA of ETS2. In some embodiments, the SMSM compounds and methods of their use described herein can modulate splicing of a pre-mRNA of ETV4. In some embodiments, the SMSM compounds and methods of their use described herein can modulate splicing of a pre-mRNA of EVC2. In some embodiments, the SMSM compounds and methods of their use described herein can modulate splicing of a pre-mRNA of EXO1. In some embodiments, the SMSM compounds and methods of their use described herein can modulate splicing of a pre-mRNA of EXOC4. In some embodiments, the SMSM compounds and methods of their use described herein can modulate splicing of a pre-mRNA of F11. In some embodiments, the SMSM compounds and methods of their use described herein can modulate splicing of a pre-mRNA of F13A1. In some embodiments, the SMSM compounds and methods of their use described herein can modulate splicing of a pre-mRNA of F3. In some embodiments, the SMSM compounds and methods of their use described herein can modulate splicing of a pre-mRNA of F5. In some embodiments, the SMSM compounds and methods of their use described herein can modulate splicing of a pre-mRNA of F7. In some embodiments, the SMSM compounds and methods of their use described herein can modulate splicing of a pre-mRNA of F8. In some embodiments, the SMSM compounds and methods of their use described herein can modulate splicing of a pre-mRNA of FAH. In some embodiments, the SMSM compounds and methods of their use described herein can modulate splicing of a pre-mRNA of FAM134A. In some embodiments, the SMSM compounds and methods of their use described herein can modulate splicing of a pre-mRNA of FAM13A1. In some embodiments, the SMSM compounds and methods of their use described herein can modulate splicing of a pre-mRNA of FAM13B1. In some embodiments, the SMSM compounds and methods of their use described herein can modulate splicing of a pre-mRNA of FAM13C1. In some embodiments, the SMSM compounds and methods of their use described herein can modulate splicing of a pre-mRNA of FAM161A. In some embodiments, the SMSM compounds and methods of their use described herein can modulate splicing of a pre-mRNA of FAM176B. In some embodiments, the SMSM compounds and methods of their use described herein can modulate splicing of a pre-mRNA of FAM184A. In some embodiments, the SMSM compounds and methods of their use described herein can modulate splicing of a pre-mRNA of FAM19A1. In some embodiments, the SMSM compounds and methods of their use described herein can modulate splicing of a pre-mRNA of FAM20A. In some embodiments, the SMSM compounds and methods of their use described herein can modulate splicing of a pre-mRNA of FAM23B. In some embodiments, the SMSM compounds and methods of their use described herein can modulate splicing of a pre-mRNA of FAM65C. In some embodiments, the SMSM compounds and methods of their use described herein can modulate splicing of a pre-mRNA of FANCA. In some embodiments, the SMSM compounds and methods of their use described herein can modulate splicing of a pre-mRNA of FANCC. In some embodiments, the SMSM compounds and methods of their use described herein can modulate splicing of a pre-mRNA of FANCG. In some embodiments, the SMSM compounds and methods of their use described herein can modulate splicing of a pre-mRNA of FANCM. In some embodiments, the SMSM compounds and methods of their use described herein can modulate splicing of a pre-mRNA of FANK1. In some embodiments, the SMSM compounds and methods of their use described herein can modulate splicing of a pre-mRNA of FAR2. In some embodiments, the SMSM compounds and methods of their use described herein can modulate splicing of a pre-mRNA of FBN1. In some embodiments, the SMSM compounds and methods of their use described herein can modulate splicing of a pre-mRNA of FBXO15. In some embodiments, the SMSM compounds and methods of their use described herein can modulate splicing of a pre-mRNA of FBXO18. In some embodiments, the SMSM compounds and methods of their use described herein can modulate splicing of a pre-mRNA of FBXO38. In some embodiments, the SMSM compounds and methods of their use described herein can modulate splicing of a pre-mRNA of FCGBP. In some embodiments, the SMSM compounds and methods of their use described herein can modulate splicing of a pre-mRNA of FECH. In some embodiments, the SMSM compounds and methods of their use described herein can modulate splicing of a pre-mRNA of FEZ2. In some embodiments, the SMSM compounds and methods of their use described herein can modulate splicing of a pre-mRNA of FGA. In some embodiments, the SMSM compounds and methods of their use described herein can modulate splicing of a pre-mRNA of FGD6. In some embodiments, the SMSM compounds and methods of their use described herein can modulate splicing of a pre-mRNA of FGFR1OP. In some embodiments, the SMSM compounds and methods of their use described herein can modulate splicing of a pre-mRNA of FGFR1OP2. In some embodiments, the SMSM compounds and methods of their use described herein can modulate splicing of a pre-mRNA of FGFR2. In some embodiments, the SMSM compounds and methods of their use described herein can modulate splicing of a pre-mRNA of FGG. In some embodiments, the SMSM compounds and methods of their use described herein can modulate splicing of a pre-mRNA of FGR. In some embodiments, the SMSM compounds and methods of their use described herein can modulate splicing of a pre-mRNA of FIX. In some embodiments, the SMSM compounds and methods of their use described herein can modulate splicing of a pre-mRNA of FKBP3. In some embodiments, the SMSM compounds and methods of their use described herein can modulate splicing of a pre-mRNA of FLJ35848. In some embodiments, the SMSM compounds and methods of their use described herein can modulate splicing of a pre-mRNA of FLJ36070. In some embodiments, the SMSM compounds and methods of their use described herein can modulate splicing of a pre-mRNA of FLNA. In some embodiments, the SMSM compounds and methods of their use described herein can modulate splicing of a pre-mRNA of FN1. In some embodiments, the SMSM compounds and methods of their use described herein can modulate splicing of a pre-mRNA of FNBP1L. In some embodiments, the SMSM compounds and methods of their use described herein can modulate splicing of a pre-mRNA of FOLH1. In some embodiments, the SMSM compounds and methods of their use described herein can modulate splicing of a pre-mRNA of FOXM1. In some embodiments, the SMSM compounds and methods of their use described herein can modulate splicing of a pre-mRNA of FRAS1. In some embodiments, the SMSM compounds and methods of their use described herein can modulate splicing of a pre-mRNA of FUT9. In some embodiments, the SMSM compounds and methods of their use described herein can modulate splicing of a pre-mRNA of FZD3. In some embodiments, the SMSM compounds and methods of their use described herein can modulate splicing of a pre-mRNA of FZD6. In some embodiments, the SMSM compounds and methods of their use described herein can modulate splicing of a pre-mRNA of GAB1. In some embodiments, the SMSM compounds and methods of their use described herein can modulate splicing of a pre-mRNA of GALC. In some embodiments, the SMSM compounds and methods of their use described herein can modulate splicing of a pre-mRNA of GALNT3. In some embodiments, the SMSM compounds and methods of their use described herein can modulate splicing of a pre-mRNA of GAPDH. In some embodiments, the SMSM compounds and methods of their use described herein can modulate splicing of a pre-mRNA of GART. In some embodiments, the SMSM compounds and methods of their use described herein can modulate splicing of a pre-mRNA of GAS2L3. In some embodiments, the SMSM compounds and methods of their use described herein can modulate splicing of a pre-mRNA of GBA. In some embodiments, the SMSM compounds and methods of their use described herein can modulate splicing of a pre-mRNA of GBGT1. In some embodiments, the SMSM compounds and methods of their use described herein can modulate splicing of a pre-mRNA of GCG. In some embodiments, the SMSM compounds and methods of their use described herein can modulate splicing of a pre-mRNA of GCGR. In some embodiments, the SMSM compounds and methods of their use described herein can modulate splicing of a pre-mRNA of GCK. In some embodiments, the SMSM compounds and methods of their use described herein can modulate splicing of a pre-mRNA of GFM1. In some embodiments, the SMSM compounds and methods of their use described herein can modulate splicing of a pre-mRNA of GH1. In some embodiments, the SMSM compounds and methods of their use described herein can modulate splicing of a pre-mRNA of GHR. In some embodiments, the SMSM compounds and methods of their use described herein can modulate splicing of a pre-mRNA of GHV. In some embodiments, the SMSM compounds and methods of their use described herein can modulate splicing of a pre-mRNA of GJA1. In some embodiments, the SMSM compounds and methods of their use described herein can modulate splicing of a pre-mRNA of GLA. In some embodiments, the SMSM compounds and methods of their use described herein can modulate splicing of a pre-mRNA of GLT8D1. In some embodiments, the SMSM compounds and methods of their use described herein can modulate splicing of a pre-mRNA of GNAS. In some embodiments, the SMSM compounds and methods of their use described herein can modulate splicing of a pre-mRNA of GNB5. In some embodiments, the SMSM compounds and methods of their use described herein can modulate splicing of a pre-mRNA of GOLGB1. In some embodiments, the SMSM compounds and methods of their use described herein can modulate splicing of a pre-mRNA of GOLT1A. In some embodiments, the SMSM compounds and methods of their use described herein can modulate splicing of a pre-mRNA of GOLT1B. In some embodiments, the SMSM compounds and methods of their use described herein can modulate splicing of a pre-mRNA of GPATCH1. In some embodiments, the SMSM compounds and methods of their use described herein can modulate splicing of a pre-mRNA of GPR158. In some embodiments, the SMSM compounds and methods of their use described herein can modulate splicing of a pre-mRNA of GPR160. In some embodiments, the SMSM compounds and methods of their use described herein can modulate splicing of a pre-mRNA of GRAMD3. In some embodiments, the SMSM compounds and methods of their use described herein can modulate splicing of a pre-mRNA of GRHPR. In some embodiments, the SMSM compounds and methods of their use described herein can modulate splicing of a pre-mRNA of GRIA1. In some embodiments, the SMSM compounds and methods of their use described herein can modulate splicing of a pre-mRNA of GRIA3. In some embodiments, the SMSM compounds and methods of their use described herein can modulate splicing of a pre-mRNA of GRIA4. In some embodiments, the SMSM compounds and methods of their use described herein can modulate splicing of a pre-mRNA of GRIN2B. In some embodiments, the SMSM compounds and methods of their use described herein can modulate splicing of a pre-mRNA of GRM3. In some embodiments, the SMSM compounds and methods of their use described herein can modulate splicing of a pre-mRNA of GRM4. In some embodiments, the SMSM compounds and methods of their use described herein can modulate splicing of a pre-mRNA of GRN. In some embodiments, the SMSM compounds and methods of their use described herein can modulate splicing of a pre-mRNA of GSDMB. In some embodiments, the SMSM compounds and methods of their use described herein can modulate splicing of a pre-mRNA of GSTCD. In some embodiments, the SMSM compounds and methods of their use described herein can modulate splicing of a premRNA of GSTO2. In some embodiments, the SMSM compounds and methods of their use described herein can modulate splicing of a pre-mRNA of GTPBP4. In some embodiments, the SMSM compounds and methods of their use described herein can modulate splicing of a pre-mRNA of HADHA. In some embodiments, the SMSM compounds and methods of their use described herein can modulate splicing of a pre-mRNA of HBA2. In some embodiments, the SMSM compounds and methods of their use described herein can modulate splicing of a pre-mRNA of HBB. In some embodiments, the SMSM compounds and methods of their use described herein can modulate splicing of a pre-mRNA of HCK. In some embodiments, the SMSM compounds and methods of their use described herein can modulate splicing of a pre-mRNA of HDAC3. In some embodiments, the SMSM compounds and methods of their use described herein can modulate splicing of a pre-mRNA of HDAC5. In some embodiments, the SMSM compounds and methods of their use described herein can modulate splicing of a pre-mRNA of HDX. In some embodiments, the SMSM compounds and methods of their use described herein can modulate splicing of a pre-mRNA of HEPACAM2. In some embodiments, the SMSM compounds and methods of their use described herein can modulate splicing of a pre-mRNA of HERC1. In some embodiments, the SMSM compounds and methods of their use described herein can modulate splicing of a pre-mRNA of HEXA. In some embodiments, the SMSM compounds and methods of their use described herein can modulate splicing of a pre-mRNA of HEXB. In some embodiments, the SMSM compounds and methods of their use described herein can modulate splicing of a pre-mRNA of HIPK3. In some embodiments, the SMSM compounds and methods of their use described herein can modulate splicing of a pre-mRNA of HLA-DPB1. In some embodiments, the SMSM compounds and methods of their use described herein can modulate splicing of a pre-mRNA of HLA-G. In some embodiments, the SMSM compounds and methods of their use described herein can modulate splicing of a pre-mRNA of HLCS. In some embodiments, the SMSM compounds and methods of their use described herein can modulate splicing of a pre-mRNA of HLTF. In some embodiments, the SMSM compounds and methods of their use described herein can modulate splicing of a pre-mRNA of HMBS. In some embodiments, the SMSM compounds and methods of their use described herein can modulate splicing of a pre-mRNA of HMGCL. In some embodiments, the SMSM compounds and methods of their use described herein can modulate splicing of a pre-mRNA of HNF1A. In some embodiments, the SMSM compounds and methods of their use described herein can modulate splicing of a pre-mRNA of HNRNPH1. In some embodiments, the SMSM compounds and methods of their use described herein can modulate splicing of a pre-mRNA of HP1BP3. In some embodiments, the SMSM compounds and methods of their use described herein can modulate splicing of a pre-mRNA of HPGD. In some embodiments, the SMSM compounds and methods of their use described herein can modulate splicing of a pre-mRNA of HPRT1. In some embodiments, the SMSM compounds and methods of their use described herein can modulate splicing of a pre-mRNA of HPRT2. In some embodiments, the SMSM compounds and methods of their use described herein can modulate splicing of a pre-mRNA of HSF2BP. In some embodiments, the SMSM compounds and methods of their use described herein can modulate splicing of a pre-mRNA of HSF4. In some embodiments, the SMSM compounds and methods of their use described herein can modulate splicing of a pre-mRNA of HSPA9. In some embodiments, the SMSM compounds and methods of their use described herein can modulate splicing of a pre-mRNA of HSPG2. In some embodiments, the SMSM compounds and methods of their use described herein can modulate splicing of a pre-mRNA of HTT. In some embodiments, the SMSM compounds and methods of their use described herein can modulate splicing of a pre-mRNA of HXA. In some embodiments, the SMSM compounds and methods of their use described herein can modulate splicing of a pre-mRNA of ICA1. In some embodiments, the SMSM compounds and methods of their use described herein can modulate splicing of a pre-mRNA of IDH1. In some embodiments, the SMSM compounds and methods of their use described herein can modulate splicing of a pre-mRNA of IDS. In some embodiments, the SMSM compounds and methods of their use described herein can modulate splicing of a pre-mRNA of IFI44L. In some embodiments, the SMSM compounds and methods of their use described herein can modulate splicing of a pre-mRNA of IKBKAP. In some embodiments, the SMSM compounds and methods of their use described herein can modulate splicing of a pre-mRNA of IL1R2. In some embodiments, the SMSM compounds and methods of their use described herein can modulate splicing of a pre-mRNA of IL5RA. In some embodiments, the SMSM compounds and methods of their use described herein can modulate splicing of a pre-mRNA of IL7RA. In some embodiments, the SMSM compounds and methods of their use described herein can modulate splicing of a pre-mRNA of IMMT. In some embodiments, the SMSM compounds and methods of their use described herein can modulate splicing of a pre-mRNA of INPP5D. In some embodiments, the SMSM compounds and methods of their use described herein can modulate splicing of a pre-mRNA of INSR. In some embodiments, the SMSM compounds and methods of their use described herein can modulate splicing of a pre-mRNA of INTS3. In some embodiments, the SMSM compounds and methods of their use described herein can modulate splicing of a pre-mRNA of INTU. In some embodiments, the SMSM compounds and methods of their use described herein can modulate splicing of a pre-mRNA of IP04. In some embodiments, the SMSM compounds and methods of their use described herein can modulate splicing of a pre-mRNA of IP08. In some embodiments, the SMSM compounds and methods of their use described herein can modulate splicing of a pre-mRNA of IQGAP2. In some embodiments, the SMSM compounds and methods of their use described herein can modulate splicing of a pre-mRNA of ISL2. In some embodiments, the SMSM compounds and methods of their use described herein can modulate splicing of a pre-mRNA of ITFG1. In some embodiments, the SMSM compounds and methods of their use described herein can modulate splicing of a pre-mRNA of ITGAL. In some embodiments, the SMSM compounds and methods of their use described herein can modulate splicing of a pre-mRNA of ITGB1. In some embodiments, the SMSM compounds and methods of their use described herein can modulate splicing of a pre-mRNA of ITGB2. In some embodiments, the SMSM compounds and methods of their use described herein can modulate splicing of a pre-mRNA of ITGB3. In some embodiments, the SMSM compounds and methods of their use described herein can modulate splicing of a pre-mRNA of ITGB4. In some embodiments, the SMSM compounds and methods of their use described herein can modulate splicing of a pre-mRNA of ITIH1. In some embodiments, the SMSM compounds and methods of their use described herein can modulate splicing of a pre-mRNA of ITPR2. In some embodiments, the SMSM compounds and methods of their use described herein can modulate splicing of a pre-mRNA of IWS1. In some embodiments, the SMSM compounds and methods of their use described herein can modulate splicing of a pre-mRNA of JAG1. In some embodiments, the SMSM compounds and methods of their use described herein can modulate splicing of a pre-mRNA of JAK1. In some embodiments, the SMSM compounds and methods of their use described herein can modulate splicing of a pre-mRNA of JAK2. In some embodiments, the SMSM compounds and methods of their use described herein can modulate splicing of a pre-mRNA of JMJD1C. In some embodiments, the SMSM compounds and methods of their use described herein can modulate splicing of a pre-mRNA of KALRN. In some embodiments, the SMSM compounds and methods of their use described herein can modulate splicing of a pre-mRNA of KATNAL2. In some embodiments, the SMSM compounds and methods of their use described herein can modulate splicing of a pre-mRNA of KCNN2. In some embodiments, the SMSM compounds and methods of their use described herein can modulate splicing of a pre-mRNA of KCNT2. In some embodiments, the SMSM compounds and methods of their use described herein can modulate splicing of a pre-mRNA of KIAA0256. In some embodiments, the SMSM compounds and methods of their use described herein can modulate splicing of a pre-mRNA of KIAA0528. In some embodiments, the SMSM compounds and methods of their use described herein can modulate splicing of a pre-mRNA of KIAA0564. In some embodiments, the SMSM compounds and methods of their use described herein can modulate splicing of a pre-mRNA of KIAA0586. In some embodiments, the SMSM compounds and methods of their use described herein can modulate splicing of a pre-mRNA of KIAA1033. In some embodiments, the SMSM compounds and methods of their use described herein can modulate splicing of a pre-mRNA of KIAA1166. In some embodiments, the SMSM compounds and methods of their use described herein can modulate splicing of a pre-mRNA of KIAA1219. In some embodiments, the SMSM compounds and methods of their use described herein can modulate splicing of a pre-mRNA of KIAA1409. In some embodiments, the SMSM compounds and methods of their use described herein can modulate splicing of a pre-mRNA of KIAA1622. In some embodiments, the SMSM compounds and methods of their use described herein can modulate splicing of a pre-mRNA of KIAA1787. In some embodiments, the SMSM compounds and methods of their use described herein can modulate splicing of a pre-mRNA of KIF15. In some embodiments, the SMSM compounds and methods of their use described herein can modulate splicing of a pre-mRNA of KIF16B. In some embodiments, the SMSM compounds and methods of their use described herein can modulate splicing of a pre-mRNA of KIF3B. In some embodiments, the SMSM compounds and methods of their use described herein can modulate splicing of a pre-mRNA of KIF5A. In some embodiments, the SMSM compounds and methods of their use described herein can modulate splicing of a pre-mRNA of KIF5B. In some embodiments, the SMSM compounds and methods of their use described herein can modulate splicing of a pre-mRNA of KIF9. In some embodiments, the SMSM compounds and methods of their use described herein can modulate splicing of a pre-mRNA of KIN. In some embodiments, the SMSM compounds and methods of their use described herein can modulate splicing of a pre-mRNA of KIR2DL5B. In some embodiments, the SMSM compounds and methods of their use described herein can modulate splicing of a pre-mRNA of KIR3DL2. In some embodiments, the SMSM compounds and methods of their use described herein can modulate splicing of a pre-mRNA of KIR3DL3. In some embodiments, the SMSM compounds and methods of their use described herein can modulate splicing of a pre-mRNA of KLF12. In some embodiments, the SMSM compounds and methods of their use described herein can modulate splicing of a pre-mRNA of KLF3. In some embodiments, the SMSM compounds and methods of their use described herein can modulate splicing of a pre-mRNA of KLHL20. In some embodiments, the SMSM compounds and methods of their use described herein can modulate splicing of a pre-mRNA of KLK12. In some embodiments, the SMSM compounds and methods of their use described herein can modulate splicing of a pre-mRNA of KLKB1. In some embodiments, the SMSM compounds and methods of their use described herein can modulate splicing of a pre-mRNA of KPNA5. In some embodiments, the SMSM compounds and methods of their use described herein can modulate splicing of a pre-mRNA of KRAS. In some embodiments, the SMSM compounds and methods of their use described herein can modulate splicing of a pre-mRNA of KREMEN1. In some embodiments, the SMSM compounds and methods of their use described herein can modulate splicing of a pre-mRNA of KRIT1. In some embodiments, the SMSM compounds and methods of their use described herein can modulate splicing of a pre-mRNA of KRT5. In some embodiments, the SMSM compounds and methods of their use described herein can modulate splicing of a pre-mRNA of KRTCAP2. In some embodiments, the SMSM compounds and methods of their use described herein can modulate splicing of a pre-mRNA of L1CAM. In some embodiments, the SMSM compounds and methods of their use described herein can modulate splicing of a pre-mRNA of L3MBTL. In some embodiments, the SMSM compounds and methods of their use described herein can modulate splicing of a pre-mRNA of L3MBTL2. In some embodiments, the SMSM compounds and methods of their use described herein can modulate splicing of a pre-mRNA of LACE1. In some embodiments, the SMSM compounds and methods of their use described herein can modulate splicing of a pre-mRNA of LAMA1. In some embodiments, the SMSM compounds and methods of their use described herein can modulate splicing of a pre-mRNA of LAMA2. In some embodiments, the SMSM compounds and methods of their use described herein can modulate splicing of a pre-mRNA of LAMA3. In some embodiments, the SMSM compounds and methods of their use described herein can modulate splicing of a pre-mRNA of LAMB1. In some embodiments, the SMSM compounds and methods of their use described herein can modulate splicing of a pre-mRNA of LARP7. In some embodiments, the SMSM compounds and methods of their use described herein can modulate splicing of a pre-mRNA of LDLR. In some embodiments, the SMSM compounds and methods of their use described herein can modulate splicing of a pre-mRNA of LENG1. In some embodiments, the SMSM compounds and methods of their use described herein can modulate splicing of a pre-mRNA of LGALS3. In some embodiments, the SMSM compounds and methods of their use described herein can modulate splicing of a pre-mRNA of LGMN. In some embodiments, the SMSM compounds and methods of their use described herein can modulate splicing of a pre-mRNA of LHCGR. In some embodiments, the SMSM compounds and methods of their use described herein can modulate splicing of a pre-mRNA of LHX6. In some embodiments, the SMSM compounds and methods of their use described herein can modulate splicing of a pre-mRNA of LIMCH1. In some embodiments, the SMSM compounds and methods of their use described herein can modulate splicing of a pre-mRNA of LIMK2. In some embodiments, the SMSM compounds and methods of their use described herein can modulate splicing of a pre-mRNA of LMBRD1. In some embodiments, the SMSM compounds and methods of their use described herein can modulate splicing of a pre-mRNA of LMBRD2. In some embodiments, the SMSM compounds and methods of their use described herein can modulate splicing of a pre-mRNA of LMLN. In some embodiments, the SMSM compounds and methods of their use described herein can modulate splicing of a pre-mRNA of LMNA. In some embodiments, the SMSM compounds and methods of their use described herein can modulate splicing of a pre-mRNA of LMO2. In some embodiments, the SMSM compounds and methods of their use described herein can modulate splicing of a pre-mRNA of LOC389634. In some embodiments, the SMSM compounds and methods of their use described herein can modulate splicing of a pre-mRNA of LOC390110. In some embodiments, the SMSM compounds and methods of their use described herein can modulate splicing of a pre-mRNA of LPA. In some embodiments, the SMSM compounds and methods of their use described herein can modulate splicing of a pre-mRNA of LPCAT2. In some embodiments, the SMSM compounds and methods of their use described herein can modulate splicing of a pre-mRNA of LPL. In some embodiments, the SMSM compounds and methods of their use described herein can modulate splicing of a pre-mRNA of LRP4. In some embodiments, the SMSM compounds and methods of their use described herein can modulate splicing of a pre-mRNA of LRPPRC. In some embodiments, the SMSM compounds and methods of their use described herein can modulate splicing of a pre-mRNA of LRRC19. In some embodiments, the SMSM compounds and methods of their use described herein can modulate splicing of a pre-mRNA of LRRC42. In some embodiments, the SMSM compounds and methods of their use described herein can modulate splicing of a pre-mRNA of LRRK2. In some embodiments, the SMSM compounds and methods of their use described herein can modulate splicing of a pre-mRNA of LRWD1. In some embodiments, the SMSM compounds and methods of their use described herein can modulate splicing of a pre-mRNA of LUM. In some embodiments, the SMSM compounds and methods of their use described herein can modulate splicing of a pre-mRNA of LVRN. In some embodiments, the SMSM compounds and methods of their use described herein can modulate splicing of a pre-mRNA of LYN. In some embodiments, the SMSM compounds and methods of their use described herein can modulate splicing of a pre-mRNA of LYST. In some embodiments, the SMSM compounds and methods of their use described herein can modulate splicing of a pre-mRNA of MADD. In some embodiments, the SMSM compounds and methods of their use described herein can modulate splicing of a pre-mRNA of MAGI1. In some embodiments, the SMSM compounds and methods of their use described herein can modulate splicing of a pre-mRNA of MAGT1. In some embodiments, the SMSM compounds and methods of their use described herein can modulate splicing of a pre-mRNA of MALT1. In some embodiments, the SMSM compounds and methods of their use described herein can modulate splicing of a pre-mRNA of MAP2K1. In some embodiments, the SMSM compounds and methods of their use described herein can modulate splicing of a pre-mRNA of MAP4K4. In some embodiments, the SMSM compounds and methods of their use described herein can modulate splicing of a pre-mRNA of MAPK8IP3. In some embodiments, the SMSM compounds and methods of their use described herein can modulate splicing of a pre-mRNA of MAPK9. In some embodiments, the SMSM compounds and methods of their use described herein can modulate splicing of a pre-mRNA of MAPT. In some embodiments, the SMSM compounds and methods of their use described herein can modulate splicing of a pre-mRNA of MATN2. In some embodiments, the SMSM compounds and methods of their use described herein can modulate splicing of a pre-mRNA of MCF2L2. In some embodiments, the SMSM compounds and methods of their use described herein can modulate splicing of a pre-mRNA of MCM6. In some embodiments, the SMSM compounds and methods of their use described herein can modulate splicing of a pre-mRNA of MDGA2. In some embodiments, the SMSM compounds and methods of their use described herein can modulate splicing of a pre-mRNA of MEGF10. In some embodiments, the SMSM compounds and methods of their use described herein can modulate splicing of a pre-mRNA of MEGF11. In some embodiments, the SMSM compounds and methods of their use described herein can modulate splicing of a pre-mRNA of MEMO1. In some embodiments, the SMSM compounds and methods of their use described herein can modulate splicing of a pre-mRNA of MET. In some embodiments, the SMSM compounds and methods of their use described herein can modulate splicing of a pre-mRNA of MGAM. In some embodiments, the SMSM compounds and methods of their use described herein can modulate splicing of a pre-mRNA of MGAT4A. In some embodiments, the SMSM compounds and methods of their use described herein can modulate splicing of a pre-mRNA of MGAT5. In some embodiments, the SMSM compounds and methods of their use described herein can modulate splicing of a pre-mRNA of MGC16169. In some embodiments, the SMSM compounds and methods of their use described herein can modulate splicing of a pre-mRNA of MGC34774. In some embodiments, the SMSM compounds and methods of their use described herein can modulate splicing of a pre-mRNA of MIB1. In some embodiments, the SMSM compounds and methods of their use described herein can modulate splicing of a pre-mRNA of MIER2. In some embodiments, the SMSM compounds and methods of their use described herein can modulate splicing of a pre-mRNA of MKKS. In some embodiments, the SMSM compounds and methods of their use described herein can modulate splicing of a pre-mRNA of MKL2. In some embodiments, the SMSM compounds and methods of their use described herein can modulate splicing of a pre-mRNA of MLANA. In some embodiments, the SMSM compounds and methods of their use described herein can modulate splicing of a pre-mRNA of MLH1. In some embodiments, the SMSM compounds and methods of their use described herein can modulate splicing of a pre-mRNA of MLL5. In some embodiments, the SMSM compounds and methods of their use described herein can modulate splicing of a pre-mRNA of MLX. In some embodiments, the SMSM compounds and methods of their use described herein can modulate splicing of a pre-mRNA of MME. In some embodiments, the SMSM compounds and methods of their use described herein can modulate splicing of a pre-mRNA of MPDZ. In some embodiments, the SMSM compounds and methods of their use described herein can modulate splicing of a pre-mRNA of MPI. In some embodiments, the SMSM compounds and methods of their use described herein can modulate splicing of a pre-mRNA of MRAP2. In some embodiments, the SMSM compounds and methods of their use described herein can modulate splicing of a pre-mRNA of MRPL11. In some embodiments, the SMSM compounds and methods of their use described herein can modulate splicing of a pre-mRNA of MRPL39. In some embodiments, the SMSM compounds and methods of their use described herein can modulate splicing of a pre-mRNA of MRPS28. In some embodiments, the SMSM compounds and methods of their use described herein can modulate splicing of a pre-mRNA of MRPS35. In some embodiments, the SMSM compounds and methods of their use described herein can modulate splicing of a pre-mRNA of MS4A13. In some embodiments, the SMSM compounds and methods of their use described herein can modulate splicing of a pre-mRNA of MSH2. In some embodiments, the SMSM compounds and methods of their use described herein can modulate splicing of a pre-mRNA of MSMB. In some embodiments, the SMSM compounds and methods of their use described herein can modulate splicing of a pre-mRNA of MST1R. In some embodiments, the SMSM compounds and methods of their use described herein can modulate splicing of a pre-mRNA of MTDH. In some embodiments, the SMSM compounds and methods of their use described herein can modulate splicing of a pre-mRNA of MTF2. In some embodiments, the SMSM compounds and methods of their use described herein can modulate splicing of a pre-mRNA of MTHFR. In some embodiments, the SMSM compounds and methods of their use described herein can modulate splicing of a pre-mRNA of MTIF2. In some embodiments, the SMSM compounds and methods of their use described herein can modulate splicing of a pre-mRNA of MUC2. In some embodiments, the SMSM compounds and methods of their use described herein can modulate splicing of a pre-mRNA of MUT. In some embodiments, the SMSM compounds and methods of their use described herein can modulate splicing of a pre-mRNA of MVK. In some embodiments, the SMSM compounds and methods of their use described herein can modulate splicing of a pre-mRNA of MYB. In some embodiments, the SMSM compounds and methods of their use described herein can modulate splicing of a pre-mRNA of MYCBP2. In some embodiments, the SMSM compounds and methods of their use described herein can modulate splicing of a pre-mRNA of MYH2. In some embodiments, the SMSM compounds and methods of their use described herein can modulate splicing of a pre-mRNA of MYO19. In some embodiments, the SMSM compounds and methods of their use described herein can modulate splicing of a pre-mRNA of MYO3A. In some embodiments, the SMSM compounds and methods of their use described herein can modulate splicing of a pre-mRNA of MYO9B. In some embodiments, the SMSM compounds and methods of their use described herein can modulate splicing of a pre-mRNA of MYOM2. In some embodiments, the SMSM compounds and methods of their use described herein can modulate splicing of a pre-mRNA of MYOM3. In some embodiments, the SMSM compounds and methods of their use described herein can modulate splicing of a pre-mRNA of NAG. In some embodiments, the SMSM compounds and methods of their use described herein can modulate splicing of a pre-mRNA of NARG1. In some embodiments, the SMSM compounds and methods of their use described herein can modulate splicing of a pre-mRNA of NARG2. In some embodiments, the SMSM compounds and methods of their use described herein can modulate splicing of a pre-mRNA of NCOA1. In some embodiments, the SMSM compounds and methods of their use described herein can modulate splicing of a pre-mRNA of NDC80. In some embodiments, the SMSM compounds and methods of their use described herein can modulate splicing of a pre-mRNA of NDFIP2. In some embodiments, the SMSM compounds and methods of their use described herein can modulate splicing of a pre-mRNA of NEB. In some embodiments, the SMSM compounds and methods of their use described herein can modulate splicing of a pre-mRNA of NEDD4. In some embodiments, the SMSM compounds and methods of their use described herein can modulate splicing of a pre-mRNA of NEK1. In some embodiments, the SMSM compounds and methods of their use described herein can modulate splicing of a pre-mRNA of NEK11. In some embodiments, the SMSM compounds and methods of their use described herein can modulate splicing of a pre-mRNA of NEK5. In some embodiments, the SMSM compounds and methods of their use described herein can modulate splicing of a pre-mRNA of NF1. In some embodiments, the SMSM compounds and methods of their use described herein can modulate splicing of a pre-mRNA of NF2. In some embodiments, the SMSM compounds and methods of their use described herein can modulate splicing of a pre-mRNA of NFE2L2. In some embodiments, the SMSM compounds and methods of their use described herein can modulate splicing of a pre-mRNA of NFIA. In some embodiments, the SMSM compounds and methods of their use described herein can modulate splicing of a pre-mRNA of NFIX. In some embodiments, the SMSM compounds and methods of their use described herein can modulate splicing of a pre-mRNA of NFKBIL2. In some embodiments, the SMSM compounds and methods of their use described herein can modulate splicing of a pre-mRNA of NFRKB. In some embodiments, the SMSM compounds and methods of their use described herein can modulate splicing of a pre-mRNA of NKAIN2. In some embodiments, the SMSM compounds and methods of their use described herein can modulate splicing of a pre-mRNA of NKAP. In some embodiments, the SMSM compounds and methods of their use described herein can modulate splicing of a pre-mRNA of NLRC3. In some embodiments, the SMSM compounds and methods of their use described herein can modulate splicing of a pre-mRNA of NLRC5. In some embodiments, the SMSM compounds and methods of their use described herein can modulate splicing of a pre-mRNA of NLRP13. In some embodiments, the SMSM compounds and methods of their use described herein can modulate splicing of a pre-mRNA of NLRP7. In some embodiments, the SMSM compounds and methods of their use described herein can modulate splicing of a pre-mRNA of NLRP8. In some embodiments, the SMSM compounds and methods of their use described herein can modulate splicing of a pre-mRNA of NME7. In some embodiments, the SMSM compounds and methods of their use described herein can modulate splicing of a pre-mRNA of NOL10. In some embodiments, the SMSM compounds and methods of their use described herein can modulate splicing of a pre-mRNA of NOS1. In some embodiments, the SMSM compounds and methods of their use described herein can modulate splicing of a pre-mRNA of NOS2A. In some embodiments, the SMSM compounds and methods of their use described herein can modulate splicing of a pre-mRNA of NOTCH1. In some embodiments, the SMSM compounds and methods of their use described herein can modulate splicing of a pre-mRNA of NPM1. In some embodiments, the SMSM compounds and methods of their use described herein can modulate splicing of a pre-mRNA of NR1H4. In some embodiments, the SMSM compounds and methods of their use described herein can modulate splicing of a pre-mRNA of NR4A3. In some embodiments, the SMSM compounds and methods of their use described herein can modulate splicing of a pre-mRNA of NRXN1. In some embodiments, the SMSM compounds and methods of their use described herein can modulate splicing of a pre-mRNA of NSMAF. In some embodiments, the SMSM compounds and methods of their use described herein can modulate splicing of a pre-mRNA of NSMCE2. In some embodiments, the SMSM compounds and methods of their use described herein can modulate splicing of a pre-mRNA of NT5C. In some embodiments, the SMSM compounds and methods of their use described herein can modulate splicing of a pre-mRNA of NT5C3. In some embodiments, the SMSM compounds and methods of their use described herein can modulate splicing of a pre-mRNA of NUBP1. In some embodiments, the SMSM compounds and methods of their use described herein can modulate splicing of a pre-mRNA of NUBPL. In some embodiments, the SMSM compounds and methods of their use described herein can modulate splicing of a pre-mRNA of NUDT5. In some embodiments, the SMSM compounds and methods of their use described herein can modulate splicing of a pre-mRNA of NUMAL. In some embodiments, the SMSM compounds and methods of their use described herein can modulate splicing of a pre-mRNA of NUP160. In some embodiments, the SMSM compounds and methods of their use described herein can modulate splicing of a pre-mRNA of NUP88. In some embodiments, the SMSM compounds and methods of their use described herein can modulate splicing of a pre-mRNA of NUP98. In some embodiments, the SMSM compounds and methods of their use described herein can modulate splicing of a pre-mRNA of NUPL1. In some embodiments, the SMSM compounds and methods of their use described herein can modulate splicing of a pre-mRNA of OAT. In some embodiments, the SMSM compounds and methods of their use described herein can modulate splicing of a pre-mRNA of OBFC2A. In some embodiments, the SMSM compounds and methods of their use described herein can modulate splicing of a pre-mRNA of OBFC2B. In some embodiments, the SMSM compounds and methods of their use described herein can modulate splicing of a pre-mRNA of OLIG2. In some embodiments, the SMSM compounds and methods of their use described herein can modulate splicing of a pre-mRNA of OPA1. In some embodiments, the SMSM compounds and methods of their use described herein can modulate splicing of a pre-mRNA of OPN4. In some embodiments, the SMSM compounds and methods of their use described herein can modulate splicing of a pre-mRNA of OPTN. In some embodiments, the SMSM compounds and methods of their use described herein can modulate splicing of a pre-mRNA of OSBPL11. In some embodiments, the SMSM compounds and methods of their use described herein can modulate splicing of a pre-mRNA of OSBPL8. In some embodiments, the SMSM compounds and methods of their use described herein can modulate splicing of a pre-mRNA of OSGEPL1. In some embodiments, the SMSM compounds and methods of their use described herein can modulate splicing of a pre-mRNA of OTC. In some embodiments, the SMSM compounds and methods of their use described herein can modulate splicing of a pre-mRNA of OXT. In some embodiments, the SMSM compounds and methods of their use described herein can modulate splicing of a pre-mRNA of PADI4. In some embodiments, the SMSM compounds and methods of their use described herein can modulate splicing of a pre-mRNA of PAH. In some embodiments, the SMSM compounds and methods of their use described herein can modulate splicing of a pre-mRNA of PAN2. In some embodiments, the SMSM compounds and methods of their use described herein can modulate splicing of a pre-mRNA of PAPOLG. In some embodiments, the SMSM compounds and methods of their use described herein can modulate splicing of a pre-mRNA of PARD3. In some embodiments, the SMSM compounds and methods of their use described herein can modulate splicing of a pre-mRNA of PARVB. In some embodiments, the SMSM compounds and methods of their use described herein can modulate splicing of a pre-mRNA of PAWR. In some embodiments, the SMSM compounds and methods of their use described herein can modulate splicing of a pre-mRNA of PBGD. In some embodiments, the SMSM compounds and methods of their use described herein can modulate splicing of a pre-mRNA of PBRM1. In some embodiments, the SMSM compounds and methods of their use described herein can modulate splicing of a pre-mRNA of PCBP4. In some embodiments, the SMSM compounds and methods of their use described herein can modulate splicing of a pre-mRNA of PCCA. In some embodiments, the SMSM compounds and methods of their use described herein can modulate splicing of a pre-mRNA of PCNX. In some embodiments, the SMSM compounds and methods of their use described herein can modulate splicing of a pre-mRNA of PCOTH. In some embodiments, the SMSM compounds and methods of their use described herein can modulate splicing of a pre-mRNA of PDCD4. In some embodiments, the SMSM compounds and methods of their use described herein can modulate splicing of a pre-mRNA of PDE10A. In some embodiments, the SMSM compounds and methods of their use described herein can modulate splicing of a pre-mRNA of PDE8B. In some embodiments, the SMSM compounds and methods of their use described herein can modulate splicing of a pre-mRNA of PDH1. In some embodiments, the SMSM compounds and methods of their use described herein can modulate splicing of a pre-mRNA of PDIA3. In some embodiments, the SMSM compounds and methods of their use described herein can modulate splicing of a pre-mRNA of PDK4. In some embodiments, the SMSM compounds and methods of their use described herein can modulate splicing of a pre-mRNA of PDLIM5. In some embodiments, the SMSM compounds and methods of their use described herein can modulate splicing of a pre-mRNA of PDS5A. In some embodiments, the SMSM compounds and methods of their use described herein can modulate splicing of a pre-mRNA of PDS5B. In some embodiments, the SMSM compounds and methods of their use described herein can modulate splicing of a pre-mRNA of PDXK. In some embodiments, the SMSM compounds and methods of their use described herein can modulate splicing of a pre-mRNA of PDZRN3. In some embodiments, the SMSM compounds and methods of their use described herein can modulate splicing of a pre-mRNA of PELI2. In some embodiments, the SMSM compounds and methods of their use described herein can modulate splicing of a pre-mRNA of PGK1. In some embodiments, the SMSM compounds and methods of their use described herein can modulate splicing of a pre-mRNA of PGM2. In some embodiments, the SMSM compounds and methods of their use described herein can modulate splicing of a pre-mRNA of PHACTR4. In some embodiments, the SMSM compounds and methods of their use described herein can modulate splicing of a pre-mRNA of PHEX. In some embodiments, the SMSM compounds and methods of their use described herein can modulate splicing of a pre-mRNA of PHKB. In some embodiments, the SMSM compounds and methods of their use described herein can modulate splicing of a pre-mRNA of PHLDB2. In some embodiments, the SMSM compounds and methods of their use described herein can modulate splicing of a pre-mRNA of PHTF1. In some embodiments, the SMSM compounds and methods of their use described herein can modulate splicing of a pre-mRNA of PIAS1. In some embodiments, the SMSM compounds and methods of their use described herein can modulate splicing of a pre-mRNA of PIGF. In some embodiments, the SMSM compounds and methods of their use described herein can modulate splicing of a pre-mRNA of PIGN. In some embodiments, the SMSM compounds and methods of their use described herein can modulate splicing of a pre-mRNA of PIGT. In some embodiments, the SMSM compounds and methods of their use described herein can modulate splicing of a pre-mRNA of PIK3C2G. In some embodiments, the SMSM compounds and methods of their use described herein can modulate splicing of a pre-mRNA of PIK3CG. In some embodiments, the SMSM compounds and methods of their use described herein can modulate splicing of a pre-mRNA of PIK3R1. In some embodiments, the SMSM compounds and methods of their use described herein can modulate splicing of a pre-mRNA of PIP5K1A. In some embodiments, the SMSM compounds and methods of their use described herein can modulate splicing of a pre-mRNA of PITRM1. In some embodiments, the SMSM compounds and methods of their use described herein can modulate splicing of a pre-mRNA of PIWIL3. In some embodiments, the SMSM compounds and methods of their use described herein can modulate splicing of a pre-mRNA of PKD1. In some embodiments, the SMSM compounds and methods of their use described herein can modulate splicing of a pre-mRNA of PKD2. In some embodiments, the SMSM compounds and methods of their use described herein can modulate splicing of a pre-mRNA of PKHD1L1. In some embodiments, the SMSM compounds and methods of their use described herein can modulate splicing of a pre-mRNA of PKIB. In some embodiments, the SMSM compounds and methods of their use described herein can modulate splicing of a pre-mRNA of PKLR. In some embodiments, the SMSM compounds and methods of their use described herein can modulate splicing of a pre-mRNA of PKM1. In some embodiments, the SMSM compounds and methods of their use described herein can modulate splicing of a pre-mRNA of PKM2. In some embodiments, the SMSM compounds and methods of their use described herein can modulate splicing of a pre-mRNA of PLCB1. In some embodiments, the SMSM compounds and methods of their use described herein can modulate splicing of a pre-mRNA of PLCB4. In some embodiments, the SMSM compounds and methods of their use described herein can modulate splicing of a pre-mRNA of PLCG1. In some embodiments, the SMSM compounds and methods of their use described herein can modulate splicing of a pre-mRNA of PLD1. In some embodiments, the SMSM compounds and methods of their use described herein can modulate splicing of a pre-mRNA of PLEKHA5. In some embodiments, the SMSM compounds and methods of their use described herein can modulate splicing of a pre-mRNA of PLEKHA7. In some embodiments, the SMSM compounds and methods of their use described herein can modulate splicing of a pre-mRNA of PLEKHM1. In some embodiments, the SMSM compounds and methods of their use described herein can modulate splicing of a pre-mRNA of PLKR. In some embodiments, the SMSM compounds and methods of their use described herein can modulate splicing of a pre-mRNA of PLXNC1. In some embodiments, the SMSM compounds and methods of their use described herein can modulate splicing of a pre-mRNA of PMFBP1. In some embodiments, the SMSM compounds and methods of their use described herein can modulate splicing of a pre-mRNA of POLN. In some embodiments, the SMSM compounds and methods of their use described herein can modulate splicing of a pre-mRNA of POLR3D. In some embodiments, the SMSM compounds and methods of their use described herein can modulate splicing of a pre-mRNA of POMT2. In some embodiments, the SMSM compounds and methods of their use described herein can modulate splicing of a pre-mRNA of POSTN. In some embodiments, the SMSM compounds and methods of their use described herein can modulate splicing of a pre-mRNA of PPFIA2. In some embodiments, the SMSM compounds and methods of their use described herein can modulate splicing of a pre-mRNA of PPP1R12A. In some embodiments, the SMSM compounds and methods of their use described herein can modulate splicing of a pre-mRNA of PPP3CB. In some embodiments, the SMSM compounds and methods of their use described herein can modulate splicing of a pre-mRNA of PPP4C. In some embodiments, the SMSM compounds and methods of their use described herein can modulate splicing of a pre-mRNA of PPP4R1L. In some embodiments, the SMSM compounds and methods of their use described herein can modulate splicing of a pre-mRNA of PPP4R2. In some embodiments, the SMSM compounds and methods of their use described herein can modulate splicing of a pre-mRNA of PRAME. In some embodiments, the SMSM compounds and methods of their use described herein can modulate splicing of a pre-mRNA of PRC1. In some embodiments, the SMSM compounds and methods of their use described herein can modulate splicing of a pre-mRNA of PRDM1. In some embodiments, the SMSM compounds and methods of their use described herein can modulate splicing of a pre-mRNA of PRIM1. In some embodiments, the SMSM compounds and methods of their use described herein can modulate splicing of a pre-mRNA of PRIM2. In some embodiments, the SMSM compounds and methods of their use described herein can modulate splicing of a pre-mRNA of PRKAR1A. In some embodiments, the SMSM compounds and methods of their use described herein can modulate splicing of a pre-mRNA of PRKCA. In some embodiments, the SMSM compounds and methods of their use described herein can modulate splicing of a pre-mRNA of PRKG1. In some embodiments, the SMSM compounds and methods of their use described herein can modulate splicing of a pre-mRNA of PRMT7. In some embodiments, the SMSM compounds and methods of their use described herein can modulate splicing of a pre-mRNA of PROC. In some embodiments, the SMSM compounds and methods of their use described herein can modulate splicing of a pre-mRNA of PROCR. In some embodiments, the SMSM compounds and methods of their use described herein can modulate splicing of a pre-mRNA of PRODH. In some embodiments, the SMSM compounds and methods of their use described herein can modulate splicing of a pre-mRNA of PROSC. In some embodiments, the SMSM compounds and methods of their use described herein can modulate splicing of a pre-mRNA of PROX1. In some embodiments, the SMSM compounds and methods of their use described herein can modulate splicing of a pre-mRNA of PRPF40B. In some embodiments, the SMSM compounds and methods of their use described herein can modulate splicing of a pre-mRNA of PRPF4B. In some embodiments, the SMSM compounds and methods of their use described herein can modulate splicing of a pre-mRNA of PRRG2. In some embodiments, the SMSM compounds and methods of their use described herein can modulate splicing of a pre-mRNA of PRUNE2.

In some embodiments, the SMSM compounds and methods of their use described herein can modulate splicing of a pre-mRNA of PSD3. In some embodiments, the SMSM compounds and methods of their use described herein can modulate splicing of a pre-mRNA of PSEN1. In some embodiments, the SMSM compounds and methods of their use described herein can modulate splicing of a pre-mRNA of PSMA1. In some embodiments, the SMSM compounds and methods of their use described herein can modulate splicing of a pre-mRNA of PTCH1. In some embodiments, the SMSM compounds and methods of their use described herein can modulate splicing of a pre-mRNA of PTEN. In some embodiments, the SMSM compounds and methods of their use described herein can modulate splicing of a pre-mRNA of PTK2. In some embodiments, the SMSM compounds and methods of their use described herein can modulate splicing of a pre-mRNA of PTK2B. In some embodiments, the SMSM compounds and methods of their use described herein can modulate splicing of a pre-mRNA of PTPN11. In some embodiments, the SMSM compounds and methods of their use described herein can modulate splicing of a pre-mRNA of PTPN22. In some embodiments, the SMSM compounds and methods of their use described herein can modulate splicing of a pre-mRNA of PTPN3. In some embodiments, the SMSM compounds and methods of their use described herein can modulate splicing of a pre-mRNA of PTPN4. In some embodiments, the SMSM compounds and methods of their use described herein can modulate splicing of a pre-mRNA of PTPRD. In some embodiments, the SMSM compounds and methods of their use described herein can modulate splicing of a pre-mRNA of PTPRK. In some embodiments, the SMSM compounds and methods of their use described herein can modulate splicing of a pre-mRNA of PTPRM. In some embodiments, the SMSM compounds and methods of their use described herein can modulate splicing of a pre-mRNA of PTPRN2. In some embodiments, the SMSM compounds and methods of their use described herein can modulate splicing of a pre-mRNA of PTPRT. In some embodiments, the SMSM compounds and methods of their use described herein can modulate splicing of a pre-mRNA of PUS10. In some embodiments, the SMSM compounds and methods of their use described herein can modulate splicing of a pre-mRNA of PVRL2. In some embodiments, the SMSM compounds and methods of their use described herein can modulate splicing of a pre-mRNA of PYGM. In some embodiments, the SMSM compounds and methods of their use described herein can modulate splicing of a pre-mRNA of QRSL1. In some embodiments, the SMSM compounds and methods of their use described herein can modulate splicing of a pre-mRNA of RAB11FIP2. In some embodiments, the SMSM compounds and methods of their use described herein can modulate splicing of a pre-mRNA of RAB23. In some embodiments, the SMSM compounds and methods of their use described herein can modulate splicing of a pre-mRNA of RALBP 1. In some embodiments, the SMSM compounds and methods of their use described herein can modulate splicing of a pre-mRNA of RALGDS. In some embodiments, the SMSM compounds and methods of their use described herein can modulate splicing of a pre-mRNA of RBICC1. In some embodiments, the SMSM compounds and methods of their use described herein can modulate splicing of a pre-mRNA of RBL2. In some embodiments, the SMSM compounds and methods of their use described herein can modulate splicing of a pre-mRNA of RBM39. In some embodiments, the SMSM compounds and methods of their use described herein can modulate splicing of a pre-mRNA of RBM45. In some embodiments, the SMSM compounds and methods of their use described herein can modulate splicing of a pre-mRNA of REC8. In some embodiments, the SMSM compounds and methods of their use described herein can modulate splicing of a pre-mRNA of RFC4. In some embodiments, the SMSM compounds and methods of their use described herein can modulate splicing of a pre-mRNA of RFT1. In some embodiments, the SMSM compounds and methods of their use described herein can modulate splicing of a pre-mRNA of RFTN1. In some embodiments, the SMSM compounds and methods of their use described herein can modulate splicing of a pre-mRNA of RHPN2. In some embodiments, the SMSM compounds and methods of their use described herein can modulate splicing of a pre-mRNA of RIF1. In some embodiments, the SMSM compounds and methods of their use described herein can modulate splicing of a pre-mRNA of RLN3. In some embodiments, the SMSM compounds and methods of their use described herein can modulate splicing of a pre-mRNA of RMND5B. In some embodiments, the SMSM compounds and methods of their use described herein can modulate splicing of a pre-mRNA of RNF11. In some embodiments, the SMSM compounds and methods of their use described herein can modulate splicing of a pre-mRNA of RNF32. In some embodiments, the SMSM compounds and methods of their use described herein can modulate splicing of a pre-mRNA of RNFT1. In some embodiments, the SMSM compounds and methods of their use described herein can modulate splicing of a pre-mRNA of RNGTT. In some embodiments, the SMSM compounds and methods of their use described herein can modulate splicing of a pre-mRNA of ROCK1. In some embodiments, the SMSM compounds and methods of their use described herein can modulate splicing of a pre-mRNA of ROCK2. In some embodiments, the SMSM compounds and methods of their use described herein can modulate splicing of a pre-mRNA of RP 1. In some embodiments, the SMSM compounds and methods of their use described herein can modulate splicing of a pre-mRNA of RP11-265F1. In some embodiments, the SMSM compounds and methods of their use described herein can modulate splicing of a pre-mRNA of RP13-36C9. In some embodiments, the SMSM compounds and methods of their use described herein can modulate splicing of a pre-mRNA of RP6KA3. In some embodiments, the SMSM compounds and methods of their use described herein can modulate splicing of a pre-mRNA of RPAP3. In some embodiments, the SMSM compounds and methods of their use described herein can modulate splicing of a pre-mRNA of RPGR. In some embodiments, the SMSM compounds and methods of their use described herein can modulate splicing of a pre-mRNA of RPN1. In some embodiments, the SMSM compounds and methods of their use described herein can modulate splicing of a pre-mRNA of RPS6KA6. In some embodiments, the SMSM compounds and methods of their use described herein can modulate splicing of a pre-mRNA of RRM1. In some embodiments, the SMSM compounds and methods of their use described herein can modulate splicing of a pre-mRNA of RRP1B. In some embodiments, the SMSM compounds and methods of their use described herein can modulate splicing of a pre-mRNA of RSK2. In some embodiments, the SMSM compounds and methods of their use described herein can modulate splicing of a pre-mRNA of RTEL1. In some embodiments, the SMSM compounds and methods of their use described herein can modulate splicing of a pre-mRNA of RTF1. In some embodiments, the SMSM compounds and methods of their use described herein can modulate splicing of a premRNA of RUFY1. In some embodiments, the SMSM compounds and methods of their use described herein can modulate splicing of a pre-mRNA of RYR3. In some embodiments, the SMSM compounds and methods of their use described herein can modulate splicing of a pre-mRNA of SAAL1. In some embodiments, the SMSM compounds and methods of their use described herein can modulate splicing of a pre-mRNA of SAE1. In some embodiments, the SMSM compounds and methods of their use described herein can modulate splicing of a pre-mRNA of SBCAD. In some embodiments, the SMSM compounds and methods of their use described herein can modulate splicing of a pre-mRNA of SCN11A. In some embodiments, the SMSM compounds and methods of their use described herein can modulate splicing of a pre-mRNA of SCN1A. In some embodiments, the SMSM compounds and methods of their use described herein can modulate splicing of a pre-mRNA of SCN2A. In some embodiments, the SMSM compounds and methods of their use described herein can modulate splicing of a pre-mRNA of SCN3A. In some embodiments, the SMSM compounds and methods of their use described herein can modulate splicing of a pre-mRNA of SCN4A. In some embodiments, the SMSM compounds and methods of their use described herein can modulate splicing of a pre-mRNA of SCN5A. In some embodiments, the SMSM compounds and methods of their use described herein can modulate splicing of a pre-mRNA of SCN8A. In some embodiments, the SMSM compounds and methods of their use described herein can modulate splicing of a pre-mRNA of SCNA. In some embodiments, the SMSM compounds and methods of their use described herein can modulate splicing of a pre-mRNA of SCO1. In some embodiments, the SMSM compounds and methods of their use described herein can modulate splicing of a pre-mRNA of SCYL3. In some embodiments, the SMSM compounds and methods of their use described herein can modulate splicing of a pre-mRNA of SDK1. In some embodiments, the SMSM compounds and methods of their use described herein can modulate splicing of a pre-mRNA of SDK2. In some embodiments, the SMSM compounds and methods of their use described herein can modulate splicing of a pre-mRNA of SEC24A. In some embodiments, the SMSM compounds and methods of their use described herein can modulate splicing of a pre-mRNA of SEC24D. In some embodiments, the SMSM compounds and methods of their use described herein can modulate splicing of a pre-mRNA of SEC31A. In some embodiments, the SMSM compounds and methods of their use described herein can modulate splicing of a pre-mRNA of SEL1L. In some embodiments, the SMSM compounds and methods of their use described herein can modulate splicing of a pre-mRNA of SENP3. In some embodiments, the SMSM compounds and methods of their use described herein can modulate splicing of a pre-mRNA of SENP6. In some embodiments, the SMSM compounds and methods of their use described herein can modulate splicing of a pre-mRNA of SENP7. In some embodiments, the SMSM compounds and methods of their use described herein can modulate splicing of a pre-mRNA of SERPINA1. In some embodiments, the SMSM compounds and methods of their use described herein can modulate splicing of a pre-mRNA of SETD3. In some embodiments, the SMSM compounds and methods of their use described herein can modulate splicing of a pre-mRNA of SETD4. In some embodiments, the SMSM compounds and methods of their use described herein can modulate splicing of a pre-mRNA of SEZ6. In some embodiments, the SMSM compounds and methods of their use described herein can modulate splicing of a pre-mRNA of SFRS12. In some embodiments, the SMSM compounds and methods of their use described herein can modulate splicing of a pre-mRNA of SGCE. In some embodiments, the SMSM compounds and methods of their use described herein can modulate splicing of a pre-mRNA of SGOL2. In some embodiments, the SMSM compounds and methods of their use described herein can modulate splicing of a pre-mRNA of SGPL1. In some embodiments, the SMSM compounds and methods of their use described herein can modulate splicing of a pre-mRNA of SH2D1A. In some embodiments, the SMSM compounds and methods of their use described herein can modulate splicing of a pre-mRNA of SH3BGRL2. In some embodiments, the SMSM compounds and methods of their use described herein can modulate splicing of a pre-mRNA of SH3PXD2A. In some embodiments, the SMSM compounds and methods of their use described herein can modulate splicing of a pre-mRNA of SH3PXD2B. In some embodiments, the SMSM compounds and methods of their use described herein can modulate splicing of a pre-mRNA of SH3RF2. In some embodiments, the SMSM compounds and methods of their use described herein can modulate splicing of a pre-mRNA of SH3TC2. In some embodiments, the SMSM compounds and methods of their use described herein can modulate splicing of a pre-mRNA of SIPA1L2. In some embodiments, the SMSM compounds and methods of their use described herein can modulate splicing of a pre-mRNA of SIPA1L3. In some embodiments, the SMSM compounds and methods of their use described herein can modulate splicing of a pre-mRNA of SIVA1. In some embodiments, the SMSM compounds and methods of their use described herein can modulate splicing of a pre-mRNA of SKAP1. In some embodiments, the SMSM compounds and methods of their use described herein can modulate splicing of a pre-mRNA of SKIV2L2. In some embodiments, the SMSM compounds and methods of their use described herein can modulate splicing of a pre-mRNA of SLC12A3. In some embodiments, the SMSM compounds and methods of their use described herein can modulate splicing of a pre-mRNA of SLC13A1. In some embodiments, the SMSM compounds and methods of their use described herein can modulate splicing of a pre-mRNA of SLC22A17. In some embodiments, the SMSM compounds and methods of their use described herein can modulate splicing of a pre-mRNA of SLC25A14. In some embodiments, the SMSM compounds and methods of their use described herein can modulate splicing of a pre-mRNA of SLC28A3. In some embodiments, the SMSM compounds and methods of their use described herein can modulate splicing of a pre-mRNA of SLC38A1. In some embodiments, the SMSM compounds and methods of their use described herein can modulate splicing of a pre-mRNA of SLC38A4. In some embodiments, the SMSM compounds and methods of their use described herein can modulate splicing of a pre-mRNA of SLC39A10. In some embodiments, the SMSM compounds and methods of their use described herein can modulate splicing of a pre-mRNA of SLC4A2. In some embodiments, the SMSM compounds and methods of their use described herein can modulate splicing of a pre-mRNA of SLC6A 11. In some embodiments, the SMSM compounds and methods of their use described herein can modulate splicing of a pre-mRNA of SLC6A13. In some embodiments, the SMSM compounds and methods of their use described herein can modulate splicing of a pre-mRNA of SLC6A6. In some embodiments, the SMSM compounds and methods of their use described herein can modulate splicing of a pre-mRNA of SLC6A8. In some embodiments, the SMSM compounds and methods of their use described herein can modulate splicing of a pre-mRNA of SMARCA1. In some embodiments, the SMSM compounds and methods of their use described herein can modulate splicing of a pre-mRNA of SMARCA5. In some embodiments, the SMSM compounds and methods of their use described herein can modulate splicing of a pre-mRNA of SMC5. In some embodiments, the SMSM compounds and methods of their use described herein can modulate splicing of a pre-mRNA of SMN2. For example, the SMSM compounds and methods of their use described herein can modulate splicing of exon 7 of a pre-mRNA of SMN2. In some embodiments, the SMSM compounds and methods of their use described herein can modulate splicing of a pre-mRNA of SMTN. In some embodiments, the SMSM compounds and methods of their use described herein can modulate splicing of a pre-mRNA of SNCA1P. In some embodiments, the SMSM compounds and methods of their use described herein can modulate splicing of a pre-mRNA of SNRK. In some embodiments, the SMSM compounds and methods of their use described herein can modulate splicing of a pre-mRNA of SNRP70. In some embodiments, the SMSM compounds and methods of their use described herein can modulate splicing of a pre-mRNA of SNX6. In some embodiments, the SMSM compounds and methods of their use described herein can modulate splicing of a pre-mRNA of SOD1. In some embodiments, the SMSM compounds and methods of their use described herein can modulate splicing of a pre-mRNA of SPAG9. In some embodiments, the SMSM compounds and methods of their use described herein can modulate splicing of a pre-mRNA of SPATA13. In some embodiments, the SMSM compounds and methods of their use described herein can modulate splicing of a pre-mRNA of SPATA4. In some embodiments, the SMSM compounds and methods of their use described herein can modulate splicing of a pre-mRNA of SPATS1. In some embodiments, the SMSM compounds and methods of their use described herein can modulate splicing of a pre-mRNA of SPECC1L. In some embodiments, the SMSM compounds and methods of their use described herein can modulate splicing of a pre-mRNA of SPINK5. In some embodiments, the SMSM compounds and methods of their use described herein can modulate splicing of a pre-mRNA of SPP2. In some embodiments, the SMSM compounds and methods of their use described herein can modulate splicing of a pre-mRNA of SPTA1. In some embodiments, the SMSM compounds and methods of their use described herein can modulate splicing of a pre-mRNA of SRP72. In some embodiments, the SMSM compounds and methods of their use described herein can modulate splicing of a pre-mRNA of SSX3. In some embodiments, the SMSM compounds and methods of their use described herein can modulate splicing of a pre-mRNA of SSX5. In some embodiments, the SMSM compounds and methods of their use described herein can modulate splicing of a pre-mRNA of SSX9. In some embodiments, the SMSM compounds and methods of their use described herein can modulate splicing of a pre-mRNA of STAG1. In some embodiments, the SMSM compounds and methods of their use described herein can modulate splicing of a pre-mRNA of STAMBPL1. In some embodiments, the SMSM compounds and methods of their use described herein can modulate splicing of a pre-mRNA of STARD6. In some embodiments, the SMSM compounds and methods of their use described herein can modulate splicing of a pre-mRNA of STAT6. In some embodiments, the SMSM compounds and methods of their use described herein can modulate splicing of a pre-mRNA of STK17B. In some embodiments, the SMSM compounds and methods of their use described herein can modulate splicing of a pre-mRNA of STX3. In some embodiments, the SMSM compounds and methods of their use described herein can modulate splicing of a pre-mRNA of STXBP1. In some embodiments, the SMSM compounds and methods of their use described herein can modulate splicing of a pre-mRNA of SUCLG2. In some embodiments, the SMSM compounds and methods of their use described herein can modulate splicing of a pre-mRNA of SULF2. In some embodiments, the SMSM compounds and methods of their use described herein can modulate splicing of a pre-mRNA of SUPT16H. In some embodiments, the SMSM compounds and methods of their use described herein can modulate splicing of a pre-mRNA of SUPT6H. In some embodiments, the SMSM compounds and methods of their use described herein can modulate splicing of a pre-mRNA of SV2C. In some embodiments, the SMSM compounds and methods of their use described herein can modulate splicing of a pre-mRNA of SYCP1. In some embodiments, the SMSM compounds and methods of their use described herein can modulate splicing of a pre-mRNA of SYCP2. In some embodiments, the SMSM compounds and methods of their use described herein can modulate splicing of a pre-mRNA of SYT6. In some embodiments, the SMSM compounds and methods of their use described herein can modulate splicing of a pre-mRNA of SYTL5. In some embodiments, the SMSM compounds and methods of their use described herein can modulate splicing of a pre-mRNA of TAF2. In some embodiments, the SMSM compounds and methods of their use described herein can modulate splicing of a pre-mRNA of TBC1D26. In some embodiments, the SMSM compounds and methods of their use described herein can modulate splicing of a pre-mRNA of TBC1D29. In some embodiments, the SMSM compounds and methods of their use described herein can modulate splicing of a pre-mRNA of TBC1D3G. In some embodiments, the SMSM compounds and methods of their use described herein can modulate splicing of a pre-mRNA of TBC1D8B. In some embodiments, the SMSM compounds and methods of their use described herein can modulate splicing of a pre-mRNA of TBCEL. In some embodiments, the SMSM compounds and methods of their use described herein can modulate splicing of a pre-mRNA of TBK1. In some embodiments, the SMSM compounds and methods of their use described herein can modulate splicing of a pre-mRNA of TBPL1. In some embodiments, the SMSM compounds and methods of their use described herein can modulate splicing of a pre-mRNA of TCEB3. In some embodiments, the SMSM compounds and methods of their use described herein can modulate splicing of a pre-mRNA of TCF 12. In some embodiments, the SMSM compounds and methods of their use described herein can modulate splicing of a pre-mRNA of TCP11L2. In some embodiments, the SMSM compounds and methods of their use described herein can modulate splicing of a pre-mRNA of TDRD3. In some embodiments, the SMSM compounds and methods of their use described herein can modulate splicing of a pre-mRNA of TEAD1. In some embodiments, the SMSM compounds and methods of their use described herein can modulate splicing of a pre-mRNA of TECTB. In some embodiments, the SMSM compounds and methods of their use described herein can modulate splicing of a pre-mRNA of TEK. In some embodiments, the SMSM compounds and methods of their use described herein can modulate splicing of a pre-mRNA of TET2. In some embodiments, the SMSM compounds and methods of their use described herein can modulate splicing of a pre-mRNA of TFRC. In some embodiments, the SMSM compounds and methods of their use described herein can modulate splicing of a pre-mRNA of TG. In some embodiments, the SMSM compounds and methods of their use described herein can modulate splicing of a pre-mRNA of TGM7. In some embodiments, the SMSM compounds and methods of their use described herein can modulate splicing of a pre-mRNA of TGS1. In some embodiments, the SMSM compounds and methods of their use described herein can modulate splicing of a pre-mRNA of THOC2. In some embodiments, the SMSM compounds and methods of their use described herein can modulate splicing of a pre-mRNA of TIAL1. In some embodiments, the SMSM compounds and methods of their use described herein can modulate splicing of a pre-mRNA of TIAM2. In some embodiments, the SMSM compounds and methods of their use described herein can modulate splicing of a pre-mRNA of TIMM50. In some embodiments, the SMSM compounds and methods of their use described herein can modulate splicing of a pre-mRNA of TLK2. In some embodiments, the SMSM compounds and methods of their use described herein can modulate splicing of a pre-mRNA of TM4SF20. In some embodiments, the SMSM compounds and methods of their use described herein can modulate splicing of a pre-mRNA of TM6SF1. In some embodiments, the SMSM compounds and methods of their use described herein can modulate splicing of a pre-mRNA of TMEM156. In some embodiments, the SMSM compounds and methods of their use described herein can modulate splicing of a pre-mRNA of TMEM194A. In some embodiments, the SMSM compounds and methods of their use described herein can modulate splicing of a pre-mRNA of TMEM27. In some embodiments, the SMSM compounds and methods of their use described herein can modulate splicing of a pre-mRNA of TMEM77. In some embodiments, the SMSM compounds and methods of their use described herein can modulate splicing of a pre-mRNA of TMF1. In some embodiments, the SMSM compounds and methods of their use described herein can modulate splicing of a pre-mRNA of TMPRSS6. In some embodiments, the SMSM compounds and methods of their use described herein can modulate splicing of a pre-mRNA of TNFRSF10A. In some embodiments, the SMSM compounds and methods of their use described herein can modulate splicing of a pre-mRNA of TNFRSF10B. In some embodiments, the SMSM compounds and methods of their use described herein can modulate splicing of a pre-mRNA of TNFRSF8. In some embodiments, the SMSM compounds and methods of their use described herein can modulate splicing of a pre-mRNA of TNK2. In some embodiments, the SMSM compounds and methods of their use described herein can modulate splicing of a pre-mRNA of TNKS. In some embodiments, the SMSM compounds and methods of their use described herein can modulate splicing of a pre-mRNA of TNKS2. In some embodiments, the SMSM compounds and methods of their use described herein can modulate splicing of a pre-mRNA of TOM1L1. In some embodiments, the SMSM compounds and methods of their use described herein can modulate splicing of a pre-mRNA of TOM1L2. In some embodiments, the SMSM compounds and methods of their use described herein can modulate splicing of a pre-mRNA of TOP2B. In some embodiments, the SMSM compounds and methods of their use described herein can modulate splicing of a pre-mRNA of TP53. In some embodiments, the SMSM compounds and methods of their use described herein can modulate splicing of a pre-mRNA of TP53BP2. In some embodiments, the SMSM compounds and methods of their use described herein can modulate splicing of a pre-mRNA of TP53I3. In some embodiments, the SMSM compounds and methods of their use described herein can modulate splicing of a pre-mRNA of TP53INP1. In some embodiments, the SMSM compounds and methods of their use described herein can modulate splicing of a pre-mRNA of TP63. In some embodiments, the SMSM compounds and methods of their use described herein can modulate splicing of a pre-mRNA of TRAF3IP3. In some embodiments, the SMSM compounds and methods of their use described herein can modulate splicing of a pre-mRNA of TRAPPC2. In some embodiments, the SMSM compounds and methods of their use described herein can modulate splicing of a pre-mRNA of TRIM44. In some embodiments, the SMSM compounds and methods of their use described herein can modulate splicing of a pre-mRNA of TRIM65. In some embodiments, the SMSM compounds and methods of their use described herein can modulate splicing of a pre-mRNA of TRIML1. In some embodiments, the SMSM compounds and methods of their use described herein can modulate splicing of a pre-mRNA of TRIML2. In some embodiments, the SMSM compounds and methods of their use described herein can modulate splicing of a pre-mRNA of TRPM3. In some embodiments, the SMSM compounds and methods of their use described herein can modulate splicing of a pre-mRNA of TRPM5. In some embodiments, the SMSM compounds and methods of their use described herein can modulate splicing of a pre-mRNA of TRPM7. In some embodiments, the SMSM compounds and methods of their use described herein can modulate splicing of a pre-mRNA of TSC1. In some embodiments, the SMSM compounds and methods of their use described herein can modulate splicing of a pre-mRNA of TSC2. In some embodiments, the SMSM compounds and methods of their use described herein can modulate splicing of a pre-mRNA of TSHB. In some embodiments, the SMSM compounds and methods of their use described herein can modulate splicing of a pre-mRNA of TSPAN7. In some embodiments, the SMSM compounds and methods of their use described herein can modulate splicing of a pre-mRNA of TTC17. In some embodiments, the SMSM compounds and methods of their use described herein can modulate splicing of a pre-mRNA of TTLL5. In some embodiments, the SMSM compounds and methods of their use described herein can modulate splicing of a pre-mRNA of TTLL9. In some embodiments, the SMSM compounds and methods of their use described herein can modulate splicing of a pre-mRNA of TTN. In some embodiments, the SMSM compounds and methods of their use described herein can modulate splicing of a pre-mRNA of TTPAL. In some embodiments, the SMSM compounds and methods of their use described herein can modulate splicing of a pre-mRNA of TTR. In some embodiments, the SMSM compounds and methods of their use described herein can modulate splicing of a pre-mRNA of TUSC3. In some embodiments, the SMSM compounds and methods of their use described herein can modulate splicing of a pre-mRNA of TXNDC10. In some embodiments, the SMSM compounds and methods of their use described herein can modulate splicing of a pre-mRNA of UBE3A. In some embodiments, the SMSM compounds and methods of their use described herein can modulate splicing of a pre-mRNA of UCK1. In some embodiments, the SMSM compounds and methods of their use described herein can modulate splicing of a pre-mRNA of UGT1A1. In some embodiments, the SMSM compounds and methods of their use described herein can modulate splicing of a pre-mRNA of UHRF1BP1. In some embodiments, the SMSM compounds and methods of their use described herein can modulate splicing of a pre-mRNA of UNC45B. In some embodiments, the SMSM compounds and methods of their use described herein can modulate splicing of a pre-mRNA of UNC5C. In some embodiments, the SMSM compounds and methods of their use described herein can modulate splicing of a pre-mRNA of USH2A. In some embodiments, the SMSM compounds and methods of their use described herein can modulate splicing of a pre-mRNA of USP1. In some embodiments, the SMSM compounds and methods of their use described herein can modulate splicing of a pre-mRNA of USP38. In some embodiments, the SMSM compounds and methods of their use described herein can modulate splicing of a pre-mRNA of USP39. In some embodiments, the SMSM compounds and methods of their use described herein can modulate splicing of a pre-mRNA of USP6. In some embodiments, the SMSM compounds and methods of their use described herein can modulate splicing of a pre-mRNA of UTP15. In some embodiments, the SMSM compounds and methods of their use described herein can modulate splicing of a pre-mRNA of UTP18. In some embodiments, the SMSM compounds and methods of their use described herein can modulate splicing of a pre-mRNA of UTP20. In some embodiments, the SMSM compounds and methods of their use described herein can modulate splicing of a pre-mRNA of UTRN. In some embodiments, the SMSM compounds and methods of their use described herein can modulate splicing of a pre-mRNA of UTX. In some embodiments, the SMSM compounds and methods of their use described herein can modulate splicing of a pre-mRNA of UTY. In some embodiments, the SMSM compounds and methods of their use described herein can modulate splicing of a pre-mRNA of UVRAG. In some embodiments, the SMSM compounds and methods of their use described herein can modulate splicing of a pre-mRNA of UXT. In some embodiments, the SMSM compounds and methods of their use described herein can modulate splicing of a pre-mRNA of VAPA. In some embodiments, the SMSM compounds and methods of their use described herein can modulate splicing of a pre-mRNA of VPS29. In some embodiments, the SMSM compounds and methods of their use described herein can modulate splicing of a pre-mRNA of VPS35. In some embodiments, the SMSM compounds and methods of their use described herein can modulate splicing of a pre-mRNA of VPS39. In some embodiments, the SMSM compounds and methods of their use described herein can modulate splicing of a pre-mRNA of VTI1A. In some embodiments, the SMSM compounds and methods of their use described herein can modulate splicing of a pre-mRNA of VTI1B. In some embodiments, the SMSM compounds and methods of their use described herein can modulate splicing of a pre-mRNA of VWA3B. In some embodiments, the SMSM compounds and methods of their use described herein can modulate splicing of a pre-mRNA of WDFY2. In some embodiments, the SMSM compounds and methods of their use described herein can modulate splicing of a pre-mRNA of WDR16. In some embodiments, the SMSM compounds and methods of their use described herein can modulate splicing of a pre-mRNA of WDR17. In some embodiments, the SMSM compounds and methods of their use described herein can modulate splicing of a pre-mRNA of WDR26. In some embodiments, the SMSM compounds and methods of their use described herein can modulate splicing of a pre-mRNA of WDR44. In some embodiments, the SMSM compounds and methods of their use described herein can modulate splicing of a pre-mRNA of WDR67. In some embodiments, the SMSM compounds and methods of their use described herein can modulate splicing of a pre-mRNA of WDTC1. In some embodiments, the SMSM compounds and methods of their use described herein can modulate splicing of a pre-mRNA of WRNIP1. In some embodiments, the SMSM compounds and methods of their use described herein can modulate splicing of a pre-mRNA of WWC3. In some embodiments, the SMSM compounds and methods of their use described herein can modulate splicing of a pre-mRNA of XRN1. In some embodiments, the SMSM compounds and methods of their use described herein can modulate splicing of a pre-mRNA of XRN2. In some embodiments, the SMSM compounds and methods of their use described herein can modulate splicing of a pre-mRNA of XX-FW88277. In some embodiments, the SMSM compounds and methods of their use described herein can modulate splicing of a pre-mRNA of YARS. In some embodiments, the SMSM compounds and methods of their use described herein can modulate splicing of a pre-mRNA of YGM. In some embodiments, the SMSM compounds and methods of their use described herein can modulate splicing of a pre-mRNA of ZBTB20. In some embodiments, the SMSM compounds and methods of their use described herein can modulate splicing of a pre-mRNA of ZC3H7A. In some embodiments, the SMSM compounds and methods of their use described herein can modulate splicing of a pre-mRNA of ZC3HAV1. In some embodiments, the SMSM compounds and methods of their use described herein can modulate splicing of a pre-mRNA of ZC3HC1. In some embodiments, the SMSM compounds and methods of their use described herein can modulate splicing of a pre-mRNA of ZFYVE1. In some embodiments, the SMSM compounds and methods of their use described herein can modulate splicing of a pre-mRNA of ZNF114. In some embodiments, the SMSM compounds and methods of their use described herein can modulate splicing of a pre-mRNA of ZNF169. In some embodiments, the SMSM compounds and methods of their use described herein can modulate splicing of a pre-mRNA of ZNF326. In some embodiments, the SMSM compounds and methods of their use described herein can modulate splicing of a pre-mRNA of ZNF365. In some embodiments, the SMSM compounds and methods of their use described herein can modulate splicing of a pre-mRNA of ZNF37A. In some embodiments, the SMSM compounds and methods of their use described herein can modulate splicing of a pre-mRNA of ZNF618. In some embodiments, the SMSM compounds and methods of their use described herein can modulate splicing of a pre-mRNA of ZWINT.

In some embodiments, the SMSM compounds and methods of their use described herein can modulate splicing, such as alternative splicing of a polynucleotide encoded by MAPT gene. In some embodiments, alternative splicing of the MAPT pre-mRNA may lead to the expression of 1, 2, 3, 4, 5, 6, 7, 8, 9 or 10 isoforms of the tau protein. In some embodiments, alternative splicing of the MAPT pre-mRNA may lead to the expression of 6 isoforms of the tau protein. In some embodiments, the 6 isoforms of tau include 3 four-repeat (4R) isoforms and 3 three-repeat (3R) isoforms of the tau protein. In the 3R tau isoforms exon 10 is excluded from the splice variants. For example, a 3R tau isoform in which exon 10 is excluded may include exon 2 and/or exon 3. In the 4R tau isoforms exon 10 is included in the splice variants. For example, a 4R tau isoform in which exon 10 is included may include exon 2 and/or exon 3. The inclusion or exclusion of exon 10 may depend on alternative splicing events in a stem loop occurring at the exon 10 intron 10 junction. In some embodiments, a mutation occurring at the 5'ss results in inclusion of exon 10 in an mRNA encoding the tau protein. In some embodiments, a mutation in an ISS region of the stem loop results in exclusion of exon 10 from the mRNA encoding the tau protein. In some embodiments, a mutation at the 5'ss destabilizes the stem loop, thereby decreasing exon 10 inclusion in the mRNA of tau. In some embodiments, a mutation at the 5'ss inhibits binding of a spliceosome component to the pre-mRNA, thereby decreasing exon 10 inclusion in the mRNA of tau. In some embodiments, a mutation at the ISS region of the stem loop inhibits binding of a spliceosome component to the pre-mRNA, thereby increasing exon 10 inclusion in the mRNA of tau.

The ratio of 3R to 4R tau isoforms may contribute to a number of conditions or diseases. In some embodiments, a subject without a condition or disease has a 3R to 4R ratio of 1:1. In some embodiments, a subject with a condition or disease described herein has a 3R to 4R ratio of about 1:1.2, 1:1.4, 1:1.6, 1:1.8, 1:2, 1:2.5, 1:3, 1:3.5, 1:4, 1:4.5 or 1:5. In some embodiments, a subject with a condition or disease described herein has a 3R to 4R ratio from about 1:1 to about 1:1.1, about 1:1 to about 1:1.2, about 1:1 to about 1:1.3, about 1:1 to about 1:1.4, about 1:1 to about 1:1.5, about 1:1 to about 1:1.6, about 1:1 to about 1:1.8, about 1:1 to about 1:2, about 1:1 to about 1:3, about 1:1 to about 1:3.5, about 1:1 to about 1:4, about 1:1 to about 1:4.5, about 1:1 to about 1:5, 1:2 to about 1:3, about 1:2 to about 1:4, about 1:2 to about 1:5, about 1:3 to about 1:4, about 1:3 to about 1:5, or about 1:4 to about 1:5. In some embodiments, a subject with a condition or disease described herein has a 4R to 3R ratio of about 1:1.2, 1:1.4, 1:1.6, 1:1.8, 1:2, 1:2.5, 1:3, 1:3.5, 1:4, 1:4.5 or 1:5. In some embodiments, a subject with a condition or disease described herein has a 4R to 3R ratio from about 1:1 to about 1:1.1, about 1:1 to about 1:1.2, about 1:1 to about 1:1.3, about 1:1 to about 1:1.4, about 1:1 to about 1:1.5, about 1:1 to about 1:1.6, about 1:1 to about 1:1.8, about 1:1 to about 1:2, about 1:1 to about 1:3, about 1:1 to about 1:3.5, about 1:1 to about 1:4, about 1:1 to about 1:4.5, about 1:1 to about 1:5, 1:2 to about 1:3, about 1:2 to about 1:4, about 1:2 to about 1:5, about 1:3 to about 1:4, about 1:3 to about 1:5, or about 1:4 to about 1:5.

In some aspects, the SMSM compounds are used to modulate alternative splicing of tau pre-mRNA. In some embodiments, the SMSM compound binds to the stem loop of exon 10 of the tau pre-mRNA, reducing binding affinity of a spliceosome component to the 5'ss, thereby increasing exclusion of exon 10 in the mRNA of tau and increasing the ratio of 3R:4R tau isoforms. In some embodiments, the SMSM compound binds to the stem loop of exon 10 of the tau pre-mRNA, increasing binding affinity of a spliceosome component to the 5'ss, thereby increasing inclusion of exon 10 in the mRNA of tau and decreasing the ratio of 3R:4R tau isoforms. In some embodiments, the SMSM compound binds to the stem loop of exon 10 of the tau pre-mRNA, reducing binding affinity of a spliceosome component to the ISS region, thereby increasing inclusion of exon 10 in the mRNA of tau and decreasing the ratio of 3R:4R tau isoforms. In some embodiments, the SMSM compound binds to the stem loop of exon 10 of the tau pre-mRNA, increasing binding affinity of a spliceosome component to the ISS region, thereby reducing inclusion of exon 10 in the mRNA of tau and increasing the ratio of 3R:4R tau isoforms. In some embodiments, the SMSM compound restores the ratio of 3R:4R to 1:1. In some embodiments, the SMSM compound alters the ratio from 3R>4R to 4R>3R. In some embodiments, the SMSM compound alters the ratio from 3R<4R to 4R<3R. In some embodiments, the SMSM compound binds to the stem loop of exon 10 of the tau pre-mRNA, increasing the thermodynamic stability of the stem loop, thereby reducing inclusion of exon 10 in the mRNA of tau and increasing the ratio of 3R:4R tau isoforms. In some embodiments, the SMSM compound binds to the stem loop of exon 10 of the tau pre-mRNA, decreasing the thermodynamic stability of the stem loop, thereby increasing inclusion of exon 10 in the mRNA of tau and decreasing the ratio of 3R:4R tau isoforms.

Mutations and/or aberrant secondary or tertiary RNA structures in cis-acting elements of splicing can alter splicing patterns. Mutations and/or aberrant secondary or tertiary RNA structures can be found in core consensus sequences, including 5'ss, 3'ss, and BP regions, or other regulatory elements, including ESEs, ESSs, ISEs, and ISSs. Mutations in cis-acting elements can result in multiple diseases. Exemplary diseases are described below. The present disclosure provides splice modulating compounds and methods that target pre-mRNA containing one or more mutations and/or aberrant secondary or tertiary RNA structures in cis-acting elements. In some embodiments, the present disclosure provides methods and small molecule binding agents that target pre-mRNA containing one or more mutations and/or aberrant secondary or tertiary RNA structures in splice sites or BP regions. In some embodiments, the present disclosure provides methods and small molecule binding agents that target pre-mRNA containing one or more mutations and/or aberrant secondary or tertiary RNA structures in other regulatory elements, for example, ESEs, ESSs, ISEs, and ISSs.

In some embodiments, splicing at a splice site sequence of a polynucleotide of primary cells is modulated. In some embodiments, splicing at a splice site sequence of a polynucleotide of cells of a tumor is modulated. In some embodiments, the SMSM modulates splicing at a cryptic splice site sequence. In some embodiments, an SMSM modulates splicing of splice site of a polynucleotide. In some embodiments, wherein the polynucleotide is transcribed from the gene. In some embodiments, SMSM modulates exon inclusion in the polynucleotide and splicing of the splice site sequence. In some embodiments, the SMSM modulates pseudoexons inclusion in the polynucleotide and splicing of the splice site sequence. In some embodiments, the SMSM modulates splicing at a cryptic splice site sequence of a polynucleotide.

In some embodiments, an SMSM modulates splicing by preventing, inhibiting or reducing splicing of the polynucleotide. In some embodiments, an SMSM modulates splicing by preventing, inhibiting or reducing splicing at the splice site sequence. In some embodiments, an SMSM decreases affinity of a splicing complex component to the polynucleotide. In some embodiments, an SMSM decreases affinity of a splicing complex component to the polynucleotide at the splice site sequence, upstream of the splice site sequence or downstream of the splice site sequence. In some embodiments, an SMSM inhibits or reduces a rate of catalysis of splicing of the polynucleotide. In some embodiments, an SMSM inhibits or reduces a rate of catalysis of splicing of the polynucleotide at the splice site sequence. In some embodiments, an SMSM increases steric hindrance between a splicing complex component and the polynucleotide. In some embodiments, an SMSM increases steric hindrance between a splicing complex component and the polynucleotide at the splice site sequence, upstream of the splice site sequence or downstream of the splice site sequence. In some embodiments, an SMSM increases steric hindrance between a first splicing complex component and a second splicing complex component. In some embodiments, an SMSM prevents, inhibits, disrupts or reduces binding of a first splicing complex component and a second splicing complex component.

In some embodiments, an SMSM decreases affinity of a first splicing complex component to a second splicing complex component. In some embodiments, an SMSM prevents, inhibits, disrupts or reduces binding of a splicing complex component to the polynucleotide. In some embodiments, an SMSM prevents, inhibits, disrupts or reduces binding of a splicing complex component to the polynucleotide at the splice site sequence, upstream of the splice site sequence or downstream of the splice site sequence.

In some embodiments, an SMSM modulates splicing by promoting or increasing splicing of the polynucleotide. In some embodiments, an SMSM modulates splicing by promoting or increasing splicing the splice site sequence. In some embodiments, an SMSM increases affinity of a splicing complex component to the polynucleotide. In some embodiments, an SMSM increases affinity of a splicing complex component to the polynucleotide at the splice site sequence, upstream of the splice site sequence or downstream of the splice site sequence. In some embodiments, an SMSM increases a rate of catalysis of splicing of the polynucleotide. In some embodiments, an SMSM increases a rate of catalysis of splicing of the polynucleotide at the splice site sequence. In some embodiments, an SMSM decreases or reduces steric hindrance between a splicing complex component and the polynucleotide. In some embodiments, an SMSM decreases steric hindrance between a splicing complex component and the polynucleotide at the splice site sequence, 1-1000 nucleobases bases upstream of the splice site sequence or 1-1000 nucleobases downstream of the splice site sequence. In some embodiments, an SMSM decreases or reduces steric hindrance between a first splicing complex component and a second splicing complex component. In some embodiments, an SMSM promotes or increases binding of a first splicing complex component and a second splicing complex component. In some embodiments, an SMSM increases affinity of a first splicing complex component to a second splicing complex component. In some embodiments, an SMSM promotes or increases binding of a splicing complex component to the polynucleotide. In some embodiments, an SMSM promotes or increases binding of a splicing complex component to the polynucleotide at the splice site sequence, 1-1000 nucleobases upstream of the splice site sequence or 1-1000 nucleobases downstream of the splice site sequence. In some embodiments, an SMSM binds to a splicing complex component, the polynucleotide, or a combination thereof. In some embodiments, an SMSM binds to the polynucleotide at the splice site sequence, 1-1000 nucleobases upstream of the splice site sequence or 1-1000 nucleobases downstream of the splice site sequence. In some embodiments, an SMSM structurally modulates a splicing complex component, the polynucleotide, or both. In some embodiments, an SMSM promotes or increases steric hindrance, steric shielding, steric attraction, chain crossing, steric repulsions, steric inhibition of resonance, steric inhibition of protonation, or a combination thereof of the polynucleotide, a splicing complex component or a combination thereof. In some embodiments, binding of an SMSM to a polynucleotide or a splicing complex component decreases conformational stability of a splice site sequence. In some embodiments, binding of an SMSM to a polynucleotide increases conformational stability of a splice site sequence.

In some embodiments, an SMSM modulates exon skipping of a target polynucleotide, such as a pre-mRNA. For example, an SMSM can inhibit exon skipping of a target polynucleotide, such as a pre-mRNA. For example, an SMSM can promote exon skipping of a target polynucleotide, such as a pre-mRNA. In some embodiments, an SMSM modulates splicing at a splice site sequence of a polynucleotide in a cell of a subject with a disease or condition associated with exon skipping of the polynucleotide, such as a pre-mRNA. In some embodiments, an SMSM modulates splicing at a splice site sequence of a polynucleotide in a cell of a subject with a disease or condition associated with aberrant exon skipping of the polynucleotide, such as a pre-mRNA.

In some embodiments, an SMSM modulates exon inclusion of a target polynucleotide, such as a pre-mRNA. For example, an SMSM can inhibit exon inclusion of a target polynucleotide, such as a pre-mRNA. For example, an SMSM can promote exon inclusion of a target polynucleotide, such as a pre-mRNA. In some embodiments, an SMSM modulates splicing at a splice site sequence of a polynucleotide in a cell of a subject with a disease or condition associated with exon inclusion of the polynucleotide, such as a pre-mRNA. In some embodiments, an SMSM modulates splicing at a splice site sequence of a polynucleotide in a cell of a subject with a disease or condition associated with aberrant exon inclusion of the polynucleotide, such as a pre-mRNA.

In some embodiments, an SMSM modulates nonsense mediated degradation (NMD) of a target polynucleotide, such as a pre-mRNA. For example, an SMSM can inhibit nonsense mediated degradation (NMD) of a target polynucleotide, such as a pre-mRNA or an mRNA. In some embodiments, an SMSM modulates splicing at a splice site sequence of a polynucleotide in a cell of a subject with a disease or condition associated with NMD of the polynucleotide, such as a pre-mRNA or an mRNA.

In some embodiments, an SMSM modulates intron inclusion of a target polynucleotide. For example, an SMSM can inhibit intron inclusion of a target polynucleotide, such as a pre-mRNA. For example, an SMSM can promote intron inclusion of a target polynucleotide, such as a pre-mRNA. In some embodiments, an SMSM modulates splicing at a splice site sequence of a polynucleotide in a cell of a subject with a disease or condition associated with intron inclusion of the polynucleotide. In some embodiments, the SMSM modulates splicing at a splice site sequence of a polynucleotide in a cell of a subject with a disease or condition associated with intron inclusion of the polynucleotide.

In some embodiments, an SMSM modulates splicing at splice site sequence of a polynucleotide, such as a pre-mRNA, wherein the splice site sequence comprises a sequence selected from the group consisting of NGAgunvrn, NHAdddddn, NNBnnnnnn, and NHAddmhvk; wherein N or n is A, U, G or C; B is C, G, or U; H or h is A, C, or U; d is a, g, or u; m is a or c; r is a or g; v is a, c or g; k is g or u.

In some embodiments, an SMSM modulates splicing of a splice site sequence comprising a sequence NNBgunnnn, NNBhunnnn, or NNBgvnnnn. In some embodiments, an SMSM modulates splicing of a splice site sequence comprising a sequence NNBgurrrn, NNBguwwdn, NNBguvmvn, NNBguvbbn, NNBgukddn, NNBgubnbd, NNBhunngn, NNBhurmhd, or NNBgvdnvn; wherein N or n is A, U, G or C; B is C, G, or U; H or h is A, C, or U; d is a, g, or u; m is a or c; r is a or g; v is a, c or g; k is g or u.

In some embodiments, an SMSM modulates splicing of a splice site sequence comprising a sequence of Table 2A, Table 2B, Table 2C or Table 2D. In some embodiments, an SMSM modulates splicing of a splice site sequence comprising a sequence AAAauaagu, AAAguaagua (SEQ ID NO: 1), AAAguacau, AAAguaga, AAAguaug, AAAguaugu, AAAgugagug (SEQ ID NO: 2), AAAgugaguu (SEQ ID NO: 3), AACaugagga (SEQ ID NO: 4), AACguaagu, AACgugacu, AACgugauu, AAGaugagc, AAGauuugu, AAGgaugag, AAGgcaaaa, AAGgcagggg (SEQ ID NO: 5), AAGgcaggga (SEQ ID NO: 6), AAGgggaaaa, AAGguauag (SEQ ID NO: 7), AAGguaaag, AAGguaaau, AAGguaaca, AAGguaacaug (SEQ ID NO: 8), AAGguaacu, AAGguaagcc (SEQ ID NO: 9), AAGguaagcg (SEQ ID NO: 10), AAGguaauaa (SEQ ID NO: 11), AAGguaaugu (SEQ ID NO: 12), AAGguaaugua (SEQ ID NO: 13), AAGguacag, AAGguacgg, AAGguacug, AAGguagacc (SEQ ID NO: 14), AAGguagag, AAGguagcg, AAGguagua, AAGguagug, AAGguauac, AAGguauau, AAGguauauu (SEQ ID NO: 15), AAGguauca, AAGguaucg, AAGguaucu, AAGguauga, AAGguaugg, AAGguaugu, AAGguauuu, AAGgucaag, AAGgucaau, AAGgucucu, AAGgucuggg (SEQ ID NO: 16), AAGgucugu, AAGgugaccuu (SEQ ID NO: 17), AAGgugagau (SEQ ID NO: 18), AAGgugaguc (SEQ ID NO: 19), AAGgugccu, AAGgugggcc (SEQ ID NO: 20), AAGguggu, AAGguggua, AAGguguau, AAGgugucu, AAGgugugc, AAGgugugu, AAGguguua, AAGguuaag, AAGguuagc, AAGguuagug (SEQ ID NO: 21), AAGguuca, AAGguuuaa, AAGguuuau, AAGguuugg, AAGguuaaua, AAGguuagga, AAUguaaau, AAUguaagc, AAUguaagg, AAUguaauu, AAUguaugu, AAUgugagn, AAUgugugu, ACAguaaau, ACAgugagg, ACAguuagu, ACAguuuga, ACCaugagu, ACCgugaguu (SEQ ID NO: 22), ACGauaagg, ACGcuaagc, ACGguagcu, ACGgugaac, ACGgugagug (SEQ ID NO: 23), ACUguaaau, ACUguaacu, ACUguauu, ACUgugagug (SEQ ID NO: 24), AGAguaag, AGAguaaga, AGAguaagg, AGAguaagu, AGAguagau, AGAguaggu, AGAgugaau, AGAgugagc, AGAgugagu, AGAgugcgu, AGCguaagg, AGCguaagu, AGCguacgu, AGCguaggu, AGCgugagu, AGGguaauga (SEQ ID NO: 25), AGGguagac, AGGguauau, AGGgugaau, AGGgugagg, AGGgugauc, AGGgugcaa, AGGgugucu, AGUguaagc, AGUguaagu, AGUgugagu, AGUgugaguac (SEQ ID NO: 26), AUAgucagu, AUAgugaau, AUCgguaaaa (SEQ ID NO: 27), AUCguuaga, AUGguaaaa, AUGguaacc, AUGguacau, AUGguaugu, AUGguauuu, AUGgucauu, AUGgugacc, AUUuuaagc, CAAGguaccu (SEQ ID NO: 28), CAAguaaac, CAAguaacu, CAAguaagc, CAAguaagg, CAAguaagua (SEQ ID NO: 29), CAAguaau, CAAguaugu, CAAguauuu, CAAgugaaa, CAAgugagu, CACgugagc, CACguuggu, CAGauaacu, CAGaugagg, CAGaugagu, CAGauuggu, CAGcugugu, CAGgcgagu, CAGgcuggu, CAGguaaggc (SEQ ID NO: 30), CAGguaaaa, CAGguaaag, CAGguaaccuc (SEQ ID NO: 31), CAGguaagac (SEQ ID NO: 32), CAGguaagc, CAGguaagu, CAGguaau, CAGguaaugc (SEQ ID NO: 33), CAGguaaugu (SEQ ID NO: 34), CAGguacaa, CAGguacag, CAGguacagu (SEQ ID NO: 35), CAGguaccg, CAGguacug, CAGguagag, CAGguagcaa (SEQ ID NO: 36), CAGguaggagg (SEQ ID NO: 37), CAGguaggc, CAGguagguga (SEQ ID NO: 38), CAGguagua, CAGguagug, CAGguauag, CAGguauau, CAGguaucc, CAGguauga, CAGguaugg, CAGguaugu, CAGguauug, CAGgucaau, CAGgucagug (SEQ ID NO: 39), CAGgucuga, CAGgucugga (SEQ ID NO: 40), CAGgucuggu (SEQ ID NO: 41), CAGgucuuu, CAGgugacu, CAGgugagc, CAGgugaggg (SEQ ID NO: 42), CAGgugagugg (SEQ ID NO: 43), CAGgugaua, CAGgugcac, CAGgugcag, CAGgugcgc, CAGgugcug, CAGguggau, CAGgugggug (SEQ ID NO: 44), CAGgugua, CAGguguag, CAGguguau, CAGguguga, CAGgugugu, CAGguuaag, CAGguugau, CAGguugcu, CAGguuggc, CAGguuguc, CAGguuguu, CAGguuuagu (SEQ ID NO: 45), CAGguuugc, CAGguuugg, CAGuuuggu, CAUggaagac (SEQ ID NO: 46), CAUguaau, CAUguaauu, CAUguaggg, CAUguauuu, CCAguaaac, CCAgugaga, CCGguaacu, CCGgugaau, CCGgugacu, CCGgugagg, CCUauaagu, CCUaugagu, CCUguaaau, CCUguaagc, CCUguaauu, CCUgugaau, CCUgugauu, CGAguccgu, CGCauaagu, CGGguaau, CGGguauau, CGGguaugg, CGGgucauaauc (SEQ ID NO: 47), CGGgugggu, CGGguguau, CGGgugugu, CGUgugaau, CGUgugggu, CUGguauga, CUGgugaau, CUGgugaguc (SEQ ID NO: 48), CUGgugaguuc (SEQ ID NO: 49), CUGgugcau, CUGgugcuu, CUGguguga, CUGguuugu, CUGuuaag, CUGuugaga, GAAggaagu, GAAguaaac, GAAguaaau, GAAgucugg, GAAguggg, GAAgugugu, GAAuaaguu, GACaugagg, GAGaucugg, GAGaugagg, GAGCAGguaagcu (SEQ ID NO: 50), GAGcugcag, GAGgcaggu, GAGgcgugg, GAGgcuccc, GAGguggguuu (SEQ ID NO: 51), GAGguaaag, GAGguaaga, GAGguaagag (SEQ ID NO: 52), GAGguaagcg (SEQ ID NO: 53), GAGguaauac (SEQ ID NO: 54), GAGguaauau (SEQ ID NO: 55), GAGguaaugu (SEQ ID NO: 56), GAGguacaa, GAGguagga, GAGguauau, GAGguauga, GAGguaugg, GAGgucuggu (SEQ ID NO: 57), GAGgugaag, GAGgugagg, GAGgugca, GAGgugccu, GAGgugcggg (SEQ ID NO: 58), GAGgugcug, GAGguguac, GAGguguau, GAGgugugc, GAGgugugu, GAGuuaagu, GAUaugagu, GAUguaaau, GAUguaagu, GAUguaauu, GAUguaua, GAUgugacu, GAUgugagg, GAUgugauu, GCAguaaau, GCAguagga, GCAguuagu, GCGaugagu, GCGgagagu, GCGguaaaa, GCGguaauca (SEQ ID NO: 59), GCGgugacu, GCGgugagca (SEQ ID NO: 60), GCGgugagcu (SEQ ID NO: 61), GCGguggga, GCGguuagu, GCUguaaau, GCUguaacu, GCUguaauu, GGAguaag, GGAguaagg, GGAguaagu, GGAguaggu, GGAgugagu, GGAguuagu, GGCguaagu, GGCgucagu, GGGauaagu, GGGaugagu, GGGguaagug (SEQ ID NO: 62), GGGguaaau, GGGguaacu, GGGguacau, GGGgugacg, GGGgugagug (SEQ ID NO: 63), GGGgugcau, GGGguuggga (SEQ ID NO: 64), GGUguaagu, GUAgugagu, GUGguaagu, GUGguaagug (SEQ ID NO: 65), GUGgugagc, GUGgugagu, GUGgugauc, GUGguugua, GUUauaagu, GUUCUCAgugug (SEQ ID NO: 66), GUUguaaau, GUUuugguga (SEQ ID NO: 67), uAGCAGguaagca (SEQ ID NO: 68), uGGguaccug (SEQ ID NO: 69), UAGaugcgu, UAGguaaag, UAGguaccc, UAGguaggu, UAGguauau, UAGguauc, UAGguauga, UAGguauug, UAGgucaga, UAGgugcau, UAGguguau, UCAguaaac, UCAguaaau, UCAguaagu, UCAgugauu, UCAgugug, UCCgugaau, UCCgugacu, UCCgugagc, UCUguaaau, UGAgugaau, UGGauaagg, UGGguaaag, UGGguacca, UGGguaugc, UGGguggau, UGGgugggg (SEQ ID NO: 70), UGGguggggug (SEQ ID NO: 71), UGGgugugg, UGGguuagu, UGUgcaagu, UGUguaaau, UGUguacau, UUAguaaau, UUCauaagu, UUGguaaag, UUGguaaca, UUGguacau, UUGguagau, UUGgugaau, UUGgugagc, UUUauaagc or UUUgugagc.

ABCA4, ABCA9, ABCB1, ABCB5, ABCC9, ABCD1, ACADL, ACADM, ACADSB, ACSS2, ACTG2, ADA, ADAL, ADAM10, ADAM15, ADAM22, ADAM32, ADAMTS12, ADAMTS13, ADAMTS20, ADAMTS6, ADAMTS9, ADCY10, ADCY3, ADCY8, ADRBK2, AFP, AGL, AGT, AHCTF1, AKAP10, AKAP3, AKNA, ALAS1, ALB, ALDH3A2, ALG6, ALS2CL, AMBRA1, ANGPTL3, ANK3, ANTXR2, ANXA10, ANXA11, AP2A2, AP4E1, APC, APOA1, APOB, APOC3, APOH, AR, ARFGEF1, ARFGEF2, ARHGAP1, ARHGAP18, ARHGAP26, ARHGAP8, ARHGEF18, ARHGEF2, ARPC3, ARS2,

ASH1L, ASNSD1, ASPM, ATAD5, ATG16L2, ATG4A, ATM, ATP11C, ATP13A5, ATP6V1G3, ATP7A, ATP7B, ATR, ATXN2, ATXN3, B2M, B4GALNT3, BBOX1, BBS4, BCL2-like 11 (BIM), BCS1L, BMP2K, BMPR2, BRCA1, BRCA2, BRCC3, BRSK1, BRSK2, BTAF1, BTK, C10orf137, C11orf30, C11orf65, C11orf70, C12orf51, C13orf1, C13orf15, C14orf101, C14orf118, C15orf29, C15orf42, C15orf60, C16orf33, C16orf38, C16orf48, C18orf8, C19orf42, C1orf107, C1orf114, C1orf130, C1orf149, C1orf27, C1orf71, C1orf87, C1orf94, C1R, C20orf74, C21orf70, C2orf55, C3, C3orf23, C4orf18, C4orf29, C5orf34, C6orf118, C8B, C8orf33, C9orf114, C9orf43, C9orf86, C9orf98, CA11, CAB39, CACHD1, CACNA1B, CACNA1C, CACNA1G, CACNA1H, CACNA2D1, CALCA, CALCOCO2, CAMK1D, CAMKK1, CAPN3, CAPN9, CAPSL, CARKD, CAT, CBX1, CBX3, CCDC102B, CCDC11, CCDC131, CCDC146, CCDC15, CCDC18, CCDC5, CCDC81, CD1B, CD33, CD4, CD46, CDC14A, CDC16, CDC2L5, CDC42BPB, CDCA8, CDH1, CDH10, CDH11, CDH23, CDH24, CDH8, CDH9, CDK5RAP2, CDK6, CDK8, CEL, CELSR3, CENP1, CENTB2, CENTG2, CEP110, CEP170, CEP192, CETP, CFB, CFH, CFTR, CGN, CGNL1, CHAF1A, CHD9, CHIC2, CHL1, CHM, CHN1, CLCN1, CLEC16A, CLIC2, CLINT1, CLK1, CLPB, CLPTM1, CMIP, CMYA5, CNGA3, CNOT1, CNOT7, CNTN6, COG3, COL11A1, COL11A2, COL12A1, COL14A1, COL15A1, COL17A1, COL19A1, COL1A1, COL1A2, COL22A1, COL24A1, COL25A1, COL29A1, COL2A1, COL3A1, COL4A1, COL4A2, COL4A5, COL4A6, COL5A2, COL6A1, COL7A1, COL9A1, COL9A2, COLQ, COMTD1, COPA, COPB2, COPS7B, COPZ2, CPSF2, CPXM2, CR¹, CREBBP, CRKRS, CRYZ, CSE1L, CSTB, CSTF3, CT45-6, CUBN, CUL4B, CUL5, CXorf41, CYBB, CYFIP2, CYP17, CYP19, CYP24A1, CYP27A1, CYP3A4, CYP3A43, CYP3A5, CYP4F2, CYP4F3, DAZ2, DCBLD1, DCC, DCTN3, DCUN1D4, DDA1, DDEF1, DDX1, DDX24, DDX4, DENND2D, DEPDC2, DES, DGAT2, DHFR, DHRS7, DHRS9, DIP2A, DMD, DMTF1, DNAH3, DNAH8, DNAI1, DNAJA4, DNAJC13, DNAJC7, DNT-TIP2, DOCK10, DOCK11, DOCK4, DPP3, DPP4, DPY19L2P2, DSCC1, DUX4, DVL3, DYNC1H1, DYSF, ECM2, EDEM3, EFCAB3, EFCAB4B, EFNA4, EFTUD2, EGFR, EIF3A, ELA1, ELA2A, EMCN, EMD, EML5, ENPP3, EPB41L5, EPHA3, EPHA4, EPHB1, EPHB2, EPHB3, EPS15, ERBB4, ERCC1, ERCC8, ERGIC3, ERMN, ERMP1, ERN1, ERN2, ETS2, ETV4, EVC2, EXO1, EXOC4, F11, F13A1, F3, F5, F7, F8, FAH, FAM134A, FAM13A1, FAM13B1, FAM13C1, FAM161A, FAM176B, FAM184A, FAM19A1, FAM20A, FAM23B, FAM65C, FANCA, FANCC, FANCG, FANCM, FANK1, FAR2, FBN1, FBXO15, FBXO18, FBXO38, FCGBP, FECH, FEZ2, FGA, FGD6, FGFR1OP, FGFR1OP2, FGFR2, FGG, FGR, FIX, FKBP3, FLJ35848, FLJ36070, FLNA, FN1, FNBP1L, FOLH1, FOXM1, FRAS1, FUT9, FZD3, FZD6, GAB1, GALC, GALNT3, GAPDH, GART, GAS2L3, GBA, GBGT1, GCG, GCGR, GCK, GFM1, GH1, GHR, GHV, GJA1, GLA, GLT8D1, GNAS, GNB5, GOLGB1, GOLT1A, GOLT1B, GPATCH1, GPR158, GPR160, GRAMD3, GRHPR, GRIA1, GRIA3, GRIA4, GRIN2B, GRM3, GRM4, GRN, GSDMB, GSTCD, GSTO2, GTPBP4, HADHA, HBA2, HBB, HCK, HDAC3, HDAC5, HDX, HEPACAM2, HERC1, HEXA, HEXB, HIPK3, HLA-DPB1, HLA-G, HLCS, HLTF, HMBS, HMGCL, HNF1A, HNRNPH1, HP1BP3, HPGD, HPRT1, HPRT2, HSF2BP, HSF4, HSPA9, HSPG2, HTT, HXA, ICA1, IDH1, IDS, IFI44L, IKBKAP, IL1R2, IL5RA, IL7RA, IMMT, INPP5D, INSR, INTS3, INTU, IP04, IP08, IQGAP2, ISL2, ITFG1, ITGAL, ITGB1, ITGB2, ITGB3, ITGB4, ITIH1, ITPR2, IWS1, JAG1, JAK1, JAK2, JMJD1C, KALRN, KATNAL2, KCNN2, KCNT2, KIAA0256, KIAA0528, KIAA0564, KIAA0586, KIAA1033, KIAA1166, KIAA1219, KIAA1409, KIAA1622, KIAA1787, KIF15, KIF16B, KIF3B, KIF5A, KIF5B, KIF9, KIN, KIR2DL5B, KIR3DL2, KIR3DL3, KLF12, KLF3, KLHL20, KLK12, KLKB1, KPNA5, KRAS, KREMEN1, KRIT1, KRT5, KRTCAP2, L1CAM, L3MBTL, L3MBTL2, LACE1, LAMA1, LAMA2, LAMA3, LAMB1, LARP7, LDLR, LENG1, LGALS3, LGMN, LHCGR, LHX6, LIMCH1, LIMK2, LMBRD1, LMBRD2, LMLN, LMNA, LMO2, LOC389634, LOC390110, LPA, LPCAT2, LPL, LRP4, LRPPRC, LRRC19, LRRC42, LRRK2, LRWD1, LUM, LVRN, LYN, LYST, MADD, MAGI1, MAGT1, MALT1, MAP2K1, MAP4K4, MAPK8IP3, MAPK9, MAPT, MATN2, MCF2L2, MCM6, MDGA2, MEGF10, MEGF11, MEMO1, MET, MGAM, MGAT4A, MGAT5, MGC16169, MGC34774, MIB1, MIER2, MKKS, MKL2, MLANA, MLH1, MLL5, MLX, MME, MPDZ, MPI, MRAP2, MRPL11, MRPL39, MRPS28, MRPS35, MS4A13, MSH2, MSMB, MST1R, MTDH, MTF2, MTHFR, MTIF2, MUC2, MUT, MVK, MYB, MYCBP2, MYH2, MYO19, MYO3A, MYO9B, MYOM2, MYOM3, NAG, NARG1, NARG2, NCOA1, NDC80, NDFIP2, NEB, NEDD4, NEK1, NEK11, NEK5, NF1, NF2, NFE2L2, NFIA, NFIX, NFKBIL2, NFRKB, NKAIN2, NKAP, NLRC3, NLRC5, NLRP13, NLRP7, NLRP8, NME7, NOL10, NOS1, NOS2A, NOTCH1, NPM1, NR1H4, NR4A3, NRXN1, NSMAF, NSMCE2, NT5C, NT5C3, NUBP1, NUBPL, NUDT5, NUMA1, NUP160, NUP88, NUP98, NUPL1, OAT, OBFC2A, OBFC2B, OLIG2, OPA1, OPN4, OPTN, OSBPL11, OSBPL8, OSGEPL1, OTC, OXT, PADI4, PAH, PAN2, PAPOLG, PARD3, PARVB, PAWR, PBGD, PBRM1, PCBP4, PCCA, PCNX, PCOTH, PDCD4, PDE10A, PDE8B, PDH1, PDIA3, PDK4, PDLIM5, PDS5A, PDS5B, PDXK, PDZRN3, *PELI*2, PGK1, PGM2, PHACTR4, PHEX, PHKB, PHLDB2, PHTF1, PIAS1, PIGF, PIGN, PIGT, PIK3C2G, PIK3CG, PIK3R1, PIP5K1A, PITRM1, PIWIL3, PKD1, PKD2, PKHD1L1, PKIB, PKLR, PKM1, PKM2, PLCB1, PLCB4, PLCG1, PLD1, PLEKHA5, PLEKHA7, PLEKHM1, PLKR, PLXNC1, PMFBP1, POLN, POLR3D, POMT2, POSTN, PPFIA2, PPP1R12A, PPP3CB, PPP4C, PPP4R1L, PPP4R2, PRAME, PRC1, PRDM1, PRIM1, PRIM2, PRKAR1A, PRKCA, PRKG1, PRMT7, PROC, PROCR, PRODH, PROSC, PROX1, PRPF40B, PRPF4B, PRRG2, PRUNE2, PSD3, PSEN1, PSMAL, PTCH1, PTEN, PTK2, PTK2B, PTPN11, PTPN22, PTPN3, PTPN4, PTPRD, PTPRK, PTPRM, PTPRN2, PTPRT, PUS10, PVRL2, PYGM, QRSL1, RAB11FIP2, RAB23, RALBP1, RALGDS, RB1CC1, RBL2, RBM39, RBM45, REC8, RFC4, RFT1, RFTN1, RHPN2, RIF1, RLN3, RMND5B, RNF11, RNF32, RNFT1, RNGTT, ROCK1, ROCK2, RP1, RP11-265F1, RP13-36C9, RP6KA3, RPAP3, RPGR, RPN1, RPS6KA6, RRM1, RRP1B, RSK2, RTEL1, RTF1, RUFY1, RYR3, SAAL1, SAE1, SBCAD, SCN11A, SCN1A, SCN2A, SCN3A, SCN4A, SCN5A, SCN8A, SCNA, SCO1, SCYL3, SDK1, SDK2, SEC24A, SEC24D, SEC31A, SEL1L, SENP3, SENP6, SENP7, SERPINA1, SETD3, SETD4, SEZ6, SFRS12, SGCE, SGOL2, SGPL1, SH2D1A, SH3BGRL2, SH3PXD2A, SH3PXD2B, SH3RF2, SH3TC2, SIPA1L2, SIPA1L3, SIVA1, SKAP1, SKIV2L2, SLC12A3, SLC13A1, SLC22A17, SLC25A14, SLC28A3, SLC38A1, SLC38A4, SLC39A10, SLC4A2, SLC6A11, SLC6A13, SLC6A6, SLC6A8, SMARCA1, SMARCA5, SMC5, SMN2, SMTN, SNCA1P, SNRK, SNRP70, SNX6, SOD1, SPAG9, SPATA13, SPATA4, SPATS1, SPECC1L, SPINK5, SPP2, SPTA1, SRP72, SSX3, SSX5, SSX9, STAG1, STAMBPL1, STARD6, STAT6, STK17B, STX3, STXBP1, SUCLG2, SULF2, SUPT16H, SUPT6H, SV2C, SYCP1, SYCP2, SYT6, SYTL5, TAF2, TBC1D26, TBC1D29, TBC1D3G, TBC1D8B, TBCEL, TBK1, TBPL1, TCEB3, TCF12, TCP11L2, TDRD3, TEAD1, TECTB, TEK, TET2, TFRC, TG, TGM7, TGS1, THOC2, TIAL1, TIAM2, TIMM50, TLK2, TM4SF20, TM6SF1, TMEM156, TMEM194A, TMEM27, TMEM77, TMF1, TMPRSS6, TNFRSF10A, TNFRSF10B, TNFRSF8, TNK2, TNKS, TNKS2, TOM1L1, TOM1L2, TOP2B, TP53, TP53BP2, TP53I3, TP53INP1, TP63, TRAF3IP3, TRAPPC2, TRIM44, TRIM65, TRIML1, TRIML2, TRPM3, TRPM5, TRPM7, TSC1, TSC2, TSHB, TSPAN7, TTC17, TTLL5, TTLL9, TTN, TTPAL, TTR, TUSC3, TXNDC10, UBE3A, UCK1, UGT1A1, UHRF1BP1, UNC45B, UNC5C, USH2A, USP1, USP38, USP39, USP6, UTP15, UTP18, UTP20, UTRN, UTX, UTY, UVRAG, UXT, VAPA, VPS29, VPS35, VPS39, VTI1A, VTI1B, VWA3B, WDFY2, WDR16, WDR17, WDR26, WDR44, WDR67, WDTC1, WRNIP1, WWC3, XRN1, XRN2, XX-FW88277, YARS, YGM, ZBTB20, ZC3H7A, ZC3HAV1, ZC3HC1, ZFYVE1, ZNF114, ZNF169, ZNF326, ZNF365, ZNF37A, ZNF618 or a ZWINT In some embodiments, an SMSM modulates splicing of a splice site sequence comprising a sequence of Table 2A. In some embodiments, an SMSM modulates splicing of a splice site sequence comprising a sequence AAAauaagu, AAAguaagua (SEQ ID NO: 1), AAAguacau, AAAguaga, AAAguauug, AAAguaugu, AAAgugagug (SEQ ID NO: 2), AAAgugaguu (SEQ ID NO: 3), AACaugagga (SEQ ID NO: 4), AACguaagu, AACgugacu, AACgugauu, AAGaugagc, AAGauuugu, AAGgaugag, AAGgcaaaa, AAGgcaaggg (SEQ ID NO: 5), AAGgcaggga (SEQ ID NO: 6), AAGgaaaaa, AAGgtatgag (SEQ ID NO: 72), AAGguaaagg, AAGguaaau, AAGguaaca, AAGguaacaug (SEQ ID NO: 8), AAGguaacu, AAGguaagcc (SEQ ID NO: 9), AAGguaagcg (SEQ ID NO: 10), AAGguaauaa (SEQ ID NO: 11), AAGguaaugu (SEQ ID NO: 12), AAGguaaugua (SEQ ID NO: 13), AAGguacag, AAGguacgg, AAGguacug, AAGguagacc (SEQ ID NO: 14), AAGguagag, AAGguagcg, AAGguagua, AAGguagug, AAGguauac, AAGguauau, AAGguauauu (SEQ ID NO: 15), AAGguauca, AAGguaucg, AAGguaucu, AAGguauga, AAGguaugg, AAGguaugu, AAGguauuu, AAGgucaag, AAGgucaau, AAGgucucu, AAGgucuggg (SEQ ID NO: 16), AAGgucugu, AAGgugaccuu (SEQ ID NO: 17), AAGgugagau (SEQ ID NO: 18), AAGgugaguc (SEQ ID NO: 19), AAGgugccu, AAGgugggcc (SEQ ID NO: 20), AAGgugggu, AAGguggua, AAGguguau, AAGgugucu, AAGgugugc, AAGgugugu, AAGguguua, AAGguuaag, AAGguuagc, AAGguuagug (SEQ ID NO: 21), AAGguuca, AAGguuuaa, AAGguuuau, AAGguuugg, AAGuuaagg, AAGuuaaua, AAGuuagga, AAUguaaau, AAUguaagc, AAUguaagg, AAUguaauu, AAUguaugu, AAUgugagu, AAUgugugu, ACAguaaau, ACAgugagg, ACAguuagu, ACAguuuga, ACCaugagu, ACCgugaguu (SEQ ID NO: 22), ACGauaagg, ACGcuaagc, ACGguagcu, ACGgugaac, ACGgugagug (SEQ ID NO: 23), ACUguaaau, ACUguaacu, ACUguauu, ACUgugagug (SEQ ID NO: 24), AGAguaaga, AGAguaagg, AGAguaagu, AGAguagau, AGAguaggu, AGAgugaau, AGAgugagc, AGAgugagu, AGAgugcgu, AGCguaagg, AGCguacgu, AGCguaggu, AGCgugagu, AGGguaauga (SEQ ID NO: 25), AGGguagac, AGGguauau, AGGgugaau, AGGgugagg, AGGgugauc, AGGgugcaa, AGGgugucu, AGUguaagc, AGUguaagu, AGUgugagu, AGUgugaguac (SEQ ID NO: 26), AUAgucagu, AUAgugaau, AUCgguaaaa (SEQ ID NO: 27), AUCguuaga, AUGguaaaa, AUGguaacc, AUGguacau, AUGguaugu, AUGguauuu, AUGgucauu, AUGgugacc, AUUuuaagc, CAAGguaccu (SEQ ID NO: 28), CAAguaaac, CAAguaacu, CAAguaagc, CAAguaagg, CAAguaagua (SEQ ID NO: 29), CAAguaau, CAAguaugu, CAAguauuu, CAAgugaaa, CAAgugagu, CACgugagc, CACguuggu, CAGauaacu, CAGaugagg, CAGauuggu, CAGcugugu, CAGgcuggu, CAGgtaaggc (SEQ ID NO: 73), CAGguaaaa, CAGguaaag, CAGguaaccuc (SEQ ID NO: 31), CAGguaagac (SEQ ID NO: 32), CAGguaagc, CAGguaagu, CAGguaau, CAGguaaugc (SEQ ID NO: 33), CAGguaaugu (SEQ ID NO: 34), CAGguacaa, CAGguacag, CAGguacagu (SEQ ID NO: 35), CAGguaccg, CAGguacug, CAGguagag, CAGguagcaa (SEQ ID NO: 36), CAGguaggagg (SEQ ID NO: 37), CAGguaggc, CAGguagguga (SEQ ID NO: 38), CAGguagua, CAGguagug, CAGguauag, CAGguauau, CAGguaucc, CAGguauga, CAGguaugg, CAGguaugu, CAGguauug, CAGgucaau, CAGgucagug (SEQ ID NO: 39), CAGgucuga, CAGgucugga (SEQ ID NO: 40), CAGgucuggu (SEQ ID NO: 41), CAGgucuuu, CAGgugagc, CAGgugaggg (SEQ ID NO: 42), CAGgugagugg (SEQ ID NO: 43), CAGgugaua, CAGgugcac, CAGgugcag, CAGgugcgc, CAGgugcug, CAGguggau, CAGguggggug (SEQ ID NO: 44), CAGgugua, CAGguguag, CAGguguau, CAGguguga, CAGgugugu, CAGguuaag, CAGguugau, CAGguugcu, CAGguuggc, CAGguuguc, CAGguuguu, CAGguuuagu (SEQ ID NO: 45), CAGguuugc, CAGguuugg, CAGuuuggu, CAUggaagac (SEQ ID NO: 46), CAUguaau, CAUguaauu, CAUguaggg, CAUguauuu, CCAguaaac, CCAgugaga, CCGguaacu, CCGgugaau, CCGgugacu, CCGgugagg, CCUauaagu, CCUaugagu, CCUguaaau, CCUguaagc, CCUguaauu, CCUgugaau, CCUgugauu, CGAguccgu, CGCauaagu, CGGguaau, CGGguauau, CGGguaugg, CGGgucauaac (SEQ ID NO: 47), CGGgugggu, CGGguguau, CGGgugugu, CGUgugaau, CGUgugggu, CUGguauga, CUGgugaau, CUGgugaguc (SEQ ID NO: 48), CUGgugaguuc (SEQ ID NO: 49), CUGgugcau, CUGgugcuu, CUGguguga, CUGguuugu, CUGuuaag, CUGuugaga, GAAggaagu, GAAguaaac, GAAguaaau, GAAgucugg, GAAguggg, GAAgugugu, GAAuaaguu, GACaugagg, GAUcugagg, GAGaugagg, GAGCAGguaagcu (SEQ ID NO: 50), GAGcugcag, GAGgcaggu, GAGgcgugg, GAGgcuccc, GAGgtgggttt (SEQ ID NO: 74), GAGguaaag, GAGguaaga, GAGguaagag (SEQ ID NO: 52), GAGguaagcg (SEQ ID NO: 53), GAGguaauac (SEQ ID NO: 54), GAGguaauau (SEQ ID NO: 55), GAGguaaugu (SEQ ID NO: 56), GAGguacaa, GAGguagga, GAGguauau, GAGguauga, GAGguaugg, GAGgucuggu (SEQ ID NO: 57), GAGgugaag, GAGgugagg, GAGgugca, GAGgugccu, GAGgugcggg (SEQ ID NO: 58), GAGgugcug, GAGguguac, GAGguguau, GAGgugugc, GAGgugugu, GAGuuaagu, GAUaugagu, GAUguaaau, GAUguaagu, GAUguaauu, GAUguaua, GAUgugacu, GAUgugagg, GAUgugauu, GCAguaaau, GCAguagga, GCAguuagu, GCGaugagu, GCGgagagu, GCGguaaaa, GCGguaauca (SEQ ID NO: 59), GCGgugacu, GCGgugagca (SEQ ID NO: 60), GCGgugagcu (SEQ ID NO: 61), GCGguggga, GCGguuagu, GCUguaaau, GCUguaacu, GCUguaauu, GGAguaagg, GGAguaagu, GGAguaggu, GGAgugagu, GGAguuagu, GGCguaagu, GGCgucagu, GGGauaagu, GGGaugagu, GGGgtaagtg (SEQ ID NO: 75), GGGguaaau, GGGguaacu, GGGguacau, GGGgugacg, GGGgugagug (SEQ ID NO: 63), GGGgugcau, GGGguuggga (SEQ ID NO: 64), GGUguaagu, GUUCUCAgugug (SEQ ID NO: 66), UCAgugug, GUAgugagu, GUGguaagu, GUGguaagug (SEQ ID NO: 65), GUGgugagc, GUGgugagu, GUGgugauc, GUGguugua, GUUauaagu, GUUguaaau, GUUuugguga (SEQ ID NO: 67), UAGCAGguaagca (SEQ ID NO: 68), TGGgtacctg (SEQ ID NO: 76), UAGaugcgu, UAGguaaag, UAGguaccc, UAGguaggu, UAGguauau, UAGguauc, UAGguauga, UAGguauug, UAGgucaga, UAGgugcau, UAGguguau, UCAguaaac, UCAguaaau, UCAguaagu, UCAgugauu, UCCgugaau, UCCgugacu, UCCgugagc, UCUguaaau, UGAgugaau, UGGauaagg, UGGguaaag, UGGguacca, UGGguaugc, UGGguggau, UGGguggggg (SEQ ID NO: 70), UGGguggggug (SEQ ID NO: 71), UGGgugugg, UGGguuagu, UGUgcaagu, UGUguaaau, UGUguacau, UUAguaaau, UUCauaagu, UUGguaaag, UUGguaaca, UUGguacau, UUGguagau, UUGgugaau, UUGgugagc, UUUauaagc or UUUgugagc.

In some embodiments, an SMSM modulates splicing of a splice site sequence comprising a sequence of Table 2B. In some embodiments, an SMSM modulates splicing of a splice site sequence comprising a sequence AAAauaagu, AAGaugagc, AAGauuugu, AAGgaugag, AAGgcaaaa, AAGuuaagg, AAGuuaaua, AAGuuagga, ACCaugagu, ACGauaagg, ACGcuaagc, AGGguauau, AGGgugagg, AGGgugauc, AGGgugucu, AUGgugacc, AUUuuaagc, CAAgugagu, CACgugagc, CACguuggu, CAGauaacu, CAGaugagg, CAGaugagu, CAGauuggu, CAGcugugu, CAGgcgagu, CAGgcuggu, CAGgugacu, CAGguugau, CAGguugcu, CAGguuggc, CAGguuguu, CAGuuuggu, CAUguaggg, CAUguauuu, CCGgugaau, CCUauaagu, CCUaugagu, CCUgugaau, CGCauaagu, CGGguguau, CUGuuaag, CUGuugaga, GAAggaagu, GAAguaaau, GAAgucugg, GAAgugggg, GAAgugugu, GAAuaaguu, GACaugagg, GAGaucugg, GAGaugagg, GAGgcaggu, GAGgcgugg, GAGgcuccc, GAGguaaga, GAGguagga, GAGgugagg, GAGuuaagu, GAUaugagu, GAUaugagu, GCAguagga, GCGaugagu, GCGgagagu, GCGgugacu, GCGguuagu, GCUguaacu, GGGaugagu, GUAgugagu, GUGgugagc, GUGgugauc, UAGaugcgu, UGGauaagg, UGGguacca, UGGguggau, UGGguggggug (SEQ ID NO: 71), UGUgcaagu, UUCauaagu, UUGguaaca, UUUauaagc or UUUgugagc.

In some embodiments, an SMSM modulates splicing of a splice site sequence comprising a sequence of Table 2C or Table 2D. In some embodiments, an SMSM modulates splicing of a splice site sequence comprising a sequence NGAguaag.

In some embodiments, an SMSM modulates splicing of a splice site sequence comprising a sequence of Table 2C. In some embodiments, an SMSM modulates splicing of a splice site sequence comprising a sequence AGAguaag.

In some embodiments, an SMSM modulates splicing of a splice site sequence comprising a sequence of Table 2D. In some embodiments, an SMSM modulates splicing of a splice site sequence comprising a sequence GGAguaag.

TABLE 2A

Exemplary targets

| Gene | Disease | Splice Site Sequence | SEQ ID NO: | Description | Exon |
|---|---|---|---|---|---|
| ABCA4 | Stargardt disease, Macular Degeneration, Age-Related | GAGguaaag | | Non-mutated 5' bulge | 3 |
| | | CGGguaugg | | Non-mutated 5' bulge | 4 |
| | | AGUguaagc | | Non-mutated 5' bulge | 13 |
| | | CCAguaaac | | IVS20+5G>A | 20 |
| | | CAGgugcac | | IVS28+5G>A | 28 |
| | | AUGguacau | | IVS40+5G>A | 40 |
| | | AGAguaggu | | Non-mutated 5' bulge | 6 |
| | | AAGguacug | | Non-mutated 5' bulge | 11 |
| | | GGAguaggu | | Non-mutated 5' bulge | 20 |
| ABCD1 | X-linked adrenoleukodystrophy (X-ALD) | GAAguggg | | IVS1-1G>A | 1 |
| ACADM | Medium-chain acyl-coA DH deficiency | AAGguaaau | | IVS7+6G>U Mutated 5' bulge | 8 |
| ACADSB | 2-methylbutyryl-CoA dehydrogenase deficiency | GGGgugcau | | IVS3+3A>G | 3 |
| ADA | Adenosine deaminase deficiency | CCAgugaga | | IVS5+6U>A | 5 |
| ADAMTS13 | Thrombotic thrombocytopenic purpura | AGGguagac | | IVS13+5G>A | 13 |
| AGL | Glycogen Storage Disease Type III | GGCguaagu | | Non-mutated 5' bulge | 1 |
| | | CUGguauga | | IVS6+3A>G | 6 |
| | | AAGguagug | | Non-mutated 5' bulge | 28 |
| | | AGAguaagu | | Non-mutated 5' bulge | 31 |
| AGT | Treatment Resistant Hypertension | AAGguaagcc | 9 | Non-mutated 5'ss | 1 |
| ALB | Analbuminemia | AACaugagga | 4 | c.1652+1 G>A | 12 |
| ALDH3A2 | Cancer, non-small cell lung cancer, Sjögren-Larrson syndrome | CAGgucuggu | 41 | Non-mutated 5' bulge | 2 |
| | | AAGguuuau | | IVS5+5G>A | 5 |
| ALG6 | ALG6-congenital disorder of glycosylation, ALG6-CDG | UGUguaaau | | IVS3+5G>A | 3 |
| ANGPTL3 | Lipid disorders, Rare hyperlipidemias. Nonalcoholic fatty liver disease (NAFLD), Metabolic complications, Homozygous familial hypercholesterolemia (HoFH), Familial chylomicronemia syndrome (FCS) | AAAguaagua | 1 | Non-mutated 5'ss | 1 |
| APC | Colorectal cancer, Familial adenomatous polyposis | CAAguaugu | | IVS9+3A>G | 9 |
| | | CAAguauuu | | IVS9+5G>U | 9 |
| | | CAGguauau | | IVS14+3A>G | 14 |
| APOA1 | | UGGguaccug | 69 | Non-mutated 5'ss | 1 |
| APOB | Familial hypercholesterolemia, hypercholesterolemia Homozygous hypobetalipoproteinemia, familial hypercholesterolemia | AGAguaagu | | Non-mutated 5' bulge | 13 |
| | | AAGgcaaaa | | IVS24+2 U>C | 24 |
| APOC3 | Familial Chylomicronemia Syndrome (FCS) and familial partial lipodystrophy (FPL) | CAGguaaugc | 33 | Non-mutated 5'ss | 1 |

TABLE 2A-continued

Exemplary targets

| Gene | Disease | Splice Site Sequence | SEQ ID NO: | Description | Exon |
|---|---|---|---|---|---|
| AR | Androgen Sensitivity, prostate cancer | CUGuuaag | | IVS4+1G>U | 4 |
| | | UUAguaaau | | IVS6+5G>A | 6 |
| ATM | Ataxia-Telangiectasia, cancer | AAGguagua | | Non-mutated 5' bulge | 2 |
| | | UAGguauau | | IVS7+5^dG>A | 7 |
| | | CAGguacag | | Non-mutated 5' bulge | 8 |
| | | UUGguaaag | | Non-mutated 5' bulge | 9 |
| | | AAGguuuaa | | IVS9+3A>U | 9 |
| | | AUCguuaga | | IVS21+3A>U | 21 |
| | | AUCgguaaaa | 27 | IVS21+5^dG>A | 21 |
| | | AAGgucucu | | Non-mutated 5' bulge | 35 |
| | | GAGguaaugu | 56 | Non-mutated 5' bulge | 38 |
| | | CAGauaacu | | IVS45+1G>A | 45 |
| | | GAGguaaag | | Non-mutated 5' bulge | 61 |
| ATP7A | Occipital Horn Syndrome, Menkes Disease | AAGguaaugu | 12 | Non-mutated 5' bulge | 3 |
| | Occipital Horn Syndrome | GUUguaaau | | IVS6+5G>A | 6 |
| | Menkes Disease | GUUauaagu | | IVS6+1G>A | 6 |
| | Occipital Horn Syndrome, Menkes Disease | AAGguaaag | | Non-mutated 5' bulge | 10 |
| | Occipital horn syndrome | AAGguaaag | | IVS10+3A>U Mutated 5' bulge | 10 |
| | Menkes Disease | CAGgucuuu | | IVS11+3A>C (mouse model), consistent with patient | 11 |
| | Occipital Horn Syndrome, Menkes Disease | CAAguaaac | | IVS17+5G>A | 17 |
| | | CUGguuugu | | IVS21+3A>U | 21 |
| ATP7B | Wilson's disease | AAAgugaguu | 3 | Non-mutated 5'ss | 1 |
| ATR | Seckel syndrome 1 | CAGguauug | | Non-mutated 5' bulge | 19 |
| | | CAGgucuga | | Non-mutated 5' bulge | 28 |
| ATXN2 | Spinocerebellar ataxia type 2 (SCA2), ALS | CAGgugggug | 44 | Non-mutated 5'ss | 1 |
| | | GAGguggguuu | 51 | Non-mutated 5'ss | 5 |
| ATXN3 | Spinocerebellar ataxia type 3 (SCA3) | AAAgugagug | 2 | Non-mutated 5'ss | 1 |
| B2M | Cancer, colorectal cancer | AGCgugagu | | Non-mutated 5' bulge | 1 |
| BCL2-like 11 (BIM) | Autoimmune disease, tumor development, Chronic Myeloid Leukemia drug resistance | AGGguaauga | 25 | Non-mutated 5'ss | 3,4 |
| | | GUUuugguga | 67 | | |
| BMP2K | Cancer | CAAguaagg | | Mutation inducing loss of U1snRNA affinity | 14 |
| BRCA1 | Breast Cancer | UGGguaaag | | Non-mutated 5' bulge | 1 |
| | | AAGguguau | | IVS5+3A>G | 5 |
| | | AGGguauau | | IVS5-2A>G | 5 |
| | | AAGgugugc | | IVS13+6U>C | 13 |
| | | UUUgugagc | | IVS16+6U>C | 16 |
| | | UCUguaaau | | IVS18+5G>A | 18 |
| | | ACAguaaau | | IVS22+5G>A | 22 |
| BRCA2 | Breast Cancer | CAGguguga | | IVS5+3A>G | 5 |
| | | UAGguauug | | Non-mutated 5' bulge | 14 |
| | | CAGguauga | | Non-mutated 5' bulge | 19 |
| BTK | Isolated growth hormone deficiency type III, X-linked agammaglobulinemia (XLA), Cancer, Autoimmune disorders | AAGguggua | | Non-mutated 5' bulge | 2 |
| | | GAAguaaac | | IVS6+5G>A | 6 |
| | | GAUguagagg | | IVS14+6U>G | 14 |
| C3 | Hereditary C3 deficiency | UGGguaagg | | IVS18+1G>A | 18 |
| CACNA1B | Pain, tactile neuropathic allodynia | GUGguaagug | 65 | Non-mutated 5'ss | 37a |
| | | AAGguagacc | 14 | Non-mutated 5'ss | 37b |
| CACNA1C | Type 1 Timothy's syndrome | GAGCAGguaagcu | 50 | G406R (G>A) | 8a |
| | Type 2 Timothy's syndrome | UAGCAGguaagca | 68 | G406R (G>A) | 8 |
| | | GUUCUCAgugug | 66 | G402R (G>A) | 8 |
| CALCA | CGRP-related migraines | CAUggaagac | 46 | Non-mutated 5'ss | 4 |
| CAT | Acatalasemia and Pityriasis Versicolor, Autoimmune disease, cancer | UUGguagau | | IVS4+5G>A | 4 |
| CD33 | Alzheimer's disease, acute myeloid leukemia | CAGgugagugg | 43 | Non-mutated 5'ss | 1 |
| CD46 | Autoimmune disorders, cancer, atypical hemolytic uremic syndrome (aHUS), multiple sclerosis, rheumatoid arthritis, age-related macular degeneration, asthma | CAGguuuagu | 45 | Non-mutated 5'ss | 7 |
| | | CAGguuuagu | 45 | Non-mutated 5'ss | 8 |
| | | AAGguaucu | | Non-mutated 5'ss | 13 |
| CDH1 | Cancer, hereditary diffuse gastric cancer syndrome | CAGguggau | | IVS14+5G>A | 14 |
| CDH23 | Usher Syndrome and Nonsyndromic Deafness | ACGgugaac | | IVS51+5G>A | 51 |
| | | AGCguaagg | | Non-mutated 5' bulge | 54 |
| CFB (Complement factor B) | Hemolytic Uremic Syndrome, Atypical 4 and Complement Factor B Deficiency | GAGguaagcg | 53 | Non-mutated 5'ss | 1 |
| CFTR | Cystic Fibrosis | CAUguaau | | -1G>U Mutated 5' bulge | 8 |
| | | AAAguaug | | -1G>A Mutated 5' bulge | 19 |
| | | AAGuuaaua | | IVS4+1G>U | 4 |
| | | ACAguauagu | | IVS6b+3^d | 6b |

TABLE 2A-continued

Exemplary targets

| Gene | Disease | Splice Site Sequence | SEQ ID NO: | Description | Exon |
|---|---|---|---|---|---|
| | | CAGguaaugu | 34 | Non-mutated 5' bulge | 8 |
| | | AAAguaugu | | c.1766–1G>A | 12 |
| | | AAUguaugu | | c.1766–1G>U | 12 |
| | | AAGguauuu | | IVS12+5G>U | 12 |
| | | AAGgugugu | | c. 1766+3A>G | 12 |
| | | AAGgucugu | | c. 1766+3A>C | 12 |
| | | AAGguauga | | Non-mutated 5' bulge | 19 |
| | | CACgugagc | | IVS20–1G>C | 20 |
| CHM | Choroideremia | UAGgucaga | | IVS13+3A>C | 13 |
| CLCNI | Myotonia congenita | CAGguuaag | | IVS1+3A>U Mutated 5' bulge | 1 |
| COL11A1 | Stickler syndrome, Cancer, Marshall syndrome | GAGguaauac | 54 | Non-mutated 5' bulge | 7 |
| | | AGCguaagu | | Non-mutated 5' bulge | 8 |
| | | AGAguaagu | | Non-mutated 5' bulge | 29 |
| | | AAGguauca | | Non-mutated 5' bulge | 34 |
| | | GGCguaagu | | Non-mutated 5' bulge | 50 |
| | | GGCgucagu | | IVS50+3A>C | 50 |
| | | GGAguaagu | | Non-mutated 5' bulge | 64 |
| COL11A2 | Otospondylomegaepiphyseal Dysplasia, Stickler syndrome | CCUgugaau | | IVS53+5G>A | 53 |
| COL1A1 | Severe type III osteogenesis imperfecta | GGAguaagu | | Non-mutated 5' bulge | 5 |
| | | UCAguaaac | | IVS8+5G>A | 8 |
| | | CCUaugagu | | IVS8+1G>A | 8 |
| | | AGAgugagu | | Non-mutated 5' bulge | 11 |
| | | GCUguaaau | | IVS14+5G>A | 14 |
| | | AGCgugagu | | Non-mutated 5' bulge | 19 |
| | | AGAguaagu | | Non-mutated 5' bulge | 30 |
| COL1A2 | Osteogenesis imperfecta | AGAguagau | | IVS21+5G>A Mutated 5' bulge | 21 |
| | | GAUguaaau | | IVS9+5G>A | 9 |
| | | AGAguaggu | | Non-mutated 5' bulge | 21 |
| | | AGAguaagu | | Non-mutated 5' bulge | 23 |
| | | CGGgugggu | | IVS26+3A>G | 26 |
| | | AGAguaagu | | Non-mutated 5' bulge | 30 |
| | | CGUgugaau | | IVS33+5G>A | 33 |
| | | CGUgugggu | | IVS33+4A>G | 33 |
| | | GCUguaaau | | IVS40+5G>A | 40 |
| COL2A1 | Chondrodysplasias, familial osteoarthritis | GUGguugua | | Non-mutated 5' bulge | 2 |
| | | GGAguaagu | | Non-mutated 5' bulge | 7 |
| | | AGAguaagu | | Non-mutated 5' bulge | 13 |
| | | CCUgugauu | | IVS20+5G>U | 20 |
| | | UCUguaaau | | IVS24+5G>A | 24 |
| | | AGAguaagu | | Non-mutated 5' bulge | 49 |
| COL3A1 | Ehlers-Danlos syndrome | CCUguaagc | | IVS7+6U>C | 7 |
| | | UCAguaaau | | IVS8+5G>A | 8 |
| | | AGAguaagu | | Non-mutated 5' bulge | 10 |
| | | GCAguuagu | | IVS14+3G>U | 14 |
| | Ehlers-Danlos syndrome IV | CCUauaagu | | IVS16+1G>A | 16 |
| | | CGCauaagu | | IVS20+1G>A | 20 |
| | Ehlers-Danlos syndrome | GAUgugauu | | IVS25+5G>U | 25 |
| | | ACUguaaau | | IVS27+5G>A | 27 |
| | | ACUguauu | | IVS27+5G>U | 27 |
| | | AAGguagua | | Non-mutated 5' bulge | 29 |
| | | GCUguaauu | | IVS37+5G>U | 37 |
| | | CCUguaaau | | IVS38+5G>A | 38 |
| | | CCUguaauu | | IVS38+5G>U | 38 |
| | | GAUgugacu | | IVS42+5G>C | 42 |
| | Ehlers-Danlos syndrome IV | GAUaugagu | | IVS42+1G>A | 42 |
| | Ehlers-Danlos syndrome | CCUguaaau | | IVS45+5G>A | 45 |
| | | AGAguaagu | | Non-mutated 5' bulge | 46 |
| COL4A5 | Alport syndrome | AGAguaagu | | Non-mutated 5' bulge | 4 |
| | | AGAguaagu | | Non-mutated 5' bulge | 15 |
| | | AAGgucuggg | 16 | Non-mutated 5' bulge | 28 |
| | | CAGgugcug | | Non-mutated 5' bulge | 39 |
| | | CAGguaaag | | Non-mutated 5' bulge | 52 |
| COL6A1 | Mild Bethlem myopathy | GGGgaugagu | | IVS3+1G>A | 3 |
| | Autosomal-recessive isolated dystonia, dystonia | AAGguaugg | | Non-mutated 5' bulge | 4 |
| | | CAGguaugg | | Non-mutated 5' bulge | 6 |
| | | AAGguacgg | | Non-mutated 5' bulge | 14 |
| | | AAAguacau | | IVS29+5G>A | 29 |
| | | AGUguaagu | | Non-mutated 5' bulge | 38 |

TABLE 2A-continued

Exemplary targets

| Gene | Disease | Splice Site Sequence | SEQ ID NO: | Description | Exon |
|---|---|---|---|---|---|
| COL7A1 | Recessive dystrophic epidermolysis bullosa | AGGgugauc | | IVS3−2A>G | 3 |
| | Dominant dystrophic epidermolysis bullosa | CAGguauag | | Non-mutated 5' bulge | 23 |
| | | CAGguuugg | | Non-mutated 5' bulge | 24 |
| | | CAGguuugg | | Non-mutated 5' bulge | 27 |
| | | AGGgugagg | | Non-mutated 5'ss | 73 |
| | Recessive dystrophic epidermolysis bullosa | GUAgugagu | | IVS95−1G>A | 95 |
| COL9A2 | Multiple epiphyseal dysplasia | CCGgugagg | | IVS3+6U>G | 3 |
| | | CCGgugacu | | IVS3+5G>C | 3 |
| COLQ | Congenital acetylcholinesterase deficiency | UGGguggggg | 70 | IVS16+3A>G | 16 |
| CREBBP | Rubinstein-Taybi syndrome | AAGguuca | | +3A>U Mutated 5' bulge | 18 |
| CSTB | Epilepsy progressive myoclonus | AAAguaga | | −1G>A Mutated 5' bulge | 2 |
| CUL4B | X-linked intellectual disability, cancer | CAGguaaaa | | Non-mutated 5' bulge | 14 |
| CYBB | X-linked chronic granulomatous disease | GGGguaaau | | IVS2+5G>A | 2 |
| | | GCGguaaaa | | IVS3+5G>A | 3 |
| | | AAGguuagc | | IVS5+3A>U | 5 |
| | | UGAgugaau | | IVS6+5G>A | 6 |
| CYP17 | Congenital adrenal hyperplasia and 17-hydroxylase deficiency | UCAgugauu | | IVS2+5G>U | 2 |
| | | CUGgugaau | | IVS7+5G>A | 7 |
| CYP19 | Placental aromatase deficiency | UGUgcaagu | | IVS6+2U>C | 6 |
| CYP27A1 | Cerebrotendineous xanthomatosis | AACgugauu | | IVS7+5G>U | 7 |
| | | GAGguagga | | IVS6−2C>A | 6 |
| | | GCAguagga | | IVS6−1G>A | 6 |
| DES | Desmin-related myopathy | GAGguguac | | IVS3+3A>G | 3 |
| DGAT2 | Nonalcoholic steatohepatitis (NASH) | GGGgugagug | 63 | Non-mutated 5'ss | 1 |
| DMD | Duchenne's muscular dystrophy, Duchenne and Becker muscular dystrophy | GAUguaagu | | Non-mutated 5' bulge | 5 |
| | | CAGguaaag | | Non-mutated 5' bulge | 8 |
| | | CAGgugugu | | Non-mutated 5' bulge | 14 |
| | | AUGgucauu | | IVS19+3A>C | 19 |
| | | AGAguaaga | | Non-mutated 5' bulge | 24 |
| | | AAGggaaaa | | IVS26+2U>G | 26 |
| | | CAGguauau | | c.4250U>A | 31 |
| | | CAGguauau | | Non-mutated 5' bulge | 31 |
| | | AAGguaugag | 7 | Non-mutated 5'ss | 51 |
| | | CAAguaacu | | IVS62+5G>C | 62 |
| | | GCUguaacu | | IVS64+5G>C | 64 |
| | | GCUguaacu | | IVS64+5G>C | 64 |
| | | GAUguaauu | | IVS66+5G>U | 66 |
| | | CCGguaacu | | IVS69+5G>C | 69 |
| | | AACgugacu | | IVS70+5G>C | 70 |
| DUX4 | FSHD | GGGguuggga | 64 | Non-mutated 5'ss | 1 |
| DYSF | Limb Girdle Muscular Dystrophy 2B, Miyoshi myopathy, Miyoshi Muscular Dystrophy 1 | AGAgugcgu | | Non-mutated 5' bulge | 13 |
| | | UGUguacau | | IVS45+5G>A | 45 |
| EGFR | Cancer | AACguaagu | | Non-mutated 5'ss | 4 |
| | | ACAguuuga | | Non-mutated 5' bulge | 9 |
| | | GUGgugagu | | Non-mutated 5' bulge | 22 |
| EMD | Emery-Dreifuss muscular dystrophy | UAGguaccc | | IVS1+5G>C | 1 |
| ETV4 | Ovarian Cancer | GAGcugcag | | Non-mutated 5' bulge | 5 |
| F13A1 | Cancer | UUGgugagc | | IVS3+6C>U | 3 |
| | | UUGgugaau | | IVS3+5G>A | 3 |
| F5 | Factor V deficiency | AAGguaacu | | Non-mutated 5' bulge | 1 |
| | | CAUguauuu | | IVS10−1G>U | 10 |
| | | AAGguuugg | | Non-mutated 5' bulge | 13 |
| | | UGGguuagu | | IVS19+3A>U | 19 |
| | | AAGgucaag | | Non-mutated 5' bulge | 23 |
| | | AAGguagag | | Non-mutated 5' bulge | 24 |
| F7 | Factor VII deficiency | UGGgugggau | | IVS7+5G>A | 7 |
| | | UGGgugggug | 71 | IVS7+7A>G | 7 |
| | | UGGguacca | | IVS7del[+3:+6] | 7 |
| F8 | Hemophilia A | AGGgugaau | | IVS3+5G>A | 3 |
| | | CAGgugugu | | IVS6+3A>G | 6 |
| | | CAGguguga | | IVS14+3A>G | 14 |
| | | AUUgugaau | | IVS19+5G>A | 19 |
| | | AUGguauuu | | IVS22+5G>U | 22 |
| | | AUAgucagu | | IVS23+3A>C | 23 |

TABLE 2A-continued

Exemplary targets

| Gene | Disease | Splice Site Sequence | SEQ ID NO: | Description | Exon |
|---|---|---|---|---|---|
| F11 | Factor XI, clotting disorders | CAGguacagu | 35 | Non-mutated 5' ss | 1 |
| FAH | Tyrosinemia type 1, Chronic Tyrosinemia Type 1 | AAGguaugu | | Non-mutated 5' bulge | 11 |
| | | CCGgugaau | | IVS12+5G>A | 12 |
| FANCA | Fanconi Anemia | AGAguaaga | | Non-mutated 5' bulge | 4 |
| | | AAGguagcg | | Non-mutated 5' bulge | 6 |
| | | CUGgugcau | | IVS7+5G>A | 7 |
| | | CUGgugcuu | | IVS7+5G>U | 7 |
| | | GAGgugcug | | Non-mutated 5' bulge | 10 |
| | | CGAguccgu | | IVS16+3A>C | 16 |
| FANCC | Fanconi anemia | AAUgugugu | | IVS4+4A>U | 4 |
| FANCG | Fanconi Anemia, Complementation Group G and Fanconi Anemia, Complementation Group A | CAGgugaua | | IVS4+3A>G | 4 |
| FBN1 | Marfan Syndrome | UUGguacau | | IVS11+5G>A | 11 |
| | | GAGguaugg | | Non-mutated 5' bulge | 13 |
| | | AAGguaauaa | 11 | Non-mutated 5' bulge | 14 |
| | | CAGgucaau | | IVS25+5G>A | 25 |
| | | CAUguaauu | | IVS37+5G>U | 37 |
| | | UAGgugcau | | IVS46+5G>A | 46 |
| | | UAGaugcgu | | IVS46+1G>A | 46 |
| | | AAGguaaag | | Non-mutated 5' bulge | 60 |
| FECH | Erythropoietic protoporphyria | UAGguauc | | −3A>U Mutated 5' bulge | 10 |
| | | GAGguauga | | Non-mutated 5' bulge | 2 |
| | | CAGguaugg | | Non-mutated 5' bulge | 4 |
| | | AAGgugucu | | IVS10+3A>G | 10 |
| | | AAGguaucu | | Non-mutated 5' bulge | 10 |
| FGA | Common congenital afibrinogenemia | UGGgugugg | | IVS1+3A>G | 1 |
| | | GAGguuaagu | | IVS4+1G>U | 4 |
| FGFR2 | Craniosynostosis syndromes, cancer | AGAguaagu | | Non-mutated 5' bulge | 3 |
| | | CAGguguau | | IVS3c+3A>G | 3c |
| FGG | Dysfibrinogenaemia | GCAguaaau | | IVS1+5G>A | 1 |
| | | CAAgugaaa | | IVS3+5G>A | 3 |
| FIX | Haemophilia B deficiency (coagulation factor IX deficiency) | CGGgucauaauc | 47 | c.519A>G | 5 |
| FLNA | X-linked cardiac valvular dysplasia | AGAguaagu | | Non-mutated 5' bulge | 19 |
| FOXM1 | Cancer | AAGguaaugu | 12 | Non-mutated 5' bulge | 4 |
| | | UCAguaagu | | Non-mutated bulge | 9 |
| FRAS1 | Fraser syndrome | AAGguacgg | | Non-mutated 5' bulge | 3 |
| | | GGAguagagu | | Non-mutated 5' bulge | 5 |
| | | AAGguauuu | | Non-mutated 5' bulge | 8 |
| | | AAGguaucg | | Non-mutated 5' bulge | 17 |
| | | AGCguaggu | | Non-mutated 5' bulge | 22 |
| | | AGAguaagu | | Non-mutated 5' bulge | 24 |
| | | CAGguacaa | | Non-mutated 5' bulge | 53 |
| GALC | NASH | GGAguuagu | | Non-mutated 5' bulge | 5 |
| GBA | Gaucher's disease | GAGguaagag | 52 | Non-mutated 5' ss | 2 |
| GCGR | Diabetes | GCGgugagca | 60 | Non-mutated 5' ss | 1 |
| GH1 | Growth hormone deficiency | UCCgugagc | | IVS3+6U>C | 3 |
| | | UCCgugaau | | IVS3+5G>A | 3 |
| | | UCCgugacu | | IVS3+5G>C | 3 |
| | | GGGgugacg | | IVS4+5G>C | 4 |
| | | GGGgugacg | | IVS4+5G>A | 4 |
| GHR | Acromegaly | GGGguaagug | 62 | Non-mutated 5' ss | 1 |
| GHV | Mutation in placenta | UUUauaagc | | IVS2+1G>A | 2 |
| GLA | Fabry's disease | AAGgugagau | 18 | Non-mutated 5' ss | 4 |
| HADHA | Trifunctional protein deficiency or LCHAD | AAGgugucu | | IVS3+3A>G | 3 |
| | | AGUguaagu | | Non-mutated 5' bulge | 18 |
| HBA2 | Alpha-thalassemia | GAGgcuccc | | IVS1 del[+2:+6] | 1 |
| HBB | Beta-thalassemia | CAGguuuguu | | IVS1+5G>U | 1 |
| | | CACguuggu | | IVS1−1G>C | 1 |
| | | CAGguuggc | | IVS1+6U>C | 1 |
| | | CAGauuggu | | IVS1+1G>A | 1 |
| | | CAGuuuggu | | IVS1+1G>U | 1 |
| | | CAGgcuggu | | IVS1+2U>C | 1 |
| | | CAGguugau | | IVS1+5G>A | 1 |
| | | CAGguugcu | | IVS1+5G>C | 1 |
| | | AGGgugucu | | IVS2 del[+4:+5] | 2 |
| HEXA | Tay-Sachs Syndrome | ACAguaaau | | IVS4+5G>A | 4 |
| | | CUGguguga | | IVS8+3A>G | 8 |
| | | GACaugagg | | IVS9+1G>A | 9 |

TABLE 2A-continued

Exemplary targets

| Gene | Disease | Splice Site Sequence | SEQ ID NO: | Description | Exon |
|---|---|---|---|---|---|
| HEXB | Sandhoff disease | UUGguaaca | | IVS8+5G>C | 8 |
| HLCS | Holocarboxylase synthetase deficiency | AAGgucaau | | IVS10+5G>A | 10 |
| HMBS | Acute intermittent porphyria | GCGguuagu | | IVS1+3G>U | 1 |
| | | GCGgugacu | | IVS1+5G>C | 1 |
| HMGCL | Hereditary HL deficiency | ACGcuaagc | | IVS7+1G>C | 7 |
| HNF1A | diabetes | AGCguaagu | | Non-mutated 5' bulge | 2 |
| HPRT1 | Somatic mutations in kidney tubular epithelial cells | GUGgugagc | | IVS1del[−2:+34] | 1 |
| | | GUGgugauc | | IVS1+5G>U | 1 |
| | Lesch-Nyhan syndrome | GAAggaagu | | IVS5+2U>G | 5 |
| | | GAAgugugu | | IVS5+3:4AA>GU | 5 |
| | | GAAguaaau | | IVS5+5G>A | 5 |
| | | GAAuaaguu | | IVS5del[G1] | 5 |
| | | ACUguaaau | | IVS7+5G>A | 7 |
| | Hypoxanthine phospho ribosyltransferase deficiency | ACUguaacu | | IVS7+5G>C | 7 |
| | | AAUguaagc | | IVS8+6U>C Mutation inducing loss of U1snRNA affinity | 8 |
| | | AAUguaagg | | IVS8+6U>G | 8 |
| | | AAUguaaau | | IVS8+5G>A | 8 |
| | | AAUguaauu | | IVS8+5G>U | 8 |
| HPRT2 | Primary hyperthyroidism | GGGauaagu | | IVS1+1G>A | 1 |
| HSF4 | Congenital cataracts | CAGguagug | | IVS12+4A>G | 12 |
| HSPG2 | Schwartz-Jampel syndrome type 1 | AGAgugagu | | Non-mutated 5'ss | 30 |
| | | AGAguaagu | | Non-mutated 5' ss | 40 |
| | | CAGguacag | | Non-mutated 5' ss | 61 |
| HTT | Huntington's disease | CAGguacug | | Non-mutated 5' ss | 25 |
| | | AAGguaaau | | Non-mutated 5'ss | 32 |
| | | AGAguaagu | | Non-mutated 5' ss | 51 |
| | | CUGgugaguc | 48 | Non-mutated 5' ss | 52 |
| | | ACCgugaguu | 22 | Non-mutated 5' ss | 1 |
| IDH1 | Gliomas | CAGguaaccuc | 31 | Non-mutated 5' ss | 1 |
| | | ACUgugagug | 24 | Non-mutated 5' ss | 1 |
| IDS | Mucopolysaccharidosis type II (Hunter syndrome) | AUGguaacc | | IVS7+5G>C | 7 |
| | | AUUuuaagc | | IVS7−1:+1GG>UU | 7 |
| IKBKAP | Familial Dysautonomia, Dysautonomia | CAAguaagc | | IVS20+6U>C Mutation inducing loss of U1snRNA affinity | 20 |
| | | CAGguaugu | | Non-mutated 5' ss | 27 |
| | | AGCguacgu | | Non-mutated 5' ss | 33 |
| IL7RA | Encodes IL7RA, Multiple sclerosis | AAGgugaccuu | 17 | Non-mutated 5'ss | 6 |
| INSR | Breast Cancer | GGCguaagu | | Non-mutated 5' bulge | 7 |
| | | AGUguaagu | | Non-mutated 5' bulge | 20 |
| ITGB2 | Leukocyte adhesion deficiency | UUCauaagu | | IVS7+1G>A | 7 |
| ITGB3 | Glanzmann thrombasthenia | GAUaugagu | | IVS4+1G>A | 4 |
| ITGB4 | Epidermolysis bullosa with congenital pyloric atresia | GAGgugccu | | Non-mutated 5' bulge | 4 |
| | | CAGguagua | | Non-mutated 5' bulge | 33 |
| JAG1 | Alagille syndrome | CGGgugugu | | IVS11+3A>G | 11 |
| | | AGAgugagu | | Non-mutated 5' bulge | 18 |
| KLKB1 | Hereditary angioedema | CAGguagcaa | 36 | Non-mutated 5'ss | 1 |
| KRAS | Cancer | CAGguaagu | | Splice switching on isoforms | 4a |
| KRT5 | Dowling-Meara epidermolysis bullosa simplex | AAGaugagc | | IVS1+1G>A | 1 |
| L1CAM | Cancer | AAUgugagu | | Non-mutated 5' bulge | 2 |
| | | AGAguaaga | | Non-mutated 5' bulge | 14 |
| | | CAGgugagc | | Non-mutated 5' bulge | 27 |
| | | CAGguaaggc | 30 | Non-mutated 5'ss | 1 |
| LAMA2 | Muscular dystrophy: merosin deficient | GAGgugca | | +3A>G Mutated 5' bulge | 1 |
| LAMA3 | Cancer, Junctional epidermolysis bullosa | CAGguaaag | | Non-mutated 5' bulge | 16 |
| | | AAGguaaugu | 12 | Non-mutated 5' bulge | 26 |
| | | CAGguagug | | Non-mutated 5' bulge | 27 |
| | | AGCguaagu | | Non-mutated 5' bulge | 31 |
| | | CAGguaccg | | Non-mutated 5' bulge | 40 |
| | | AAGguaaugu | 12 | Non-mutated 5' bulge | 45 |
| | | AGAgugagu | | Non-mutated 5' bulge | 50 |
| | | GAGguacaa | | Non-mutated 5' bulge | 57 |
| | | UGGguaugc | | Non-mutated 5' bulge | 64 |

TABLE 2A-continued

Exemplary targets

| Gene | Disease | Splice Site Sequence | SEQ ID NO: | Description | Exon |
|---|---|---|---|---|---|
| LDLR | Familial hypercholesterolemia | GAGgcgugg | | IVS12+2U>C | 12 |
| LGALS3 | NASH | GCGggagcu | 61 | Non-mutated 5'ss | 1 |
| LMNA | Hutchinson-Gilford progeria syndrome (HGPS) | CAAgugagu | | c.1968−1G>A | 10 |
| LPA | Hyperlipoproteinemia, Type Iii and Familial Hyperlipidemia | CAGguaagac | 32 | Non-mutated 5'ss | 1 |
| LPL | Familial hypercholesterolemia | ACGauaagg | | IVS2+1G>A | 2 |
| LRRK2 | Parkinson's disease | GCGguaauca | 59 | Non-mutated 5'ss | 1 |
| | | AAGguaacaug | 8 | Non-mutated 5'ss | 31 |
| | | CAGguagguga | 38 | Non-mutated 5'ss | 41 |
| MADD | Cancer, Glioblastoma | AAGguacag | | Non-mutated 5' bulge | 3 |
| | | AAGgugggu | | Non-mutated 5' bulge | 16 |
| | | AGAguaagg | | Non-mutated 5' bulge | 21 |
| MAPT | Frontotemporal Dementia | AGUguaagu | | IVS10+3G>A Mutated 5' bulge | 10 |
| | Alzheimer's disease, Frontotemporal dementia and parkinsonism linked to chromosome 17, Progressive supranuclear palsy (PSP), Corticobasal degeneration (CBD), Argyrophilic grain disease, Pick's disease | AGUgugagu | | Non-mutated 5' bulge | 10 |
| | | AGUgugaguac | 26 | Non-mutated 5'bulge | 10 |
| | | AAGguuagug | 21 | Non-mutated 5'ss | 1 |
| | | AAGgugggcc | 20 | Non-mutated 5'ss | 2 |
| | | CAGgugaggg | 42 | Non-mutated 5'ss | 3 |
| | | AAGguaagcg | 10 | Non-mutated 5'bulge | 5 |
| MET | Cancer | AAGguauauu | 15 | Non-mutated 5'ss | 14 |
| MLH1 | Colorectal cancer: non-polyposis | CGGguaau | | −2A>G Mutated 5' bulge | 6 |
| | | CAAguaau | | −1G>A Mutated 5' bulge | 18 |
| | Hereditary nonpolyposis colorectal cancer; Colorectal cancer: non-polyposis | CAGgugcag | | IVS6+3A>G Mutated 5' bulge | 6 |
| | Hereditary nonpolyposis colorectal cancer | CAGgugcag | | IVS18+3A>G | 18 |
| | | CAGguauag | | Non-mutated 5' bulge | 4 |
| | | CAGguacag | | Non-mutated 5' bulge | 6 |
| | | CAGguaaugu | 34 | Non-mutated 5' bulge | 10 |
| | | CAGguacag | | Non-mutated 5' bulge | 18 |
| MSH2 | Lynch syndrome | AAGguaaca | | Non-mutated 5' bulge | 7 |
| | | CAGguuugc | | Non-mutated 5' bulge | 10 |
| MST1R | Cancer, Breast cancer, Colon cancer | CAGguaggc | | Non-mutated | 11 |
| MTHFR | Severe deficiency of MTHFR | CAGaugagg | | IVS4+1G>A | 4 |
| MUT | Methylmalonic acidemia | AAGguauac | | Non-mutated 5' bulge | 3 |
| | | AAGguguua | | ISV8+3A>G | 8 |
| | | GAGguaauau | 55 | Non-mutated 5' bulge | 10 |
| MVK | Mevalonic aciduria | CAGguaucc | | Non-mutated 5' bulge | 4 |
| NF1 | Neurofibromatosis, Neurofibromatosis type 1 | UAGguguau | | IVS11+3A>G Mutated 5' bulge | 11 |
| | | GGGguaacu | | IVS3+5G>C | 3 |
| | Neurofibromatosis, Neurofibromatosis type I, Neurofibromatosis type II | CGGguguau | | IVS7+5G>A | 7 |
| | Neurofibromatosis, Neurofibromatosis type 1 | UAGguauau | | Non-mutated 5' bulge | 15 |
| | | CAGguaaag | | Non-mutated 5' bulge | 21 |
| | | GAGguaaga | | IVS27b del[+1:+10] | 27b |
| | | AAAauaagu | | IVS28+1G>A | 28 |
| | Neurofibromatosis | UAGguaaag | | Non-mutated 5' bulge | 34 |
| | | CAAGguaccu | 28 | c.6724−4C>U | 36 |
| | | AAGgugccu | | IVS36+3A>G | 36 |
| NF2 | Neurofibromatosis, Neurofibromatosis type II | GAGgugagg | | IVS12 del[−14:+2] | 12 |
| | | GAGaugagg | | IVS12+1G>A | 12 |
| NR1H4 | Nonalcoholic steatohepatitis (NASH) | CAAguaagua | 29 | Non-mutated 5'ss | 1 |
| OAT | OAT deficiency | CAGguuguc | | Non-mutated 5' bulge | 5 |
| OPA1 | Autosomal dominant optic atrophy | CGGguauau | | IVS8+5G>A | 8 |
| OTC | Ornithine transcarbamylase deficiency | GAGgugugc | | IVS7+3A>G | 7 |
| OXT | Pain, endometritis, Chorioamnionitis | AAGgugaguc | 19 | Non-mutated 5'ss | 1 |
| PAH | Phenylketonuria | CAGguguga | | IVS5+3A>G | 5 |
| | | AGAguaagu | | Non-mutated 5' bulge | 6 |
| | | CAGguguga | | IVS10+3A>G | 10 |
| | | GAGgugcggg | 58 | Non-mutated 5'ss | 1 |
| PBGD | Acute intermittent porphyria | GCGaugagu | | IVS1+1G>A | 1 |
| | | GCGgagagu | | IVS1+2U>A | 1 |
| | | GCGgugacu | | IVS1+5G>C | 1 |
| | | GCGguuagu | | IVS1+3G>U | 1 |
| | | CAUguaggg | | IVS10−1G>U | 10 |
| PCCA | Propionic acidemia | GGGguaagu | | Non-mutated 5' bulge | 14 |
| | | AAGguaugg | | Non-mutated 5' bulge | 18 |
| PDH1 | Pyruvate dehydrogenase deficiency | AAGguacag | | Non-mutated 5' bulge | 11 |
| PGK1 | Pyruvate dehydrogenase deficiency | AAGguuagga | | IVS4+1G>U | 4 |
| PHEX | X-linked hypophosphatemic rickets | AGAgugagu | | Non-mutated 5' bulge | 4 |
| | | AGAgugagu | | Non-mutated 5' bulge | 14 |

TABLE 2A-continued

Exemplary targets

| Gene | Disease | Splice Site Sequence | SEQ ID NO: | Description | Exon |
|---|---|---|---|---|---|
| PKD2 | Polycystic kidney disease | AGUguaagu | | Non-mutated 5' bulge | 13 |
| PKLR | Pyruvate kinase deficiency | CAGgucugga | 40 | Non-mutated 5' bulge | 7 |
| | | GCGguggga | | IVS9+3A>G | 9 |
| PKM1 | Cancer Cancer metabolism | CUGgugaguuc | 49 | Non-mutated 5'ss | 9 |
| PKM2 | Cancer, Cancer metabolism | CAGguaggagg | 37 | Non-mutated 5'ss | 10 |
| PLEKHM1 | Autosomal recessive osteopetrosis type 6 | AGAgugagu | | Non-mutated 5' bulge | 4 |
| PLKR | Lymphoblastic leukemia | AGUgugagu | | Non-mutated 5' bulge | 25 |
| POMT2 | Limb-girdle muscular dystrophy | GGAguaagg | | Non-mutated 5' bulge | 3 |
| | | CAGguaaugu | 34 | Non-mutated 5' bulge | 10 |
| | | AGAguaagu | | Non-mutated 5' bulge | 11 |
| | | AGUgugagu | | Non-mutated 5' bulge | 14 |
| PRDM1 | B-cell lymphoma | CAGgugcgc | | Non-mutated 5' bulge | 6 |
| PRKARIA | Carney complex. | GAGgugaag | | IVS8+3A>G | 8 |
| PROC | Protein C deficiency | ACAgugagg | | IVS3+3A>G | 3 |
| PSEN1 | Alzheimer's disease | CAGguacag | | Non-mutated 5' bulge | 3 |
| PTCHI | Basal cell carcinoma | GAGgugugu | | Non-mutated 5' bulge | 1 |
| PTEN | Cowden syndrome | GAGgcaggu | | IVS4+2U>C | 4 |
| | | AAGauuugu | | IVS7+1G>A | 7 |
| PYGM | Myophosphorylase deficiency (McArdle disease) | ACCaugagu | | IVS14+1G>A | 14 |
| RP6KA3 | Coffin Lowry Syndrome | GAGguguau | | IVS6+3A>G | 6 |
| RPGR | Retinitis pigmentosa | CAGgugua | | +3A>G Mutated 5' bulge | 4 |
| | | AAGguuugg | | Non-mutated 5' bulge | 3 |
| | | CAGguauag | | Non-mutated 5' bulge | 4 |
| | | CAGguguag | | IVS4+3A>G | 4 |
| | X-linked retinitis pigmentosa (RP3) | CUGuugaga | | IVS5+1G>U | 5 |
| | Retinitis pigmentosa | AGGgugcaa | | IVS10+3A>G | 10 |
| RSK2 | Coffin Lowry Syndrome | GAGguauau | | IVS6+3A>G | 6 |
| SBCAD | SBCAD deficiency | GGGguacau | | IVS3+3A>G | 3 |
| SCNA | Alpha-synuclein, Parkinson's disease, Dementia with Lewy bodies (DLB) | UAGguaggu | | Non-mutated 5'ss | 2 |
| | | CAGguaagc | | Non-mutated 5'bulge | 3 |
| | | GAGguagga | | Non-mutated 5'bulge | 5 |
| SCN5A | Cardiomyopathies | GGCguaagu | | Non-mutated 5' bulge | 4 |
| | | CAGgugugu | | Non-mutated 5' bulge | 8 |
| SERPINA1 | Emphysema | AAGguuaagg | | IVS2+1G>U | 2 |
| SH2D1A | Lymphoproliferative syndrome: X-linked | GAUguaua | | −1G>U Mutated 5' bulge | 2 |
| SLC12A3 | Gitelman syndrome | GGCguaagu | | Non-mutated 5' bulge | 22 |
| SLC6A8 | X-linked mental retardation | GGAguagagu | | Non-mutated 5' bulge | 3 |
| | | ACGguagcu | | IVS10+5G>C | 10 |
| SMN2 | Spinal muscular atrophy | GGAguaagu | | IVS7+6C>U Mutation inducing loss of U1snRNA affinity | 7 |
| SOD1 | Familial ALS | AAGgcaaggg | 5 | Non-mutated 5'ss | 1 |
| | | GUGgguaagu | | Non-mutated 5'ss | 4 |
| SPINK5 | Netherton syndrome | CAGguaau | | IVS2+5G>A | 2 |
| | | AAGguagua | | Non-mutated 5' bulge | 20 |
| SPTA1 | Hereditary blood disorders, Elliptocytosis-2, Pyropoikilocytosis, Spherocytosis type 3 | AAGguauau | | Non-mutated 5' bulge | 3 |
| | Hereditary blood disorders, Elliptocytosis-2, Pyropoikilocytosis | CAGguagag | | Non-mutated 5' bulge | 27 |
| | | UAGguauga | | Non-mutated 5' bulge | 41 |
| TMPRSS6 | Beta-thalassemia, Iron toxicity | AAGgcaggga | 6 | Non-mutated 5'ss | 1 |
| TP53 | Cancers | GAGgucuggu | 57 | Non-mutated 5' bulge | 5 |
| | Colorectal tumors | AUGgugacc | | IVS5+5G>C | 5 |
| | Squamous cell carcinoma | GAAgucugg | | IVS6−1G>A | 6 |
| | | GAGgucugg | | IVS6+1G>A | 6 |
| TRAPPC2 | Spondyloepiphyseal dysplasia tarda | AAGguaegg | | +4U>C Mutated 5' bulge | 5 |
| | | AAGguaugg | | Non-mutated 5' bulge | 4 |
| TSC1 | Tuberous sclerosis | AUGguaaaa | | Non-mutated 5' bulge | 9 |
| | | AAGguaaugua | 13 | Non-mutated 5' bulge | 14 |
| TSC2 | | AGAgugaau | | +5G>A Mutated 5' bulge | 2 |
| | Familial tuberous sclerosis | AAGgaugag | | IVS37+2 ins[A] | 37 |
| TSHB | Thyroid stimulating hormone. | CGGguauau | | IVS2+5G>A | 2 |
| TTN | Dilated cardiomyopathy | CAGgugagc | | Non-mutated 5'ss | 1 |
| TTR | TTR amyloidosis | ACGgugagug | 23 | Non-mutated 5'ss | 1 |

TABLE 2A-continued

Exemplary targets

| Gene | Disease | Splice Site Sequence | SEQ ID NO: | Description | Exon |
|---|---|---|---|---|---|
| UBE3A | Dup15q, Angelman's | CAGgucagug | 39 | Non-mutated 5'ss | 1 |
| UGT1A1 | Crigler-Najjar syndrome type 1 | CAGcugugu | | IVS1+1G>C | 1 |
| USH2A | Usher syndrome type IIa | CAGguauug | | Non-mutated 5' bulge | 19 |
| | | CAGguaaugu | 34 | Non-mutated 5' bulge | 28 |
| | | AAGguaaag | | Non-mutated 5' bulge | 31 |
| | | GGAguaagu | | Non-mutated 5' bulge | 34 |
| | | AGAgugagc | | Non-mutated 5' bulge | 39 |
| | | AUGguaugu | | Non-mutated 5' bulge | 70 |

TABLE 2B

Exemplary targets

| Gene | Disease | Mutated Authentic Splice Site Sequence | Authentic Splice Site Mutation | Exon | Cryptic Splice Site sequence (Location) |
|---|---|---|---|---|---|
| HBB | Beta-thalassemia | CACguuggu | IVS1−1G>C | 1 | GUGgugagg (IVS1 −16) |
| | | CAGguuggc | IVS1+6U>C | 1 | AUGguuaag (IVS2 +48) |
| | | CAGauuggu | IVS1+1G>A | 1 | AAGgugaac (IVS1 −38) |
| | | CAGuuuggu | IVS1+1G>U | 1 | AAGgugaag (Exon2 −135) |
| | | CAGgcuggu | IVS1+2U>C | 1 | |
| | | CAGguugau | IVS1+5G>A | 1 | |
| | | CAGguugcu | IVS1+5G>C | 1 | |
| | | CAGguuguu | IVS1+5G>U | 1 | |
| | | AGGgugucu | IVS2 del[+4:+5] | 2 | |
| PBGD | Acute intermittent porphyria | GCGaugagu | IVS1+1G>A | 1 | CGGgugggg (Exon 10 −9) |
| | | CAUguaggg | IVS10−1G>U | 10 | |
| | | GCGgagagu | IVS1+2U>A | 1 | |
| | | GCGgugacu | IVS1+5G>C | 1 | |
| | | GCGguuagu | IVS1+3G>U | 1 | |
| HBA2 | Alpha-thalassemia | GAGgcuccc | IVS1 del[+2:+6] | 1 | GGGguaagg (Exon1 −49) |
| AR | Androgen Sensitivity | CUGuuaag | IVS4+1G>U | 4 | |
| ATM | Ataxia-telangiectasia | CAGauaacu | IVS45+1G>A | 45 | AGAgugacu (IVS45 +72) |
| BRCA1 | Breast Cancer | UUUgugagc | IVS16+6U>C | 16 | UAUguaaga (Exon5 −22) |
| | | AGGguauau | IVS5−2A>G | 5 | UAGguauug (IVS16 +70) |
| CYP27A1 | Cerebrotendinous xanthomatosis | GAGguagga | IVS6−2C>A | 6 | GUGgugggu (Exon6 −89) |
| | | GCAguagga | IVS6−1G>A | 6 | |
| FAH | Chronic Tyrosinemia Type 1 | CCGgugaau | IVS12+5G>A | 12 | GAGgugggu (IVS112 +106) |
| TP53 | Colorectal tumors | AUGgugacc | IVS5+5G>C | 5 | |
| FGA | Common congenital afibrinogenemia | GAGguuagu | IVS4+1G>U | 4 | GGAguuaag (Exon4 −66) UAAguauua (Exon4 −36) |
| PTEN | Cowden syndrome | AAGauuugu | IVS7+1G>A | 7 | CAUguaagg (IVS7 +76) |
| | | GAGgcaggu | IVS4+2U>C | 4 | |
| UGT1A1 | Crigler-Najjar syndrome type 1 | CAGcugugu | IVS1+1G>C | 1 | GAGgugacu (Exon1 −141) |
| CFTR | Cystic Fibrosis | CACgugagc | IVS20−1G>C | 20 | AUUgugagg (Exon4 −93) |
| | | AAGguuaaua | IVS4+1G>U | 4 | |
| COL7A1 | Dominant Dystrophic epidermolysis bullosa | AGGgugagg | Exon73 del[−98: −71] | 73 | CUGguauuc (Exon73 −62) |
| KRT5 | Dowling-Meara epidermolysis bullosa simplex | AAGaugagc | IVS1+1G>A | 1 | AGGgugagg (Exon1 −66) |
| DMD | Duchenne and Becker muscular dystrophy | GCUguaacu | IVS64+5G>C | 64 | AAGggaaaa (IVS26+2U>G) |
| COL3A1 | Ehlers-Danlos syndrome IV | GAUaugagu | IVS42+1G>A | 42 | GGAguaagc (IVS16 +24) |
| | | CCUauaagu | IVS16+1G>A | 16 | |
| | | CGCauaagu | IVS20+1G>A | 20 | |

TABLE 2B-continued

Exemplary targets

| Gene | Disease | Mutated Authentic Splice Site Sequence | Authentic Splice Site Mutation | Exon | Cryptic Splice Site sequence (Location) |
|---|---|---|---|---|---|
| LPL | Familial hypercholesterolemia | ACGauaagg | IVS2+1G>A | 2 | CAGgugggga (IVS2 +143)<br>GAGguuggu (IVS2 +247)<br>AGAgugagg (IVS2 +383) |
| LDLR | Familial hypercholesterolemia | GAGgcgugg | IVS12+2U>C | 12 | UACguacga (IVS12 +12) |
| TSC2 | Familial tuberous sclerosis | AAGgaugag | IVS37+2 ins[A] | 37 | CCGgugagg (Exon37 −29) |
| F7 | FVII deficiency | UGGgugggug (SEQ ID NO: 71) | IVS7+7A>G | 7 | UGGgugggu (IVS7 +38) |
|  |  | UGGguggau | IVS7+5G>A | 7 |  |
|  |  | UGGguacca | IVS7del[+3:+6] | 7 |  |
| ITGB3 | Glanzmann thrombasthenia | GAUaugagu | IVS4+1G>A | 4 | CAGgugugg (IVS4 +28) |
| C3 | Hereditary C3 deficiency | UGGauaagg | IVS18+1G>A | 18 | GAAgugagu (Exon18 −61) |
| HMGCL | Hereditary HL deficiency | ACGcuaagc | IVS7+1G>C | 7 | GGGguauuu (IVS7 +79) |
| APOB | Homozygous hypobetalipoproteinemia | AAGgcaaaa | IVS24+2U>C | 24 |  |
| LMNA | Hutchinson-Gilford progeria syndrome (HGPS) | CAAgugagu | IVS11−1G>A | 11 | CAGgugggc (Exon 11) |
|  |  | CAGgugacu | IVS11+5G>C | 11 | CAGgugggc (Exon 11) |
|  |  | CAGgaugau | IVS11+1G>A | 11 | CAGgugggc (Exon 11) |
|  |  | CAGgcgagu | IVS11+2U>C | 11 | CAGgugggc (Exon 11) |
| HPRT1 | Lesch-Nyhan syndrome | GAAggaagu | IVS5+2U>G | 5 | AAGguaagc (IVS5 +68) |
|  |  | GAAgugugu | IVS5+3:4AA>GU | 5 |  |
|  |  | GAAguaaau | IVS5+5G>A | 5 |  |
|  |  | GAAuaaguu | IVS5del[G1] | 5 |  |
| ITGB2 | Leukocyte adhesion deficiency | UUCauaagu | IVS7+1G>A | 7 | AGGgugggg (IVS7 +65) |
| FBN1 | Marfan syndrome | UAGaugcgu | IVS46+1G>A | 46 | GAAgucagu (IVS46 +34) |
| GCK | Maturity onset diabetes of the young (MODY) |  |  |  | CCUgugagg (Exon4 −24) |
| COL6A1 | Mild Bethlem myopathy | GGGaugagu | IVS3+1G>A | 3 | CAAguacuu (Exon3 −66) |
| IDS | Mucopolysaccharidosis type II (Hunter syndrome) | AUUuuaagc | IVS7−1:+1GG>UU | 7 | CUGgugagu (IVS7 +23) |
| GHV | Mutation in placenta | UUUauaagc | IVS2+1G>A | 2 | UGGguaaug (IVS2 +13) |
| YGM | Myophosphorylase deficiency (McArdle disease) | ACCaugagu | IVS14+1 G>A | 14 | CAGgugaag (Exon 14 −67) |
| NF1 | Neurofibromatosis type I | AAAauaagu | IVS28+1G>A | 28 | AACguuaag (Exon27b −69) |
|  |  | GAGguaaga | IVS27b del[+1:+10] | 27b | AAGguacuu (Exon28 −4) |
| NF2 | Neurofibromatosis type II | GAGgugagg | IVS12 del[−14:+2] | 12 | GAUguacgg (Exon7 −23) |
|  |  | GAGgaugagg | IVS12+1G>A | 12 | AAGgucug (Exon 12 −38) |
|  |  | CGGguguau | IVS7+5 G>A | 7 | GAGgucug (Exon 12 −53)<br>ACGguguga (Exon7 −28) |
| PGK1 | Phosphoglycerate kinase deficiency | AAGuuagga | IVS4+1G>U | 4 | GGGgugagg (IVS4 +31) |
| CYP19 | Placental aromatase deficiency | UGUgcaagu | IVS6+2U>C | 6 |  |
| PKD1 | Polycystic kidney disease 1 |  |  |  | CAGguggcg (Exon43 −66) |
| COL7A1 | Recessive dystrophic epidermolysis bullosa | GUAgugagu | IVS95−1G>A | 95 | GGGgucagu (Exon95 −7) |
|  |  | AGGgugauc | IVS3−2A>G | 3 | UCCgugagc (Exon 3 −104) |
|  | Risk for emphysema | AAGuuaagg | IVS2+1G>U | 2 | AGGguacuc (Exon2 −84) |
|  | Sandhoff disease | UUGguaaca | IVS8+5G>C | 8 | AAUguuggu (Exon8 −4) |
| MTHFR | Severe deficiency of MTHFR | CAGaugagg | IVS4+1G>A | 4 |  |

TABLE 2B-continued

Exemplary targets

| Gene | Disease | Mutated Authentic Splice Site Sequence | Authentic Splice Site Mutation | Exon | Cryptic Splice Site sequence (Location) |
|---|---|---|---|---|---|
| F5 | Severe factor V deficiency | CAUguauuu | IVS10−1G>U | 10 | UCUguaaga (Exon 10 −35) |
| COL1A1 | Severe type III osteogenesis imperfecta | CCUaugagu<br>CCUgugaau | IVS8+1G>A<br>IVS8+5G>A | 8<br>8 | UUGguaaga<br>(IVS8 G +97; exon 8 +26)<br>CUGgugagc (IVS8 +97)<br>CUGgugaca (Exon34 −8) |
| HPRT1 | Somatic mutations in kidney tubular epithelial cells | GUGgugagc<br>GUGgugauc | IVS1del[−2:+34]<br>IVS1+5G>U | 1<br>1 | CAGguggcg (IVS1 +50) |
| TP53 | Squamous cell carcinoma | GAAgucugg<br>GAGaucugg | IVS6−1G>A<br>IVS6+1G>A | 6<br>6 | |
| HXA | Tay-Sachs Syndrome | GACaugagg | IVS9+1 G>A | 9 | AGGgugggu (IVS9 +18) |
| ABCD1 | X-linked adrenoleukodystrophy (X-ALD) | GAAguggg | IVS1−1G>A | 1 | CAGguuggg (IVS1 +10) |
| RPGR | X-linked retinitis pigmentosa (RP3) | CUGuugaga | IVS5+1G>U | 5 | CAUguaauu (Exon5 −76) |

<sup>A</sup> TABLE 2C

Exemplary targets with AGAguaag splice site sequence

| Gene | Chr | Genomic Location | Genomic Location | Strand |
|---|---|---|---|---|
| EPHA3 | 3 | 89604444 | 89604474 | + |
| PCOTH | 13 | 23361677 | 23361707 | + |
| NDFIP2 | 13 | 79005577 | 79005607 | + |
| FZD6 | 8 | 104409805 | 104409835 | + |
| PTPN3 | 9 | 111222509 | 111222539 | − |
| AFP | 4 | 74537190 | 74537220 | + |
| CBX3 | 7 | 26212640 | 26212670 | + |
| PHACTR4 | 1 | 28675375 | 28675405 | + |
| TAF2 | 8 | 120826286 | 120826316 | − |
| KCNT2 | 1 | 194552885 | 194552915 | − |
| PRIM1 | 12 | 55431073 | 55431103 | − |
| CDH9 | 5 | 26941809 | 26941839 | − |
| SLC38A1 | 12 | 44883044 | 44883074 | − |
| HDX | X | 83643077 | 83643107 | − |
| RAB23 | 6 | 57194060 | 57194090 | − |
| STX3 | 11 | 59312981 | 59313011 | + |
| DNAH3 | 16 | 21053065 | 21053095 | − |
| SSX3 | X | 48100997 | 48101027 | − |
| NSMAF | 8 | 59670657 | 59670687 | − |
| XRN2 | 20 | 21283495 | 21283525 | + |
| EVC2 | 4 | 5715719 | 5715749 | − |
| ERCC8 | 5 | 60223605 | 60223635 | − |
| QRSL1 | 6 | 107210285 | 107210315 | + |
| CEP110 | 9 | 122943672 | 122943702 | + |
| FANCA | 16 | 88404822 | 88404852 | − |
| DYNC1H1 | 14 | 101544412 | 101544442 | + |
| TRIML1 | 4 | 189298099 | 189298129 | + |
| MKL2 | 16 | 14213752 | 14213782 | + |
| CHAF1A | 19 | 4369058 | 4369088 | + |
| CCDC11 | 18 | 46031110 | 46031140 | − |
| ALS2CL | 3 | 46704576 | 46704606 | − |
| C13orf1 | 13 | 49390214 | 49390244 | − |
| JAK1 | 1 | 65079706 | 65079736 | − |
| PAN2 | 12 | 54998272 | 54998302 | − |
| PRKG1 | 10 | 52897587 | 52897617 | + |
| KREMEN1 | 22 | 27824926 | 27824956 | + |
| ADAMTS9 | 3 | 64611717 | 64611747 | − |
| PDS5B | 13 | 32228079 | 32228109 | + |
| PTPRM | 18 | 8374669 | 8374699 | + |
| DPP4 | 2 | 162570485 | 162570515 | − |
| L3MBTL2 | 22 | 39955591 | 39955621 | + |
| EFCAB3 | 17 | 57837751 | 57837781 | + |
| GRHPR | 9 | 37412815 | 37412845 | + |
| ARHGEF18 | 19 | 7434826 | 7434856 | + |
| MLX | 17 | 37977597 | 37977627 | + |
| ABCB5 | 7 | 20649508 | 20649538 | + |
| MAP4K4 | 2 | 101814730 | 101814760 | + |
| L1CAM | X | 152786433 | 152786463 | − |
| CLPB | 11 | 71683001 | 71683031 | + |
| GNB5 | 15 | 50203946 | 50203976 | − |
| TRAF3IP3 | 1 | 208021411 | 208021441 | + |
| WDR26 | 1 | 222673827 | 222673857 | − |
| ARHGAP1 | 11 | 46675131 | 46675161 | − |
| PPP4C | 16 | 30001341 | 30001371 | + |
| MRPS35 | 12 | 27768371 | 27768401 | + |
| WDR17 | 4 | 177254715 | 177254745 | + |
| CLIC2 | X | 154162429 | 154162459 | − |
| ARS2 | 7 | 100323401 | 100323431 | + |
| MYO3A | 10 | 26483743 | 26483773 | + |
| EPS15 | 1 | 51701917 | 51701947 | − |
| ANK3 | 10 | 61570100 | 61570130 | − |
| CNOT1 | 16 | 57148251 | 57148281 | − |
| FBXO38 | 5 | 147770506 | 147770536 | + |
| PLXNC1 | 12 | 93142207 | 93142237 | + |
| DMD | X | 32392608 | 32392638 | − |
| TMEM27 | X | 15587044 | 15587074 | − |
| CDH10 | 5 | 24570962 | 24570992 | − |
| GOLT1B | 12 | 21546134 | 21546164 | + |
| NUMA1 | 11 | 71412952 | 71412982 | + |
| IMMT | 2 | 86226686 | 86226716 | + |
| SSX9 | X | 48050476 | 48050506 | − |
| SSX5 | X | 47941095 | 47941125 | − |
| PPP1R12A | 12 | 78790703 | 78790733 | − |
| TBCEL | 11 | 120429636 | 120429666 | + |
| MYO9B | 19 | 17167267 | 17167297 | + |
| PRPF40B | 12 | 48316028 | 48316058 | + |
| C10orf137 | 10 | 127414448 | 127414478 | + |
| PDK4 | 7 | 95060931 | 95060961 | − |
| MEGF11 | 15 | 63995524 | 63995554 | + |
| FLJ35848 | 17 | 40102396 | 40102426 | + |
| SLC13A1 | 7 | 122556119 | 122556149 | − |
| MADD | 11 | 47270708 | 47270738 | + |
| ADAM10 | 15 | 56723361 | 56723391 | − |
| MYH2 | 17 | 10380556 | 10380586 | − |

TABLE 2C-continued

Exemplary targets with AGAguaag splice site sequence

| Gene | Chr | Genomic Location | Genomic Location | Strand |
|---|---|---|---|---|
| IL5RA | 3 | 3121571 | 3121601 | − |
| RLN3 | 19 | 14002153 | 14002183 | + |
| CCDC81 | 11 | 85803988 | 85804018 | + |
| SENP3 | 17 | 7408890 | 7408920 | + |
| ACSS2 | 20 | 32977730 | 32977760 | + |
| TRIM65 | 17 | 71399473 | 71399503 | − |
| LOC390110 | 11 | 44028232 | 44028262 | + |
| SENP6 | 6 | 76388046 | 76388076 | + |
| PIK3C2G | 12 | 18607684 | 18607714 | + |
| SLC38A4 | 12 | 45458323 | 45458353 | − |
| HDAC5 | 17 | 39526192 | 39526222 | − |
| MGAM | 7 | 141380633 | 141380663 | + |
| YARS | 1 | 33020576 | 33020606 | − |
| C1R | 12 | 7132560 | 7132590 | − |
| TIMM50 | 19 | 44670682 | 44670712 | + |
| SEC24A | 5 | 134038791 | 134038821 | − |
| NOS2A | 17 | 23138815 | 23138845 | − |
| FBXO18 | 10 | 6003311 | 6003341 | + |
| PKHD1L1 | 8 | 110482978 | 110483008 | + |
| GSDMB | 17 | 35315874 | 35315904 | − |
| C8orf33 | 8 | 146249321 | 146249351 | + |
| PROCR | 20 | 33222668 | 33222698 | + |
| FEZ2 | 2 | 36661921 | 36661951 | − |
| KIAA1033 | 12 | 104025754 | 104025784 | + |
| FANK1 | 10 | 127575199 | 127575229 | + |
| COMTD1 | 10 | 76664358 | 76664388 | − |
| REC8 | 14 | 23716414 | 23716444 | + |
| ATG4A | X | 107267755 | 107267785 | + |
| GTPBP4 | 10 | 1045505 | 1045535 | + |
| PLCG1 | 20 | 39234328 | 39234358 | + |
| CDH24 | 14 | 22593539 | 22593569 | − |
| PRRG2 | 19 | 54783686 | 54783716 | + |
| KIF5A | 12 | 56256413 | 56256443 | + |
| C1orf130 | 1 | 24794575 | 24794605 | + |
| ARFGEF2 | 20 | 47038591 | 47038621 | + |
| NME7 | 1 | 167534402 | 167534432 | − |
| SEL1L | 14 | 81022370 | 81022400 | − |
| MME | 3 | 156369265 | 156369295 | + |
| PRIM2 | 6 | 57293302 | 57293332 | + |
| DNAJC13 | 3 | 133724516 | 133724546 | + |
| PPP4R1L | 20 | 56246657 | 56246687 | − |
| LUM | 12 | 90026010 | 90026040 | − |
| ZNF37A | 10 | 38424723 | 38424753 | + |
| SNRK | 3 | 43348791 | 43348821 | + |
| SPAG9 | 17 | 46511928 | 46511958 | − |
| JAK2 | 9 | 5063770 | 5063800 | + |
| C1orf114 | 1 | 167654859 | 167654889 | − |
| CSE1L | 20 | 47140951 | 47140981 | + |
| MRPS28 | 8 | 81077773 | 81077803 | − |
| NSMCE2 | 8 | 126183896 | 126183926 | + |
| NUBPL | 14 | 31138321 | 31138351 | + |
| C5orf34 | 5 | 43544988 | 43545018 | − |
| MRPL39 | 21 | 25886979 | 25887009 | − |
| MTF2 | 1 | 93353748 | 93353778 | + |
| FANCM | 14 | 44720643 | 44720673 | + |
| EPB41L5 | 2 | 120601882 | 120601912 | + |
| ADAMTS20 | 12 | 42146706 | 42146736 | − |
| RFC4 | 3 | 187995125 | 187995155 | − |
| PIAS1 | 15 | 66226077 | 66226107 | + |
| CUL5 | 11 | 107465545 | 107465575 | + |
| COL5A2 | 2 | 189615675 | 189615705 | − |
| FN1 | 2 | 215951121 | 215951157 | − |
| PROSC | 8 | 37749550 | 37749580 | + |
| LHX6 | 9 | 124015690 | 124015720 | − |
| SCYL3 | 1 | 168114383 | 168114413 | − |
| MALT1 | 18 | 54518788 | 54518818 | + |
| C15orf42 | 15 | 87944905 | 87944935 | + |
| DIP2A | 21 | 46773509 | 46773539 | + |
| WDR44 | X | 117454800 | 117454830 | + |
| KIN | 10 | 7865034 | 7865064 | − |
| FGFR2 | 10 | 123313990 | 123314020 | − |
| OSBPL8 | 12 | 75287532 | 75287562 | − |
| TCEB3 | 1 | 23956187 | 23956217 | + |
| MYO19 | 17 | 31929016 | 31929046 | − |
| APOB | 2 | 21104688 | 21104718 | − |
| RP13-36C9. | X | 134715052 | 134715082 | + |
| RP13-36C9. | X | 134777728 | 134777758 | − |
| CT45-6 | X | 134794978 | 134795008 | − |
| XX-FW88277 | X | 134680521 | 134680551 | + |
| CEP110 | 9 | 122959964 | 122959994 | + |
| SPATS1 | 6 | 44428573 | 44428603 | + |
| C9orf114 | 9 | 130631194 | 130631224 | − |
| STK17B | 2 | 196712573 | 196712603 | − |
| CCDC18 | 1 | 93455999 | 93456029 | + |
| NCOA1 | 2 | 24803064 | 24803094 | + |
| TTLL5 | 14 | 75199304 | 75199334 | + |
| SH3PXD2A | 10 | 105474002 | 105474032 | − |
| DOCK4 | 7 | 111192394 | 111192424 | − |
| MTDH | 8 | 98804424 | 98804454 | + |
| COL24A1 | 1 | 86145449 | 86145479 | − |
| ADAMTS6 | 5 | 64631552 | 64631582 | + |
| SENP7 | 3 | 102529996 | 102530026 | + |
| PIGN | 18 | 57928031 | 57928061 | − |
| TOP2B | 3 | 25623650 | 25623680 | + |
| NUPL1 | 13 | 24787590 | 24787620 | + |
| OSBPL11 | 3 | 126761897 | 126761927 | − |
| CCDC5 | 18 | 41954009 | 41954039 | + |
| COPS7B | 2 | 232364112 | 232364142 | + |
| POLN | 4 | 2200608 | 2200638 | − |
| VTI1A | 10 | 114418022 | 114418052 | + |
| SYTL5 | X | 37833769 | 37833799 | + |
| CETP | 16 | 55561399 | 55561429 | + |
| LMLN | 3 | 199185727 | 199185757 | + |
| C11orf70 | 11 | 101442577 | 101442607 | + |
| LMBRD2 | 5 | 36145788 | 36145818 | − |
| DNTTIP2 | 1 | 94111247 | 94111277 | − |
| ECM2 | 9 | 94304600 | 94304630 | − |
| PRKG1 | 10 | 53563656 | 53563686 | + |
| C16orf38 | 16 | 1477302 | 1477332 | − |
| RBM45 | 2 | 178696609 | 178696639 | + |
| C1orf94 | 1 | 34416282 | 34416312 | + |
| GRIA1 | 5 | 152869544 | 152869574 | + |
| HDAC3 | 5 | 140988294 | 140988324 | − |
| IPO4 | 14 | 23727246 | 23727276 | − |
| MYOM2 | 8 | 2077714 | 2077744 | + |
| NARG1 | 4 | 140501217 | 140501247 | + |
| HEPACAM2 | 7 | 92659487 | 92659517 | − |
| SDK2 | 17 | 68955333 | 68955363 | + |
| FBXO15 | 18 | 69958923 | 69958953 | + |
| SNX6 | 14 | 34120502 | 34120532 | − |
| BBOX1 | 11 | 27097953 | 27097983 | + |
| C3orf23 | 3 | 44417815 | 44417845 | + |
| ETS2 | 21 | 39108171 | 39108201 | + |
| CDC16 | 13 | 114040792 | 114040822 | + |
| CFH | 1 | 194908901 | 194908931 | + |
| ANTXR2 | 4 | 81171785 | 81171815 | − |
| PIK3CG | 7 | 106300268 | 106300298 | + |
| EDEM3 | 1 | 182968578 | 182968608 | − |
| IL1R2 | 2 | 102002691 | 102002721 | + |
| KPNA5 | 6 | 117133001 | 117133031 | + |
| LHCGR | 2 | 48779242 | 48779272 | − |
| NOL10 | 2 | 10720520 | 10720550 | + |
| CYP3A4 | 7 | 99205311 | 99205341 | − |
| TTC17 | 11 | 43369687 | 43369717 | + |
| FAR2 | 12 | 29366109 | 29366139 | + |
| COL3A1 | 2 | 189563316 | 189563346 | + |
| ZBTB20 | 3 | 115826398 | 115826428 | − |
| COL19A1 | 6 | 70907587 | 70907617 | + |
| NUP160 | 11 | 47797486 | 47797516 | + |
| SCO1 | 17 | 10539767 | 10539797 | − |
| VWA3B | 2 | 98283096 | 98283126 | + |
| COL3A1 | 2 | 189580894 | 189580924 | + |
| CYP3A43 | 7 | 99283798 | 99283828 | + |
| DHRS7 | 14 | 59690414 | 59690444 | − |
| MIB1 | 18 | 17687162 | 17687192 | + |
| NLRC5 | 16 | 55670690 | 55670720 | + |
| POLR3D | 8 | 22160707 | 22160737 | + |
| ATP11C | X | 138696982 | 138697012 | − |
| ADAM15 | 1 | 153296186 | 153296216 | + |
| FAM65C | 20 | 48645297 | 48645327 | − |

TABLE 2C-continued

Exemplary targets with AGAguaag splice site sequence

| Gene | Chr | Genomic Location | Genomic Location | Strand |
|---|---|---|---|---|
| SCN3A | 2 | 165733476 | 165733506 | − |
| CYP3A5 | 7 | 99102144 | 99102174 | − |
| COL1A1 | 17 | 45624324 | 45624354 | − |
| FGR | 1 | 27820641 | 27820671 | − |
| MIER2 | 19 | 276619 | 276649 | − |
| SIPA1L3 | 19 | 43283691 | 43283721 | + |
| CDH11 | 16 | 63583156 | 63583186 | − |
| SYCP1 | 1 | 115203939 | 115203969 | + |
| ASH1L | 1 | 153652143 | 153652173 | − |
| FAM13B1 | 5 | 137351846 | 137351876 | − |
| COL4A5 | X | 107693797 | 107693827 | + |
| PRPF4B | 6 | 3966684 | 3966714 | + |
| PTPN11 | 12 | 111424428 | 111424458 | + |
| LAMB1 | 7 | 107367654 | 107367684 | − |
| PIK3R1 | 5 | 67627057 | 67627087 | + |
| FLNA | X | 153243216 | 153243246 | − |
| SKIV2L2 | 5 | 54698445 | 54698475 | + |
| RNFT1 | 17 | 55394667 | 55394697 | − |
| PDCD4 | 10 | 112644255 | 112644285 | + |
| AHCTF1 | 1 | 245137460 | 245137490 | − |
| DHFR | 5 | 79965436 | 79965466 | − |
| UTP15 | 5 | 72899893 | 72899923 | + |
| TMEM156 | 4 | 38666850 | 38666880 | − |
| TNKS | 8 | 9604951 | 9604981 | + |
| NFIA | 1 | 61570831 | 61570861 | + |
| NT5C3 | 7 | 33021791 | 33021821 | − |
| TNKS2 | 10 | 93580736 | 93580766 | + |
| COL11A1 | 1 | 103227646 | 103227676 | − |
| PCNX | 14 | 70583560 | 70583590 | + |
| MEMO1 | 2 | 31999355 | 31999385 | − |
| LMBRD1 | 6 | 70467362 | 70467392 | − |
| NEDD4 | 15 | 54030850 | 54030880 | − |
| PPP3CB | 10 | 74901216 | 74901246 | − |
| C1orf71 | 1 | 244864497 | 244864527 | + |
| CAB39 | 2 | 231383266 | 231383296 | + |
| POMT2 | 14 | 76848378 | 76848408 | − |
| TP53INP1 | 8 | 96013458 | 96013488 | − |
| CDC14A | 1 | 100706223 | 100706253 | + |
| KLF3 | 4 | 38367880 | 38367910 | + |
| NEK1 | 4 | 170760224 | 170760254 | − |
| PPP4R2 | 3 | 73192686 | 73192916 | + |
| KLF12 | 13 | 73285274 | 73285304 | − |
| PHTF1 | 1 | 114042391 | 114042421 | − |
| COL2A1 | 12 | 46674028 | 46674058 | − |
| KIAA1622 | 14 | 93792679 | 93792709 | + |
| TTN | 2 | 179343016 | 179343046 | − |
| PSD3 | 8 | 18534387 | 18534417 | − |
| LACE1 | 6 | 108905173 | 108905203 | + |
| SLC28A3 | 9 | 86104330 | 86104330 | − |
| COPA | 1 | 158533741 | 158533771 | − |
| PAPOLG | 2 | 60849514 | 60849544 | + |
| CENPI | X | 100268896 | 100268926 | + |
| ARFGEF1 | 8 | 68328224 | 68328254 | − |
| EXOC4 | 7 | 133273347 | 133273377 | + |
| TIAM2 | 6 | 155607594 | 155607624 | + |
| MDGA2 | 14 | 46384703 | 46384733 | − |
| BRCC3 | X | 153972293 | 153972323 | + |
| MEGF10 | 5 | 126804443 | 126804473 | + |
| WDTC1 | 1 | 27481348 | 27481378 | + |
| EMCN | 4 | 101605587 | 101605617 | − |
| FUT9 | 6 | 96575555 | 96575585 | + |
| NPM1 | 5 | 170752572 | 170752602 | + |
| GPR160 | 3 | 171280364 | 171280394 | + |
| OSGEPL1 | 2 | 190334602 | 190334632 | − |
| SGPL1 | 10 | 72274386 | 72274416 | + |
| CEP192 | 18 | 13028563 | 13028593 | + |
| CHN1 | 2 | 175491492 | 175491522 | − |
| FLJ36070 | 19 | 53911758 | 53911788 | − |
| CELSR3 | 3 | 48652095 | 48652125 | − |
| GLT8D1 | 3 | 52704461 | 52704491 | − |
| COL14A1 | 8 | 121423851 | 121423881 | + |
| SAAL1 | 11 | 18074878 | 18074908 | − |
| SH3TC2 | 5 | 148386600 | 148386630 | − |
| SEC31A | 4 | 84014772 | 84014802 | − |
| LVRN | 5 | 115357435 | 115357465 | + |
| TLK2 | 17 | 57984833 | 57984863 | + |
| KIF5B | 10 | 32349940 | 32349970 | − |
| EML5 | 14 | 88282266 | 88282296 | − |
| TMF1 | 3 | 69176317 | 69176347 | − |
| TMF1 | 3 | 69155880 | 69155910 | − |
| TRIM44 | 11 | 35641889 | 35641919 | + |
| PTK2 | 8 | 141925525 | 141925555 | − |
| MLL5 | 7 | 104468691 | 104468721 | + |
| ABCB1 | 7 | 87034021 | 87034051 | − |
| SGOL2 | 2 | 201148414 | 201148444 | + |
| PAWR | 12 | 78512224 | 78512254 | − |
| NUBP1 | 16 | 10769375 | 10769405 | + |
| PHLDB2 | 3 | 113142167 | 113142197 | + |
| ISL2 | 15 | 74416322 | 74416352 | + |
| CNOT7 | 8 | 17145306 | 17145336 | − |
| UTX | X | 44823525 | 44823555 | + |
| COL5A2 | 2 | 189631804 | 189631834 | − |
| DSCC1 | 8 | 120925014 | 120925044 | − |
| RB1CC1 | 8 | 53705567 | 53705597 | − |
| PLCB4 | 20 | 9401479 | 9401509 | + |
| ASPM | 1 | 195328789 | 195328819 | − |
| ERMP1 | 9 | 5801095 | 5801125 | − |
| LIMK2 | 22 | 29986048 | 29986078 | + |
| HERC1 | 15 | 61733355 | 61733385 | − |
| CHD9 | 16 | 51854495 | 51854525 | + |
| THOC2 | X | 122599559 | 122599589 | − |
| SCN11A | 3 | 38961890 | 38961920 | − |
| SLC39A10 | 2 | 196281798 | 196281828 | + |
| PLCB1 | 20 | 8717354 | 8717384 | + |
| CXorf41 | X | 106348840 | 106348870 | + |
| CENTB2 | 3 | 196547261 | 196547291 | − |
| UNC5C | 4 | 96382587 | 96382617 | − |
| DNAH8 | 6 | 39060046 | 39060076 | + |
| POMT2 | 14 | 76824842 | 76824872 | − |
| MAGT1 | X | 76983383 | 76983413 | − |
| HSPA9 | 5 | 137921441 | 137921471 | − |
| PTPRK | 6 | 128339479 | 128339509 | − |
| RP1 | 8 | 55697386 | 55697416 | + |
| PTPN4 | 2 | 120434984 | 120435014 | + |
| C19orf42 | 19 | 16627033 | 16627063 | − |
| TG | 8 | 133982965 | 133982995 | + |
| PIGT | 20 | 43481629 | 43481659 | + |
| CDC42BPB | 14 | 102495705 | 102495735 | − |
| TOM1L1 | 17 | 50382471 | 50382501 | + |
| USP39 | 2 | 85716749 | 85716779 | + |
| POSTN | 13 | 37058903 | 37058933 | − |
| PAH | 12 | 101773028 | 101773058 | − |
| ARHGEF2 | 1 | 154191301 | 154191331 | − |
| RBM39 | 20 | 33773060 | 33773090 | − |
| C21orf70 | 21 | 45204496 | 45204526 | + |
| GAS2L3 | 12 | 99540276 | 99540306 | + |
| UXT | X | 47401510 | 47401540 | + |
| C16orf48 | 16 | 66257459 | 66257489 | − |
| CMIP | 16 | 80282931 | 80282961 | + |
| CA11 | 19 | 53834602 | 53834632 | − |
| PHKB | 16 | 46251964 | 46251994 | + |
| ADAMTS9 | 3 | 64602548 | 64602578 | − |
| SETD3 | 14 | 99001777 | 99001807 | − |
| DENND2D | 1 | 111532831 | 111532861 | − |
| GAB1 | 4 | 144600066 | 144600096 | + |
| COL4A2 | 13 | 109888370 | 109888400 | + |
| PADI4 | 1 | 17555526 | 17555556 | + |
| MYOM3 | 1 | 24260121 | 24260151 | − |
| ARPC3 | 12 | 109367624 | 109367654 | − |
| TBC1D3G | 17 | 31873637 | 31873667 | + |
| USP6 | 17 | 4981754 | 4981784 | + |
| COG3 | 13 | 44958696 | 44958726 | + |
| ATP6V1G3 | 1 | 196776306 | 196776336 | − |
| KIR2DL5B | 19 | 237531 | 237561 | + |
| KIR3DL2 | 19 | 60069191 | 60069191 | + |
| KIR3DL3 | 19 | 59938621 | 59938651 | + |
| HTT | 4 | 3186721 | 3186751 | + |
| CEP192 | 18 | 13086291 | 13086321 | + |
| TEAD1 | 11 | 12859159 | 12859189 | + |
| CD4 | 12 | 6775799 | 6775829 | + |

TABLE 2C-continued

Exemplary targets with AGAguaag splice site sequence

| Gene | Chr | Genomic Location | Genomic Location | Strand |
|---|---|---|---|---|
| SUCLG2 | 3 | 67662185 | 67662215 | − |
| VTI1B | 14 | 67192870 | 67192900 | − |
| L3MBTL | 20 | 41598497 | 41598527 | + |
| GCG | 2 | 162710280 | 162710310 | − |
| MCF2L2 | 3 | 184428763 | 184428793 | − |
| MYCBP2 | 13 | 76590460 | 76590490 | − |
| AP2A2 | 11 | 971284 | 971314 | + |
| GRAMD3 | 5 | 125829912 | 125829942 | + |
| ATAD5 | 17 | 26245279 | 26245309 | + |
| PDS5A | 4 | 39540218 | 39540248 | − |
| GRM3 | 7 | 86307142 | 86307172 | + |
| TG | 8 | 134030355 | 134030385 | + |
| SPAG9 | 17 | 46430788 | 46430818 | − |
| PLEKHA7 | 11 | 16849206 | 16849236 | − |
| KATNAL2 | 18 | 42840008 | 42840038 | + |
| COL5A2 | 2 | 189629928 | 189629958 | − |
| ERN2 | 16 | 23629322 | 23629352 | − |
| TFRC | 3 | 197264670 | 197264700 | − |
| TET2 | 4 | 106384369 | 106384399 | + |
| KRTCAP2 | 1 | 153411649 | 153411679 | − |
| MEGF10 | 5 | 126802143 | 126802173 | + |
| IWS1 | 2 | 127977417 | 127977447 | − |
| COL2A1 | 12 | 46656548 | 46656578 | − |
| FAM20A | 17 | 64062497 | 64062527 | − |
| PDIA3 | 15 | 41842681 | 41842711 | + |
| CDC2L5 | 7 | 40084960 | 40084990 | + |
| SMARCA1 | X | 128473446 | 128473476 | − |
| NFRKB | 11 | 129257540 | 129257570 | − |
| CPXM2 | 10 | 125629701 | 125629731 | − |
| BCS1L | 2 | 219235631 | 219235661 | + |
| NFIX | 19 | 13045295 | 13045325 | + |
| SPECC1L | 22 | 23050380 | 23050410 | + |
| NAG | 2 | 15350096 | 15350126 | − |
| KIF16B | 20 | 16426242 | 16426272 | − |
| AKAP3 | 12 | 4621310 | 4621340 | − |
| PROX1 | 1 | 212228672 | 212228702 | + |
| MATN2 | 8 | 99102716 | 99102746 | + |
| STAMBPL1 | 10 | 90663180 | 90663210 | + |
| EPHB1 | 3 | 136451008 | 136451038 | + |
| TTPAL | 20 | 42548745 | 42548775 | + |
| PVRL2 | 19 | 50077446 | 50077476 | + |
| ZNF618 | 9 | 115837321 | 115837351 | + |
| COL4A5 | X | 107710609 | 107710639 | + |
| FAM13C1 | 10 | 60792149 | 60792179 | − |
| VPS35 | 16 | 45272068 | 45272098 | − |
| SPP2 | 2 | 234624463 | 234624493 | + |
| FAM19A1 | 3 | 68670706 | 68670736 | + |
| NRXN1 | 2 | 50576531 | 50576561 | − |
| HIPK3 | 11 | 33326925 | 33326955 | + |
| CAPN9 | 1 | 228992543 | 228992573 | + |
| CEP170 | 1 | 241406611 | 241406641 | − |
| FGFR1OP | 6 | 167358357 | 167358387 | + |
| ADCY8 | 8 | 131917689 | 131917719 | − |
| MAGI1 | 3 | 65403491 | 65403521 | − |
| UNC45B | 17 | 30505858 | 30505888 | + |
| C16orf33 | 16 | 46598 | 46628 | + |
| GRN | 17 | 39783979 | 39784009 | + |
| KIF9 | 3 | 47293760 | 47293790 | + |
| LMO2 | 11 | 33847452 | 33847482 | − |
| C13orf15 | 13 | 40930591 | 40930621 | + |
| FNBP1L | 1 | 93771198 | 93771228 | + |
| CCDC102B | 18 | 64657218 | 64657158 | + |
| C15orf29 | 15 | 32226677 | 32226707 | − |
| ARHGAP18 | 6 | 129970715 | 129970745 | − |
| C9orf98 | 9 | 134692499 | 134692529 | − |
| GRIA3 | X | 122389656 | 122389686 | + |
| DNAI1 | 9 | 34473463 | 34473493 | + |
| PIWIL3 | 22 | 23475355 | 23475385 | − |
| SLC4A2 | 7 | 150394766 | 150394796 | + |
| CRKRS | 17 | 34929851 | 34929881 | + |
| OBFC2B | 12 | 54905731 | 54905761 | + |
| C14orf118 | 14 | 75712771 | 75712801 | + |
| DCTN3 | 9 | 34608657 | 34608687 | − |
| COL4A1 | 13 | 109656997 | 109657027 | − |
| CDCA8 | 1 | 37938765 | 37938795 | + |
| PARVB | 22 | 42863716 | 42863746 | + |
| FGFR1OP2 | 12 | 26982895 | 26982925 | + |
| STXBP1 | 9 | 129414525 | 129414555 | + |
| BMPR2 | 2 | 203129484 | 203129514 | + |
| SNRP70 | 19 | 54293758 | 54293788 | + |
| ACADL | 2 | 210793600 | 210793630 | − |
| TBC1D8B | X | 105950866 | 105950896 | + |
| MUC2 | 11 | 1073587 | 1073617 | + |
| POMT2 | 14 | 76823313 | 76823343 | − |
| CAPSL | 5 | 35946209 | 35946239 | − |
| BRSK2 | 11 | 1429210 | 1429240 | + |
| ERGIC3 | 20 | 33605556 | 33605586 | + |
| DDA1 | 19 | 17286183 | 17286213 | + |
| CDK8 | 13 | 25872672 | 25872702 | + |
| TP63 | 3 | 191068410 | 191068440 | + |
| INPP5D | 2 | 233757891 | 233757921 | + |
| MAPK8IP3 | 16 | 1714664 | 1714694 | + |
| TNFRSF8 | 1 | 12108681 | 12108711 | + |
| AMBRA1 | 11 | 46396023 | 46396053 | − |
| F3 | 1 | 94774093 | 94774123 | − |
| HSPG2 | 1 | 22059241 | 22059271 | − |
| RHPN2 | 19 | 38209234 | 38209264 | − |
| RP11-265F1 | 1 | 15682467 | 15682497 | + |
| ELA2A | 1 | 15662589 | 15662619 | + |
| GRM4 | 6 | 34115917 | 34115947 | + |
| GOLT1A | 1 | 202449617 | 202449647 | − |
| LGMN | 14 | 92254829 | 92254859 | + |
| TNK2 | 3 | 197080749 | 197080779 | − |
| LRP4 | 11 | 46867522 | 46867552 | + |
| SEC24A | 5 | 134041726 | 134041756 | + |
| EFCAB4B | 12 | 3658326 | 3658356 | − |
| MAPK9 | 5 | 179621274 | 179621304 | + |
| SH3RF2 | 5 | 145415954 | 145415984 | + |
| NKAP | X | 118956705 | 118956735 | − |
| CALCOCO2 | 17 | 44274233 | 44274263 | + |
| DDX1 | 2 | 15677956 | 15677986 | + |
| PRMT7 | 16 | 66912851 | 66912881 | + |
| TDRD3 | 13 | 59939499 | 59939529 | + |
| PPFIA2 | 12 | 80375659 | 80375689 | − |
| COL24A1 | 1 | 86021751 | 86021781 | − |
| STAMBPL1 | 10 | 90671147 | 90671147 | + |
| KIF15 | 3 | 44865039 | 44865069 | + |
| ANXA11 | 10 | 81906098 | 81906128 | − |
| PIK3C2G | 12 | 18415497 | 18415527 | + |
| COL29A1 | 3 | 131625419 | 131625449 | + |
| ERMN | 2 | 157892215 | 157892245 | − |
| GNAS | 20 | 56904119 | 56904149 | + |
| SULF2 | 20 | 45734333 | 45734363 | + |
| TRPM7 | 15 | 48654325 | 48654355 | − |
| ALAS1 | 3 | 52208481 | 52208511 | + |
| COPZ2 | 17 | 43466212 | 43466242 | − |
| OLIG2 | 21 | 33320189 | 33320219 | + |
| FAM13A1 | 4 | 89889929 | 89889959 | − |
| RPN1 | 3 | 129823681 | 129823711 | + |
| SRP72 | 4 | 57028652 | 57028682 | + |
| LPCAT2 | 16 | 54137215 | 54137245 | + |
| SGCE | 7 | 94066929 | 94066959 | − |
| C1orf107 | 1 | 208070996 | 208071026 | + |
| UTP18 | 17 | 46698625 | 46698655 | + |
| UVRAG | 11 | 75405657 | 75405687 | + |
| PRC1 | 15 | 89318803 | 89318833 | − |
| CUBN | 10 | 17125916 | 17125846 | − |
| NEK5 | 13 | 51574054 | 51574084 | − |
| EPHB3 | 3 | 185781875 | 185781905 | + |
| ZNF114 | 19 | 53466882 | 53466912 | + |
| CAMK1D | 10 | 12906542 | 12906572 | + |
| NOTCH1 | 9 | 138517439 | 138517469 | − |
| ADAL | 15 | 41415301 | 41415331 | + |
| SPATA13 | 13 | 23758516 | 23758546 | + |
| CAMKK1 | 17 | 3740720 | 3740750 | − |
| C9orf86 | 9 | 138837917 | 138837947 | + |
| FRAS1 | 4 | 79513021 | 79513051 | + |
| CENTG2 | 2 | 236614209 | 236614239 | + |
| PTPRD | 9 | 8330327 | 8330357 | − |
| UHRF1BP1 | 6 | 34910601 | 34910631 | + |

TABLE 2C-continued

Exemplary targets with AGAguaag splice site sequence

| Gene | Chr | Genomic Location | Genomic Location | Strand |
|---|---|---|---|---|
| JAK1 | 1 | 65084904 | 65084934 | − |
| LYST | 1 | 233985385 | 233985415 | − |
| CPSF2 | 14 | 91697328 | 91697358 | + |
| PUS10 | 2 | 61041015 | 61041045 | − |
| COL1A2 | 7 | 93882503 | 93882533 | + |
| DPP4 | 2 | 162587495 | 162587525 | − |
| SEC24D | 4 | 119905389 | 119905419 | − |
| ADCY10 | 1 | 166139733 | 166139763 | − |
| CDH8 | 16 | 60627469 | 60627499 | − |
| ZC3HAV1 | 7 | 138396306 | 138396336 | − |
| SKAP1 | 17 | 43620188 | 43620218 | − |
| FAM23B | 10 | 18105150 | 18105180 | + |
| RTEL1 | 20 | 61779965 | 61779995 | + |
| ZNF365 | 10 | 63806686 | 63806716 | + |
| SAE1 | 19 | 52348122 | 52348152 | + |
| STARD6 | 18 | 50109699 | 50109729 | − |
| TBK1 | 12 | 63170151 | 63170181 | + |
| SETD4 | 21 | 36335959 | 36335989 | − |
| ZWINT | 10 | 57790947 | 57790977 | − |
| GRIN2B | 12 | 13611210 | 13611240 | − |
| TNFRSF10A | 8 | 23110574 | 23110604 | − |
| TNFRSF10B | 8 | 22937630 | 22937660 | − |
| ROCK2 | 2 | 11251817 | 11251847 | − |
| ABCA9 | 17 | 64568586 | 64568616 | − |
| GRIA4 | 11 | 105302860 | 105302890 | + |
| EXO1 | 1 | 240082321 | 240082351 | + |
| PRAME | 22 | 21231362 | 21231392 | − |
| C8B | 1 | 57170055 | 57170085 | − |
| PAPOLG | 2 | 60867690 | 60867720 | + |
| CDH8 | 16 | 60416401 | 60416431 | − |
| KIAA0586 | 14 | 58025330 | 58025360 | + |
| GSTCD | 4 | 106907867 | 106907897 | + |
| STAG1 | 3 | 137635072 | 137635102 | − |
| CLINT1 | 5 | 157148933 | 157148963 | − |
| KCNN2 | 5 | 113836745 | 113836775 | + |
| GART | 21 | 33800135 | 33800165 | − |
| DDX24 | 14 | 93596181 | 93596211 | − |
| AKAP10 | 17 | 19785715 | 19785745 | − |
| LRPPRC | 2 | 43980093 | 43980123 | − |
| DOCK11 | X | 117654388 | 117654418 | + |
| LAMA2 | 6 | 129506903 | 129506933 | + |
| HNRNPH1 | 5 | 178975689 | 178975719 | + |
| RAB11FIP2 | 10 | 119795296 | 119795326 | − |
| COL9A1 | 6 | 71036722 | 71036752 | − |
| LRRC42 | 1 | 54186227 | 54186257 | + |
| KRIT1 | 7 | 91693760 | 91693790 | − |
| PLEKHA5 | 12 | 19299351 | 19299381 | + |
| MLANA | 9 | 5882536 | 5882566 | + |
| CCDC15 | 11 | 124334355 | 124334385 | + |
| CACNA2D1 | 7 | 81437911 | 81437941 | − |
| SCN1A | 2 | 166621151 | 166621181 | − |
| SENP6 | 6 | 76480002 | 76480032 | + |
| DNAJA4 | 15 | 76345675 | 76345705 | + |
| AP4E1 | 15 | 49063619 | 49063649 | + |
| LAMB1 | 7 | 107413687 | 107413717 | − |
| TCP11L2 | 12 | 105254106 | 105254136 | + |
| GOLGB1 | 3 | 122884438 | 122884468 | − |
| C20orf74 | 20 | 20513493 | 20513523 | − |
| WDFY2 | 13 | 51228584 | 51228614 | + |
| MGC34774 | 7 | 77817519 | 77817549 | + |
| DNAJC7 | 17 | 37394932 | 37394962 | − |
| RPAP3 | 12 | 46347014 | 46347044 | − |
| PTK2B | 8 | 27343574 | 27343604 | + |
| RNF32 | 7 | 156128527 | 156128557 | + |
| COL22A1 | 8 | 139862336 | 139862366 | − |
| VAPA | 18 | 9940550 | 9940580 | + |
| MGAT4A | 2 | 98641097 | 98641127 | − |
| RYR3 | 15 | 31920361 | 31920391 | + |
| MYB | 6 | 135552699 | 135552729 | + |
| SPATA4 | 4 | 177351087 | 177351117 | − |
| FZD3 | 8 | 28465172 | 28465202 | + |
| CR1 | 1 | 205847289 | 205847319 | + |
| C18orf8 | 18 | 19360712 | 19360742 | + |
| CHIC2 | 4 | 54609863 | 54609893 | − |
| TRIML2 | 4 | 189255193 | 189255223 | − |
| WRNIP1 | 6 | 2715579 | 2715609 | + |
| INTU | 4 | 128814803 | 128814833 | + |
| WDR67 | 8 | 124231534 | 124231564 | + |
| C1orf149 | 1 | 37747450 | 37747480 | − |
| ELA1 | 12 | 50021279 | 50021309 | − |
| C12orf51 | 12 | 111115232 | 111115262 | − |
| LIMCH1 | 4 | 41335726 | 41335756 | + |
| ROCK1 | 18 | 16793783 | 16793813 | − |
| COL4A6 | X | 107440618 | 107440648 | − |
| AGL | 1 | 100153615 | 100153645 | + |
| WWC3 | X | 10062621 | 10062651 | + |
| GPATCH1 | 19 | 38295344 | 38295374 | + |
| IFI44L | 1 | 78867257 | 78867287 | + |
| NLRC3 | 16 | 3538120 | 3538150 | − |
| DCC | 18 | 48995950 | 48995980 | + |
| ARHGEF18 | 19 | 7433205 | 7433235 | + |
| MPI | 15 | 72972181 | 72972211 | + |
| PTPN22 | 1 | 114169271 | 114169301 | − |
| KIAA1622 | 14 | 93744641 | 93744671 | + |
| DEPDC2 | 8 | 69158162 | 69158192 | + |
| NARG2 | 15 | 58527445 | 58527475 | − |
| COL25A1 | 4 | 109972969 | 109972999 | − |
| ENPP3 | 6 | 132040758 | 132040788 | + |
| UTRN | 6 | 144900531 | 144900561 | + |
| CUBN | 10 | 17022021 | 17022051 | − |
| TIAL1 | 10 | 121326097 | 121326127 | − |
| USP38 | 4 | 144346814 | 144346844 | + |
| SIPA1L2 | 1 | 230686145 | 230686175 | − |
| NUPL1 | 13 | 24791473 | 24791503 | + |
| SUPT16H | 14 | 20901216 | 20901246 | − |
| KIAA1219 | 20 | 36608472 | 36608502 | + |
| JAK2 | 9 | 5070365 | 5070395 | + |
| GALNT3 | 2 | 166323487 | 166323517 | − |
| ZC3HC1 | 7 | 129477503 | 129477533 | − |
| COL1A2 | 7 | 93878387 | 93878417 | + |
| CBX1 | 17 | 43509210 | 43509240 | − |
| SMC5 | 9 | 72102942 | 72102972 | + |
| ANXA10 | 4 | 169342392 | 169342422 | + |
| XRN1 | 3 | 143566826 | 143566856 | − |
| CREBBP | 16 | 3734880 | 3734910 | − |
| NOS1 | 12 | 116186061 | 116186091 | − |
| SMARCA5 | 4 | 144667048 | 144667078 | + |
| VPS29 | 12 | 109421707 | 109421737 | + |
| PLD1 | 3 | 172935333 | 172935363 | − |
| PIGF | 2 | 46694321 | 46694351 | − |
| C1orf27 | 1 | 184621823 | 184621853 | + |
| TCF12 | 15 | 55143298 | 55143328 | + |
| COL24A1 | 1 | 85999651 | 85999681 | − |
| MRAP2 | 6 | 84829415 | 84829445 | + |
| FOLH1 | 11 | 49161261 | 49161291 | − |
| PSMAL | 11 | 89035044 | 89035074 | + |
| SH3PXD2B | 5 | 171741629 | 171741659 | − |
| KIAA0256 | 15 | 47088689 | 47088719 | − |
| C4orf18 | 4 | 159271372 | 159271402 | − |
| NR4A3 | 9 | 101635542 | 101635572 | + |
| FAM184A | 6 | 119342986 | 119343016 | − |
| PDE8B | 5 | 76743287 | 76743317 | + |
| DDX4 | 5 | 55116914 | 55116944 | + |
| ERN1 | 17 | 59511851 | 59511881 | − |
| COL12A1 | 6 | 75868020 | 75868050 | − |
| COPB2 | 3 | 140573239 | 140573269 | − |
| ICA1 | 7 | 8147904 | 8147934 | − |
| NUP98 | 11 | 3759832 | 3759862 | − |
| GJA1 | 6 | 121798662 | 121798692 | + |
| LRRC19 | 9 | 26989596 | 26989626 | − |
| IPO8 | 12 | 30709405 | 30709435 | − |
| CDK5RAP2 | 9 | 122255539 | 122255569 | − |
| UTY | Y | 13944813 | 13944843 | − |
| EIF3A | 10 | 120806226 | 120806256 | − |
| ASNSD1 | 2 | 190238407 | 190238437 | + |

[A] *Homo sapiens* (human) genome assembly GRCh37 (hg19) from Genome Reference Consortium

TABLE 2D

Exemplary SMSM Splice Site Targets with GGAguaag splice site sequence

| Gene | Chr | Genomic location | Genomic location | Strand |
|---|---|---|---|---|
| CD1B | 1 | 156565768 | 156565798 | − |
| ZFYVE1 | 14 | 72514372 | 72514402 | − |
| LENG1 | 19 | 59352297 | 59352327 | − |
| PRUNE2 | 9 | 78424060 | 78424090 | − |
| HLA-DPB1 | 6 | 33161542 | 33161572 | + |
| GSTO2 | 10 | 106047417 | 106047447 | + |
| BRSK1 | 19 | 60506032 | 60506062 | + |
| GAPDH | 12 | 6517578 | 6517608 | + |
| TTLL9 | 20 | 29950014 | 29950044 | + |
| CACHD1 | 1 | 64820560 | 64820590 | + |
| DPP3 | 11 | 66019521 | 66019551 | + |
| LRWD1 | 7 | 101892597 | 101892627 | + |
| CYFIP2 | 5 | 156685209 | 156685239 | + |
| KIAA1787 | 17 | 7165139 | 7165169 | − |
| KCNN2 | 5 | 113850384 | 113850414 | + |
| SLC25A14 | X | 129301993 | 129302023 | + |
| CEL | 9 | 134934051 | 134934081 | + |
| TRPM3 | 9 | 72443834 | 72443864 | − |
| DPY19L2P2 | 7 | 102707805 | 102707835 | − |
| COL17A1 | 10 | 105787368 | 105787398 | − |
| TRPM5 | 11 | 2383317 | 2383347 | − |
| ITGB1 | 10 | 33254789 | 33254819 | − |
| ACTG2 | 2 | 73982140 | 73982130 | + |
| TECTB | 10 | 114049297 | 114049327 | + |
| SYCP2 | 20 | 57890379 | 57890409 | − |
| KIAA1166 | X | 64056670 | 64056700 | − |
| RTF1 | 15 | 39549867 | 39549897 | + |
| MGAM | 7 | 141368693 | 141368723 | + |
| PCBP4 | 3 | 51970789 | 51970819 | − |
| ERCC1 | 19 | 50609045 | 50609075 | − |
| CGN | 1 | 149764875 | 149764905 | + |
| CACNA1G | 17 | 46040364 | 46040394 | + |
| NT5C | 17 | 70638855 | 70638885 | − |
| MGAT5 | 2 | 134815785 | 134815815 | + |
| SDK1 | 7 | 3975567 | 3975597 | + |
| RMND5B | 5 | 177503319 | 177503349 | + |
| HLA-G | 6 | 29905434 | 29905464 | + |
| HP1BP3 | 1 | 20975661 | 20975691 | − |
| KIAA0564 | 13 | 41191711 | 41191741 | − |
| SLC6A6 | 3 | 14464313 | 14464343 | + |
| NFKBIL2 | 8 | 145638852 | 145638882 | − |
| PRODH | 22 | 17298487 | 17298517 | − |
| CACNA1H | 16 | 1202124 | 1202154 | + |
| INTS3 | 1 | 152003306 | 152003336 | + |
| POMT2 | 14 | 76842417 | 76842447 | − |
| KLK12 | 19 | 56226928 | 56226958 | − |
| FAM134A | 2 | 219754156 | 219754186 | + |
| MKKS | 20 | 10360316 | 10360346 | − |
| HPGD | 4 | 175650861 | 175650891 | − |
| FKBP3 | 14 | 44659824 | 44659854 | − |
| TXNDC10 | 18 | 64501126 | 64501156 | − |
| NUP88 | 17 | 5230736 | 5230766 | − |
| SV2C | 5 | 75622897 | 75622927 | + |
| ADAM32 | 8 | 39222827 | 39222857 | + |
| SEZ6 | 17 | 24307287 | 24307317 | − |
| NUDT5 | 10 | 12277759 | 12277789 | − |
| PDZRN3 | 3 | 73535973 | 73536003 | − |
| TP53I3 | 2 | 24161089 | 24161119 | − |
| SCN8A | 12 | 50366493 | 50366523 | + |
| NLRC3 | 16 | 3547579 | 3547609 | − |
| CDK6 | 7 | 92090270 | 92090300 | − |
| RFT1 | 3 | 53128924 | 53128954 | − |
| GSTCD | 4 | 106966391 | 106966421 | + |
| DAZ2 | Y | 23782988 | 23783018 | + |
| DAZ2 | Y | 25408223 | 25408253 | + |
| FCGBP | 19 | 45124790 | 45124820 | − |
| ZNF326 | 1 | 90245882 | 90245912 | + |
| ITPR2 | 12 | 26483311 | 26483341 | − |
| CHL1 | 3 | 411540 | 411570 | + |
| NKAIN2 | 6 | 124645972 | 124646002 | + |
| COL11A1 | 1 | 103121327 | 103121357 | − |
| CNGA3 | 2 | 98366321 | 98366351 | + |
| SYT6 | 1 | 114437864 | 114437894 | − |
| ARHGAP26 | 5 | 142373859 | 142373889 | + |
| PTPRN2 | 7 | 157596266 | 157596296 | − |
| EPHA4 | 2 | 221999412 | 221999442 | − |
| RUFY1 | 5 | 178936728 | 178936758 | + |
| ATP13A5 | 3 | 194534217 | 194534247 | − |
| PELI2 | 14 | 55825090 | 55825120 | + |
| BTAF1 | 10 | 93681242 | 93681272 | + |
| SIVA1 | 14 | 104294127 | 104294157 | + |
| APOH | 17 | 61655880 | 61655910 | − |
| TGS1 | 8 | 56848817 | 56848847 | + |
| CMYA5 | 5 | 79122633 | 79122663 | + |
| NLRP7 | 19 | 60141208 | 60141238 | − |
| CYP24A1 | 20 | 52208016 | 52208046 | − |
| B4GALNT3 | 12 | 439957 | 439987 | + |
| UTP20 | 12 | 100203775 | 100203805 | + |
| NEK11 | 3 | 132475093 | 132475123 | + |
| CARKD | 13 | 110072699 | 110072729 | + |
| C15orf60 | 15 | 71630529 | 71630559 | + |
| PIP5K1A | 1 | 149478263 | 149478293 | + |
| NLRC5 | 16 | 55662016 | 55662046 | + |
| SCN2A | 2 | 165872678 | 165872708 | + |
| PITRM1 | 10 | 3192024 | 3192054 | − |
| RRM1 | 11 | 4105047 | 4105077 | + |
| PKIB | 6 | 122996196 | 122996226 | + |
| C9orf43 | 9 | 115225584 | 115225614 | + |
| ADAM22 | 7 | 87630416 | 87630446 | + |
| HCK | 20 | 30126170 | 30126200 | + |
| MRPL11 | 11 | 65961135 | 65961165 | − |
| COL2A1 | 12 | 46677640 | 46677670 | − |
| TBPL1 | 6 | 134343076 | 134343106 | + |
| TM4SF20 | 2 | 227943859 | 227943889 | − |
| KIAA0528 | 12 | 22567611 | 22567641 | − |
| C11orf65 | 11 | 107783017 | 107783047 | − |
| PTPRT | 20 | 40377761 | 40377791 | − |
| ITFG1 | 16 | 46044129 | 46044159 | − |
| MAP2K1 | 15 | 64466804 | 64466834 | + |
| HSF2BP | 21 | 43877565 | 43877595 | − |
| RFTN1 | 3 | 16394213 | 16394243 | − |
| ITPR2 | 12 | 26759936 | 26759966 | − |
| OBFC2A | 2 | 192254973 | 192255003 | + |
| WDR16 | 17 | 9442360 | 9442390 | − |
| OPTN | 10 | 13191006 | 13191036 | + |
| C14orf101 | 14 | 56121488 | 56121518 | + |
| ADRBK2 | 22 | 24404867 | 24404897 | + |
| TOM1L2 | 17 | 17710899 | 17710929 | − |
| C6orf118 | 6 | 165614944 | 165614974 | − |
| PDLIM5 | 4 | 95794799 | 95794829 | + |
| USP1 | 1 | 62686910 | 62686940 | + |
| HLTF | 3 | 150250693 | 150250723 | − |
| ERBB4 | 2 | 211960899 | 211960929 | − |
| C4orf29 | 4 | 129161828 | 129161858 | + |
| UTP20 | 12 | 100293650 | 100293680 | + |
| CRYZ | 1 | 74952835 | 74952865 | − |
| DCBLD1 | 6 | 117960234 | 117960264 | + |
| KIF3B | 20 | 30378333 | 30378363 | + |
| AKNA | 9 | 116161679 | 116161709 | − |
| RALGDS | 9 | 134965460 | 134965490 | − |
| TM6SF1 | 15 | 81579422 | 81579452 | + |
| PMFBP1 | 16 | 70714298 | 70714328 | − |
| TBC1D29 | 17 | 25911845 | 25911875 | + |
| FAM161A | 2 | 61927382 | 61927412 | − |
| TBC1D26 | 17 | 15587032 | 15587062 | + |
| ZNF169 | 9 | 96088900 | 96088930 | − |
| KIAA1409 | 14 | 93218778 | 93218808 | + |
| NFE2L2 | 2 | 177807182 | 177807212 | − |
| PRKCA | 17 | 62213539 | 62213569 | + |
| CLPTM1 | 19 | 50172542 | 50172572 | − |
| MCM6 | 2 | 136350283 | 136350313 | − |
| TMEM194A | 12 | 55750708 | 55750738 | + |
| SCN4A | 17 | 59403212 | 59403242 | − |
| TUSC3 | 8 | 15645477 | 15645507 | + |
| GBGT1 | 9 | 135028946 | 135028976 | − |
| CCDC146 | 7 | 76721801 | 76721831 | + |
| GFM1 | 3 | 159853935 | 159853965 | + |
| MSMB | 10 | 51225827 | 51225857 | + |

TABLE 2D-continued

Exemplary SMSM Splice Site Targets with GGAguaag splice site sequence

| Gene | Chr | Genomic location | Genomic location | Strand |
|---|---|---|---|---|
| STAT6 | 12 | 55778539 | 55778569 | − |
| FAM176B | 1 | 36562065 | 36562095 | − |
| NEB | 2 | 152054715 | 152054745 | − |
| MTIF2 | 2 | 55349202 | 55349232 | − |
| CLEC16A | 16 | 10974404 | 10974434 | + |
| ADAMTS12 | 5 | 33685400 | 33685430 | − |
| LOC389634 | 12 | 8434117 | 8434147 | − |
| TGM7 | 15 | 41356336 | 41356366 | − |
| SLC6A13 | 12 | 217337 | 217367 | − |
| C11orf30 | 11 | 75911968 | 75911998 | + |
| DCUN1D4 | 4 | 52469883 | 52469913 | + |
| TEK | 9 | 27159612 | 27159642 | + |
| RRP1B | 21 | 43920630 | 43920660 | + |
| MGC16169 | 4 | 107450517 | 107450547 | − |
| TMEM77 | 1 | 111464661 | 111464691 | − |
| ADCY3 | 2 | 24915204 | 24915234 | − |
| RALBP1 | 18 | 9503272 | 9503302 | + |
| EPHB2 | 1 | 23111664 | 23111694 | + |
| PDXK | 21 | 43996923 | 43996953 | + |
| SLC22A17 | 14 | 22891679 | 22891709 | − |
| GPR158 | 10 | 25724933 | 25724963 | + |
| LYN | 8 | 57022821 | 57022851 | + |
| SFRS12 | 5 | 65476106 | 65476136 | + |
| DHRS9 | 2 | 169632008 | 169632038 | + |
| CLK1 | 2 | 201437053 | 201437083 | − |
| SLC6A11 | 3 | 10840062 | 10840092 | + |
| COL1A1 | 17 | 45631570 | 45631600 | − |
| DVL3 | 3 | 185367140 | 185367170 | + |
| ITIH1 | 3 | 52796653 | 52796683 | + |
| NLRP8 | 19 | 61179466 | 61179496 | + |
| SNCAIP | 5 | 121808311 | 121808341 | + |
| SH3BGRL2 | 6 | 80440220 | 80440250 | + |
| PDE10A | 6 | 165768699 | 165768729 | − |
| OPN4 | 10 | 88408409 | 88408439 | + |
| C1orf87 | 1 | 60227396 | 60227426 | − |
| EFNA4 | 1 | 153306525 | 153306555 | + |
| KLHL20 | 1 | 172011589 | 172011619 | + |
| LAMA1 | 18 | 6948460 | 6948490 | − |
| BBS4 | 15 | 70804034 | 70804064 | + |
| SUPT6H | 17 | 24025743 | 24025773 | + |
| MEGF10 | 5 | 126797085 | 126797115 | + |
| FGD6 | 12 | 94026394 | 94026424 | − |
| SMTN | 22 | 29825867 | 29825897 | + |
| PBRM1 | 3 | 52671173 | 52671203 | − |
| ATG16L2 | 11 | 72212800 | 72212830 | + |
| KALRN | 3 | 125859073 | 125859103 | + |
| DDEF1 | 8 | 131269521 | 131269551 | − |
| CSTF3 | 11 | 33077714 | 33077744 | − |
| ARHGAP8 | 22 | 43576693 | 43576723 | + |
| ZC3H7A | 16 | 11759772 | 11759802 | − |
| LARP7 | 4 | 113777829 | 113777859 | + |
| EFTUD2 | 17 | 40318134 | 40318164 | − |
| UCK1 | 9 | 133391637 | 133391667 | − |
| CAPN3 | 15 | 40465431 | 40465461 | + |
| CNTN6 | 3 | 1389143 | 1389173 | + |
| PARD3 | 10 | 34730744 | 34730774 | − |
| TAF2 | 8 | 120866606 | 120866636 | − |
| TSPAN7 | X | 38310537 | 38310567 | + |
| TP53BP2 | 1 | 222038424 | 222038454 | − |
| JMJD1C | 10 | 64638813 | 64638843 | − |
| GRIA1 | 5 | 153058811 | 153058841 | + |
| RNGTT | 6 | 89567986 | 89568016 | − |
| ABCC9 | 12 | 21957057 | 21957087 | − |
| SNX6 | 14 | 34168848 | 34168878 | − |
| CGNL1 | 15 | 55531764 | 55531794 | + |
| ITGAL | 16 | 30429943 | 30429973 | + |
| CYP4F3 | 19 | 15621076 | 15621106 | + |
| CYP4F2 | 19 | 15862106 | 15862136 | − |
| MS4A13 | 11 | 60047987 | 60048017 | + |
| C2orf55 | 2 | 98820998 | 98821028 | − |
| AFP | 4 | 74534033 | 74534063 | + |
| COL15A1 | 9 | 100851846 | 100851876 | + |
| RIF1 | 2 | 152023655 | 152023685 | + |
| RPS6KA6 | X | 83246147 | 83246177 | − |
| DDX1 | 2 | 15670844 | 15670874 | + |
| MPDZ | 9 | 13129970 | 13130000 | − |
| PGM2 | 4 | 37526652 | 37526682 | + |
| RBL2 | 16 | 52058567 | 52058597 | + |
| CCDC131 | 12 | 70294865 | 70294895 | − |
| NDC80 | 18 | 2598814 | 2598844 | + |
| USH2A | 1 | 214238836 | 214238866 | − |
| VPS39 | 15 | 40243100 | 40243130 | − |
| DMTF1 | 7 | 86648578 | 86648608 | + |
| RNF11 | 1 | 51508370 | 51508400 | + |
| DOCK10 | 2 | 225378003 | 225378033 | − |
| IQGAP2 | 5 | 75942749 | 75942779 | + |
| NLRP13 | 19 | 61108104 | 61108134 | − |

$^A$ Homo sapiens (human) genome assembly GRCh37 (hg19) from Genome Reference Consortium Methods of Treatment The compositions and methods described herein can be used for treating a human disease or disorder associated with aberrant splicing, such as aberrant pre-mRNA splicing. The compositions and methods described herein can be used for treating a human disease or disorder by modulating mRNA, such as pre-mRNA. In some embodiments, the compositions and methods described herein can be used for treating a human disease or disorder by modulating splicing of a nucleic acid even when that nucleic acid is not aberrantly spliced in the pathogenesis of the disease or disorder being treated.

Provided herein are methods of treating cancer or a non-cancer disease or condition in a mammal in need thereof. The method can comprise administering a therapeutically effective amount of a compound described herein or a pharmaceutically acceptable salt thereof, to a mammal with a cancer or a non-cancer disease or condition. In some embodiments, the present disclosure relates to the use of an SMSM as described herein for the preparation of a medicament for the treatment, prevention and/or delay of progression of cancer or a non-cancer disease or condition. In some embodiments, the present disclosure relates to the use of a steric modulator as described herein for the treatment, prevention and/or delay of progression of cancer or a non-cancer disease or condition.

In some embodiments, an effective amount in the context of the administration of an SMSM compound or a pharmaceutically acceptable salt thereof, or composition or medicament thereof refers to an amount of an SMSM compound or a pharmaceutically acceptable salt thereof to a patient which has a therapeutic effect and/or beneficial effect. In certain specific embodiments, an effective amount in the context of the administration of an SMSM compound or a pharmaceutically acceptable salt thereof, or composition or medicament thereof to a patient results in one, two or more of the following effects: (i) reduces or ameliorates the severity of a disease; (ii) delays onset of a disease; (iii) inhibits the progression of a disease; (iv) reduces hospitalization of a subject; (v) reduces hospitalization length for a subject; (vi) increases the survival of a subject; (vii) improves the quality of life of a subject; (viii) reduces the number of symptoms associated with a disease; (ix) reduces or ameliorates the severity of a symptom associated with a disease; (x) reduces the duration of a symptom associated with a disease associated; (xi) prevents the recurrence of a symptom associated with a disease; (xii) inhibits the development or onset of a symptom of a disease; and/or (xiii) inhibits of the progression of a symptom associated with a disease. In some embodiments, an effective amount of an SMSM compound or a pharmaceutically acceptable salt thereof is an amount effective to restore the amount of a RNA transcript of a gene to the amount of the RNA transcript detectable in healthy patients or cells from healthy patients. In other embodiments, an effective amount of an SMSM compound or a pharmaceutically acceptable salt thereof is an amount effective to restore the amount an RNA isoform and/or protein isoform of gene to the amount of the RNA isoform and/or protein isoform detectable in healthy patients or cells from healthy patients.

In some embodiments, an effective amount of an SMSM compound or a pharmaceutically acceptable salt thereof is an amount effective to decrease the aberrant amount of an RNA transcript of a gene which associated with a disease. In some embodiments, an effective amount of an SMSM compound or a pharmaceutically acceptable salt thereof is an amount effective to decrease the amount of the aberrant expression of an isoform of a gene. In some embodiments, an effective amount of an SMSM compound or a pharmaceutically acceptable salt thereof is an amount effective to result in a substantial change in the amount of an RNA transcript (e.g., mRNA transcript), alternative splice variant or isoform.

In some embodiments, an effective amount of an SMSM compound or a pharmaceutically acceptable salt thereof is an amount effective to increase or decrease the amount of an RNA transcript (e.g., an mRNA transcript) of gene which is beneficial for the prevention and/or treatment of a disease. In some embodiments, an effective amount of an SMSM compound or a pharmaceutically acceptable salt thereof is an amount effective to increase or decrease the amount of an alternative splice variant of an RNA transcript of gene which is beneficial for the prevention and/or treatment of a disease. In some embodiments, an effective amount of an SMSM compound or a pharmaceutically acceptable salt thereof is an amount effective to increase or decrease the amount of an isoform of gene which is beneficial for the prevention and/or treatment of a disease.

A method of treating cancer in a subject in need thereof can comprise administering to the subject a therapeutically effective amount of a compound described herein or a pharmaceutically acceptable salt thereof. A method of treating a non-cancer disease or condition in a subject in need thereof can comprise administering to the subject a therapeutically effective amount of a compound described herein or a pharmaceutically acceptable salt thereof.

In some embodiments, the present disclosure relates to a method for the treatment, prevention and/or delay of progression of cancer or a non-cancer disease or condition comprising administering an effective amount of a SMSM as described herein to a subject, in particular to a mammal.

In some embodiments, an effective amount in the context of the administration of an SMSM compound or a pharmaceutically acceptable salt thereof, or composition or medicament thereof refers to an amount of an SMSM compound or a pharmaceutically acceptable salt thereof to a patient which has a therapeutic effect and/or beneficial effect. In certain specific embodiments, an effective amount in the context of the administration of an SMSM compound or a pharmaceutically acceptable salt thereof, or composition or medicament thereof to a patient results in one, two or more of the following effects: (i) reduces or ameliorates the severity of a disease; (ii) delays onset of a disease; (iii) inhibits the progression of a disease; (iv) reduces hospitalization of a subject; (v) reduces hospitalization length for a subject; (vi) increases the survival of a subject; (vii) improves the quality of life of a subject; (viii) reduces the number of symptoms associated with a disease; (ix) reduces or ameliorates the severity of a symptom associated with a disease; (x) reduces the duration of a symptom associated with a disease associated; (xi) prevents the recurrence of a symptom associated with a disease; (xii) inhibits the development or onset of a symptom of a disease; and/or (xiii) inhibits of the progression of a symptom associated with a disease. In some embodiments, an effective amount of an SMSM compound or a pharmaceutically acceptable salt thereof is an amount effective to restore the amount of a RNA transcript of a gene to the amount of the RNA transcript detectable in healthy patients or cells from healthy patients. In other embodiments, an effective amount of an SMSM compound or a pharmaceutically acceptable salt thereof is an amount effective to restore the amount an RNA isoform and/or protein isoform of gene to the amount of the RNA isoform and/or protein isoform detectable in healthy patients or cells from healthy patients.

In some embodiments, an effective amount of an SMSM compound or a pharmaceutically acceptable salt thereof is an amount effective to decrease the aberrant amount of an RNA transcript of a gene which associated with a disease. In some embodiments, an effective amount of an SMSM compound or a pharmaceutically acceptable salt thereof is an amount effective to decrease the amount of the aberrant expression of an isoform of a gene. In some embodiments, an effective amount of an SMSM compound or a pharmaceutically acceptable salt thereof is an amount effective to result in a substantial change in the amount of an RNA transcript (e.g., mRNA transcript), alternative splice variant or isoform.

In some embodiments, an effective amount of an SMSM compound or a pharmaceutically acceptable salt thereof is an amount effective to increase or decrease the amount of an RNA transcript (e.g., an mRNA transcript) of gene which is beneficial for the prevention and/or treatment of a disease. In some embodiments, an effective amount of an SMSM compound or a pharmaceutically acceptable salt thereof is an amount effective to increase or decrease the amount of an alternative splice variant of an RNA transcript of gene which is beneficial for the prevention and/or treatment of a disease. In some embodiments, an effective amount of an SMSM compound or a pharmaceutically acceptable salt thereof is an amount effective to increase or decrease the amount of an isoform of gene which is beneficial for the prevention and/or treatment of a disease. Non-limiting examples of effective amounts of an SMSM compound or a pharmaceutically acceptable salt thereof are described herein. For example, the effective amount may be the amount required to prevent and/or treat a disease associated with the aberrant amount of an mRNA transcript of gene in a human subject. In general, the effective amount will be in a range of from about 0.001 mg/kg/day to about 500 mg/kg/day for a patient having a weight in a range of between about 1 kg to about 200 kg. The typical adult subject is expected to have a median weight in a range of between about 70 and about 100 kg.

In one embodiment, an SMSM described herein can be used in the preparation of medicaments for the treatment of diseases or conditions described herein. In addition, a method for treating any of the diseases or conditions described herein in a subject in need of such treatment, can involve administration of pharmaceutical compositions that includes at least one SMSM described herein or a pharmaceutically acceptable salt, thereof, in a therapeutically effective amount to a subject.

In certain embodiments, an SMSM described herein can be administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial. In prophylactic applications, compositions containing an SMSM described herein can be administered to a patient susceptible to or otherwise at risk of a particular disease, disorder or condition. In certain embodiments, the dose of drug being administered may be temporarily reduced or temporarily suspended for a certain length of time (i.e., a "drug holiday"). Doses employed for adult human treatment typically range of 0.01 mg-5000 mg per day or from about 1 mg to about 1000 mg per day. In some embodiments, a desired dose is conveniently presented in a single dose or in divided doses.

For combination therapies described herein, dosages of the co-administered compounds can vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially. If administration is simultaneous, the multiple therapeutic agents can be, by way of example only, provided in a single, unified form, or in multiple forms.

Conditions and Diseases

The present disclosure relates to a pharmaceutical composition comprising a SMSM described herein for use in the treatment, prevention and/or delay of progression of a disease, disorder or condition. In some embodiments, the present disclosure relates to a pharmaceutical composition comprising a SMSM described herein for use in the treatment, prevention and/or delay of progression of a disease, disorder or condition in Table 2A, Table 2B, Table 2C and Table 2D.

A method of treating, preventing, or delaying a non-cancer disease or condition disease can comprise administering a therapeutically effective amount of a compound described herein or a pharmaceutically acceptable salt thereof to a subject with a disease, disorder or condition in Table 2A, Table 2B, Table 2C and Table 2D.

In some embodiments, the present disclosure relates to a pharmaceutical composition comprising a SMSM described herein for use in the treatment, prevention and/or delay of progression of cancer.

A method of treating, preventing, or delaying cancer can comprise administering a therapeutically effective amount of a compound described herein or a pharmaceutically acceptable salt thereof to a subject with a liquid cancer. A method of treating, preventing, or delaying cancer can comprise administering a therapeutically effective amount of a compound described herein or a pharmaceutically acceptable salt thereof to a subject with a leukemia or lymphoma. A method of treating, preventing, or delaying cancer can comprise administering a therapeutically effective amount of a compound described herein or a pharmaceutically acceptable salt thereof to a subject with a leukemia, acute myeloid leukemia, colon cancer, gastric cancer, macular degeneration, acute monocytic leukemia, breast cancer, hepatocellular carcinoma, cone-rod dystrophy, alveolar soft part sarcoma, myeloma, skin melanoma, prostatitis, pancreatitis, pancreatic cancer, retinitis, adenocarcinoma, adenoiditis, adenoid cystic carcinoma, cataract, retinal degeneration, gastrointestinal stromal tumor, Wegener's granulomatosis, sarcoma, myopathy, prostate adenocarcinoma, Hodgkin's lymphoma, ovarian cancer, non-Hodgkin's lymphoma, multiple myeloma, chronic myeloid leukemia, acute lymphoblastic leukemia, renal cell carcinoma, transitional cell carcinoma, colorectal cancer, chronic lymphocytic leukemia, anaplastic large cell lymphoma, kidney cancer, breast cancer, cervical cancer.

A method of treating, preventing, or delaying cancer can comprise administering a therapeutically effective amount of a compound described herein or a pharmaceutically acceptable salt thereof to a subject with a solid cancer or solid tumor.

In some embodiments, the tumor is selected from the group consisting of adenocarcinoma, melanoma (e.g., metastatic melanoma), liver cancer (e.g., hepatocellular carcinoma, hepatoblastoma, liver carcinoma), prostate cancer (e.g., prostate adenocarcinoma, androgen-independent prostate cancer, androgen-dependent prostate cancer, prostate carcinoma), sarcoma (e.g., leiomyosarcoma, rhabdomyosarcoma), brain cancer (e.g., glioma, a malignant glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma, anaplastic astrocytoma, juvenile pilocytic astrocytoma, a mixture of oligodendroglioma and astrocytoma elements), breast cancer (e.g., triple negative breast cancer, metastatic breast cancer, breast carcinoma, breast sarcoma, adenocarcinoma, lobular (small cell) carcinoma, intraductal carcinoma, medullary breast cancer, mucinous breast cancer, tubular breast cancer, papillary breast cancer, inflammatory breast cancer), Paget's disease, juvenile Paget's disease, lung cancer (e.g., KRAS-mutated non-small cell lung cancer, non-small cell lung cancer, squamous cell carcinoma (epidermoid carcinoma), adenocarcinoma, large-cell carcinoma, small cell lung cancer, lung carcinoma), pancreatic cancer (e.g., insulinoma, gastrinoma, glucagonoma, vipoma, somatostatin-secreting tumor, carcinoid tumor, islet cell tumor, pancreas carcinoma), skin cancer (e.g., skin melanoma, basal cell carcinoma, squamous cell carcinoma, melanoma, superficial spreading melanoma, nodular melanoma, lentigo malignant melanoma, acrallentiginous melanoma, skin carcinoma), cervical cancer (e.g., squamous cell carcinoma, adenocarcinoma, cervical carcinoma), ovarian cancer (e.g., ovarian epithelial carcinoma, borderline tumor, germ cell tumor, stromal tumor, ovarian carcinoma), cancer of the mouth, cancer of the nervous system (e.g., cancer of the central nervous system, a CNS germ cell tumor), goblet cell metaplasia, kidney cancer (e.g., renal cell cancer, adenocarcinoma, hypernephroma, Wilms' tumor, fibrosarcoma, transitional cell cancer (renal pelvis and/or uterer), renal cell carcinoma, renal carcinoma), bladder cancer (e.g., transitional cell carcinoma, squamous cell cancer, carcinosarcoma), stomach cancer (e.g., fungating (polypoid), ulcerating, superficial spreading, diffusely spreading, liposarcoma, fibrosarcoma, carcinosarcoma), uterine cancer (e.g., endometrial cancer, endometrial carcinoma, uterine sarcoma), cancer of the esophagus (e.g., squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma, esophageal carcinomas), colon cancer (e.g., colon carcinoma, cancer of the rectum (e.g., rectal cancers), colorectal cancer (e.g., colorectal carcinoma, metastatic colorectal cancer, hereditary nonpolyposis colorectal cancer, KRAS mutated colorectal cancer), gallbladder cancer (e.g., adenocarcinoma, cholangiocarcinoma, papillary cholangiocarcinoma, nodular cholangiocarcinoma, diffuse cholangiocarcinoma), testicular cancer (e.g., germinal tumor, seminoma, anaplastic testicular cancer, classic (typical) testicular cancer, spermatocytic testicular cancer, nonseminoma testicular cancer), embryonal carcinoma (e.g., teratoma carcinoma, choriocarcinoma (yolk-sac tumor)), gastric cancer (e.g., gastrointestinal stromal tumor, cancer of other gastrointestinal tract organs, gastric carcinomas), bone cancer (e.g., connective tissue sarcoma, bone sarcoma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcoma, angiosarcoma (hemangiosarcoma), fibrosarcoma, Kaposi's sarcoma, leiomyosarcoma, alveolar soft part sarcoma), liposarcoma, lymphangiosarcoma, neurilemmoma, rhabdomyosarcoma, synovial sarcoma, cancer of the lymph node (e.g., lymphangioendotheliosarcoma), adenoid cystic carcinoma, vaginal cancer (e.g., squamous cell carcinoma, adenocarcinoma, melanoma), vulvar cancer (e.g., squamous cell carcinoma, melanoma, adenocarcinoma, sarcoma, Paget's disease), cancer of other reproductive organs, thyroid cancer (e.g., papillary thyroid cancer, follicular thyroid cancer, medullary thyroid cancer, anaplastic thyroid cancer, thyroid carcinoma), salivary gland cancer (e.g., adenocarcinoma, mucoepidermoid carcinoma), eye cancer (e.g., ocular melanoma, iris melanoma, choroidal melanoma, cilliary body melanoma, retinoblastoma), penal cancers, oral cancer (e.g. squamous cell carcinoma, basal cancer), pharynx cancer (e.g., squamous cell cancer, verrucous pharynx cancer), cancer of the head, cancer of the neck, cancer of the throat, cancer of the chest, cancer of the spleen, cancer of skeletal muscle, cancer of subcutaneous tissue, adrenal cancer, pheochromocytoma, adrenocortical carcinoma, pituitary cancer, Cushing's disease, prolactin-secreting tumor, acromegaly, diabetes insipidus, myxosarcoma, osteogenic sarcoma, endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, papillary adenocarcinomas, ependyoma, optic nerve glioma, primitive neuroectodermal tumor, rhabdoid tumor, renal cancer, glioblastoma multiforme, neurofibroma, neurofibromatosis, pediatric cancer, neuroblastoma, malignant melanoma, carcinoma of the epidermis, polycythemia vera, Waldenstrom's macroglobulinemia, monoclonal gammopathy of undetermined significance, benign monoclonal gammopathy, heavy chain disease, pediatric solid tumor, Ewing's sarcoma, Wilms tumor, carcinoma of the epidermis, HIV-related Kaposi's sarcoma, rhabdomyosarcoma, thecomas, arrhenoblastomas, endometrial carcinoma, endometrial hyperplasia, endometriosis, fibrosarcomas, choriocarcinoma, nasopharyngeal carcinoma, laryngeal carcinoma, hepatoblastoma, Kaposi's sarcoma, hemangioma, cavernous hemangioma, hemangioblastoma, retinoblastoma, glioblastoma, Schwannoma, neuroblastoma, rhabdomyosarcoma, osteogenic sarcoma, leiomyosarcoma, urinary tract carcinoma, abnormal vascular proliferation associated with phakomatoses, edema (such as that associated with brain tumors), Meigs' syndrome, pituitary adenoma, primitive neuroectodermal tumor, medullblastoma, and acoustic neuroma.

A method of treating, preventing, or delaying cancer can comprise administering a therapeutically effective amount of a compound described herein or a pharmaceutically acceptable salt thereof to a subject with basal cell carcinoma, goblet cell metaplasia, or a malignant glioma. A method of treating, preventing, or delaying cancer can comprise administering a therapeutically effective amount of a compound described herein or a pharmaceutically acceptable salt thereof to a subject with a cancer of the liver, breast, lung, prostate, cervix, uterus, colon, pancreas, kidney, stomach, bladder, ovary, or brain.

A method of treating, preventing, or delaying cancer can comprise administering a therapeutically effective amount of a compound described herein or a pharmaceutically acceptable salt thereof to a subject with a cancer of the head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, and brain or central nervous system.

Specific examples of cancers that can be prevented and/or treated in accordance with present disclosure include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangio sarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; KRAS mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acrallentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

A method of treating, preventing, or delaying cancer can comprise administering a therapeutically effective amount of a compound described herein or a pharmaceutically acceptable salt thereof to a subject with a pediatric solid tumor, Ewing's sarcoma, Wilms tumor, neuroblastoma, neurofibroma, carcinoma of the epidermis, malignant melanoma, cervical carcinoma, colon carcinoma, lung carcinoma, renal carcinoma, breast carcinoma, breast sarcoma, metastatic breast cancer, HIV-related Kaposi's sarcoma, prostate cancer, androgen-independent prostate cancer, androgen-dependent prostate cancer, neurofibromatosis, lung cancer, non-small cell lung cancer, KRAS-mutated non-small cell lung cancer, malignant melanoma, melanoma, colon cancer, KRAS-mutated colorectal cancer, glioblastoma multiforme, renal cancer, kidney cancer, bladder cancer, ovarian cancer, hepatocellular carcinoma, thyroid carcinoma, rhabdomyosarcoma, acute myeloid leukemia, or multiple myeloma.

In some embodiments, cancers and conditions associated therewith that are prevented and/or treated in accordance with the present disclosure are breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), or Meigs' syndrome. In specific embodiment, the cancer an astrocytoma, an oligodendroglioma, a mixture of oligodendroglioma and an astrocytoma elements, an ependymoma, a meningioma, a pituitary adenoma, a primitive neuroectodermal tumor, a medullblastoma, a primary central nervous system (CNS) lymphoma, or a CNS germ cell tumor.

In some embodiments, the cancer treated in accordance with the present disclosure is an acoustic neuroma, an anaplastic astrocytoma, a glioblastoma multiforme, or a meningioma. In some embodiments, the cancer treated in accordance with the present disclosure is a brain stem glioma, a craniopharyngioma, an ependyoma, a juvenile pilocytic astrocytoma, a medulloblastoma, an optic nerve glioma, primitive neuroectodermal tumor, or a rhabdoid tumor.

A method of treating, preventing, or delaying a condition or disease can comprise administering a therapeutically effective amount of a compound described herein or a pharmaceutically acceptable salt thereof to a subject with acute myeloid leukemia, ALS, Alzheimer's disease, argyrophilic grain disease, cancer metabolism, chronic lymphocytic leukemia, colorectal carcinoma, corticobasal degeneration, cystic fibrosis, dilated cardiomyopathy, Duchenne muscular dystrophy, Ehlers-Danlos syndrome, endometrial cancer, Fabry's disease, familial dysautonomia, familial hypercholesterolemia, familial persistent hyperinsulinemic hypoglycemia, frontotemporal dementia, FTDP-17, gucher's disease, glioma, globular glial tauopathy, HIV-1, Huntington's disease, Hutchinson-Gilford progeria syndrome, hypercholesterolemia, Leber congenital amaurosis, migraine, multiple sclerosis, myelodysplastic syndromes, NASH, Niemann-Pick's, non-small cell lung cancer, pain, Parkinson's disease, phenylketonuria, Pick's disease, progressive supranuclear palsy, spinal muscular atrophy, spinocerebellar ataxia type 2, or Wilson's disease.

A method of treating, preventing, or delaying a non-cancer disease or condition disease can comprise administering a therapeutically effective amount of a compound described herein or a pharmaceutically acceptable salt thereof to a subject with atypical hemolytic uremic syndrome (aHUS), cystic fibrosis, muscular dystrophy, polycystic autosomal-dominant kidney disease, cancer-induced cachexia, benign prostatic hyperplasia, rheumatoid arthritis, psoriasis, atherosclerosis, obesity, retinopathies (including diabetic retinopathy and retinopathy of prematurity), retrolental fibroplasia, neovascular glaucoma, age-related macular degeneration, exudative macular degeneration, thyroid hyperplasias (including Grave's disease), corneal and other tissue transplantation, epidemic keratoconjunctivitis, Vitamin A deficiency, contact lens overwear, atopic keratitis, superior limbic keratitis, and pterygium keratitis sicca, viral infections, inflammation associated with viral infections, chronic inflammation, lung inflammation, nephrotic syndrome, preeclampsia, ascites, pericardial effusion (such as that associated with pericarditis), pleural effusion, Sjogren's syndrome, acne rosacea, phylectenulosis, syphilis, lipid degeneration, chemical burns, bacterial ulcers, fungal ulcers, Herpes simplex infection, Herpes zoster infections, protozoan infections, Mooren's ulcer, Terrien's marginal degeneration, marginal keratolysis, systemic lupus, polyarteritis, trauma, Wegener's sarcoidosis, Paget's disease, scleritis, Stevens-Johnson's disease, pemphigoid, radial keratotomy, Eales' disease, Behcet's disease, sickle cell anemia, pseudoxanthoma elasticum, Stargardt's disease, pars planitis, chronic retinal detachment, vein occlusion, artery occlusion, carotid obstructive disease, chronic uveitis/vitritis, ocular histoplasmosis, Mycobacteria infections, Lyme's disease, Best's disease, myopia, optic pits, hyperviscosity syndromes, toxoplasmosis, sarcoidosis, trauma, post-laser complications, diseases associated with rubeosis (neovascularization of the iris and of the angle), and diseases caused by the abnormal proliferation of fibrovascular or fibrous tissue, including all forms of prolific vitreoretinopathy. Certain examples of non-neoplastic conditions that can be prevented and/or treated in accordance with the methods described herein include viral infections, including but not limited to, those associated with viruses belonging to Flaviviridae, flavivirus, pestivirus, hepacivirus, West Nile virus, hepatitis C virus (HCV) or human papilloma virus (HPV), cone-rod dystrophy, prostatitis, pancreatitis, retinitis, cataract, retinal degeneration, Wegener's granulomatosis, myopathy, adenoiditis, germ cell tumors, combined methylmalonic aciduria and homocystinuria, cb1C type, Alzheimer's disease, hyperprolinemia, acne, tuberculosis, succinic semialdehyde dehydrogenase deficiency, esophagitis, mental retardation, glycine encephalopathy, Crohn's disease, spina bifida, autosomal recessive disease, schizophrenia, neural tube defects, myelodysplastic syndromes, amyotropic lateral sclerosis, neuronitis, Parkinson's disease, talipes equinovarus, dystrophinopathies, cerebritis, bladder related disorders, cleft lip, cleft palate, cervicitis, spasticity, lipoma, scleroderma, Gitelman syndrome, poliomyelitis, paralysis, Aagenaes syndrome, oculomotor nerve paralysis, and spinal muscular atrophy.

A method of treating, preventing, or delaying a non-cancer disease or condition disease can comprise administering a therapeutically effective amount of a compound described herein or a pharmaceutically acceptable salt thereof to a subject with atypical hemolytic uremic syndrome (aHUS), Hutchinson-Gilford progeria syndrome (HGPS), Limb girdle muscular dystrophy type 1B, Familial partial lipodystrophy type 2, Frontotemporal dementia with parkinsonism chromosome 17, Richardson's syndrome, PSP-Parkinsonism, Argyrophilic grain disease, Corticobasal degeneration, Pick's disease, Globular glial tauopathy, Guadeloupean Parkinsonism, Myotonic dystrophy, Down Syndrome, Neonatal Hypoxia-Ischemia, Familial Dysautonomia, Spinal muscular atrophy, Hypoxanthine phosphoribosyltransferase deficiency, Ehlers-Danlos syndrome, Occipital Horn Syndrome, Fanconi Anemia, Marfan Syndrome, thrombotic thrombocytopenic purpura, glycogen Storage Disease Type III, cystic fibrosis, neurofibromatosis, Tyrosinemia (type I), Menkes Disease, Analbuminemia, Congenital acetylcholinesterase deficiency, Haemophilia B deficiency (coagulation factor IX deficiency), Recessive dystrophic epidermolysis bullosa, Dominant dystrophic epidermolysis bullosa, Somatic mutations in kidney tubular epithelial cells, Neurofibromatosis type II, X-linked adrenoleukodystrophy (X-ALD), FVII deficiency, Homozygous hypobetalipoproteinemia, Ataxia-telangiectasia, Androgen Sensitivity, Common congenital afibrinogenemia, Risk for emphysema, Mucopolysaccharidosis type II (Hunter syndrome), Severe type III osteogenesis imperfecta, Ehlers-Danlos syndrome IV, Glanzmann thrombasthenia, Mild Bethlem myopathy, Dowling-Meara epidermolysis bullosa simplex, Severe deficiency of MTHFR, Acute intermittent porphyria, Tay-Sachs Syndrome, Myophosphorylase deficiency (McArdle disease), Chronic Tyrosinemia Type 1, Mutation in placenta, Leukocyte adhesion deficiency, Hereditary C3 deficiency, Neurofibromatosis type I, Placental aromatase deficiency, Cerebrotendinous xanthomatosis, Duchenne and Becker muscular dystrophy, Severe factor V deficiency, Alpha-thalassemia, Beta-thalassemia, Hereditary HL deficiency, Lesch-Nyhan syndrome, Familial hypercholesterolemia, Phosphoglycerate kinase deficiency, Cowden syndrome, X-linked retinitis pigmentosa (RP3), Crigler-Najjar syndrome type 1, Chronic tyrosinemia type I, Sandhoff disease, Maturity onset diabetes of the young (MODY), Familial tuberous sclerosis, Polycystic kidney disease 1, or Primary Hyperthyroidism.

In some embodiments, non-cancer diseases that can be prevented and/or treated in accordance with the disclosure of WO2016/19638$_6$ al, WO2016/12834$_3$ al, WO2015/02487$_6$ a2 and EP3053577A1. In some embodiments, non-cancer diseases that can be prevented and/or treated include, but are not limited to, atypical hemolytic uremic syndrome (aHUS), Hutchinson-Gilford progeria syndrome (HGPS), Limb girdle muscular dystrophy type 1B, Familial partial lipodystrophy type 2, Frontotemporal dementia with parkinsonism chromosome 17, Richardson's syndrome, PSP-Parkinsonism, Argyrophilic grain disease, Corticobasal degeneration, Pick's disease, Globular glial tauopathy, Guadeloupean Parkinsonism, Myotonic dystrophy, Down Syndrome, Neonatal Hypoxia-Ischemia, Familial Dysautonomia, Spinal muscular atrophy, Hypoxanthine phosphoribosyltransferase deficiency, Ehlers-Danlos syndrome, Occipital Horn Syndrome, Fanconi Anemia, Marfan Syndrome, thrombotic thrombocytopenic purpura, glycogen Storage Disease Type III, cystic fibrosis, neurofibromatosis, Tyrosinemia (type I), Menkes Disease, Analbuminemia, Congenital acetylcholinesterase deficiency, Haemophilia B deficiency (coagulation factor IX deficiency), Recessive dystrophic epidermolysis bullosa, Dominant dystrophic epidermolysis bullosa, Somatic mutations in kidney tubular epithelial cells, Neurofibromatosis type II, X-linked adrenoleukodystrophy (X-ALD), FVII deficiency, Homozygous hypobetalipoproteinemia, Ataxia-telangiectasia, Androgen Sensitivity, Common congenital afibrinogenemia, Risk for emphysema, Mucopolysaccharidosis type II (Hunter syndrome), Severe type III osteogenesis imperfecta, Ehlers-Danlos syndrome IV, Glanzmann thrombasthenia, Mild Bethlem myopathy, Dowling-Meara epidermolysis bullosa simplex, Severe deficiency of MTHFR, Acute intermittent *porphyria*, Tay-Sachs Syndrome, Myophosphorylase deficiency (McArdle disease), Chronic Tyrosinemia Type 1, Mutation in placenta, Leukocyte adhesion deficiency, Hereditary C3 deficiency, Neurofibromatosis type I, Placental aromatase deficiency, Cerebrotendinous xanthomatosis, Duchenne and Becker muscular dystrophy, Severe factor V deficiency, Alpha-thalassemia, Beta-thalassemia, Hereditary HL deficiency, Lesch-Nyhan syndrome, Familial hypercholesterolemia, Phosphoglycerate kinase deficiency, Cowden syndrome, X-linked retinitis pigmentosa (RP3), Crigler-Najjar syndrome type 1, Chronic tyrosinemia type I, Sandhoff disease, Maturity onset diabetes of the young (MODY), Familial tuberous sclerosis, or Polycystic kidney disease 1.

Methods of Administering

The compositions described herein can be administered to the subject in a variety of ways, including parenterally, intravenously, intradermally, intramuscularly, colonically, rectally or intraperitoneally. In some embodiments, the small molecule splicing modulator or a pharmaceutically acceptable salt thereof is administered by intraperitoneal injection, intramuscular injection, subcutaneous injection, or intravenous injection of the subject. In some embodiments, the pharmaceutical compositions can be administered parenterally, intravenously, intramuscularly or orally. The oral agents comprising a small molecule splicing modulator can be in any suitable form for oral administration, such as liquid, tablets, capsules, or the like. The oral formulations can be further coated or treated to prevent or reduce dissolution in stomach. The compositions of the present invention can be administered to a subject using any suitable methods known in the art. Suitable formulations for use in the present invention and methods of delivery are generally well known in the art. For example, the small molecule splicing modulators described herein can be formulated as pharmaceutical compositions with a pharmaceutically acceptable diluent, carrier or excipient. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

Pharmaceutical formulations described herein can be administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the pharmaceutical compositions described herein are administered orally. In some embodiments, the pharmaceutical compositions described herein are administered topically. In such embodiments, the pharmaceutical compositions described herein are formulated into a variety of topically administrable compositions, such as solutions, suspensions, lotions, gels, pastes, shampoos, scrubs, rubs, smears, medicated sticks, medicated bandages, balms, creams or ointments. In some embodiments, the pharmaceutical compositions described herein are administered topically to the skin. In some embodiments, the pharmaceutical compositions described herein are administered by inhalation. In some embodiments, the pharmaceutical compositions described herein are formulated for intranasal administration. Such formulations include nasal sprays, nasal mists, and the like. In some embodiments, the pharmaceutical compositions described herein are formulated as eye drops. In some embodiments, the pharmaceutical compositions described herein are: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal. In some embodiments, the pharmaceutical compositions described herein are administered orally to the mammal. In certain embodiments, an SMSM described herein is administered in a local rather than systemic manner. In some embodiments, an SMSM described herein is administered topically. In some embodiments, an SMSM described herein is administered systemically.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

SMSMs suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against contamination from microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition.

Dosing and Schedules

The SMSMs utilized in the methods of the invention can be, e.g., administered at dosages that may be varied depending upon the requirements of the subject the severity of the condition being treated and/or imaged, and/or the SMSM being employed. For example, dosages can be empirically determined considering the type and stage of disease diagnosed in a particular subject and/or the type of imaging modality being used in conjunction with the SMSMs. The dose administered to a subject, in the context of the present invention should be sufficient to affect a beneficial diagnostic or therapeutic response in the subject. The size of the dose also can be determined by the existence, nature, and extent of any adverse side-effects that accompany the administration of a SMSM in a particular subject.

It is advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Toxicity and therapeutic efficacy of such compounds can be determined by procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue to minimize potential damage to uninfected cells and, thereby, reduce side effects.

Therapeutic index data obtained from cell culture assays and/or animal studies can be used in predicting the therapeutic index in vivo and formulating a range of dosages for use in subjects, such as human subjects. The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the concentration of the test compound which achieves a half-maximal inhibition of symptoms as determined in cell culture. Such information can be used to more accurately determine useful doses in humans. Levels in plasma may be measured, for example, by high performance liquid chromatography. Various animal models and clinical assays for evaluating effectiveness of a particular SMSM in preventing or reducing a disease or condition are known in the art may be used in the present invention. The dosage may vary within this range depending upon the dosage form employed and the route of administration utilized. The exact formulation, route of administration and dosage can be chosen by the individual physician in view of the patient's condition. (See e.g. Fingl et al, 1975, In: The Pharmacological Basis of Therapeutics. Ch. 1 pi).

In some aspects, the SMSMs provided have a therapeutic index ($LD_{50}/ED_{50}$) of at least about 1, 2, 3, 4, 5, 6, 7, 8, 9, 10, 11, 12, 13, 14, 15, 16, 17, 18, 19, 20, 40, 50, 60, 70, 80, 90, 100, 200, 300, 400, 500, 600, 700, 800, 900, 1000, 10000, or 100000 or more. In some aspects, the SMSMs provided have a therapeutic index ($LD_{50}/ED_{50}$) of at least about 1, 2, 3, 4, 5, 6, 7, 8, 9, 10, 11, 12, 13, 14, 15, 16, 17, 18, 19, 20, 40, 50, 60, 70, 80, 90, 100, 200, 300, 400, 500, 600, 700, 800, 900, 1000, 10000, or 100000 or more as determined in cell culture.

In some aspects, the SMSMs provided have an $IC_{50}$ viability/$EC_{50}$ splicing value of at least about 1, 2, 3, 4, 5, 6, 7, 8, 9, 10, 11, 12, 13, 14, 15, 16, 17, 18, 19, 20, 40, 50, 60, 70, 80, 90, 100, 200, 300, 400, 500, 600, 700, 800, 900, 1000, 10000, or 100000 or more. In some aspects, the SMSMs provided have an $IC_{50}$ viability/$EC_{50}$ splicing value of at least about 1, 2, 3, 4, 5, 6, 7, 8, 9, 10, 11, 12, 13, 14, 15, 16, 17, 18, 19, 20, 40, 50, 60, 70, 80, 90, 100, 200, 300, 400, 500, 600, 700, 800, 900, 1000, 10000, or 100000 or more as determined in cell culture.

A dosage of using an SMSM when administered may be at least 1, 2, 3, 4, 5, 6, 7, 8, 9, 10, 11, 12, 13, 14, 15, 16, 17, 18, 19, or 20 grams/m² in humans, or a dosage in another subject comparable to that in humans. A dosage ("dosage X") of an SMSM in a subject other than a human is comparable to a dosage ("dosage Y") of the SMSM in humans if the serum concentration of the scavenger in the subject post administration of the SMSM at dosage X is equal to the serum concentration of the SMSM in humans post administration of the compound at dosage Y.

Within the scope of the present description, the effective amount of an SMSM compound or a pharmaceutically acceptable salt thereof for use in the manufacture of a medicament, the preparation of a pharmaceutical kit or in a method for preventing and/or treating a disease in a human subject in need thereof, is intended to include an amount in a range of from about 1 pg to about 50 grams.

The compositions of the present invention can be administered as frequently as necessary, including hourly, daily, weekly or monthly.

In any of the aforementioned aspects are further embodiments comprising single administrations of an effective amount of an SMSM described herein, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of an SMSM described herein, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of an SMSM described herein is temporarily suspended or the dose of the compound being administered is temporarily reduced; at the end of the drug holiday, dosing of the compound is resumed. In one embodiment, the length of the drug holiday varies from 2 days to 1 year.

Combination Therapies

In certain instances, it is appropriate to administer at least one SMSM described herein in combination with another therapeutic agent. For example, a compound SMSM described herein can be co-administered with a second therapeutic agent, wherein SMSM and the second therapeutic agent modulate different aspects of the disease, disorder or condition being treated, thereby providing a greater overall benefit than administration of either therapeutic agent alone.

In some embodiments, an SMSM described herein can be used in combination with an anti-cancer therapy. In some embodiments, a steric modulator is used in combination with conventional chemotherapy, radiotherapy, hormonal therapy, and/or immunotherapy. In some embodiments, an SMSM described herein can be used in combination with conventional chemotherapeutic agents including alkylating agents (e.g., temozolomide, cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), EGFR inhibitors (e.g., gefitinib, erlotinib, etc.), and the like.

In some embodiments, an SMSM may be administered in combination with one or more other SMSMs.

A SMSM may be administered to a subject in need thereof prior to, concurrent with, or following the administration of chemotherapeutic agents. For instance, SMSMs may be administered to a subject at least 8 hours, 7 hours, 6 hours, 5 hours, 4 hours, 3 hours, 2 hours, 1.5 hours, 1 hour, or 30 minutes before the starting time of the administration of chemotherapeutic agent(s). In certain embodiments, they may be administered concurrent with the administration of chemotherapeutic agent(s). In other words, in these embodiments, SMSMs are administrated at the same time when the administration of chemotherapeutic agent(s) starts. In other embodiments, SMSMs may be administered following the starting time of administration of chemotherapeutic agent(s) (e.g., at least 30 minutes, 1 hour, 2 hours, 3 hours, 4 hours, 5 hours, 6 hours, 7 hours or 8 hours after the starting time of administration of chemotherapeutic agents). Alternatively, SMSMs may be administered at least 30 minutes, 1 hour, 2 hours, 3 hours, 4 hours, 5 hours, 6 hours, 7 hours or 8 hours after the completion of administration of chemotherapeutic agents. Generally, these SMSMs are administered for a sufficient period of time so that the disease or condition is prevented or reduced. Such sufficient period of time may be identical to, or different from, the period during which chemotherapeutic agent(s) are administered. In certain embodiments, multiple doses of SMSMs are administered for each administration of a chemotherapeutic agent or a combination of multiple chemotherapeutic agents.

In certain embodiments, an appropriate dosage of a SMSM is combined with a specific timing and/or a particular route to achieve the optimum effect in preventing or reducing the disease or condition. For instance, an SMSM may be administered to a human orally at least 1 hour, 2 hours, 3 hours, 4 hours, 5 hours, 6 hours, 7 hours 8 hours, 9 hours, 10 hours, 11 hours or 12 hours; or at least 1 day, 2 days, 3 days, 4 days, 5 days, 6 days, 7 days, 8 days, 9 days, 10 days, 11 days, 12 days; or at least 1 week, 2 weeks, 3 weeks or 4 weeks; or at least 1 month, 2 months, 3 months, 4 months, 5 months, 6 months, 7 months, 8 months, 9 months, 10 months, 11 months or 12 months; prior to or after the beginning or the completion, of the administration of a chemotherapeutic agent or a combination of chemotherapeutic agents.

Subjects

The subjects that can be treated with the SMSMs and methods described herein can be any subject that produces mRNA that is subject to alternative splicing, e.g., the subject may be a eukaryotic subject, such as a plant or an animal. In some embodiments, the subject is a mammal, e.g., human. In some embodiments, the subject is a human. In some embodiments, the subject is a non-human animal. In some embodiments, the subject is a fetus, an embryo, or a child. In some embodiments, the subject is a non-human primate such as chimpanzee, and other apes and monkey species; farm animals such as cattle, horses, sheep, goats, swine; domestic animals such as rabbits, dogs, and cats; laboratory animals including rodents, such as rats, mice and guinea pigs, and the like.

In some embodiments, the subject is prenatal (e.g., a fetus), a child (e.g., a neonate, an infant, a toddler, a preadolescent), a pubescent, or an adult (e.g., an early adult, a middle aged adult, a senior citizen). The human subject can be between about 0 months and about 120 years old, or older. The human subject can be between about 0 and about 12 months old; for example, about 1, 2, 3, 4, 5, 6, 7, 8, 9, 10, 11, or 12 months old. The human subject can be between about 0 and 12 years old; for example, between about 0 and 30 days old; between about 1 month and 12 months old; between about 1 year and 3 years old; between about 4 years and 5 years old; between about 4 years and 12 years old; about 1, 2, 3, 4, 5, 6, 7, 8, 9, 10, 11, or 12 years old. The human subject can be between about 13 years and 19 years old; for example, about 13, 14, 15, 16, 17, 18, or 19 years old. The human subject can be between about 20 and about 39 year old; for example, about 20, 21, 22, 23, 24, 25, 26, 27, 28, 29, 30, 31, 32, 33, 34, 35, 36, 37, 38, or 39 years old. The human subject can be between about 40 to about 59 years old; for example, about 40, 41, 42, 43, 44, 45, 46, 47, 48, 49, 50, 51, 52, 53, 54, 55, 56, 57, 58, or 59 years old. The human subject can be greater than 59 years old; for example, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old. The human subjects can include living subjects or deceased subjects. The human subjects can include male subjects and/or female subjects.

Assays

Gene expression experiments often involve measuring the relative amount of gene expression products, such as mRNA, expressed in two or more experimental conditions. This is because altered levels of a specific sequence of a gene expression product can suggest a changed need for the protein coded for by the gene expression product, perhaps indicating a homeostatic response or a pathological condition.

In some embodiments, a method can comprise measuring, assaying or obtaining expression levels of one or more genes. In some cases, the method provides a number or a range of numbers, of genes that the expression levels of the genes can be used to diagnose, characterize or categorize a biological sample. In some embodiments, the gene expression data corresponds to data of an expression level of one or more biomarkers that are related to a disease or condition. The number of genes used can be between about 1 and about 500; for example about 1-500, 1-400, 1-300, 1-200, 1-100, 1-50, 1-25, 1-10, 10-500, 10-400, 10-300, 10-200, 10-100, 10-50, 10-25, 25-500, 25-400, 25-300, 25-200, 25-100, 25-50, 50-500, 50-400, 50-300, 50-200, 50-100, 100-500, 100-400, 100-300, 100-200, 200-500, 200-400, 200-300, 300-500, 300-400, 400-500, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, or any included range or integer. For example, at least about 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, 500 or more total genes can be used. The number of genes used can be less than or equal to about 1, 2, 3, 4, 5, 6, 7, 8, 9, 10, 15, 20, 25, 30, 33, 35, 38, 40, 43, 45, 48, 50, 53, 58, 63, 65, 68, 100, 120, 140, 142, 145, 147, 150, 152, 157, 160, 162, 167, 175, 180, 185, 190, 195, 200, 300, 400, 500, or more.

In some embodiments, relative gene expression, as compared to normal cells and/or tissues of the same organ, can be determined by measuring the relative rates of transcription of RNA, such as by production of corresponding cDNAs and then analyzing the resulting DNA using probes developed from the gene sequences as corresponding to a genetic marker. Thus, the levels of cDNA produced by use of reverse transcriptase with the full RNA complement of a cell suspected of being cancerous produces a corresponding amount of cDNA that can then be amplified using polymerase chain reaction, or some other means, such as linear amplification, isothermal amplification, NASB, or rolling circle amplification, to determine the relative levels of resulting cDNA and, thereby, the relative levels of gene expression. General methods for determining gene expression product levels are known to the art and may include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, SAGE, enzyme linked immuno-absorbance assays, mass-spectrometry, immunohistochemistry, blotting, microarray, RT-PCR, quantitative PCR, sequencing, RNA sequencing, DNA sequencing (e.g., sequencing of cDNA obtained from RNA); Next-Gen sequencing, nanopore sequencing, pyrosequencing, or Nanostring sequencing. Gene expression product levels may be normalized to an internal standard such as total mRNA or the expression level of a particular gene including but not limited to glyceraldehyde 3-phosphate dehydrogenase, or tubulin.

Gene expression data generally comprises the measurement of the activity (or the expression) of a plurality of genes, to create a picture of cellular function. Gene expression data can be used, for example, to distinguish between cells that are actively dividing, or to show how the cells react to a particular treatment. Microarray technology can be used to measure the relative activity of previously identified target genes and other expressed sequences. Sequence based techniques, like serial analysis of gene expression (SAGE, SuperSAGE) are also used for assaying, measuring or obtaining gene expression data. SuperSAGE is especially accurate and can measure any active gene, not just a predefined set. In an RNA, mRNA or gene expression profiling microarray, the expression levels of thousands of genes can be simultaneously monitored to study the effects of certain treatments, diseases, and developmental stages on gene expression.

Figure 4:
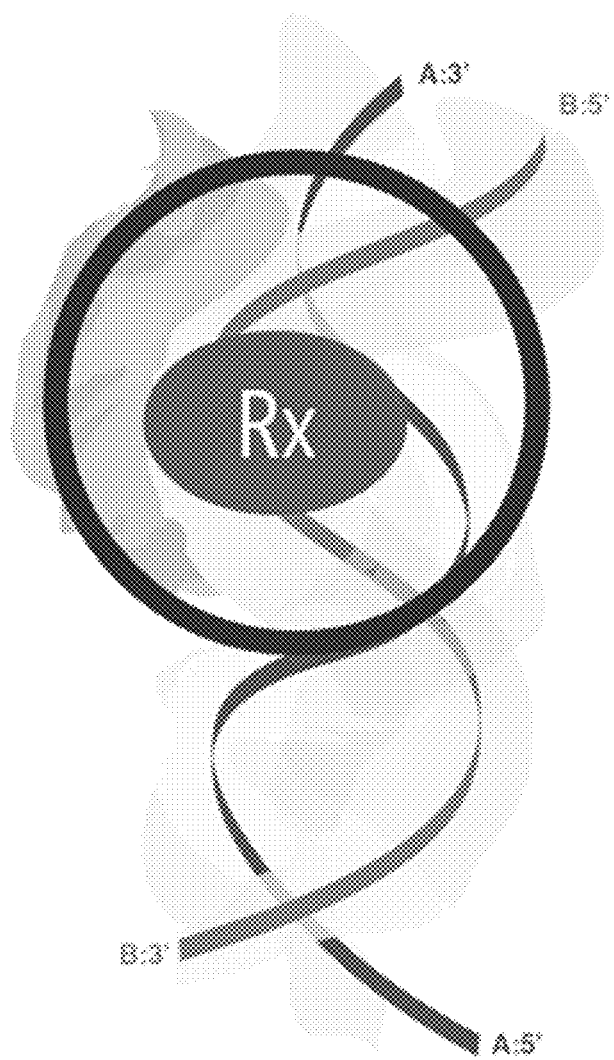
FIG. 4 depicts a diagram of an exemplary small molecule splicing modulator bound to a complex comprising a polynucleotide and splicing complex protein.
Figure 5:
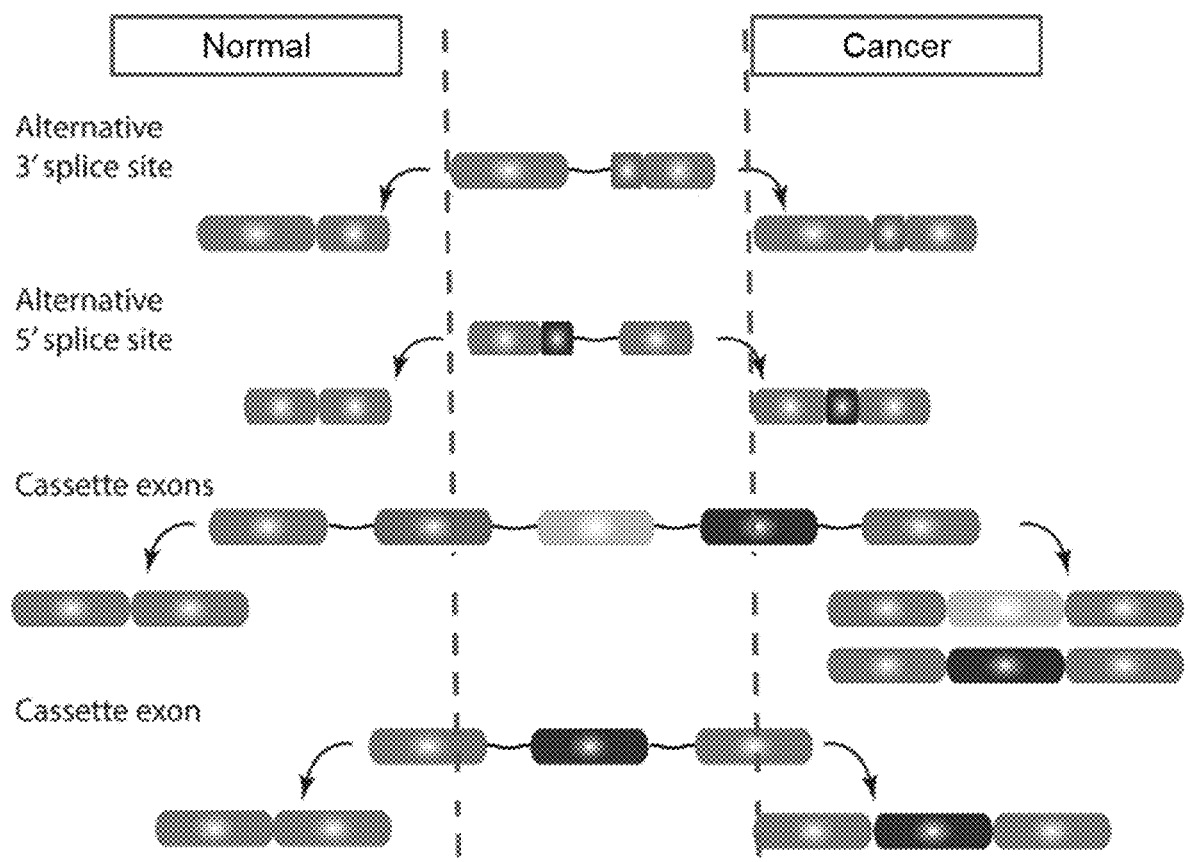
FIG. 5 depicts a diagram of alternative splicing of exemplary pre-mRNAs transcribed from the indicated genes. mRNA isoforms depicted on the left are normal; mRNA isoforms depicted on the right promote cancer.

In accordance with the foregoing, the expression level of a gene, marker, gene expression product, mRNA, pre-mRNA, or a combination thereof may be determined using northern blotting and employing the sequences as identified herein to develop probes for this purpose. Such probes may be composed of DNA or RNA or synthetic nucleotides or a combination of these and may advantageously be comprised of a contiguous stretch of nucleotide residues matching, or complementary to, a sequence corresponding to a genetic marker identified in FIG. 4. Such probes will most usefully comprise a contiguous stretch of at least 15-200 residues or more including 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, 100, 110, 120, 130, 140, 150, 160, 175, or 200 nucleotides or more. Thus, where a single probe binds multiple times to the transcriptome of experimental cells, whereas binding of the same probe to a similar amount of transcriptome derived from the genome of control cells of the same organ or tissue results in observably more or less binding, this is indicative of differential expression of a gene, marker, gene expression product, mRNA, or pre-mRNA comprising, or corresponding to, sequences corresponding to a genetic marker from which the probe sequence was derived.

In some embodiments of the present invention, gene expression may be determined by microarray analysis using, for example, Affymetrix arrays, cDNA microarrays, oligonucleotide microarrays, spotted microarrays, or other microarray products from Biorad, Agilent, or Eppendorf. Microarrays provide particular advantages because they may contain a large number of genes or alternative splice variants that may be assayed in a single experiment. In some cases, the microarray device may contain the entire human genome or transcriptome or a substantial fraction thereof allowing a comprehensive evaluation of gene expression patterns, genomic sequence, or alternative splicing. Markers may be found using standard molecular biology and microarray analysis techniques as described in Sambrook *Molecular Cloning a Laboratory Manual* 2001 and Baldi, P., and Hatfield, W. G., *DNA Microarrays and Gene Expression* 2002.

Microarray analysis generally begins with extracting and purifying nucleic acid from a biological sample, (e.g. a biopsy or fine needle aspirate) using methods known to the art. For expression and alternative splicing analysis it may be advantageous to extract and/or purify RNA from DNA. It may further be advantageous to extract and/or purify mRNA from other forms of RNA such as tRNA and rRNA. In some embodiments, RNA samples with RIN ≤5.0 are typically not used for multi-gene microarray analysis, and may instead be used only for single-gene RT-PCR and/or TaqMan assays. Microarray, RT-PCR and TaqMan assays are standard molecular techniques well known in the relevant art. TaqMan probe-based assays are widely used in real-time PCR including gene expression assays, DNA quantification and SNP genotyping.

Various kits can be used for the amplification of nucleic acid and probe generation of the subject methods. In some embodiments, Ambion WT-expression kit can be used. Ambion WT-expression kit allows amplification of total RNA directly without a separate ribosomal RNA (rRNA) depletion step. With the Ambion® WT Expression Kit, samples as small as 50 ng of total RNA can be analyzed on Affymetrix® GeneChip® Human, Mouse, and Rat Exon and Gene 1.0 ST Arrays. In addition to the lower input RNA requirement and high concordance between the Affymetrix® method and TaqMan® real-time PCR data, the Ambion® WT Expression Kit provides a significant increase in sensitivity. For example, a greater number of probe sets detected above background can be obtained at the exon level with the Ambion® WT Expression Kit as a result of an increased signal-to-noise ratio. Ambion WT-expression kit may be used in combination with additional Affymetrix labeling kit.

In some embodiments, AmpTec Trinucleotide Nano mRNA Amplification kit (6299-A15) can be used in the subject methods. The ExpressArt® TRinucleotide mRNA amplification Nano kit is suitable for a wide range, from 1 ng to 700 ng of input total RNA. According to the amount of input total RNA and the required yields of a RNA, it can be used for 1-round (input >300 ng total RNA) or 2-rounds (minimal input amount 1 ng total RNA), with a RNA yields in the range of >10 μg. AmpTec's proprietary TRinucleotide priming technology results in preferential amplification of mRNAs (independent of the universal eukaryotic 3'-poly (A)-sequence), combined with selection against rRNAs. This kit can be used in combination with cDNA conversion kit and Affymetrix labeling kit.

In some embodiments, gene expression levels can be obtained or measured in an individual without first obtaining a sample. For example, gene expression levels may be determined in vivo, that is in the individual. Methods for determining gene expression levels in vivo are known to the art and include imaging techniques such as CAT, MRI; NMR; PET; and optical, fluorescence, or biophotonic imaging of protein or RNA levels using antibodies or molecular beacons. Such methods are described in US 2008/0044824, US 2008/0131892, herein incorporated by reference. Additional methods for in vivo molecular profiling are contemplated to be within the scope of the present invention.

Provided herein are methods for determining whether an SMSM compound or a pharmaceutically acceptable salt thereof modulates the amount of one, two, three or more RNA transcripts (e.g., pre-mRNA or mRNA transcripts or isoforms thereof) of one, two, three or more genes.

In one embodiment, provided herein is a method for determining whether an SMSM compound or a pharmaceutically acceptable salt thereof modulates the amount of an RNA transcript, comprising: (a) contacting a cell with an SMSM compound or a pharmaceutically acceptable salt thereof, and (b) determining the amount of the RNA transcript produced by the cell, wherein an alteration in the amount of the RNA transcript in the presence of an SMSM compound or a pharmaceutically acceptable salt thereof relative to the amount of the RNA transcript in the absence of an SMSM compound or a pharmaceutically acceptable salt thereof or the presence of a negative control (e.g., a vehicle control such as PBS or DMSO) indicates that an SMSM compound or a pharmaceutically acceptable salt thereof modulates the amount of the RNA transcript. In some embodiments, provided herein is a method for determining whether an SMSM compound or a pharmaceutically acceptable salt thereof modulates the amount of an RNA transcript (e.g., an mRNA transcript), comprising: (a) contacting a first cell with an SMSM compound or a pharmaceutically acceptable salt thereof, (b) contacting a second cell with a negative control (e.g., a vehicle control, such as PBS or DMSO); and (c) determining the amount of the RNA transcript produced by the first cell and the second cell; and (d) comparing the amount of the RNA transcript produced by the first cell to the amount of the RNA transcript expressed by the second cell, wherein an alteration in the amount of the RNA transcript produced by the first cell relative to the amount of the RNA transcript produced by the second cell indicates that an SMSM compound or a pharmaceutically acceptable salt thereof modulates the amount of the RNA transcript. In some embodiments, the contacting of the cell with the compound occurs in cell culture. In other embodiments, the contacting of the cell with the compound occurs in a subject, such as a non-human animal subject. In some embodiments, provided herein is a method for determining whether an SMSM compound or a pharmaceutically acceptable salt thereof modulates the splicing of an RNA transcript (e.g., an mRNA transcript), comprising: (a) culturing a cell in the presence of an SMSM compound or a pharmaceutically acceptable salt thereof, and (b) determining the amount of the two or more RNA transcripts splice variants produced by the cell, wherein an alteration in the amount of the two or more RNA transcripts in the presence of the compound relative to the amount of the two or more RNA transcripts splice variants in the absence of the compound or the presence of a negative control (e.g., a vehicle control such as PBS or DMSO) indicates that an SMSM compound or a pharmaceutically acceptable salt thereof modulates the splicing of the RNA transcript.

In some embodiments, provided herein is a method for determining whether an SMSM compound or a pharmaceutically acceptable salt thereof modulates the splicing of an RNA transcript (e.g., an mRNA transcript), comprising: (a) culturing a cell in the presence of an SMSM compound or a pharmaceutically acceptable salt thereof, (b) isolating two or more RNA transcript splice variants from the cell after a certain period of time; and (c) determining the amount of the two or more RNA transcript splice variants produced by the cell, wherein an alteration in the amount of the two or more RNA transcript in the presence of the compound relative to the amount of the two or more RNA transcript splice variants in the absence of the compound or the presence of a negative control (e.g., a vehicle control such as PBS or DMSO) indicates that an SMSM compound or a pharmaceutically acceptable salt thereof modulates the splicing of the RNA transcript. In some embodiments, provided herein is a method for determining whether an SMSM compound or a pharmaceutically acceptable salt thereof modulates the splicing of an RNA transcript (e.g., an mRNA transcript), comprising (a) culturing a first cell in the presence of an SMSM compound or a pharmaceutically acceptable salt thereof, (b) culturing a second cell in the presence of a negative control (e.g., a vehicle control, such as PBS or DMSO); (c) isolating two or more RNA transcript splice variants produced by the first cell and isolating two or more RNA transcript splice variants produced by the second cell; (d) determining the amount of the two or more RNA transcript splice variants produced by the first cell and the second cell; and (e) comparing the amount of the two or more RNA transcript splice variants produced by the first cell to the amount of the two or more RNA transcript splice variants produced by the second cell, wherein an alteration in the amount of the two or more RNA transcript splice variants produced by the first cell relative to the amount of the two or more RNA transcript splice variants produced by the second cell indicates that an SMSM compound or a pharmaceutically acceptable salt thereof modulates the splicing of the RNA transcript.

In some embodiments, provided herein is a method for determining whether an SMSM compound or a pharmaceutically acceptable salt thereof modulates the amount of an RNA transcript (e.g., an mRNA transcript), comprising: (a) contacting a cell-free system with an SMSM compound or a pharmaceutically acceptable salt thereof, and (b) determining the amount of the RNA transcript produced by the cell-free system, wherein an alteration in the amount of the RNA transcript in the presence of the compound relative to the amount of the RNA transcript in the absence of the compound or the presence of a negative control (e.g., a vehicle control such as PBS or DMSO) indicates that an SMSM compound or a pharmaceutically acceptable salt thereof modulates the amount of the RNA transcript. In some embodiments, provided herein is a method for determining whether an SMSM compound or a pharmaceutically acceptable salt thereof modulates the amount of an RNA transcript (e.g., an mRNA transcript), comprising: (a) contacting a first cell-free system with an SMSM compound or a pharmaceutically acceptable salt thereof, (b) contacting a second cell-free system with a negative control (e.g., a vehicle control, such as PBS or DMSO); and (c) determining the amount of the RNA transcript produced by the first cell-free system and the second cell-free system; and (d) comparing the amount of the RNA transcript produced by the first cell-free system to the amount of the RNA transcript expressed by the second cell-free system, wherein an alteration in the amount of the RNA transcript produced by the first cell-free system relative to the amount of the RNA transcript produced by the second cell-free system indicates that an SMSM compound or a pharmaceutically acceptable salt thereof modulates the amount of the RNA transcript. In some embodiments, the cell-free system comprises purely synthetic RNA, synthetic or recombinant (purified) enzymes, and protein factors. In other embodiments, the cell-free system comprises RNA transcribed from a synthetic DNA template, synthetic or recombinant (purified) enzymes, and protein factors. In other embodiments, the cell-free system comprises purely synthetic RNA and nuclear extract. In other embodiments, the cell-free system comprises RNA transcribed from a synthetic DNA template and nuclear extract. In other embodiments, the cell-free system comprises purely synthetic RNA and whole cell extract. In other embodiments, the cell-free system comprises RNA transcribed from a synthetic DNA template and whole cell extract. In some embodiments, the cell-free system additionally comprises regulatory RNAs (e.g., microRNAs).

In some embodiments, provided herein is a method for determining whether an SMSM compound or a pharmaceutically acceptable salt thereof modulates the splicing of an RNA transcript (e.g., an mRNA transcript), comprising: (a) contacting a cell-free system with an SMSM compound or a pharmaceutically acceptable salt thereof, and (b) determining the amount of two or more RNA transcript splice variants produced by the cell-free system, wherein an alteration in the amount of the two or more RNA transcript splice variants in the presence of the compound relative to the amount of the two or more RNA transcript splice variants in the absence of the compound or the presence of a negative control (e.g., a vehicle control such as PBS or DMSO) indicates that an SMSM compound or a pharmaceutically acceptable salt thereof modulates the splicing of the RNA transcript. In some embodiments, provided herein is a method for determining whether an SMSM compound or a pharmaceutically acceptable salt thereof modulates the splicing of an RNA transcript (e.g., an mRNA transcript), comprising: (a) contacting a first cell-free system with an SMSM compound or a pharmaceutically acceptable salt thereof; (b) contacting a second cell-free system with a negative control (e.g., a vehicle control, such as PBS or DMSO); and (c) determining the amount of two or more RNA transcript splice variants produced by the first cell-free system and the second cell-free system; and (d) comparing the amount of the two or more RNA transcript splice variants produced by the first cell-free system to the amount of the RNA transcript expressed by the second cell-free system, wherein an alteration in the amount of the two or more RNA transcript splice variants produced by the first cell-free system relative to the amount of the two or more RNA transcript splice variants produced by the second cell-free system indicates that an SMSM compound or a pharmaceutically acceptable salt thereof modulates the splicing of the RNA transcript. In some embodiments, the cell-free system comprises purely synthetic RNA, synthetic or recombinant (purified) enzymes, and protein factors. In other embodiments, the cell-free system comprises RNA transcribed from a synthetic DNA template, synthetic or recombinant (purified) enzymes, and protein factors. In other embodiments, the cell-free system comprises purely synthetic RNA and nuclear extract. In other embodiments, the cell-free system comprises RNA transcribed from a synthetic DNA template and nuclear extract. In other embodiments, the cell-free system comprises purely synthetic RNA and whole cell extract. In other embodiments, the cell-free system comprises RNA transcribed from a synthetic DNA template and whole cell extract. In some embodiments, the cell-free system additionally comprises regulatory RNAs (e.g., microRNAs).

In some embodiments, provided herein is a method for determining whether an SMSM compound or a pharmaceutically acceptable salt thereof modulates the amount of an RNA transcript (e.g., an mRNA transcript), comprising: (a) culturing a cell in the presence of an SMSM compound or a pharmaceutically acceptable salt thereof, (b) isolating the RNA transcript from the cell after a certain period of time; and (c) determining the amount of the RNA transcript produced by the cell, wherein an alteration in the amount of the RNA transcript in the presence of the compound relative to the amount of the RNA transcript in the absence of the compound or the presence of a negative control (e.g., a vehicle control such as PBS or DMSO) indicates that an SMSM compound or a pharmaceutically acceptable salt thereof modulates the amount of the RNA transcript. In some embodiments, provided herein is a method for determining whether an SMSM compound or a pharmaceutically acceptable salt thereof modulates the amount of an RNA transcript (e.g., an mRNA transcript), comprising (a) culturing a first cell in the presence of an SMSM compound or a pharmaceutically acceptable salt thereof, (b) culturing a second cell in the presence of a negative control (e.g., a vehicle control, such as PBS or DMSO); (c) isolating the RNA transcript produced by the first cell and isolating the RNA transcript produced by the second cell; (d) determining the amount of the RNA transcript produced by the first cell and the second cell; and (e) comparing the amount of the RNA transcript produced by the first cell to the amount of the RNA transcript produced by the second cell, wherein an alteration in the amount of the RNA transcript produced by the first cell relative to the amount of the RNA transcript produced by the second cell indicates that an SMSM compound or a pharmaceutically acceptable salt thereof modulates the amount of the RNA transcript.

In some embodiments, the cell contacted or cultured with an SMSM compound or a pharmaceutically acceptable salt thereof is a primary cell from a subject. In some embodiments, the cell contacted or cultured with an SMSM compound or a pharmaceutically acceptable salt thereof is a primary cell from a subject with a disease. In specific embodiments, the cell contacted or cultured with an SMSM compound or a pharmaceutically acceptable salt thereof is a primary cell from a subject with a disease associated with an aberrant amount of an RNA transcript for a particular gene. In some specific embodiments, the cell contacted or cultured with an SMSM compound or a pharmaceutically acceptable salt thereof is a primary cell from a subject with a disease associated with an aberrant amount of an isoform of a particular gene. In some embodiments, the cell contacted or cultured with an SMSM compound or a pharmaceutically acceptable salt thereof is a fibroblast, an immune cell, or a muscle cell. In some embodiments, the cell contacted or cultured with an SMSM compound or a pharmaceutically acceptable salt thereof is a diseased cell.

In some embodiments, the cell contacted or cultured with an SMSM compound or a pharmaceutically acceptable salt thereof is from a cell line. In some embodiments, the cell contacted or cultured with an SMSM compound or a pharmaceutically acceptable salt thereof is a cell line derived from a subject with a disease. In some embodiments, the cell contacted or cultured with an SMSM compound or a pharmaceutically acceptable salt thereof is from a cell line known to have aberrant RNA transcript levels for a particular gene. In specific embodiments, the cell contacted or cultured with an SMSM compound or a pharmaceutically acceptable salt thereof is from a cell line derived from a subject with a disease known to have aberrant RNA transcript levels for a particular gene. In some embodiments, the cell contacted or cultured with an SMSM compound or a pharmaceutically acceptable salt thereof is a diseased cell line. In some specific embodiments, the cell contacted or cultured with an SMSM compound or a pharmaceutically acceptable salt thereof is from a cell line derived from a subject with a disease known to have an aberrant amount of an RNA isoform and/or protein isoform of a particular gene. Non-limiting examples of cell lines include 293, 3T3, 4T1, 721, 9L, A2780, A172, A20, A253, A431, A-549, A-673, ALC, B 16, B35, BCP-1, BEAS-2B, bEnd.3, BHK, BR 293, BT20, BT483, BxPC3, C2C12, C3h-10T1/2, C6/36, C6, Cal-27, CHO, COR-L23, COS, COV-434, CML T1, CMT, CRL7030, CT26, D17, DH82, DU145, DuCaP, EL4, EM2, EM3, EMT6, FM3, H1299, H69, HB54, HB55, HCA2, HEK-293, HeLa, Hepalclc7, HL-60, HMEC, Hs578T, HsS78Bst, HT-29, HTB2, HUVEC, Jurkat, J558L, JY, K562, Ku812, KCL22, KG1, KYOl, LNCap, Ma-Mel, MC-38, MCF-7, MCF-IOA, MDA-MB-231, MDA-MB-468, MDA-MB-435, MDCK, MG63, MOR/0.2R, MONO-MAC 6, MRC5, MTD-1A, NCI-H69, NIH-3T3, NALM-1, NSO, NW-145, OPCN, OPCT, PNT-1A, PNT-2, Raji, RBL, RenCa, RIN-5F, RMA, Saos-2, Sf21, Sf9, SiHa, SKBR3, SKOV-3, T2, T-47D, T84, THP1, U373, U87, U937, VCaP, Vero, VERY, W138, WM39, WT-49, X63, YAC-1, and YAR cells. In one embodiment, the cells are from a patient.

In some embodiments, a dose-response assay is performed. In one embodiment, the dose response assay comprises: (a) contacting a cell with a concentration of an SMSM compound or a pharmaceutically acceptable salt thereof, (b) determining the amount of the RNA transcript produced by the cell, wherein an alteration in the amount of the RNA transcript in the presence of the compound relative to the amount of the RNA transcript in the absence of the compound or the presence of a negative control (e.g., a vehicle control such as PBS or DMSO) indicates that an SMSM compound or a pharmaceutically acceptable salt thereof modulates the amount of the RNA transcript; (c) repeating steps (a) and (b), wherein the only experimental variable changed is the concentration of the compound or a form thereof, and (d) comparing the amount of the RNA transcript produced at the different concentrations of the compound or a form thereof. In some embodiments, the dose response assay comprises: (a) culturing a cell in the presence of an SMSM compound or a pharmaceutically acceptable salt thereof, (b) isolating the RNA transcript from the cell after a certain period of time; (c) determining the amount of the RNA transcript produced by the cell, wherein an alteration in the amount of the RNA transcript in the presence of the compound relative to the amount of the RNA transcript in the absence of the compound or the presence of a negative control (e.g., a vehicle control such as PBS or DMSO) indicates that an SMSM compound or a pharmaceutically acceptable salt thereof modulates the amount of the RNA transcript; (d) repeating steps (a), (b), and (c), wherein the only experimental variable changed is the concentration of the compound or a form thereof, and (e) comparing the amount of the RNA transcript produced at the different concentrations of the compound or a form thereof. In some embodiments, the dose-response assay comprises: (a) contacting each well of a microtiter plate containing cells with a different concentration of an SMSM compound or a pharmaceutically acceptable salt thereof, (b) determining the amount of an RNA transcript produced by cells in each well; and (c) assessing the change of the amount of the RNA transcript at the different concentrations of the compound or form thereof.

In some embodiments described herein, the cell is contacted or cultured with an SMSM compound or a pharmaceutically acceptable salt thereof, or a tissue sample is contacted with an SMSM compound or a pharmaceutically acceptable salt thereof, or a negative control for a period of 15 minutes, 30 minutes, 45 minutes, 1 hour, 2 hours, 3 hours, 4 hours, 5 hours, 6 hours, 8 hours, 12 hours, 18 hours, 24 hours, 48 hours, 72 hours or more. In other embodiments described herein, the cell is contacted or cultured with an SMSM compound or a pharmaceutically acceptable salt thereof, or a tissue sample is contacted with an SMSM compound or a pharmaceutically acceptable salt thereof, or a negative control for a period of 15 minutes to 1 hour, 1 to 2 hours, 2 to 4 hours, 6 to 12 hours, 12 to 18 hours, 12 to 24 hours, 28 to 24 hours, 24 to 48 hours, 48 to 72 hours.

In some embodiments described herein, the cell is contacted or cultured with a concentration of an SMSM compound or a pharmaceutically acceptable salt thereof, or a tissue sample is contacted with a concentration of an SMSM compound or a pharmaceutically acceptable salt thereof, wherein the concentration is 0.01 µM, 0.05 µM, 1 µM, 2 µM, 5 µM, 10 µM, 15 µM, 20 µM, 25 µM, 50 µM, 75 µM, 100 µM, or 150 µM. In other embodiments described herein, the cell is contacted or cultured with concentration of an SMSM compound or a pharmaceutically acceptable salt thereof, or a tissue sample is contacted with a concentration of an SMSM compound or a pharmaceutically acceptable salt thereof, wherein the concentration is 175 µM, 200 µM, 250 µM, 275 µM, 300 µM, 350 µM, 400 µM, 450 µM, 500 µM, 550 µM 600 µM, 650 µM, 700 µM, 750 µM, 800 µM, 850 µM, 900 µM, 950 µM or 1 mM. In some embodiments described herein, the cell is contacted or cultured with concentration of an SMSM compound or a pharmaceutically acceptable salt thereof, or a tissue sample is contacted with a concentration of an SMSM compound or a pharmaceutically acceptable salt thereof, wherein the concentration is 5 nM, 10 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, or 950 nM. In some embodiments described herein, the cell is contacted or cultured with concentration of an SMSM compound or a pharmaceutically acceptable salt thereof, or a tissue sample is contacted with a concentration of an SMSM compound or a pharmaceutically acceptable salt thereof, wherein the concentration is between 0.01 µM to 0.1 µM, 0.1 µM to 1 µM, 1 µM to 50 µM, 50 µM to 100 µM, 100 µM to 500 µM, 500 µM to 1 nM, 1 nM to 10 nM, 10 nM to 50 nM, 50 nM to 100 nM, 100 nM to 500 nM, 500 nM to 1000 nM.

Techniques known to one skilled in the art may be used to determine the amount of an RNA transcript. In some embodiments, the amount of one, two, three or more RNA transcripts is measured using deep sequencing, such as ILLUMINA® RNASeq, ILLUMINA® next generation sequencing (NGS), ION TORRENT™ RNA next generation sequencing, 454™ pyrosequencing, or Sequencing by Oligo Ligation Detection (SOLID™). In other embodiments, the amount of multiple RNA transcripts is measured using an exon array, such as the GENECHIP® human exon array. In some embodiments, the amount of one, two, three or more RNA transcripts is determined by RT-PCR. In other embodiments, the amount of one, two, three or more RNA transcripts is measured by RT-qPCR. Techniques for conducting these assays are known to one skilled in the art.

In some embodiments, a statistical analysis or other analysis is performed on data from the assay utilized to measure an RNA transcript. In some embodiments, a student t-test statistical analysis is performed on data from the assay utilized to measure an RNA transcript to determine those RNA transcripts that have an alternation in amount in the presence of the compound relative to the amount in the absence of the compound or presence of a negative control. In specific embodiments, the student t-test value of those RNA transcripts with the alternation is 10%, 5%, 4%, 3%, 2%, 1%, 0.5% or 0.1%. In some specific embodiments, p value of those RNA transcripts with the alternation is 10%, 5%, 4%, 3%, 2%, 1%, 0.5% or 0.1%. In certain specific embodiments, the student t-test and p values of those RNA transcripts with the alteration are 10%, 5%, 4%, 3%, 2%, 1%, 0.5% or 0.1% and 10%, 5%, 4%, 3%, 2%, 1%, 0.5% or 0.1%), respectively.

In some embodiments, a further analysis is performed to determine how an SMSM compound or a pharmaceutically acceptable salt thereof is changing the amount of an RNA transcript. In specific embodiments, a further analysis is performed to determine if an alternation in the amount of an RNA transcript in the presence of an SMSM compound or a pharmaceutically acceptable salt thereof relative the amount of the RNA transcript in the absence of the compound or a form thereof, or the presence of a negative control is due to changes in transcription, splicing, and/or stability of the RNA transcript. Techniques known to one skilled in the art may be used to determine whether an SMSM compound or a pharmaceutically acceptable salt thereof changes, e.g., the transcription, splicing and/or stability of an RNA transcript.

In some embodiments, the stability of one or more RNA transcripts is determined by serial analysis of gene expression (SAGE), differential display analysis (DD), RNA arbitrarily primer (RAP)-PCR, restriction endonuclease-lytic analysis of differentially expressed sequences (READS), amplified restriction fragment-length polymorphism (ALFP), total gene expression analysis (TOGA), RT-PCR, RT-qPCR, high-density cDNA filter hybridization analysis (HDFCA), suppression subtractive hybridization (SSH), differential screening (DS), cDNA arrays, oligonucleotide chips, or tissue microarrays. In other embodiments, the stability of one or more RNA transcripts is determined by Northern blots, RNase protection, or slot blots.

In some embodiments, the transcription in a cell or tissue sample is inhibited before (e.g., 5 minutes, 10 minutes, 30 minutes, 1 hour, 2 hours, 4 hours, 6 hours, 8 hours, 12 hours, 18 hours, 24 hours, 36 hours, 48 hours, or 72 hours before) or after (e.g., 5 minutes, 10 minutes, 30 minutes, 1 hour, 2 hours, 4 hours, 6 hours, 8 hours, 12 hours, 18 hours, 24 hours, 36 hours, 48 hours, or 72 hours after) the cell or the tissue sample is contacted or cultured with an inhibitor of transcription, such as a-amanitin, DRB, flavopiridol, triptolide, or actinomycin-D. In other embodiments, the transcription in a cell or tissue sample is inhibited with an inhibitor of transcription, such as a-amanitin, DRB, flavopiridol, triptolide, or actinomycin-D, while the cell or tissue sample is contacted or cultured with an SMSM compound or a pharmaceutically acceptable salt thereof.

In some embodiments, the level of transcription of one or more RNA transcripts is determined by nuclear run-on assay or an in vitro transcription initiation and elongation assay. In some embodiments, the detection of transcription is based on measuring radioactivity or fluorescence. In some embodiments, a PCR-based amplification step is used.

In some embodiments, the amount of alternatively spliced forms of the RNA transcripts of a particular gene are measured to see if there is an alteration in the amount of one, two or more alternatively spliced forms of the RNA transcripts of the gene. In some embodiments, the amount of an isoform encoded by a particular gene is measured to see if there is an alteration in the amount of the isoform. In some embodiments, the levels of spliced forms of RNA are quantified by RT-PCR, RT-qPCR, or northern blotting. In other embodiments, sequence-specific techniques may be used to detect the levels of an individual splice form. In some embodiments, splicing is measured in vitro using nuclear extracts. In some embodiments, detection is based on measuring radioactivity or fluorescence. Techniques known to one skilled in the art may be used to measure alterations in the amount of alternatively spliced forms of an RNA transcript of a gene and alterations in the amount of an isoform encoded by a gene.

Biological Samples

A sample, e.g., a biological sample can be taken from a subject and examined to determine whether the subject produces mRNA that is subject to alternative splicing. A biological sample can comprise a plurality of biological samples. The plurality of biological samples can contain two or more biological samples; for examples, about 2-1000, 2-500, 2-250, 2-100, 2-75, 2-50, 2-25, 2-10, 10-1000, 10-500, 10-250, 10-100, 10-75, 10-50, 10-25, 25-1000, 25-500, 25-250, 25-100, 25-75, 25-50, 50-1000, 50-500, 50-250, 50-100, 50-75, 60-70, 100-1000, 100-500, 100-250, 250-1000, 250-500,500-1000, 2, 3, 4, 5, 6, 7, 8, 9, 10, 11, 12, 13, 14, 15, 16, 17, 18, 19, 20, 21, 22, 23, 24, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, 1000, or more biological samples. The biological samples can be obtained from a plurality of subjects, giving a plurality of sets of a plurality of samples. The biological samples can be obtained from about 2 to about 1000 subjects, or more; for example, about 2-1000, 2-500, 2-250, 2-100, 2-50, 2-25, 2-20, 2-10, 10-1000, 10-500, 10-250, 10-100, 10-50, 10-25, 10-20, 15-20, 25-1000, 25-500, 25-250, 25-100, 25-50, 50-1000, 50-500, 50-250, 50-100, 100-1000, 100-500, 100-250, 250-1000, 250-500, 500-1000, or at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 68, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, 550, 600, 650, 700, 750, 800, 850, 900, 950, to 1000 or more subjects.

The biological samples can be obtained from human subjects. The biological samples can be obtained from human subjects at different ages. The human subject can be prenatal (e.g., a fetus), a child (e.g., a neonate, an infant, a toddler, a preadolescent), an adolescent, a pubescent, or an adult (e.g., an early adult, a middle aged adult, a senior citizen). The human subject can be between about 0 months and about 120 years old, or older. The human subject can be between about 0 and about 12 months old; for example, about 1, 2, 3, 4, 5, 6, 7, 8, 9, 10, 11, or 12 months old. The human subject can be between about 0 and 12 years old; for example, between about 0 and 30 days old; between about 1 month and 12 months old; between about 1 year and 3 years old; between about 4 years and 5 years old; between about 4 years and 12 years old; about 1, 2, 3, 4, 5, 6, 7, 8, 9, 10, 11, or 12 years old. The human subject can be between about 13 years and 19 years old; for example, about 13, 14, 15, 16, 17, 18, or 19 years old. The human subject can be between about 20 and about 39 year old; for example, about 20, 21, 22, 23, 24, 25, 26, 27, 28, 29, 30, 31, 32, 33, 34, 35, 36, 37, 38, or 39 years old. The human subject can be between about 40 to about 59 years old; for example, about 40, 41, 42, 43, 44, 45, 46, 47, 48, 49, 50, 51, 52, 53, 54, 55, 56, 57, 58, or 59 years old. The human subject can be greater than 59 years old; for example, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old. The human subjects can include living subjects or deceased subjects. The human subjects can include male subjects and/or female subjects.

Biological samples can be obtained from any suitable source that allows determination of expression levels of genes, e.g., from cells, tissues, bodily fluids or secretions, or a gene expression product derived therefrom (e.g., nucleic acids, such as DNA or RNA; polypeptides, such as protein or protein fragments). The nature of the biological sample can depend upon the nature of the subject. If a biological sample is from a subject that is a unicellular organism or a multicellular organism with undifferentiated tissue, the biological sample can comprise cells, such as a sample of a cell culture, an excision of the organism, or the entire organism. If a biological sample is from a multicellular organism, the biological sample can be a tissue sample, a fluid sample, or a secretion.

The biological samples can be obtained from different tissues. The term tissue is meant to include ensembles of cells that are of a common developmental origin and have similar or identical function. The term tissue is also meant to encompass organs, which can be a functional grouping and organization of cells that can have different origins. The biological sample can be obtained from any tissue. Suitable tissues from a plant can include, but are not limited to, epidermal tissue such as the outer surface of leaves; vascular tissue such as the xylem and phloem, and ground tissue. Suitable plant tissues can also include leaves, roots, root tips, stems, flowers, seeds, cones, shoots, stobili, pollen, or a portion or combination thereof.

The biological samples can be obtained from different tissue samples from one or more humans or non-human animals. Suitable tissues can include connective tissues, muscle tissues, nervous tissues, epithelial tissues or a portion or combination thereof. Suitable tissues can also include all or a portion of a lung, a heart, a blood vessel (e.g., artery, vein, capillary), a salivary gland, a esophagus, a stomach, a liver, a gallbladder, a pancreas, a colon, a rectum, an anus, a hypothalamus, a pituitary gland, a pineal gland, a thyroid, a parathyroid, an adrenal gland, a kidney, a ureter, a bladder, a urethra, a lymph node, a tonsil, an adenoid, a thymus, a spleen, skin, muscle, a brain, a spinal cord, a nerve, an ovary, a fallopian tube, a uterus, vaginal tissue, a mammary gland, a testicle, a vas deferens, a seminal vesicle, a prostate, penile tissue, a pharynx, a larynx, a trachea, a bronchi, a diaphragm, bone marrow, a hair follicle, or a combination thereof. A biological sample from a human or non-human animal can also include a bodily fluid, secretion, or excretion; for example, a biological sample can be a sample of aqueous humour, vitreous humour, bile, blood, blood serum, breast milk, cerebrospinal fluid, endolymph, perilymph, female ejaculate, amniotic fluid, gastric juice, menses, mucus, peritoneal fluid, pleural fluid, saliva, sebum, semen, sweat, tears, vaginal secretion, vomit, urine, feces, or a combination thereof. The biological sample can be from healthy tissue, diseased tissue, tissue suspected of being diseased, or a combination thereof.

In some embodiments, the biological sample is a fluid sample, for example a sample of blood, serum, sputum, urine, semen, or other biological fluid. In certain embodiments the sample is a blood sample. In some embodiments the biological sample is a tissue sample, such as a tissue sample taken to determine the presence or absence of disease in the tissue. In certain embodiments the sample is a sample of thyroid tissue.

The biological samples can be obtained from subjects in different stages of disease progression or different conditions. Different stages of disease progression or different conditions can include healthy, at the onset of primary symptom, at the onset of secondary symptom, at the onset of tertiary symptom, during the course of primary symptom, during the course of secondary symptom, during the course of tertiary symptom, at the end of the primary symptom, at the end of the secondary symptom, at the end of tertiary symptom, after the end of the primary symptom, after the end of the secondary symptom, after the end of the tertiary symptom, or a combination thereof. Different stages of disease progression can be a period of time after being diagnosed or suspected to have a disease; for example, at least about, or at least, 1, 2, 3, 4, 5, 6, 7, 8, 9, 10, 11, 12, 13, 14, 15, 16, 17, 18, 19, 20, 21, 22, 23 or 24 hours; 1, 2, 3, 4, 5, 6, 7, 8, 9, 10, 11, 12, 13, 14, 15, 16, 17, 18, 19, 20, 21, 22, 23, 24, 25, 26, 27 or 28 days; 1, 2, 3, 4, 5, 6, 7, 8, 9, 10, 11, 12, 13, 14, 15, 16, 17, 18, 19 or 20 weeks; 1, 2, 3, 4, 5, 6, 7, 8, 9, 10, 11 or 12 months; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 years after being diagnosed or suspected to have a disease. Different stages of disease progression or different conditions can include before, during or after an action or state; for example, treatment with drugs, treatment with a surgery, treatment with a procedure, performance of a standard of care procedure, resting, sleeping, eating, fasting, walking, running, performing a cognitive task, sexual activity, thinking, jumping, urinating, relaxing, being immobilized, being emotionally traumatized, being shock, and the like.

The methods of the present disclosure provide for analysis of a biological sample from a subject or a set of subjects. The subject(s) may be, e.g., any animal (e.g., a mammal), including but not limited to humans, non-human primates, rodents, dogs, cats, pigs, fish, and the like. The present methods and compositions can apply to biological samples from humans, as described herein.

A biological sample can be obtained by methods known in the art such as the biopsy methods provided herein, swabbing, scraping, phlebotomy, or any other suitable method. The biological sample can be obtained, stored, or transported using components of a kit of the present disclosure. In some cases, multiple biological samples, such as multiple thyroid samples, can be obtained for analysis, characterization, or diagnosis according to the methods of the present disclosure. In some cases, multiple biological samples, such as one or more samples from one tissue type (e.g., thyroid) and one or more samples from another tissue type (e.g., buccal) can be obtained for diagnosis or characterization by the methods of the present disclosure. In some cases, multiple samples, such as one or more samples from one tissue type (e.g., thyroid) and one or more samples from another tissue (e.g., buccal) can be obtained at the same or different times. In some cases, the samples obtained at different times are stored and/or analyzed by different methods. For example, a sample can be obtained and analyzed by cytological analysis (e.g., using routine staining). In some cases, a further sample can be obtained from a subject based on the results of a cytological analysis. The diagnosis of cancer or other condition can include an examination of a subject by a physician, nurse or other medical professional. The examination can be part of a routine examination, or the examination can be due to a specific complaint including, but not limited to, one of the following: pain, illness, anticipation of illness, presence of a suspicious lump or mass, a disease, or a condition. The subject may or may not be aware of the disease or condition. The medical professional can obtain a biological sample for testing. In some cases the medical professional can refer the subject to a testing center or laboratory for submission of the biological sample. The methods of obtaining provided herein include methods of biopsy including fine needle aspiration, core needle biopsy, vacuum assisted biopsy, incisional biopsy, excisional biopsy, punch biopsy, shave biopsy or skin biopsy. In some cases, the methods and compositions provided herein are applied to data only from biological samples obtained by FNA. In some cases, the methods and compositions provided herein are applied to data only from biological samples obtained by FNA or surgical biopsy. In some cases, the methods and compositions provided herein are applied to data only from biological samples obtained by surgical biopsy. A biological sample can be obtained by non-invasive methods, such methods including, but not limited to: scraping of the skin or cervix, swabbing of the cheek, saliva collection, urine collection, feces collection, collection of menses, tears, or semen. The biological sample can be obtained by an invasive procedure, such procedures including, but not limited to: biopsy, alveolar or pulmonary lavage, needle aspiration, or phlebotomy. The method of biopsy can further include incisional biopsy, excisional biopsy, punch biopsy, shave biopsy, or skin biopsy. The method of needle aspiration can further include fine needle aspiration, core needle biopsy, vacuum assisted biopsy, or large core biopsy. Multiple biological samples can be obtained by the methods herein to ensure a sufficient amount of biological material. Methods of obtaining suitable samples of thyroid are known in the art and are further described in the ATA Guidelines for thyroid nodule management (Cooper et al. Thyroid Vol. 16 No. 2 2006), herein incorporated by reference in its entirety. Generic methods for obtaining biological samples are also known in the art and further described in for example Ramzy, Ibrahim *Clinical Cytopathology and Aspiration Biopsy* 2001 which is herein incorporated by reference in its entirety. The biological sample can be a fine needle aspirate of a thyroid nodule or a suspected thyroid tumor. The fine needle aspirate sampling procedure can be guided by the use of an ultrasound, X-ray, or other imaging device.

In some cases, the subject can be referred to a specialist such as an oncologist, surgeon, or endocrinologist for further diagnosis. The specialist can likewise obtain a biological sample for testing or refer the individual to a testing center or laboratory for submission of the biological sample. In any case, the biological sample can be obtained by a physician, nurse, or other medical professional such as a medical technician, endocrinologist, cytologist, phlebotomist, radiologist, or a pulmonologist. The medical professional can indicate the appropriate test or assay to perform on the sample, or the molecular profiling business of the present disclosure can consult on which assays or tests are most appropriately indicated. The molecular profiling business can bill the individual or medical or insurance provider thereof for consulting work, for sample acquisition and or storage, for materials, or for all products and services rendered.

A medical professional need not be involved in the initial diagnosis or sample acquisition. An individual can alternatively obtain a sample through the use of an over the counter kit. The kit can contain a means for obtaining said sample as described herein, a means for storing the sample for inspection, and instructions for proper use of the kit. In some cases, molecular profiling services are included in the price for purchase of the kit. In other cases, the molecular profiling services are billed separately.

A biological sample suitable for use by the molecular profiling business can be any material containing tissues, cells, nucleic acids, genes, gene fragments, expression products, gene expression products, and/or gene expression product fragments of an individual to be tested. Methods for determining sample suitability and/or adequacy are provided. The biological sample can include, but is not limited to, tissue, cells, and/or biological material from cells or derived from cells of an individual. The sample can be a heterogeneous or homogeneous population of cells or tissues. The biological sample can be obtained using any method known to the art that can provide a sample suitable for the analytical methods described herein.

Obtaining a biological sample can be aided by the use of a kit. A kit can be provided containing materials for obtaining, storing, and/or shipping biological samples. The kit can contain, for example, materials and/or instruments for the collection of the biological sample (e.g., sterile swabs, sterile cotton, disinfectant, needles, syringes, scalpels, anesthetic swabs, knives, curette blade, liquid nitrogen, etc.). The kit can contain, for example, materials and/or instruments for the storage and/or preservation of biological samples (e.g., containers; materials for temperature control such as ice, ice packs, cold packs, dry ice, liquid nitrogen; chemical preservatives or buffers such as formaldehyde, formalin, paraformaldehyde, glutaraldehyde, alcohols such as ethanol or methanol, acetone, acetic acid, HOPE fixative (Hepesglutamic acid buffer-mediated organic solvent protection effect), heparin, saline, phosphate buffered saline, TAPS, bicine, Tris, tricine, TAPSO, HEPES, TES, MOPS, PIPES, cadodylate, SSC, MES, phosphate buffer; protease inhibitors such as aprotinin, bestatin, calpain inhibitor I and II, chymostatin, E-64, leupeptin, alpha-2-macroglobulin, pefabloc SC, pepstatin, phenylmethanesufonyl fluoride, trypsin inhibitors; DNAse inhibitors such as 2-mercaptoethanol, 2-nitro-5-thicyanobenzoic acid, calcium, EGTA, EDTA, sodium dodecyl sulfate, iodoacetate, etc.; RNAse inhibitors such as ribonuclease inhibitor protein; double-distilled water; DEPC (diethyprocarbonate) treated water, etc.). The kit can contain instructions for use. The kit can be provided as, or contain, a suitable container for shipping. The shipping container can be an insulated container. The shipping container can be self-addressed to a collection agent (e.g., laboratory, medical center, genetic testing company, etc.). The kit can be provided to a subject for home use or use by a medical professional. Alternatively, the kit can be provided directly to a medical professional.

One or more biological samples can be obtained from a given subject. In some cases, between about 1 and about 50 biological samples are obtained from the given subject; for example, about 1-50, 1-40, 1-30, 1-25, 1-20, 1-15, 1-10, 1-7, 1-5, 5-50, 5-40, 5-30, 5-25, 5-15, 5-10, 10-50, 10-40, 10-25, 10-20, 25-50, 25-40, or at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 biological samples can be obtained from the given subject. Multiple biological samples from the given subject can be obtained from the same source (e.g., the same tissue), e.g., multiple blood samples, or multiple tissue samples, or from multiple sources (e.g., multiple tissues). Multiple biological samples from the given subject can be obtained at the same time or at different times. Multiple biological samples from the given subject can be obtained at the same condition or different condition. Multiple biological samples from the given subject can be obtained at the same disease progression or different disease progression of the subject. If multiple biological samples are collected from the same source (e.g., the same tissue) from the particular subject, the samples can be combined into a single sample. Combining samples in this way can ensure that enough material is obtained for testing and/or analysis.

EXAMPLES

These examples are provided for illustrative purposes only and not to limit the scope of the claims provided herein. The starting materials and reagents used for the synthesis of the compounds described herein may be synthesized or can be obtained from commercial sources, such as, but not limited to, Sigma-Aldrich, Acros Organics, Fluka, and Fischer Scientific.

Example 1: 2-(6-(cyclopropyl(2,2,6,6-tetramethylpiperidin-4-yl)amino)pyridazin-3-yl)-5-(1H-pyrazol-4-yl)phenol

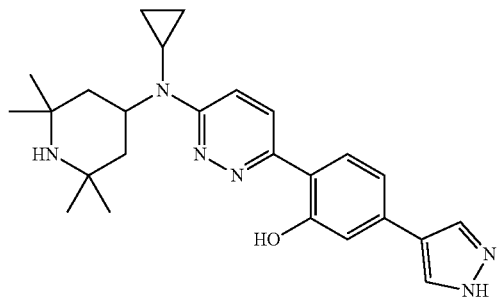 [SMILES: CC1(C)CC(N(c2ccc(-c3ccc(-c4cn[nH]c4)cc3O)nn2)C2CC2)CC(C)(C)N1]

Step 1: Synthesis of 6-chloro-N-(2,2,6,6-tetramethylpiperidin-4-yl)pyridazin-3-amine

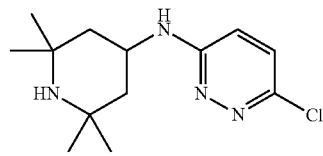 [SMILES: CC1(C)CC(Nc2ccc(Cl)nn2)CC(C)(C)N1]

A mixture of 2,2,6,6-tetramethylpiperidin-4-amine (2.1 g, 14.1 mmol), 3,6-dichloropyridazine (2 g, 12.8 mmol) and diisopropylethylamine (3.6 g, 28.2 mmol) in 50 mL of n-butyl alcohol was stirred at 120° C. for 4 h. The mixture was concentrated and ethyl acetate (60 mL) was added. The resulting mixture was washed with 10 mL of $H_2O$, concentrated and triturated in ethyl acetate/petroleum ether which gave 2.3 g of 6-chloro-N-(2,2,6,6-tetramethylpiperidin-4-yl) pyridazin-3-amine as white solid (67% yield). LCMS: m/z 269.2 [M+H]$^+$; $t_R$=1.46 min.

Step 2: Synthesis of 6-chloro-N-cyclopropyl-N-(2,2,6,6-tetramethylpiperidin-4-yl)pyridazin-3-amine

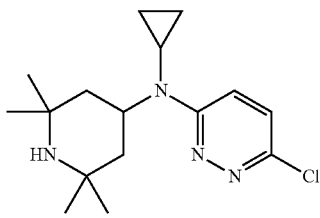 [SMILES: CC1(C)CC(N(c2ccc(Cl)nn2)C2CC2)CC(C)(C)N1]

A mixture of 6-chloro-N-(2,2,6,6-tetramethylpiperidin-4-yl)pyridazin-3-amine (400 mg, 1.5 mmol), cyclopropylboronic acid (387 mg, 4.5 mmol), Cu(OAc)$_2$ (273 mg, 1.5 mmol), Na$_2$CO$_3$ (318 mg, 3 mmol) and triethylamine (303 mg, 3 mmol) in 10 mL of 1,2-dichloroethane was stirred at room temperature for 16 h. The mixture was filtered, concentrated and purified by silica gel column (methanol/dichloromethane=0-20%) which gave 210 mg of 6-chloro-N-cyclopropyl-N-(2,2,6,6-tetramethylpiperidin-4-yl)pyridazin-3-amine as black solid (34% yield). LCMS: m/z 309.2 [M+H]$^+$; $t_R$=1.77 min.

Step 3: Synthesis of 6-(4-chloro-2-methoxyphenyl)-N-cyclopropyl-N-(2,2,6,6-tetramethylpiperidin-4-yl)pyridazin-3-amine

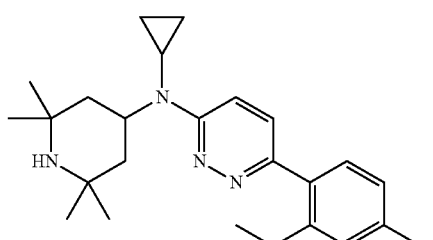

A mixture of 6-chloro-N-cyclopropyl-N-(2,2,6,6-tetramethylpiperidin-4-yl)pyridazin-3-amine (160 mg, 0.52 mmol), 4-chloro-2-methoxyphenylboronic acid (106 mg, 0.57 mmol), [1,1'-Bis(diphenylphosphino)ferrocene]dichloropalladium(II) (42 mg, 0.05 mmol) and K$_2$CO$_3$ (144 mg, 1.04 mmol) in 3 mL of 1,4-dioxane and 0.3 mL of water was degassed and stirred at 105° C. for 8 h under nitrogen atmosphere. The mixture was then concentrated and purified by silica gel chromatography (0-20% methanol/dichloromethane) which gave 150 mg of 6-(4-chloro-2-methoxyphenyl)-N-cyclopropyl-N-(2,2,6,6-tetramethylpiperidin-4-yl)pyridazin-3-amine as black solid (53% yield). LCMS: m/z 415.1 [M+H]$^+$; $t_R$=1.51 min.

Step 4: Synthesis of N-cyclopropyl-6-(2-methoxy-4-(1H-pyrazol-4-yl)phenyl)-N-(2,2,6,6-tetramethylpiperidin-4-yl)pyridazin-3-amine

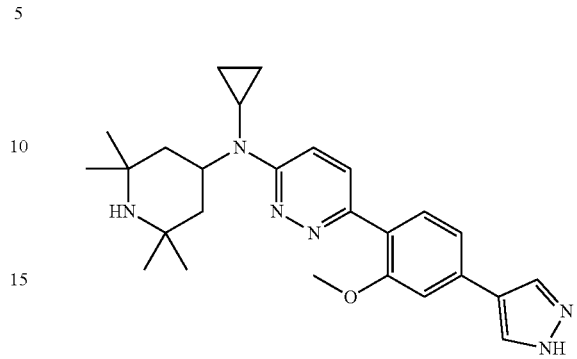

A mixture of 6-(4-chloro-2-methoxyphenyl)-N-cyclopropyl-N-(2,2,6,6-tetramethylpiperidin-4-yl)pyridazin-3-amine (110 mg, 0.27 mmol), 4-(4,4,5,5-tetramethyl-1,3,2-dioxaborolan-2-yl)-1H-pyrazole (78 mg, 0.4 mmol), 1,1'-Bis(diphenylphosphino)ferrocene]dichloropalladium(II) (22 mg, 0.03 mmol) and K$_2$CO$_3$ (73 mg, 0.53 mmol) in 4 mL of 1,4-dioxane and 0.4 mL of water was purged with nitrogen and sealed. The mixture was stirred at 130° C. under microwave irradiation for 2 h, concentrated and purified by silica gel chromatography (0-20% MeOH/CH$_2$Cl$_2$) which gave 100 mg of N-cyclopropyl-6-(2-methoxy-4-(1H-pyrazol-4-yl)phenyl)-N-(2,2,6,6-tetramethylpiperidin-4-yl)pyridazin-3-amine as white solid (25% yield). LCMS: m/z 447.3 [M+H]$^+$; $t_R$=1.78 min.

Step 5: Synthesis of Title Compound, 2-(6-(cyclopropyl(2,2,6,6-tetramethylpiperidin-4-yl)amino)pyridazin-3-yl)-5-(1H-pyrazol-4-yl)phenol

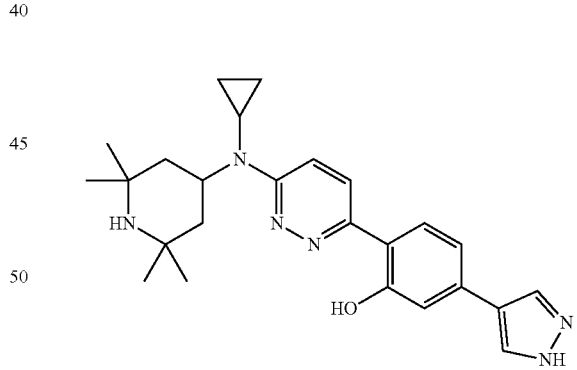

A mixture of N-cyclopropyl-6-(2-methoxy-4-(1H-pyrazol-4-yl)phenyl)-N-(2,2,6,6-tetramethylpiperidin-4-yl)pyridazin-3-amine (80 mg, 0.18 mmol) and sodium ethane thiolate (30 mg, 0.36 mmol) was dissolved in N-Methyl-2-pyrrolidone (2 mL). The mixture was stirred at 185° C. for 8 h. After cooling to room temperature, the mixture was purified by reverse HPLC which gave 33 mg of 2-(6-(cyclopropyl(2,2,6,6-tetramethylpiperidin-4-yl)amino)pyridazin-3-yl)-5-(1H-pyrazol-4-yl)phenol as yellow solid (34% yield).

Example 2: Synthesis of 2-(6-(((1R,3s,5S)-8-azabi-cyclo[3.2.1]octan-3-yl)(methyl)amino)pyridazin-3-yl)-5-(1H-pyrazol-4-yl)phenol

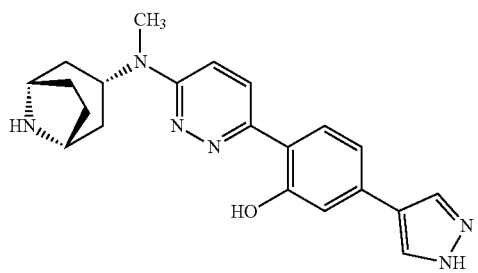 [SMILES: CN(c1ccc(-c2ccc(-c3cn[nH]c3)cc2O)nn1)[C@@H]1C[C@H]2CC[C@@H](C1)N2]

Step 1: Synthesis of tert-butyl (1R,3S,5S)-3-((6-chloropyridazin-3-yl)amino)-8-azabicyclo[3.2.1]octane-8-carboxylate

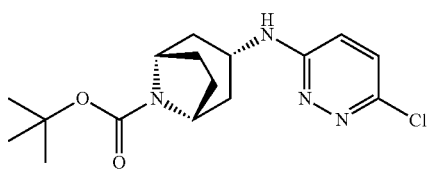 [SMILES: CC(C)(C)OC(=O)N1[C@@H]2CC[C@H]1C[C@H](Nc1ccc(Cl)nn1)C2]

A mixture of tert-butyl (1R,3S,5S)-3-amino-8-azabicyclo[3.2.1]octane-8-carboxylate (400 mg, 1.77 mmol), 3,6-dichloropyridazine (489 mg, 3.28 mmol) and DIPEA (652 mg, 5.1 mmol) in 4 mL of DMSO was stirred at 120° C. for 18 h. After cooling to room temperature, the mixture was quenched with 10 mL of water, extracted with EtOAc (20 mL×3). The combined organic solvents were washed with water (10 mL), concentrated and purified by silica gel column (5-80% EtOAc/petroleum ether) which gave 320 mg of tert-butyl (1R,3S,5S)-3-((6-chloropyridazin-3-yl)amino)-8-azabicyclo[3.2.1]octane-8-carboxylate as white solid (53% yield). LCMS: m/z 339.2 [M+H]$^+$; $t_R$=1.41 min.

Step 2: Synthesis of tert-butyl (1R,3s,5S)-3-((6-chloropyridazin-3-yl)(methyl)amino)-8-azabicyclo[3.2.1]octane-8-carboxylate

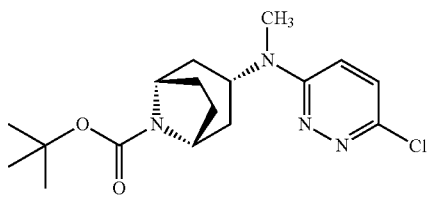 [SMILES: CN(c1ccc(Cl)nn1)[C@@H]1C[C@H]2CC[C@@H](C1)N2C(=O)OC(C)(C)C]

Sodium hydride (89 mg, 2.23 mmol, 60% in mineral oil) was added to a stirred solution tert-butyl (1R,3S,5S)-3-((6-chloropyridazin-3-yl)amino)-8-azabicyclo[3.2.1]octane-8-carboxylate (300 mg, 0.89 mmol) in 4 mL of DMF at 0° C. After stirring at 0° C. for 40 min, Methyl Iodide (253 mg, 1.78 mmol) was added. The mixture was then allowed to warm up to room temperature and stirred for 2 h. The mixture was quenched with water (10 mL), extracted with EtOAc (30 mL×3), concentrated and purified by silica gel column (5-60% EtOAc/petroleum ether) which gave 300 mg tert-butyl (1R,3s,5S)-3-((6-chloropyridazin-3-yl)(methyl)amino)-8-azabicyclo[3.2.1]octane-8-carboxylate as white solid (96% yield). LCMS: m/z 353.0 [M+H]$^+$; $t_R$=1.43 min.

Step 3: Synthesis of tert-butyl (1R,3s,5S)-3-((6-(4-chloro-2-methoxyphenyl)pyridazin-3-yl)(methyl)amino)-8-azabicyclo[3.2.1]octane-8-carboxylate.

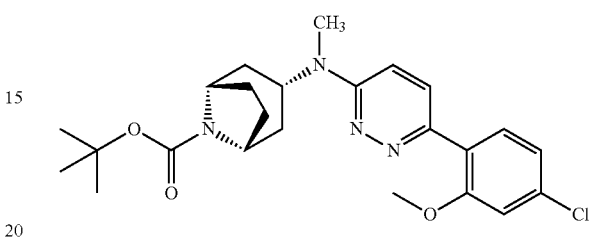

A mixture tert-butyl (1R,3s,5S)-3-((6-chloropyridazin-3-yl)(methyl)amino)-8-azabicyclo[3.2.1]octane-8-carboxylate (300 mg, 0.85 mmol), 4-chloro-2-methoxyphenylboronic acid (158 mg, 0.85 mmol), Pd(dppf)Cl$_2$ (78 mg, 0.1 mmol) and K$_2$CO$_3$ (265 mg, 1.92 mmol) in 4 mL of 1,4-dioxane and 0.4 mL of water was degassed and stirred at 105° C. for 6 h under nitrogen atmosphere. The mixture was then concentrated and purified by silica gel chromatography (5-60% EtOAc/petroleum ether) which gave 130 mg of tert-butyl (1R,3s,5S)-3-((6-(4-chloro-2-methoxyphenyl)pyridazin-3-yl)(methyl)amino)-8-azabicyclo[3.2.1]octane-8-carboxylate as white solid (34% yield). LCMS: m/z 459.1 [M+H]$^+$; $t_R$=1.64 min.

Step 4: Synthesis of tert-butyl (1R,3s,5S)-3-((6-(2-methoxy-4-(1H-pyrazol-4-yl)phenyl)pyridazin-3-yl)(methyl)amino)-8-azabicyclo[3.2.1]octane-8-carboxylate

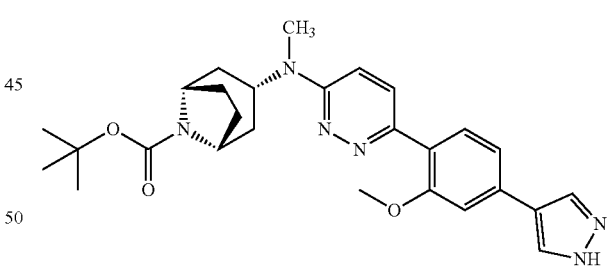

A mixture of tert-butyl (1R,3s,5S)-3-((6-(4-chloro-2-methoxyphenyl)pyridazin-3-yl)(methyl)amino)-8-azabicyclo[3.2.1]octane-8-carboxylate (130 mg, 0.28 mmol), 4-(4,4,5,5-tetramethyl-1,3,2-dioxaborolan-2-yl)-1H-pyrazole (66 mg, 0.34 mmol), Pd(dppf)Cl$_2$ (20 mg, 0.028 mmol) and K$_2$CO$_3$ (77 mg, 0.56 mmol) in 2 mL of 1,4-dioxane and 0.4 mL of water was purged with nitrogen and sealed. The mixture was stirred at 130° C. under MW for 2 h, concentrated and purified by silica gel chromatography (0-50% MeOH/CH$_2$Cl$_2$) which gave 120 mg of tert-butyl (1R,3s,5S)-3-((6-(2-methoxy-4-(1H-pyrazol-4-yl)phenyl)pyridazin-3-yl)(methyl)amino)-8-azabicyclo[3.2.1]octane-8-carboxylate as white solid (87% yield). LCMS: m/z 491.3 [M+H]$^+$; $t_R$=1.98 min.

Step 5: Synthesis of tert-butyl (1R,3s,5S)-3-((6-(2-hydroxy-4-(1H-pyrazol-4-yl)phenyl)pyridazin-3-yl)(methyl)amino)-8-azabicyclo[3.2.1]octane-8-carboxylate

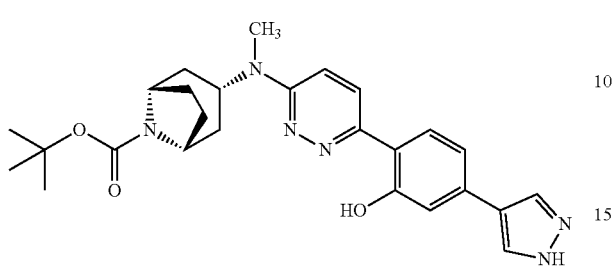

A mixture of tert-butyl (1R,3s,5S)-3-((6-(2-methoxy-4-(1H-pyrazol-4-yl)phenyl)pyridazin-3-yl)(methyl)amino)-8-azabicyclo[3.2.1]octane-8-carboxylate (120 mg, 0.24 mmol) and EtSNa (41 mg, 0.48 mmol) was dissolved in NMP (2 mL). The mixture was stirred at 180° C. for 6 h. After cooling to room temperature, the mixture was purified by reverse HPLC $(NH_4)_2CO_3$ which gave 70 mg of tert-butyl (1R,3s,5S)-3-((6-(2-hydroxy-4-(1H-pyrazol-4-yl)phenyl)pyridazin-3-yl)(methyl)amino)-8-azabicyclo[3.2.1]octane-8-carboxylate as yellow solid (61% yield). LCMS: m/z 477.2 [M+H]$^+$; $t_R$=1.58 min.

Step 6: Synthesis of Title Compound: 2-(6-(((1R,3s,5S)-8-azabicyclo[3.2.1]octan-3-yl)(methyl)amino)pyridazin-3-yl)-5-(1H-pyrazol-4-yl)phenol

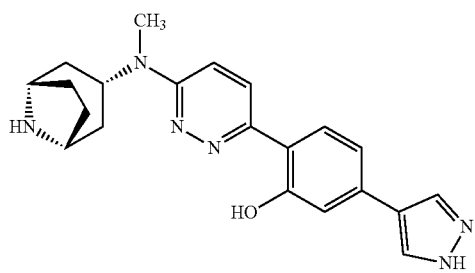 [SMILES: CN(c1ccc(-c2ccc(-c3cn[nH]c3)cc2O)nn1)[C@@H]1C[C@H]2CC[C@@H](C1)N2]

A 2 ml solution of 4 N Hydrogen Chloride in dioxane was added to a solution of tert-butyl (1R,3s,5S)-3-((6-(2-hydroxy-4-(1H-pyrazol-4-yl)phenyl)pyridazin-3-yl)(methyl)amino)-8-azabicyclo[3.2.1]octane-8-carboxylate (70 mg, 0.15 mmol) in 1 mL of $CH_2Cl_2$ at room temperature. After stirring at room temperature for 1 h, the mixture was concentrated, neutralized with ammonium hydroxide and purified by prep-HPLC $(NH_4HCO_3)$ which gave 36 mg of 2-(6-(((1R,3s,5S)-8-azabicyclo[3.2.1]octan-3-yl)(methyl)amino)pyridazin-3-yl)-5-(1H-pyrazol-4-yl)phenol as yellow solid (45% yield).

Example 3: Synthesis of 2-(6-(((1R,3s,5S)-9-azabicyclo[3.3.1]nonan-3-yl)(methyl)amino)pyridazin-3-yl)-5-(1H-pyrazol-4-yl)phenol

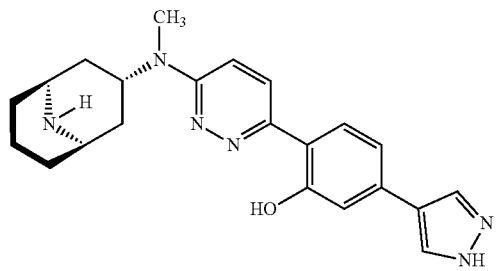

Step 1: Synthesis of tert-butyl (1R,3s,5S)-3-((6-chloropyridazin-3-yl)amino)-9-azabicyclo[3.3.1]nonane-9-carboxylate

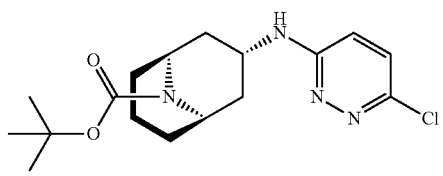

A mixture of tert-butyl (1R,3s,5S)-3-amino-9-azabicyclo[3.3.1]nonane-9-carboxylate (2.5 g, 10.42 mmol), 3,6-dichloropyridazine (2.02 g, 13.55 mmol) and DIPEA (2.96 g, 22.92 mmol) in 50 mL of DMSO was stirred at 120° C. for 6 h. The mixture was cooled to room temperature, quenched with $H_2O$ and extracted with ethyl acetate (160 mL×3). The combined organic layers were washed with brine, dried over anhydrous $Na_2SO_4$ and concentrated under reduced pressure. After removal of solvent, the crude product was purified by silica gel column (50% EtOAc/petroleum ether) which gave 2.3 g of tert-butyl (1R,3s,5S)-3-((6-chloropyridazin-3-yl)amino)-9-azabicyclo[3.3.1]nonane-9-carboxylate as yellow solid (yield: 63%). LCMS: m/z 353.2 [M+H]$^+$; $t_R$=1.93 min.

Step 2: Synthesis of tert-butyl (1R,3s,5S)-3-((6-chloropyridazin-3-yl)(methyl)amino)-9-azabicyclo[3.3.1]nonane-9-carboxylate

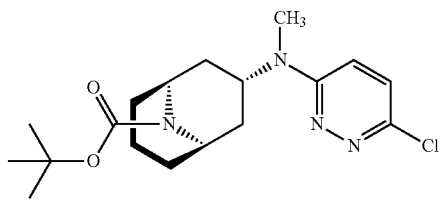

Sodium hydride (784 mg, 19.60 mmol, 60% in mineral oil) was added to a stirred solution of tert-butyl (1R,3s,5S)-3-((6-chloropyridazin-3-yl)amino)-9-azabicyclo[3.3.1]nonane-9-carboxylate (2.3 g, 6.54 mmol) in 40 mL of DMF at 0° C. After stirring for 20 min at 0° C., $CH_3I$ (1.9 g, 13.08 mmol) was added. The mixture was then stirred at room temperature for 1 h, quenched with H$_2$O and extracted with EtOAc (80 mL×3). The combined organic phases were washed with brine, dried over anhydrous Na$_2$SO$_4$, concentrated under reduced pressure and purified by silica gel column (50% EtOAc/petroleum ether) which gave 2.0 g of tert-butyl (1R,3s,5S)-3-((6-chloropyridazin-3-yl)(methyl)amino)-9-azabicyclo[3.3.1]nonane-9-carboxylate as yellow solid (84% yield). LCMS: m/z 367.2 [M+H]$^+$; t$_R$=2.11 min.

Step 3: Synthesis of 1-bromo-4-iodo-2-(methoxymethoxy)benzene

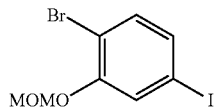

Bromomethyl methyl ether (1.25 g, 10 mmol) was added to a stirred solution of 2-bromo-5-iodophenol (1.5 g, 5 mmol) and K$_2$CO$_3$ (1.38 g, 10 mmol) in 20 mL of DMF at 0° C. The mixture was then stirred at room temperature for 16 h, quenched with 20 mL of H$_2$O and extracted with EtOAc (20 mL×3). The combined organic solvents were dried over anhydrous Na$_2$SO$_4$, concentrated and purified by silica gel column (0-5% EtOAc/petroleum ether) which gave 1.45 g of 1-bromo-4-iodo-2-(methoxymethoxy)benzene as colorless liquid (79% yield). LCMS: t$_R$=1.50 min.

Step 4: Synthesis of 4-(4-bromo-3-(methoxymethoxy)phenyl)-1-(tetrahydro-2H-pyran-2-yl)-1H-pyrazole

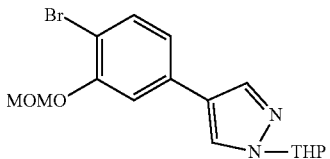

A mixture of 1-bromo-4-iodo-2-(methoxymethoxy)benzene (3.3 g, 9.6 mmol), 1-(tetrahydro-2H-pyran-2-yl)-4-(4,4,5,5-tetramethyl-1,3,2-dioxaborolan-2-yl)-1H-pyrazole (2.67 g, 9.6 mmol), Pd(dppf)Cl$_2$ (866 mg, 1 mmol) and K$_2$CO$_3$ (2.66 g, 19.3 mmol) in 40 mL of dioxane and 4 mL of H$_2$O was degassed and stirred at 105° C. for 8 h. After cooling to room temperature, the mixture was extracted with EtOAc (30 mL×3). The combined organic solvents were concentrated and purified by silica gel column (10-50% EtOAc/petroleum ether) which gave 2.5 g of 4-(4-bromo-3-(methoxymethoxy)phenyl)-1-(tetrahydro-2H-pyran-2-yl)-1H-pyrazole as colorless oil (69% yield). LCMS: m/z 367.1 [M+H]f; t$_R$=2.03 min.

Step 5: Synthesis of 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole

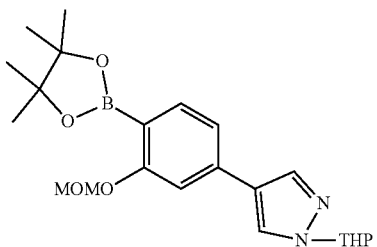

A mixture of 4-(4-bromo-3-(methoxymethoxy)phenyl)-1-(tetrahydro-2H-pyran-2-yl)-1H-pyrazole (1.5 g, 4.1 mmol), 4,4,4',4',5,5,5',5'-octamethyl-2,2'-bi(1,3,2-dioxaborolane) (2.1 g, 8.2 mmol), Pd(dppf)Cl$_2$ (369 mg, 0.41 mmol) and KOAc (804 mg, 8.2 mmol) in 20 mL of dioxane was degassed and stirred at 105° C. for 8 h. The mixture was filtered, concentrated and purified by silica gel column which gave 0.81 g of 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole as colorless oil (48% yield). LCMS: m/z 415.3 [M+H]$^+$; t$_R$=2.10 min.

Step 6: Synthesis of tert-butyl (1R,3s,5S)-3-((6-(2-(methoxymethoxy)-4-(1-(tetrahydro-2H-pyran-2-yl)-1H-pyrazol-4-yl)phenyl)pyridazin-3-yl)(methyl)amino)-9-azabicyclo[3.3.1]nonane-9-carboxylate

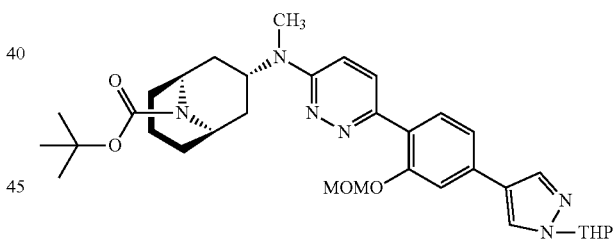

A mixture of tert-butyl (1R,3s,5S)-3-((6-chloropyridazin-3-yl)(methyl)amino)-9-azabicyclo[3.3.1]nonane-9-carboxylate (1.7 g, 4.64 mmol), 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole (2.5 g, 6.04 mmol), Pd(dppf)Cl$_2$ (339 mg, 0.46 mmol) and K$_2$CO$_3$ (1.28 g, 9.28 mmol) in 40 mL of 1,4-dioxane and 8 mL of water was degassed and stirred at 105° C. for 2 h under nitrogen atmosphere. The mixture was then concentrated and purified by silica gel chromatography (5-60% EtOAc/petroleum ether) which gave 2.2 g of tert-butyl (1R,3s,5S)-3-((6-(2-(methoxymethoxy)-4-(1-(tetrahydro-2H-pyran-2-yl)-1H-pyrazol-4-yl)phenyl)pyridazin-3-yl)(methyl)amino)-9-azabicyclo[3.3.1]nonane-9-carboxylate as pale yellow solid (77% yield). LCMS(A039): m/z 619.3 [M+H]$^+$; t$_R$=2.17 min.

Step 7: Synthesis of Title Compound: 2-(6-(((1R,3s,5S)-9-azabicyclo[3.3.1]nonan-3-yl)(methyl)amino)pyridazin-3-yl)-5-(1H-pyrazol-4-yl)phenol

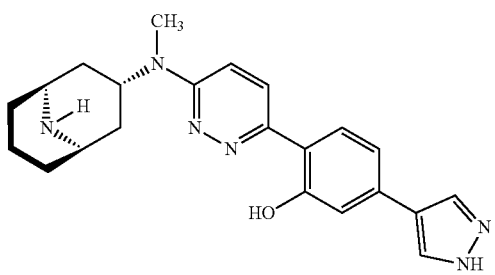

A 10 mL solution of 4N HCl in dioxane was added to a stirred solution of tert-butyl (1R,3s,5S)-3-((6-(2-(methoxymethoxy)-4-(1-(tetrahydro-2H-pyran-2-yl)-1H-pyrazol-4-yl)phenyl)pyridazin-3-yl)(methyl)amino)-9-azabicyclo[3.3.1]nonane-9-carboxylate (2.2 g, 3.56 mmol) in 4 mL of CH$_2$Cl$_2$. The mixture was stirred at room temperature for 2 h, concentrated under reduced pressure, neutralized with NH$_3$/MeOH and purified by prep-HPLC which gave 900 mg of 2-(6-(((1R,3s,5S)-9-azabicyclo[3.3.1]nonan-3-yl)(methyl)amino)pyridazin-3-yl)-5-(1H-pyrazol-4-yl)phenol as a yellow solid (65% yield).

Example 4: Synthesis of 2-(6-(((1R,3s,5S)-1,5-dimethyl-8-azabicyclo[3.2.1]octan-3-yl)(methyl)amino)pyridazin-3-yl)-5-(1H-pyrazol-4-yl)phenol

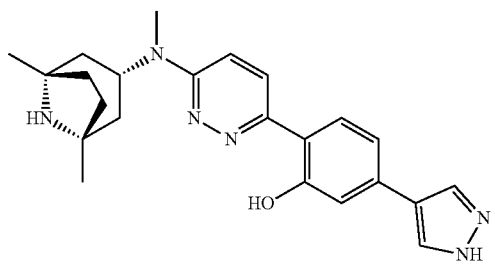 [SMILES: CN(c1ccc(-c2ccc(-c3cn[nH]c3)cc2O)nn1)[C@H]1C[C@]2(C)CC[C@](C)(C1)N2]

Step 1: Synthesis of 1,5-dimethyl-8-azabicyclo[3.2.1]octan-3-one

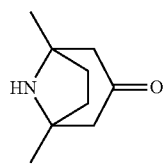

A solution of potassium hydroxide (108 g, 1.93 mol) in 70 mL of H$_2$O was added to a stirred solution of 3-oxopentanedioic acid (120 g, 822 mmol) and hexane-2,5-dione (49.2 g, 432 mmol) in 350 mL of H$_2$O at 0° C. Ammonium chloride (70.1 g, 1.32 mol) and NaOAc trihydrate (70.1 g, 515 mmol) in 667 mL of H$_2$O was then added with stirring. The pH of the resulting solution was adjusted to ~9 using 1 N NaOH aqueous solution. The mixture was stirred at room temperature for about 72 h during which time the pH was maintained at approximately 9 by using additional 1 N NaOH. The mixture was extracted with CH$_2$Cl$_2$ (1 L×5). The combined organic solvents were dried over anhydrous Na$_2$SO$_4$, concentrated and purified by silica gel chromatography (0-25% MeOH/CH$_2$Cl$_2$) which gave 16.7 g of 1,5-dimethyl-8-azabicyclo[3.2.1]octan-3-one as black oil (25% yield). LCMS(039): m/z 154.2 [M+H]$^+$; t$_R$=1.20 min; purity: 85%.

Step 2: Synthesis of tert-butyl 1,5-dimethyl-3-oxo-8-azabicyclo[3.2.1]octane-8-carboxylate

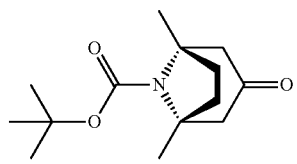

A mixture of 1,5-dimethyl-8-azabicyclo[3.2.1]octan-3-one (24 g, 163 mmol), di-tert-butyl dicarbonate (35.6 g, 326 mmol) and DIPEA (31.5 g, 244 mmol) in 500 mL of 1,4-dioxane was stirred at 70° C. for 6 h. The mixture was concentrated and purified by silica gel chromatography (0-30% EtOAc/petroleum ether) which gave 16.7 of tert-butyl 1,5-dimethyl-3-oxo-8-azabicyclo[3.2.1]octane-8-carboxylate as white solid (yield: 42%). LCMS(042): m/z 198.1 [M−55]$^+$; t$_R$=1.40 min; purity: 1000.

Step 3: Synthesis of tert-butyl 3-(hydroxyimino)-1,5-dimethyl-8-azabicyclo[3.2.1]octane-8-carboxylate

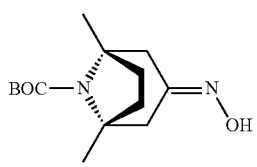

A mixture of tert-butyl 1,5-dimethyl-3-oxo-8-azabicyclo[3.2.1]octane-8-carboxylate (16.7 g, 66 mmol), hydroxylamine hydrochloride (18.2 g, 26.4 mmol) and sodium acetate (10.8 g, 132 mmol) in 250 mL of ethanol was stirred at 70° C. for 4 h. The mixture was concentrated. 200 mL of EtOAc and 60 mL of H$_2$O was added. The organic phase was separated, washed with brine (50 mL), dried over anhydrous Na$_2$SO$_4$, concentrated to give 16.7 g of tert-butyl 3-(hydroxyimino)-1,5-dimethyl-8-azabicyclo[3.2.1]octane-8-carboxylate as yellow solid which was used directly to next step (93% yield). LCMS (039): m/z 269.2 [M+H]$^+$; t$_R$=1.92 min; purity: 100%.

Step 4: Synthesis of tert-butyl (1R,3s,5S)-3-amino-1,5-dimethyl-8-azabicyclo[3.2.1]octane-8-carboxylate

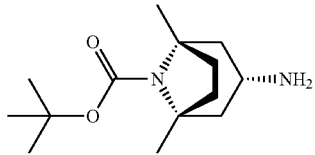

Sodium metal (40.2 g, 1.75 mol) was added portion wise to a mixture of tert-butyl 3-(hydroxyimino)-1,5-dimethyl-8-azabicyclo[3.2.1]octane-8-carboxylate (26.8 g, 0.1 mol) in 1000 mL of n-PrOH was heated to 110° C. over 1 h. After addition, the mixture was stirred at reflux for additional 1 h. The mixture was cooled to room temperature and quenched carefully with H₂O (500 mL). The organic layer was separated and concentrated. DCM (500 mL) was added to the residue. The solid was filtered off and the filtrate was concentrated under reduced pressure to afford 20 g of tert-butyl (1R,3s,5S)-3-amino-1,5-dimethyl-8-azabicyclo[3.2.1]octane-8-carboxylate as a yellow oil, which was used directly to next step (yield: 79%). LCMS(A038): m/z 255.3 $[M+H]^+$; $t_R$=1.37 min; purity: 99%.

Step 5: Synthesis of tert-butyl (1R,3s,5S)-3-((6-chloropyridazin-3-yl)amino)-1,5-dimethyl-8-azabicyclo[3.2.1]octane-8-carboxylate

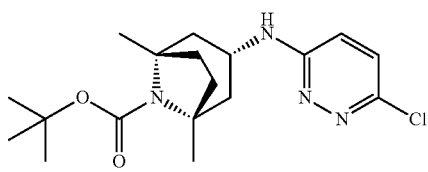 [SMILES: CC(C)(C)OC(=O)N1[C@@]2(C)CC[C@]1(C)C[C@@H](Nc1ccc(Cl)nn1)C2]

A mixture of tert-butyl (1R,3s,5S)-3-amino-1,5-dimethyl-8-azabicyclo[3.2.1]octane-8-carboxylate (20 g, 78.7 mmol), 3,6-dichloropyridazine (23.3 g, 157.5 mmol) and DIPEA (20.48 g, 157.5 mmol) in 500 mL of DMSO was stirred at 120° C. for 24 h. The mixture was cooled to room temperature, quenched with H₂O and extracted with ethyl acetate (500 mL×3). The combined organic layers were washed with brine, dried over anhydrous Na₂SO₄ and concentrated under reduced pressure. After removal of solvent, the crude product was purified by silica gel column (50% EtOAc/petroleum ether) to afford 17.5 g of tert-butyl (1R,3s,5S)-3-((6-chloropyridazin-3-yl)amino)-1,5-dimethyl-8-azabicyclo[3.2.1]octane-8-carboxylate as yellow solid (yield: 61%). LCMS(038): m/z 367.2 $[M+H]^+$; $t_R$=1.88 min; purity: 99%.

Step 6: Synthesis of tert-butyl (1R,3s,5S)-3-((6-chloropyridazin-3-yl)(methyl)amino)-1,5-dimethyl-8-azabicyclo[3.2.1]octane-8-carboxylate

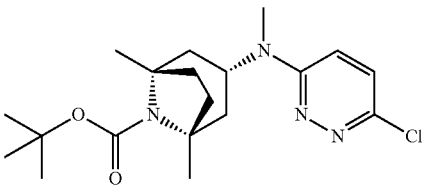 [SMILES: CN(c1ccc(Cl)nn1)[C@H]1C[C@]2(C)CC[C@](C)(C1)N2C(=O)OC(C)(C)C]

Sodium hydride (2.87 g, 71.7 mmol) was added to a stirred solution of tert-butyl (1R,3s,5S)-3-((6-chloropyridazin-3-yl)amino)-1,5-dimethyl-8-azabicyclo[3.2.1]octane-8-carboxylate (17.5 g, 47.8 mmol) in 400 mL of DMF at 0° C. After stirring for 20 min at 0° C., CH₃I (13.58 g, 95.6 mmol) was added. The mixture was then stirred at room temperature for 1 h, quenched with H₂O and extracted with EtOAc (300 mL×3). The combined organic phases were washed with brine, dried over anhydrous Na₂SO₄, concentrated under reduced pressure and purified by silica gel column (30% EtOAc/petroleum ether) to afford 14.5 g of tert-butyl (1R,3s,5S)-3-((6-chloropyridazin-3-yl)(methyl)amino)-1,5-dimethyl-8-azabicyclo[3.2.1]octane-8-carboxylate as yellow solid (80% yield). LCMS(039): m/z 381.2 $[M+H]^+$; $t_R$=2.17 min; purity: 99%.

Step 7: Synthesis of 1-bromo-4-chloro-2-(methoxymethoxy)benzene

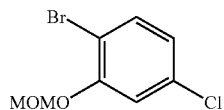

Sodium hydride (1.85 g, 46.3 mmol, 60% in mineral oil) was added to a stirred solution of 2-bromo-5-chlorophenol (8 g, 38.6 mmol) in 150 mL of DMF at 0° C. After stirring at 0° C. for 30 min, Methoxy Methyl Bromide (7.25 g, 58 mmol) was added. The mixture was then stirred at room temperature for 2 h, quenched with NH₄Cl aqueous solution (15 mL), extracted with EtOAc (30 mL×3). The combined organic layer was dried over anhydrous Na₂SO₄, concentrated and purified by silica gel chromatography (0-10% EtOAc/petroleum ether) which gave 8.1 g of 1-bromo-4-chloro-2-(methoxymethoxy)benzene as colorless oil (84% yield). ¹H NMR (500 MHz, Chloroform-d) δ 7.45 (d, J=8.5 Hz, 1H), 7.17 (d, J=2.3 Hz, 1H), 6.89 (dd, J=8.4, 2.3 Hz, 1H), 5.24 (s, 2H). LCMS: $t_R$=1.51 min.

Step 8: Synthesis of 4-chloro-2-(methoxymethoxy)phenylboronic acid

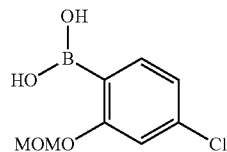

A THF solution of n-BuLi (5.76 mL, 14.4 mmol) was added to a stirred solution of 1-bromo-4-chloro-2-(methoxymethoxy)benzene (3 g, 12 mmol) in 40 mL of THF under nitrogen at −78° C. After stirring at −78° C. for 40 min, B(OMe)₃ (2 g, 19.2 mmol) was added. The mixture was allowed to warm up to room temperature and stirred for 16 h. NH₄Cl aqueous solution (10 mL) was added to the mixture. The mixture was extracted with EtOAc (20 mL×3). The combined organic solvents were washed with brine (10 mL), dried over Na₂SO₄, concentrated and recrystallized from 3% EtOAc/petroleum ether to give 1.6 g of 4-chloro-2-(methoxymethoxy)phenylboronic acid as off white solid (62% yield). LCMS: m/z 199.1 [M-OH]⁺; $t_R$=1.65 min.

Step 9: Synthesis of tert-butyl (1R,3s,5S)-3-((6-(4-chloro-2-(methoxymethoxy)phenyl)pyridazin-3-yl)(methyl)amino)-1,5-dimethyl-8-azabicyclo[3.2.1]octane-8-carboxylate

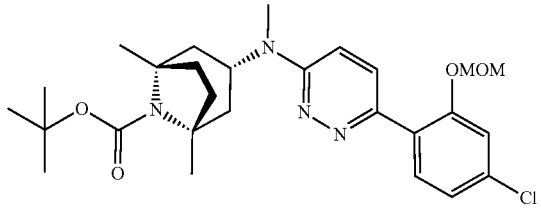

A mixture of tert-butyl (1R,3s,5S)-3-((6-chloropyridazin-3-yl)(methyl)amino)-1,5-dimethyl-8-azabicyclo[3.2.1]octane-8-carboxylate (6 g, 16.4 mmol), 4-chloro-2-(methoxymethoxy)phenylboronic acid (5.3 g, 24.6 mmol), Pd(dppf)Cl₂ (1.6 mg, 2 mmol) and K₂CO₃ (4.53 mg, 32.8 mmol) in 80 mL of dioxane and 8 mL of H₂O was degassed and stirred at 100° C. for 7 h. After cooling to room temperature, the mixture was concentrated and purified by silica gel column (10-60% EtOAc/petroleum ether) which gave 4.52 g of tert-butyl (1R,3s,5S)-3-((6-(4-chloro-2-(methoxymethoxy)phenyl)pyridazin-3-yl)(methyl)amino)-1,5-dimethyl-8-azabicyclo[3.2.1]octane-8-carboxylate as white solid (57% yield). LCMS: m/z 517.3 [M+H]⁺; $t_R$=1.86 min.

Step 10: Synthesis of tert-butyl (1R,3s,5S)-3-((6-(2-(methoxymethoxy)-4-(1H-pyrazol-4-yl)phenyl)pyridazin-3-yl)(methyl)amino)-1,5-dimethyl-8-azabicyclo[3.2.1]octane-8-carboxylate

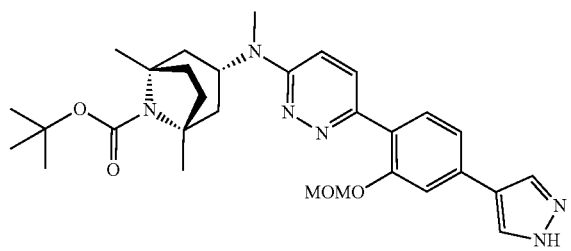

A mixture of tert-butyl (1R,3s,5S)-3-((6-(4-chloro-2-(methoxymethoxy)phenyl)pyridazin-3-yl)(methyl)amino)-1,5-dimethyl-8-azabicyclo[3.2.1]octane-8-carboxylate (14.5 g, 28.1 mmol), 4-(4,4,5,5-tetramethyl-1,3,2-dioxaborolan-2-yl)-1H-pyrazole (10.9 g, 56.2 mmol), catalyst (2.21 g, 2.82 mmol) and K₃PO₄ (11.9 g, 56.2 mmol) in 100 mL of dioxane and 50 mL of H₂O was degassed and stirred at 100° C. for 5 h. The mixture was concentrated and purified by silica gel column (10-80% EtOAc/petroleum ether) which gave 11.1 g of tert-butyl (1R,3s,5S)-3-((6-(2-(methoxymethoxy)-4-(1H-pyrazol-4-yl)phenyl)pyridazin-3-yl)(methyl)amino)-1,5-dimethyl-8-azabicyclo[3.2.1]octane-8-carboxylate as white solid (72% yield). LCMS: m/z 549.2 [M+H]⁺; $t_R$=2.09 min.

Step 10: Synthesis of Title Compound: 2-(6-(((1R,3s,5S)-1,5-dimethyl-8-azabicyclo[3.2.1]octan-3-yl)(methyl)amino)pyridazin-3-yl)-5-(1H-pyrazol-4-yl)phenol

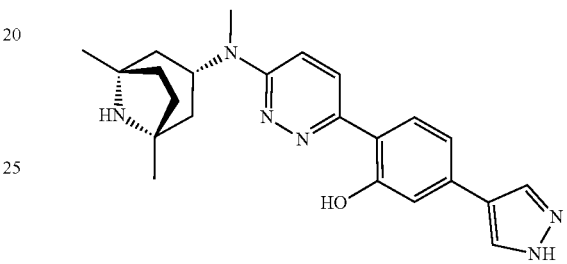

A solution of 4N HCl in dioxane (80 ml) was added to a stirred solution of tert-butyl (1R,3s,5S)-3-((6-(2-(methoxymethoxy)-4-(1H-pyrazol-4-yl)phenyl)pyridazin-3-yl)(methyl)amino)-1,5-dimethyl-8-azabicyclo[3.2.1]octane-8-carboxylate (16 g, 29.2 mmol) in 80 mL of CH₂Cl₂ at room temperature. The mixture was stirred at room temperature for 3 h and concentrated. The residue was dissolved in water. pH value was adjusted to 9. The mixture was extracted with CH₂Cl₂/MeOH (4/1, v/v). The combined organic solvents were concentrated and purified by silica gel chromatography (0-60% MeOH/CH₂Cl₂) to give 11.2 g of 2-(6-(((1R,3s,5S)-1,5-dimethyl-8-azabicyclo[3.2.1]octan-3-yl)(methyl)amino)pyridazin-3-yl)-5-(1H-pyrazol-4-yl)phenol as yellow solid (84% yield).

Example 5: Synthesis of 2-(6-(((1R,3s,5S)-1,5-dimethyl-9-azabicyclo[3.3.1]nonan-3-yl)(methyl)amino)pyridazin-3-yl)-5-(1H-pyrazol-4-yl)phenol

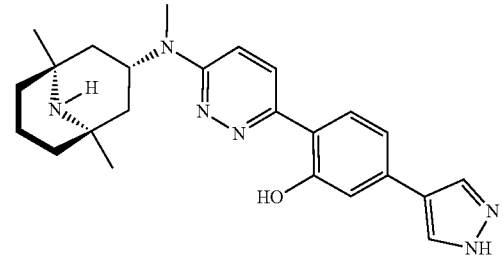

Step 1: Synthesis of 1-bromo-4-iodo-2-(methoxymethoxy)benzene

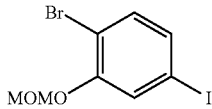

Methoxymethyl bromide (1.25 g, 10 mmol) was added to a stirred solution of 2-bromo-5-iodophenol (1.5 g, 5 mmol) and $K_2CO_3$ (1.38 g, 10 mmol) in 20 mL of DMF at 0° C. The mixture was then stirred at room temperature for 16 h, quenched with 20 mL of $H_2O$ and extracted with EtOAc (20 mL×3). The combined organic solvents were dried over anhydrous $Na_2SO_4$, concentrated and purified by silica gel column (0-5% EtOAc/petroleum ether) to give 1.45 g of 1-bromo-4-iodo-2-(methoxymethoxy)benzene as colorless liquid (79% yield). LCMS: $t_R$=1.50 min.

Step 2: Synthesis of 4-(4-bromo-3-(methoxymethoxy)phenyl)-1-(tetrahydro-2H-pyran-2-yl)-1H-pyrazole

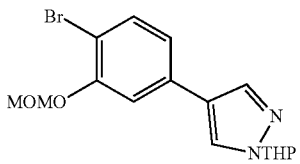

A mixture of 1-bromo-4-iodo-2-(methoxymethoxy)benzene (3.3 g, 9.6 mmol), 1-(tetrahydro-2H-pyran-2-yl)-4-(4,4,5,5-tetramethyl-1,3,2-dioxaborolan-2-yl)-1H-pyrazole (2.67 g, 9.6 mmol), Pd(dppf)Cl$_2$ (866 mg, 1 mmol) and $K_2CO_3$ (2.66 g, 19.3 mmol) in 40 mL of dioxane and 4 mL of $H_2O$ was degassed and stirred at 105° C. for 8 h. After cooling to room temperature, the mixture was extracted with EtOAc (30 mL×3). The combined organic solvents were concentrated and purified by silica gel column (10-50% EtOAc/petroleum ether) to give 2.5 g of 4-(4-bromo-3-(methoxymethoxy)phenyl)-1-(tetrahydro-2H-pyran-2-yl)-1H-pyrazole as colorless oil (69% yield). LCMS: m/z 367.1 [M+H]$^+$; $t_R$=2.03 min.

Step 3: Synthesis of 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole

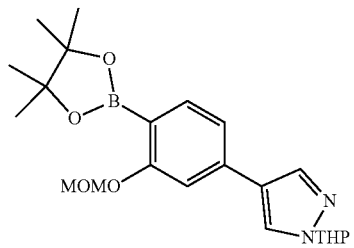

A mixture of 4-(4-bromo-3-(methoxymethoxy)phenyl)-1-(tetrahydro-2H-pyran-2-yl)-1H-pyrazole (1.5 g, 4.1 mmol), 4,4,4',4',5,5,5',5'-octamethyl-2,2'-bi(1,3,2-dioxaborolane) (2.1 g, 8.2 mmol), Pd(dppf)Cl$_2$ (369 mg, 0.41 mmol) and KOAc (804 mg, 8.2 mmol) in 20 mL of dioxane was degassed and stirred at 105° C. for 8 h. The mixture was filtered, concentrated and purified by silica gel column which gave 0.81 g of 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole as colorless oil (48% yield). LCMS: m/z 415.3 [M+H]$^+$; $t_R$=2.10 min.

Step 4: Synthesis of N1,N5-dimethoxy-N1,N5-dimethylglutarimide

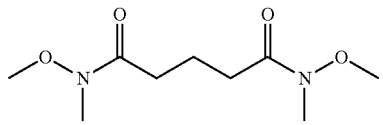

Glutaroyl dichloride (50 g, 0.299 mol) was added to a stirred solution of NO-dimethylhydroxylamine hydrochloride (64 g, 0.658 mmol) and Et$_3$N (121.2 g, 1.2 mmol) in 1000 mL of $CH_2Cl_2$ at 0° C. over 30 min. The reaction mixture was allowed to room temperature and stirred for 3 h. 500 mL of water was added to the mixture, which was extracted with $CH_2Cl_2$ (1000 mL×3). The combined organic layers were washed with 1% HCl solution, brine, dried over anhydrous $Na_2SO_4$ and concentrated under reduced pressure to afford 55 g of N1,N5-dimethoxy-N1,N5-dimethylglutarimide as brown oil (85% yield), which was used for next step without further purification. LCMS: m/z 219.2 [M+H]$^+$; $t_R$=1.26 min.

Step 5: Synthesis of heptane-2,6-dione

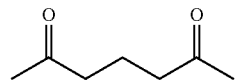

Methyl magnesium bromide (250 mL, 0.756 mol) was added to a stirred solution of N1,N5-dimethoxy-N1,N5-dimethylglutarimide (55 g, 0.252 mol) in 800 mL of dry THF at 0° C. over 30 min. After all the Grignard reagent was added, the reaction mixture was allowed to warm to room temperature and stirred for 2 h. Water, 50 mL, was added to the mixture followed by 1% HCl aqueous solution 300 mL. The mixture was extracted with ethyl acetate (1000 mL×3). The combined organic layers were washed with 1% HCl aqueous solution, brine, dried over anhydrous $Na_2SO_4$, concentrated under reduced pressure and purified by silica gel column (10-50% ethyl acetate in petroleum ether) to afford 13 g of heptane-2,6-dione as brownish solid (40% yield). LCMS: m/z 129.1 [M+H]$^+$; $t_R$=1.24 min.

Step 6: Synthesis of 1,5-dimethyl-9-azabicyclo[3.3.1]nonan-3-one

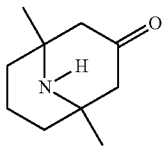

Ammonium Acetate (18.3 g, 0.238 mol) and acetone dicarboxylic acid (34.7 g, 0.238 mol) were added to a stirred solution of heptane-2,6-dione (5.07 g, 39.6 mmol) in AcOH (49 mL) at room temperature. The reaction mixture was then stirred for 3 h at 80° C. The mixture was cooled to 0° C. and diluted with $CH_2Cl_2$ and water. The aqueous phase was separated and acidified with 10% HCl aqueous solution (pH=1) and then diluted with EtOAc. The resultant mixture was extracted with water. The combined aqueous layers were basified with 20% NaOH (pH=11) and extracted with $CH_2Cl_2$ (three times). The combined organic layers were dried over $K_2CO_3$ and concentrated under reduced pressure. The residue was purified by flash silica gel column chromatography (50% ethyl acetate in petroleum ether to 10% MeOH in $CH_2Cl_2$) to afford 1,5-dimethyl-9-azabicyclo[3.3.1]nonan-3-one (2.0 g, 30% yield) as dark red oil. LCMS: m/z 168.2 [M+H]$^+$; $t_R$=1.24 min.

Step 7: Synthesis of 9-(4-methoxybenzyl)-1,5-dimethyl-9-azabicyclo[3.3.1]nonan-3-one

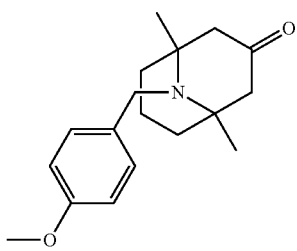 [SMILES: COc1ccc(CN2C3(C)CCCC2(C)CC(=O)C3)cc1]

A solution of 1,5-dimethyl-9-azabicyclo[3.3.1]nonan-3-one (2.0 g, 11.98 mmol), $K_2CO_3$ (3.3 g, 24 mmol) and 1-(chloromethyl)-4-methoxybenzene (2.2 g, 14.4 mmol.) in 50 mL of acetone was heated to reflux for 16 h under nitrogen protection. The reaction mixture was cooled to room temperature, 50 mL of water was added to this mixture which was extracted with ethyl acetate (50 mL×3). The combined organic layers were washed with brine, dried over anhydrous $Na_2SO_4$, concentrated and purified by silica gel chromatography (10-30% ethyl acetate in petroleum ether) which gave 9-(4-methoxybenzyl)-1,5-dimethyl-9-azabicyclo[3.3.1]nonan-3-one as yellowish solid (2.4 g, 70% yield). LCMS: m/z 288.2 [M+H]$^+$; $t_R$=1.22 min.

Step 8: Synthesis of 9-(4-methoxybenzyl)-1,5-dimethyl-9-azabicyclo[3.3.1]nonan-3-one oxime

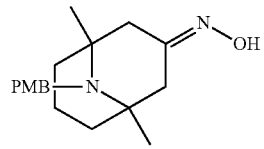

A solution of 9-(4-methoxybenzyl)-1,5-dimethyl-9-azabicyclo[3.3.1]nonan-3-one (8.5 g, 29.62 mmol) and $NH_2OH$ HCl (4.1 g, 60 mmol) in 150 mL of ethanol was heated to 85° C. for 3 h. Then the mixture was concentrated to residue which was dissolved in water and adjusted pH to 8 with aqueous solution of $Na_2CO_3$. The mixture was extracted with ethyl acetate (200 mL×3). The combined organic layers were washed with brine, dried over anhydrous $Na_2SO_4$ and concentrated which gave 9-(4-methoxybenzyl)-1,5-dimethyl-9-azabicyclo[3.3.1]nonan-3-one oxime as white solid (8.1 g, 90% yield). LCMS: m/z 303.1 [M+H]$^+$; $t_R$=1.19 min.

Step 9: Synthesis of (1R,3s,5S)-9-(4-methoxybenzyl)-1,5-dimethyl-9-azabicyclo[3.3.1]nonan-3-amine

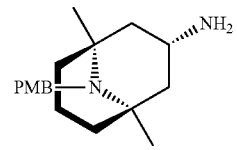

Sodium (6.72 g, 280 mmol) was added to a stirred solution of 9-(4-methoxybenzyl)-1,5-dimethyl-9-azabicyclo[3.3.1]nonan-3-one oxime (8.1 g, 26.82 mmol) in 100 mL of propanol in portions at 105° C. After the addition, the reaction was stirred at 105° C. for 1 h. The reaction mixture was concentrated and 100 mL of water was added. The mixture was extracted with ethyl acetate (150 mL×3). The combined organic layers were washed with brine, dried over anhydrous $Na_2SO_4$ and concentrated to afford (1R,3s,5S)-9-(4-methoxybenzyl)-1,5-dimethyl-9-azabicyclo[3.3.1]nonan-3-amine as colorless oil (6.3 g, 82% yield). LCMS: m/z 289.1 [M+H]$^+$; $t_R$=1.18 min.

Step 10: Synthesis of (1R,3s,5S)—N-(6-chloropyridazin-3-yl)-9-(4-methoxybenzyl)-1,5-dimethyl-9-azabicyclo[3.3.1]nonan-3-amine

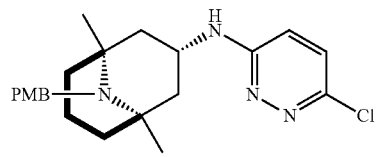

A solution of (1R,3s,5S)-9-(4-methoxybenzyl)-1,5-dimethyl-9-azabicyclo[3.3.1]nonan-3-amine (6.3 g, 21.88 mmol), 3,6-dichloropyridazine (3.9 g, 26.26 mmol) and DIPEA (5.4 g, 42 mmol) in 100 mL of DMSO was heated to 140° C. for 6 h under nitrogen protection. The reaction mixture was cooled to room temperature. 100 mL of water was added to this mixture and extracted with ethyl acetate (105 mL×3). The combined organic layers were washed with saturated NH₄Cl aqueous solution, brine, dried over anhydrous Na₂SO₄, concentrated and purified by silica gel chromatography (10-50% ethyl acetate in petroleum ether) which gave (1R,3s,5S)—N-(6-chloropyridazin-3-yl)-9-(4-methoxybenzyl)-1,5-dimethyl-9-azabicyclo[3.3.1]nonan-3-amine as brown solid (4.2 g, 50% yield). LCMS: m/z 401.2 [M+H]⁺; $t_R$=1.39 min.

Step 11: Synthesis of (1R,3s,5S)—N-(6-chloro-pyridazin-3-yl)-9-(4-methoxybenzyl)-N,1,5-trimethyl-9-azabicyclo[3.3.1]nonan-3-amine

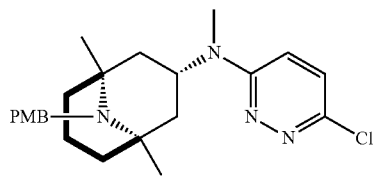

Sodium hydride (768 mg, 16 mmol, 60% in mineral oil) was added to a stirred solution of (1R,3s,5S)—N-(6-chloropyridazin-3-yl)-9-(4-methoxybenzyl)-1,5-dimethyl-9-azabicyclo[3.3.1]nonan-3-amine (4.2 g, 10.5 mmol) in 100 mL of THF at room temperature. After the reaction was stirred for 30 min, methyl iodide (1.78 g, 12.6 mmol) was added to the mixture. The reaction was heated to 50° C. for 6 h. The reaction mixture was cooled to room temperature, quenched with 50 mL of water and extracted with ethyl acetate (100 mL×3). The combined organic layers were washed with brine, dried over anhydrous Na₂SO₄, concentrated and purified by silica gel chromatography (10-60% ethyl acetate in petroleum ether) which gave (1R,3s,5S)—N-(6-chloropyridazin-3-yl)-9-(4-methoxybenzyl)-N,1,5-trimethyl-9-azabicyclo[3.3.1]nonan-3-amine as brown solid (2.7 g, 60% yield). LCMS: m/z 415.2 [M+H]⁺; $t_R$=1.42 min.

Step 12: Synthesis of (1R,3s,5S)-9-(4-methoxybenzyl)-N-(6-(2-(methoxymethoxy)-4-(1-(tetrahydro-2H-pyran-2-yl)-1H-pyrazol-4-yl)phenyl)pyridazin-3-yl)-N,1,5-trimethyl-9-azabicyclo[3.3.1]nonan-3-amine

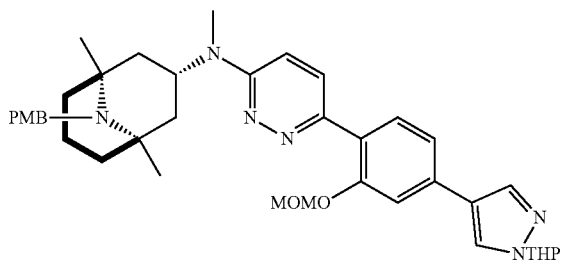

A mixture of (1R,3s,5S)—N-(6-chloropyridazin-3-yl)-9-(4-methoxybenzyl)-N,1,5-trimethyl-9-azabicyclo[3.3.1]nonan-3-amine (120 mg, 0.3 mmol), 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole (120 mg, 0.3 mmol), Pd(dppf)Cl₂ (22 mg, 0.03 mmol) and K₂CO₃ (81 mg, 0.6 mmol) in 5 mL of dioxane and 1 mL of H₂O was degassed and stirred at 85° C. for 6 h. After cooling to room temperature, the mixture was extracted with EtOAc (30 mL×3). The combined organic solvents were concentrated and purified by silica gel column (10-50% EtOAc/petroleum ether) which gave 100 mg g of (1R,3s,5S)-9-(4-methoxybenzyl)-N-(6-(2-(methoxymethoxy)-4-(1-(tetrahydro-2H-pyran-2-yl)-1H-pyrazol-4-yl)phenyl)pyridazin-3-yl)-N,1,5-trimethyl-9-azabicyclo[3.3.1]nonan-3-amine as yellowish solid (50% yield). LCMS: m/z 667.5 [M+H]⁺; $t_R$=1.51 min.

Step 13: Synthesis of (1R,3s,5S)—N-(6-(2-(methoxymethoxy)-4-(1-(tetrahydro-2H-pyran-2-yl)-1H-pyrazol-4-yl)phenyl)pyridazin-3-yl)-N,1,5-trimethyl-9-azabicyclo[3.3.1]nonan-3-amine

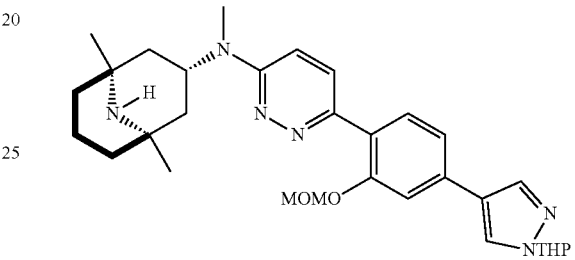

A solution of (1R,3s,5S)-9-(4-methoxybenzyl)-N-(6-(2-(methoxymethoxy)-4-(1-(tetrahydro-2H-pyran-2-yl)-1H-pyrazol-4-yl)phenyl)pyridazin-3-yl)-N,1,5-trimethyl-9-azabicyclo[3.3.1]nonan-3-amine (100 mg, 0.15 mmol) and Pd(OH)₂ (100 mg) in MeOH (5 mL) was stirred at room temperature under a balloon of hydrogen for 6 h. The mixture was filtered through a pad of celite and concentrated which gave (1R,3s,5S)—N-(6-(2-(methoxymethoxy)-4-(1-(tetrahydro-2H-pyran-2-yl)-1H-pyrazol-4-yl)phenyl)pyridazin-3-yl)-N,1,5-trimethyl-9-azabicyclo[3.3.1]nonan-3-amine as yellowish solid (52 mg, 78% in yield). LCMS: m/z 547.3 [M+H]⁺; $t_R$=1.54 min.

Step 13: Synthesis of 2-(6-(((1R,3s,5S)-1,5-dimethyl-9-azabicyclo[3.3.1]nonan-3-yl)(methyl)amino)pyridazin-3-yl)-5-(1H-pyrazol-4-yl)phenol

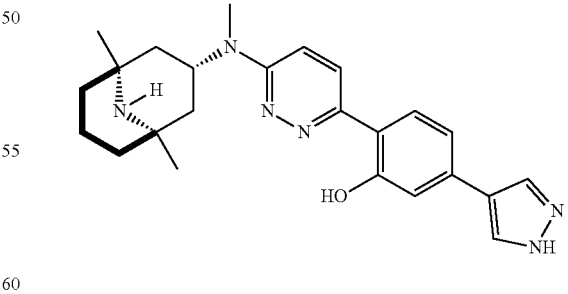

A solution of (1R,3s,5S)—N-(6-(2-(methoxymethoxy)-4-(1-(tetrahydro-2H-pyran-2-yl)-1H-pyrazol-4-yl)phenyl)pyridazin-3-yl)-N,1,5-trimethyl-9-azabicyclo[3.3.1]nonan-3-amine (52 mg, 0.095 mmol) in 10 mL of HCl in dioxane (4N) was stirred at room temperature for 3 h. The reaction mixture was concentrated. A solution of Ammonia in methanol (7 N) was added to adjust the pH to 9. The mixture was concentrated and purified by silica gel column (80% MeOH/EtOAc) which gave 25 mg of 2-(6-(((1R,3s,5S)-1,5-dimethyl-9-azabicyclo[3.3.1]nonan-3-yl)(methyl)amino)pyridazin-3-yl)-5-(1H-pyrazol-4-yl)phenol as yellow solid (60% yield). $^1$H NMR (500 MHz, Methanol-d$_4$) δ 8.15 (d, J=9.9 Hz, 1H), 8.09 (s, 1H), 7.95 (s, 1H), 7.78 (d, J=8.0 Hz, 1H), 7.33 (d, J=9.8 Hz, 1H), 7.21-7.20 (m, 2H), 6.08-6.03 (m, 1H), 2.99 (s, 3H), 2.45-2.42 (m, 1H), 2.15-1.76 (m, 9H), 1.48 (s, 6H). LCMS: m/z 419.2.0 [M+H]f; t$_R$=1.34 min.

Example 6: Synthesis of 2-(6-(((1R,3s,5S)-1,5-dimethyl-8-azabicyclo[3.2.1]octan-3-yl)(methyl)amino)pyridazin-3-yl)-4-fluoro-5-(1H-pyrazol-4-yl)phenol

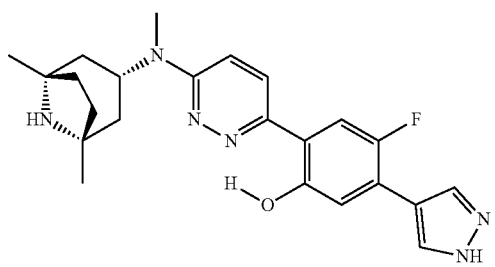 [SMILES: CN(c1ccc(-c2cc(F)c(-c3cn[nH]c3)cc2O)nn1)[C@H]1C[C@]2(C)CC[C@](C)(C1)N2]

Step 1: Synthesis of 1,5-dimethyl-8-azabicyclo[3.2.1]octan-3-one

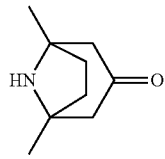

Potassium hydroxide (108 g, 1.93 mol) in 70 mL of H$_2$O was added to a stirred solution of 3-oxopentanedioic acid (120 g, 822 mmol) and hexane-2,5-dione (49.2 g, 432 mmol) in 350 mL of H$_2$O and 0° C. After the addition, NH$_4$Cl (70.1 g, 1.32 mol) and NaOAc trihydrate (70.1 g, 515 mmol) in 667 mL of H$_2$O was added. The pH value was adjusted to ~9 by using 1 N NaOH aqueous solution. The mixture was stirred at room temperature for 72 h during which time the pH value was adjusted to ~9 by using additional 1 N NaOH aqueous solution. The mixture was extracted with CH$_2$Cl$_2$ (1 L×5). The combined organic solvents were dried over anhydrous Na$_2$SO$_4$, concentrated and purified by silica gel chromatography (0-25% MeOH/CH$_2$Cl$_2$) which gave 16.7 g of 1,5-dimethyl-8-azabicyclo[3.2.1]octan-3-one as black oil (25% yield). LCMS: m/z 154.2 [M+H]$^+$; t$_R$=1.20 min.

Step 2: Synthesis of tert-butyl 1,5-dimethyl-3-oxo-8-azabicyclo[3.2.1]octane-8-carboxylate

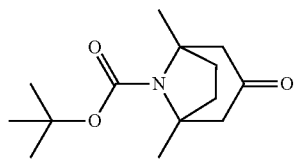 [SMILES: CC(C)(C)OC(=O)N1C2(C)CCC1(C)CC(=O)C2]

A mixture of 1,5-dimethyl-8-azabicyclo[3.2.1]octan-3-one (24 g, 163 mmol), di-tert-butyl dicarbonate (35.6 g, 326 mmol) and DIPEA (31.5 g, 244 mmol) in 500 mL of 1,4-dioxane was stirred at 70° C. for 6 h. The mixture was concentrated and purified by silica gel chromatography (0-30% EtOAc/petroleum ether) which gave 16.7 of tert-butyl 1,5-dimethyl-3-oxo-8-azabicyclo[3.2.1]octane-8-carboxylate as white solid (yield: 42%). LCMS: m/z 198.1 [M−55]$^+$; t$_R$=1.40 min.

Step 3: Synthesis of tert-butyl 3-(hydroxyimino)-1,5-dimethyl-8-azabicyclo[3.2.1]octane-8-carboxylate

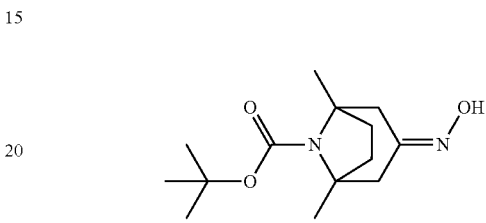

A mixture of tert-butyl 1,5-dimethyl-3-oxo-8-azabicyclo[3.2.1]octane-8-carboxylate (16.7 g, 66 mmol), hydroxylamine hydrochloride (18.2 g, 26.4 mmol) and NaOAc (10.8 g, 132 mmol) in 250 mL of EtOH was stirred at 70° C. for 4 h. The mixture was concentrated. 200 mL of EtOAc and 60 mL of H$_2$O was added. The organic phase was separated, washed with brine (50 mL), dried over anhydrous Na$_2$SO$_4$, concentrated to give 16.7 g of tert-butyl 3-(hydroxyimino)-1,5-dimethyl-8-azabicyclo[3.2.1]octane-8-carboxylate as yellow solid which was used directly to next step (93% yield). LCMS: m/z 269.2 [M+H]$^+$; t$_R$=1.92 min.

Step 4: Synthesis of tert-butyl (1R,3s,5S)-3-amino-1,5-dimethyl-8-azabicyclo[3.2.1]octane-8-carboxylate

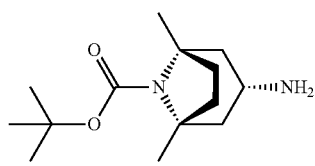

Sodium (40.2 g, 1.75 mol) was added in portions to a mixture of tert-butyl 3-(hydroxyimino)-1,5-dimethyl-8-azabicyclo[3.2.1]octane-8-carboxylate (26.8 g, 0.1 mol) in 1000 mL of n-PrOH was heated to 110° C. over 1 h. After addition, the mixture was stirred at reflux for additional 1 h. The mixture was cooled to room temperature, quenched with H$_2$O (500 mL). The organic layer was separated and concentrated. DCM (500 mL) was added to the residue. The solid was filtered off and the filtrate was concentrated under reduced pressure to afford 20 g of tert-butyl (1R,3s,5S)-3-amino-1,5-dimethyl-8-azabicyclo[3.2.1]octane-8-carboxylate as a yellow oil, which was used directly to next step (yield: 79%). LCMS: m/z 255.3 [M+H]$^+$; t$_R$=1.37 min.

Step 5: Synthesis of tert-butyl (1R,3s,5S)-3-((6-chloropyridazin-3-yl)amino)-1,5-dimethyl-8-azabicyclo[3.2.1]octane-8-carboxylate

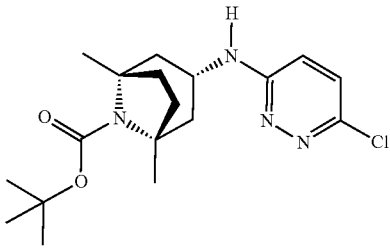

A mixture of tert-butyl (1R,3s,5S)-3-amino-1,5-dimethyl-8-azabicyclo[3.2.1]octane-8-carboxylate (20 g, 78.7 mmol), 3,6-dichloropyridazine (23.3 g, 157.5 mmol) and DIPEA (20.48 g, 157.5 mmol) in 500 mL of DMSO was stirred at 120° C. for 24 h. The mixture was cooled to room temperature, quenched with H$_2$O and extracted with ethyl acetate (500 mL×3). The combined organic layers were washed with brine, dried over anhydrous Na$_2$SO$_4$ and concentrated under reduced pressure. After removal of solvent, the crude product was purified by silica gel column (50% EtOAc/petroleum ether) to afford 17.5 g of tert-butyl (1R,3s,5S)-3-((6-chloropyridazin-3-yl)amino)-1,5-dimethyl-8-azabicyclo[3.2.1]octane-8-carboxylate as yellow solid (yield: 61%). LCMS: m/z 367.2 [M+H]$^+$; $t_R$=1.88 min.

Step 6: Synthesis of tert-butyl (1R,3s,5S)-3-((6-chloropyridazin-3-yl)(methyl)amino)-1,5-dimethyl-8-azabicyclo[3.2.1]octane-8-carboxylate

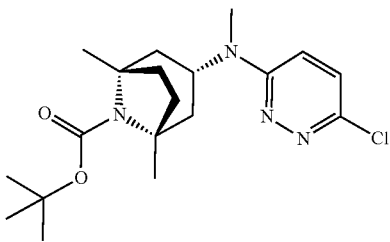

Sodium hydride (2.87 g, 71.7 mmol, 60% in mineral oil) was added to a stirred solution of tert-butyl (1R,3s,5S)-3-((6-chloropyridazin-3-yl)amino)-1,5-dimethyl-8-azabicyclo[3.2.1]octane-8-carboxylate (17.5 g, 47.8 mmol) in 400 mL of DMF at 0° C. After stirring for 20 min at 0° C., CH$_3$I (13.58 g, 95.6 mmol) was added. The mixture was then stirred at room temperature for 1 h, quenched with H$_2$O and extracted with EtOAc (300 mL×3). The combined organic phases were washed with brine, dried over anhydrous Na$_2$SO$_4$, concentrated under reduced pressure and purified by silica gel column (30% EtOAc/petroleum ether) to afford 14.5 g of tert-butyl (1R,3s,5S)-3-((6-chloropyridazin-3-yl)(methyl)amino)-1,5-dimethyl-8-azabicyclo[3.2.1]octane-8-carboxylate as yellow solid (80% yield). LCMS: m/z 381.2 [M+H]$^+$; $t_R$=2.17 min.

Step 7: Synthesis of 2-bromo-5-chloro-4-fluorophenol

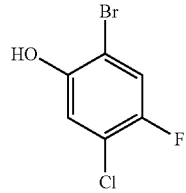

Bromine (3.52 g, 22 mmol) was added to a stirred solution of 3-chloro-4-fluorophenol (4.02 g, 20 mmol) in 80 mL of CH$_2$Cl$_2$ at room temperature. The mixture was stirred at room temperature for 18 h and quenched with 10 mL of aqueous Na$_2$S$_2$O$_3$ solution. The organic phase was collected, concentrated and purified by silica gel chromatography (0-10% EtOAc/petroleum ether) to afford 2.5 g of 2-bromo-5-chloro-4-fluorophenol as white solid (44% yield). $^1$H NMR (500 MHz, Chloroform-d) δ 7.29 (d, J=8.0 Hz, 1H), 7.08 (d, J=6.6 Hz, 1H), 5.45 (s, 1H). LCMS: $t_R$=1.44 min.

Step 8: Synthesis of 1-bromo-4-chloro-5-fluoro-2-(methoxymethoxy)benzene

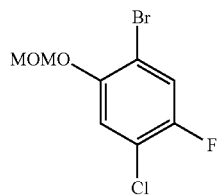

Sodium hydride (215 mg, 5.4 mmol) was added to a stirred solution of 2-bromo-5-chloro-4-fluorophenol (1 g, 4.48 mmol) in 14 mL of DMF at 0° C. After stirring for 30 min, bromo(methoxy)methane (428 mg, 8 mmol) was added. The mixture was then stirred at room temperature for 2 h, quenched with 10 mL of saturated NH$_4$Cl aqueous solution and extracted with EtOAc (30 mL×3). The combined organic solvents were concentrated and purified by silica gel silica gel column (0-8% EtOAc/petroleum ether) to give 1.01 g of 1-bromo-4-chloro-5-fluoro-2-(methoxymethoxy)benzene as white solid (70% yield). $^1$H NMR (500 MHz, Chloroform-d) δ 7.37 (d, J=8.1 Hz, 1H), 7.23 (d, J=6.6 Hz, 1H), 5.20 (s, 2H), 3.52 (s, 3H).

Step 9: Synthesis of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate

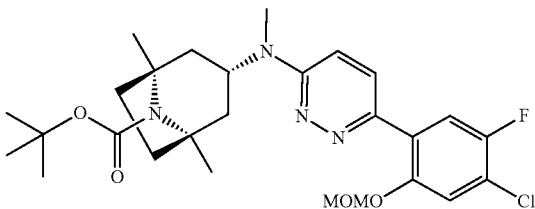

A mixture of 1-bromo-4-chloro-5-fluoro-2-(methoxymethoxy)benzene (8.5 g, 31.7 mmol), 4,4,4',4',5,5,5',5'-octamethyl-2,2'-bi(1,3,2-dioxaborolane) (12.1 g, 47.5 mmol), Pd(dppf)Cl$_2$ (1.86 g, 2.54 mmol) and potassium acetate (6.2 g, 63.4 mmol) in 200 mL of dioxane was degassed and stirred at 100° C. for 8 h. After cooling to room temperature, tert-butyl (1R,3s,5S)-3-((6-chloropyridazin-3-yl)(methyl)amino)-1,5-dimethyl-8-azabicyclo[3.2.1]octane-8-carboxylate (8 g, 21.2 mmol), K$_2$CO$_3$ (5.8 g, 42.3 mmol) and H$_2$O (30 mL) were added. The mixture was stirred at 100° C. for 3 h, concentrated and purified by silica gel column (10-25% EtOAc/petroleum ether) which gave 6 g of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate as light yellow solid (53% yield). LCMS: m/z 535.2 [M+H]$^+$; t$_R$=2.40 min.

Step 10: Synthesis of tert-butyl (1R,3s,5S)-3-((6-(5-fluoro-2-(methoxymethoxy)-4-(1H-pyrazol-4-yl)phenyl)pyridazin-3-yl)(methyl)amino)-1,5-dimethyl-8-azabicyclo[3.2.1]octane-8-carboxylate

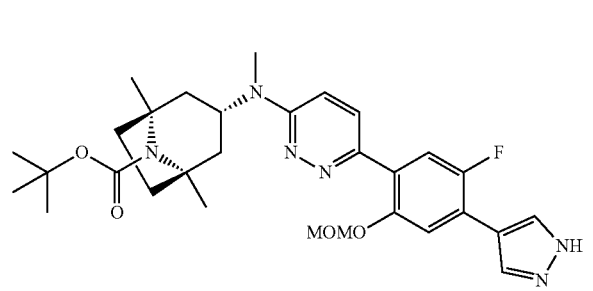

A mixture of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate (120 mg, 0.22 mmol), 4-(4,4,5,5-tetramethyl-1,3,2-dioxaborolan-2-yl)-1H-pyrazole (66 mg, 0.34 mmol), Pd(dppf)Cl$_2$ (20 mg, 0.028 mmol) and K$_2$CO$_3$ (77 mg, 0.56 mmol) in 2 mL of 1,4-dioxane and 0.4 mL of water was purged with nitrogen and sealed. The mixture was stirred at 130° C. under MW for 2 h, concentrated and purified by silica gel chromatography (0-20% MeOH/CH$_2$Cl$_2$) which gave 90 mg of tert-butyl (1R,3s,5S)-3-((6-(5-fluoro-2-(methoxymethoxy)-4-(1H-pyrazol-4-yl)phenyl)pyridazin-3-yl)(methyl)amino)-1,5-dimethyl-8-azabicyclo[3.2.1]octane-8-carboxylate as white solid (72% yield). LCMS: m/z 567.2 [M+H]$^+$; t$_R$=1.59 min.

Step 11: Synthesis of 2-(6-(((1R,3s,5S)-1,5-dimethyl-8-azabicyclo[3.2.1]octan-3-yl)(methyl)amino)pyridazin-3-yl)-4-fluoro-5-(1H-pyrazol-4-yl)phenol

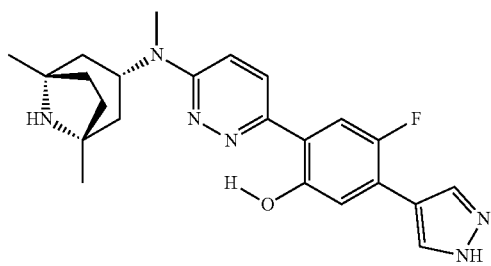

A solution HCl in dioxane (4 N, 4 ml) was added to a stirred solution of tert-butyl (1R,3s,5S)-3-((6-(5-fluoro-2-(methoxymethoxy)-4-(1H-pyrazol-4-yl)phenyl)pyridazin-3-yl)(methyl)amino)-1,5-dimethyl-8-azabicyclo[3.2.1]octane-8-carboxylate (90 mg, 0.16 mmol) in 2 mL of CH$_2$Cl$_2$. The mixture was stirred at room temperature for 2 h, concentrated under reduced pressure, neutralized with NH$_3$/MeOH and purified by prep-HPLC to give 32 mg of 2-(6-(((1R,3s,5S)-1,5-dimethyl-8-azabicyclo[3.2.1]octan-3-yl)(methyl)amino)pyridazin-3-yl)-4-fluoro-5-(1H-pyrazol-4-yl)phenol as a yellow solid (54% yield). $^1$H NMR (500 MHz, DMSO-d$_6$) δ 13.56 (s, 1H), 13.14 (s, 1H), 8.21 (d, J=9.9 Hz, 1H), 8.11 (s, 2H), 7.81 (d, J=12.6 Hz, 1H), 7.35 (d, J=9.9 Hz, 1H), 7.30 (d, J=7.0 Hz, 1H), 5.00-4.87 (m, 1H), 2.93 (s, 3H), 1.83-1.77 (m, 2H), 1.56-1.39 (m, 6H), 1.17 (s, 6H). LCMS (A038): m/z 423.3[M+H]$^+$; t$_R$=1.36 min.

Example 7: Synthesis of 2-(6-(((1R,3s,5S)-1,5-dimethyl-9-azabicyclo[3.3.1]nonan-3-yl)(methyl)amino)pyridazin-3-yl)-4-fluoro-5-(1H-pyrazol-4-yl)phenol

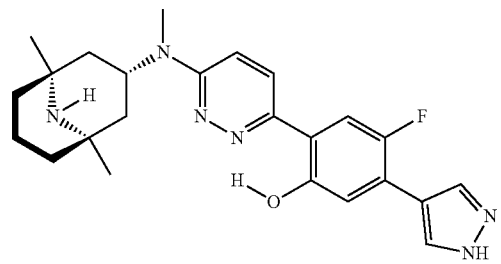

Step 1: Synthesis of N1,N5-dimethoxy-N1,N5-dimethylglutarimide

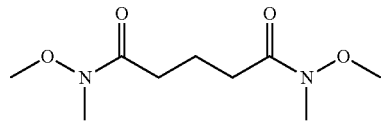

Glutaroyl dichloride (50 g, 0.299 mol) was added to a stirred solution of NO-dimethylhydroxylamine hydrochloride (64 g, 0.658 mmol) and Et$_3$N (121.2 g, 1.2 mmol) in 1000 mL of CH$_2$Cl$_2$ at 0° C. over 30 min. The reaction mixture was allowed to room temperature and stirred for 3 h. 500 mL of water was added to the mixture, which was extracted with CH$_2$Cl$_2$ (1000 mL×3). The combined organic layers were washed with 1% HCl solution, brine, dried over anhydrous Na$_2$SO$_4$ and concentrated under reduced pressure which gave 55 g of N1,N5-dimethoxy-N1,N5-dimethylglutarimide as brown oil (85% yield), which was used for next step without further purification. LCMS: m/z 219.2 [M+H]$^+$; t$_R$=1.26 min.

Step 2: Synthesis of heptane-2,6-dione

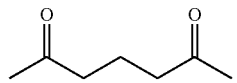

Methyl magnesium bromide (250 mL, 0.756 mol) was added to a stirred solution of N1,N5-dimethoxy-N1,N5-dimethylglutarimide (55 g, 0.252 mol) in 800 mL of THF at 0° C. over 30 min. The reaction mixture was allowed to warm to room temperature and stirred for 2 h. 50 mL of water was added to the mixture followed by 1% HCl aqueous solution 300 mL. The mixture was extracted with ethyl acetate (1000 mL×3). The combined organic layers were washed with 1% HCl aqueous solution, brine, dried over anhydrous $Na_2SO_4$, concentrated under reduced pressure and purified by silica gel column (10-50% ethyl acetate in petroleum ether) which gave 13 g of heptane-2,6-dione as brownish solid (40% yield). LCMS: m/z 129.1 [M+H]$^+$; $t_R$=1.24 min.

Step 3: Synthesis of 1,5-dimethyl-9-azabicyclo[3.3.1]nonan-3-one

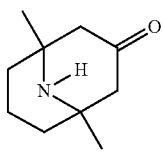

Ammonium acetate (18.3 g, 0.238 mol) and acetone dicarboxylic acid (34.7 g, 0.238 mol) were added to a stirred solution of heptane-2,6-dione (5.07 g, 39.6 mmol) in AcOH (49 mL) at room temperature. The reaction mixture was then stirred for 3 h at 80° C. The mixture was cooled to 0° C. and diluted with $CH_2Cl_2$ and water. The aqueous phase was separated and acidified with 10% HCl aqueous solution (pH=1) and then diluted with AcOEt. The resultant mixture was extracted with water. The combined aqueous layers were basified with 20% NaOH (pH=11) and extracted with $CH_2Cl_2$ (three times). The combined organic layers were dried over $K_2CO_3$ and concentrated under reduced pressure. The residue was purified by flash silica gel column chromatography (50% ethyl acetate in petroleum ether to 10% MeOH in $CH_2Cl_2$) which gave 1,5-dimethyl-9-azabicyclo[3.3.1]nonan-3-one (2.0 g, 30% yield) as dark red oil. LCMS: m/z 168.2 [M+H]$^+$; $t_R$=1.24 min.

Step 4: Synthesis of 9-(4-methoxybenzyl)-1,5-dimethyl-9-azabicyclo[3.3.1]nonan-3-one

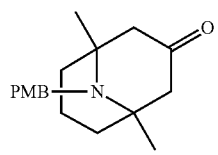

A solution of 1,5-dimethyl-9-azabicyclo[3.3.1]nonan-3-one (2.0 g, 11.98 mmol), $K_2CO_3$ (3.3 g, 24 mmol) and 1-(chloromethyl)-4-methoxybenzene (2.2 g, 14.4 mmol.) in 50 mL of acetone was heated to reflux for 16 h under nitrogen protection. The reaction mixture was cooled to room temperature, 50 mL of water was added to this mixture which was extracted with ethyl acetate (50 mL×3). The combined organic layers were washed with brine, dried over anhydrous $Na_2SO_4$, concentrated and purified by silica gel chromatography (10-30% ethyl acetate in petroleum ether) which gave 9-(4-methoxybenzyl)-1,5-dimethyl-9-azabicyclo[3.3.1]nonan-3-one as yellowish solid (2.4 g, 70% yield). LCMS: m/z 288.2 [M+H]$^+$; $t_R$=1.22 min.

Step 5: Synthesis of 9-(4-methoxybenzyl)-1,5-dimethyl-9-azabicyclo[3.3.1]nonan-3-one oxime

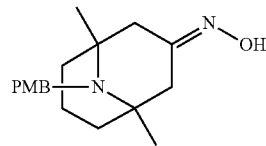

A solution of 9-(4-methoxybenzyl)-1,5-dimethyl-9-azabicyclo[3.3.1]nonan-3-one (8.5 g, 29.62 mmol) and $NH_2OH$ HCl (4.1 g, 60 mmol) in 150 mL of ethanol was heated to 85° C. for 3 h. Then the mixture was concentrated to residue which was dissolved in water and adjusted pH to 8 with aqueous solution of $Na_2CO_3$. Tithe mixture was extracted with ethyl acetate (200 mL×3). The combined organic layers were washed with brine, dried over anhydrous $Na_2SO_4$ and concentrated which gave 9-(4-methoxybenzyl)-1,5-dimethyl-9-azabicyclo[3.3.1]nonan-3-one oxime as white solid (8.1 g, 90% yield). LCMS: m/z 303.1 [M+H]$^+$; $t_R$=1.19 min.

Step 6: Synthesis of (1R,3s,5S)-9-(4-methoxybenzyl)-1,5-dimethyl-9-azabicyclo[3.3.1]nonan-3-amine

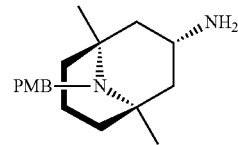

Sodium (6.72 g, 280 mmol) was added to a stirred solution of 9-(4-methoxybenzyl)-1,5-dimethyl-9-azabicyclo[3.3.1]nonan-3-one oxime (8.1 g, 26.82 mmol) in 100 mL of propanol in portions at 105° C. After the addition, the reaction was stirred at 105° C. for 1 h. The reaction mixture was concentrated and 100 mL of water was added. The mixture was extracted with ethyl acetate (150 mL×3). The combined organic layers were washed with brine, dried over anhydrous $Na_2SO_4$ and concentrated which gave (1R,3s,5S)-9-(4-methoxybenzyl)-1,5-dimethyl-9-azabicyclo[3.3.1]nonan-3-amine as colorless oil (6.3 g, 82% yield). LCMS: m/z 289.1 [M+H]$^+$; $t_R$=1.18 min.

Step 7: Synthesis of (1R,3s,5S)—N-(6-chloropyridazin-3-yl)-9-(4-methoxybenzyl)-1,5-dimethyl-9-azabicyclo[3.3.1]nonan-3-amine

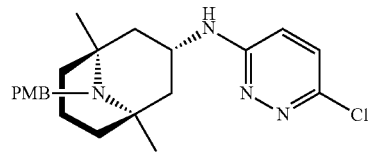

A solution of (1R,3s,5S)-9-(4-methoxybenzyl)-1,5-dimethyl-9-azabicyclo[3.3.1]nonan-3-amine (6.3 g, 21.88 mmol), 3,6-dichloropyridazine (3.9 g, 26.26 mmol) and DIPEA (5.4 g, 42 mmol) in 100 mL of DMSO was heated to 140° C. for 6 h under nitrogen protection. The reaction mixture was cooled to room temperature. 100 mL of water was added to this mixture and extracted with ethyl acetate (105 mL×3). The combined organic layers were washed with saturated NH$_4$Cl aqueous solution, brine, dried over anhydrous Na$_2$SO$_4$, concentrated and purified by silica gel chromatography (10-50% ethyl acetate in petroleum ether) which gave (1R,3s,5S)—N-(6-chloropyridazin-3-yl)-9-(4-methoxybenzyl)-1,5-dimethyl-9-azabicyclo[3.3.1]nonan-3-amine as brown solid (4.2 g, 50% yield). LCMS: m/z 401.2 [M+H]$^+$; t$_R$=1.39 min.

Step 8: Synthesis of (1R,3s,5S)—N-(6-chloropyridazin-3-yl)-9-(4-methoxybenzyl)-N,1,5-trimethyl-9-azabicyclo[3.3.1]nonan-3-amine

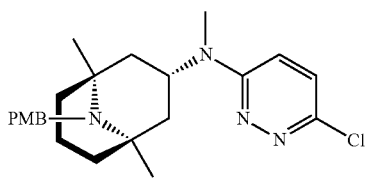

Sodium hydride (768 mg, 16 mmol, 60% in mineral oil) was added to a stirred solution of (1S,3R)—N-(6-chloropyridazin-3-yl)-9-(4-methoxybenzyl)-1,5-dimethyl-9-azabicyclo[3.3.1]nonan-3-amine (4.2 g, 10.5 mmol) in 100 mL of THF at room temperature. After the reaction was stirred for 30 min, methyl iodide (1.78 g, 12.6 mmol) was added to the mixture. The reaction was heated to 50° C. for 6 h. The reaction mixture was cooled to room temperature, quenched with 50 mL of water and extracted with ethyl acetate (100 mL×3). The combined organic layers were washed with brine, dried over anhydrous Na$_2$SO$_4$, concentrated and purified by silica gel chromatography (10-60% ethyl acetate in petroleum ether) which gave (1S,3R)—N-(6-chloropyridazin-3-yl)-9-(4-methoxybenzyl)-N,1,5-trimethyl-9-azabicyclo[3.3.1]nonan-3-amine as brown solid (2.7 g, 60% yield). LCMS: m/z 415.2 [M+H]$^+$; t$_R$=1.42 min.

Step 9: Synthesis of 2-bromo-5-chloro-4-fluorophenol

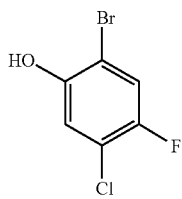

Bromine (3.52 g, 22 mmol) was added to a stirred solution of 3-chloro-4-fluorophenol (4.02 g, 20 mmol) in 80 mL of CH$_2$Cl$_2$ at room temperature. The mixture was stirred at room temperature for 18 h and quenched with 10 mL of aqueous Na$_2$S$_2$O$_3$ solution. The organic phase was collected, concentrated and purified by silica gel chromatography (0-10% EtOAc/petroleum ether) which gave 2.5 g of 2-bromo-5-chloro-4-fluorophenol as white solid (44% yield). $^1$H NMR (500 MHz, Chloroform-d) δ 7.29 (d, J=8.0 Hz, 1H), 7.08 (d, J=6.6 Hz, 1H), 5.45 (s, 1H). LCMS: t$_R$=1.44 min.

Step 10: Synthesis of 1-bromo-4-chloro-5-fluoro-2-(methoxymethoxy)benzene

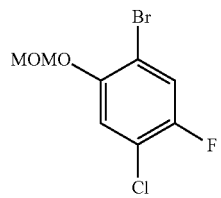

Sodium hydride (215 mg, 5.4 mmol, 60% in mineral oil) was added to a stirred solution of 2-bromo-5-chloro-4-fluorophenol (1 g, 4.48 mmol) in 14 mL of DMF at 0° C. After stirring for 30 min, bromo(methoxy)methane (428 mg, 8 mmol) was added. The mixture was then stirred at room temperature for 2 h, quenched with 10 mL of saturated NH$_4$Cl aqueous solution and extracted with EtOAc (30 mL×3). The combined organic solvents were concentrated and purified by silica gel silica gel column (0-8% EtOAc/petroleum ether) which gave 1.01 g of 1-bromo-4-chloro-5-fluoro-2-(methoxymethoxy)benzene as white solid (70% yield). $^1$H NMR (500 MHz, Chloroform-d) δ 7.37 (d, J=8.1 Hz, 1H), 7.23 (d, J=6.6 Hz, 1H), 5.20 (s, 2H), 3.52 (s, 3H).

Step 11: Synthesis of (1R,3s,5S)—N-(6-(4-chloro-5-fluoro-2-(methoxymethoxy)phenyl) pyridazin-3-yl)-9-(4-methoxybenzyl)-N,1,5-trimethyl-9-azabicyclo[3.3.1]nonan-3-amine

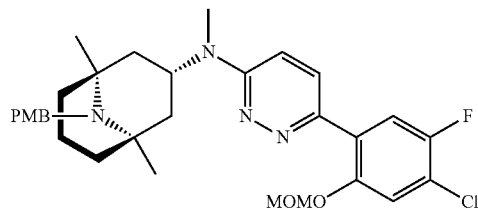

A mixture of 1-bromo-4-chloro-5-fluoro-2-(methoxymethoxy)benzene (600 mg, 2.22 mmol), 4,4,4',4',5,5,5',5'-octamethyl-2,2'-bi(1,3,2-dioxaborolane) (677 mg, 2.66 mmol), Pd(dppf)Cl$_2$ (325 mg, 0.44 mmol) and KOAc (435 mg, 4.44 mmol) in 8 mL of dioxane was degassed and stirred at 100° C. for 6 h. The mixture was cooled to room temperature, (1R,3s,5S)—N-(6-chloropyridazin-3-yl)-9-(4-methoxybenzyl)-N,1,5-trimethyl-9-azabicyclo[3.3.1]nonan-3-amine (735 mg, 1.78 mmol), Pd(dppf)Cl$_2$ (325 mg, 0.44 mmol), K$_2$CO$_3$ (613 mg, 4.44 mmol) and 1 mL of H$_2$O was added. The mixture was degassed and stirred at 100° C. for 2 h, concentrated and purified by silica gel column (40% EtOAc/petroleum ether) which gave 615 mg of (1R,3s,5S)—N-(6-(4-chloro-5-fluoro-2-(methoxymethoxy)phenyl) pyridazin-3-yl)-9-(4-methoxybenzyl)-N,1,5-trimethyl-9-azabicyclo[3.3.1]nonan-3-amine as brown solid (49% yield). LCMS: m/z 569.0 [M+H]$^+$; t$_R$=2.54 min.

Step 12: Synthesis of (1R,3s,5S)—N-(6-(5-fluoro-2-(methoxymethoxy)-4-(1H-pyrazol-4-yl) phenyl) pyridazin-3-yl)-9-(4-methoxybenzyl)-N,1,5-trimethyl-9-azabicyclo[3.3.1]nonan-3-amine

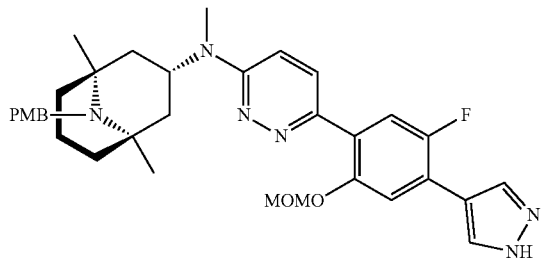

A mixture of (1R,3s,5S)—N-(6-(4-chloro-5-fluoro-2-(methoxymethoxy)phenyl) pyridazin-3-yl)-9-(4-methoxybenzyl)-N,1,5-trimethyl-9-azabicyclo[3.3.1]nonan-3-amine (188 mg, 0.33 mmol), 4-(4,4,5,5-tetramethyl-1,3,2-dioxaborolan-2-yl)-1H-pyrazole (65 mg, 0.33 mmol), catalyst (52 mg, 0.07 mmol) and K₃PO₄ (141 mg, 0.66 mmol) in 2 mL of dioxane and 0.3 mL of H₂O was degassed and stirred at 100° C. for 16 h. The mixture was filtered, concentrated and purified by silica gel column (40-100% EtOAc/petroleum ether) which gave 113 mg of (1R,3s,5S)—N-(6-(5-fluoro-2-(methoxymethoxy)-4-(1H-pyrazol-4-yl) phenyl) pyridazin-3-yl)-9-(4-methoxybenzyl)-N,1,5-trimethyl-9-azabicyclo[3.3.1]nonan-3-amine as white solid (57% yield). LCMS: m/z 601.2 [M+H]⁺; $t_R$=2.27 min.

Step 13: Synthesis of 2-(6-(((1R,3s,5S)-1,5-dimethyl-9-azabicyclo[3.3.1]nonan-3-yl)(methyl)amino)pyridazin-3-yl)-4-fluoro-5-(1H-pyrazol-4-yl)phenol

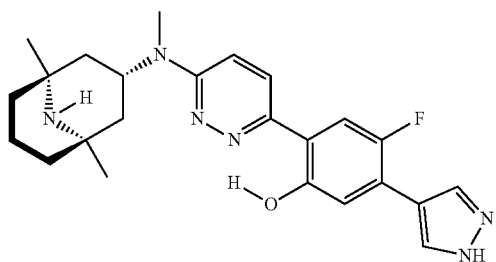

A mixture of (1R,3s,5S)—N-(6-(5-fluoro-2-(methoxymethoxy)-4-(1H-pyrazol-4-yl) phenyl)pyridazin-3-yl)-9-(4-methoxybenzyl)-N,1,5-trimethyl-9-azabicyclo[3.3.1]nonan-3-amine (113 mg, 0.19 mmol) in 10 mL of TFA was stirred at 70° C. for 72 h. The reaction mixture was concentrated, NH₃/MeOH (7 N) was added to make pH=9, concentrated and purified by silica gel column (80% MeOH/EtOAc) which gave 2-(6-(((1R,3s,5S)-1,5-dimethyl-9-azabicyclo[3.3.1]nonan-3-yl)(methyl)amino)pyridazin-3-yl)-4-fluoro-5-(1H-pyrazol-4-yl)phenol (13 mg, 16% yield). H NMR (500 MHz, DMSO-d₆) δ 13.52 (s, 1H), 13.13 (s, 1H), 8.22 (d, J=10.1 Hz, 1H), 8.18-7.91 (m, 2H), 7.80 (d, J=12.7 Hz, 1H), 7.29 (dd, J=11.7, 8.3 Hz, 2H), 5.74 (m, 1H), 2.88 (s, 2H), 2.15-1.99 (m, 1H), 1.63 (s, 5H), 1.56-1.24 (m, 4H), 1.05 (s, 6H). LCMS: m/z 437.0 [M+H]⁺; $t_R$=1.77 min.

Example 8: Synthesis of 4-(4-(6-(((1R,3s,5S)-1,5-dimethyl-8-azabicyclo[3.2.1]octan-3-yl)(methyl)amino)pyridazin-3-yl)-3-hydroxyphenyl)-1-methylpyridin-2(1H)-one

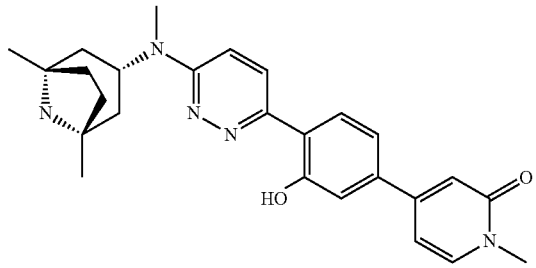

Step 1: Synthesis of 1,5-dimethyl-8-azabicyclo[3.2.1]octan-3-one

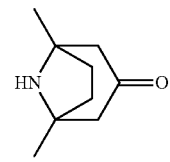

Potassium hydride (108 g, 1.93 mol) in 70 mL of H₂O was added to a stirred solution of 3-oxopentanedioic acid (120 g, 822 mmol) and hexane-2,5-dione (49.2 g, 432 mmol) in 350 mL of H₂O and 0° C. After the addition, NH₄Cl (70.1 g, 1.32 mol) and NaOAc trihydrate (70.1 g, 515 mmol) in 667 mL of H₂O was added. The pH value was adjusted to ~9 by using 1 N NaOH aqueous solution. The mixture was stirred at room temperature for 72 h during which time the pH value was adjusted to ~9 by using additional 1 N NaOH aqueous solution. The mixture was extracted with CH₂Cl₂ (1 L×5). The combined organic solvents were dried over anhydrous Na₂SO₄, concentrated and purified by silica gel chromatography (0-25% MeOH/CH₂Cl₂) which gave 16.7 g of 1,5-dimethyl-8-azabicyclo[3.2.1]octan-3-one as black oil (25% yield). LCMS: m/z 154.2 [M+H]⁺; $t_R$=1.20 min; purity: 85%.

Step 2: Synthesis of tert-butyl 1,5-dimethyl-3-oxo-8-azabicyclo[3.2.1]octane-8-carboxylate

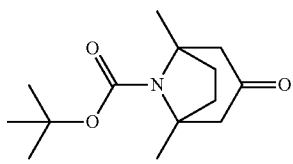 [SMILES: CC(C)(C)OC(=O)N1C2(C)CCC1(C)CC(=O)C2]

A mixture of 1,5-dimethyl-8-azabicyclo[3.2.1]octan-3-one (24 g, 163 mmol), di-tert-butyl dicarbonate (35.6 g, 326 mmol) and DIPEA (31.5 g, 244 mmol) in 500 mL of 1,4-dioxane was stirred at 70° C. for 6 h. The mixture was concentrated and purified by silica gel chromatography (0-30% EtOAc/petroleum ether) which gave 16.7 of tert-butyl 1,5-dimethyl-3-oxo-8-azabicyclo[3.2.1]octane-8-carboxylate as white solid (yield: 42%). LCMS: m/z 198.1 [M−55]$^+$; $t_R$=1.40 min; purity: 100%.

Step 3: Synthesis of tert-butyl 3-(hydroxyimino)-1,5-dimethyl-8-azabicyclo[3.2.1]octane-8-carboxylate

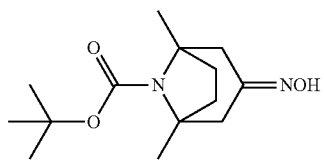

A mixture of tert-butyl 1,5-dimethyl-3-oxo-8-azabicyclo[3.2.1]octane-8-carboxylate (16.7 g, 66 mmol), hydroxylamine hydrochloride (18.2 g, 26.4 mmol) and NaOAc (10.8 g, 132 mmol) in 250 mL of EtOH was stirred at 70° C. for 4 h. The mixture was concentrated. 200 mL of EtOAc and 60 mL of H$_2$O was added. The organic phase was separated, washed with brine (50 mL), dried over anhydrous Na$_2$SO$_4$, concentrated to give 16.7 g of tert-butyl 3-(hydroxyimino)-1,5-dimethyl-8-azabicyclo[3.2.1]octane-8-carboxylate as yellow solid which was used directly to next step (93% yield). LCMS: m/z 269.2 [M+H]$^+$; $t_R$=1.92 min; purity: 100%.

Step 4: Synthesis of tert-butyl (1R,3s,5S)-3-amino-1,5-dimethyl-8-azabicyclo[3.2.1]octane-8-carboxylate

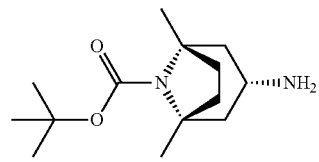 [SMILES: CC(C)(C)OC(=O)N1[C@@]2(C)CC[C@]1(C)C[C@@H](N)C2]

Sodium (40.2 g, 1.75 mol) was added in portions to a mixture of tert-butyl 3-(hydroxyimino)-1,5-dimethyl-8-azabicyclo[3.2.1]octane-8-carboxylate (26.8 g, 0.1 mol) in 1000 mL of n-PrOH was heated to 110° C. over 1 h. After addition, the mixture was stirred at reflux for additional 1 h. The mixture was cooled to room temperature, quenched with H$_2$O (500 mL). The organic layer was separated and concentrated. DCM (500 mL) was added to the residue. The solid was filtered off and the filtrate was concentrated under reduced pressure which gave 20 g of tert-butyl (1R,3s,5S)-3-amino-1,5-dimethyl-8-azabicyclo[3.2.1]octane-8-carboxylates a yellow oil, which was used directly to next step (yield: 79%). LCMS: m/z 255.3 [M+H]$^+$; $t_R$=1.37 min; purity: 99%.

Step 5: Synthesis of tert-butyl (1R,3s,5S)-3-((6-chloropyridazin-3-yl)amino)-1,5-dimethyl-8-azabicyclo[3.2.1]octane-8-carboxylate

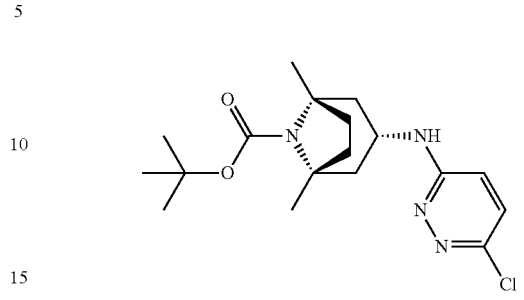

A mixture of tert-butyl (1R,3s,5S)-3-amino-1,5-dimethyl-8-azabicyclo[3.2.1]octane-8-carboxylate (20 g, 78.7 mmol), 3,6-dichloropyridazine (23.3 g, 157.5 mmol) and DIPEA (20.48 g, 157.5 mmol) in 500 mL of DMSO was stirred at 120° C. for 24 h. The mixture was cooled to room temperature, quenched with H$_2$O and extracted with ethyl acetate (500 mL×3). The combined organic layers were washed with brine, dried over anhydrous Na$_2$SO$_4$ and concentrated under reduced pressure. After removal of solvent, the crude product was purified by silica gel column (50% EtOAc/petroleum ether) which gave 17.5 g of tert-butyl (1R,3s,5S)-3-((6-chloropyridazin-3-yl)amino)-1,5-dimethyl-8-azabicyclo[3.2.1]octane-8-carboxylate as yellow solid (yield: 61%). LCMS: m/z 367.2 [M+H]$^+$; $t_R$=1.88 min; purity: 99%.

Step 6: Synthesis of tert-butyl (1R,3s,5S)-3-((6-chloropyridazin-3-yl)(methyl)amino)-1,5-dimethyl-8-azabicyclo[3.2.1]octane-8-carboxylate

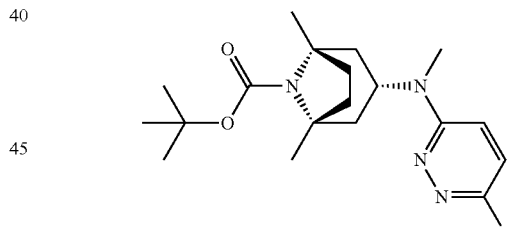

Sodium hydride (2.87 g, 71.7 mmol) was added to a stirred solution of tert-butyl (1R,3s,5S)-3-((6-chloropyridazin-3-yl)amino)-1,5-dimethyl-8-azabicyclo[3.2.1]octane-8-carboxylate (17.5 g, 47.8 mmol) in 400 mL of DMF at 0° C. After stirring for 20 min at 0° C., iodomethane (13.58 g, 95.6 mmol) was added. The mixture was then stirred at room temperature for 1 h, quenched with H$_2$O and extracted with EtOAc (300 mL×3). The combined organic phases were washed with brine, dried over anhydrous Na$_2$SO$_4$, concentrated under reduced pressure and purified by silica gel column (30% EtOAc/petroleum ether) which gave 14.5 g of tert-butyl (1R,3s,5S)-3-((6-chloropyridazin-3-yl)(methyl)amino)-1,5-dimethyl-8-azabicyclo[3.2.1]octane-8-carboxylate as yellow solid (80% yield). LCMS: m/z 381.2 [M+H]$^+$; $t_R$=2.17 min; purity: 99%.

Step 7: Synthesis of 1-bromo-4-chloro-2-(methoxymethoxy)benzene

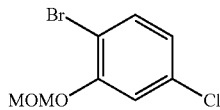

Sodium hydride (185 g, 46.3 mmol, 60% in mineral oil) was added to a stirred solution of 2-bromo-5-chlorophenol (8 g, 38.6 mmol) in 150 mL of DMF at 0° C. After stirring at 0° C. for 30 min, MOMBr (7.25 g, 58 mmol) was added. The mixture was then stirred at room temperature for 2 h, quenched with NH$_4$Cl aqueous solution (15 mL), extracted with EtOAc (30 mL×3). The combined organic solvents were dried over anhydrous Na$_2$SO$_4$, concentrated and purified by silica gel chromatography (0-10% EtOAc/petroleum ether) which gave 8.1 g of 1-bromo-4-chloro-2-(methoxymethoxy)benzene as colorless oil (84% yield). $^1$H NMR (500 MHz, Chloroform-d) δ 7.45 (d, J=8.5 Hz, 1H), 7.17 (d, J=2.3 Hz, 1H), 6.89 (dd, J=8.4, 2.3 Hz, 1H), 5.24 (s, 2H). LCMS: $t_R$=1.51 min.

Step 8: Synthesis of 4-chloro-2-(methoxymethoxy)phenylboronic acid

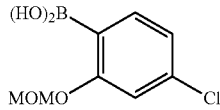

A solution of n-BuLi in hexane (5.76 mL, 14.4 mmol) was added to a stirred solution of 1-bromo-4-chloro-2-(methoxymethoxy)benzene (3 g, 12 mmol) in 40 mL of THF under nitrogen at −78° C. After stirring at −78° C. for 40 min, B(OMe)$_3$ (2 g, 19.2 mmol) was added. The mixture was allowed to warm up to room temperature and stirred for 16 h. NH$_4$Cl aqueous solution (10 mL) was added to the mixture. The mixture was extracted with EtOAc (20 mL×3). The combined organic solvents were washed with brine (10 mL), dried over Na$_2$SO$_4$, concentrated and recrystallized from 3% EtOAc/petroleum ether which gave 1.6 g of 4-chloro-2-(methoxymethoxy)phenylboronic acid as off white solid (62% yield). LCMS: m/z 199.1 [M-OH]$^+$; $t_R$=1.65 min.

Step 9: Synthesis of tert-butyl (1R,3s,5S)-3-((6-(4-chloro-2-(methoxymethoxy)phenyl) pyridazin-3-yl)(methyl)amino)-1,5-dimethyl-8-azabicyclo[3.2.1]octane-8-carboxylate

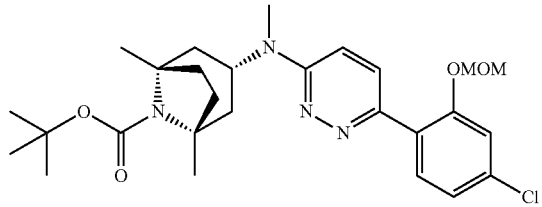

A mixture of tert-butyl (1R,3s,5S)-3-((6-chloropyridazin-3-yl)(methyl)amino)-1,5-dimethyl-8-azabicyclo[3.2.1]octane-8-carboxylate (6 g, 16.4 mmol), 4-chloro-2-(methoxymethoxy)phenylboronic acid (5.3 g, 24.6 mmol), Pd(dppf)Cl$_2$(1.6 mg, 2 mmol) and K$_2$CO$_3$ (4.53 mg, 32.8 mmol) in 80 mL of dioxane and 8 mL of H$_2$O was degassed and stirred at 100° C. for 7 h. After cooling to room temperature, the mixture was concentrated and purified by silica gel column (10-60% EtOAc/petroleum ether) which gave 4.52 g of tert-butyl (1R,3s,5S)-3-((6-(4-chloro-2-(methoxymethoxy)phenyl)pyridazin-3-yl)(methyl)amino)-1,5-dimethyl-8-azabicyclo[3.2.1]octane-8-carboxylate as white solid (57% yield). LCMS: m/z 517.3 [M+H]$^+$; $t_R$=1.86 min.

Step 10: Synthesis of tert-butyl (1R,3s,5S)-3-((6-(2-(methoxymethoxy)-4-(1-methyl-2-oxo-1,2-dihydropyridin-4-yl)phenyl)pyridazin-3-yl)(methyl)amino)-1,5-dimethyl-8-azabicyclo[3.2.1]octane-8-carboxylate

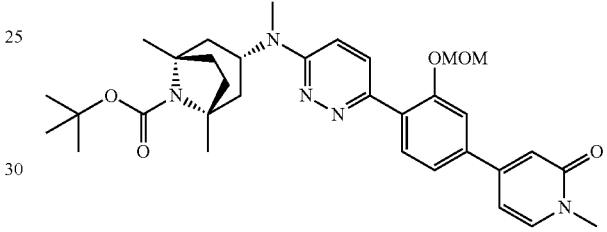

A mixture of tert-butyl (1R,3s,5S)-3-((6-(4-chloro-2-(methoxymethoxy)phenyl)pyridazin-3-yl)(methyl)amino)-1,5-dimethyl-8-azabicyclo[3.2.1]octane-8-carboxylate (4 g, 7.75 mmol), 1-methyl-2-oxo-1,2-dihydropyridin-4-ylboronic acid (1.77 g, 11.6 mmol), catalyst (610 mg mg, 0.78 mmol) and K$_3$PO$_4$ (3.29 g, 15.5 mmol) in 30 mL of dioxane and 10 mL of H$_2$O was degassed and stirred at 100° C. for 6 h. The mixture was filtered, concentrated and purified by silica gel column (0-15% MeOH/EtOAc) which gave 4.2 g of tert-butyl (1R,3s,5S)-3-((6-(2-(methoxymethoxy)-4-(1-methyl-2-oxo-1,2-dihydropyridin-4-yl)phenyl)pyridazin-3-yl)(methyl)amino)-1,5-dimethyl-8-azabicyclo[3.2.1]octane-8-carboxylate as white solid (77% yield). LCMS: m/z 590.2 [M+H]$^+$; $t_R$=2.09 min.

Step 11: Synthesis of 4-(4-(6-(((1R,3s,5S)-1,5-dimethyl-8-azabicyclo[3.2.1]octan-3-yl)(methyl)amino) pyridazin-3-yl)-3-hydroxyphenyl)-1-methylpyridin-2 (1H)-one

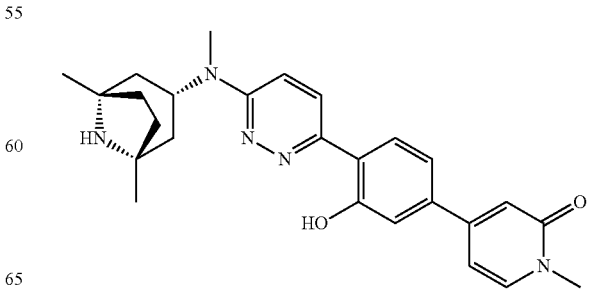

A solution of 30 mL of 4N HCl in dioxane was added to a stirred solution of (1R,3s,5S)-tert-butyl 3-((6-(2-(methoxymethoxy)-4-(1-methyl-2-oxo-1,2-dihydropyridin-4-yl)phenyl)pyridazin-3-yl)(methyl)amino)-1,5-dimethyl-8-azabicyclo[3.2.1]octane-8-carboxylate (3 g, 5.1 mmol) in 20 mL of CH$_2$Cl$_2$ and 20 mL of MeOH. The mixture was stirred at room temperature for 3 h, concentrated under reduced pressure. The residue was dissolved in water. K$_2$CO$_3$ aqueous solution was added to adjust pH=9. The solid was collected and dried in vacuo which gave 2.15 g of 4-(4-(6-(((1R,3s,5S)-1,5-dimethyl-8-azabicyclo[3.2.1]octan-3-yl)(methyl)amino) pyridazin-3-yl)-3-hydroxyphenyl)-1-methylpyridin-2(1H)-one as yellow solid (80% yield).

$^1$H NMR (500 MHz, DMSO-d$_6$) δ 13.75 (s, 1H), 8.25 (d, J=10.0 Hz, 1H), 7.97 (d, J=8.2 Hz, 1H), 7.78 (d, J=7.1 Hz, 1H), 7.38 (d, J=9.9 Hz, 1H), 7.29-7.22 (m, 2H), 6.70 (s, 1H), 6.61 (d, J=7.2 Hz, 1H), 4.94 (s, 1H), 3.46 (s, 3H), 2.94 (s, 3H), 1.88-1.83 (m, 2H), 1.61-1.42 (m, 6H), 1.23 (s, 6H). LCMS: m/z 446.1 [M+H]$^+$; t$_R$=1.72 min.

Example 9: Synthesis of 4-(4-(6-(((1R,3s,5S)-1,5-dimethyl-8-azabicyclo[3.2.1]octan-3-yl)(methyl) amino)pyridazin-3-yl)-2-fluoro-5-hydroxyphenyl)-1-methylpyridin-2(1H)-one

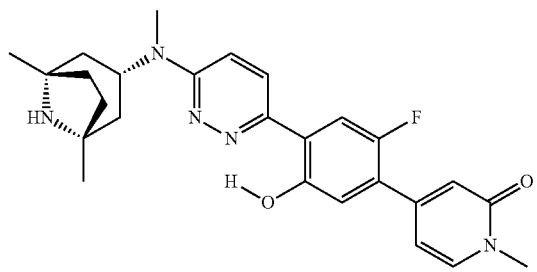 [SMILES: CN(c1ccc(-c2cc(F)c(-c3ccn(C)c(=O)c3)cc2O)nn1)[C@H]1C[C@]2(C)CC[C@](C)(C1)N2]

Step 1: Synthesis of 1,5-dimethyl-8-azabicyclo [3.2.1]octan-3-one

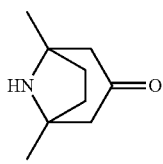

Potassium hydroxide (108 g, 1.93 mol) in 70 mL of H$_2$O was added to a stirred solution of 3-oxopentanedioic acid (120 g, 822 mmol) and hexane-2,5-dione (49.2 g, 432 mmol) in 350 mL of H$_2$O and 0° C. After the addition, NH$_4$Cl (70.1 g, 1.32 mol) and NaOAc trihydrate (70.1 g, 515 mmol) in 667 mL of H$_2$O was added. The pH value was adjusted to ~9 by using 1 N NaOH aqueous solution. The mixture was stirred at room temperature for 72 h during which time the pH value was adjusted to ~9 by using additional 1 N NaOH aqueous solution. The mixture was extracted with CH$_2$Cl$_2$ (1 L×5). The combined organic solvents were dried over anhydrous Na$_2$SO$_4$, concentrated and purified by silica gel chromatography (0-25% MeOH/CH$_2$Cl$_2$) to give 16.7 g of 1,5-dimethyl-8-azabicyclo[3.2.1]octan-3-one as black oil (25% yield). LCMS: m/z 154.2 [M+H]$^+$; t$_R$=1.20 min.

Step 2: Synthesis of tert-butyl 1,5-dimethyl-3-oxo-8-azabicyclo[3.2.1]octane-8-carboxylate

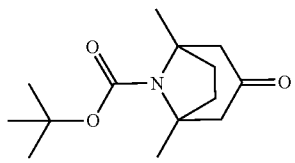 [SMILES: CC(C)(C)OC(=O)N1C2(C)CCC1(C)CC(=O)C2]

A mixture of 1,5-dimethyl-8-azabicyclo[3.2.1]octan-3-one (24 g, 163 mmol), di-tert-butyl dicarbonate (35.6 g, 326 mmol) and DIPEA (31.5 g, 244 mmol) in 500 mL of 1,4-dioxane was stirred at 70° C. for 6 h. The mixture was concentrated and purified by silica gel chromatography (0-30% EtOAc/petroleum ether) to give 16.7 of tert-butyl 1,5-dimethyl-3-oxo-8-azabicyclo[3.2.1]octane-8-carboxylate as white solid (yield: 42%). LCMS: m/z 198.1 [M−55]$^+$; t$_R$=1.40 min.

Step 3: Synthesis of tert-butyl 3-(hydroxyimino)-1,5-dimethyl-8-azabicyclo[3.2.1]octane-8-carboxylate

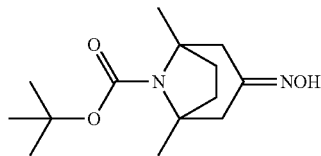

A mixture of tert-butyl 1,5-dimethyl-3-oxo-8-azabicyclo [3.2.1]octane-8-carboxylate (16.7 g, 66 mmol), hydroxylamine hydrochloride (18.2 g, 26.4 mmol) and NaOAc (10.8 g, 132 mmol) in 250 mL of EtOH was stirred at 70° C. for 4 h. The mixture was concentrated. 200 mL of EtOAc and 60 mL of H$_2$O was added. The organic phase was separated, washed with brine (50 mL), dried over anhydrous Na$_2$SO$_4$, concentrated to give 16.7 g of tert-butyl 3-(hydroxyimino)-1,5-dimethyl-8-azabicyclo[3.2.1]octane-8-carboxylate as yellow solid which was used directly to next step (93% yield). LCMS: m/z 269.2 [M+H]$^+$; t$_R$=1.92 min.

Step 4: Synthesis of tert-butyl (1R,3s,5S)-3-amino-1,5-dimethyl-8-azabicyclo[3.2.1]octane-8-carboxylate

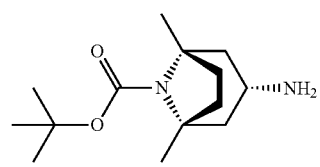

Sodium (40.2 g, 1.75 mol) was added in portions to a mixture of tert-butyl 3-(hydroxyimino)-1,5-dimethyl-8-azabicyclo[3.2.1]octane-8-carboxylate (26.8 g, 0.1 mol) in 1000 mL of n-PrOH was heated to 110° C. over 1 h. After addition, the mixture was stirred at reflux for additional 1 h. The mixture was cooled to room temperature, quenched with H$_2$O (500 mL). The organic layer was separated and concentrated. DCM (500 mL) was added to the residue. The solid was filtered off and the filtrate was concentrated under reduced pressure to afford 20 g of tert-butyl (1R,3s,5S)-3-amino-1,5-dimethyl-8-azabicyclo[3.2.1]octane-8-carboxylate as a yellow oil, which was used directly to next step (yield: 79%). LCMS: m/z 255.3 [M+H]$^+$; $t_R$=1.37 min.

Step 5: Synthesis of tert-butyl (1R,3s,5S)-3-((6-chloropyridazin-3-yl)amino)-1,5-dimethyl-8-azabicyclo[3.2.1]octane-8-carboxylate

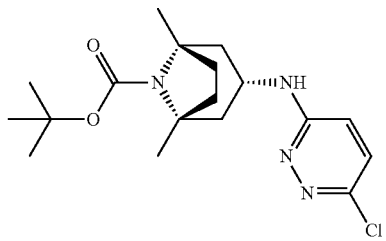 [SMILES: CC(C)(C)OC(=O)N1[C@@]2(C)CC[C@]1(C)C[C@@H](Nc1ccc(Cl)nn1)C2]

A mixture of tert-butyl (1R,3s,5S)-3-amino-1,5-dimethyl-8-azabicyclo[3.2.1]octane-8-carboxylate (20 g, 78.7 mmol), 3,6-dichloropyridazine (23.3 g, 157.5 mmol) and DIPEA (20.48 g, 157.5 mmol) in 500 mL of DMSO was stirred at 120° C. for 24 h. The mixture was cooled to room temperature, quenched with H$_2$O and extracted with ethyl acetate (500 mL×3). The combined organic layers were washed with brine, dried over anhydrous Na$_2$SO$_4$ and concentrated under reduced pressure. After removal of solvent, the crude product was purified by silica gel column (50% EtOAc/petroleum ether) to afford 17.5 g of tert-butyl (1R,3s,5S)-3-((6-chloropyridazin-3-yl)amino)-1,5-dimethyl-8-azabicyclo[3.2.1]octane-8-carboxylate as yellow solid (yield: 61%). LCMS: m/z 367.2 [M+H]$^+$; $t_R$=1.88 min.

Step 6: Synthesis of tert-butyl (1R,3s,5S)-3-((6-chloropyridazin-3-yl)(methyl)amino)-1,5-dimethyl-8-azabicyclo[3.2.1]octane-8-carboxylate

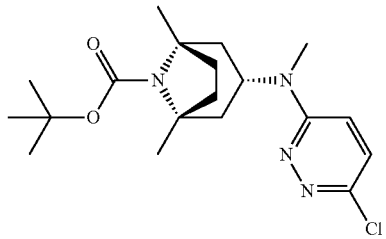 [SMILES: CN(c1ccc(Cl)nn1)[C@H]1C[C@]2(C)CC[C@](C)(C1)N2C(=O)OC(C)(C)C]

Sodium hydride (2.87 g, 71.7 mmol, 60% in mineral oil) was added to a stirred solution of tert-butyl (1R,3s,5S)-3-((6-chloropyridazin-3-yl)amino)-1,5-dimethyl-8-azabicyclo[3.2.1]octane-8-carboxylate (17.5 g, 47.8 mmol) in 400 mL of DMF at 0° C. After stirring for 20 min at 0° C., CH$_3$I (13.58 g, 95.6 mmol) was added. The mixture was then stirred at room temperature for 1 h, quenched with H$_2$O and extracted with EtOAc (300 mL×3). The combined organic phases were washed with brine, dried over anhydrous Na$_2$SO$_4$, concentrated under reduced pressure and purified by silica gel column (30% EtOAc/petroleum ether) to afford 14.5 g of tert-butyl (1R,3s,5S)-3-((6-chloropyridazin-3-yl) (methyl)amino)-1,5-dimethyl-8-azabicyclo[3.2.1]octane-8-carboxylate as yellow solid (80% yield). LCMS: m/z 381.2 [M+H]$^+$; $t_R$=2.17 min.

Step 7: Synthesis of 2-bromo-5-chloro-4-fluorophenol

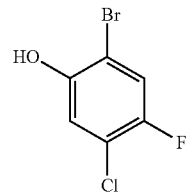

Bromine (3.52 g, 22 mmol) was added to a stirred solution of 3-chloro-4-fluorophenol (4.02 g, 20 mmol) in 80 mL of CH$_2$Cl$_2$ at room temperature. The mixture was stirred at room temperature for 18 h and quenched with 10 mL of aqueous Na$_2$S$_2$O$_3$ solution. The organic phase was collected, concentrated and purified by silica gel chromatography (0-10% EtOAc/petroleum ether) to afford 2.5 g of 2-bromo-5-chloro-4-fluorophenol as white solid (44% yield). $^1$H NMR (500 MHz, Chloroform-d) δ 7.29 (d, J=8.0 Hz, 1H), 7.08 (d, J=6.6 Hz, 1H), 5.45 (s, 1H). LCMS: $t_R$=1.44 min.

Step 8: Synthesis of 1-bromo-4-chloro-5-fluoro-2-(methoxymethoxy)benzene

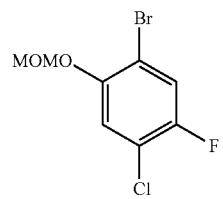

Sodium hydride (215 mg, 5.4 mmol) was added to a stirred solution of 2-bromo-5-chloro-4-fluorophenol (1 g, 4.48 mmol) in 14 mL of DMF at 0° C. After stirring for 30 min, bromo(methoxy)methane (428 mg, 8 mmol) was added. The mixture was then stirred at room temperature for 2 h, quenched with 10 mL of saturated NH$_4$Cl aqueous solution and extracted with EtOAc (30 mL×3). The combined organic solvents were concentrated and purified by silica gel silica gel column (0-8% EtOAc/petroleum ether) to give 1.01 g of 1-bromo-4-chloro-5-fluoro-2-(methoxymethoxy)benzene as white solid (70% yield). $^1$H NMR (500 MHz, Chloroform-d) δ 7.37 (d, J=8.1 Hz, 1H), 7.23 (d, J=6.6 Hz, 1H), 5.20 (s, 2H), 3.52 (s, 3H).

Step 9: Synthesis of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate

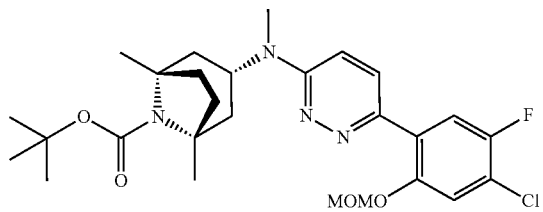

A mixture of 1-bromo-4-chloro-5-fluoro-2-(methoxymethoxy)benzene (8.5 g, 31.7 mmol), 4,4,4',4',5,5,5',5'-octamethyl-2,2'-bi(1,3,2-dioxaborolane) (12.1 g, 47.5 mmol), Pd(dppf)Cl$_2$ (1.86 g, 2.54 mmol) and KOAc (6.2 g, 63.4 mmol) in 200 mL of dioxane was degassed and stirred at 100° C. for 8 h. After cooling to room temperature, tert-butyl (1R,3s,5S)-3-((6-chloropyridazin-3-yl)(methyl)amino)-1,5-dimethyl-8-azabicyclo[3.2.1]octane-8-carboxylate (8 g, 21.2 mmol), K$_2$CO$_3$ (5.8 g, 42.3 mmol) and H$_2$O (30 mL) were added. The mixture was stirred at 100° C. for 3 h, concentrated and purified by silica gel column (10-25% EtOAc/petroleum ether) which gave 6 g of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate as light yellow solid (53% yield). LCMS: m/z 535.2 [M+H]$^+$; t$_R$=2.40 min.

Step 10: Synthesis of tert-butyl (1R,3s,5S)-3-((6-(5-fluoro-2-(methoxymethoxy)-4-(1-methyl-2-oxo-1,2-dihydropyridin-4-yl)phenyl)pyridazin-3-yl)(methyl)amino)-1,5-dimethyl-8-azabicyclo[3.2.1]octane-8-carboxylate

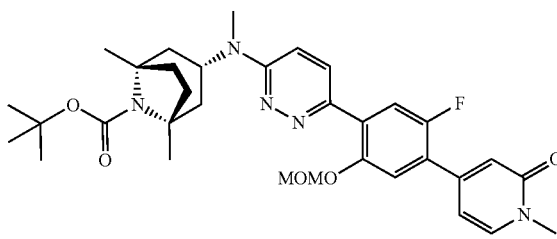

A mixture of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate (120 mg, 0.22 mmol), 1-methyl-2-oxo-1,2-dihydropyridin-4-ylboronic acid (63 mg, 0.27 mmol), Pd(dppf)Cl$_2$ (20 mg, 0.028 mmol) and K$_2$CO$_3$ (77 mg, 0.56 mmol) in 2 mL of 1,4-dioxane and 0.4 mL of water was purged with nitrogen and sealed. The mixture was stirred at 130° C. under MW for 2 h, concentrated and purified by silica gel chromatography (0-10% MeOH/CH$_2$Cl$_2$) which gave 110 mg of tert-butyl (1R,3s,5S)-3-((6-(5-fluoro-2-(methoxymethoxy)-4-(1-methyl-2-oxo-1,2-dihydropyridin-4-yl)phenyl)pyridazin-3-yl)(methyl)amino)-1,5-dimethyl-8-azabicyclo[3.2.1]octane-8-carboxylate as white solid (82% yield). LCMS: m/z 608.2 [M+H]$^+$; t$_R$=1.59 min.

Step 11: Synthesis of 4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1-methylpyridin-2(1H)-one

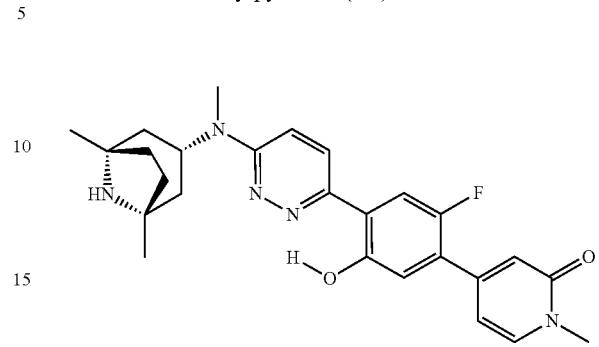

To a stirred solution of tert-butyl (1R,3s,5S)-3-((6-(5-fluoro-2-(methoxymethoxy)-4-(1-methyl-2-oxo-1,2-dihydropyridin-4-yl)phenyl)pyridazin-3-yl)(methyl)amino)-1,5-dimethyl-8-azabicyclo[3.2.1]octane-8-carboxylate (100 mg, 0.16 mmol) in 2 mL of CH$_2$Cl$_2$ was added 4 mL of a 4N solution of HCl in dioxane. The mixture was stirred at room temperature for 2 h, concentrated under reduced pressure, neutralized with NH$_3$/MeOH and purified by prep-HPLC to give 37 mg of 4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1-methylpyridin-2(1H)-one as a yellow solid (50% yield).

Example 10: Synthesis of 2-(6-((1R,3s,5S)-1,5-dimethyl-8-azabicyclo[3.2.1]octan-3-yloxy)pyridazin-3-yl)-5-(1H-pyrazol-4-yl)phenol

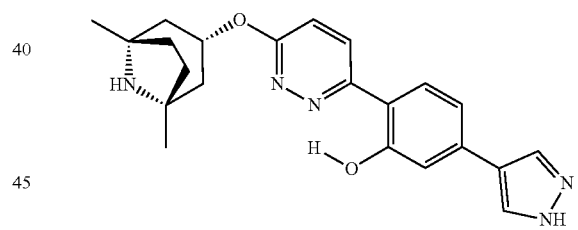

Step 1: Synthesis of 1,5-dimethyl-8-azabicyclo[3.2.1]octan-3-one

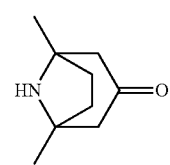

Potassium hydroxide (108 g, 1.93 mol) in 70 mL of H$_2$O was added to a stirred solution of 3-oxopentanedioic acid (120 g, 822 mmol) and hexane-2,5-dione (49.2 g, 432 mmol) in 350 mL of H$_2$O and 0° C. After the addition, NH$_4$Cl (70.1 g, 1.32 mol) and NaOAc trihydrate (70.1 g, 515 mmol) in 667 mL of H$_2$O was added. The pH value was adjusted to ~9 by using 1 N NaOH aqueous solution. The mixture was stirred at room temperature for 72 h during which time the pH value was adjusted to ~9 by using additional 1 N NaOH aqueous solution. The mixture was extracted with CH₂Cl₂ (1 L×5). The combined organic solvents were dried over anhydrous Na₂SO₄, concentrated and purified by silica gel chromatography (0-25% MeOH/CH₂Cl₂) which gave 16.7 g of 1,5-dimethyl-8-azabicyclo[3.2.1]octan-3-one as black oil (25% yield). LCMS: m/z 154.2 [M+H]⁺; $t_R$=1.20 min.

Step 2: Synthesis of 1,5-dimethyl-8-azabicyclo [3.2.1]octan-3-ol

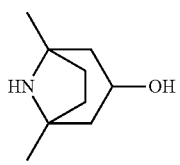

Sodium borohydride (224 mg, 5.88 mmol) was added to a stirred solution of 1,5-dimethyl-8-azabicyclo[3.2.1]octan-3-one (600 mg, 3.92 mmol) in 10 mL of methanol at 0° C. The mixture was stirred at room temperature for 3 h and concentrated. 100 mL of EtOAc and 60 mL of H₂O was added. The organic phase was separated, washed with brine (50 mL), dried over anhydrous Na₂SO₄ and concentrated which gave 600 mg of a mixture of isomers of 1,5-dimethyl-8-azabicyclo[3.2.1]octan-3-ol as white solid (yield: 99%). LCMS: m/z 156.3 [M+H]⁺; $t_R$=0.28 min.

Step 3: Synthesis of(1R,3s,5S)-3-(6-chloro-pyridazin-3-yloxy)-1,5-dimethyl-8-azabicyclo[3.2.1] octane

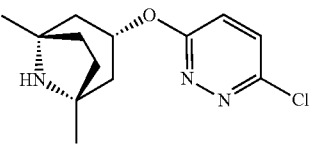 [SMILES: C[C@]12CC[C@](C)(C[C@@H](Oc3ccc(Cl)nn3)C1)N2]

Sodium hydride (129 mg, 3.23 mmol, 60% in mineral oil) was added to a mixture of 1,5-dimethyl-8-azabicyclo[3.2.1] octan-3-ol (200 mg, 1.29 mmol) in THF (10 mL) at room temperature. The mixture was stirred at room temperature for 30 minutes. Then 3,6-dichloropyridazine (210 mg, 1.42 mmol) was added. The mixture was stirred at 50° C. for 18 hours. After cooling to room temperature, the mixture was quenched with 20 mL of water, extracted with EtOAc (20 mL×3). The combined organic solvents were washed with water (10 mL), concentrated and isomers were purified by silica gel column (0-10% MeOH/DCM) which gave 45 mg of (1R,3s,5S)-3-(6-chloropyridazin-3-yloxy)-1,5-dimethyl-8-azabicyclo[3.2.1]octane as white solid (13% yield). LCMS: m/z 268.1 [M+H]⁺; $t_R$=1.56 min.

Step 4: Synthesis of 1-bromo-4-iodo-2-(methoxymethoxy)benzene

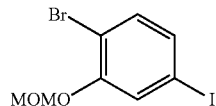

Methoxymethyl bromide (1.25 g, 10 mmol) was added to a stirred solution of 2-bromo-5-iodophenol (1.5 g, 5 mmol) and K₂CO₃ (1.38 g, 10 mmol) in 20 mL of DMF at 0° C. The mixture was then stirred at room temperature for 16 h, quenched with 20 mL of H₂O and extracted with EtOAc (20 mL×3). The combined organic solvents were dried over anhydrous Na₂SO₄, concentrated and purified by silica gel column (0-5% EtOAc/petroleum ether) to give 1.45 g of 1-bromo-4-iodo-2-(methoxymethoxy)benzene as colorless liquid (79% yield). LCMS: $t_R$=1.50 min.

Step 5: Synthesis of 4-(4-bromo-3-(methoxymethoxy)phenyl)-1-(tetrahydro-2H-pyran-2-yl)-1H-pyrazole

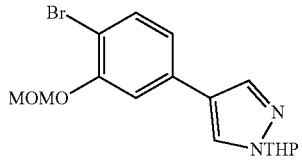

A mixture of 1-bromo-4-iodo-2-(methoxymethoxy)benzene (3.3 g, 9.6 mmol), 1-(tetrahydro-2H-pyran-2-yl)-4-(4, 4,5,5-tetramethyl-1,3,2-dioxaborolan-2-yl)-1H-pyrazole (2.67 g, 9.6 mmol), Pd(dppf)Cl₂ (866 mg, 1 mmol) and K₂CO₃ (2.66 g, 19.3 mmol) in 40 mL of dioxane and 4 mL of H₂O was degassed and stirred at 105° C. for 8 h. After cooling to room temperature, the mixture was extracted with EtOAc (30 mL×3). The combined organic solvents were concentrated and purified by silica gel column (10-50% EtOAc/petroleum ether) which gave 2.5 g of 4-(4-bromo-3-(methoxymethoxy)phenyl)-1-(tetrahydro-2H-pyran-2-yl)-1H-pyrazole as colorless oil (69% yield). LCMS: m/z 367.1 [M+H]⁺; $t_R$=2.03 min.

Step 6: Synthesis of 4-(3-(methoxymethoxy)-4-(4,4, 5,5-tetramethyl-1,3,2-dioxaborolan-2-yl)phenyl)-1-(tetrahydro-2H-pyran-2-yl)-1H-pyrazole

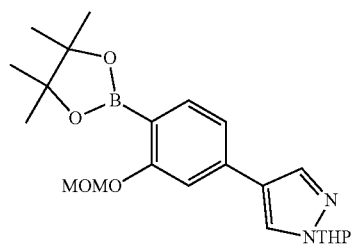

A mixture of 4-(4-bromo-3-(methoxymethoxy)phenyl)-1-(tetrahydro-2H-pyran-2-yl)-1H-pyrazole (1.5 g, 4.1 mmol), 4,4,4',4',5,5,5',5'-octamethyl-2,2'-bi(1,3,2-dioxaborolane) (2.1 g, 8.2 mmol), Pd(dppf)Cl$_2$ (369 mg, 0.41 mmol) and KOAc (804 mg, 8.2 mmol) in 20 mL of dioxane was degassed and stirred at 105° C. for 8 h. The mixture was filtered, concentrated and purified by silica gel column to give 0.81 g of 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole as colorless oil (48% yield). LCMS: m/z 415.3 [M+H]$^+$; t$_R$=2.10 min.

Step 7: Synthesis of (1R,3s,5S)-3-((6-(2-(methoxymethoxy)-4-(1-(tetrahydro-2H-pyran-2-yl)-1H-pyrazol-4-yl)phenyl)pyridazin-3-yl)oxy)-1,5-dimethyl-8-azabicyclo[3.2.1]octane

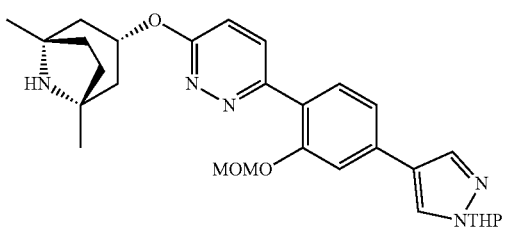

A mixture of (1R,3s,5S)-3-(6-chloropyridazin-3-yloxy)-1,5-dimethyl-8-azabicyclo[3.2.1]octane (40 mg, 0.15 mmol), 4-(3-(methoxymethoxy)-4-(4,4,5,5-tetramethyl-1,3,2-dioxaborolan-2-yl)phenyl)-1-(tetrahydro-2H-pyran-2-yl)-1H-pyrazole (81 mg, 0.20 mmol), Pd(dppf)Cl$_2$ (15 mg, 0.021 mmol) and K$_2$CO$_3$ (42 mg, 0.30 mmol) in 1.5 mL of 1,4-dioxane and 0.5 mL of water was degassed and stirred at 105° C. for 2 h under nitrogen atmosphere. The mixture was then concentrated and purified by silica gel chromatography (1-15% MeOH/DCM) which gave 60 mg of (1R,3s,5S)-3-((6-(2-(methoxymethoxy)-4-(1-(tetrahydro-2H-pyran-2-yl)-1H-pyrazol-4-yl)phenyl)pyridazin-3-yl)oxy)-1,5-dimethyl-8-azabicyclo[3.2.1]octane as white solid (78% yield). LCMS: m/z 520.3 [M+H]$^+$; t$_R$=1.89 min.

Step 8: Synthesis of 2-(6-(((1R,3s,5S)-1,5-dimethyl-8-azabicyclo[3.2.1]octan-3-yl)oxy)pyridazin-3-yl)-5-(1H-pyrazol-4-yl)phenol

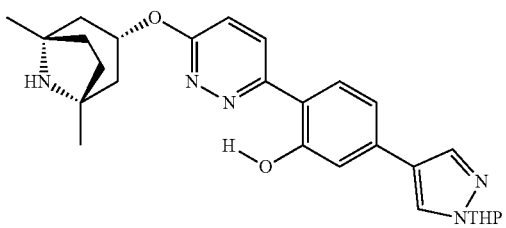

A 1 mL solution of 4 N HCl in dioxane was added to a solution of (1R,3s,5S)-3-((6-(2-(methoxymethoxy)-4-(1-(tetrahydro-2H-pyran-2-yl)-1H-pyrazol-4-yl)phenyl)pyridazin-3-yl)oxy)-1,5-dimethyl-8-azabicyclo[3.2.1]octane (60 mg, 0.12 mmol) in 1 mL of CH$_2$Cl$_2$ at room temperature. After stirring at room temperature for 1 h, the mixture was concentrated, neutralized with ammonium hydroxide and purified by prep-HPLC (NH$_4$HCO$_3$) which gave 30 mg of 2-(6-(((1R,3s,5S)-1,5-dimethyl-8-azabicyclo[3.2.1]octan-3-yl)oxy)pyridazin-3-yl)-5-(1H-pyrazol-4-yl)phenol as yellow solid (67% yield).

Example 11: Synthesis of 2-(6-(((1R,3s,5S)-1,5-dimethyl-8-azabicyclo[3.2.1]octan-3-yl)(methyl)amino)pyridazin-3-yl)-5-(6-methoxypyridazin-4-yl)phenol

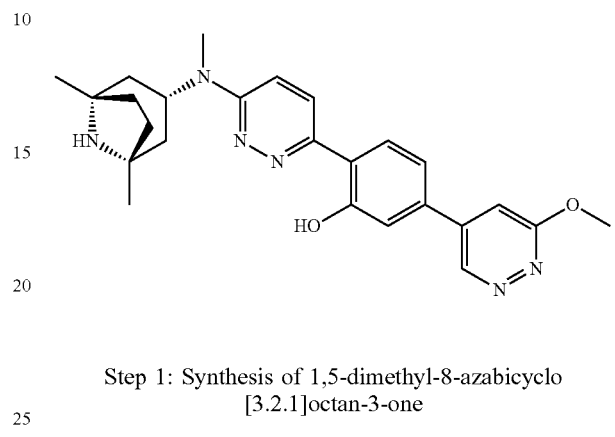

Step 1: Synthesis of 1,5-dimethyl-8-azabicyclo[3.2.1]octan-3-one

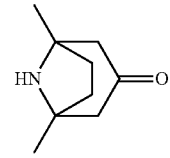

Potassium hydroxide (108 g, 1.93 mol) in 70 mL of H$_2$O was added to a stirred solution of 3-oxopentanedioic acid (120 g, 822 mmol) and hexane-2,5-dione (49.2 g, 432 mmol) in 350 mL of H$_2$O and 0° C. After the addition, NH$_4$Cl (70.1 g, 1.32 mol) and NaOAc trihydrate (70.1 g, 515 mmol) in 667 mL of H$_2$O was added. The pH value was adjusted to ~9 by using 1 N NaOH aqueous solution. The mixture was stirred at room temperature for 72 h during which time the pH value was adjusted to ~9 by using additional 1 N NaOH aqueous solution. The mixture was extracted with CH$_2$Cl$_2$ (1 L×5). The combined organic solvents were dried over anhydrous Na$_2$SO$_4$, concentrated and purified by silica gel chromatography (0-25% MeOH/CH$_2$Cl$_2$) which gave 16.7 g of 1,5-dimethyl-8-azabicyclo[3.2.1]octan-3-one as black oil (25% yield). LCMS: m/z 154.2 [M+H]$^+$; t$_R$=1.20 min; purity: 85%.

Step 2: Synthesis of tert-butyl 1,5-dimethyl-3-oxo-8-azabicyclo[3.2.1]octane-8-carboxylate

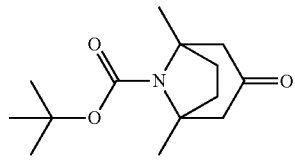 [SMILES: CC(C)(C)OC(=O)N1C2(C)CCC1(C)CC(=O)C2]

A mixture of 1,5-dimethyl-8-azabicyclo[3.2.1]octan-3-one (24 g, 163 mmol), di-tert-butyl dicarbonate (35.6 g, 326 mmol) and DIPEA (31.5 g, 244 mmol) in 500 mL of 1,4-dioxane was stirred at 70° C. for 6 h. The mixture was concentrated and purified by silica gel chromatography (0-30% EtOAc/petroleum ether) which gave 16.7 of tert-butyl 1,5-dimethyl-3-oxo-8-azabicyclo[3.2.1]octane-8-carboxylate as white solid (yield: 42%). LCMS: m/z 198.1 [M−55]$^+$; t$_R$=1.40 min; purity: 100%.

Step 3: Synthesis of tert-butyl 3-(hydroxyimino)-1, 5-dimethyl-8-azabicyclo[3.2.1]octane-8-carboxylate

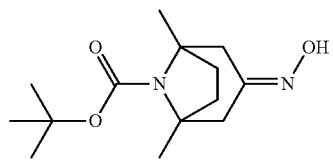 [SMILES: CC(C)(C)OC(=O)N1C2(C)CCC1(C)CC(=NO)C2]

A mixture of tert-butyl 1,5-dimethyl-3-oxo-8-azabicyclo [3.2.1]octane-8-carboxylate (16.7 g, 66 mmol), hydroxylamine hydrochloride (18.2 g, 26.4 mmol) and NaOAc (10.8 g, 132 mmol) in 250 mL of EtOH was stirred at 70° C. for 4 h. The mixture was concentrated. 200 mL of EtOAc and 60 mL of H$_2$O was added. The organic phase was separated, washed with brine (50 mL), dried over anhydrous Na$_2$SO$_4$, concentrated which gave 16.7 g of tert-butyl 3-(hydroxyimino)-1,5-dimethyl-8-azabicyclo[3.2.1]octane-8-carboxylate as yellow solid which was used directly to next step (93% yield). LCMS: m/z 269.2 [M+H]$^+$; t$_R$=1.92 min; purity: 100%.

Step 4: Synthesis of tert-butyl (1R,3s,5S)-3-amino-1,5-dimethyl-8-azabicyclo[3.2.1]octane-8-carboxylate

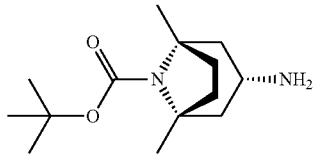

Sodium (40.2 g, 1.75 mol) was in portions added to a mixture of tert-butyl 3-(hydroxyimino)-1,5-dimethyl-8-azabicyclo[3.2.1]octane-8-carboxylate (26.8 g, 0.1 mol) in 1000 mL of n-PrOH was heated to 110° C. over 1 h. After addition, the mixture was stirred at reflux for additional 1 h. The mixture was cooled to room temperature, quenched with H$_2$O (500 mL). The organic layer was separated and concentrated. DCM (500 mL) was added to the residue. The solid was triturated filtered off and the filtrate was concentrated under reduced pressure to afford 20 g of tert-butyl (1R,3s,5S)-3-amino-1,5-dimethyl-8-azabicyclo[3.2.1]octane-8-carboxylate as a yellow oil, which was used directly in next step (yield: 79%). LCMS: m/z 255.3 [M+H]$^+$; t$_R$=1.37 min; purity: 99%.

Step 5: Synthesis of tert-butyl (1R,3s,5S)-3-((6-chloropyridazin-3-yl)amino)-1,5-dimethyl-8-azabicyclo[3.2.1]octane-8-carboxylate

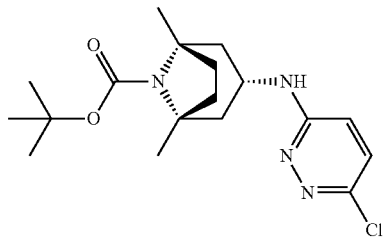

A mixture of tert-butyl (1R,3s,5S)-3-amino-1,5-dimethyl-8-azabicyclo[3.2.1]octane-8-carboxylate (20 g, 78.7 mmol), 3,6-dichloropyridazine (23.3 g, 157.5 mmol) and DIPEA (20.48 g, 157.5 mmol) in 500 mL of DMSO was stirred at 120° C. for 24 h. The mixture was cooled to room temperature, quenched with H$_2$O and extracted with ethyl acetate (500 mL×3). The combined organic layers were washed with brine, dried over anhydrous Na$_2$SO$_4$ and concentrated under reduced pressure. After removal of solvent, the crude product was purified by silica gel column (50% EtOAc/ petroleum ether) which gave 17.5 g of tert-butyl (1R,3s,5S)-3-((6-chloropyridazin-3-yl)amino)-1,5-dimethyl-8-azabicyclo[3.2.1]octane-8-carboxylate as yellow solid (yield: 61%). LCMS: m/z 367.2 [M+H]$^+$; t$_R$=1.88 min; purity: 99%.

Step 6: Synthesis of tert-butyl (1R,3s,5S)-3-((6-chloropyridazin-3-yl)(methyl)amino)-1,5-dimethyl-8-azabicyclo[3.2.1]octane-8-carboxylate

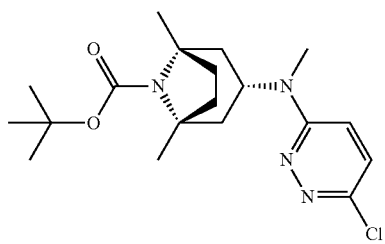 [SMILES: CN(c1ccc(Cl)nn1)[C@H]1C[C@]2(C)CC[C@](C)(C1)N2C(=O)OC(C)(C)C]

Sodium hydride (2.87 g, 71.7 mmol) was added to a stirred solution of tert-butyl (1R,3s,5S)-3-((6-chloropyridazin-3-yl)amino)-1,5-dimethyl-8-azabicyclo[3.2.1]octane-8-carboxylate (17.5 g, 47.8 mmol) in 400 mL of DMF at 0° C. After stirring for 20 min at 0° C., CH$_3$I (13.58 g, 95.6 mmol) was added. The mixture was then stirred at room temperature for 1 h, quenched with H$_2$O and extracted with EtOAc (300 mL×3). The combined organic phases were washed with brine, dried over anhydrous Na$_2$SO$_4$, concentrated under reduced pressure and purified by silica gel column (30% EtOAc/petroleum ether) which gave 14.5 g of tert-butyl (1R,3s,5S)-3-((6-chloropyridazin-3-yl)(methyl) amino)-1,5-dimethyl-8-azabicyclo[3.2.1]octane-8-carboxylate as yellow solid (80% yield). LCMS: m/z 381.2 [M+H]$^+$; t$_R$=2.17 min; purity: 99%.

Step 7: Synthesis of 1-bromo-4-chloro-2-(methoxymethoxy)benzene

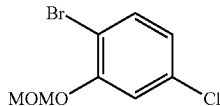

Sodium hydride (185 g, 46.3 mmol, 60% in mineral oil) was added to a stirred solution of 2-bromo-5-chlorophenol (8 g, 38.6 mmol) in 150 mL of DMF at 0° C. After stirring at 0° C. for 30 min, MOMBr (7.25 g, 58 mmol) was added. The mixture was then stirred at room temperature for 2 h, quenched with NH$_4$Cl aqueous solution (15 mL), extracted with EtOAc (30 mL×3). The combined organic solvents were dried over anhydrous Na$_2$SO$_4$, concentrated and purified by silica gel chromatography (0-10% EtOAc/petroleum ether) which gave 8.1 g of 1-bromo-4-chloro-2-(methoxymethoxy)benzene as colorless oil (84% yield). $^1$H NMR (500 MHz, Chloroform-d) δ 7.45 (d, J=8.5 Hz, 1H), 7.17 (d, J=2.3 Hz, 1H), 6.89 (dd, J=8.4, 2.3 Hz, 1H), 5.24 (s, 2H). LCMS: $t_R$=1.51 min.

Step 8: Synthesis of 4-chloro-2-(methoxymethoxy)phenylboronic acid

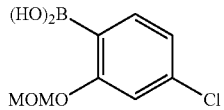

To a stirred solution of 1-bromo-4-chloro-2-(methoxymethoxy)benzene (3 g, 12 mmol) in 40 mL of THF under nitrogen at −78° C. was added n-BuLi (5.76 mL, 14.4 mmol). After stirring at −78° C. for 40 min, B(OMe)$_3$ (2 g, 19.2 mmol) was added. The mixture was allowed to warm up to room temperature and stirred for 16 h. NH$_4$Cl aqueous solution (10 mL) was added to the mixture. The mixture was extracted with EtOAc (20 mL×3). The combined organic solvents were washed with brine (10 mL), dried over Na$_2$SO$_4$, concentrated and recrystallized from 3% EtOAc/petroleum ether which gave 1.6 g of 4-chloro-2-(methoxymethoxy)phenylboronic acid as off white solid (62% yield). LCMS: m/z 199.1 [M-OH]$^+$; $t_R$=1.65 min.

Step 9: Synthesis of tert-butyl (1R,3s,5S)-3-((6-(4-chloro-2-(methoxymethoxy)phenyl)pyridazin-3-yl)(methyl)amino)-1,5-dimethyl-8-azabicyclo[3.2.1]octane-8-carboxylate

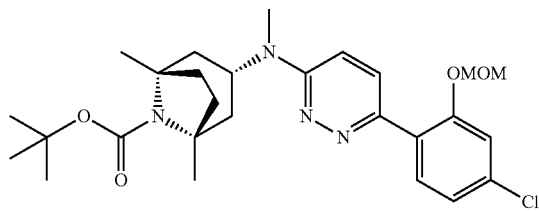

A mixture of tert-butyl (1R,3s,5S)-3-((6-chloropyridazin-3-yl)(methyl)amino)-1,5-dimethyl-8-azabicyclo[3.2.1]octane-8-carboxylate (6 g, 16.4 mmol), 4-chloro-2-(methoxymethoxy)phenylboronic acid (5.3 g, 24.6 mmol), Pd(dppf)Cl$_2$(1.6 mg, 2 mmol) and K$_2$CO$_3$ (4.53 mg, 32.8 mmol) in 80 mL of dioxane and 8 mL of H$_2$O was degassed and stirred at 100° C. for 7 h. After cooling to room temperature, the mixture was concentrated and purified by silica gel column (10-60% EtOAc/petroleum ether) which gave 4.52 g of tert-butyl (1R,3s,5S)-3-((6-(4-chloro-2-(methoxymethoxy)phenyl)pyridazin-3-yl)(methyl)amino)-1,5-dimethyl-8-azabicyclo[3.2.1]octane-8-carboxylate as white solid (57% yield). LCMS: m/z 517.3 [M+H]$^+$; $t_R$=1.86 min.

Step 10: Synthesis of 5-chloro-3-methoxypyridazine

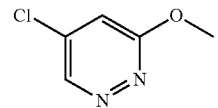

Sodium methoxide (5.84 g, 0.108 mol) was added to a stirred solution of 3,5-dichloropyridazine (8 g, 0.054 mol) in 350 mL of THF at 0° C. After the addition, the mixture was stirred at room temperature for 16 h. The mixture was quenched with water (100 mL), extracted with EA (300 mL×2). The combined organic solvents were dried over anhydrous Na$_2$SO$_4$, concentrated and purified by silica gel chromatography (0-40% EtOAc/petroleum ether) which gave 1.5 g of 5-chloro-3-methoxypyridazine as yellow solid (17% yield). LCMS: m/z 145.1 [M+H]$^+$; $t_R$=1.42 min.

Step 11: Synthesis of tert-butyl (1R,3s,5S)-3-((6-(2-(methoxymethoxy)-4-(6-methoxypyridazin-4-yl)phenyl)pyridazin-3-yl)(methyl)amino)-1,5-dimethyl-8-azabicyclo[3.2.1]octane-8-carboxylate

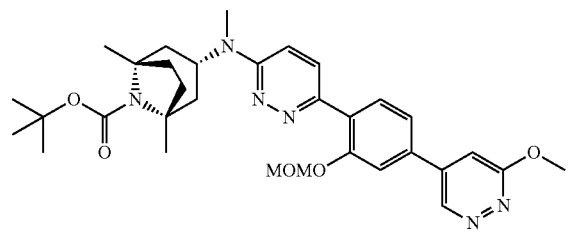

A mixture of tert-butyl (1R,3s,5S)-3-((6-(4-chloro-2-(methoxymethoxy)phenyl)pyridazin-3-yl)(methyl)amino)-1,5-dimethyl-8-azabicyclo[3.2.1]octane-8-carboxylate (200 mg, 0.39 mmol), 4,4,4',4',5,5,5',5'-octamethyl-2,2'-bi(1,3,2-dioxaborolane) (197 mg, 0.77 mmol), Pd$_2$(dba)$_3$ (32 mg, 0.04 mmol), X-Phos (20 mg, 0.04 mmol) and KOAc (115 mg, 1.2 mmol) in 4 mL of 1,4-dioxane was degassed and stirred at 90° C. for 2 h. After cooling to room temperature, Pd(dppf)Cl$_2$ (61 mg, 0.08), 5-chloro-3-methoxypyridazine (113 mg, 0.78 mmol), K$_2$CO$_3$ (163 mg, 1.2 mmol) and H$_2$O (0.3 mL) were added. The mixture was stirred at 110° C. for 2 h, concentrated and purified by silica gel column (10-80% EtOAc/petroleum ether) to give 230 mg of tert-butyl (1R, 3s,5S)-3-((6-(2-(methoxymethoxy)-4-(6-methoxypyridazin-4-yl)phenyl)pyridazin-3-yl)(methyl)amino)-1,5-dimethyl-8- azabicyclo[3.2.1]octane-8-carboxylate as light yellow solid (78% yield). LCMS: m/z 591.2 [M+H]+; $t_R$=2.20 min.

Step 12: Synthesis of 2-(6-(((1R,3s,5S)-1,5-dimethyl-8-azabicyclo[3.2.1]octan-3-yl)(methyl)amino)pyridazin-3-yl)-5-(6-methoxypyridazin-4-yl)phenol

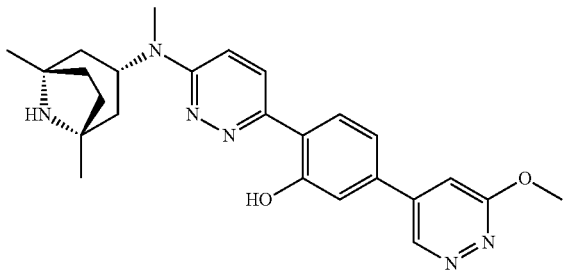

A solution 4 N HCl in dioxane 4 mL was added to a stirred solution of tert-butyl (1R,3s,5S)-3-((6-(2-(methoxymethoxy)-4-(6-methoxypyridazin-4-yl)phenyl)pyridazin-3-yl)(methyl)amino)-1,5-dimethyl-8-azabicyclo[3.2.1]octane-8-carboxylate (180 mg, 0.3 mmol) in 4 mL of $CH_2CO_2$. The mixture was stirred at room temperature for 3 h, concentrated under reduced pressure, neutralized with $NH_3$/MeOH and purified by prep-HPLC which gave 58 mg of 2-(6-(((1R,3s,5S)-1,5-dimethyl-8-azabicyclo[3.2.1]octan-3-yl)(methyl)amino)pyridazin-3-yl)-5-(6-methoxypyridazin-4-yl)phenol as a yellow solid (43% yield).

Example 12: Synthesis of 4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1-(fluoromethyl)pyridin-2(1H)-one

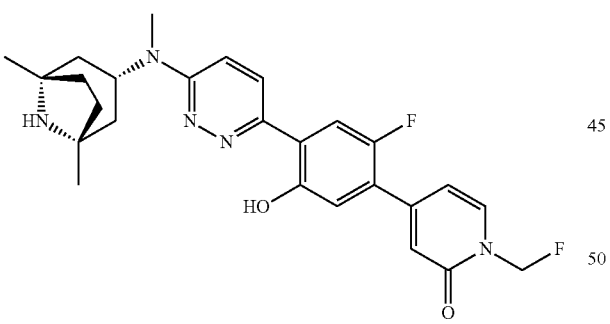

Step 1: Synthesis of 1,5-dimethyl-8-azabicyclo[3.2.1]octan-3-one

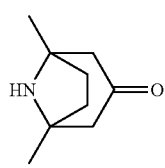

Potassium hydroxide (108 g, 1.93 mol) in 70 mL of $H_2O$ was added to a stirred solution of 3-oxopentanedioic acid (120 g, 822 mmol) and hexane-2,5-dione (49.2 g, 432 mmol) in 350 mL of $H_2O$ and 0° C. After the addition, $NH_4Cl$ (70.1 g, 1.32 mol) and NaOAc trihydrate (70.1 g, 515 mmol) in 667 mL of $H_2O$ was added. The pH value was adjusted to ~9 by using 1 N NaOH aqueous solution. The mixture was stirred at room temperature for 72 h during which time the pH value was adjusted to ~9 by using additional 1 N NaOH aqueous solution. The mixture was extracted with $CH_2Cl_2$ (1 L×5). The combined organic solvents were dried over anhydrous $Na_2SO_4$, concentrated and purified by silica gel chromatography (0-25% MeOH/$CH_2Cl_2$) which gave 16.7 g of 1,5-dimethyl-8-azabicyclo[3.2.1]octan-3-one as black oil (25% yield). LCMS: m/z 154.2 [M+H]+; $t_R$=1.20 min.

Step 2: Synthesis of tert-butyl 1,5-dimethyl-3-oxo-8-azabicyclo[3.2.1]octane-8-carboxylate

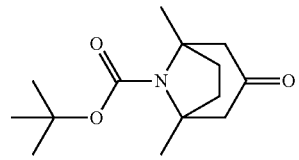

A mixture of 1,5-dimethyl-8-azabicyclo[3.2.1]octan-3-one (24 g, 163 mmol), di-tert-butyl dicarbonate (35.6 g, 326 mmol) and DIPEA (31.5 g, 244 mmol) in 500 mL of 1,4-dioxane was stirred at 70° C. for 6 h. The mixture was concentrated and purified by silica gel chromatography (0-30% EtOAc/petroleum ether) which gave 16.7 of tert-butyl 1,5-dimethyl-3-oxo-8-azabicyclo[3.2.1]octane-8-carboxylate as white solid (yield: 42%). LCMS: m/z 198.1 [M−55]+; $t_R$=1.40 min.

Step 3: Synthesis of tert-butyl 3-(hydroxyimino)-1,5-dimethyl-8-azabicyclo[3.2.1]octane-8-carboxylate

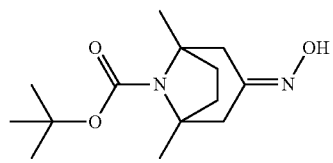 [SMILES: CC(C)(C)OC(=O)N1C2(C)CCC1(C)CC(=NO)C2]

A mixture of tert-butyl 1,5-dimethyl-3-oxo-8-azabicyclo[3.2.1]octane-8-carboxylate (16.7 g, 66 mmol), hydroxylamine hydrochloride (18.2 g, 26.4 mmol) and NaOAc (10.8 g, 132 mmol) in 250 mL of EtOH was stirred at 70° C. for 4 h. The mixture was concentrated. 200 mL of EtOAc and 60 mL of $H_2O$ was added. The organic phase was separated, washed with brine (50 mL), dried over anhydrous $Na_2SO_4$, concentrated to give 16.7 g of tert-butyl 3-(hydroxyimino)-1,5-dimethyl-8-azabicyclo[3.2.1]octane-8-carboxylate as yellow solid which was used directly to next step (93% yield). LCMS: m/z 269.2 [M+H]+; $t_R$=1.92 min.

Step 4: Synthesis of tert-butyl (1R,3s,5S)-3-amino-1,5-dimethyl-8-azabicyclo[3.2.1]octane-8-carboxylate

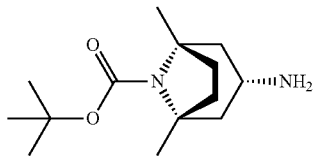

Sodium (40.2 g, 1.75 mol) was added in portions to a mixture of tert-butyl 3-(hydroxyimino)-1,5-dimethyl-8-azabicyclo[3.2.1]octane-8-carboxylate (26.8 g, 0.1 mol) in 1000 mL of n-PrOH was heated to 110° C. over 1 h. After addition, the mixture was stirred at reflux for additional 1 h. The mixture was cooled to room temperature, quenched with H$_2$O (500 mL). The organic layer was separated and concentrated. DCM (500 mL) was added to the residue. The solid was filtered off and the filtrate was concentrated under reduced pressure which gave 20 g of tert-butyl (1R,3s,5S)-3-amino-1,5-dimethyl-8-azabicyclo[3.2.1]octane-8-carboxylate as a yellow oil, which was used directly to next step (yield: 79%). LCMS: m/z 255.3 [M+H]$^+$; t$_R$=1.37 min.

Step 5: Synthesis of tert-butyl (1R,3s,5S)-3-((6-chloropyridazin-3-yl)amino)-1,5-dimethyl-8-azabicyclo[3.2.1]octane-8-carboxylate

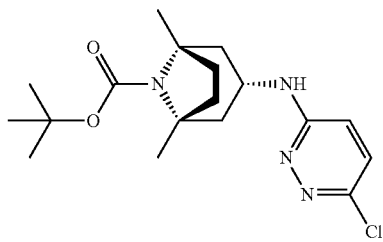

A mixture of tert-butyl (1R,3s,5S)-3-amino-1,5-dimethyl-8-azabicyclo[3.2.1]octane-8-carboxylate (20 g, 78.7 mmol), 3,6-dichloropyridazine (23.3 g, 157.5 mmol) and DIPEA (20.48 g, 157.5 mmol) in 500 mL of DMSO was stirred at 120° C. for 24 h. The mixture was cooled to room temperature, quenched with H$_2$O and extracted with ethyl acetate (500 mL×3). The combined organic layers were washed with brine, dried over anhydrous Na$_2$SO$_4$ and concentrated under reduced pressure. After removal of solvent, the crude product was purified by silica gel column (50% EtOAc/petroleum ether) which gave 17.5 g of tert-butyl (1R,3s,5S)-3-((6-chloropyridazin-3-yl)amino)-1,5-dimethyl-8-azabicyclo[3.2.1]octane-8-carboxylate as yellow solid (yield: 61%). LCMS: m/z 367.2 [M+H]$^+$; t$_R$=1.88 min.

Step 6: Synthesis of tert-butyl (1R,3s,5S)-3-((6-chloropyridazin-3-yl)(methyl)amino)-1,5-dimethyl-8-azabicyclo[3.2.1]octane-8-carboxylate

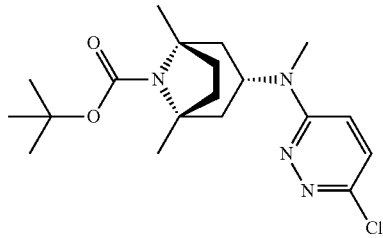

Sodium hydride (2.87 g, 71.7 mmol, 60% in mineral oil) was added to a stirred solution of tert-butyl (1R,3s,5S)-3-((6-chloropyridazin-3-yl)amino)-1,5-dimethyl-8-azabicyclo[3.2.1]octane-8-carboxylate (17.5 g, 47.8 mmol) in 400 mL of DMF at 0° C. After stirring for 20 min at 0° C., CH$_3$I (13.58 g, 95.6 mmol) was added. The mixture was then stirred at room temperature for 1 h, quenched with H$_2$O and extracted with EtOAc (300 mL×3). The combined organic phases were washed with brine, dried over anhydrous Na$_2$SO$_4$, concentrated under reduced pressure and purified by silica gel column (30% EtOAc/petroleum ether) which gave 14.5 g of tert-butyl (1R,3s,5S)-3-((6-chloropyridazin-3-yl)(methyl)amino)-1,5-dimethyl-8-azabicyclo[3.2.1]octane-8-carboxylate as yellow solid (80% yield). LCMS: m/z 381.2 [M+H]$^+$; t$_R$=2.17 min.

Step 7: Synthesis of 2-bromo-5-chloro-4-fluorophenol

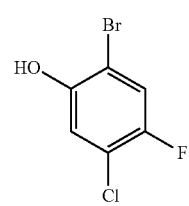

Bromine (3.52 g, 22 mmol) was added to a stirred solution of 3-chloro-4-fluorophenol (4.02 g, 20 mmol) in 80 mL of CH$_2$Cl$_2$ at room temperature. The mixture was stirred at room temperature for 18 h and quenched with 10 mL of aqueous Na$_2$S$_2$O$_3$ solution. The organic phase was collected, concentrated and purified by silica gel chromatography (0-10% EtOAc/petroleum ether) which gave 2.5 g of 2-bromo-5-chloro-4-fluorophenol as white solid (44% yield). $^1$H NMR (500 MHz, Chloroform-d) δ 7.29 (d, J=8.0 Hz, 1H), 7.08 (d, J=6.6 Hz, 1H), 5.45 (s, 1H). LCMS: t$_R$=1.44 min.

Step 8: Synthesis of 1-bromo-4-chloro-5-fluoro-2-(methoxymethoxy)benzene

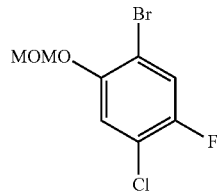

Sodium hydride (215 mg, 5.4 mmol, 60% in mineral oil) was added to a stirred solution of 2-bromo-5-chloro-4-fluorophenol (1 g, 4.48 mmol) in 14 mL of DMF at 0° C. After stirring for 30 min, bromo(methoxy)methane (428 mg, 8 mmol) was added. The mixture was then stirred at room temperature for 2 h, quenched with 10 mL of saturated NH$_4$Cl aqueous solution and extracted with EtOAc (30 mL×3). The combined organic solvents were concentrated and purified by silica gel silica gel column (0-8% EtOAc/petroleum ether) which gave 1.01 g of 1-bromo-4-chloro-5-fluoro-2-(methoxymethoxy)benzene as white solid (70% yield). $^1$H NMR (500 MHz, Chloroform-d) δ 7.37 (d, J=8.1 Hz, 1H), 7.23 (d, J=6.6 Hz, 1H), 5.20 (s, 2H), 3.52 (s, 3H).

Step 9: Synthesis of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate

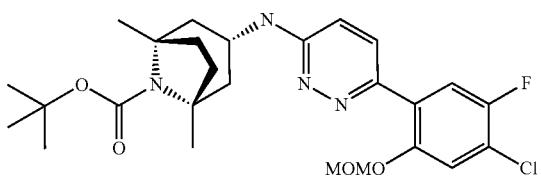

A mixture of 1-bromo-4-chloro-5-fluoro-2-(methoxymethoxy)benzene (8.5 g, 31.7 mmol), 4,4,4',4',5,5,5',5'-octamethyl-2,2'-bi(1,3,2-dioxaborolane) (12.1 g, 47.5 mmol), Pd(dppf)Cl$_2$ (1.86 g, 2.54 mmol) and KOAc (6.2 g, 63.4 mmol) in 200 mL of dioxane was degassed and stirred at 100° C. for 8 h. After cooling to room temperature, tert-butyl (1R,3s,5S)-3-((6-chloropyridazin-3-yl)(methyl)amino)-1,5-dimethyl-8-azabicyclo[3.2.1]octane-8-carboxylate (8 g, 21.2 mmol), K$_2$CO$_3$ (5.8 g, 42.3 mmol) and H$_2$O (30 mL) were added. The mixture was stirred at 100° C. for 3 h, concentrated and purified by silica gel column (10-25% EtOAc/petroleum ether) which gave 6 g of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate as light yellow solid (53% yield). LCMS: m/z 535.2 [M+H]$^+$; t$_R$=2.40 min.

Step 10: Synthesis of 4-bromo-1-(fluoromethyl)pyridin-2(1H)-one

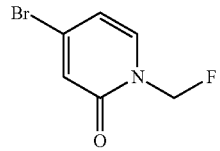

Sodium hydride (111 mg, 4.62 mmol, 60% in mineral oil) was added to a stirred solution of 4-bromopyridin-2(1H)-one (400 mg, 2.31 mmol) in 15 mL of THF at 0° C. After stirring for 20 min at 0° C., bromofluoromethane (517 mg, 4.62 mmol) was added. The mixture was then stirred at 50° C. for 1 h, quenched with H$_2$O and extracted with EtOAc (30 mL×3). The combined organic phases were washed with brine, dried over anhydrous Na$_2$SO$_4$, concentrated under reduced pressure and purified by silica gel column (50% EtOAc/petroleum ether) which gave 400 mg of 4-bromo-1-(fluoromethyl)pyridin-2(1H)-one as white solid (84% yield). LCMS: m/z 207.9 [M+H]$^+$; t$_R$=1.46 min.

Step 11: Synthesis of tert-butyl (1R,3s,5S)-3-((6-(5-fluoro-4-(1-(fluoromethyl)-2-oxo-1,2-dihydropyridin-4-yl)-2-(methoxymethoxy)phenyl)pyridazin-3-yl)(methyl)amino)-1,5-dimethyl-8-azabicyclo[3.2.1]octane-8-carboxylate

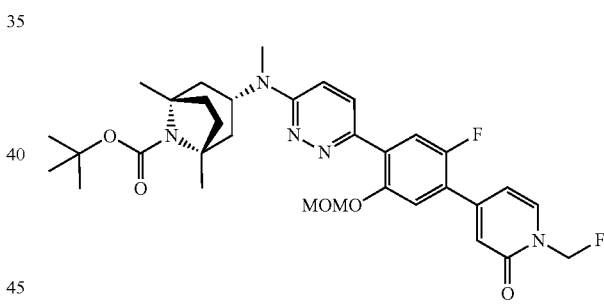

A mixture of 4-bromo-1-(fluoromethyl)pyridin-2(1H)-one (65 mg, 0.32 mmol), 4,4,4',4',5,5,5',5'-octamethyl-2,2'-bi(1,3,2-dioxaborolane) (97 mg, 0.38 mmol), Pd$_2$(dba)$_3$ (27 mg, 0.03 mmol), X-Phos (29 mg, 0.06 mmol) and KOAc (63 mg, 0.64 mmol) in 4 mL of 1,4-dioxane was degassed and stirred at 90° C. for 8 h. After cooling to room temperature, tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate (100 mg, 0.19 mmol), K$_2$CO$_3$ (52 mg, 0.38 mmol) and H$_2$O (0.8 mL) were added. The mixture was stirred at 110° C. for 3 h, concentrated and purified by silica gel column (10-80% EtOAc/petroleum ether) which gave 90 mg of tert-butyl (1R,3s,5S)-3-((6-(5-fluoro-4-(1-(fluoromethyl)-2-oxo-1,2-dihydropyridin-4-yl)-2-(methoxymethoxy)phenyl)pyridazin-3-yl)(methyl)amino)-1,5-dimethyl-8-azabicyclo[3.2.1]octane-8-carboxylate as light yellow oil (77% yield). LCMS: m/z 626.1 [M+H]$^+$; t$_R$=2.19 min.

Step 12: Synthesis of 4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1-(fluoromethyl)pyridin-2(1H)-one

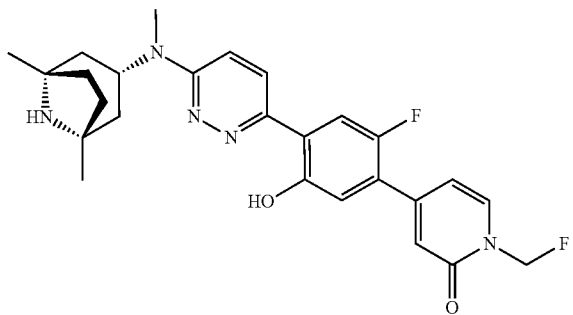

A solution of 4N HCl in dioxane (4 mL) was added to a stirred solution of tert-butyl (1R,3s,5S)-3-((6-(4-chloro-5-fluoro-2-(methoxymethoxy)phenyl)pyridazin-3-yl)(methyl)amino)-1,5-dimethyl-8-azabicyclo[3.2.1]octane-8-carboxylate (90 mg, 0.14 mmol) in 4 mL of $CH_2Cl_2$. The mixture was stirred at room temperature for 2 h, concentrated under reduced pressure, neutralized with $NH_3$/MeOH and purified by prep-HPLC which gave 32 mg of 4-(4-(6-(((1R,3s,5S)-1,5-dimethyl-8-azabicyclo[3.2.1]octan-3-yl)(methyl)amino)pyridazin-3-yl)-2-fluoro-5-hydroxyphenyl)-1-(fluoromethyl)pyridin-2(1H)-one as a yellow solid (46% yield).

Example 13: Splicing Assay (MAPTau, MADD, FOXM1)

Various cells lines were treated with the SMSMs described herein. RNA was then isolated, cDNA synthesized, qPCR performed and the levels of various mRNA targets of the SMSMs were determined. In some instances, RNA was isolated, cDNA synthesized, qPCR performed and the levels of mRNA isoforms in the various cell samples were determined.

Materials

Cells to Ct kit: ThermoFisher, AM1728. TaqMan Gene Expression Master Mix: ThermoFisher, 4369542. PPIA probe/primer: ThermoFisher, Hs03045993_gH, VIC-MGB_PL.

```
Probe/primer sequences:

FoxM1
FOXM1 A2 probe/primer: IDT DNA
                                          (SEQ ID NO: 77)
Primer 1: ACA GGT GGT GTT TGG TTA CA (SEQ ID NO: 78)
Primer 2: AAA TTA AAC AAG CTG GTG ATG GG (SEQ ID NO: 79)
Probe: /56-FAM/AG TTC TTT A/Zen/G TGG CGA
TCT GCG AGA /3IABkFQ/

FOXM1 BC probe/primer: IDT DNA
                                          (SEQ ID NO: 80)
Primer 1: GAG CTT GCC CGC CAT AG (SEQ ID NO: 81)
Primer 2: CTG GTC CTG CAG AAG AAA GAG
```

```
Probe/primer sequences:
                                          (SEQ ID NO: 82)
Probe: /5HEX/CC AAG GTG C/ZEN/T GCT AGC
TGA GGA /3IABkFQ/

MADD
Isoform 4 (WT)
                                          (SEQ ID NO: 83)
Primer 1: GGC TAA ATA CTC TAA TGG AGA TTG TTA C (SEQ ID NO: 84)
Primer 2: GGC TGT GTT TAA TGA CAG ATG AC (SEQ ID NO: 85)
Probe: /5HEX/AG TGG TGA A/ZEN/G GAA ACA GGA
GGG CGT TAG /3IABkFQ/

Isoform 3 (Ex16)
                                          (SEQ ID NO: 86)
Primer 1: CAC TGT TGG GCT GTG TTT AAT G (SEQ ID NO: 87)
Primer 2: ACA GTA CCA GCT TCA GTC TTT C (SEQ ID NO: 88)
Probe: /56-FAM/TC TGA AAG G/ZEN/A AAC AGG
AGG GCG TT/3IABkFQ/

MAPTau
MAPT Full length (4R) probe/primer: IDT DNA
                                          (SEQ ID NO: 89)
Primer 1: CCA TGC CAG ACC TGA AGA AT (SEQ ID NO: 90)
Primer 2: TTG GAC TGG ACG TTG CTA AG (SEQ ID NO: 91)
Probe: /5HEX/AA TTA TCT G/ZEN/C ACC TTC CCG
CCT CC/3IABkFQ/

MAPT Truncation (3R) probe/primer: IDT DNA
                                          (SEQ ID NO: 92)
Primer 1: AGA TCG GCT CCA CTG AGA A (SEQ ID NO: 93)
Primer 2: GGT TTA TGA TGG ATG TTG CCT AAT G (SEQ ID NO: 94)
Probe: /56-FAM/CA ACT GGT T/ZEN/T GTA GAC TAT TTG
CAC CTT CCC /3IABkFQ/
```

Cells:

Cells used included 93-T449, A-375, A-673, ASPC-1, BxPC-3, CCL-136, Daoy, DU-145, G-401, Hep-3B, IMR-32, K-562, LP-LoVo, MDA-MB-157, MDA-MB-231-luc, MDA-MB-468, MG-63, Ms751, NCI-H358, PACA-2, PANC-1, PC-3, RGX-MPC-11, RGX-PACA-2, SH-SY5Y, SJSA, SKOV3, SNU-16, SW872 (HTB-92), TOLEDO, T.T, U-118, U-251MG, U-87MG, and Z-138 cells.

On the day of the experiment, a 96-well plate was seeded with the cell lines of interest. The cells were diluted with full growth media to a concentration of $2.0 \times 10^5$ cells/mL and 100 µL of cells were added to each well (20,000 cells per well). The cells were treated with a compound immediately after plating.

The compounds were then added to the cell plate using the HP compound dispenser. In the initial experiment, atop concentration of 10 µM and an 8 point 4-fold dilution scheme was used. The stock compounds were made at a concentration of 5 mM, and the DMSO concentration was set to 0.2%. DMSO was used to normalize all the compound-containing wells and the untreated cells.

The treated cells were incubated at 37° C. in a 5% $CO_2$ incubator for the desired amount of time. Plates were placed in a plastic bag with a wet paper towel to prevent evaporation.

RNA was isolated using the Cells to $C_T$ kit (ThermoFisher, AM1728). The cells were washed once with 100 µL cold PBS. 50 µL of lysis buffer was added to each well/tube (49.5 µL lysis buffer+0.5 µL DNase I per well/tube). The lysis reaction was mixed and incubated at room temperature for 5 minutes. 5 µL of stop solution was added directly into each cell lysis reaction and mixed by pipetting up and down 5 times. The plates/tubes were incubated at room temperature for 2 minutes then placed on ice if the cDNA synthesis was to be performed immediately. Otherwise, the plates/tubes were stored at −80° C. cDNA synthesis reactions were then performed. Reverse Transcription (RT) Master mix was prepared according to the table below.

| Component | Each reaction |
| --- | --- |
| 2x RT Buffer | 25 µL |
| 20x RT Enzyme Mix | 2.5 µL |
| Nuclease-free water | 12.5 µL |

40 µL RT master mix was added to PCR tubes or plate wells. 10 µL of RNA was added to each tube/well. The RT thermal cycler program was then run and tubes or plate wells were incubated at 37° C. for 1 hour, then at 95° C. for 5 minutes to deactivate the enzyme.

The qPCR was performed using a QuantStudio 6 instrument (ThermoFisher) and the following cycling conditions and according to the tables below. All samples and standards were analyzed in triplicate. Cycle 1: 2 minutes at 50° C. Cycle 2: 10 minutes at 95° C. Cycle 3 (repeat 40 times): 15 seconds at 95° C., 1 minute at 60° C.

| Isoform 1 or isoform 2 standard samples | |
| --- | --- |
| Component | Per qPCR well |
| 2x TaqMan Gene Expression Master Mix | 10 µL |
| 40x isoform 1 or isoform 2 probe/primer | 0.5 µL |
| Nuclease-free water | 4.5 µL |
| Standard DNA | 5 µL |
| Unknown sample (FOXM1 isoform A2/FOXM1 isoform BC quantitation) | |
| 2x TaqMan Gene Expression Master Mix | 10 µL |
| 40x isoform 1 probe/primer | 0.5 µL |
| 40x isoform 2 probe/primer | 0.5 µL |
| Nuclease-free water | 5 µL |
| Sample DNA | 4 µL |
| PPIA Standard sample | |
| 2x TaqMan Gene Expression Master Mix | 10 µL |
| 60x PPIA probe/primer | 0.33 µL |
| Nuclease-free water | 4.67 µL |
| Standard DNA | 5 µL |
| Unknown sample (PPIA quantitation) | |
| 2x TaqMan Gene Expression Master Mix | 10 µL |
| 60x PPIA probe/primer | 0.33 µL |
| Nuclease-free water | 5.67 µL |
| Sample DNA | 4 µL |

The determined isoform 2 and isoform 1 quantities were then be used to determine the isoform 2: isoform 2 ratio at the various compound concentrations. The PPIA quantities were used in the normalization to account of cell proliferation effects of the compounds.

Standard Construction

PPIA Standard (5834 bps)

G Block sequence (IDT DNA)
(SEQ ID NO: 95)
GAATTCGGCCAGGCTCGTGCCGTTTTGCAGACGCCACCGCCGAGGAAA

ACCGTGTACTATTAGCCATGGTCAACCCCACCGTGTTCTTCGACATTG

CCGTCGACGGCGAGCCCTTGGGCCGCGTCTCCTTTGAGCTGTTTGCAG

ACAAGGTCCCAAAGACAGCAGAAAATTTTCGTGCTCTGAGCACTGGAG

AGAAAGGATTTGGTTATAAGGGTTCCTGCTTTCACAGAATTATTCCAG

GGTTTATGTGTCAGGGTGGTGACTTCACACGCCATAATGGCACTGGTG

GCAAGTCCATCTATGGGGAGAAATTTGAAGATGAGAACTTCATCCTAA

AGCATACGGGTCCTGGCATCTTGTCCATGGCAAATGCTGGACCCAACA

CAAATGGTTCCCGCGGCCGC.

FoxM1 A2 (5558 bps)
G Block sequence (IDT DNA)
(SEQ ID NO: 96)
GAATTCGTTTTTGGGGAACAGGTGGTGTTTGGTTACATGAGTAAGTTC

TTTAGTGGCGATCTGCGAGATTTTGGTACACCCATCACCAGCTTGTTT

AATTTTATCTTTCTTTGTTTATCAGCGGCCGC

FoxM2 BC (6439 bps)
G Block sequence (IDT DNA)
(SEQ ID NO: 97)
GAATTCGGCGGAAGATGAAGCCACTGCTACCACGGGTCAGCTCATACC

TGGTACCTATCCAGTTCCCGGTGAACCAGTCACTGGTGTTGCAGCCCT

CGGTGAAGGTGCCATTGCCCCTGGCGGCTTCCCTCATGAGCTCAGAGC

TTGCCCGCCATAGCAAGCGAGTCCGCATTGCCCCCAAGGTGCTGCTAG

CTGAGGAGGGGATAGCTCCTCTTTCTTCTGCAGGACCAGGGAAAGAGG

AGAAACTCCTGTTTGGAGAAGGGTTTTCTCCTTTGCTTCCAGTTCAGA

CTATCAAGGAGGAAGAAATCCAGCCTGGGGAGGAAATGCCACACTTAG

CGAGACCCATCAAAGTGGAGAGCCCTCCCTTGGAAGAGTGGCCCTCCC

CGGCCCCATCTTTCAAAGAGGAATCATCTCACTCCTGGGAGGATTCGT

CCCAATCTCCCACCCCAAGACCCAAGAAGTCCTACAGTGGGCTTAGGT

CCCCAACCCGGTGTGTCTCGGAAATGCTTGTGATTCAACACAGGGAGA

GGAGGGAGAGGAGCCGGTCTCGGAGGAAACAGCATCTACTGCCTCCCT

GTGTGGATGAGCCGGAGCTGCTCTTCTCAGAGGGGCCCAGTACTTCCC

GCTGGGCCGCAGAGCTCCCGTTCCCAGCAGACTCCTCTGACCCTGCCT

CCCAGCTCAGCTACTCCCAGGAAGTGGGAGGACCTTTTAAGACACCCA

TTAAGGAAACGCTGCCCATCTCCTCCACCCCGAGCAAATCTGTCCTCC

CCAGAACCCCTGAATCCTGGAGGCTCACGCCCCCAGCCAAAGTAGGGG

GACTGGATTTCAGCCCAGTACAAACCTCCCAGGGTGCCTCTGACCCCT

TGCCTGACCCCCTGGGGCTGATGGATCTCAGCACCACTCCCTTGCAAA

GTGCTCCCCCCCTTGAATCACCGCAAAGGCTCCTCAGTTCAGAACCCT

TAGACCTCATCTCCGTCCCCTTTGGCAACTCTTCTCCCTCAGCGGCCG

C

MADD Isoform 4 (WT) (5668 bps)
G Block sequence (IDT DNA)
(SEQ ID NO: 98)
GAATTCAAAGGTGCCCGAGAGAAGGCCACGCCCTTCCCCAGTCTGAAA

GTATTTGGGCTAAATACTCTAATGGAGATTGTTACTGAAGCCGGCCCC

GGGAGTGGTGAAGGAAACAGGAGGGCGTTAGTGGATCAGAAGTCATCT

GTCATTAAACACAGCCCAACAGTGAAAAGAGAACCTCCATCACCCCAG

GGTCGATCCAGCAATTCTAGTGAGAACCAGCAGTTCCTGCGGCCGC

MADD Isoform 3 (Ex16) (5689 bps)
G Block sequence (IDT DNA)
(SEQ ID NO: 99)
GAATTCACCGAGGGCTTCGGGGGCATCATGTCTTTTGCCAGCAGCCTC

TATCGGAACCACAGTACCAGCTTCAGTCTTTCAAACCTCACACTGCCC

ACCAAAGGTGCCCGAGAGAAGGCCACGCCCTTCCCCAGTCTGAAAGGA

AACAGGAGGGCGTTAGTGGATCAGAAGTCATCTGTCATTAAACACAGC

CCAACAGTGAAAAGAGAACCTCCATCACCCCAGGGTCGATCCAGCAAT

TCTAGTGAGAAGCGGCCGC

MAPTau Full length (4R) (5654 bps)
G Block sequence (IDT DNA)
(SEQ ID NO: 100)
GAATTCTCCGCCAAGAGCCGCCTGCAGACAGCCCCCGTGCCCATGCCA

GACCTGAAGAATGTCAAGTCCAAGATCGGCTCCACTGAGAACCTGAAG

CACCAGCCGGGAGGCGGGAAGGTGCAGATAATTAATAAGAAGCTGGAT

CTTAGCAACGTCCAGTCCAAGTGTGGCTCAAAGGATAATATCAAACAC

GTCCCGGGAGGCGGCAGTGTGCAAGCGGCCGC

MAPTau Truncation (3R) (5644 bps)
G Block sequence (IDT DNA)
(SEQ ID NO: 101)
GAATTCTCAAGTCCAAGATCGGCTCCACTGAGAACCTGAAGCACCAGC

CGGGAGGCGGGAAGGTGCAAATAGTCTACAAACCAGTTGACCTGAGCA

AGGTGACCTCCAAGTGTGGCTCATTAGGCAACATCCATCATAAACCAG

GAGGTGGCCAGGTGGAAGTAAAATCTGAGAAGCTTGACTTCAAGGACA

GAGTCCAGTCGAAGGCGGCCGC

The G Blocks were inserted into the pCI-neo mammalian expression vector (Promega) at the EcoRI and NotI restriction sites (bolded) using Infusion cloning technology (Clontech). The plasmids were then purified using standard miniprep or maxiprep kits (Macherey Nagel).

Standard Curve Preparation

The dilution necessary to make the top standard is calculated. A top concentration 200,000,000 copies/µL of the stock plasmid was prepared in TE buffer. A series of 10-fold dilutions, also in TE, were then made. A total of 5 µL of each standard was used in a qPCR well to generate samples containing $10^9$ copies, $10^8$ copies, $10^7$ copies, $10^6$ copies, $10^5$ copies, $10^4$ copies, $10^3$ copies, $10^2$ copies, 101copies, and 0 copies.

An assay to measure the $FOXM1^{A2}$ mRNA and $FOXM1^{BC}$ mRNA, or $MADD^{WT\ (isoform\ 4)}$ mRNA and $MADD^{Ex16\ (isoform\ 3)}$ mRNA, or $MAPTau^{4R}$ mRNA and $MAPTau^{3R}$ mRNA simultaneously in cell wells was performed. The RNA values were measured relative to DMSO control and also included a housekeeping gene, PPIA to ensure data was consistent. The mRNA values were measured after 24 hours of incubation with the SMSM compounds. The SMSMs dose dependently increased $FOXM1^{A2}$ levels while concomitantly decreasing $FOXM1^{BC}$ levels with $EC_{50}$ and $IC_{50}$ values in the nanomolar range. This assay was performed in the cell lines shown in Table 3A. Exemplary FOXM1 results are shown in Table 3A.

TABLE 3A

| Cell Line | FOXM1 | | | | | | | |
|---|---|---|---|---|---|---|---|---|
| | SMSM-129 | SMSM-138 | SMSM-223 | SMSM-167 | SMSM-151 | SMSM-191 | SMSM-168 | SMSM-160 |
| A-375 | <1 | 1-10 | 11-100 | <1 | 1-10 | 1-10 | 1-10 | <1 |
| A-673 | <1 | 11-100 | — | <1 | 1-10 | <1 | 1-10 | 1-10 |
| BxPC-3 | — | 101-200 | 200-500 | — | — | — | — | 11-100 |
| Daoy | — | 11-100 | 101-200 | — | — | — | — | — |
| DU-145 | — | 11-100 | 200-500 | — | — | — | — | — |
| G-401 | — | 101-200 | 11-100 | — | — | — | — | — |
| Hep-3B | — | — | — | 11-100 | 101-200 | — | 101-200 | — |
| K-562 | — | — | — | 1-10 | 11-100 | 1-10 | 11-100 | — |
| LP-LoVo | 1-10 | — | — | — | — | — | — | — |
| MDA-MB-157 | <1 | — | — | — | — | — | — | — |
| MDA-MB-231-luc | <1 | 11-100 | — | — | — | — | — | 11-100 |
| MDA-MB-468 | — | — | — | 1-10 | 11-100 | 1-10 | 11-100 | — |
| NCI-H358 | — | — | — | <1 | 1-10 | 1-10 | 1-10 | — |
| PANC-1 | — | — | — | 11-100 | 101-200 | 101-200 | 101-200 | — |
| PC-3 | — | — | — | 11-100 | 11-100 | 11-100 | 11-100 | — |
| SH-SY5Y | — | 11-100 | 11-100 | — | — | — | — | — |
| SKOV3 | 1-10 | — | — | — | — | — | — | — |
| T.T | — | 11-100 | 101-200 | — | — | — | — | — |
| U-118 | — | 11-100 | — | — | — | — | — | 1-10 |
| U-87MG | — | — | — | 11-100 | 11-100 | 11-100 | 11-100 | — |
| Z-138 | <1 | 11-100 | — | — | — | — | — | 1-10 |

Example 14: SMN2 Splicing Assay—Monitoring Expression Levels of SMN2 Splice Variant Using Real-Time Quantitative PCR Various cells lines were treated with the SMSMs described herein. RNA was then isolated, cDNA synthesized, qPCR performed and the levels of various mRNA targets of the SMSMs were determined. In some instances, RNA was isolated, cDNA synthesized, qPCR performed and the levels of mRNA isoforms in the various cell samples were determined.

Materials

Cells to Ct kit: ThermoFisher, AM1728. TaqMan Gene Expression Master Mix: ThermoFisher, 4369542. PPIA probe/primer: ThermoFisher, Hs03045993_gH, VIC-MGB_PL.

Probe/Primer Sequences:

The table below summarizes the primers used.

| Sequence (5'-3') | Primer | Primer | 5'-Mod. | 3'-Mod. | Species |
|---|---|---|---|---|---|
| GCT CAC ATT CCT TAA ATT AAG GAG AAA (SEQ ID NO: 102) | FL | 0.04 µmol Forward Primer | None | None | Human |
| TGG CTA TCA TAC TGG CTA TTA TAT GGA A (SEQ ID NO: 103) | Δ7 | 0.04 µmol Forward Primer | None | None | Human |
| TCC AGA TCT GTC TGA TCG TTT CTT (SEQ ID NO: 104) | Reverse Primer | 0.04 µmol | None | None | Human |
| CTG GCA TAG AGC AGC ACT AAA TGA CAC CAC (SEQ ID NO: 105) | Probe | 0.2 µmol | FAM (Fluorescein) | BHQ-1 | Human |

Cells:

SMA type I patient cells (GM03813 (Coriell))

Protocol

On the day of the experiment, a 96-well plate was seeded with the cell lines of interest. The cells were diluted with full growth media to a concentration of $2.0 \times 10^5$ cells/mL and 100 µL of cells were added to each well (20,000 cells per well). The cells were treated with a compound immediately after plating.

The compounds were then added to the cell plate using the HP compound dispenser. In the initial experiment, atop concentration of 10 µM and an 8 point 4-fold dilution scheme was used. The stock compounds were made at a concentration of 5 mM, and the DMSO concentration was set to 0.2%. DMSO was used to normalize all the compound-containing wells and the untreated cells.

The treated cells were incubated at 37° C. in a 500 $CO_2$ incubator for the desired amount of time. Plates were placed in a plastic bag with a wet paper towel to prevent evaporation.

RNA was isolated using the Cells to $C_T$ kit (ThermoFisher, AM1728). The cells were washed once with 100 µL cold PBS. 50 µL of lysis buffer was added to each well/tube (49.5 µL lysis buffer+0.5 µL DNase I per well/tube). The lysis reaction was mixed and incubated at room temperature for 5 minutes. 5 µL of stop solution was added directly into each cell lysis reaction and mixed by pipetting up and down 5 times. The plates/tubes were incubated at room temperature for 2 minutes then placed on ice if the cDNA synthesis was to be performed immediately. Otherwise, the plates/tubes were stored at −80° C.

cDNA synthesis reactions were then performed. 40 µL RT master mix was added to PCR tubes or plate wells. 10 µL of RNA was added to each tube/well. The RT thermal cycler program was then run and tubes or plate wells were incubated at 37° C. for 1 hour, then at 95° C. for 5 minutes to deactivate the enzyme.

The qPCR was performed using a QuantStudio 6 instrument (ThermoFisher) and the following cycling conditions and according to the tables below. All samples and standards were analyzed in triplicate. Cycle 1: 2 minutes at 50° C. Cycle 2: 10 minutes at 95° C. Cycle 3 (repeat 40 times): 15 seconds at 95° C., 1 minute at 60° C.

| $SMN2^{FL}$ or $SMN2^{\Delta 7}$ standard samples | |
|---|---|
| Component | Per qPCR well |
| 2x TaqMan Gene Expression Master Mix | 10 µL |
| 40x $SMN2^{FL}$ or $SMN2^{\Delta 7}$ probe/primer | 0.5 µL |
| Nuclease-free water | 4.5 µL |
| Standard DNA | 5 µL |

| Unknown sample (FOXM1 isoform A2/ FOXM1 isoform BC quantitation) | |
|---|---|
| Component | Per qPCR well |
| 2x TaqMan Gene Expression Master Mix | 10 µL |
| 40x $SMN2^{FL}$ probe/primer | 0.5 µL |
| 40x $SMN2^{\Delta 7}$ probe/primer | 0.5 µL |
| Nuclease-free water | 5 µL |
| Sample DNA | 4 µL |

| PPIA Standard sample | |
| --- | --- |
| Component | Per qPCR well |
| 2x TaqMan Gene Expression Master Mix | 10 μL |
| 60x PPIA probe/primer | 0.33 μL |
| Nuclease-free water | 4.67 μL |
| Standard DNA | 5 μL |

| Unknown sample (PPIA quantitation) | |
| --- | --- |
| Component | Per qPCR well |
| 2x TaqMan Gene Expression Master Mix | 10 μL |
| 60x PPIA probe/primer | 0.33 μL |
| Nuclease-free water | 5.67 μL |
| Sample DNA | 4 μL |

The determined SMN2$^{\Delta 7}$ and SMN2$^{FL}$ quantities were then be used to determine the SMN2$^{\Delta 7}$:SMN2$^{FL}$ ratio at the various compound concentrations. The PPIA quantities were used in the normalization to account of cell proliferation effects of the compounds.

Standard Construction
PPIA Standard (5834 bps)

```
G Block sequence (IDT DNA)
                                  (SEQ ID NO: 95)
GAATTCGGCCAGGCTCGTGCCGTTTTGCAGACGCCACCGCCGAGGAA

AACCGTGTACTATTAGCCATGGTCAACCCCACCGTGTTCTTCGACAT

TGCCGTCGACGGCGAGCCCTTGGGCCGCGTCTCCTTTGAGCTGTTTG

CAGACAAGGTCCCAAAGACAGCAGAAAATTTTCGTGCTCTGAGCACT

GGAGAGAAAGGATTTGGTTATAAGGGTTCCTGCTTTCACAGAATTAT

TCCAGGGTTTATGTGTCAGGGTGGTGACTTCACACGCCATAATGGCA

CTGGTGGCAAGTCCATCTATGGGGAGAAATTTGAAGATGAGAACTTC

ATCCTAAAGCATACGGGTCCTGGCATCTTGTCCATGGCAAATGCTGG

ACCCAACACAAATGGTTCCCGCGGCCGC
```

SMN2$^{FL}$ standard G Block sequence (IDT DNA) were used
SMN2$^{\Delta 7}$ standard G Block sequence (IDT DNA) were used The G Blocks were inserted into the pCI-neo mammalian expression vector (Promega) at the EcoRI and NotI restriction sites (bolded) using Infusion cloning technology (Clontech). The plasmids were then purified using standard miniprep or maxiprep kits (Macherey Nagel).

Standard Curve Preparation

The dilution to make the top standard was calculated. A top concentration 200,000,000 copies/μL of the stock plasmid was prepared in TE buffer. A series of 10-fold dilutions, also in TE, were then made. A total of 5 μL of each standard was used in a qPCR well to generate samples containing $10^9$ copies, $10^8$ copies, $10^7$ copies, $10^6$ copies, $10^5$ copies, $10^4$ copies, $10^3$ copies, $10^2$ copies, 101 copies, and 0 copies.

An assay to measure the SMN2$^{FL}$ mRNA and SMN2$^{\Delta 7}$ mRNA simultaneously in cell wells was performed. The RNA values were measured relative to DMSO control and also included a housekeeping gene, PPIA to ensure data was consistent. The mRNA values were measured after 24 hours of incubation with the SMSM compounds. The SMSMs dose dependently increased the the SMN2$^{FL}$ values while concomitantly decreasing the SMN2$^{\Delta 7}$ values at the same with EC$_{50}$ and IC$_{50}$ values in the nanomolar range.

Additionally, to monitor expression levels of SMN2 splice variant using real-time quantitative PCR, SMA type I patient cells (GM03813 (Coriell)) were plated at 5,000 cells/well in 200 μl Dulbecco's modified Eagle's medium (DMEM) with GlutaMAX and 10% fetal bovine serum (FBS) (Life Technologies, Inc.) in 96-well plates, and incubated for 6 hours in a cell culture incubator. Cells were then treated with SMSMs at different concentrations (0.5% DMSO) in duplicate for 24 hours. After removal of the supernatant, cells were lysed in Cells-To-Ct lysis buffer (Life Technologies, Inc.) according to the manufacturer's recommendations. The mRNA levels of SMN2 FL, SMN2 Δ7 were quantified using Taqman-based RT-qPCR and SMN2-specific primers and probes. The SMN2 forward and reverse primers were each used at a final concentration of 0.4 μM. The SMN2 probe was used at a final concentration of 0.15 μM. RT-qPCR was carried out at the following temperatures for indicated times: Step 1: 48° C. (15 min); Step 2: 95° C. (10 min); Step 3: 95° C. (15 sec); Step 4: 60° C. (1 min); Steps 3 and 4 were repeated for 40 cycles. The Ct values for each mRNA were converted to mRNA abundance using actual PCR efficiencies.

Exemplary results of the assays described in the examples above are shown in Table 3B.

TABLE 3B

| SMSM # | GM03813$^{FL}$ EC$_{50}$ (nM) | GM03813$^{\Delta 7}$ IC$_{50}$ (nM) |
| --- | --- | --- |
| 138 | 1 | 1 |
| 160 | 0.6 | 0.7 |
| 151 | 0.7 | 0.9 |
| 289 | 4 | 4 |

Example 15: IKBKAP Splicing Assay

Various cells lines were treated with the SMSMs described herein. RNA was then isolated, cDNA synthesized, qPCR performed and the levels of IKBKAP targets of the SMSMs were determined.

Materials

Cells to Ct kit: ThermoFisher, AM1728. TaqMan Gene Expression Master Mix: ThermoFisher, 4369542. PPIA probe/primer: ThermoFisher, Hs03045993_gH, VIC-MGB_PL.

Probe/Primer Sequences:

```
IKBKAP
IKBKAP WT probe/primer: IDT DNA
                                 (SEQ ID NO: 106)
Primer 1: ACC AGG GCT CGA TGA TGA A (SEQ ID NO: 107)
Primer 2: GCA GCA ATC ATG TGT CCC A (SEQ ID NO: 108)
Probe: /56-FAM/GT TCA CGG A/ZEN/T TGT CAC
TGT TGT GCC /3IABkFQ/
IKBKAP MU probe/primer: IDT DNA
                                 (SEQ ID NO: 109)
Primer 1: GAA GGT TTC CAC ATT TCC AAG
```

-continued (SEQ ID NO: 110)
Primer 2: CAC AAA GCT TGT ATT ACA GAC T (SEQ ID NO: 111)
Probe: /5HEX/CT CAA TCT G/ZEN/A TTT ATG ATC
ATA ACC CTA AGG TG/3IABkFQ/

Protocol

On the day of the experiment, a 96-well plate was seeded with the cell lines of interest. The cells were diluted with full growth media to a concentration of $2.0 \times 10^5$ cells/mL and 100 μL of cells were added to each well (20,000 cells per well). The cells were treated with a compound immediately after plating.

The compounds were then added to the cell plate using the HP compound dispenser. In the initial experiment, atop concentration of 10 μM and an 8 point 4-fold dilution scheme was used. The stock compounds were made at a concentration of 5 mM, and the DMSO concentration was set to 0.2%. DMSO was used to normalize all the compound-containing wells and the untreated cells.

The treated cells were incubated at 37° C. in a 500 $CO_2$ incubator for the desired amount of time. Plates were placed in a plastic bag with a wet paper towel to prevent evaporation.

RNA was isolated using the Cells to $C_T$ kit (ThermoFisher, AM1728). The cells were washed once with 100 μL cold PBS. 50 μL of lysis buffer was added to each well/tube (49.5 μL lysis buffer+0.5 μL DNase I per well/tube). The lysis reaction was mixed and incubated at room temperature for 5 minutes. 5 μL of stop solution was added directly into each cell lysis reaction and mixed by pipetting up and down 5 times. The plates/tubes were incubated at room temperature for 2 minutes then placed on ice if the cDNA synthesis was to be performed immediately. Otherwise, the plates/tubes were stored at −80° C.

cDNA synthesis reactions were then performed. 40 μL RT master mix was added to PCR tubes or plate wells. 10 μL of RNA was added to each tube/well. The RT thermal cycler program was then run and tubes or plate wells were incubated at 37° C. for 1 hour, then at 95° C. for 5 minutes to deactivate the enzyme.

The qPCR was performed using a QuantStudio 6 instrument (ThermoFisher) and the following cycling conditions and according to the tables below. All samples and standards were analyzed in triplicate. Cycle 1: 2 minutes at 50° C. Cycle 2: 10 minutes at 95° C. Cycle 3 (repeat 40 times): 15 seconds at 95° C., 1 minute at 60° C.

| IKBKAP$^{FL}$ or IKBKAP$^{\Delta 20}$ standard samples | |
|---|---|
| Component | Per qPCR well |
| 2x TaqMan Gene Expression Master Mix | 10 μL |
| 40x IKBKAP$^{FL}$ or IKBKAP$^{\Delta 20}$ probe/primer | 0.5 μL |
| Nuclease-free water | 4.5 μL |
| Standard DNA | 5 μL |

| Unknown sample (IKBKAP$^{FL}$/IKBKAP$^{\Delta 20}$ quantitation) | |
|---|---|
| Component | Per qPCR well |
| 2x TaqMan Gene Expression Master Mix | 10 μL |
| 40x IKBKAP$^{FL}$ probe/primer | 0.5 μL |
| 40x IKBKAP$^{\Delta 20}$ probe/primer | 0.5 μL |
| Nuclease-free water | 5 μL |
| Sample DNA | 4 μL |

| PPIA Standard sample | |
|---|---|
| Component | Per qPCR well |
| 2x TaqMan Gene Expression Master Mix | 10 μL |
| 60x PPIA probe/primer | 0.33 μL |
| Nuclease-free water | 4.67 μL |
| Standard DNA | 5 μL |

| Unknown sample (PPIA quantitation) | |
|---|---|
| Component | Per qPCR well |
| 2x TaqMan Gene Expression Master Mix | 10 μL |
| 60x PPIA probe/primer | 0.33 μL |
| Nuclease-free water | 5.67 μL |
| Sample DNA | 4 μL |

The determined IKBKAP$^{FL}$ and IKBKAP$^{\Delta 20}$ isoform quantities were then used to determine the IKBKAP$^{FL}$: IKBKAP$^{\Delta 20}$ ratio at increasing SMSM compound concentrations. The PPIA quantities were used in the normalization to account of cell proliferation effects of the compounds.

Standard Construction

PPIA standard (5834 bps)
G Block sequence (IDT DNA (SEQ ID NO: 95)
GAATTCGGCCAGGCTCGTGCCGTTTTGCAGACGCCACCGCCGAGGAA

AACCGTGTACTATTAGCCATGGTCAACCCCACCGTGTTCTTCGACAT

TGCCGTCGACGGCGAGCCCTTGGGCCGCGTCTCCTTTGAGCTGTTTG

CAGACAAGGTCCCAAAGACAGCAGAAAATTTTCGTGCTCTGAGCACT

GGAGAGAAAGGATTTGGTTATAAGGGTTCCTGCTTTCACAGAATTAT

TCCAGGGTTTATGTGTCAGGGTGGTGACTTCACACGCCATAATGGCA

CTGGTGGCAAGTCCATCTATGGGAGAAATTTGAAGATGAGAACTTC

ATCCTAAAGCATACGGGTCCTGGCATCTTGTCCATGGCAAATGCTGG

ACCCAACACAAATGGTTCCCGCGGCCGC

IKBKAP WT (5639 bps)

(SEQ ID NO: 112)
GAATTCCTTCATTTAAAACATTACAGGCCGGCCTGAGCAGCAATCAT

GTGTCCCATGGGGAAGTTCTGCGGAAAGTGGAGAGGGGTTCACGGAT

TGTCACTGTTGTGCCCCAGGACACAAAGCTTGTATTACAGATGCCAA

GGGGAAACTTAGAAGTTGTTCATCATCGAGCCCTGGTTTTAGCTCAG

ATTCGGAAGTGGTGCGGCCGC

-continued

IKBKAP MU (5645 bps)
(SEQ ID NO: 113)
GAATTCCGGATTGTCACTGTTGTGCCCCAGGACACAAAGCTTGTATT

ACAGACTTATGTTTAAAGAGGCATTTGAATGCATGAGAAAGCTGAGA

ATCAATCTCAATCTGATTTATGATCATAACCCTAAGGTGTTTCTTGG

AAATGTGGAAACCTTCATTAAACAGATAGATTCTGTGAATCATATTA

ACTTGTTTTTTACAGAATTGCGGCCGC

The G Blocks were inserted into the pCI-neo mammalian expression vector (Promega) at the EcoRI and NotI restriction sites (bolded) using Infusion cloning technology (Clontech). The plasmids were then purified using standard miniprep or maxiprep kits (Macherey Nagel).

Standard Curve Preparation

The dilution necessary to make the top standard is calculated. A top concentration 200,000,000 copies/μL of the stock plasmid was prepared in TE buffer. A series of 10-fold dilutions, also in TE, were then made. A total of 5 μL of each standard was used in a qPCR well to generate samples containing $10^9$ copies, $10^8$ copies, $10^7$ copies, $10^6$ copies, $10^5$ copies, $10^4$ copies, $10^3$ copies, $10^2$ copies, $10^1$ copies, and 0 copies.

An assay to measure the IKBKAP$^{FL}$ mRNA and IKBKAP$^{\Delta 20}$ mRNA simultaneously in cell wells was performed. The RNA values were measured relative to DMSO control and also included a housekeeping gene, PPIA to ensure data was consistent. The mRNA values were measured after 24 hours of incubation with the SMSM compounds. The SMSMs dose dependently increased the IKBKAP$^{FL}$ values while concomitantly decreasing the IKBKAP$^{\Delta 20}$ values at the same with EC$_{50}$ and IC$_{50}$ values in the nanomolar range.

Exemplary results of the assays are shown in Table 3C:

TABLE 3C

| SMSM # | IKBKAP$^{FL}$ EC$_{50}$ (nM) | IKBKAP$^{\Delta 20}$ IC$_{50}$ (nM) |
|---|---|---|
| 266 | <100 | <200 |
| 162 | — | 201-1000 |
| 138 | 101-350 | 201-1000 |
| 152 | 351-1000 | >1000 |
| 217 | 351-1000 | 201-1000 |
| 315 | >1000 | >1000 |
| 160 | <100 | <200 |
| 161 | <100 | <200 |
| 223 | 101-350 | >1000 |
| 238 | 101-350 | 201-1000 |
| 154 | 351-1000 | — |
| 278 | 101-350 | <200 |
| 282 | 101-350 | 201-1000 |
| 218 | 351-1000 | >1000 |
| 228 | 351-1000 | >1000 |
| 240 | 101-350 | 201-1000 |

Example 16: Cell Viability and Proliferation

Small molecule splicing modulators were tested in a dose-response assay using different cancer cell lines. Cells were first plated in 96-well plastic tissue culture plates (10,000 cells per well). The cells were treated with 500 nM of SMSM or vehicle alone (DMSO) for 48 hours. Following treatment, the cells were washed with PBS, stained with a crystal violet staining solution, and allowed to dry for 48-72 hrs. After drying, sodium citrate buffer was added to each well and allowed to incubate for 5 min at room temperature. The absorbance was measured at 450 nM using a microplate reader (Biorad; Hercules, Calif.). The relative cell proliferation for each of the cancer cell lines was determined.

To measure cell viability, cells were plated in 96-well plastic tissue culture plates at a density of $5 \times 10^3$ cells/well. Twenty-four hours after plating, cells were treated with various SMSMs. After 72 hours, the cell culture media were removed and plates were stained with 100 mL/well of a solution containing 0.5% crystal violet and 25% methanol, rinsed with deionized water, dried overnight, and resuspended in 100 mL citrate buffer (0.1 M sodium citrate in 50% ethanol) to assess plating efficiency. Intensity of crystal violet staining, assessed at 570 nm and quantified using a Vmax Kinetic Microplate Reader and Softmax software (Molecular Devices Corp., Menlo Park, Calif.), were directly proportional to cell number. Data were normalized to vehicle-treated cells and were presented as the mean±SE from representative experiments. SMSMs that are effective were determined for various cells lines.

Small molecule splicing modulators were tested in a dose-response assay using A673 cells and NHDF cells.

A673 cells or NHDF cells were first plated in 96-well plastic tissue culture plates (10,000 cells per well). The cells were treated with vehicle alone (DMSO), or increasing concentrations of SMSM compounds for 72 h. Following treatment, cell proliferation was determined using a crystal violet assay. The relative cell proliferation at each concentration was determined.

Exemplary results are shown in the table below and FIGS. 9A-9H.

| SMSM #/drug | Ratio NHDF/A673 IC$_{50}$ |
|---|---|
| 160 | >225 |
| 151 | >350 |
| 167 | >2,500 |
| 168 | >500 |
| Panobinostat | ≤10 |
| Belinostat | ≤10 |
| Vorinostat | ≤10 |
| Mocetinostat | ≤10 |
| Trichostatin A | ≤10 |

Example 17: Monitoring Expression Levels of FOXM1 Splice Variants Using Real-Time Quantitative PCR Human fibroblasts were plated at 10,000 cells/well in 200 μL DMEM with GlutaMAX and 10% FBS in 96-well plates in a cell culture incubator (37° C., 5% CO$_2$, 100% relative humidity). Cells were then treated with SMSMs in Table 1B at different concentrations (0.1-1000 nM, each in 0.5% DMSO) in triplicate for 24 hours. RNA extraction was performed as per instructions in the Cells-to-CT™ Kits (Ambion®, Applied Biosystems). RNA samples were frozen at −20° C. until further analysis. Relative expression levels of full-length FOXM1 (FOXM1$^{FL}$) or FOXM1 lacking exon VIIa (FOXM1$^{\Delta VIIa}$) with GAPDH for internal control, was measured using one-step multiplex reverse transcription-polymerase chain reaction (RT-PCR). TaqMan® FAM probes were used for relative quantitation of FOXM1$^{FL}$ or FOXM1$^{\Delta VIIa}$ expression levels and TaqMan® VIC probes were used for relative quantitation of human GAPDH levels. The fidelity of the amplification methods was determined using the ΔΔCt relative quantification method for quantitative PCR. The data shows that the compounds induced alternative splicing of FOXM1 towards full-length FOXM1.

Figure 7:
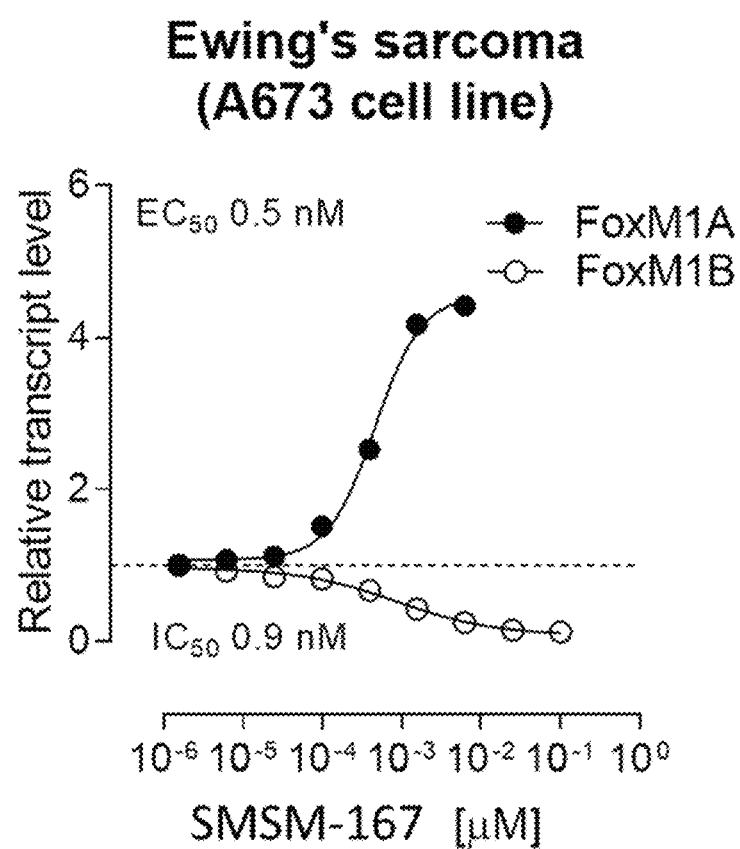
FIG. 7 depicts a graph of relative transcript levels of FOXM1 isoform A (represses cancer) and FOXM1 isoform B (promotes cancer) in A-673 cells incubated with the indicated concentrations of an SMSM.
Figure 8:
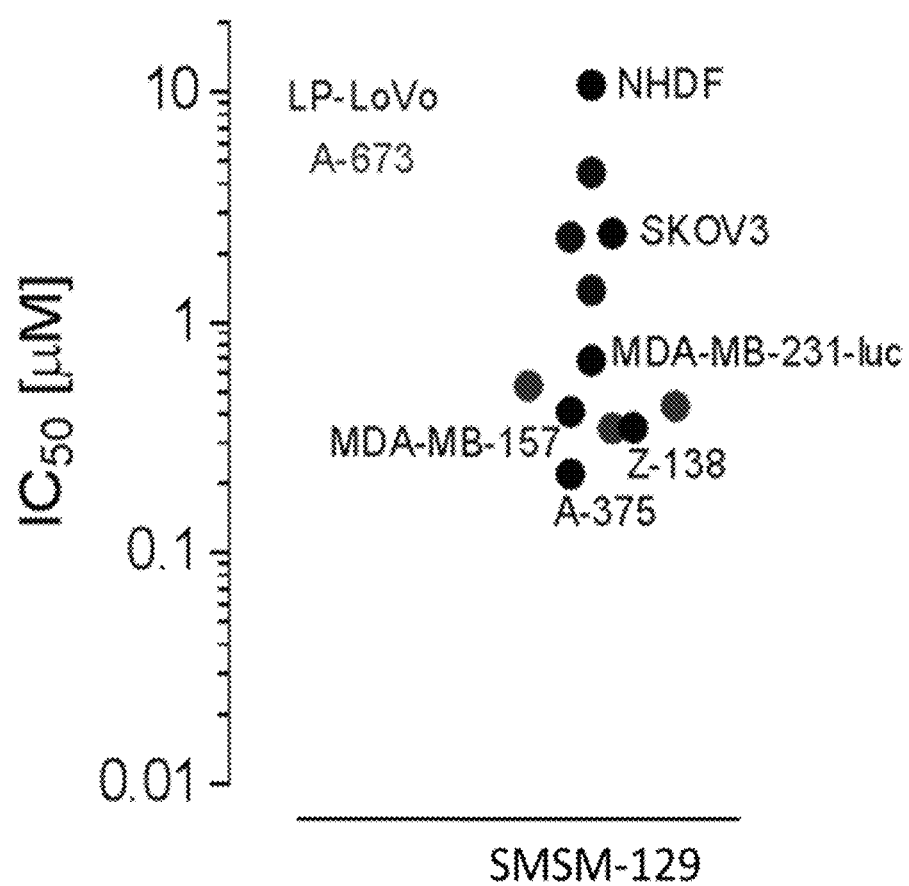
FIG. 8 depicts a plot of the measured $IC_{50}$ of cell viability of an SMSM for the indicated cells.
Figure 9A:
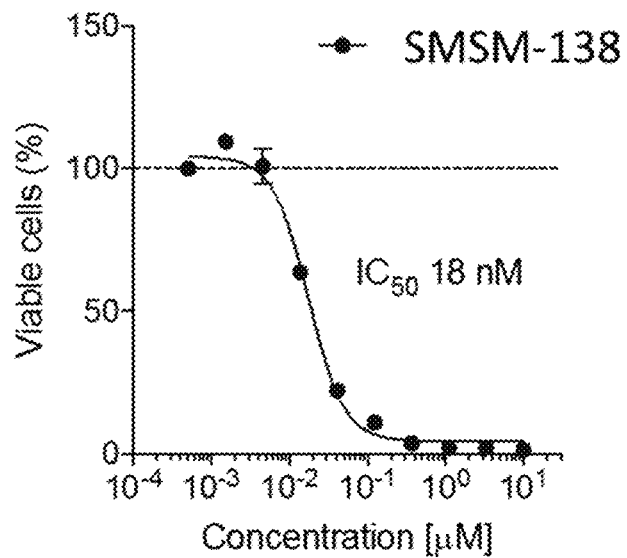
FIG. 9A depicts a graph of viable A-673 cells when incubated with the indicated concentrations of an SMSM.
Figure 9B:
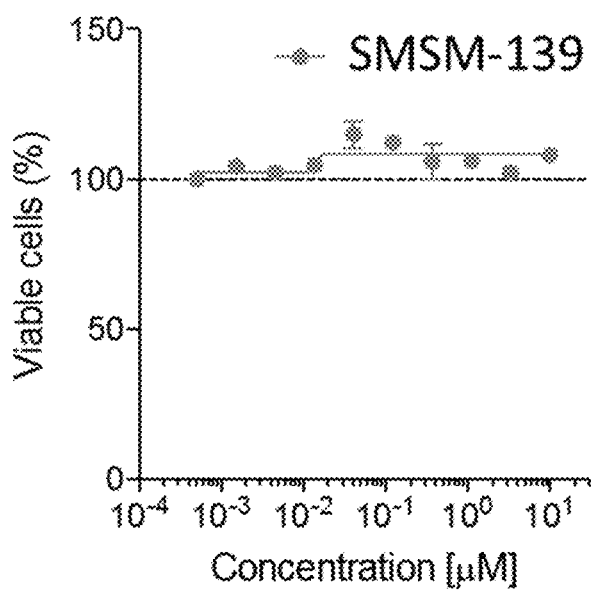
FIG. 9B depicts a graph of viable A-673 cells when incubated with the indicated concentrations of an SMSM.
Figure 9C:
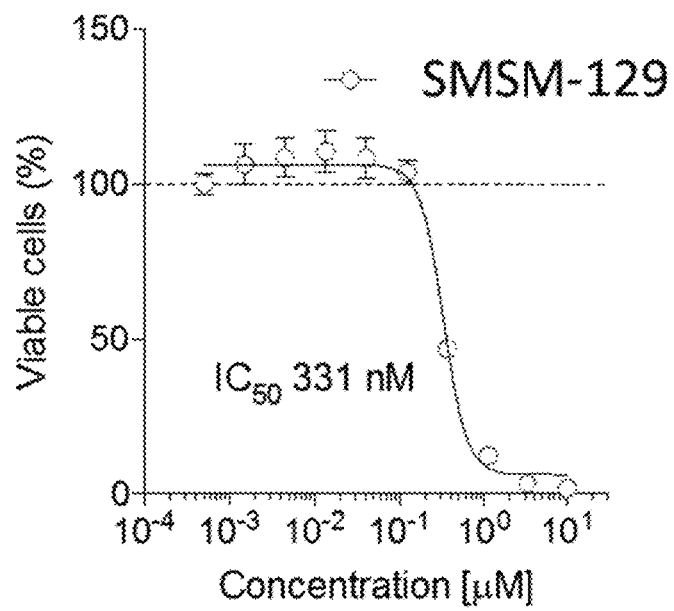
FIG. 9C depicts a graph of viable A-673 cells when incubated with the indicated concentrations of an SMSM.
Figure 9D:
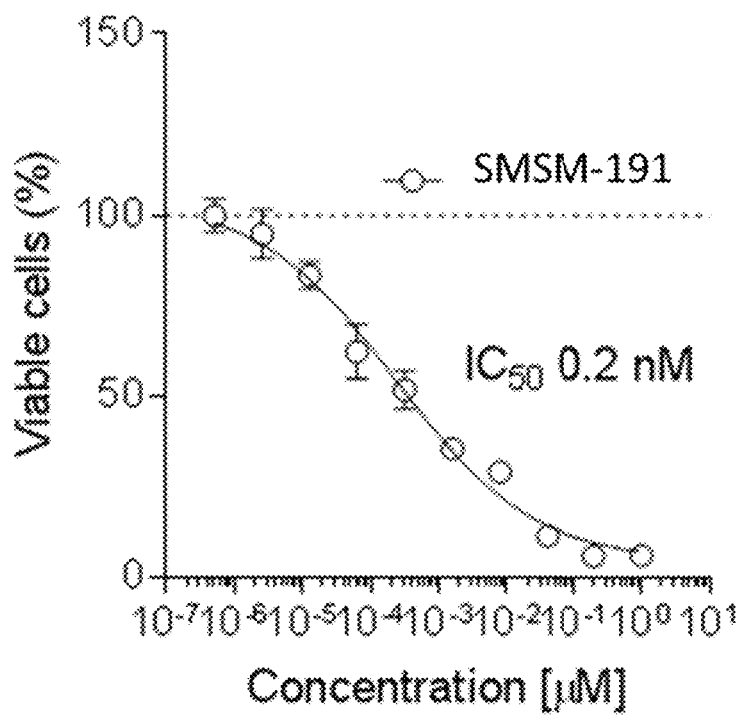
FIG. 9D depicts a graph of viable A-673 cells when incubated with the indicated concentrations of an SMSM.
Figure 9E:
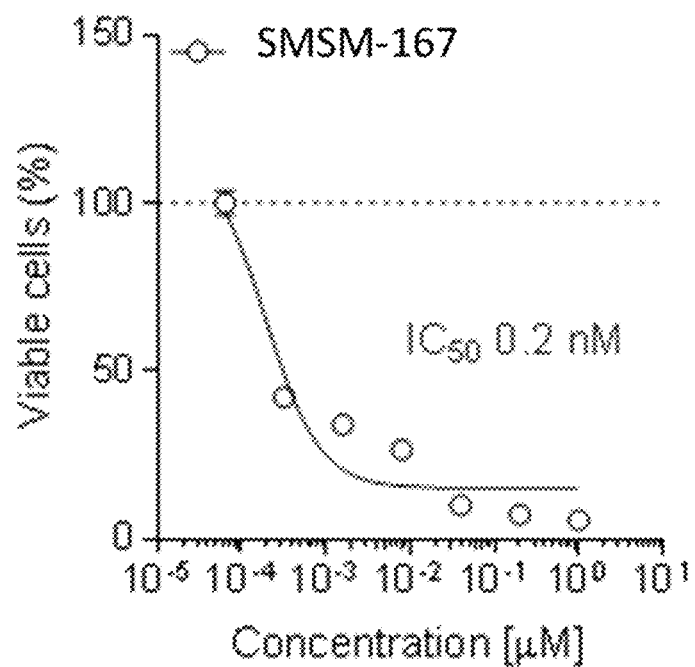
FIG. 9E depicts a graph of viable A-673 cells when incubated with the indicated concentrations of an SMSM.
Figure 9F:
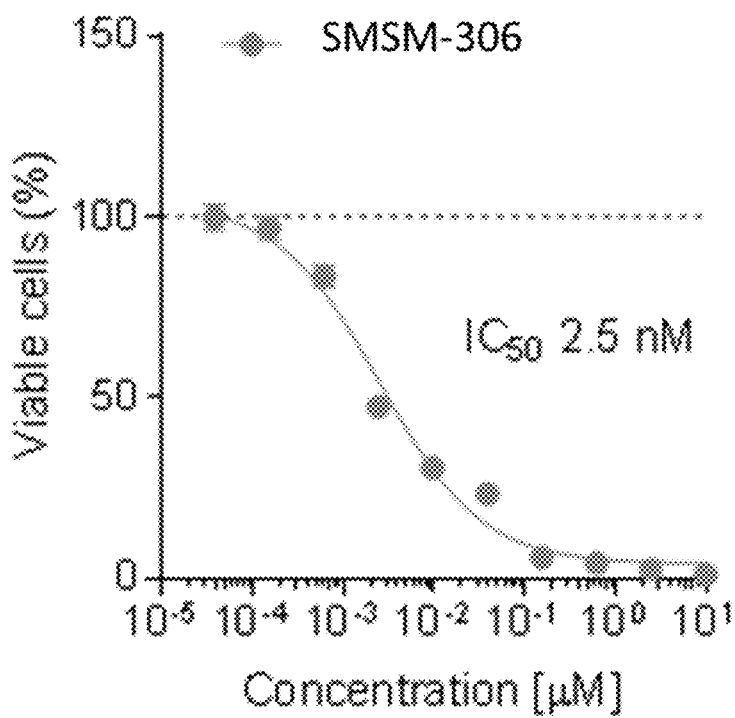
FIG. 9F depicts a graph of viable A-673 cells when incubated with the indicated concentrations of an SMSM.
Figure 9G:
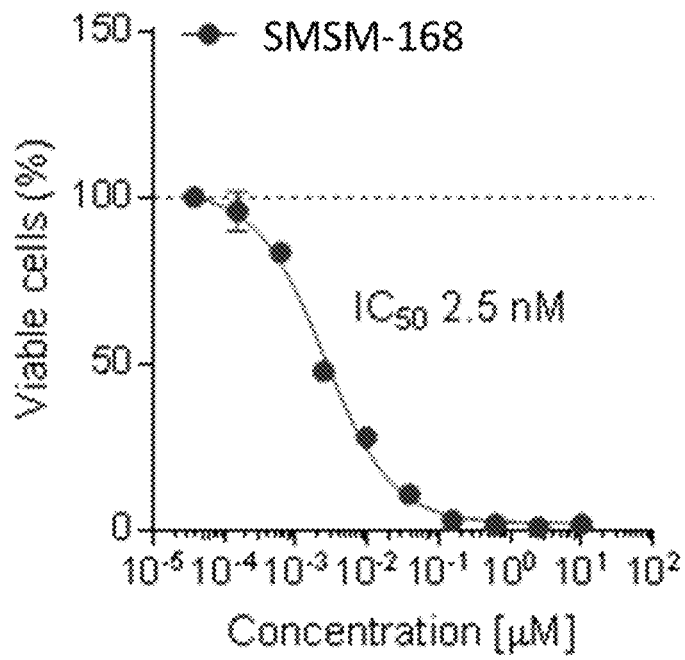
FIG. 9G depicts a graph of viable A-673 cells when incubated with the indicated concentrations of an SMSM.
Figure 9H:
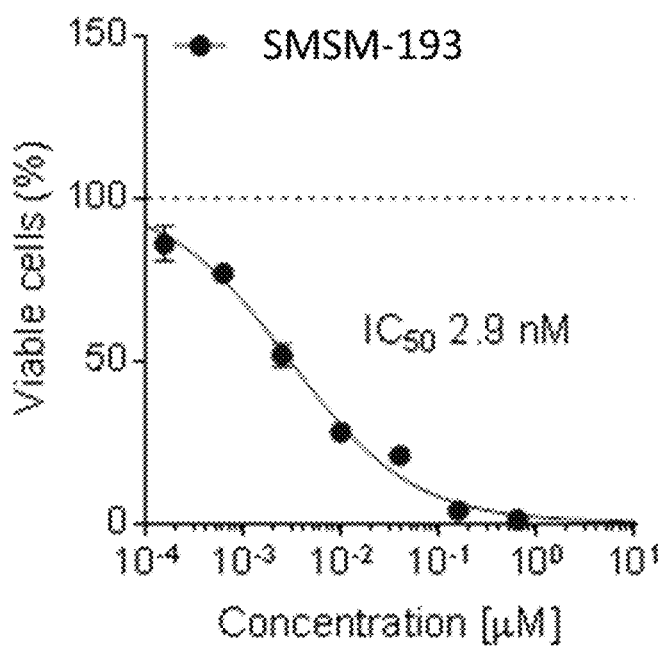
FIG. 9H depicts a graph of viable A-673 cells when incubated with the indicated concentrations of an SMSM.
Figure 10:
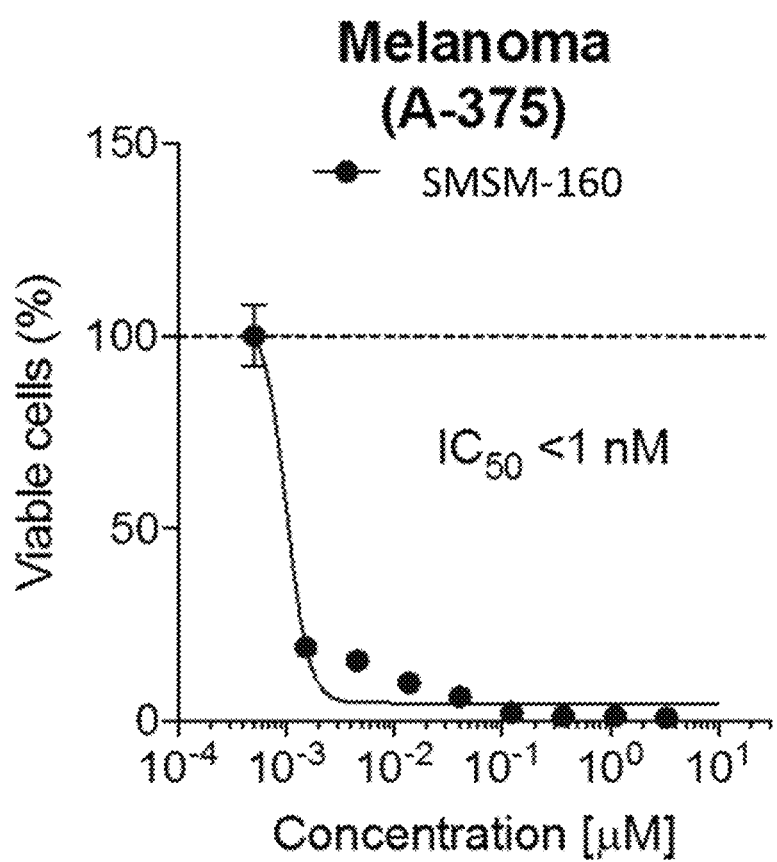
FIG. 10 depicts a graph of viable A-375 cells when incubated with the indicated concentrations of an SMSM.
Figure 11A:
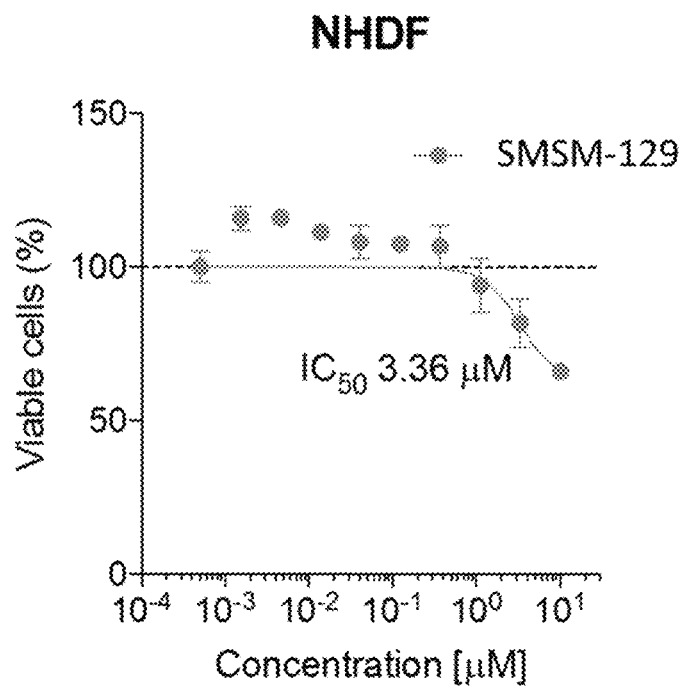
FIG. 11A depicts a graph of viable normal human dermal fibroblasts (NHDFs) cells when incubated with the indicated concentrations of an SMSM has a 100-fold higher therapeutic index compared to HDAC inhibitors.
Figure 11B:
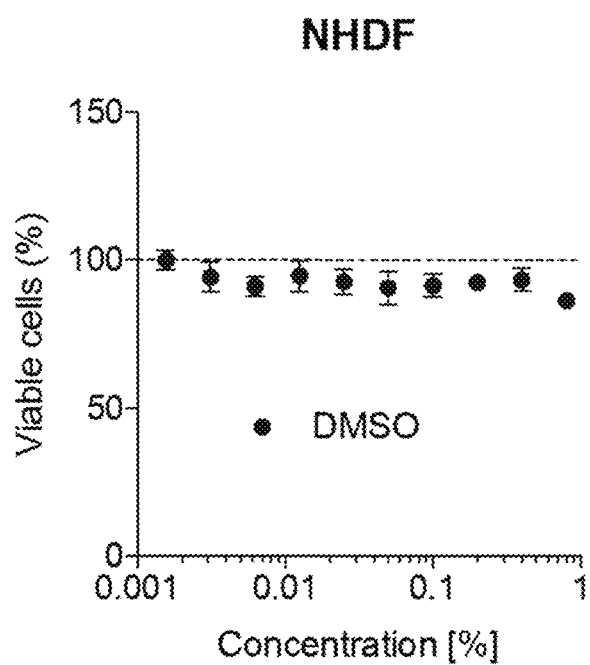
FIG. 11B depicts a graph of viable normal human dermal fibroblasts (NHDFs) cells when incubated with the indicated concentrations of DMSO.
Figure 12:
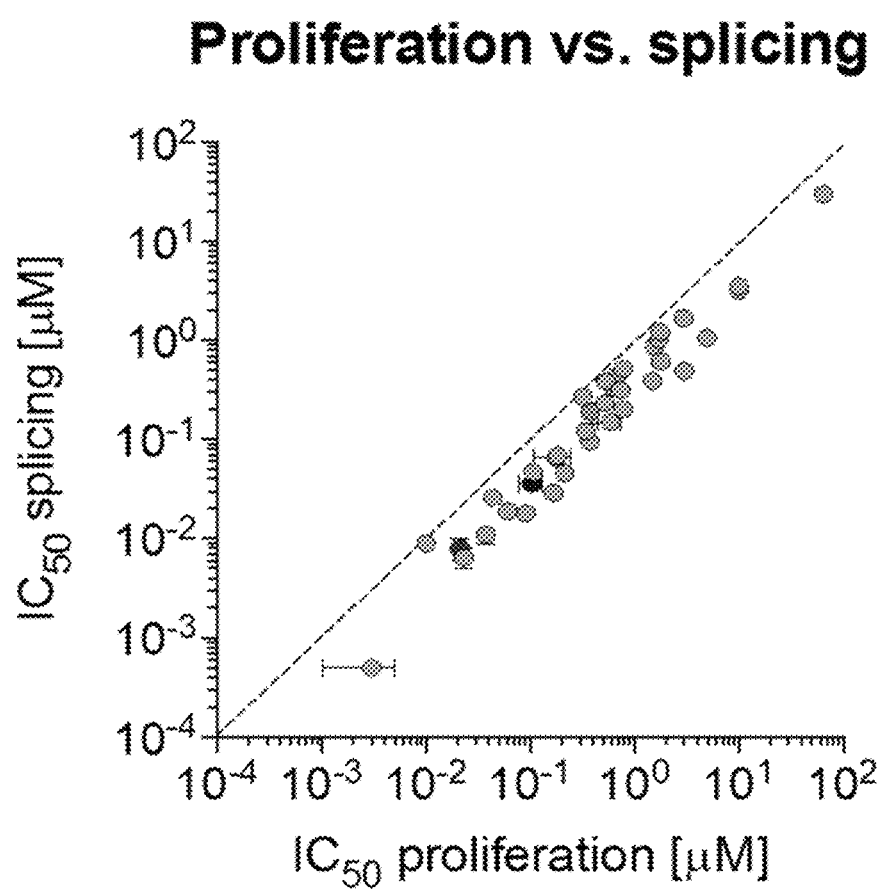
FIG. 12 depicts a graph of $IC_{50}$ splicing vs $IC_{50}$ proliferation for SMSMs disclosed herein. The results show viability potency correlates with cell splicing.
Figure 13:
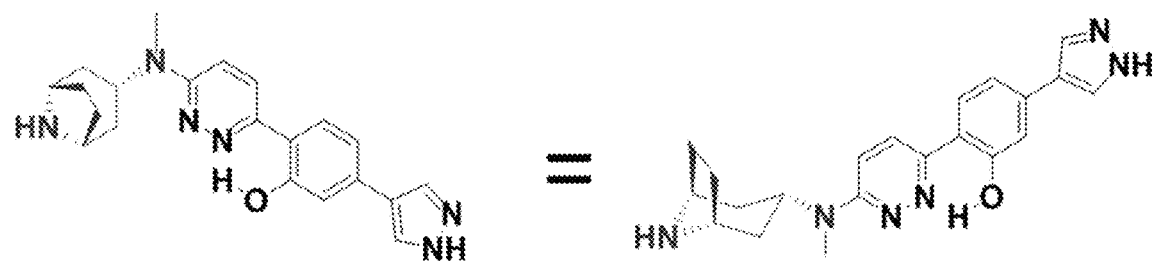
FIG. 13 illustrates representative impact of stereochemistry of depicted compound 1 and compound 2 on cell activity.
Figure 13:
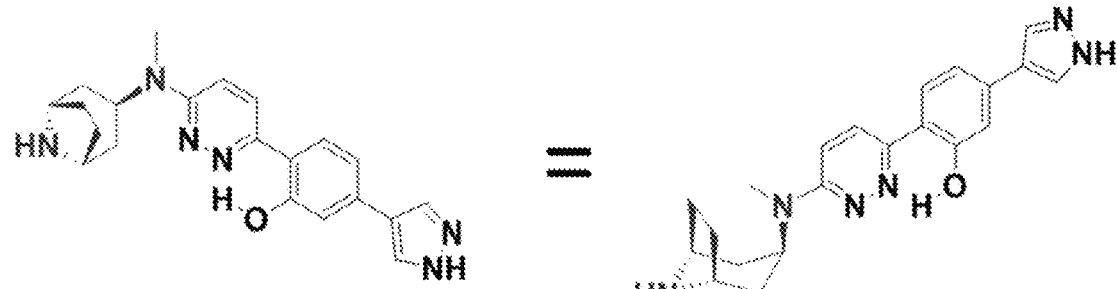

The SMSMs increased expression of the FOXM1$^{FL}$ mRNA. Correspondingly, the mRNAs for FOXM1$^{\Delta VIIa}$ declined. The data demonstrate that upregulation of FOXM1$^{FL}$ with downregulation of FOXM1$^{\Delta VIIa}$ by treatment with the SMSMs of the present disclosure were directly correlated, indicating an effect of the SMSMs on alternative splicing of FOXM1. The resulting concentration dependence curves of the FOXM1$\Delta^{VIIa}$ splice variant are fitted to a Hill binding equation to yield IC$_{50}$ values. Taken together, the data underline a splicing modifying activity in the FOXM1 gene. This may result in arrest of cell cycle and induction of apoptosis, as the FOXM1$^{FL}$ variant created by SMSM treatment is functionally inactive, and antagonizes the pro-proliferating. effect of functional FOXM1. Exemplary results are shown in FIG. 7 and FIG. 12.

Example 18: Maximum Tolerable Dose Study

Survival of mice after administration of SMSMs after 10 or 11 days was assessed.

Tolerance of the drug treatments was determined by measuring the weight of the mice during the period of drug administration. Body weight was measured prior to tumor inoculation and prior to the treatment administration and then daily. The changes in the final weight of the mice for the SMSM treatments were determined. Results are summarized in the table below:

| Group Treatment (3 per group) | Group # | Outcome | Route of Administration | Dose (mg/kg) | Dosing Schedule |
|---|---|---|---|---|---|
| Vehicle | 1 | All survived | IP | NA | QD x 11 |
| SMSM-151 | 2 | All survived | IP | 1 | QD x 11 |
| Vehicle | 3 | All survived | PO | NA | QD x 11 |
| SMSM-151 | 4 | All survived | PO | 10 | QD x 11 |
| SMSM-151 | 5 | All survived | PO | 10 | BID x 11 |
| Vehicle | 1 | All survived | IP | NA | QD x 12 |
| SMSM-167 | 2 | All survived | IP | 1 | QD x 12 |
| SMSM-167 | 3 | All survived | IP | 0.1 | BID x 12 |
| SMSM-167 | 4 | All survived | IP | 0.3 | BID x 12 |
| Vehicle | 5 | All survived | PO | NA | QD x 12 |
| SMSM-167 | 6 | All survived | PO | 5 | QD x 12 |
| SMSM-167 | 7 | BW loss in one animal | PO | 5 | BID x 12 |

Example 19: Dose Range and Time Course Studies

Dose range and time course studies comparing antineoplastic effects of SMSM-167 and SMSM-151 against vehicle were conducted.

Figure 14A:
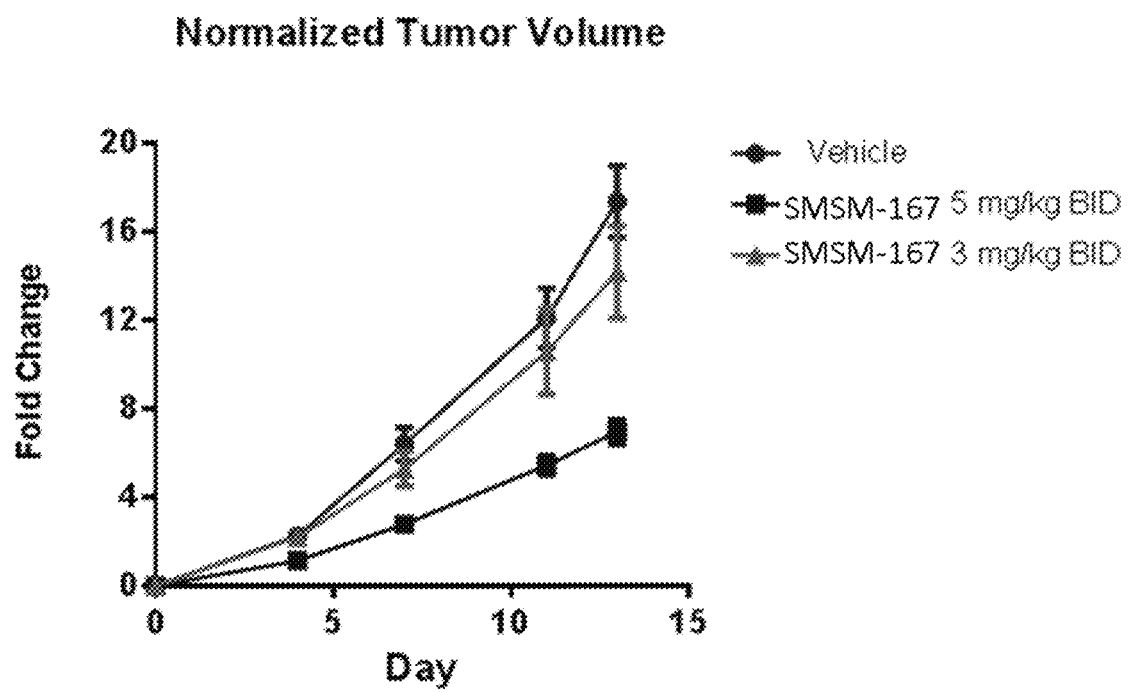
FIG. 14A depicts a graph showing normalized fold change in A-673 xenograft tumor volumes after treatment of mice with the indicated doses of an SMSM for the indicated time.
Figure 14B:
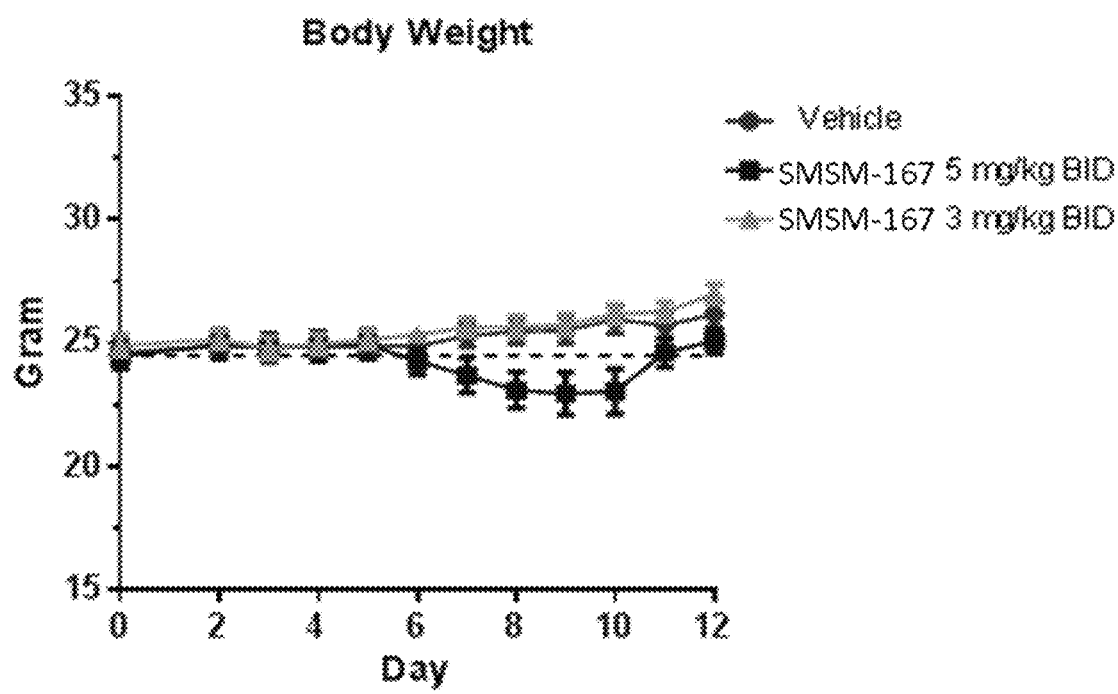
FIG. 14B depicts a graph of percent body weight change of mice post treatment with the indicated doses of an SMSM.
Figure 14C:
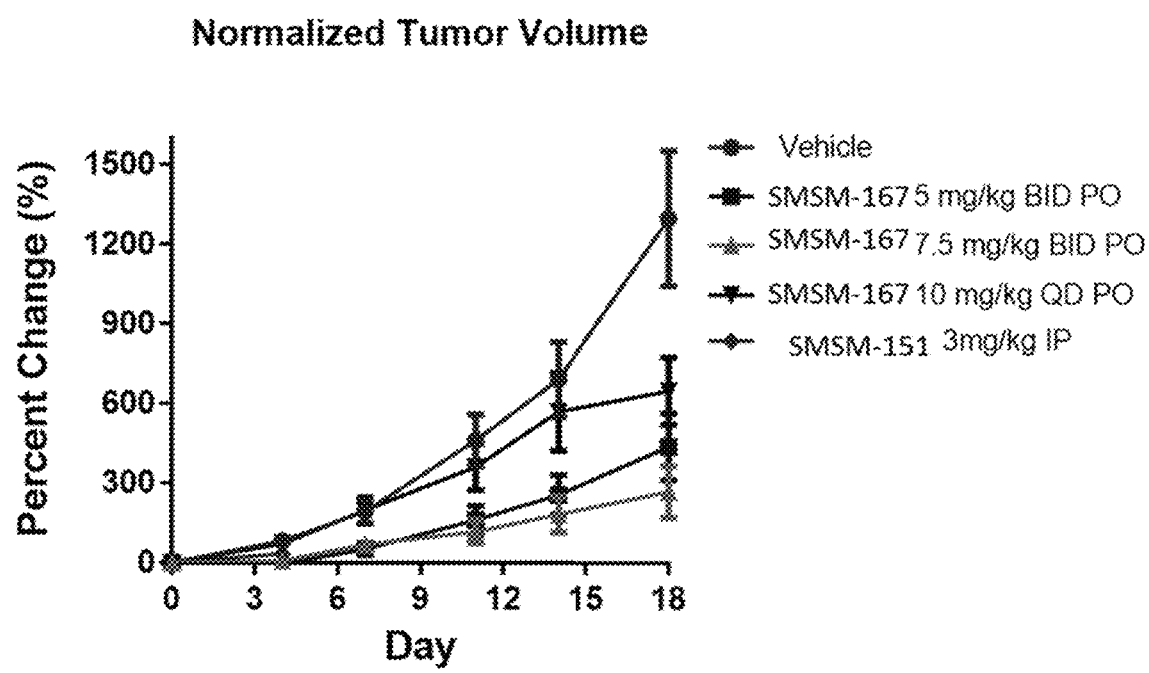
FIG. 14C depicts a graph showing normalized percent change in A-673 xenograft tumor volumes post treatment of mice with the indicated doses of an SMSM.

Experimental groups used for this study are shown in the table below and FIGS. 14A-C.

| Group | Group Treatment | Dose (mg/kg) | Dosing Schedule | Route of Administration | # Mice |
|---|---|---|---|---|---|
| 1 | Vehicle | NA | QD x 14 | PO | 10 |
| 2 | SMSM-151 | 3 mg/kg | BID x 14 | IP | 10 |
| 3 | SMSM-167 | 5 mg/kg | BID x 14 | PO | 10 |
| 4 | SMSM-167 | 7.5 mg/kg | BID x 14 | PO | 10 |
| 5 | SMSM-167 | 10 mg/kg | QD x 14 | PO | 10 |

Female NCrNu mice were used. Age range of enrolment was 7-10 weeks. A total of 75 animals were for the studies.

The A673 tumor cell line was maintained in vitro as a monolayer culture. The tumor cells were routinely subcultured twice weekly by Tryp1E, and did not to exceed 4-5 passages. The cells growing in an exponential growth phase were harvested and counted for tumor inoculation.

Each mouse were inoculated into a right flank with the single cell suspension of 950 viable tumor cells (5×10$^6$ cells/mouse) in serum-free RPMI 1640 Media for tumor development. Treatments were administered when mean tumor size reached approximately 75 mm$^3$.

An acclimation period of a minimum of 72 hrs was allowed between animal receipt and tumor inoculation in order to accustom the animals to the laboratory environment. Immunodeficient NCrNu mice were maintained in a pathogen-free environment. Animals were fed a diet of Irradiated Mouse pellet feed Purina rodent diet #5053 (Fisher Feeds, Bound Brook, N.J.) and chlorinated water from a reverse osmosis (RO) system (4-6 ppm).

Before commencement of treatment, all animals were weighed and assigned to treatment groups using a randomization procedure. Mice were randomized into groups based upon their tumor sizes to ensure that each group had approximately the same mean tumor size and range of tumor size.

After inoculation, the animals were checked daily for morbidity and mortality. At the time of routine monitoring, the animals were checked for any effects of tumor growth on normal behavior such as mobility, food and water consumption, body weight gain/loss, eye/hair matting and any other abnormal effects. Deaths and observed clinical signs were recorded. Animals that were observed to be in a continuing deteriorating condition or bearing a tumor exceeding 2,000 mm$^3$ in size were euthanized.

Body weight were measured prior to tumor inoculation and prior to the treatment administration and then daily. Tumor size were measured 2-3 times per week in two dimensions using a caliper, and the volume were expressed in mm$^3$ using the formula: V=0.5×a×b$^2$ where a and b are the long and short diameters of the tumor, respectively.

Studies were terminated when the tumor size in the vehicle treated group reached 2,000 mm$^3$. Each mouse was bled at 2 hrs after the last dose and at least 50 µl of plasma were collected from each mouse. All of the collected plasma samples and retainer dosing solutions for each dose level were used for bioanalytical measurements. All tumors were also collected and weighed. One necrosis-free tumor fragment of approximately 50 mg was taken from each tumor and flash-frozen for RNA isolation. The remaining tumor was flash frozen for PK analysis.

Example 20: Subcutaneous U87-Luc Brain Tumor Model in Ncr Nude Mice

The efficacy of SMSM-167, SMSM-160 and SMSM-151 in a subcutaneous U87-Luc brain tumor model in C.B-17 SCID mice was assessed.

Figure 15A:
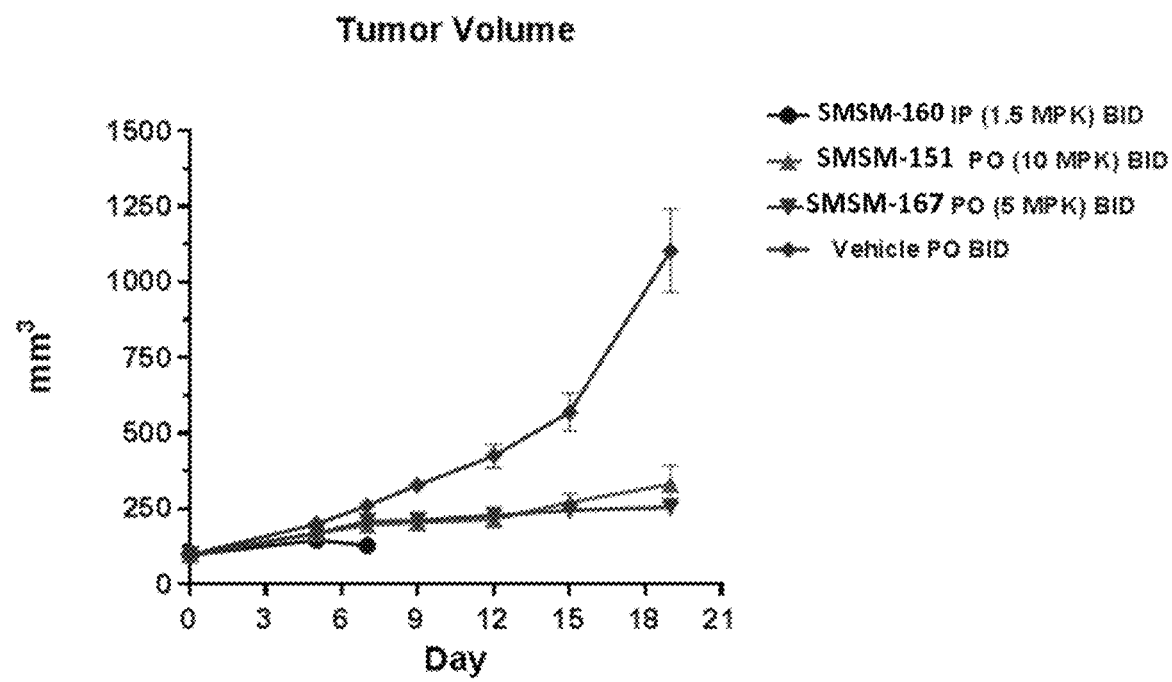
FIG. 15A depicts a graph showing change in A-673 xenograft tumor volumes post treatment of mice with the indicated doses of an SMSM.
Figure 15B:
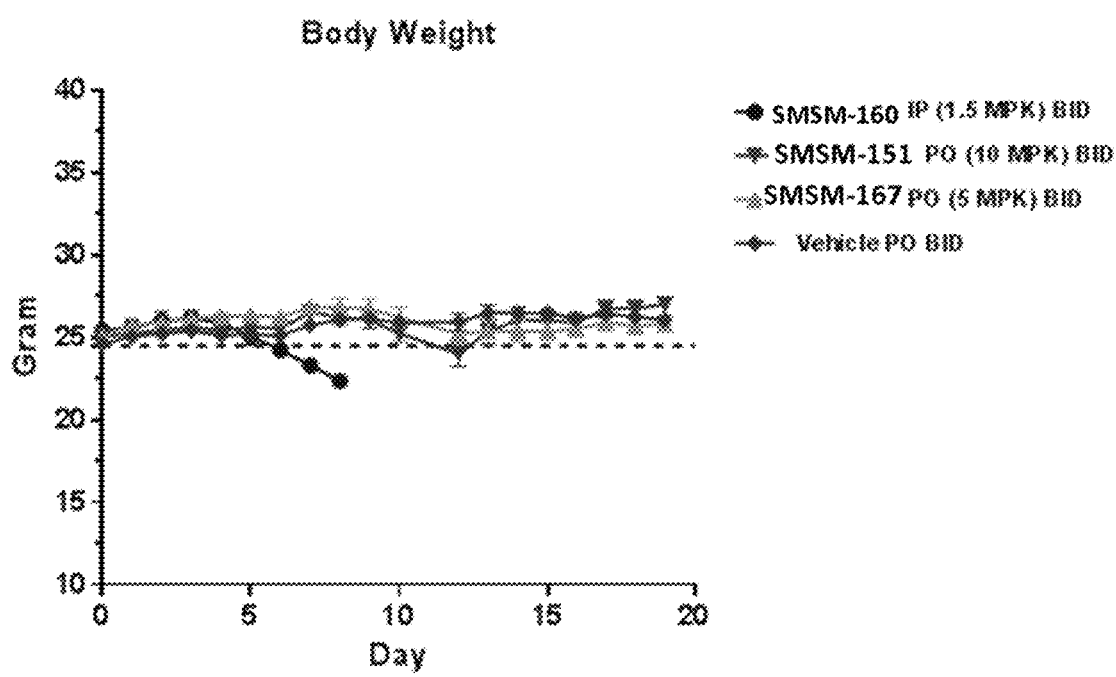
FIG. 15B depicts a graph of percent body weight change of mice post treatment with the indicated doses of an SMSM.

Experimental groups to be used for this study are shown in the table below and FIGS. 15A-B.

| Group | Group Treatment | Dose (mg/kg) | Dosing Schedule | Routeof Administration | # Mice/ Group |
|---|---|---|---|---|---|
| 1 | Vehicle | — | BID x 14 | PO | 10 |
| 2 | SMSM-160 | 1.5 mg/kg | BID x 14 | IP | 10 |
| 3 | SMSM-151 | 10 mg/kg | BID x 14 | PO | 10 |
| 4 | SMSM-167 | 5 mg/kg | BID x 14 | PO | 10 |

Tumor inoculation began on day 0. Treatments were administered when mean tumor size reached approximately 100 mm$^3$. 100 mice were used for this study.

An acclimation period of a minimum of 72 hrs was allowed between animal receipt and tumor inoculation in order to accustom the animals to the laboratory environment. Animals were fed a diet of Irradiated Mouse pellet feed Purina rodent diet #5053 (Fisher Feeds, Bound Brook, N.J.) and chlorinated water from a reverse osmosis (RO) system (4-6 ppm).

Before commencement of treatment, all animals were weighed and assigned to treatment groups using a randomization procedure. Mice were randomized into groups based upon their tumor sizes, as measured by caliper to ensure that each group had approximately the same mean tumor size and range of tumor size.

After inoculation, the animals were checked daily for morbidity and mortality. At the time of routine monitoring, the animals were checked for any effects of tumor growth on normal behavior such as mobility, food and water consumption, body weight gain/loss, eye/hair matting and any other abnormal effects. Deaths and observed clinical signs were recorded. Animals that were observed to be in a continuing deteriorating condition or bearing a tumor exceeding 2,000 mm$^3$ in size were euthanized.

Body weight was measured prior to tumor inoculation and prior to the treatment administration and then daily. Tumor size was measured 2 times per week in two dimensions using a caliper. Studies were terminated when the tumor size in the vehicle treated group reached 2,000 mm$^3$. Each mouse was bled at 2 hrs after the last dose and at least 50 μl of plasma was collected from each mouse. All of the collected plasma samples and retainer dosing solutions for each dose level were used for bioanalytical measurements. All tumors were also collected and weighed. One necrosis-free tumor fragment of approximately 50 mg was taken from each tumor and flash-frozen for RNA isolation. The remaining tumor was flash frozen for PK analysis.

Example 21: In Vivo SMSM Treatment Inhibits Tumor Growth

Studies were performed to assess the effects of in vivo SMSM treatment on glioblastoma, breast, pancreatic, prostate, melanoma, lymphoma and Ewing sarcoma tumors. Studies were also performed to assess the effects of in vivo SMSM treatment on mRNA levels. Immunocompromised nude mice with pre-existing glioblastoma, breast, pancreatic, prostate, melanoma, lymphoma and Ewing sarcoma xenografts were treated with vehicle or SMSMs. Tumor tissues from subcutaneous xenografts were broken into a powder using a BioPulverizer (Biospec Products, Inc.). After SMSM treatment, mRNA was isolated from the xenografts and was analyzed by qRT-PCR.

Tumor size was measured 2 times per week in two dimensions using a caliper. Studies were terminated when the tumor size in the vehicle treated group reached 2,000 mm$^3$. Each mouse was bled at 2 hrs after the last dose and at least 50 μl of plasma was collected from each mouse. All of the collected plasma samples and retainer dosing solutions for each dose level were used for bioanalytical measurements. All tumors were also collected and weighed. One necrosis-free tumor fragment of approximately 50 mg was taken from each tumor and flash-frozen for RNA isolation. The remaining tumor was flash frozen for PK analysis.

The effects of in vivo SMSM treatments on pre-existing subcutaneous glioblastoma, breast, pancreatic, prostate, melanoma, lymphoma and Ewing sarcoma xenografts were assessed. For these in vivo experiments, 1×10$^6$ Raji, A375, A673, MDA-MB-231, BxPC-3, PC-3 or U87 (cells re- suspended in 100 μl PBS were subcutaneously injected into the flanks of nude mice. When the tumor reached approximately 100 mm$^3$ (volume=(3/4)(π)(length/2)(width/2)$^2$), the treatments indicated in the tables below were initiated.

As shown in the table below and FIGS. 14A, 14B and 14C, SMSM-160 treatment of immunocompromised nude mice with pre-existing A673 xenografts led to tumor growth inhibition (TGI). (TGI (%)=(1−(TV$_{Treatment/Dx}$−TV$_{Treatment/D1}$)/(TV$_{Control/Dx}$−TV$_{Control/D1}$))×100).

|  |  | TGI(%) | | | |
| --- | --- | --- | --- | --- | --- |
| Group |  | Day 7 | Day 11 | Day 14 | Day 18 |
| SMSM-167 5 mg/kg BID PO | 1 | 65.56% | 56.92% | 55.14% | 59.68% |
| SMSM-167 7.5 mg/kg BID PO | 2 | 59.45% | 64.75% | 64.43% | 72.80% |
| SMSM-167 10 mg/kg QD PO | 3 | −32.72% | 3.85% | −2.13% | 41.77% |

Figure 16A:
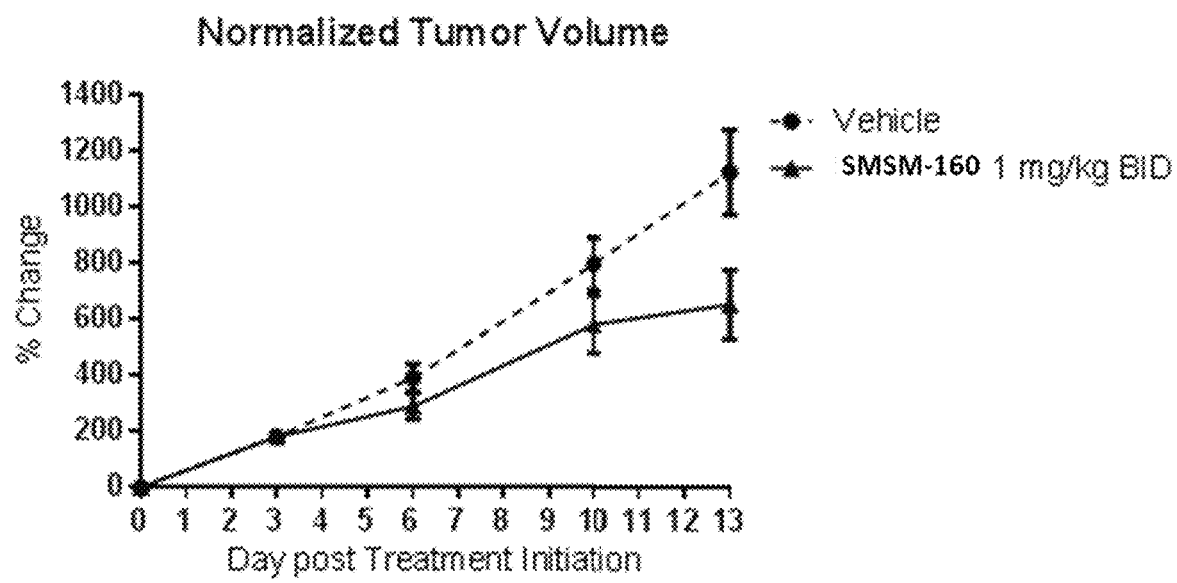
FIG. 16A depicts a graph showing normalized percent change in A-673 xenograft tumor volumes post treatment of mice with the indicated doses of an SMSM.
Figure 16B:
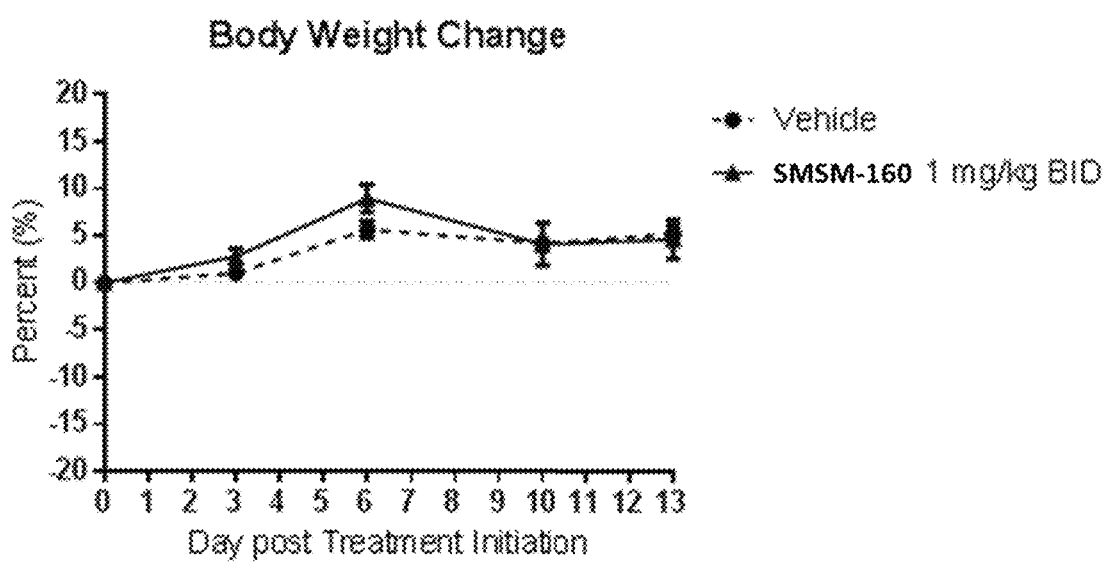
FIG. 16B depicts a graph of percent body weight change of mice post treatment with the indicated doses of an SMSM.
Figure 16C:
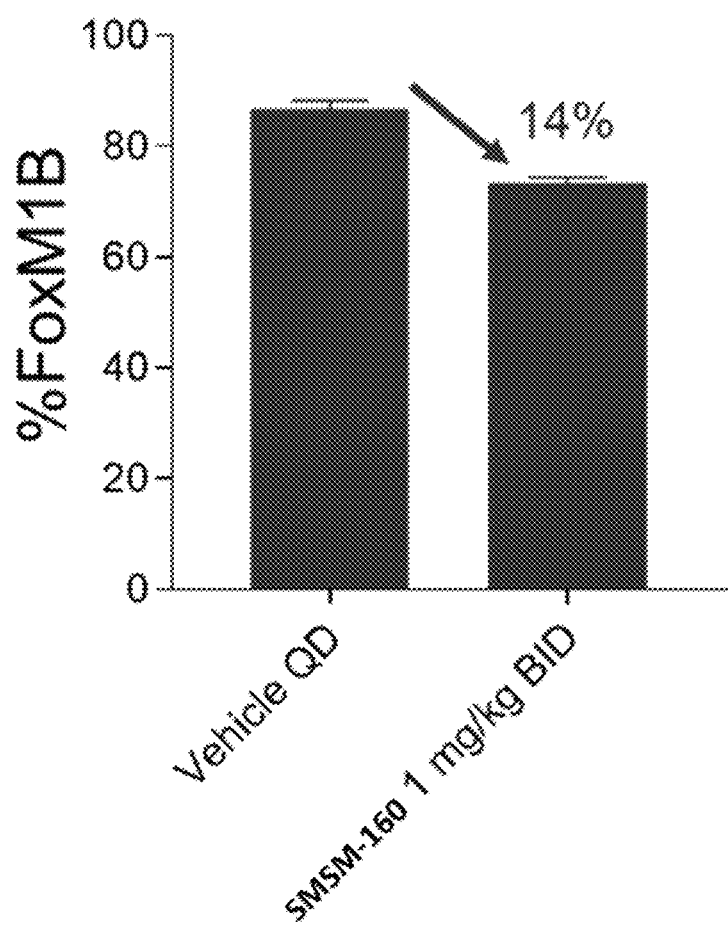
FIG. 16C depicts a graph showing normalized relative transcript levels of FOXM1 isoform B in the mice post treatment with the indicated dose of an SMSM.

As shown in the table below and FIGS. 16A, 16B and 16C, SMSM-160 treatment of immunocompromised nude mice with pre-existing A673 xenografts led to tumor growth inhibition (TGI). (TGI (%)=(1−(TV$_{Treatment/Dx}$−TV$_{Treatment/D1}$)/(TV$_{Control/Dx}$−TV$_{Control/D1}$))×100).

|  |  | Tumor Growth Inhibition (TGI) (%) | | | |
| --- | --- | --- | --- | --- | --- |
| Group |  | Day 3 | Day 6 | Day 10 | Day 13 |
| SMSM-160; 1 mg/kg; BID | 2 | −0.94% | 25.67% | 25.67% | 42.90% |

Figure 17A:
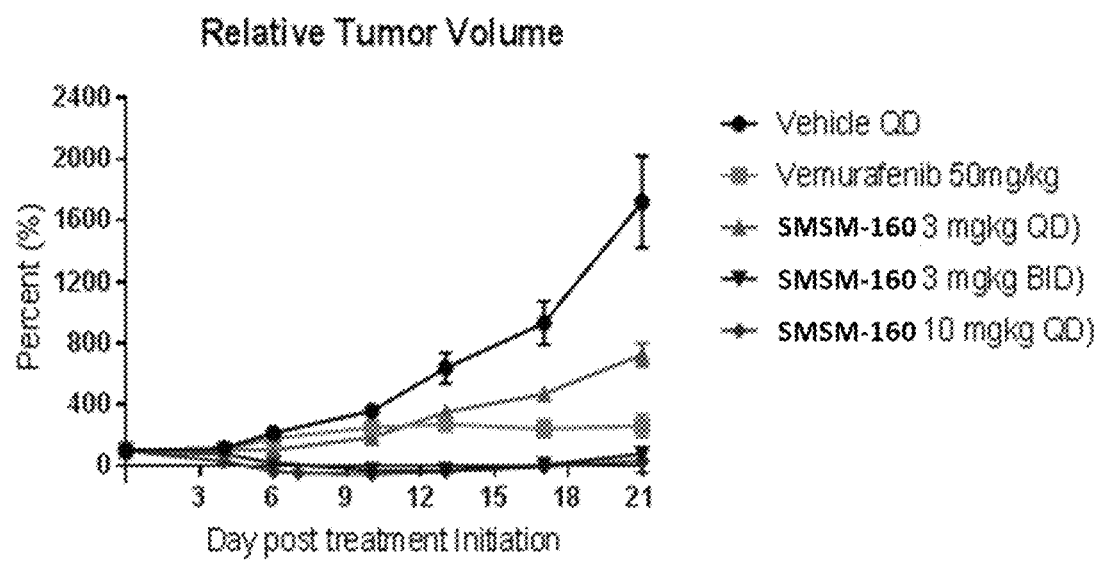
FIG. 17A depicts a graph showing normalized fold change in A-375 xenograft tumor volumes post treatment of mice with the indicated doses of an SMSM or vemurafenib.
Figure 17B:
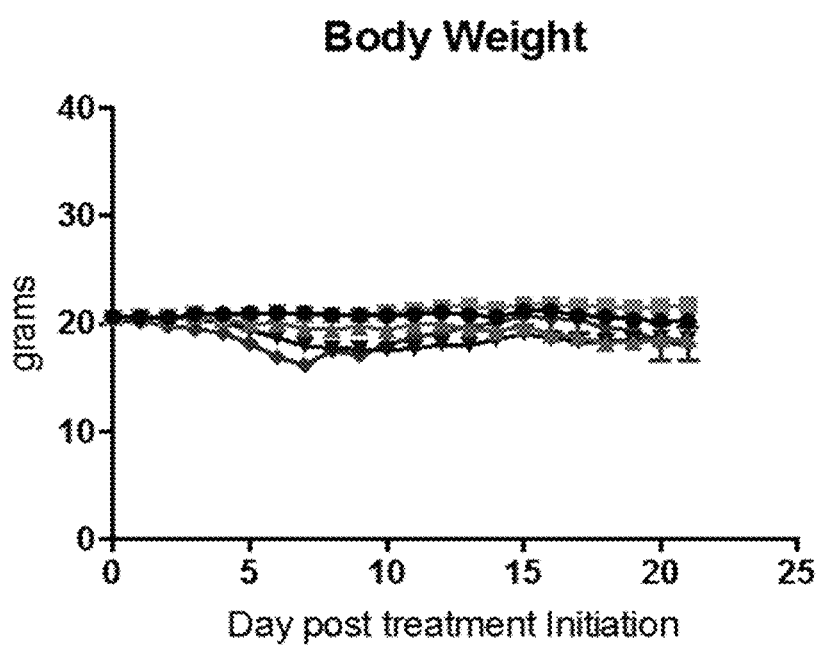
FIG. 17B depicts a graph of percent body weight change of mice post treatment with the indicated doses of an SMSM or vemurafenib.
Figure 17C:
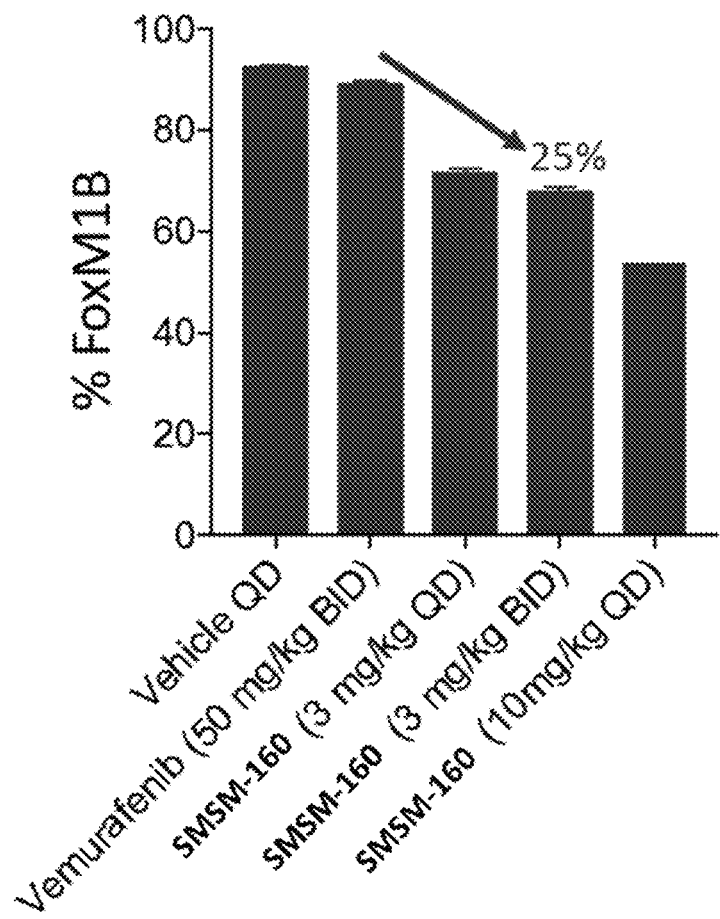
FIG. 17C depicts a graph showing normalized relative transcript levels of FOXM1 isoform B in the mice post treatment with the indicated doses of SMSMs or vemurafenib.
Figure 18A:
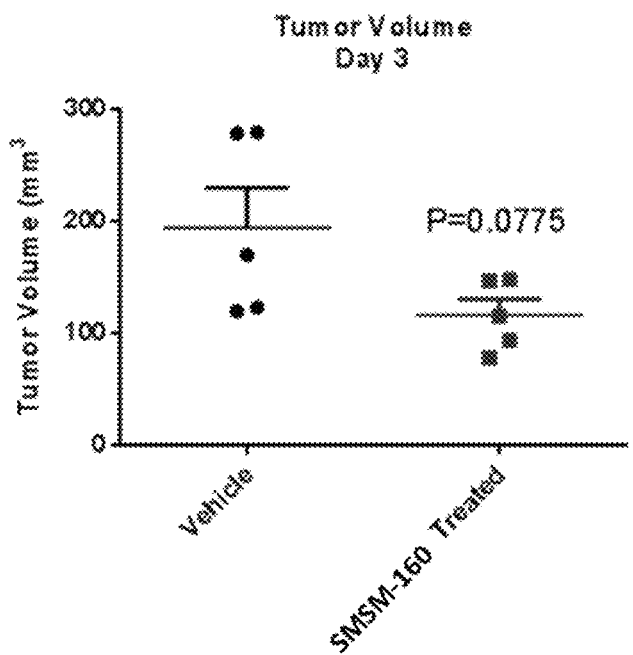
FIG. 18A depicts a graph showing fold change in U87 (glioblastoma) xenograft tumor volumes three days post treatment of severe combined immunodeficiency (SCID) mice with the indicated doses of an SMSM.
Figure 18B:
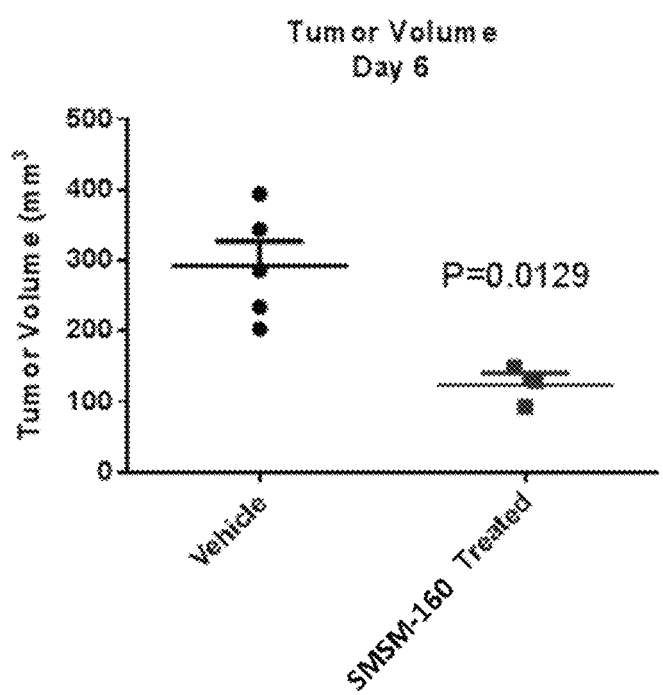
FIG. 18B depicts a graph showing fold change in U87 (glioblastoma) xenograft tumor volumes three days post treatment of SCID mice with the indicated doses of an SMSM.
Figure 19A:
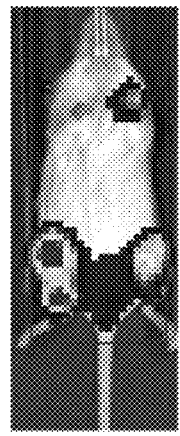
FIG. 19A depicts dorsal and ventral bioluminescence in Raji (lymphoma) xenograft SCID mice post treatment with an SMSM.
Figure 19A:
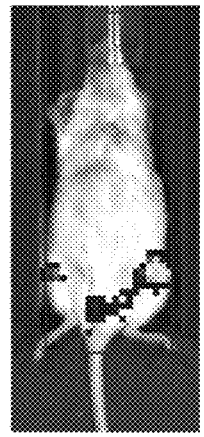
Figure 19A:
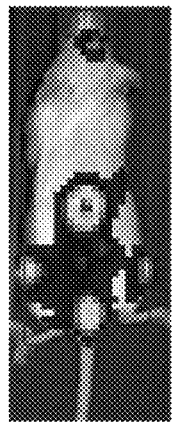
Figure 19A:
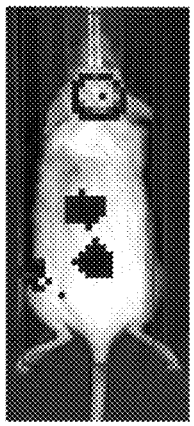
Figure 19B:
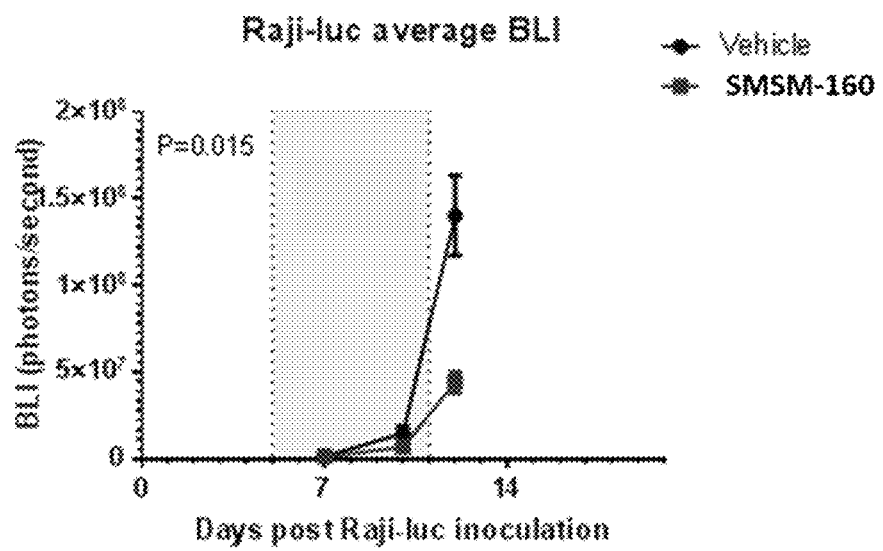
FIG. 19B depicts a graph of ventral bioluminescence in Raji (lymphoma) xenograft SCID mice post treatment with an SMSM.
Figure 19C:
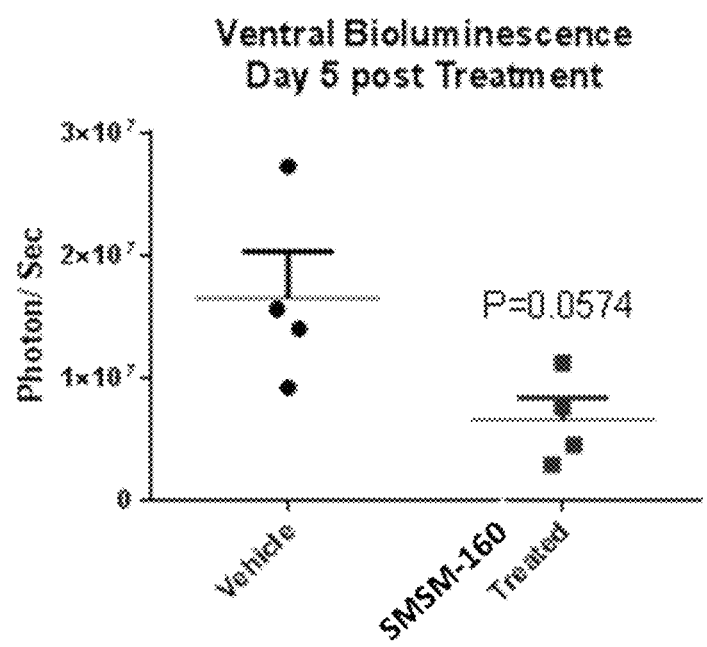
FIG. 19C depicts of ventral bioluminescence in Raji (lymphoma) xenograft SCID mice five days post treatment with an SMSM.

As shown in the table below and FIGS. 17A and 17B, SMSM-160 treatment of immunocompromised nude mice with pre-existing A375 xenografts led to tumor growth inhibition (TGI).

|  | Tumor Growth Inhibition (TGI) (%) | | | | | |
| --- | --- | --- | --- | --- | --- | --- |
| Group | D4 | D6 | D10 | D13 | D17 | D21 |
| Vemurafenib; 50 mg/kg; p.o.; BID | 9.47% | 9.98% | 24.32% | 50.53% | 69.66% | 82.03% |
| SMSM-160; 3 mg/kg; ip.; QD | 3.40% | 47.56% | 44.13% | 40.08% | 45.12% | 53.98% |
| SMSM-160; 3 mg/kg; ip.; BID | 33.09% | 92.99% | 109.59% | 105.98% | 99.59% | 94.68% |
| SMSM-160; 10 mg/kg; ip.; QD*5 day | 72.84% | 118.42% | 112.78% | 103.12% | 97.84% | 95.59% |

Figure 20A:
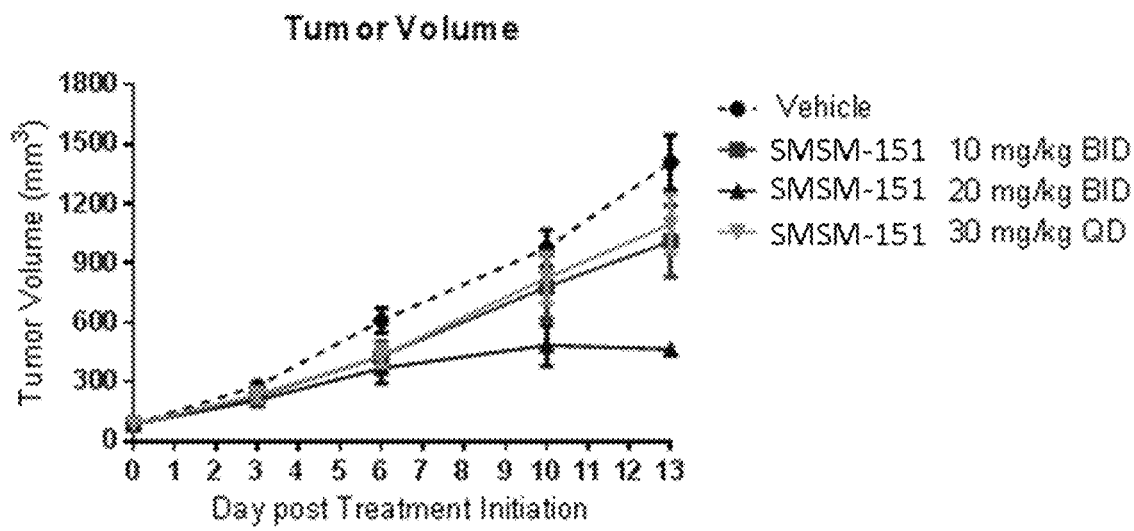
FIG. 20A depicts a graph showing fold change in A-673 xenograft tumor volumes post treatment with of mice with the indicated doses of an SMSM.
Figure 20B:
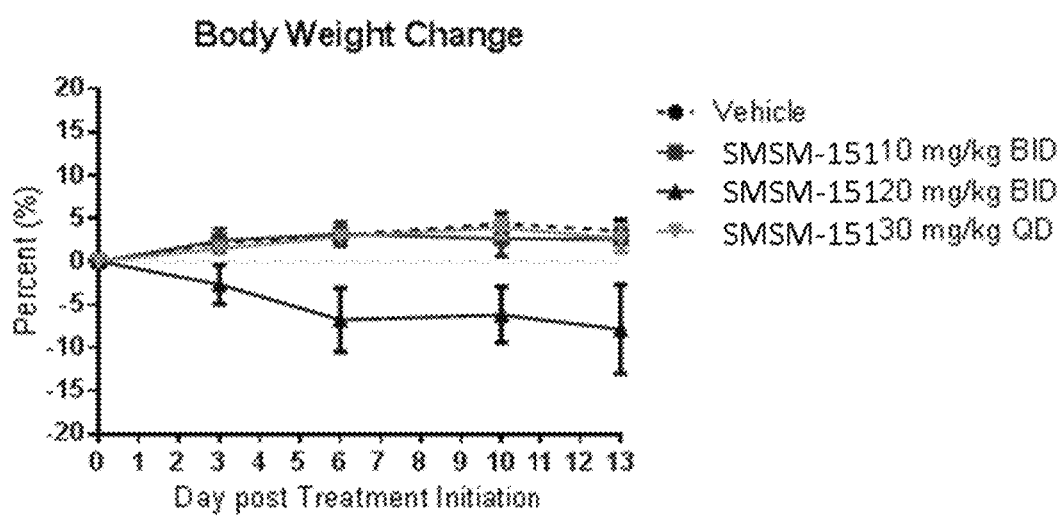
FIG. 20B depicts a graph of percent body weight change of mice post treatment with the indicated doses of an SMSM.

As shown in the table below and FIGS. 20A and 20B, SMSM-151 treatment of immunocompromised nude mice with pre-existing A673 xenografts led to tumor growth inhibition (TGI).

| Group | Tumor Growth Inhibition (TGI) (%) | | | |
| --- | --- | --- | --- | --- |
| | Day 3 | Day 6 | Day 10 | Day 13 |
| SMSM-151 10 mg/kg BID p.o. | 28.03% | 34.29% | 22.09% | 30.12% |
| SMSM-151 20 mg/kg BID p.o. | 37.61% | 45.97% | 55.24% | 71.29% |
| SMSM-151 30 mg/kg QD p.o. | 23.90% | 34.28% | 17.11% | 23.52% |

Figure 21A:
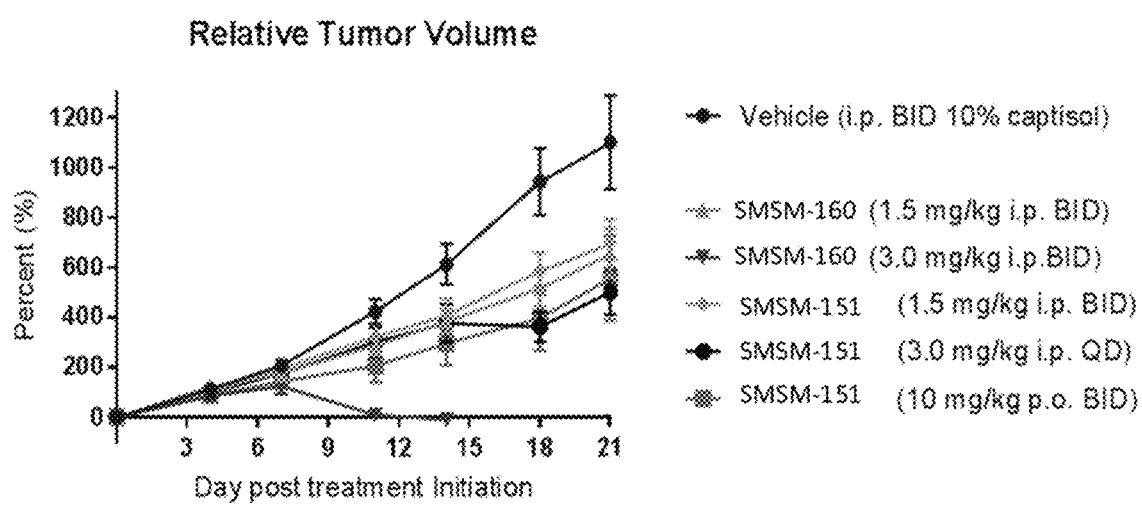
FIG. 21A depicts a graph showing normalized percent change in A-375 xenograft tumor volumes post treatment with of mice with the indicated doses of SMSMs.
Figure 21B:
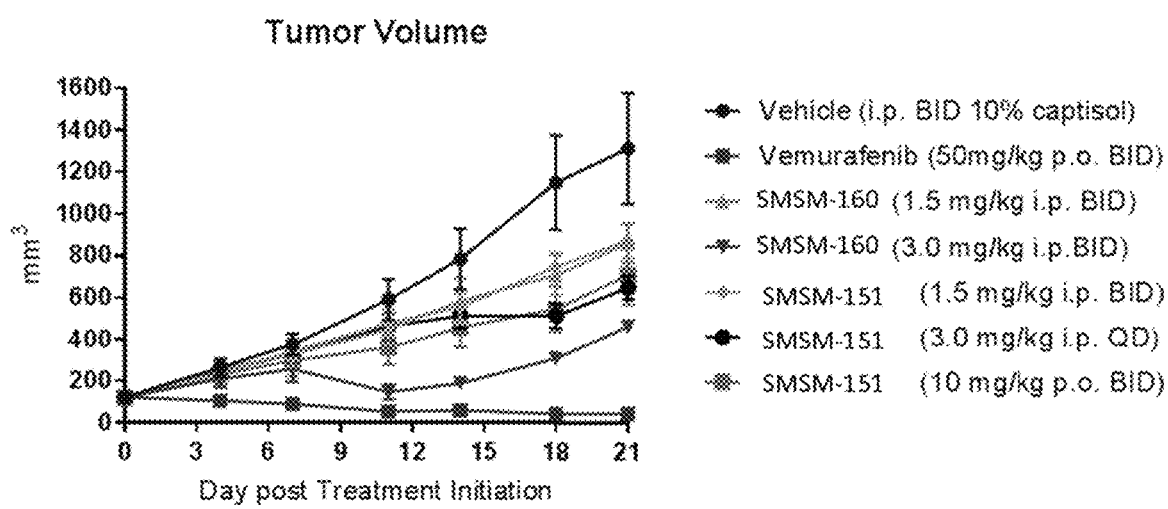
FIG. 21B depicts a graph showing volumes of tumors in A-375 xenograft mice post treatment with the indicated doses of SMSMs.
Figure 21C:
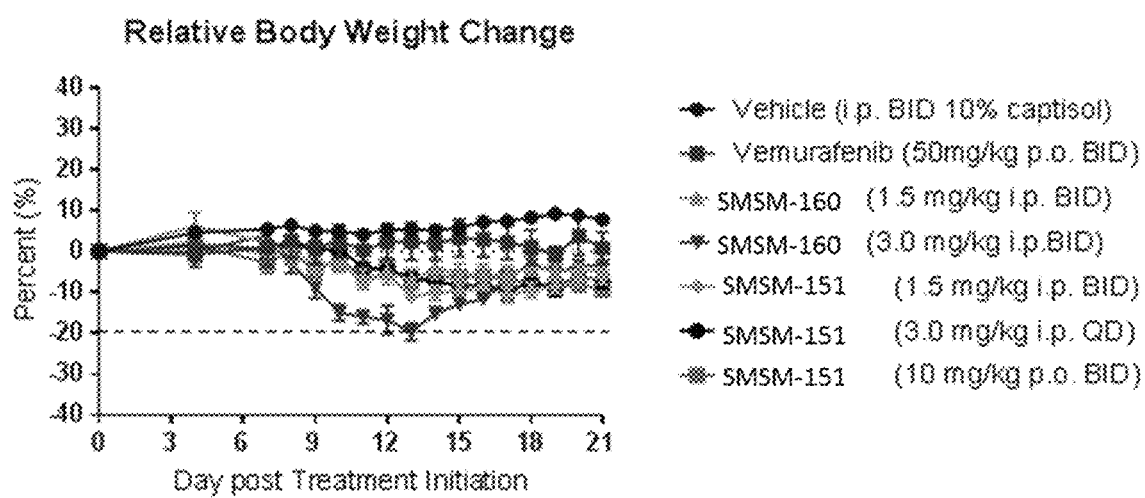
FIG. 21C depicts a graph of percent body weight change of mice post treatment with the indicated doses of an SMSM or vemurafenib.
Figure 22:
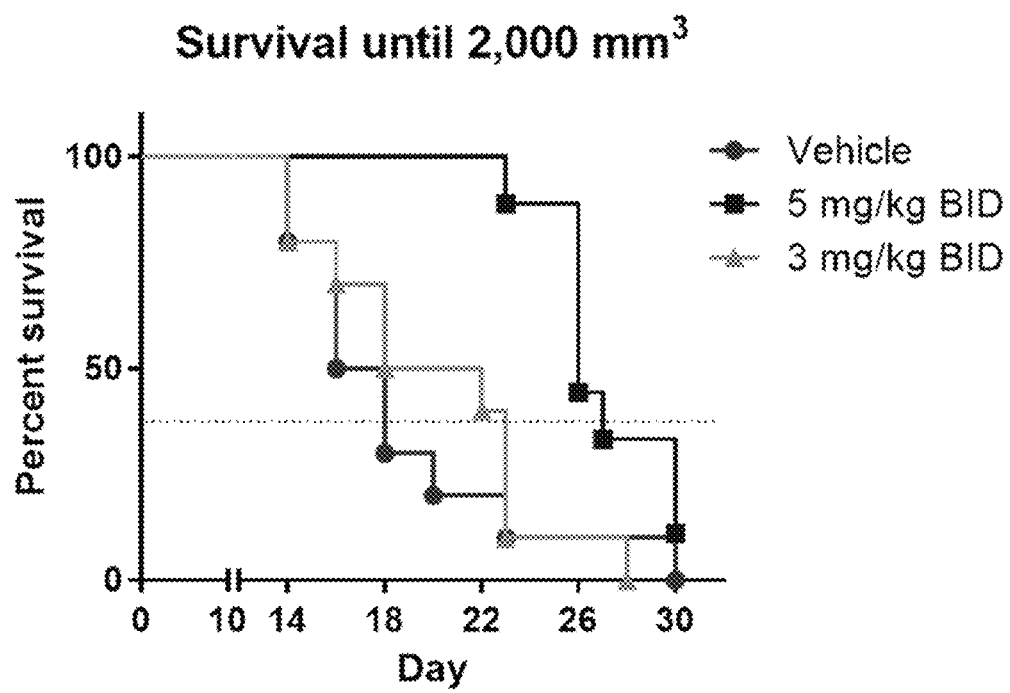
FIG. 22 depicts a Kaplan-Meier plot of percent survival over time of A-673 Ewing's sarcoma mice mean after treatment with the indicated doses of an SMSM administered twice a day (b.i.d.).
Figure 23:
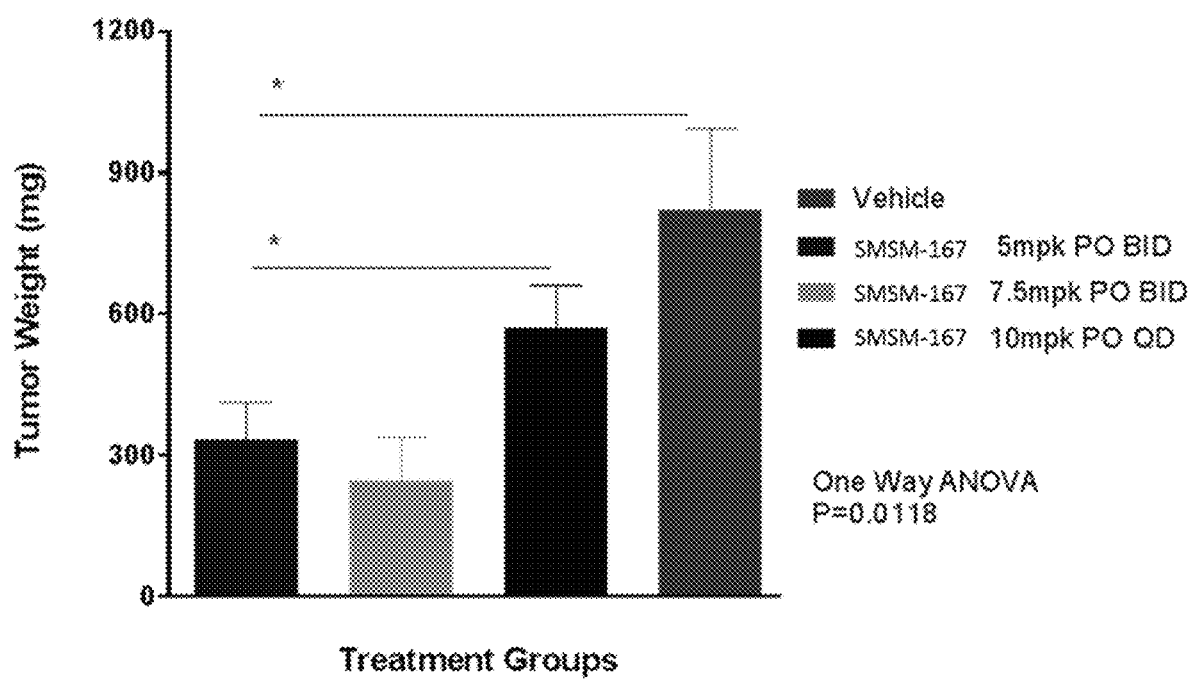
FIG. 23 depicts a graph of A-673 xenograft tumor weights post treatment of mice with the indicated doses of SMSMs.

As shown in the table below and FIGS. 21A and 21B, SMSM-160 or SMSM-151 treatment of immunocompromised nude mice with pre-existing A-375 xenografts led to tumor growth inhibition (TGI).

| Group | Tumor Growth Inhibition (TGI) (%) | | | | | |
| --- | --- | --- | --- | --- | --- | --- |
| | D 4 | D 7 | D 11 | D 14 | D 18 | D 21 |
| Vemurafenib, 50 mg/kg, p.o., BID *21 days | 111.22% | 112.77% | 114.44% | 109.55% | 107.72% | 106.56% |
| SMSM-160 1.5 mg/kg, i.p., BID *21 days | 3.60% | 18.11% | 30.05% | 30.28% | 42.80% | 37.88% |
| SMSM-160 3 mg/kg, i.p., BID *21 days | 38.68% | 46.64% | 94.46% | 89.78% | 81.80% | 71.33% |
| SMSM-151 1.5 mg/kg, i.p., BID *21 days | 21.81% | 13.08% | 24.17% | 34.70% | 39.27% | 36.89% |
| SMSM-151 3 mg/kg, i.p., QD *21 days | 15.21% | 18.86% | 27.48% | 41.30% | 62.06% | 55.77% |
| SMSM-151 10 mg/kg, p.o., BID *21 days | 22.49% | 28.98% | 48.28% | 49.06% | 58.41% | 50.32% |

Example 22: Pharmacodynamics

A-673 cell viability ($IC_{50}$), Splicing ($IC_{50}$) and brain AUC/Plasma AUC of SMSMs were determined. As shown in the tables below SMSMs had high CNS exposure.

| Compound | A-673 cell viability ($IC_{50}$) | Splicing ($IC_{50}$) | Brain/Plasma AUC |
| --- | --- | --- | --- |
| SMSM-151 | ≤5 nM | <1 nM | 1.4 (PO, rat) |
| SMSM-160 | ≤5 nM | <1 nM | 0 |
| SMSM-167 | <0.5 nM | <1 nM | 0.5 (PO, rat); 0.27 (PO, mouse) |
| SMSM-168 | ≤5 nM | <1 nM | 3.7 (PO, rat); 0.46 (PO, mouse) |
| SMSM-169 | ≤5 nM | <1 nM | 0.6 (PO, rat); 0.17 (PO, mouse) |
| SMSM-191 | <1 nM | | 0.43 (IP, mouse) |
| SMSM-193 | <3 nM | | |
| SMSM-306 | <3 nM | | |
| SMSM-259 | <1 nM | | 0.05 (IP, mouse) |
| SMSM-245 | | 30 | |
| SMSM-251 | | 150 | |
| SMSM-257 | | 121 | |
| SMSM-258 | | 149 | |
| SMSM-182 | | | 0.1 (IP, mouse) |
| SMSM-187 | | | 0.1 (IP, mouse) |
| SMSM-265 | | | 0.08 (IP, mouse) |
| SMSM-205 | | | 0.34 (IP, mouse) |

Example 23: Efficacy of SMSMs in Subcutaneous U87-Luc Brain Tumor Model in Combination with Radiotherapy Study Aim To evaluate efficacy of SMSMs in Subcutaneous U87-Luc Brain Tumor Model in combination with radiotherapy Experimental Design Subcutaneous U87-Luc Brain Tumor Model in NcrNude Mice: tumor inoculation on Day 0; compound treatment initiation at 100 mm³ (Day 0), twice daily by oral gavage; radiotherapy treatment on Day 3. The radiotherapy treatment (10 Gy) was conducted using Image Guided Small Animal Radiation Research Platform (SARRP) irradiator (Xstrahl Limited, GU15 3YL).

Experimental Groups

Figure 24A:
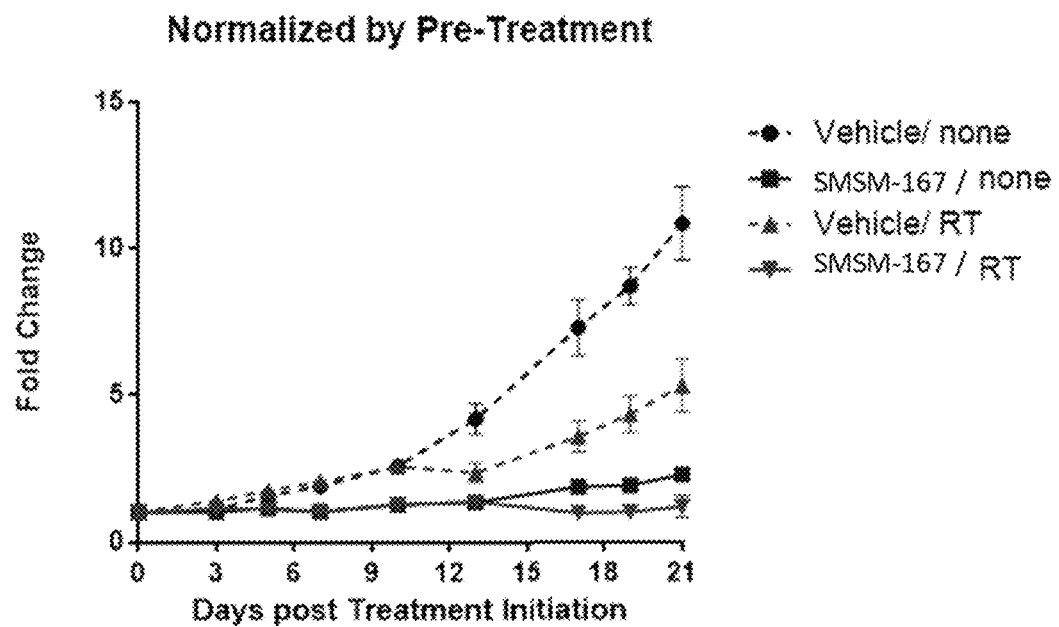
FIG. 24A depicts a graph showing volumes of tumors in A-375 xenograft mice post treatment with the indicated doses of vehicle, an SMSM, vehicle+radiation therapy (RT), and SMSM+radiation therapy.
Figure 24B:
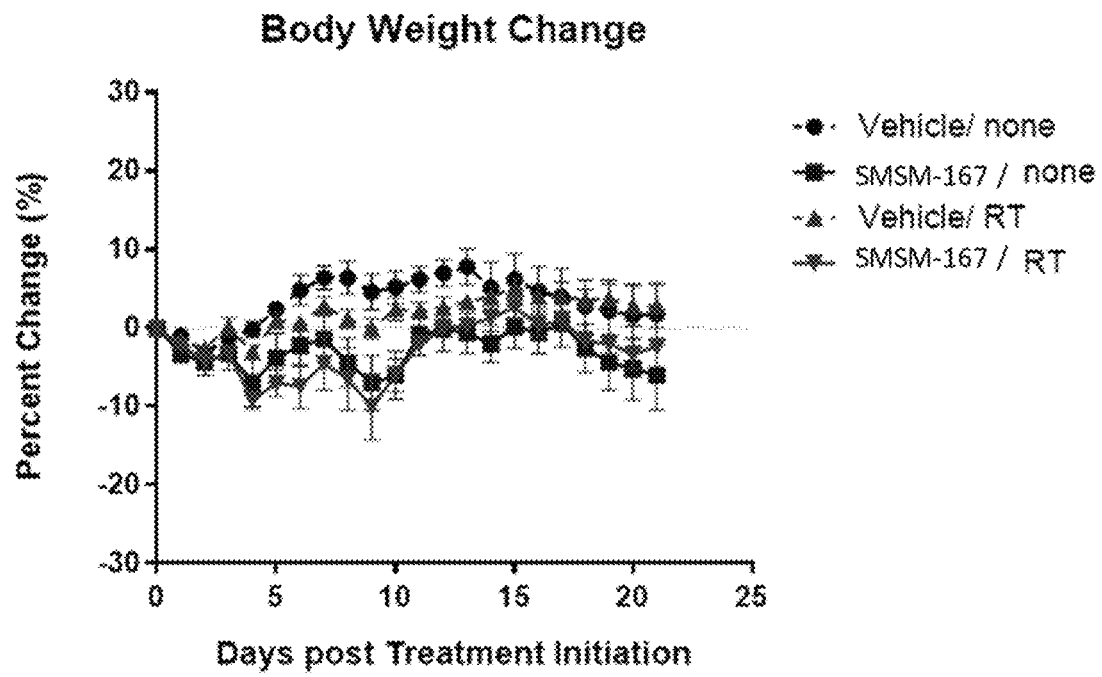
FIG. 24B depicts a graph of percent body weight change of mice post treatment with the indicated doses of vehicle, an SMSM, vehicle+radiation therapy (RT), and SMSM+radiation therapy.

The experimental groups used in this study are shown in the table below. Results are shown in FIGS. 24A and 24B.

| Group | # Mice | Treatment 1 | Treatment 1 Schedule | Treatment 2 | Treatment 2 Schedule |
| --- | --- | --- | --- | --- | --- |
| Group 1 | 5 | None | NA | Vehicle | BID from Day 0 for the duration of the study |
| Group 2 | 5 | None | NA | SMSM-167, 5 mg/kg | BID from Day 0 for the duration of the study |
| Group 3 | 5 | 10 Gy | Day 3 | Vehicle | BID from Day 0 for the duration of the study |
| Group 4 | 5 | 10 Gy | Day 3 | SMSM-167, 5 mg/kg | BID from Day 0 for the duration of the study |

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt thereof:

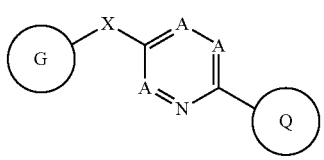

Formula (I)

wherein,

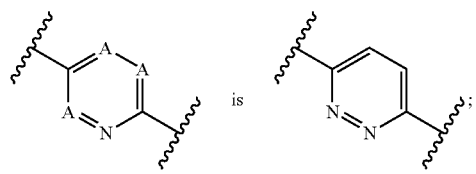

is ring Q is monocyclic heteroaryl, or fused bicyclic heteroaryl, wherein ring Q is optionally substituted;

X is —$NR^3$—;

each $R^1$ is independently H, D, substituted or unsubstituted $C_1$-$C_6$ alkyl, substituted or unsubstituted $C_1$-$C_6$ haloalkyl, substituted or unsubstituted $C_1$-$C_6$ heteroalkyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl;

$R^3$ is —$OR^1$, —$N(R^1)_2$, $C_1$-$C_6$ alkyl, $C_1$-$C_6$ haloalkyl, $C_1$-$C_6$ heteroalkyl, or $C_3$-$C_8$ cycloalkyl;

ring G is a group of the Formula

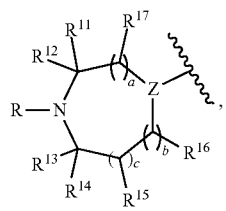

wherein

Z is $CR^7$; $R^7$ is substituted or unsubstituted $C_1$-$C_6$ alkyl, substituted or unsubstituted $C_1$-$C_6$ haloalkyl or —$CH_2OR^1$; and $R^3$ and $R^7$ taken together with the intervening atoms to which they are attached form a 4, 5, or 6-membered ring;

R is H;

a, b, and c are each independently selected from 0, 1, and 2;

$R^{11}$, $R^{12}$, $R^{13}$, $R^{14}$, $R^{15}$, $R^{16}$, and $R^{17}$ are each independently selected from the group consisting of H, F, $OR^1$, substituted or unsubstituted $C_{1-6}$ alkyl, a substituted or unsubstituted $C_{1-6}$ fluoroalkyl, substituted or unsubstituted $C_1$-$C_6$ heteroalkyl, wherein alkyl is optionally substituted with hydroxy, amino, methoxy, substituted or unsubstituted mono-$C_{1-6}$ alkylamino, and substituted or unsubstituted di-$C_{1-6}$ alkylamino; or $R^{11}$ and $R^{13}$, taken in combination form a substituted or unsubstituted $C_{1-3}$ alkylene group; or $R^{11}$ and $R^{15}$, taken in combination form a substituted or unsubstituted $C_{1-3}$ alkylene group; or $R^{11}$ and $R^{17}$, taken in combination form a substituted or unsubstituted $C_{1-3}$ alkylene group; or $R^{16}$ and $R^{17}$, taken in combination form a substituted or unsubstituted $C_{1-3}$ alkylene group; or $R^{16}$ and $R^{17}$, taken in combination form a bond; or $R^{13}$ and $R^{14}$, taken in combination with the carbon atom to which they attach, form a spirocyclic $C_{3-8}$ cycloalkyl.

2. The compound of claim 1, or a pharmaceutically acceptable salt thereof, wherein ring G is

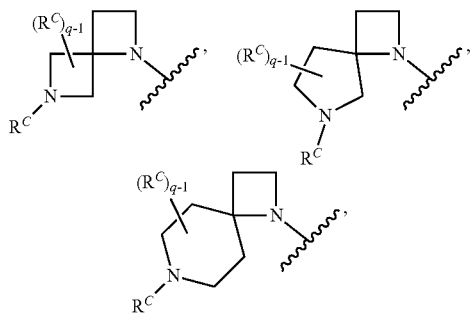

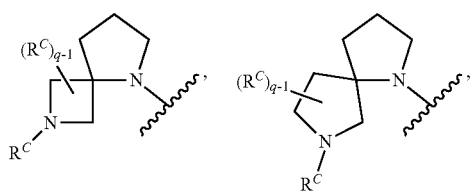

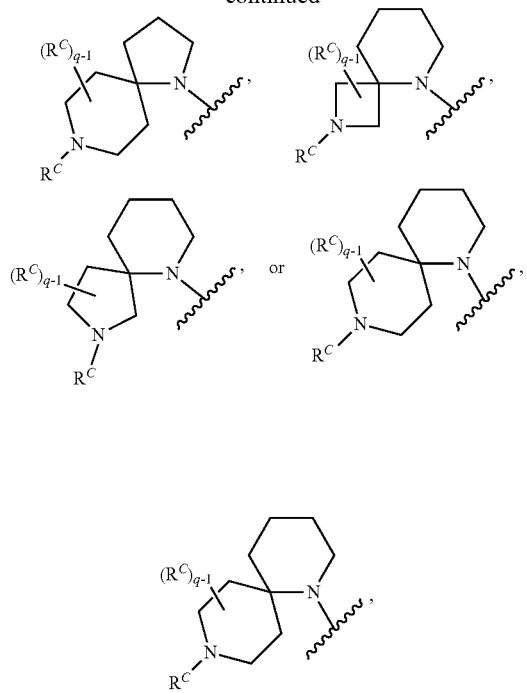

or wherein each $R^C$ is independently selected from H, D, F, —CN, —OH, —OR$^1$, —SR$^1$, —S(=O)R$^1$, —S(=O)$_2$R$^1$, —N(R$^1$)$_2$, —CH$_2$—N(R$^1$)$_2$, —NHS(=O)$_2$R$^1$, —S(=O)$_2$N(R$^1$)$_2$, —C(=O)R$^1$, —OC(=O)R$^1$, —CO$_2$R$^1$, —OCO$_2$R$^1$, —C(=O)N(R$^1$)$_2$, —OC(=O)N(R$^1$)$_2$, —NR$^1$C(=O)N(R$^1$)$_2$, —NR$^1$C(=O)R$^1$, —NR$^1$C(=O)OR$^1$, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, and substituted or unsubstituted C$_2$-C$_8$ heterocycloalkyl; and q is 0, 1, 2, 3, 4, 5, or 6.

3. The compound of claim 2, or a pharmaceutically acceptable salt thereof, wherein ring G is

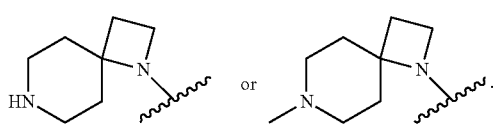 [SMILES: *N1CCC12CCNCC2 ; "or" ; *N1CCC12CCN(C)CC2 ; "."]

4. The compound of claim 1, or a pharmaceutically acceptable salt thereof, wherein ring Q is a 6 membered monocyclic heteroaryl selected from the group consisting of:

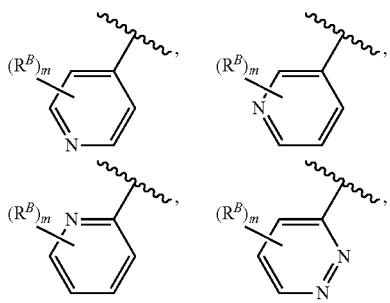

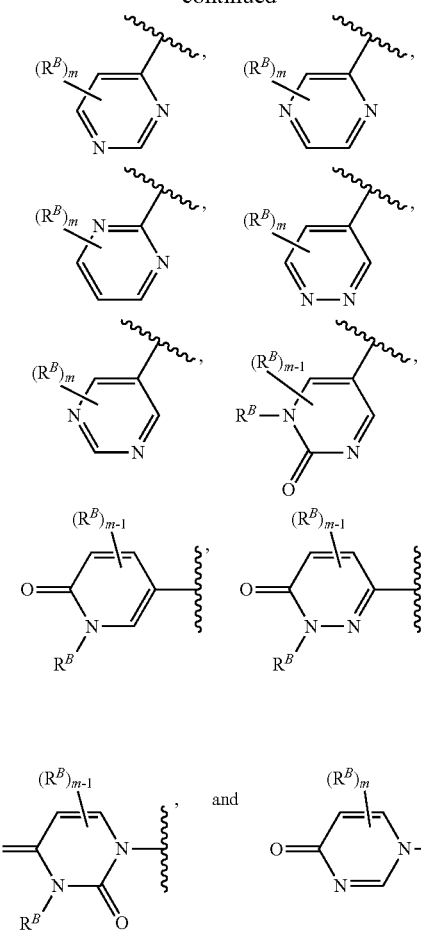

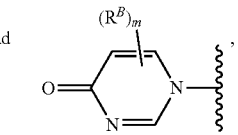

wherein each $R^B$ is independently selected from cyano, halogen, hydroxy, substituted or unsubstituted C$_{1-6}$ alkyl, —OCH$_3$, —OCD$_3$, substituted or unsubstituted C$_{2-6}$ alkenyl, substituted or unsubstituted C$_{2-6}$ alkynyl, substituted or unsubstituted C$_{1-6}$ alkoxy, substituted or unsubstituted C$_{3-7}$ cycloalkyl, substituted or unsubstituted C$_{2-8}$ heterocycloalkyl, substituted or unsubstituted heteroaryl, substituted or unsubstituted heterocycloalkyl-C$_{1-6}$ alkyl, substituted or unsubstituted C$_{1-6}$ alkyl-aryl, substituted or unsubstituted C$_{1-6}$ alkyl-heterocycloalkyl, substituted or unsubstituted C$_{1-6}$ alkyl-heteroaryl, substituted or unsubstituted C$_{1-6}$ alkoxy-aryl, substituted or unsubstituted C$_{1-6}$ alkoxy-heterocycloalkyl, and substituted or unsubstituted C$_{1-6}$ alkoxy-heteroaryl; and m is 0, 1, 2, or 3.

5. The compound of claim 4, or a pharmaceutically acceptable salt thereof, wherein ring Q is a 6 membered monocyclic heteroaryl selected from the group consisting of:

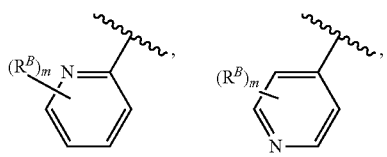

-continued

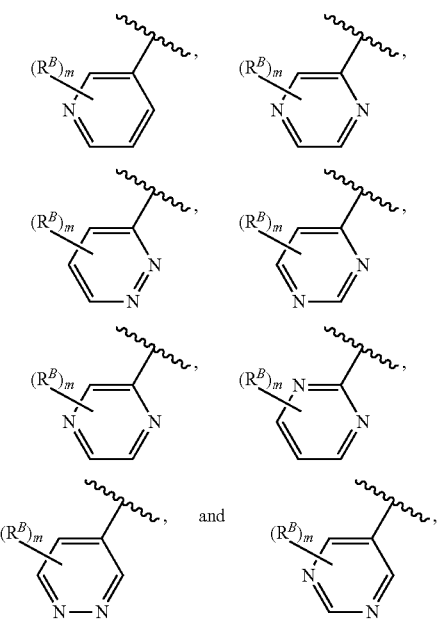

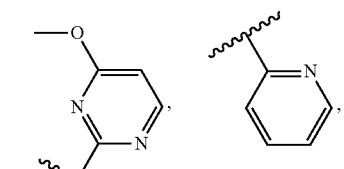

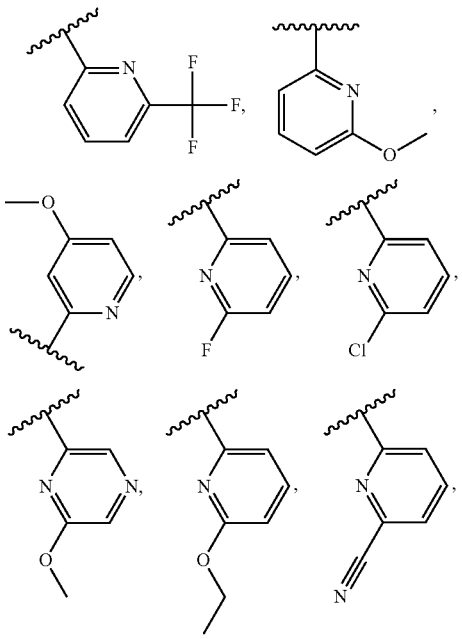

wherein
each $R^B$ is independently selected from cyano, halogen, hydroxy, substituted or unsubstituted $C_{1-6}$ alkyl, —OCH$_3$, —OCD$_3$, substituted or unsubstituted $C_{1-6}$ alkoxy, substituted or unsubstituted heteroaryl, and substituted or unsubstituted $C_{1-6}$ alkoxy-heterocycloalkyl.

6. The compound of claim 5, or a pharmaceutically acceptable salt thereof, wherein ring Q is

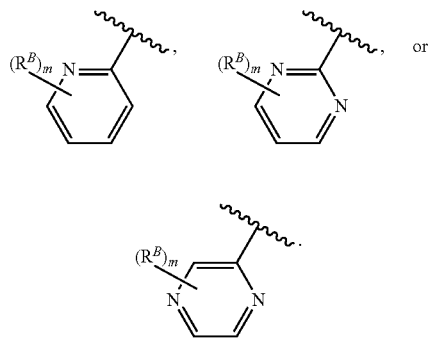

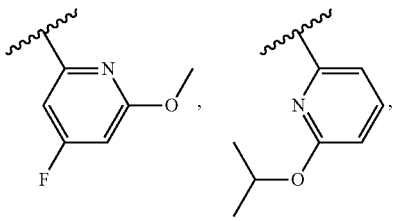

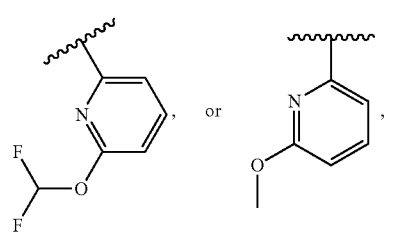

wherein each of which is optionally substituted with a 5 or 6 membered heteroaryl.

8. The compound of claim 1, or a pharmaceutically acceptable salt thereof, wherein ring Q is a fused bicyclic heteroaryl having 8 to 10 ring atoms, 1, 2, or 3 ring heteroatoms independently selected from N, O, and S, and 7. The compound of claim 1, or a pharmaceutically acceptable salt thereof, wherein ring Q is

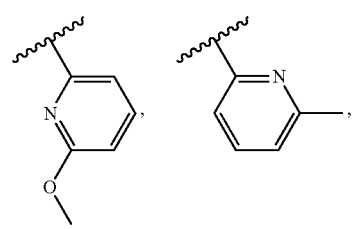

which is substituted with 0, 1, or 2 substituents independently selected from cyano, oxo, oxime, halogen, hydroxy, $C_{1-6}$ alkyl, $C_{1-6}$ alkoxy, $C_{1-6}$ alkoxy substituted with hydroxy, amino, mono-$C_{1-6}$ alkylamino, di-$C_{1-6}$ alkylamino, $C_{3-7}$ cycloalkyl, $C_{2-8}$ heterocycloalkyl, and heteroaryl.

9. The compound of claim 1, or a pharmaceutically acceptable salt thereof, wherein ring Q is 6-5 fused heteroaryl, wherein the 6-5 fused heteroaryl is substituted with 1, 2 or 3 $R^B$, wherein each $R^B$ is independently selected from cyano, halogen, oxo, hydroxy, substituted or unsubstituted $C_{1-6}$ alkyl, —OCH$_3$, —OCD$_3$, substituted or unsubstituted $C_{2-6}$ alkenyl, substituted or unsubstituted $C_{2-6}$ alkynyl, substituted or unsubstituted $C_{1-6}$ alkoxy, substituted or unsubstituted $C_{3-7}$ cycloalkyl, substituted or unsubstituted $C_{2-8}$ heterocycloalkyl, heteroaryl, substituted or unsubstituted heterocycloalkyl-$C_{1-6}$ alkyl, substituted or unsubstituted $C_{1-6}$ alkyl-aryl, substituted or unsubstituted $C_{1-6}$ alkyl-heterocycloalkyl, substituted or unsubstituted $C_{1-6}$ alkyl-heteroaryl, substituted or unsubstituted $C_{1-6}$ alkoxy-aryl, substituted or unsubstituted $C_{1-6}$ alkoxy-heterocycloalkyl, and substituted or unsubstituted $C_{1-6}$ alkoxy-heteroaryl.

10. The compound of claim 9, or a pharmaceutically acceptable salt thereof, wherein ring Q is 6-5 fused heteroaryl substituted with 1, 2 or 3 $R^B$, wherein each $R^B$ is independently selected from cyano, halogen, oxo, hydroxy, and 5 or 6 membered heteroaryl.

11. The compound of claim 9, or a pharmaceutically acceptable salt thereof, wherein ring Q is indazole, indole, benzothiophene, or benzothiazole, each substituted with 1 or 2 substituents selected from halogen and 5 or 6 membered heteroaryl.

12. The compound of claim 1, or a pharmaceutically acceptable salt thereof, wherein ring Q is a monocyclic heteroaryl or 6-5 fused bicyclic heteroaryl substituted with:

0, 1, 2, or 3 substituents independently selected from $C_1$-$C_6$ alkyl, oxo, oxime, halo-$C_1$-$C_6$ alkyl, dihalo-$C_1$-$C_6$ alkyl, trihalo-$C_1$-$C_6$ alkyl, $C_1$-$C_6$ alkoxy, $C_1$-$C_6$ alkoxy-$C_3$-$C_7$ cycloalkyl, halo-$C_1$-$C_6$ alkoxy, dihalo-$C_1$-$C_6$ alkoxy, trihalo-$C_1$-$C_6$ alkoxy, hydroxy, cyano, halogen, amino, mono-$C_1$-$C_6$ alkylamino, di-$C_1$-$C_6$ alkylamino, aryl, heteroaryl, $C_1$-$C_6$ alkyl substituted with hydroxy, $C_1$-$C_6$ alkoxy substituted with aryl, —C(=O)NH—$C_1$-$C_6$ alkyl-heteroaryl, —NHC(=O)—$C_1$-$C_6$ alkyl heteroaryl, $C_1$-$C_6$ alkyl-C(=O)NH-heteroaryl, $C_1$-$C_6$ alkyl-NHC(=O)-heteroaryl, $C_3$-$C_7$ cycloalkyl, 5-7 membered cycloalkenyl, and 5, 6 or 9 membered heterocycle containing 1 or 2 heteroatoms independently, selected from S, O, and N;

wherein two $C_1$-$C_6$ alkyl groups can combine with the atoms to which they are bound to form a 5-6 membered ring; and wherein the heteroaryl has 5, 6, 9, or 10 ring atoms, 1, 2 or 3 ring heteroatoms selected from N, O, and S, and is substituted with 0, 1, or 2 substituents independently selected from oxo, hydroxy, nitro, halogen, $C_1$-$C_6$ alkyl, $C_1$-$C_6$ alkenyl, $C_1$-$C_6$ alkoxy, $C_3$-$C_7$ cycloalkyl, $C_1$-$C_6$ alkyl-OH, trihalo-$C_1$-$C_6$ alkyl, mono-$C_1$-$C_6$ alkylamino, di-$C_1$-$C_6$ alkylamino, —C(=O)NH$_2$, —NH$_2$, —NO$_2$, hydroxy-$C_1$-$C_6$ alkylamino, hydroxy-$C_1$-$C_6$ alkyl, 4-7 membered heterocycle-$C_1$-$C_6$ alkyl, amino-$C_1$-$C_6$ alkyl, mono-$C_1$-$C_6$ alkylamino-$C_1$-$C_6$ alkyl, and di-$C_1$-$C_6$ alkylamino-$C_1$-$C_6$ alkyl.

13. The compound of claim 12, or a pharmaceutically acceptable salt thereof, wherein:

ring Q is selected from the group consisting of

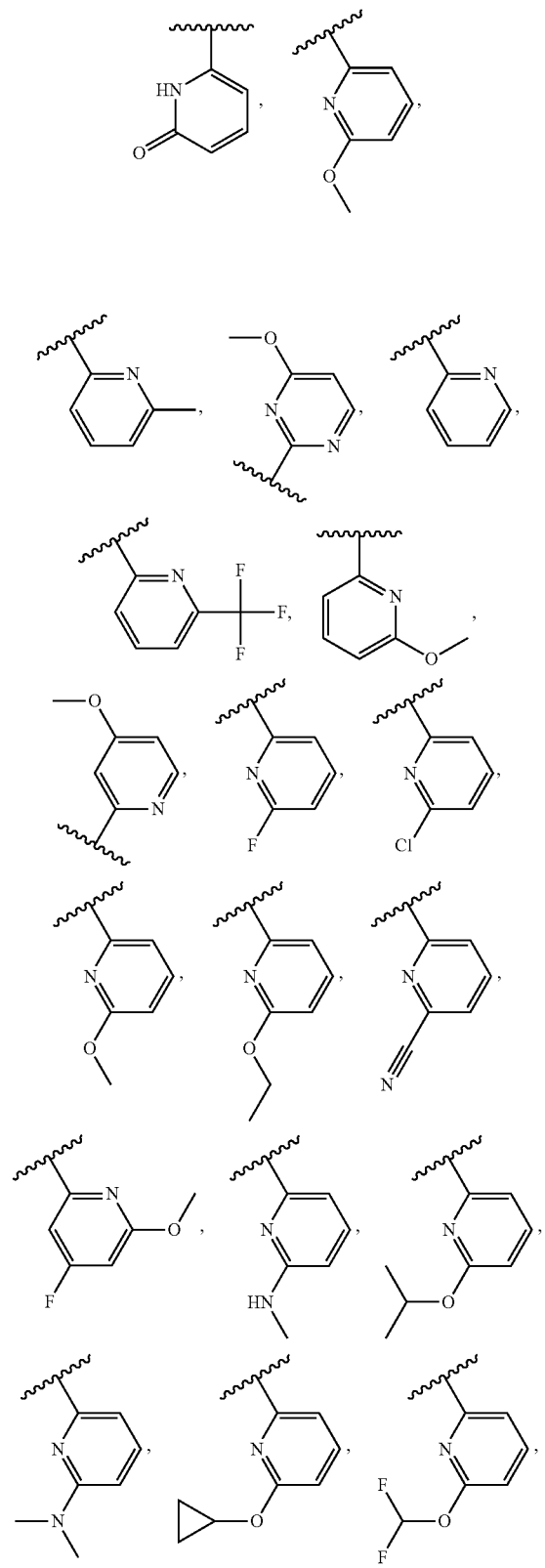

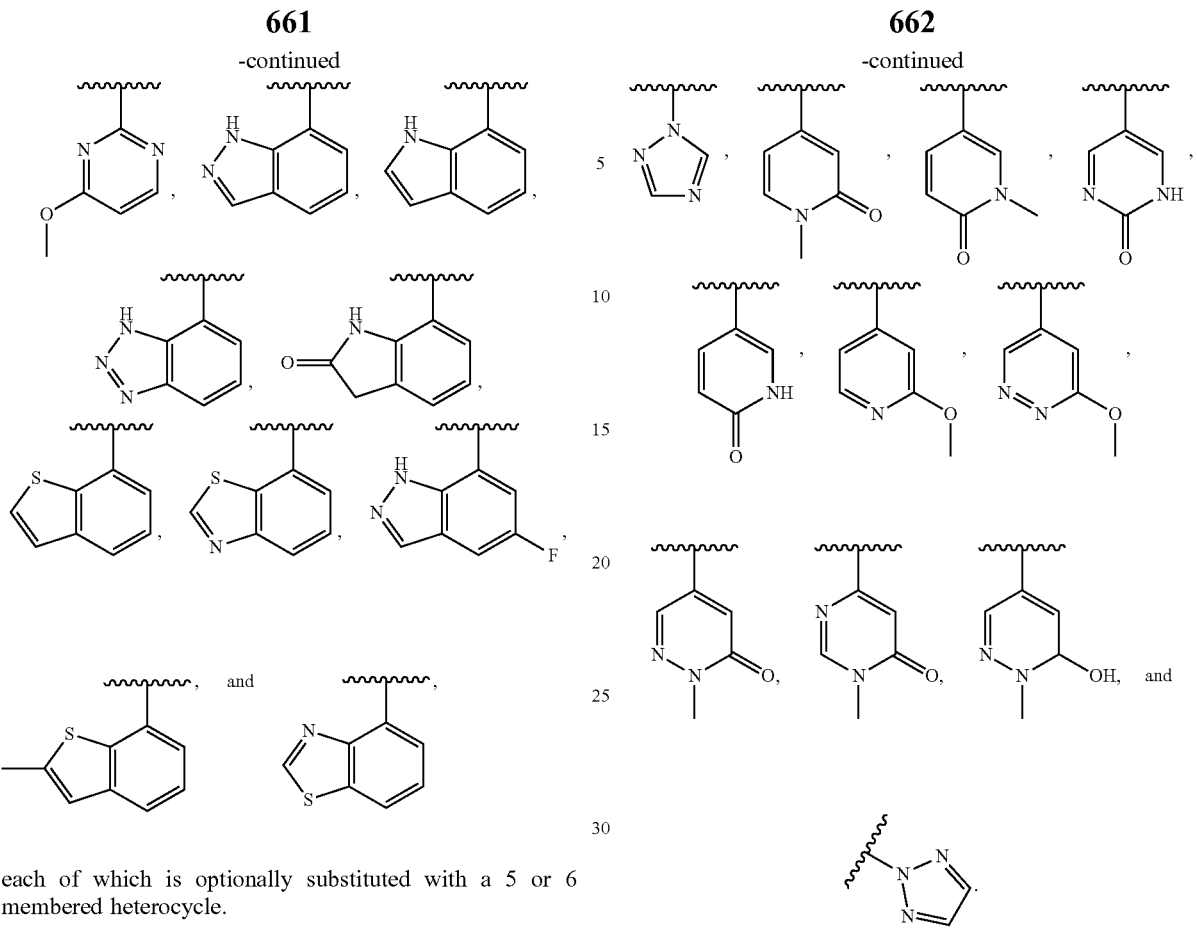

each of which is optionally substituted with a 5 or 6 membered heterocycle.

14. The compound of claim 13, or a pharmaceutically acceptable salt thereof, wherein ring Q is substituted with a heteroaryl selected from the group consisting of:

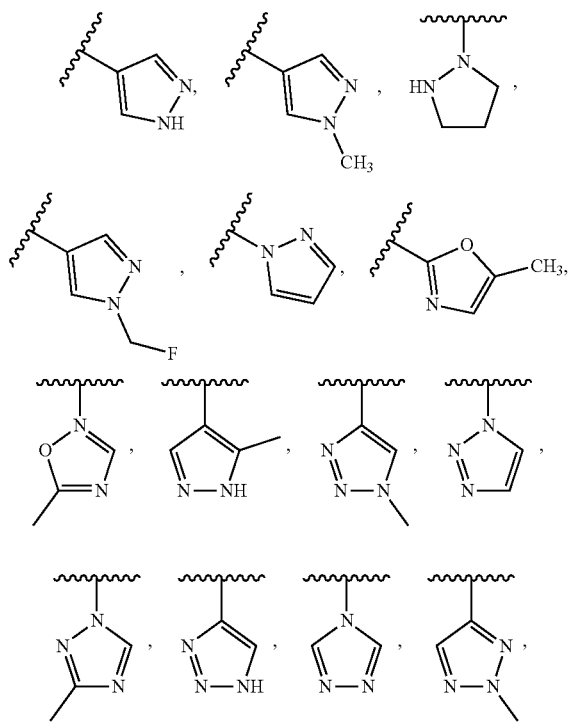

15. The compound of claim 1, or a pharmaceutically acceptable salt thereof, wherein X is —NR³—, and R³ is —CH₃, —CH₂CH₃, —CH₂CD₃ or —CD₃, or cyclopropyl.

16. A pharmaceutical composition that comprises a compound according to claim 1, or a pharmaceutically acceptable salt thereof, and a pharmaceutically acceptable carrier or excipient.

17. A compound of Formula (I), or a pharmaceutically acceptable salt thereof:

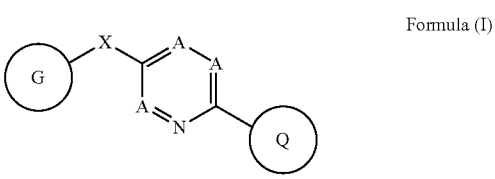

Formula (I)

wherein,

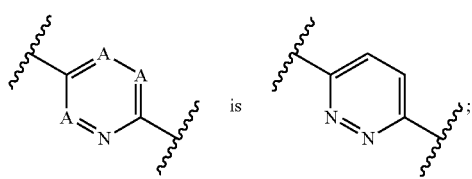

is ring Q is

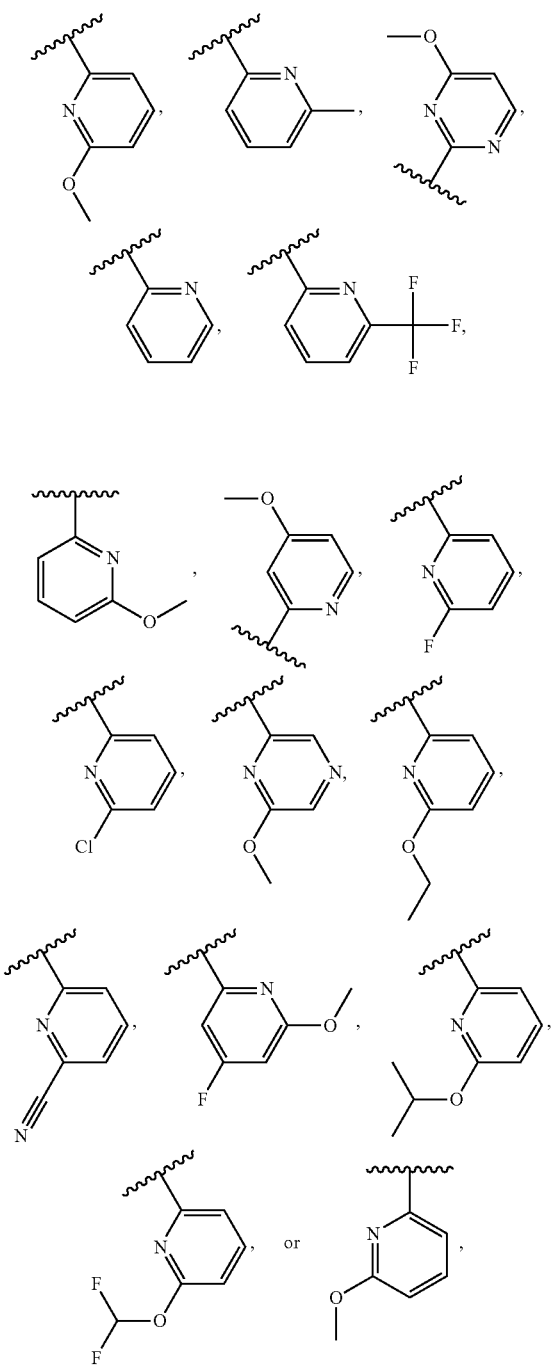

wherein each of which is optionally substituted with a 5 or 6 membered heteroaryl;

X is —NR$^3$—;

R$^3$ is H, —OR$^1$, —N(R$^1$)$_2$, C$_1$-C$_6$ alkyl, C$_1$-C$_6$ haloalkyl, C$_1$-C$_6$ heteroalkyl, or C$_3$-C$_8$ cycloalkyl;

each R$^1$ is independently H, D, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;

ring G is a group of the Formula

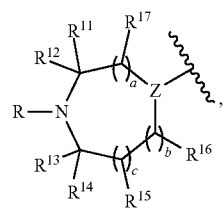

wherein

Z is CR$^7$; R$^7$ is H, D, substituted or unsubstituted C$_1$-C$_6$ alkyl, substituted or unsubstituted C$_1$-C$_6$ haloalkyl or —CH$_2$OR$^1$;

R is H;

a, b, and c are each independently selected from 0, 1, and 2;

R$^{11}$, R$^{12}$, R$^{13}$, R$^{14}$, R$^{15}$, R$^{16}$, and R$^{17}$ are each independently selected from the group consisting of H, F, OR$^1$, substituted or unsubstituted C$_{1-6}$ alkyl, a substituted or unsubstituted C$_{1-6}$ fluoroalkyl, substituted or unsubstituted C$_1$-C$_6$ heteroalkyl, wherein alkyl is optionally substituted with hydroxy, amino, methoxy, substituted or unsubstituted mono-C$_{1-6}$ alkylamino, and substituted or unsubstituted di-C$_{1-6}$ alkylamino; or R$^{11}$ and R$^{13}$, taken in combination form a substituted or unsubstituted C$_{1-3}$ alkylene group; or R$^{11}$ and R$^{15}$, taken in combination form a substituted or unsubstituted C$_{1-3}$ alkylene group; or R$^{11}$ and R$^{17}$, taken in combination form a substituted or unsubstituted C$_{1-3}$ alkylene group; or R$^{16}$ and R$^{17}$, taken in combination form a substituted or unsubstituted C$_{1-3}$ alkylene group; or R$^{16}$ and R$^{17}$, taken in combination form a bond; or R$^{13}$ and R$^{14}$, taken in combination with the carbon atom to which they attach, form a spirocyclic C$_{3-8}$ cycloalkyl; or R$^3$ and R$^7$ are optionally taken together with the intervening atoms to which they are attached form a 4, 5, or 6-membered ring; or R$^3$ and R$^{16}$ are optionally taken together with the intervening atoms to which they are attached form a 4, 5, or 6-membered ring.

18. The compound of claim 17, or a pharmaceutically acceptable salt thereof, wherein ring G is

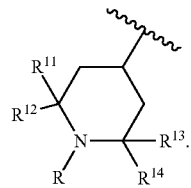

19. The compound of claim 17, or a pharmaceutically acceptable salt thereof, wherein ring G is

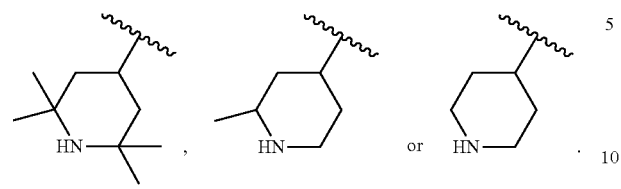

20. A compound of Formula (I), or a pharmaceutically acceptable salt thereof:

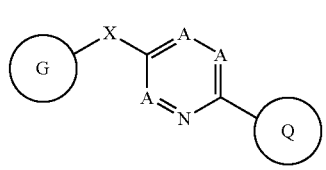

Formula (I)

wherein,

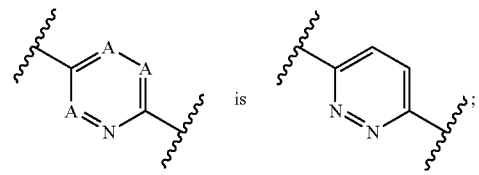 is 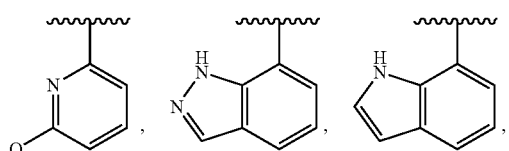;

ring Q:
(i) is indazole, indole, benzothiophene, or benzothiazole, each substituted with 1 or 2 substituents selected from halogen and 5 or 6 membered heteroaryl, or
(ii) is selected from the group consisting of

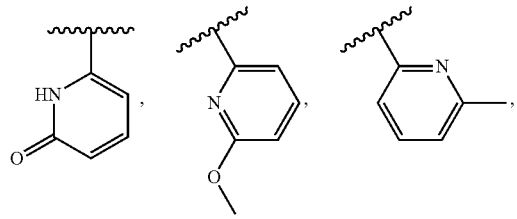

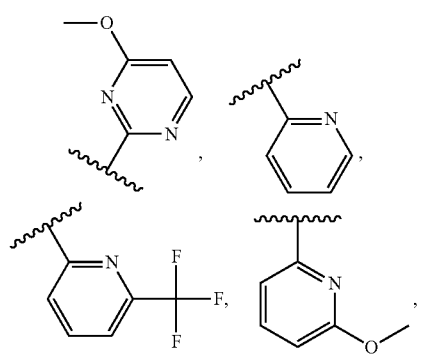

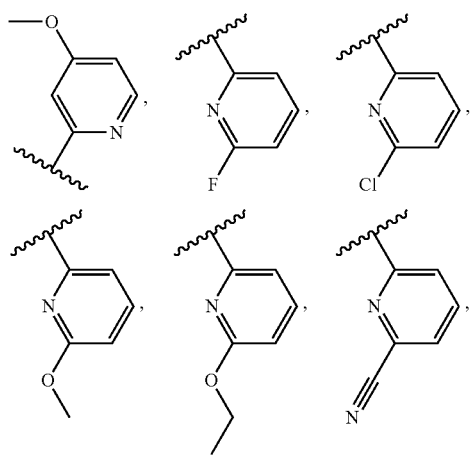

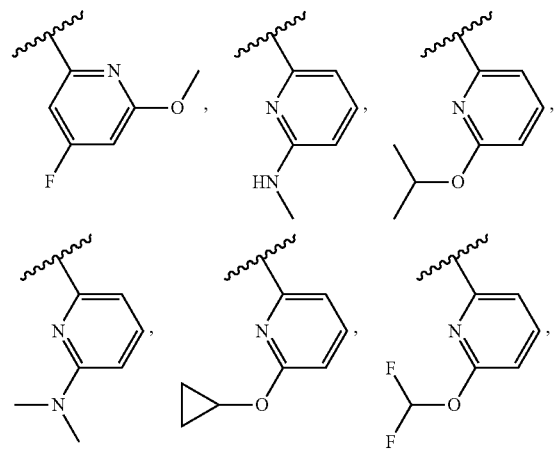

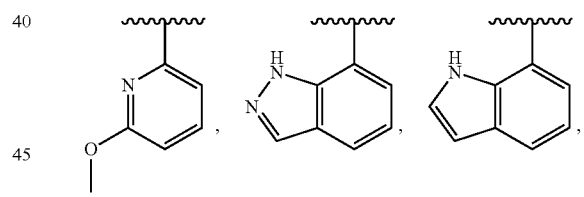

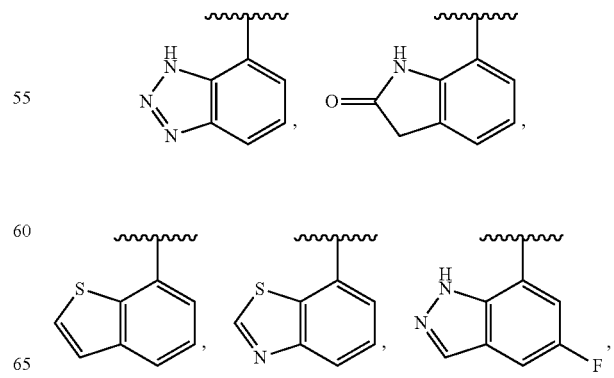

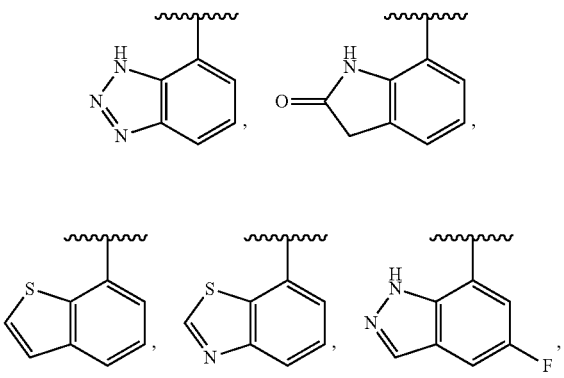

-continued

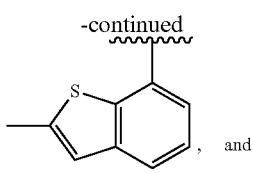, and

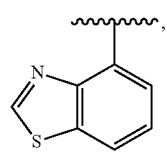 [SMILES: *c1cccc2scnc12], each of which is optionally substituted with a 5 or 6 membered heterocycle;

X is —NR$^3$—;

each R$^1$ is independently H, D, substituted or unsubstituted C$_1$-C$_6$ alkyl, substituted or unsubstituted C$_1$-C$_6$ haloalkyl, substituted or unsubstituted C$_1$-C$_6$ heteroalkyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl;

R$^3$ is H, —OR$^1$, —N(R$^1$)$_2$, C$_1$-C$_6$ alkyl, C$_1$-C$_6$ haloalkyl, C$_1$-C$_6$ heteroalkyl, or C$_3$-C$_8$ cycloalkyl;

ring G is a group of the Formula

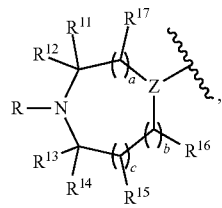, wherein

Z is CR$^7$; R$^7$ is H, D, substituted or unsubstituted C$_1$-C$_6$ alkyl, substituted or unsubstituted C$_1$-C$_6$ haloalkyl or —CH$_2$OR$^1$;

R is H;

a, b, and c are each independently selected from 0, 1, and 2;

R$^{11}$, R$^{12}$, R$^{13}$, R$^{14}$, R$^{15}$, R$^{16}$, and R$^{17}$ are each independently selected from the group consisting of H, F, OR$^1$, substituted or unsubstituted C$_{1-6}$ alkyl, a substituted or unsubstituted C$_{1-6}$ fluoroalkyl, and substituted or unsubstituted C$_1$-C$_6$ heteroalkyl, wherein alkyl is optionally substituted with hydroxy, amino, methoxy, substituted or unsubstituted mono-C$_{1-6}$ alkylamino, and substituted or unsubstituted di-C$_{1-6}$ alkylamino; or R$^{11}$ and R$^{13}$, taken in combination form a substituted or unsubstituted C$_{1-3}$ alkylene group; or R$^{11}$ and R$^{15}$, taken in combination form a substituted or unsubstituted C$_{1-3}$ alkylene group; or R$^{11}$ and R$^{17}$, taken in combination form a substituted or unsubstituted C$_{1-3}$ alkylene group; or R$^{16}$ and R$^{17}$, taken in combination form a substituted or unsubstituted C$_{1-3}$ alkylene group; or R$^{16}$ and R$^{17}$, taken in combination form a bond; or R$^{13}$ and R$^{14}$, taken in combination with the carbon atom to which they attach, form a spirocyclic C$_{3-8}$ cycloalkyl;

R$^3$ and R$^7$ are optionally taken together with the intervening atoms to which they are attached form a 4, 5, or 6-membered ring; or R$^3$ and R$^{16}$ are optionally taken together with the intervening atoms to which they are attached form a 4, 5, or 6-membered ring.

21. The compound of claim 20, or a pharmaceutically acceptable salt thereof, wherein ring G is

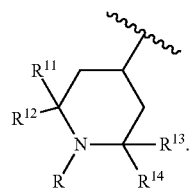

22. The compound of claim 20, or a pharmaceutically acceptable salt thereof, wherein ring G is

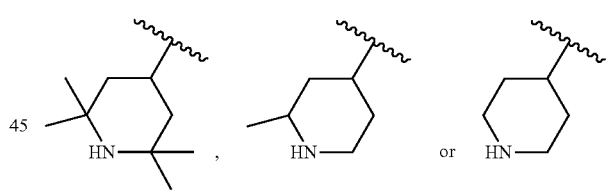

\* \* \* \* \*

SEQUENCE LISTING

<160> NUMBER OF SEQ ID NOS: 121

<210> SEQ ID NO 1
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 1
aaaguaagua                                                           10

<210> SEQ ID NO 2
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 2
aaagugagug                                                           10

<210> SEQ ID NO 3
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 3
aaagugaguu                                                           10

<210> SEQ ID NO 4
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 4
aacaugagga                                                           10

<210> SEQ ID NO 5
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 5
aaggcaaggg                                                           10

<210> SEQ ID NO 6
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 6
aaggcaggga                                                           10

```
<210> SEQ ID NO 7
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 7
aagguaugag                                                              10

<210> SEQ ID NO 8
<211> LENGTH: 11
<212> TYPE: RNA
<213> ORGANISM: Unknown
<220> FEATURE:
<223> OTHER INFORMATION: Description of Unknown:
      Splice site sequence

<400> SEQUENCE: 8
aagguaacau g                                                            11

<210> SEQ ID NO 9
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 9
aagguaagcc                                                              10

<210> SEQ ID NO 10
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 10
aagguaagcg                                                              10

<210> SEQ ID NO 11
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 11
aagguaauaa                                                              10

<210> SEQ ID NO 12
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 12
aagguaaugu                                                              10
```

```
<210> SEQ ID NO 13
<211> LENGTH: 11
<212> TYPE: RNA
<213> ORGANISM: Unknown
<220> FEATURE:
<223> OTHER INFORMATION: Description of Unknown:
      Splice site sequence

<400> SEQUENCE: 13
aagguaaugu a                                                              11

<210> SEQ ID NO 14
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 14
aagguagacc                                                                10

<210> SEQ ID NO 15
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 15
aagguauauu                                                                10

<210> SEQ ID NO 16
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 16
aaggucuggg                                                                10

<210> SEQ ID NO 17
<211> LENGTH: 11
<212> TYPE: RNA
<213> ORGANISM: Unknown
<220> FEATURE:
<223> OTHER INFORMATION: Description of Unknown:
      Splice site sequence

<400> SEQUENCE: 17
aaggugaccu u                                                              11

<210> SEQ ID NO 18
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 18
aaggugagau                                                                10
```

```
<210> SEQ ID NO 19
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 19
aaggugaguc                                                              10

<210> SEQ ID NO 20
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 20
aaggugggcc                                                              10

<210> SEQ ID NO 21
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 21
aagguuagug                                                              10

<210> SEQ ID NO 22
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 22
accgugaguu                                                              10

<210> SEQ ID NO 23
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 23
acggugagug                                                              10

<210> SEQ ID NO 24
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 24
acugugagug                                                              10

<210> SEQ ID NO 25
```

```
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 25
aggguaauga                                                                 10

<210> SEQ ID NO 26
<211> LENGTH: 11
<212> TYPE: RNA
<213> ORGANISM: Unknown
<220> FEATURE:
<223> OTHER INFORMATION: Description of Unknown:
      Splice site sequence

<400> SEQUENCE: 26
agugugagua c                                                               11

<210> SEQ ID NO 27
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 27
aucgguaaaa                                                                 10

<210> SEQ ID NO 28
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 28
caagguaccu                                                                 10

<210> SEQ ID NO 29
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 29
caaguaagua                                                                 10

<210> SEQ ID NO 30
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 30
cagguaaggc                                                                 10

<210> SEQ ID NO 31
<211> LENGTH: 11
```

```
<212> TYPE: RNA
<213> ORGANISM: Unknown
<220> FEATURE:
<223> OTHER INFORMATION: Description of Unknown:
      Splice site sequence

<400> SEQUENCE: 31
cagguaaccu c                                                         11

<210> SEQ ID NO 32
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 32
cagguaagac                                                           10

<210> SEQ ID NO 33
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 33
cagguaaugc                                                           10

<210> SEQ ID NO 34
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 34
cagguaaugu                                                           10

<210> SEQ ID NO 35
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 35
cagguacagu                                                           10

<210> SEQ ID NO 36
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 36
cagguagcaa                                                           10

<210> SEQ ID NO 37
<211> LENGTH: 11
<212> TYPE: RNA
```

```
<213> ORGANISM: Unknown
<220> FEATURE:
<223> OTHER INFORMATION: Description of Unknown:
      Splice site sequence

<400> SEQUENCE: 37
cagguaggag g                                                              11

<210> SEQ ID NO 38
<211> LENGTH: 11
<212> TYPE: RNA
<213> ORGANISM: Unknown
<220> FEATURE:
<223> OTHER INFORMATION: Description of Unknown:
      Splice site sequence

<400> SEQUENCE: 38
cagguaggug a                                                              11

<210> SEQ ID NO 39
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 39
caggucagug                                                                10

<210> SEQ ID NO 40
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 40
caggucugga                                                                10

<210> SEQ ID NO 41
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 41
caggucuggu                                                                10

<210> SEQ ID NO 42
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 42
caggugaggg                                                                10

<210> SEQ ID NO 43
<211> LENGTH: 11
<212> TYPE: RNA
<213> ORGANISM: Unknown
```

```
<220> FEATURE:
<223> OTHER INFORMATION: Description of Unknown:
      Splice site sequence

<400> SEQUENCE: 43
caggugagug g                                                              11

<210> SEQ ID NO 44
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 44
caggugggug                                                                10

<210> SEQ ID NO 45
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 45
cagguuuagu                                                                10

<210> SEQ ID NO 46
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 46
cauggaagac                                                                10

<210> SEQ ID NO 47
<211> LENGTH: 12
<212> TYPE: RNA
<213> ORGANISM: Unknown
<220> FEATURE:
<223> OTHER INFORMATION: Description of Unknown:
      Splice site sequence

<400> SEQUENCE: 47
cgggucauaa uc                                                             12

<210> SEQ ID NO 48
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 48
cuggugaguc                                                                10

<210> SEQ ID NO 49
<211> LENGTH: 11
<212> TYPE: RNA
<213> ORGANISM: Unknown
<220> FEATURE:
```

```
<223> OTHER INFORMATION: Description of Unknown:
      Splice site sequence

<400> SEQUENCE: 49
cuggugaguu c                                                              11

<210> SEQ ID NO 50
<211> LENGTH: 13
<212> TYPE: RNA
<213> ORGANISM: Unknown
<220> FEATURE:
<223> OTHER INFORMATION: Description of Unknown:
      Splice site sequence

<400> SEQUENCE: 50
gagcagguaa gcu                                                            13

<210> SEQ ID NO 51
<211> LENGTH: 11
<212> TYPE: RNA
<213> ORGANISM: Unknown
<220> FEATURE:
<223> OTHER INFORMATION: Description of Unknown:
      Splice site sequence

<400> SEQUENCE: 51 gaggugggguu u                                                             11

<210> SEQ ID NO 52
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 52
gagguaagag                                                                10

<210> SEQ ID NO 53
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 53
gagguaagcg                                                                10

<210> SEQ ID NO 54
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 54
gagguaauac                                                                10

<210> SEQ ID NO 55
<211> LENGTH: 10
<212> TYPE: RNA
<213> ORGANISM: Unknown
<220> FEATURE:
<223> OTHER INFORMATION: Description of Unknown:
```

Splice site sequence

<400> SEQUENCE: 55
gagguaauau                                                                10

<210> SEQ ID NO 56
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 56
gagguaaugu                                                                10

<210> SEQ ID NO 57
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 57
gaggucuggu                                                                10

<210> SEQ ID NO 58
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 58
gaggugcggg                                                                10

<210> SEQ ID NO 59
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 59
gcgguaauca                                                                10

<210> SEQ ID NO 60
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 60
gcggugagca                                                                10

<210> SEQ ID NO 61
<211> LENGTH: 10
<212> TYPE: RNA
<213> ORGANISM: Unknown
<220> FEATURE:
<223> OTHER INFORMATION: Description of Unknown:
      Splice site sequence -continued

<400> SEQUENCE: 61
gcggugagcu                                                                     10

<210> SEQ ID NO 62
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 62
gggguaagug                                                                     10

<210> SEQ ID NO 63
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 63
ggggugagug                                                                     10

<210> SEQ ID NO 64
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 64
gggguuggga                                                                     10

<210> SEQ ID NO 65
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 65
gugguaagug                                                                     10

<210> SEQ ID NO 66
<211> LENGTH: 12
<212> TYPE: RNA
<213> ORGANISM: Unknown
<220> FEATURE:
<223> OTHER INFORMATION: Description of Unknown:
      Splice site sequence

<400> SEQUENCE: 66
guucucagug ug                                                                  12

<210> SEQ ID NO 67
<211> LENGTH: 10
<212> TYPE: RNA
<213> ORGANISM: Unknown
<220> FEATURE:
<223> OTHER INFORMATION: Description of Unknown:
      Splice site sequence

```
<400> SEQUENCE: 67
guuuugguga                                                              10

<210> SEQ ID NO 68
<211> LENGTH: 13
<212> TYPE: RNA
<213> ORGANISM: Unknown
<220> FEATURE:
<223> OTHER INFORMATION: Description of Unknown:
      Splice site sequence

<400> SEQUENCE: 68
uagcagguaa gca                                                          13

<210> SEQ ID NO 69
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 69
uggguaccug                                                              10

<210> SEQ ID NO 70
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 70 ugggugggggg                                                             10

<210> SEQ ID NO 71
<211> LENGTH: 10
<212> TYPE: RNA
<213> ORGANISM: Unknown
<220> FEATURE:
<223> OTHER INFORMATION: Description of Unknown:
      Splice site sequence

<400> SEQUENCE: 71
ugggugggug                                                              10

<210> SEQ ID NO 72
<211> LENGTH: 10
<212> TYPE: DNA
<213> ORGANISM: Unknown
<220> FEATURE:
<223> OTHER INFORMATION: Description of Unknown:
      Splice site sequence

<400> SEQUENCE: 72
aaggtatgag                                                              10

<210> SEQ ID NO 73
<211> LENGTH: 10
<212> TYPE: DNA
<213> ORGANISM: Unknown
<220> FEATURE:
<223> OTHER INFORMATION: Description of Unknown:
      Splice site sequence

<400> SEQUENCE: 73
```
caggtaaggc                                                              10

<210> SEQ ID NO 74
<211> LENGTH: 11
<212> TYPE: DNA
<213> ORGANISM: Unknown
<220> FEATURE:
<223> OTHER INFORMATION: Description of Unknown:
      Splice site sequence

<400> SEQUENCE: 74
gaggtgggtt t                                                            11

<210> SEQ ID NO 75
<211> LENGTH: 10
<212> TYPE: DNA
<213> ORGANISM: Unknown
<220> FEATURE:
<223> OTHER INFORMATION: Description of Unknown:
      Splice site sequence

<400> SEQUENCE: 75
ggggtaagtg                                                              10

<210> SEQ ID NO 76
<211> LENGTH: 10
<212> TYPE: DNA
<213> ORGANISM: Unknown
<220> FEATURE:
<223> OTHER INFORMATION: Description of Unknown:
      Splice site sequence

<400> SEQUENCE: 76
tgggtacctg                                                              10

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
acaggtggtg tttggttaca                                                   20

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aaattaaaca agctggtgat ggg                                               23

<210> SEQ ID NO 79
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
gtggcgatct gcgaga                                                     16

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 80
gagcttgccc gccatag                                                    17

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 81
ctggtcctgc agaagaaaga g                                               21

<210> SEQ ID NO 82
<211> LENGTH: 13
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 82
tgctagctga gga                                                        13

<210> SEQ ID NO 83
<211> LENGTH: 28
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 83
ggctaaatac tctaatggag attgttac                                        28

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 84
ggctgtgttt aatgacagat gac                                             23

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
     probe

<400> SEQUENCE: 85
ggaaacagga gggcgttag                                                  19

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cactgttggg ctgtgtttaa tg                                             22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acagtaccag cttcagtctt tc                                             22

<210> SEQ ID NO 88
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
aaacaggagg gcgtt                                                     15

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccatgccaga cctgaagaat                                                20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ttggactgga cgttgctaag                                                20

<210> SEQ ID NO 91
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
caccttcccg cctcc                                                     15

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
agatcggctc cactgagaa                                                    19

<210> SEQ ID NO 93
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ggtttatgat ggatgttgcc taatg                                             25

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 94
tgtagactat ttgcaccttc cc                                                22

<210> SEQ ID NO 95
<211> LENGTH: 404
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
gaattcggcc aggctcgtgc cgttttgcag acgccaccgc cgaggaaaac cgtgtactat        60
tagccatggt caaccccacc gtgttcttcg acattgccgt cgacggcgag cccttgggcc       120
gcgtctcctt tgagctgttt gcagacaagg tcccaaagac agcagaaaat tttcgtgctc       180
tgagcactgg agagaaagga tttggttata agggttcctg ctttcacaga attattccag       240
ggtttatgtg tcagggtggt gacttcacac gccataatgg cactggtggc aagtccatct       300
atggggagaa atttgaagat gagaacttca tcctaaagca tacgggtcct ggcatcttgt       360
ccatggcaaa tgctggaccc aacacaaatg gttcccgcgg ccgc                        404

<210> SEQ ID NO 96
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gaattcgttt ttggggaaca ggtggtgttt ggttacatga gtaagttctt tagtggcgat        60
ctgcgagatt ttggtacacc catcaccagc ttgtttaatt ttatctttct ttgtttatca       120

```
gcggccgc                                                            128
```

<210> SEQ ID NO 97
<211> LENGTH: 1009
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
gaattcggcg gaagatgaag ccactgctac cacgggtcag ctcatacctg gtacctatcc     60
agttcccggt gaaccagtca ctggtgttgc agccctcggt gaaggtgcca ttgcccctgg    120
cggcttccct catgagctca gagcttgccc gccatagcaa gcgagtccgc attgccccca    180
aggtgctgct agctgaggag gggatagctc ctctttcttc tgcaggacca gggaaagagg    240
agaaactcct gtttggagaa gggttttctc ctttgcttcc agttcagact atcaaggagg    300
aagaaatcca gctggggag gaaatgccac acttagcgag acccatcaaa gtggagagcc    360
ctcccttgga agagtggccc tccccggccc catctttcaa agaggaatca tctcactcct    420
gggaggattc gtcccaatct cccacccaa gacccaagaa gtcctacagt gggcttaggt     480
ccccaacccg gtgtgtctcg gaaatgcttg tgattcaaca cagggagagg agggagagga    540
gccggtctcg gaggaaacag catctactgc ctccctgtgt ggatgagccg gagctgctct    600
tctcagaggg gcccagtact tcccgctggg ccgcagagct cccgttccca gcagactcct    660
ctgaccctgc ctcccagctc agctactccc aggaagtggg aggacctttt aagacaccca    720
ttaaggaaac gctgcccatc tcctccaccc cgagcaaatc tgtcctcccc agaacccctg    780
aatcctggag gctcacgccc ccagccaaag taggggact ggatttcagc ccagtacaaa     840
cctcccaggg tgcctctgac ccccttgcctg acccctggg gctgatggat ctcagcacca    900
ctcccttgca aagtgctccc cccccttgaat caccgcaaag gctcctcagt tcagaacccct   960 tagacctcat ctccgtcccc tttggcaact cttctccctc agcggccgc                1009
```

<210> SEQ ID NO 98
<211> LENGTH: 238
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
gaattcaaag gtgcccgaga aaggccacg cccttcccca gtctgaaagt atttgggcta     60
aatactctaa tggagattgt tactgaagcc ggccccggga gtggtgaagg aaacaggagg    120
gcgttagtgg atcagaagtc atctgtcatt aaacacagcc caacagtgaa aagagaacct    180 ccatcaccc agggtcgatc cagcaattct agtgagaacc agcagttcct gcggccgc      238
```

<210> SEQ ID NO 99
<211> LENGTH: 259
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
gaattcaccg agggcttcgg gggcatcatg tcttttgcca gcagcctcta tcggaaccac    60
```

```
agtaccagct tcagtctttc aaacctcaca ctgcccacca aaggtgcccg agagaaggcc      120
acgcccttcc ccagtctgaa aggaaacagg agggcgttag tggatcagaa gtcatctgtc      180
attaaacaca gcccaacagt gaaagagaa cctccatcac cccagggtcg atccagcaat       240
tctagtgaga agcggccgc                                                   259
```

<210> SEQ ID NO 100
<211> LENGTH: 224
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100

```
gaattctccg ccaagagccg cctgcagaca gcccccgtgc ccatgccaga cctgaagaat      60
gtcaagtcca agatcggctc cactgagaac ctgaagcacc agccgggagg cgggaaggtg     120
cagataatta ataagaagct ggatcttagc aacgtccagt ccaagtgtgg ctcaaaggat     180
aatatcaaac acgtcccggg aggcggcagt gtgcaagcgg ccgc                      224
```

<210> SEQ ID NO 101
<211> LENGTH: 214
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101

```
gaattctcaa gtccaagatc ggctccactg agaacctgaa gcaccagccg ggaggcggga      60
aggtgcaaat agtctacaaa ccagttgacc tgagcaaggt gacctccaag tgtggctcat     120
taggcaacat ccatcataaa ccaggaggtg gccaggtgga agtaaaatct gagaagcttg     180
acttcaagga cagagtccag tcgaaggcgg ccgc                                 214
```

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102

```
gctcacattc cttaaattaa ggagaaa                                          27
```

<210> SEQ ID NO 103
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103

```
tggctatcat actggctatt atatggaa                                         28
```

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
tccagatctg tctgatcgtt tctt                                           24

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
ctggcataga gcagcactaa atgacaccac                                     30

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
accagggctc gatgatgaa                                                 19

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gcagcaatca tgtgtccca                                                 19

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
ttgtcactgt tgtgcc                                                    16

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gaaggtttcc acatttccaa g                                              21

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cacaaagctt gtattacaga ct                                             22

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
atttatgatc ataaccctaa ggtg                                           24

<210> SEQ ID NO 112
<211> LENGTH: 209
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
gaattccttc atttaaaaca ttacaggccg gcctgagcag caatcatgtg tcccatgggg    60
aagttctgcg gaaagtggag aggggttcac ggattgtcac tgttgtgccc caggacacaa  120
agcttgtatt acagatgcca aggggaaact tagaagttgt tcatcatcga gccctggttt  180
tagctcagat tcggaagtgg tgcggccgc                                     209

<210> SEQ ID NO 113
<211> LENGTH: 215
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
gaattccgga ttgtcactgt tgtgcccag gacacaaagc ttgtattaca gacttatgtt    60
taaagaggca tttgaatgca tgagaaagct gagaatcaat ctcaatctga tttatgatca  120
taaccctaag gtgtttcttg gaaatgtgga aaccttcatt aaacagatag attctgtgaa  180
tcatattaac ttgttttta cagaattgcg gccgc                               215

<210> SEQ ID NO 114
<211> LENGTH: 12
<212> TYPE: RNA
<213> ORGANISM: Unknown
<220> FEATURE:
<223> OTHER INFORMATION: Description of Unknown:
      primary RNA sequence

<400> SEQUENCE: 114
gcgcuguguc ga                                                        12

<210> SEQ ID NO 115
<211> LENGTH: 11
<212> TYPE: RNA
<213> ORGANISM: Unknown
<220> FEATURE:
<223> OTHER INFORMATION: Description of Unknown:
      pre-mRNA sequence
<220> FEATURE:
<221> NAME/KEY: modified_base

```
<222> LOCATION: (5)..(6)
<223> OTHER INFORMATION: Pseudouridine

<400> SEQUENCE: 115
auacuuaccu g                                                         11

<210> SEQ ID NO 116
<211> LENGTH: 11
<212> TYPE: RNA
<213> ORGANISM: Unknown
<220> FEATURE:
<223> OTHER INFORMATION: Description of Unknown:
      pre-mRNA sequence

<400> SEQUENCE: 116
ggaguaaguc u                                                         11

<210> SEQ ID NO 117
<211> LENGTH: 10
<212> TYPE: RNA
<213> ORGANISM: Unknown
<220> FEATURE:
<223> OTHER INFORMATION: Description of Unknown:
      pre-mRNA sequence
<220> FEATURE:
<221> NAME/KEY: modified_base
<222> LOCATION: (5)..(6)
<223> OTHER INFORMATION: Pseudouridine

<400> SEQUENCE: 117
auacuuacug                                                           10

<210> SEQ ID NO 118
<211> LENGTH: 12
<212> TYPE: RNA
<213> ORGANISM: Unknown
<220> FEATURE:
<223> OTHER INFORMATION: Description of Unknown:
      pre-mRNA sequence
<220> FEATURE:
<221> NAME/KEY: modified_base
<222> LOCATION: (12)..(12)
<223> OTHER INFORMATION: a, c, u, or g

<400> SEQUENCE: 118
caguaagucu gn                                                        12

<210> SEQ ID NO 119
<211> LENGTH: 10
<212> TYPE: RNA
<213> ORGANISM: Unknown
<220> FEATURE:
<223> OTHER INFORMATION: Description of Unknown:
      pre-mRNA sequence

<400> SEQUENCE: 119
caaguaagug                                                           10

<210> SEQ ID NO 120
<211> LENGTH: 9
<212> TYPE: RNA
<213> ORGANISM: Unknown
<220> FEATURE:
<223> OTHER INFORMATION: Description of Unknown:
      pre-mRNA sequence

<400> SEQUENCE: 120 aggugggu                                                              9
```

```
<210> SEQ ID NO 121
<211> LENGTH: 10
<212> TYPE: RNA
<213> ORGANISM: Unknown
<220> FEATURE:
<223> OTHER INFORMATION: Description of Unknown:
      pre-mRNA sequence

<400> SEQUENCE: 121
cagguaagua                                                         10
```